US010689388B1

(12) United States Patent
Castro et al.

(10) Patent No.: US 10,689,388 B1
(45) Date of Patent: Jun. 23, 2020

(54) INDOLE AHR INHIBITORS AND USES THEREOF

(71) Applicant: Kyn Therapeutics, Boston, MA (US)

(72) Inventors: Alfredo C. Castro, Somerville, MA (US); Catherine Anne Evans, Somerville, MA (US)

(73) Assignee: Ikena Oncology, Inc., Boston, MA (US)

( * ) Notice: Subject to any disclaimer, the term of this patent is extended or adjusted under 35 U.S.C. 154(b) by 0 days.

(21) Appl. No.: 16/668,070

(22) Filed: Oct. 30, 2019

Related U.S. Application Data

(62) Division of application No. 15/958,586, filed on Apr. 20, 2018, now Pat. No. 10,570,133.

(60) Provisional application No. 62/658,454, filed on Apr. 16, 2018, provisional application No. 62/592,542, filed on Nov. 30, 2017, provisional application No. 62/488,476, filed on Apr. 21, 2017.

(51) Int. Cl.

| | |
|---|---|
| ***C07D 487/04*** | (2006.01) |
| ***C07D 473/34*** | (2006.01) |
| ***C07D 495/04*** | (2006.01) |
| ***C07D 519/00*** | (2006.01) |
| ***C07D 401/14*** | (2006.01) |
| ***A61P 35/00*** | (2006.01) |
| ***A61P 29/00*** | (2006.01) |
| *A61K 9/00* | (2006.01) |

(52) U.S. Cl.
CPC ............ *C07D 487/04* (2013.01); *A61P 29/00* (2018.01); *A61P 35/00* (2018.01); *C07D 401/14* (2013.01); *C07D 473/34* (2013.01); *C07D 495/04* (2013.01); *C07D 519/00* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 8,906,682 | B2 | 12/2014 | June et al. |
| 2004/0009978 | A1 | 1/2004 | Hayakawa et al. |
| 2004/0235877 | A1 | 11/2004 | Ishizuka et al. |
| 2006/0128729 | A1 | 6/2006 | Pal et al. |
| 2011/0281863 | A1 | 11/2011 | Bearss et al. |
| 2018/0298013 | A1 | 10/2018 | Romero et al. |

FOREIGN PATENT DOCUMENTS

| | | | |
|---|---|---|---|
| WO | WO-2006029879 | A2 | 3/2006 |
| WO | WO-2006105021 | A2 | 10/2006 |
| WO | WO-2006122150 | A1 | 11/2006 |
| WO | WO-2007005874 | A2 | 1/2007 |
| WO | WO-2007075598 | A2 | 7/2007 |
| WO | WO-2008036642 | A2 | 3/2008 |
| WO | WO-2008036653 | A2 | 3/2008 |
| WO | WO-2008132601 | A1 | 11/2008 |
| WO | WO-2009009116 | A2 | 1/2009 |
| WO | WO-2009044273 | A2 | 4/2009 |
| WO | WO-2009073620 | A2 | 6/2009 |
| WO | WO-2010019570 | A2 | 2/2010 |
| WO | WO-2010077634 | A1 | 7/2010 |
| WO | WO-2011028683 | A1 | 3/2011 |
| WO | WO-2011056652 | A1 | 5/2011 |
| WO | WO-2011070024 | A1 | 6/2011 |
| WO | WO-2011107553 | A1 | 9/2011 |
| WO | WO-2011109400 | A2 | 9/2011 |
| WO | WO-2011131407 | A1 | 10/2011 |
| WO | WO-2011140249 | A2 | 11/2011 |
| WO | WO-2012032433 | A1 | 3/2012 |
| WO | WO-2012142237 | A1 | 10/2012 |
| WO | WO-2012145493 | A1 | 10/2012 |
| WO | WO-2013079174 | A1 | 6/2013 |
| WO | WO-2013087699 | A1 | 6/2013 |
| WO | WO-2013119716 | A1 | 8/2013 |
| WO | WO-2013132044 | A1 | 9/2013 |
| WO | WO-2013169264 | A1 | 11/2013 |
| WO | WO-2014008218 | A1 | 1/2014 |
| WO | WO-2014036357 | A1 | 3/2014 |
| WO | WO-2014138485 | A1 | 9/2014 |

OTHER PUBLICATIONS

Adams et al., "Big Opportunities for Small Molecules in Immuno-oncology," Nature Reviews Drug Discovery, vol. 14, No. 9, Sep. 2015 (pp. 603-622).
Berge et al., "Pharmaceutical Salts," Journal of Pharmaceutical Sciences, vol. 66, No. 1, Jan. 1977 (pp. 1-19).
Esser et al., The Aryl Hydrocarbon Receptor in Immunity, Trends in Immunology, vol. 30, No. 9, Sep. 2009 (pp. 447-454).
Funatake et al., "Cutting Edge: Activation of the Aryl Hydrocarbon Receptor by 2, 3, 7, 8-Tetachlorodibenzo-p-dioxin Generates a Population of CD4+ CD25+ Cells With Characteristics of Regulatory T Cells," Journal of Immunology, vol. 175, No. 7, Oct. 2005 (pp. 4184-4188).
Gandhi et al., "Activation of the Aryl Hydrocarbon Receptor Induces Human Type 1 Regulatory T Cell-like and Foxp3(=) Regulatory T Cells," Nature Immunology, vol. 11, No. 9, Sep. 2010 (pp. 846-853).
Head et al., "The Aryl Hydrocarbon Receptor is a Modulator of Anti-Viral Immunity," Biochemical Pharmacology, vol. 77, No. 4, Feb. 2009 (pp. 642-653).
Ishida et al., "Activation of Aryl Hydrocarbon Receptor Promotes Invasion of Clear Cell Renal Cell Carcinoma and is Associated With Poor Prognosis and Cigarette Smoke," International Journal of Cancer, vol. 137, No. 2, Jul. 2015 (pp. 299-310).
Ishida et al., "Activation of the Aryl Hydrocarbon Receptor Pathway Enhances Cancer Cell Invasion by Upregulating the MMP Expression and is Associated With poor Prognosis in Upper Urinary TractUrothelial Cancer," Carcinogenesis, vol. 31, No. 2, Feb. 2010 (pp. 287-295).

(Continued)

*Primary Examiner* — Po-Chih Chen
(74) *Attorney, Agent, or Firm* — Andrea L. C. Reid; Dechert LLP

(57) ABSTRACT

The present invention provides compounds useful as inhibitors of AHR, compositions thereof, and methods of using the same.

20 Claims, 4 Drawing Sheets

(56) References Cited

OTHER PUBLICATIONS

Jin et al, "Aryl Hydrocarbon Receptor Activation Reduces Dendritic Cell function During Influenza Virus Infection," Toxicological Sciences, vol. 116, No. 2, Aug. 2010 (pp. 512-522).
Jin et al., "New Insightsinto the Role of the Aryl Hydrocarbon Receptor in the Function of CD11c+ Cells During Respiratory Viral Infection," European Journal of Immunology, vol. 44, No. 6, Jun. 2014 (pp. 1685-1698).
Menzrich et al., "An Interaction Between Kynurenine and the Aryl Hydrocarbon Receptor Can Generate Regulatory T Cells," Journal of Immunology, vol. 185, No. 6, Sep. 2010 (pp. 3190-3198).
Moon et al., "Targeting the Indoleamine 2,3-Dioxygenase Pathway in Cancer," Journal for Immunotherapy of Cancer, vol. 3, No. 51, Dec. 2015 (10 pages).
Murray et al., "Ah Receptor Ligands in Cancer: friend of Foe," Nature Reviews Cancer, vol. 14, No. 12, Dec. 2014 (pp. 801-814).
Nguyen et al., "The Roles of Aryl Hydrocarbon Receptor in Immune Responses," International Immunology, vol. 25, No. 6, Jun. 2013 (pp. 335-343).
Nguyen et al., "Aryl Hydrocarbon Receptor and Kynurenine: Recent Advances in Autoimmune Disease Research," Frontiers in Immunology, vol. 5, No. 551, Oct. 2014 (6 pages).
Okazaki et al., "A Rheostat for Immune Responses: the Unique Properties of PD-1 and Their Advantages for clinical Application," Nature Immunology, vol. 14, No. 12, Dec. 2013 (pp. 1212-1218).
Opitz et al., "An Endogenous Tumour-Promoting Ligand of the Human Aryl Hydrocarbon Receptor," Nature, vol. 478, No. 7368, Oct. 2011 (pp. 197-203).
Peng et al., "Aryl Hydrocarbon Receptor pathway Activation Enhances Gastric Cancer Cell Invasiveness Likely Through a c-Jun-dependent Induction of Matri Metalloproteinase-9," BMC Cell Biology, vol. 10, No. 27, Apr. 2009 (7 pages).
Ross et al., "Bispecific T Cell Engager (BiTE®) Antibody Constructs Can Mediate Bystander Tumor Cell Killing," PLoS One, vol. 12, No. 8, Aug. 2017 (24 pages).
Su et al., "Prognostic Value of Nuclear Translocation of Aryl Hydrocarbon Receptor for non-Small Cell Lung Cancer," Anticancer Research, vol. 33, No. 9, Sep. 2013 (pp. 3953-3961).
Togood, "Small Molecule Immuno-Oncology Therapeutic Agents," Bioorganic and Medicinal Chemistry Letters, vol. 28, No. 3, Feb. 2018 (pp. 319-329).
Uyttenhove et al., "Evidence for a Tumoral Immune Resistance Mechanism Based on Tryptophan Degradation by Indoleamine 2.3-Dioxygenase," Nature Medicine, vol. 9, No. 10, Oct. 2003 (pp. 1269-1274).
Vogel et al.,"Cross-talk Between Aryl Hydrocarbon Receptor and the Inflammatory Response: A Role for Nuclear Factor-kB," Journal of Biological Chemistry, vol. 289, No. 3, Jan. 2014 (pp. 1866-1875).
Wagage et al., "The Aryl Hydrocarbon Receptor Promotes IL-10 Production by NK Cells," Journal of Immunology, vol. 192, No. 4, Feb. 2014 pp. 1661-1670).
Zou et al., "PD-L1 (B7-H1) and PD-1 Pathway Blockade for Cancer Therapy: Mechanisms, Response Biomarkers and Combinations," Science Translational Medicine, vol. 8, No. 328, Mar. 2016 (34 pages).
International Search Report and Written Opinion for International Application No. PCT/US2018/028532 dated Oct. 30, 2018 (10 pages).
Pubmed Compound Summary for CID 56889663, 'FEUZRBLRMMOWLUUHFFFAOYSA-N', U.S. National Library of Medicine, Mar. 30, 2012 (pp. 1-11), p. 3 (https://pubchem.ncbi.nim.nih.gov/compound/56889663).
Pubmed Compound Summary for CID 56913247, 'BIPWCZYHWSCQMCUHFFFAOYSA-N', U.S. National Library of Medicine, Mar. 30, 2012 (pp. 1-11); p. 3 (https://pubchem.ncbi.nlm.nih.gov/compound/56913247).
Pubmed Compound Summary for CID 71138224, 'HFJKTMMVPWAAQQUHFFFAOYSA-N', U.S. National Library of Medicine, Mar. 21, 2013 (pp. 1-8); p. 3 (https://pubchem.ncbi.nlm.nih.gov/mcompound/71138224).

INDOLE AHR INHIBITORS AND USES THEREOF

BACKGROUND OF THE INVENTION

The aryl hydrocarbon receptor (AHR) is a transcription factor that without ligand exists in the inactive state in the cytoplasm bound to HSP90. Upon ligand binding, AHR translocates to the nucleus where it dimerizes with ARNT forming a functional transcription factor. AHR/ARNT binds dioxin response elements (DRE) in the promotor of many genes where it modulates gene transcription. The most well documented genes regulated by AHR are the cytochrome P450 genes Cyp1b1 and Cyp1a1, where activation of AHR greatly increases expression of these genes. Therefore, Cyp1b1 and Cyp1a1 mRNA levels are a selective readout of AHR activation (reviewed in Murray et al., 2014).

Many exogenous and endogenous agonists of AHR exist that activate the receptor. The best characterized exogenous ligand class are the dioxins. One of the first endogenous ligands to be characterized is kynurenine, generated by TDO (Opitz 2011) or IDO (Mezrich 2010). Kynurenine is a stable metabolite in the IDO/TDO pathway and is the product of tryptophan degradation. Kynurenine has been shown to activate AHR as measured by an increase in Cyp1a1 and/or Cyp1b1 mRNA levels in multiple cell types, along with other DRE-driven genes.

AHR activation has pro-tumor effects by acting directly on the tumor cells and indirectly by causing immunosuppression, therefore not allowing the body's own immune system to attack the tumor. For example, AHR activation through multiple ligands leads to increased expression of FoxP3 and results in a polarization of CD4+ T-cells toward a suppressive subset called Foxp3+T-regulatory cells (Tregs). These T-reg cells inhibit the proliferation of activated T cells (Funatake 2005, other refs). Interestingly, kynurenine has been shown to induce immunosuppressive Tregs through AHR. Kynurenine does not affect T-reg generation in AHR-null T cells or when an AHR antagonist is added (Mezrich). In addition to T-regs, AHR activation also leads to expansion of suppressive Tr1 T cells (Gandhi 2010). It has also been shown that expression of IDO is regulated by AHR activation in both tumor cells and T cells, leading to increased immune suppression (Vogel). It is likely there is also a role for AHR in immune suppressive myeloid cells (Nguyen 2013). Immune suppression is often associated with high levels of anti-inflammatory cytokines and there is evidence that AHR is involved in activation of many of these cytokines, such as IL-10 (Gandhi 2010, Wagage 2014).

There remains an unmet need to develop inhibitors of AHR for treating diseases, disorders and conditions associated therewith.

SUMMARY OF THE INVENTION

It has now been found that compounds of this invention, and pharmaceutically acceptable compositions thereof, are effective as inhibitors of AHR. Such compounds have the general formula I:

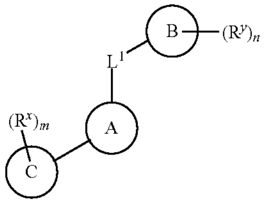

I or a pharmaceutically acceptable salt thereof, wherein each variable is as defined and described herein.

Compounds of the present invention, and pharmaceutically acceptable compositions thereof, are useful for treating a variety of diseases, disorders or conditions, associated with AHR. Such diseases, disorders, or conditions include those described herein.

Compounds provided by this invention are also useful for the study of AHR in biological and pathological phenomena; the study of intracellular signal transduction pathways; and the comparative evaluation of new AHR inhibitors in vitro or in vivo.

DETAILED DESCRIPTION OF CERTAIN EMBODIMENTS

Figure 1:
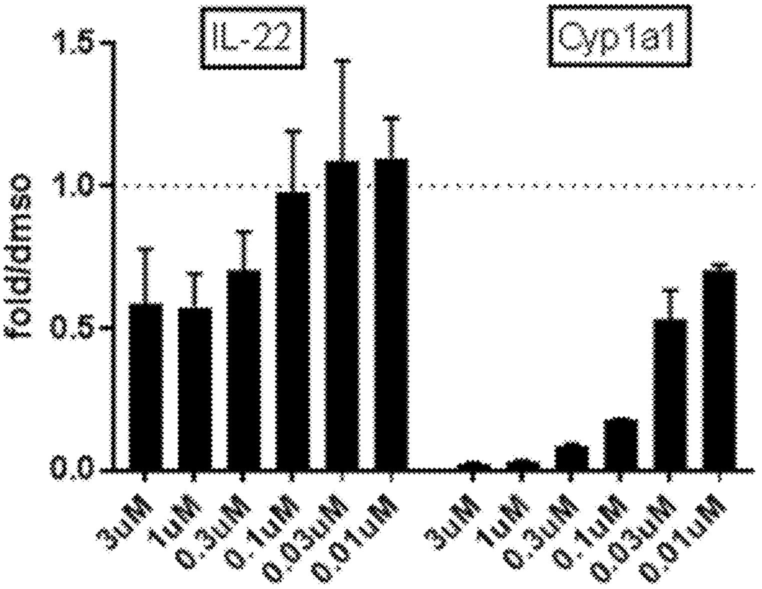
FIG. 1 depicts a plot showing inhibition of IL22 and cyp1a1 RNA expression levels with a compound described herein.

1. General Description of Compounds of the Invention

In certain embodiments, the present invention provides inhibitors of AHR. In some embodiments, such compounds include those of formula I:

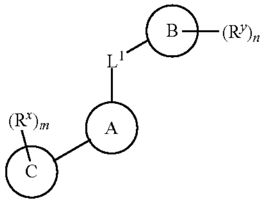

I or a pharmaceutically acceptable salt thereof, wherein: Ring A is selected from:

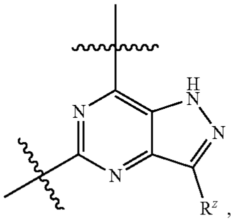
,
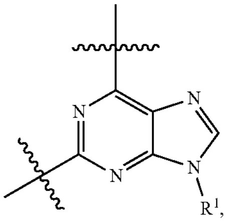
,
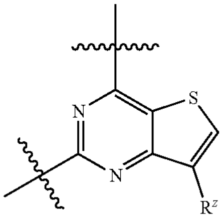
,
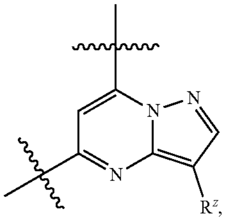
,
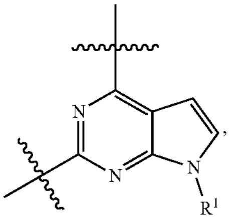
,
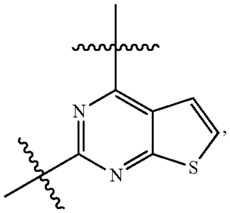
,
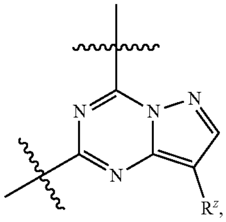
,
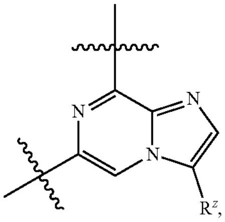
,
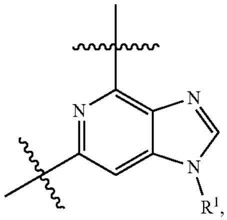
,
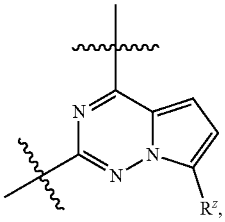
, and
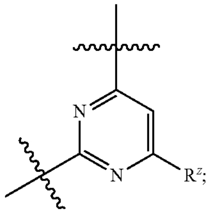
;

each $R^1$ is independently selected from R, —C(O)R, —C(O)OR, —$SO_2$R, —C(O)N(R)$_2$, or —$SO_2$RN(R)$_2$;

each R is independently hydrogen, deuterium, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each or $R^x$, $R^y$, and $R^z$ is independently selected from R, halogen, cyano, nitro, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)$SO_2$R, —$SO_2$RN(R)$_2$, —C(O)R, —C(O)OR, —OC(O)R, —C(O)OR, —S(O)R, or —$SO_2$R, or:

two $R^x$ on the same carbon are taken together to form =O or =S; or:

two $R^y$ on the same carbon are taken together to form =O or =S;

each of m and n is independently 1, 2, 3, 4, or 5;

Ring B is phenyl, a 5-6 membered monocyclic heteroaromatic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

Ring C is phenyl or a 5-6 membered heteroaryl ring having 1-4 heteroatoms independently selected from nitrogen, oxygen, or sulfur; or an 8-10 membered bicyclic heteroaryl ring having 1-4 heteroatoms independently selected from nitrogen, oxygen, or sulfur;

$L^1$ is a covalent bond or an optionally substituted $C_{1-6}$ membered straight or branched bivalent hydrocarbon chain wherein a methylene unit of $L^1$ is optionally replaced with -Cy-, —O—, —S—, —NR—, —C(O)—, —C(O)O—, —OC(O)—, —C(O)N(R)—, —N(R)C(O)—, —$SO_2$—, —N(R)$SO_2$—, or —$SO_2$N(R)—S; and -Cy- is a 3-8 membered bivalent saturated, partially unsaturated, or aromatic monocyclic ring having 0-2 heteroatoms independently selected from nitrogen, oxygen, or sulfur, or an 8-10 membered bivalent saturated, partially unsaturated, or aromatic bicyclic ring having 0-3 heteroatoms independently selected from nitrogen, oxygen, or sulfur.

In some embodiments, the present invention provides inhibitors of AHR, such compounds include those of formula I':

I'

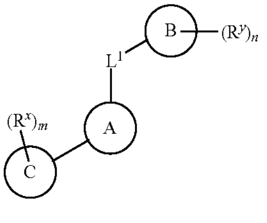

or a pharmaceutically acceptable salt thereof, wherein: Ring A is selected from:

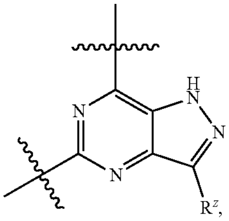
,
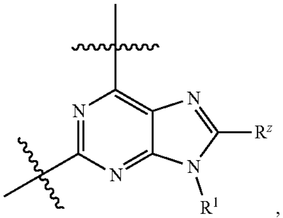
,

-continued

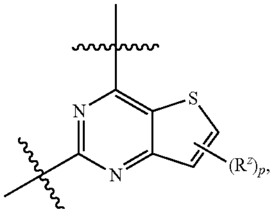
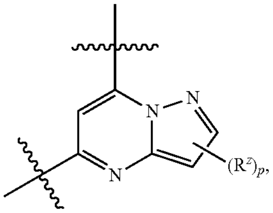
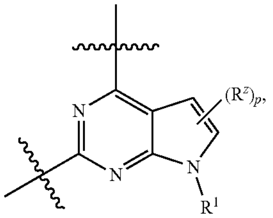
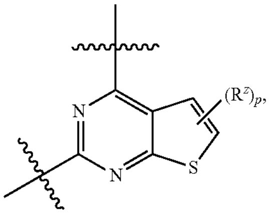
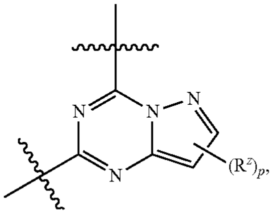
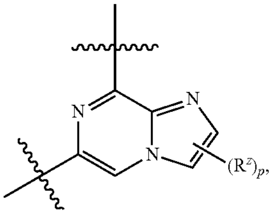
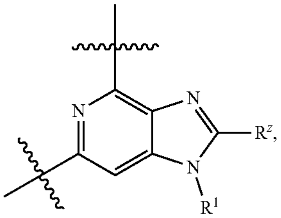
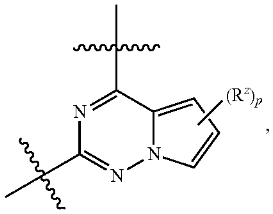
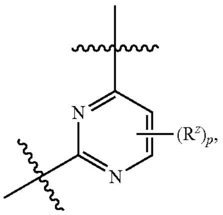
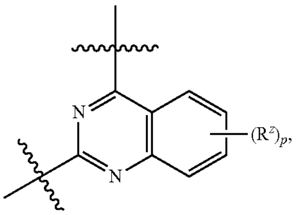
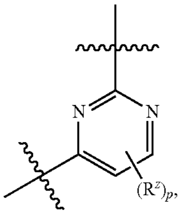
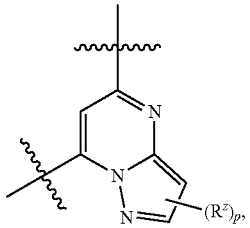
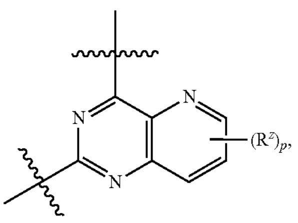
and
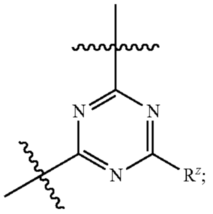

each p is independently 0, 1, or 2, as valency will allow;

each $R^1$ is independently selected from R, —C(O)R, —C(O)OR, —$SO_2$R, —C(O)N$(R)_2$, or —$SO_2$RN$(R)_2$;

each R is independently hydrogen, deuterium, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or two R on the same nitrogen are taken together with their intervening atoms to form a 4-7 membered saturated, partially unsaturated, or aromatic ring having 1-2 heteroatoms in addition to the nitrogen independently selected from oxygen, nitrogen, or sulfur;

each or $R^x$, $R^y$, and $R^z$ is independently selected from R, halogen, cyano, nitro, —OR, —SR, —N$(R)_2$, —N(R)C(O)R, —C(O)N$(R)_2$, —C(O)N(R)OR, —N(R)C(O)N$(R)_2$, —N(R)C(O)OR, —OC(O)N$(R)_2$, —N(R)$SO_2$R, —$SO_2$RN$(R)_2$, —C(O)R, —C(O)OR, —OC(O)R, —C(O)OR, —S(O)R, or —$SO_2$R, or:

two $R^x$ on the same carbon are taken together to form =O or =S; or:

two $R^y$ on the same carbon are taken together to form =O or =S;

each of m and n is independently 1, 2, 3, 4, or 5;

Ring B is phenyl, a 7-10 membered bicyclic partially unsaturated or aromatic carbocyclic ring, a 5-6 membered monocyclic heteroaromatic ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, or a 12-15 membered partially unsaturated or aromatic tricyclic ring having 1-4 heteroatoms independently selected from nitrogen, oxygen, or sulfur;

Ring C is phenyl or a 5-6 membered heteroaryl ring having 1-4 heteroatoms independently selected from nitrogen, oxygen, or sulfur;

$L^1$ is a covalent bond or an optionally substituted $C_{1-6}$ membered straight or branched bivalent hydrocarbon chain wherein a methylene unit of $L^1$ is optionally replaced with -Cy-, —O—, —S—, —NR—, —C(O)—, —C(O)O—, —OC(O)—, —C(O)N(R)—, —N(R)C(O)—, —$SO_2$—, —N(R)$SO_2$—, or —$SO_2$N(R)—S; and -Cy- is a 3-8 membered bivalent saturated, partially unsaturated, or aromatic monocyclic ring having 0-2 heteroatoms independently selected from nitrogen, oxygen, or sulfur, or an 8-10 membered bivalent saturated, partially unsaturated, or aromatic bicyclic ring having 0-3 heteroatoms independently selected from nitrogen, oxygen, or sulfur.

In some embodiments, the present invention provides a compound of formula I or formula I', with the proviso that when Ring A is

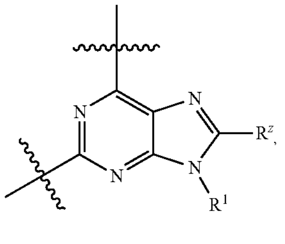

Ring B is not
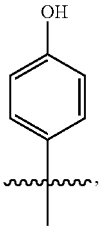, 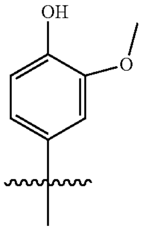, 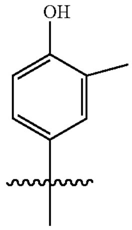,
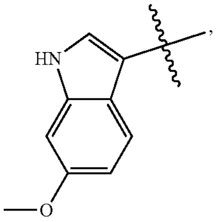, 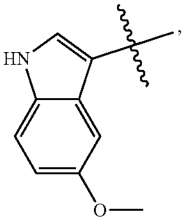,
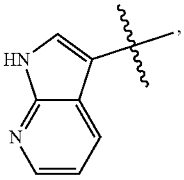, 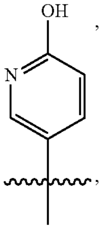, 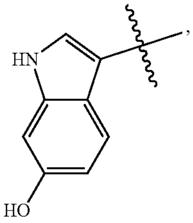,
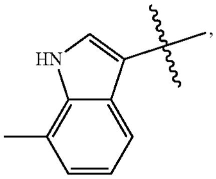, 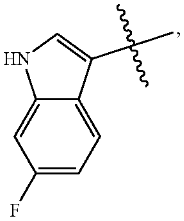,
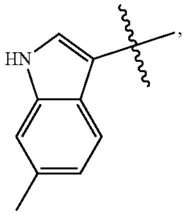, 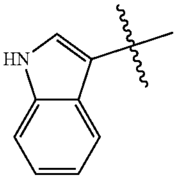 or
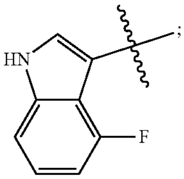; and/or
Ring C is not
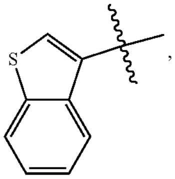, 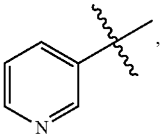, 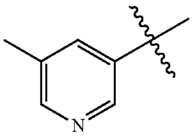 or
-continued
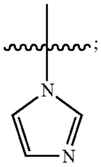; and/or
$R^1$ is not
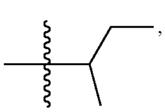, 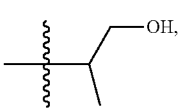 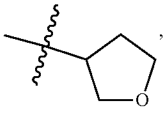,
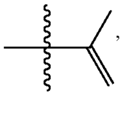, or 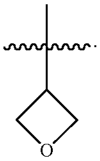.
As generally defined above, Ring A is selected from:
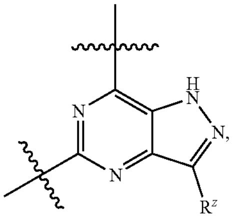 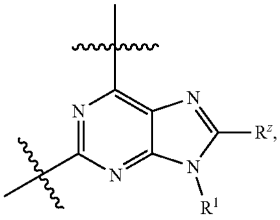
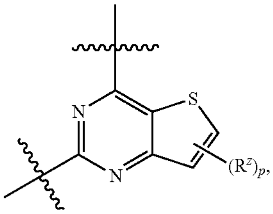 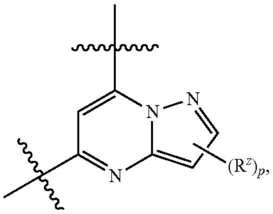
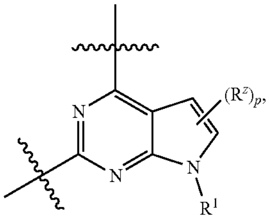 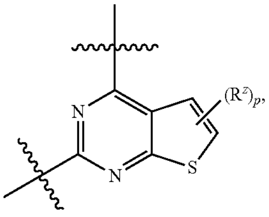
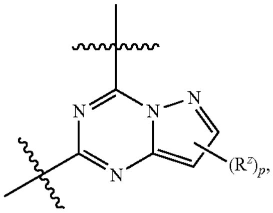 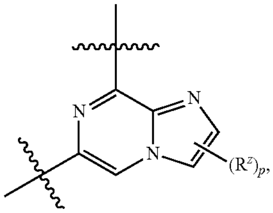

-continued

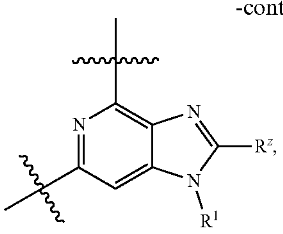

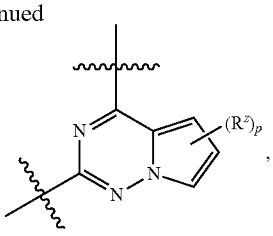

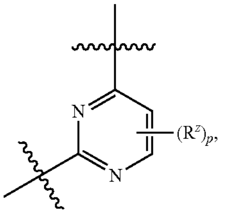

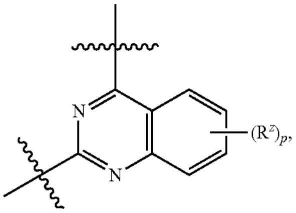

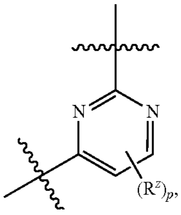

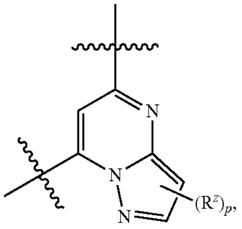

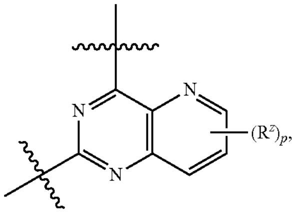

and

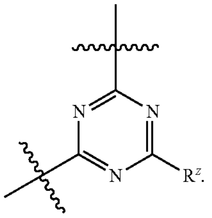

One of ordinary skill in the art would readily understand and appreciate that there are multiple orientations of Ring A. For example, and for the purposes of clarity, when Ring A is selected to be

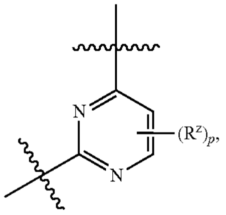

embodiments may be envisioned whereby Ring A is oriented in formula I or formula I' as

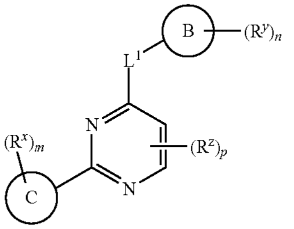

or as

-continued

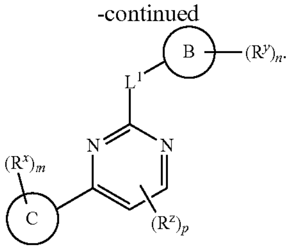

Accordingly, both such orientations are contemplated by the present invention.

In some embodiments, the present invention provides a compound of formula I or formula I', with the proviso that $L^1$ is not —$NHCH_2CH_2$—. In some embodiments, the present invention provides a compound of formula I or formula I', with the proviso that when Ring A is

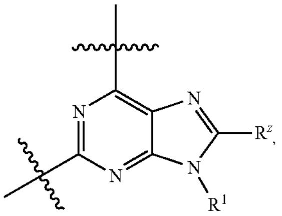

$L^1$ is not —$NHCH_2CH_2$—.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

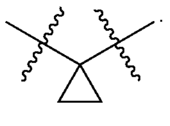 [SMILES: *C1(*)CC1]

As used herein, the term "cyclobutylenyl" refers to a bivalent cyclobutyl group of the following structure:

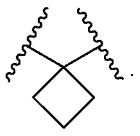 [SMILES: *C1(*)CCC1]

As used herein, the term "oxetanyl" refers to a bivalent oxetanyl group of the following structure:

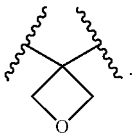 [SMILES: *C1(*)COC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^o$; $—(CH_2)_{0-4}OR^o$; $—O(CH_2)_{0-4}R^o$, $—O—(CH_2)_{0-4}C(O)OR^o$; $—(CH_2)_{0-4}CH(OR^o)_2$; $—(CH_2)_{0-4}SR^o$; $—(CH_2)_{0-4}Ph$, which may be substituted with $R^o$; $—(CH_2)_{0-4}O(CH_2)_{0-1}Ph$ which may be substituted with $R^o$; $—CH{=}CHPh$, which may be substituted with $R^o$; $—(CH_2)_{0-4}O(CH_2)_{0-1}$-pyridyl which may be substituted with $R^o$; $—NO_2$; $—CN$; $—N_3$; $—(CH_2)_{0-4}N(R^o)_2$; $—(CH_2)_{0-4}N(R^o)C(O)R^o$; $—N(R^o)C(S)R^o$; $—(CH_2)_{0-4}N(R^o)C(O)NR^o_2$; $—N(R^o)C(S)NR^o_2$; $—(CH_2)_{0-4}N(R^o)C(O)OR^o$; $—N(R^o)N(R^o)C(O)R^o$; $—N(R^o)N(R^o)C(O)NR^o_2$; $—N(R^o)N(R^o)C(O)OR^o$; $—(CH_2)_{0-4}C(O)R^o$; $—C(S)R^o$; $—(CH_2)_{0-4}C(O)OR^o$; $—(CH_2)_{0-4}C(O)SR^o$; $—(CH_2)_{0-4}C(O)OSiR^o_3$; $—(CH_2)_{0-4}OC(O)R^o$; $—OC(O)(CH_2)_{0-4}SR—$, $SC(S)SR^o$; $—(CH_2)_{0-4}SC(O)R^o$; $—(CH_2)_{0-4}C(O)NR^o_2$; $—C(S)NR^o_2$; $—C(S)SR^o$; $—SC(S)SR^o$, $—(CH_2)_{0-4}OC(O)NR^o_2$; $—C(O)N(OR^o)R^o$; $—C(O)C(O)R^o$; $—C(O)CH_2C(O)R^o$; $—C(NOR^o)R^o$; $—(CH_2)_{0-4}SSR^o$; $—(CH_2)_{0-4}S(O)_2R^o$; $—(CH_2)_{0-4}S(O)_2OR^o$; $—(CH_2)_{0-4}OS(O)_2R^o$; $—S(O)_2NR^o_2$; $—(CH_2)_{0-4}S(O)R^o$; $—N(R^o)S(O)_2NR^o_2$; $—N(R^o)S(O)_2R^o$; $—N(OR)R^o$; $—C(NH)NR^o_2$; $—P(O)_2R^o$; $—P(O)R^o_2$; $—OP(O)R^o_2$; $—OP(O)(OR^o)_2$; $SiR^o_3$; $—(C_{1-4}$ straight or branched alkylene)$O—N(R^o)_2$; or $—(C_{1-4}$ straight or branched alkylene) $C(O)O—N(R^o)_2$, wherein each $R^o$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), are independently halogen, $—(CH_2)_{0-2}R^•$, -(halo$R^•$), $—(CH_2)_{0-2}OH$, $—(CH_2)_{0-2}OR^•$, $—(CH_2)_{0-2}CH(OR^•)_2$; —O(halo$R^•$), $—CN$, $—N_3$, $—(CH_2)_{0-2}C(O)R^•$, $—(CH_2)_{0-2}C(O)OH$, $—(CH_2)_{0-2}C(O)OR^•$, $—(CH_2)_{0-2}SR^•$, $—(CH_2)_{0-2}SH$, $—(CH_2)_{0-2}NH_2$, $—(CH_2)_{0-2}NHR^•$, $—(CH_2)_{0-2}NR^•_2$, $—NO_2$, $—SiR^•_3$, $—OSiR^•_3$, $—C(O)SR^•$, $—(C_{1-4}$ straight or branched alkylene)$C(O)OR^•$, or $—SSR^•$ wherein each $R^•$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^o$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $—O(C(R^*_2))_{2-3}O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $—R^•$, -(halo$R^•$), $—OH$, $—OR^•$, —O(halo$R^•$), $—CN$, $—C(O)OH$, $—C(O)OR^•$, $—NH_2$, $—NHR^•$, $—NR^•_2$, or $—NO_2$, wherein each $R^•$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^\dagger$, $—NR^\dagger_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\dagger_2$, or $—N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $—R^\bullet$, -(halo$R^\bullet$), —OH, $—OR^\bullet$, —O(halo$R^\bullet$), —CN, —C(O)OH, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

3. Description of Exemplary Embodiments

In certain embodiments, the present invention provides inhibitors of AHR. In some embodiments, such compounds include those of formula I:

I

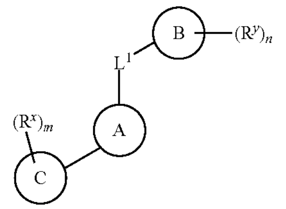

or a pharmaceutically acceptable salt thereof, wherein:

Ring A is selected from:

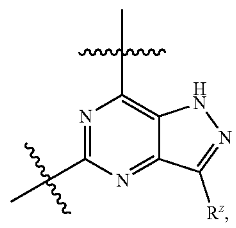
,
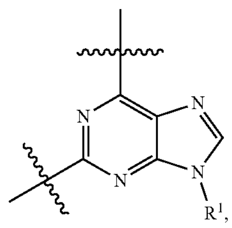
,
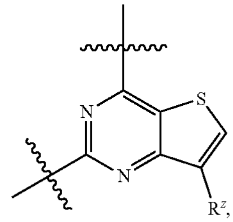
,
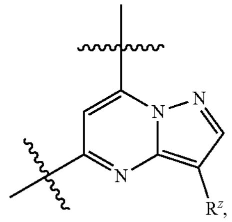
,
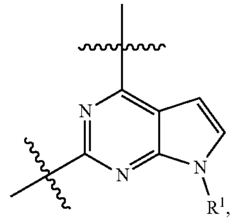
,
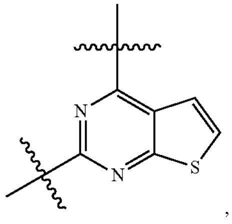
,

-continued

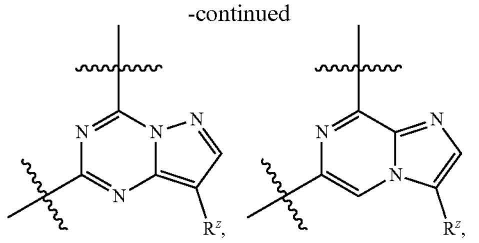

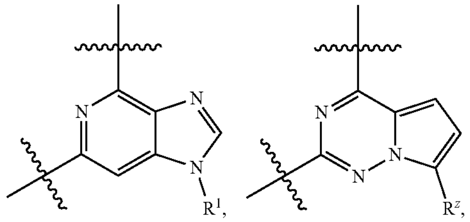

and

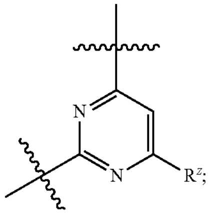

each $R^1$ is independently selected from R, —C(O)R, —C(O)OR, —$SO_2$R, —C(O)N$(R)_2$, or —$SO_2$RN$(R)_2$;

each R is independently hydrogen, deuterium, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each or $R^x$, $R^y$, and $R^z$ is independently selected from R, halogen, cyano, nitro, —OR, —SR, —N$(R)_2$, —N(R)C(O)R, —C(O)N$(R)_2$, —N(R)C(O)N$(R)_2$, —N(R)C(O)OR, —OC(O)N$(R)_2$, —N(R)$SO_2$R, —$SO_2$RN$(R)_2$, —C(O)R, —C(O)OR, —OC(O)R, —C(O)OR, —S(O)R, or —$SO_2$R, or:

two $R^x$ on the same carbon are taken together to form =O or =S; or:

two $R^y$ on the same carbon are taken together to form =O or =S;

each of m and n is independently 1, 2, 3, 4, or 5;

Ring B is phenyl, a 5-6 membered monocyclic heteroaromatic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

Ring C is phenyl or a 5-6 membered heteroaryl ring having 1-4 heteroatoms independently selected from nitrogen, oxygen, or sulfur; or an 8-10 membered bicyclic heteroaryl ring having 1-4 heteroatoms independently selected from nitrogen, oxygen, or sulfur;

$L^1$ is a covalent bond or an optionally substituted $C_{1-6}$ membered straight or branched bivalent hydrocarbon chain wherein a methylene unit of $L^1$ is optionally replaced with -Cy-, —O—, —S—, —NR—, —C(O)—, —C(O)O—, —OC(O)—, —C(O)N(R)—, —N(R)C(O)—, —$SO_2$—, —N(R)$SO_2$—, or —$SO_2$N(R)—S; and -Cy- is a 3-8 membered bivalent saturated, partially unsaturated, or aromatic monocyclic ring having 0-2 heteroatoms independently selected from nitrogen, oxygen, or sulfur, or an 8-10 membered bivalent saturated, partially unsaturated, or aromatic bicyclic ring having 0-3 heteroatoms independently selected from nitrogen, oxygen, or sulfur.

In some embodiments, the present invention provides inhibitors of AHR, such compounds include include those of formula I':

I'

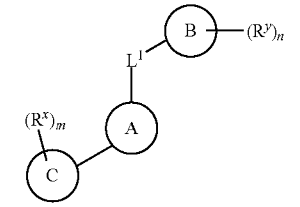

or a pharmaceutically acceptable salt thereof, wherein:

Ring A is selected from:

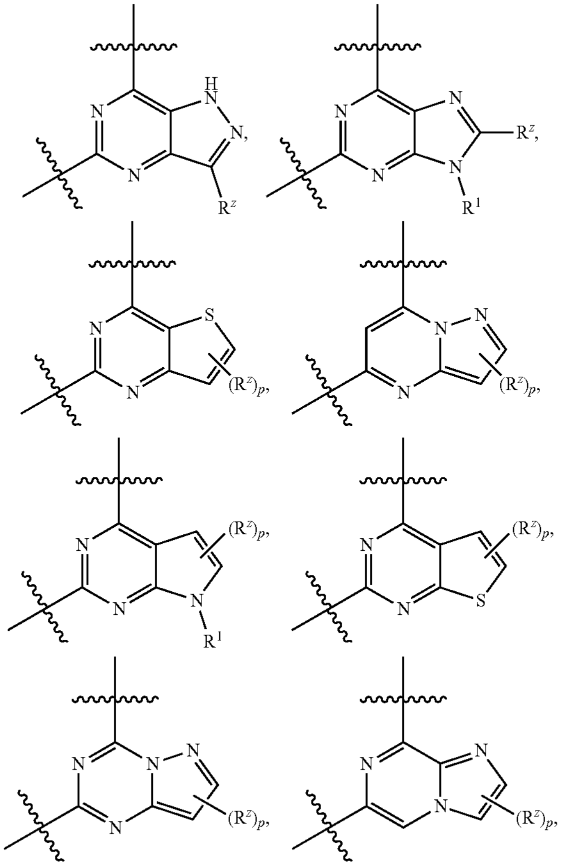

-continued

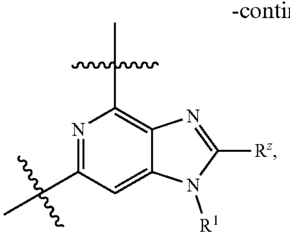

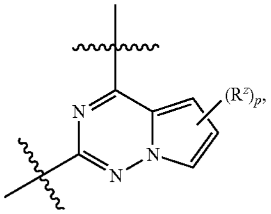

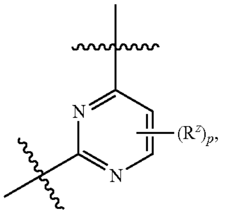

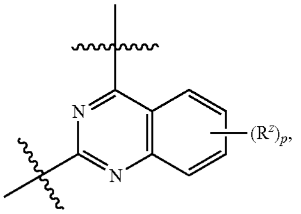

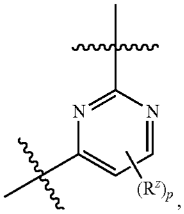

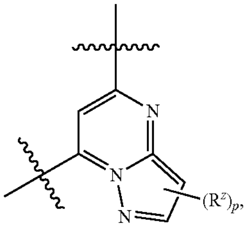

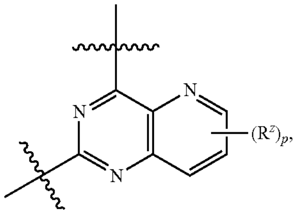

and

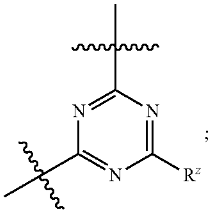

;

each p is independently 0, 1, or 2, as valency will allow;

each $R^1$ is independently selected from R, —C(O)R, —C(O)OR, —$SO_2$R, —C(O)N$(R)_2$, or —$SO_2$RN$(R)_2$;

each R is independently hydrogen, deuterium, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or two R on the same nitrogen are taken together with their intervening atoms to form a 4-7 membered saturated, partially unsaturated, or aromatic ring having 1-2 heteroatoms in addition to the nitrogen independently selected from oxygen, nitrogen, or sulfur;

each or $R^x$, $R^y$, and $R^z$ is independently selected from R, halogen, cyano, nitro, —OR, —SR, —N$(R)_2$, —N(R)C(O)R, —C(O)N$(R)_2$, —C(O)N(R)OR, —N(R)C(O)N$(R)_2$, N(R)C(O)OR, —OC(O)N$(R)_2$, —N(R)$SO_2$R, —$SO_2$RN$(R)_2$, —C(O)R, —C(O)OR, —OC(O)R, —C(O)OR, —S(O)R, or —$SO_2$R, or:

two $R^x$ on the same carbon are taken together to form =O or =S; or:

two $R^y$ on the same carbon are taken together to form =O or =S;

each of m and n is independently 1, 2, 3, 4, or 5;

Ring B is phenyl, a 7-10 membered bicyclic partially unsaturated or aromatic carbocyclic ring, a 5-6 membered monocyclic heteroaromatic ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, or a 12-15 membered partially unsaturated or aromatic tricyclic ring having 1-4 heteroatoms independently selected from nitrogen, oxygen, or sulfur;

Ring C is phenyl or a 5-6 membered heteroaryl ring having 1-4 heteroatoms independently selected from nitrogen, oxygen, or sulfur;

$L^1$ is a covalent bond or an optionally substituted $C_{1-6}$ membered straight or branched bivalent hydrocarbon chain wherein a methylene unit of $L^1$ is optionally replaced with -Cy-, —O—, —S—, —NR—, —C(O)—, —C(O)O—, —OC(O)—, —C(O)N(R)—, —N(R)C(O)—, —$SO_2$—, —N(R)$SO_2$—, or —$SO_2$N(R)—S; and -Cy- is a 3-8 membered bivalent saturated, partially unsaturated, or aromatic monocyclic ring having 0-2 heteroatoms independently selected from nitrogen, oxygen, or sulfur, or an 8-10 membered bivalent saturated, partially unsaturated, or aromatic bicyclic ring having 0-3 heteroatoms independently selected from nitrogen, oxygen, or sulfur.

In some embodiments, the present invention provides a compound of formula I or formula I', with the proviso that when Ring A is

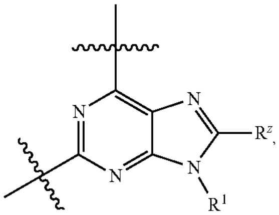

Ring B is not

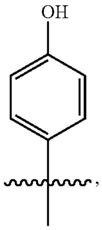

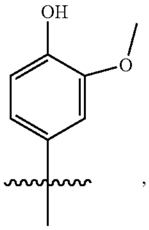

,

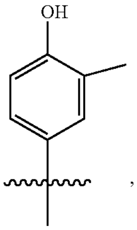

,

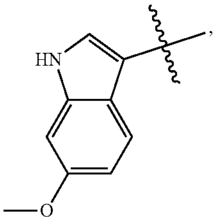

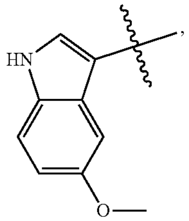

-continued

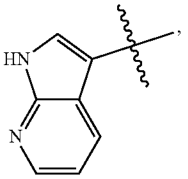

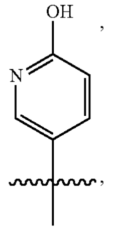

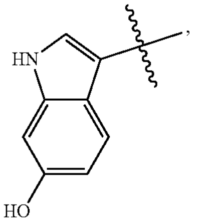

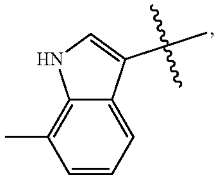

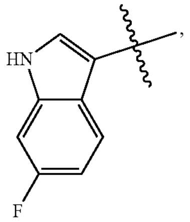

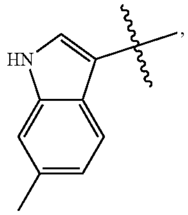

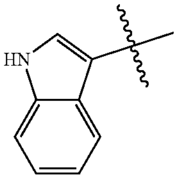

or

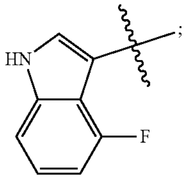

; and/or

Ring C is not

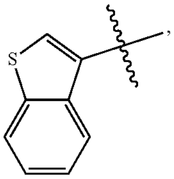

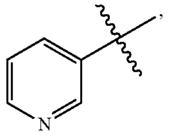

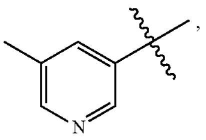

, or

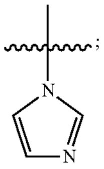

; and/or $R^1$ is not

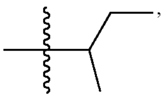

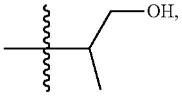

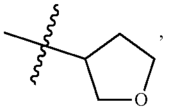

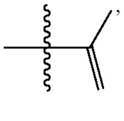

, or

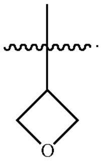

In some embodiments, the present invention provides a compound of formula I or formula I', with the proviso that $L^1$ is not $—NHCH_2CH_2—$. In some embodiments, the present invention provides a compound of formula I or formula I', with the proviso that when Ring A is

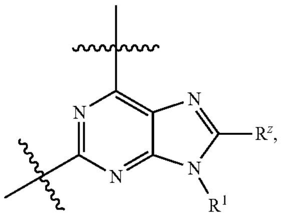

$L^1$ is not $—NHCH_2CH_2—$.

In some embodiments, the present invention provides a compound of formula I or formula I', with the proviso that the compound is other than:

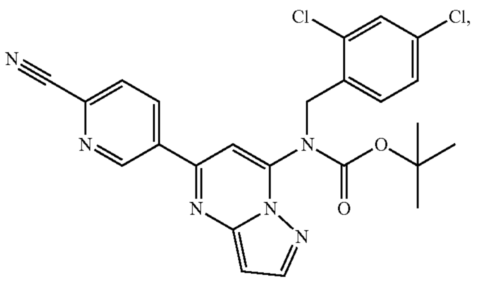

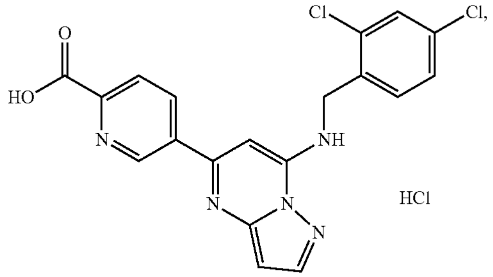

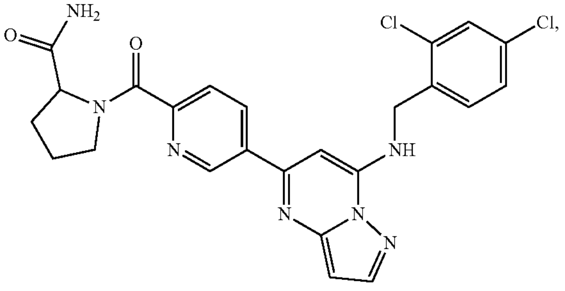

-continued
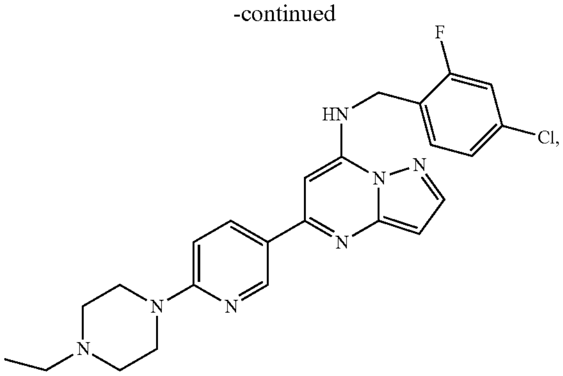
,
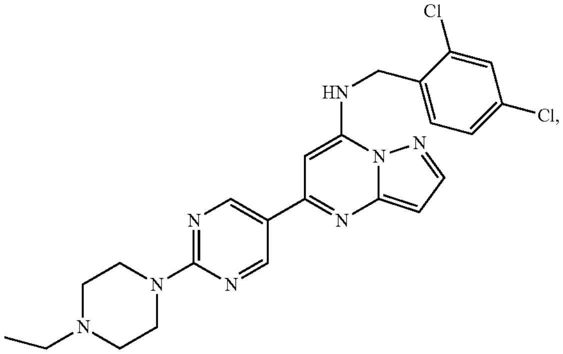
,
or
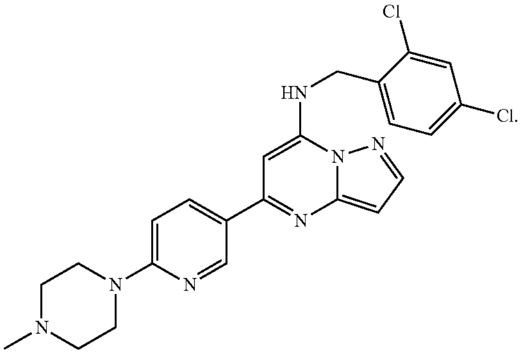 [SMILES: CN1CCN(c2ccc(-c3cc(NCc4ccc(Cl)cc4Cl)n4nccc4n3)cn2)CC1]
.
In some embodiments, a provided compound is other than
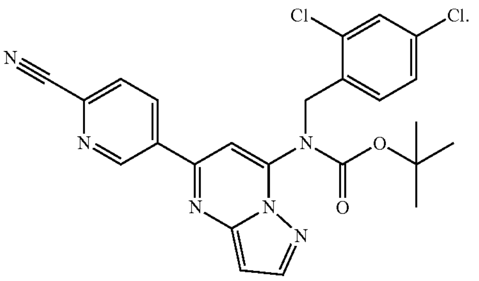 [SMILES: CC(C)(C)OC(=O)N(Cc1ccc(Cl)cc1Cl)c1cc(-c2ccc(C#N)nc2)nc2ccnn12]
.
In some embodiments, a provided compound is other than
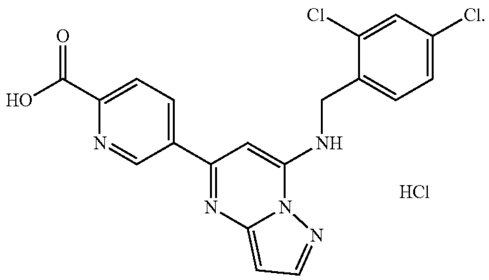 [SMILES: O=C(O)c1ccc(-c2cc(NCc3ccc(Cl)cc3Cl)n3nccc3n2)cn1 ; Cl]
.
In some embodiments, a provided compound is other than
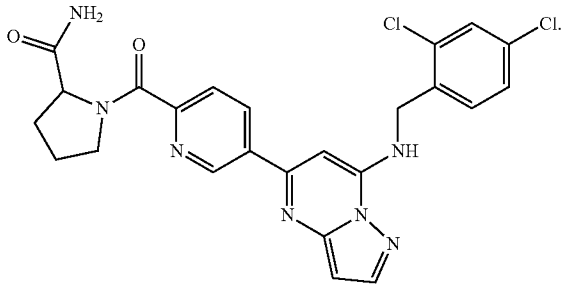 [SMILES: NC(=O)C1CCCN1C(=O)c1ccc(-c2cc(NCc3ccc(Cl)cc3Cl)n3nccc3n2)cn1]
.
In some embodiments, a provided compound is other than
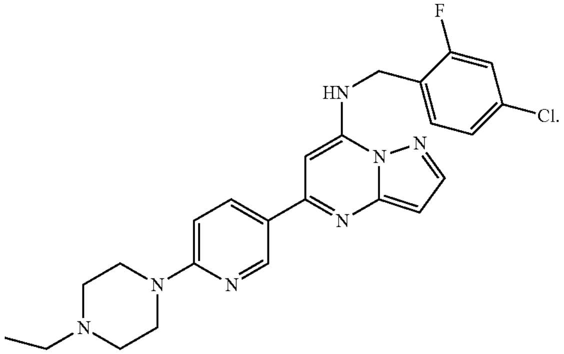 [SMILES: CCN1CCN(c2ccc(-c3cc(NCc4ccc(Cl)cc4F)n4nccc4n3)cn2)CC1]
.
In some embodiments, a provided compound is other than
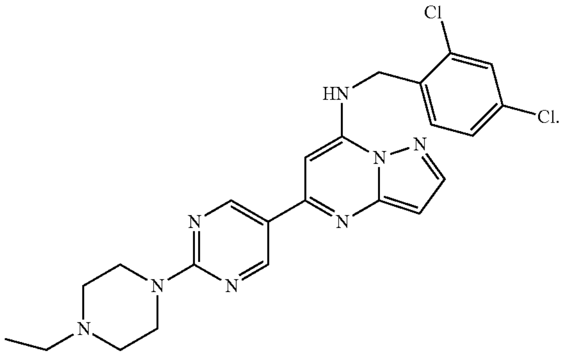 [SMILES: CCN1CCN(c2ncc(-c3cc(NCc4ccc(Cl)cc4Cl)n4nccc4n3)cn2)CC1]
.

In some embodiments, a provided compound is other than

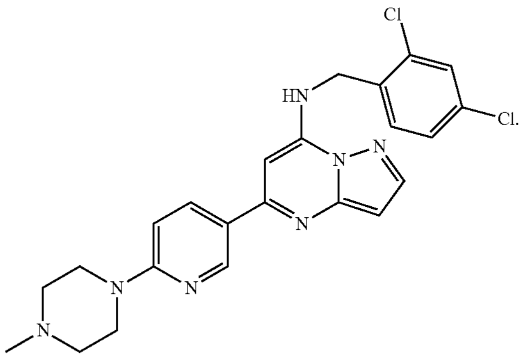 [SMILES: CN1CCN(c2ccc(-c3cc(NCc4ccc(Cl)cc4Cl)n4nccc4n3)cn2)CC1]

As defined generally above, $R^1$ is R, —C(O)R, —C(O)OR, —$SO_2$R, —C(O)N(R)$_2$, or —$SO_2$RN(R)$_2$. In some embodiments, $R^1$ is hydrogen. In some embodiments, $R^1$ is R. In some embodiments, $R^1$ is —C(O)R. In some embodiments, $R^1$ is —C(O)OR. In some embodiments, $R^1$ is —$SO_2$R. In some embodiments, $R^1$ is —C(O)N(R)$_2$. In some embodiments, $R^1$ is —$SO_2$RN(R)$_2$. In some embodiments, $R^1$ is hydrogen. In some embodiments, $R^1$ is deuterium. In some embodiments, $R^1$ is an optionally substituted group selected from $C_{1-6}$ aliphatic. In some embodiments, $R^1$ is selected from those depicted in Table 1, below.

As defined generally above, each $R^x$ is independently R, halogen, cyano, nitro, —OR, —SR, —N(R)$_2$, —N(R)C(O)R, —C(O)N(R)$_2$, —C(O)N(R)OR, —N(R)C(O)N(R)$_2$, N(R)C(O)OR, —OC(O)N(R)$_2$, —N(R)$SO_2$R, —$SO_2$RN(R)$_2$, —C(O)R, —C(O)OR, —OC(O)R, —C(O)OR, —S(O)R, or —$SO_2$R, or two $R^x$ on the same carbon are taken together to form =O or =S. In some embodiments, each $R^x$ is the same. In some embodiments, each $R^x$ is different. In some embodiments, $R^x$ is hydrogen. In some embodiments, $R^x$ is R. In some embodiments, $R^x$ is halogen. In some embodiments, $R^x$ is cyano. In some embodiments, $R^x$ is nitro. In some embodiments, $R^x$ is —OR. In some embodiments, $R^x$ is —SR. In some embodiments, $R^x$ is —N(R)$_2$. In some embodiments, $R^x$ is —N(R)C(O)R. In some embodiments, $R^x$ is —C(O)N(R)$_2$. In some embodiments, $R^x$ is —C(O)N(R)OR. In some embodiments, $R^x$ is —N(R)C(O)N(R)$_2$. In some embodiments, $R^x$ is —N(R)C(O)OR. In some embodiments, $R^x$ is —OC(O)N(R)$_2$. In some embodiments, $R^x$ is —N(R)$SO_2$R. In some embodiments, $R^x$ is —$SO_2$RN(R)$_2$. In some embodiments, $R^x$ is —C(O)R. In some embodiments, $R^x$ is —C(O)OR. In some embodiments, $R^x$ is —CO(O)R. In some embodiments, $R^x$ is —S(O)R. In some embodiments, $R^x$ is —$SO_2$R. In some embodiments, two $R^x$ on the same carbon are taken together to form =O or =S. In some embodiments, $R^x$ is hydrogen. In some embodiments, $R^x$ is deuterium. In some embodiments, $R^x$ is an optionally substituted group selected from $C_{1-6}$ aliphatic. In some embodiments, $R^x$ is selected from those depicted in Table 1, below.

As defined generally above, each $R^y$ is independently R, halogen, cyano, nitro, —OR, —SR, —N(R)$_2$, —N(R)C(O)R, —C(O)N(R)$_2$, —C(O)N(R)OR, —N(R)C(O)N(R)$_2$, —N(R)C(O)OR, —OC(O)N(R)$_2$, —N(R)$SO_2$R, —$SO_2$RN(R)$_2$, —C(O)R, —C(O)OR, —OC(O)R, —C(O)OR, —S(O)R, or —$SO_2$R, or two $R^y$ on the same carbon are taken together to form =O or =S. In some embodiments, each $R^y$ is the same. In some embodiments, each $R^y$ is different. In some embodiments, $R^y$ is hydrogen. In some embodiments, $R^y$ is R. In some embodiments, $R^y$ is halogen. In some embodiments, $R^y$ is cyano. In some embodiments, $R^y$ is nitro. In some embodiments, $R^y$ is —OR. In some embodiments, $R^y$ is —SR. In some embodiments, $R^y$ is —N(R)$_2$. In some embodiments, $R^y$ is —C(O)N(R)OR. In some embodiments, $R^y$ is —N(R)C(O)R. In some embodiments, $R^y$ is —C(O)N(R)$_2$. In some embodiments, $R^y$ is —N(R)C(O)N(R)$_2$. In some embodiments, $R^y$ is —N(R)C(O)OR. In some embodiments, $R^y$ is —OC(O)N(R)$_2$. In some embodiments, $R^y$ is —N(R)$SO_2$R. In some embodiments, $R^y$ is —$SO_2$RN(R)$_2$. In some embodiments, $R^y$ is —C(O)R. In some embodiments, $R^y$ is —C(O)OR. In some embodiments, $R^y$ is —CO(O)R. In some embodiments, $R^y$ is —S(O)R. In some embodiments, $R^y$ is —$SO_2$R. In some embodiments, two $R^y$ on the same carbon are taken together to form =O or =S. In some embodiments, $R^y$ is hydrogen. In some embodiments, $R^y$ is deuterium. In some embodiments, $R^y$ is an optionally substituted group selected from $C_{1-6}$ aliphatic. In some embodiments, $R^y$ is selected from those depicted in Table 1, below.

As defined generally above, each $R^z$ is independently R, halogen, cyano, nitro, —OR, —SR, —N(R)$_2$, —N(R)C(O)R, —C(O)N(R)$_2$, —C(O)N(R)OR, —N(R)C(O)N(R)$_2$, —N(R)C(O)OR, —OC(O)N(R)$_2$, —N(R)$SO_2$R, —$SO_2$RN(R)$_2$, —C(O)R, —C(O)OR, —OC(O)R, —C(O)OR, —S(O)R, or —$SO_2$R. In some embodiments, $R^z$ is hydrogen. In some embodiments, $R^z$ is R. In some embodiments, $R^z$ is halogen. In some embodiments, $R^z$ is cyano. In some embodiments, $R^z$ is nitro. In some embodiments, $R^z$ is —OR. In some embodiments, $R^z$ is —SR. In some embodiments, $R^z$ is —N(R)$_2$. In some embodiments, $R^z$ is —C(O)N(R)OR. In some embodiments, $R^z$ is —N(R)C(O)R. In some embodiments, $R^z$ is —C(O)N(R)$_2$. In some embodiments, $R^z$ is —N(R)C(O)N(R)$_2$. In some embodiments, $R^z$ is —N(R)C(O)OR. In some embodiments, $R^z$ is —OC(O)N(R)$_2$. In some embodiments, $R^z$ is —N(R)$SO_2$R. In some embodiments, $R^z$ is —$SO_2$RN(R)$_2$. In some embodiments, $R^z$ is —C(O)R. In some embodiments, $R^z$ is —C(O)OR. In some embodiments, $R^z$ is —CO(O)R. In some embodiments, $R^z$ is —S(O)R. In some embodiments, $R^z$ is —$SO_2$R. In some embodiments, $R^z$ is hydrogen. In some embodiments, $R^z$ is deuterium. In some embodiments, $R^z$ is an optionally substituted group selected from $C_{1-6}$ aliphatic. In some embodiments, $R^z$ is selected from those depicted in Table 1, below.

As defined generally above, p is 0, 1 or 2. In some embodiments, p is 0. In some embodiments, p is 1. In some embodiments, p is 2. In some embodiments, p is selected from those depicted in Table 1, below.

As defined generally above, n is 1, 2, 3, 4 or 5. In some embodiments, n is 1. In some embodiments, n is 2. In some embodiments, n is 3. In some embodiments, n is 4. In some embodiments, n is 5. In some embodiments, n is selected from those depicted in Table 1, below.

As defined generally above, m is 1, 2, 3, 4 or 5. In some embodiments, m is 1. In some embodiments, m is 2. In some embodiments, m is 3. In some embodiments, m is 4. In some embodiments, m is 5. In some embodiments, m is selected from those depicted in Table 1, below.

As defined generally above, Ring B is phenyl, a 7-10 membered bicyclic partially unsaturated or aromatic carbocyclic ring, a 5-6 membered monocyclic heteroaromatic ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, or a 12-15 membered partially unsaturated or aromatic tricyclic ring having 1-4 heteroatoms independently selected from nitrogen, oxygen, or sulfur. In some embodiments, Ring B is a 7-10 membered bicyclic partially unsaturated or aromatic carbocyclic ring. In some embodiments, Ring B is a 12-15 membered partially unsaturated or aromatic tricyclic ring having 1-4 heteroatoms independently selected from nitrogen, oxygen, or sulfur. In some embodiments, Ring B is a 5-6 membered monocyclic heteroaromatic ring having 1-4 heteroatoms independently selected from nitrogen, oxygen, or sulfur. In some embodiments, Ring B is an 8-10 membered bicyclic heteroaryl ring having 1-4 heteroatoms independently selected from nitrogen, oxygen, or sulfur. In some embodiments, Ring B is phenyl. In some embodiments, Ring B is thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl or pteridinyl, indolycarl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, tetrahydroquinolinyl, tetrahydroisoquinolinyl, or pyrido[2,3-b]-1,4-oxazin-3(4H)-one. In some embodiments, Ring B is selected from those depicted in Table 1, below.

As defined generally above, Ring C is phenyl, a 5-6 membered monocyclic heteroaromatic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur. In some embodiments, Ring C is phenyl. In some embodiments, Ring C is a 5-6 membered heteroaryl ring having 1-4 heteroatoms independently selected from nitrogen, oxygen, or sulfur. In some embodiments, Ring C is thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl or pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, tetrahydroquinolinyl, tetrahydroisoquinolinyl, or pyrido[2,3-b]-1,4-oxazin-3(4H)-one. In some embodiments, Ring C is selected from those depicted in Table 1, below.

As defined generally above, $L^1$ is a covalent bond or an optionally substituted $C_1$-6 membered straight or branched bivalent hydrocarbon chain wherein a methylene unit of $L^1$ is optionally replaced with -Cy-, —O—, —S—, —NR—, —C(O)—, —C(O)O—, —OC(O)—, —C(O)N(R)—, —N(R)C(O)—, —$SO_2$—, —N(R)$SO_2$—, or —$SO_2$N(R)—S. In some embodiments, $L^1$ is a covalent bond. In some embodiments, $L^1$ is an optionally substituted $C_{1-6}$ membered straight or branched bivalent hydrocarbon chain. In some embodiments, $L^1$ is -Cy-. In some embodiments, $L^1$ is phenylene, heterocyclylene, heteroarylene, cyclopropylene, cyclobutylenyl, cyclopentylene, cyclohexylene or oxetanyl. In some embodiments, $L^1$ is —NR—. In some embodiments, $L^1$ is —N($CH_2$)$_2$—. In some embodiments, $L^1$ is selected from those depicted in Table 1, below.

In some embodiments, -Cy- is phenylene, heterocyclylene, heteroarylene, cyclopropylene, cyclobutylenyl, cyclopentylene, cyclohexylene and oxetanyl. In some embodiments, -Cy- is selected from:

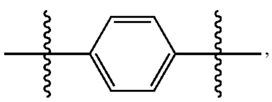,
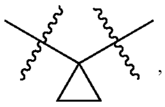,

-continued

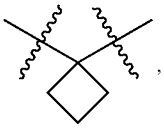,
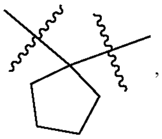,
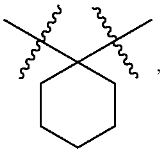,
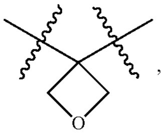,
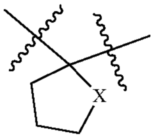,
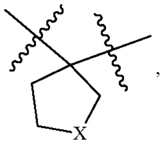,
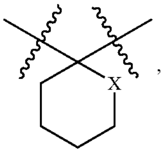,
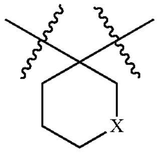,
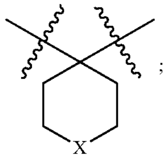;

wherein X is a heteroatom selected from nitrogen, oxygen, or sulfur. In some embodiments, -Cy- is selected from those depicted in Table 1, below.

In some embodiments, the present invention provides a compound selected from any of formulae I-a, I-b, I-c, I-d, I-e, I-f, I-g, I-h, I-i, I-j, I-k, I-l, I-m, I-n, I-o and I-p:

I-a

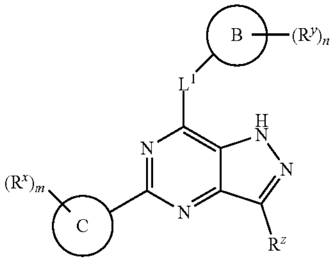

I-b

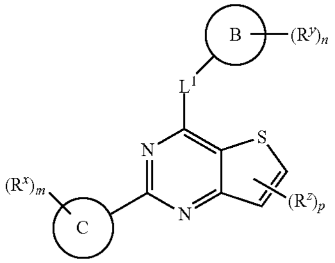

I-c

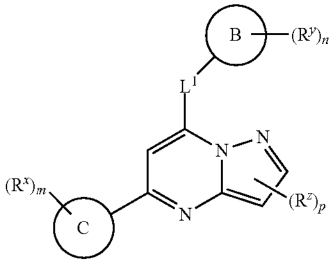

-continued
I-d
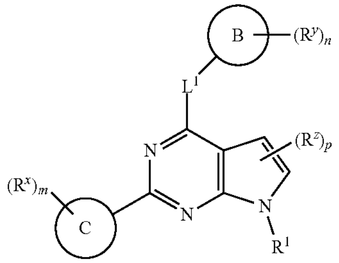
I-e
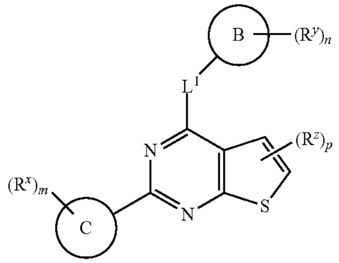
I-f
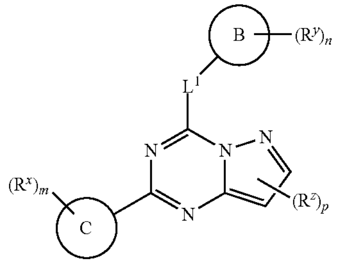
I-g
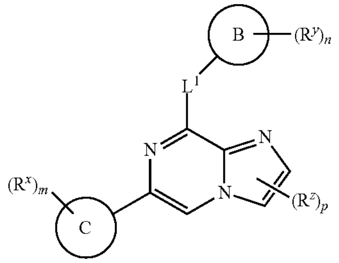
I-h
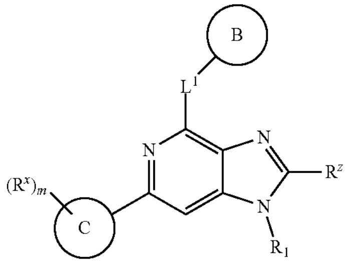
I-i
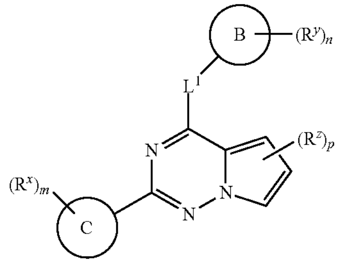
-continued
I-j
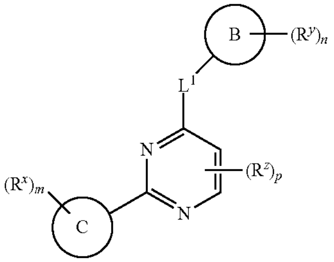
I-k
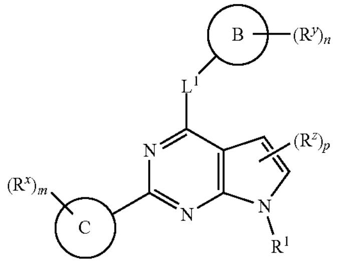
I-l
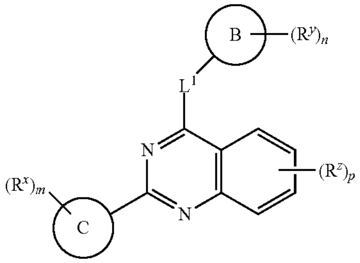
I-m
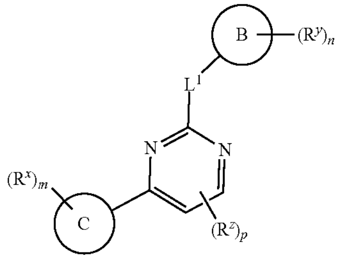
I-n
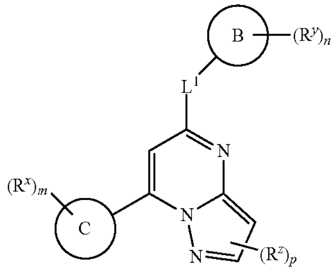
I-o
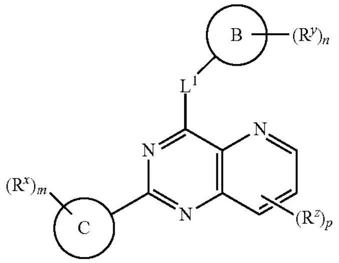
and -continued I-p

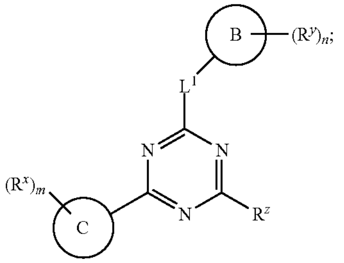

or a pharmaceutically acceptable salt thereof; wherein each variable is as defined herein and described in embodiments for formula I and formula I', supra, or described in embodiments herein, both singly and in combination.

In some embodiments, the present invention provides a compound selected from any of formulae II-a, II-b, II-c, II-d, II-e, II-f, II-g, II-h, II-i, II-j, II-k, II-l, II-m, II-n, II-o and II-p:

II-a

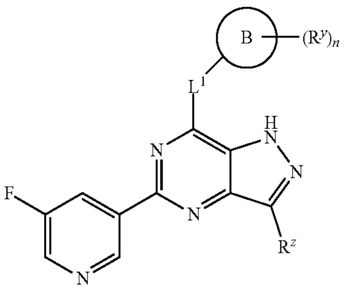

II-b

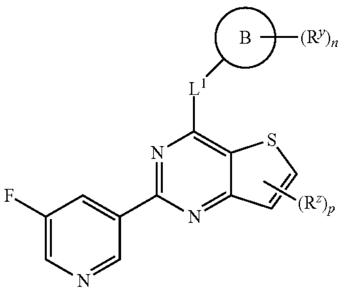

II-c

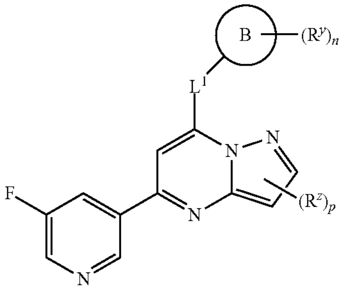

-continued

II-d

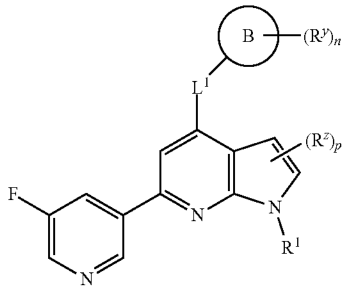

II-e

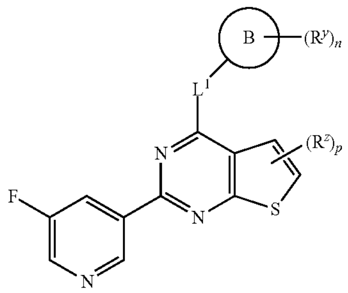

II-f

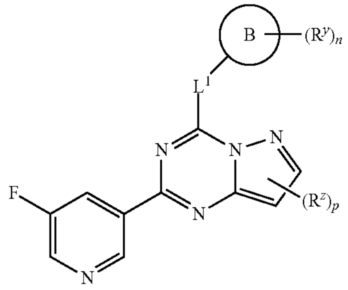

II-g

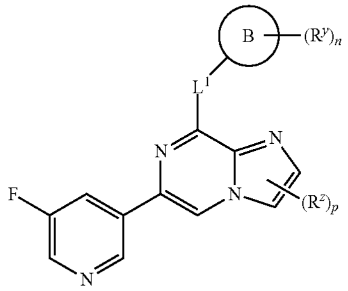

II-h

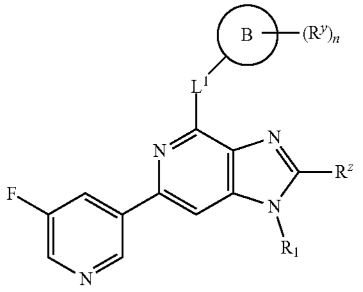

-continued

II-i

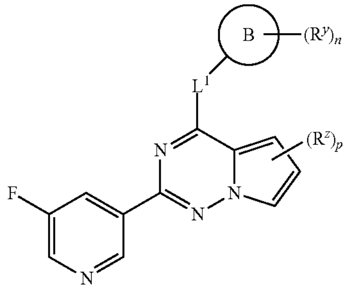

II-j

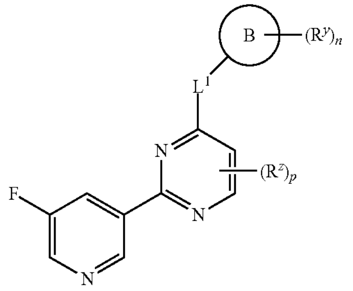

II-k

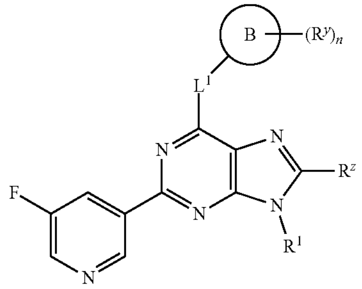

II-l

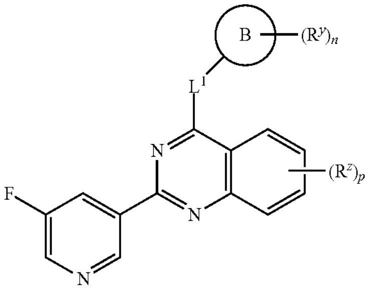

II-m

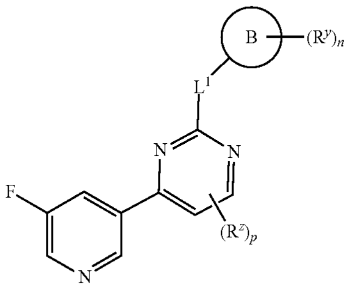

-continued

II-n

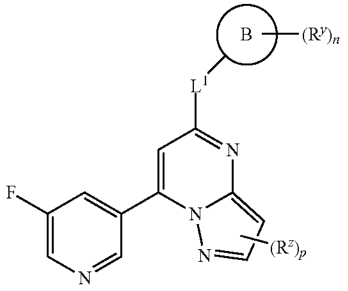

II-o

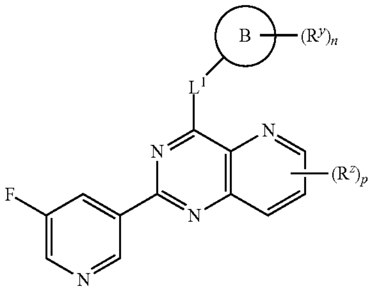

II-p

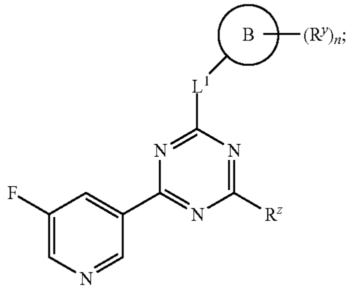

or a pharmaceutically acceptable salt thereof; wherein each variable is as defined herein and described in embodiments for formula I and formula I', supra, or described in embodiments herein, both singly and in combination.

In some embodiments, the present invention provides a compound selected from any of formulae III-a, III-b, III-c, III-d, III-e, III-f, III-g, III-h, III-i, III-j, III-k, III-l, III-m, III-n, III-o, III-p, III-q, III-r, III-s, III-t, III-u, III-v, III-w, III-x, III-y, III-z, III-aa, III-bb, III-cc, III-dd, III-ee, III-ff, III-gg, III-hh, III-ii, III-jj and III-kk:

III-a

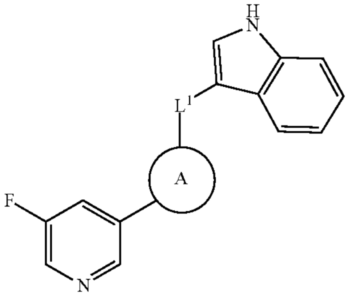

-continued
III-b
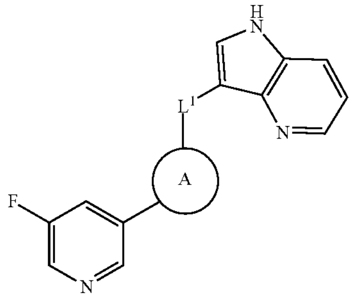
III-c
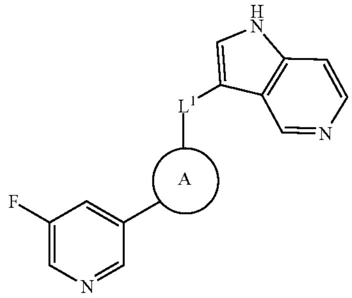
III-d
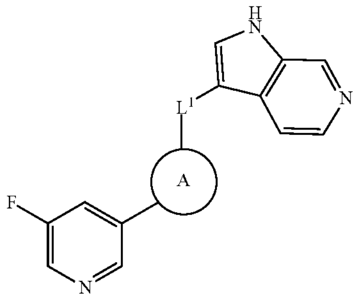
III-e
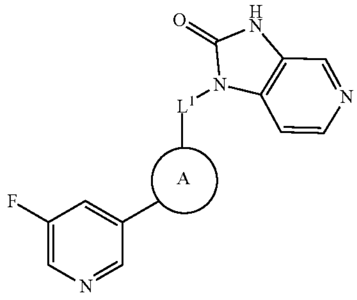
III-f
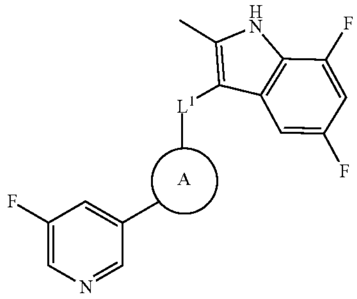
-continued
III-g
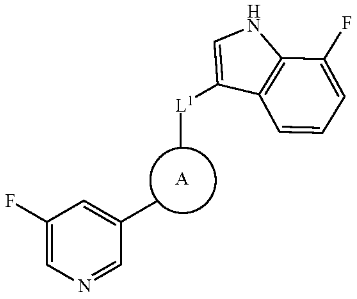
III-h
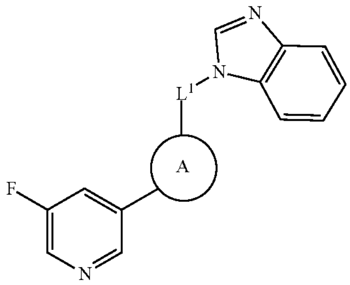
III-i
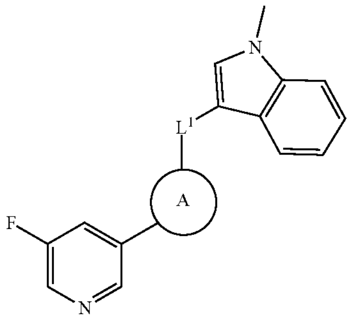
III-j
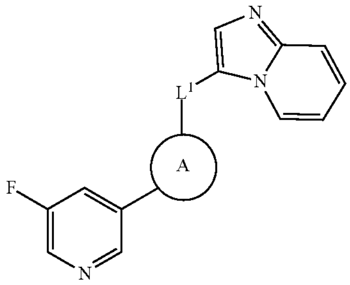
III-k
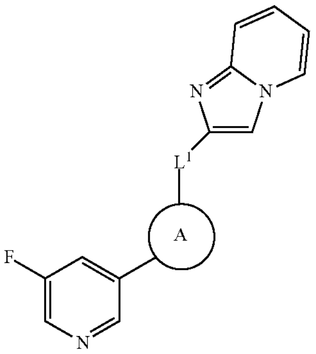

-continued
III-l
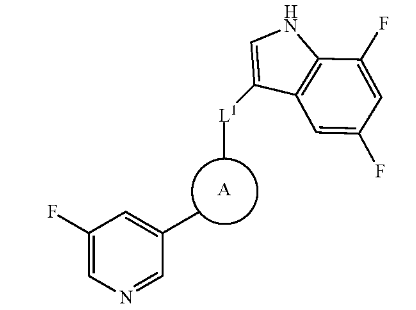
III-m
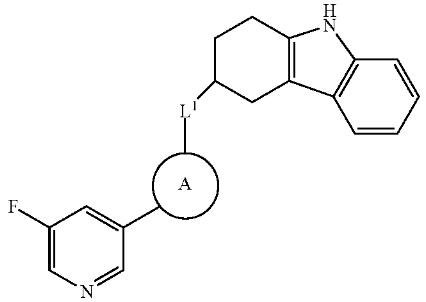
III-n
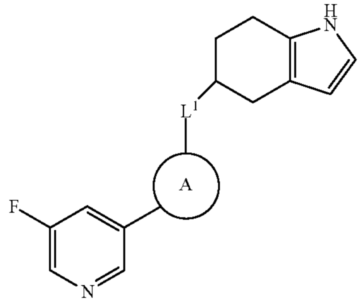
III-o
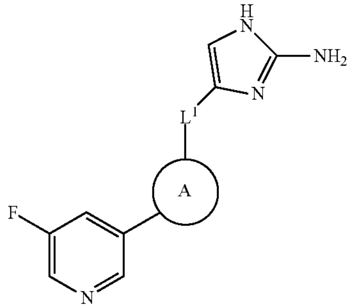
III-p
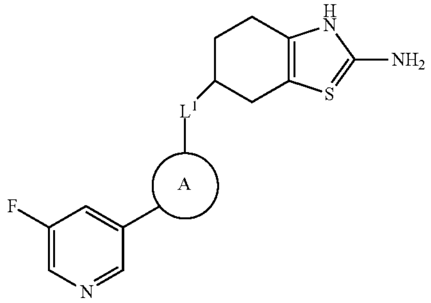
-continued
III-q
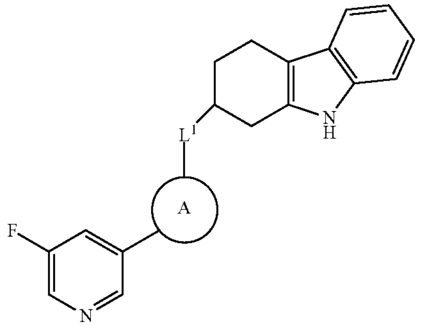
III-r
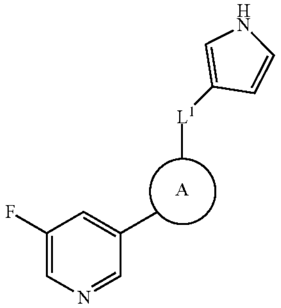
III-s
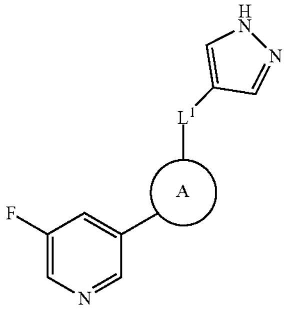
III-t
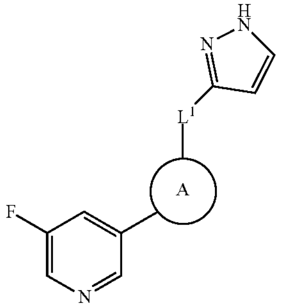
III-u
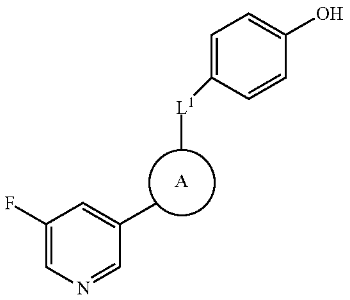

-continued
III-v
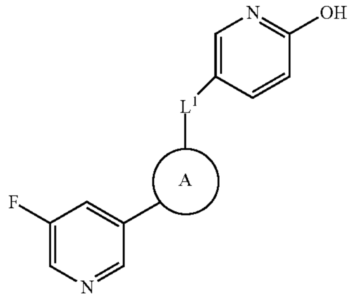
III-w
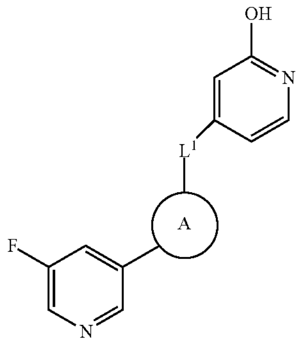
III-x
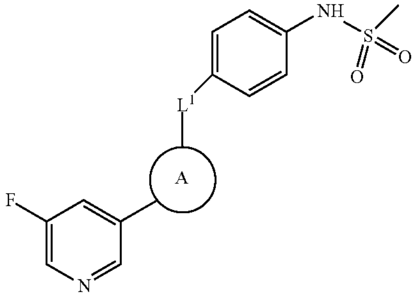
III-y
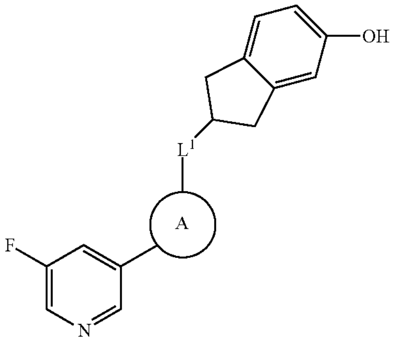
III-z
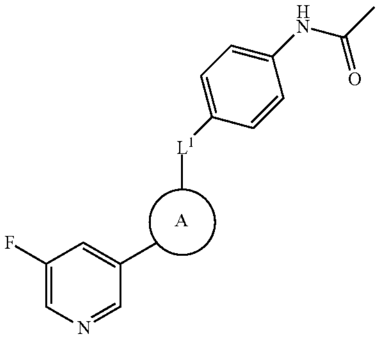
-continued
III-aa
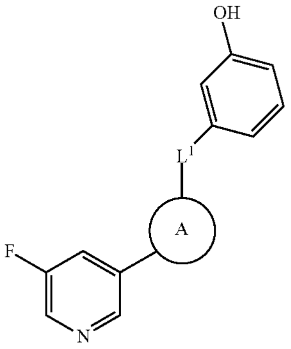
III-bb
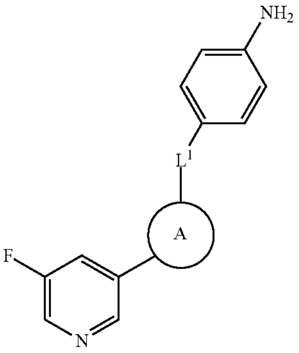
III-cc
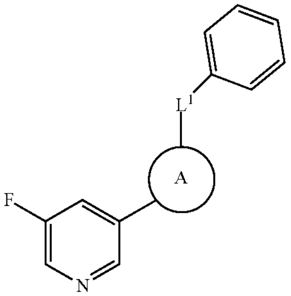
III-dd
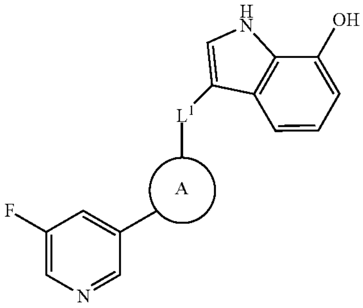
III-ee
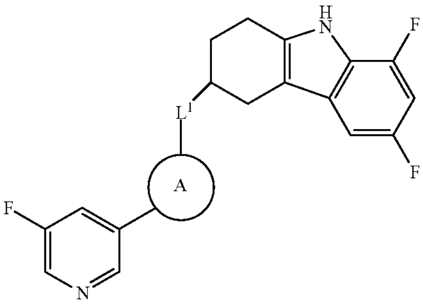

-continued

III-ff

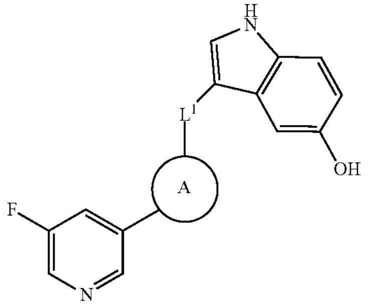

III-gg

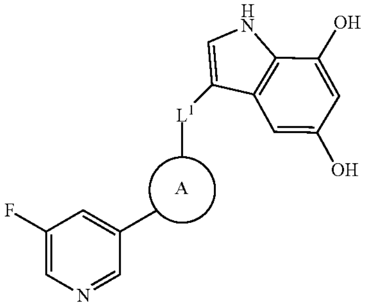

III-hh

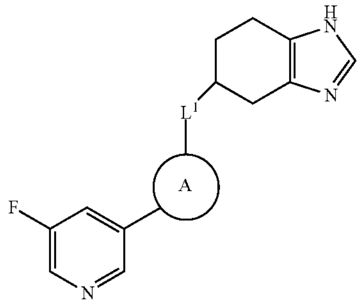

III-ii

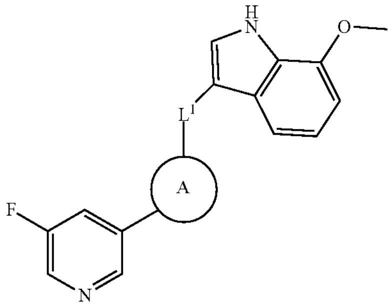

III-jj

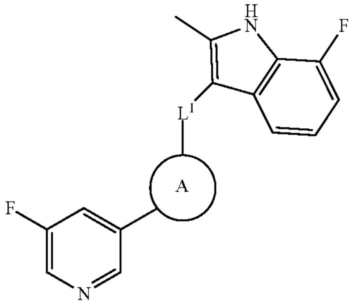

-continued

III-kk

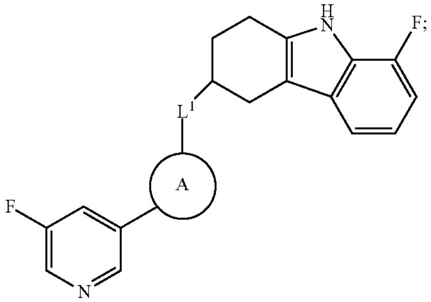

or a pharmaceutically acceptable salt thereof, wherein each variable is as defined herein and described in embodiments for formula I and formula I', supra, or described in embodiments herein, both singly and in combination.

In some embodiments, the present invention provides a compound selected from any of formulae IV-a, IV-b, IV-c, IV-d, IV-e, IV-f, IV-g, IV-h, IV-i, IV-j, IV-k, IV-l, IV-m, IV-n, IV-o, IV-p and IV-q:

IV-a

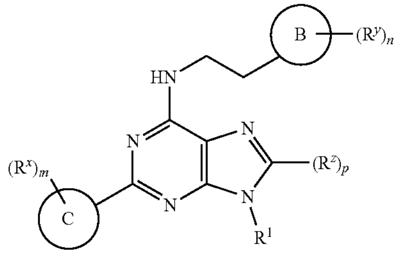

IV-b

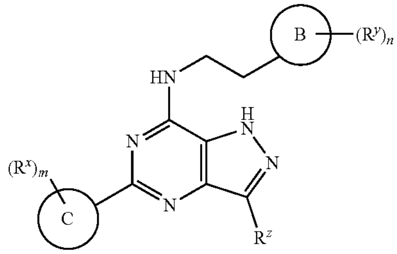

IV-c

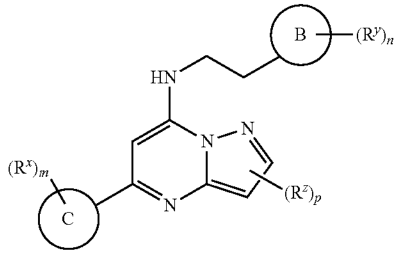

IV-d

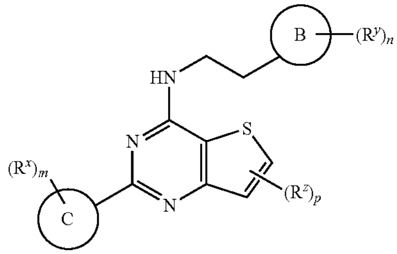

-continued
IV-e
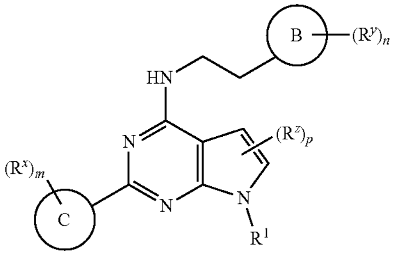
IV-f
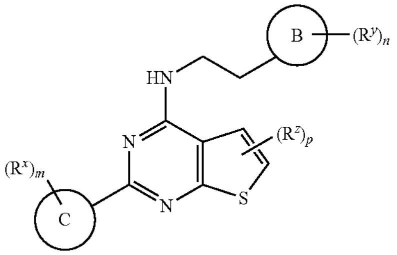
IV-g
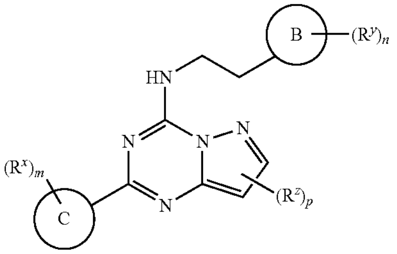
IV-h
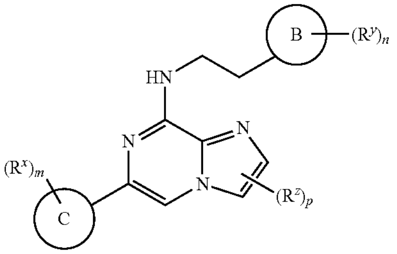
IV-i
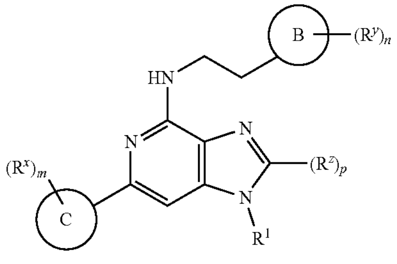
IV-j
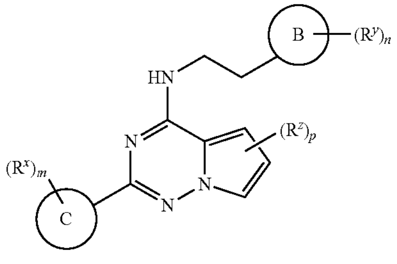
-continued
IV-k
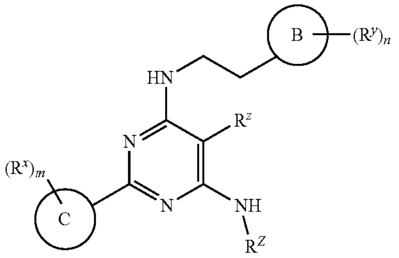
IV-l
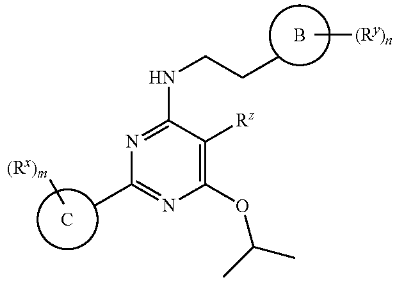
IV-m
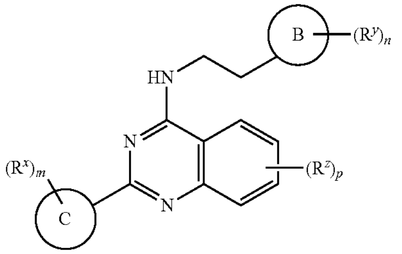
IV-n
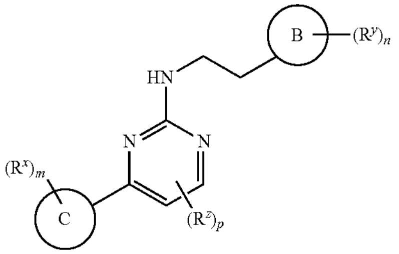
IV-o
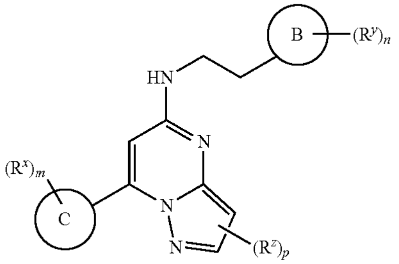
IV-p
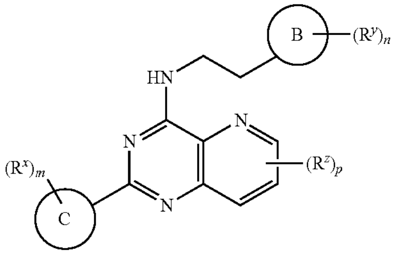

-continued

IV-q

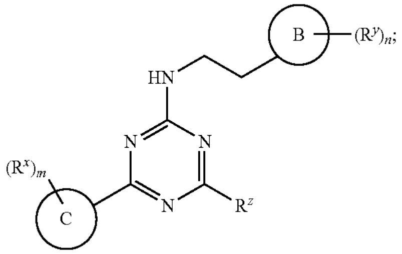

or a pharmaceutically acceptable salt thereof, wherein each variable is as defined herein and described in embodiments for formula I and formula I', supra, or described in embodiments herein, both singly and in combination.

In some embodiments, the present invention provides a compound selected from any of formulae V-a, V-b, V-c, V-d, V-e, V-f, V-g, V-h, V-i, V-j, V-k and V-l:

V-a

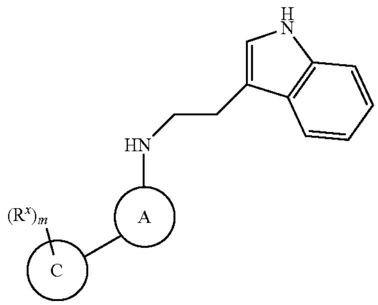

V-b

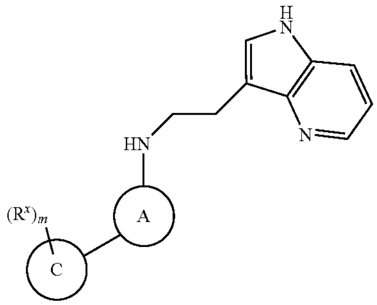

V-c

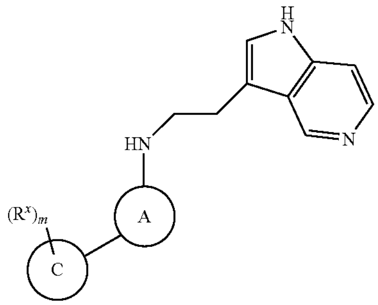

-continued

V-d

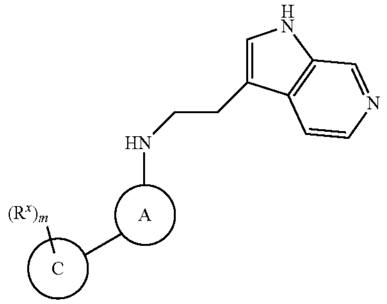

V-e

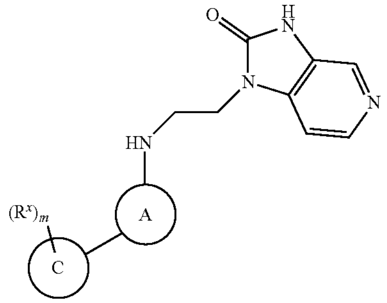

V-f

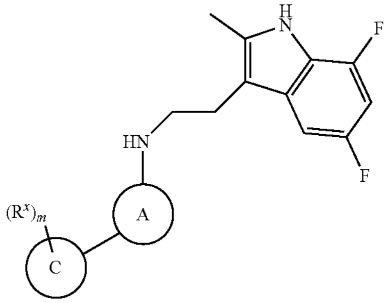

V-g

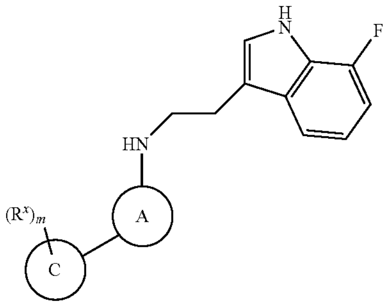

V-h

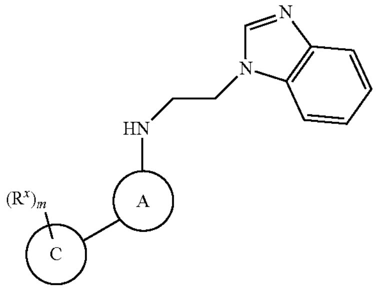

-continued

V-i

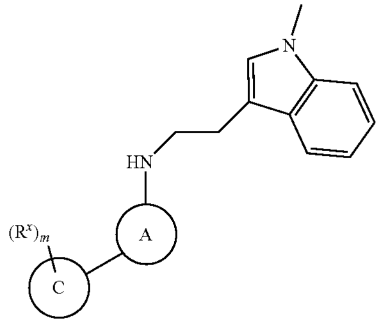

V-j

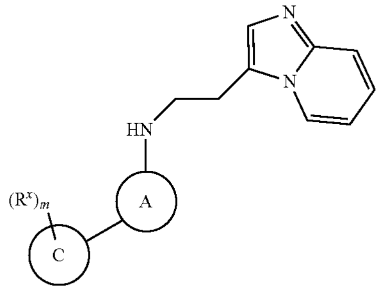

V-k

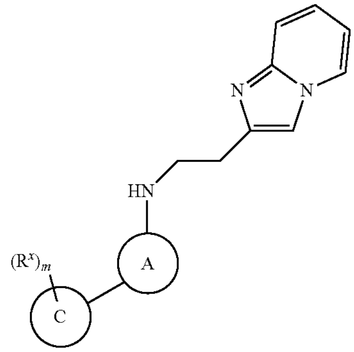

V-l

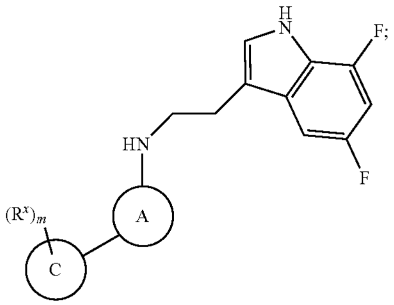

or a pharmaceutically acceptable salt thereof, wherein each variable is as defined herein and described in embodiments for formula I and formula I', supra, or described in embodiments herein, both singly and in combination.

In some embodiments, the present invention provides a compound selected from any of formulae VI-a, VI-b, VI-c, VI-d, VI-e and VI-f:

VI-a

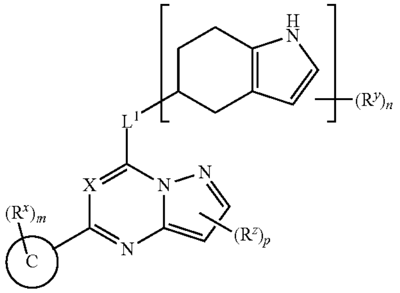

VI-b

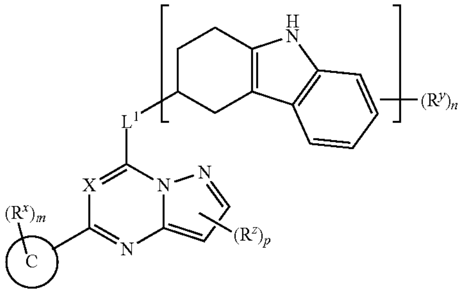

VI-c

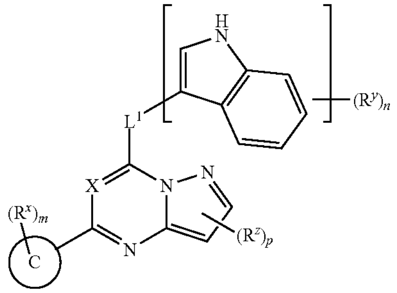

VI-d

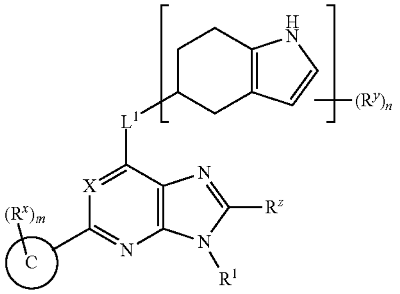

VI-e

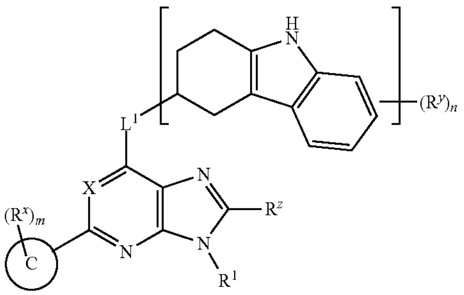

and

-continued

VI-f

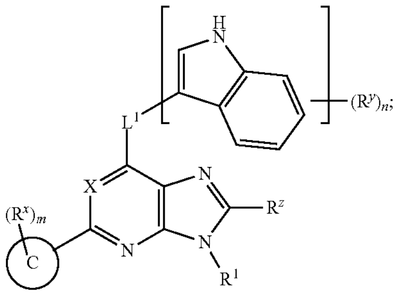

or a pharmaceutically acceptable salt thereof wherein X is N or CH; wherein each variable is as defined herein and described in embodiments for formula I and formula I', supra, or described in embodiments herein, both singly and in combination.

In some embodiments, the present invention provides a compound selected from any of formulae VII-a, VII-b, VII-c, VII-d, VII-e, VII-f and VII-g:

VII-a

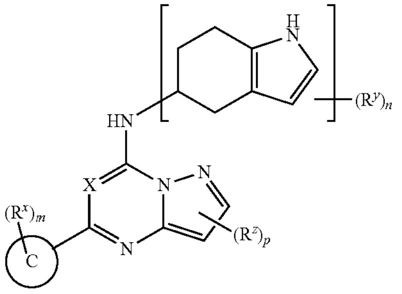

VII-b

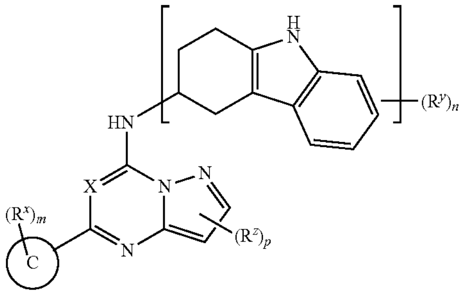

VII-c

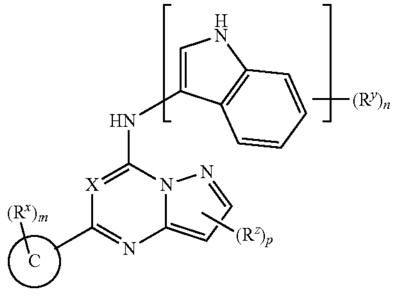

-continued

VII-d

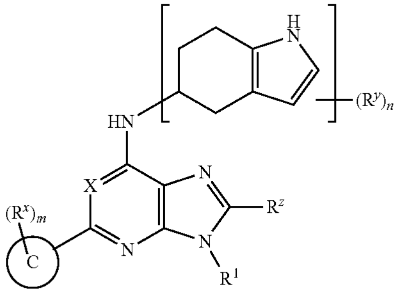

VII-e

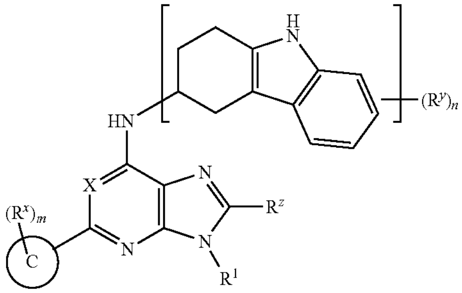

VII-f

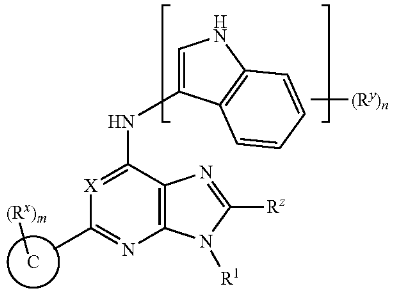

and

VII-g

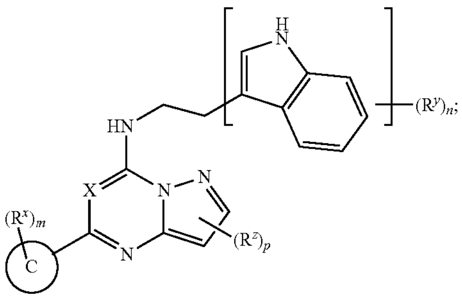

or a pharmaceutically acceptable salt thereof wherein X is N or CH; wherein each variable is as defined herein and described in embodiments for formula I and formula I', supra, or described in embodiments herein, both singly and in combination.

In some embodiments, the present invention provides a compound selected from any of formulae VIII-a, VIII-b, VIII-c, VIII-d, VIII-e and VIII-f:

VIII-a

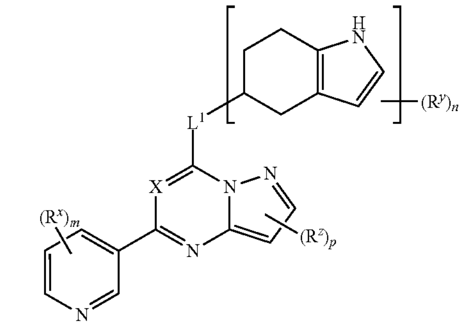

VIII-b

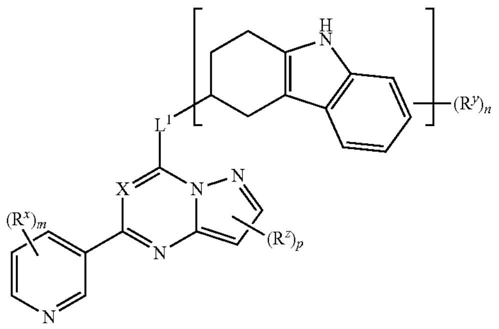

VIII-c

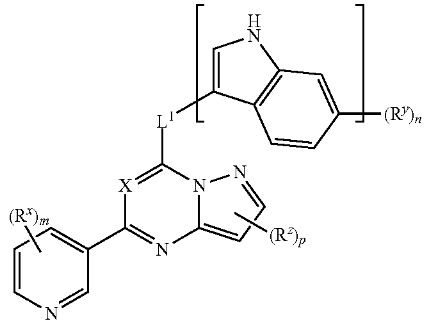

VIII-d

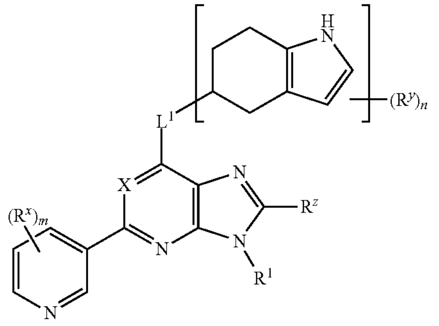

-continued

VIII-e

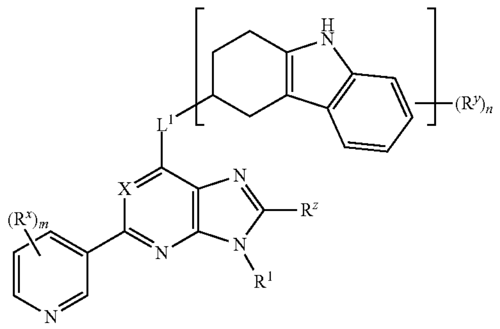

and

VIII-f

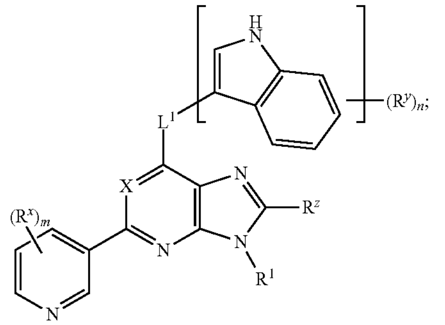

or a pharmaceutically acceptable salt thereof wherein X is N or CH; wherein each variable is as defined herein and described in embodiments for formula I and formula I', supra, or described in embodiments herein, both singly and in combination.

In some embodiments, the present invention provides a compound selected from any of formulae IX-a, IX-b and IX-c:

IX-a

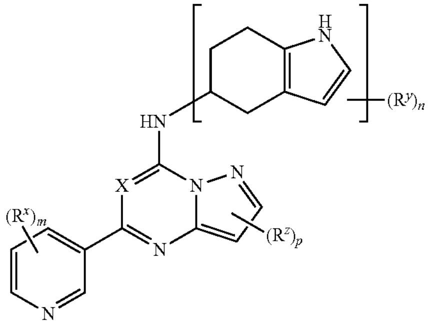

IX-b

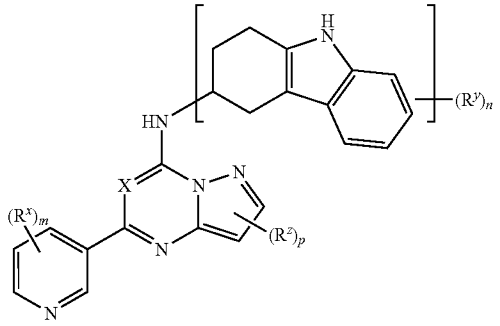

and

-continued

IX-c

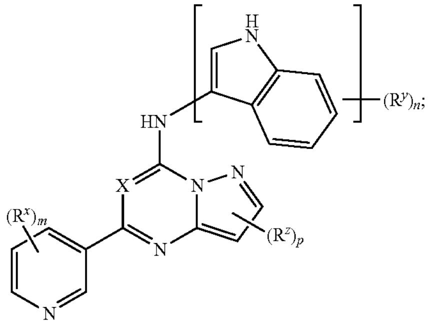

or a pharmaceutically acceptable salt thereof wherein X is N or CH; wherein each variable is as defined herein and described in embodiments for formula I and formula I', supra, or described in embodiments herein, both singly and in combination.

In some embodiments, the present invention provides a compound selected from any of formulae X-a, X-b, X-c, X-d, X-e, X-f, X-g, X-h and X-i:

X-a

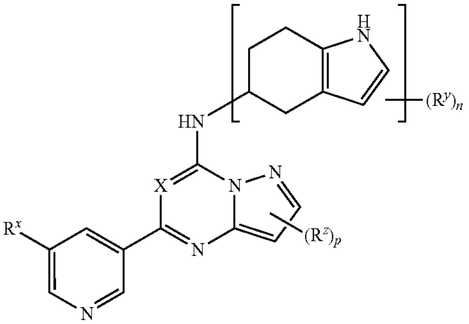

X-b

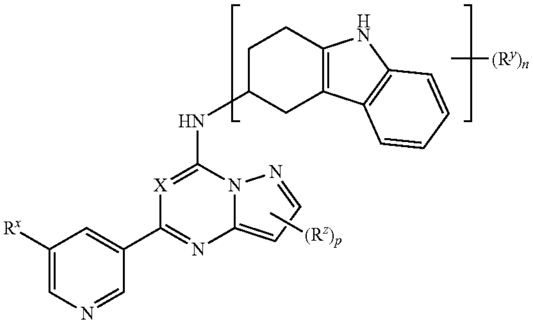

X-c

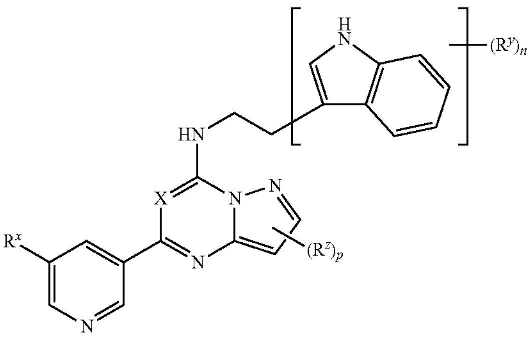

-continued

X-d

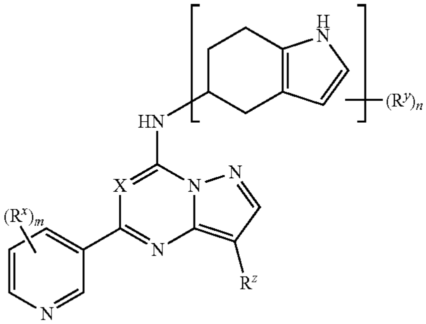

X-e

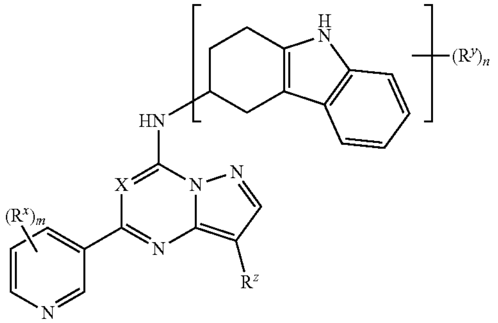

X-f

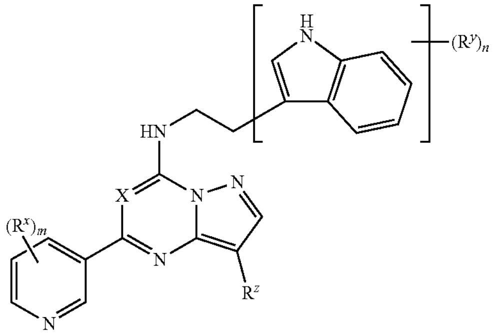

X-g

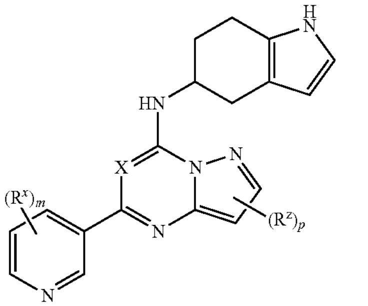

X-h

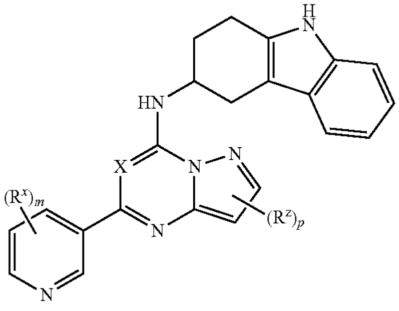

-continued

X-i

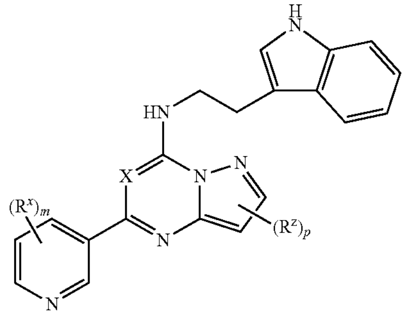

;

or a pharmaceutically acceptable salt thereof wherein X is N or CH; wherein each variable is as defined herein and described in embodiments for formula I and formula I', supra, or described in embodiments herein, both singly and in combination.

In some embodiments, the present invention provides a compound selected from any of formulae XI-a, XI-b, XI-c, XI-d, XI-e, XI-f, XI-g, XI-h and XI-i:

XI-a

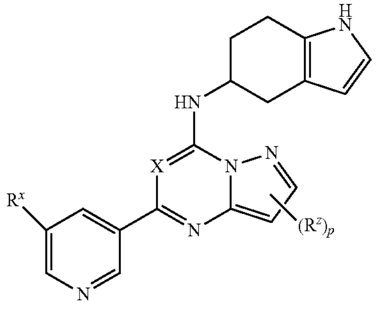

XI-b

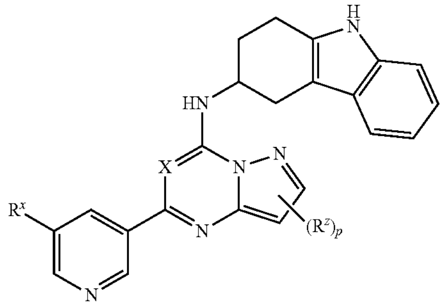

XI-c

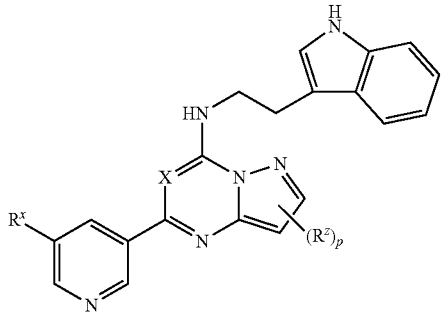

-continued

XI-d

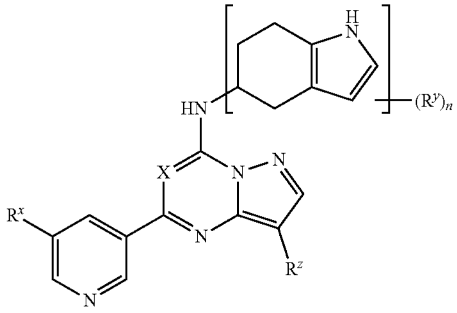

XI-e

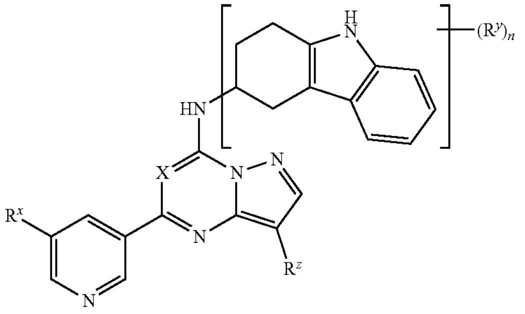

XI-f

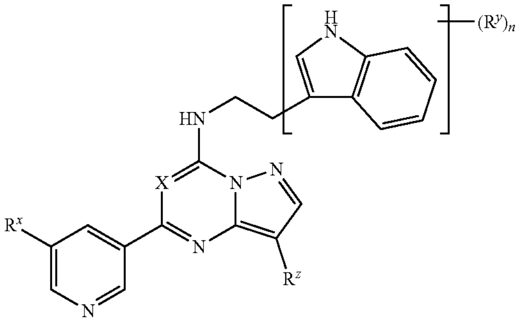

XI-g

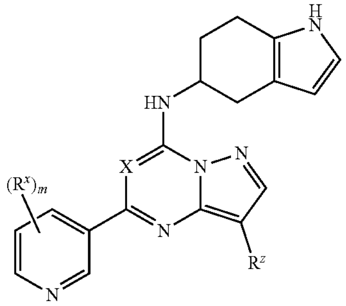

XI-h

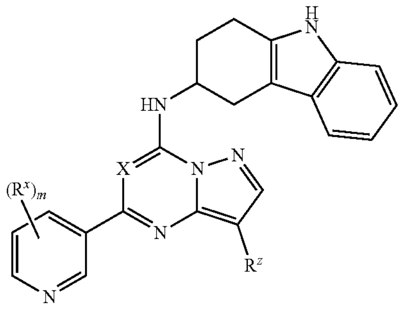

and

-continued

XI-i

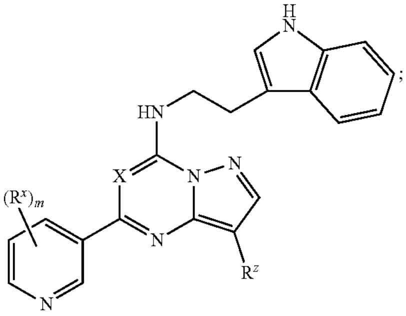

;

or a pharmaceutically acceptable salt thereof wherein X is N or CH; wherein each variable is as defined herein and described in embodiments for formula I and formula I', supra, or described in embodiments herein, both singly and in combination.

In some embodiments, the present invention provides a compound selected from any of formulae XII-a, XII-b and XI-c:

XII-a

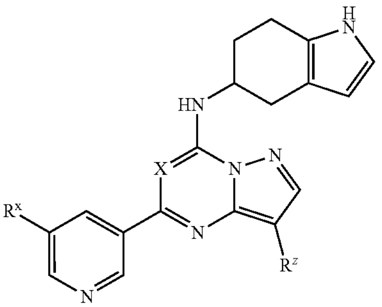

XII-b

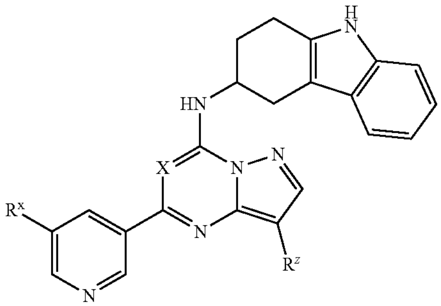

and

XII-c

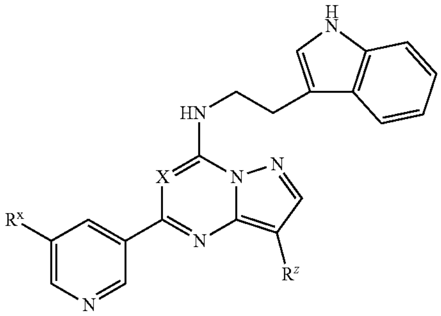

;

or a pharmaceutically acceptable salt thereof wherein X is N or CH; wherein each variable is as defined herein and described in embodiments for formula I and formula I', supra, or described in embodiments herein, both singly and in combination.

In some embodiments, the present invention provides a compound of formula I and formula I' provided that when Ring A is

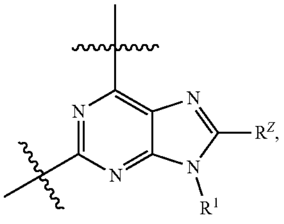

Ring B is not

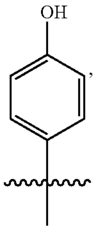
,
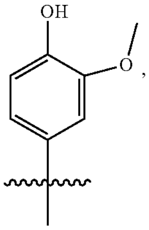
,
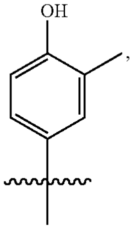
,
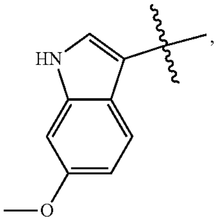
,
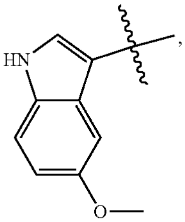
,
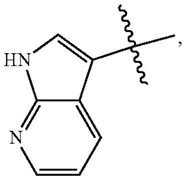
,
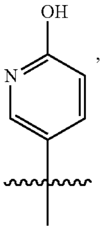
,
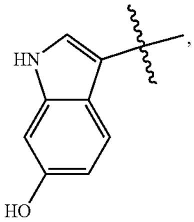
,
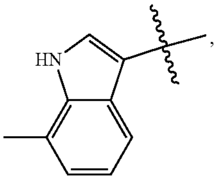
,
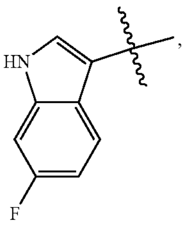
,
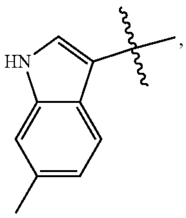
,
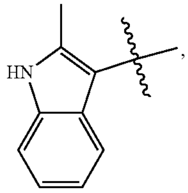
, or -continued

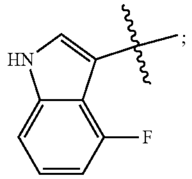

and/or Ring C is not

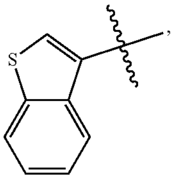 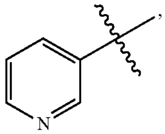

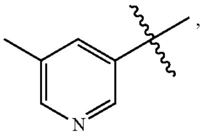 or 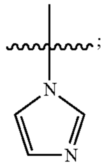 and/or $R^1$ is not

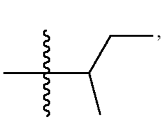 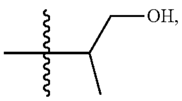 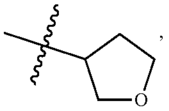

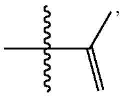 or 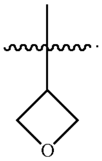

In some embodiments, the present invention provides a compound of formula I and formula I' provided that $L^1$ is not —$NHCH_2CH_2$—. In some embodiments, the present invention provides a compound of formula I and formula I' provided that when Ring A is

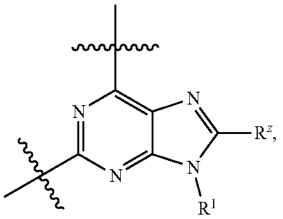

$L^1$ is not —$NHCH_2CH_2$—.

Exemplary compounds of the present invention are set forth in Table 1, below:

TABLE 1

| Exemplary Compounds of Formula I | |
|---|---|
| I-1 | 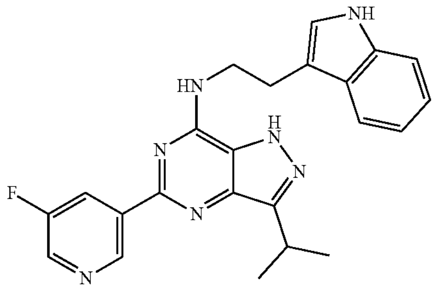 [SMILES: CC(C)c1n[nH]c2c(NCCc3c[nH]c4ccccc34)nc(-c3cncc(F)c3)nc12] |
| I-2 | 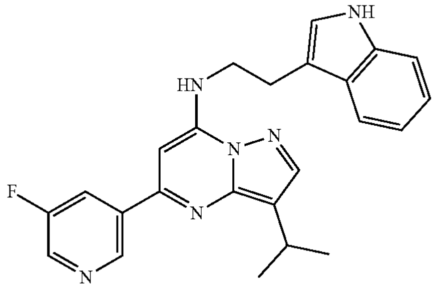 [SMILES: CC(C)c1cnn2c(NCCc3c[nH]c4ccccc34)cc(-c3cncc(F)c3)nc12] |
| I-3 | 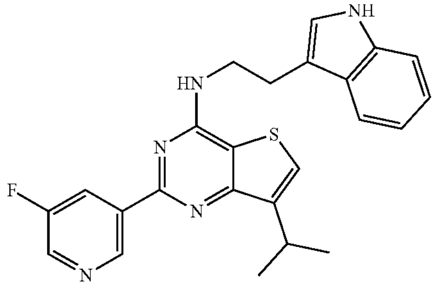 [SMILES: CC(C)c1csc2c(NCCc3c[nH]c4ccccc34)nc(-c3cncc(F)c3)nc12] |
| I-4 | 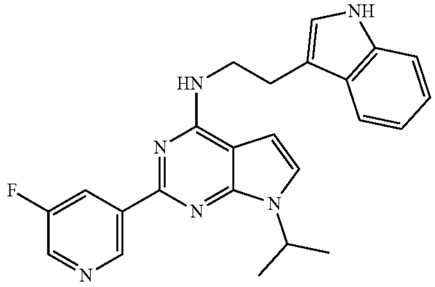 [SMILES: CC(C)n1ccc2c(NCCc3c[nH]c4ccccc34)nc(-c3cncc(F)c3)nc21] |
| I-5 | 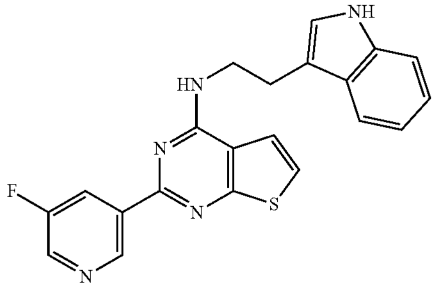 [SMILES: Fc1cncc(-c2nc(NCCc3c[nH]c4ccccc34)c3ccsc3n2)c1] |

TABLE 1-continued
Exemplary Compounds of Formula I
I-6
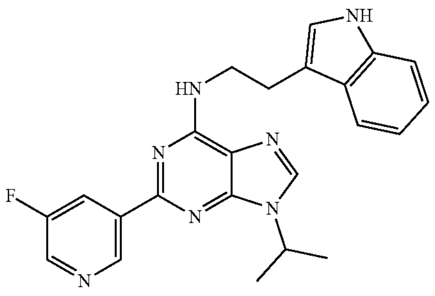 [SMILES: CC(C)n1cnc2c(NCCc3c[nH]c4ccccc34)nc(-c3cncc(F)c3)nc21]
I-7
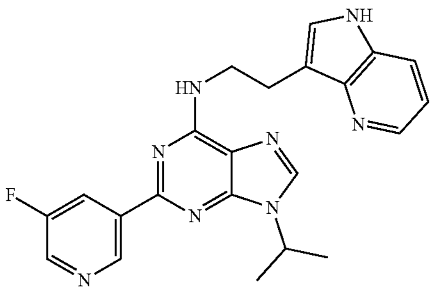 [SMILES: CC(C)n1cnc2c(NCCc3c[nH]c4cccnc34)nc(-c3cncc(F)c3)nc21]
I-8
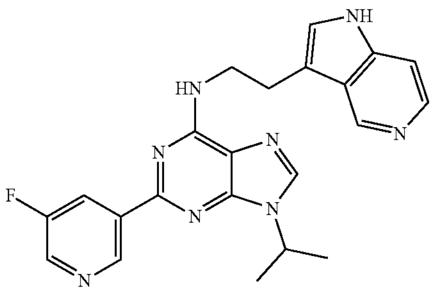 [SMILES: CC(C)n1cnc2c(NCCc3c[nH]c4ccncc34)nc(-c3cncc(F)c3)nc21]
I-9
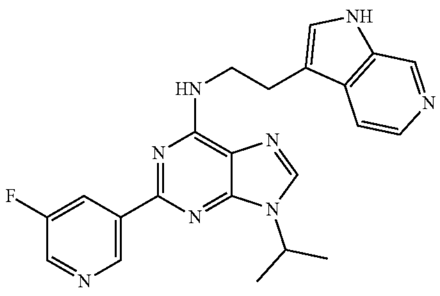 [SMILES: CC(C)n1cnc2c(NCCc3c[nH]c4cnccc34)nc(-c3cncc(F)c3)nc21]
I-10
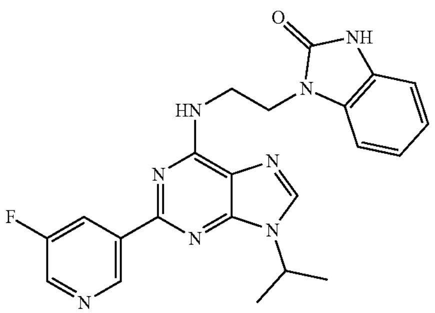 [SMILES: CC(C)n1cnc2c(NCCn3c(=O)[nH]c4ccccc43)nc(-c3cncc(F)c3)nc21]
TABLE 1-continued
Exemplary Compounds of Formula I
I-11
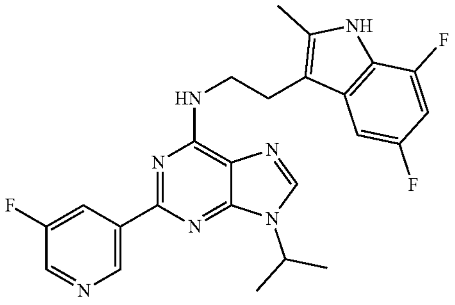 [SMILES: Cc1[nH]c2c(F)cc(F)cc2c1CCNc1nc(-c2cncc(F)c2)nc2c1ncn2C(C)C]
I-12
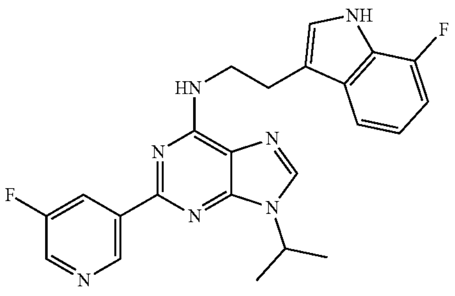 [SMILES: CC(C)n1cnc2c(NCCc3c[nH]c4c(F)cccc34)nc(-c3cncc(F)c3)nc21]
I-13
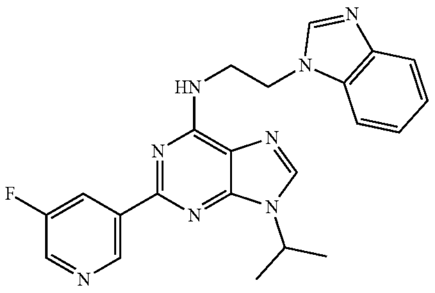 [SMILES: CC(C)n1cnc2c(NCCn3cnc4ccccc43)nc(-c3cncc(F)c3)nc21]
I-14
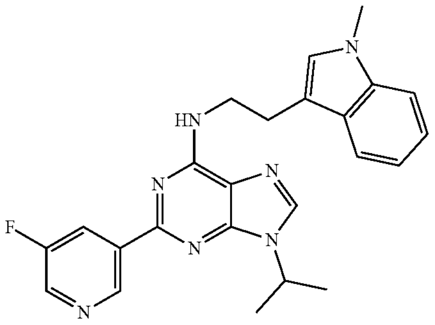 [SMILES: CC(C)n1cnc2c(NCCc3cn(C)c4ccccc34)nc(-c3cncc(F)c3)nc21]
I-15
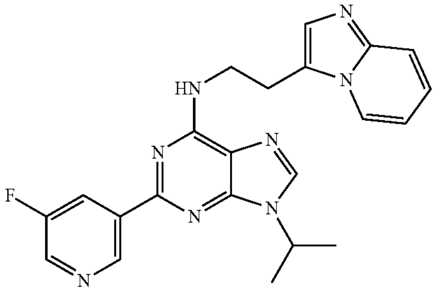 [SMILES: CC(C)n1cnc2c(NCCc3cnc4ccccn34)nc(-c3cncc(F)c3)nc21]

TABLE 1-continued
| Exemplary Compounds of Formula I | |
|---|---|
| I-16 | 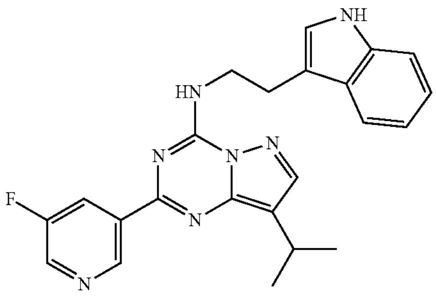 [SMILES: CC(C)c1cnn2c(NCCc3c[nH]c4ccccc34)nc(-c3cncc(F)c3)nc12] |
| I-17 | 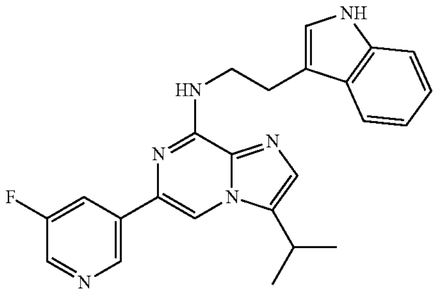 [SMILES: CC(C)c1cnc2c(NCCc3c[nH]c4ccccc34)nc(-c3cncc(F)c3)cn12] |
| I-18 | 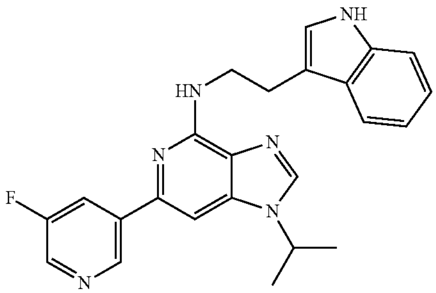 [SMILES: CC(C)n1cnc2c(NCCc3c[nH]c4ccccc34)nc(-c3cncc(F)c3)cc21] |
| I-19 | 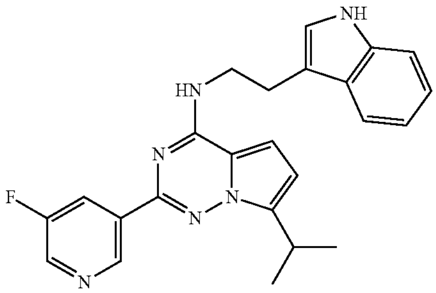 [SMILES: CC(C)c1ccc2c(NCCc3c[nH]c4ccccc34)nc(-c3cncc(F)c3)nn12] |
| I-20 | 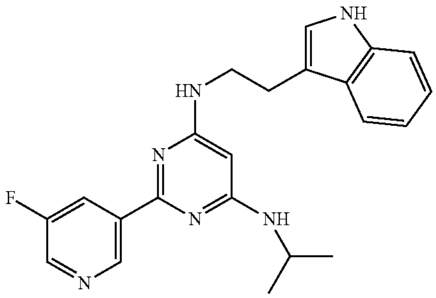 [SMILES: CC(C)Nc1cc(NCCc2c[nH]c3ccccc23)nc(-c2cncc(F)c2)n1] |
TABLE 1-continued
| Exemplary Compounds of Formula I | |
|---|---|
| I-21 | 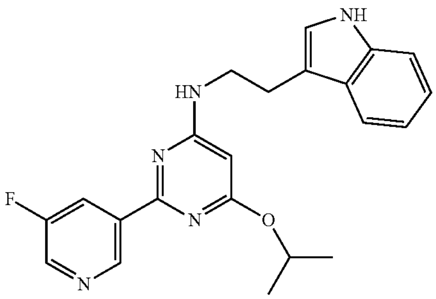 [SMILES: CC(C)Oc1cc(NCCc2c[nH]c3ccccc23)nc(-c2cncc(F)c2)n1] |
| I-22 | 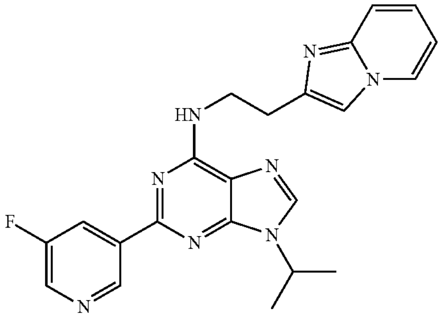 [SMILES: CC(C)n1cnc2c(NCCc3cn4ccccc4n3)nc(-c3cncc(F)c3)nc21] |
| I-23 | 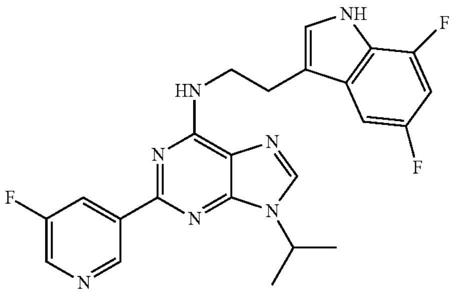 [SMILES: CC(C)n1cnc2c(NCCc3c[nH]c4c(F)cc(F)cc34)nc(-c3cncc(F)c3)nc21] |
| I-24 | 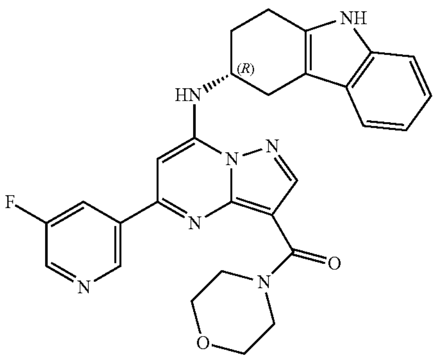 |

TABLE 1-continued
| Exemplary Compounds of Formula I |
| --- |
I-25
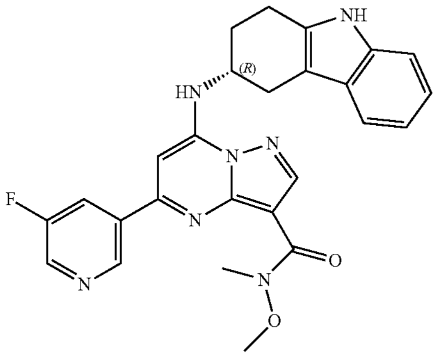
I-26
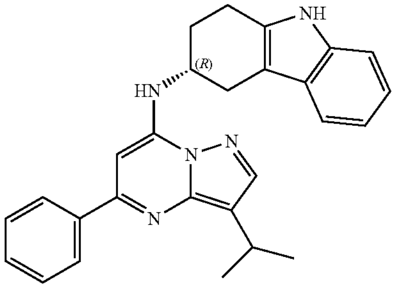
I-27a
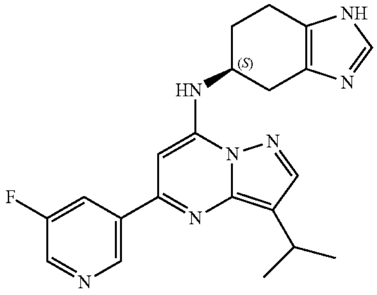
I-27b
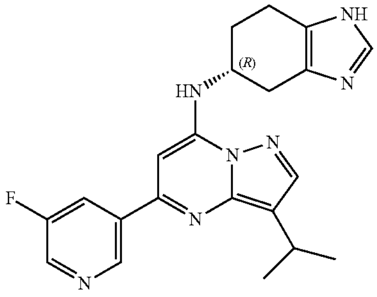
TABLE 1-continued
| Exemplary Compounds of Formula I |
| --- |
I-28a
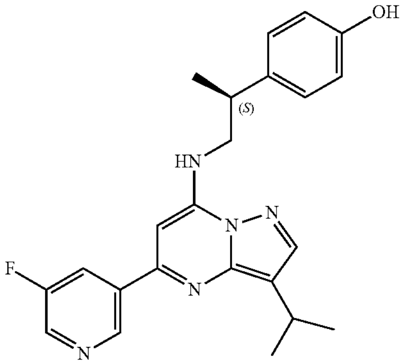
I-28b
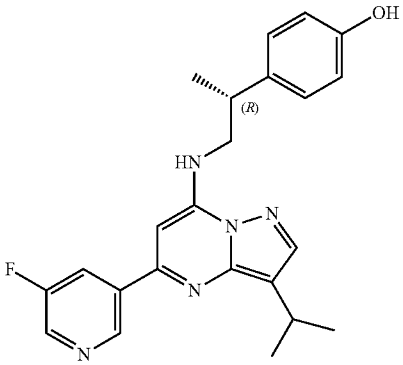
I-29
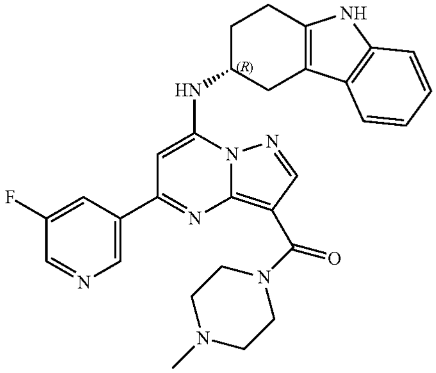
I-30
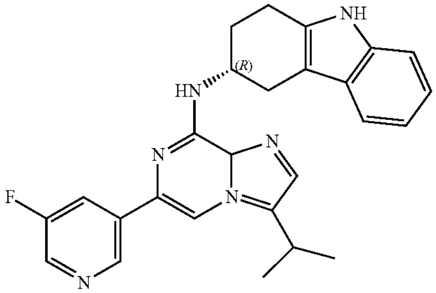

TABLE 1-continued
| Exemplary Compounds of Formula I | |
|---|---|
| I-31 | 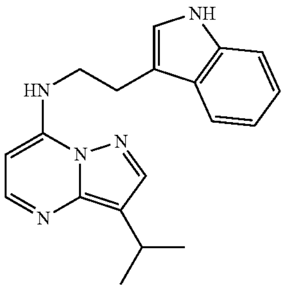 [SMILES: CC(C)c1cnn2c(NCCc3c[nH]c4ccccc34)ccnc12] |
| I-32a | 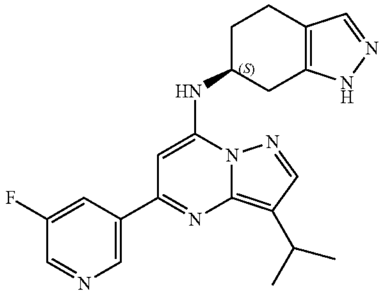 |
| I-32b | 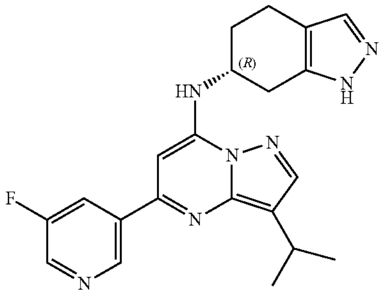 |
| I-33 | 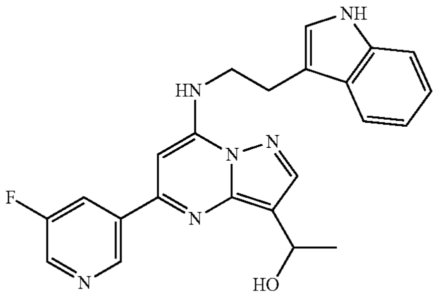 [SMILES: CC(O)c1cnn2c(NCCc3c[nH]c4ccccc34)cc(-c3cncc(F)c3)nc12] |
| I-34 | 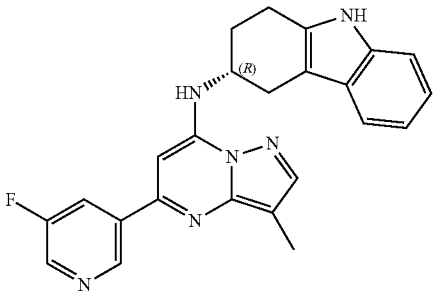 |
TABLE 1-continued
| Exemplary Compounds of Formula I | |
|---|---|
| I-35 | 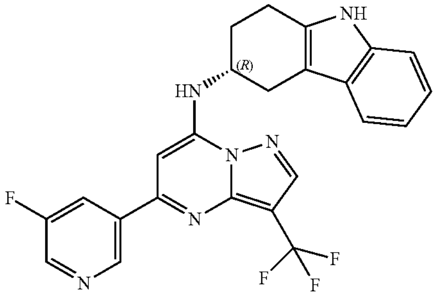 |
| I-36 | 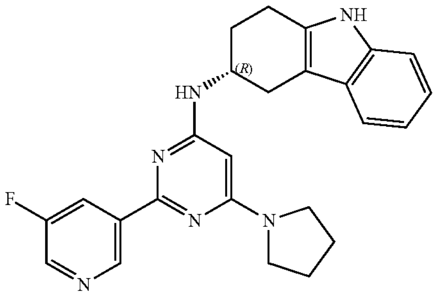 |
| I-37a | 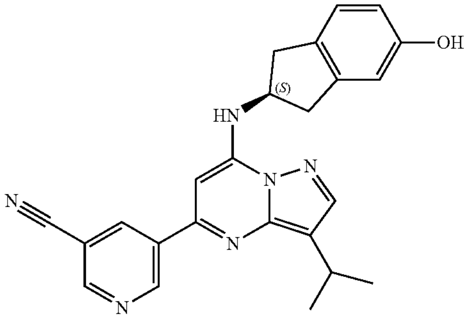 |
| I-37b | 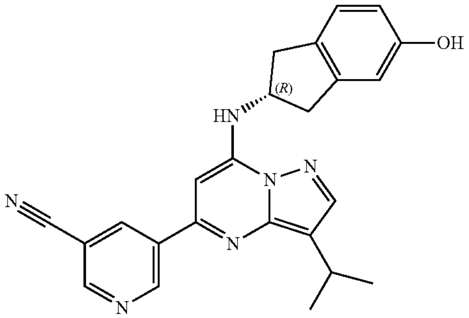 |
| I-38 | 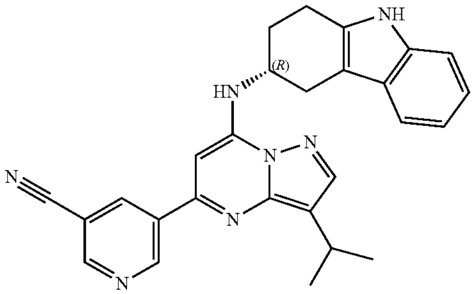 |

TABLE 1-continued
Exemplary Compounds of Formula I
I-39
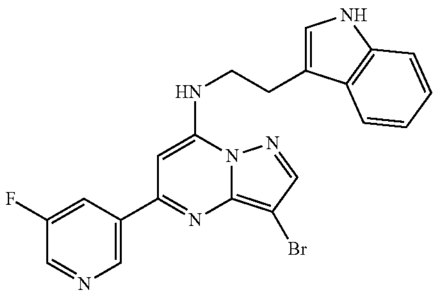 [SMILES: Fc1cncc(-c2cc(NCCc3c[nH]c4ccccc34)n3ncc(Br)c3n2)c1]
I-40
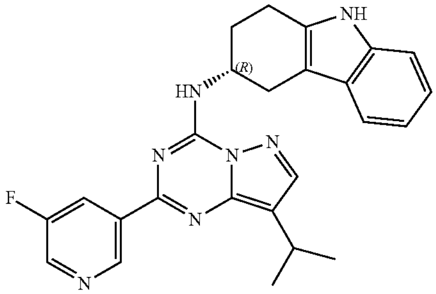
I-41
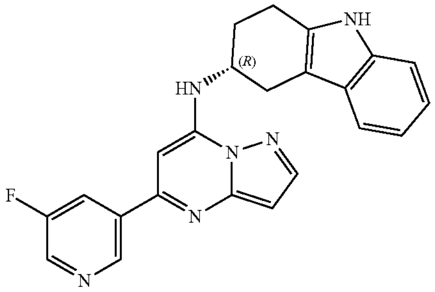
I-42a
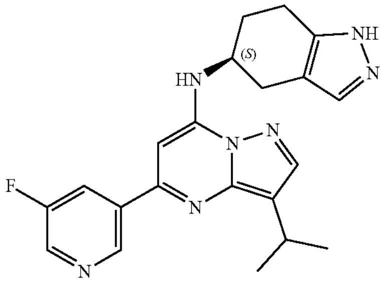
I-42b
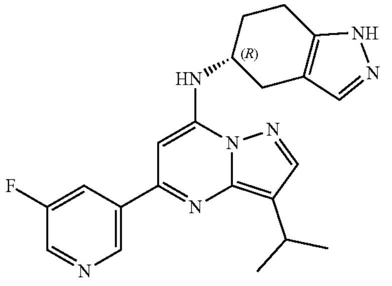
TABLE 1-continued
Exemplary Compounds of Formula I
I-43
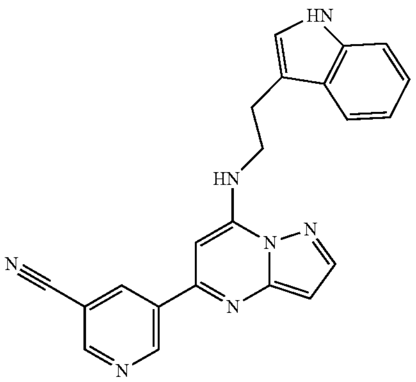 [SMILES: N#Cc1cncc(-c2cc(NCCc3c[nH]c4ccccc34)n3nccc3n2)c1]
I-44
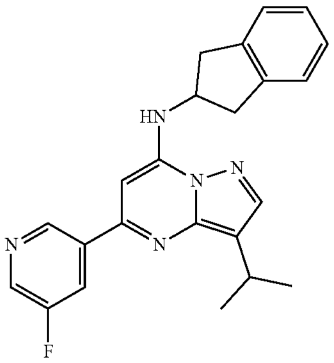 [SMILES: CC(C)c1cnn2c(NC3Cc4ccccc4C3)cc(-c3cncc(F)c3)nc12]
I-45
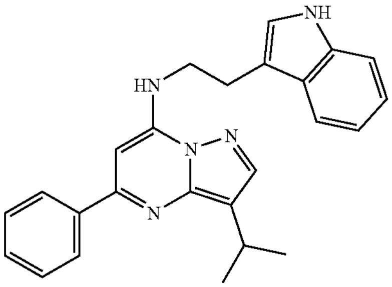
I-46
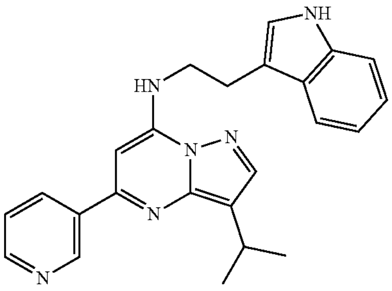 [SMILES: CC(C)c1cnn2c(NCCc3c[nH]c4ccccc34)cc(-c3cccnc3)nc12]

TABLE 1-continued
| Exemplary Compounds of Formula I |
|---|
I-47
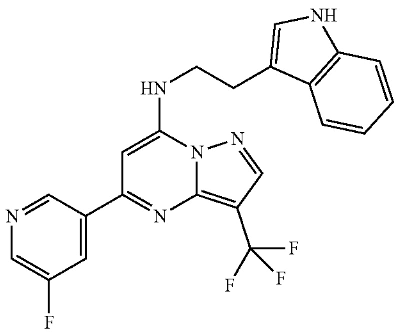 [SMILES: Fc1cncc(-c2cc(NCCc3c[nH]c4ccccc34)n3ncc(C(F)(F)F)c3n2)c1]
I-48
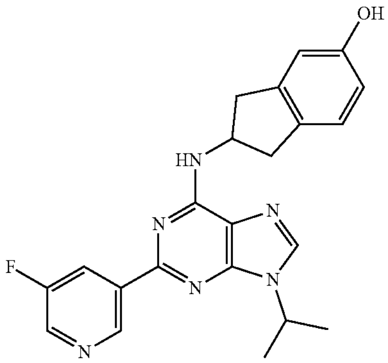 [SMILES: CC(C)n1cnc2c(NC3Cc4ccc(O)cc4C3)nc(-c3cncc(F)c3)nc21]
I-49
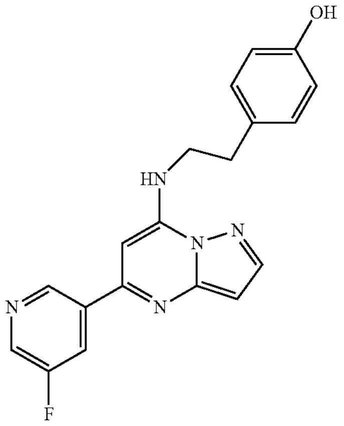 [SMILES: Oc1ccc(CCNc2cc(-c3cncc(F)c3)nc3ccnn23)cc1]
I-50
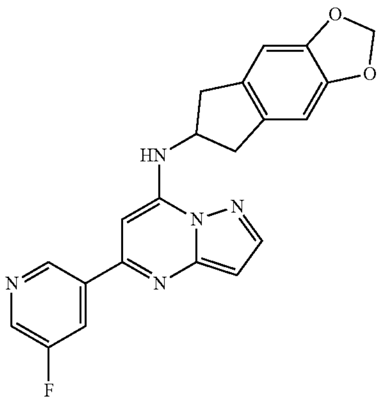 [SMILES: Fc1cncc(-c2cc(NC3Cc4cc5c(cc4C3)OCO5)n3nccc3n2)c1]
TABLE 1-continued
| Exemplary Compounds of Formula I |
|---|
I-51
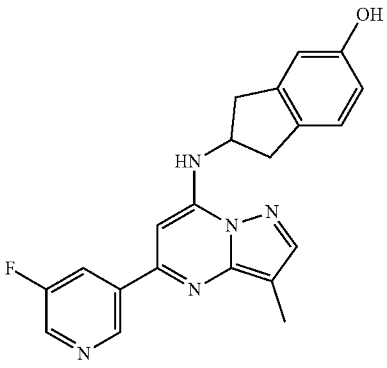 [SMILES: Cc1cnn2c(NC3Cc4ccc(O)cc4C3)cc(-c3cncc(F)c3)nc12]
I-52
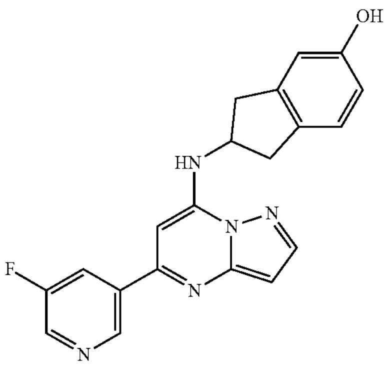 [SMILES: Oc1ccc2c(c1)CC(Nc1cc(-c3cncc(F)c3)nc3ccnn13)C2]
I-53
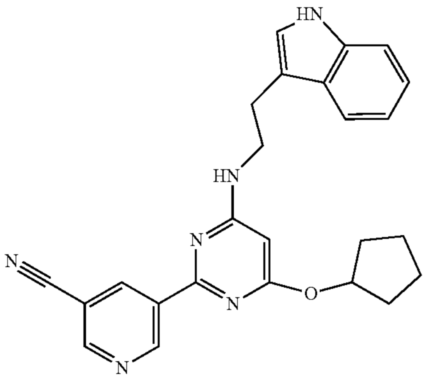 [SMILES: N#Cc1cncc(-c2nc(NCCc3c[nH]c4ccccc34)cc(OC3CCCC3)n2)c1]
I-54
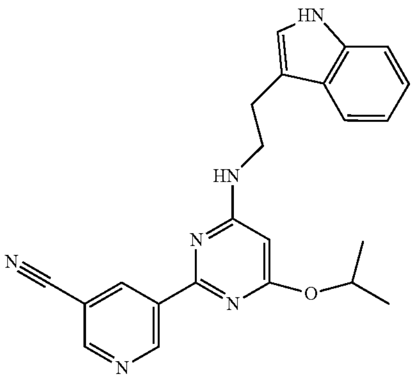 [SMILES: CC(C)Oc1cc(NCCc2c[nH]c3ccccc23)nc(-c2cncc(C#N)c2)n1]

TABLE 1-continued
| Exemplary Compounds of Formula I |
| --- |
I-55
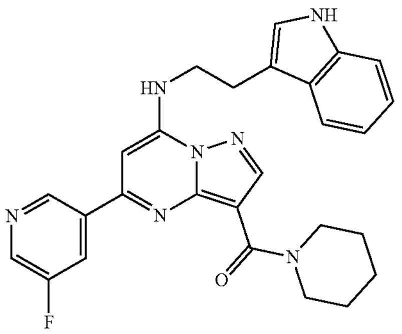 [SMILES: O=C(c1cnn2c(NCCc3c[nH]c4ccccc34)cc(-c3cncc(F)c3)nc12)N1CCCCC1]
I-56
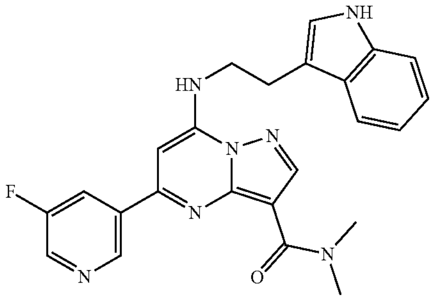 [SMILES: CN(C)C(=O)c1cnn2c(NCCc3c[nH]c4ccccc34)cc(-c3cncc(F)c3)nc12]
I-57
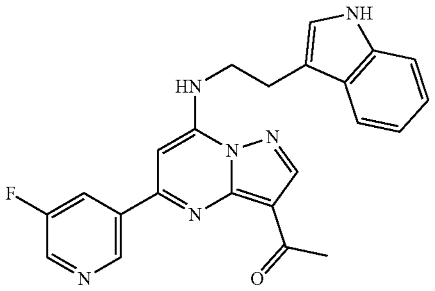 [SMILES: CC(=O)c1cnn2c(NCCc3c[nH]c4ccccc34)cc(-c3cncc(F)c3)nc12]
I-58
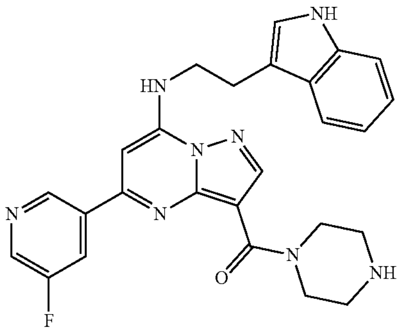 [SMILES: O=C(c1cnn2c(NCCc3c[nH]c4ccccc34)cc(-c3cncc(F)c3)nc12)N1CCNCC1]
I-59
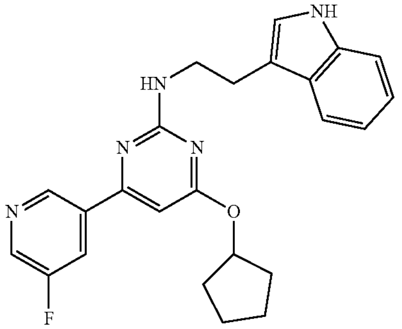 [SMILES: Fc1cncc(-c2cc(OC3CCCC3)nc(NCCc3c[nH]c4ccccc34)n2)c1]
TABLE 1-continued
| Exemplary Compounds of Formula I |
| --- |
I-60
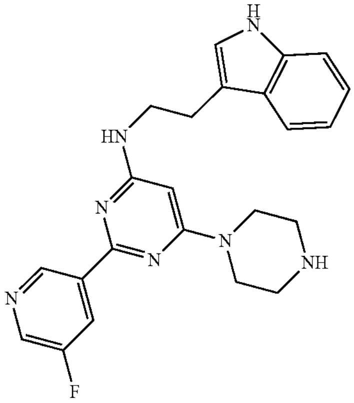 [SMILES: Fc1cncc(-c2nc(NCCc3c[nH]c4ccccc34)cc(N3CCNCC3)n2)c1]
I-61
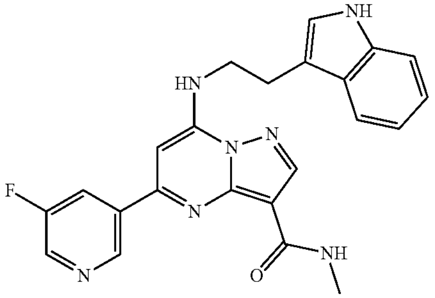 [SMILES: CNC(=O)c1cnn2c(NCCc3c[nH]c4ccccc34)cc(-c3cncc(F)c3)nc12]
I-62
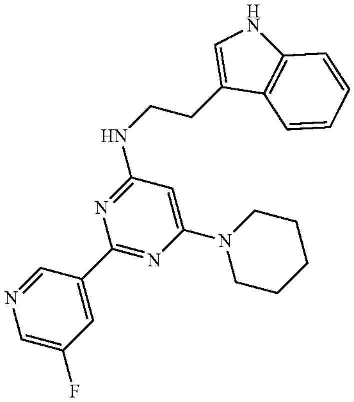 [SMILES: Fc1cncc(-c2nc(NCCc3c[nH]c4ccccc34)cc(N3CCCCC3)n2)c1]
I-63
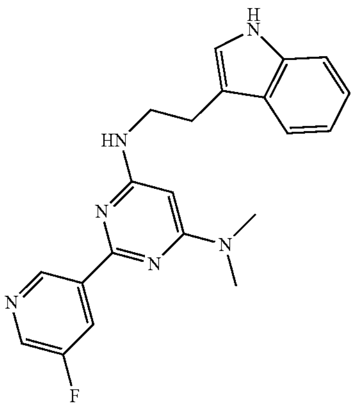 [SMILES: CN(C)c1cc(NCCc2c[nH]c3ccccc23)nc(-c2cncc(F)c2)n1]

TABLE 1-continued
| Exemplary Compounds of Formula I | |
|---|---|
| I-64 | 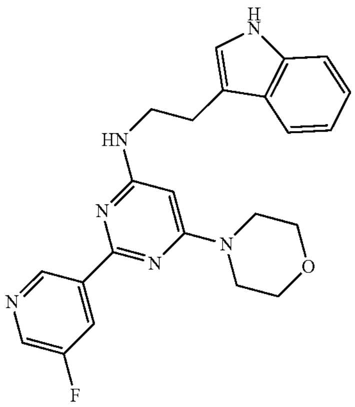 [SMILES: Fc1cncc(-c2nc(NCCc3c[nH]c4ccccc34)cc(N3CCOCC3)n2)c1] |
| I-65 | 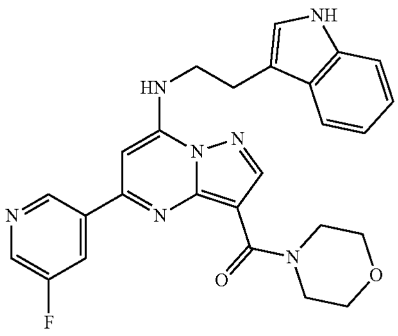 [SMILES: O=C(c1cnn2c(NCCc3c[nH]c4ccccc34)cc(-c3cncc(F)c3)nc12)N1CCOCC1] |
| I-66 | 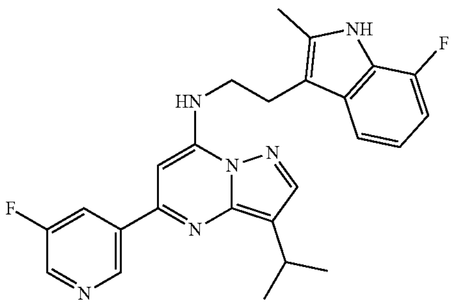 [SMILES: Cc1[nH]c2c(F)cccc2c1CCNc1cc(-c2cncc(F)c2)nc2c(C(C)C)cnn12] |
| I-67 | 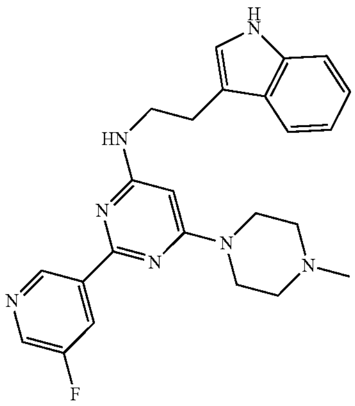 [SMILES: CN1CCN(c2cc(NCCc3c[nH]c4ccccc34)nc(-c3cncc(F)c3)n2)CC1] |
TABLE 1-continued
| Exemplary Compounds of Formula I | |
|---|---|
| I-68 | 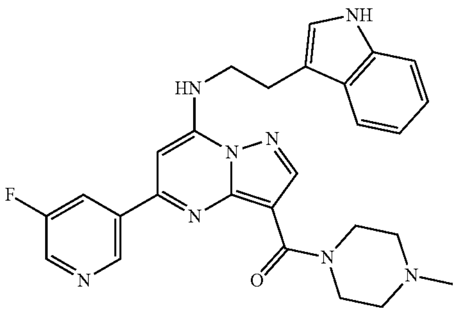 [SMILES: CN1CCN(C(=O)c2cnn3c(NCCc4c[nH]c5ccccc45)cc(-c4cncc(F)c4)nc23)CC1] |
| I-69 | 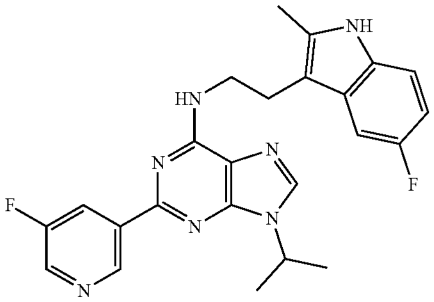 [SMILES: Cc1[nH]c2ccc(F)cc2c1CCNc1nc(-c2cncc(F)c2)nc2c1ncn2C(C)C] |
| I-70 | 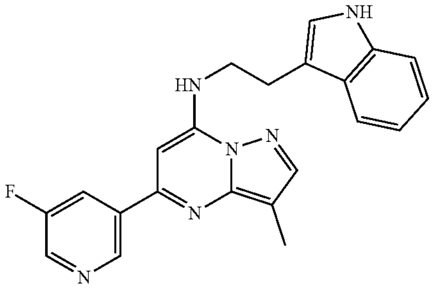 [SMILES: Cc1cnn2c(NCCc3c[nH]c4ccccc34)cc(-c3cncc(F)c3)nc12] |
| I-71 | 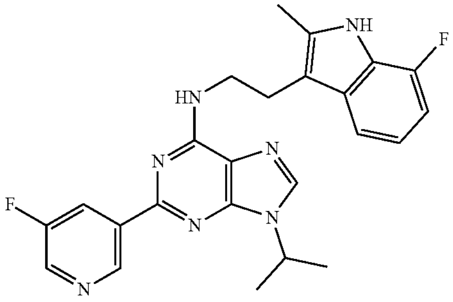 |
| I-72 | 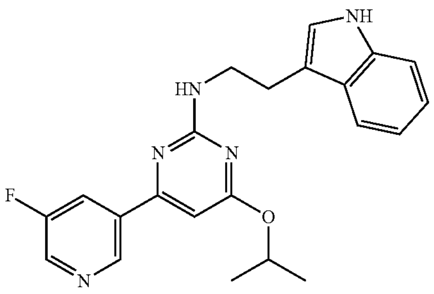 [SMILES: CC(C)Oc1cc(-c2cncc(F)c2)nc(NCCc2c[nH]c3ccccc23)n1] |

TABLE 1-continued
Exemplary Compounds of Formula I
I-73
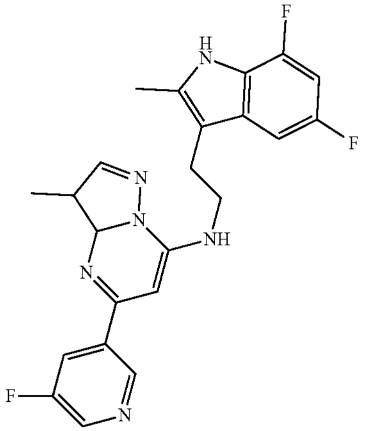 [SMILES: Cc1[nH]c2c(F)cc(F)cc2c1CCNC1=CC(c2cncc(F)c2)=NC2C(C)C=NN12]
I-74
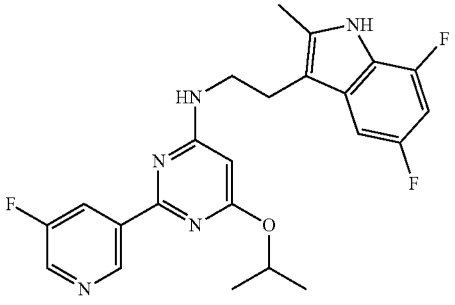 [SMILES: Cc1[nH]c2c(F)cc(F)cc2c1CCNc1cc(OC(C)C)nc(-c2cncc(F)c2)n1]
I-75a
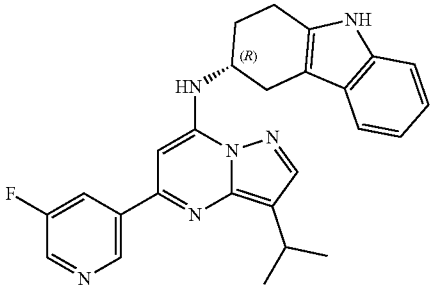
I-75b
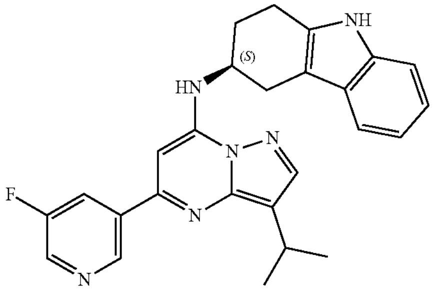
TABLE 1-continued
Exemplary Compounds of Formula I
I-75c
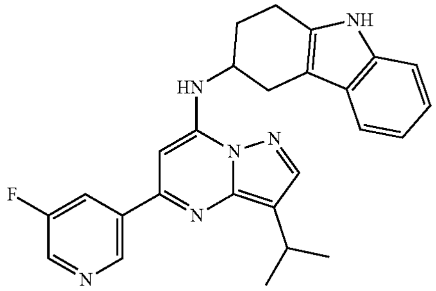 [SMILES: CC(C)c1cnn2c(NC3CCc4[nH]c5ccccc5c4C3)cc(-c3cncc(F)c3)nc12]
I-76
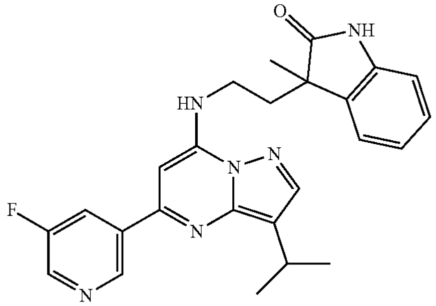 [SMILES: CC(C)c1cnn2c(NCCC3(C)C(=O)Nc4ccccc43)cc(-c3cncc(F)c3)nc12]
I-77
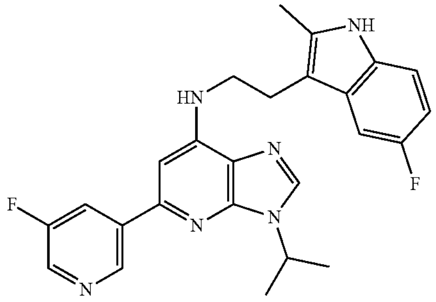 [SMILES: Cc1[nH]c2ccc(F)cc2c1CCNc1cc(-c2cncc(F)c2)nc2c1ncn2C(C)C]
I-78
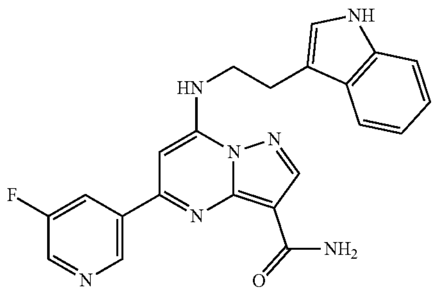 [SMILES: NC(=O)c1cnn2c(NCCc3c[nH]c4ccccc34)cc(-c3cncc(F)c3)nc12]
I-79
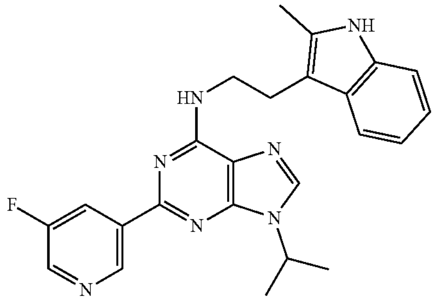 [SMILES: Cc1[nH]c2ccccc2c1CCNc1nc(-c2cncc(F)c2)nc2c1ncn2C(C)C]

TABLE 1-continued
Exemplary Compounds of Formula I
I-80
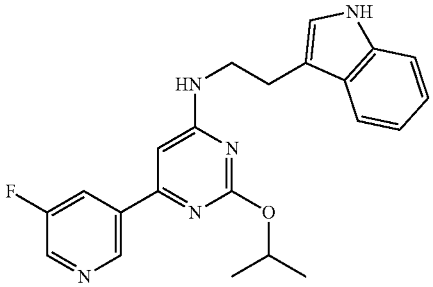 [SMILES: CC(C)Oc1nc(NCCc2c[nH]c3ccccc23)cc(-c2cncc(F)c2)n1]
I-81
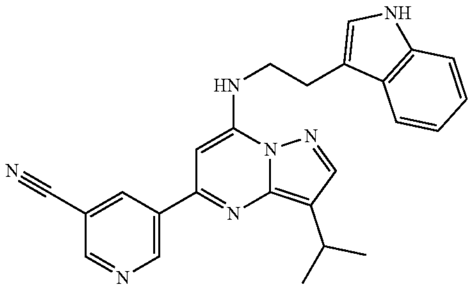 [SMILES: CC(C)c1cnn2c(NCCc3c[nH]c4ccccc34)cc(-c3cncc(C#N)c3)nc12]
I-82a
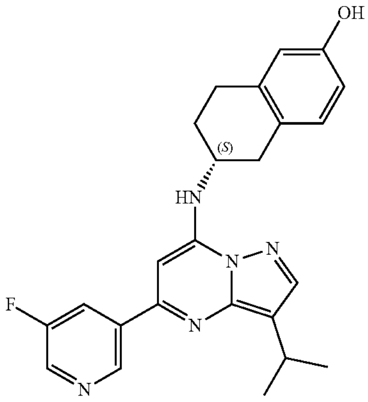
I-82b
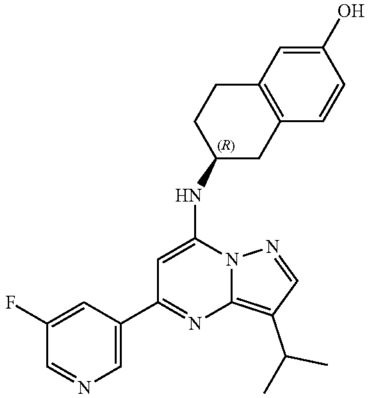
TABLE 1-continued
Exemplary Compounds of Formula I
I-82c
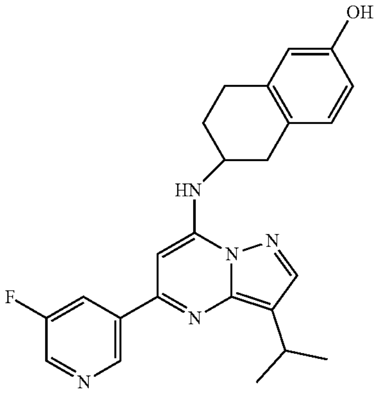 [SMILES: CC(C)c1cnn2c(NC3CCc4cc(O)ccc4C3)cc(-c3cncc(F)c3)nc12]
I-83
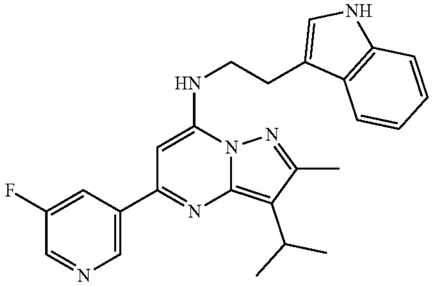 [SMILES: Cc1nn2c(NCCc3c[nH]c4ccccc34)cc(-c3cncc(F)c3)nc2c1C(C)C]
I-84
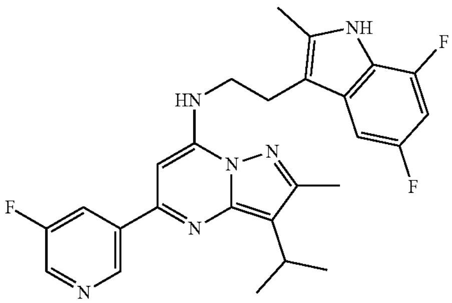 [SMILES: Cc1nn2c(NCCc3c(C)[nH]c4c(F)cc(F)cc34)cc(-c3cncc(F)c3)nc2c1C(C)C]
I-85
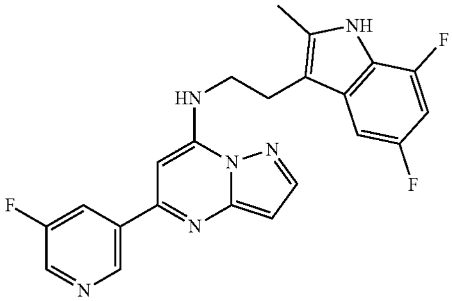
I-86
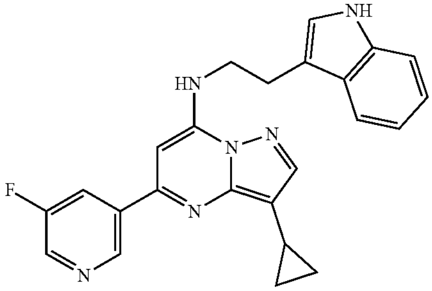 [SMILES: Fc1cncc(-c2cc(NCCc3c[nH]c4ccccc34)n3ncc(C4CC4)c3n2)c1]

TABLE 1-continued
Exemplary Compounds of Formula I
I-87
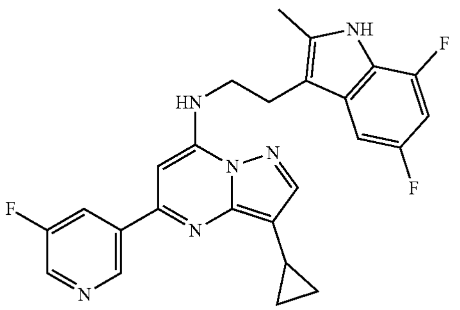 [SMILES: Cc1[nH]c2c(F)cc(F)cc2c1CCNc1cc(-c2cncc(F)c2)nc2c(C3CC3)cnn12]
I-88
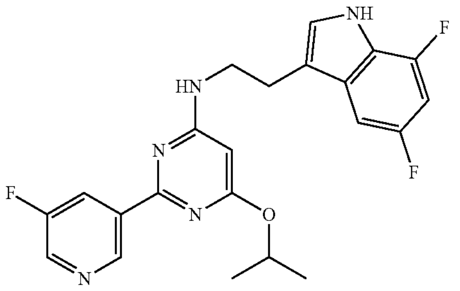 [SMILES: CC(C)Oc1cc(NCCc2c[nH]c3c(F)cc(F)cc23)nc(-c2cncc(F)c2)n1]
I-89
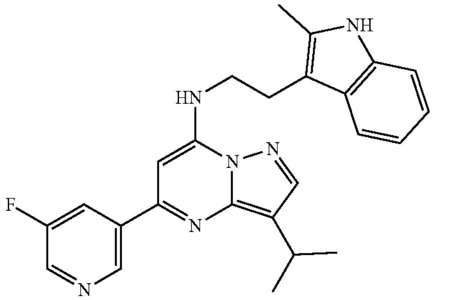 [SMILES: Cc1[nH]c2ccccc2c1CCNc1cc(-c2cncc(F)c2)nc2c(C(C)C)cnn12]
I-90
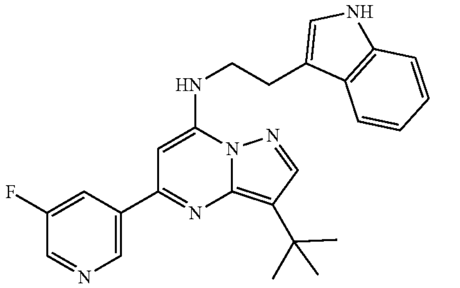 [SMILES: CC(C)(C)c1cnn2c(NCCc3c[nH]c4ccccc34)cc(-c3cncc(F)c3)nc12]
I-91
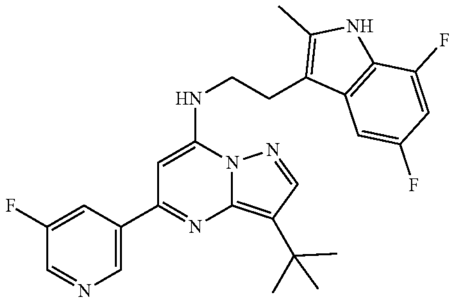 [SMILES: Cc1[nH]c2c(F)cc(F)cc2c1CCNc1cc(-c2cncc(F)c2)nc2c(C(C)(C)C)cnn12]
TABLE 1-continued
Exemplary Compounds of Formula I
I-92
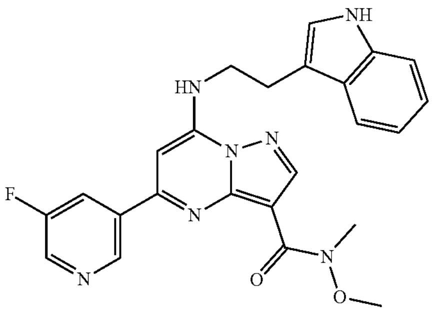 [SMILES: CON(C)C(=O)c1cnn2c(NCCc3c[nH]c4ccccc34)cc(-c3cncc(F)c3)nc12]
I-93
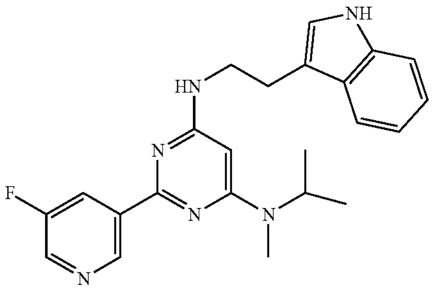 [SMILES: CC(C)N(C)c1cc(NCCc2c[nH]c3ccccc23)nc(-c2cncc(F)c2)n1]
I-94a
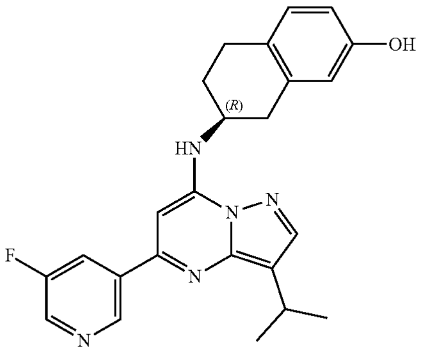
I-94b
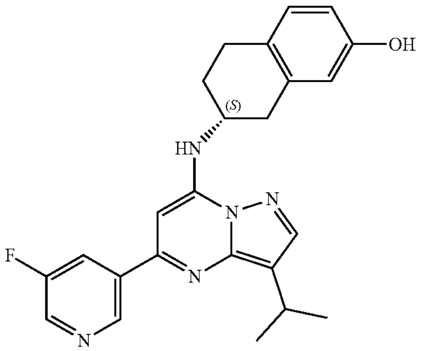

TABLE 1-continued
Exemplary Compounds of Formula I
I-95
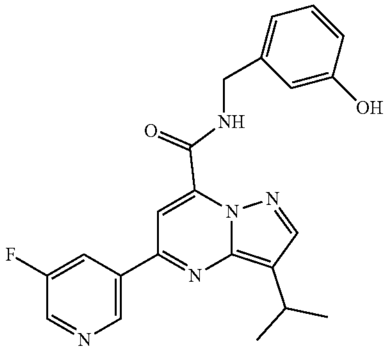 [SMILES: CC(C)c1cnn2c(C(=O)NCc3cccc(O)c3)cc(-c3cncc(F)c3)nc12]
I-96
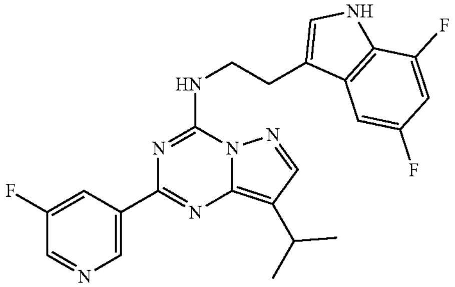 [SMILES: CC(C)c1cnn2c(NCCc3c[nH]c4c(F)cc(F)cc34)nc(-c3cncc(F)c3)nc12]
I-97a
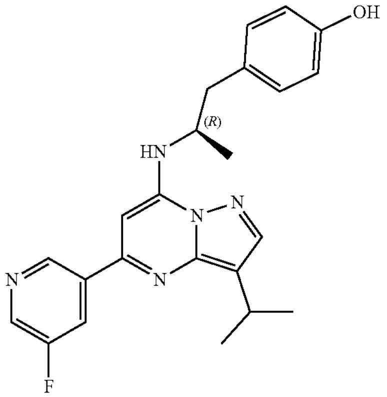
I-97b
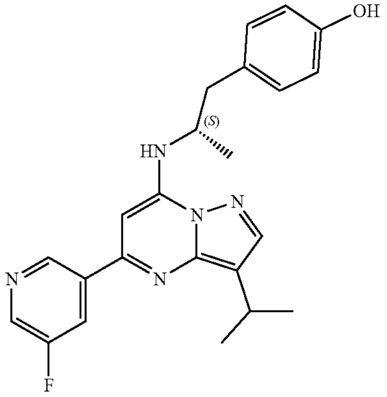
TABLE 1-continued
Exemplary Compounds of Formula I
I-98a
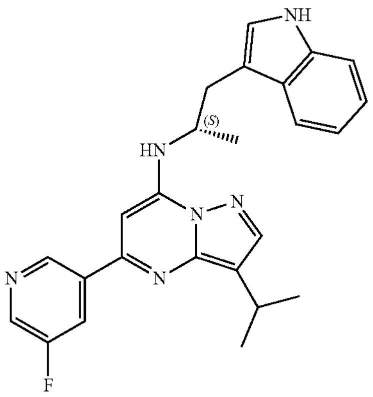
I-98b
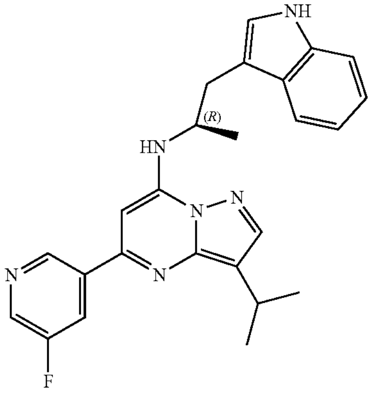
I-99
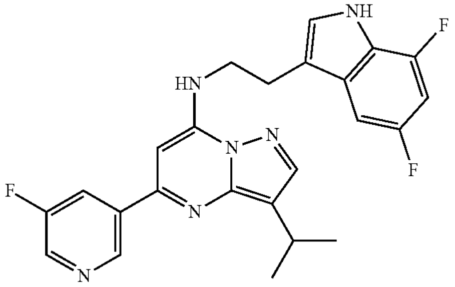 [SMILES: CC(C)c1cnn2c(NCCc3c[nH]c4c(F)cc(F)cc34)cc(-c3cncc(F)c3)nc12]
I-100
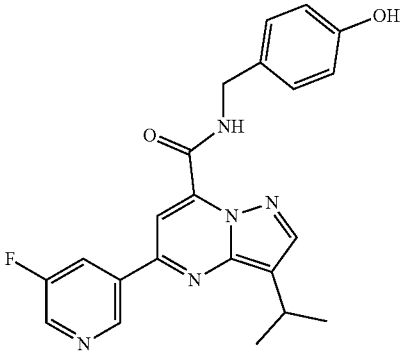 [SMILES: CC(C)c1cnn2c(C(=O)NCc3ccc(O)cc3)cc(-c3cncc(F)c3)nc12]

TABLE 1-continued
Exemplary Compounds of Formula I
I-101
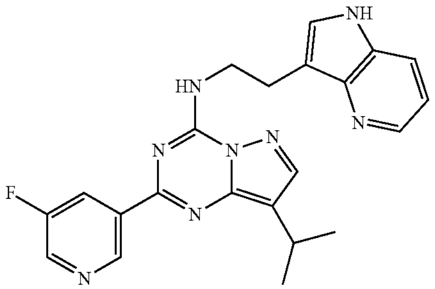 [SMILES: CC(C)c1cnn2c(NCCc3c[nH]c4cccnc34)nc(-c3cncc(F)c3)nc12]
I-102
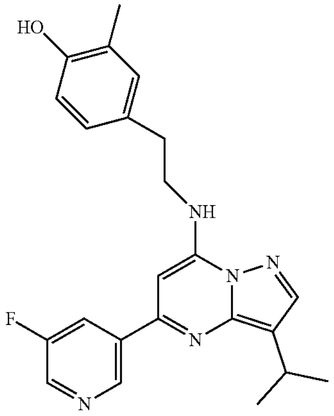 [SMILES: Cc1cc(CCNc2cc(-c3cncc(F)c3)nc3c(C(C)C)cnn23)ccc1O]
I-103
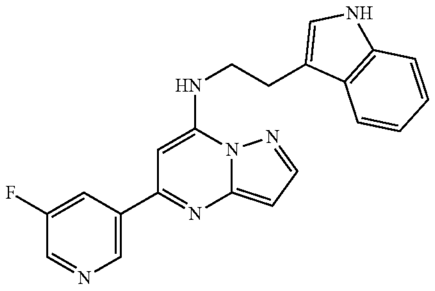 [SMILES: Fc1cncc(-c2cc(NCCc3c[nH]c4ccccc34)n3nccc3n2)c1]
I-104
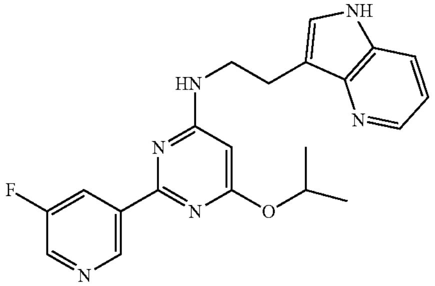 [SMILES: CC(C)Oc1cc(NCCc2c[nH]c3cccnc23)nc(-c2cncc(F)c2)n1]
I-105
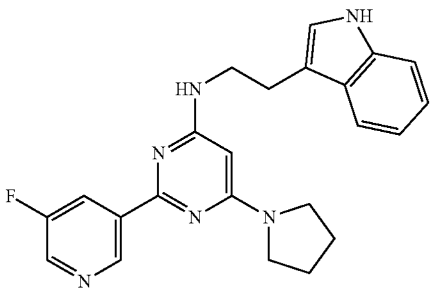 [SMILES: Fc1cncc(-c2nc(NCCc3c[nH]c4ccccc34)cc(N3CCCC3)n2)c1]
TABLE 1-continued
Exemplary Compounds of Formula I
I-106
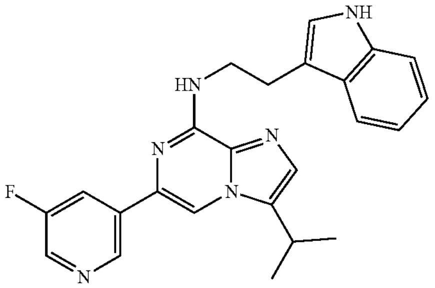 [SMILES: CC(C)c1cnc2c(NCCc3c[nH]c4ccccc34)nc(-c3cncc(F)c3)cn12]
I-107
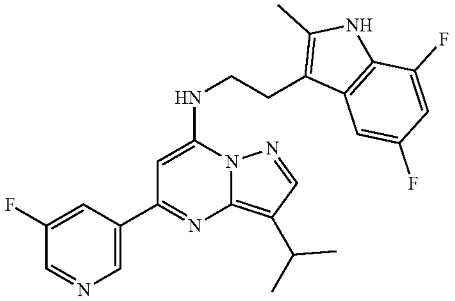 [SMILES: Cc1[nH]c2c(F)cc(F)cc2c1CCNc1cc(-c2cncc(F)c2)nc2c(C(C)C)cnn12]
I-108
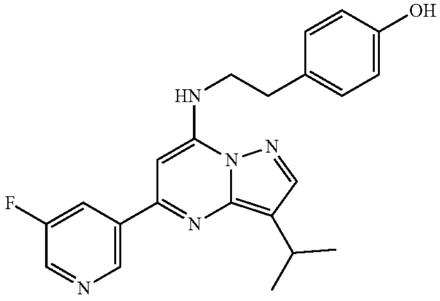 [SMILES: CC(C)c1cnn2c(NCCc3ccc(O)cc3)cc(-c3cncc(F)c3)nc12]
I-109
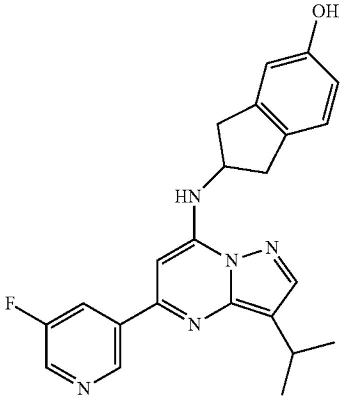 [SMILES: CC(C)c1cnn2c(NC3Cc4ccc(O)cc4C3)cc(-c3cncc(F)c3)nc12]
I-110
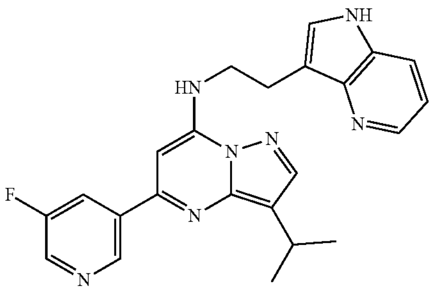 [SMILES: CC(C)c1cnn2c(NCCc3c[nH]c4cccnc34)cc(-c3cncc(F)c3)nc12]

TABLE 1-continued
Exemplary Compounds of Formula I
I-111
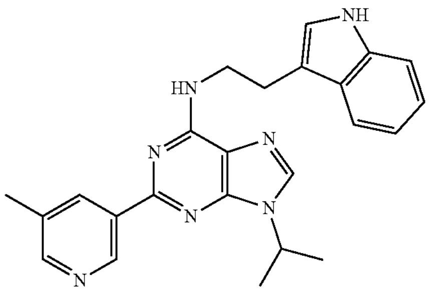 [SMILES: Cc1cncc(-c2nc(NCCc3c[nH]c4ccccc34)c3ncn(C(C)C)c3n2)c1]
I-112
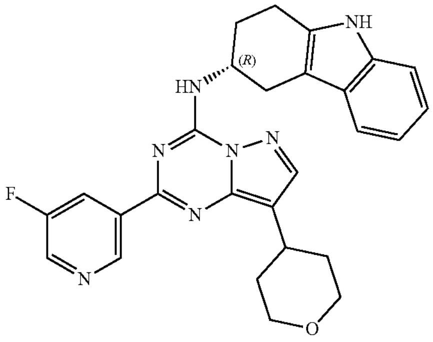
I-113
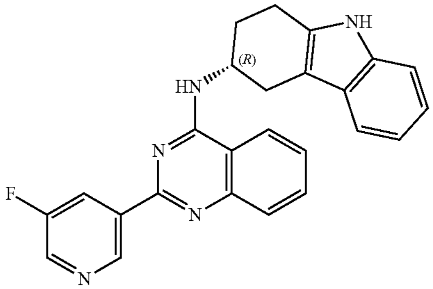
I-114
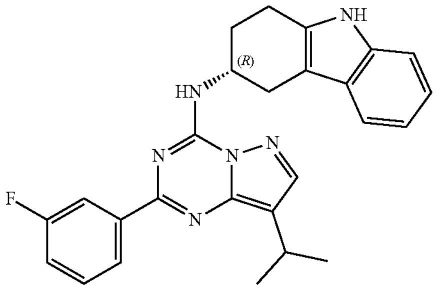
I-115
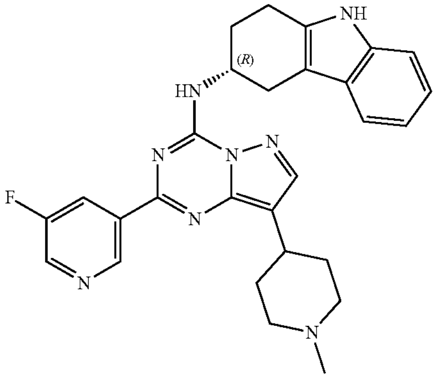
I-116
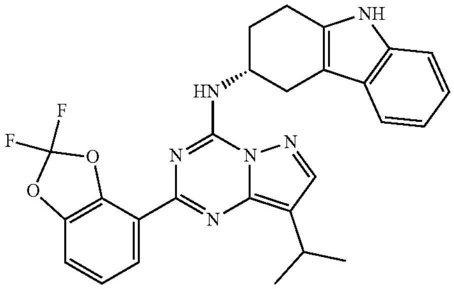 [SMILES: CC(C)c1cnn2c(N[C@@H]3CCc4[nH]c5ccccc5c4C3)nc(-c3cccc4c3OC(F)(F)O4)nc12]
I-117
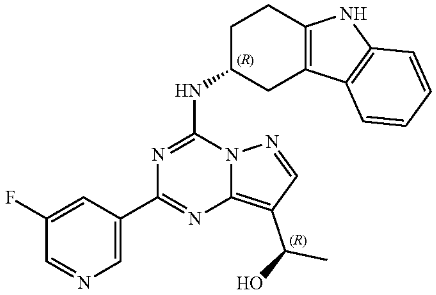
I-118
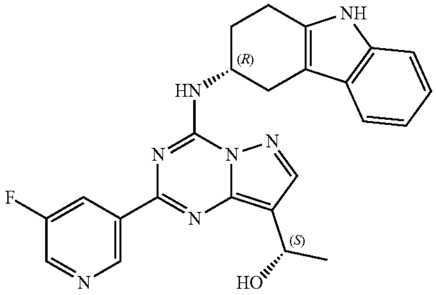
I-119
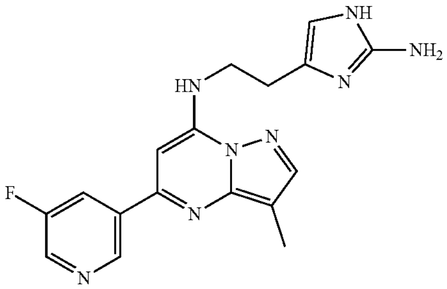 [SMILES: Cc1cnn2c(NCCc3c[nH]c(N)n3)cc(-c3cncc(F)c3)nc12]

TABLE 1-continued
Exemplary Compounds of Formula I
I-120
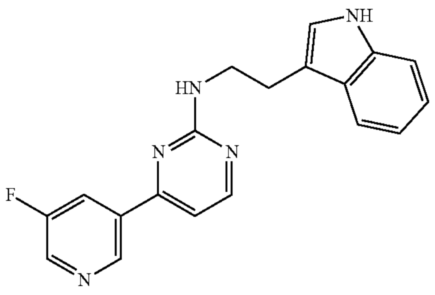 [SMILES: Fc1cncc(-c2ccnc(NCCc3c[nH]c4ccccc34)n2)c1]
I-121
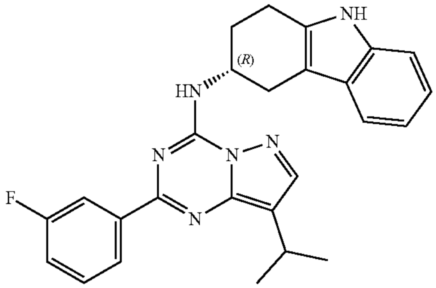
I-122
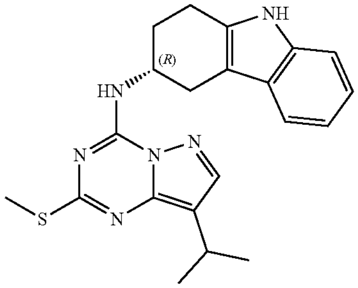
I-123
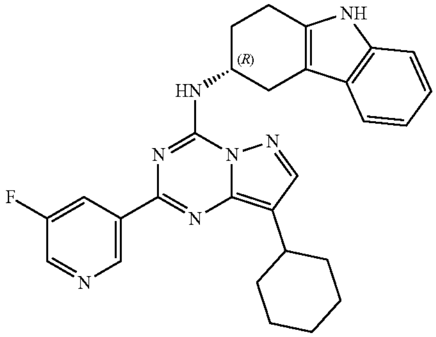
I-124
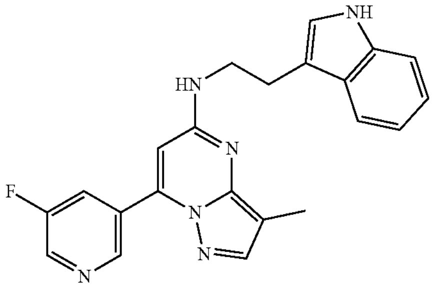 [SMILES: Cc1cnn2c(-c3cncc(F)c3)cc(NCCc3c[nH]c4ccccc34)nc12]
I-125
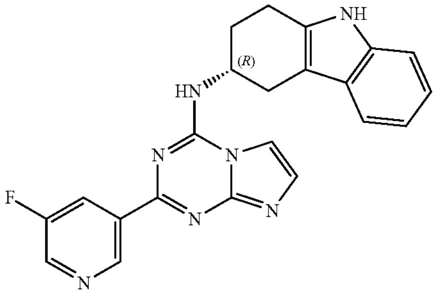
I-126
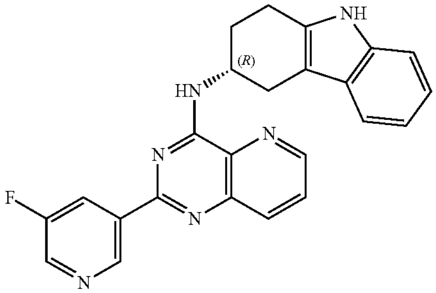
I-128a
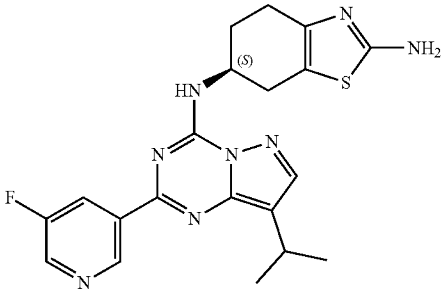
I-128b
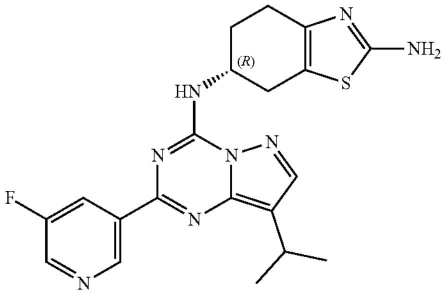
I-129
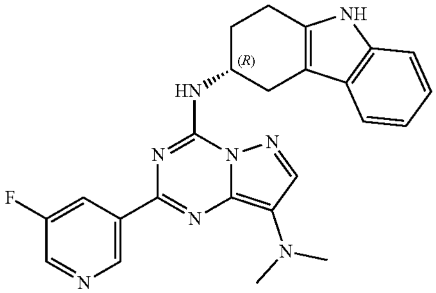

TABLE 1-continued
Exemplary Compounds of Formula I
I-130
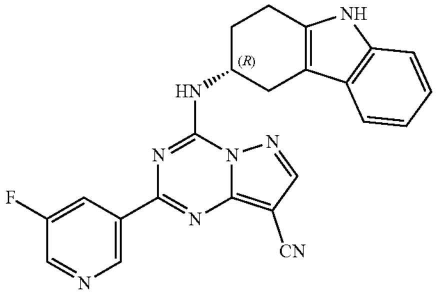
I-131
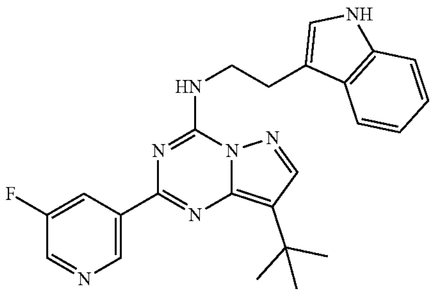 [SMILES: CC(C)(C)c1cnn2c(NCCc3c[nH]c4ccccc34)nc(-c3cncc(F)c3)nc12]
I-132
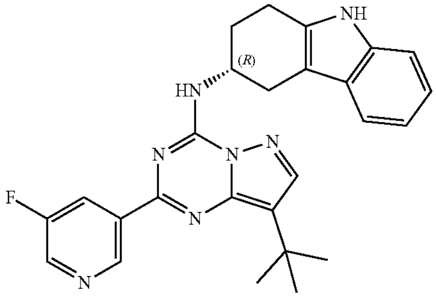
I-133
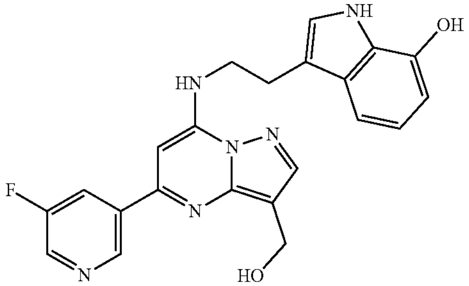 [SMILES: OCc1cnn2c(NCCc3c[nH]c4c(O)cccc34)cc(-c3cncc(F)c3)nc12]
I-134
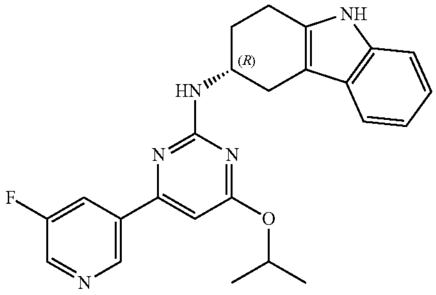
I-135
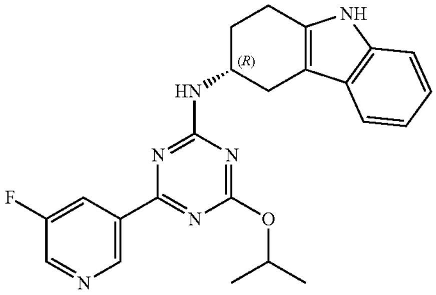
I-136
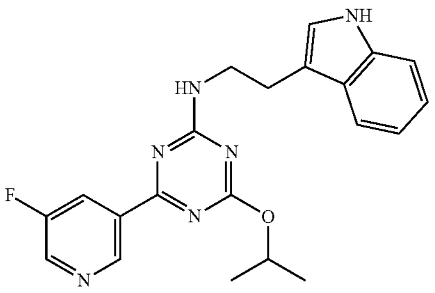 [SMILES: CC(C)Oc1nc(NCCc2c[nH]c3ccccc23)nc(-c2cncc(F)c2)n1]
I-137a
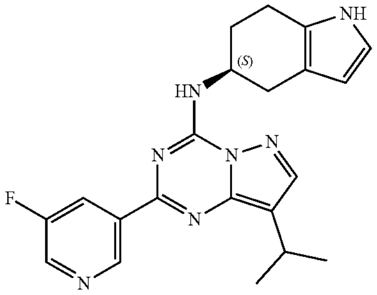
I-137b
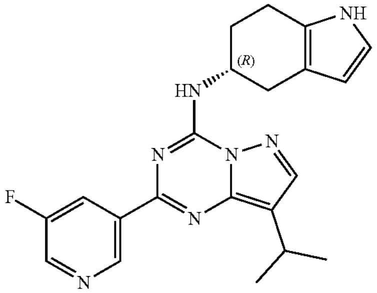
I-137c
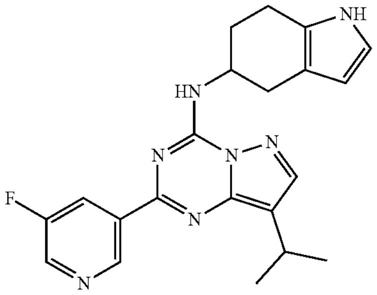 [SMILES: CC(C)c1cnn2c(NC3CCc4[nH]ccc4C3)nc(-c3cncc(F)c3)nc12]

TABLE 1-continued
Exemplary Compounds of Formula I
I-139a
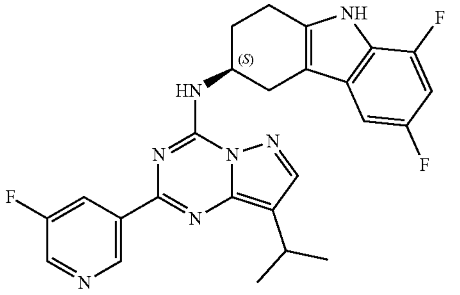
I-139b
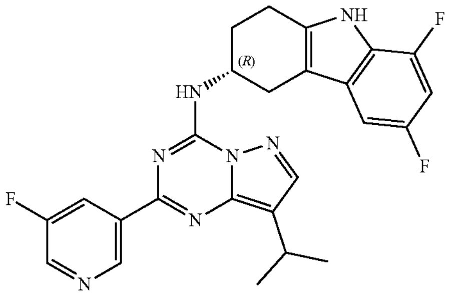
I-139c
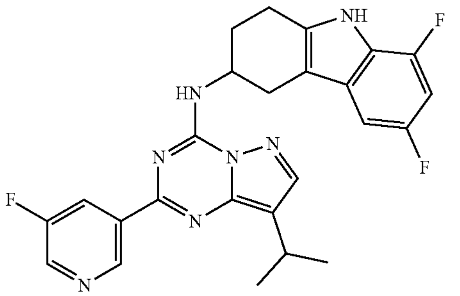 [SMILES: CC(C)c1cnn2c(NC3CCc4[nH]c5c(F)cc(F)cc5c4C3)nc(-c3cncc(F)c3)nc12]
I-141
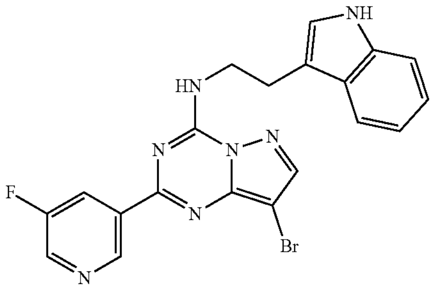 [SMILES: Fc1cncc(-c2nc(NCCc3c[nH]c4ccccc34)n3ncc(Br)c3n2)c1]
I-142
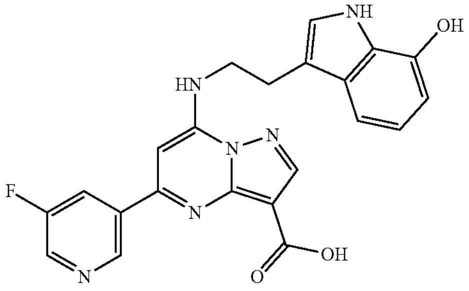 [SMILES: O=C(O)c1cnn2c(NCCc3c[nH]c4c(O)cccc34)cc(-c3cncc(F)c3)nc12]
TABLE 1-continued
Exemplary Compounds of Formula I
I-143
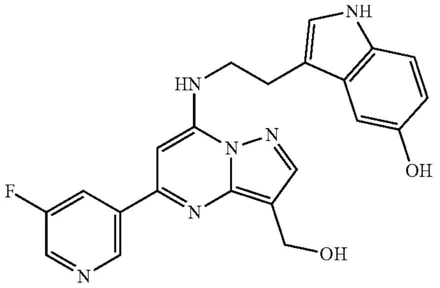 [SMILES: OCc1cnn2c(NCCc3c[nH]c4ccc(O)cc34)cc(-c3cncc(F)c3)nc12]
I-144a
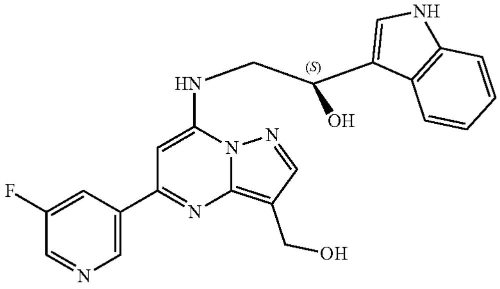
I-144b
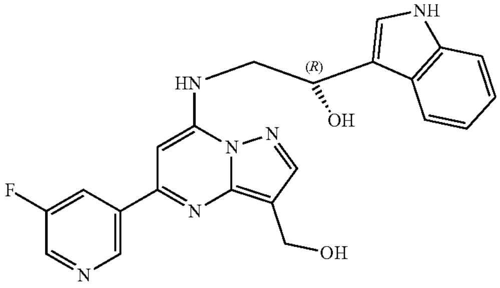
I-146a
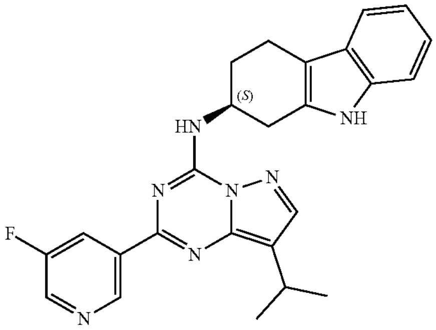
I-146b
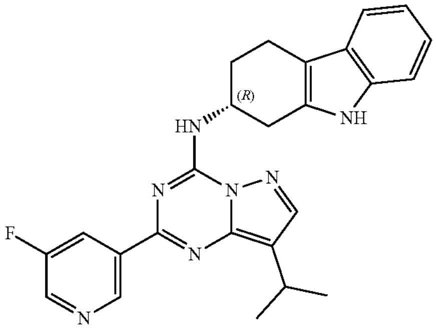

TABLE 1-continued
| Exemplary Compounds of Formula I | |
|---|---|
| I-148 | 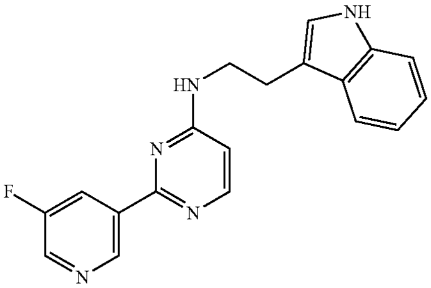 [SMILES: Fc1cncc(-c2nccc(NCCc3c[nH]c4ccccc34)n2)c1] |
| I-149 | 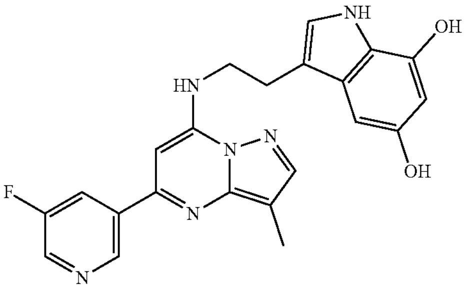 [SMILES: Cc1cnn2c(NCCc3c[nH]c4c(O)cc(O)cc34)cc(-c3cncc(F)c3)nc12] |
| I-150a | 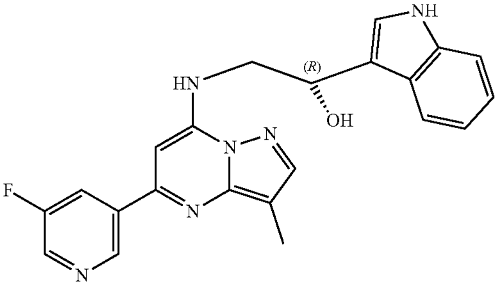 |
| I-150b | 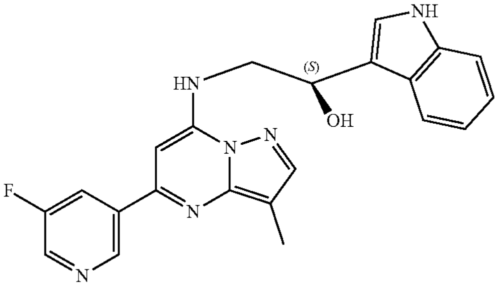 |
| I-152a | 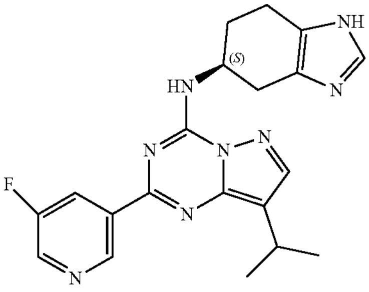 |
TABLE 1-continued
| Exemplary Compounds of Formula I | |
|---|---|
| I-152b | 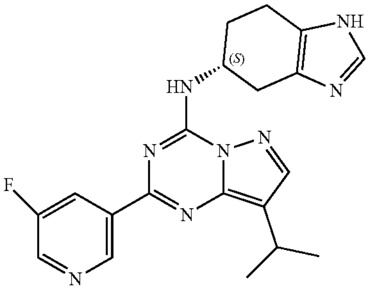 |
| I-152c | 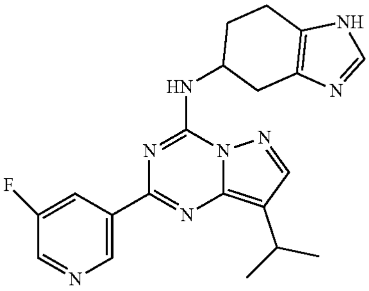 [SMILES: CC(C)c1cnn2c(NC3CCc4[nH]cnc4C3)nc(-c3cncc(F)c3)nc12] |
| I-154 | 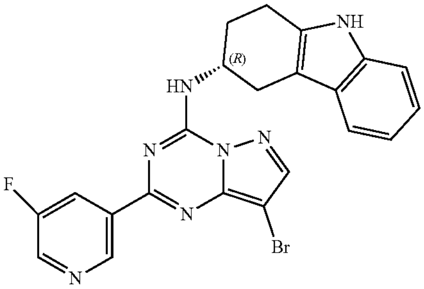 |
| I-155 | 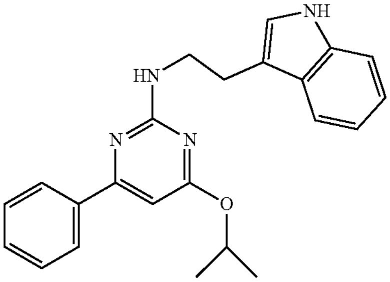 [SMILES: CC(C)Oc1cc(-c2ccccc2)nc(NCCc2c[nH]c3ccccc23)n1] |
| I-156 | 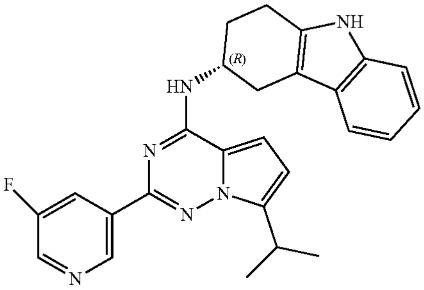 |

TABLE 1-continued
| Exemplary Compounds of Formula I | |
|---|---|
| I-157 | 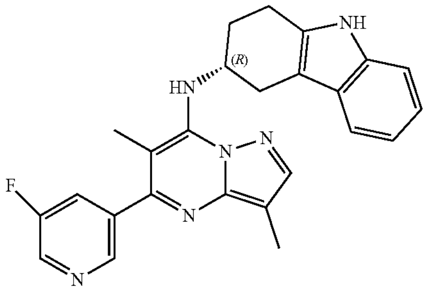 |
| I-158a | 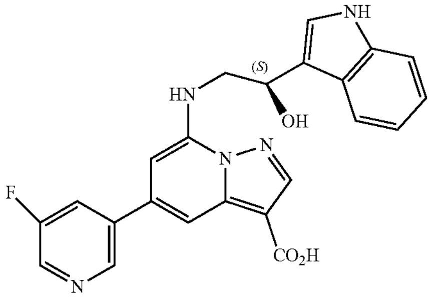 |
| I-158b | 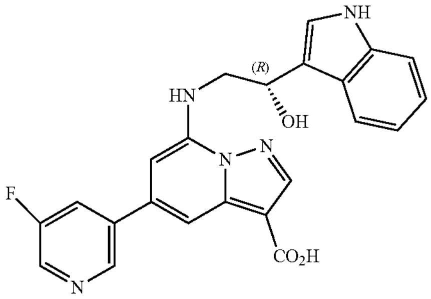 |
| I-160a | 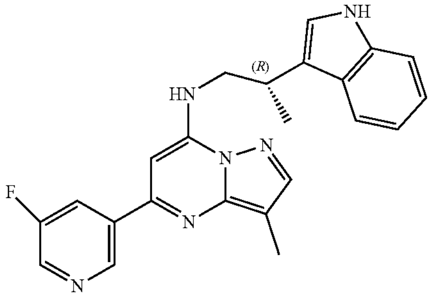 |
| I-160b | 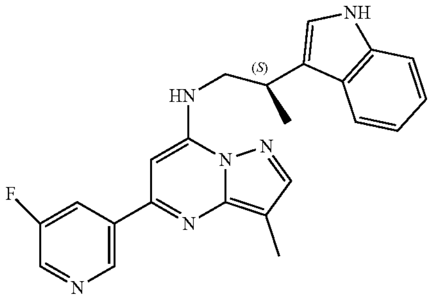 |
TABLE 1-continued
| Exemplary Compounds of Formula I | |
|---|---|
| I-160c | 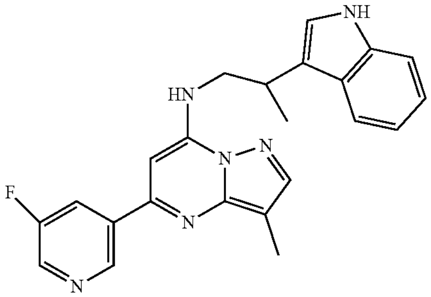 [SMILES: Cc1cnn2c(NCC(C)c3c[nH]c4ccccc34)cc(-c3cncc(F)c3)nc12] |
| I-162 | 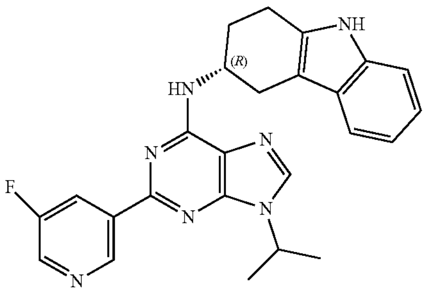 |
| I-163 | 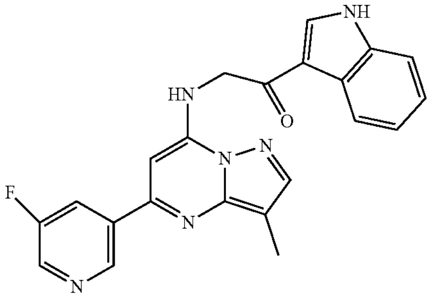 [SMILES: Cc1cnn2c(NCC(=O)c3c[nH]c4ccccc34)cc(-c3cncc(F)c3)nc12] |
| I-164 | 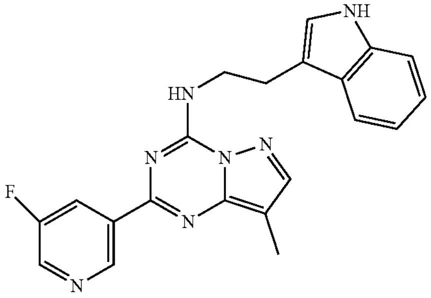 [SMILES: Cc1cnn2c(NCCc3c[nH]c4ccccc34)nc(-c3cncc(F)c3)nc12] |
| I-165 | 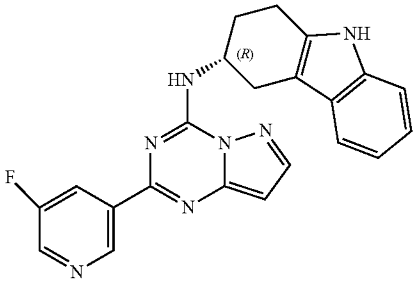 |

TABLE 1-continued
| Exemplary Compounds of Formula I | |
|---|---|
| I-166 | 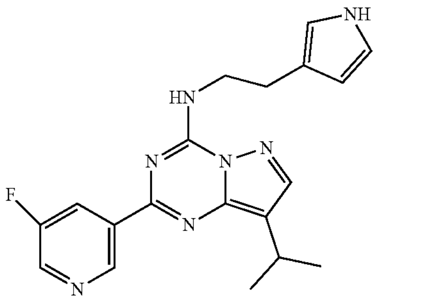 [SMILES: CC(C)c1cnn2c(NCCc3cc[nH]c3)nc(-c3cncc(F)c3)nc12] |
| I-167 | 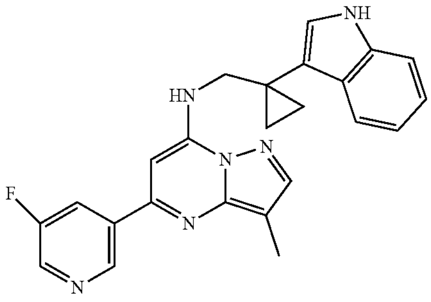 [SMILES: Cc1cnn2c(NCC3(c4c[nH]c5ccccc45)CC3)cc(-c3cncc(F)c3)nc12] |
| I-168 | 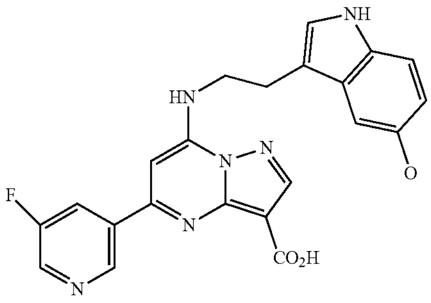 [SMILES: O=C(O)c1cnn2c(NCCc3c[nH]c4ccc(O)cc34)cc(-c3cncc(F)c3)nc12] |
| I-169 | 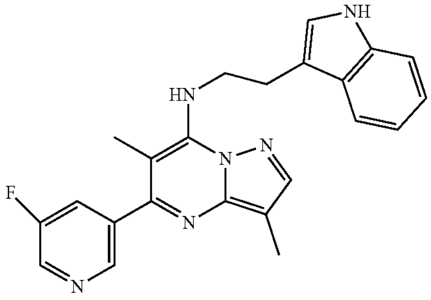 [SMILES: Cc1c(-c2cncc(F)c2)nc2c(C)cnn2c1NCCc1c[nH]c2ccccc12] |
| I-170 | 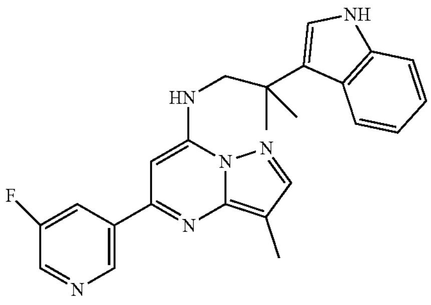 [SMILES: Cc1cnn2c(NCC(C)(C)c3c[nH]c4ccccc34)cc(-c3cncc(F)c3)nc12] |
TABLE 1-continued
| Exemplary Compounds of Formula I | |
|---|---|
| I-171 | 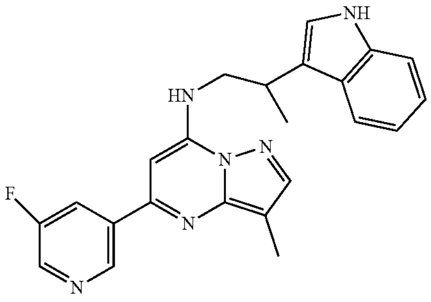 [SMILES: Cc1cnn2c(NCC(C)c3c[nH]c4ccccc34)cc(-c3cncc(F)c3)nc12] |
| I-172 | 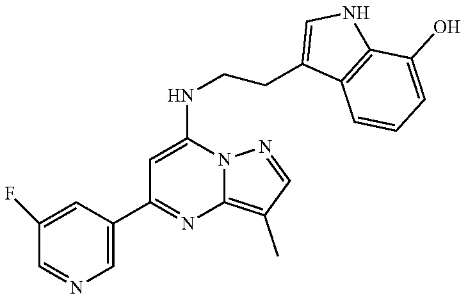 [SMILES: Cc1cnn2c(NCCc3c[nH]c4c(O)cccc34)cc(-c3cncc(F)c3)nc12] |
| I-173 | 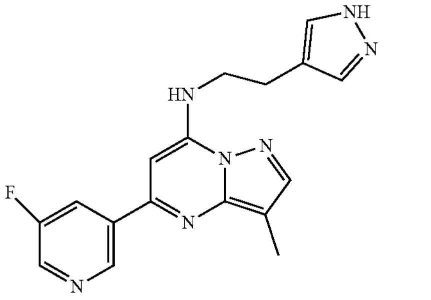 [SMILES: Cc1cnn2c(NCCc3cn[nH]c3)cc(-c3cncc(F)c3)nc12] |
| I-174 | 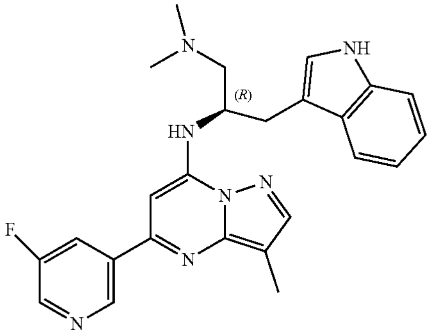 |
| I-175 | 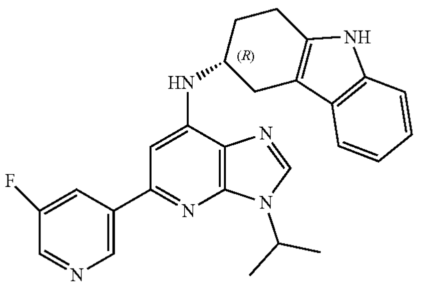 |

TABLE 1-continued
Exemplary Compounds of Formula I
I-175
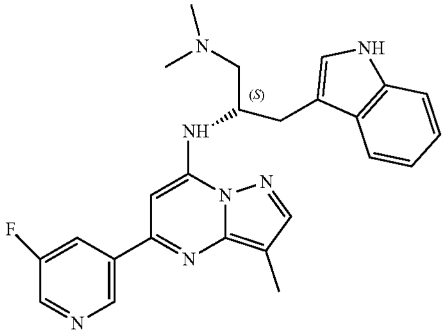
I-177
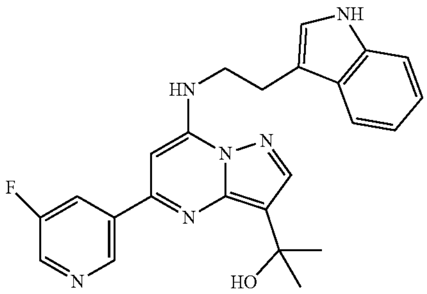 [SMILES: CC(C)(O)c1cnn2c(NCCc3c[nH]c4ccccc34)cc(-c3cncc(F)c3)nc12]
I-178
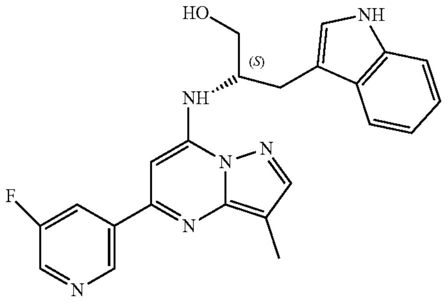
I-179
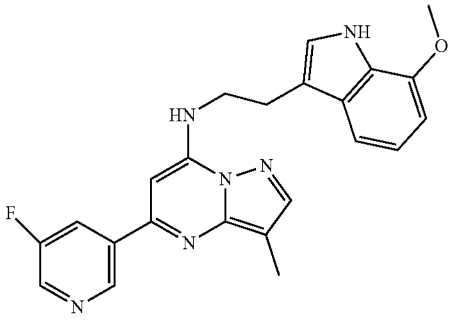 [SMILES: COc1cccc2c(CCNc3cc(-c4cncc(F)c4)nc4c(C)cnn34)c[nH]c12]
I-180
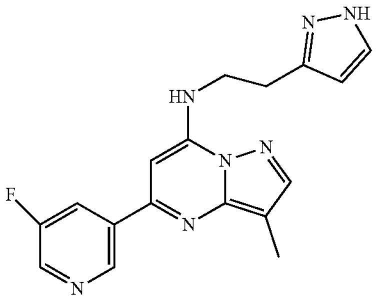 [SMILES: Cc1cnn2c(NCCc3cc[nH]n3)cc(-c3cncc(F)c3)nc12]
TABLE 1-continued
Exemplary Compounds of Formula I
I-181
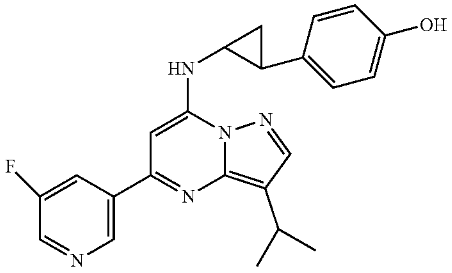 [SMILES: CC(C)c1cnn2c(NC3CC3c3ccc(O)cc3)cc(-c3cncc(F)c3)nc12]
I-182
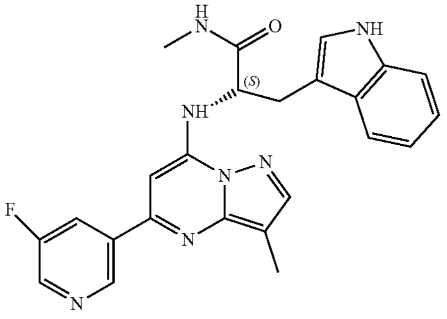
I-183
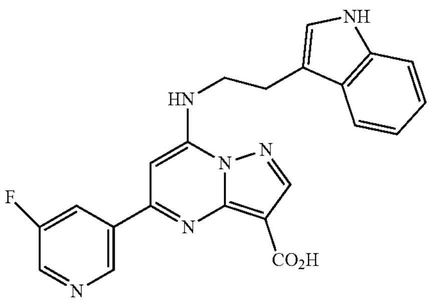 [SMILES: O=C(O)c1cnn2c(NCCc3c[nH]c4ccccc34)cc(-c3cncc(F)c3)nc12]
I-184
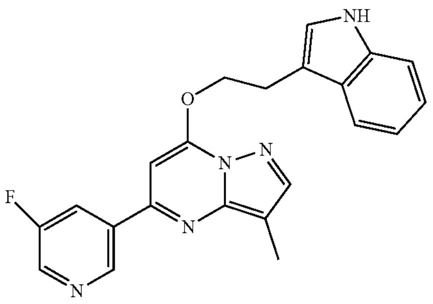 [SMILES: Cc1cnn2c(OCCc3c[nH]c4ccccc34)cc(-c3cncc(F)c3)nc12]
I-185
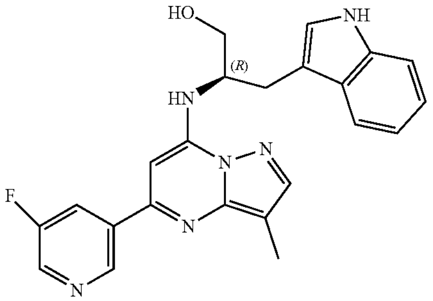

TABLE 1-continued
Exemplary Compounds of Formula I
I-186
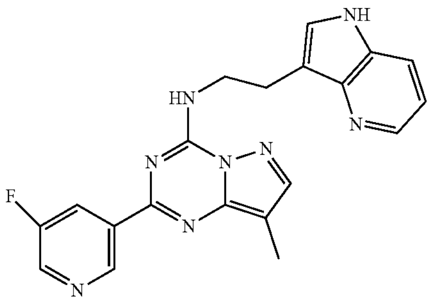 [SMILES: Cc1cnn2c(NCCc3c[nH]c4cccnc34)nc(-c3cncc(F)c3)nc12]
I-187a
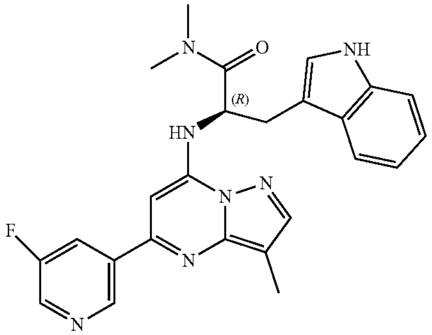
I-187b
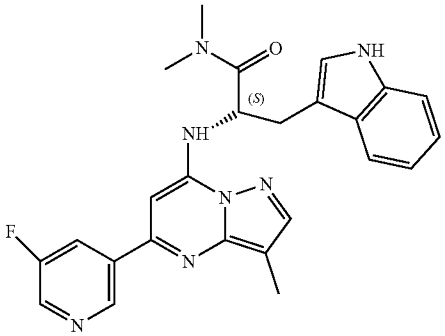
I-189
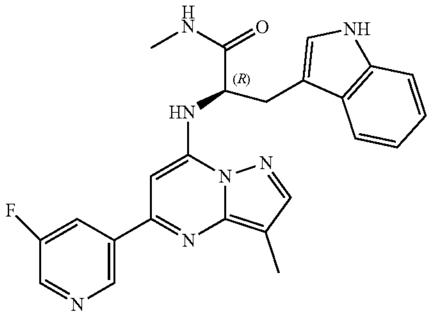
I-190a
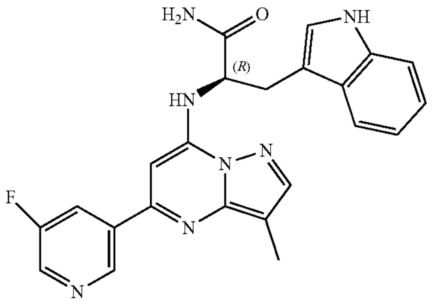
TABLE 1-continued
Exemplary Compounds of Formula I
I-190b
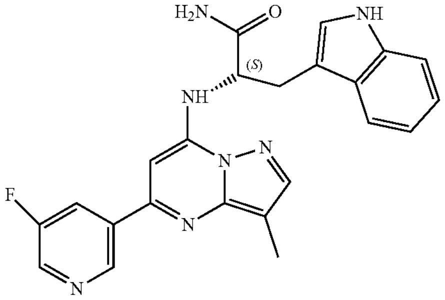
I-192
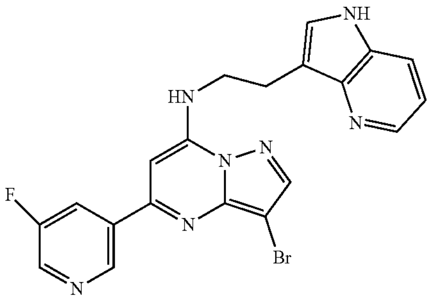 [SMILES: Fc1cncc(-c2cc(NCCc3c[nH]c4cccnc34)n3ncc(Br)c3n2)c1]
I-193
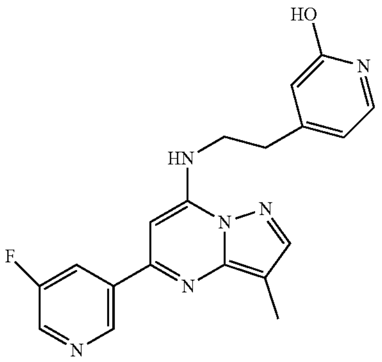
I-194
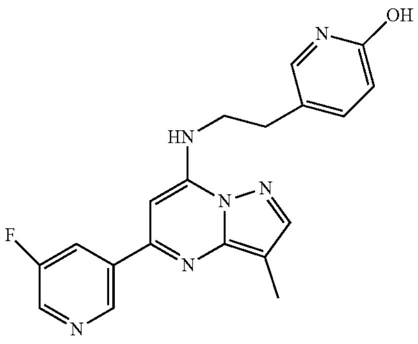 [SMILES: Cc1cnn2c(NCCc3ccc(O)nc3)cc(-c3cncc(F)c3)nc12]

TABLE 1-continued
| Exemplary Compounds of Formula I | |
|---|---|
| I-195 | 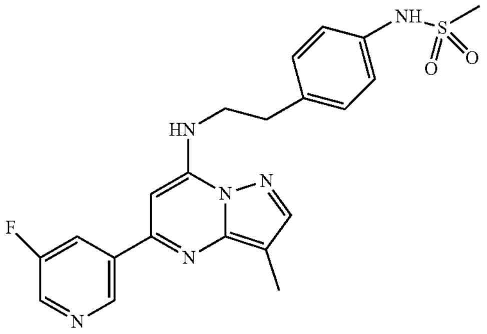 [SMILES: Cc1cnn2c(NCCc3ccc(NS(C)(=O)=O)cc3)cc(-c3cncc(F)c3)nc12] |
| I-196 | 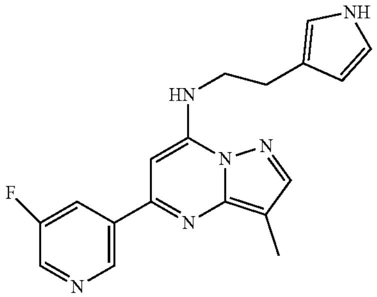 |
| I-197 | 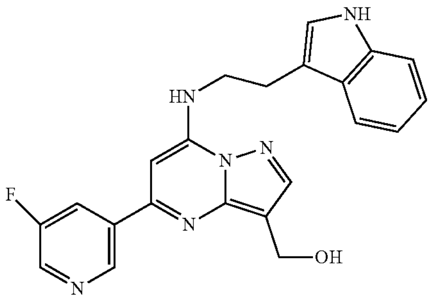 [SMILES: OCc1cnn2c(NCCc3c[nH]c4ccccc34)cc(-c3cncc(F)c3)nc12] |
| I198a | 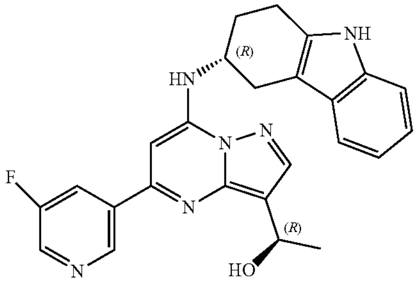 |
| I-198b | 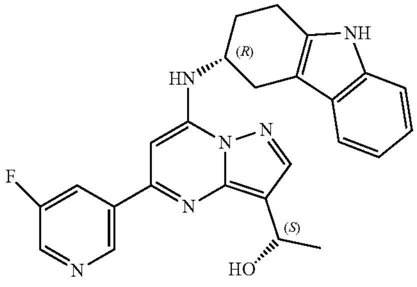 |
TABLE 1-continued
| Exemplary Compounds of Formula I | |
|---|---|
| I-198c | 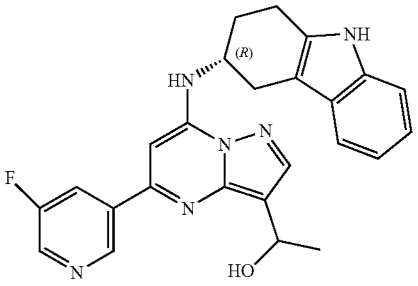 |
| I-200 | 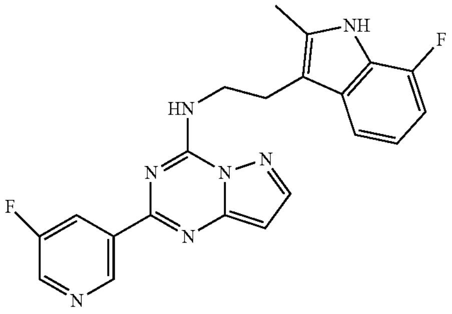 [SMILES: Cc1[nH]c2c(F)cccc2c1CCNc1nc(-c2cncc(F)c2)nc2ccnn12] |
| I-201 | 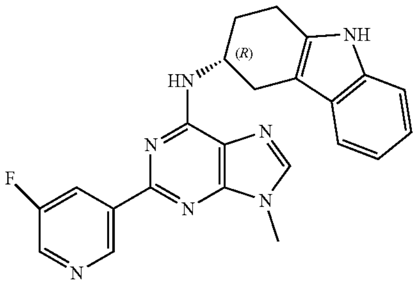 |
| I-202 | 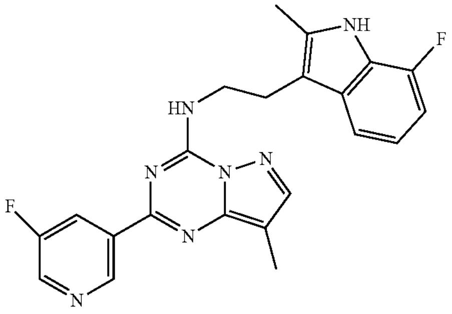 [SMILES: Cc1[nH]c2c(F)cccc2c1CCNc1nc(-c2cncc(F)c2)nc2c(C)cnn12] |
| I-203 | 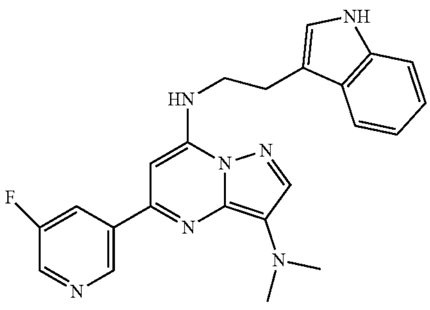 [SMILES: CN(C)c1cnn2c(NCCc3c[nH]c4ccccc34)cc(-c3cncc(F)c3)nc12] |

TABLE 1-continued
Exemplary Compounds of Formula I
I-204a
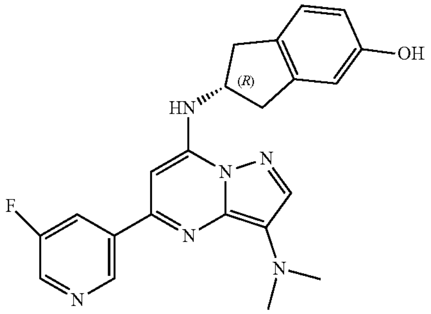
I-204b
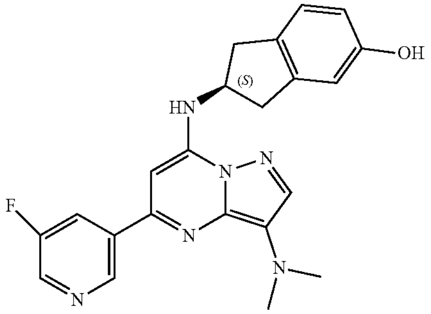
I-206
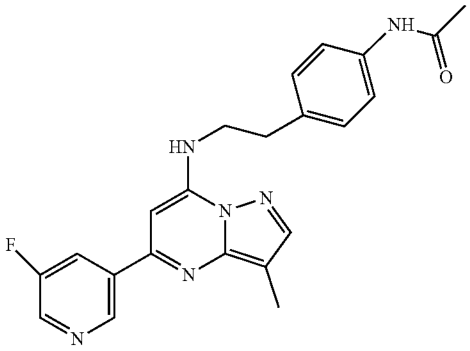 [SMILES: CC(=O)Nc1ccc(CCNc2cc(-c3cncc(F)c3)nc3c(C)cnn23)cc1]
I-207
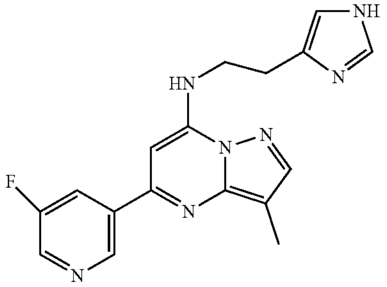 [SMILES: Cc1cnn2c(NCCc3c[nH]cn3)cc(-c3cncc(F)c3)nc12]
I-208
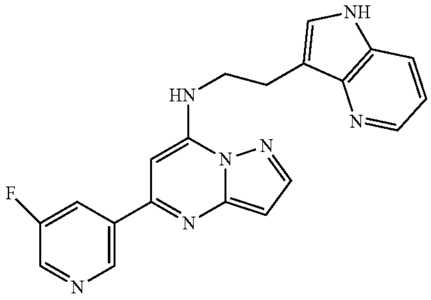 [SMILES: Fc1cncc(-c2cc(NCCc3c[nH]c4cccnc34)n3nccc3n2)c1]
TABLE 1-continued
Exemplary Compounds of Formula I
I-209
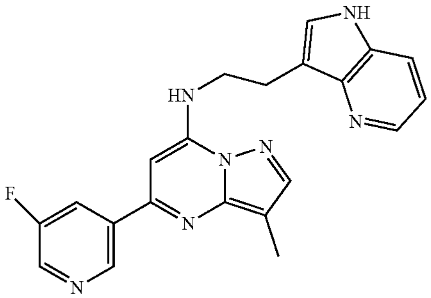 [SMILES: Cc1cnn2c(NCCc3c[nH]c4cccnc34)cc(-c3cncc(F)c3)nc12]
I-210
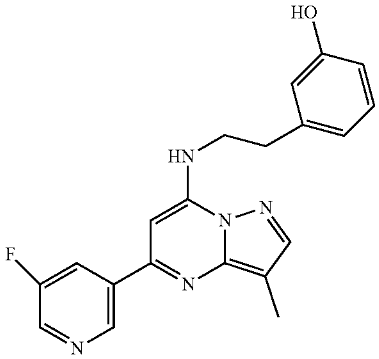 [SMILES: Cc1cnn2c(NCCc3cccc(O)c3)cc(-c3cncc(F)c3)nc12]
I-211
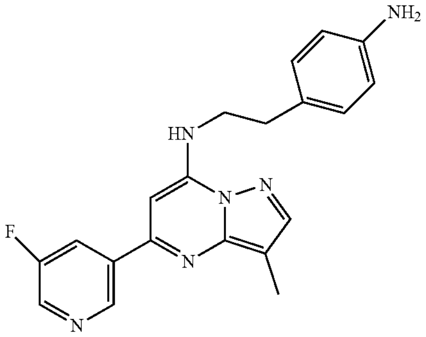 [SMILES: Cc1cnn2c(NCCc3ccc(N)cc3)cc(-c3cncc(F)c3)nc12]
I-212
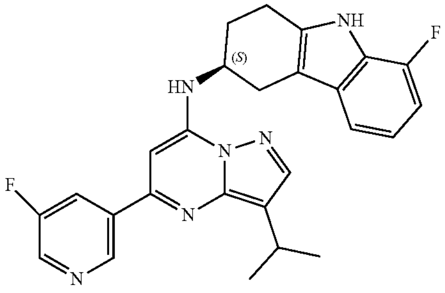

TABLE 1-continued
Exemplary Compounds of Formula I
I-213
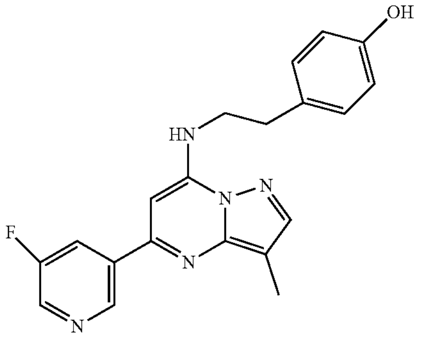 [SMILES: Cc1cnn2c(NCCc3ccc(O)cc3)cc(-c3cncc(F)c3)nc12]
I-214
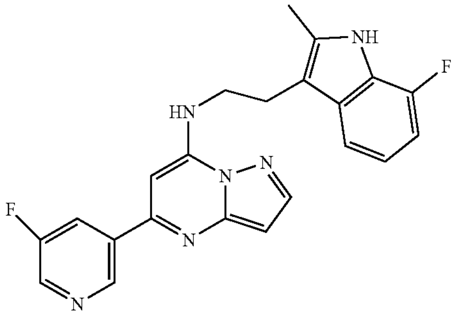 [SMILES: Cc1[nH]c2c(F)cccc2c1CCNc1cc(-c2cncc(F)c2)nc2ccnn12]
I-215
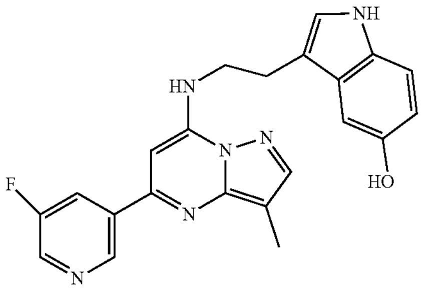 [SMILES: Cc1cnn2c(NCCc3c[nH]c4ccc(O)cc34)cc(-c3cncc(F)c3)nc12]
I-216a
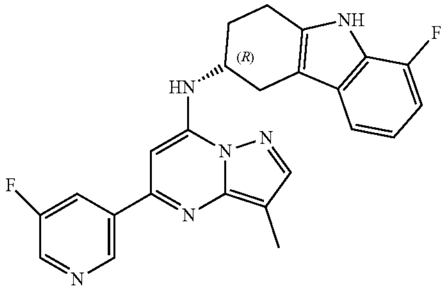
I-216b
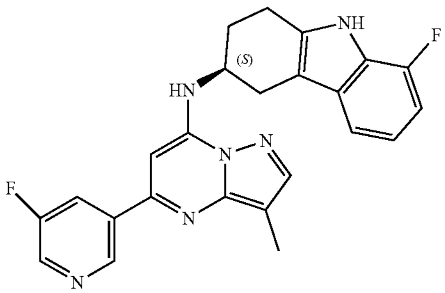
TABLE 1-continued
Exemplary Compounds of Formula I
I-218
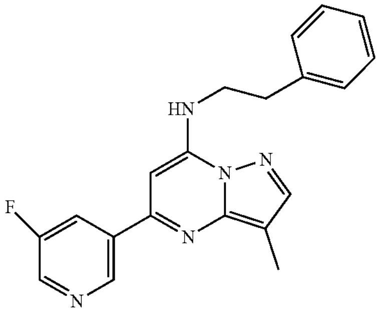 [SMILES: Cc1cnn2c(NCCc3ccccc3)cc(-c3cncc(F)c3)nc12]
I-219
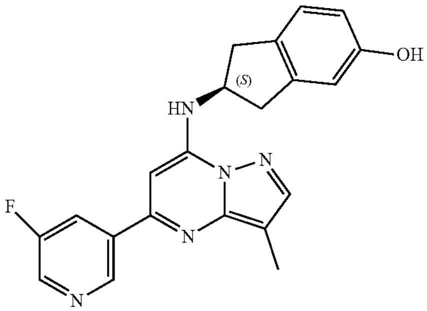
I-220
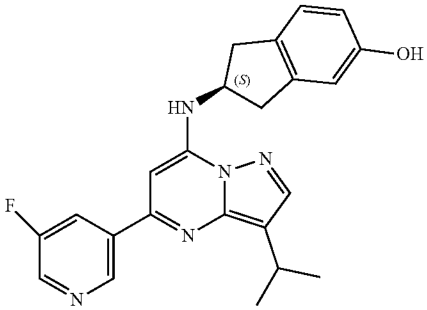
I-221
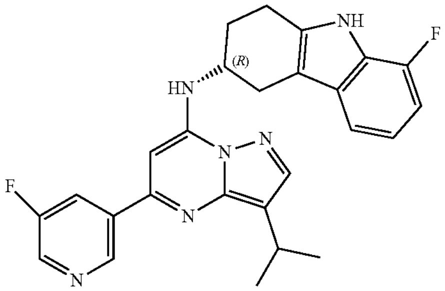
I-222a
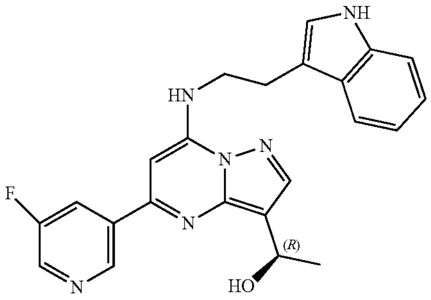

TABLE 1-continued
Exemplary Compounds of Formula I
I-222b
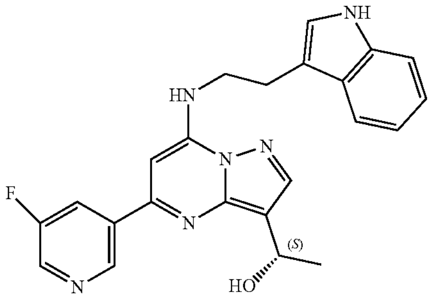
I-222c
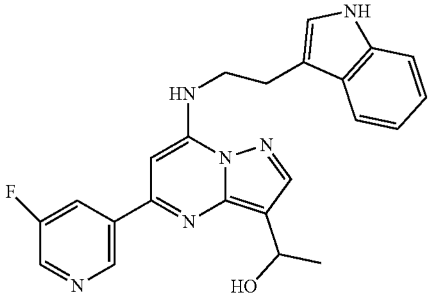 [SMILES: CC(O)c1cnn2c(NCCc3c[nH]c4ccccc34)cc(-c3cncc(F)c3)nc12]
I-224
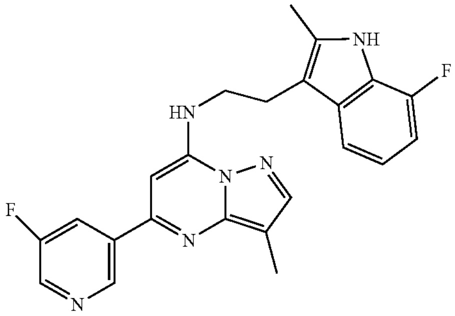 [SMILES: Cc1[nH]c2c(F)cccc2c1CCNc1cc(-c2cncc(F)c2)nc2c(C)cnn12]
I-225
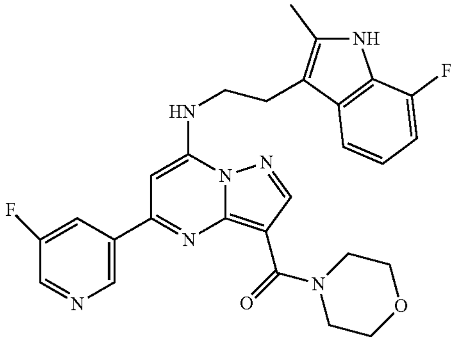 [SMILES: Cc1[nH]c2c(F)cccc2c1CCNc1cc(-c2cncc(F)c2)nc2c(C(=O)N3CCOCC3)cnn12]
I-226
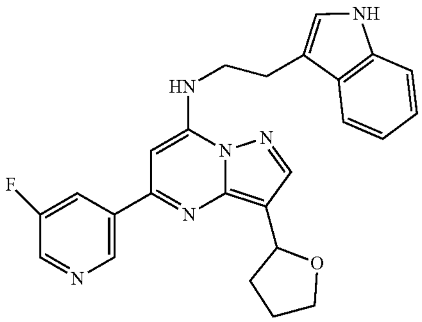 [SMILES: Fc1cncc(-c2cc(NCCc3c[nH]c4ccccc34)n3ncc(C4CCCO4)c3n2)c1]
TABLE 1-continued
Exemplary Compounds of Formula I
I-227
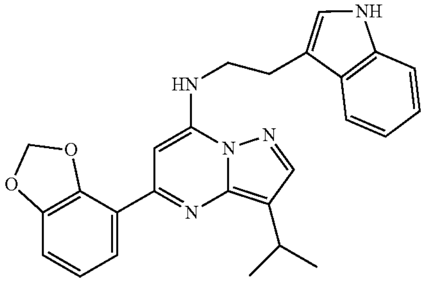 [SMILES: CC(C)c1cnn2c(NCCc3c[nH]c4ccccc34)cc(-c3cccc4c3OCO4)nc12]
I-228
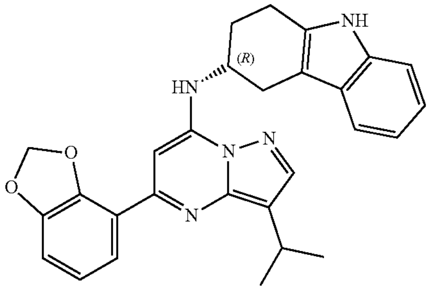
I-229
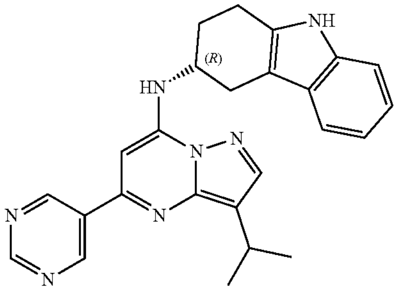
I-230
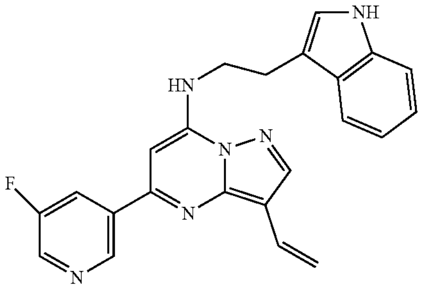 [SMILES: C=Cc1cnn2c(NCCc3c[nH]c4ccccc34)cc(-c3cncc(F)c3)nc12]
I-231
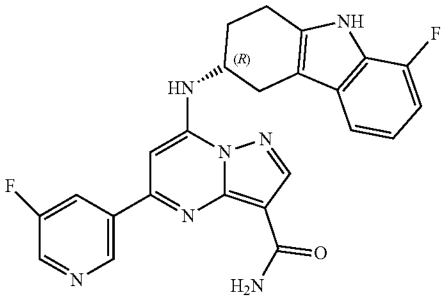

TABLE 1-continued
| Exemplary Compounds of Formula I | |
| --- | --- |
| I-232 | 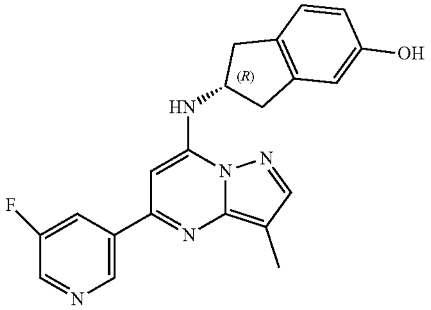 |
| I-233 | 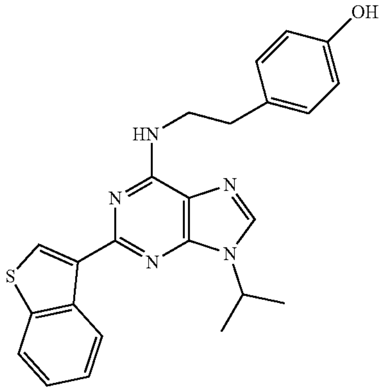 [SMILES: CC(C)n1cnc2c(NCCc3ccc(O)cc3)nc(-c3csc4ccccc34)nc21] |
| I-234 | 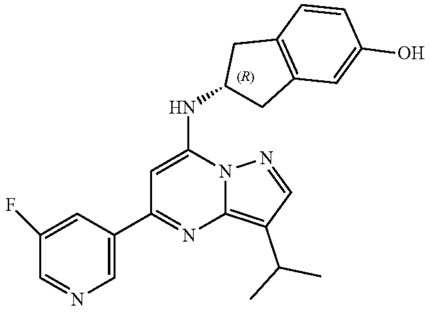 |
| I-235 | 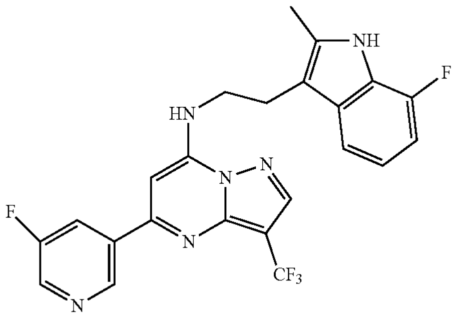 [SMILES: Cc1[nH]c2c(F)cccc2c1CCNc1cc(-c2cncc(F)c2)nc2c(C(F)(F)F)cnn12] |
TABLE 1-continued
| Exemplary Compounds of Formula I | |
| --- | --- |
| I-236 | 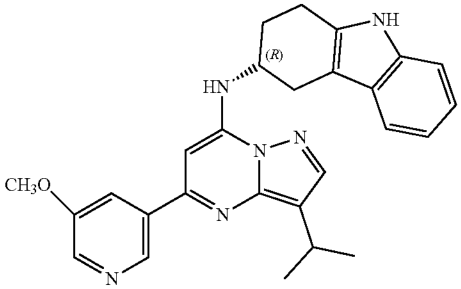 |
| I-237 | 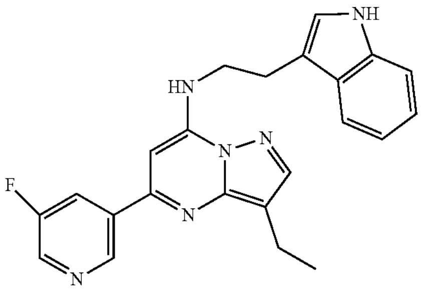 [SMILES: CCc1cnn2c(NCCc3c[nH]c4ccccc34)cc(-c3cncc(F)c3)nc12] |
| I-238 | 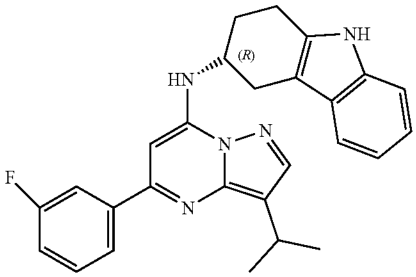 |
| I-239 | 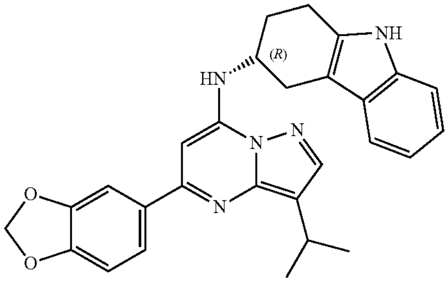 |
| I-240 | 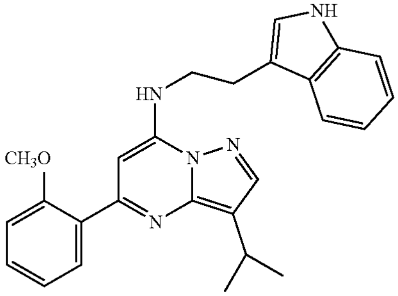 |

TABLE 1-continued
| Exemplary Compounds of Formula I | |
|---|---|
| I-241 | 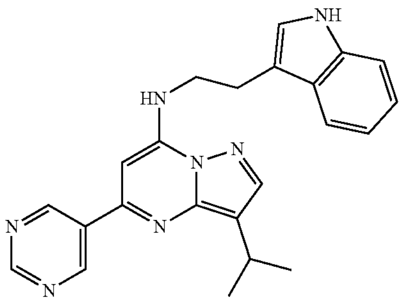 [SMILES: CC(C)c1cnn2c(NCCc3c[nH]c4ccccc34)cc(-c3cncnc3)nc12] |
| I-242 | 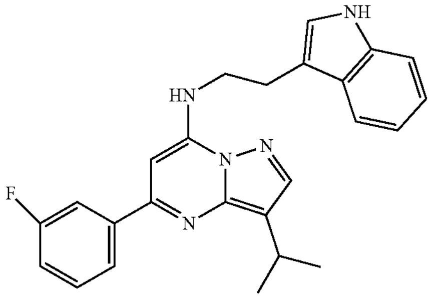 [SMILES: CC(C)c1cnn2c(NCCc3c[nH]c4ccccc34)cc(-c3cccc(F)c3)nc12] |
| I-243a | 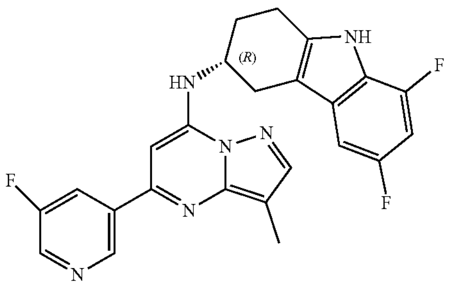 |
| I-243b | 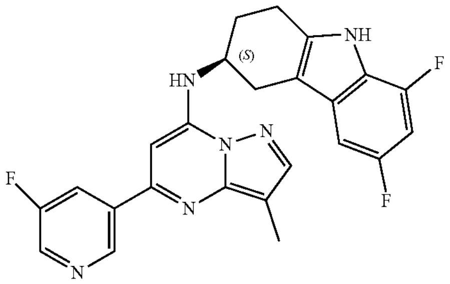 |
| I-245 | 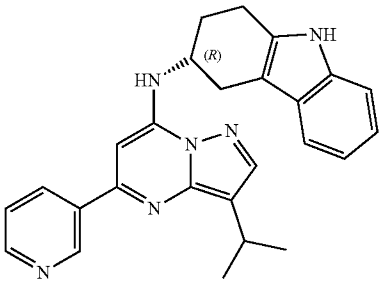 |
TABLE 1-continued
| Exemplary Compounds of Formula I | |
|---|---|
| I-246 | 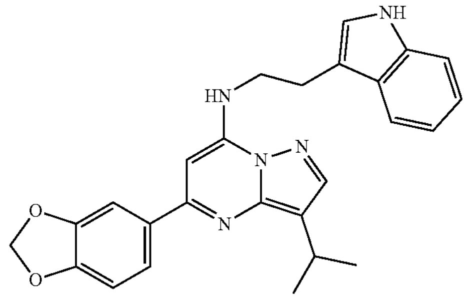 [SMILES: CC(C)c1cnn2c(NCCc3c[nH]c4ccccc34)cc(-c3ccc4c(c3)OCO4)nc12] |
| I-247a | 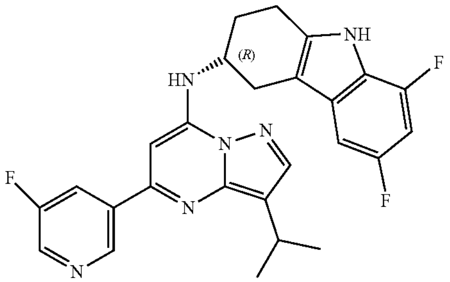 |
| I-247b | 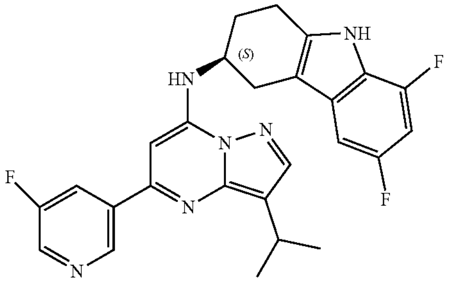 |
| I-249a | 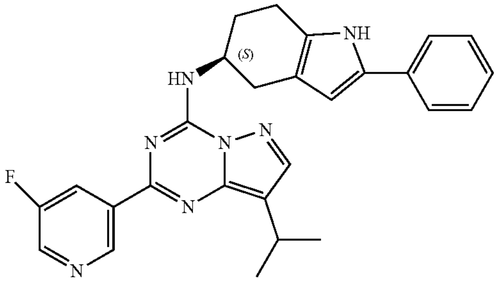 |
| I-249b | 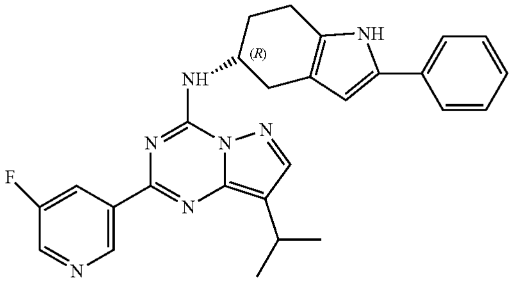 |

TABLE 1-continued
Exemplary Compounds of Formula I
I-249c
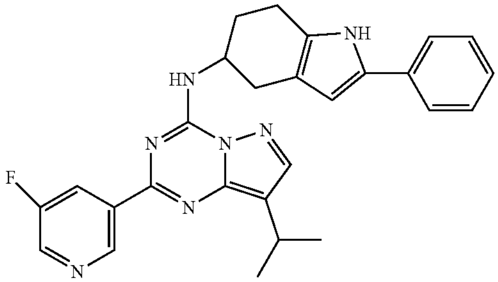 [SMILES: CC(C)c1cnn2c(NC3CCc4[nH]c(-c5ccccc5)cc4C3)nc(-c3cncc(F)c3)nc12]
I-250
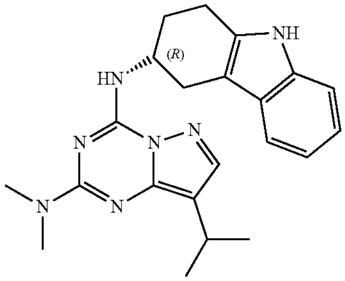
I-251
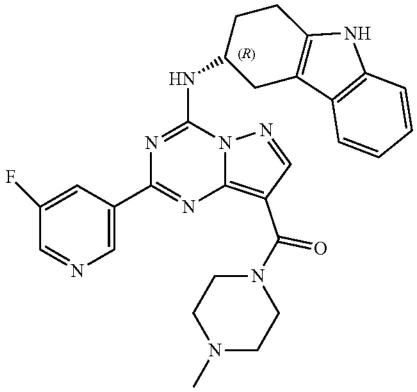
I-252a
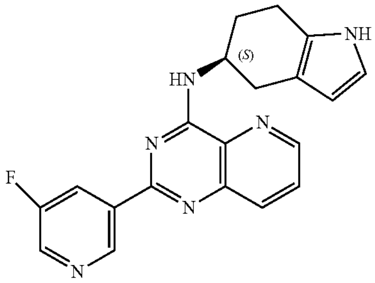 [SMILES: Fc1cncc(-c2nc(N[C@H]3CCc4[nH]ccc4C3)c3ncccc3n2)c1]
I-252b
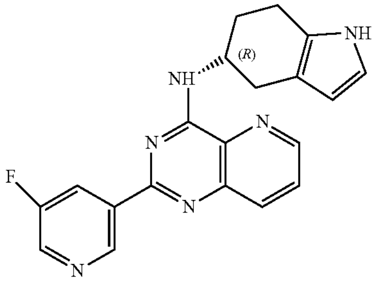
TABLE 1-continued
Exemplary Compounds of Formula I
I-252c
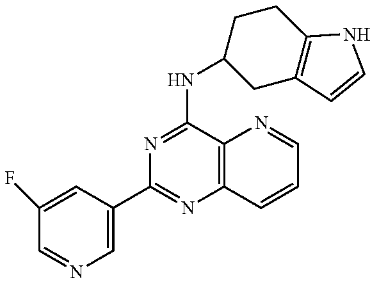 [SMILES: Fc1cncc(-c2nc(NC3CCc4[nH]ccc4C3)c3ncccc3n2)c1]
I-253
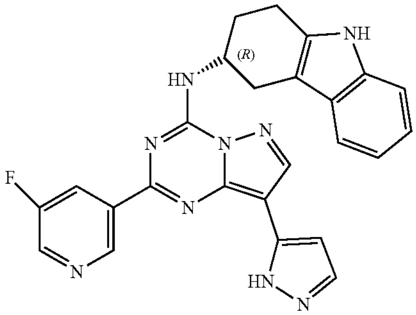
I-254
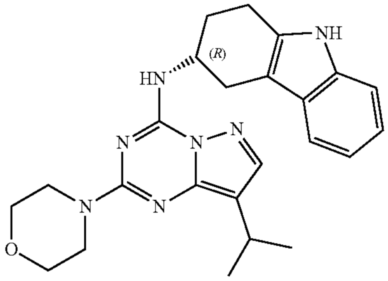
I-255
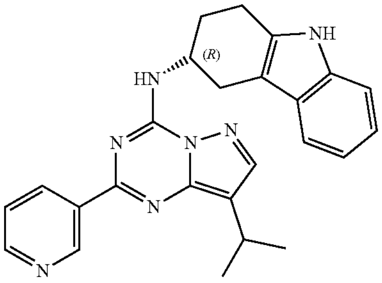
I-256
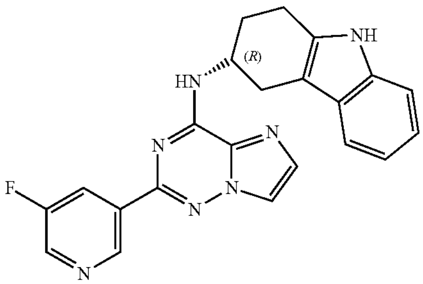

TABLE 1-continued
| Exemplary Compounds of Formula I |
| --- |
I-257
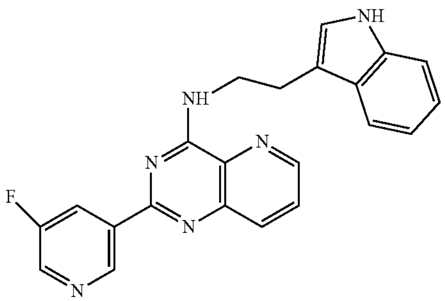 [SMILES: Fc1cncc(-c2nc(NCCc3c[nH]c4ccccc34)c3ncccc3n2)c1]
I-258
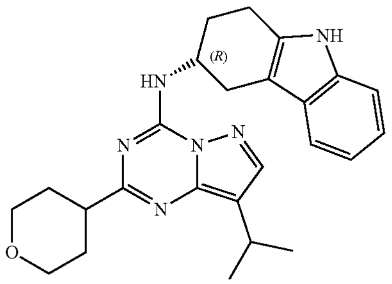
I-259a
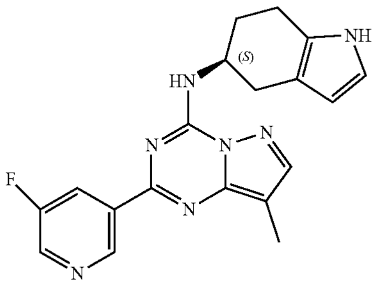 [SMILES: Cc1cnn2c(N[C@H]3CCc4[nH]ccc4C3)nc(-c3cncc(F)c3)nc12]
I-259b
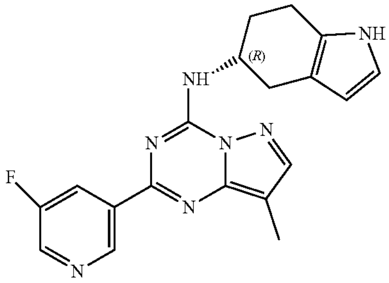
I-259c
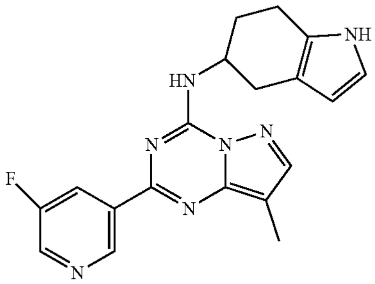 [SMILES: Cc1cnn2c(NC3CCc4[nH]ccc4C3)nc(-c3cncc(F)c3)nc12]
TABLE 1-continued
| Exemplary Compounds of Formula I |
| --- |
I-260
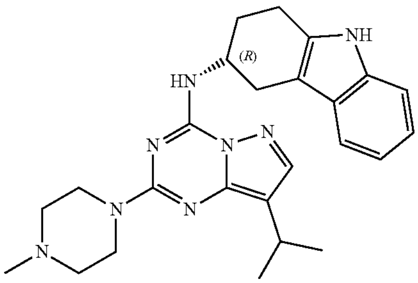
I-261
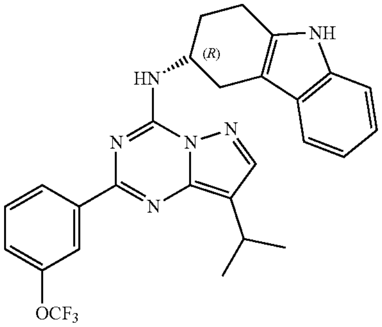
I-262
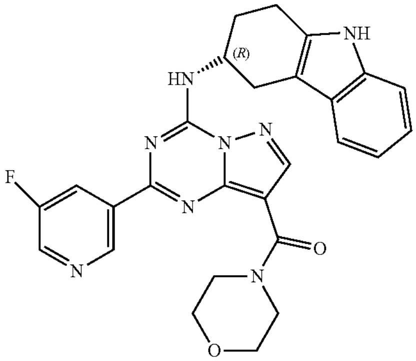
I-263a
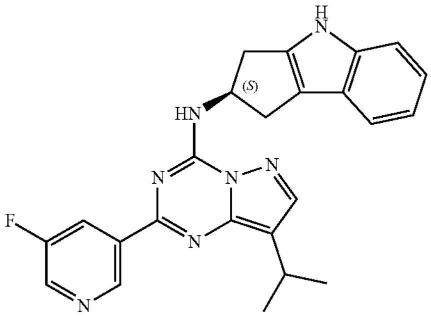

TABLE 1-continued
| Exemplary Compounds of Formula I | |
|---|---|
| I-263b | 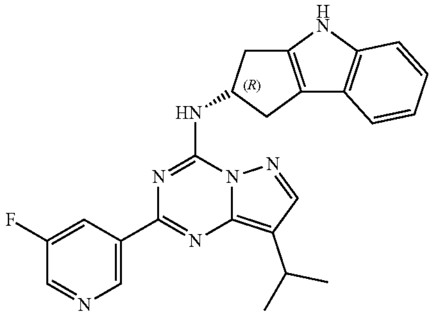 |
| I-263c | 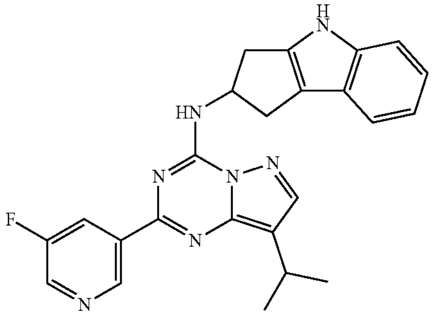 [SMILES: CC(C)c1cnn2c(NC3Cc4[nH]c5ccccc5c4C3)nc(-c3cncc(F)c3)nc12] |
| I-264 | 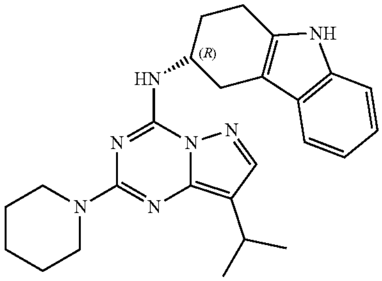 |
| I-265 | 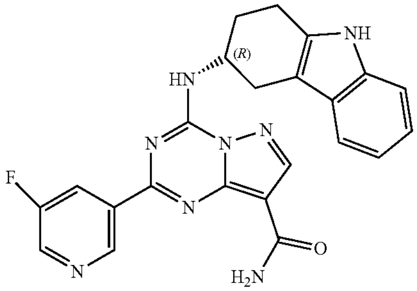 |
| I-266 | 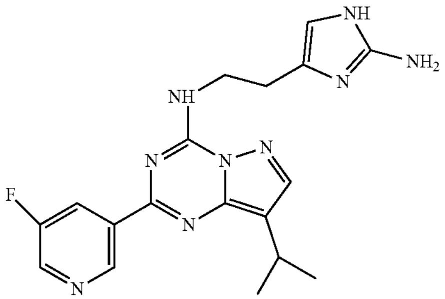 [SMILES: CC(C)c1cnn2c(NCCc3c[nH]c(N)n3)nc(-c3cncc(F)c3)nc12] |
TABLE 1-continued
| Exemplary Compounds of Formula I | |
|---|---|
| I-267 | 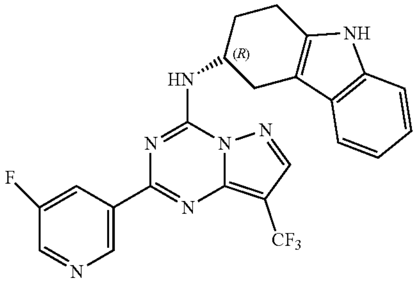 |
| I-268 | 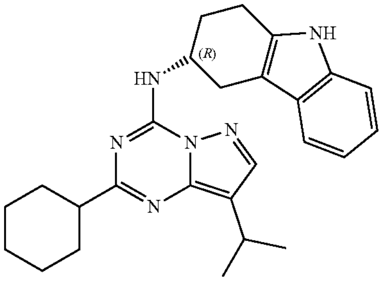 |
| I-269 | 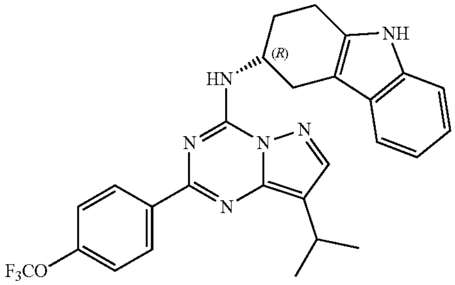 |
| I-270 | 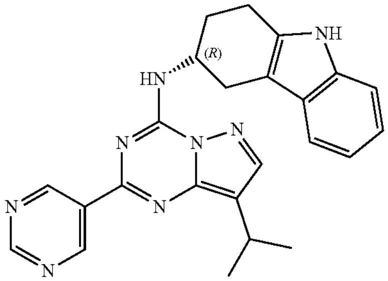 |
| I-271 | 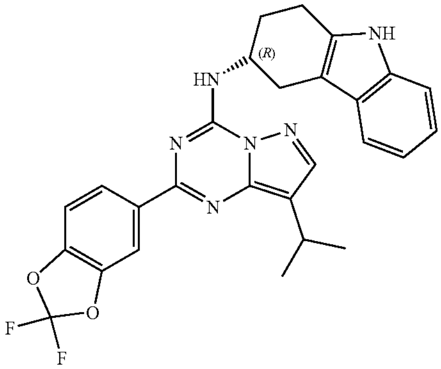 |

TABLE 1-continued
Exemplary Compounds of Formula I
I-272
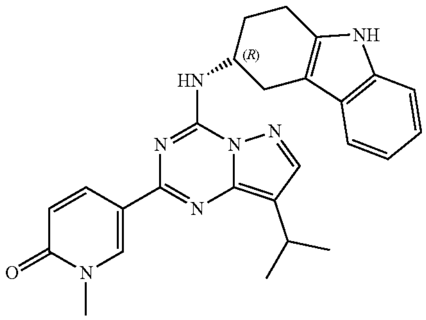
I-273
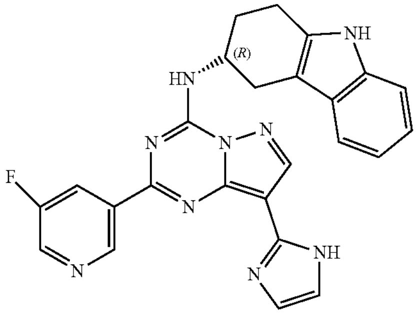
I-274
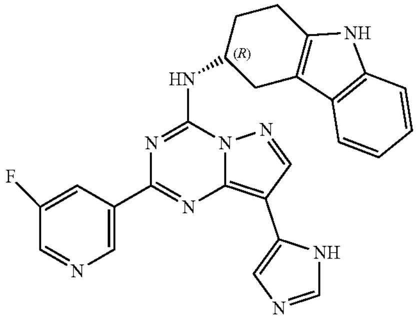
I-275
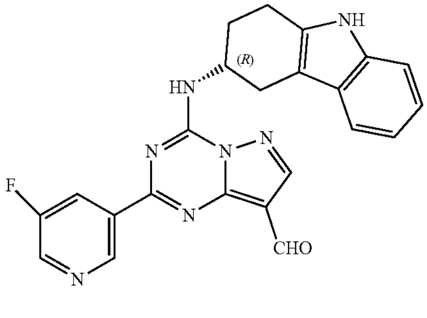
TABLE 1-continued
Exemplary Compounds of Formula I
I-276
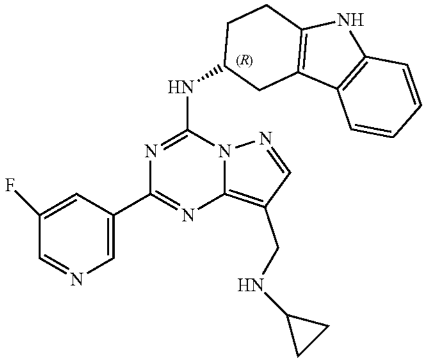
I-277
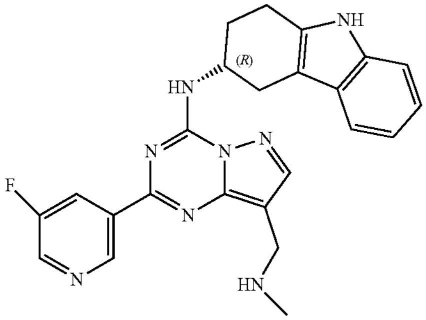
I-278
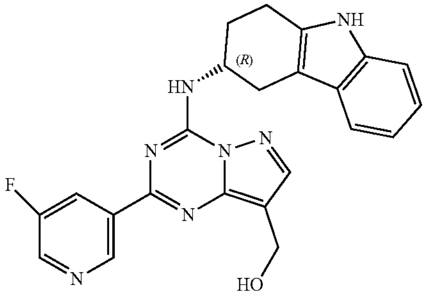
I-279
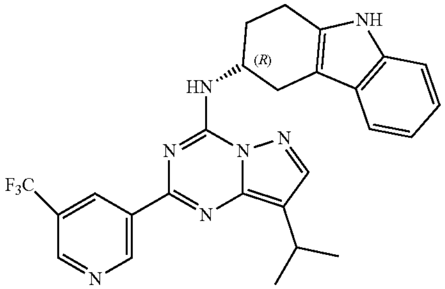
I-280
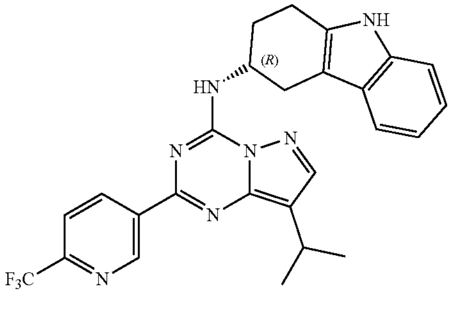

TABLE 1-continued

Exemplary Compounds of Formula I

I-281

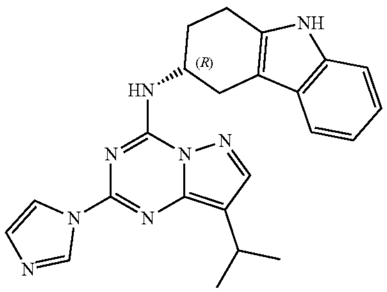

I-282

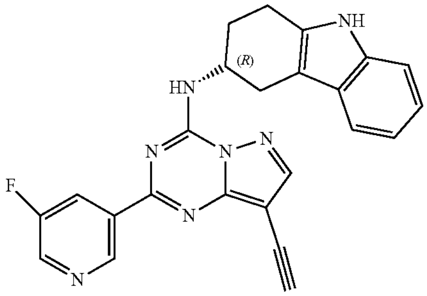

I-283

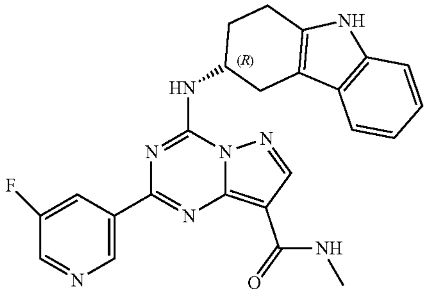

I-284

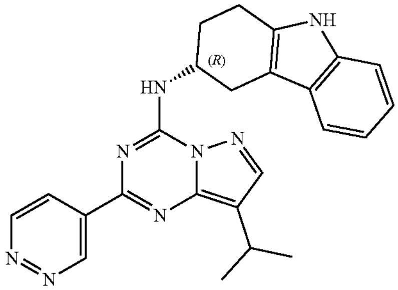

I-285

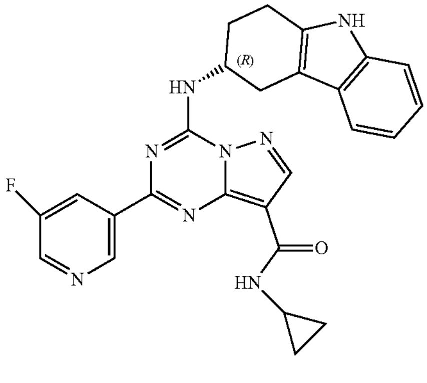

I-286

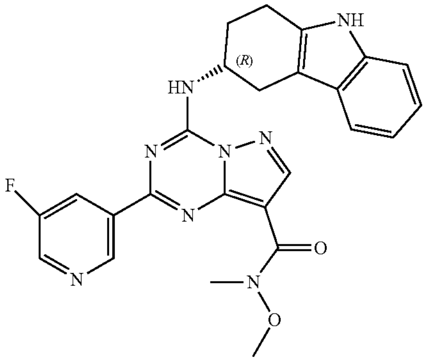

I-287

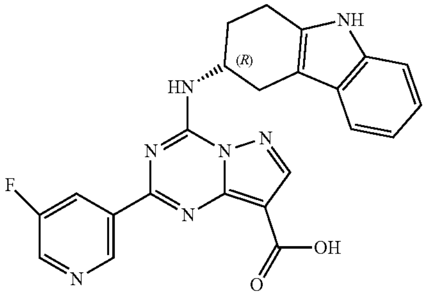

I-288

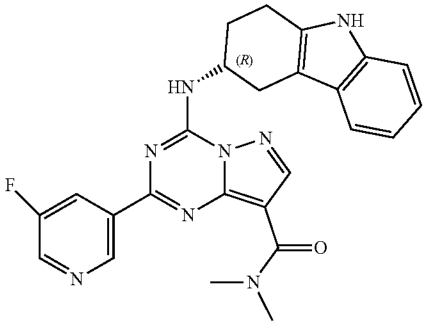

I-289

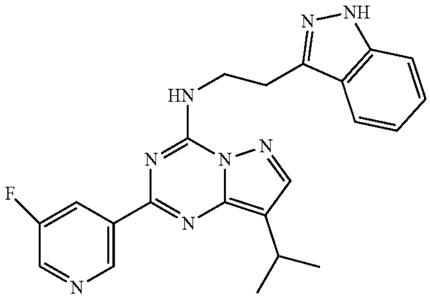 [SMILES: CC(C)c1cnn2c(NCCc3n[nH]c4ccccc34)nc(-c3cncc(F)c3)nc12]

In certain embodiments, the present invention provides any compound selected from those depicted in Table 1, above, or a pharmaceutically acceptable salt thereof.

4. Uses, Formulation and Administration and Pharmaceutically Acceptable Compositions According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit AHR, in a biological sample or in a patient. In certain embodiments, the amount of compound in compositions of this invention is such that is effective to measurably inhibit AHR, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The activity of a compound utilized in this invention as an inhibitor of AHR may be assayed in vitro or in vivo. An in vivo assessment of the efficacy of the compounds of the invention may be made using an animal model of obesity or metabolic syndrome, e.g., a rodent or primate model. Cell-based assays may be performed using, e.g., a cell line isolated from a tissue that expresses AHR. Additionally, biochemical or mechanism-based assays, e.g., transcription assays using a purified protein, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with compounds of the invention. Alternate in vitro assays quantitate the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this invention as an inhibitor of AHR are set forth in the Examples below. The aforementioned assays are exemplary and not intended to limit the scope of the invention. The skilled practitioner can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating or lessening the severity of a metabolic disorder or condition, cancer, a bacterial infection, a fungal infection, a parasitic infection (e.g. malaria), an autoimmune disorder, a neurodegenerative or neurological disorder, schizophrenia, a bone-related disorder, liver disease, or a cardiac disorder.

In some embodiments, the compounds and compositions, according to the method of the present invention, may be administered using any amount and any route of administration effective for treating or lessening the severity of a disease associated with AHR.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses and Methods of Treatment

According to one embodiment, the invention relates to a method of inhibiting AHR in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of enzymes in a biological sample is useful for a variety of purposes that are known to one of skill in the art. Examples of such purposes include, but are not limited to biological assays, gene expression studies, and biological target identification.

Another embodiment of the present invention relates to a method of inhibiting AHR in a patient comprising the step of administering to said patient a compound of the present invention, or a composition comprising said compound.

Provided compounds are inhibitors of AHR and are therefore useful for treating one or more disorders associated with activity of AHR. Thus, in certain embodiments, the present invention provides a method for treating an AHR-mediated disorder comprising the step of administering to a patient in need thereof a compound of the present invention, or pharmaceutically acceptable composition thereof.

As used herein, the terms "AHR-mediated" disorders, diseases, and/or conditions as used herein means any disease or other deleterious condition in which AHR, or a mutant thereof, are known to play a role. Accordingly, another embodiment of the present invention relates to treating or lessening the severity of one or more diseases in which AHR, or a mutant thereof, are known to play a role.

AHR mediated disorders are well established in the art. The nexus between AHR and AHR mediated disorders diseases and/or conditions as recited herein is well established in the relevant arts. For example, see: Uyttenhove et al., "Evidence for a tumoral immune resistance mechanism based on tryptophan degradation by indoleamine 2,3-dioxygenase" *Nature Medicine,* 2003 vol. 9(10), 1038; Murray et al., "AH RECEPTOR LIGANDS IN CANCER: FRIEND AND FOE" *Nat. Rev. Cancer* December 2014, vol. 14(12), pages 801-814; Moon et al., "Targeting the indoleamine 2,3-dioxygenase pathway in cancer" *J. ImmunoTherapy of Cancer,* 2015 vol 3, page 51; Ishida et al., "Activation of aryl hydrocarbon receptor promotes invasion of clear cell renal cell carcinoma and is associated with poor prognosis and cigarette smoke" *Int. J. Cancer* July 2015 vol. 15, no. 137(2), pages 299-310; Ishida et al., "Activation of the aryl hydrocarbon receptor pathway enhances cancer cell invasion by upregulating the MMP expression and is associated with poor prognosis in upper urinary tract urothelial cancer" *Carcinogenesis* February 2010 vol. 31(2), pages 287-295. Su et al., "Prognostic value of nuclear translocation of aryl hydrocarbon receptor for non-small cell lung cancer" *Anticancer Res*. September 2013, vol. 33(9), pages 3953-3961; Peng et al., "Aryl hydrocarbon receptor pathway activation enhances gastric cancer cell invasiveness likely through a c-Jun-dependent induction of matrix metalloproteinase-9" *BMC Cell Biol.* April 2009 vol. 16; pages 10-27; Jin et al., "Aryl Hydrocarbon Receptor Activation Reduces Dendritic Cell Function during Influenza Virus Infection" Toxicol Sci. August 2010, vol. 116(2), pages 514-522; Head et al., "The aryl hydrocarbon receptor is a modulator of anti-viral immunity" *Biochem. Pharmacol.* Febraury 2009 vol. 15; no. 77(4), pages 642-53; Jin et al., "New insights into the role of the aryl hydrocarbon receptor in the function of $CD11c^+$ cells during respiratory viral infection" *Eur J. Immunol.* June 2014, vol. 44(6), pages 1685-98; Nguyen et al., "Aryl hydrocarbon receptor and kynurenine: recent advances in autoimmune disease research" *Front Immunol.* October 2014, vol. 29, no. 5, page 551; Esser et al., "The aryl hydrocarbon receptor in immunity" *Trends in Immunology*, Vol. 30, No. 9.

In some embodiments, the present invention provides a method for treating one or more disorders, diseases, and/or conditions wherein the disorder, disease, or condition is a proliferative disease such as cancer, an inflammatory disorder, or a viral infection.

In certain embodiments, the present invention provides a method of treating cancer or another proliferative disorder, comprising administering a compound or composition of the present invention to a patient with cancer or another proliferative disorder. In certain embodiments, the method of treating cancer or another proliferative disorder comprises administering compounds and compositions of the present invention to a mammal. In certain embodiments, the mammal is a human.

As used herein, the terms "inhibition of cancer" and "inhibition of cancer cell proliferation" refer to the inhibition of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the compounds and compositions described herein and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by compounds or compositions of the invention is a melanoma, liposarcoma, lung cancer, breast cancer, prostate cancer, leukemia, kidney cancer, esophageal cancer, brain cancer, lymphoma or colon cancer. In certain embodiments, the cancer is a primary effusion lymphoma (PEL).

Compounds of the current invention are useful in the treatment of a proliferative disease selected from a benign or malignant tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, Waldenström's macroglobulinemia, a mammary carcinoma, follicular carcinoma, undifferentiated carcinoma, papillary carcinoma, seminoma, melanoma, an MYD88-driven disorder, DLBCL, ABC DLBCL, an IL-1-driven disorder, Smoldering of indolent multiple myeloma, or a leukemia.

Cancer includes, in some embodiments, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is a solid tumor, such as a sarcoma, carcinoma, or lymphoma. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, the cancer is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CML), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Clear cell renal cell carcinoma, Renal Pelvis Cancer, Ureter Cancer, Transitional Cell Cancer, Retinoblastoma, Rhabdomyosarcoma, Salivary Gland Cancer, Sarcoma, Sezary Syndrome, Skin Cancer, Small Cell Lung Cancer, Small Intestine Cancer, Soft Tissue Sarcoma, Squamous Cell Carcinoma, Squamous Neck Cancer with Occult Primary, Squamous Cell Carcinoma of the Head and Neck (HNSCC), Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Triple Negative Breast Cancer (TNBC), Gestational Trophoblastic Tumor, Unknown Primary, Unusual Cancer of Childhood, Urethral Cancer, Uterine Cancer, Uterine Sarcoma, Waldenstrom Macroglobulinemia, or Wilms Tumor.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Graves' disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, dermatomyositis, polymyositis, inclusion body myositis, myasthenia gravis, thyroiditis, Addison's disease, lichen planus, Type 1 diabetes, or Type 2 diabetes.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin-Associated Periodic Syndromes (CAPS), or osteoarthritis.

In some embodiments, the inflammatory disease which can be treated according to the methods of this invention is selected from a TH17-mediated disease. In some embodiments, the TH17-mediated disease is selected from Systemic lupus erythematosus, Multiple sclerosis, inflammatory bowel disease including Crohn's or ulcerative colitis.

In some embodiments, the inflammatory disease which can be treated according to the methods of this invention is selected from Sjogren's syndrome allergic disorders, osteoarthritis. Conditions of the eye such as ocular allergy, conjunctivitis, keratoconjunctivitis sicca, and vernal conjunctivitis, diseases affecting the nose including allergic rhinitis.

In some embodiments, the inflammatory disease which can be treated according to the methods of this invention is selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In certain embodiments, a provided compound is useful for treating a viral infection, disease, or condition. In some embodiments, the present invention provides a method of treating a viral disease selected from retroviral diseases, such as, HIV-1, HIV-2, human T-cell leukemia virus-I (HTLV-I), HTLV-II, HTLV-III, simian immunodeficiency virus (SIV), lymphadenopathy-associated virus (LAV-2), simian T-lymphotrophic virus-I (STLV-I), STLV-II, STLV-III, simian B-lymphotrophic (SBL) virus, Gibbon ape leukemia virus (GALV), bovine leukemia virus (BLV), equine infectious anemia virus (EIAV), feline leukemia virus (FELV), murine leukemia virus (MuLV), avian leukosis virus (ALV); other virus infections such as hepadnaviridae (Hepatitis B); herpesviridae (Herpes simplex I, Herpes simplex II, Varicella-Zoster, Epstein-Barr virus and cytomegalovirus); parvoviridae (human parvovirus B-19); papovaviridae (human papilloma virus types 1 to 60, JC and BK viruses); pox viruses (variola major, variola minor, vaccinia, monkey pox, cowpox, paravaccinia or milker's node virus, parapox or ORF virus, molluscum contagiosum) and cancers, lymphomas and other leukemias.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or a composition thereof, is administered in combination with another anti-cancer, cytotoxin, or chemotherapeutic agent, to a patient in need thereof.

In certain embodiments, the anti-cancer or chemotherapeutic agents used in combination with compounds or compositions of the invention include, but are not limited to metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™ Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SUl11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

In certain embodiments, an immuno-oncology agent can be administered with a compound as described herein for treatment of a proliferative disorder as described herein. As used herein, the term "an immuno-oncology agent" refers to an agent which is effective to enhance, stimulate, and/or up-regulate immune responses in a subject. In some embodiments, the administration of an immuno-oncology agent with a compound as described herein has a synergic effect in treating cancer.

In some embodiments, a compound as described herein is sequentially administered prior to administration of an immuno-oncology agent. In some embodiments, a compound as described herein is administered concurrently with an immuno-oncology agent. In some embodiments, a compound as described herein is sequentially administered after administration of an immuno-oncology agent.

In some embodiments, a compound as described herein may be co-formulated with an immuno-oncology agent.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fnl4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound as described herein, and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an IDO antagonist. In some embodiments, an IDO antagonist is INCB-024360 (WO2006/122150, WO07/75598, WO08/

36653, WO08/36642), indoximod, or NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiment, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

In certain embodiments, a combination of 2 or more therapeutic agents may be administered together with compounds of the invention. In certain embodiments, a combination of 3 or more therapeutic agents may be administered with compounds of the invention.

Other examples of agents the inhibitors of this invention may also be combined with include, without limitation: vitamins and nutritional supplements, cancer vaccines, treatments for neutropenia (e.g. G-CSF, filgrastim, lenograstim), treatments for thrombocytopenia (e.g. blood transfusion, erythropoietin), PI3 kinase (PI3K) inhibitors, MEK inhibitors, mTOR inhibitors, CPT1 inhibitors, AMPK activators, PCSK9 inhibitors, SREBP site 1 protease inhibitors, HMG CoA-reductase inhibitors, antiemetics (e.g. 5-$HT_3$ receptor antagonists, dopamine antagonists, NK1 receptor antagonists, histamine receptor antagonists, cannabinoids, benzodiazepines, or anticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, compounds of the present invention, or a pharmaceutically acceptable composition thereof, are administered in combination with antisense agents, a monoclonal or polyclonal antibody or an siRNA therapeutic.

In another embodiment, the present invention provides a method of treating an inflammatory disease, disorder or condition by administering to a patient in need thereof a compound of the present invention and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In some embodiments, a provided compound is administered in combination with an antiviral agent, including, e.g., acyclovir, pencyclovir, cidofovir, idoxuridine, zidovudine, ribavarin, amantadine, foscarnet, didanosine, acyclovir, ganciclovir, cidofovir, zalcitabine, rimantadine, calacyclovir, famiciclovir, abacavir, didanosine, emtricitabine, lamivudine, stavudine, tenofovir, zalcitabine, zidovudine, zidovudine-lamivudine, TRIZIVIR (zidovudine, lamivudine, abacavir), EPZICOM (aba-cavir-lamivudine), TRUVADA (tenofovir-emtricitabine), efavirenz, nevirapine, and delavirdine, amprenavir, atazanavir, fosamprenavir, indinavir, lopinavir-ritonavir, nelfinavir, ritonavir, saquinavir, and tipranavir. In some embodiments, the antiviral agent is anti-influenza agent including, e.g., rimantadine, amantadine, oseltamivir, and zanamivir.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the present invention, an additional therapeutic agent, and a pharmaceutically acceptable carrier, adjuvant, or vehicle.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of the present invention and one or more additional therapeutic agents. The therapeutic agent may be administered together with a compound of the present invention, or may be administered prior to or following administration of a compound of the present invention. Suitable therapeutic agents are described in further detail below. In certain embodiments, a compound of the present invention may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I' may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In some embodiments, the present invention provides a medicament comprising at least one compound of the present invention or a pharmaceutically acceptable salt thereof and a pharmaceutically acceptable carrier.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1A

DRE-Luciferase Reporter Assay

AHR binds to Dioxin Responsive Elements (DRE) upstream of genes that it activates. One measure of AHR activity is activation of a reporter gene, such as luciferase, downstream of one or multiple DRE elements. Luciferase activity will reflect activation and inhibition of AHR in the cells expressing his reporter.

Murine Hepa1-6 or Hepa-1c1c7 or other murine cell line with a DRE-luciferase reporter either stably or transiently transfected were plated in media in plates (96-well, 384-well or other plates) and incubated overnight at 37° C. in a $CO_2$ incubator. Likewise, human HepG2 or other human cell line with a DRE-luciferase reporter either stably or transiently transfected were plated in media in plates (96-well, 384-well or other plates) and incubated overnight at 37° C. in a $CO_2$ incubator.

The next day, an AHR activating ligand, such as TCDD, kynurenine, ITE (2-(1H-indole-3-yl carbonyl)-4-thiazole-carboxylic methyl ester), VAF347, BNF (beta-naphthoflavone), FICZ (6-formylindolo(3,2-b) carbazole or other AHR ligands, was added with or without AHR antagonist.

Cells were incubated for 4, 15 or 24 hours or another time point and then lysed for determination of luciferase activity as a read-out of the AHR activation or inhibition. Luciferase was measured with a commercial kit such as the Promega Luciferase kit or any kit or reagents that provide the luciferin substrate for measuring luciferase activity. The level of luciferase with only activating ligand added was the maximum signal while the luciferase with no ligand was the minimum signal. $IC_{50}$ values were determined as the concentration which inhibits half of the luciferase activity. Compounds assayed and their $IC_{50}$ values are shown in Table 2, below.

In some embodiments, compounds have an $IC_{50}$ of 5-20 μM. In some embodiments, compounds have an $IC_{50} \leq 5$ μM. In some embodiments, compounds have an $IC_{50} \leq 1$ μM. In some embodiments, compounds have an $IC_{50} \leq 0.1$ μM. In some embodiments, compounds have an $IC_{50} \leq 0.01$ μM. In some embodiments, compounds have an $IC_{50} \leq 0.001$ μM.

Activity of certain compounds of the present invention as obtained by the above assay is set forth in Table 2, below.

In Table 2, IC50 values are reported as A, B, C and D, whereby A represents an IC50 of <0.5 μM; B represents an IC50 of between 0.5 and 1.0 μM; and C represents an IC50 of between 1.0 and 1.5 μM; and D represents an IC50 of >1.5 μM.

TABLE 2

$IC_{50}$ Values for Select Compounds Assayed According to Example 1A.

| Compound | $IC_{50}$ |
|---|---|
| I-1 | C |
| I-2 | A |
| I-3 | C |
| I-4 | A |
| I-5 | D |
| I-6 | A |
| I-7 | A |
| I-9 | C |
| I-19 | B |

Example 1B

DRE-Luciferase Reporter Assay (Alternate Method)

AHR binds to Dioxin Responsive Elements (DRE) upstream of genes that it activates. One measure of AHR activity is activation of a reporter gene, such as luciferase, downstream of one or multiple DRE elements. Luciferase activity will reflect activation and inhibition of AHR in the cells expressing his reporter.

Murine Hepa1-6 or Hepa-1c1c7 or other murine cell line with a DRE-luciferase reporter either stably or transiently transfected were plated in media in plates (96-well, 384-well or other plates) and incubated overnight at 37° C. in a $CO_2$ incubator or compound and agonist were added at the time of plating. Likewise, human HepG2 or other human cell line with a DRE-luciferase reporter either stably or transiently transfected were plated in media in plates (96-well, 384-well or other plates) and incubated overnight at 37° C. in a $CO_2$ incubator or compound and agonist were added at the time of plating.

At the time that cells are plated or following incubation overnight, an AHR activating ligand, such as TCDD, kynurenine, ITE (2-(1H-indole-3-ylcarbonyl)-4-thiazolecarboxylic methyl ester), VAF347, BNF (beta-naphthoflavone), FICZ (6-formylindolo(3,2-b) carbazole or other AHR ligands, was added with or without AHR antagonist.

Cells were incubated for 4, 15 or 24 hours or another time point and then lysed for determination of luciferase activity as a read-out of the AHR activation or inhibition. Luciferase was measured with a commercial kit such as the Promega Luciferase kit or any kit or reagents that provide the luciferin substrate for measuring luciferase activity. The level of luciferase with only activating ligand added was the maximum signal while the luciferase with no ligand was the minimum signal. $IC_{50}$ values were determined as the concentration which inhibits half of the luciferase activity. Compounds assayed and their $IC_{50}$ values are shown in Table 3, below.

In some embodiments, compounds have an $IC_{50}$ of 5-20 μM. In some embodiments, compounds have an $IC_{50} \leq 5$ μM. In some embodiments, compounds have an $IC_{50} \leq 1$ μM. In some embodiments, compounds have an $IC_{50} \leq 0.1$ μM. In some embodiments, compounds have an $IC_{50} \leq 0.01$ μM. In some embodiments, compounds have an $IC_{50} < 0.001$ μM.

Activity of certain compounds of the present invention as obtained by the above assay is set forth in Table 3, below.

In Table 3, $IC_{50}$ values are reported as A, B, C and D, whereby A represents an $IC_{50}$ of ≤0.5 μM; B represents an $IC_{50}$ of between 0.5 and 1.0 μM; and C represents an $IC_{50}$ of between 1.0 and 1.5 μM; and D represents an $IC_{50}$ of >1.5 μM.

TABLE 3

$IC_{50}$ Values for Select Compounds Assayed According to Example 1B.

| Compound | $IC_{50}$ | Compound | $IC_{50}$ |
|---|---|---|---|
| I-1 | A | I-58 | D |
| I-2 | A | I-59 | A |
| I-3 | A | I-60 | B |
| I-4 | A | I-61 | A |
| I-5 | A | I-62 | A |
| I-6 | A | I-63 | A |
| I-7 | D | I-64 | A |
| I-8 | D | I-65 | A |
| I-9 | B | I-66 | A |
| I-10 | D | I-67 | A |
| I-11 | A | I-68 | B |

TABLE 3-continued $IC_{50}$ Values for Select Compounds Assayed According to Example 1B.

| Compound | $IC_{50}$ | Compound | $IC_{50}$ |
|---|---|---|---|
| I-13 | D | I-69 | A |
| I-14 | D | I-70 | A |
| I-15 | A | I-71 | A |
| I-16 | A | I-72 | A |
| I-19 | A | I-73 | A |
| I-20 | A | I-74 | B |
| I-21 | A | I-75a | D |
| I-22 | A | I-75b | D |
| I-23 | A | I-77 | A |
| I-24 | D | I-78 | A |
| I-25 | D | I-79 | A |
| I-26 | D | I-80 | B |
| I-27a | B | I-81 | A |
| I-28a | D | I-82b | D |
| I-29 | D | I-83 | A |
| I-30 | A | I-84 | D |
| I-31 | D | I-85 | B |
| I-32a | D | I-86 | A |
| I-33 | A | I-87 | A |
| I-34 | D | I-88 | B |
| I-35 | D | I-89 | A |
| I-36 | D | I-90 | A |
| I-37a | D | I-91 | A |
| I-38 | D | I-92 | A |
| I-39 | A | I-93 | A |
| I-40 | A | I-94a | D |
| I-41 | D | I-95 | D |
| I-42a | D | I-96 | A |
| I-43 | B | I-97a | D |
| I-44 | D | I-98a | D |
| I-45 | A | I-99 | A |
| I-46 | A | I-100 | D |
| I-47 | A | I-101 | A |
| I-48 | A | I-102 | A |
| I-49 | A | I-103 | A |
| I-50 | D | I-104 | B |
| I-51 | A | I-105 | A |
| I-52 | B | I-106 | A |
| I-53 | A | I-107 | A |
| I-54 | A | I-108 | A |
| I-55 | A | I-109 | A |
| I-56 | A | I-110 | B |
| I-57 | A | I-111 | A |
| I-120 | D | I-185 | D |
| I-121 | D | I-186 | B |
| I-122 | D | I-187a | D |
| I-123 | C | I-187b | D |
| I-124 | D | | |
| I-125 | D | I-189 | D |
| I-126 | A | I-190a | D |
| I-128a | D | I-190b | D |
| I-128b | D | I-192 | B |
| I-129 | A | I-193 | D |
| I-130 | A | I-194 | D |
| I-131 | A | I-195 | D |
| I-132 | B | I-196 | A |
| I-133 | A | I-197 | A |
| I-134 | D | I-198a | A |
| I-135 | A | I-198b | B |
| I-136 | A | I-200 | A |
| I-137a | A | I-201 | A |
| I-137b | A | I-202 | A |
| I-139a | A | I-203 | A |
| I-139b | A | I-204a | A |
| I-141 | A | I-204b | A |
| I-142 | D | I-206 | D |
| I-143 | D | I-207 | D |
| I-144a | C | I-208 | D |
| I-144b | A | I-209 | B |
| I-146a | D | I-210 | C |
| I-146b | D | I-211 | D |
| I-148 | D | I-212 | D |
| I-149 | D | I-213 | A |
| I-150a | A | I-214 | A |
| I-150b | C | I-215 | D |
| I-152a | D | I-216a | B |

TABLE 3-continued

IC$_{50}$ Values for Select Compounds Assayed According to Example 1B.

| Compound | IC$_{50}$ | Compound | IC$_{50}$ |
|---|---|---|---|
| I-152b | A | I-216b | D |
| I-154 | A | I-218 | A |
| I-155 | B | I-219 | A |
| I-156 | D | I-220 | A |
| I-157 | D | I-221 | D |
| I-158a | D | I-222a | A |
| I-158b | D | I-222b | A |
| I-160a | D | I-224 | A |
| I-160b | D | I-225 | A |
| I-162 | A | I-226 | A |
| I-163 | A | I-227 | A |
| I-164 | A | I-228 | D |
| I-165 | A | I-229 | D |
| I-166 | A | I-230 | A |
| I-167 | D | I-231 | D |
| I-168 | D | I-232 | A |
| I-169 | B | I-233 | B |
| I-170 | D | I-234 | B |
| I-171 | C | I-235 | A |
| I-172 | C | I-236 | D |
| I-173 | D | I-237 | A |
| I-174 | D | I-238 | D |
| I-175 | D | I-239 | D |
| I-176 | D | I-240 | D |
| I-177 | A | I-241 | A |
| I-178 | D | I-242 | A |
| I-179 | A | I-243a | D |
| I-180 | B | I-243b | D |
| I-181 | D | I-245 | D |
| I-182 | D | I-246 | C |
| I-183 | D | I-247 | D |
| I-184 | D | I-248 | D |
| I-249a | A | I-249b | A |
| I-250 | D | I-251 | D |
| I-252a | A | I-252b | A |
| I-253 | A | I-254 | D |
| I-255 | A | I-256 | A |
| I-257 | A | I-258 | D |
| I-259a | A | I-259b | A |
| I-260 | D | I-261 | D |
| I-262 | A | I-263a | C |
| I-263b | C | I-264 | D |
| I-265 | A | I-266 | D |

TABLE 3-continued

IC$_{50}$ Values for Select Compounds Assayed According to Example 1B.

| Compound | IC$_{50}$ | Compound | IC$_{50}$ |
|---|---|---|---|
| I-267 | A | I-268 | D |
| I-269 | D | I-270 | A |
| I-271 | D | I-272 | D |
| I-273 | C | I-274 | A |
| I-275 | A | I-276 | A |
| I-277 | A | I-278 | A |
| I-279 | D | I-280 | D |
| I-281 | A | I-282 | A |
| I-283 | D | I-284 | B |
| I-285 | D | I-286 | A |
| I-287 | D | I-288 | A |
| I-289 | A | | |

Example 1C

Mouse Pharmacokinetics Study

Formulations of compounds set forth in Table 4 were administered intravenously or orally via gavage to CD-1 mice. Typically, at 0.167, 0.5, 1, 2, 4, 6, 12, and 24 hours post-dose, blood was collected and processed to plasma by centrifugation and stored at −80° C. until analysis.

Internal standard was added to each sample prior to protein precipitation with acetonitrile. The precipitates were filtered through a Phree phospholipid removal filter plate and the samples were analyzed by LC/MS/MS. A standard curve was prepared in plasma from typically from 1.0 ng/mL to 3000 ng/mL and processed in the same manner as the samples. Sample analysis was typically performed on a suitable LC/MS/MS system fitted with an analytical UPLC column and compounds eluted from the analytical column with a gradient from 30-95% 0.1% formic acid (v/v) in ACN: 0.1% formic acid (v/v) in water. Mass spectrometric detection of test compound and the internal standard was performed by MRM in positive mode. The pharmacokinetics of each compound were analyzed by Phoenix WinNonlin software (Pharsight, St. Louis, Mo.) via non-compartmental analysis. The results are summarized in Table 4 below.

TABLE 4

Mouse Pharmacokinetic Data According to Example 1C.

| Compound | Dose (mg/kg) | Route | Formulation | $C_{max}$ (ng/mL) | $T_{max}$ (h) | $T^{1/2}$ (h) | Vdss (L/kg) | Cl (mL/min/kg) | $T_{last}$ (h) | AUC 0-last (ng * h/mL) | AUC 0-inf (ng * h/mL) | Bioavailability (%) |
|---|---|---|---|---|---|---|---|---|---|---|---|---|
| I-137a | 3 | iv | 1.5 mg/mL in DMSO:PEG400:Water = 5:75:20, solution | | | 8.2 | 6.6 | 25 | 24 | 1921 | 2008 | |
| I-137a | 30 | po | 3 mg/mL in 0.5% methylcellulose and 0.2% Tween 80, suspension | 953 | 0.5 | 3.5 | | | 24 | 3782 | 3835 | 19 |
| I-137b | 3 | iv | 1.5 mg/mL in DMSO:PEG400:Water = 5:75:20, solution | | | 11.2 | 16.6 | 37 | 24 | 1220 | 1352 | |
| I-137b | 30 | po | 3 mg/mL in 0.5% methylcellulose and | 476 | 2 | 5.9 | | | 24 | 3630 | 3828 | 28 |

TABLE 4-continued

Mouse Pharmacokinetic Data According to Example 1C.

| Compound | Dose (mg/kg) | Route | Formulation | $C_{max}$ (ng/mL) | $T_{max}$ (h) | $T^{1/2}$ (h) | Vdss (L/kg) | Cl (mL/min/kg) | $T_{last}$ (h) | AUC 0-last (ng * h/mL) | AUC 0-inf (ng * h/mL) | Bioavail-ability (%) |
|---|---|---|---|---|---|---|---|---|---|---|---|---|
| | | | 0.2% Tween 80, suspension | | | | | | | | | |
| I-144b | 30 | po | 1.5 mg/mL in DMSO:PEG400:Water = 5:75:20, solution | | | 1.3 | 0.8 | 44 | 6 | 1140 | 1145 | |
| I-144b | 30 | po | 3 mg/mL in 0.5% methyl-cellulose and 0.2% Tween 80, suspension | 599 | 0.2 | 2 | | | 6 | 613 | 727 | 6 |
| I-154 | 3 | iv | 1.5 mg/mL in DMSO:PEG400:Water = 5:75:20, solution | | | 12 | 13.7 | 16.5 | 24 | 2414 | 3034 | |
| I-154 | 30 | po | 3 mg/mL in 0.5% methyl-cellulose and 0.2% Tween 80, suspension | 840 | 2 | 9.6 | | | 24 | 9358 | 11207 | 39 |
| I-198a | 3 | iv | 1.5 mg/mL in DMSO:PEG400:Water = 5:75:20, solution | | | 4.3 | 12.1 | 64.8 | 24 | 765 | 772 | |
| I-198a | 30 | po | 3.00 mg/mL in 0.5% Methyl-cellulose, suspension | 721 | 1 | 4.2 | | | 24 | 3961 | 4048 | 52 |
| I-201 | 3 | iv | 1.5 mg/mL in DMSO:PEG400:Water = 5:75:20, solution | | | 8.52 | 19.6 | 37.5 | 24 | 1203 | 1334 | |
| I-201 | 30 | po | 3.00 mg/mL in 0.5% Methyl-cellulose, suspension | 1413 | 1 | 7.16 | | | 24 | 9653 | 10558 | 79 |
| I-203 | 3 | iv | 1.5 mg/mL in DMSO:PEG400:Water = 5:75:20, solution | | | 2.3 | 5.8 | 88.5 | 12 | 555 | 565 | |
| I-203 | 30 | po | 3.00 mg/mL in 0.5% Methyl-cellulose, suspension | 604 | 0.2 | 0.7 | | | 6 | 656 | 657 | 12 |
| I-204b | 3 | iv | 1.5 mg/mL in DMSO:PEG400:Water = 5:75:20, solution | | | 0.9 | 4 | 110 | 6 | 454 | 455 | |
| I-204b | 30 | po | 3.00 mg/mL in 0.5% Methyl-cellulose, suspension | 55 | 0.2 | 3.2 | | | 12 | 63 | 67 | 2 |
| I-219 | 3 | iv | 1.5 mg/mL in DMSO:PEG400:Water = 5:75:20, solution | | | 0.7 | 2.4 | 73.3 | 6 | 678 | 682 | |
| I-219 | 30 | po | 3.00 mg/mL in 30% PEG400/10% solutol/60% water, suspension | 48.9 | 0.2 | | | | 12 | 132 | 215 | 2 |

TABLE 4-continued

| Compound | Dose (mg/kg) | Route | Formulation | $C_{max}$ (ng/mL) | $T_{max}$ (h) | $T^{1/2}$ (h) | Vdss (L/kg) | Cl (mL/min/ kg) | $T_{last}$ (h) | AUC 0-last (ng * h/ mL) | AUC 0-inf (ng * h/ mL) | Bioavail-ability (%) |
|---|---|---|---|---|---|---|---|---|---|---|---|---|
| Mouse Pharmacokinetic Data According to Example 1C. | | | | | | | | | | | | |
| I-222a | 3 | iv | 1.5 mg/mL in DMSO:PEG400:Water = 5:75:20, solution | | | 2.4 | 1.5 | 36.9 | 6 | 1329 | 1329 | |
| I-222a | 30 | po | 3.00 mg/mL in 30% PEG400/10% solutol/60% water, solution | 2873 | 0.2 | 1.7 | | | 12 | 2231 | 2239 | 16 |
| I-222b | 3 | iv | 1.5 mg/mL in DMSO:PEG400:Water = 5:75:20, solution | | | 1.8 | 2 | 88.1 | 6 | 564 | 567 | |
| I-222b | 30 | po | 3.00 mg/mL in 30% PEG400/10% solutol/60% water, solution | 2167 | 0.2 | 3.3 | | | 24 | 2865 | 2870 | 51 |
| I-39 | 3 | iv | 1.5 mg/mL in DMSO:PEG400:Water = 5:75:20, solution | | | 1.31 | 3.5 | 53.7 | 6 | 908 | 931 | |
| I-39 | 30 | po | 3.00 mg/mL in DMSO:PEG400:Water = 5:75:20, solution | 799 | | 3.35 | | | 24 | 1597 | 1609 | 17 |
| I-40 | 3 | iv | 1.5 mg/mL in DMSO:PEG400:Water = 5:75:20, solution | | | 8.4 | 24 | 41.2 | 24 | 1066 | 1213 | |
| I-40 | 30 | po | 3.00 mg/mL in 30% PEG400/10% solutol/60% water, solution | 853 | 2 | 8.8 | | | 24 | 7560 | 9142 | 75 |
| I-65 | 3 | iv | 1.5 mg/mL in DMSO:PEG400:Water = 5:75:20, solution | | | 0.7 | 2.7 | 93.1 | 4 | 522 | 537 | |
| I-65 | 30 | po | 3.00 mg/mL in DMSO:PEG400:Water = 5:75:20, solution | 574 | 0.2 | 0.8 | | | 6 | 370 | 373 | 7 |
| I-70 | 3 | iv | 1.5 mg/mL in DMSO:PEG400:Water = 5:75:20, solution | | | 1.08 | 3.2 | 54.9 | 6 | 862 | 872 | |
| I-70 | 30 | po | 10.0 mg/mL in 30% PEG/70% (20% hp-?-CD) solution, clear solution | 900 | 0.5 | 2.26 | | | 12 | 1944 | 1993 | 26 |
| I-73 | 3 | iv | 1.5 mg/mL in DMSO:PEG400:Water = 5:75:20, solution | | | 2 | 7.7 | 90 | 12 | 553 | 556 | |
| I-73 | 30 | po | 3.00 mg/mL in 0.5% Methyl-cellulose, suspension | 37.5 | 1 | 2.1 | 6 | | 24 | 96 | 108 | 2 |
| I-75a | 3 | iv | 1.5 mg/mL in DMSO:PEG400:Water = 5:75:20, solution | | | 13.8 | 13.7 | 14.4 | 24 | 2666 | 2265 | |
| I-75a | 30 | po | 3.0 mg/mL in | 969 | 2 | 9.8 | | | 24 | 13579 | 936 | 51 |

TABLE 4-continued

Mouse Pharmacokinetic Data According to Example 1C.

| Compound | Dose (mg/kg) | Route | Formulation | $C_{max}$ (ng/mL) | $T_{max}$ (h) | $T^{1/2}$ (h) | Vdss (L/kg) | Cl (mL/min/kg) | $T_{last}$ (h) | AUC 0-last (ng * h/mL) | AUC 0-inf (ng * h/mL) | Bioavail-ability (%) |
|---|---|---|---|---|---|---|---|---|---|---|---|---|
| | | | DMSO:PEG400:Water = 5:75:20, solution | | | | | | | | | |
| I-103 | 3 | iv | 3.00 mg/mL in 40% PEG400/10% solutol/50% water, solution | | | 0.62 | 1.4 | 43.9 | 6 | 1137 | 1140 | |
| I-103 | 30 | po | 6.00 mg/mL in 40% PEG400/10% solutol/50% water, solution | 713 | 0.2 | 2.15 | | | 12 | 649 | 671 | 6 |
| I-107 | 3 | iv | 3.00 mg/mL in DMSO:solutol:water = 5:10:85, solution | | | 2.18 | 43.2 | 540 | 6 | 88 | 92 | |
| I-107 | 15 | po | 3.00 mg/mL in DMSO:solutol:water = 5:10:85, solution | 0 | 0 | | | | 0 | 0 | 0 | 0 |
| I-2 | 3 | iv | 3.00 mg/mL in DMSO:PEG400:Water = 5:75:20, solution | | | 1.99 | 9.6 | 82 | 6 | 554 | 610 | |
| I-2 | 30 | po | 6.00 mg/mL in DMSO:PEG400:Water = 5:75:20, solution | 182 | 0.2 | 3.9 | | | 24 | 730 | 743 | 12 |
| I-259a | 3 | iv | 1.5 mg/mL in DMSO:PEG400:Water = 5:75:20, clear solution | | | 1.2 | 4.7 | 59 | 6 | 825 | 842 | |
| I-259a | 30 | po | 3.0 mg/mL in 0.5% methylcellulose, homogenous opaque suspension | 82 | 0.5 | 1.2 | | | 6 | 237 | 249 | 3 |
| I-118 | 3 | iv | 1.5 mg/mL in DMSO:PEG400:Water = 5:75:20, clear solution | | | 0.6 | 4.9 | 136 | 4 | 364 | 368 | |
| I-118 | 30 | po | 3.0 mg/mL in 0.5% methylcellulose, homogenous opaque suspension | 41 | 1 | 1.9 | | | 6 | 107 | 121 | 3 |
| I-126 | 3 | iv | 1.5 mg/mL in DMSO:PEG400:Water = 5:75:20, clear solution | | | 8.8 | 17 | 30 | 24 | 1463 | 1651 | |
| I-126 | 30 | po | 3.0 mg/mL in 0.5% methylcellulose, homogenous opaque suspension | 1870 | 1 | 6.1 | | | 24 | 13748 | 14741 | 100 |
| I-129 | 3 | iv | 1.5 mg/mL in DMSO:PEG400:Water = 5:75:20, clear solution | | | 14 | 22 | 31 | 24 | 1339 | 1615 | |
| I-129 | 30 | po | 3.0 mg/mL in 0.5% methylcellulose, homogenous | 1043 | 2 | 6.4 | | | 24 | 7034 | 7532 | 53 |

TABLE 4-continued

Mouse Pharmacokinetic Data According to Example 1C.

| Compound | Dose (mg/kg) | Route | Formulation | $C_{max}$ (ng/mL) | $T_{max}$ (h) | $T^{1/2}$ (h) | Vdss (L/kg) | Cl (mL/min/kg) | $T_{last}$ (h) | AUC 0-last (ng * h/mL) | AUC 0-inf (ng * h/mL) | Bioavailability (%) |
|---|---|---|---|---|---|---|---|---|---|---|---|---|
| | | | opaque suspension | | | | | | | | | |
| I-130 | 3 | iv | 1.5 mg/mL in DMSO:PEG400:Water = 5:75:20, clear solution | | | 2.6 | 7.5 | 39 | 12 | 1223 | 1272 | |
| I-130 | 30 | po | 3.0 mg/mL in 0.5% methylcellulose, homogenous opaque suspension | 936 | 2 | 3.5 | | | 24 | 6624 | 6689 | 53 |
| I-59 | 3 | iv | 1.5 mg/mL in DMSO:PEG400:Water = 5:75:20, clear solution | | | 6.6 | 11.2 | 53 | 24 | 925 | 949 | |
| I-59 | 30 | po | 3.0 mg/mL in 0.5% methylcellulose, homogenous opaque suspension | 719 | 0.5 | 4.3 | | | 24 | 2110 | 2130 | 22 |

Example 1D

In Vitro Mouse Liver S9 Metabolic Stability Assay

CD-1 mouse liver S9 were purchased from Corning or XenoTech LLC or BioreclamationIVT, LLC or WuXi prepared. The cells were stored at −80° C. in a freezer before use. β-Nicotinamide adenine dinucleotide phosphate (NADP), Glucose 6-phosphate (G6P), Glucose 6-phosphate dehydrogenase from yeast (G6PDH), Uridine 5'-diphophoglucuronic acid trisodium salt (UDPGA) and Adenosine 3'-phosphate 5'-phosphosulfate lithium salt hydrate (PAPS) were available commercially from Sigma.

Compounds were diluted in DMSO to make 10 mM stock solution. 5 μL of this stock solution (10 mM, DMSO) was diluted with 45 μL DMSO and 450 μL 50% Methanol/Water to make intermediate stock solution (100 μM, 45% MeOH, 10% DMSO). 50 μL of intermediate stock solution was diluted with 450 μL 100 mM phosphate buffer to make a final stock solution (10 μM, 4.5% MeOH, 1% DMSO). 10 uL of final stock solution was added to 90 uL liver S9 system (final concentration of 1 μM, 0.45% MeOH, 0.1% DMSO).

Test compounds were incubated at 37° C. with liver S9 (pooled from multiple donors) at 1 μM in the presence of a NADPH regenerating system, UDPGA, and PAPS at 1 mg/mL S9 protein. Time samples (0 and 60 minutes) were removed and immediately mixed with cold acetonitrile containing internal standard (IS). Samples were analyzed by LC/MS/MS and disappearance of test compounds were assessed based on peak area ratios of analyte /IS (no standard curve). All samples were injected and analyzed using LC-MS/MS. The analyte/internal standard peak area ratios were converted to percentage remaining (% Remaining) with the following equation: % Remaining at 60 min=(Peak area ratio of analyte to IS at 60 min/Peak area ratio of analyte to IS at t=0)×100%. The results are summarized in Table 5 below.

TABLE 5

Mouse Stability Data According to Example 1D.

| Compound | Mouse S9 Stability: % Remaining After 60 Minutes | Compound | Mouse S9 Stability: % Remaining After 60 Minutes |
|---|---|---|---|
| I-6 | 0 | I-40 | 87 |
| I-2 | 13 | I-39 | 30 |
| I-4 | 0 | I-36 | 29 |
| I-21 | 26 | I-30 | 11 |
| I-16 | 2 | I-235 | 2 |
| I-109 | 10 | I-224 | 0 |
| I-107 | 0 | I-222b | 0 |
| I-106 | 1 | I-222a | 1 |
| I-105 | 8 | I-219 | 5 |
| I-103 | 7 | I-214 | 0 |
| I-101 | 1 | I-209 | 0 |
| I-98b | 0 | I-208 | 0 |
| I-96 | 36 | I-204b | 0 |
| I-92 | 0 | I-203 | 0 |
| I-90 | 11 | I-202 | 0 |
| I-81 | 2 | I-201 | 34 |
| I-78 | 1 | I-200 | 0 |
| I-75a | 65 | I-198a | 30 |
| I-73 | 11 | I-196 | 0 |
| I-72 | 3 | I-177 | 2 |
| I-70 | 0 | I-166 | 4 |
| I-68 | 4 | I-165 | 3 |
| I-67 | 5 | I-164 | 0 |
| I-67 | 1 | I-162 | 54 |
| I-65 | 0 | I-156 | 28 |
| I-59 | 11 | I-154 | 13 |
| I-47 | 50 | I-152b | 3 |
| I-45 | 19 | I-152a | 2 |

Example 1E

In Vivo Mouse Liver and Spleen Cyp1a1 Modulation Assay

C57BL/6 mice, female, 6-8 weeks old, weighing approximately 18-20 g were purchased from Shanghai Lingchang Biological Technology Co., Ltd or other certified vendors and used in the studies. Animal husbandry, feeding and health conditions are according to animal welfare guidelines. VAG539 (30 mg/kg, po) was used as AHR agonist, and test compounds were formulated in suitable vehicles, typically 0.5% methylcellulose).

C57BL/6 mice (n=3 per group) were treated with AHR agonist alone or with AHR agonist and test compounds. Animals were sacrificed at 4 or 10 hours after treatment upon which their livers and spleens were collected and subsequently analyzed by qPCR. Normalized fold induction of cyp1a1 was determined by comparing mCYP1A1 and mGAPDH counts (ct) according to: normalized fold=$2^{-\Delta\Delta Ct}$. The percent inhibition was calculated according to:

$$\left[1-\frac{\text{average normalized fold for } AHR \text{ agonist and compound treated}}{\text{average normalized fold for } AHR \text{ agonist treated}}\right]\times 100=\%$$

inhibition

The results are summarized in Table 6 below.

TABLE 6

Cyp1a1 Inhibition Data According to Example 1E.

| | | Cyp1a1 inhibition | | |
|---|---|---|---|---|
| | | Liver | | Spleen |
| Compound | Dose | 4 h | 10 h | 4 h |
| I-2 | 30 mg/kg | 50% | | |
| I-103 | 30 mg/kg | 94% | 0% | |
| I-75a | 30 mg/kg | 55% | | |
| I-57 | 30 mg/kg | 77% | | 66% |
| I-46 | 30 mg/kg | 96% | | 94% |
| I-39 | 30 mg/kg | 90% | | 69% |
| I-70 | 30 mg/kg | 98% | | |
| | 10 mg/kg | 99% | 81% | |
| | 10 mg/kg | 98% | 98% | 88% |
| | 5 mg/kg | 93% | 96% | 79% |
| | 2 mg/kg | 83% | 63% | 65% |
| | 1 mg/kg | 52% | 34% | 38% |
| I-40 | 25 mg/kg | 98% | 97% | 96% |
| | 10 mg/kg | 93% | 75% | 74% |
| | 5 mg/kg | 77% | 48% | 34% |
| I-201 | 25 mg/kg | 86% | 97% | 72% |
| | 10 mg/kg | 72% | 59% | 46% |
| | 5 mg/kg | 58% | 44% | 40% |

Example 1F

T-Cell Study with I-70

Human T cells were isolated by CD3 negative selection after isolation of PBMCs from blood of human donors via ficoll density gradient centrifugation. One million T cells were activated with 25 uL of CD3/CD28 tetramer (Stemcell) in the presence or absence of 1-70 for 24 hours, after which media was removed and stored at −80 C for later cytokine analysis. Cells were then washed 2× with PBS, before isolating RNA according to the manufacturer's instructions for the RNAeasy mini kit (Qiagen).

RNA was converted to cDNA using VILO-IV RT mastermix (Thermofisher), and q-RT-PCR was performed to determine levels of IL-22 (Hs01574154_m1), Cyp1a1 (Hs01054797_g1), and GAPDH (Hs00266705_g1). Data was analyzed using the ddCT method whereby each sample is first normalized to GAPDH housekeeping gene before being normalized to control treatment. IL22 and cyp1a1 RNA expression levels are inhibited by treatment with I-70, as shown in FIG. 1.

Figure 2:
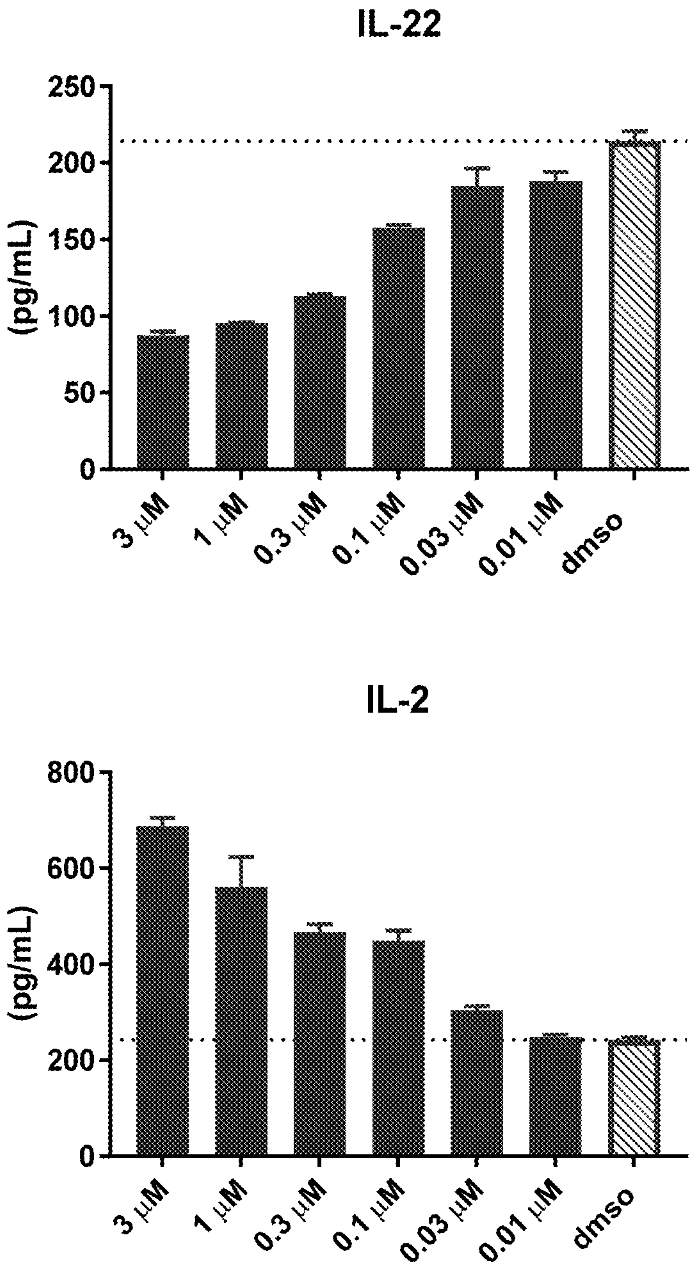
FIG. 2 depicts a plot showing decrease in IL-22 protein (top) and increase in IL-2 (bottom) by treatment of activated T cells with a compound described herein.

Cytokine levels were determined utilizing the mesoscale discovery (MSD) platform (K15067L-2) and MSD analysis software according to the manufacturer's instructions. IL-22 protein levels are decreased and pro-inflammatory IL-2 protein levels are increased by treatment with 1-70, as shown in FIG. 2.

CD3/CD28 activated T cells are AHR activated as measured by gene expression and cytokine production. Treatment with the AHR inhibitor lead to inhibition of cyp1a1 and IL22 gene expression and cytokine IL-22 production. AHR inhibition also increases production of the pro-inflammatory cytokine IL-2.

Example 1G

Efficacy Study of 1-70 and Checkpoint Inhibitor Anti-PD-1 in the Mouse Colorectal Cancer Model CT26 in Balb/c Mice CT26 is a murine colon carcinoma cell line obtained from ATCC. CT26 cells were cultured in RPMI supplemented with 10% FBS. $5\times10^5$ CT26 cells in 100 μl PBS were implanted subcutaneously in 6-8 week old female, Balb/c mice. Dosing for the efficacy study starts 4 days post implant: AHR antagonist was dosed orally, every day (QD) at or 10 mg/kg for 3 weeks. anti-PD-1 (BioXcell RMP1-14) was twice a week, intraperitoneally (IP) at 10 mg/kg for five total doses. Tumors were monitored by caliper measurement every 2-3 days and body weight measured three times per week.

Figure 3:
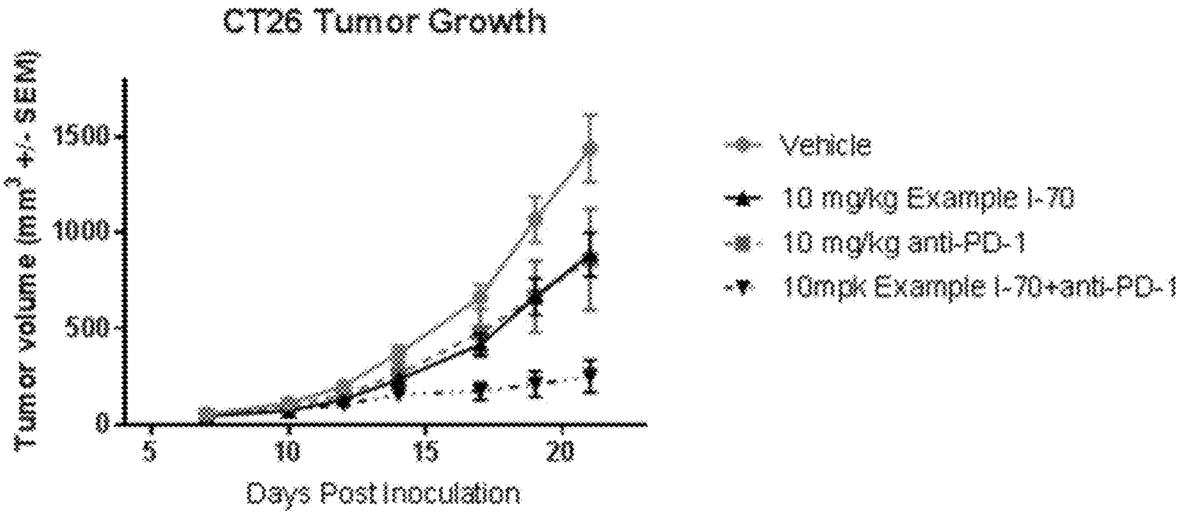
FIG. 3 depicts a plot showing CT26 efficacy study with a vehicle, a compound described herein, anti-PD-1 and a combination thereof.

Tumor growth is inhibited by AHR antagonist 1-70 alone or in combination with anti-PD-1, as shown in FIG. 3. Tumor growth inhibition is statistically significant with 1-70 as single agent compared to vehicle, with p value=0.0166. In addition, the tumor growth inhibition in the combination group was significant compared to the anti-PD-1 alone, p value=0.0420. p values determined by Student's T-test analysis.

Example 1H

Efficacy Study of 1-70 and Checkpoint Inhibitor Anti-PD-1 in the Mouse Melanoma Model B16-IDO in C57BL/6 Mice B16-IDO is a murine melanoma carcinoma cell line that has been engineered to overexpress IDO1 (Holmgaard, 2015 Cell Reports). B16-IDO cells were cultured in DMEM supplemented with 10% FBS. $2\times10^5$ B16-IDO cells in 50 μl PBS were implanted intradermally in 6-8 week old female, C57BL/6 mice. Dosing for the efficacy study starts 7 days post implant: AHR antagonist 1-70 was dosed orally, every day (QD) at or 10 mg/kg for 2 weeks. Anti-PD-1 (BioXcell RMP1-14) was administered every $3^{rd}$ day, intraperitoneally (IP) at 250 μg/mouse for five total doses. Tumors were monitored by caliper measurement every 2-3 days and body weight measured three times per week.

Figure 4:
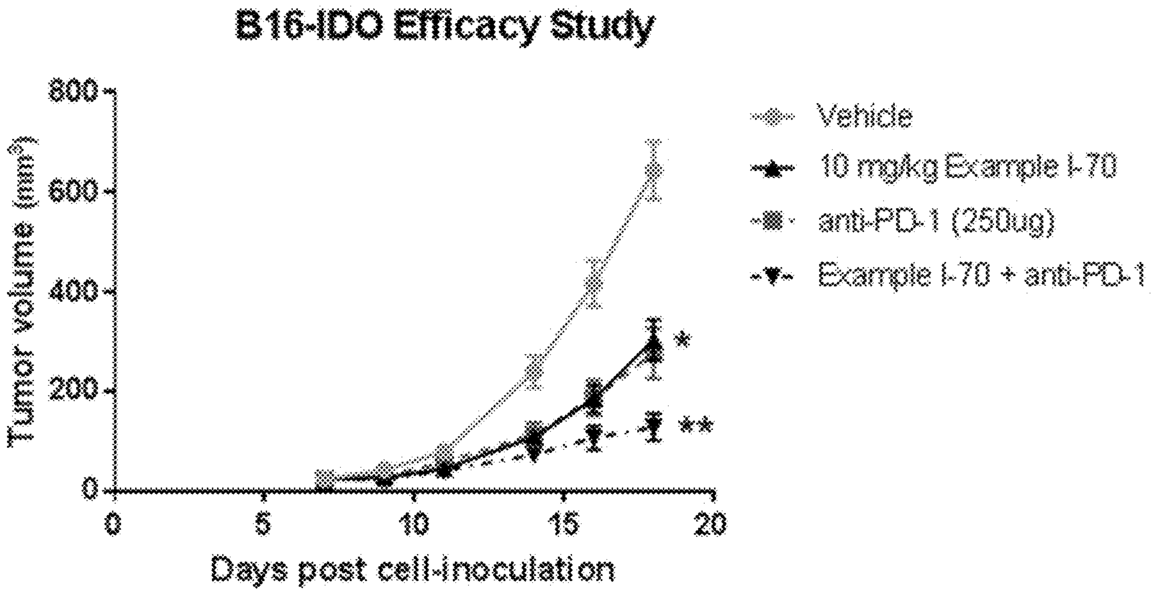
FIG. 4 depicts a plot showing B16-IDO efficacy study with a vehicle, a compound described herein, anti-PD-1 and a combination thereof.

Tumor growth was inhibited by AHR antagonist 1-70 alone or in combination with anti-PD-1, as shown in FIG. 4. Tumor growth inhibition was statistically significant with 1-70 as single agent compared to vehicle, with p value <0.001. In addition, the tumor growth inhibition in the combination group was significant compared to the anti-PD-1 alone, p value <0.03. p values determined by Student's T-test analysis.

Example 2

AHR-Dependent Gene Expression

Murine Hepal-6 or Hepa-1c1c7 or other murine cell line are plated in media in plates (6, well, 12 well or other plates) and incubated overnight at 37° C. in a $CO_2$ incubator; or human HepG2 or other human cell line are plated in media in plates (6-well, 12-well or other plates) and incubated overnight at 37° C. in a $CO_2$ incubator.

The next day AHR activating ligand, such as TCDD, kynurenine, ITE (2-(1H-indole-3-ylcarbonyl)-4-thiazolecarboxylic methyl ester), VAF347, BNF (beta-naphthoflavone), ICZ (6-Formylindolo(3,2-b) carbazole or other AHR ligands added with or without AHR antagonist. Cells are incubated for 4, 15 or 24 hours or another time point and then cells are lysed for RNA collection. RNA can be collected via a RNAisolation kit such as Qiagen or any other RNAisolation method. Gene expression is determined by quantitative RT-PCR using probes for specific genes including a housekeeping gene such as Gapdh, β-actin or other constitutively expressed genes for normalization. AHR-dependent genes to be examined include but are not limited to: cyp1a1, cyp1b1, AHRR, IDO1, IDO2, cox2, IL6, VEGFA, cyclinD1, cdc2, MMP-9, c-myc.

Example 3

AHR-dependent gene expression is measured in tissue samples such as tumor or liver. RNA is extracted from the tissue via methods such as RNA isolation kit such as Qiagen or any other RNA isolation method known to one of ordinary skill in the art. The RNA extraction could be done from total cells or cells post-sorting for specific populations of cells such as tumor cells, tumor associated-T cells, tumor associated-myeloid cells or others. Gene expression is determined by quantitative RT-PCR using probes for specific genes including a housekeeping gene such as Gapdh, β-actin or other constitutively expressed genes for normalization. AHR-dependent genes to be examined include but are not limited to: cyp1a1, cyp1b1, AHRR, IDO1, IDO2, cox2, IL6, VEGFA, cyclinD1, cdc2, MMP-9, c-myc.

Example 4

Synthesis of I-5

I-5

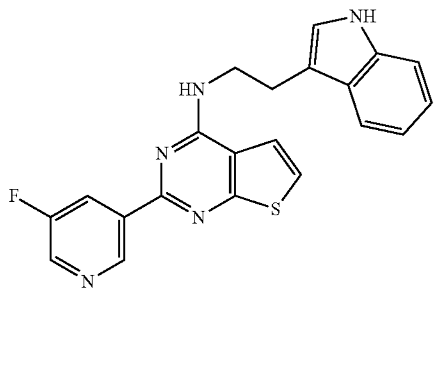

Synthetic Scheme:

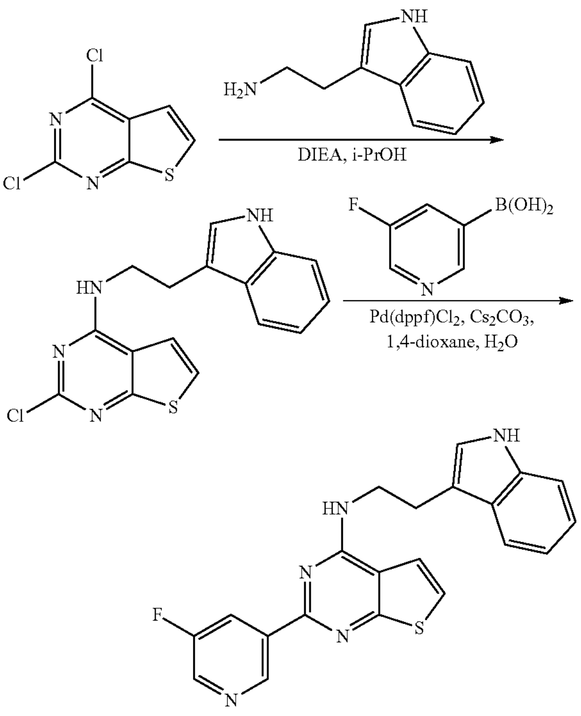

I-5

Step 1: N-(2-(1H-indol-3-yl)ethyl)-2-chlorothieno[2,3-d]pyrimidin-4-amine

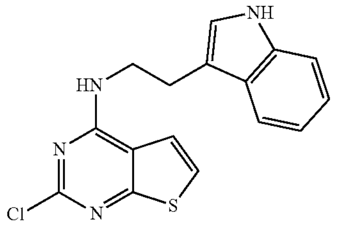 [SMILES: Clc1nc(NCCc2c[nH]c3ccccc23)c2ccsc2n1]

To a solution of 2,4-dichlorothieno[2,3-d]pyrimidine (200 mg, 975.31 umol, 1 eq) in i-PrOH (15 mL) was added DIPEA (630.24 mg, 4.88 mmol, 849.38 uL, 5.0 eq) and 2-(1H-indol-3-yl)ethanamine (203.14 mg, 1.27 mmol, 1.3 eq). The mixture was stirred at 50° C. for 3 h. LC-MS showed the starting material was consumed completely and one main peak with desired MS was detected. The reaction mixture was diluted with $H_2O$ (15 mL) and extracted with DCM (15 mL×3). The combined organic layers were dried over $Na_2SO_4$, filtered and concentrated under reduced pressure to give a residue which was purified by flash silica gel chromatography (ISCO®; 12 g SepaFlash® Silica Flash Column, Eluent of 20-30% EtOAc/PE gradient @50 mL/min) to give 2-chloro-N-[2-(1H-indol-3-yl)ethyl]thieno[2,3-d]pyrimidin-4-amine (260 mg, 774.90 umol, 79.4% yield) as a yellow solid. $^1H$ NMR (400 MHz, $CD_3OD$) δ ppm 7.67 (d, J=7.9 Hz, 1H), 7.40-7.35 (m, 2H), 7.31 (d, J=8.2 Hz, 1H), 7.10-7.05 (m, 2H), 7.00-6.93 (m, 1H), 3.86-3.79 (m, 2H), 3.11 (t, J=7.4 Hz, 2H); ES-LCMS m/z 329.0, 331.0 $[M+H]^+$.

Step 2: N-(2-(1H-indol-3-yl)ethyl)-2-(5-fluoropyridin-3-yl)thieno[2,3-d]pyrimidin-4-amine (I-5)

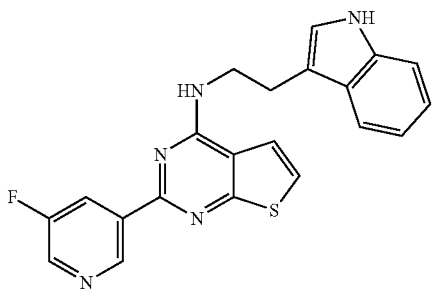 [SMILES: Fc1cncc(-c2nc(NCCc3c[nH]c4ccccc34)c3ccsc3n2)c1]

To a solution of 2-chloro-N-[2-(1H-indol-3-yl)ethyl]thieno[2,3-d]pyrimidin-4-amine (100 mg, 298.04 umol, 1 eq) in 1,4-dioxane (3 mL) and $H_2O$ (1 mL) was added (5-fluoro-3-pyridyl)boronic acid (75.59 mg, 536.47 umol, 1.8 eq), $Cs_2CO_3$ (291.32 mg, 894.11 umol, 3.0 eq) and Pd(dppf)$Cl_2$ (32.71 mg, 44.71 umol, 0.15 eq). The mixture was stirred at 120° C. under microwave for 1 h. LC-MS showed the starting material was consumed completely and one main peak with desired MS was detected. The reaction mixture was filtered. The filtrate was diluted with $H_2O$ (15 mL) and extracted with EtOAc (15 mL×3). The combined organic layers were dried over $Na_2SO_4$, filtered and concentrated under reduced pressure to give a residue which was purified by preparative HPLC (HCl condition; column: Phenomenex Kinetex XB-C18 150 mm*30 mm, 5 am; mobile phase: [water(0.05% HCl)-ACN]; B %: 50%-75%, 12 min) and the desired fraction was lyophilized to yield 2-(5-fluoro-3-pyridyl)-N-[2-(1H-indol-3-yl)ethyl]thieno[2,3-d]pyrimidin-4-amine (54.40 mg, 109.05 umol, 36.59% yield, 100% purity, 3HCl salt) as a yellow solid. $^1H$ NMR (400 MHz, $CD_3OD$) δ ppm 9.19 (s, 1H), 8.84 (s, 1H), 8.58 (d, J=9.3 Hz, 1H), 7.63-7.57 (m, 2H), 7.54 (d, J=5.7 Hz, 1H), 7.19 (d, J=7.7 Hz, 1H), 7.02-6.90 (m, 3H), 4.08 (t, J=6.8 Hz, 2H), 3.19 (t, J=6.7 Hz, 2H); ES-LCMS m/z 390.0 $[M+H]^+$.

Example 5

Synthesis of I-4

I-4

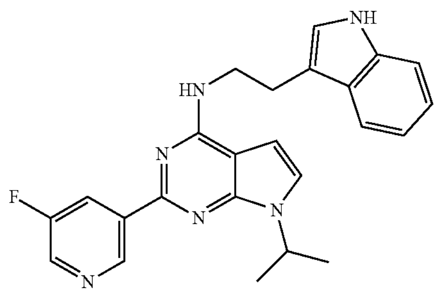

Synthesis Scheme:

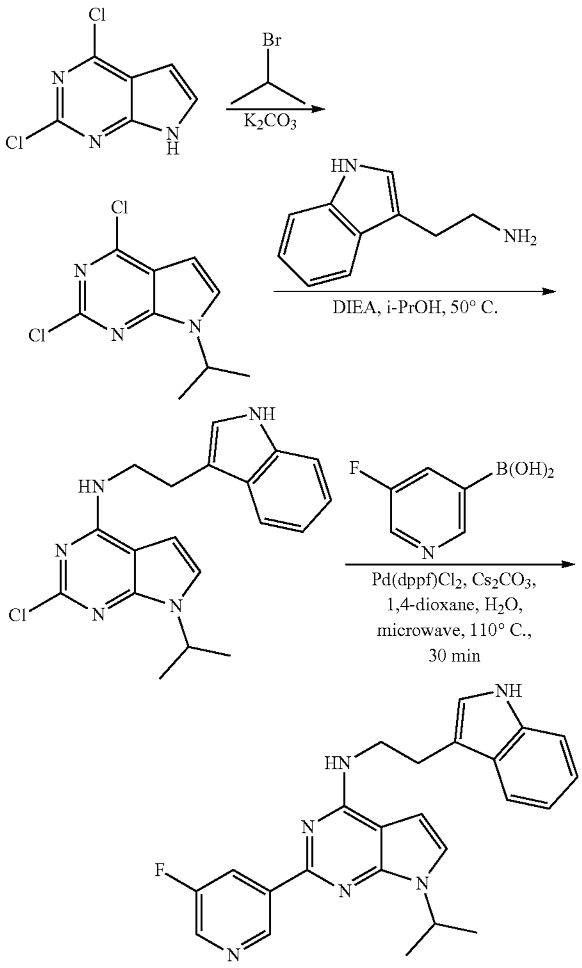

I-4

Step 1: 2,4-Dichloro-7-isopropyl-7H-pyrrolo[2,3-d]pyrimidine

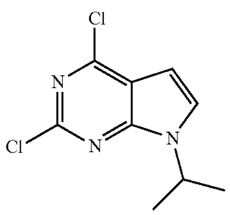

A mixture of 2,4-dichloro-7H-pyrrolo[2,3-d]pyrimidine (1 g, 5.32 mmol, 1 eq), 2-bromopropane (3.27 g, 26.59 mmol, 2.50 mL, 5.0 eq) and $K_2CO_3$ (3.68 g, 26.59 mmol, 5 eq) in DMSO (20 mL) was degassed and purged with $N_2$ for 3 times then the mixture was stirred at 10-20° C. for 48 h under $N_2$ atmosphere. TLC (PE/EA=3/1, $R_f$=0.50) indicated starting material was consumed, and one major new spot with larger polarity was detected. The reaction mixture was diluted with $H_2O$ (50 mL) and extracted with EtOAc (50 mL×3). The combined organic layers were dried over anhydrous $Na_2SO_4$, filtered and concentrated under reduced pressure to give a residue which was purified on silica gel column chromatography (from PE/EtOAc=1/0 to 4/1, TLC: PE/EtOAc=3/1, $R_f$=0.50) to give the product 2,4-dichloro-7-isopropyl-pyrrolo[2,3-d]pyrimidine (650 mg, 2.71 mmol, 50.99% yield, 96% purity) as a white solid. $^1H$ NMR (400 MHz, $CDCl_3$) δ ppm 7.33 (d, J=3.7 Hz, 1H), 6.62 (d, J=3.5 Hz, 1H), 5.20-5.01 (m, 1H), 1.53 (d, J=6.8 Hz, 6H); ES-LCMS m/z 230.0, 232.0 $[M+H]^+$.

Step 2: 2-Chloro-N-[2-(1H-indol-3-yl)ethyl]-7-isopropyl-pyrrolo[2,3-d]pyrimidin-4-amine

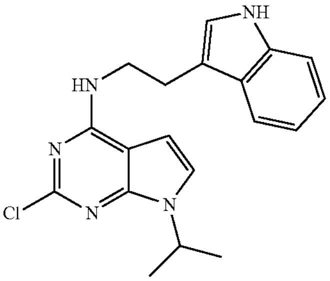 [SMILES: CC(C)n1ccc2c(NCCc3c[nH]c4ccccc34)nc(Cl)nc21]

A mixture of 2,4-dichloro-7-isopropyl-pyrrolo[2,3-d]pyrimidine (100 mg, 417.22 umol, 1 eq), 2-(1H-indol-3-yl)ethanamine (100 mg, 620 umol, 1.2 eq) and DIEA (161.77 mg, 1.25 mmol, 218.02 uL, 3 eq) in i-PrOH (5 mL) was degassed and purged with $N_2$ for 3 times. Then the mixture was stirred at 50° C. for 11 h under $N_2$ atmosphere. LC-MS showed 15% of starting material was remained. The reaction mixture was concentrated under reduced pressure to give a residue which was purified on silica gel column chromatography (from PE/EtOAc=1/0 to 1/1, TLC: PE/EtOAc=3/1, $R_f$=0.28) to give the product 2-chloro-N-[2-(1H-indol-3-yl)ethyl]-7-isopropyl-pyrrolo[2,3-d]pyrimidin-4-amine (120 mg, 315.39 umol, 75.59% yield, 93% purity) as light red oil. $^1H$ NMR (400 MHz, $CDCl_3$) δ ppm 8.06 (s, 1H), 7.69 (d, J=7.9 Hz, 1H), 7.41 (d, J=7.9 Hz, 1H), 7.26-7.20 (m, 1H), 7.18-7.13 (m, 1H), 7.09 (d, J=2.4 Hz, 1H), 6.96 (d, J=3.5 Hz, 1H), 6.23 (s, 1H), 5.22 (s, 1H), 5.03 (d, J=6.8, 13.5 Hz, 1H), 3.99 (q, J=6.6 Hz, 2H), 3.17 (t, J=6.6 Hz, 2H), 1.46 (d, J=6.8 Hz, 6H); ES-LCMS m/z 353.8, 354.9 $[M+H]^+$.

Step 3: 2-(5-Fluoro-3-pyridyl)-N-[2-(1H-indol-3-yl)ethyl]-7-isopropyl-pyrrolo[2,3-d]pyrimidin-4-amine (I-4)

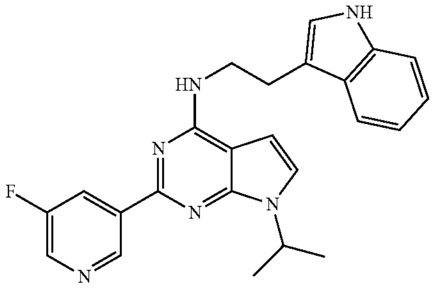 [SMILES: CC(C)n1ccc2c(NCCc3c[nH]c4ccccc34)nc(-c3cncc(F)c3)nc21]

2-Chloro-N-[2-(1H-indol-3-yl)ethyl]-7-isopropyl-pyrrolo[2,3-d]pyrimidin-4-amine (80 mg, 210.26 umol, 1 eq), (5-fluoro-3-pyridyl)boronic acid (44.44 mg, 315.39 umol, 1.5 eq), Pd(dppf)$Cl_2$ (15.38 mg, 21.03 umol, 0.1 eq) and $Cs_2CO_3$ (205.52 mg, 630.78 umol, 3 eq) in 1,4-dioxane (2 mL) and $H_2O$ (0.5 mL) were taken up into a microwave tube. The reaction mixture was bubbled with $N_2$ for 3 min then sealed and heated at 110° C. for 30 min under microwave. LC-MS showed 90% of desired compound was detected. The reaction mixture was concentrated under reduced pressure to give a residue which was purified by preparative HPLC (MeCN/$H_2O$ as eluents, acidic condition, Instrument: DC/Phenomenex Kinetex XB-C18 150 mm*30 mm, 5 μm/Mobile phase: water(0.05% HCl)-ACN/Gradient: B from 47% to 77% in 10 min/Flow rate: 25 mL/min) followed by lyophilization to yield 2-(5-fluoro-3-pyridyl)-N-[2-(1H-indol-3-yl)ethyl]-7-isopropyl-pyrrolo[2,3-d]pyrimidin-4-amine (51.57 mg, 120.95 umol, 57.52% yield, 97.21% purity, 3HCl salt) as a yellow solid. $^1H$ NMR (400 MHz, DMSO-$d_6$) δ ppm 9.41 (s, 1H), 8.72 (s, 1H), 8.50 (d, J=8.6 Hz, 1H), 8.09 (s, 1H), 7.64 (d, J=7.7 Hz, 1H), 7.40 (s, 1H), 7.35 (d, J=8.2 Hz, 1H), 7.23 (s, 1H), 7.07 (t, J=7.4 Hz, 1H), 7.02-6.93 (m, 1H), 6.69 (s, 1H), 5.06 (s, 1H), 3.89 (s, 1H), 3.80-3.77 (m, 2H), 3.20-3.00 (m, 2H), 1.48 (d, J=6.6 Hz, 6H); ES-LCMS m/z 414.9 $[M+H]^+$.

Example 6

Synthesis of I-3

I-3

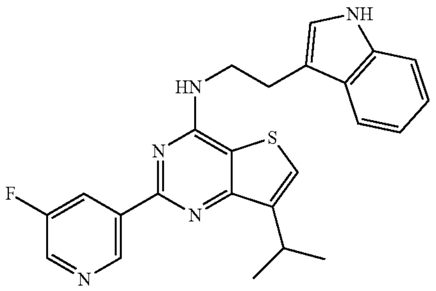

Synthesis Scheme:

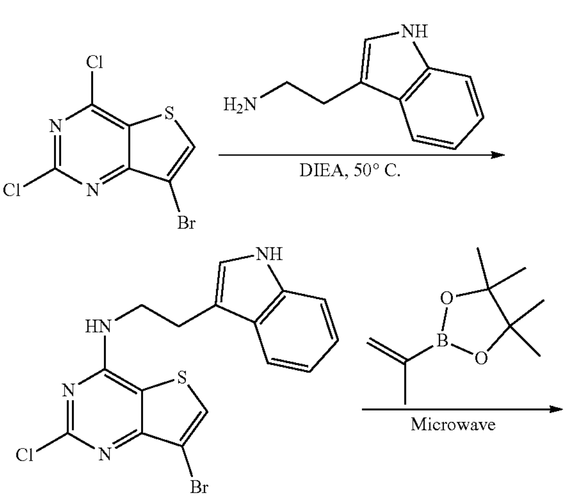

-continued

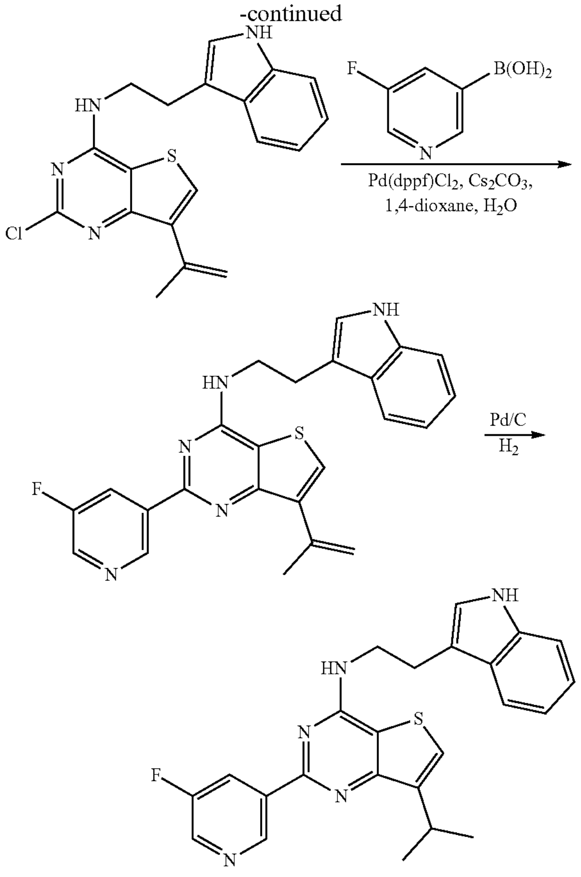

I-3

Step 1: N-(2-(1H-indol-3-yl)ethyl)-7-bromo-2-chlorothieno[3,2-d]pyrimidin-4-amine

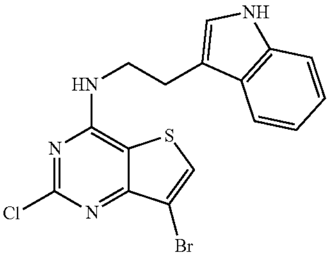 [SMILES: Clc1nc(NCCc2c[nH]c3ccccc23)c2scc(Br)c2n1]

To a solution of 7-bromo-2,4-dichloro-thieno[3,2-d]pyrimidine (100 mg, 352.16 umol, 1 eq) and 2-(1H-indol-3-yl)ethanamine (84.63 mg, 528.24 umol, 1.5 eq) in i-PrOH (3 mL) was added DIEA (136.54 mg, 1.06 mmol, 184.02 uL, 3 eq). The mixture was stirred at 50° C. for 3 h. LC-MS showed no starting material was remained and 93% of desired compound was detected. The reaction mixture was concentrated under reduced pressure to give a residue which was purified on silica gel column chromatography (from DCM/MeOH=1/0 to 100/1, TLC: PE/EtOAc=3/1, $R_f$=0.42) to give 7-bromo-2-chloro-N-[2-(1H-indol-3-yl)ethyl]thieno[3,2-d]pyrimidin-4-amine (140 mg, 339.94 umol, 96.53% yield, 99% purity) as gray solid. $^1$H NMR (400 MHz, $CDCl_3$) δ ppm 8.11 (s, 1H), 7.69-7.66 (m, 2H), 7.43 (d, J=8.2 Hz, 1H), 7.25-7.23 (m, 1H), 7.18-7.14 (m, 1H), 7.09 (d, J=2.2 Hz, 1H), 5.25 (s, 1H), 4.01 (q, J=6.4 Hz, 2H), 3.18 (t, J=6.5 Hz, 2H); ES-LCMS m/z 406.9, 408.9 $[M+H]^+$.

Step 2: N-(2-(1H-indol-3-yl)ethyl)-2-chloro-7-(prop-1-en-2-yl)thieno[3,2-d]pyrimidin-4-amine

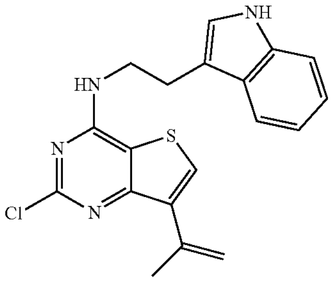 [SMILES: C=C(C)c1csc2c(NCCc3c[nH]c4ccccc34)nc(Cl)nc12]

7-Bromo-2-chloro-N-[2-(1H-indol-3-yl)ethyl]thieno[3,2-d]pyrimidin-4-amine (120 mg, 291.38 umol, 1 eq), 2-isopropenyl-4,4,5,5-tetramethyl-1,3,2-dioxaborolane (39.17 mg, 233.10 umol, 0.8 eq), $Pd(dppf)Cl_2$ (42.64 mg, 58.28 umol, 0.2 eq) and $Cs_2CO_3$ (284.81 mg, 874.14 umol, 3.0 eq) in 1,4-dioxane (5 mL) and $H_2O$ (1 mL) were taken up into a microwave tube. The tube was purged with $N_2$ for 3 min then sealed and heated at 80° C. for 10 min under microwave. LC-MS showed most of starting material was consumed and 68% of desired compound was detected. The combined reaction mixture was diluted with $H_2O$ (20 mL) and extracted with EtOAc (20 mL×3). The combined organic layers were dried over anhydrous $Na_2SO_4$, filtered and concentrated under reduced pressure to give a residue which was purified on silica gel column chromatography (from PE/EtOAc=1/0 to 10/3, TLC: PE/EtOAc=3/1, $R_f$=0.45) to give the product N-(2-(1H-indol-3-yl)ethyl)-2-chloro-7-(prop-1-en-2-yl)thieno[3,2-d]pyrimidin-4-amine (95 mg, 73.85% yield, 98% purity) as light yellow oil; $^1$H NMR (400 MHz, $CDCl_3$) δ ppm 8.10 (s, 1H), 7.69 (d, J=7.8 Hz, 1H), 7.51 (s, 1H), 7.42 (d, J=8.0 Hz, 1H), 7.26-7.22 (m, 1H), 7.20-7.13 (m, 1H), 7.09 (d, J=2.3 Hz, 1H), 6.37 (s, 1H), 5.38 (s, 1H), 5.11 (s, 1H), 4.00 (q, J=6.4 Hz, 2H), 3.18 (t, J=6.7 Hz, 2H), 2.21 (s, 3H); ES-LCMS m/z 369.0, 371.0 $[M+H]^+$.

Step 3: N-(2-(1H-indol-3-yl)ethyl)-2-(5-fluoropyridin-3-yl)-7-(prop-1-en-2-yl)thieno[3,2-d]pyrimidin-4-amine

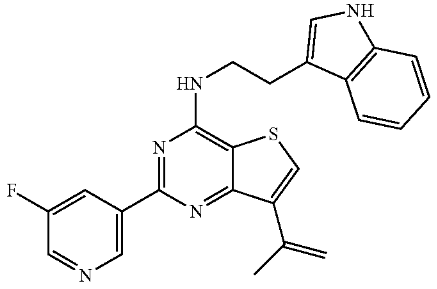 [SMILES: C=C(C)c1csc2c(NCCc3c[nH]c4ccccc34)nc(-c3cncc(F)c3)nc12]

2-Chloro-N-[2-(1H-indol-3-yl)ethyl]-7-isopropenyl-thieno[3,2-d]pyrimidin-4-amine (95 mg, 252.38 umol, 1 eq), (5-fluoro-3-pyridyl)boronic acid (53.34 mg, 378.58 umol, 1.5 eq), Pd(dppf)$Cl_2$ (18.47 mg, 25.24 umol, 0.1 eq) and $Cs_2CO_3$ (246.69 mg, 757.15 umol, 3 eq) in 1,4-dioxane (2 mL) and $H_2O$ (0.5 mL) were taken up into a microwave tube. The sealed tube was purged with $N_2$ for 3 min then heated at 110° C. for 30 min under microwave. LC-MS showed most of starting material was consumed and 85% of desired compound was detected. The reaction mixture was concentrated under reduced pressure to give a residue which was purified on silica gel column chromatography (from PE/EtOAc=1/0 to 10/3, TLC: PE/EtOAc=3/1, $R_f$=0.44) to give the product 2-(5-fluoro-3-pyridyl)-N-[2-(1H-indol-3-yl)ethyl]-7-isopropenyl-thieno[3,2-d]pyrimidin-4-amine (85 mg, 188.00 umol, 74.49% yield, 95% purity) as oil. $^1$H NMR (400 MHz, $CDCl_3$) δ ppm 9.59 (s, 1H), 8.55 (d, J=2.6 Hz, 1H), 8.48 (d, J=10.1 Hz, 1H), 8.07 (s, 1H), 7.69 (d, J=7.9 Hz, 1H), 7.56 (s, 1H), 7.42 (d, J=7.9 Hz, 1H), 7.26-7.22 (m, 1H), 7.20-7.15 (m, 1H), 7.11 (s, 1H), 6.70 (s, 1H), 5.46 (s, 1H), 5.06 (s, 1H), 4.14 (q, J=6.5 Hz, 2H), 3.26 (t, J=6.5 Hz, 2H), 2.30 (s, 3H); ES-LCMS m/z 430.0 $[M+H]^+$.

Step 4: N-(2-(1H-indol-3-yl)ethyl)-2-(5-fluoropyridin-3-yl)-7-isopropylthieno[3,2-d]pyrimidin-4-amine (I-3)

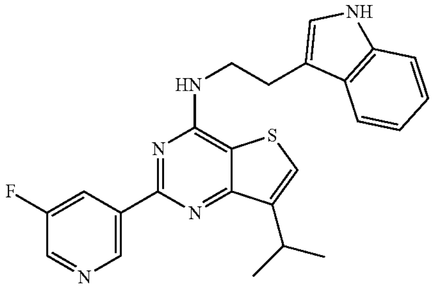 [SMILES: CC(C)c1csc2c(NCCc3c[nH]c4ccccc34)nc(-c3cncc(F)c3)nc12]

To a solution of 2-(5-fluoro-3-pyridyl)-N-[2-(1H-indol-3-yl)ethyl]-7-isopropenyl-thieno[3,2-d]pyrimidin-4-amine (50 mg, 110.59 umol, 1 eq) in MeOH (20 mL) and THF (2 mL) was added Pd/C (10%, 50 mg) under $N_2$. The suspension was degassed under vacuum and purged with $H_2$ for 3 times. The mixture was stirred under $H_2$ (15 psi) at 10-15° C. for 0.5 h. LC-MS showed no starting material was remained and 95% of desired compound was detected. The reaction mixture was filtered and the filtrate was concentrated under reduced pressure. The residue was purified by preparative HPLC (MeCN/$H_2O$ as eluents, acidic condition, Instrument: DC/Phenomenex Kinetex XB-C18 150 mm*30 mm, 5 am/Mobile phase: water(0.05% HCl)-ACN/Gradient: B from 62% to 92% in 10 min/Flow rate: 25 mL/min) followed by lyophilization to yield 2-(5-fluoro-3-pyridyl)-N-[2-(1H-indol-3-yl)ethyl]-7-isopropyl-thieno[3,2-d]pyrimidin-4-amine (40.32 mg, 74.05 umol, 66.96% yield, 99.34% purity, 3HCl salt) as a yellow solid. 1H NMR (400 MHz, DMSO-$d_6$) δ ppm 10.85 (s, 1H), 9.46 (s, 1H), 8.69 (d, J=2.8 Hz, 1H), 8.42 (d, J=10.0 Hz, 1H), 8.19 (t, J=5.6 Hz, 1H), 7.77 (s, 1H), 7.64 (d, J=8.0 Hz, 1H), 7.34 (d, J=8.0 Hz, 1H), 7.22 (d, J=2.0 Hz, 1H), 7.07 (t, J=7.4 Hz, 1H), 6.99-6.95 (m, 1H), 3.93-3.87 (m, 2H), 3.46-3.41 (m, 1H), 3.12 (t, J=7.4 Hz, 2H), 1.37 (d, J=6.8 Hz, 6H); ES-LCMS m/z 432.0 $[M+H]^+$.

Example 7

Synthesis of I-2

I-2

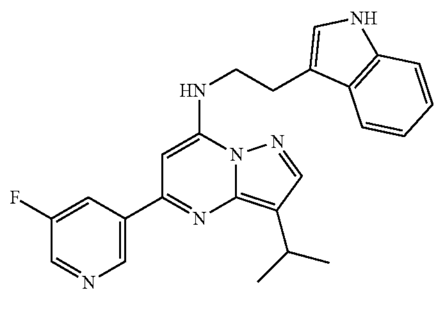

Synthesis Scheme:

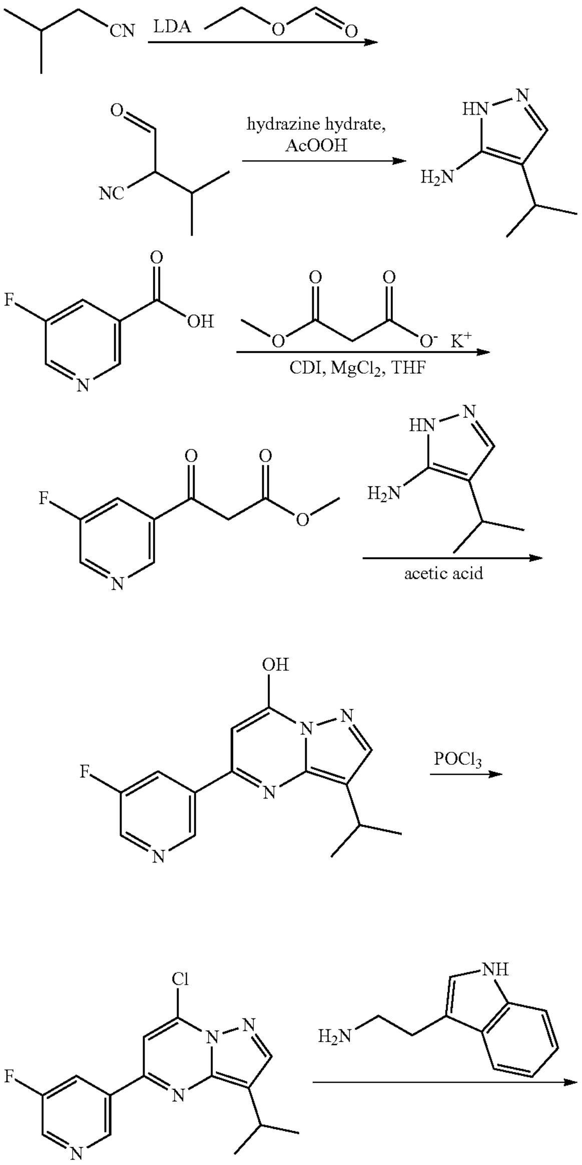

-continued

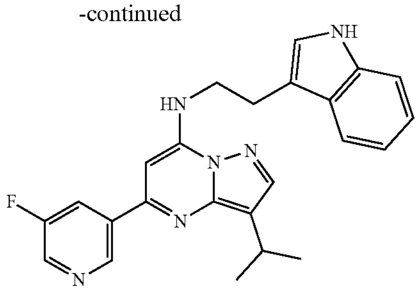

I-2

Step 1: 2-Formyl-3-methylbutanenitrile

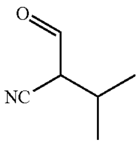

To a mixture of diisopropylamine (2.43 g, 24.06 mmol, 3.40 mL, 1 eq) in THF (20 mL) was added n-BuLi (2.5 M, 10.10 mL, 1.05 eq) dropwise at −78° C. under $N_2$. The mixture was stirred at −78° C. for 10 min, then warmed up to 0° C. and stirred for 1 h. The mixture was cooled to −78° C., 3-methylbutanenitrile (2 g, 24.06 mmol, 2.53 mL, 1 eq) dissolved in THF (15 mL, anhydrous) was added dropwise and stirred at −78° C. for 10 min. A solution of ethyl formate (1.87 g, 25.26 mmol, 2.03 mL, 1.05 eq) in THF (15 mL, anhydrous) was added dropwise and stirred at −78° C. for 40 min, then the mixture was warmed to 5-14° C. for 16 h. TLC (PE/EA=3/1, $R_f$=0.34) indicated one major new spot was detected. The reaction mixture was quenched by addition 1 N HCl solution (50 mL) at −78° C., and extracted with EtOAc (50 mL×3). The combined organic layers were dried over anhydrous $Na_2SO_4$, filtered and concentrated under reduced pressure to give a residue which was purified on silica gel column chromatography (from PE/EtOAc=1/0 to 1/4, TLC: PE/EtOAc=3/1, $R_f$=0.34) to give 2-formyl-3-methyl-butanenitrile (2 g, 16.20 mmol, 67.32% yield, 90% purity) as light yellow oil. $^1H$ NMR (400 MHz, $CDCl_3$) δ ppm 9.57 (s, 1H), 3.43 (d, J=4.4 Hz, 1H), 2.56-2.40 (m, 1H), 1.20 (d, J=6.8 Hz, 3H), 1.12 (d, J=6.8 Hz, 3H).

Step 2: 4-Isopropyl-1H-pyrazol-5-amine

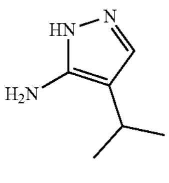

A mixture of 2-formyl-3-methyl-butanenitrile (500 mg, 4.05 mmol, 1 eq), hydrazine hydrate (168.67 mg, 5.26 mmol, 190.37 uL, 1.3 eq) and AcOH (425.50 mg, 7.09 mmol, 405.24 uL, 1.75 eq) in EtOH (20 mL) was degassed and purged with $N_2$ for 3 times. The mixture was stirred at 80-90° C. (reflux) for 16 h under $N_2$ atmosphere then concentrated under reduced pressure. The residue was diluted with sat. $NaHCO_3$ solution (20 mL) and extracted with DCM (20 mL×3). The combined organic layers were dried over anhydrous $Na_2SO_4$, filtered and concentrated under reduced pressure to give the crude product 4-isopropyl-1H-pyrazol-5-amine (420 mg, 3.02 mmol, 74.58% yield, 90% purity) as yellow solid, which was used in the next step without further purification. $^1H$ NMR (400 MHz, $CDCl_3$) δ ppm 7.13 (s, 1H), 2.69 (t, J=6.9 Hz, 1H), 1.21 (d, J=6.8 Hz, 6H).

Step 3: Methyl 3-(5-fluoropyridin-3-yl)-3-oxopropanoate

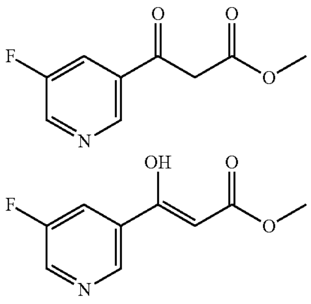

To a solution of 5-fluoropyridine-3-carboxylic acid (500 mg, 3.54 mmol, 1 eq) in THF (20 mL) was added CDI (689.51 mg, 4.25 mmol, 1.2 eq). The mixture was stirred at 5-14° C. for 2 h. (3-Methoxy-3-oxo-propanoyl)oxypotassium (553.43 mg, 3.54 mmol, 1 eq) and $MgCl_2$ (337.39 mg, 3.54 mmol, 1 eq) was added and the reaction was stirred at 5-14° C. for 16 h. TLC (PE/EA=1/1, $R_f$=0.58) indicated the starting material was consumed and one major new spot with larger polarity was detected. The reaction mixture was diluted with 3 N HCl solution (20 mL) and extracted with EtOAc (20 mL×3). The combined organic layers were dried over anhydrous $Na_2SO_4$, filtered and concentrated under reduced pressure to give a residue. The residue was purified on silica gel column chromatography (from PE/EtOAc=1/0 to 1/4, TLC: PE/EtOAc=1/1, $R_f$=0.58) to give methyl 3-(5-fluoro-3-pyridyl)-3-oxo-propanoate (175 mg, 843.21 umol, 23.80% yield, 95% purity) as a white solid and methyl 3-(5-fluoro-3-pyridyl)-3-oxo-propanoate (175 mg, 843.21 umol, 23.80% yield, 95% purity) as a white solid. $^1H$ NMR (400 MHz, $CDCl_3$) δ ppm 12.48 (s, 1H), 8.97 (s, 1H), 8.82 (s, 1H), 8.70 (d, J=2.6 Hz, 1H), 8.56 (d, J=2.6 Hz, 1H), 7.96 (d, J=2.2, 8.6 Hz, 1H), 7.86-7.73 (m, 1H), 5.75 (s, 1H), 4.04 (s, 2H), 3.84 (s, 3H), 3.78 (s, 3H); ES-LCMS m/z 198.1 $[M+H]^+$.

Step 4: 5-(5-Fluoropyridin-3-yl)-3-isopropylpyrazolo[1,5-a]pyrimidin-7-ol

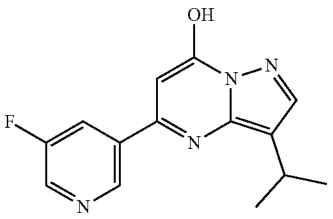 [SMILES: CC(C)c1cnn2c(O)cc(-c3cncc(F)c3)nc12]

To a solution of methyl 3-(5-fluoro-3-pyridyl)-3-oxo-propanoate (200 mg, 963.67 umol, 1 eq) in AcOH (5 mL) was added 4-isopropyl-1H-pyrazol-5-amine (134.03 mg, 963.67 umol, 1 eq). The mixture was stirred at 120° C. for 0.5 h. LCMS showed starting material was consumed completely and one main peak with desired MS was detected. The reaction mixture was concentrated under reduced pressure to give the crude product 5-(5-fluoro-3-pyridyl)-3-isopropyl-pyrazolo[1,5-a]pyrimidin-7-ol (300 mg, 639.05 umol, 66.31% yield, 58% purity) as yellow oil, which was used in the next step without further purification. $^1$H NMR (400 MHz, $CD_3OD$) δ ppm 8.79 (m, 1H), 8.63-8.67 (m, 1H), 8.09-8.06 (m, 1H), 7.87 (m, 1H), 6.06 (m, 1H), 3.26-3.25 (m, 1H), 2.75-2.70 (m, 1H), 1.30 (d, J=6.8 Hz, 3H), 1.15-1.09 (m, 3H); ES-LCMS m/z 567.0 $[2M+Na]^+$.

Step 5: 7-Chloro-5-(5-fluoropyridin-3-yl)-3-isopropylpyrazolo[1,5-a]pyrimidine

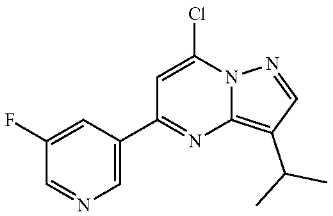 [SMILES: CC(C)c1cnn2c(Cl)cc(-c3cncc(F)c3)nc12]

A solution of 5-(5-fluoropyridin-3-yl)-3-isopropylpyrazolo[1,5-a]pyrimidin-7-ol (300 mg, 639.05 umol, 1 eq) in $POCl_3$ (4.95 g, 32.28 mmol, 3 mL, 50.52 eq) was stirred at 110° C. for 3 h. LC-MS showed no starting material was remained and 67% of desired compound was detected. The reaction mixture was concentrated under reduced pressure then diluted with DCM (20 mL×2), concentrated under reduced pressure to give a residue which was purified on silica gel column chromatography (from PE/EtOAc=1/0 to 2/5, TLC: PE/EtOAc=1/1, $R_f$=0.64) to give the product 7-chloro-5-(5-fluoropyridin-3-yl)-3-isopropylpyrazolo[1,5-a]pyrimidine (140 mg, 385.25 umol, 60.28% yield, 80% purity) as a yellow solid. $^1$H NMR (400 MHz, $CDCl_3$) δ ppm 9.10 (s, 1H), 8.61-8.60 (m, 1H), 8.22-8.14 (m, 2H), 7.41-7.27 (m, 1H), 3.47-3.38 (m, 1H), 1.48-1.44 (m, 6H); ES-LCMS m/z 291.0, 293.0$[M+H]^+$.

Step 6: N-(2-(1H-indol-3-yl)ethyl)-5-(5-fluoropyridin-3-yl)-3-isopropylpyrazolo[1,5-a]pyrimidin-7-amine (I-2)

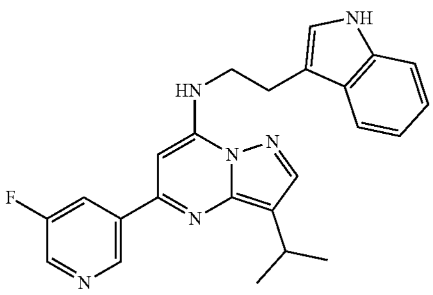 [SMILES: CC(C)c1cnn2c(NCCc3c[nH]c4ccccc34)cc(-c3cncc(F)c3)nc12]

To a solution of 7-chloro-5-(5-fluoro-3-pyridyl)-3-isopropyl-pyrazolo[1,5-a]pyrimidine (80 mg, 220.14 umol, 1 eq) and 2-(1H-indol-3-yl)ethanamine (52.90 mg, 330.21 umol, 1.5 eq) in i-PrOH (3 mL) was added DIEA (85.36 mg, 660.42 umol, 115.03 uL, 3.0 eq). The mixture was stirred at 50° C. for 3 h. LCMS showed no starting material was remained and 92% of desired compound was detected. The reaction mixture was concentrated under reduced pressure and the residue was purified by preparative HPLC (MeCN/$H_2O$ as eluents, acidic condition, Instrument: DC/Phenomenex Kinetex XB-C18 150 mm*30 mm, 5 μm/Mobile phase: water(0.05% HCl)-ACN/Gradient: B from 47% to 57% in 10 min/Flow rate: 25 mL/min) followed by lyophilization to yield 5-(5-fluoro-3-pyridyl)-N-[2-(1H-indol-3-yl)ethyl]-3-isopropyl-pyrazolo[1,5-a]pyrimidin-7-amine (88.45 mg, 168.66 umol, 76.61% yield, 99.89% purity, 3HCl salt) as a yellow solid. $^1$H NMR (400 MHz, $CD_3OD$) δ ppm 8.73 (d, J=2.2 Hz, 1H), 8.34 (s, 1H), 8.15 (s, 1H), 7.55 (d, J=8.6 Hz, 1H), 7.43 (d, J=7.9 Hz, 1H), 7.07 (d, J=8.2 Hz, 1H), 6.94 (s, 1H), 6.86 (t, J=7.2 Hz, 1H), 6.72 (t, J=7.4 Hz, 1H), 5.71 (s, 1H), 3.95 (t, J=5.7 Hz, 2H), 3.17-3.12 (m, 3H), 1.26 (d, J=6.8 Hz, 6H); ES-LCMS m/z 415.2 $[M+H]^+$.

Example 8

Synthesis of I-10

I-10

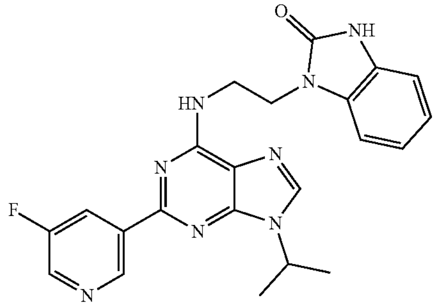

Synthesis Scheme:

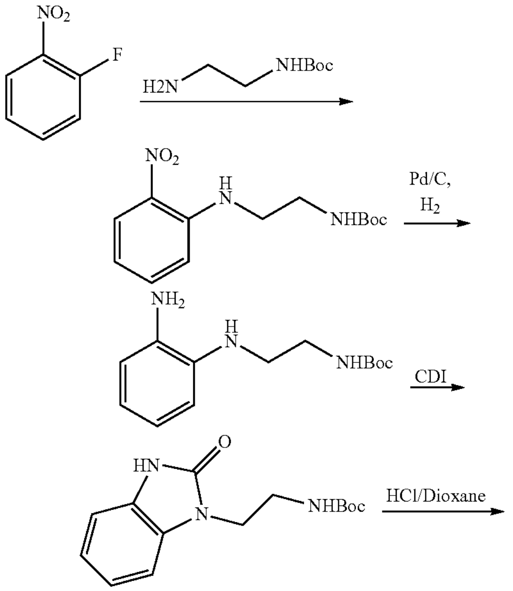

-continued

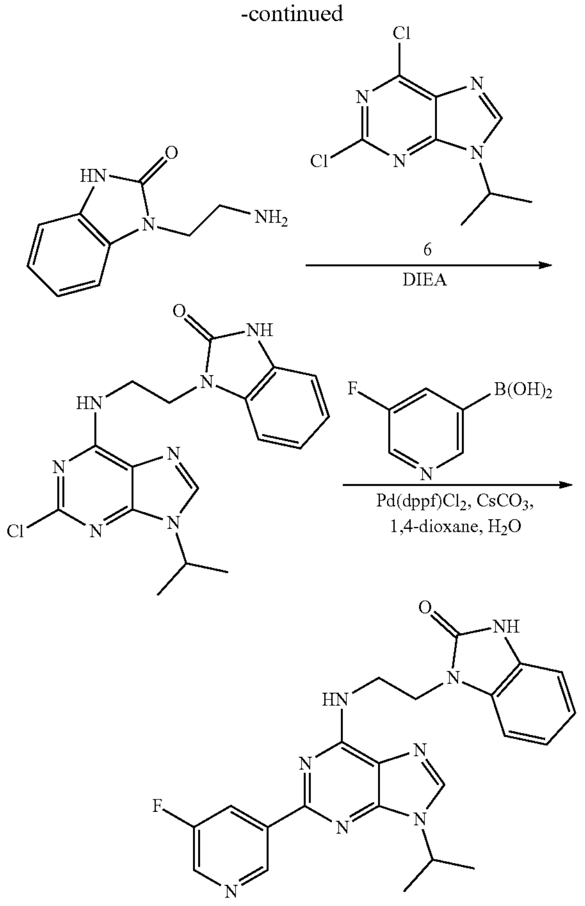

I-10

Step 1: tert-Butyl N-[2-(2-nitroanilino)ethyl]carbamate

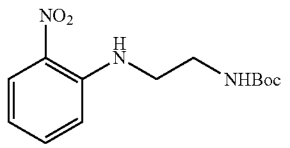 [SMILES: CC(C)(C)OC(=O)NCCNc1ccccc1[N+](=O)[O-]]

To a solution of 1-fluoro-2-nitro-benzene (10 g, 70.87 mmol, 7.46 mL, 1 eq) and tert-butyl N-(2-aminoethyl) carbamate (11.35 g, 70.87 mmol, 11.13 mL, 1 eq) in DMF (50 mL) was added $K_2CO_3$ (15.67 g, 113.39 mmol, 1.6 eq). The mixture was stirred at 70° C. for 18 h. TLC (PE/EtOAc=5/1, $R_f$=0.69) showed most starting material was consumed. The mixture was diluted with $H_2O$ (100 mL), extracted with EtOAc (100 mL×3). The combined orangic layers were dried over anhydrous $Na_2SO_4$, filtered and concentrated under reduced pressure. The crude material was purified on silica gel column chromatography (from PE/EtOAc=1/0 to 5/4, TLC: PE/EtOAc=5/1, $R_f$=0.69) to give tert-butyl N-[2-(2-nitroanilino)ethyl]carbamate (19 g, 67.54 mmol, 95.3% yield, 100% purity) as an orange solid. $^1$H NMR (400 MHz, $CDCl_3$) δ ppm 8.19 (d, J=8.8 Hz, 1H), 7.47-7.43 (m, 1H), 6.95 (d, J=8.4 Hz, 1H), 6.69-6.65 (m, 1H), 3.50-3.43 (m, 4H), 1.46 (s, 9H); ES-LCMS m/z 304.0 $[M+Na]^+$.

Step 2: tert-Butyl N-[2-(2-aminoanilino)ethyl]carbamate

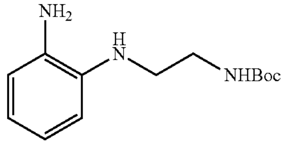 [SMILES: CC(C)(C)OC(=O)NCCNc1ccccc1N]

To a solution of tert-butyl N-[2-(2-nitroanilino)ethyl]carbamate (5 g, 17.77 mmol, 1 eq) in MeOH (50 mL) was added Pd/C (10%, 500 mg) under $N_2$ atmosphere. The suspension was degassed and purged with $H_2$ for 3 times. The mixture was stirred under $H_2$ (15 Psi) at 2-9° C. for 18 h. LC-MS showed the staring material was consumed completely and one main peak with desired MS was detected. The mixture was filtered and concentrated under reduced pressure to give crude tert-butyl N-[2-(2-aminoanilino)ethyl]carbamate (4.4 g, 17.51 mmol, 98.50% yield, crude) as dark red oil which was used in the next step without further purification. $^1$H NMR (400 MHz, $CD_3OD$) δ ppm 6.70-6.67 (m, 2H), 6.62 (d, J=7.6 Hz, 1H), 6.56 (t, J=7.2 Hz, 1H), 3.29-3.26 (m, 2H), 3.18-3.17 (m, 2H), 1.42 (s, 9H); ES-LCMS m/z 252.2 $[M+H]^+$.

Step 3: tert-Butyl N-[2-(2-oxo-3H-benzimidazol-1-yl)ethyl]carbamate

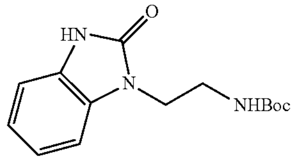 [SMILES: CC(C)(C)OC(=O)NCCn1c(=O)[nH]c2ccccc21]

To a solution of tert-butyl N-[2-(2-aminoanilino)ethyl]carbamate (2 g, 7.96 mmol, 1 eq) in THF (20 mL) was added CDI (1.55 g, 9.55 mmol, 1.2 eq). The mixture was stirred at 80° C. for 2 h. LC-MS showed starting material was consumed completely and one main peak with desired MS was detected. The mixture was diluted with EtOAc (50 mL), washed with citric acid solution (aq., 20 mL×2), dried over anhydrous $Na_2SO_4$, filtered and concentrated under reduced pressure to give a residue which was purified on silica gel column chromatography (from PE/EtOAc=1/0 to 5/4, TLC: PE/EtOAc=1/1, $R_f$=0.31). The slight yellow oil obtained was diluted with 1 NHCl solution (5 mL), filtered and collected the solid. The solid was triturated with isopropyl ether (20 mL), filtered and collected the product tert-butyl N-[2-(2-oxo-3H-benzimidazol-1-yl)ethyl]carbamate (1.63 g, 5.73 mmol, 72.0% yield, 97.52% purity) as a white solid. $^1$H NMR (400 MHz, $CD_3OD$) δ ppm 7.13-7.01 (m, 4H), 3.93 (t, J=6.0 Hz, 2H), 3.35-3.31 (m, 2H), 1.29, 1.17 (s, 9H); ES-LCMS m/z 300.1 $[M+H]^+$.

Step 4: 3-(2-Aminoethyl)-1H-benzimidazol-2-one

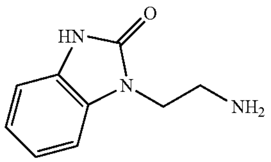 [SMILES: NCCn1c(=O)[nH]c2ccccc21]

To a solution of tert-butyl N-[2-(2-oxo-3H-benzimidazol-1-yl)ethyl]carbamate (646.02 mg, 2.27 mmol, 1 eq) in DCM (10 mL) was added HCl/1,4-dioxane (4 M, 5.00 mL, 8.80 eq) dropwise at 0° C. After addition, the mixture was stirred at 4-12° C. for 1 h. LC-MS showed most of starting material was consumed. The reaction mixture was concentrated under reduced pressure to give crude 3-(2-aminoethyl)-1H-benzimidazol-2-one (400 mg, 1.87 mmol, 82.4% yield, HCl salt) as a white solid, which was used in the next step without further purification. $^1$H NMR (400 MHz, $CD_3OD$) δ ppm 7.18-7.17 (m, 1H), 7.11-7.08 (m, 3H), 4.19-4.16 (m, 2H), 3.31-3.28 (m, 2H); ES-LCMS m/z 178.1 $[M+H]^+$.

Step 5: 3-[2-[(2-Chloro-9-isopropyl-purin-6-yl)amino]ethyl]-1H-benzimidazol-2-one

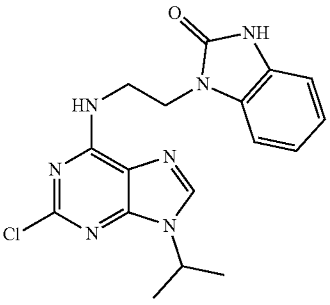 [SMILES: CC(C)n1cnc2c(NCCn3c(=O)[nH]c4ccccc43)nc(Cl)nc21]

To a solution of 2,6-dichloro-9-isopropyl-purine (200 mg, 827.24 umol, 1 eq) in isopropanol (10 mL) was added DIEA (427.65 mg, 3.31 mmol, 576.35 uL, 4.0 eq) and 3-(2-aminoethyl)-1H-benzimidazol-2-one (265.13 mg, 1.24 mmol, 1.5 eq, HCl). The mixture was stirred at 50° C. for 5 h. LC-MS showed most of starting material was consumed. The reaction mixture was concentrated under reduced pressure to remove isopropanol. The residue was diluted with $H_2O$ (20 mL) and extracted with DCM/isopropanol (20 mL×3, v/v=3/1). The combined organic layers were dried over anhydrous $Na_2SO_4$, filtered and concentrated under reduced pressure to give a residue. The residue was purified on silica gel column chromatography (from DCM/MeOH=1/0 to 10/1, TLC: DCM/MeOH=10/1, $R_f$=0.15) to give 3-[2-[(2-chloro-9-isopropyl-purin-6-yl)amino]ethyl]-1H-benzimidazol-2-one (280 mg, 730.45 umol, 88.3% yield, 97% purity) as a white solid; $^1$H NMR (400 MHz, $CD_3OD$) δ ppm 8.14 (s, 1H), 7.28 (d, J=7.2 Hz, 1H), 7.06-6.97 (m, 3H), 4.78-4.75 (m, 1H), 4.22 (t, J=6.0 Hz, 2H), 3.97 (t, J=6.0 Hz, 2H), 1.62 (d, J=6.4 Hz, 6H); ES-LCMS m/z 372.1, 374.0 $[M+H]^+$.

Step 6: 3-[2-[[2-(5-Fluoro-3-pyridyl)-9-isopropyl-purin-6-yl]amino]ethyl]-1H-benzimidazol-2-one (I-10)

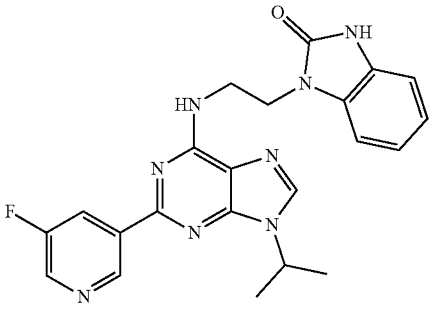 [SMILES: CC(C)n1cnc2c(NCCn3c(=O)[nH]c4ccccc43)nc(-c3cncc(F)c3)nc21]

To a solution of 3-[2-[(2-chloro-9-isopropyl-purin-6-yl)amino]ethyl]-1H-benzimidazol-2-one (100 mg, 260.88 umol, 1 eq) and (5-fluoro-3-pyridyl)boronic acid (73.52 mg, 521.75 umol, 2 eq) in 1,4-dioxane (2 mL) and $H_2O$ (0.5 mL) was added Pd(dppf)$Cl_2$ (9.54 mg, 13.04 umol, 0.05 eq) and $Cs_2CO_3$ (255.00 mg, 782.63 umol, 3 eq). The mixture was purged with $N_2$ for 3 min and stirred at 120° C. for 0.5 h under microwave. LC-MS showed most of starting material was consumed and desired compound was detected. The reaction mixture was concentrated under reduced pressure. The residue was diluted with EtOAc/MeOH/THF (10 mL/10 mL/10 mL) and stirred for 5 min, filtered. The filtrate was concentrated under reduced pressure to give a residue which was purified by preparative HPLC (MeCN/$H_2O$ as eluents, acidic condition, Instrument: DC/Phenomenex Kinetex XB-C18 150 mm*30 mm, 5 μm/Mobile phase: water(0.05% HCl)-ACN/Gradient: B from 20% to 50% in 12 min/Flow rate: 25 mL/min) followed by lyophilization to yield 3-[2-[[2-(5-fluoro-3-pyridyl)-9-isopropyl-purin-6-yl]amino]ethyl]-1H-benzimidazol-2-one (11.08 mg, 21.29 umol, 8.16% yield, 97.1% purity, 2HCl salt, 10.85 mg was delivered) as a light yellow solid. $^1$H NMR (400 MHz, $CD_3OD$) δ ppm 9.51-9.27 (m, 2H), 9.15-8.90 (m, 2H), 7.23 (d, J=7.8 Hz, 1H), 6.92 (t, J=7.8 Hz, 1H), 6.75 (t, J=7.5 Hz, 1H), 6.63 (d, J=7.8 Hz, 1H), 5.19-4.97 (m, 1H), 4.30-4.15 (m, 4H), 1.67 (d, J=6.8 Hz, 6H); ES-LCMS m/z 433.1 $[M+H]^+$.

Example 9

Synthesis of I-19

I-19

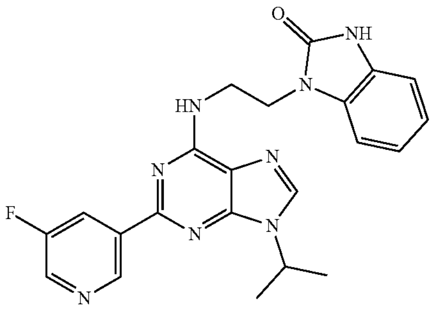

Synthetic Scheme:

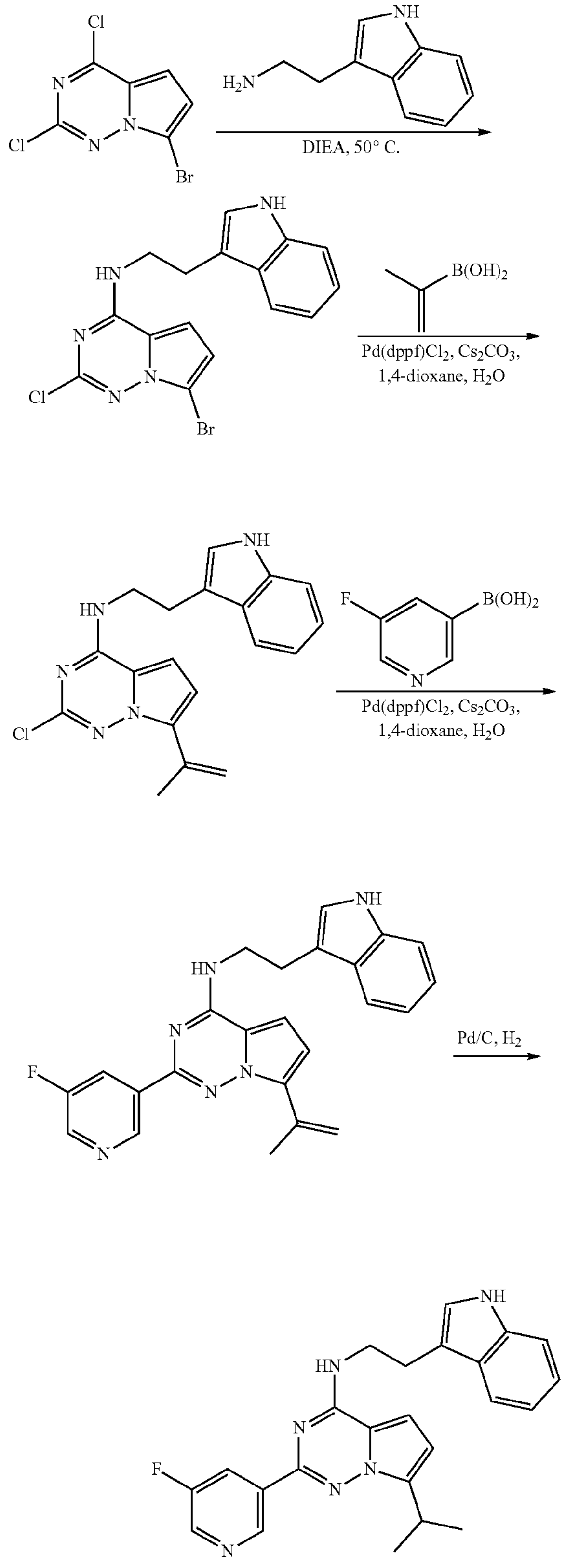

I-19

Step 1: N-(2-(1H-Indol-3-yl)ethyl)-7-bromo-2-chloropyrrolo[2,1-f][1,2,4]triazin-4-amine

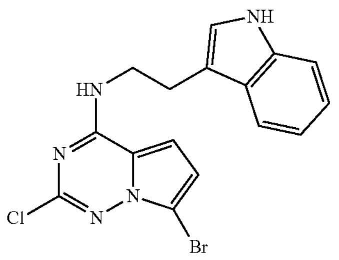 [SMILES: Clc1nc(NCCc2c[nH]c3ccccc23)c2ccc(Br)n2n1]

To a solution of 7-bromo-2,4-dichloro-pyrrolo[2,1-f][1,2,4]triazine (100 mg, 374.66 umol, 1 eq) in i-PrOH (3 mL) was added DIEA (242.10 mg, 1.87 mmol, 326.29 uL, 5.0 eq) and 2-(1H-indol-3-yl)ethanamine (78.03 mg, 487.06 umol, 1.3 eq). The mixture was stirred at 50° C. for 1.5 h. LC-MS showed the starting material was consumed completely and one main peak with desired MS was detected. The reaction mixture was diluted with $H_2O$ (15 mL) and extracted with DCM (15 mL×3). The combined organic layers were dried over $Na_2SO_4$, filtered and concentrated under reduced pressure to give a residue which was purified by flash silica gel chromatography (ISCO®; 4 g SepaFlash® Silica Flash Column, Eluent of 20-25% Ethyl acetate/Petroleum ether gradient @55 mL/min) to give 7-bromo-2-chloro-N-[2-(1H-indol-3-yl)ethyl]pyrrolo[2,1-f][1,2,4]triazin-4-amine (140 mg, 354.78 umol, 94.7% yield) as a white solid. $^1$H NMR (400 MHz, $CDCl_3$) δ ppm 8.08 (s, 1H), 7.66 (d, J=7.7 Hz, 1H), 7.42 (d, J=8.2 Hz, 1H), 7.26-7.23 (m, 1H), 7.19-7.14 (m, 1H), 7.09 (d, J=2.2 Hz, 1H), 6.59 (d, J=4.6 Hz, 1H), 6.40 (br s, 1H), 5.55 (m, 1H), 3.99 (q, J=6.2 Hz, 2H), 3.17 (t, J=6.6 Hz, 2H); ES-LCMS m/z 389.9, 392.0 $[M+H]^+$.

Step 2: N-(2-(1H-Indol-3-yl)ethyl)-2-chloro-7-(prop-1-en-2-yl)pyrrolo[2,1-f][1,2,4]triazin-4-amine

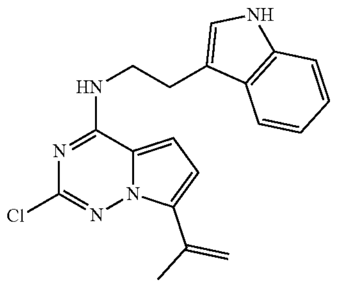 [SMILES: C=C(C)c1ccc2c(NCCc3c[nH]c4ccccc34)nc(Cl)nn12]

To a solution of 7-bromo-2-chloro-N-[2-(1H-indol-3-yl)ethyl]pyrrolo[2,1-f][1,2,4]triazin-4-amine (90 mg, 228.07 umol, 1 eq) in 1,4-dioxane (2 mL) and $H_2O$ (0.5 mL) was added 2-isopropenyl-4,4,5,5-tetramethyl-1,3,2-dioxaborolane (38.33 mg, 228.07 umol, 1.0 eq), $Pd(dppf)Cl_2$ (33.38 mg, 45.61 umol, 0.2 eq) and $Cs_2CO_3$ (222.93 mg, 684.22 umol, 3.0 eq). The mixture was stirred under microwave at 80° C. for 30 min. LCMS showed 67% of desired product was found. The reaction mixture was filtered and the filtrate was diluted with $H_2O$ (15 mL) then extracted with EtOAc (15 mL×3). The combined organic layers were dried over $Na_2SO_4$, filtered and concentrated under reduced pressure to give a residue which was purified by flash silica gel chromatography (ISCO®; 12 g SepaFlash® Silica Flash Column, Eluent of 10-13% Ethyl acetate/Petroleum ether gradient @50 mL/min) to give 2-chloro-N-[2-(1H-indol-3-yl)ethyl]-7-isopropenyl-pyrrolo[2,1-f][1,2,4]triazin-4-amine (65 mg, 144.10 umol, 63.2% yield) as colorless oil. $^1$H NMR (400 MHz, $CDCl_3$) δ ppm 8.08 (br s, 1H), 7.67 (d, J=7.7 Hz, 1H), 7.41 (d, J=8.2 Hz, 1H), 7.26-7.23 (m, 1H), 7.20-7.14 (m, 1H), 7.09 (d, J=2.2 Hz, 1H), 6.58 (d, J=4.6 Hz, 1H), 6.36 (br s, 1H), 6.25 (s, 1H), 5.50 (br s, 1H), 5.35 (s, 1H), 4.02-3.96 (m, 2H), 3.16 (t, J=6.5 Hz, 2H), 2.20 (s, 3H); ES-LCMS m/z 352.0, 354.0 $[M+H]^+$.

Step 3: N-(2-(1H-Indol-3-yl)ethyl)-2-(5-fluoropyridin-3-yl)-7-(prop-1-en-2-yl)pyrrolo[2,1-f][1,2,4]triazin-4-amine

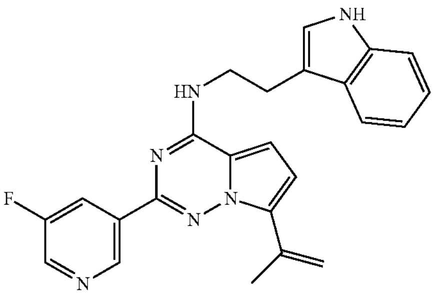 [SMILES: C=C(C)c1ccc2c(NCCc3c[nH]c4ccccc34)nc(-c3cncc(F)c3)nn12]

To a solution of 2-chloro-N-[2-(1H-indol-3-yl)ethyl]-7-isopropenyl-pyrrolo[2,1-f][1,2,4]triazin-4-amine (65 mg, 144.10 umol, 1 eq) in 1,4-dioxane (3 mL) and $H_2O$ (1 mL) was added (5-fluoro-3-pyridyl)boronic acid (30.46 mg, 216.15 umol, 1.5 eq), Pd(dppf)$Cl_2$ (15.82 mg, 21.62 umol, 0.15 eq) and $Cs_2CO_3$ (140.85 mg, 432.31 umol, 3.0 eq). The mixture was stirred at 110° C. under microwave for 0.5 h. LCMS showed about 72% of desired product was detected. The reaction mixture was filtered and the filtrate was diluted with $H_2O$ (15 mL) then extracted with EtOAc (15 mL×3). The combined organic layers were dried over $Na_2SO_4$, filtered and concentrated under reduced pressure to give a residue which was purified by preparative TLC (PE/EtOAc=1.5/1, $R_f$=0.6) to give 2-(5-fluoro-3-pyridyl)-N-[2-(1H-indol-3-yl)ethyl]-7-isopropenyl-pyrrolo[2,1-f][1,2,4]triazin-4-amine (40 mg, 76.61 umol, 53.2% yield) as a yellow solid. $^1$H NMR (400 MHz, $CDCl_3$) δ ppm 9.29 (s, 1H), 8.38 (d, J=2.9 Hz, 1H), 8.23-8.16 (m, 1H), 8.05 (br s, 1H), 7.55 (d, J=7.7 Hz, 1H), 7.30-7.27 (m, 1H), 7.30-7.24 (m, 1H), 7.14-7.09 (m, 1H), 7.07-7.02 (m, 1H), 6.95 (d, J=2.2 Hz, 1H), 6.54 (d, J=4.6 Hz, 1H), 6.34-6.23 (m, 2H), 5.45 (t, J=5.6 Hz, 1H), 5.27 (s, 1H), 3.95 (q, J=6.5 Hz, 2H), 3.09 (t, J=6.6 Hz, 2H), 2.15 (s, 3H); ES-LCMS m/z 413.1 $[M+H]^+$.

Step 4: N-(2-(1H-Indol-3-yl)ethyl)-2-(5-fluoropyridin-3-yl)-7-isopropylpyrrolo[2,1-f][1,2,4]triazin-4-amine (I-19)

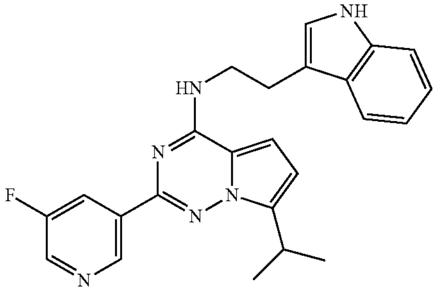 [SMILES: CC(C)c1ccc2c(NCCc3c[nH]c4ccccc34)nc(-c3cncc(F)c3)nn12]

To a solution of 2-(5-fluoro-3-pyridyl)-N-[2-(1H-indol-3-yl)ethyl]-7-isopropenyl-pyrrolo[2,1-f][1,2,4]triazin-4-amine (30 mg, 57.46 umol, 1 eq) in MeOH (8 mL) was added Pd/C (10%, 40 mg). The suspension was degassed under vacuum and purged with $H_2$ several times then the mixture was stirred at $H_2$ (15 psi) at 20° C. for 0.5 h. LC-MS showed the starting material was consumed completely and one main peak with desired MS was detected. The reaction mixture was filtered and concentrated under reduced pressure to give a residue which was purified by preparative HPLC (HCl condition; column: Phenomenex Kinetex XB-C18 150 mm*30 mm, 5 m; mobile phase: [water(0.05% HCl)-ACN]; B %: 75%-95%, 12 min) and the desired fraction was lyophilized to yield 2-(5-fluoro-3-pyridyl)-N-[2-(1H-indol-3-yl)ethyl]-7-isopropyl-pyrrolo[2,1-f][1,2,4]triazin-4-amine (6.75 mg, 12.89 umol, 17.72% yield, 100% purity, 3HCl salt) as a white solid. $^1$H NMR (400 MHz, $CD_3OD$) δ ppm 9.05 (s, 1H), 8.76 (br s, 1H), 8.42 (d, J=8.8 Hz, 1H), 7.63 (d, J=7.3 Hz, 1H), 7.23 (d, J=7.7 Hz, 1H), 7.06-6.97 (m, 3H), 6.92 (d, J=4.0 Hz, 1H), 6.54 (d, J=4.0 Hz, 1H), 4.01 (t, J=7.1 Hz, 2H), 3.55 (d, J=7.0, 14.1 Hz, 1H), 3.17 (t, J=6.8 Hz, 2H); ES-LCMS m/z 415.1 $[M+H]^+$.

Example 10

Synthesis of I-22

I-22

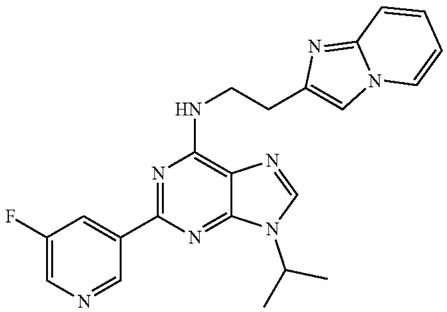

Step 1: 2-(Chloromethyl)imidazo[1,2-a]pyridine

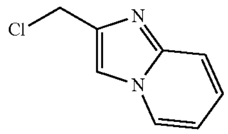 [SMILES: ClCc1cn2ccccc2n1]

To a solution of pyridin-2-amine (5 g, 53.13 mmol, 1 eq) in DME (10 mL) was added 1,3-dichloropropan-2-one (13.49 g, 106.25 mmol, 2 eq). The mixture was stirred at 20° C. for 1 h. The reaction mixture was concentrated under reduced pressure. The residue was dissolved in EtOH (50 mL) then stirred at 90° C. for 16 h. LC-MS showed the starting material was consumed completely and desired MS was detected. The reaction mixture was concentrated and the residue was hydrolyzed with saturated solution of sodium carbonate (100 mL). The reaction mixture was extracted with DCM (60 mL×3), combined, dried with $Na_2SO_4$, filtered, and concentrated under reduced pressure to yield 2-(chloromethyl)imidazo[1,2-a]pyridine (8.85 g, crude), which was used in the next step without further purification. $^1$H NMR (400 MHz, $CDCl_3$) δ ppm 8.14 (d, J=6.8 Hz, 1H), 7.70-7.59 (m, 2H), 7.26-7.20 (m, 1H), 6.85 (t, J=6.8 Hz, 1H), 4.79 (s, 2H); ES-LCMS m/z 167.2, 169.5 $[M+H]^+$.

Step 2: 2-Imidazo[1,2-a]pyridin-2-ylacetonitrile

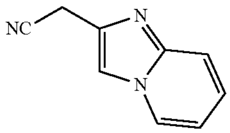 [SMILES: N#CCc1cn2ccccc2n1]

A mixture of 2-(chloromethyl)imidazo[1,2-a]pyridine (3 g, 18.01 mmol, 1 eq) and KCN (1.52 g, 23.41 mmol, 1.3 eq) in DMSO (50 mL) was degassed and purged with $N_2$ for 3 times. Then the mixture was stirred at 80° C. for 16 h under $N_2$ atmosphere. LC-MS showed 27% of the starting material was remained and 17% of desired compound was detected. The reaction mixture was quenched with water (200 mL) then extracted with EtOAc (100 mL×3). The combined organic layers were washed with brine (50 mL), dried over $Na_2SO_4$, filtered and concentrated under reduced pressure to give a residue which was purified by flash silica gel chromatography (from DCM/MeOH=1/0 to 10/1, TLC: DCM/MeOH=10/1, $R_f$=0.49) to yield 2-imidazo[1,2-a]pyridin-2-ylacetonitrile (200 mg, 890.75 umol, 5.0% yield, 70% purity) as a yellow solid. $^1$H NMR (400 MHz, DMSO-$d_6$) δ ppm 8.59-8.49 (m, 1H), 7.92 (s, 1H), 7.55-7.49 (m, 1H), 7.28-7.11 (m, 1H), 6.92-6.85 (m, 1H), 4.12 (s, 3H); ES-LCMS m/z 158.1 $[M+H]^+$.

Step 3: 2-Imidazo[1,2-a]pyridin-2-ylethanamine

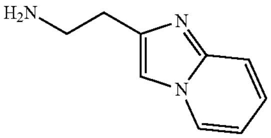 [SMILES: NCCc1cn2ccccc2n1]

To a solution of 2-imidazo[1,2-a]pyridin-2-ylacetonitrile (100 mg, 445.37 umol, 1 eq) in THF (5 mL) was added $BH_3$-$Me_2S$ (10 M, 445.37 uL, 10 eq). The mixture was stirred at 80° C. for 2 h until LC-MS showed the starting material was consumed completely and desired MS was detected. The reaction mixture was quenched with MeOH at 10° C. followed by stirring at 80° C. for 1 h. The resulting mixture was concentrated under reduced pressure to yield 2-imidazo[1,2-a]pyridin-2-ylethanamine (71.8 mg, crude) as a white solid, which was used in the next step without further purification. $^1$H NMR (400 MHz, $CD_3OD$) δ ppm 8.82-8.61 (m, 1H), 8.21-8.06 (m, 1H), 8.02-7.61 (m, 2H), 7.52-7.21 (m, 1H), 3.61-3.38 (m, 2H), 3.35-3.28 (m, 2H); ES-LCMS m/z 162.1 $[M+H]^+$.

Step 4: 2-(5-Fluoro-3-pyridyl)-N-(2-imidazo[1,2-a]pyridin-2-ylethyl)-9-isopropyl-purin-6-amine (I-22)

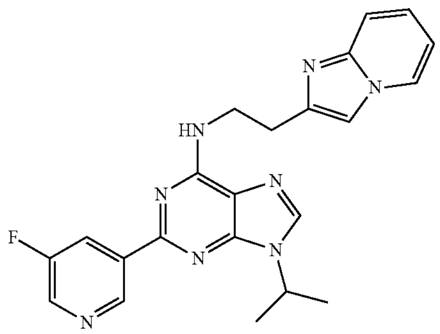 [SMILES: CC(C)n1cnc2c(NCCc3cn4ccccc4n3)nc(-c3cncc(F)c3)nc21]

To a solution of 6-chloro-2-(5-fluoro-3-pyridyl)-9-isopropyl-purine (50 mg, 164.55 umol, 1 eq) in i-PrOH (5 mL) was added DIEA (106.33 mg, 822.73 umol, 143.31 uL, 5 eq) and 2-imidazo[1,2-a]pyridin-2-ylethanamine (71.8 mg, 445.40 umol, 2.71 eq). The mixture was stirred at 90° C. for 16 h. LC-MS showed the starting material was consumed completely and one main peak with desired MS was detected. The reaction mixture was concentrated under reduced pressure to give a residue which was purified by preparative HPLC (column: Phenomenex Kinetex XB-C18 150 mm×30 mm, 5 m; mobile phase: [water (0.05% HCl)-ACN]; B %: 10%-38%, 12 min) and the desired fraction was lyophilized to yield 2-(5-fluoro-3-pyridyl)-N-(2-imidazo[1,2-a]pyridin-2-ylethyl)-9-isopropyl-purin-6-amine (22.38 mg, 41.71 umol, 25.4% yield, 98% purity, 3HCl) as a yellow solid. $^1$H NMR (400 MHz, $CD_3OD$) δ ppm 9.62 (s, 1H), 9.36 (s, 1H), 9.18-8.90 (m, 2H), 8.71 (d, J=6.2 Hz, 1H), 8.17 (s, 1H), 7.96-7.76 (m, 2H), 7.43 (t, J=6.8 Hz, 1H), 5.16 (s, 1H), 4.30 (s, 2H), 3.43 (t, J=6.4 Hz, 2H), 1.75 (d, J=6.8 Hz, 6H); ES-LCMS m/z 417.1 $[M+H]^+$.

Example 11

Synthesis of I-20

I-20

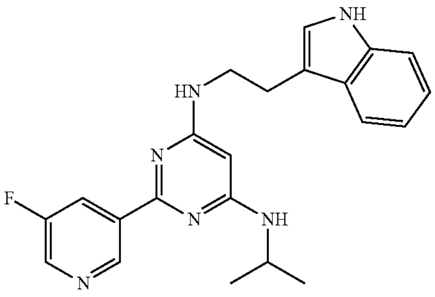

Synthetic Scheme:

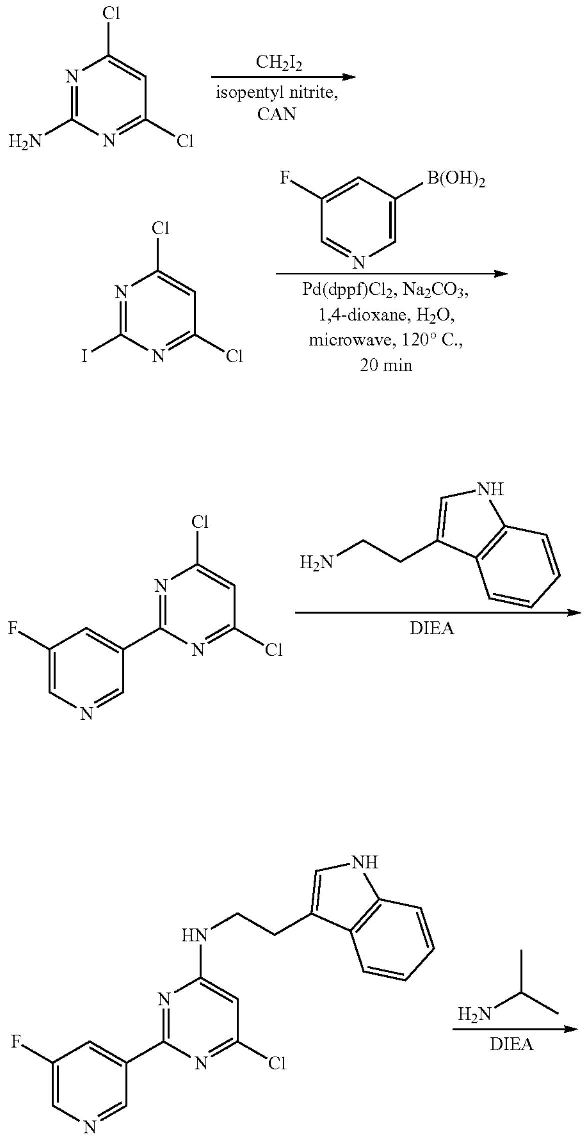

-continued

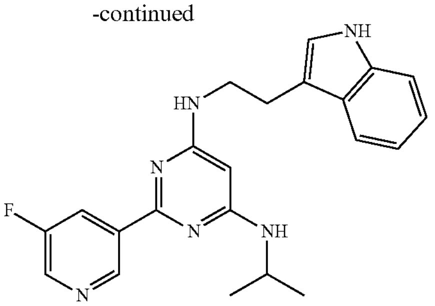

I-20

Step 1: 4,6-Dichloro-2-iodo-pyrimidine

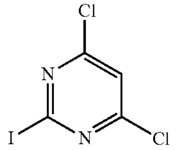

To a solution of 4,6-dichloropyrimidin-2-amine (5 g, 30.49 mmol, 1 eq) in acetonitrile (40 mL) was added $CH_2I_2$ (8.98 g, 33.54 mmol, 2.71 mL, 1.1 eq) and isopentyl nitrite (17.86 g, 152.45 mmol, 20.53 mL, 5.0 eq). The mixture was stirred at 80° C. for 3.5 h. LCMS showed the starting material was consumed completely and one main peak was detected. The reaction mixture was concentrated under reduced pressure to remove acetonitrile. The residue was diluted with EtOAc (50 mL), washed with $Na_2SO_3$ solution (50 mL×2), dried over $Na_2SO_4$, filtered and concentrated under reduced pressure to give a residue which was purified by flash silica gel chromatography (from PE/EtOAc=100/1 to 10/1, TLC: PE/EtOAc=3/1, $R_f$=0.90) to yield 4,6-dichloro-2-iodo-pyrimidine (6.32 g, 22.60 mmol, 74.1% yield, 98.3% purity) as a white solid. $^1H$ NMR (400 MHz, $CD_3OD$) δ ppm 7.79-7.76 (m, 1H); ES-LCMS m/z 274.7, 276.8 $[M+H]^+$.

Step 2: 4,6-Dichloro-2-(5-fluoro-3-pyridyl)pyrimidine

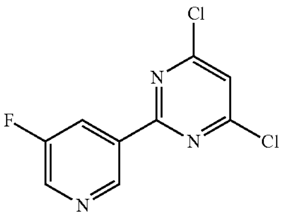 [SMILES: Fc1cncc(-c2nc(Cl)cc(Cl)n2)c1]

4,6-Dichloro-2-iodo-pyrimidine (500 mg, 1.79 mmol, 1 eq), (5-fluoro-3-pyridyl)boronic acid (251.96 mg, 1.79 mmol, 1 eq), $Na_2CO_3$ (568.55 mg, 5.36 mmol, 3.0 eq) and $Pd(dppf)Cl_2$ (130.84 mg, 178.81 umol, 0.1 eq) in 1,4-dioxane (6 mL) and water (1.2 mL) were taken up into a microwave tube. The sealed tube was heated at 80° C. for 30 min under microwave. LCMS showed 53% of desired compound was detected. The reaction mixture was diluted with EtOAc (30 mL) and filtered through a pad of celite. The filtrate was concentrated under reduced pressure to give a residue which was purified by flash silica gel chromatography (from PE/EtOAc=100/1 to 10/3, TLC: PE/EtOAc=3/1, $R_f$=0.80) to yield 4,6-dichloro-2-(5-fluoro-3-pyridyl)pyrimidine (165 mg, 676.08 umol, 37.8% yield, 100% purity) as a white solid. $^1$H NMR (400 MHz, $CD_3OD$) δ ppm 9.36 (s, 1H), 8.67 (d, J=2.9 Hz, 1H), 8.52-8.44 (m, 1H), 7.76 (s, 1H); ES-LCMS m/z 243.9, 245.9 $[M+H]^+$.

Step 3: 6-Chloro-2-(5-fluoro-3-pyridyl)-N-[2-(1H-indol-3-yl)ethyl]pyrimidin-4-amine

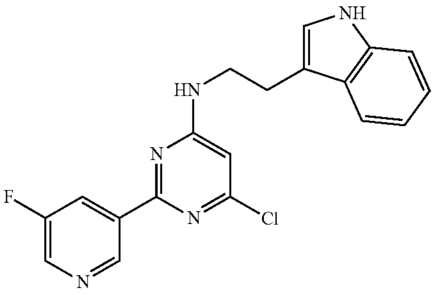 [SMILES: Fc1cncc(-c2nc(Cl)cc(NCCc3c[nH]c4ccccc34)n2)c1]

To a solution of 4,6-dichloro-2-(5-fluoro-3-pyridyl)pyrimidine (165 mg, 676.08 umol, 1.0 eq) in i-PrOH (10 mL) was added DIEA (262.13 mg, 2.03 mmol, 353.28 uL, 3.0 eq) and 2-(1H-indol-3-yl)ethanamine (108.32 mg, 676.08 umol, 1.0 eq). The mixture was stirred at 50° C. for 3 h. LCMS showed 88% of desired compound was detected. The reaction mixture was concentrated to yield 6-chloro-2-(5-fluoro-3-pyridyl)-N-[2-(1H-indol-3-yl)ethyl]pyrimidin-4-amine (240 mg, crude) as brown oil which was used in the next step without further purification. $^1$H NMR (400 MHz, DMSO-$d_6$) δ ppm 9.31-9.23 (m, 1H), 8.86-8.20 (m, 2H), 8.11 (s, 1H), 7.92 (s, 1H), 7.57 (dd, J=7.8, 11.8 Hz, 1H), 7.42-7.29 (m, 1H), 7.26-7.17 (m, 1H), 7.13-6.93 (m, 2H), 6.55 (s, 1H), 3.83-3.70 (m, 2H), 3.04-2.95 (m, 2H); ES-LCMS m/z 368.0, 369.0 $[M+H]^+$.

Step 4: 2-(5-Fluoro-3-pyridyl)-N6-[2-(1H-indol-3-yl)ethyl]-N4-isopropyl-pyrimidine-4,6-diamine (I-20)

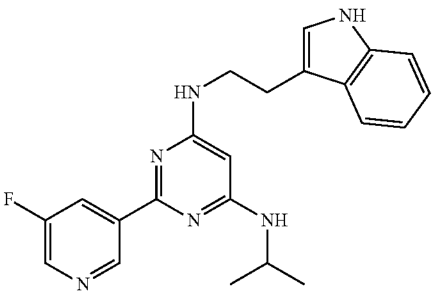 [SMILES: CC(C)Nc1cc(NCCc2c[nH]c3ccccc23)nc(-c2cncc(F)c2)n1]

6-Chloro-2-(5-fluoro-3-pyridyl)-N-[2-(1H-indol-3-yl)ethyl]pyrimidin-4-amine (60 mg, 140.62 umol, 1.0 eq), propan-2-amine (1.03 g, 17.46 mmol, 1.5 mL, 124.16 eq) and DIEA (90.87 mg, 703.10 umol, 122.46 uL, 5.0 eq) were taken up into a microwave tube in i-PrOH (3 mL). The sealed tube was heated at 125° C. for 6 h under microwave. LCMS showed 66% of desired compound was detected. The reaction mixture was concentrated under reduced pressure to remove i-PrOH. The residue was purified by preparative HPLC (HCl condition; column: Phenomenex Gemini 150×25 mm×10 um; mobile phase: [water (0.05% HCl)-ACN]; B %: 25%-55%, 10 min) and the desired fraction was lyophilized to yield 2-(5-fluoro-3-pyridyl)-N6-[2-(1H-indol-3-yl)ethyl]-N4-isopropyl-pyrimidine-4,6-diamine (19.11 mg, 38.19 umol, 27.16% yield, 99.90% purity, 3HCl salt) as a yellow solid. $^1$H NMR (400 MHz, $CD_3OD$) δ ppm 8.99 (s, 1H), 8.75 (d, J=2.6 Hz, 1H), 8.18 (s, 1H), 7.62 (d, J=7.9 Hz, 1H), 7.31 (s, 1H), 7.17-6.98 (m, 4H), 3.73 (s, 2H), 3.13 (t, J=6.4 Hz, 3H), 1.21 (s, 6H); ES-LCMS m/z 391.3 $[M+H]^+$.

Example 12

Synthesis of I-15

I-15

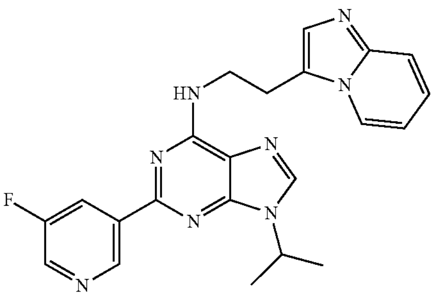

Synthetic Scheme:

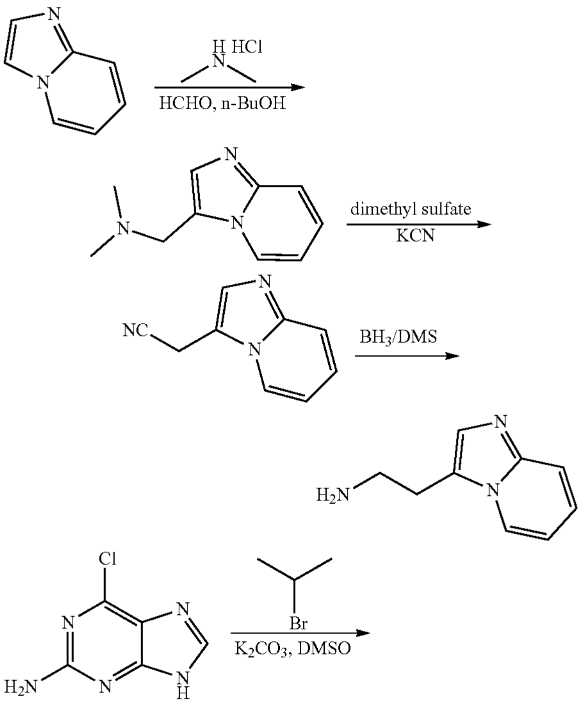

-continued

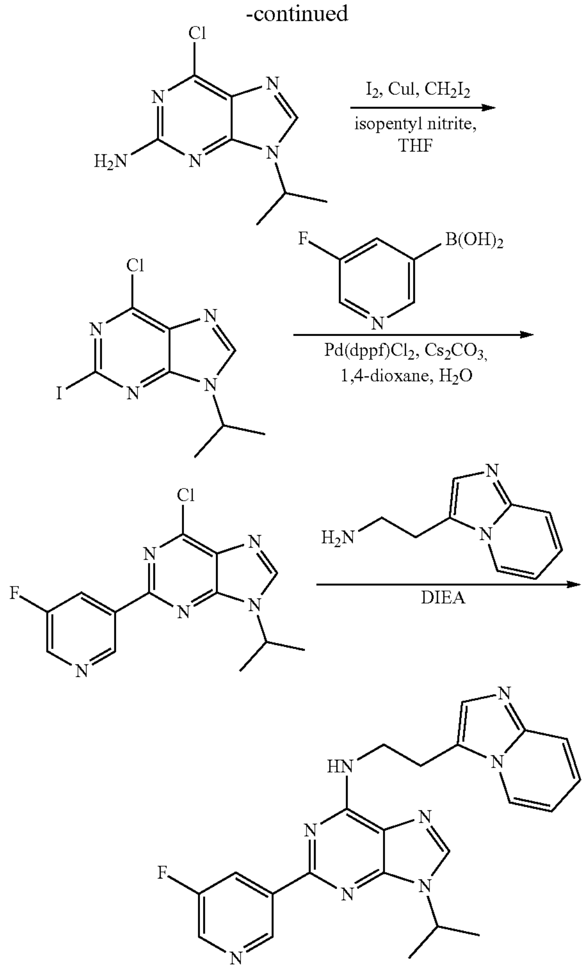

I-15

Step 1: 1-Imidazo[1,2-a]pyridin-3-yl-N,N-dimethyl-methanamine

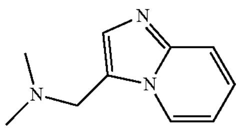

A mixture of imidazo[1,2-a]pyridine (500 mg, 4.23 mmol, 1 eq), N-methylmethanamine (414.16 mg, 5.08 mmol, 1.2 eq, HCl), and HCHO (412.16 mg, 5.08 mmol, 378.13 uL, 37% in water, 1.2 eq) in n-BuOH (5 mL) was degassed and purged with $N_2$ for 3 times. Then the mixture was stirred at 120° C. for 3 h under $N_2$ atmosphere. LC-MS showed the starting material was consumed completely and one main peak with desired MS was detected. The reaction mixture was concentrated under reduced pressure to give 1-imidazo[1,2-a]pyridin-3-yl-N,N-dimethyl-methanamine (742 mg, crude) as a yellow solid, which was used in the next step without further purification. $^1$H NMR (400 MHz, $CDCl_3$) δ ppm 8.85 (d, J=6.8 Hz, 1H), 8.27 (d, J=6.8 Hz, 1H), 7.85-7.73 (m, 2H), 7.68 (s, 1H), 4.41 (s, 2H), 2.64 (s, 6H); ES-LCMS m/z 176.2 $[M+H]^+$.

Step 2: 2-Imidazo[1,2-a]pyridin-3-ylacetonitrile

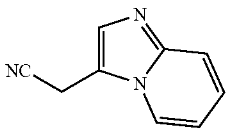 [SMILES: N#CCc1cnc2ccccn12]

To a solution of 1-imidazo[1,2-a]pyridin-3-yl-N,N-dimethyl-methanamine (742.00 mg, 4.23 mmol, 1 eq) in THF (6 mL) was added dimethyl sulfate (534.10 mg, 4.23 mmol, 401.58 uL, 1 eq) dropwise. The resulting mixture was heated at 70° C. for 30 minutes. The solvent was removed and the residue was dissolved in $H_2O$ (5 mL). To the mixture was added KCN (303.30 mg, 4.66 mmol, 1.1 eq) and the mixture was heated at 110° C. for 3 h. LC-MS showed 27% of the starting mixture was remained and 33% of desired compound was detected. The reaction mixture was quenched by addition of $NaHCO_3$ (30 mL) then extracted with EtOAc (20 mL×3). The combined organic layers were washed with brine (10 mL), dried over anhydrous $Na_2SO_4$, filtered and concentrated under reduced pressure to give a residue. The residue was purified by flash silica gel chromatography (from DCM/MeOH=1/0 to 10/1, TLC: DCM/MeOH=10/1, $R_f$=0.48) to yield 2-imidazo[1,2-a]pyridin-3-ylacetonitrile (900 mg, 50.4% yield, 87.6% purity) as a yellow solid. $^1$H NMR (400 MHz, $CDCl_3$) δ ppm 8.39 (d, J=6.8 Hz, 1H), 7.63 (d, J=9.0 Hz, 1H), 7.58 (s, 1H), 7.32 (ddd, J=1.1, 6.7, 9.0 Hz, 1H), 7.06 (dt, J=0.9, 6.8 Hz, 1H), 4.47 (s, 2H); ES-LCMS m/z 158.1 $[M+H]^+$.

Step 3: 2-Imidazo[1,2-a]pyridin-3-ylethanamine

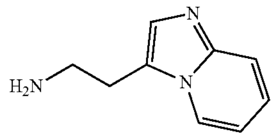 [SMILES: NCCc1cnc2ccccn12]

To a solution of 2-imidazo[1,2-a]pyridin-3-ylacetonitrile (80 mg, 421.70 umol, 1 eq) in THF (8 mL) was added $BH_3$-$Me_2S$ (10 M, 421.70 uL, 10 eq) dropwise. The mixture was stirred at 70° C. for 2 h. LC-MS showed the starting material was consumed completely and desired MS was detected. The reaction mixture was quenched by addition of MeOH (20 mL) and HCl/MeOH (4 M, 0.1 mL) slowly followed by stirring at 70° C. for 3 h. The mixture was concentrated under reduced pressure to give 2-imidazo[1,2-a]pyridin-3-ylethanamine (68 mg, crude) as colorless oil, which was used for the next step without further purification. $^1$H NMR (400 MHz, $CD_3OD$) δ ppm 8.48-8.43 (m, 1H), 7.89-7.65 (m, 1H), 7.69-7.44 (m, 1H), 7.46 (s, 1H), 7.26-7.17 (m, 1H), 3.17-3.10 (m, 2H), 3.09-3.01 (m, 2H); ES-LCMS m/z 162.1 $[M+H]^+$.

Step 4: 6-Chloro-9-isopropyl-purin-2-amine

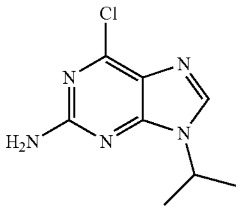

To a solution of 6-chloro-9H-purin-2-amine (27 g, 159.22 mmol, 1 eq) in DMSO (220 mL) was added $K_2CO_3$ (66.02 g, 477.67 mmol, 3 eq) and 2-bromopropane (97.92 g, 796.12 mmol, 74.75 mL, 5 eq). The mixture was stirred at 15° C. for 88 h. LC-MS showed the starting material was consumed completely and one main peak with desired MS was detected. The reaction mixture was quenched by addition of water (1000 mL) then extracted with EtOAc (500 mL×3). The combined organic layers were washed with water (100 mL×2), brine (100 mL), dried over $Na_2SO_4$, filtered and concentrated under reduced pressure to give a residue as a yellow solid. The residue was added with PE/EtOAc (5/1, 500 mL) then stirred at 15° C. for 2 h. The slurry was filtered and the cake was rinsed with PE (30 mL×2). The solid was collected and dried in vacuo to yield crude 6-chloro-9-isopropyl-purin-2-amine (28 g, 130.97 mmol, 82.2% yield, 99% purity) as a light yellow solid, which was used for the next step without further purification. $^1H$ NMR (400 MHz, $CDCl_3$) δ ppm 7.84 (s, 1H), 5.20 (s, 2H), 4.74-4.64 (m, 1H), 1.57 (d, J=6.8 Hz, 6H); ES-LCMS m/z 212.0, 214.0 $[M+H]^+$.

Step 5: 6-Chloro-2-iodo-9-isopropyl-purine

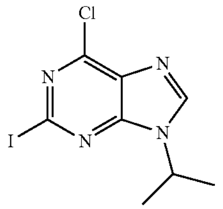

To a mixture of 6-chloro-9-isopropyl-purin-2-amine (10 g, 46.78 mmol, 1 eq), $I_2$ (11.87 g, 46.78 mmol, 1 eq), CuI (8.91 g, 46.78 mmol, 1 eq), and $CH_2I_2$ (125.28 g, 467.75 mmol, 37.73 mL, 10 eq) in THF (400 mL) was added isopentyl nitrite (16.44 g, 140.33 mmol, 18.89 mL, 3 eq). The mixture was stirred at 70° C. for 3 h. LC-MS showed the starting material was consumed completely and desired MS was detected. The reaction mixture was filtered through celite and the cake was rinsed with EtOAc (100 mL×2). The filtrate was concentrated under reduced pressure and the residue was diluted with EtOAc (300 mL), washed with $Na_2SO_3$ (100 mL), brine (100 mL), dried over $Na_2SO_4$, filtered and concentrated under reduced pressure to give a residue which was purified by flash silica gel chromatography (from PE/EtOAc=1/0 to 1/1, TLC: PE/EtOAc=1/1, $R_f$=0.58) to yield 6-chloro-2-iodo-9-isopropyl-purine (12.5 g, 31.39 mmol, 67.1% yield, 81% purity) as a yellow solid. $^1H$ NMR (400 MHz, $CDCl_3$) δ ppm 8.09 (s, 1H), 4.98-4.82 (m, 1H), 1.63 (d, J=7.0 Hz, 6H); ES-LCMS m/z 322.8, 324.8 $[M+H]_+$.

Step 6: 6-Chloro-2-(5-fluoro-3-pyridyl)-9-isopropyl-purine

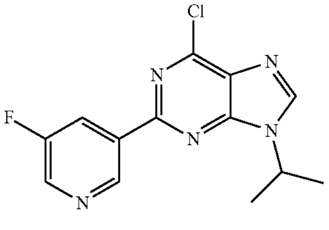 [SMILES: CC(C)n1cnc2c(Cl)nc(-c3cncc(F)c3)nc21]

6-Chloro-2-iodo-9-isopropyl-purine (3 g, 8.28 mmol, 1 eq), (5-fluoro-3-pyridyl)boronic acid (1.17 g, 8.28 mmol, 1 eq), Pd(dppf)$Cl_2$ (302.86 mg, 413.91 umol, 0.05 eq) and $Cs_2CO_3$ (2.70 g, 8.28 mmol, 1 eq) in 1,4-dioxane (50 mL) and $H_2O$ (10 mL) was de-gassed and then heated at 80° C. for 16 h under $N_2$. LCMS showed the starting material was consumed completely. The reaction mixture was poured into $H_2O$ (100 mL) then extracted with EtOAc (80 mL×3). The organic phase was washed with brine (30 mL), dried over anhydrous $Na_2SO_4$, concentrated under reduced pressure to give a residue which was purified by flash silica gel chromatography (from PE/EtOAc=1/0 to 1/1, TLC: PE/EtOAc=1/1, $R_f$=0.58) to yield 6-chloro-2-(5-fluoro-3-pyridyl)-9-isopropyl-purine (1.71 g, 5.63 mmol, 68.0% yield, 96% purity) as a yellow solid. $^1H$ NMR (400 MHz, $CDCl_3$) δ ppm 9.54 (s, 1H), 8.58 (d, J=2.8 Hz, 1H), 8.48 (td, J=2.1, 9.5 Hz, 1H), 8.21 (s, 1H), 5.10-4.93 (m, 1H), 1.73 (d, J=6.8 Hz, 6H); ES-LCMS m/z 292.0, 294.0 $[M+H]^+$.

Step 7: 2-(5-Fluoro-3-pyridyl)-N-(2-imidazo[1,2-a]pyridin-3-ylethyl)-9-isopropyl-purin-6-amine (I-15)

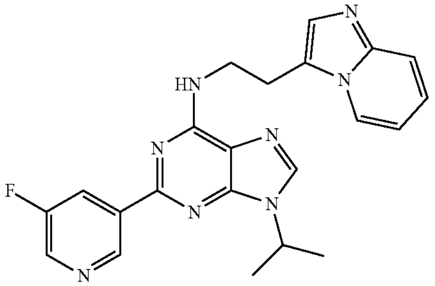 [SMILES: CC(C)n1cnc2c(NCCc3cnc4ccccn34)nc(-c3cncc(F)c3)nc21]

To a solution of 6-chloro-2-(5-fluoro-3-pyridyl)-9-isopropyl-purine (50 mg, 164.55 umol, 1 eq), and 2-imidazo[1,2-a]pyridin-3-ylethanamine (68 mg, 421.83 umol, 2.56 eq) in i-PrOH (5 mL) was added DIEA (106.33 mg, 822.73 umol, 143.31 uL, 5 eq). The mixture was stirred at 95° C. for 16 h. LC-MS showed the starting material was consumed completely and desired MS (m/z=M12+H) was detected. The reaction mixture was concentrated under reduced pressure and the residue was purified by preparative HPLC (column: Phenomenex Kinetex XB-C18 150 mm×30 mm, 5 m; mobile phase: [water (0.05% HCl)-ACN]; B %: 7%-37%, 12 min) and the desired fraction was lyophilized to yield 2-(5-fluoro-3-pyridyl)-N-(2-imidazo[1,2-a]pyridin-3-ylethyl)-9-isopropyl-purin-6-amine (34.09 mg, 63.53 umol, 38.6% yield, 98% purity, 3HCl salt) as a yellow solid. $^1$H NMR (400 MHz, $CD_3OD$) δ ppm 9.50 (s, 1H), 9.33 (s, 1H), 9.03-8.88 (m, 3H), 8.00 (s, 1H), 7.96-7.88 (m, 1H), 7.86-7.79 (m, 1H), 7.54 (t, J=6.8 Hz, 1H), 5.21-5.07 (m, 1H), 4.32 (t, J=6.2 Hz, 2H), 3.58 (t, J=6.3 Hz, 2H), 1.74 (d, J=6.6 Hz, 6H); ES-LCMS m/z 416.9 [M+H]$^+$.

Example 13

Synthesis of I-1

I-1

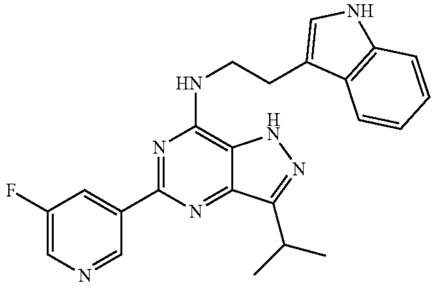

Synthetic Scheme:

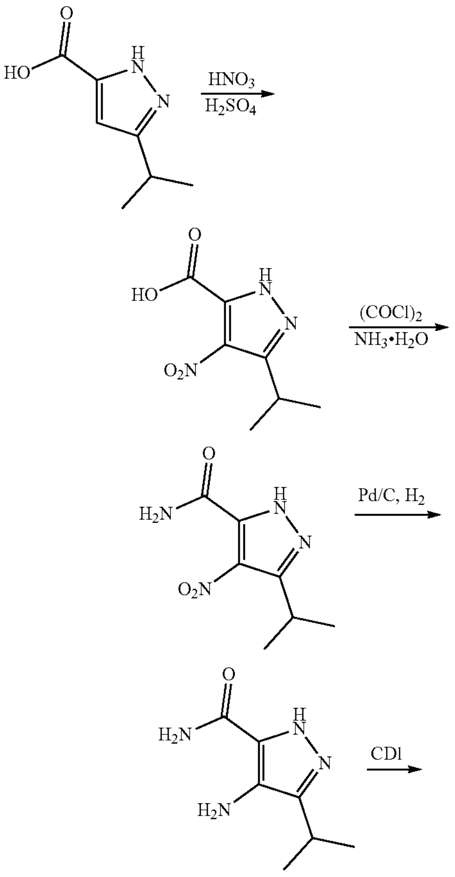

-continued

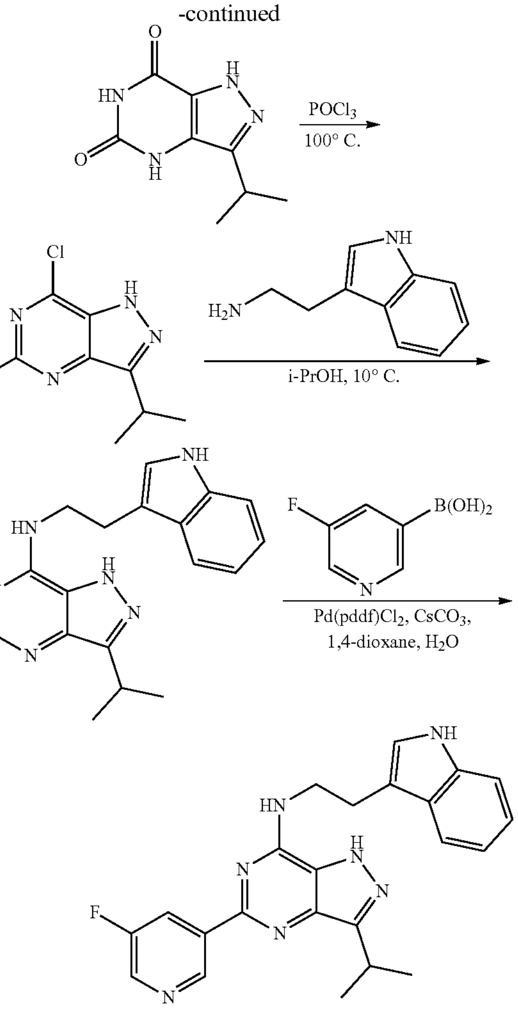

I-1

Step 1:
3-Isopropyl-4-nitro-1H-pyrazole-5-carboxylic Acid

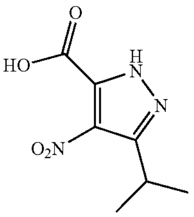

To an ice-bath and stirred solution of fuming $HNO_3$ (700.00 mg, 11.11 mmol, 0.5 mL, 1.71 eq) and fuming $H_2SO_4$ (1.88 g, 18.76 mmol, 1.02 mL, 98% purity, 2.89 eq) was added 3-isopropyl-1H-pyrazole-5-carboxylic acid (1 g, 6.49 mmol, 1 eq) in portionwise at 0° C. over 5 min. After addition, the mixture was stirred at this temperature for 1 h then at 100° C. for 6 h. LC-MS showed the starting material was consumed completely and one main peak with desired MS was detected. The mixture was poured into ice-water (30 g), the white precipitate was filtered and dried to yield 3-isopropyl-4-nitro-1H-pyrazole-5-carboxylic acid (700 mg, 3.20 mmol, 49.36% yield, 91.1% purity) as a white solid. $^1$H NMR (400 MHz, $CD_3OD$) δ ppm 3.56 (spt, J=7.0 Hz, 1H), 1.35 (d, J=7.1 Hz, 6H); ES-LCMS m/z 200.1 $[M+H]^+$.

Step 2: 3-Isopropyl-4-nitro-1H-pyrazole-5-carboxamide

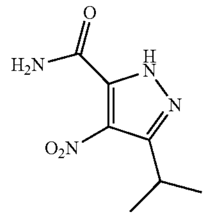

To a solution of 3-isopropyl-4-nitro-1H-pyrazole-5-carboxylic acid (700 mg, 3.20 mmol, 1 eq) in DCM (15 mL) and DMF (0.1 mL) was added oxalyl chloride (1.22 g, 9.61 mmol, 840.83 uL, 3 eq) dropwise over 5 min. After addition, the mixture was stirred at 15° C. for 1 h then the resulting mixture was concentrated. The residue was dissolved in THF (10 mL) and cooled to 0° C. $NH_3H_2O$ (9.75 g, 77.90 mmol, 10.71 mL, 28% purity, 24.33 eq) was added in dropwise. After addition, the mixture was stirred at 15° C. for 1 h. LC-MS showed the starting material was consumed completely and one main peak with desired MS was detected. The reaction mixture was concentrated under reduced pressure and the residue was diluted with EtOAc (50 mL) and extracted with EtOAc (50 mL×2). The combined organic layers were washed with brine (30 mL), dried over $Na_2SO_4$, filtered and concentrated under reduced pressure to give 3-isopropyl-4-nitro-1H-pyrazole-5-carboxamide (0.6 g, 2.91 mmol, 90.96% yield, 96.2% purity) as a white solid. $^1$H NMR (400 MHz, $CD_3OD$) δ ppm 3.68-3.60 (m, 1H), 1.34 (d, J=6.8 Hz, 6H); ES-LCMS m/z 199.1 $[M+H]^+$.

Step 3: 4-Amino-3-isopropyl-1H-pyrazole-5-carboxamide

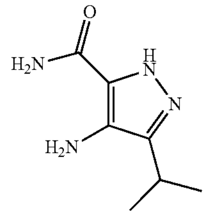

To a mixture of 3-isopropyl-4-nitro-1H-pyrazole-5-carboxamide (600 mg, 2.91 mmol, 1 eq) in MeOH (20 mL) was added Pd/C (10%, 0.1 g) under $N_2$. The suspension was degassed under vacuum and purged with $H_2$ several times. The mixture was stirred under $H_2$ (15 psi) at 15° C. for 3 h. TLC (PE/EA=1/1, $R_f$=0.1) showed the starting material was consumed completely. The reaction mixture was filtered and the filtrate was concentrated to yield 4-amino-3-isopropyl-1H-pyrazole-5-carboxamide (500 mg, 2.68 mmol, 91.86% yield, 90% purity) as an off white solid. $^1$H NMR (400 MHz, $CD_3OD$) δ ppm 3.02 (spt, J=7.0 Hz, 1H), 1.27 (d, J=7.1 Hz, 6H); ES-LCMS m/z 169.1 $[M+H]^+$.

Step 4: 3-Isopropyl-1,4-dihydropyrazolo[4,3-d]pyrimidine-5,7-dione

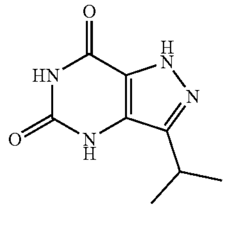

To a solution of 4-amino-3-isopropyl-1H-pyrazole-5-carboxamide (500 mg, 2.68 mmol, 1 eq) in DMF (10 mL) was added CDI (477.20 mg, 2.94 mmol, 1.1 eq) and the mixture was stirred at 80° C. for 12 h. LC-MS showed starting material was consumed completely and one main peak with desired MS was detected. The reaction mixture was concentrated to yield 3-isopropyl-1,4-dihydropyrazolo[4,3-d]pyrimidine-5,7-dione (550 mg, crude) as a brown solid. $^1$H NMR (400 MHz, $CD_3OD$) δ ppm 3.22-3.13 (m, 1H), 1.30 (d, J=6.8 Hz, 6H); ES-LCMS m/z 195.1 $[M+H]^+$.

Step 5: 5,7-Dichloro-3-isopropyl-1H-pyrazolo[4,3-d]pyrimidine

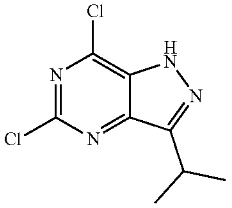

A solution of 3-isopropyl-1,4-dihydropyrazolo[4,3-d]pyrimidine-5,7-dione (500 mg, 2.57 mmol, 1 eq) in $POCl_3$ (10 mL) was stirred at 100° C. for 2 h. LC-MS showed starting material was consumed completely. The reaction mixture was concentrated under reduced pressure. The residue was diluted with EtOAc (50 mL), adjusted pH to 8 and extracted with EtOAc (50 mL×2). The combined organic layers were washed with brine (30 mL), dried over $Na_2SO_4$, filtered and concentrated under reduced pressure to give a residue which was purified by flash silica gel chromatography (ISCO®; 4 g SepaFlash® Silica Flash Column, Eluent of 0-30% Ethyl acetate/Petroleum ether gradient @ 15 mL/min) to yield 5,7-dichloro-3-isopropyl-1H-pyrazolo[4,3-d]pyrimidine (110 mg, 442.22 umol, 17.18% yield, 92.9% purity) as a white solid. $^1$H NMR (400 MHz, $CDCl_3$) δ ppm 10.39 (br s, 1H), 3.51 (spt, J=6.9 Hz, 1H), 1.47 (d, J=6.8 Hz, 6H); ES-LCMS m/z 231.3, 233.3 $[M+H]^+$.

Step 6: 5-Chloro-N-[2-(1H-indol-3-yl)ethyl]-3-isopropyl-1H-pyrazolo[4,3-d]pyrimidin-7-amine

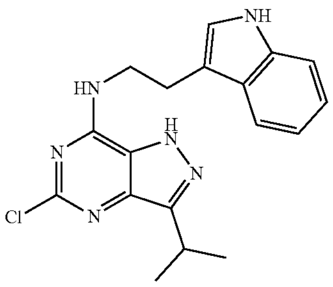 [SMILES: CC(C)c1n[nH]c2c(NCCc3c[nH]c4ccccc34)nc(Cl)nc12]

To a solution of 5,7-dichloro-3-isopropyl-1H-pyrazolo[4,3-d]pyrimidine (110 mg, 442.22 umol, 1 eq), 2-(1H-indol-3-yl)ethanamine (85.02 mg, 530.67 umol, 1.2 eq) in i-PrOH (5 mL) was added DIEA (171.46 mg, 1.33 mmol, 231.08 uL, 3 eq). The mixture was stirred at 8° C. for 16 h. LC-MS showed starting material was consumed completely and one main peak with desired MS was detected. The reaction mixture was concentrated under reduced pressure to give 5-chloro-N-[2-(1H-indol-3-yl)ethyl]-3-isopropyl-1H-pyrazolo[4,3-d]pyrimidin-7-amine (160 mg, 392.29 umol, 88.71% yield, 87% purity) as a brown solid. $^1$H NMR (400 MHz, $CD_3OD$) δ ppm 7.67 (br s, 1H), 7.35 (d, J=8.0 Hz, 1H), 7.14-7.08 (m, 2H), 7.04-6.98 (m, 1H), 3.94 (q, J=6.2 Hz, 2H), 3.43 (br s, 1H), 3.17 (t, J=7.2 Hz, 2H), 1.39 (s, 6H); ES-LCMS m/z 355.2, 357.1 $[M+H]^+$.

Step 7: 5-(5-Fluoro-3-pyridyl)-N-[2-(1H-indol-3-yl)ethyl]-3-isopropyl-1H-pyrazolo[4,3-d]pyrimidin-7-amine (I-1)

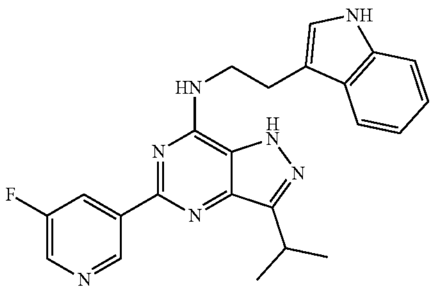 [SMILES: CC(C)c1n[nH]c2c(NCCc3c[nH]c4ccccc34)nc(-c3cncc(F)c3)nc12]

To a mixture of 5-chloro-N-[2-(1H-indol-3-yl)ethyl]-3-isopropyl-1H-pyrazolo[4,3-d]pyrimidin-7-amine (80 mg, 196.15 umol, 1 eq), (5-fluoro-3-pyridyl)boronic acid (33.17 mg, 235.38 umol, 1.2 eq), $Cs_2CO_3$ (159.77 mg, 490.37 umol, 2.5 eq) in 1,4-dioxane (2 mL) and water (0.5 mL) was added $Pd(dppf)Cl_2$ (7.18 mg, 9.81 umol, 0.05 eq) under $N_2$. The mixture was stirred under $N_2$ at 120° C. for 30 min under microwave. LC-MS showed 82.5% of product was detected. The reaction mixture was concentrated under reduced pressure and the residue was diluted with DCM (20 mL) and extracted with DCM (20 mL×2). The combined organic layers were washed with brine (30 mL), dried over $Na_2SO_4$, filtered and concentrated under reduced pressure to give a residue which was purified by preparative HPLC (column: Phenomenex Gemini 150*25 mm*10 um; mobile phase: [water (0.05% HCl)-ACN]; B %: 40%-70%, 10 min). The desired fraction was lyophilized to yield 5-(5-fluoro-3-pyridyl)-N-[2-(1H-indol-3-yl)ethyl]-3-isopropyl-1H-pyrazolo[4,3-d]pyrimidin-7-amine (66.84 mg, 123.15 umol, 62.78% yield, 96.7% purity, 3HCl salt) as a yellow solid. $^1$H NMR (400 MHz, $CD_3OD$) δ ppm 8.93 (s, 1H), 8.74 (d, J=2.6 Hz, 1H), 8.01 (d, J=8.8 Hz, 1H), 7.55 (d, J=7.9 Hz, 1H), 7.16 (d, J=7.9 Hz, 1H), 7.04 (s, 1H), 6.94 (t, J=7.7 Hz, 1H), 6.88-6.81 (m, 1H), 4.18 (t, J=6.6 Hz, 2H), 3.57 (d, J=7.0, 13.9 Hz, 1H), 3.21 (t, J=6.6 Hz, 2H), 1.44 (d, J=7.1 Hz, 6H); ES-LCMS m/z 415.9 $[M+H]^+$.

Example 14

Synthesis of I-9

I-9

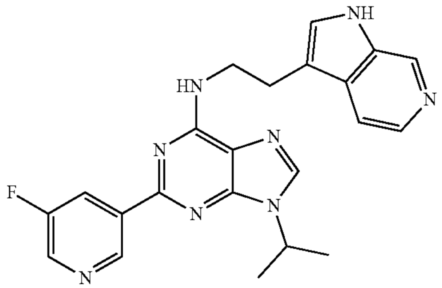

Synthetic Scheme:

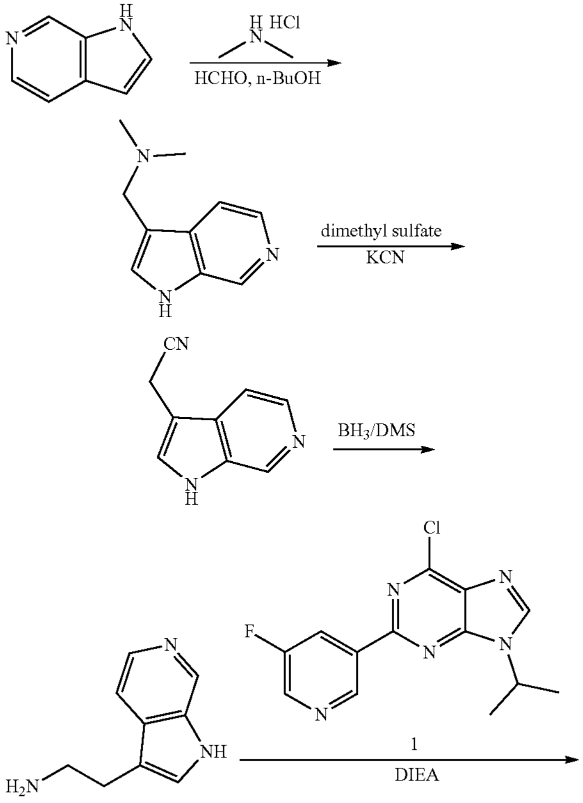

-continued

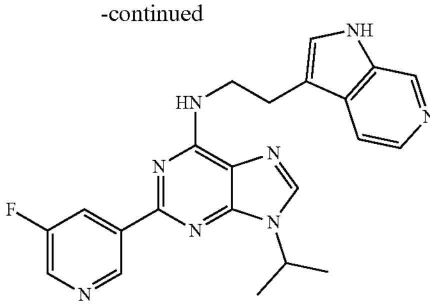

I-9

Step 1: N,N-Dimethyl-1-(1H-pyrrolo[2,3-c]pyridin-3-yl)methanamine

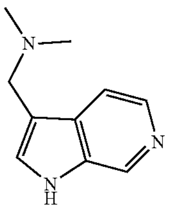

To a solution of 1H-pyrrolo[2,3-c]pyridine (900 mg, 7.62 mmol, 1 eq) in n-BuOH (15 mL) was added HCHO (680.06 mg, 8.38 mmol, 623.91 uL, 37% in water, 1.1 eq) and N-methylmethanamine hydrochloride (695.78 mg, 8.53 mmol, 1.12 eq). The mixture was stirred at 120° C. for 3 h. TLC (DCM/MeOH=10/1, $R_f$=0.06) indicated the starting material was consumed completely and one major new spot was detected. The reaction mixture was concentrated under reduced pressure to yield N,N-dimethyl-1-(1H-pyrrolo[2,3-c]pyridin-3-yl)methanamine (1.85 g, crude) as a yellow oil which was used into the next step without further purification. $^1$H NMR (400 MHz, $CD_3OD$) δ ppm 8.83 (d, J=1.1 Hz, 1H), 8.22 (d, J=5.7 Hz, 1H), 7.97 (s, 1H), 7.91 (d, J=0.7 Hz, 1H), 4.56 (s, 2H), 2.87 (s, 6H); ES-LCMS m/z 176.2 $[M+H]^+$.

Step 2: 2-(1H-Pyrrolo[2,3-c]pyridin-3-yl)acetonitrile

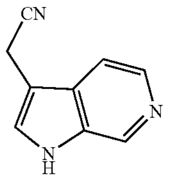 [SMILES: N#CCc1c[nH]c2cnccc12]

To a solution of N,N-dimethyl-1-(1H-pyrrolo[2,3-c]pyridin-3-yl)methanamine (2.75 g, 8.55 mmol, 1 eq) in THF (20 mL) was added dimethyl sulfate (1.08 g, 8.55 mmol, 810.81 uL, 1.0 eq) dropwise. The resulting mixture was stirred at 70° C. for 30 min. THF was removed and the residue was dissolved in water (15 mL). To the mixture was added KCN (612.44 mg, 9.40 mmol, 1.1 eq) and the mixture was stirred at 110° C. for 3 h. LCMS showed the starting material was consumed completely and one main peak with desired MS was detected. The reaction mixture was diluted with water (40 mL) and extracted with EtOAc (45 mL×3). The combined organic layers were dried over $Na_2SO_4$, filtered and concentrated under reduced pressure to yield 2-(1H-pyrrolo[2,3-c]pyridin-3-yl)acetonitrile (417.0 mg, crude) as a yellow solid which was used in the next step without further purification. $^1$H NMR (400 MHz, $CD_3OD$) δ ppm 8.70 (s, 1H), 8.13 (d, J=5.8 Hz, 1H), 7.67 (d, J=5.8 Hz, 1H), 7.58 (s, 1H), 4.01 (s, 2H); ES-LCMS m/z 158.1 $[M+H]^+$.

Step 3: 2-(1H-Pyrrolo[2,3-c]pyridin-3-yl)ethanamine

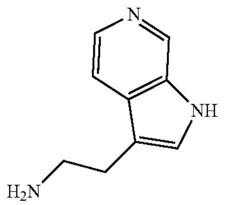 [SMILES: NCCc1c[nH]c2cnccc12]

To a solution of 2-(1H-pyrrolo[2,3-c]pyridin-3-yl)acetonitrile (417.0 mg, 2.65 mmol, 1 eq) in THF (20 mL) was added $BH_3$-$Me_2S$ (10 M, 2.65 mL, 10 eq). The mixture was stirred at 70° C. for 2 h. LCMS showed the starting material was consumed completely and one main peak was detected. MeOH (50 mL) was added into the reaction mixture dropwise and it was stirred at 70° C. for 2 h. The mixture was concentrated under reduced pressure to yield 2-(1H-pyrrolo[2,3-c]pyridin-3-yl)ethanamine (423.9 mg, crude) as a yellow solid which was used into the next step without further purification. $^1$H NMR (400 MHz, $CD_3OD$) δ ppm 8.71-8.59 (m, 1H), 8.08-8.00 (m, 1H), 7.73-7.64 (m, 1H), 7.63-7.53 (m, 1H), 3.09-2.92 (m, 4H); ES-LCMS m/z 162.1 $[M+H]^+$.

Step 4: 2-(5-Fluoro-3-pyridyl)-9-isopropyl-N-[2-(1H-pyrrolo[2,3-c]pyridin-3-yl)ethyl]purin-6-amine (I-9)

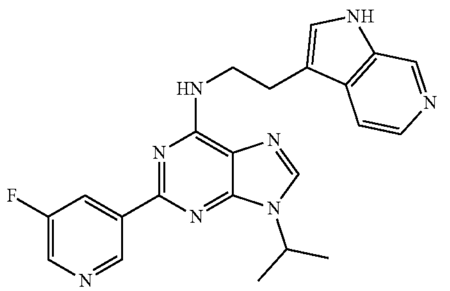 [SMILES: CC(C)n1cnc2c(NCCc3c[nH]c4cnccc34)nc(-c3cncc(F)c3)nc21]

To a solution of 6-chloro-2-(5-fluoro-3-pyridyl)-9-isopropyl-purine (49.35 mg, 148.88 umol, 1.0 eq) in i-PrOH (5 mL) was added DIEA (57.72 mg, 446.64 umol, 77.79 uL, 3.0 eq) and 2-(1H-pyrrolo[2,3-c]pyridin-3-yl)ethanamine (72.00 mg, 446.64 umol, 3.0 eq). The mixture was stirred at 50° C. for 15 h. LCMS showed 71% of desired compound was detected. The reaction mixture was concentrated under reduced pressure to remove i-PrOH. The residue was purified by preparative HPLC (HCl condition; column: Phenomenex Gemini 150×25 mm×10 um; mobile phase: [water (0.05% HCl)-ACN]; B %: 30%-60%, 10 min) and the desired fraction was lyophilized to yield 2-(5-fluoro-3- pyridyl)-9-isopropyl-N-[2-(1H-pyrrolo[2,3-c]pyridin-3-yl) ethyl]purin-6-amine (11.84 mg, 21.76 umol, 14.62% yield, 96.66% purity, 3HCl salt) as a yellow solid. $^1$H NMR (400 MHz, $CD_3OD$) δ ppm 9.54 (s, 1H), 9.36 (s, 1H), 9.05-8.98 (m, 2H), 8.96 (s, 1H), 8.27-8.22 (m, 1H), 8.21-8.16 (m, 2H), 5.15 (td, J=6.7, 13.6 Hz, 1H), 4.21 (t, J=6.4 Hz, 2H), 3.39 (t, J=6.7 Hz, 2H), 1.74 (d, J=6.8 Hz, 6H); ES-LCMS m/z 417.0 $[M+H]^+$.

Example 15

Synthesis of I-11

I-11

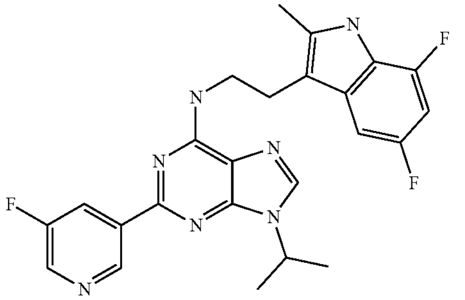

Synthetic Scheme:

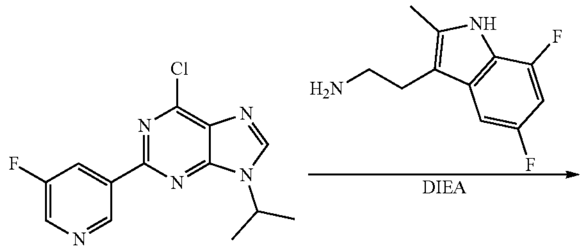

1

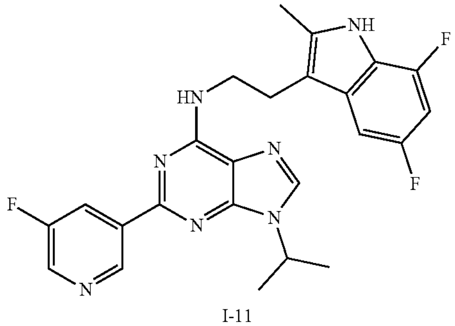

I-11

Step 1: N-(2-(5,7-Difluoro-2-methyl-1H-indol-3-yl) ethyl)-2-(5-fluoropyridin-3-yl)-9-isopropyl-9H-purin-6-amine (I-11)

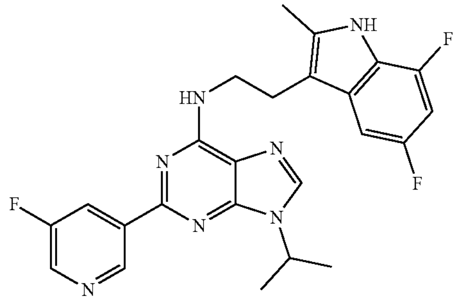 [SMILES: Cc1[nH]c2c(F)cc(F)cc2c1CCNc1nc(-c2cncc(F)c2)nc2c1ncn2C(C)C]

To a solution of 6-chloro-2-(5-fluoro-3-pyridyl)-9-isopropyl-purine (50 mg, 150.83 umol, 1 eq) in i-PrOH (2 mL) was added DIEA (97.47 mg, 754.17 umol, 131.36 uL, 5 eq) and 2-(5,7-difluoro-2-methyl-H-indol-3-yl)ethanamine (45.29 mg, 150.83 umol, 1 eq, oxalic acid). The mixture was stirred at 50° C. for 16 h. LCMS showed 65% of desired compound was detected. The reaction mixture was concentrated under reduced pressure to give a residue which was purified by preparative HPLC (column: Phenomenex Gemini 150×25 mm×10 um; mobile phase: [water (0.05% HCl)-ACN]; B %: 50%-80%, 10 min) and the desired fraction was lyophilized to yield N-(2-(5,7-difluoro-2-methyl-1H-indol-3-yl)ethyl)-2-(5-fluoropyridin-3-yl)-9-isopropyl-9H-purin-6-amine (53.81 mg, 36.8% yield, 100% purity, 3HCl salt) as a light yellow solid. $^1$H NMR (400 MHz, $CD_3OD$) δ ppm 9.36 (s, 1H), 8.85 (s, 1H), 8.76 (s, 1H), 8.61 (d, J=8.8 Hz, 1H), 6.95 (d, J=7.3 Hz, 1H), 6.49 (t, J=10.2 Hz, 1H), 5.11-4.99 (m, 1H), 4.03 (s, 2H), 3.08 (t, J=6.5 Hz, 2H), 2.31 (s, 3H), 1.70 (d, J=6.8 Hz, 6H); ES-LCMS m/z 466.0 $[M+H]^+$.

Example 16

Synthesis of I-14

I-14

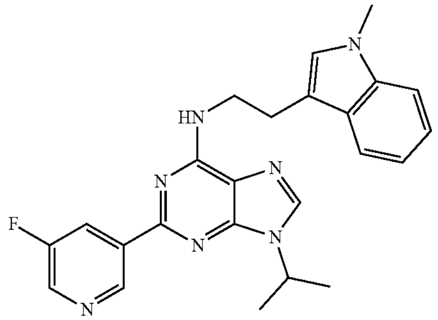

Synthesis Scheme:

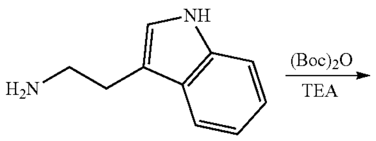

-continued

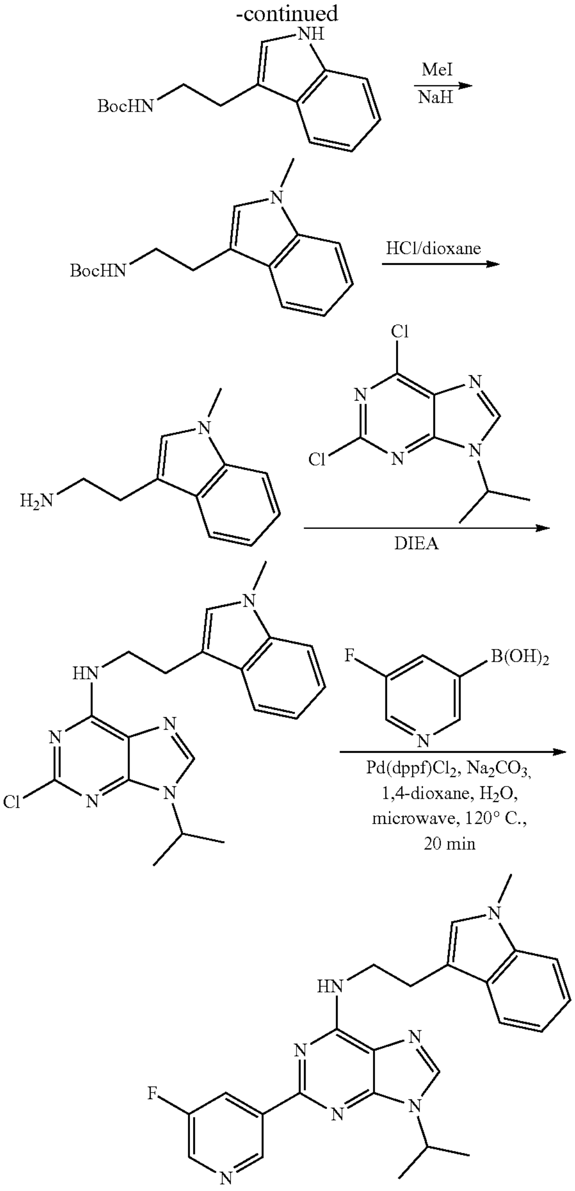

I-14

Step 1: tert-Butyl (2-(1H-indol-3-yl)ethyl)carbamate

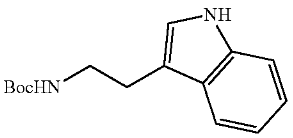 [SMILES: CC(C)(C)OC(=O)NCCc1c[nH]c2ccccc12]

To a solution of 2-(1H-indol-3-yl)ethanamine (2.8 g, 17.48 mmol, 1 eq) in anhydrous DCM (30 mL) was added TEA (5.31 g, 52.44 mmol, 7.30 mL, 3 eq) and $(Boc)_2O$ (4.58 g, 20.98 mmol, 4.82 mL, 1.2 eq). The mixture was stirred at 15° C. for 3 h. LCMS showed the starting material was consumed completely and one main peak with desired MS was detected. $H_2O$ (20 mL) was added, and the mixture was extracted with DCM (20 mL×3). The combined organic layers were washed with brine (20 mL×2), dried over anhydrous $Na_2SO_4$, filtered and concentrated under reduced pressure to give a residue which was purified on silica gel column chromatography (from PE/EtOAc=1/0 to 3/1, TLC: PE/EtOAc=2/1, $R_f$=0.45) to yield tert-butyl (2-(1H-indol-3-yl)ethyl)carbamate (3.55 g, 13.50 mmol, 77.2% yield, 99% purity) as a yellow solid. $^1$H NMR (400 MHz, $CDCl_3$) δ ppm 8.13 (br s, 1H), 7.61 (d, J=7.9 Hz, 1H), 7.35 (d, J=8.2 Hz, 1H), 7.24-7.16 (m, 1H), 7.16-7.08 (m, 1H), 7.00 (s, 1H), 4.59 (br s, 1H), 3.47 (q, J=6.4 Hz, 2H), 2.96 (t, J=6.8 Hz, 2H), 1.46 (s, 9H); ES-LCMS m/z 283.0 $[M+Na]^+$.

Step 2: tert-Butyl (2-(1-methyl-1H-indol-3-yl)ethyl) carbamate

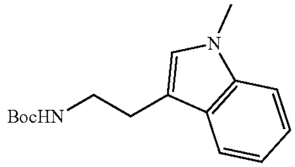 [SMILES: Cn1cc(CCNC(=O)OC(C)(C)C)c2ccccc21]

To a solution of tert-butyl N-[2-(1H-indol-3-yl)ethyl] carbamate (1.5 g, 5.70 mmol, 1 eq) in THF (30 mL) was added NaH (456.30 mg, 11.41 mmol, 60% purity, 2.0 eq) at 0° C. over 5 min. After addition, the mixture was stirred at this temperature for 20 min then MeI (809.67 mg, 5.70 mmol, 355.12 uL, 1.0 eq) was added dropwise at 0° C. The resulting mixture was stirred at 10° C. for 2 h. TLC (PE/EtOAc=3/1, $R_f$=0.49) indicated the starting material was consumed completely and two new spots formed. The reaction mixture was quenched by addition of water (50 mL) at 10° C. then extracted with EtOAc (30 mL×3). The combined organic layers were washed with brine (20 mL), dried over anhydrous $Na_2SO_4$, filtered and concentrated under reduced pressure to give a residue which was purified by flash silica gel chromatography (from PE/EA=1/0 to 3/1, TLC: PE/EA=3/1, $R_f$=0.49) to yield tert-butyl N-[2-(1-methylindol-3-yl)ethyl]carbamate (900 mg, 50.4% yield, 87.6% purity) as a colorless oil; $^1$H NMR (400 MHz, $CD_3OD$) δ ppm 7.98 (d, J=7.8 Hz, 1H), 7.74-7.57 (m, 2H), 7.55-7.43 (m, 1H), 4.99 (br s, 1H), 4.13 (s, 3H), 3.89-3.81 (m, 2H), 3.32 (t, J=6.4 Hz, 2H), 1.82 (s, 9H); ES-LCMS m/z 219.0 $[M-t-Bu+H]^+$.

Step 3: 2-(1-Methyl-1H-indol-3-yl)ethanamine

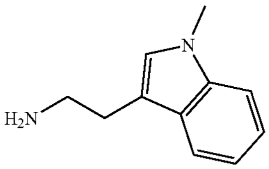

To a solution of tert-butyl N-[2-(1-methylindol-3-yl) ethyl]carbamate (700 mg, 2.24 mmol, 1 eq) in DCM (20 mL) was added HCl/MeOH (4 M, 5 mL, 8.95 eq). The mixture was stirred at 10° C. for 4 h. TLC (EtOAc, $R_f$=0.0) indicated the start material was consumed completely. The reaction mixture was concentrated under reduced pressure to give crude 2-(1-methylindol-3-yl)ethanamine (500 mg, crude, 2HCl) as a white solid which was used for the next step without further purification. $^1$H NMR (400 MHz, $CD_3OD$) δ ppm 7.58 (d, J=7.8 Hz, 1H), 7.36 (d, J=8.3 Hz, 1H), 7.20 (t, J=7.5 Hz, 1H), 7.14-7.04 (m, 2H), 3.78 (s, 3H), 3.27-3.19 (m, 2H), 3.15-3.07 (m, 2H); ES-LCMS m/z 175.1 $[M+H]^+$.

Step 4: 2-Chloro-9-isopropyl-N-(2-(1-methyl-1H-indol-3-yl)ethyl)-9H-purin-6-amine

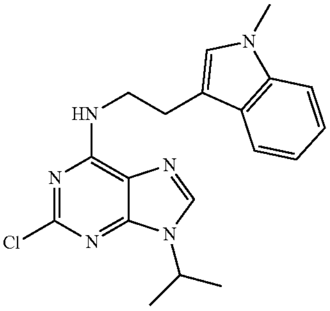 [SMILES: CC(C)n1cnc2c(NCCc3cn(C)c4ccccc34)nc(Cl)nc21]

To a solution of 2,6-dichloro-9-isopropyl-purine (200 mg, 827.24 umol, 1 eq) in i-PrOH (10 mL) was added DIEA (855.30 mg, 6.62 mmol, 1.15 mL, 8 eq) and 2-(1-methylindol-3-yl)ethanamine (306.70 mg, 992.69 umol, 1.2 eq, 2HCl). The mixture was stirred at 50° C. for 14 h. LC-MS showed the starting material was consumed completely and one main peak with desired MS was detected. The reaction mixture was concentrated under reduced pressure to remove i-PrOH (10 mL) and the residue was purified by flash silica gel chromatography (from PE/EtOAc=1/0 to 1/1, TLC: PE/EtOAc=1/2, $R_f$=0.62) to yield 2-chloro-9-isopropyl-N-[2-(1-methylindol-3-yl)ethyl]purin-6-amine (250 mg, 81.9% yield, 100% purity) as colorless oil. $^1$H NMR (400 MHz, $CD_3OD$) δ ppm 8.48-8.19 (m, 2H), 7.73 (d, J=7.5 Hz, 1H), 7.37 (d, J=8.3 Hz, 1H), 7.25-6.94 (m, 3H), 4.70-4.58 (m, 1H), 3.77-3.64 (m, 5H), 3.06-2.91 (m, 2H), 1.50 (d, J=6.5 Hz, 6H); ES-LCMS m/z 369.1, 371.1 $[M+H]^+$.

Step 5: 2-(5-Fluoropyridin-3-yl)-9-isopropyl-N-(2-(1-methyl-1H-indol-3-yl)ethyl)-9H-purin-6-amine (I-14)

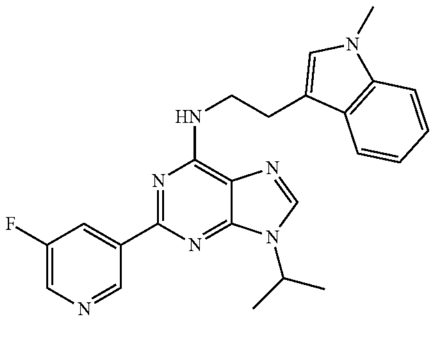 [SMILES: CC(C)n1cnc2c(NCCc3cn(C)c4ccccc34)nc(-c3cncc(F)c3)nc21]

2-Chloro-9-isopropyl-N-[2-(1-methylindol-3-yl)ethyl]purin-6-amine (100 mg, 271.10 umol, 1 eq), (5-fluoro-3-pyridyl)boronic acid (95.50 mg, 677.76 umol, 2.5 eq), $Pd(dppf)Cl_2$ (19.84 mg, 27.11 umol, 0.1 eq) and $Cs_2CO_3$ (264.99 mg, 813.31 umol, 3.0 eq) were taken up into a microwave tube in 1,4-dioxane (3 mL) and $H_2O$ (0.6 mL). The sealed tube was heated at 120° C. for 30 min under microwave. LC-MS showed the start material was consumed completely and one main peak with desired MS was detected. The reaction mixture was concentrated under reduced pressure. The residue was dissolved in EtOAc (50 mL), filtered through $SiO_2$. The cake was rinsed with EtOAc (10 mL×2). The combined organic layers were concentrated under reduced pressure to give a residue which was purified by preparative HPLC (column: Phenomenex Gemini 150*25 mm*10 um; mobile phase: [water (0.05% HCl)-ACN]; B %: 55%-85%, 10 min). The desired fraction was lyophilized to yield 2-(5-fluoro-3-pyridyl)-9-isopropyl-N-[2-(1-methylindol-3-yl)ethyl]purin-6-amine (53.81 mg, 36.8% yield, 100% purity, 3HCl salt) as a yellow solid. $^1$H NMR (400 MHz, $CD_3OD$) δ ppm 9.36 (s, 1H), 9.11 (br s, 1H), 8.84 (s, 1H), 8.75 (d, J=8.8 Hz, 1H), 7.60 (d, J=7.9 Hz, 1H), 7.20 (d, J=7.9 Hz, 1H), 7.07 (t, J=7.5 Hz, 1H), 7.02-6.93 (m, 2H), 5.09 (td, J=6.8, 13.6 Hz, 1H), 4.16-4.10 (m, 2H), 3.61 (s, 3H), 3.20 (t, J=6.6 Hz, 2H), 1.72 (d, J=6.8 Hz, 6H); ES-LCMS m/z 430.2 $[M+H]^+$.

Example 17

Synthesis of I-7

I-7

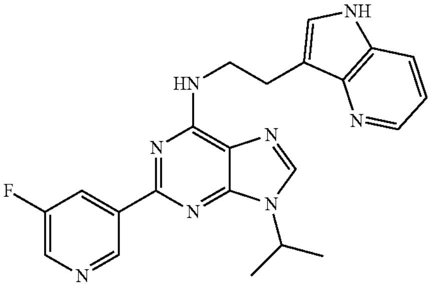

Synthetic Scheme:

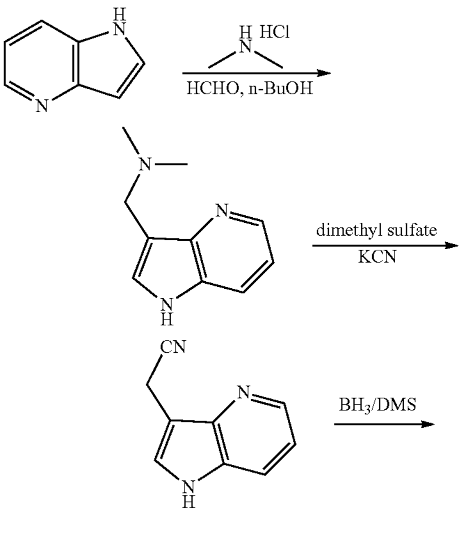

-continued

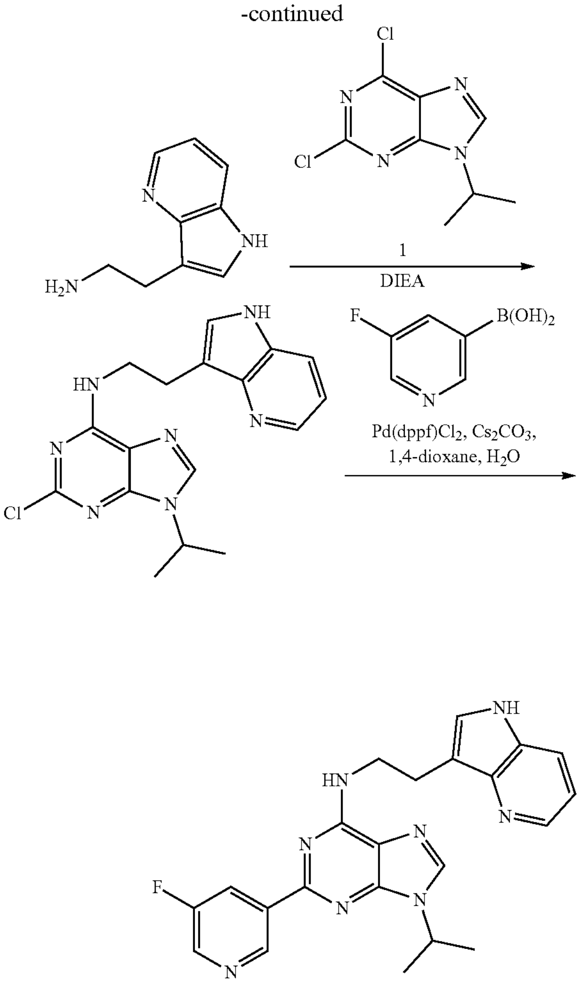

I-7

Step 1: N,N-Dimethyl-1-(1H-pyrrolo[3,2-b]pyridin-3-yl)methanamine

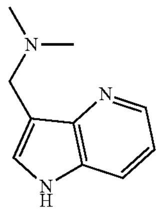

To a solution of 1H-pyrrolo[3,2-b]pyridine (500 mg, 4.23 mmol, 1 eq) in n-BuOH (5 mL) was added HCHO (377.65 mg, 4.65 mmol, 346.47 uL, 37% in water, 1.1 eq) and N-methylmethanamine (379.43 mg, 4.65 mmol, 1.1 eq, HCl salt). The mixture was stirred at 120° C. for 3 h. LC-MS showed starting material was consumed completely and one main peak with desired MS was detected. The reaction mixture was concentrated under reduced pressure to give N,N-dimethyl-1-(1H-pyrrolo[3,2-b]pyridin-3-yl)methanamine (559.7 mg, crude) as a yellow solid which was used in the next step without further purification. $^1$H NMR (400 MHz, $CD_3OD$) δ ppm 8.32 (dd, J=1.1, 4.6 Hz, 1H), 7.80 (d, J=8.3 Hz, 1H), 7.56 (s, 1H), 7.16 (dd, J=4.8, 8.3 Hz, 1H), 3.80 (s, 2H), 2.28 (s, 6H); ES-LCMS m/z 176.1 $[M+H]^+$.

Step 2: 2-(1H-Pyrrolo[3,2-b]pyridin-3-yl)acetonitrile

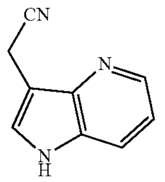 [SMILES: N#CCc1c[nH]c2cccnc12]

To a solution of N,N-dimethyl-1-(1H-pyrrolo[3,2-b]pyridin-3-yl)methanamine (200.00 mg, 1.14 mmol, 1 eq) in THF (1.5 mL) was added dimethyl sulfate (143.96 mg, 1.14 mmol, 108.24 uL, 1.0 eq) dropwise. The resulting mixture was stirred at 70° C. for 30 min. The solvent was removed and the residue was dissolved in water (1.2 mL). To the mixture was added KCN (81.76 mg, 1.26 mmol, 1.1 eq) and the mixture was stirred at 110° C. for 3 h. LC-MS showed starting material was consumed completely and one main peak with desired MS was detected. The reaction mixture was diluted with water (5 mL) and extracted with EtOAc (15 mL×3). The combined organic layers were dried over $Na_2SO_4$, filtered and concentrated under reduced pressure to give 2-(1H-pyrrolo[3,2-b]pyridin-3-yl)acetonitrile (131.7 mg, 662.72 umol, 58.1% yield, 79.1% purity) as a yellow solid which was used in the next step without further purification. $^1$H NMR (400 MHz, $CD_3OD$) δ ppm 8.37-8.29 (m, 1H), 7.87-7.78 (m, 1H), 7.64-7.51 (m, 1H), 7.25-7.14 (m, 1H), 4.01 (d, J=0.9 Hz, 2H); ES-LCMS m/z 158.1 $[M+H]^+$.

Step 3: 2-(1H-Pyrrolo[3,2-b]pyridin-3-yl)ethanamine

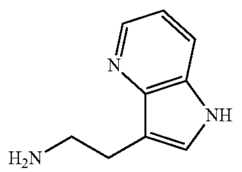 [SMILES: NCCc1c[nH]c2cccnc12]

To a solution of 2-(1H-pyrrolo[3,2-b]pyridin-3-yl)acetonitrile (131.70 mg, 662.72 umol, 1 eq) in THF (10 mL) was added $BH_3$-$Me_2S$ (1 mL, 10 M in $Me_2S$) dropwise. The reaction mixture was stirred at 70° C. for 2 h. LC-MS showed starting material was consumed completely and one main peak was detected. MeOH (30 mL) was added dropwise and the mixture was stirred at 70° C. for 2 h. The mixture was concentrated under reduced pressure to give 2-(1H-pyrrolo[3,2-b]pyridin-3-yl)ethanamine (50.00 mg, crude) as a yellow solid which was used in the next step without further purification. $^1$H NMR (400 MHz, $CD_3OD$) δ ppm 8.30 (d, J=4.6 Hz, 1H), 7.80 (d, J=8.2 Hz, 1H), 7.44 (s, 1H), 7.16 (dd, J=4.6, 8.2 Hz, 1H), 3.35 (s, 2H), 3.03 (s, 2H); ES-LCMS m/z 162.2 $[M+H]^+$.

Step 4: 2-Chloro-9-isopropyl-N-[2-(1H-pyrrolo[3,2-b]pyridin-3-yl)ethyl]purin-6-amine

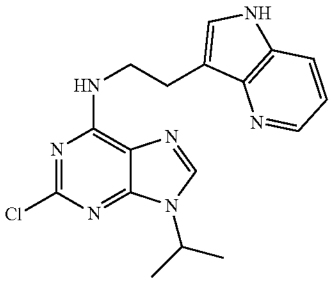 [SMILES: CC(C)n1cnc2c(NCCc3c[nH]c4cccnc34)nc(Cl)nc21]

To a solution of 2,6-dichloro-9-isopropyl-purine (76.49 mg, 320.46 umol, 1.2 eq) in i-PrOH (10 mL) was added DIEA (172.57 mg, 1.34 mmol, 232.57 uL, 5.0 eq) and 2-(1H-pyrrolo[3,2-b]pyridin-3-yl)ethanamine (50.00 mg, 267.05 umol, 1 eq). The mixture was stirred at 50° C. for 12 h. LC-MS showed starting material was consumed completely and 55% of desired compound was detected. The reaction mixture was concentrated and the residue was purified by preparative TLC ($SiO_2$, DCM/MeOH=10/1, $R_f$=0.65) to yield 2-chloro-9-isopropyl-N-[2-(1H-pyrrolo[3,2-b]pyridin-3-yl)ethyl]purin-6-amine (25.00 mg, 70.26 umol, 26.3% yield, 100% purity) as a yellow solid. $^1$H NMR (400 MHz, $CD_3OD$) δ ppm 8.30 (dd, J=1.3, 4.8 Hz, 1H), 8.08 (s, 1H), 7.77 (dd, J=1.1, 8.2 Hz, 1H), 7.44 (s, 1H), 7.14 (dd, J=4.8, 8.3 Hz, 1H), 4.79-4.68 (m, 1H), 3.96-3.87 (m, 2H), 3.20 (t, J=6.8 Hz, 2H), 1.56 (d, J=6.8 Hz, 6H); ES-LCMS m/z 356.1, 358.1 [M+H]$^+$.

Step 5: 2-(5-Fluoro-3-pyridyl)-9-isopropyl-N-[2-(1H-pyrrolo[3,2-b]pyridin-3-yl)ethyl]purin-6-amine (I-7)

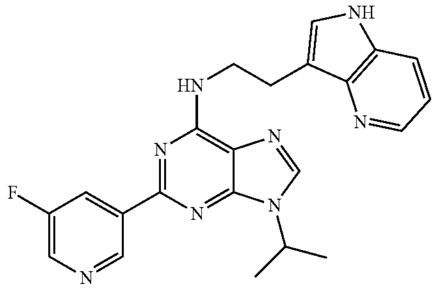 [SMILES: CC(C)n1cnc2c(NCCc3c[nH]c4cccnc34)nc(-c3cncc(F)c3)nc21]

2-Chloro-9-isopropyl-N-[2-(1H-pyrrolo[3,2-b]pyridin-3-yl)ethyl]purin-6-amine (25.00 mg, 70.26 umol, 1 eq), (5-fluoro-3-pyridyl)boronic acid (24.75 mg, 175.65 umol, 2.5 eq), $Cs_2CO_3$ (68.68 mg, 210.78 umol, 3.0 eq) and Pd(dppf)$Cl_2$ (5.14 mg, 7.03 umol, 0.1 eq) were taken up into a microwave tube in 1,4-dioxane (2 mL) and water (0.4 mL). The sealed tube was heated at 120° C. for 30 min under microwave. LC-MS showed starting material was consumed completely and 60% of desired compound was detected. The reaction mixture was diluted with EtOAc (10 mL) and filtered through a pad of celite. The filtrate was concentrated under reduced pressure to give a residue which was purified by preparative HPLC (HCl condition, column: Phenomenex Kinetex XB-C18 150 mm*30 mm, 5 m; mobile phase:

[water(0.05% HCl)-ACN]; B %: 5%-35%, 12 min) and the desired fraction was lyophilized to yield 2-(5-fluoro-3-pyridyl)-9-isopropyl-N-[2-(1H-pyrrolo[3,2-b]pyridin-3-yl)ethyl]purin-6-amine (8.83 mg, 16.14 umol, 23.0% yield, 96.1% purity, 3HCl salt) as a white solid; $^1$H NMR (400 MHz, $CD_3OD$) δ ppm 9.37 (s, 1H), 8.92 (s, 1H), 8.78 (s, 1H), 8.69 (s, 1H), 8.51 (s, 1H), 8.43 (d, J=7.3 Hz, 1H), 8.05 (s, 1H), 7.59 (s, 1H), 5.06 (td, J=6.8, 13.6 Hz, 1H), 4.22 (t, J=6.4 Hz, 2H), 3.38 (t, J=6.8 Hz, 2H), 1.70 (d, J=6.8 Hz, 6H); ES-LCMS m/z 417.2 [M+H]$^+$.

Example 18

Synthesis of I-13

I-13

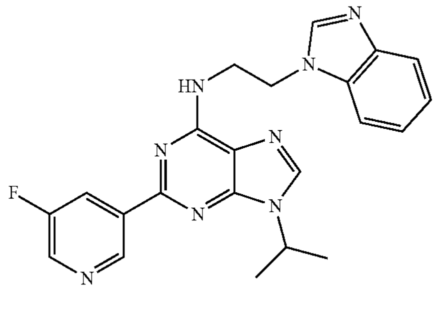

Synthetic Scheme:

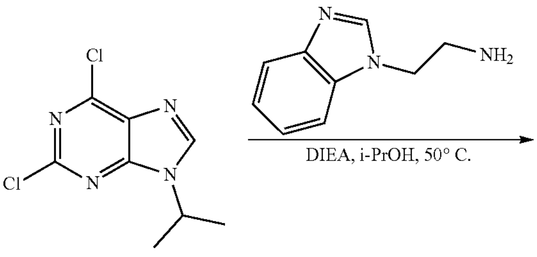

1

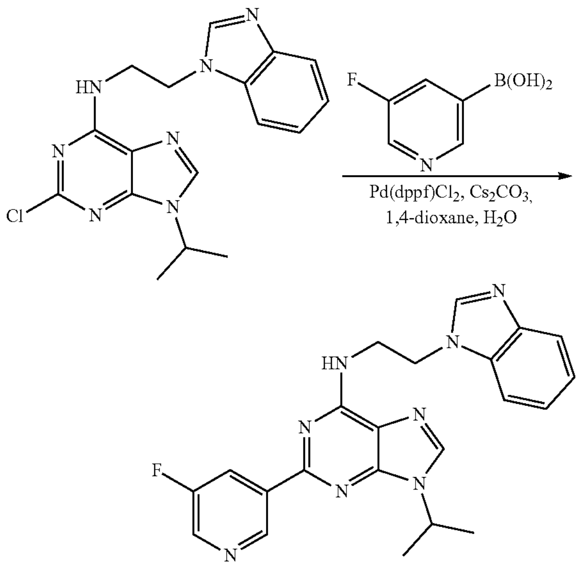

I-13

Step 1: N-(2-(1H-Benzo[d]imidazol-1-yl)ethyl)-2-chloro-9-isopropyl-9H-purin-6-amine

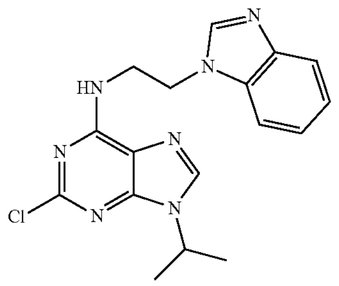 [SMILES: CC(C)n1cnc2c(NCCn3cnc4ccccc43)nc(Cl)nc21]

To a solution of 2,6-dichloro-9-isopropyl-purine (200 mg, 827.24 umol, 1 eq) in i-PrOH (8 mL) was added DIEA (106.91 mg, 827.24 umol, 144.09 uL, 1 eq) and 2-(benzimidazol-1-yl)ethanamine (160.02 mg, 992.69 umol, 1.2 eq). The mixture was stirred at 50° C. for 16 h. LC-MS showed the starting material was consumed completely and one main peak with desired MS was detected. The reaction mixture was concentrated under reduced pressure to remove i-PrOH to give a residue which was purified by flash silica gel column chromatography (from DCM/MeOH=1/0 to 10/1, TLC: DCM/MeOH=10/1, $R_f$=0.33) to yield N-[2-(benzimidazol-1-yl)ethyl]-2-chloro-9-isopropyl-purin-6-amine (275 mg, 93.4% yield, 100% purity) as a white solid. $^1$H NMR (400 MHz, $CD_3OD$) δ ppm 7.98-7.71 (m, 2H), 7.54 (d, J=7.5 Hz, 2H), 7.38-7.18 (m, 2H), 6.77 (br s, 1H), 4.86-4.67 (m, 1H), 4.53 (t, J=6.0 Hz, 2H), 4.02 (br s, 2H), 1.69-1.46 (m, 6H); ES-LCMS m/z 356.1, 357.1 $[M+H]^+$.

Step 2: N-(2-(1H-Benzo[d]imidazol-1-yl)ethyl)-2-(5-fluoropyridin-3-yl)-9-isopropyl-9H-purin-6-amine (I-13)

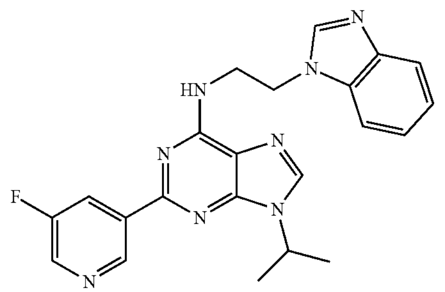 [SMILES: CC(C)n1cnc2c(NCCn3cnc4ccccc43)nc(-c3cncc(F)c3)nc21]

N-[2-(Benzimidazol-1-yl)ethyl]-2-chloro-9-isopropyl-purin-6-amine (120 mg, 337.24 umol, 1 eq), (5-fluoro-3-pyridyl)boronic acid (95.04 mg, 674.49 umol, 2 eq), $Cs_2CO_3$ (329.64 mg, 1.01 mmol, 3.0 eq) and $Pd(dppf)Cl_2$ (12.34 mg, 16.86 umol, 0.05 eq) in 1,4-dioxane (5 mL) and $H_2O$ (1 mL) was de-gassed and refilled with $N_2$. The mixture was heated to 80° C. for 12 h. LC-MS showed 58% of desired compound. The reaction mixture was poured into $H_2O$ (30 mL) then extracted with EtOAc (20 mL×3). The organic phase was combined, washed with brine (10 mL), dried over anhydrous $Na_2SO_4$ and concentrated under reduced pressure to give a residue. The residue was purified by preparative HPLC (column: Phenomenex Gemini 150*25 mm*10 um; mobile phase: [water (0.05% ammonia hydroxide v/v)-ACN]; B %: 38%-68%, 10 min) to yield N-[2-(benzimidazol-1-yl)ethyl]-2-(5-fluoro-3-pyridyl)-9-isopropyl-purin-6-amine (31.40 mg, 22.4% yield, 100% purity) as a white solid. $^1$H NMR (400 MHz, $CD_3OD$) δ ppm 9.08 (br s, 1H), 8.43 (d, J=2.6 Hz, 1H), 8.17 (s, 1H), 8.15-7.95 (m, 2H), 7.67 (d, J=8.2 Hz, 1H), 7.38 (d, J=8.2 Hz, 1H), 7.26 (t, J=7.7 Hz, 1H), 7.17-7.00 (m, 1H), 4.88-4.83 (m, 1H), 4.62 (t, J=5.4 Hz, 2H), 4.20 (br s, 2H), 1.63 (d, J=6.8 Hz, 6H); ES-LCMS m/z 417.1 $[M+H]^+$.

Example 19

Synthesis of I-8

I-8

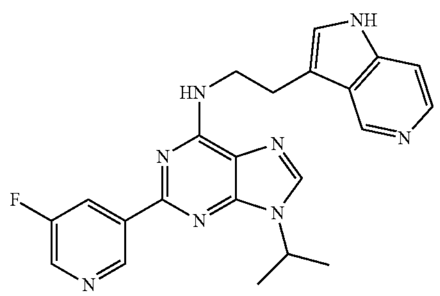 [SMILES: CC(C)n1cnc2c(NCCc3c[nH]c4ccncc34)nc(-c3cncc(F)c3)nc21]

Synthetic Scheme:

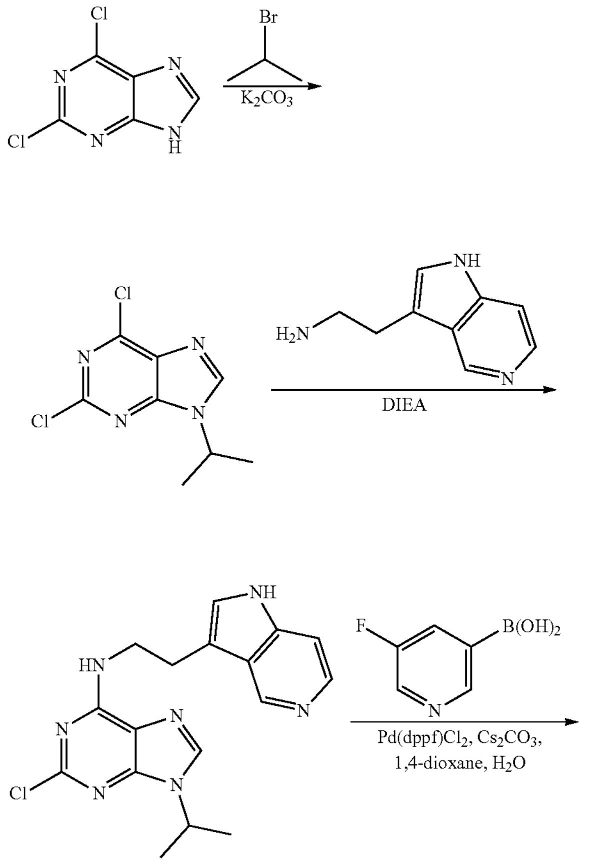

-continued

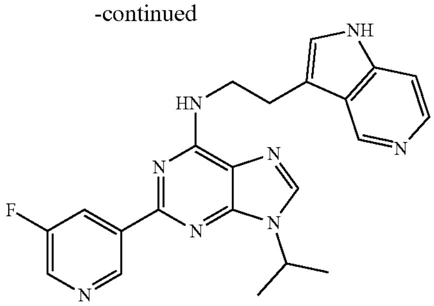

I-8

Step 1: 2,6-Dichloro-9-isopropyl-purine

I-8

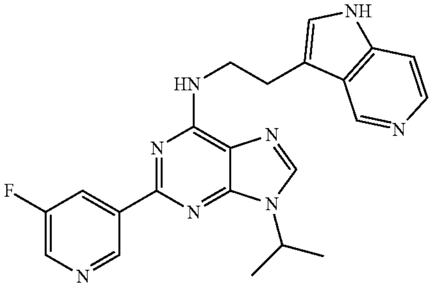

To a solution of 2,6-dichloro-9H-purine (20 g, 105.82 mmol, 1 eq) in DMSO (160 mL) was added $K_2CO_3$ (73.13 g, 529.09 mmol, 5 eq) and 2-bromopropane (65.07 g, 529.09 mmol, 49.67 mL, 5 eq). The mixture was stirred at 25° C. for 12 h. TLC (PE/EtOAc=1/1, $R_f$=0.45) indicated starting material was consumed completely and one major new spot was detected. The reaction mixture was diluted with water (200 mL) and extracted with EtOAc (100 mL×3). The combined organic layers were washed with water (80 mL×3), dried over $Na_2SO_4$, filtered and concentrated under reduced pressure to give a residue which was purified by flash silica gel column chromatography (from PE/EtOAc=5/1 to 2/1, TLC: PE/EtOAc=1/1, $R_f$=0.45) to yield 2,6-dichloro-9-isopropyl-purine (3.52 g, 14.75 mmol, 13.9% yield, 96.8% purity) as a white solid. $^1$H NMR (400 MHz, $CD_3OD$) δ ppm 8.66 (s, 1H), 4.97-4.89 (m, 1H), 1.65 (d, J=6.8 Hz, 6H); ES-LCMS m/z 231.0, 232.9 $[M+H]^+$.

Step 2: 2-Chloro-9-isopropyl-N-[2-(1H-pyrrolo[3,2-c]pyridin-3-yl)ethyl]purin-6-amine

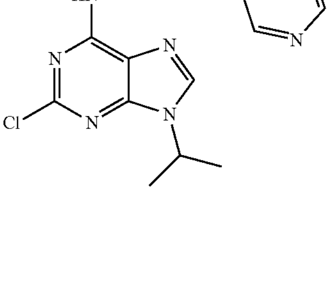

To a solution of 2,6-dichloro-9-isopropyl-purine (148.07 mg, 620.33 umol, 1 eq) in i-PrOH (10 mL) was added DIEA (400.86 mg, 3.10 mmol, 540.24 uL, 5.0 eq) and 2-(1H-pyrrolo[3,2-c]pyridin-3-yl)ethanamine (100 mg, 620.33 umol, 1 eq). The mixture was stirred at 50° C. for 12 h. LC-MS showed starting material was consumed completely and 33% of desired compound was detected. The reaction mixture was concentrated under reduced pressure to remove solvent. The residue was purified by flash silica gel chromatography (from DCM/MeOH=100/1 to 5/1, TLC: DCM/MeOH=10/1, $R_f$=0.68) to yield 2-chloro-9-isopropyl-N-[2-(1H-pyrrolo[3,2-c]pyridin-3-yl)ethyl]purin-6-amine (74.5 mg, 33.8% yield, crude) as a yellow solid; ES-LCMS m/z 356.0, 357.0 $[M+H]^+$.

Step 3: 2-(5-Fluoro-3-pyridyl)-9-isopropyl-N-[2-(1H-pyrrolo[3,2-c]pyridin-3-yl)ethyl]purin-6-amine (I-8)

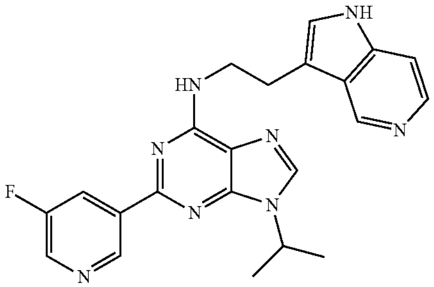

2-Chloro-9-isopropyl-N-[2-(1H-pyrrolo[3,2-c]pyridin-3-yl)ethyl]purin-6-amine (74.5 mg, 104.69 umol, 1 eq), (5-fluoro-3-pyridyl)boronic acid (36.88 mg, 261.72 umol, 2.5 eq), $Cs_2CO_3$ (102.33 mg, 314.06 umol, 3.0 eq) and $Pd(dppf)Cl_2$ (7.66 mg, 10.47 umol, 0.1 eq) were taken up into a microwave tube in 1,4-dioxane (3 mL) and water (0.6 mL). The sealed tube was heated at 120° C. for 30 min under microwave. LC-MS showed starting material was consumed completely, 56% of desired compound was detected. The reaction mixture was diluted with EtOAc (15 mL) and filtered through a pad of celite. The filtrate was concentrated under reduced pressure to give a residue which was purified by preparative HPLC (HCl condition, column: Phenomenex Gemini 150×25 mm×10 um; mobile phase: [water (0.05% HCl)-ACN]; B %: 15%-45%, 10 min) and the desired fraction was lyophilized to yield 2-(5-fluoro-3-pyridyl)-9-isopropyl-N-[2-(1H-pyrrolo[3,2-c]pyridin-3-yl)ethyl]purin-6-amine (22.19 mg, 42.20 umol, 40.3% yield, 100% purity, 3HCl salt) as a white solid; $^1$H NMR (400 MHz, $CD_3OD$) δ ppm 9.53 (s, 1H), 9.31 (s, 2H), 9.00-8.94 (m, 2H), 8.28 (d, J=6.5 Hz, 1H), 7.85 (d, J=6.8 Hz, 1H), 7.79 (s, 1H), 5.14 (d, J=6.7, 13.5 Hz, 1H), 4.23 (s, 2H), 3.41 (t, J=6.7 Hz, 2H), 1.74 (d, J=6.8 Hz, 6H); ES-LCMS m/z 417.2 $[M+H]^+$.

Example 20

Synthesis of I-21

I-21

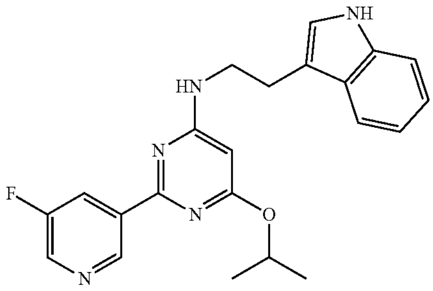

Synthesis Scheme:

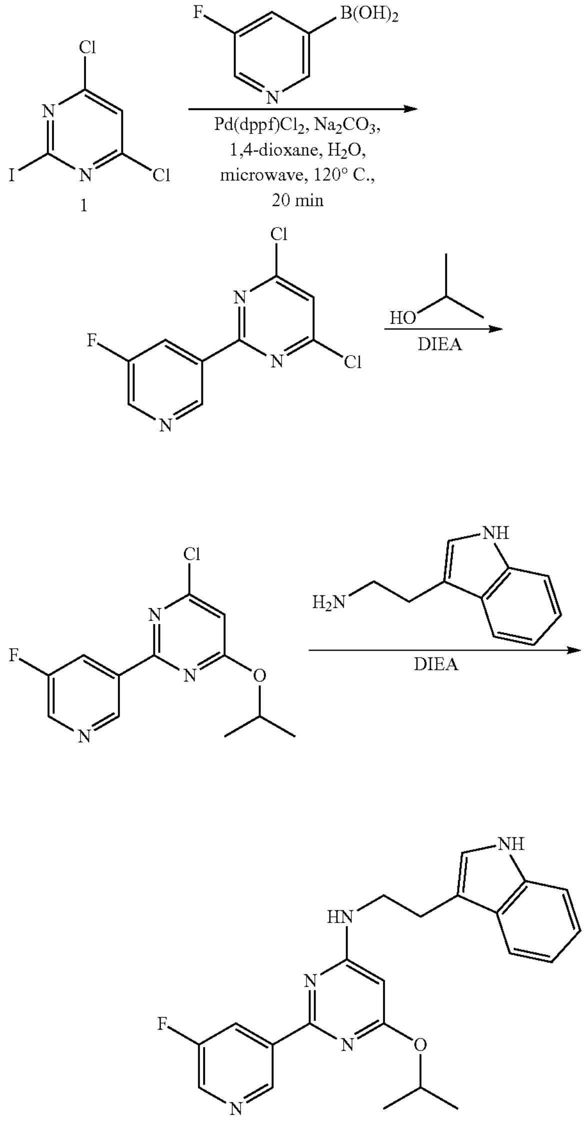

I-21

Step 1: 4,6-Dichloro-2-(5-fluoro-3-pyridyl)pyrimidine

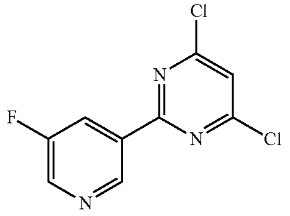 [SMILES: Fc1cncc(-c2nc(Cl)cc(Cl)n2)c1]

4,6-Dichloro-2-iodo-pyrimidine (1 g, 3.58 mmol, 1 eq), (5-fluoro-3-pyridyl)boronic acid (503.91 mg, 3.58 mmol, 1 eq), $Na_2CO_3$ (1.14 g, 10.73 mmol, 3.0 eq) and Pd(dppf)$Cl_2$ (261.67 mg, 357.62 umol, 0.1 eq) were taken up into a microwave tube in 1,4-dioxane (14 mL) and water (2.4 mL). The sealed tube was heated at 80° C. for 30 min under microwave. LCMS showed 58% of desired compound was detected. The reaction mixture was diluted with EtOAc (50 mL) and filtered through a pad of celite. The filtrate was concentrated under reduced pressure to give a residue which was purified by flash silica gel chromatography (from PE/EtOAc=100/1 to 5/1, TLC: PE/EtOAc=3/1, $R_f$=0.80) to yield 4,6-dichloro-2-(5-fluoro-3-pyridyl)pyrimidine (275 mg, 1.13 mmol, 37.8% yield, 100% purity) as a yellow solid. $^1$H NMR (400 MHz, $CD_3OD$) δ ppm 9.34 (t, J=1.4 Hz, 1H), 8.66 (d, J=2.9 Hz, 1H), 8.51-8.43 (m, 1H), 7.75 (s, 1H); ES-LCMS m/z 243.9, 245.9 $[M+H]^+$.

Step 2: 4-Chloro-2-(5-fluoro-3-pyridyl)-6-isopropoxy-pyrimidine

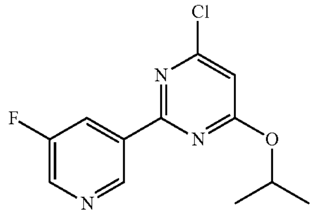 [SMILES: CC(C)Oc1cc(Cl)nc(-c2cncc(F)c2)n1]

To a solution of i-PrOH (14.78 mg, 245.85 umol, 18.82 uL, 1 eq) in THF (4 mL) was added NaH (11.80 mg, 295.02 umol, 60% in mineral oil, 1.2 eq). The mixture was stirred at 0° C. for 30 min. 4,6-dichloro-2-(5-fluoro-3-pyridyl) pyrimidine (60 mg, 245.85 umol, 1.0 eq) was added into the above solution and the mixture was stirred at 15° C. for 12 h. LCMS showed 83% of desired compound was detected. The reaction mixture was concentrated under reduced pressure to give a residue which was diluted with water (30 mL) and extracted with EtOAc (30 mL×3). The combined organic layers were dried over $Na_2SO_4$, filtered and concentrated under reduced pressure to yield 4-chloro-2-(5-fluoro-3-pyridyl)-6-isopropoxy-pyrimidine (50 mg, 167.92 umol, 68.3% yield, 89.9% purity) as a brown solid, which was used in the next step without further purification. $^1$H NMR (400 MHz, $CD_3OD$) δ ppm 9.39-9.28 (m, 1H), 8.68-8.58 (m, 1H), 8.50-8.39 (m, 1H), 6.85 (s, 1H), 5.57 (m, 1H), 1.44 (d, J=6.2 Hz, 6H); ES-LCMS m/z 268.0, 270.0 $[M+H]^+$.

Step 3: 2-(5-Fluoro-3-pyridyl)-N-[2-(1H-indol-3-yl)ethyl]-6-isopropoxy-pyrimidin-4-amine (I-21)

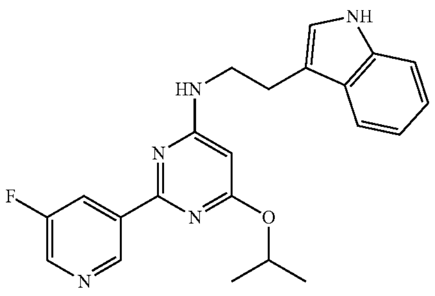 [SMILES: CC(C)Oc1cc(NCCc2c[nH]c3ccccc23)nc(-c2cncc(F)c2)n1]

To a solution of 4-chloro-2-(5-fluoro-3-pyridyl)-6-isopropoxy-pyrimidine (50 mg, 167.92 umol, 1.0 eq) in i-PrOH (4 mL) was added DIEA (65.11 mg, 503.76 umol, 87.74 uL, 3.0 eq) and 2-(1H-indol-3-yl)ethanamine (134.52 mg, 839.60 umol, 5 eq). The mixture was stirred at 70° C. for 12 h. LCMS showed the starting materials were remained and there was no desired compound. The reaction mixture was added into a microwave tube and heated at 125° C. for 3 h under microwave. LCMS showed the starting material was consumed completely and 28% of desired compound was detected. The reaction mixture was concentrated under reduced pressure to give a residue which was purified by preparative HPLC (HCl condition; column: Phenomenex Gemini 150×25 mm×10 um; mobile phase: [water(0.05% HCl)-ACN]; B %: 55%-85%, 10 min) and the desired fraction was lyophilized to yield 2-(5-fluoro-3-pyridyl)-N-[2-(1H-indol-3-yl)ethyl]-6-isopropoxy-pyrimidin-4-amine (26.35 mg, 52.45 umol, 31.2% yield, 99.7% purity, 3HCl salt) as a yellow solid. $^{1}H$ NMR (400 MHz, $CD_3OD$) δ ppm 9.15 (s, 1H), 8.66 (d, J=2.4 Hz, 1H), 8.32 (d, J=8.8 Hz, 1H), 7.60 (d, J=7.7 Hz, 1H), 7.29 (d, J=7.9 Hz, 1H), 7.13-6.95 (m, 3H), 5.69 (m, 1H), 5.04 (m, 1H), 3.78 (m, 2H), 3.09 (t, J=6.8 Hz, 2H), 1.40-1.33 (m, 6H); ES-LCMS m/z 392.1 $[M+H]^+$.

Example 21

Synthesis of I-23

I-23

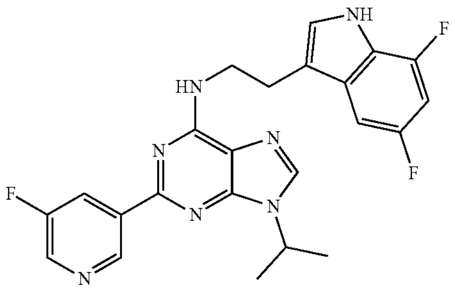

Synthesis Scheme:

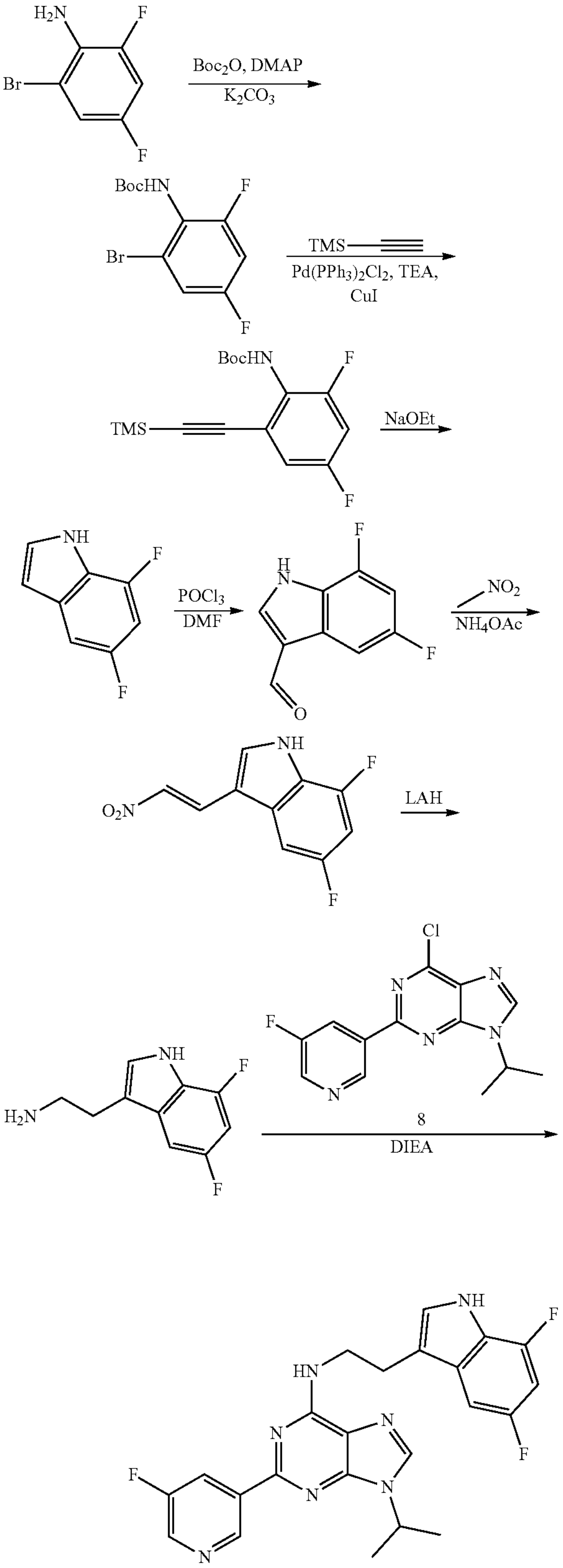

I-23

Step 1: tert-Butyl N-(2-bromo-4,6-difluoro-phenyl)carbamate

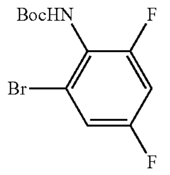 [SMILES: CC(C)(C)OC(=O)Nc1c(F)cc(F)cc1Br]

A mixture of 2-bromo-4,6-difluoro-aniline (5 g, 24.04 mmol, 1 eq), $Boc_2O$ (15.74 g, 72.11 mmol, 16.57 mL, 3 eq), DMAP (293.67 mg, 2.40 mmol, 0.1 eq) in THF (50 mL) was degassed and purged with $N_2$ for 3 times, and then the mixture was stirred at 70° C. for 16 h under $N_2$ atmosphere. LC-MS showed the starting material was consumed completely and the di-BOC intermediate was detected. The reaction mixture was concentrated under reduced pressure to give a residue which was dissolved in MeOH (50 mL) and $K_2CO_3$ (9.97 g, 72.11 mmol, 3 eq) was added. The mixture was stirred at 70° C. for 4 h. LC-MS showed the intermediate was consumed completely and one main peak with desired MS was detected. The reaction mixture was filtered, the filtrate was concentrated under reduced pressure. To the residue was added water (100 mL), extracted with EtOAc (60 mL×3). The combined organic layers were washed with brine (30 mL), dried over $Na_2SO_4$, filtered and concentrated under reduced pressure to give a residue. To the residue was added n-heptane (100 mL) then was stirred for 1 h at 15° C. The slurry was filtered, the cake was rinsed with n-heptane (30 mL×2), dried in vacuo to yield tert-butyl N-(2-bromo-4,6-difluoro-phenyl)carbamate (4.15 g, 13.47 mmol, 56.0% yield, 100% purity) as a white solid, which was used in the next step without further purification. $^1H$ NMR (400 MHz, $CDCl_3$) δ ppm 7.18 (td, J=2.3, 7.7 Hz, 1H), 6.89 (dt, J=2.8, 8.9 Hz, 1H), 5.91 (s, 1H), 1.51 (s, 9H); ES-LCMS m/z 251.9, 253.9 $[M\text{-}t\text{-}Bu+H]^+$.

Step 2: tert-Butyl N-[2,4-difluoro-6-(2-trimethylsilylethynyl)phenyl]carbamate

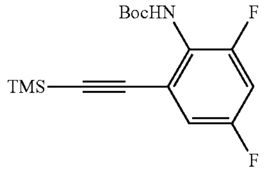 [SMILES: CC(C)(C)OC(=O)Nc1c(F)cc(F)cc1C#C[Si](C)(C)C]

A mixture of tert-butyl N-(2-bromo-4,6-difluoro-phenyl) carbamate (4 g, 12.98 mmol, 1 eq), ethynyl(trimethyl)silane (2.55 g, 25.96 mmol, 3.60 mL, 2.0 eq), TEA (3.94 g, 38.95 mmol, 5.42 mL, 3.0 eq), CuI (247.24 mg, 1.30 mmol, 0.1 eq) and $Pd(PPh_3)_2Cl_2$ (455.60 mg, 649.10 umol, 0.05 eq) in DMF (80 mL) was degassed and purged with $N_2$ for 3 times, and then the mixture was stirred at 100° C. for 16 h under $N_2$ atmosphere. LC-MS showed the starting material was consumed completely and desired MS was detected. The reaction mixture was quenched by addition water (300 mL), extracted with EtOAc (200 mL×3). The combined organic layers were washed with brine (50 mL), dried over anhydrous $Na_2SO_4$, filtered and concentrated under reduced pressure to give a residue which was purified by flash silica gel chromatography (from PE/EtOAc=1/0 to 10/1, TLC: PE/EtOAc=20/1, $R_f$=0.31) to yield tert-butyl N-[2,4-difluoro-6-(2-trimethylsilylethynyl)phenyl]carbamate (2.05 g, 5.04 mmol, 38.8% yield, 80% purity) as a black brown solid. $^1H$ NMR (400 MHz, $CDCl_3$) δ ppm 7.00-6.94 (m, 1H), 6.90-6.81 (m, 1H), 6.10 (s, 1H), 1.51 (s, 9H), 0.27 (m, 9H); ES-LCMS m/z 270.0 $[M\text{-}t\text{-}Bu+H]^+$.

Step 3: 5,7-Difluoro-1H-indole

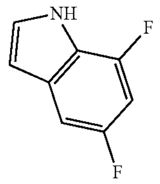 [SMILES: Fc1cc(F)c2[nH]ccc2c1]

To EtOH (100 mL) was added Na (791.23 mg, 34.42 mmol, 8 eq) slowly. After being stirred for 1 h at 15° C., tert-butyl N-[2,4-difluoro-6-(2-trimethylsilylethynyl)phenyl]carbamate (1.75 g, 4.30 mmol, 1 eq) was added to the above solution. The mixture was stirred at 85° C. for 16 h. LC-MS showed the starting material was consumed completely and desired MS was detected. The reaction mixture was concentrated under reduced pressure to remove EtOH. To the residue was added water (100 mL) and extracted with EtOAc (60 mL×3). The combined organic layers were washed with brine (30 mL), dried over $Na_2SO_4$, filtered and concentrated under reduced pressure to give a residue which was purified by flash silica gel chromatography (from PE/EtOAc=1/0 to 10/1, TLC: PE/EtOAc=20/1, $R_f$=0.17) to yield 5,7-difluoro-1H-indole (410 mg, 1.87 mmol, 43.5% yield, 70% purity) as black oil. $^1H$ NMR (400 MHz, $CD_3OD$) δ ppm 8.31 (s, 1H), 7.29-7.22 (m, 1H), 7.09 (dd, J=2.1, 9.2 Hz, 1H), 6.73 (ddd, J=2.2, 9.4, 11.1 Hz, 1H), 6.59-6.51 (m, 1H); ES-LCMS: No correct mass was found.

Step 4: 5,7-Difluoro-1H-indole-3-carbaldehyde

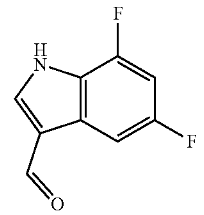 [SMILES: O=Cc1c[nH]c2c(F)cc(F)cc12]

To a solution of DMF (10 mL) was added $POCl_3$ (350.46 mg, 2.29 mmol, 212.40 uL, 2.0 eq) dropwise at −20° C. over a period of 10 mins under $N_2$. After being stirred for 1 h, 5,7-difluoro-1H-indole (250 mg, 1.14 mmol, 1 eq) in DMF (2 mL) was added to the above solution during which the temperature was maintained below −20° C. The reaction mixture was warmed to 15° C. and stirred for 1 h. LC-MS showed the starting material was consumed completely and desired MS was detected. The reaction mixture was quenched by addition $NaHCO_3$ (30 mL), extracted with EtOAc (20 mL×3). The combined organic layers were washed with brine (10 mL), dried over anhydrous $Na_2SO_4$, filtered and concentrated under reduced pressure to give a residue which was purified by flash silica gel chromatography (from PE/EtOAc=1/0 to 1/1, TLC: PE/EtOAc=1/1, $R_f$=0.40) to yield 5,7-difluoro-1H-indole-3-carbaldehyde (200 mg, 993.71 umol, 86.9% yield, 90% purity) as a yellow solid. $^1$H NMR (400 MHz, Acetone) δ ppm 11.74 (s, 1H), 10.06 (d, J=0.8 Hz, 1H), 8.38 (s, 1H), 7.74 (dd, J=2.3, 9.0 Hz, 1H), 7.03 (ddd, J=2.3, 9.5, 11.3 Hz, 1H); ES-LCMS m/z 182.1 [M+H]$^+$.

Step 5: 5,7-Difluoro-3-[(E)-2-nitrovinyl]-1H-indole

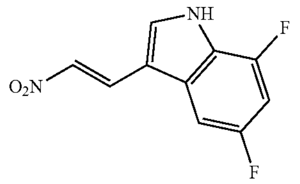 [SMILES: O=[N+]([O-])/C=C/c1c[nH]c2c(F)cc(F)cc12]

To a solution of 5,7-difluoro-1H-indole-3-carbaldehyde (200 mg, 993.71 umol, 1 eq) in nitronethane (8 mL) was added $NH_4OAc$ (229.79 mg, 2.98 mmol, 3.0 eq). The mixture was stirred at 110° C. for 16 h. LC-MS showed the starting material was consumed completely and desired MS was detected. The reaction mixture was concentrated under reduced pressure to remove nitronethane. The residue was diluted with EtOAc (50 mL), washed with water (10 mL), brine (10 mL), dried over $Na_2SO_4$, filtered and concentrated under reduced pressure to give 5,7-difluoro-3-[(E)-2-nitrovinyl]-1H-indole (160 mg, 599.56 umol, 60.3% yield, 84% purity) as a brown solid, which was used in the next step without further purification. $^1$H NMR (400 MHz, $CDCl_3$) δ ppm 8.23 (d, J=13.6 Hz, 1H), 7.74-7.58 (m, 2H), 7.26-7.11 (m, 1H), 6.91-6.75 (m, 1H); ES-LCMS m/z 225.0 [M+H]$^+$.

Step 6: 2-(5,7-Difluoro-1H-indol-3-yl)ethanamine

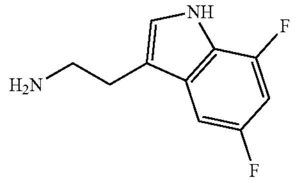 [SMILES: NCCc1c[nH]c2c(F)cc(F)cc12]

To a solution of 5,7-difluoro-3-[(E)-2-nitrovinyl]-1H-indole (50 mg, 187.36 umol, 1 eq) in THF (5 mL) was added dropwise LAH (1 M, 936.82 uL, 5 eq) at 0° C. After addition, the mixture was stirred at 80° C. for 2 h. LC-MS showed the starting material was consumed completely and one main peak with desired MS was detected. The reaction mixture was diluted with THF (50 mL), quenched by addition water (0.05 mL), follow by 10% NaOH (0.05 mL) and water (0.15 mL) in sequence at 0° C. After being stirred for 30 min, the mixture was filtered through celite. The filtrate was concentrated under reduced pressure to give 2-(5,7-difluoro-1H-indol-3-yl)ethanamine (36 mg, crude) as a yellow oil, which was used in the next step without further purification. $^1$H NMR (400 MHz, $CD_3OD$) ppm 7.18 (s, 1H), 7.13-7.01 (m, 1H), 6.73-6.67 (m, 1H), 2.97-2.79 (m, 4H); ES-LCMS m/z 197.2 [M+H]$^+$.

Step 7: N-[2-(5,7-Difluoro-1H-indol-3-yl)ethyl]-2-(5-fluoro-3-pyridyl)-9-isopropyl-purin-6-amine (I-23)

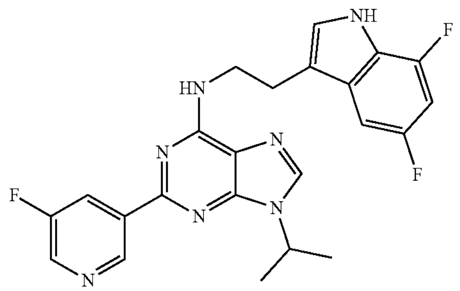 [SMILES: CC(C)n1cnc2c(NCCc3c[nH]c4c(F)cc(F)cc34)nc(-c3cncc(F)c3)nc21]

To a solution of 6-chloro-2-(5-fluoro-3-pyridyl)-9-isopropyl-purine (50 mg, 164.55 umol, 1 eq) in i-PrOH (3 mL) was added DIEA (106.33 mg, 822.73 umol, 143.30 uL, 5 eq) and 2-(5,7-difluoro-1H-indol-3-yl)ethanamine (35.51 mg, 181.00 umol, 1.1 eq). The mixture was stirred at 60° C. for 16 h. LC-MS showed 21% of the starting material was remained and 66% of desired compound was detected. The reaction mixture was concentrated under reduced pressure to remove i-PrOH to give a residue which was purified by preparative HPLC (column: Phenomenex Gemini 150×25 mm×10 um; mobile phase: [water (0.05% HCl)_ACN]; B %: 46%-76%, 10 min). The desired fraction was lyophilized to yield N-[2-(5,7-difluoro-1H-indol-3-yl)ethyl]-2-(5-fluoro-3-pyridyl)-9-isopropyl-purin-6-amine (20.82 mg, 36.75 umol, 22.3% yield, 99% purity, 3HCl salt) as a yellow solid. $^1$H NMR (400 MHz, $CD_3OD$) δ ppm 9.45 (s, 1H), 9.20 (s, 1H), 8.90 (s, 1H), 8.83 (d, J=9.0 Hz, 1H), 7.24 (s, 1H), 7.11 (d, J=8.8 Hz, 1H), 6.67-6.58 (m, 1H), 5.11 (m, 1H), 4.13 (s, 2H), 3.17 (t, J=6.6 Hz, 2H), 1.73 (d, J=6.8 Hz, 6H); ES-LCMS m/z 452.2 [M+H]$^+$.

Example 22

Synthesis of I-16

I-16

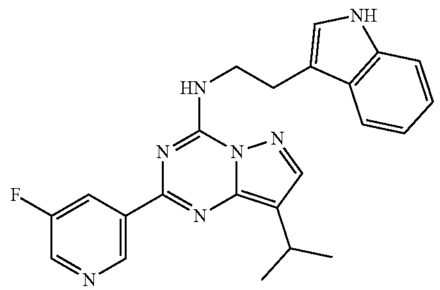

Synthesis Scheme:

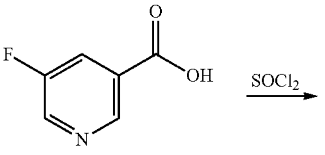

-continued

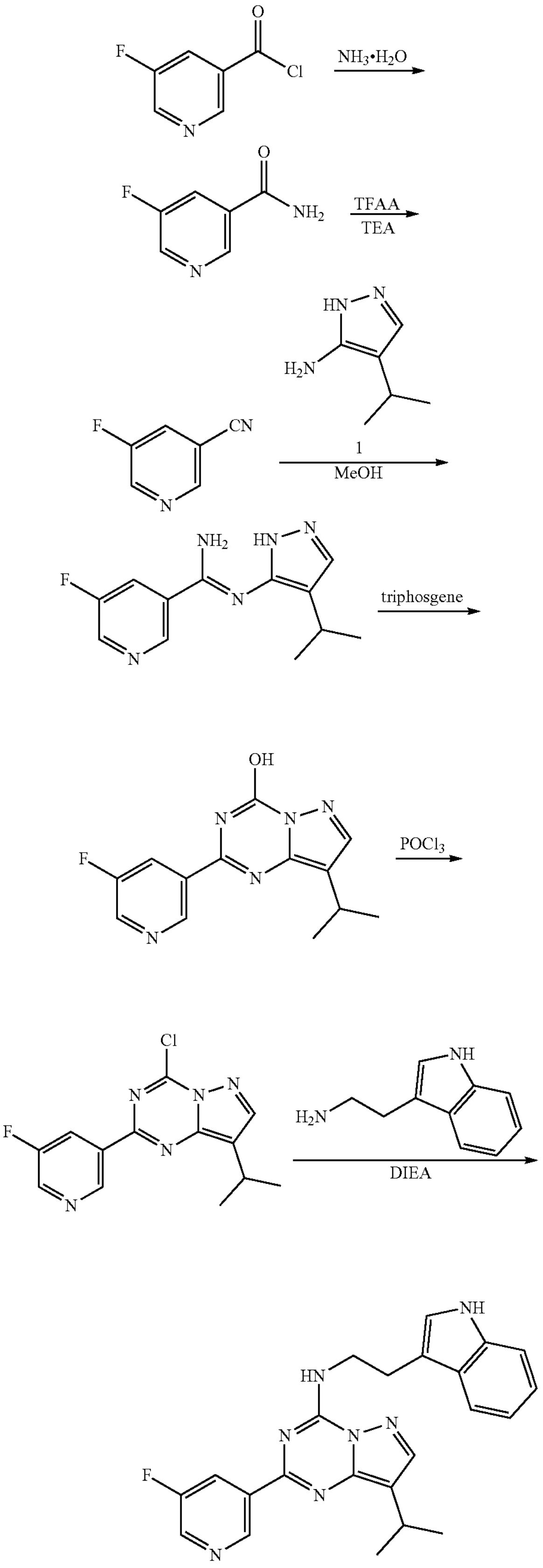

I-16

Step 1: 5-Fluoropyridine-3-carbonyl chloride

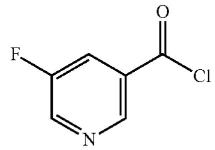

To a solution of 5-fluoropyridine-3-carboxylic acid (7 g, 49.61 mmol, 1 eq) in $SOCl_2$ (57.40 g, 482.47 mmol, 35.00 mL, 9.73 eq) was added DMF (0.1 mL) at 0° C. After addition, the mixture was stirred at 50° C. for 2 h. TLC (PE/EA=1/1, $R_f$=0.75, added MeOH) showed the starting material was consumed completely. The mixture was concentrated to yield the 5-fluoropyridine-3-carbonyl chloride (7 g, crude) as light yellow oil, which was used in the next step without further purification.

Step 2: 5-Fluoropyridine-3-carboxamide

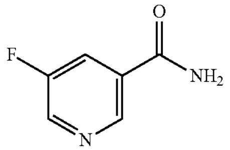

To a solution of $NH_3H_2O$ (31.85 g, 254.47 mmol, 35.00 mL, 28% purity, 5.80 eq) in THF (10 mL) was added the solution of 5-fluoropyridine-3-carbonyl chloride (7 g, 43.87 mmol, 1 eq) in THF (30 mL) dropwise at 0° C. under $N_2$. The mixture was stirred at 15° C. for 1 h. LCMS showed starting material was consumed completely and one main peak with desired MS was detected. The reaction mixture was concentrated under reduced pressure to remove solvent. The residue was diluted with EtOAc (50 mL) and extracted with EtOAc (50 mL×2). The combined organic layers were washed with brine (30 mL), dried over $Na_2SO_4$, filtered and concentrated under reduced pressure to yield 5-fluoropyridine-3-carboxamide (6 g, 42.39 mmol, 96.6% yield, 99.0% purity) as an off white solid. $^1H$ NMR (400 MHz, $CD_3OD$) δ ppm 8.87 (s, 1H), 8.62 (d, J=2.6 Hz, 1H), 8.06-8.01 (m, 1H); ES-LCMS m/z 141.1 $[M+H]^+$.

Step 3: 5-Fluoropyridine-3-carbonitrile

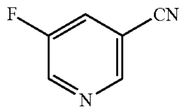

To a mixture of 5-fluoropyridine-3-carboxamide (6 g, 42.39 mmol, 1 eq) and TEA (6.43 g, 63.59 mmol, 8.85 mL, 1.5 eq) in DCM (60 mL) was added TFAA (13.36 g, 63.59 mmol, 8.85 mL, 1.5 eq) dropwise at 15° C. under $N_2$. The mixture was stirred at 15° C. for 12 h. TLC (PE/EA=1/1, $R_f$=0.89) indicated the starting material was consumed completely and one new spot formed. The reaction mixture was concentrated under reduced pressure to give a residue which was purified by flash silica gel chromatography (ISCO®; 24 g SepaFlash® Silica Flash Column, Eluent of 0-20% Ethyl acetate/Petroleum ethergradient @ 30 mL/min) to yield 5-fluoropyridine-3-carbonitrile (4.7 g, 36.57 mmol, 86.3% yield, 95.0% purity) as a white solid. $^{1}H$ NMR (400 MHz, $CD_3OD$) δ ppm 8.82-8.71 (m, 2H), 8.14-8.06 (m, 1H); ES-LCMS: No correct mass was found.

Step 4: 5-Fluoro-N-(4-isopropyl-1H-pyrazol-5-yl) pyridine-3-carboxamidine

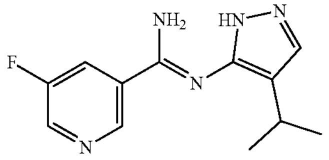 [SMILES: CC(C)c1cn[nH]c1/N=C(\N)c1cncc(F)c1]

A mixture of 5-fluoropyridine-3-carbonitrile (1.02 g, 7.91 mmol, 1 eq) and 4-isopropyl-1H-pyrazol-5-amine (880.27 mg, 6.33 mmol, 0.8 eq) in xylene (20 mL) was stirred for 30 min at 70° C. Then $AlMe_3$ (2 M, 4.75 mL, 1.2 eq) was added to above mixture in one portion at 70° C. under $N_2$. The mixture was stirred at 100° C. for 15 h. LC-MS showed 16% of desired MS was detected. The mixture was quenched by MeOH (20 mL), concentrated to yield a residue which was purified by flash silica gel chromatography (ISCO®; 12 g SepaFlash® Silica Flash Column, Eluent of 0-10%MeOH/DCM ethergradient @ 30 mL/min) to yield 5-fluoro-N-(4-isopropyl-1H-pyrazol-5-yl)pyridine-3-carboxamidine (600 mg, 1.94 mmol, 24.5% yield, 80% purity) as a yellow solid. $^{1}H$ NMR (400 MHz, $CD_3OD$) δ ppm 8.96 (s, 1H), 8.54 (d, J=2.6 Hz, 1H), 8.11 (d, J=9.5 Hz, 1H), 7.34 (s, 1H), 3.06 (m, 1H), 1.25 (d, J=6.8 Hz, 6H); ES-LCMS m/z 248.1 $[M+H]^+$.

Step 5: 2-(5-Fluoro-3-pyridyl)-8-isopropyl-pyrazolo [1,5-a][1,3,5]triazin-4-ol

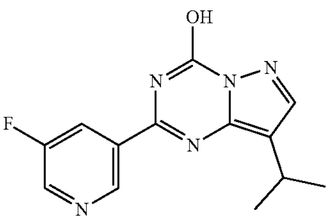 [SMILES: CC(C)c1cnn2c(O)nc(-c3cncc(F)c3)nc12]

To a mixture of 5-fluoro-N-(4-isopropyl-1H-pyrazol-5-yl) pyridine-3-carboxamidine (100 mg, 323.53 umol, 1 eq) in 1,4-dioxane (10 mL) and THF (5 mL) was added triphosgene (33.60 mg, 113.24 umol, 0.35 eq) and then the mixture was stirred for 15 h at 80° C. LC-MS showed 57.5% of desired MS was detected. The reaction mixture was concentrated under reduced pressure to give 2-(5-fluoro-3-pyridyl)-8-isopropyl-pyrazolo[1,5-a][1,3,5]triazin-4-ol (88 mg, crude) as a brown solid, which was used in the next step without further purification. $^{1}H$ NMR (400 MHz, $CD_3OD$) δ ppm 8.90-8.85 (m, 2H), 8.18 (d, J=2.3, 8.6 Hz, 1H), 7.66 (s, 1H), 3.04 (d, J=6.9, 13.7 Hz, 1H), 1.26 (d, J=6.8 Hz, 6H); ES-LCMS m/z 274.3 $[M+H]^+$.

Step 6: 4-Chloro-2-(5-fluoro-3-pyridyl)-8-isopropyl-pyrazolo[1,5-a][1,3,5]triazine

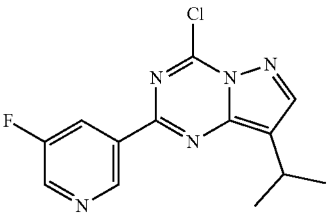 [SMILES: CC(C)c1cnn2c(Cl)nc(-c3cncc(F)c3)nc12]

A mixture of 2-(5-fluoro-3-pyridyl)-8-isopropyl-pyrazolo [1,5-a][1,3,5]triazin-4-ol (88 mg, 322.03 umol, 1 eq) in $POCl_3$ (8.1 g, 52.83 mmol, 4.91 mL, 164.04 eq) was stirred for 2 h at 100° C. LC-MS showed the starting material was consumed completely. The reaction mixture was concentrated under reduced pressure to give a residue, then diluted with DCM (20 mL) and extracted with DCM (20 mL×2). The combined organic layers were washed with brine (15 mL), dried over $Na_2SO_4$, filtered and concentrated under reduced pressure to give a residue which was purified by flash silica gel chromatography (ISCO®; 12 g SepaFlash® Silica Flash Column, Eluent of 0-15% Ethyl acetate/Petroleum ethergradient @ 30 mL/min) to yield 4-chloro-2-(5-fluoro-3-pyridyl)-8-isopropyl-pyrazolo[1,5-a][1,3,5]triazine (15 mg, 49.78 umol, 15.5% yield, 96.8% purity) as a white solid. $^{1}H$ NMR (400 MHz, $CDCl_3$) δ ppm 9.49 (s, 1H), 8.60 (d, J=2.6 Hz, 1H), 8.42 (d, J=9.5 Hz, 1H), 8.17 (s, 1H), 3.35 (d, J=6.7, 13.9 Hz, 1H), 1.43 (d, J=6.8 Hz, 6H); ES-LCMS m/z 292.0, 294.0 $[M+H]^+$.

Step 7: 2-(5-Fluoro-3-pyridyl)-N-[2-(1H-indol-3-yl) ethyl]-8-isopropyl-pyrazolo[1,5-a][1,3,5]triazin-4-amine (I-16)

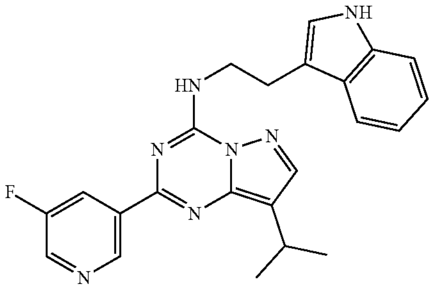

A mixture of 4-chloro-2-(5-fluoro-3-pyridyl)-8-isopropyl-pyrazolo[1,5-a][1,3,5]triazine (15 mg, 49.78 umol, 1 eq), DIEA (19.30 mg, 149.33 umol, 26.01 uL, 3 eq) and 2-(1H-indol-3-yl)ethanamine (9.57 mg, 59.73 umol, 1.2 eq) in i-PrOH (3 mL) was stirred for 3 h at 50° C. LC-MS showed the starting material was consumed completely. The reaction mixture was concentrated under reduced pressure to give a residue which was purified by preparative HPLC (HCl condition; column: Phenomenex Kinetex XB-C18 150 mm*30 mm, 5 m; mobile phase: [water(0.05% HCl)-ACN]; B %: 55%-85%, 17 min) and the desired fraction was lyophilized to yield 2-(5-fluoro-3-pyridyl)-N-[2-(1H-indol-3-yl)ethyl]-8-isopropyl-pyrazolo[1,5-a][1,3,5]triazin-4-amine (6.17 mg, 11.70 umol, 23.5% yield, 99.5% purity, 3HCl) as a white solid. $^1$H NMR (400 MHz, $CD_3OD$) δ ppm 9.14 (s, 1H), 8.81 (br s, 1H), 8.56 (d, J=9.0 Hz, 1H), 7.97 (s, 1H), 7.69-7.63 (m, 1H), 7.18-7.12 (m, 1H), 7.00-6.94 (m, 3H), 4.04 (t, J=6.7 Hz, 2H), 3.27-3.20 (m, 1H), 3.17 (t, J=6.7 Hz, 2H), 1.37 (d, J=6.8 Hz, 6H); ES-LCMS m/z 416.2 $[M+H]^+$.

Example 23

Synthesis of I-24

I-24

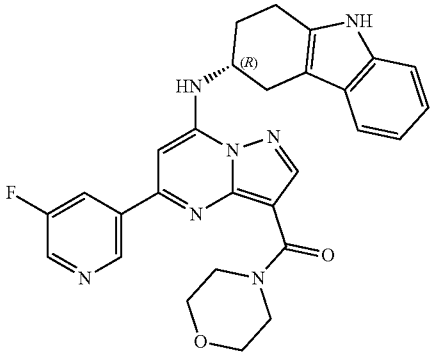

Synthesis Scheme:

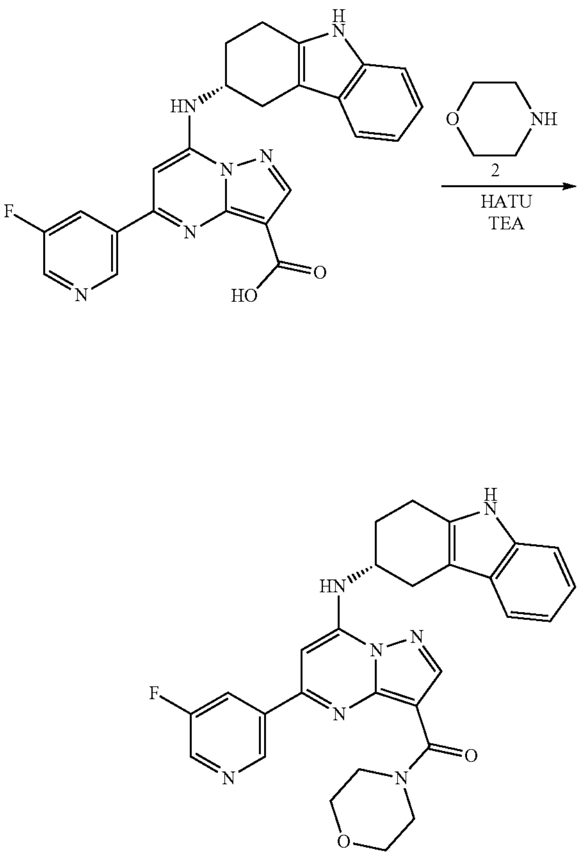

I-24

Step 1: [5-(5-Fluoro-3-pyridyl)-7-[[(3R)-2,3,4,9-tetrahydro-1H-carbazol-3-yl]amino]pyrazolo[1,5-a]pyrimidin-3-yl]-morpholino-methanone (I-24)

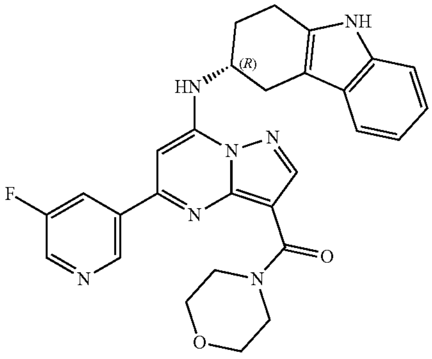

To a solution of 5-(5-fluoro-3-pyridyl)-7-[[(3R)-2,3,4,9-tetrahydro-1H-carbazol-3-yl]amino]pyrazolo[1,5-a]pyrimidine-3-carboxylic acid (25 mg, 55.60 μmol, 1 eq) in DCM (3 mL) was added HATU (31.71 mg, 83.40 μmol, 1.5 eq), TEA (11.25 mg, 111.20 μmol, 15.48 uL, 2 eq) and morpholine (9.69 mg, 111.20 μmol, 9.79 μL, 2 eq). The mixture was stirred at 25° C. for 12 h under $N_2$ atmosphere. The mixture was concentrated under reduced pressure, then water (30 mL) was added, extracted with EtOAc (20 mL×3). The combined organic layers were washed with brine (30 mL), dried over $Na_2SO_4$, filtered and concentrated. The residue was purified by preparative HPLC (column: Phenomenex Gemini 150×25 mm×10 m; mobile phase: [water(0.05% HCl)-ACN]; B %: 40%-70%, 10 min) followed by lyophilization to yield[5-(5-fluoro-3-pyridyl)-7-[[(3R)-2,3,4,9-tetrahydro-1H-carbazol-3-yl]amino]pyrazolo[1,5-a]pyrimidin-3-yl]-morpholino-methanone (8.45 mg, 13.61 μmol, 24.4% yield, 100% purity, 3HCl) as a yellow solid. $^1$H NMR (400 MHz, $CD_3OD$) δ ppm 9.24 (s, 1H), 8.66 (d, J=2.6 Hz, 1H), 8.55-8.48 (m, 1H), 8.34 (s, 1H), 7.39 (d, J=7.7 Hz, 1H), 7.28 (d, J=7.9 Hz, 1H), 7.10-7.01 (m, 2H), 6.99-6.93 (m, 1H), 4.54 (br s, 1H), 3.80 (s, 8H), 3.37-3.34 (m, 1H), 3.20-3.05 (m, 1H), 3.04-2.87 (m, 2H), 2.36 (br s, 1H), 2.28 (d, J=6.2 Hz, 1H); ES-LCMS m/z 512.3 $[M+H]^+$.

Example 24

Synthesis of I-25

I-25

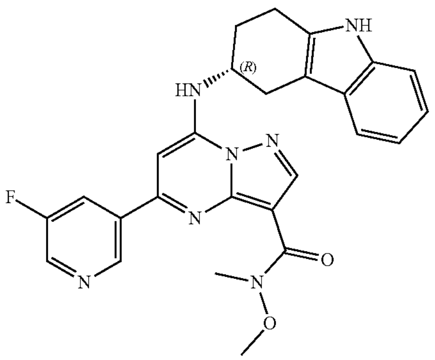

Synthetic Scheme:

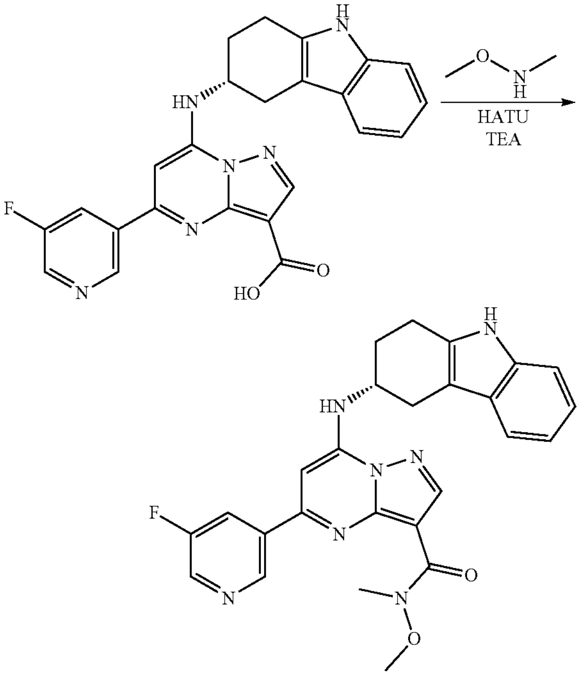

I-25

Step 1: 5-(5-Fluoro-3-pyridyl)-N-methoxy-N-methyl-7-[[(3R)-2,3,4,9-tetrahydro-1H-carbazol-3-yl]amino]pyrazolo[1,5-a]pyrimidine-3-carboxamide (I-25)

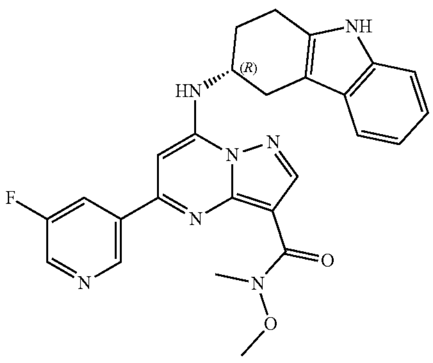

To a solution of 5-(5-fluoro-3-pyridyl)-7-[[(3R)-2,3,4,9-tetrahydro-1H-carbazol-3-yl]amino]pyrazolo[1,5-a]pyrimidine-3-carboxylic acid (30 mg, 63.06 μmol, 1 eq) in DCM (4 mL) was added HATU (35.97 mg, 94.59 μmol, 1.5 eq), TEA(12.76 mg, 126.12 μmol, 17.55 μL, 2 eq) and N-methoxymethanamine (12.30 mg, 126.12 μmol, 2 eq, HCl). The mixture was stirred at 20° C. for 1 h under $N_2$ atmosphere. The mixture was concentrated under reduced pressure, then water (30 mL) was added. The mixture was extracted with EtOAc (20 mL×3). The combined organic layers were washed with brine (30 mL), dried over $Na_2SO_4$, filtered and concentrated. The mixture was purified by preparative HPLC (column: Phenomenex Gemini 150×25 mm×10 μm; mobile phase: [water(0.05% HCl)-ACN]; B %: 40%-70%, 10 min) followed by lyophilization to yield 5-(5-fluoro-3-pyridyl)-N-methoxy-N-methyl-7-[[(3R)-2,3,4,9-tetrahydro-1H-carbazol-3-yl]amino]pyrazolo[1,5-a]pyrimidine-3-carboxamide (15.98 mg, 26.86 μmol, 42.6% yield, 100% purity, 3HCl) as a yellow solid. $^1$H NMR (400 MHz, $CD_3OD$) δ ppm 9.10 (s, 1H), 8.82 (d, J=2.8 Hz, 1H), 8.67 (s, 1H), 8.47 (d, J=9.3 Hz, 1H), 7.39 (d, J=7.5 Hz, 1H), 7.35-7.25 (m, 2H), 7.05 (t, J=7.0 Hz, 1H), 7.00-6.91 (m, 1H), 4.69 (br s, 1H), 3.87 (s, 3H), 3.43 (s, 3H), 3.18-2.95 (m, 4H), 2.37 (dd, J=5.6, 10.2 Hz, 2H); ES-LCMS m/z 486.2 $[M+H]^+$.

Example 25

Synthesis of I-26

I-26

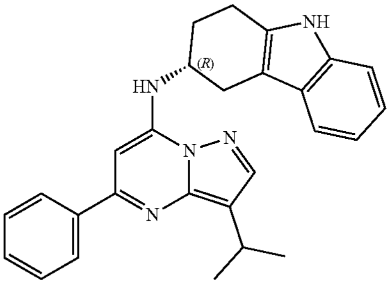

Synthetic Scheme:

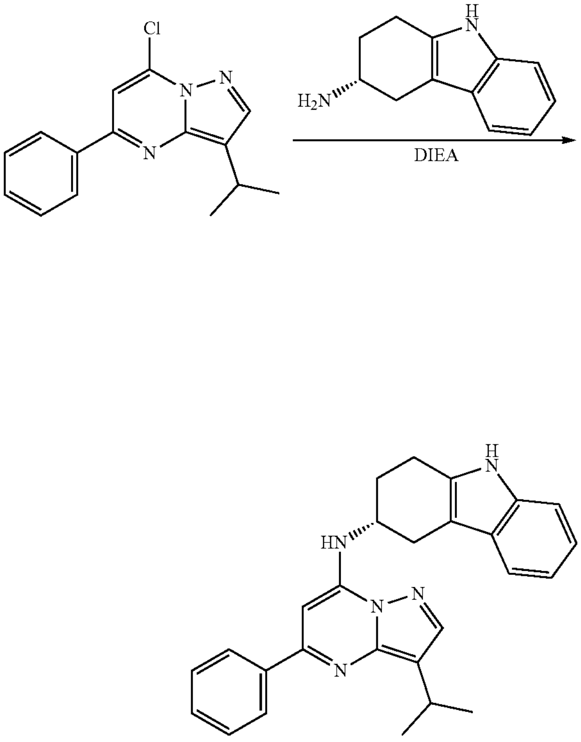

I-26

Step 1: (3R)—N-(3-isopropyl-5-phenyl-pyrazolo[1,5-a]pyrimidin-7-yl)-2,3,4,9-tetrahydro-1H-carbazol-3-amine (I-26)

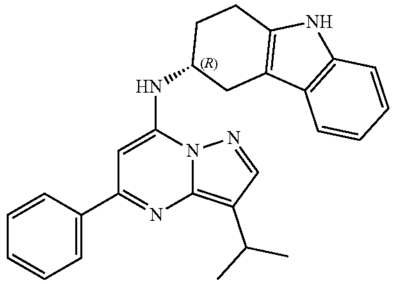

A mixture of 7-chloro-3-isopropyl-5-phenyl-pyrazolo[1,5-a]pyrimidine (60 mg, 218.15 μmol, 1 eq), (3R)-2,3,4,9-tetrahydro-1H-carbazol-3-amine (44.69 mg, 239.96 μmol, 1.1 eq), DIEA (84.58 mg, 654.44 μmol, 113.99 μL, 3 eq) in i-PrOH (2 mL) was degassed and purged with $N_2$ for 3 times, then the mixture was stirred at 80° C. for 12 h under $N_2$ atmosphere. The reaction mixture was concentrated under reduced pressure to give a residue which was purified by preparative HPLC (column: Phenomenex Gemini C18 250*50 mm*10 um; mobile phase: [water (0.05% HCl)-ACN]; B %: 35%-65%, 10 min) followed by lyophilization to yield (3R)—N-(3-isopropyl-5-phenyl-pyrazolo[1,5-a]pyrimidin-7-yl)-2,3,4,9-tetrahydro-1H-carbazol-3-amine (45.09 mg, 91.19 μmol, 41.8% yield, 100.0% purity, 2HCl) as a yellow solid. $^1$H NMR (400 MHz, $CD_3OD$) δ ppm 8.12 (s, 1H), 7.97 (d, J=7.7 Hz, 2H), 7.68-7.50 (m, 3H), 7.39 (d, J=7.9 Hz, 1H), 7.27 (d, J=8.2 Hz, 1H), 7.09-7.01 (m, 1H), 7.00-6.92 (m, 1H), 6.78 (s, 1H), 4.56 (m, 1H), 3.39-3.33 (m, 2H), 3.16-2.90 (m, 3H), 2.53-2.07 (m, 2H), 1.39 (d, J=6.8 Hz, 6H); ES-LCMS m/z 422.2 $[M+H]^+$.

Example 26

Synthesis of I-27a

I-27a

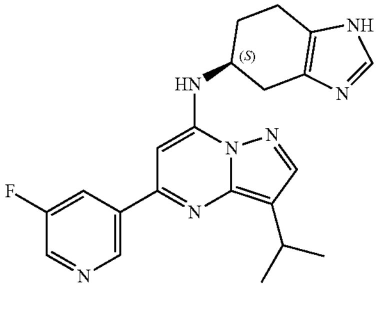

Synthetic Scheme:

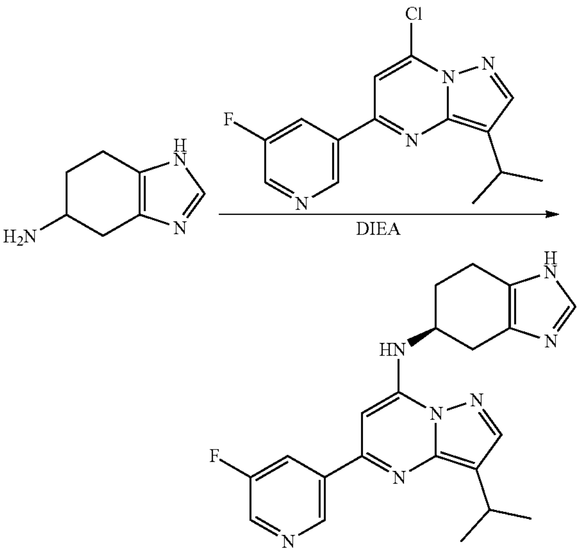

I-27

Step 1: 5-(5-Fluoro-3-pyridyl)-3-isopropyl-N-[(5S)-4,5,6,7-tetrahydro-1H-benzimidazol-5-yl]pyrazolo[1,5-a]pyrimidin-7-amine (I-27)

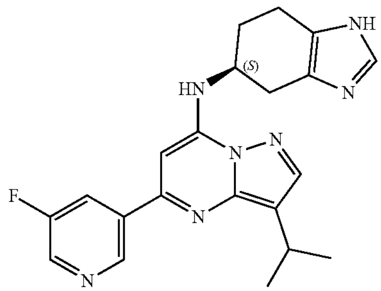

A mixture of 4,5,6,7-tetrahydro-1H-benzimidazol-5-amine (62 mg, 451.95 μmol, 1 eq), 7-chloro-5-(5-fluoro-3-pyridyl)-3-isopropyl-pyrazolo[1,5-a]pyrimidine (145.99 mg, 451.95 μmol, 1 eq) and DIEA (175.24 mg, 1.36 mmol, 236.17 μL, 3 eq) in i-PrOH (3 mL) was stirred at 90° C. for 12 h. The reaction mixture was concentrated under reduced pressure to dryness to give a residue which was purified by flash silica gel chromatography (from PE/EtOAc=20/0 to 0/1, TLC: PE/EtOAc=1/1, $R_f$=0.10). The desired fraction was dried under reduced pressure to dryness. The residue was separated by preparative SFC (column: AD (250 mm*30 mm, 5 um); mobile phase: [0.1% $NH_3H_2O$ IPA]; B %: 35%-35%, min) to give Peak 1 (Rt=5.226) and Peak 2 (Rt=5.531). Peak 1 was concentrated under reduced pressure to dryness to give a residue which was purified by preparative HPLC (column: Phenomenex Gemini 150*25 mm*10 um; mobile phase: [water (0.05% HCl)-ACN]; B %: 20%-50%, 10 min). The desired fraction was lyophilized to give 5-(5-fluoro-3-pyridyl)-3-isopropyl-N-[(5S)-4,5,6,7-tetrahydro-1H-benzimidazol-5-yl]pyrazolo[1,5-a]pyrimidin-7-amine (25.12 mg, 50.16 μmol, 11.1% yield, 100.0% purity, 3HCl) (Rt=5.226, $[\alpha]^{25.5}_D$=−18.573 (0.105 g/100 mL in MeOH, ee %=97.4%) as a yellow solid. $^1$H NMR (400 MHz, $CD_3OD$) δ ppm 9.08 (s, 1H), 8.83 (s, 1H), 8.77 (s, 1H), 8.47

(d, J=8.4 Hz, 1H), 8.25 (s, 1H), 7.07 (s, 1H), 4.72 (br s, 1H), 3.45-3.31 (m, 2H), 3.07-2.87 (m, 3H), 2.44-2.35 (m, 1H), 2.33-2.22 (m, 1H), 1.39 (d, J=6.8 Hz, 6H); ES-LCMS m/z 392.2 $[M+H]^+$.

Example 27

Synthesis of I-28a

I-28a

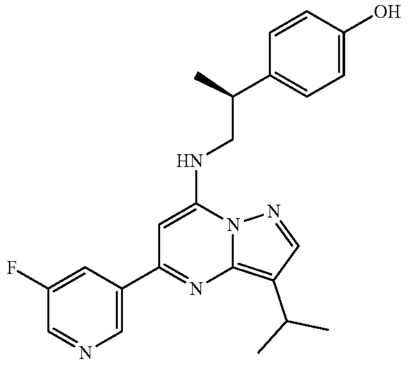

Synthetic Scheme:

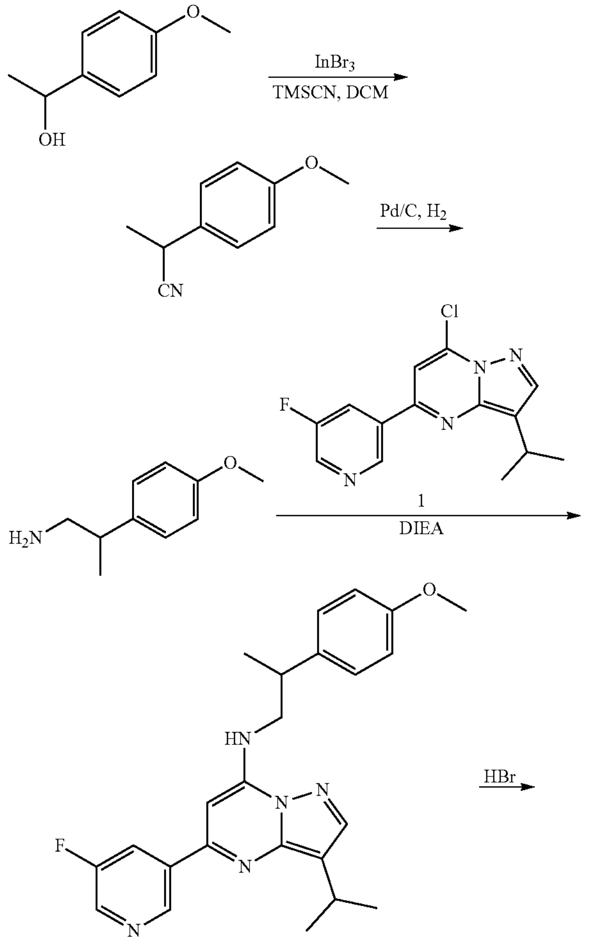

-continued

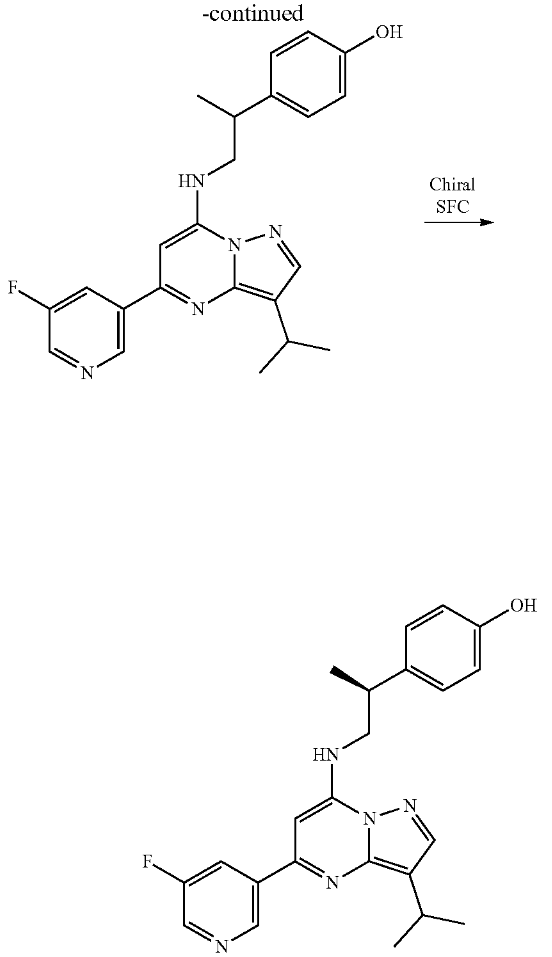

I-28

Step 1: 2-(4-Methoxyphenyl)propanenitrile

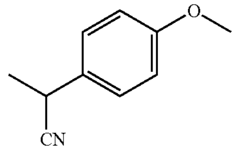

To a stirred solution of 1-(4-methoxyphenyl)ethanol (2 g, 13.14 mmol, 1 eq) in DCM (10 mL) was added the solution of TMSCN (2.61 g, 26.28 mmol, 3.29 mL, 2 eq) and tribromoindigane (465.90 mg, 1.31 mmol, 0.1 eq) in DCM (10 mL) dropwise over 30 min. Then the resulted mixture was stirred at 30° C. for 15 min. TLC (PE/EtOAc=10/1, $R_f$=0.55) showed desired compound was detected. The reaction mixture was concentrated under reduced pressure to give a residue which was purified by flash silica gel chromatography (from PE/EtOAc=100/1 to 10/1, TLC: PE/EtOAc=10/1, $R_f$=0.55) to give 2-(4-methoxyphenyl)propanenitrile (1 g, 5.58 mmol, 42.5% yield, 90.0% purity) as yellow oil. $^1$H NMR (400 MHz, $CDCl_3$) δ ppm 7.27 (s, 2H), 6.97-6.86 (m, 2H), 3.91-3.79 (m, 4H), 1.63 (d, J=7.3 Hz, 3H).

Step 2: 2-(4-Methoxyphenyl)propan-1-amine $H_2N$

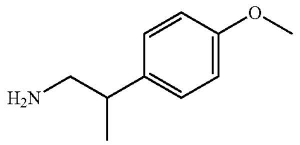

To a solution of 2-(4-methoxyphenyl)propanenitrile (800 mg, 4.47 mmol, 1 eq) in MeOH (40 mL) was added Raney-Ni (0.5 g). The mixture was degassed and purged with $H_2$ three times and the mixture was stirred at 30° C. for 5 h under $H_2$ atmosphere. TLC (PE/EtOAc=10/1, $R_f$=0.10) showed reactant 1 was almost consumed and one new spot was detected. The reaction mixture was concentrated under reduced pressure to give a residue which was purified by flash silica gel chromatography (from DCM/MeOH=10/1 to 5/1, TLC: DCM/MeOH=10/1, $R_f$=0.60) to give 2-(4-methoxyphenyl)propan-1-amine (710 mg, 3.87 mmol, 86.6% yield, 90.0% purity) as yellow oil. $^1H$ NMR (400 MHz, $CDCl_3$) δ ppm 7.13 (d, J=8.5 Hz, 2H), 6.87 (d, J=8.5 Hz, 2H), 3.80 (s, 3H), 2.88-2.69 (m, 3H), 1.23 (d, J=6.8 Hz, 3H); ES-LCMS m/z 166.1 $[M+H]^+$.

Step 3: 5-(5-Fluoro-3-pyridyl)-3-isopropyl-N-[2-(4-methoxyphenyl)propyl]pyrazolo[1,5-a]pyrimidin-7-amine

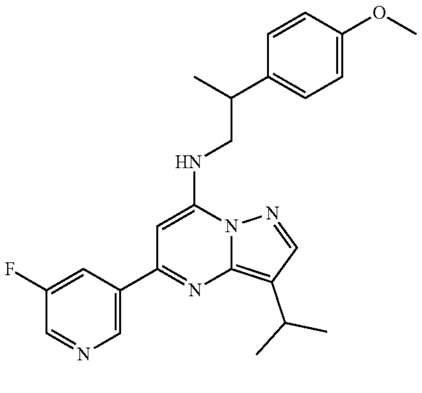 [SMILES: COc1ccc(C(C)CNc2cc(-c3cncc(F)c3)nc3c(C(C)C)cnn23)cc1]

To a solution of 7-chloro-5-(5-fluoro-3-pyridyl)-3-isopropyl-pyrazolo[1,5-a]pyrimidine (250 mg, 773.93 μmol, 1.0 eq) in i-PrOH (10 mL) was added DIEA (300.07 mg, 2.32 mmol, 404.41 μL, 3.0 eq) and 2-(4-methoxyphenyl)propan-1-amine (200 mg, 1.09 mmol, 1.41 eq). The mixture was stirred at 60° C. for 5 h. The reaction mixture was concentrated under reduced pressure to give a residue which was purified by flash silica gel chromatography (from PE/EtOAc=100/1 to 3/1, TLC: PE/EtOAc=3/1, $R_f$=0.75) to give 5-(5-fluoro-3-pyridyl)-3-isopropyl-N-[2-(4-methoxyphenyl)propyl]pyrazolo[1,5-a]pyrimidin-7-amine (300 mg, 715.15 μmol, 92.4% yield, 100.0% purity) as yellow solid. $^1H$ NMR (400 MHz, $CDCl_3$) δ ppm 9.02 (d, J=1.5 Hz, 1H), 8.53 (d, J=2.9 Hz, 1H), 8.19-8.12 (m, 1H), 7.86 (s, 1H), 7.22 (d, J=8.6 Hz, 2H), 6.94-6.86 (m, 2H), 6.38 (t, J=5.7 Hz, 1H), 6.19 (s, 1H), 3.79 (s, 3H), 3.68-3.53 (m, 2H), 3.39-3.29 (m, 1H), 3.22-3.13 (m, 1H), 1.47-1.39 (m, 9H); ES-LCMS m/z 420.2 $[M+H]^+$.

Step 4: 4-[(1S)-2-[[5-(5-fluoro-3-pyridyl)-3-isopropyl-pyrazolo[1,5-a]pyrimidin-7-yl]amino]-1-methyl-ethyl]phenol (I-28)

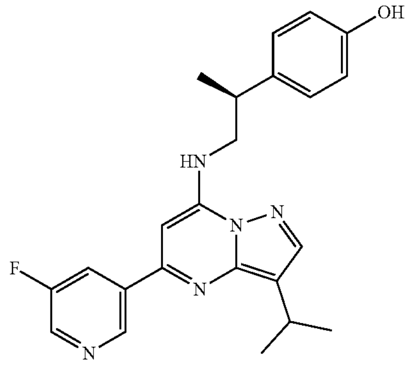 [SMILES: CC(C)c1cnn2c(NC[C@@H](C)c3ccc(O)cc3)cc(-c3cncc(F)c3)nc12]

5-(5-Fluoro-3-pyridyl)-3-isopropyl-N-[2-(4-methoxyphenyl)propyl]pyrazolo[1,5-a]pyrimidin-7-amine (290.00 mg, 691.31 μmol, 1 eq) was added into HBr (25 mL, 60% in water). The mixture was stirred at 120° C. for 2 h. The reaction mixture was concentrated under reduced pressure to give a residue which was purified by flash silica gel chromatography (from PE/EtOAc=100/1 to 2/1, TLC: PE/EtOAc=3/1, $R_f$=0.50). The compounds were separated by SFC (condition: column: OJ(250 mm×30 mm, 5 μm); mobile phase: [0.1% NH3$H_2O$ ETOH]; B %: 25%-25%, min). The solution after separation were concentrated to afford the crude products which were purified by preparative HPLC (HCl condition; column: Phenomenex Gemini 150×25 mm×10 m; mobile phase: [water (0.05% HCl)-ACN]; B %: 45%-75%, 10 min), followed by lyophilization to yield 4-[(1S)-2-[[5-(5-fluoro-3-pyridyl)-3-isopropyl-pyrazolo[1,5-a]pyrimidin-7-yl]amino]-1-methyl-ethyl]phenol (26.29 mg, 54.96 μmol, 7.9% yield, 100.0% purity, 2HCl salt ($R_t$=4.768 min, ee %=100.0 and $[\alpha]^{25}_D$=+81.522 (MeOH, c=0.104 g/100 mL)) as yellow solid. $^1H$ NMR (400 MHz, $CD_3OD$) δ ppm 8.81-8.79 (m, 2H), 8.24 (s, 1H), 8.11 (td, J=2.2, 9.0 Hz, 1H), 7.12-7.06 (m, 2H), 6.62-6.56 (m, 2H), 6.30 (s, 1H), 3.90-3.79 (m, 2H), 3.30-3.25 (m, 1H), 3.19-3.11 (m, 1H), 1.41 (d, J=7.1 Hz, 3H), 1.36 (dd, J=2.5, 6.9 Hz, 6H); ES-LCMS m/z 406.2 $[M+H]^+$.

Example 28

Synthesis of I-29

I-29

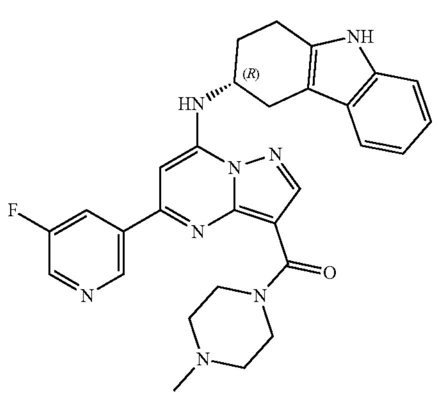

Synthetic Scheme:

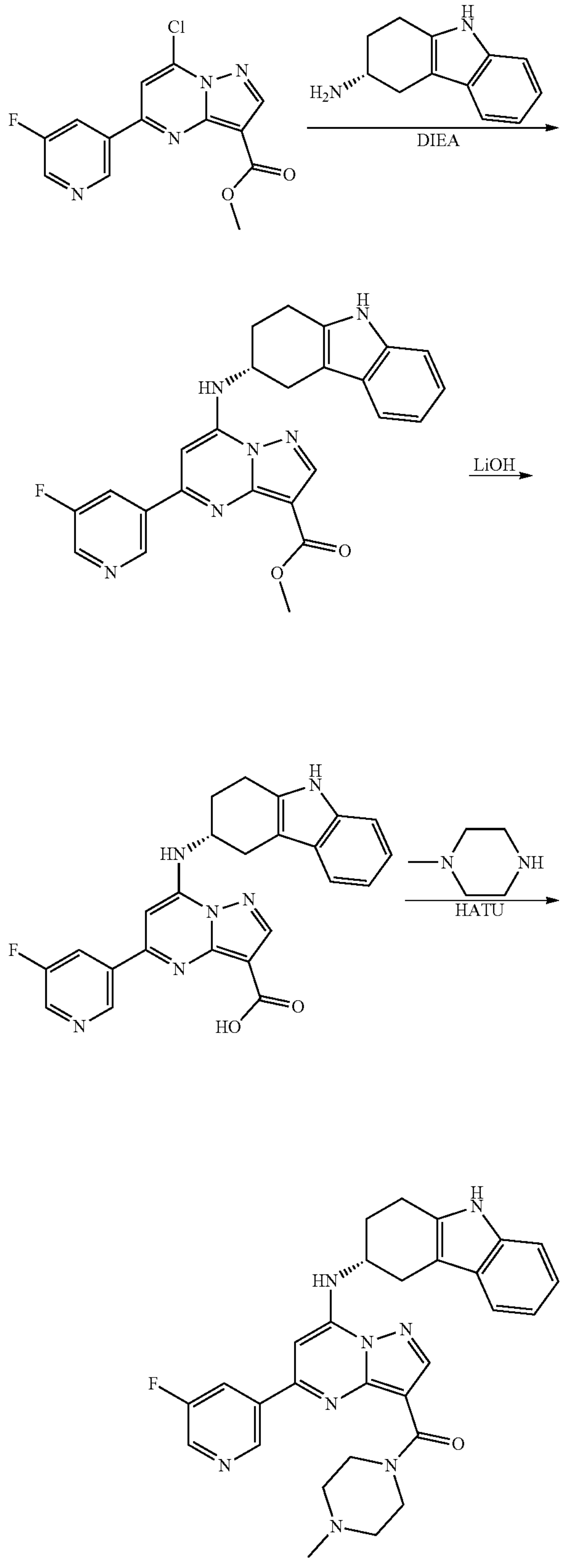

I-29

Step 1: Methyl 5-(5-fluoro-3-pyridyl)-7-[[(3R)-2,3,4,9-tetrahydro-1H-carbazol-3-yl]amino]pyrazolo[1,5-a]pyrimidine-3-carboxylate

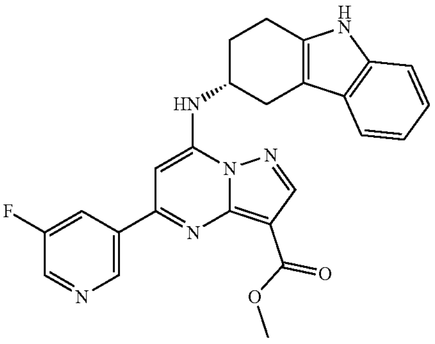 [SMILES: COC(=O)c1cnn2c(N[C@@H]3CCc4[nH]c5ccccc5c4C3)cc(-c3cncc(F)c3)nc12]

To a solution of methyl 7-chloro-5-(5-fluoro-3-pyridyl)pyrazolopyrimidine-3-carboxylate (300 mg, 929.31 μmol, 1 eq) in i-PrOH (20 mL) was added DIEA (360.32 mg, 2.79 mmol, 485.61 μL, 3 eq) and (3R)-2,3,4,9-tetrahydro-1H-carbazol-3-amine (190.39 mg, 1.02 mmol, 1.1 eq). The mixture was stirred at 60° C. for 3 h under N2 atmosphere. The mixture was concentrated under reduced pressure, then water (80 mL) was added. The mixture was extracted with EtOAc (50 mL×3). The combined organic layers were washed with brine (50 mL), dried over $Na_2SO_4$, filtered and concentrated. The residue was purified by flash silica gel chromatography (from PE/EtOAc=1/0 to 1/1, TLC: PE/EtOAc=1/1, $R_f$=0.6) to yield a product of methyl 5-(5-fluoro-3-pyridyl)-7-[[(3R)-2,3,4,9-tetrahydro-1H-carbazol-3-yl]amino]pyrazolo[1,5-a]pyrimidine-3-carboxylate (270 mg, 561.92 μmol, 60.4% yield, 95% purity) as a yellow solid. $^1H$ NMR (400 MHz, $CD_3OD$) δ ppm 9.09 (s, 1H), 8.58 (d, J=2.6 Hz, 1H), 8.47 (s, 1H), 8.37-8.25 (m, 1H), 7.95 (s, 1H), 7.47 (d, J=7.9 Hz, 1H), 7.35 (d, J=7.9 Hz, 1H), 7.22-7.06 (m, 2H), 6.79 (d, J=8.6 Hz, 1H), 6.66 (s, 1H), 4.36 (br s, 1H), 3.97 (s, 3H), 3.41 (dd, J=4.5, 15.3 Hz, 1H), 3.07-2.88 (m, 3H), 2.42-2.27 (m, 2H); ES-LCMS m/z 457.2 $[M+H]^+$.

Step 2: Methyl 5-(5-fluoro-3-pyridyl)-7-[[(3R)-2,3,4,9-tetrahydro-1H-carbazol-3-yl]amino]pyrazolo[1,5-a]pyrimidine-3-carboxylate

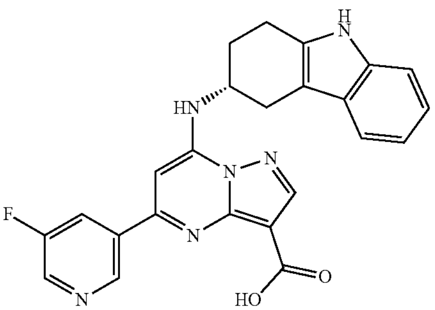 [SMILES: O=C(O)c1cnn2c(N[C@@H]3CCc4[nH]c5ccccc5c4C3)cc(-c3cncc(F)c3)nc12]

To a solution of methyl 5-(5-fluoro-3-pyridyl)-7-[[(3R)-2,3,4,9-tetrahydro-1H-carbazol-3-yl]amino]pyrazolo[1,5-a]pyrimidine-3-carboxylate (220 mg, 457.86 μmol, 1 eq) in $H_2O$ (4 mL), MeOH (2 mL) and THF (2 mL) was added LiOH—$H_2O$ (275.60 mg, 6.57 mmol, 14.34 eq). The mixture was stirred at 50° C. for 12 h under $N_2$ atmosphere. The residue was dissolved in water (30 mL), adjusted to pH to 6 by IN HCl, then extracted with EtOAc (40 mL×3). The combined organic layers were washed with brine (50 mL), dried over $Na_2SO_4$, filtered and concentrated. The residue was concentrated under reduced pressure to give methyl 5-(5-fluoro-3-pyridyl)-7-[[(3R)-2,3,4,9-tetrahydro-1H-carbazol-3-yl]amino]pyrazolo[1,5-a]pyrimidine-3-carboxylic acid (150 mg, 315.29 μmol, 68.8% yield, 93.0% purity)) as a yellow solid which was used in the next step without further purification. $^1H$ NMR (400 MHz, $CD_3OD$) δ ppm 9.25 (s, 1H), 8.59-8.50 (m, 2H), 8.49-8.40 (m, 1H), 7.38 (d, J=7.8 Hz, 1H), 7.26 (d, J=8.0 Hz, 1H), 7.09 (s, 1H), 7.06-6.87 (m, 2H), 4.50 (s, 1H), 3.28 (s, 1H), 3.15-3.02 (m, 1H), 3.00-2.83 (m, 2H), 2.43-2.31 (m, 1H), 2.30-2.15 (m, 1H); ES-LCMS m/z 443.1 $[M+H]^+$.

Step 3: [5-(5-Fluoro-3-pyridyl)-7-[[(3R)-2,3,4,9-tetrahydro-1H-carbazol-3-yl]amino]pyrazolo[1,5-a]pyrimidin-3-yl]-(4-methylpiperazin-1-yl)methanone (I-29)

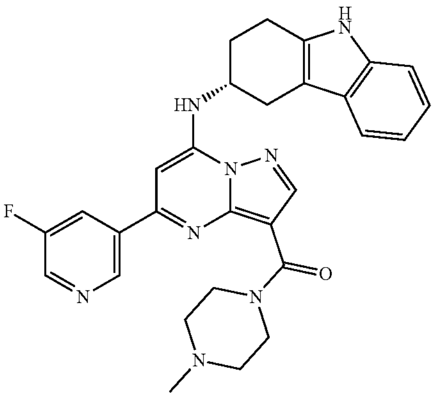 [SMILES: CN1CCN(C(=O)c2cnn3c(N[C@@H]4CCc5[nH]c6ccccc6c5C4)cc(-c4cncc(F)c4)nc23)CC1]

To a solution of 5-(5-fluoro-3-pyridyl)-7-[[(3R)-2,3,4,9-tetrahydro-1H-carbazol-3-yl]amino]pyrazolo[1,5-a]pyrimidine-3-carboxylic acid (50 mg, 105.10 μmol, 1 eq) in DCM (5 mL) was added HATU (59.94 mg, 157.65 μmol, 1.5 eq) and TEA (21.27 mg, 210.20 μmol, 29.26 μL, 2 eq) and 1-methylpiperazine (15.79 mg, 157.65 μmol, 17.49 μL, 1.5 eq). The mixture was stirred at 20° C. for 1 h under $N_2$ atmosphere. The mixture was concentrated under reduced pressure, then water (20 mL) was added. The mixture was extracted with EtOAc (20 mL×3). The combined organic layers were washed with brine (30 mL), dried over $Na_2SO_4$, filtered and concentrated. The residue was purified by preparative HPLC (column: Phenomenex Gemini C18 250×50 mm×10 m; mobile phase: [water (0.05% HCl)-ACN]; B %: 10%-40%, 10 min) followed by lyophilization to yield [5-(5-fluoro-3-pyridyl)-7-[[(3R)-2,3,4,9-tetrahydro-1H-carbazol-3-yl]amino]pyrazolo[1,5-a]pyrimidin-3-yl]-(4-methylpiperazin-1-yl)methanone (24.27 mg, 36.20 μmol, 34.4% yield, 100% purity, 4HCl) as a yellow solid. $^1H$ NMR (400 MHz, $CD_3OD$) δ ppm 9.41 (s, 1H), 9.01-8.88 (m, 2H), 8.43 (s, 1H), 7.37 (d, J=7.7 Hz, 1H), 7.27 (d, J=8.2 Hz, 1H), 7.22 (s, 1H), 7.04 (t, J=7.5 Hz, 1H), 6.99-6.93 (m, 1H), 4.79-4.51 (m, 3H), 3.60 (d, J=11.9 Hz, 4H), 3.29 (s, 3H), 3.20-3.07 (m, 1H), 3.03-2.90 (m, 5H), 2.43-2.21 (m, 2H); ES-LCMS m/z 525.3 $[M+H]^+$.

Example 29

Synthesis of I-30

I-30

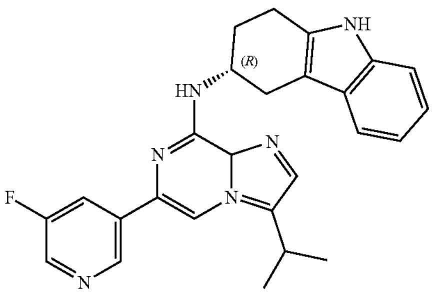

Synthetic Scheme:

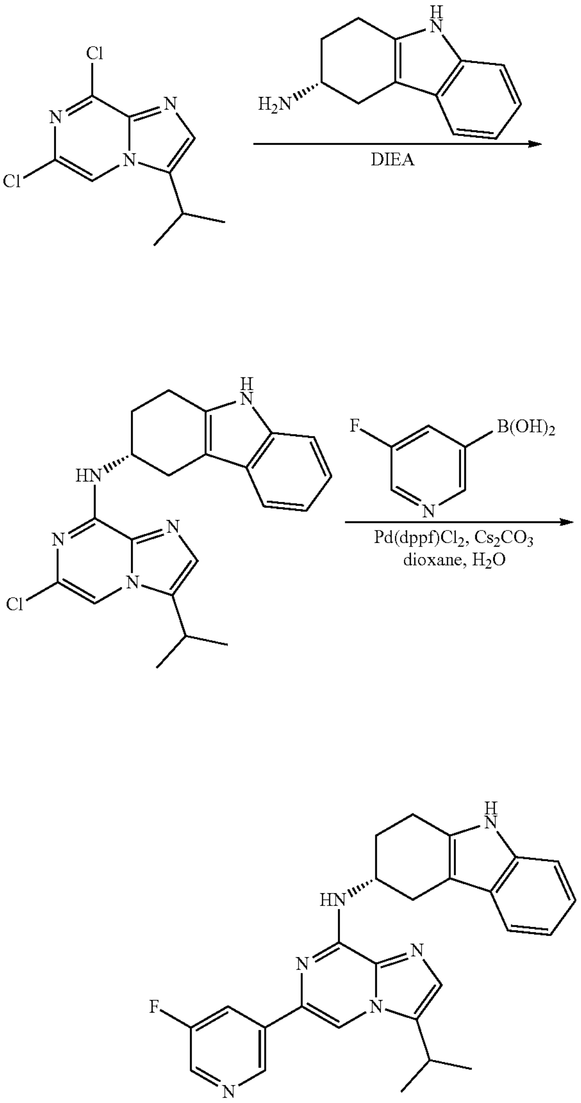

I-30

Step 1: (3R)—N-(6-Chloro-3-isopropyl-imidazo[1,2-a]pyrazin-8-yl)-2,3,4,9-tetrahydro-1H-carbazol-3-amine

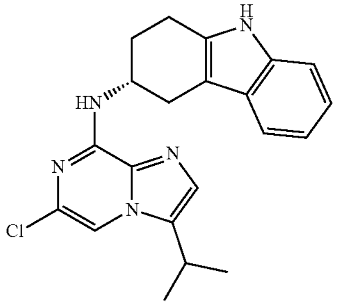 [SMILES: CC(C)c1cnc2c(N[C@@H]3CCc4[nH]c5ccccc5c4C3)nc(Cl)cn12]

To a solution of 6,8-dichloro-3-isopropyl-imidazo[1,2-a]pyrazine (45 mg, 195.57 μmol, 1 eq) and (3R)-2,3,4,9-tetrahydro-1H-carbazol-3-amine (38.25 mg, 205.35 μmol, 1.05 eq) in i-PrOH (5 mL) was added DIEA (75.83 mg, 586.72 μmol, 102.20 μL, 3 eq). The mixture was stirred at 60° C. for 3 h. LC-MS showed 55% of starting material was remained and 5% of desired compound was detected. The mixture was stirred at 60° C. for 16 h. LC-MS showed 34% of starting material was remained and 30% of desired compound was detected. The mixture was stirred at 60° C. for 16 h. LC-MS showed 21% of starting material was remained and 53% of desired compound was detected. The mixture was stirred at 60° C. for 16 h. The reaction mixture was concentrated under reduced pressure to give a residue which was purified on silica gel column chromatography (from PE/EtOAc=1/0 to 10/3, TLC: PE/EtOAc=3/1, $R_f$=0.45) to give the product (3R)—N-(6-chloro-3-isopropyl-imidazo[1,2-a]pyrazin-8-yl)-2,3,4,9-tetrahydro-1H-carbazol-3-amine (60 mg, 157.94 μmol, 80.8% yield, 100.0% purity) was obtained as light yellow oil. $^1$H NMR (400 MHz, $CDCl_3$) δ ppm 7.80 (s, 1H), 7.45 (d, J=7.5 Hz, 1H), 7.32 (s, 1H), 7.22 (s, 1H), 7.17-7.12 (m, 1H), 7.12-7.06 (m, 1H), 6.28 (d, J=9.3 Hz, 1H), 4.81 (br s, 1H), 3.29 (dd, J=5.4, 16.0 Hz, 1H), 3.15-3.04 (m, 1H), 2.99-2.89 (m, 2H), 2.81 (dd, J=6.9, 15.1 Hz, 1H), 2.28-2.25 (m, 1H), 2.23-2.15 (m, 1H), 1.37 (d, J=6.8 Hz, 6H); ES-LCMS m/z 380.2 $[M+H]^+$.

Step 2: (3R)—N-[6-(5-Fluoro-3-pyridyl)-3-isopropyl-imidazo[1,2-a]pyrazin-8-yl]-2,3,4,9-tetrahydro-1H-carbazol-3-amine (I-30)

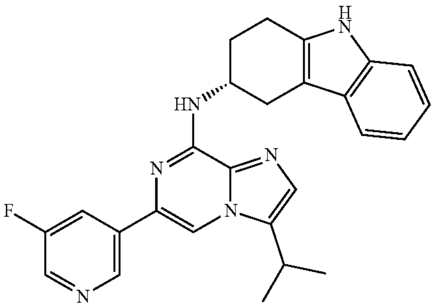 [SMILES: CC(C)c1cnc2c(N[C@@H]3CCc4[nH]c5ccccc5c4C3)nc(-c3cncc(F)c3)cn12]

To a solution of (3R)—N-(6-chloro-3-isopropyl-imidazo[1,2-a]pyrazin-8-yl)-2,3,4,9-tetrahydro-1H-carbazol-3-amine (60 mg, 157.94 μmol, 1 eq) and (5-fluoro-3-pyridyl)boronic acid (44.51 mg, 315.89 μmol, 2.0 eq) in 1,4-dioxane (2 mL) and $H_2O$ (0.5 mL) was added Pd(dppf)$Cl_2$ (11.56 mg, 15.79 μmol, 0.1 eq) and $Cs_2CO_3$ (154.38 mg, 473.83 μmol, 3.0 eq). The sealed tube was purged with $N_2$ for 3 min and heated at 110° C. for 0.5 h under microwave. The reaction mixture was filtered and concentrated under reduced pressure to give a residue which was purified by preparative HPLC twice (column: Phenomenex Gemini 150*25 mm*10 um; mobile phase: [water(0.05% HCl)-ACN]; B %: 40%-70%, 10 min; column: Gemini 150*25 5 u; mobile phase: [water (0.05% ammonia hydroxide v/v)-ACN]; B %: 50%-80%, 10 min), followed by lyophilization to yield compound (3R)—N-[6-(5-fluoro-3-pyridyl)-3-isopropyl-imidazo[1,2-a]pyrazin-8-yl]-2,3,4,9-tetrahydro-1H-carbazol-3-amine (26.85 mg, 60.59 μmol, 38.4% yield, 99.4% purity) as a white solid. $^1$H NMR (400 MHz, $CD_3OD$) δ ppm 9.07 (s, 1H), 8.38 (d, J=2.6 Hz, 1H), 8.25 (td, J=2.2, 10.2 Hz, 1H), 8.19 (s, 1H), 7.34 (d, J=7.7 Hz, 1H), 7.28-7.23 (m, 2H), 7.04-6.97 (m, 1H), 6.96-6.89 (m, 1H), 4.82-4.74 (m, 1H), 4.59 (s, 1H), 3.39-3.31 (m, 1H), 3.27-3.21 (m, 1H), 2.93 (t, J=6.2 Hz, 2H), 2.83 (dd, J=7.2, 15.1 Hz, 1H), 2.35 (dt, J=2.5, 6.4 Hz, 1H), 2.25-2.13 (m, 1H), 1.38 (dd, J=2.3, 6.7 Hz, 6H); ES-LCMS m/z 441.3 $[M+H]^+$.

Example 30

Synthesis of I-31

I-31

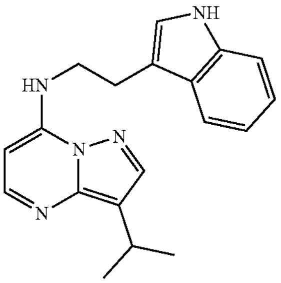

Synthetic Scheme:

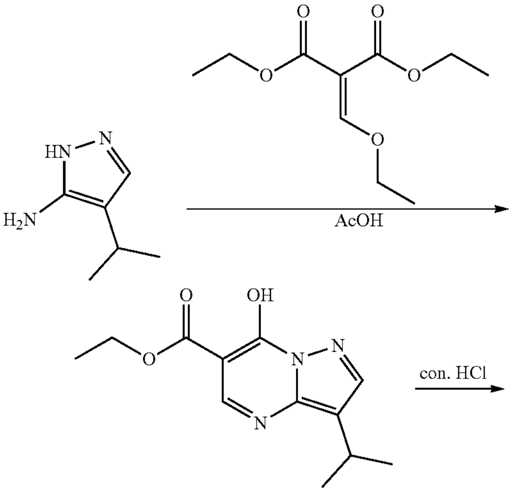

-continued

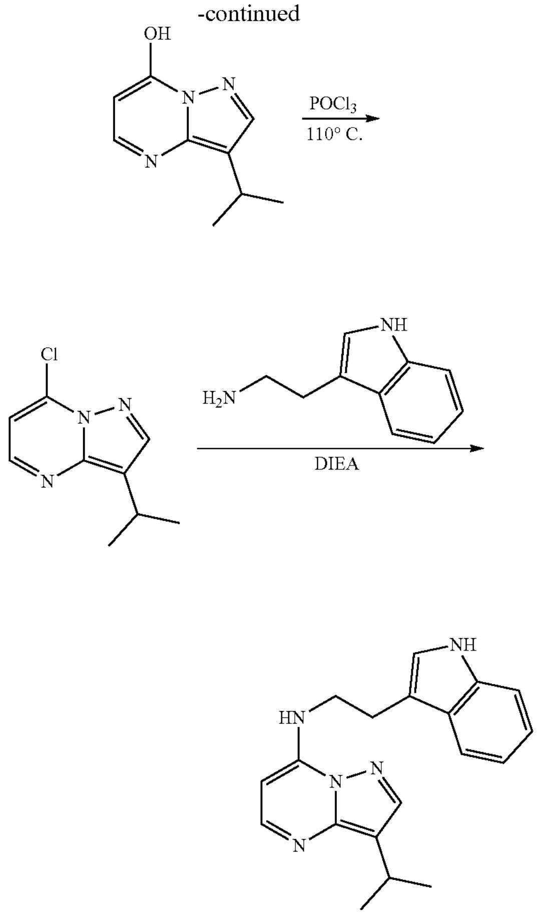

I-31

Step 1: Ethyl 7-hydroxy-3-isopropyl-pyrazolo[1,5-a]pyrimidine-6-carboxylate

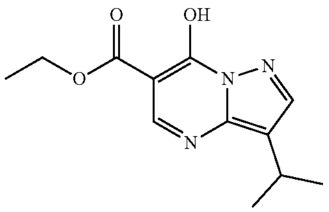 [SMILES: CCOC(=O)c1cnc2c(C(C)C)cnn2c1O]

A mixture of diethyl 2-(ethoxymethylene)propanedioate (621.89 mg, 2.88 mmol, 581.21 μL, 1 eq), 4-isopropyl-1H-pyrazol-5-amine (400 mg, 2.88 mmol, 1 eq) in AcOH (3 mL) was degassed and purged with $N_2$ for 3 times. The mixture was stirred at 120° C. for 2 h under $N_2$ atmosphere. The reaction mixture was cooled to 0° C. and filtered. The solid was washed with ethanol and petroleum ether and dried under reduced pressure to give ethyl 7-hydroxy-3-isopropyl-pyrazolo[1,5-a]pyrimidine-6-carboxylate (700 mg, 2.65 mmol, 92.3% yield, 94.5% purity) as a white solid which was used in the next step without further purification. $^1H$ NMR (400 MHz, $CD_3OD$) δ ppm 8.55 (s, 1H), 7.91 (s, 1H), 4.34 (q, J=7.2 Hz, 2H), 3.11 (m, 1H), 1.40-1.31 (m, 9H); ES-LCMS m/z 250.2 $[M+H]^+$.

Step 2: 3-Isopropylpyrazolo[1,5-a]pyrimidin-7-ol

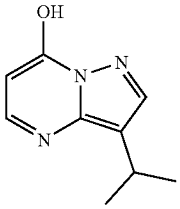

To a solution of ethyl 7-hydroxy-3-isopropyl-pyrazolo[1,5-a]pyrimidine-6-carboxylate (300 mg, 1.20 mmol, 1 eq) in $H_2O$ (3 mL) was added hydrochloric acid (6.12 g, 61.27 mmol, 6 mL, 36.5%, 50.90 eq). The mixture was stirred at 120° C. for 12 h. The reaction mixture was concentrated under reduced pressure to give 3-isopropylpyrazolo[1,5-a]pyrimidin-7-ol (200 mg, 902.92 μmol, 75.0% yield, 80.0% purity) as a black brown solid which was used in the next step without further purification. $^1H$ NMR (400 MHz, $CD_3OD$) δ ppm 8.12 (s, 1H), 7.94 (d, J=7.5 Hz, 1H), 5.98 (d, J=7.3 Hz, 1H), 2.91-2.78 (m, 1H), 1.25 (d, J=6.8 Hz, 6H); ES-LCMS m/z 178.1 $[M+H]^+$.

Step 3: 7-Chloro-3-isopropyl-pyrazolo[1,5-a]pyrimidine

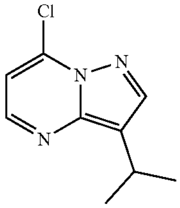

A solution of 3-isopropylpyrazolo[1,5-a]pyrimidin-7-ol (100 mg, 564.33 μmol, 1 eq) in $POCl_3$ (88.6 g, 577.83 mmol, 53.70 mL, 1023.93 eq) was stirred at 120° C. for 3 h. The reaction mixture was concentrated under reduced pressure to give a residue which was diluted with ice, then $NaHCO_3$ solid was added to above solution until pH to 8. The reaction mixture was extracted with EtOAc (30 mL×3). The combined organic layers were dried over $Na_2SO_4$, filtered and concentrated under reduced pressure to give 7-chloro-3-isopropyl-pyrazolo[1,5-a]pyrimidine (100 mg, 511.12 μmol, 90.6% yield) as brown oil which was used in the next step without further purification. $^1H$ NMR (400 MHz, $CDCl_3$) δ ppm 8.34 (d, J=4.4 Hz, 1H), 8.11 (s, 1H), 6.93 (d, J=4.4 Hz, 1H), 2.92-2.88 (m, 1H), 1.29 (d, J=6.8 Hz, 6H); ES-LCMS m/z 196.1 $[M+H]^+$ Step 4: N-[2-(1H-indol-3-yl)ethyl]-3-isopropyl-pyrazolo[1,5-a]pyrimidin-7-amine (I-31)

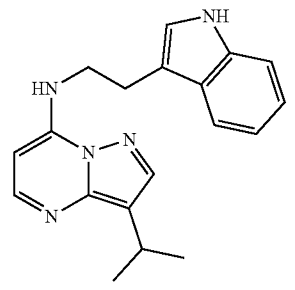 [SMILES: CC(C)c1cnn2c(NCCc3c[nH]c4ccccc34)ccnc12]

A mixture of 7-chloro-3-isopropyl-pyrazolo[1,5-a]pyrimidine (75.20 mg, 384.36 μmol, 1 eq), 2-(1H-indol-3-yl)ethanamine (73.90 mg, 461.24 μmol, 1.2 eq), DIEA (496.76 mg, 3.84 mmol, 669.49 μL, 10 eq) in i-PrOH (2 mL) was degassed and purged with $N_2$ for 3 times. The mixture was stirred at 55° C. for 3 h under $N_2$ atmosphere. The reaction mixture was concentrated under reduced pressure to give a residue which was purified by preparative HPLC (column: Syneri Max-RP C12 100*30 5 u; mobile phase: [water (0.05% HCl)-ACN]; B %: 15%-45%, 12 min), followed by lyophilization to yield N-[2-(1H-indol-3-yl)ethyl]-3-isopropyl-pyrazolo[1,5-a]pyrimidin-7-amine (22.81 mg, 54.77 μmol, 14.3% yield, 94.2% purity, 2HCl) as a yellow solid. $^1H$ NMR (400 MHz, $CD_3CD$) δ ppm 8.14 (s, 1H), 7.80 (d, J=7.1 Hz, 1H), 7.44 (d, J=7.9 Hz, 1H), 7.26 (d, J=8.2 Hz, 1H), 7.15-7.06 (m, 1H), 6.98 (t, J=7.5 Hz, 1H), 6.78 (t, J=7.2 Hz, 1H), 5.95 (d, J=7.3 Hz, 1H), 3.93 (t, J=6.5 Hz, 2H), 3.21 (t, J=6.5 Hz, 2H), 3.10 (m, 1H), 1.32 (d, J=6.8 Hz, 6H); ES-LCMS m/z 320.0 $[M+H]^+$.

Example 31

Synthesis of I-32a

I-32a

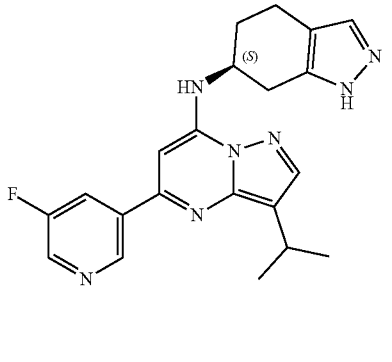

Synthetic Scheme:

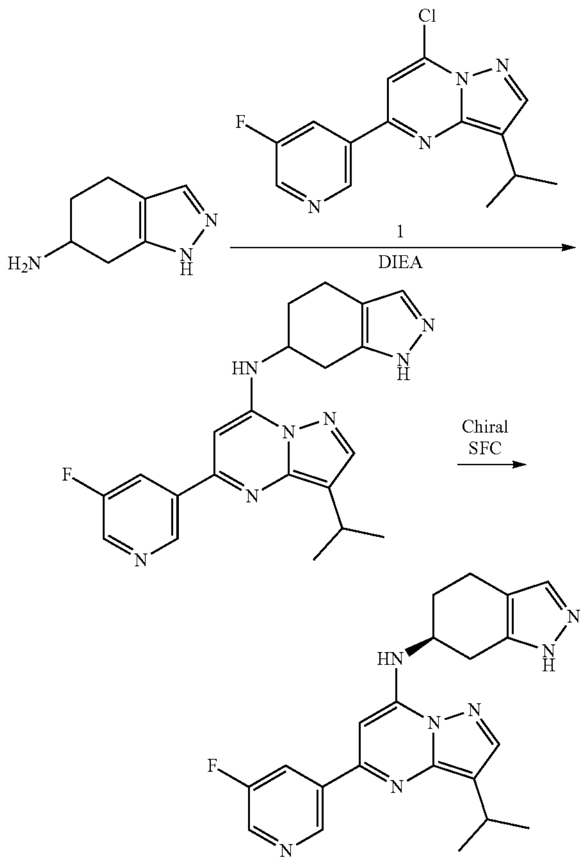

I-32

Step 1: 5-(5-Fluoro-3-pyridyl)-3-isopropyl-N-(4,5,6,7-tetrahydro-1H-indazol-6-yl)pyrazolo[1,5-a]pyrimidin-7-amine

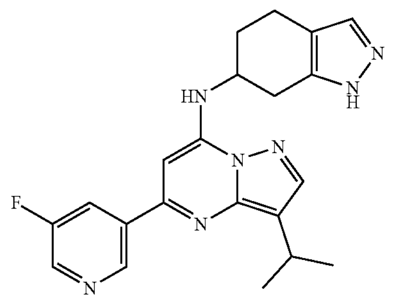 [SMILES: CC(C)c1cnn2c(NC3CCc4cn[nH]c4C3)cc(-c3cncc(F)c3)nc12]

A solution of 4,5,6,7-tetrahydro-1H-indazol-6-amine (40 mg, 291.58 μmol, 1 eq), 7-chloro-5-(5-fluoro-3-pyridyl)-3-isopropyl-pyrazolo[1,5-a]pyrimidine (84.77 mg, 291.58 μmol, 1 eq), DIEA (376.85 mg, 2.92 mmol, 507.89 μL, 10 eq) in i-PrOH (4 mL) was stirred at 120° C. for 3 h. The reaction mixture was concentrated under reduced pressure to give a residue which was purified by flash silica gel chromatography (from PE/EtOAC=100/1 to 1/1, TLC: PE/EtOAc=1/1, $R_f$=0.5) to yield 5-(5-fluoro-3-pyridyl)-3-isopropyl-N-(4,5,6,7-tetrahydro-1H-indazol-6-yl)pyrazolo

[1,5-a]pyrimidin-7-amine (90 mg, 218.42 μmol, 74.9% yield, 95.0% purity) as a yellow solid. $^1$H NMR (400 MHz, $CD_3OD$) δ ppm 9.16 (t, J=1.4 Hz, 1H), 8.52 (d, J=2.6 Hz, 1H), 8.37 (td, J=2.2, 9.9 Hz, 1H), 7.93 (s, 1H), 7.37 (s, 1H), 6.77 (s, 1H), 4.42 (s, 1H), 3.48-3.31 (m, 2H), 2.91-2.84 (m, 1H), 2.84-2.76 (m, 2H), 2.31-1.97 (m, 2H), 1.40 (d, J=6.8 Hz, 6H); ES-LCMS m/z 492.2 $[M+H]^+$.

Step 2: 5-(5-Fluoro-3-pyridyl)-3-isopropyl-N-[(6S)-4,5,6,7-tetrahydro-1H-indazol-6-yl]pyrazolo[1,5-a]pyrimidin-7-amine (I-32)

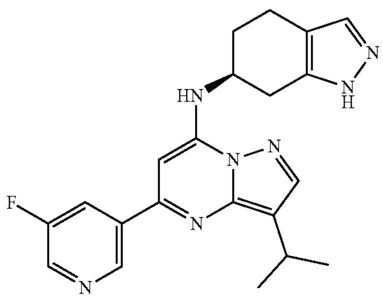 [SMILES: CC(C)c1cnn2c(N[C@H]3CCc4cn[nH]c4C3)cc(-c3cncc(F)c3)nc12]

5-(5-Fluoro-3-pyridyl)-3-isopropyl-N-(4,5,6,7-tetrahydro-1H-indazol-6-yl)pyrazolo[1,55-a]pyrimidin-7-amine (130 mg, 327.45 μmol, 1 eq) was separated by SFC (column: OD (250 mm*30 mm, 5 um); mobile phase: [0.1% $NH_3H_2O$ MeOH]; B %: 45%-45%, min) to give peak 1 ($t_R$=1.465 min) and peak 2 ($t_R$=1.687 min). The reaction mixture (peak 1) was concentrated under reduced pressure to give a residue which was purified by preparative HPLC (column: Phenomenex Gemini 150*25 mm*100 um; mobile phase: [water (0.05% HCl)-ACN]; B %: 35%-65%, 10 min), followed by lyophilization to yield 5-(5-fluoro-3-pyridyl)-3-isopropyl-N-[(6S)-4,5,6,7-tetrahydro-1H-indazol-6-yl]pyrazolo[1,5-a]pyrimidin-7-amine (39.42 mg, 76.66 μmol, 23.4% yield, 97.4% purity, 3HCl) (EE=99.3%, $t_R$=1.465 min), $[\alpha]^{26}_D$=−27.146, C=0.106 g/100 mL, MeOH) as a yellow solid. $^1$H NMR (400 MHz, $CD_3OD$) δ ppm 9.10 (s, 1H), 8.85 (d, J=2.2 Hz, 1H), 8.50 (d, J=8.8 Hz, 1H), 8.27 (s, 1H), 8.09 (s, 1H), 7.09 (s, 1H), 4.76 (s, 1H), 3.50 (dd, J=5.3, 16.5 Hz, 1H), 3.39 (m J=6.8 Hz, 1H), 3.19-3.11 (m, 1H), 2.93 (dd, J=4.4, 7.9 Hz, 2H), 2.41-2.30 (m, 1H), 2.28-2.14 (m, 1H), 1.40 (d, J=6.8 Hz, 6H); ES-LCMS m/z 392.2 $[M+H]^+$.

Example 32

Synthesis of I-33

I-33

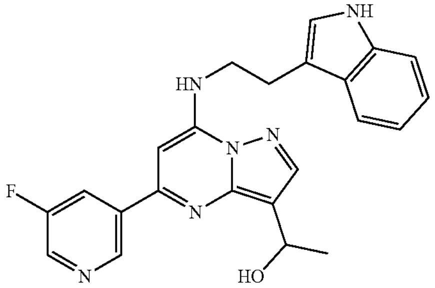

Synthetic Scheme:

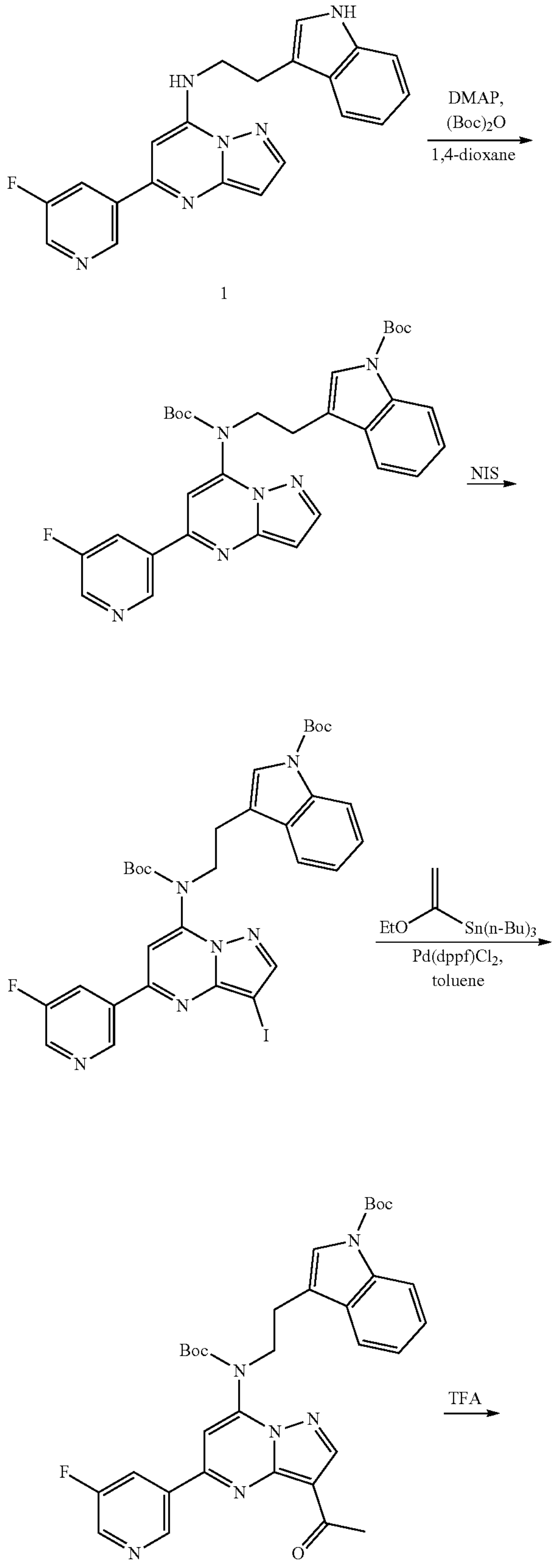

-continued

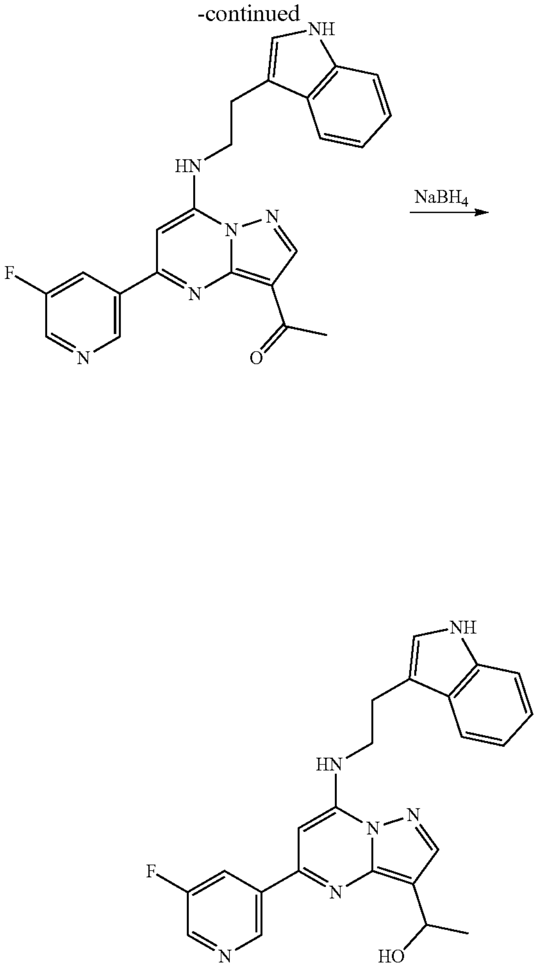

I-33

Step 1: tert-Butyl 3-[2-[tert-butoxycarbonyl-[5-(5-fluoro-3-pyridyl)pyrazolo[1,5-a]pyrimidin-7-yl]amino]ethyl]indole-1-carboxylate

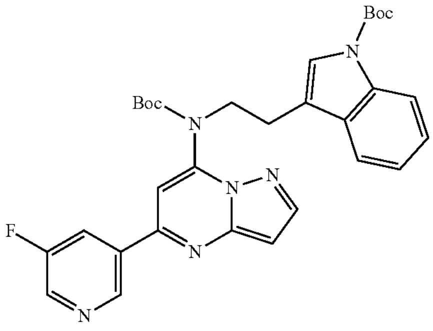

To a solution of 5-(5-fluoro-3-pyridyl)-N-[2-(1H-indol-3-yl)ethyl]pyrazolo[1,5-a]pyrimidin-7-amine (650 mg, 1.75 mmol, 1 eq) in 1,4-dioxane (30 mL) was added DMAP (639.72 mg, 5.24 mmol, 3 eq) and $(Boc)_2O$ (1.14 g, 5.24 mmol, 1.20 mL, 3 eq). The mixture was stirred at 110° C. for 12 h. The reaction mixture was concentrated under reduced pressure to give a residue which was purified by flash silica gel chromatography (from PE/EtOAc=100/1 to 3/1, TLC: PE/EtOAc=3/1, $R_f$=0.75) to give compound tert-butyl 3-[2-[tert-butoxycarbonyl-[5-(5-fluoro-3-pyridyl)pyrazolo[1,5-a]pyrimidin-7-yl]amino]ethyl]indole-1-carboxylate (575 mg, 985.06 μmol, 56.4% yield, 98.1% purity) was obtained as yellow solid. $^1H$ NMR (400 MHz, $CDCl_3$) δ ppm 8.74 (t, J=1.5 Hz, 1H), 8.55 (d, J=2.9 Hz, 1H), 8.19 (d, J=2.2 Hz, 1H), 8.01 (d, J=7.3 Hz, 1H), 7.87-7.81 (m, 1H), 7.47 (d, J=7.7 Hz, 1H), 7.27-7.23 (m, 2H), 7.20-7.14 (m, 1H), 6.77 (d, J=2.4 Hz, 1H), 6.57 (s, 1H), 4.25 (t, J=6.8 Hz, 2H), 3.13 (t, J=6.7 Hz, 2H), 1.62 (s, 9H), 1.42 (s, 9H); ES-LCMS m/z 573.3 $[M+H]^+$.

Step 2. tert-Butyl 3-[2-[tert-butoxycarbonyl-[5-(5-fluoro-3-pyridyl)-3-iodo-pyrazolo[1,5-a]pyrimidin-7-yl]amino]ethyl]indole-1-carboxylate

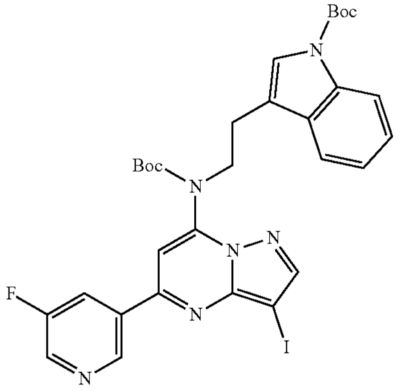 [SMILES: CC(C)(C)OC(=O)N(CCc1cn(C(=O)OC(C)(C)C)c2ccccc12)c1cc(-c2cncc(F)c2)nc2c(I)cnn12]

A mixture of tert-butyl 3-[2-[tert-butoxycarbonyl-[5-(5-fluoro-3-pyridyl)pyrazolo[1,5-a]pyrimidin-7-yl]amino]ethyl]indole-1-carboxylate (250 mg, 428.29 μmol, 1 eq) and NIS (192.72 mg, 856.58 μmol, 2 eq) in DCM (10 mL) and MeCN (10 mL) was stirred at 25° C. for 12 h. TLC (PE/EtOAc=4/1, $R_f$=0.40) showed the starting material was consumed completely. The reaction mixture was quenched with aqueous $Na_2S_2O_3$ (10 mL) and extracted with DCM (10 mL×3). The organic layer was dried over $Na_2SO_4$, filtered and concentrated under reduced pressure to dryness to give a residue which was purified by flash silica gel chromatography (from PE/EtOAc=20/1 to 5/1, TLC: PE/EtOAc=4/1, $R_f$=0.40). The desired fraction was concentrated under reduced pressure to dryness to give tert-butyl 3-[2-[tert-butoxycarbonyl-[5-(5-fluoro-3-pyridyl)-3-iodo-pyrazolo[1,5-a]pyrimidin-7-yl]amino]ethyl]indole-1-carboxylate (280 mg, 400.84 μmol, 93.6% yield, 100.0% purity) as a yellow solid. $^1H$ NMR (400 MHz, $CDCl_3$) δ ppm 8.76 (s, 1H), 8.57 (d, J=2.4 Hz, 1H), 8.18 (s, 1H), 8.00 (br s, 1H), 7.96-7.91 (m, 1H), 7.45 (d, J=7.6 Hz, 1H), 7.26 (br s, 2H), 7.20-7.15 (m, 1H), 6.58 (s, 1H), 4.23 (t, J=6.8 Hz, 2H), 3.12 (t, J=6.8 Hz, 2H), 1.62 (s, 9H), 1.42 (s, 9H); ES-LCMS m/z 699.2 $[M+H]^+$.

Step 3. tert-Butyl 3-[2-[[3-acetyl-5-(5-fluoro-3-pyridyl)pyrazolo[1,5-a]pyrimidin-7-yl]-tert-butoxycarbonyl-amino]ethyl]indole-1-carboxylate

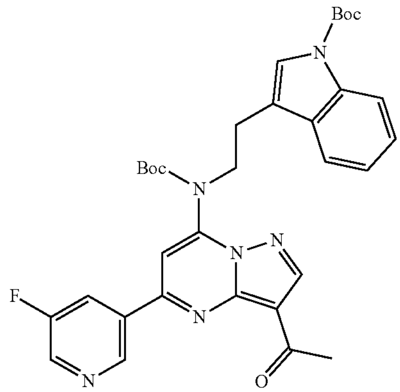 [SMILES: CC(=O)c1cnn2c(N(CCc3cn(C(=O)OC(C)(C)C)c4ccccc34)C(=O)OC(C)(C)C)cc(-c3cncc(F)c3)nc12]

A mixture of tert-butyl 3-[2-[tert-butoxycarbonyl-[5-(5-fluoro-3-pyridyl)-3-iodo-pyrazolo[1,5-a]pyrimidin-7-yl]amino]ethyl]indole-1-carboxylate (150 mg, 214.74 μmol, 1 eq), tributyl(1-ethoxyvinyl)stannane (310.21 mg, 858.95 μmol, 289.92 μL, 4 eq) and Pd(dppf)$Cl_2$ (31.43 mg, 42.95 μmol, 0.2 eq) in toluene (2 mL) was bubbled with $N_2$ for 2 min and then sealed. The reaction mixture was irradiated under microwave (1 bar) at 100° C. for 2 h. To the mixture was added aqueous KF (10 mL, 1 g/10 mL). The mixture was stirred at 25° C. for 30 min and then extracted with EtOAc (10 mL×3). The organic layer was dried over $Na_2SO_4$, filtered and concentrated under reduced pressure to dryness to give a residue which was purified by flash silica gel chromatography (from PE/EtOAc=1/0 to 2/1, TLC: PE/EtOAc=4/1, $R_f$=0.20). The desired fraction was concentrated under reduced pressure to dryness to give tert-butyl 3-[2-[[3-acetyl-5-(5-fluoro-3-pyridyl)pyrazolo[1,5-a]pyrimidin-7-yl]-tert-butoxycarbonyl-amino]ethyl]indole-1-carboxylate (80 mg, 124.17 μmol, 57.8% yield, 95.4% purity) as a yellow solid. $^1$H NMR (400 MHz, $CDCl_3$) δ ppm 8.78 (s, 1H), 8.66 (d, J=2.0 Hz, 1H), 8.61 (s, 1H), 7.96 (br s, 1H), 7.80 (d, J=8.8 Hz, 1H), 7.42 (d, J=8.0 Hz, 1H), 7.24-7.21 (m, 2H), 7.14 (t, J=7.2 Hz, 1H), 6.65 (s, 1H), 4.33-4.27 (m, 2H), 3.14 (t, J=6.4 Hz, 2H), 2.84 (s, 3H), 1.59 (s, 9H), 1.43 (s, 9H); ES-LCMS m/z 615.3 [M+H]$^+$.

Step 4: 1-[5-(5-Fluoro-3-pyridyl)-7-[2-(1H-indol-3-yl)ethylamino]pyrazolo[1,5-a]pyrimidin-3-yl]ethanone

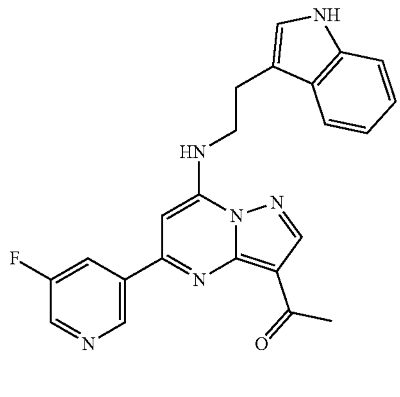 [SMILES: CC(=O)c1cnn2c(NCCc3c[nH]c4ccccc34)cc(-c3cncc(F)c3)nc12]

A mixture of tert-butyl 3-[2-[[3-acetyl-5-(5-fluoro-3-pyridyl)pyrazolo[1,5-a]pyrimidin-7-yl]-tert-butoxycarbonyl-amino]ethyl]indole-1-carboxylate (80 mg, 124.17 μmol, 1 eq) and TFA (4.62 g, 40.52 mmol, 3 mL, 326.32 eq) in DCM (9 mL) was stirred at 25° C. for 30 min. TLC (PE/EtOAc=1/1, $R_f$=0.50) showed the starting material was consumed completely. The reaction mixture was concentrated under reduced pressure at 30° C. to dryness. The residue was dissolved in water (10 mL), basified with saturated aqueous $NaHCO_3$ until pH=8 and extracted with EtOAc (15 mL×3). The organic layer was dried over $Na_2SO_4$, filtered and concentrated under reduced pressure to dryness to give 1-[5-(5-fluoro-3-pyridyl)-7-[2-(1H-indol-3-yl)ethylamino]pyrazolo[1,5-a]pyrimidin-3-yl]ethanone (50 mg, 101.34 μmol, 81.6% yield, 84.0% purity) as a yellow solid which was used in the next step without further purification. $^1$H NMR (400 MHz, DMSO-$d_6$) δ ppm 10.81 (s, 1H), 9.16 (s, 1H), 8.71 (d, J=2.8 Hz, 1H), 8.62 (t, J=6.4 Hz, 1H), 8.53 (s, 1H), 8.26-8.20 (m, 1H), 7.65 (d, J=7.6 Hz, 1H), 7.28 (d, J=8.0 Hz, 1H), 7.20 (s, 1H), 7.08-7.03 (m, 1H), 7.01-6.97 (m, 1H), 6.86 (s, 1H), 3.94-3.85 (m, 2H), 3.13 (t, J=6.8 Hz, 2H), 2.71 (s, 3H); ES-LCMS m/z 415.1 [M+H]$^+$.

Step 5: 1-[5-(5-Fluoro-3-pyridyl)-7-[2-(1H-indol-3-yl)ethylamino]pyrazolo[1,5-a]pyrimidin-3-yl]ethanol (I-33)

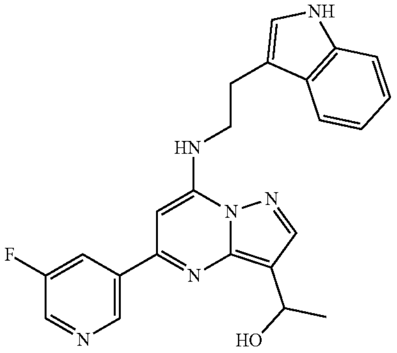 [SMILES: CC(O)c1cnn2c(NCCc3c[nH]c4ccccc34)cc(-c3cncc(F)c3)nc12]

To a solution of 1-[5-(5-fluoro-3-pyridyl)-7-[2-(1H-indol-3-yl)ethylamino]pyrazolo[1,5-a]pyrimidin-3-yl]ethanone (50 mg, 101.34 μmol, 1 eq) in MeOH (5 mL) was added $NaBH_4$ (38.34 mg, 1.01 mmol, 10 eq) and then the mixture was stirred at 25° C. for 1 h. TLC (PE/EtOAc=1/1, $R_f$=0.40) showed the starting material was consumed completely. The reaction mixture was quenched with water (10 mL) and concentrated under reduced pressure. The residue was extracted with EtOAc (15 mL×3). The organic layer was dried over $Na_2SO_4$, filtered and concentrated under reduced pressure to dryness to give a residue which was purified by preparative HPLC (column: Phenomenex Gemini 150*25 mm*10 um; mobile phase: [water (0.05% ammonia hydroxide v/v)-ACN]; B %: 36%-66%, 10 min). The desired fraction was lyophilized to give 1-[5-(5-fluoro-3-pyridyl)-7-[2-(1H-indol-3-yl)ethylamino]pyrazolo[1,5-a]pyrimidin-3-yl]ethanol (3.29 mg, 7.90 μmol, 7.8% yield, 100.0% purity) as a white solid. $^1$H NMR (400 MHz, $CDCl_3$) δ ppm 8.79 (s, 1H), 8.51 (d, J=2.8 Hz, 1H), 8.04 (br s, 1H), 7.95 (s, 1H), 7.84 (d, J=8.4 Hz, 1H), 7.69 (d, J=7.6 Hz, 1H), 7.37 (d, J=8.0 Hz, 1H), 7.22 (d, J=6.8 Hz, 2H), 7.07 (s, 1H), 6.56 (br s, 1H), 6.09 (s, 1H), 5.35 (s, 1H), 3.89-3.83 (m, 2H), 3.27 (t, J=6.4 Hz, 2H), 3.21 (d, J=3.6 Hz, 1H), 1.70 (d, J=6.4 Hz, 3H); ES-LCMS m/z 417.2 $[M+H]^+$.

Example 33

Synthesis of I-34

I-34

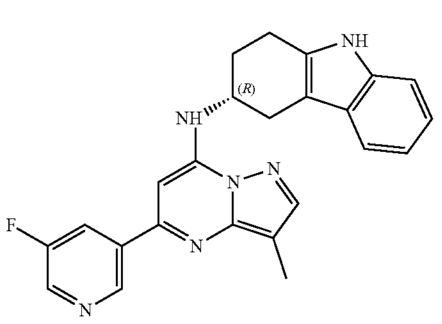

Synthetic Scheme:

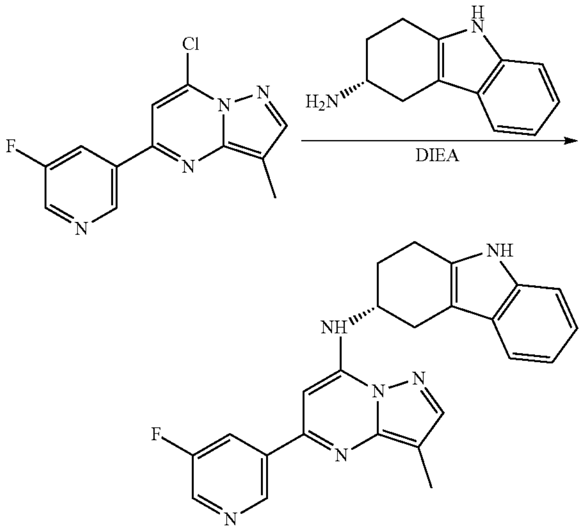

I-34

Step 1: (3R)—N-[5-(5-Fluoro-3-pyridyl)-3-methyl-pyrazolo[1,5-a]pyrimidin-7-yl]-2,3,4,9-tetrahydro-1H-carbazol-3-amine (I-34)

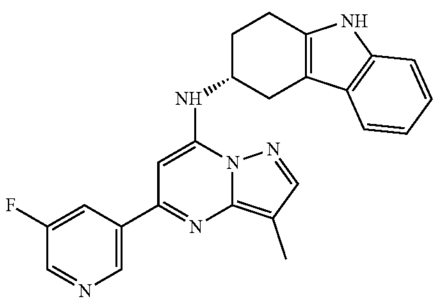 [SMILES: Cc1cnn2c(N[C@@H]3CCc4[nH]c5ccccc5c4C3)cc(-c3cncc(F)c3)nc12]

A mixture of 7-chloro-5-(5-fluoro-3-pyridyl)-3-methyl-pyrazolo[1,5-a]pyrimidine (50 mg, 171.13 μmol, 1 eq), (3R)-2,3,4,9-tetrahydro-1H-carbazol-3-amine (31.87 mg, 171.13 μmol, 1 eq) and DIEA (22.12 mg, 171.13 μmol, 29.81 μL, 1 eq) in i-PrOH (2 mL) was stirred at 80° C. for 12 h. The reaction mixture was concentrated under reduced pressure to dryness to give a residue which was purified by preparative HPLC (column: Syneri Max-RP C12 100*30 5 u; mobile phase: [water (0.05% HCl)-ACN]; B %: 50%-70%, 12 min). The desired fraction was lyophilized to give (3R)—N-[5-(5-fluoro-3-pyridyl)-3-methyl-pyrazolo[1,5-a]pyrimidin-7-yl]-2,3,4,9-tetrahydro-1H-carbazol-3-amine (29.03 mg, 55.63 μmol, 32.5% yield, 100.0% purity, 3HCl) as a yellow solid. $^1H$ NMR (400 MHz, DMSO-$d_6$) δ ppm 10.76 (s, 1H), 9.25 (s, 1H), 8.67 (d, J=2.8 Hz, 1H), 8.46 (td, J=2.0, 10.4 Hz, 1H), 8.30 (br s, 1H), 8.04 (s, 1H), 7.32 (d, J=7.6 Hz, 1H), 7.24 (d, J=8.0 Hz, 1H), 7.03 (s, 1H), 6.97 (t, J=6.8 Hz, 1H), 6.93-6.87 (m, 1H), 4.58-4.40 (m, 1H), 3.14-2.95 (m, 2H), 2.94-2.78 (m, 2H), 2.29 (s, 3H), 2.15 (br s, 2H); ES-LCMS m/z 413.2 $[M+H]^+$.

Example 34

Synthesis of I-35

I-35

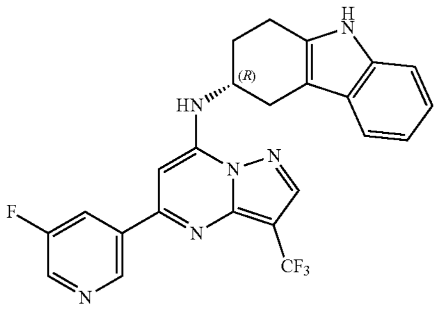 [SMILES: Fc1cncc(-c2cc(N[C@@H]3CCc4[nH]c5ccccc5c4C3)n3ncc(C(F)(F)F)c3n2)c1]

Synthetic Scheme:

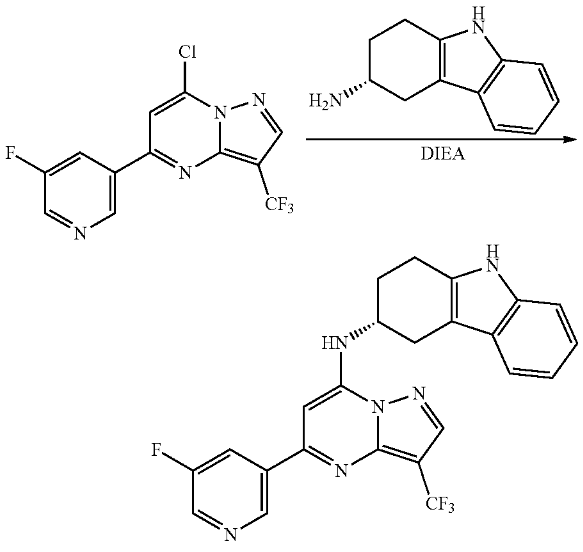

I-35

Step 1: (3R)—N-[5-(5-Fluoro-3-pyridyl)-3-(trifluoromethyl)pyrazolo[1,5-a]pyrimidin-7-yl]-2,3,4,9-tetrahydro-1H-carbazol-3-amine (I-35)

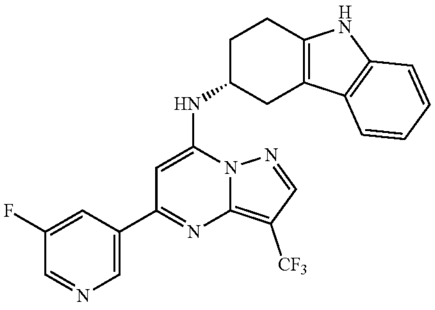

To a solution of 7-chloro-5-(5-fluoro-3-pyridyl)-3-(trifluoromethyl)pyrazolo[1,5-a]pyrimidine (35 mg, 102.58 μmol, 1 eq) and (3R)-2,3,4,9-tetrahydro-1H-carbazol-3-amine (21.02 mg, 112.83 μmol, 1.1 eq) in i-PrOH (3 mL) was added DIEA (39.77 mg, 307.73 μmol, 53.60 μL, 3.0 eq). The mixture was stirred at 60° C. for 3 h. The reaction mixture was concentrated under reduced pressure to give a residue which was purified by preparative HPLC (column: Phenomenex Gemini 150*25 mm*10 um; mobile phase: [water(0.05% HCl)-ACN]; B %: 60%-90%, 10 min), followed by lyophilization to yield (3R)—N-[5-(5-fluoro-3-pyridyl)-3-(trifluoromethyl)pyrazolo[1,5-a]pyrimidin-7-yl]-2,3,4,9-tetrahydro-1H-carbazol-3-amine (28.79 mg, 49.45 umol, 48.2% yield, 98.9% purity, 3HCl) as a yellow solid. $^1$H NMR (400 MHz, $CD_3OD$) δ ppm 9.36 (s, 1H), 8.87-8.79 (m, 2H), 8.34 (s, 1H), 7.37 (d, J=7.7 Hz, 1H), 7.26 (d, J=8.2 Hz, 1H), 7.17 (s, 1H), 7.06-6.99 (m, 1H), 6.98-6.91 (m, 1H), 4.57-4.46 (m, 1H), 3.33-3.31 (m, 1H), 3.17-3.04 (m, 1H), 3.00-2.88 (m, 2H), 2.42-2.33 (m, 1H), 2.31-2.19 (m, 1H); ES-LCMS m/z 467.2 $[M+H]^+$.

Example 35

Synthesis of I-36

I-36

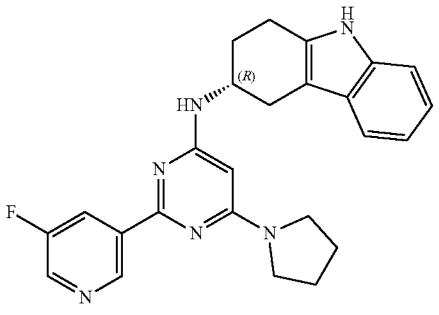

Synthetic Scheme:

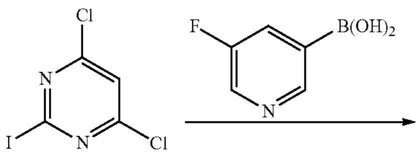

-continued

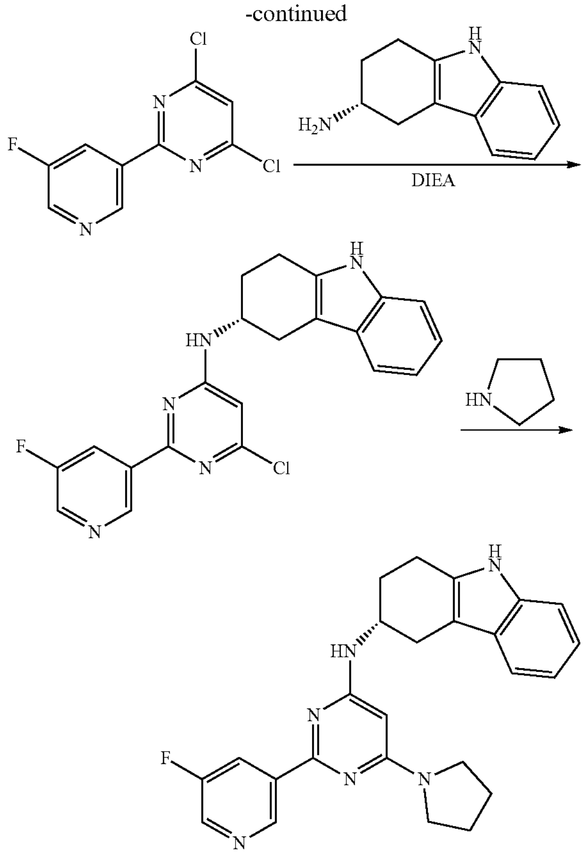

I-36

Step 1: (3R)—N-[6-Chloro-2-(5-fluoro-3-pyridyl)pyrimidin-4-yl]-2,3,4,9-tetrahydro-1H-carbazol-3-amine

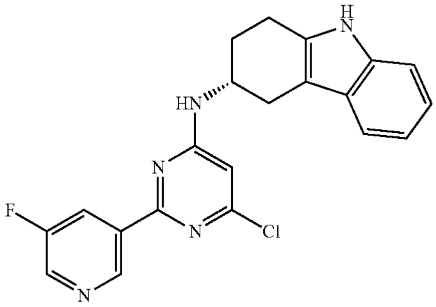 [SMILES: Fc1cncc(-c2nc(Cl)cc(N[C@@H]3CCc4[nH]c5ccccc5c4C3)n2)c1]

A mixture of 4,6-dichloro-2-(5-fluoro-3-pyridyl)pyrimidine (100 mg, 389.26 μmol, 1 eq), (3R)-2,3,4,9-tetrahydro-1H-carbazol-3-amine (79.75 mg, 428.19 μmol, 1.1 eq), DIEA(150.93 mg, 1.17 mmol, 203.41 μL, 3 eq) in i-PrOH (3 mL) was degassed and purged with $N_2$ for 3 times. The mixture was stirred at 55° C. for 12 h under $N_2$ atmosphere. The reaction mixture was concentrated under reduced pressure to give a residue which was purified by flash silica gel chromatography (from PE/EtOAC=100/1 to 3/1, TLC: PE/EtOAc=3/1, $R_f$=0.4) to yield (3R)—N-[6-chloro-2-(5-fluoro-3-pyridyl)pyrimidin-4-yl]-2,3,4,9-tetrahydro-1H-carbazol-3-amine (130 mg, 320.18 μmol, 82.3% yield, 97.0% purity) as a white solid. $^1$H NMR (400 MHz, $CDCl_3$) δ ppm 9.38 (s, 1H), 8.55 (d, J=2.9 Hz, 1H), 8.34 (d, J=9.0 Hz, 1H), 7.91 (s, 1H), 7.47 (d, J=7.7 Hz, 1H), 7.34 (d, J=7.9 Hz, 1H), 7.21-7.16 (m, 1H), 7.14-7.10 (m, 1H), 6.34 (s, 1H), 3.25 (dd, J=5.0, 15.5 Hz, 1H), 3.04-2.74 (m, 4H), 2.23 (s, 2H); ES-LCMS m/z 394.1 [M+H]$^+$.

Step 2: (3R)—N-[2-(5-Fluoro-3-pyridyl)-6-pyrrolidin-1-yl-pyrimidin-4-yl]-2,3,4,9-tetrahydro-1H-carbazol-3-amine (I-36)

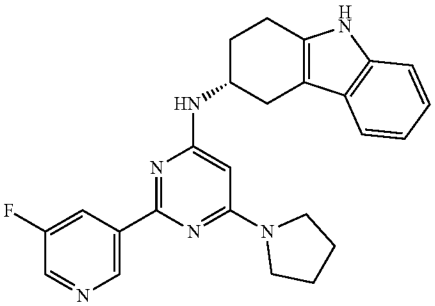 [SMILES: Fc1cncc(-c2nc(N[C@@H]3CCc4[nH]c5ccccc5c4C3)cc(N3CCCC3)n2)c1]

(3R)—N-[6-Chloro-2-(5-fluoro-3-pyridyl)pyrimidin-4-yl]-2,3,4,9-tetrahydro-1H-carbazol-3-amine (60 mg, 147.77 μmol, 1 eq) and pyrrolidine (727.50 mg, 10.23 mmol, 853.87 μL, 69.22 eq) were taken up into a microwave tube in i-PrOH (2 mL). The sealed tube was heated at 135° C. for 3 h under microwave. The reaction mixture was concentrated under reduced pressure to give a residue which was purified by preparative HPLC (column: Agela Durashell C18 150*25 5 u; mobile phase: [water(0.05% HCl)-ACN]; B %: 30%-60%, 12 min), followed by lyophilization to yield (3R)—N-[2-(5-fluoro-3-pyridyl)-6-pyrrolidin-1-yl-pyrimidin-4-yl]-2,3,4,9-tetrahydro-1H-carbazol-3-amine (42.07 mg, 78.06 μmol, 52.8% yield, 99.8% purity, 3HCl) as a brown solid. $^1$H NMR (400 MHz, DMSO-$d_6$) δ ppm 10.83 (s, 1H), 9.30 (s, 1H), 8.85 (s, 1H), 8.67-8.48 (m, 1H), 8.31 (s, 1H), 7.35 (d, J=7.5 Hz, 1H), 7.26 (d, J=7.9 Hz, 1H), 7.03-6.98 (m, 1H), 6.96-6.89 (m, 1H), 5.78 (s, 1H), 4.29 (m, 1H), 3.75-3.60 (m, 3H), 3.51 (s, 1H), 3.10 (dd, J=4.6, 15.0 Hz, 1H), 3.02-2.89 (m, 2H), 2.76-2.63 (m, 1H), 2.22-2.02 (m, 2H), 1.98 (s, 4H); ES-LCMS m/z 429.3 [M+H]$^+$.

Example 36

Synthesis of I-37a

I-37a

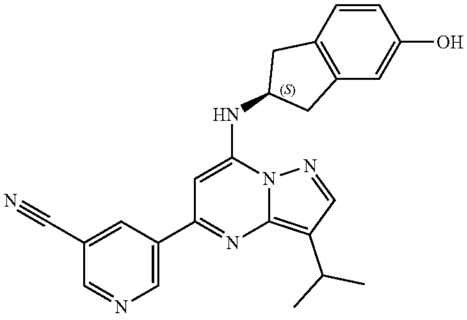

Synthetic Scheme:

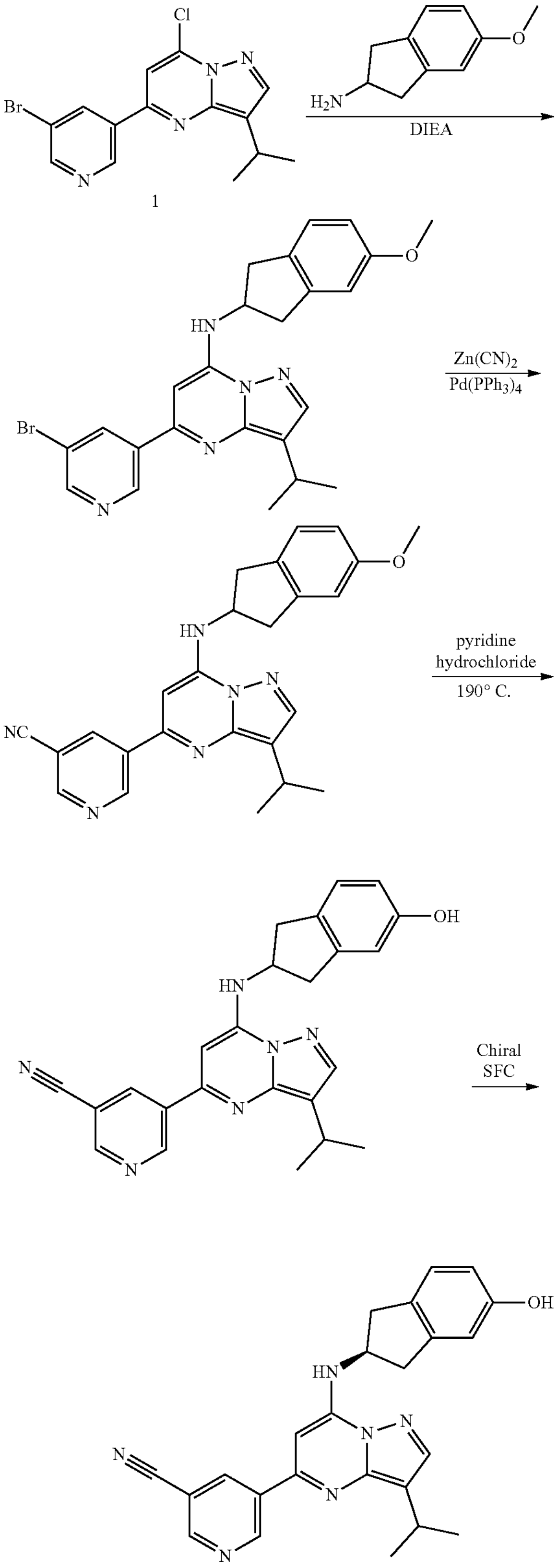

1

I-37

Step 1: 5-(5-Bromo-3-pyridyl)-3-isopropyl-N-(5-methoxyindan-2-yl)pyrazolo[1,5-a]pyrimidin-7-amine

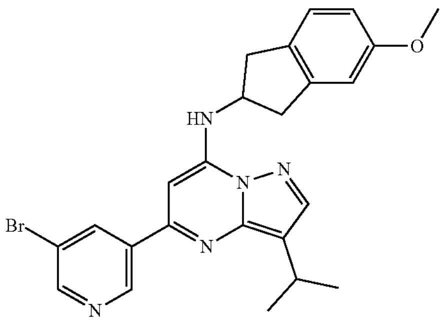 [SMILES: COc1ccc2c(c1)CC(Nc1cc(-c3cncc(Br)c3)nc3c(C(C)C)cnn13)C2]

To a solution of 5-(5-bromo-3-pyridyl)-7-chloro-3-isopropyl-pyrazolo[1,5-a]pyrimidine (100.00 mg, 264.48 μmol, 1 eq) in i-PrOH (5 mL) was added 5-methoxyindan-2-amine (52.81 mg, 264.48 μmol, 1 eq, HCl) and DIEA (341.82 mg, 2.64 mmol, 460.67 μL, 10 eq). The mixture was stirred at 90° C. for 12 h. The reaction mixture was concentrated under reduced pressure to give a residue which was purified by flash silica gel chromatography (from PE/EtOAc=1/0 to 3/1, TLC: PE/EtOAc=3/1, $R_f$=0.31) to yield 5-(5-bromo-3-pyridyl)-3-isopropyl-N-(5-methoxyindan-2-yl)pyrazolo[1,5-a]pyrimidin-7-amine (120 mg, 250.84 μmol, 94.8% yield, 100% purity) as yellow oil. $^1$H NMR (400 MHz, $CDCl_3$) δ ppm 9.18 (d, J=1.8 Hz, 1H), 8.74 (d, J=2.2 Hz, 1H), 8.58 (t, J=2.1 Hz, 1H), 7.87 (s, 1H), 7.18 (d, J=8.4 Hz, 1H), 6.83 (s, 1H), 6.79 (dd, J=2.5, 8.3 Hz, 1H), 6.58 (d, J=7.7 Hz, 1H), 6.37 (s, 1H), 4.71-4.60 (m, 1H), 3.81 (s, 3H), 3.50 (m, 2H), 3.37 (t, J=6.9 Hz, 1H), 3.08 (m, 2H), 1.42 (d, J=6.8 Hz, 6H); ES-LCMS m/z 478.1, 480.1 $[M+H]^+$.

Step 2: 5-[3-Isopropyl-7-[(5-methoxyindan-2-yl)amino]pyrazolo[1,5-a]pyrimidin-5-yl]pyridine-3-carbonitrile

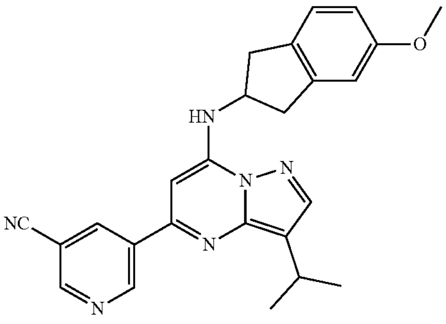 [SMILES: COc1ccc2c(c1)CC(Nc1cc(-c3cncc(C#N)c3)nc3c(C(C)C)cnn13)C2]

To a solution of 5-(5-bromo-3-pyridyl)-3-isopropyl-N-(5-methoxyindan-2-yl)pyrazolo[1,5-a]pyrimidin-7-amine (120.0 mg, 250.84 μmol, 1 eq) in DMF (6 mL) was added $Zn(CN)_2$ (117.83 mg, 1.00 mmol, 4 eq) and $Pd(PPh_3)_4$ (57.97 mg, 50.17 μmol, 0.2 eq) under $N_2$. The mixture was stirred at 85° C. for 32 h. The reaction mixture was quenched by addition of water (30 mL), then extracted with EtOAc (30 mL×3). The combined organic layers were washed with brine (10 mL), dried over $Na_2SO_4$, filtered and concentrated under reduced pressure to give a residue which was purified by flash silica gel chromatography (from PE/EtOAc=1/0 to 3/1, TLC: PE/EtOAc=3/1, $R_f$=0.55) to yield 5-[3-isopropyl-7-[(5-methoxyindan-2-yl)amino]pyrazolo[1,5-a]pyrimidin-5-yl]pyridine-3-carbonitrile (80 mg, 188.46 μmol, 75.1% yield, 100% purity) as a yellow solid. $^1$H NMR (400 MHz, $CDCl_3$) δ ppm 9.47 (d, J=2.2 Hz, 1H), 8.94 (d, J=2.0 Hz, 1H), 8.72 (t, J=2.1 Hz, 1H), 7.89 (s, 1H), 7.18 (d, J=8.2 Hz, 1H), 6.88-6.76 (m, 2H), 6.65 (d, J=7.5 Hz, 1H), 6.38 (s, 1H), 4.73-4.58 (m, 1H), 3.82 (s, 3H), 3.51 (m, 2H), 3.36 (t, J=7.0 Hz, 1H), 3.09 (m, 2H), 1.42 (d, J=6.8 Hz, 6H); ES-LCMS m/z 425.2 $[M+H]^+$.

Step 3: 5-[7-[[(2S)-5-Hydroxyindan-2-yl]amino]-3-isopropyl-pyrazolo[1,5-a]pyrimidin-5-yl]pyridine-3-carbonitrile (I-37)

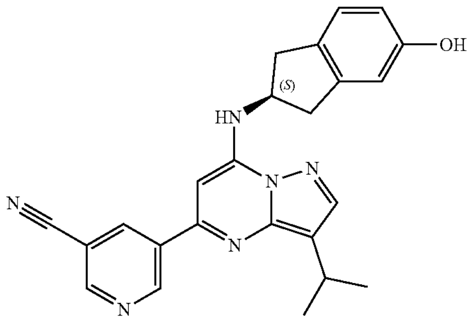

A mixture of 5-[3-isopropyl-7-[(5-methoxyindan-2-yl)amino]pyrazolo[1,5-a]pyrimidin-5-yl]pyridine-3-carbonitrile (35.00 mg, 74.21 μmol, 1 eq) and pyridine; hydrochloride (428.76 mg, 3.71 mmol, 50 eq) was stirred at 190° C. for 1 h under $N_2$. The reaction mixture was quenched by addition of sat. aq. $NaHCO_3$ (20 mL) slowly, then extracted with EtOAc (20 mL×3). The combined organic layers were washed with brine (10 mL), dried over $Na_2SO_4$, filtered and concentrated under reduced pressure to give a residue which was purified by preparative TLC (PE/EtOAc=1/1, TLC: PE/EtOAc=1/1, $R_f$=0.53) to yield 5-[7-[(5-hydroxyindan-2-yl)amino]-3-isopropyl-pyrazolo[1,5-a]pyrimidin-5-yl]pyridine-3-carbonitrile (15 mg, 34.20 μmol, 46.0% yield, 93.6% purity) as a yellow solid (Note: Tatol 80 mg of target from two batches was used for SFC separation). The racemate was separated by chiral SFC (AD (250 mm×30 mm, 10 μm); mobile phase: [0.1% $NH_3H_2O$ IPA]; B %: 55%-55%, min; peak 1 ($R_t$=1.817) and peak 2 ($R_t$=2.477)). The solution after separation was concentrated under reduced pressure to give a residue which was purified by preparative HPLC (column: Phenomenex Gemini 150×25 mm×10 μm; mobile phase: [water(0.05% HCl)-ACN]; B %: 50%-80%, 10 min) followed by lyophilization to yield 5-[7-[[(2S)-5-hydroxyindan-2-yl]amino]-3-isopropyl-pyrazolo[1,5-a]pyrimidin-5-yl]pyridine-3-carbonitrile (19.05 mg, 39.41 μmol, 22.7% yield, 100% purity, 2HCl) (EE=100%, $R_t$=1.817 min, $[\alpha]^{26}_D$=3.608 (c=1.03 mg/mL, MeOH)) as a yellow solid. $^1$H NMR (400 MHz, $CD_3OD$) δ ppm 9.44 (d, J=2.2 Hz, 1H), 9.08 (d, J=2.0 Hz, 1H), 8.84 (t, J=2.1 Hz, 1H), 8.09 (s, 1H), 7.07 (d, J=8.2 Hz, 1H), 6.88 (s, 1H), 6.71 (s, 1H), 6.64 (dd, J=2.2, 8.2 Hz, 1H), 4.96-4.90 (m, 1H), 3.50-3.41 (m, 2H), 3.38-3.33 (m, 1H), 3.19-3.03 (m, 2H), 1.40 (d, J=7.1 Hz, 6H); ES-LCMS m/z 411.2 $[M+H]^+$.

Example 37

Synthesis of I-38

I-38

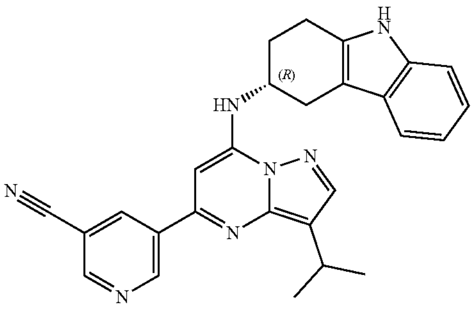

Synthetic Scheme:

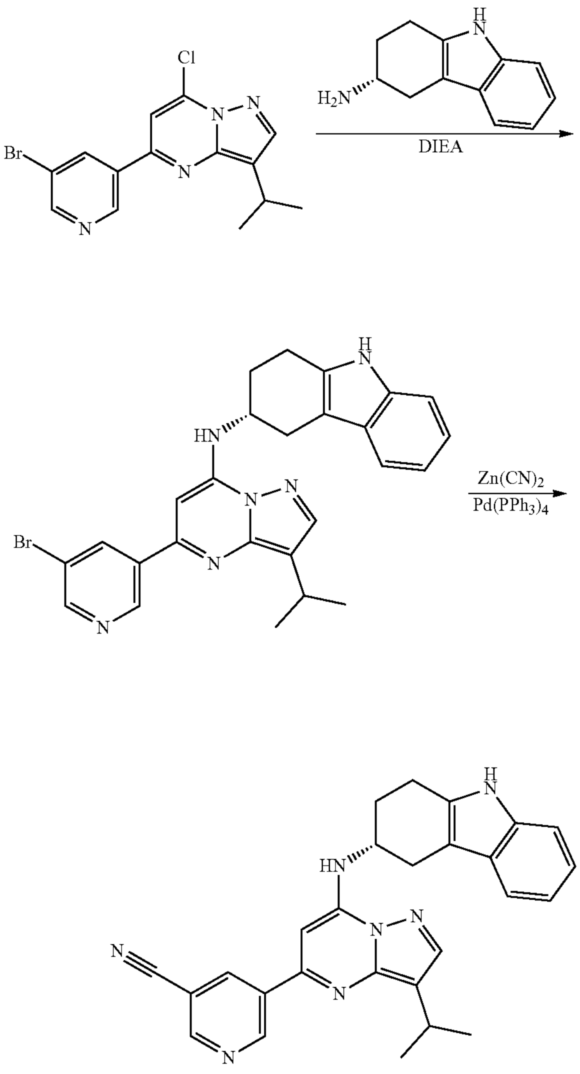

I-38

Step 1: (3R)—N-[5-(5-Bromo-3-pyridyl)-3-isopropyl-pyrazolo[1,5-a]pyrimidin-7-yl]-2,3,4,9-tetrahydro-1H-carbazol-3-amine

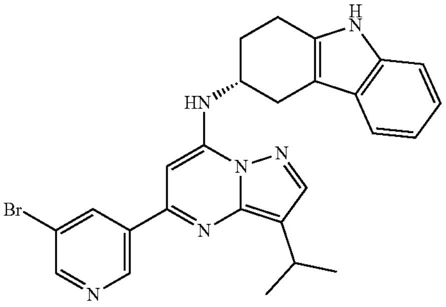 [SMILES: CC(C)c1cnn2c(N[C@@H]3CCc4[nH]c5ccccc5c4C3)cc(-c3cncc(Br)c3)nc12]

A mixture of 5-(5-bromo-3-pyridyl)-7-chloro-3-isopropyl-pyrazolo[1,5-a]pyrimidine (150 mg, 396.73 μmol, 1 eq), (3R)-2,3,4,9-tetrahydro-1H-carbazol-3-amine (77.59 mg, 416.56 μmol, 1.05 eq) and DIEA (153.82 mg, 1.19 mmol, 207.31 μL, 3 eq) in i-PrOH (10 mL) was degassed and purged with $N_2$ for 3 times. The mixture was stirred at 80° C. for 2 h under $N_2$ atmosphere. The reaction mixture was concentrated under reduced pressure to give a residue which was purified on silica gel column chromatography (from PE/EtOAc=1/0 to 10/3, TLC: PE/EtOAc=3/1, $R_f$=0.34) to give (3R)—N-[5-(5-bromo-3-pyridyl)-3-isopropyl-pyrazolo[1,5-a]pyrimidin-7-yl]-2,3,4,9-tetrahydro-1H-carbazol-3-amine (150 mg, 296.16 μmol, 74.6% yield, 99.0% purity) as a green solid. $^1H$ NMR (400 MHz, $CDCl_3$) δ ppm 9.17 (d, J=1.8 Hz, 1H), 8.73 (d, J=2.0 Hz, 1H), 8.60-8.55 (m, 1H), 7.90-7.87 (m, 1H), 7.47 (d, J=7.7 Hz, 1H), 7.34 (d, J=8.2 Hz, 1H), 7.19 (br t, J=7.6 Hz, 1H), 7.15-7.10 (m, 1H), 6.58 (br d, J=8.8 Hz, 1H), 6.40 (s, 1H), 4.32 (br s, 1H), 3.45-3.32 (m, 2H), 3.06-2.90 (m, 3H), 2.44-2.23 (m, 2H), 1.43 (d, J=6.8 Hz, 6H); ES-LCMS m/z 501.1, 503.1 $[M+H]^+$.

Step 2: 5-[3-Isopropyl-7-[[(3R)-2,3,4,9-tetrahydro-1H-carbazol-3-yl]amino]pyrazolo[1,5-a]pyrimidin-5-yl]pyridine-3-carbonitrile (I-38)

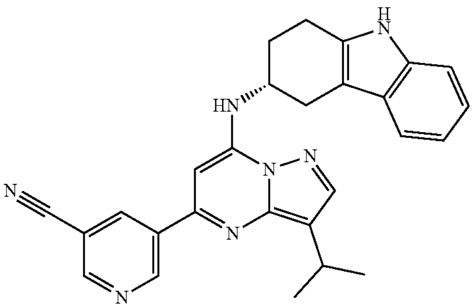 [SMILES: CC(C)c1cnn2c(N[C@@H]3CCc4[nH]c5ccccc5c4C3)cc(-c3cncc(C#N)c3)nc12]

A mixture of (3R)—N-[5-(5-bromo-3-pyridyl)-3-isopropyl-pyrazolo[1,5-a]pyrimidin-7-yl]-2,3,4,9-tetrahydro-1H-carbazol-3-amine (80 mg, 157.95 μmol, 1 eq), $Pd(PPh_3)_4$ (73.01 mg, 63.18 μmol, 0.4 eq) and $Zn(CN)_2$ (74.19 mg, 631.81 μmol, 4 eq) in DMF (5 mL) was degassed and purged with $N_2$ for 3 times. The mixture was stirred at 85° C. for 19 h under $N_2$ atmosphere. The mixture was concentrated and water (80 mL) was added, extracted with EtOAc (50 mL×3).

The combined organic layers were dried over $Na_2SO_4$, filtered and concentrated to the residue which was purified by preparative HPLC (column: Phenomenex Gemini 150*25 mm*10 μm; mobile phase: [water (0.05% ammonia hydroxide v/v)-ACN]; B %: 70%-100%, 10 min) to yield product of 5-[3-isopropyl-7-[[(3R)-2,3,4,9-tetrahydro-1H-carbazol-3-yl]amino]pyrazolo[1,5-a]pyrimidin-5-yl]pyridine-3-carbonitrile (11.7 mg, 26.14 μmol, 16.6% yield, 100.0% purity) as a yellow solid. $^1H$ NMR (400 MHz, DMSO-$d_6$) δ ppm 10.78 (s, 1H), 9.66 (d, J=2.0 Hz, 1H), 9.08-9.01 (m, 2H), 8.03 (s, 1H), 7.96 (d, J=9.5 Hz, 1H), 7.36 (d, J=7.7 Hz, 1H), 7.28 (d, J=7.9 Hz, 1H), 7.06 (s, 1H), 7.01 (t, J=7.4 Hz, 1H), 6.96-6.90 (m, 1H), 4.53-4.41 (m, 1H), 3.32-3.22 (m, 1H), 3.19-3.00 (m, 2H), 2.97-2.81 (m, 2H), 2.23-2.13 (m, 2H), 1.38 (d, J=6.8 Hz, 6H); ES-LCMS m/z 448.2 $[M+H]^+$.

Example 38

Synthesis of I-39

I-39

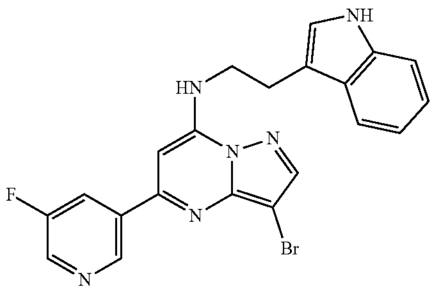

Synthetic Scheme:

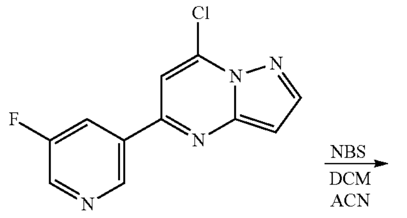

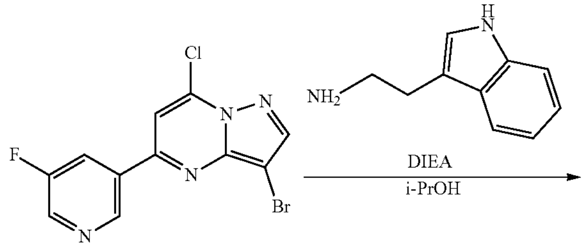

-continued

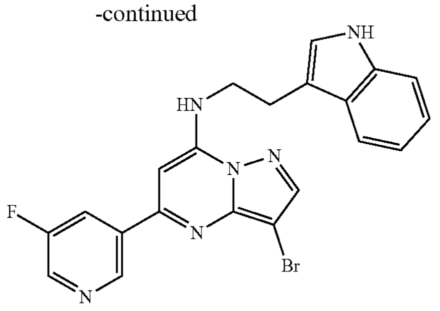

I-39

Step 1: 3-Bromo-7-chloro-5-(5-fluoro-3-pyridyl) pyrazolo[1,5-a]pyrimidine

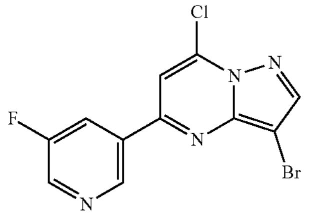 [SMILES: Fc1cncc(-c2cc(Cl)n3ncc(Br)c3n2)c1]

To a solution of 7-chloro-5-(5-fluoro-3-pyridyl)pyrazolo[1,5-a]pyrimidine (50 mg, 168.39 μmol, 1 eq) in DCM (2 mL) and ACN (4 mL) was added NBS (32.97 mg, 185.23 μmol, 1.1 eq). The mixture was stirred at 30° C. for 1 h under $N_2$ atmosphere. The reaction mixture was concentrated under reduced pressure to give 3-bromo-7-chloro-5-(5-fluoro-3-pyridyl)pyrazolo[1,5-a]pyrimidine (55.16 mg, 168.41 μmol, 100.0% yield, 100% purity) as a yellow solid which was used in the next step without further purification. $^1H$ NMR (400 MHz, $CDCl_3$) δ ppm 9.12 (s, 1H), 8.65 (d, J=2.6 Hz, 1H), 8.43-8.19 (m, 2H), 7.51 (s, 1H); ES-LCMS m/z 327.0, 329.0 $[M+H]^+$.

Step 2: 3-Bromo-5-(5-fluoro-3-pyridyl)-N-[2-(1H-indol-3-yl)ethyl]pyrazolo[1,5-a]pyrimidin-7-amine (I-39)

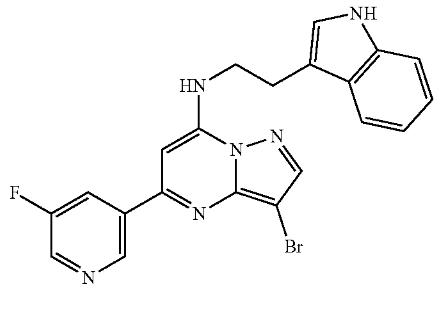 [SMILES: Fc1cncc(-c2cc(NCCc3c[nH]c4ccccc34)n3ncc(Br)c3n2)c1]

To a solution of 3-bromo-7-chloro-5-(5-fluoro-3-pyridyl) pyrazolo[1,5-a]pyrimidine (55.16 mg, 168.41 μmol, 1 eq) in i-PrOH (4 mL) was added DIEA (65.30 mg, 505.22 μmol, 88.00 μL, 3 eq) and 2-(1H-indol-3-yl)ethanamine (53.96 mg, 336.81 μmol, 2 eq). The mixture was stirred at 60° C. for 5 h under $N_2$ atmosphere. The reaction mixture was concentrated under reduced pressure to give a residue which was purified by preparative HPLC (column: Agela Durashell C18 150×25×5μ; mobile phase: [water(0.05% HCl)-ACN]; B %: 40%-70%, 12 min) followed by lyophilization to yield 3-bromo-5-(5-fluoro-3-pyridyl)-N-[2-(1H-indol-3-yl)ethyl] pyrazolo[1,5-a]pyrimidin-7-amine (65 mg, 115.93 μmol, 68.8% yield, 100% purity, 3HCl) as a yellow solid. $^1H$ NMR (400 MHz, $CD_3OD$) δ ppm 8.71 (s, 1H), 8.55 (s, 1H), 8.18 (s, 1H), 7.70 (d, J=8.8 Hz, 1H), 7.62 (d, J=8.0 Hz, 1H), 7.16 (d, J=8.3 Hz, 1H), 7.05-6.91 (m, 3H), 5.94 (s, 1H), 3.98 (t, J=5.9 Hz, 2H), 3.22 (t, J=6.0 Hz, 2H); ES-LCMS m/z 451.1, 453.1 $[M+H]^+$.

Example 39

Synthesis of I-40

I-40

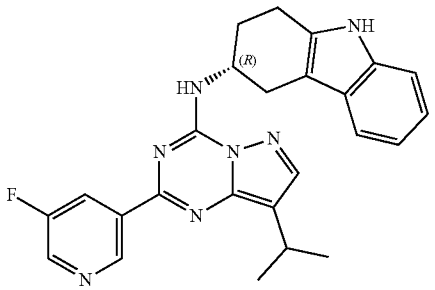

Synthetic Scheme:

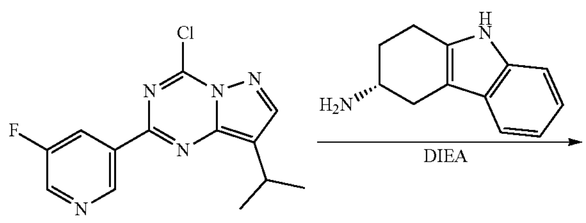

1

Step 1: (3R)—N-[2-(5-Fluoro-3-pyridyl)-8-isopropyl-pyrazolo[1,5-a][1,3,5]triazin-4-yl]-2,3,4,9-tetrahydro-1H-carbazol-3-amine (I-40)

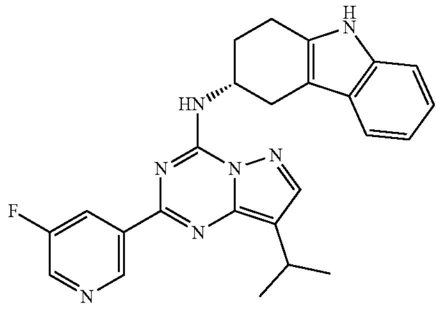 [SMILES: CC(C)c1cnn2c(N[C@@H]3CCc4[nH]c5ccccc5c4C3)nc(-c3cncc(F)c3)nc12]

A mixture of 4-chloro-2-(5-fluoro-3-pyridyl)-8-isopropyl-pyrazolo[1,5-a][1,3,5]triazine (60.00 mg, 205.68 μmol, 1 eq), (3R)-2,3,4,9-tetrahydro-1H-carbazol-3-amine (42.14 mg, 226.25 μmol, 1.1 eq), DIEA (79.75 mg, 617.05 μmol, 107.48 μL, 3 eq) in i-PrOH (4 mL) was degassed and purged with $N_2$ for 3 times. The mixture was stirred at 55° C. for 3 h under $N_2$ atmosphere. The reaction mixture was concentrated under reduced pressure to give a residue which was purified by preparative HPLC (column: Phenomenex Gemini 150*25 mm*10 um; mobile phase: [water(0.05% HCl)-ACN]; B %: 70%-100%, 10 min), followed by lyophilization to yield (3R)—N-[2-(5-fluoro-3-pyridyl)-8-isopropyl-pyrazolo[1,5-a][1,3,5]triazin-4-yl]-2,3,4,9-tetrahydro-1H-carbazol-3-amine (42.07 mg, 75.45 μmol, 36.7% yield, 98.8% purity, 3HCl) as a yellow solid. $^1H$ NMR (400 MHz, $CD_3OD$) δ ppm 9.46 (s, 1H), 8.81 (d, J=9.3 Hz, 1H), 8.76 (s, 1H), 8.12-7.92 (m, 1H), 7.37 (d, J=7.7 Hz, 1H), 7.27 (d, J=7.9 Hz, 1H), 7.08-7.00 (m, 1H), 6.99-6.90 (m, 1H), 3.34 (s, 1H), 3.31-3.25 (m, 2H), 3.18-2.79 (m, 3H), 2.44-2.21 (m, 2H), 1.42 (d, J=7.1 Hz, 6H); ES-LCMS m/z 442.2 $[M+H]^+$.

Example 40

Synthesis of I-41

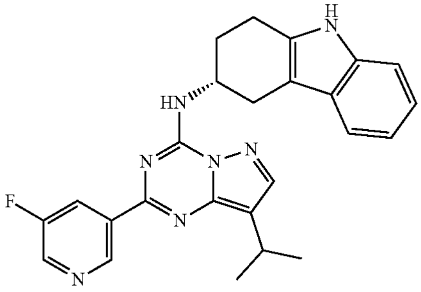

I-40

I-41

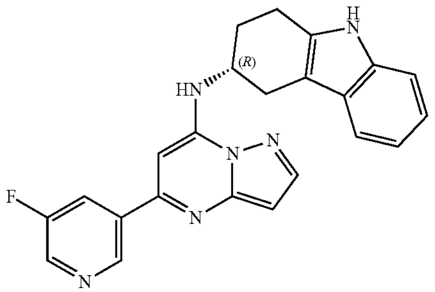

Synthetic Scheme:

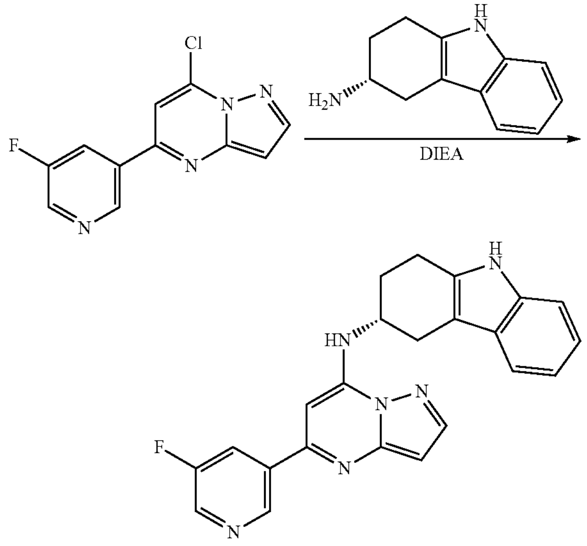

I-41

Step 1: (3R)—N-[5-(5-Fluoro-3-pyridyl)pyrazolo[1,5-a]pyrimidin-7-yl]-2,3,4,9-tetrahydro-1H-carbazol-3-amine (I-41)

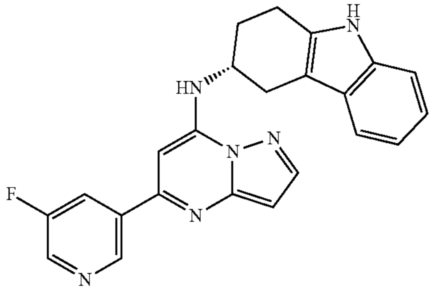 [SMILES: Fc1cncc(-c2cc(N[C@@H]3CCc4[nH]c5ccccc5c4C3)n3nccc3n2)c1]

To a solution of 7-chloro-5-(5-fluoro-3-pyridyl)pyrazolo[1,5-a]pyrimidine (50 mg, 166.91 μmol, 1.0 eq) in i-PrOH (3 mL) was added DIEA (64.71 mg, 500.72 μmol, 87.21 μL, 3.0 eq) and (3R)-2,3,4,9-tetrahydro-1H-carbazol-3-amine (37.30 mg, 200.29 μmol, 1.2 eq). The mixture was stirred at 60° C. for 12 h. The reaction mixture was concentrated under reduced pressure to give a residue which was purified by preparative HPLC (HCl condition; column: Phenomenex Gemini 150×25 mm×10 μm; mobile phase: [water (0.05% HCl)-ACN]; B %: 38%-68%, 10 min). The desired fraction was lyophilized to yield (3R)—N-[5-(5-fluoro-3-pyridyl)pyrazolo[1,5-a]pyrimidin-7-yl]-2,3,4,9-tetrahydro-1H-carbazol-3-amine (61.30 mg, 120.71 μmol, 72.3% yield, 100.0% purity, 3 HCl salt) as a yellow solid. $^1$H NMR (400 MHz, $CD_3OD$) δ ppm 9.01 (s, 1H), 8.77 (d, J=2.6 Hz, 1H), 8.34-8.27 (m, 2H), 7.39 (d, J=7.7 Hz, 1H), 7.28 (d, J=7.9 Hz, 1H), 7.13 (s, 1H), 7.09-7.01 (m, 1H), 7.00-6.93 (m, 1H), 6.66 (d, J=2.2 Hz, 1H), 4.68 (s, 1H), 3.37-3.32 (m, 2H), 3.14-3.01 (m, 2H), 2.44-2.28 (m, 2H); ES-LCMS m/z 339.2 $[M+H]^+$.

Example 41

Synthesis of I-42a

I-42a

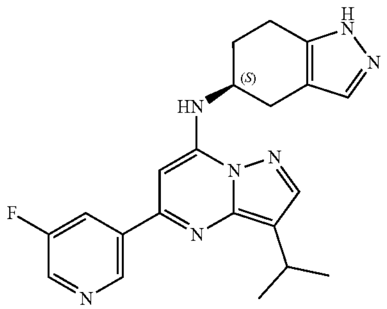

Synthetic Scheme:

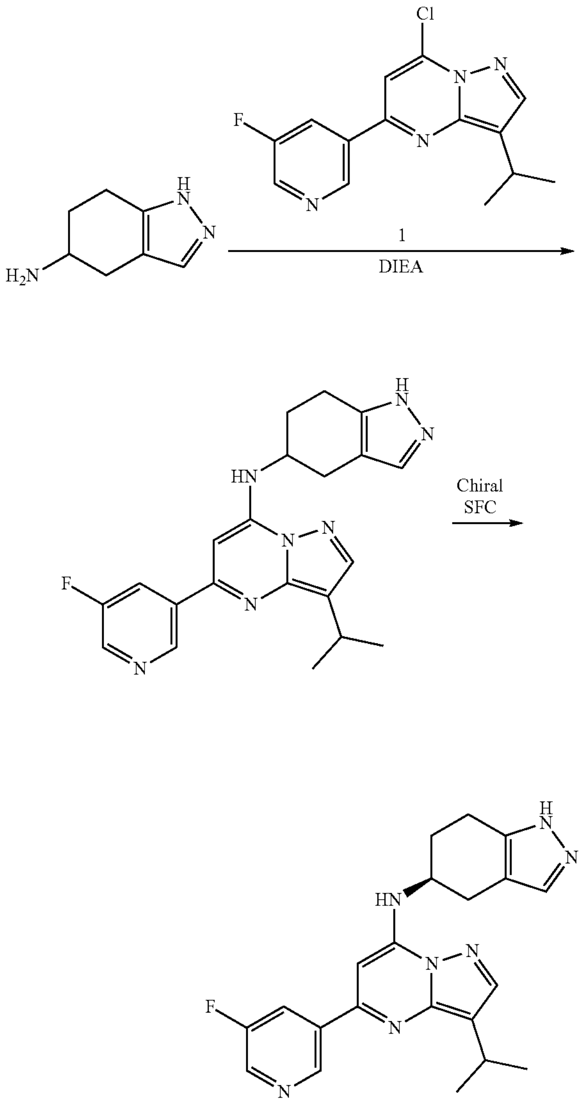

I-42

Step 1: 5-(5-Fluoro-3-pyridyl)-3-isopropyl-N-[(5S)-4,5,6,7-tetrahydro-1H-indazol-5-yl]pyrazolo[1,5-a]pyrimidin-7-amine (I-42)

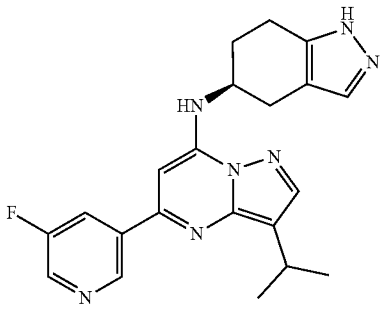 [SMILES: CC(C)c1cnn2c(N[C@H]3CCc4[nH]ncc4C3)cc(-c3cncc(F)c3)nc12]

To a solution of 7-chloro-5-(5-fluoro-3-pyridyl)-3-isopropyl-pyrazolo[1,5-a]pyrimidine (60 mg, 206.38 μmol, 1 eq) in i-PrOH (5 mL) was added DIEA (266.73 mg, 2.06 mmol, 359.47 μL, 10 eq) and 4,5,6,7-tetrahydro-1H-indazol-5-amine (43.36 mg, 206.38 μmol, 1 eq, 2HCl). The mixture was stirred at 90° C. for 12 h. The reaction mixture was concentrated under reduced pressure to give a residue which was purified by flash silica gel chromatography (from PE/EtOAc=1/0 to 0/1, TLC: PE/EtOAc=1/1, $R_f$=0.16) to yield a product. The product was separated by chiral SFC (AD (250 mm×30 mm, 5 μm); mobile phase: [0.1% $NH_3H_2O$ IPA]; B %: 35%-35%, min; peak 1 ($R_t$=5.512) and peak 2 ($R_t$=6.038)). The solution after separation was concentrated under reduced pressure to give a residue which was purified by preparative HPLC (column: Phenomenex Gemini 150×25 mm×10 μm; mobile phase: [water (0.05% HCl)-ACN]; B %: 35%-65%, 10 min) followed by lyophilization to yield 5-(5-fluoro-3-pyridyl)-3-isopropyl-N-[(5S)-4,5,6,7-tetrahydro-1H-indazol-5-yl]pyrazolo[1,5-a]pyrimidin-7-amine (29.07 mg, 58.0 μmol, 24.1% yield, 100% purity, 3HCl) (EE=94.6%, $R_t$=5.512 min, $[\alpha]^{26}_D$=−18.785 (c 1.05 mg/mL, MeOH)) as a yellow solid. $^1H$ NMR (400 MHz, $CD_3OD$) δ ppm 9.07 (s, 1H), 8.77 (d, J=2.4 Hz, 1H), 8.39 (td, J=2.2, 9.2 Hz, 1H), 8.20 (s, 1H), 7.96 (s, 1H), 6.98 (s, 1H), 4.57 (s, 1H), 3.40-3.34 (m, 1H), 3.26 (dd, J=5.2, 15.3 Hz, 1H), 3.15-3.04 (m, 2H), 2.92 (dd, J=9.6, 15.3 Hz, 1H), 2.45-2.36 (m, 1H), 2.31-2.19 (m, 1H), 1.41 (d, J=7.1 Hz, 6H); ES-LCMS m/z 392.2 $[M+H]^+$.

Example 42

Synthesis of I-43

I-43

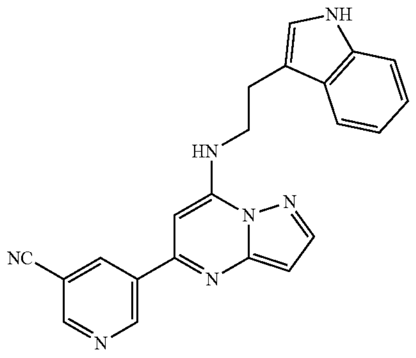

Synthetic Scheme:

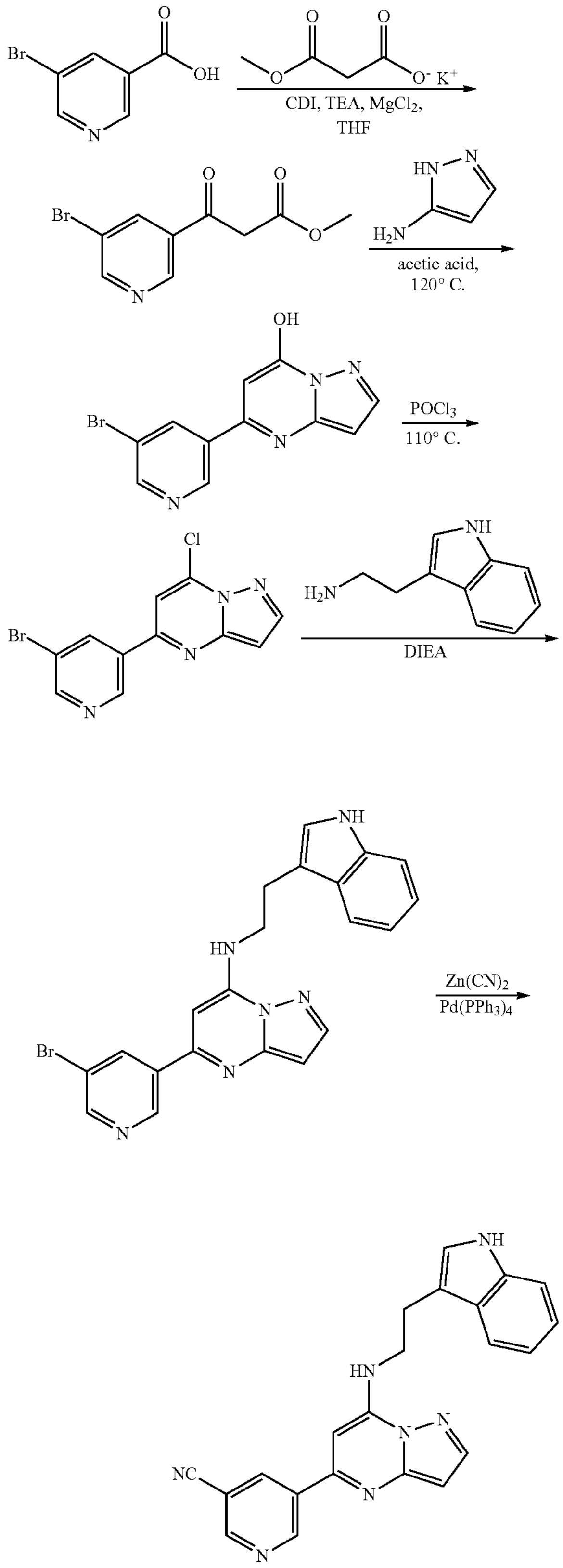

I-43

Step 1: Methyl 3-(5-bromo-3-pyridyl)-3-oxo-propanoate & methyl (Z)-3-(5-bromo-3-pyridyl)-3-hydroxy-prop-2-enoate

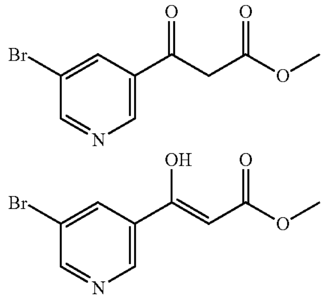

To a mixture of 5-bromopyridine-3-carboxylic acid (5 g, 24.75 mmol, 1 eq) and TEA (2.50 g, 24.75 mmol, 3.45 mL, 1 eq) in THF (100 mL) was added CDI (6.02 g, 37.13 mmol, 1.5 eq) in one portion at 30° C. under $N_2$. The mixture was stirred at 30° C. for 1 h. potassium; 3-methoxy-3-oxo-propanoate (7.73 g, 49.50 mmol, 2 eq) and $MgCl_2$ (4.71 g, 49.50 mmol, 2 eq) was added and the mixture was stirred at 30° C. for 16 h. The mixture was adjusted pH to 5-6 with 3 NHCl, extracted with EtOAc (50 mL×3). The combined organic layers were dried over $Na_2SO_4$, filtered and concentrated under reduced pressure to give a residue which was purified on silica gel column chromatography (from PE/EtOAc=1/0 to 10/3, TLC: PE/EtOAc=3/1, $R_f$=0.47) to give methyl 3-(5-bromo-3-pyridyl)-3-oxo-propanoate (1.85 g, 6.45 mmol, 26.1% yield, 90.0% purity) and methyl (Z)-3-(5-bromo-3-pyridyl)-3-hydroxy-prop-2-enoate (1.85 g, 6.45 mmol, 26.1% yield, 90.0% purity) as a white solid. $^1$H NMR (400 MHz, $CDCl_3$) δ ppm 12.46 (s, 1H), 9.05 (d, J=2.0 Hz, 1H), 8.90-8.87 (m, 2H), 8.75 (d, J=2.2 Hz, 1H), 8.39-8.36 (m, 1H), 8.21 (t, J=2.1 Hz, 1H), 5.72 (s, 1H), 4.02 (s, 2H), 3.84 (s, 3H), 3.78 (s, 3H); ES-LCMS m/z 258.0, 260.0 $[M+H]^+$.

Step 2: 5-(5-Bromo-3-pyridyl)pyrazolo[1,5-a]pyrimidin-7-ol

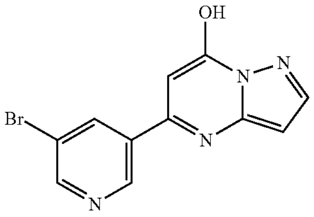 [SMILES: Oc1cc(-c2cncc(Br)c2)nc2ccnn12]

A mixture of methyl 3-(5-bromo-3-pyridyl)-3-oxo-propanoate (1.11 g, 3.87 mmol, 1 eq) and 1H-pyrazol-5-amine (386.37 mg, 4.65 mmol, 1.2 eq) in AcOH (5 mL) was stirred at 120° C. for 1 h. The reaction mixture was concentrated under reduced pressure to give 5-(5-bromo-3-pyridyl)pyrazolo[1,5-a]pyrimidin-7-ol (1 g, 3.44 mmol, 88.7% yield, crude purity) as a yellow solid. $^1$H NMR (400 MHz, $CDCl_3$) δ ppm 10.31 (s, 1H), 9.00 (d, J=2.0 Hz, 1H), 8.88 (d, J=2.0 Hz, 1H), 8.52 (t, J=2.1 Hz, 1H), 7.91 (d, J=2.0 Hz, 1H), 7.51 (s, 1H), 6.25-6.21 (m, 2H); ES-LCMS m/z 293.0, 295.0 $[M+H]^+$.

Step 3: 5-(5-Bromo-3-pyridyl)-7-chloro-pyrazolo[1,5-a]pyrimidine

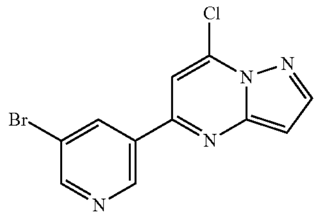 [SMILES: Clc1cc(-c2cncc(Br)c2)nc2ccnn12]

A solution of 5-(5-bromo-3-pyridyl)pyrazolo[1,5-a]pyrimidin-7-ol (1 g, 3.44 mmol, 1 eq) in $POCl_3$ (8 mL) was stirred at 100° C. for 3 h. The reaction mixture was concentrated under reduced pressure to give a residue which was purified by preparative-TLC (TLC: PE/EtOAc=3/1, $R_f$=0.65) to yield 5-(5-bromo-3-pyridyl)-7-chloro-pyrazolo[1,5-a]pyrimidine (0.8997 g, 2.91 mmol, 84.6% yield, 100.0% purity) as a yellow solid. $^1$H NMR (400 MHz, $CDCl_3$) δ ppm 9.18 (d, J=2.0 Hz, 1H), 8.81 (d, J=2.2 Hz, 1H), 8.62 (t, J=2.0 Hz, 1H), 8.30 (d, J=2.4 Hz, 1H), 7.44 (s, 1H), 6.91 (d, J=2.4 Hz, 1H); ES-LCMS m/z 309.0, 311.0 $[M+H]^+$.

Step 4: 5-(5-Bromo-3-pyridyl)-N-[2-(1H-indol-3-yl)ethyl]pyrazolo[1,5-a]pyrimidin-7-amine

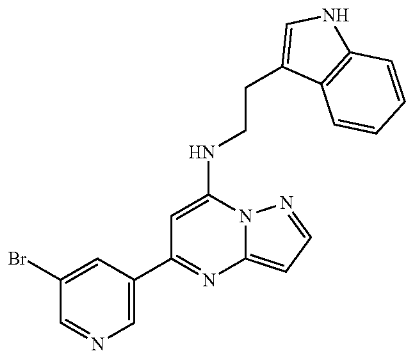 [SMILES: Brc1cncc(-c2cc(NCCc3c[nH]c4ccccc34)n3nccc3n2)c1]

To a mixture of 5-(5-bromo-3-pyridyl)-7-chloro-pyrazolo[1,5-a]pyrimidine (500 mg, 1.62 mmol, 1 eq) and 2-(1H-indol-3-yl)ethanamine (388.18 mg, 2.42 mmol, 1.5 eq) in i-PrOH (20 mL) was added DIEA (626.28 mg, 4.85 mmol, 844.04 μL, 3 eq) in one portion. The mixture was stirred at 80° C. for 2 h. The reaction mixture was concentrated under reduced pressure to give a residue which was purified on silica gel column chromatography (from PE/EtOAc=1/0 to 10/3, TLC: PE/EtOAc=3/1, $R_f$=0.35) to yield 5-(5-bromo-3-pyridyl)-N-[2-(1H-indol-3-yl)ethyl]pyrazolo[1,5-a]pyrimidin-7-amine (629 mg, 1.45 mmol, 89.9% yield, 100.0% purity) as a yellow solid. $^1$H NMR (400 MHz, $CDCl_3$) δ ppm 8.87 (d, J=1.8 Hz, 1H), 8.71 (d, J=2.2 Hz, 1H), 8.41-8.37 (m, 1H), 8.08 (br s, 1H), 8.01 (d, J=2.2 Hz, 1H), 7.68 (d, J=7.5 Hz, 1H), 7.38 (d, J=8.2 Hz, 1H), 7.23-7.17 (m, 2H), 7.11 (s, 1H), 6.61 (br s, 1H), 6.55 (d, J=2.2 Hz, 1H), 6.12 (s, 1H), 3.86 (q, J=6.2 Hz, 2H), 3.28 (t, J=6.6 Hz, 2H); ES-LCMS m/z 435.0, 437.0 $[M+H]^+$.

Step 5: 5-[7-[2-(1H-Indol-3-yl)ethylamino]pyrazolo[1,5-a]pyrimidin-5-yl]pyridine-3-carbonitrile (I-43)

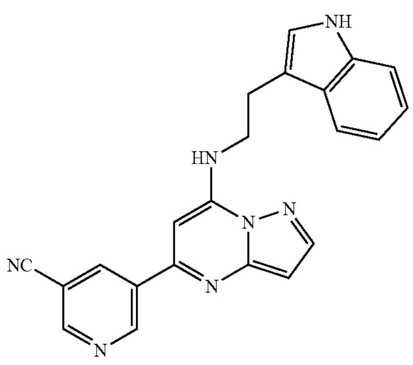 [SMILES: N#Cc1cncc(-c2cc(NCCc3c[nH]c4ccccc34)n3nccc3n2)c1]

A mixture of 5-(5-bromo-3-pyridyl)-N-[2-(1H-indol-3-yl)ethyl]pyrazolo[1,5-a]pyrimidin-7-amine (150 mg, 346.18 μmol, 1 eq), $Zn(CN)_2$ (162.60 mg, 1.38 mmol, 87.89 μL, 4 eq) and $Pd(PPh_3)4$ (80.01 mg, 69.24 μmol, 0.2 eq) in DMF (5 mL) was degassed and purged with $N_2$ for 3 times. The mixture was stirred at 85° C. for 19 h under $N_2$ atmosphere. The mixture was concentrated and saturated $NaHCO_3$ solution (10 mL) was added. The mixture was extracted with EtOAc (50 mL×3). The combined organic layers were dried over $Na_2SO_4$, filtered and concentrated. To the crude product was added MeOH (30 mL) and stirred for 10 min. The suspension was filtered and solid was collected, washed with PE/EtOAc (2/1, 30 mL×2), dried under vacuum to yield 5-[7-[2-(1H-indol-3-yl)ethylamino]pyrazolo[1,5-a]pyrimidin-5-yl]pyridine-3-carbonitrile (67.84 mg, 176.30 μmol, 50.9% yield, 98.6% purity) as a yellow solid. $^1H$ NMR (400 MHz, DMSO-$d_6$) δ ppm 10.80 (br s, 1H), 9.46 (d, J=2.2 Hz, 1H), 9.08 (d, J=2.0 Hz, 1H), 8.76 (t, J=2.1 Hz, 1H), 8.19 (br s, 1H), 8.14 (d, J=2.4 Hz, 1H), 7.65 (d, J=7.9 Hz, 1H), 7.29 (d, J=7.9 Hz, 1H), 7.21 (s, 1H), 7.09-6.97 (m, 2H), 6.70 (s, 1H), 6.52 (d, J=2.2 Hz, 1H), 3.85 (d, J=6.0 Hz, 2H), 3.14 (t, J=7.3 Hz, 2H); ES-LCMS m/z 380.2 $[M+H]^+$.

Example 43

Synthesis of I-44

I-44

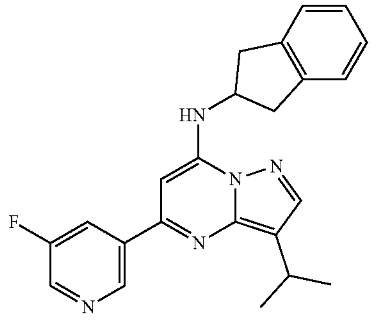

Synthetic Scheme:

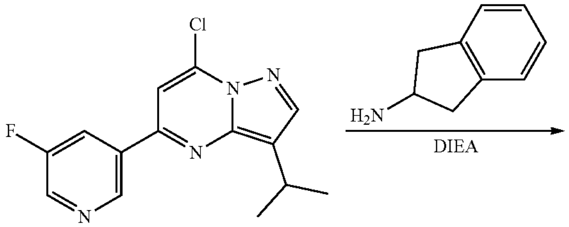

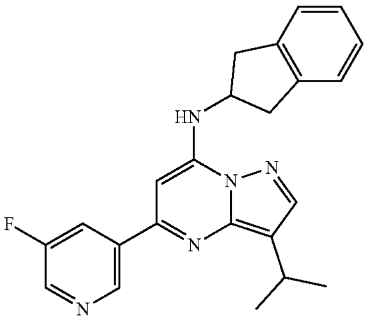 [SMILES: CC(C)c1cnn2c(NC3Cc4ccccc4C3)cc(-c3cncc(F)c3)nc12]

I-44

Step 1: 5-(5-Fluoro-3-pyridyl)-N-indan-2-yl-3-isopropyl-pyrazolo[1,5-a]pyrimidin-7-amine (I-44)

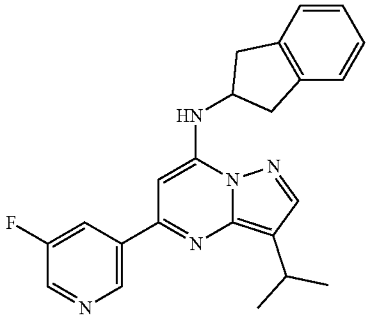

A mixture of 7-chloro-5-(5-fluoro-3-pyridyl)-3-isopropyl-pyrazolo[1,5-a]pyrimidine (50 mg, 168.55 μmol, 1 eq), indan-2-amine (26.94 mg, 202.25 μmol, 1.2 eq) and DIEA (65.35 mg, 505.64 μmol, 88.07 μL, 3 eq) in i-PrOH (5 mL) was stirred at 80° C. for 2 h. The mixture was concentrated under reduced pressure to give a residue which was purified by preparative HPLC (column: Phenomenex Gemini 150*25 mm*10 μm; mobile phase: [water(0.05% HCl)-ACN]; B %: 60%-90%, 10 min) to give 5-(5-fluoro-3-pyridyl)-N-indan-2-yl-3-isopropyl-pyrazolo[1,5-a]pyrimidin-7-amine (27.63 mg, 59.44 μmol, 35.3% yield, 99.0% purity, 2HCl) as a yellow solid. $^1H$ NMR (400 MHz, DMSO-$d_6$) δ ppm 9.32 (t, J=1.6 Hz, 1H), 8.66 (d, J=2.8 Hz, 1H), 8.50-8.46 (m, 1H), 8.16 (d, J=8.4 Hz, 1H), 8.01 (s, 1H), 7.28-7.25 (m, 2H), 7.20-7.17 (m, 2H), 7.00 (s, 1H), 4.95-4.84 (m, 1H), 3.43-3.38 (m, 2H), 3.26-3.22 (m, 1H), 3.20-3.14 (m, 2H), 1.37 (d, J=7.2 Hz, 6H); ES-LCMS m/z 388.2 $[M+H]^+$.

Example 44

Synthesis of I-45

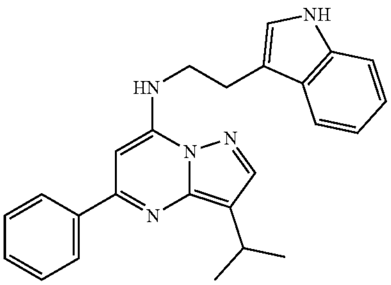

I-45

Synthetic Scheme:

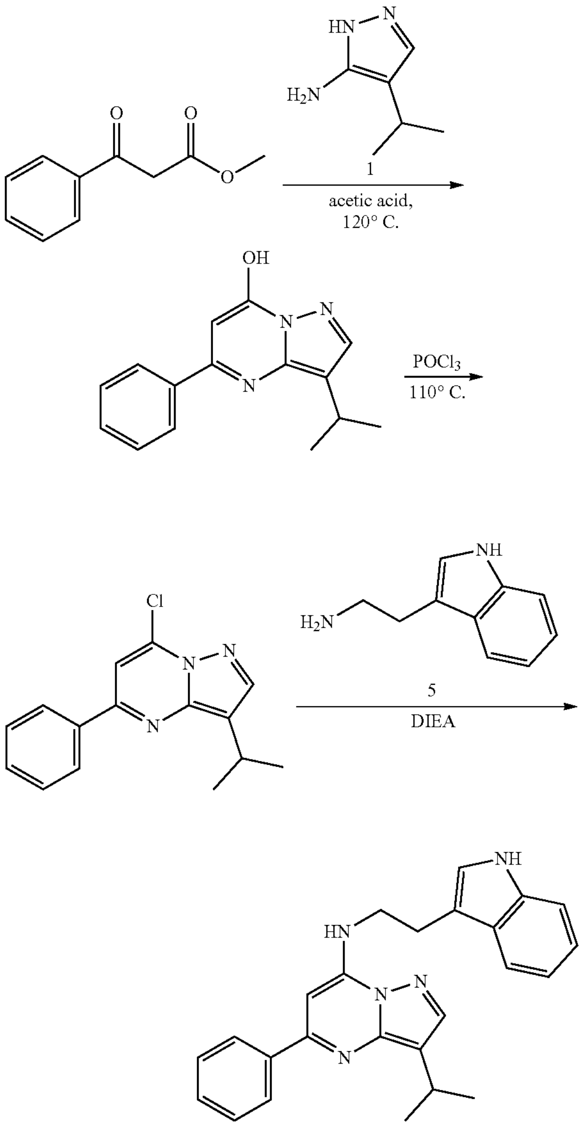

I-45

Step 1: 3-Isopropyl-5-phenyl-pyrazolo[1,5-a]pyrimidin-7-ol

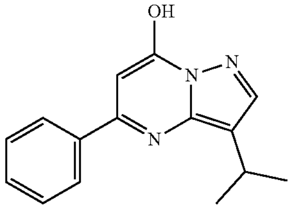 [SMILES: CC(C)c1cnn2c(O)cc(-c3ccccc3)nc12]

A mixture of methyl 3-oxo-3-phenyl-propanoate (100 mg, 561.21 μmol, 1 eq), 4-isopropyl-1H-pyrazol-5-amine (70.25 mg, 561.21 μmol, 1 eq) in AcOH (33.70 mg, 561.21 μmol, 32.10 μL, 1 eq) was degassed and purged with $N_2$ for 3 times. The mixture was stirred at 120° C. for 1 h under $N_2$ atmosphere. The reaction mixture was concentrated under reduced pressure to yield 3-isopropyl-5-phenyl-pyrazolo[1,5-a]pyrimidin-7-ol (90 mg, 355.31 μmol, 63.3% yield) as black brown oil which was used in the next step without further purification. ES-LCMS m/z 254.1 $[M+H]^+$.

Step 2: 7-Chloro-3-isopropyl-5-phenyl-pyrazolo[1,5-a]pyrimidine

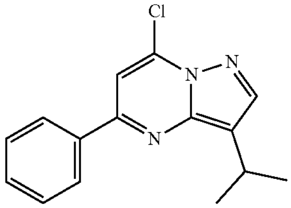 [SMILES: CC(C)c1cnn2c(Cl)cc(-c3ccccc3)nc12]

A solution of 3-isopropyl-5-phenyl-pyrazolo[1,5-a]pyrimidin-7-ol (90 mg, 355.31 μmol, 1 eq) in $POCl_3$ (2 mL) was stirred at 110° C. for 3 h. The reaction mixture was concentrated under reduced pressure, diluted with DCM (10 mL×2), concentrated under reduced pressure to give a residue which was purified by flash silica gel chromatography (from PE/EtOAC=100/1 to 10/1, TLC: PE/EtOAc=10/1, $R_f$=0.55) to yield 7-chloro-3-isopropyl-5-phenyl-pyrazolo[1,5-a]pyrimidine (60 mg, 207.11 μmol, 58.3% yield, 93.8% purity) as a yellow solid. $^1H$ NMR (400 MHz, $CD_3OD$) δ ppm 8.15-8.07 (m, 3H), 7.57-7.49 (m, 3H), 7.40 (s, 1H), 3.37-3.48 (m, 1H), 1.45 (d, J=6.8 Hz, 6H); ES-LCMS m/z 272.1 $[M+H]^+$.

Step 3: N-[2-(1H-indol-3-yl)ethyl]-3-isopropyl-5-phenyl-pyrazolo[1,5-a]pyrimidin-7-amine (I-45)

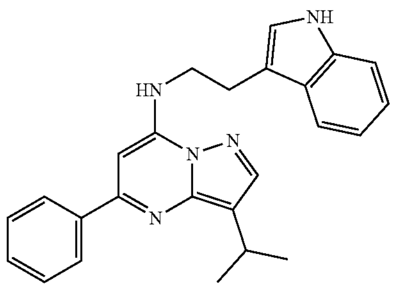 [SMILES: CC(C)c1cnn2c(NCCc3c[nH]c4ccccc34)cc(-c3ccccc3)nc12]

A mixture of 7-chloro-3-isopropyl-5-phenyl-pyrazolo[1,5-a]pyrimidine (60 mg, 207.11 μmol, 1 eq), 2-(1H-indol-3-yl)ethanamine (49.77 mg, 310.66 μmol, 1.5 eq) and DIEA (133.84 mg, 1.04 mmol, 180.37 μL, 5 eq) in i-PrOH (3 mL) was degassed and purged with $N_2$ for 3 times. The mixture was stirred at 50° C. for 3 h under $N_2$ atmosphere. The reaction mixture was concentrated under reduced pressure to give a residue which was purified by preparative HPLC (column: Phenomenex Synergi C18 250*50 mm*10 um; mobile phase: [water(0.05% HCl)-ACN]; B %: 35%-65%, 10 min), followed by lyophilization to yield N-[2-(1H-indol-3-yl)ethyl]-3-isopropyl-5-phenyl-pyrazolo[1,5-a]pyrimidin-7-amine (38.50 mg, 81.29 μmol, 39.3% yield, 98.9% purity, 2HCl) as a gray solid. $^1H$ NMR (400 MHz, $CD_3OD$) δ ppm 8.12 (s, 1H), 7.58-7.52 (m, 2H), 7.49-7.43 (m, 2H), 7.23 (d, J=8.2 Hz, 1H), 7.20-7.15 (m, 2H), 7.07-7.02 (m, 2H), 6.90-6.84 (m, 1H), 5.71 (s, 1H), 3.96 (t, J=5.8 Hz, 2H), 3.29-3.23 (m, 1H), 3.23-3.19 (m, 2H), 1.33 (d, J=6.8 Hz, 6H); ES-LCMS m/z 396.2 [M+H]+.

Example 45

Synthesis of I-46

I-46

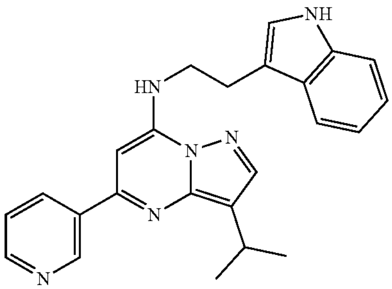

Synthetic Scheme:

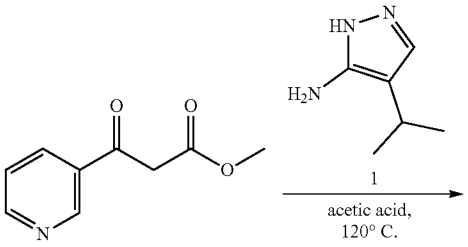

-continued

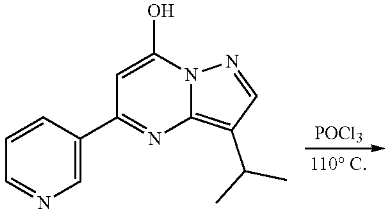

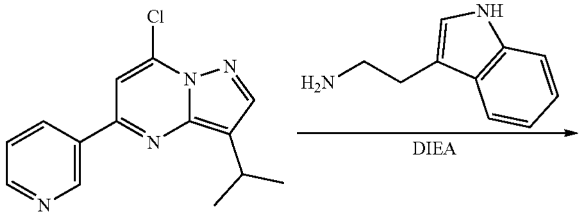

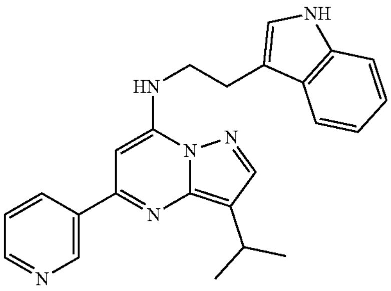

I-46

Step 1: 3-Isopropyl-5-(3-pyridyl)pyrazolo[1,5-a]pyrimidin-7-ol

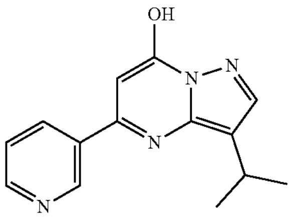 [SMILES: CC(C)c1cnn2c(O)cc(-c3cccnc3)nc12]

A mixture of methyl 3-oxo-3-(3-pyridyl)propanoate (100 mg, 558.12 μmol, 1 eq) and 4-isopropyl-1H-pyrazol-5-amine (69.86 mg, 558.12 μmol, 1 eq) in AcOH (2 mL) was stirred at 120° C. for 0.5 h. The reaction mixture was concentrated under reduced pressure to give the crude product 3-isopropyl-5-(3-pyridyl)pyrazolo[1,5-a]pyrimidin-7-ol (120 mg, 471.91 μmol, 84.6% yield, crude purity) as brown oil which was used in the next step without further purification. $^1H$ NMR (400 MHz, DMSO-$d_6$) δ ppm 9.47-8.95 (m, 1H), 8.80-8.70 (m, 1H), 8.30-8.20 (m, 1H), 7.87, 7.38 (m, 1H), 7.60-7.50 (m, 1H), 7.08, 1.24 (d, J=6.8 Hz, 3H), 1.07 (dd, J=3.5, 6.8 Hz, 3H); ES-LCMS m/z 255.1 [M+H]+.

Step 2: 7-Chloro-3-isopropyl-5-(3-pyridyl)pyrazolo[1,5-a]pyrimidine

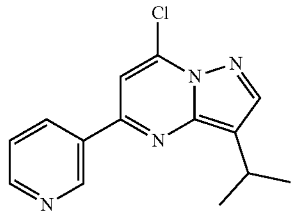 [SMILES: CC(C)c1cnn2c(Cl)cc(-c3cccnc3)nc12]

A solution of 3-Isopropyl-5-(3-pyridyl)pyrazolo[1,5-a]pyrimidin-7-ol (120.00 mg, 471.91 μmol, 1 eq) in $POCl_3$ (4.95 g, 32.28 mmol, 3 mL, 68.41 eq) was stirred at 110° C. for 3 h. The reaction mixture was concentrated under reduced pressure, diluted with DCM (20 mL) which was purified by preparative-TLC (PE/EtOAc=3/1, TLC: PE/EtOAc=3/1, $R_f$=0.40) to give 7-chloro-3-isopropyl-5-(3-pyridyl)pyrazolo[1,5-a]pyrimidine (58 mg, 212.66 μmol, 45.1% yield, 100.0% purity) as a green solid. $^1$H NMR (400 MHz, $CDCl_3$) δ ppm 9.32 (br s, 1H), 8.75 (br s, 1H), 8.45 (d, J=6.4 Hz, 1H), 8.12 (br s, 1H), 7.52-7.44 (m, 1H), 7.43-7.39 (m, 1H), 3.45-3.40 (m, 1H), 1.51-1.41 (m, 6H); ES-LCMS m/z 273.1 $[M+H]^+$.

Step 3: N-[2-(1H-Indol-3-yl)ethyl]-3-isopropyl-5-(3-pyridyl)pyrazolo[1,5-a]pyrimidin-7-amine (I-46)

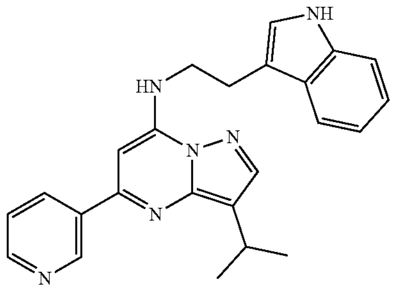 [SMILES: CC(C)c1cnn2c(NCCc3c[nH]c4ccccc34)cc(-c3cccnc3)nc12]

To a solution of 7-chloro-3-isopropyl-5-(3-pyridyl)pyrazolo[1,5-a]pyrimidine (40 mg, 146.66 μmol, 1 eq) and 2-(1H-indol-3-yl)ethanamine (35.25 mg, 220.00 μmol, 1.5 eq) in i-PrOH (5 mL) was added DIEA (56.87 mg, 439.99 μmol, 76.64 μL, 3 eq). The mixture was stirred at 60° C. for 3 h. The reaction mixture was concentrated under reduced pressure to give a residue which was purified by preparative HPLC (column: Phenomenex Gemini 150*25 mm*10 μm; mobile phase: [water (0.05% HCl)-ACN]; B %: 25%-55%, 10 min) to yield N-[2-(1H-indol-3-yl)ethyl]-3-isopropyl-5-(3-pyridyl)pyrazolo[1,5-a]pyrimidin-7-amine (31.67 mg, 60.73 μmol, 41.4% yield, 97.0% purity, 3HCl) as a yellow solid. $^1$H NMR (400 MHz, $CD_3OD$) δ ppm 8.84 (dd, J=1.2, 5.4 Hz, 1H), 8.74 (d, J=1.8 Hz, 1H), 8.11 (s, 1H), 8.04-7.98 (m, 1H), 7.91 (dd, J=5.2, 7.8 Hz, 1H), 7.57 (d, J=7.9 Hz, 1H), 7.14 (d, J=7.9 Hz, 1H), 7.01-6.95 (m, 2H), 6.91-6.86 (m, 1H), 5.81 (s, 1H), 4.00-3.94 (m, 2H), 3.24-3.16 (m, 3H), 1.32 (d, J=6.8 Hz, 6H); ES-LCMS m/z 397.2 $[M+H]^+$.

Example 46

Synthesis of I-47

I-47

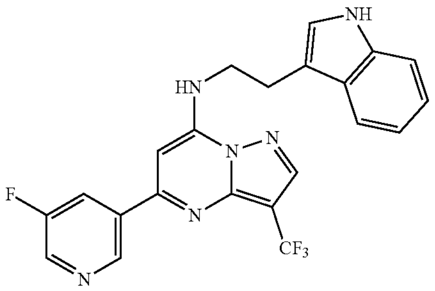

Synthetic Scheme:

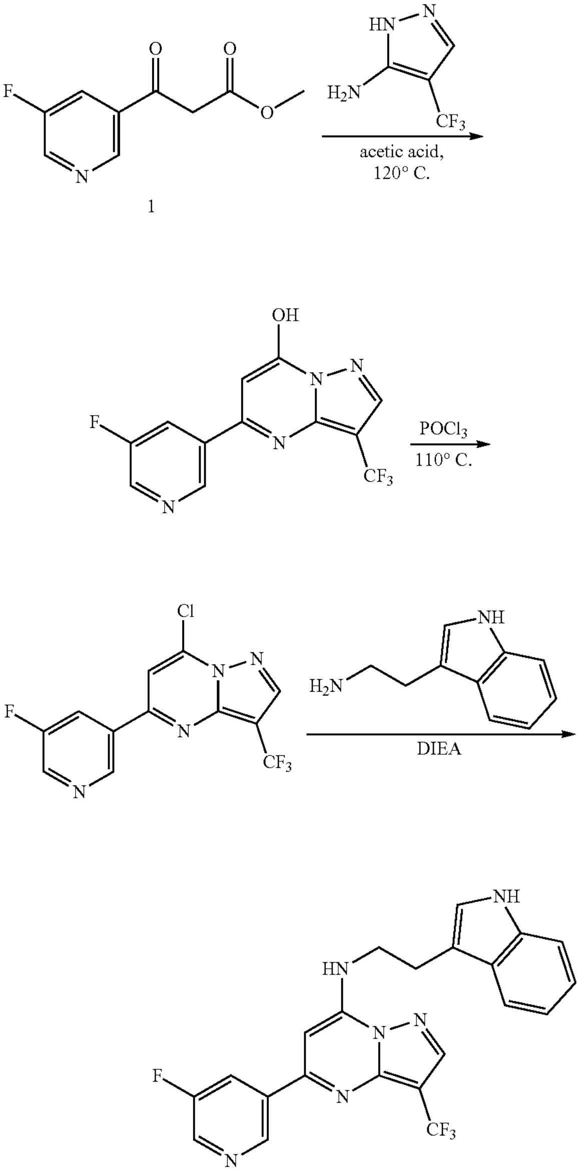

1

I-47

Step 1: 5-(5-Fluoro-3-pyridyl)-3-(trifluoromethyl)pyrazolo[1,5-a]pyrimidin-7-ol

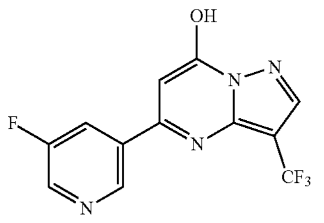 [SMILES: Oc1cc(-c2cncc(F)c2)nc2c(C(F)(F)F)cnn12]

To a solution of methyl (Z)-3-(5-fluoro-3-pyridyl)-3-hydroxy-prop-2-enoate (100.00 mg, 486.91 μmol, 1 eq) in AcOH (2 mL) was added 4-(trifluoromethyl)-1H-pyrazol-5-amine (91.32 mg, 486.91 μmol, 1 eq, HCl). The mixture was stirred at 120° C. for 2 h. The reaction mixture was concentrated under reduced pressure to give the crude product 5-(5-fluoro-3-pyridyl)-3-(trifluoromethyl)pyrazolo[1,5-a]pyrimidin-7-ol (100 mg, 335.35 μmol, 68.9% yield, crude) as a yellow solid which was used in the next step without further purification. $^1$H NMR (400 MHz, $CDCl_3$) δ ppm 9.00 (d, J=1.3 Hz, 1H), 8.87-8.79 (m, 2H), 8.35 (s, 1H), 8.23-8.11 (m, 2H); ES-LCMS m/z 299.0 $[M+H]^+$.

Step 2: 7-Chloro-5-(5-fluoro-3-pyridyl)-3-(trifluoromethyl)pyrazolo[1,5-a]pyrimidine

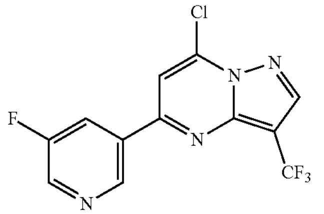 [SMILES: Fc1cncc(-c2cc(Cl)n3ncc(C(F)(F)F)c3n2)c1]

A solution of 5-(5-fluoro-3-pyridyl)-3-(trifluoromethyl)pyrazolo[1,5-a]pyrimidin-7-ol (100 mg, 335.35 μmol, 1 eq) in $POCl_3$ (18.85 g, 122.94 mmol, 11.42 mL, 366.59 eq) was stirred at 110° C. for 3 h. The reaction mixture was concentrated under reduced pressure to remove solvent. The residue was diluted with DCM (20 mL×2) and concentrated under reduced pressure to give a residue which was purified on silica gel column chromatography (from PE/EtOAc=1/0 to 3/1, TLC: PE/EtOAc=3/1, $R_f$=0.64) to give the product compound 7-chloro-5-(5-fluoro-3-pyridyl)-3-(trifluoromethyl)pyrazolo[1,5-a]pyrimidine (34 mg, 80.53 μmol, 24.0% yield, 75.0% purity) as a yellow solid. $^1$H NMR (400 MHz, $CDCl_3$) δ ppm 9.13 (s, 1H), 8.67 (s, 1H), 8.48 (s, 1H), 8.30 (d, J=6.4 Hz, 1H), 7.65 (s, 1H); ES-LCMS m/z 317.1, 319.0 $[M+H]^+$.

Step 3: 5-(5-Fluoro-3-pyridyl)-N-[2-(1H-indol-3-yl)ethyl]-3-(trifluoromethyl)pyrazolo[1,5-a]pyrimidin-7-amine (I-47)

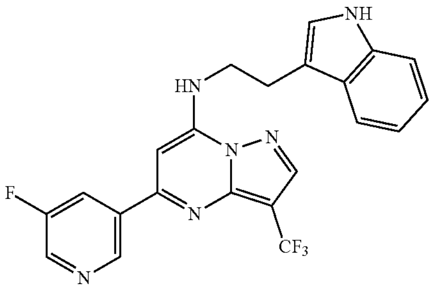 [SMILES: Fc1cncc(-c2cc(NCCc3c[nH]c4ccccc34)n3ncc(C(F)(F)F)c3n2)c1]

To a solution of 7-chloro-5-(5-fluoro-3-pyridyl)-3-(trifluoromethyl)pyrazol o[1,5-a]pyrimidine (30 mg, 71.06 μmol, 1 eq) and 2-(1H-indol-3-yl)ethanamine (17.08 mg, 106.59 μmol, 1.5 eq) in i-PrOH (5 mL) was added DIEA (27.55 mg, 213.18 μmol, 37.13 μL, 3.0 eq). The mixture was stirred at 60° C. for 3 h. The reaction mixture was concentrated under reduced pressure to give a residue which was purified by preparative HPLC (column: Phenomenex Gemini 150*25 mm*10 μm; mobile phase: [water (0.05% ammonia hydroxide v/v)-ACN]; B %: 52%-82%, 10 min) followed by lyophilization to yield 5-(5-fluoro-3-pyridyl)-N-[2-(1H-indol-3-yl)ethyl]-3-(trifluoromethyl)pyrazolo[1,5-a]pyrimidin-7-amine (24.84 mg, 45.09 μmol, 63.5% yield, 99.8% purity, 3HCl) as a yellow solid. $^1$H NMR (400 MHz, $CD_3OD$) δ ppm 8.77 (br s, 1H), 8.67 (s, 1H), 8.28 (s, 1H), 7.91 (d, J=8.2 Hz, 1H), 7.71-7.63 (m, 1H), 7.12-7.06 (m, 1H), 7.04-6.96 (m, 2H), 6.90 (s, 1H), 6.02 (s, 1H), 3.90 (t, J=6.1 Hz, 2H), 3.16 (t, J=6.1 Hz, 2H); ES-LCMS m/z 441.2 $[M+H]^+$.

Example 47

Synthesis of I-48

I-48

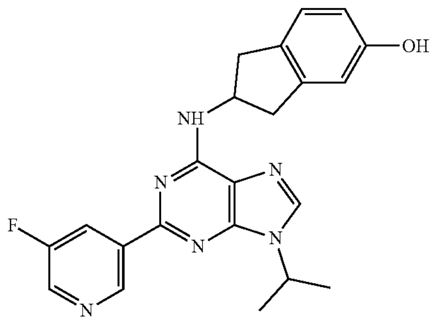

Synthetic Scheme:

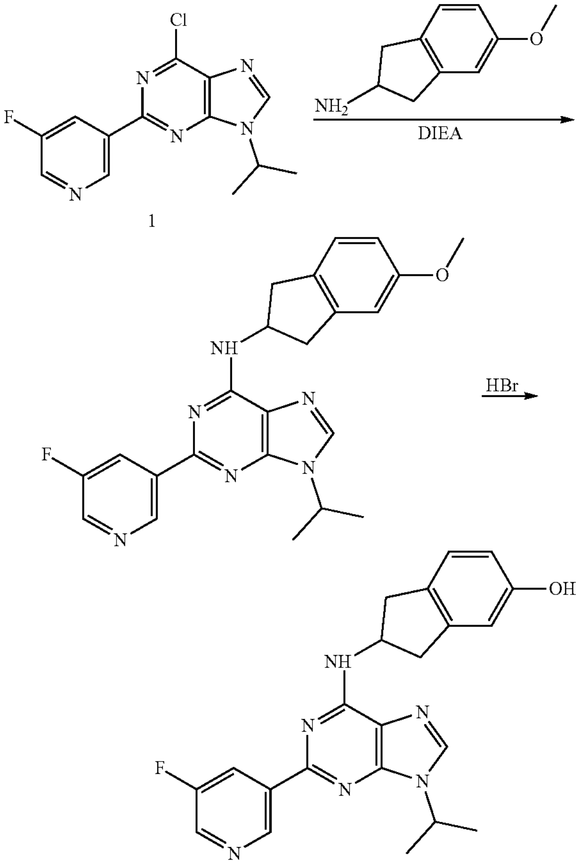

1

I-48

Step 1: 2-(5-Fluoro-3-pyridyl)-9-isopropyl-N-(5-methoxyindan-2-yl)purin-6-amine

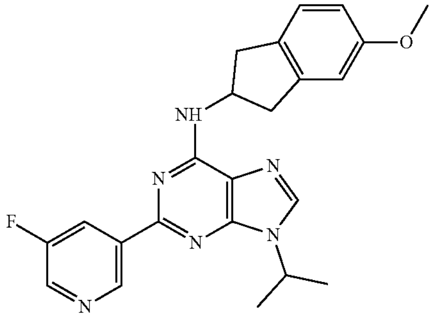 [SMILES: COc1ccc2c(c1)CC(Nc1nc(-c3cncc(F)c3)nc3c1ncn3C(C)C)C2]

To a solution of 6-chloro-2-(5-fluoro-3-pyridyl)-9-isopropyl-purine (50 mg, 164.55 μmol, 1 eq) in i-PrOH (5 mL) was added DIEA (170.13 mg, 1.32 mmol, 229.29 μL, 8 eq) and 5-methoxyindan-2-amine (33.60 mg, 168.27 μmol, 1.02 eq, HCl) under $N_2$. The mixture was stirred at 60° C. for 12 h. The reaction mixture was concentrated under reduced pressure to give crude 2-(5-fluoro-3-pyridyl)-9-isopropyl-N-(5-methoxyindan-2-yl)purin-6-amine (60 mg, 102.80 μmol, 62.4% yield, 71.7% purity) as black brown oil which was used in the next step without further purification. $^1$H NMR (400 MHz, $CDCl_3$) δ ppm 11.16 (s, 1H), 9.54 (s, 1H), 8.51 (d, J=2.9 Hz, 1H), 8.45 (d, J=9.0 Hz, 1H), 7.83 (s, 1H), 7.17 (d, J=7.9 Hz, 1H), 6.83 (s, 1H), 6.77 (dd, J=2.5, 8.3 Hz, 1H), 4.92 (m, 1H), 4.04 (td, J=6.1, 12.3 Hz, 1H), 3.84-3.79 (m, 3H), 3.48 (dt, J=7.3, 16.5 Hz, 2H), 3.05-2.92 (m, 2H), 1.22 (d, J=6.2 Hz, 6H); ES-LCMS m/z 419.2 $[M+H]^+$.

Step 2: 2-(5-Fluoro-3-pyridyl)-9-isopropyl-N-(5-methoxyindan-2-yl)purin-6-amine (I-48)

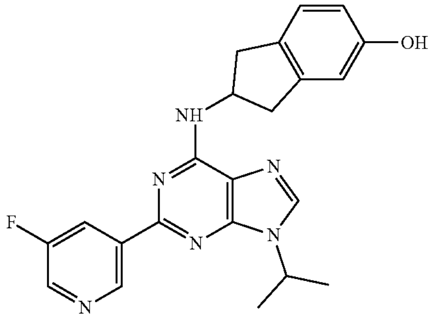

A solution of 2-(5-fluoro-3-pyridyl)-9-isopropyl-N-(5-methoxyindan-2-yl)purin-6-amine (60 mg, 102.80 μmol, 1 eq) in HBr (5 mL, 60% in water) was stirred at 120° C. for 2 h. The reaction mixture was concentrated under reduced pressure to give a residue which was purified by preparative HPLC (column: Phenomenex Gemini C18 250×50 mm×10 μm; mobile phase: [water(0.05% HCl)-ACN]; B %: 40%-70%, 10 min) followed by lyophilization to yield 2-[[2-(5-fluoro-3-pyridyl)-9-isopropyl-purin-6-yl]amino]indan-5-ol (21.36 mg, 44.75 μmol, 43.5% yield, 100% purity, 2HCl) as a yellow solid. $^1$H NMR (400 MHz, $CD_3OD$) δ ppm 9.58 (s, 1H), 9.22 (s, 1H), 8.98 (d, J=8.4 Hz, 1H), 8.90 (s, 1H), 7.09 (d, J=8.2 Hz, 1H), 6.73 (s, 1H), 6.65 (dd, J=2.4, 8.2 Hz, 1H), 5.24 (s, 1H), 5.16 (td, J=6.8, 13.6 Hz, 1H), 3.46 (ddd, J=7.2, 12.7, 15.8 Hz, 2H), 3.02 (dt, J=4.5, 14.9 Hz, 2H), 1.75 (d, J=6.1 Hz, 6H); ES-LCMS m/z 405.1 $[M+H]^+$ Example 48

Synthesis of I-49

I-49

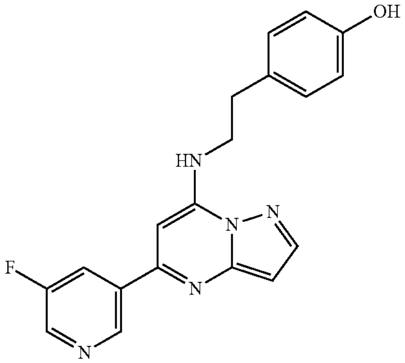

Synthetic Scheme:

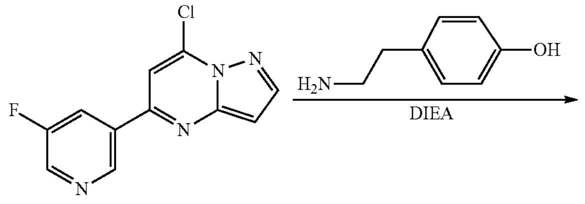

1

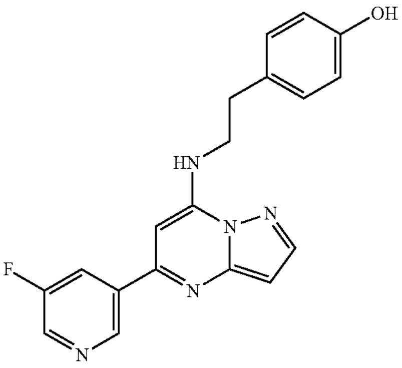

I-49

Step 1: 4-[2-[[5-(5-Fluoro-3-pyridyl)pyrazolo[1,5-a]pyrimidin-7-yl]amino]ethyl]phenol (I-49)

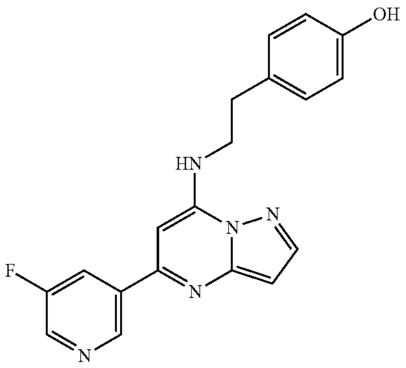 [SMILES: Oc1ccc(CCNc2cc(-c3cncc(F)c3)nc3ccnn23)cc1]

To a solution of 7-chloro-5-(5-fluoro-3-pyridyl)pyrazolo[1,5-a]pyrimidine (50 mg, 164.89 μmol, 1 eq) in i-PrOH (5 mL) was added DIEA (170.49 mg, 1.32 mmol, 229.77 μL, 8 eq) and 4-(2-aminoethyl)phenol (33.93 mg, 247.34 μmol, 1.50 eq) under $N_2$. The mixture was stirred at 80° C. for 12 h. The reaction mixture was concentrated under reduced pressure to give a residue which was purified by preparative HPLC (column: Phenomenex Gemini 150×25 mm×10 m; mobile phase: [water(0.05% HCl)-ACN]; B %: 20%-50%, 10 min), followed by lyophilization to yield 4-[2-[[5-(5-fluoro-3-pyridyl)pyrazolo[1,5-a]pyrimidin-7-yl]amino]ethyl]phenol (46.38 mg, 109.83 μmol, 66.6% yield, 100% purity, 2HCl) as a yellow solid. $^1H$ NMR (400 MHz, $CD_3OD$) δ ppm 8.85-8.75 (m, 2H), 8.27 (d, J=2.2 Hz, 1H), 8.09 (td, J=2.3, 9.2 Hz, 1H), 7.07 (d, J=8.6 Hz, 2H), 6.65-6.56 (m, 3H), 6.46 (s, 1H), 3.97 (t, J=6.6 Hz, 2H), 3.00 (t, J=6.5 Hz, 2H); ES-LCMS m/z 350.2 $[M+H]^+$.

Example 49

Synthesis of I-50

I-50

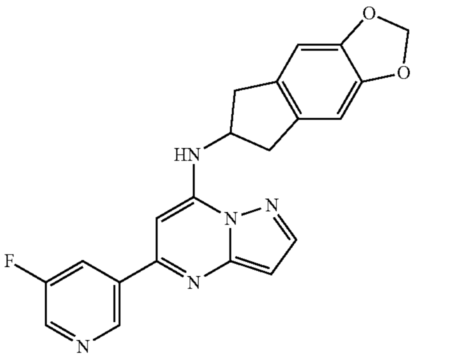

Synthetic Scheme:

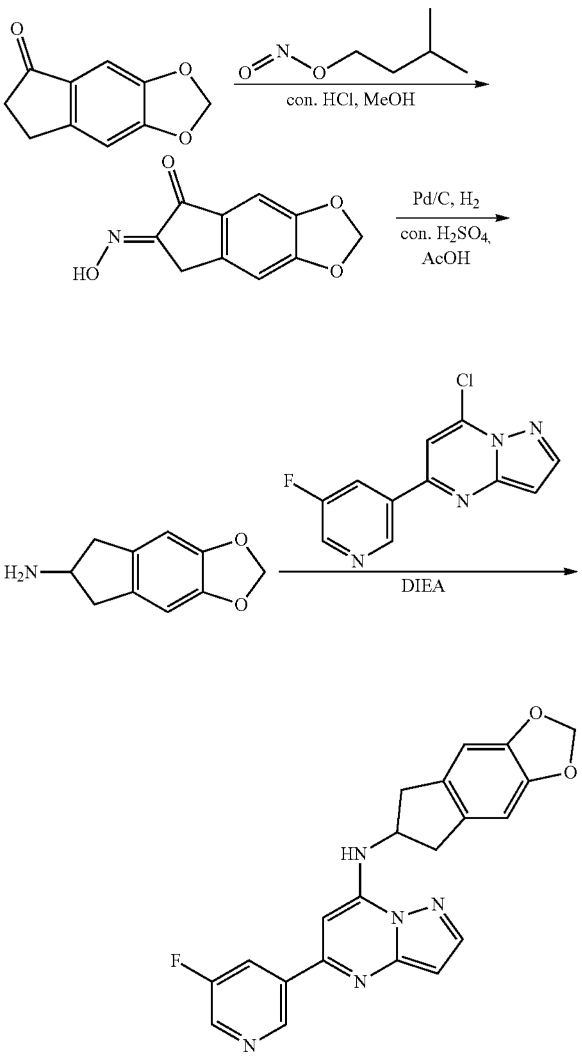

I-50

Step 1: (6E)-6-Hydroxyimino-5H-cyclopenta[f][1,3]benzodioxol-7-one

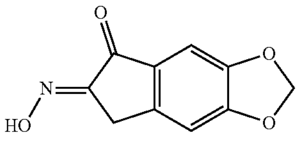 [SMILES: O=C1/C(=N/O)Cc2cc3c(cc21)OCO3]

A suspension of 5,6-dihydrocyclopenta[f][1,3]benzodioxol-7-one (0.5 g, 2.84 mmol, 1 eq) in MeOH (45 mL) was heated to 45° C., then isopentyl nitrite (539.40 mg, 4.60 mmol, 0.62 mL, 1.62 eq) and con. HCl (12 M in water, 0.47 mL, 1.99 eq) were added. The mixture was stirred at 45° C. for 1.5 h. The mixture was filtered, the cake was washed with cold MeOH (5 mL×2), dried in vacuo to give a product (300 mg). The filtrate was concentrate under reduced pressure to give a residue which was added MeOH (5 mL), then was filtered, dried in vacuo to give a product (200 mg). Compound (6E)-6-hydroxyimino-5H-cyclopenta[f][1,3]benzodioxol-7-one (500 mg, 2.44 mmol, 85.8% yield, 100% purity) was obtained as a yellow solid which was used in the next step without further purification. $^1H$ NMR (400 MHz, DMSO-$d_6$) δ ppm 12.47 (s, 1H), 7.14 (d, J=10.4 Hz, 2H), 6.18 (s, 2H), 3.64 (s, 2H); ES-LCMS m/z 206.1 $[M+H]^+$.

Step 2: 6,7-Dihydro-5H-cyclopenta[f][1,3]benzodioxol-6-amine

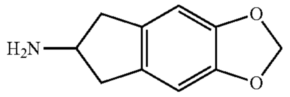 [SMILES: NC1Cc2cc3c(cc2C1)OCO3]

To a solution of (6E)-6-hydroxyimino-5H-cyclopenta[f][1,3]benzodioxol-7-one (500 mg, 2.44 mmol, 1 eq) in AcOH (25 mL) and con. $H_2SO_4$ (0.3 mL) was added Pd/C (0.13 g, 10%). The mixture was stirred at 25° C. for 12 h under $H_2$ (30 psi). The mixture was filtered, the filtrate was concentrated under reduced pressure to give a residue which was added water (50 mL), adjusted pH to 10-11 with 2 N aq. NaOH, extracted with DCM (30 mL×3). The combined organic layers were washed with brine (20 mL), dried over $Na_2SO_4$, filtered and concentrated under reduced pressure to give 6,7-dihydro-5H-cyclopenta[f][1,3]benzodioxol-6-amine (250 mg, 1.13 mmol, 46.3% yield, 80% purity) as a yellow solid which was used in the next step without further purification. $^1H$ NMR (400 MHz, $CDCl_3$) δ ppm 6.68 (s, 2H), 5.90 (s, 2H), 3.91-3.76 (m, 1H), 3.09 (dd, J=6.8, 15.3 Hz, 2H), 2.58 (dd, J=4.9, 15.4 Hz, 2H); ES-LCMS m/z No correct mass was found.

Step 3: N-(6,7-Dihydro-5H-cyclopenta[f][1,3]benzodioxol-6-yl)-5-(5-fluoro-3-pyridyl)pyrazolo[1,5-a]pyrimidin-7-amine (I-50)

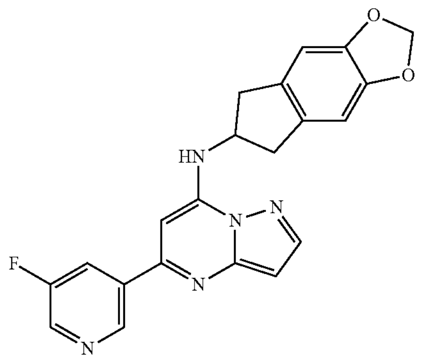 [SMILES: Fc1cncc(-c2cc(NC3Cc4cc5c(cc4C3)OCO5)n3nccc3n2)c1]

To a solution of 7-chloro-5-(5-fluoro-3-pyridyl)pyrazolo[1,5-a]pyrimidine (60 mg, 197.87 μmol, 1 eq) in i-PrOH (3 mL) was added DIEA (127.87 mg, 989.37 μmol, 172.33 μL, 5 eq) and 6,7-dihydro-5H-cyclopenta[f][1,3]benzodioxol-6-amine (65.74 mg, 296.81 μmol, 1.5 eq). The mixture was stirred at 90° C. for 12 h. The reaction mixture was concentrated under reduced pressure to give a residue which was purified by preparative HPLC (column: Phenomenex Gemini C18 250×50 mm×10 μm; mobile phase: [water (0.05% HCl)-ACN]; B %: 40%-70%, 10 min) followed by lyophilization to yield N-(6,7-dihydro-5H-cyclopenta[f][1,3]benzodioxol-6-yl)-5-(5-fluoro-3-pyridyl)pyrazolo[1,5-a]pyrimidin-7-amine (21.53 mg, 46.43 μmol, 23.4% yield, 99.7% purity, 2HCl) as a yellow solid. $^1H$ NMR (400 MHz, $CD_3OD$) δ ppm 9.02 (t, J=1.3 Hz, 1H), 8.81 (d, J=2.6 Hz, 1H), 8.34-8.29 (m, 1H), 8.28 (d, J=2.2 Hz, 1H), 7.05 (s, 1H), 6.76 (s, 2H), 6.66 (d, J=2.2 Hz, 1H), 5.94-5.90 (m, 2H), 5.08 (t, J=6.8 Hz, 1H), 3.46 (dd, J=7.7, 15.4 Hz, 2H), 3.18 (dd, J=6.3, 15.5 Hz, 2H); ES-LCMS m/z 390.1 $[M+H]^+$.

Example 50

Synthesis of I-51

I-51

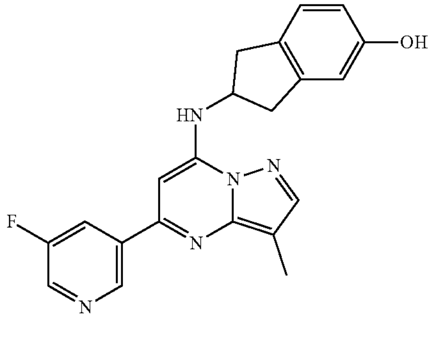 [SMILES: COc1ccc2c(c1)CC(Nc1cc(-c3cncc(F)c3)nc3c(C)cnn13)C2]

Synthetic Scheme:

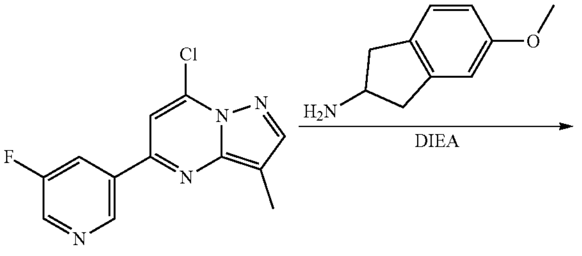

1

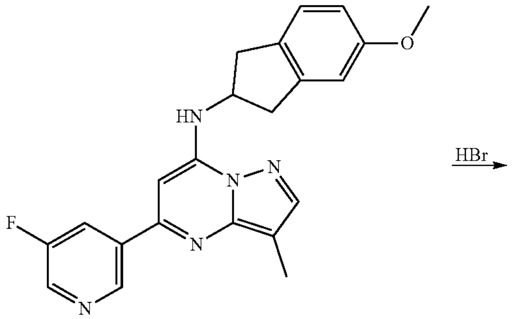

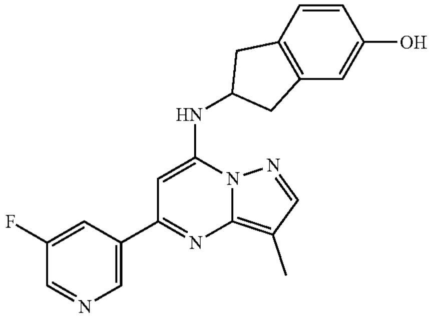 [SMILES: Cc1cnn2c(NC3Cc4ccc(O)cc4C3)cc(-c3cncc(F)c3)nc12]

I-51

Step 1: 5-(5-Fluoro-3-pyridyl)-N-(5-methoxyindan-2-yl)-3-methyl-pyrazolo[1,5-a]pyrimidin-7-amine

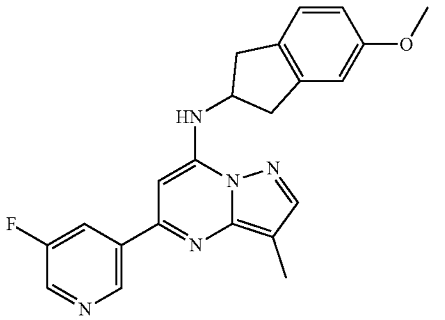

To a solution of 7-chloro-5-(5-fluoro-3-pyridyl)-3-methyl-pyrazolo[1,5-a]pyrimidine (35 mg, 133.25 μmol, 1.0 eq) in i-PrOH (4 mL) was added DIEA (86.10 mg, 666.24 μmol, 116.04 μL, 5.0 eq) and 5-methoxyindan-2-amine (30 mg, 150.24 μmol, 1.13 eq, HCl salt). The mixture was stirred at 60° C. for 12 h. The reaction mixture was concentrated under reduced pressure to give 5-(5-fluoro-3-pyridyl)-N-(5-methoxyindan-2-yl)-3-methyl-pyrazolo[1,5-a]pyrimidin-7-amine (50 mg, 113.24 μmol, 85.0% yield, 88.2% purity) was obtained as yellow oil which was used in the next step without further purification. $^1$H NMR (400 MHz, $CDCl_3$) δ ppm 9.07 (s, 1H), 8.55 (d, J=2.6 Hz, 1H), 8.21 (d, J=9.9 Hz, 1H), 7.86 (s, 1H), 7.18 (d, J=8.8 Hz, 1H), 6.87-6.75 (m, 2H), 6.60 (m, 1H), 6.39 (s, 1H), 4.66 (s, 1H), 3.81 (s, 3H), 3.70-3.64 (m, 4H), 2.39 (s, 3H); ES-LCMS m/z 390.2 $[M+H]^+$.

Step 2: 2-[[5-(5-Fluoro-3-pyridyl)-3-methyl-pyrazolo[1,5-a]pyrimidin-7-yl]amino]indan-5-ol (I-51)

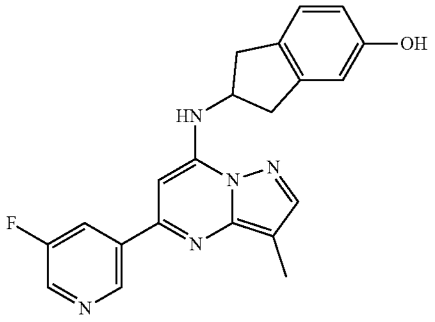

5-(5-Fluoro-3-pyridyl)-N-(5-methoxyindan-2-yl)-3-methy-pyrazolo[1,5-a]pyrimidin-7-amine (50 mg, 113.24 μmol, 1 eq) was added into HBr (5 mL, 60% in water) and the mixture was stirred at 120° C. for 2 h. The reaction mixture was concentrated under reduced pressure to give a residue which was purified by preparative HPLC (HCl condition; column: Phenomenex Gemini 150×25 mm×10 um; mobile phase: [water(0.05% HCl)-ACN]; B %: 35%-65%, 10 min). The desired fraction was lyophilized to yield 2-[[5-(5-fluoro-3-pyridyl)-3-methyl-pyrazolo[1,5-a]pyrimidin-7-yl]amino]indan-5-ol (15.05 mg, 33.46 μmol, 29.5% yield, 99.6% purity, 2 HCl salt) as a yellow solid. $^1$H NMR (400 MHz, $CD_3OD$) δ ppm 9.03 (s, 1H), 8.75 (d, J=2.5 Hz, 1H), 8.31 (td, J=2.3, 9.3 Hz, 1H), 8.07 (s, 1H), 7.08 (d, J=8.3 Hz, 1H), 6.89 (s, 1H), 6.72 (s, 1H), 6.68-6.62 (m, 1H), 4.99-4.95 (m, 1H), 3.50-3.41 (m, 2H), 3.21-3.10 (m, 2H), 2.37 (s, 3H); ES-LCMS m/z 376.1 $[M+H]^+$.

Example 51

Synthesis of I-52

I-52

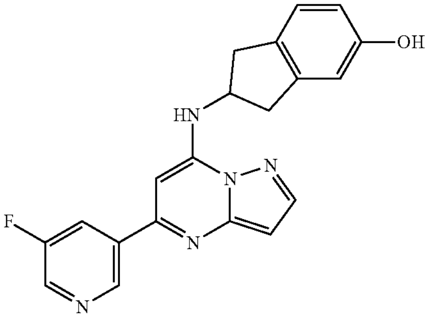

Synthetic Scheme:

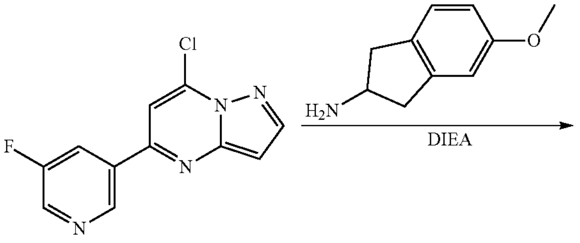

1

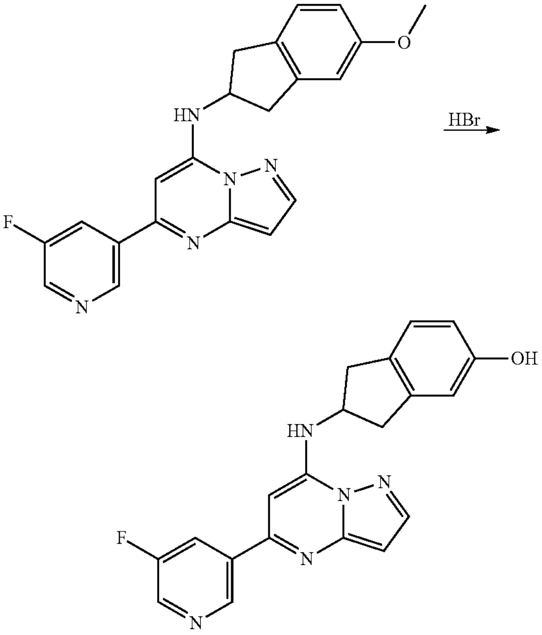

I-52

Step 1: 5-(5-Fluoro-3-pyridyl)-N-(5-methoxyindan-2-yl)pyrazolo[1,5-a]pyrimidin-7-amine

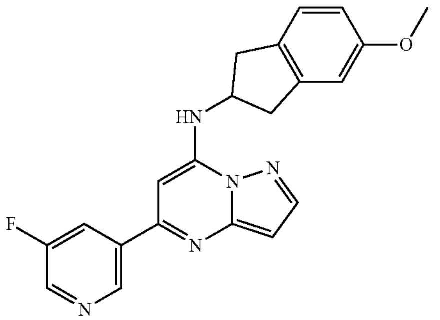 [SMILES: COc1ccc2c(c1)CC(Nc1cc(-c3cncc(F)c3)nc3ccnn13)C2]

To a solution of 7-chloro-5-(5-fluoro-3-pyridyl)pyrazolo[1,5-a]pyrimidine (50 mg, 164.89 μmol, 1.0 eq) in i-PrOH (6 mL) was added DIEA (106.56 mg, 824.47 μmol, 143.61 μL, 5.0 eq) and 5-methoxyindan-2-amine (35 mg, 175.28 μmol, 1.06 eq, HCl salt). The mixture was stirred at 60° C. for 12 h. The reaction mixture was concentrated under reduced pressure to give a residue which was used in the next step without further purification. Compound 5-(5-fluoro-3-pyridyl)-N-(5-methoxyindan-2-yl)pyrazolo[1,5-a]pyrimidin-7-amine (60 mg, 139.21 μmol, 84.4% yield, 87.1% purity) was obtained as a yellow oil. $^1$H NMR (400 MHz, $CDCl_3$) δ ppm 8.97 (s, 1H), 8.49 (d, J=2.9 Hz, 1H), 8.09 (td, J=2.3, 9.5 Hz, 1H), 7.94 (d, J=2.2 Hz, 1H), 7.11 (d, J=8.4 Hz, 1H), 6.79-6.69 (m, 2H), 6.51 (d, J=2.2 Hz, 1H), 6.37 (s, 1H), 4.63-4.55 (m, 1H), 3.77-3.68 (m, 3H), 3.59 (dt, J=3.0, 6.6 Hz, 4H); ES-LCMS m/z 376.2 $[M+H]^+$.

Step 2: 2-[[5-(5-Fluoro-3-pyridyl)pyrazolo[1,5-a]pyrimidin-7-yl]amino]indan-5-ol

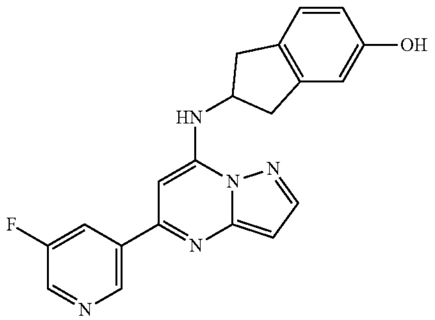

5-(5-Fluoro-3-pyridyl)-N-(5-methoxyindan-2-yl)pyrazolo[1,5-a]pyrimidin-7-amine (60 mg, 139.21 μmol, 1 eq) was added into HBr (6 mL, 60% in water) and the mixture was stirred at 120° C. for 2 h. The reaction mixture was concentrated under reduced pressure to give a residue which was purified by preparative HPLC (HCl condition; column: Phenomenex Gemini 150×25 mm×10 um; mobile phase: [water (0.05% HCl)-ACN]; B %: 30%-60%, 10 min). The desired fraction was lyophilized to yield 2-[[5-(5-fluoro-3-pyridyl)pyrazolo[1,5-a]pyrimidin-7-yl]amino]indan-5-ol (32.33 mg, 72.95 μmol, 52.4% yield, 98.0% purity, 2 HCl salt) as a yellow solid. $^1$H NMR (400 MHz, $CD_3OD$) δ ppm 9.01 (s, 1H), 8.82 (s, 1H), 8.34-8.26 (m, 2H), 7.12-7.05 (m, 2H), 6.73 (s, 1H), 6.69-6.63 (m, 2H), 5.06 (s, 1H), 3.47 (td, J=8.3, 15.9 Hz, 2H), 3.27-3.15 (m, 2H); ES-LCMS m/z 362.1 $[M+H]^+$.

Example 52

Synthesis of I-53

I-53

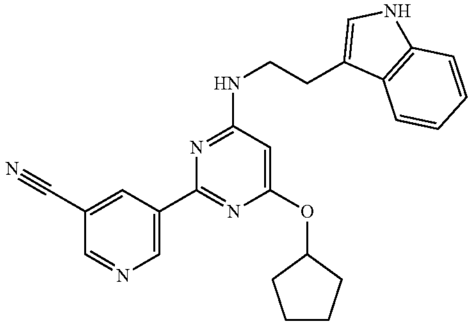

Synthetic Scheme:

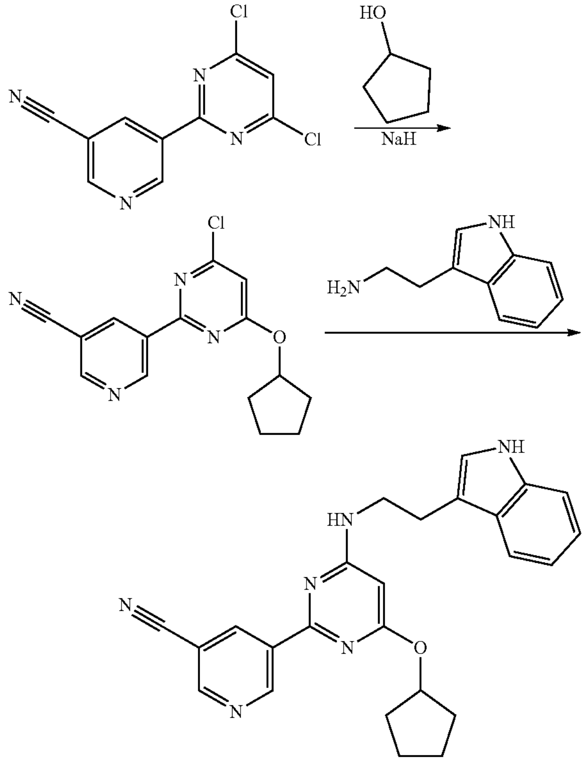

I-53

Step 1: 5-[4-Chloro-6-(cyclopentoxy)pyrimidin-2-yl]pyridine-3-carbonitrile

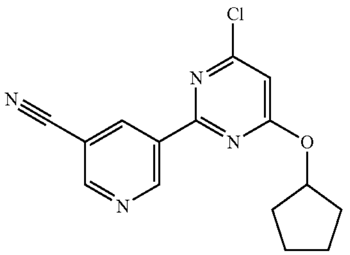 [SMILES: N#Cc1cncc(-c2nc(Cl)cc(OC3CCCC3)n2)c1]

To a solution of cyclopentanol (20.84 mg, 241.96 umol, 21.96 μL, 1.5 eq) in THF (3 mL) was added NaH (9.68 mg, 241.96 μmol, 60% in mineral oil, 1.5 eq). The mixture was stirred at 0° C. for 30 min. 5-(4,6-dichloropyrimidin-2-yl)pyridine-3-carbonitrile (50 mg, 161.31 μmol, 1 eq) was added into the above solution and the mixture was stirred at 28° C. for 12 h. The reaction mixture was quenched by addition $NH_4Cl$ (2 mL) and water (1 mL), then extracted with EtOAc (20 mL×3). The combined organic layers were dried over $Na_2SO_4$, filtered and concentrated under reduced pressure to give a residue which was purified by preparative TLC (PE/EtOAc=13/1, TLC: PE/EtOAc=13/1, $R_f$=0.54) to yield 5-[4-chloro-6-(cyclopentoxy) pyrimidin-2-yl]pyridine-3-carbonitrile (35 mg, 108.23 μmol, 67.1% yield, 93.0% purity) as a white solid. $^1$H NMR (400 MHz, $CD_3OD$) δ ppm 9.70 (d, J=2.2 Hz, 1H), 9.04 (d, J=2.0 Hz, 1H), 9.01 (t, J=2.1 Hz, 1H), 6.91 (s, 1H), 5.72-5.67 (m, J=3.1, 6.0 Hz, 1H), 2.15-2.08 (m, 2H), 1.95-1.88 (m, 2H), 1.87-1.83 (m, 2H), 1.77-1.70 (m, 2H); ES-LCMS m/z 301.1 $[M+H]^+$.

Step 2: 5-[4-(Cyclopentoxy)-6-[2-(1H-indol-3-yl)ethylamino]pyrimidin-2-yl]pyridine-3-carbonitrile (I-53)

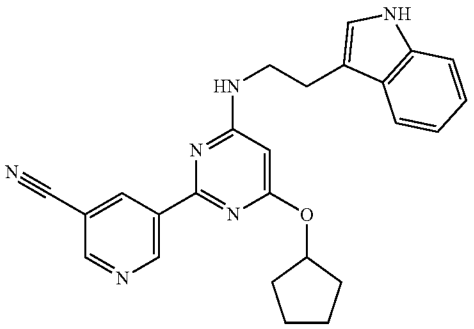 [SMILES: N#Cc1cncc(-c2nc(NCCc3c[nH]c4ccccc34)cc(OC3CCCC3)n2)c1]

5-[4-Chloro-6-(cyclopentoxy)pyrimidin-2-yl]pyridine-3-carbonitrile (60 mg, 185.54 μmol, 1 eq), 2-(1H-indol-3-yl)ethanamine (74.32 mg, 463.85 μmol, 2.5 eq) and DIEA (23.98 mg, 185.54 μmol, 32.32 uL, 1 eq) were taken up into a microwave tube in i-PrOH (4 mL). The sealed tube was heated at 135° C. for 3 h under microwave. The reaction mixture was concentrated under reduced pressure to give a residue which was purified by preparative HPLC (column: Phenomenex Synergi C18 250*50 mm*10 um; mobile phase: [water(0.05% HCl)-ACN]; B %: 60%-90%, 10 min), followed by lyophilization to yield 5-[4-(cyclopentoxy)-6-[2-(1H-indol-3-yl)ethylamino]pyrimidin-2-yl]pyridine-3-carbonitrile (21.28 mg, 39.58 μmol, 21.3% yield, 99.3% purity, 3HCl) as a yellow solid. $^1$H NMR (400 MHz, $CD_3OD$) δ ppm 10.81 (br s, 1H), 9.61 (s, 1H), 9.10 (d, J=2.0 Hz, 1H), 8.87 (s, 1H), 7.56 (d, J=7.9 Hz, 1H), 7.46 (br s, 1H), 7.31 (d, J=8.2 Hz, 1H), 7.21-7.15 (m, 1H), 7.07-7.01 (m, 1H), 7.00-6.94 (m, 1H), 5.72 (s, 1H), 5.39 (br s, 1H), 3.68 (br s, 2H), 2.96 (t, J=7.4 Hz, 2H), 1.96 (d, J=6.0 Hz, 2H), 1.74-1.64 (m, 4H), 1.62-1.52 (m, 2H); ES-LCMS m/z 425.2 $[M+H]^+$.

Example 53

Synthesis of I-54

I-54

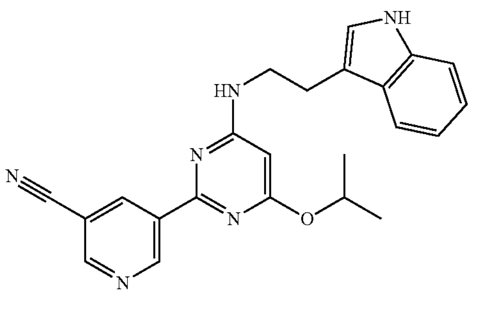

Synthetic Scheme:

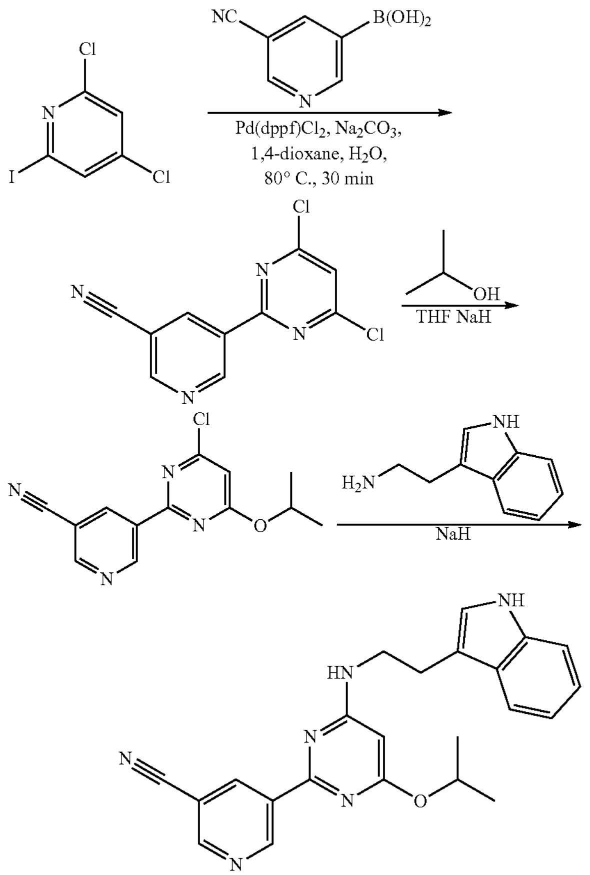

I-54

Step 1: 5-(4,6-Dichloropyrimidin-2-yl)pyridine-3-carbonitrile

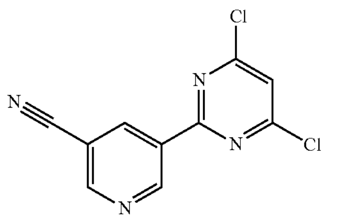 [SMILES: N#Cc1cncc(-c2nc(Cl)cc(Cl)n2)c1]

A mixture of 4,6-dichloro-2-iodo-pyrimidine (813.84 mg, 2.91 mmol, 1 eq), (5-cyano-3-pyridyl)boronic acid (409.00 mg, 2.76 mmol, 0.95 eq), Pd(dppf)$Cl_2$ (212.96 mg, 291.04 μmol, 0.1 eq), $Na_2CO_3$ (925.42 mg, 8.73 mmol, 3.0 eq) and water (2.4 mL) in 1,4-dioxane (12 mL) was degassed and purged with $N_2$ for 3 times, then the mixture was stirred at 80° C. for 1 h under $N_2$ atmosphere. The reaction mixture was diluted with EtOAc (50 mL) and filtered through a pad of celite. The filtrate was concentrated under reduced pressure to give a residue which was purified by flash silica gel chromatography (from PE/EtOAC=100/1 to 5/1, TLC: PE/EtOAc=5/1, $R_f$=0.7) to yield 5-(4,6-dichloropyrimidin-2-yl)pyridine-3-carbonitrile (180 mg, 580.71 μmol, 20.0% yield, 81.0% purity) as a yellow solid. $^1H$ NMR (400 MHz, $CDCl_3$) δ ppm 9.81 (d, J=2.4 Hz, 1H), 9.03 (d, J=2.0 Hz, 1H), 8.99 (d, J=2.0 Hz, 1H), 7.44 (s, 1H); ES-LCMS m/z 250.9, 252.9 $[M+H]^+$.

Step 2: 5-(4-Chloro-6-isopropoxy-pyrimidin-2-yl) pyridine-3-carbonitrile

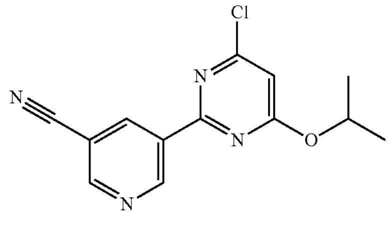 [SMILES: CC(C)Oc1cc(Cl)nc(-c2cncc(C#N)c2)n1]

To a solution of i-PrOH (9.69 mg, 161.31 μmol, 12.35 μL, 1 eq) in THF (3 mL) was added NaH (6.45 mg, 161.31 μmol, 60%, 1 eq). The mixture was stirred at 0° C. for 30 min. 5-(4,6-dichloropyrimidin-2-yl)pyridine-3-carbonitrile (50 mg, 161.31 μmol, 1 eq) was added into the above solution. The mixture was stirred at 28° C. for 12 h. The reaction mixture was concentrated under reduced pressure to give a residue which was diluted with $NH_4Cl$ (30 mL) and extracted with EtOAc (30 mL×3). The combined organic layers were dried over $Na_2SO_4$, filtered and concentrated under reduced pressure to give a residue which was purified by preparative TLC (PE/EtOAc=10/1, TLC: PE/EtOAc=10/1, $R_f$=0.55) to yield 5-(4-chloro-6-isopropoxy-pyrimidin-2-yl) pyridine-3-carbonitrile (25 mg, 87.37 μmol, 54.2% yield, 96.0% purity) as a white solid. $^1H$ NMR (400 MHz, $CD_3OD$) δ ppm 9.70 (s, 1H), 9.05 (d, J=2.0 Hz, 1H), 9.01 (t, J=2.1 Hz, 1H), 6.90 (s, 1H), 5.61 (td, J=6.3, 12.4 Hz, 1H), 1.44 (d, J=6.2 Hz, 6H); ES-LCMS m/z 275.1 $[M+H]^+$.

Step 3: 5-[4-[2-(1H-indol-3-yl)ethylamino]-6-isopropoxy-pyrimidin-2-yl]pyridine-3-carbonitrile (I-54)

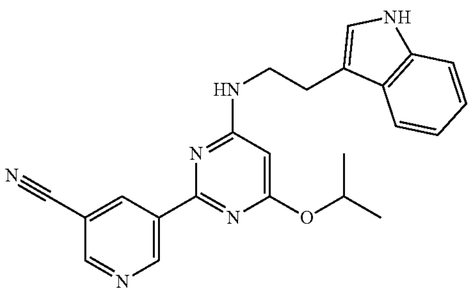 [SMILES: CC(C)Oc1cc(NCCc2c[nH]c3ccccc23)nc(-c2cncc(C#N)c2)n1]

5-(4-chloro-6-isopropoxy-pyrimidin-2-yl) pyridine-3-carbonitrile (25 mg, 91.01 μmol, 1 eq), 2-(1H-indol-3-yl) ethanamine (21.87 mg, 136.51 μmol, 1.5 eq) and DIEA (35.29 mg, 273.02 μmol, 47.56 μL, 3 eq) were taken up into a microwave tube in i-PrOH (3 mL). The sealed tube was heated at 135° C. for 5 h under microwave. The reaction mixture was concentrated under reduced pressure to give a residue which was purified by preparative HPLC (column: Phenomenex Synergi C18 250*50 mm*10 um; mobile phase: [water(0.05% HCl)-ACN]; B %: 55%-85%, 10 min), followed by lyophilization to yield 5-[4-[2-(1H-indol-3-yl)ethylamino]-6-isopropoxy-pyrimidin-2-yl]pyridine-3-carbonitrile (16.5 mg, 32.17 μmol, 35.3% yield, 99.0% purity, 3HCl) as a yellow solid. $^1$H NMR (400 MHz, DMSO-$d_6$) δ ppm 10.84 (s, 1H), 9.62 (s, 1H), 9.12 (d, J=2.0 Hz, 1H), 8.90 (s, 1H), 7.58 (d, J=8.4 Hz, 1H), 7.33 (d, J=7.9 Hz, 1H), 7.20 (s, 1H), 7.09-7.02 (m, 1H), 7.01-6.95 (m, 1H), 5.74 (s, 1H), 5.41-5.30 (m, 1H), 3.71 (m, 2H), 2.97 (t, J=7.3 Hz, 2H), 1.31 (d, J=6.2 Hz, 6H); ES-LCMS m/z 399.2 $[M+H]^+$.

Example 54

Synthesis of I-55

I-55

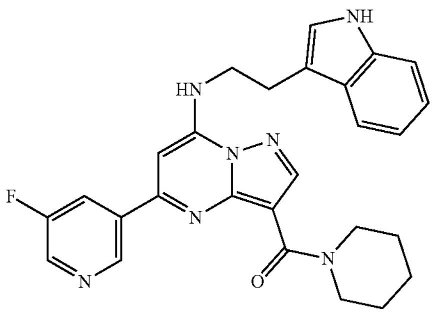

Synthetic Scheme:

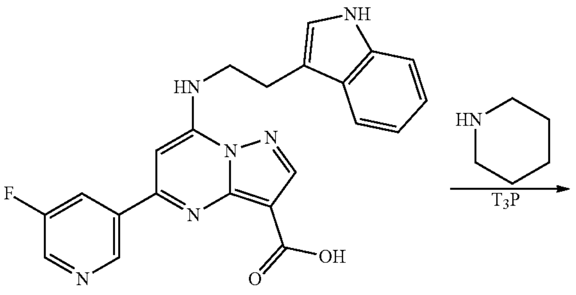

1

Step 1: [5-(5-Fluoro-3-pyridyl)-7-[2-(1H-indol-3-yl)ethylamino]pyrazolo[1,5-a]pyrimidin-3-yl]-(1-piperidyl)methanone (I-55)

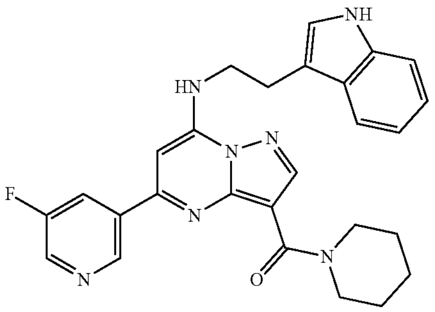

To a solution of 5-(5-fluoro-3-pyridyl)-7-[2-(1H-indol-3-yl)ethylamino]pyrazolo[1,5-a]pyrimidine-3-carboxylic acid (50 mg, 120.07 μmol, 1 eq) in pyridine (2 mL) was added piperidine (15.34 mg, 180.11 μmol, 17.79 μL, 1.5 eq) and $T_3P$ (152.82 mg, 240.15 μmol, 142.82 μL, 50%, 2 eq). The mixture was stirred at 25° C. for 12 h under $N_2$ atmosphere. The reaction mixture was concentrated under reduced pressure to give a residue which was diluted with EtOAc (10 mL) and extracted with EtOAc (30 mL×3). The combined organic layers were washed with brine (10 mL), dried over $Na_2SO_4$, filtered and concentrated under reduced pressure to give a residue which was purified by preparative HPLC (column: Phenomenex Gemini 150*25 mm*10 um; mobile phase: [water(0.05% HCl)-ACN]; B %: 42%-72%, 10 min), followed by lyophilization to yield [5-(5-fluoro-3-pyridyl)-7-[2-(1H-indol-3-yl)ethylamino]pyrazolo[1,5-a]pyrimidin-3-yl]-(1-piperidyl)methanone (12.74 mg, 21.49 μmol, 17.9% yield, 100.0% purity, 3HCl) as a white solid. $^1$H NMR (400 MHz, $CD_3OD$) δ ppm 8.72-8.68 (m, 1H), 8.57 (s, 1H), 8.34 (s, 1H), 7.71 (td J=2.4, 8.9 Hz, 1H), 7.60 (d, J=7.9 Hz, 1H), 7.14 (d, J=7.9 Hz, 1H), 7.02-6.96 (m, 2H), 6.94-6.89 (m, 1H), 6.03 (s, 1H), 4.00 (t, J=6.0 Hz, 2H), 3.71 (m, 4H), 3.23 (t, J=6.1 Hz, 2H), 1.75 (m, 2H), 1.68 (m, 4H); ES-LCMS m/z 484.2 $[M+H]^+$.

Example 55

Synthesis of I-56

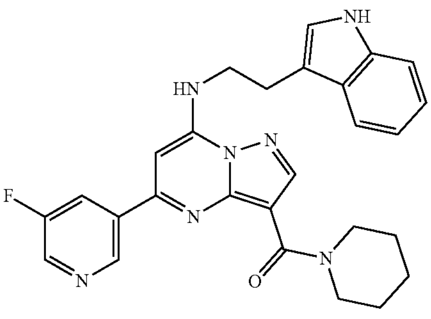 [SMILES: O=C(c1cnn2c(NCCc3c[nH]c4ccccc34)cc(-c3cncc(F)c3)nc12)N1CCCCC1]

I-55

I-56

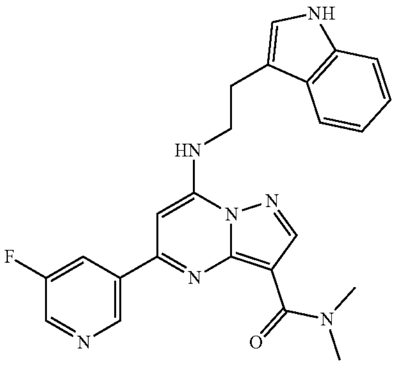 [SMILES: CN(C)C(=O)c1cnn2c(NCCc3c[nH]c4ccccc34)cc(-c3cncc(F)c3)nc12]

Synthetic Scheme:

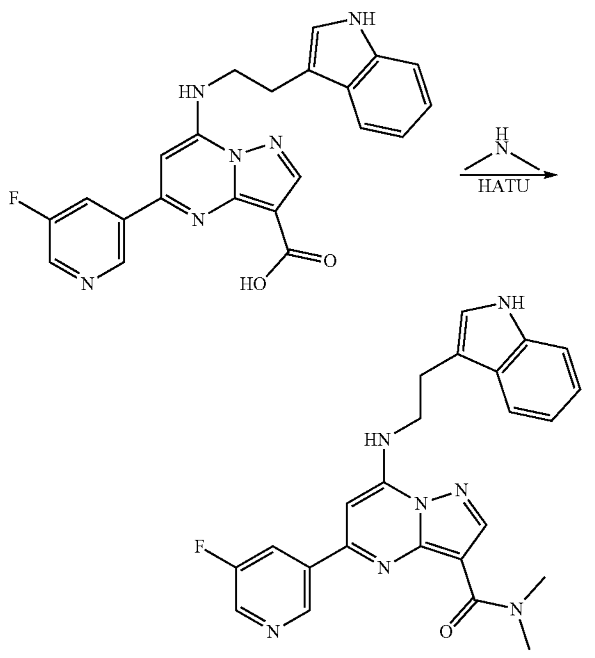

I-56

Step 1: 5-(5-Fluoro-3-pyridyl)-7-[2-(1H-indol-3-yl)ethylamino]-N,N-dimethyl-pyrazolo[1,5-a]pyrimidine-3-carboxamide (I-56)

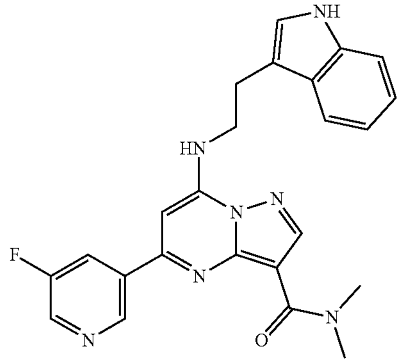

A mixture of 5-(5-fluoro-3-pyridyl)-7-[2-(1H-indol-3-yl)ethylamino]pyrazolo[1,5-a]pyrimidine-3-carboxylic acid (40 mg, 96.06 μmol, 1 eq), N-methylmethanamine (23.50 mg, 288.18 μmol, 3 eq, HCl) and $T_3P$ (611.29 mg, 960.60 μmol, 571.30 μL, 50% in EtOAc, 10 eq) in pyridine (5 mL) was stirred at 30° C. for 12 h. The mixture was concentrated under reduced pressure to give a residue which was diluted with EtOAc (20 mL) and water (20 mL), extracted with EtOAc (20 mL×3), dried over $Na_2SO_4$, filtered and concentrated under reduced pressure to give a residue which was purified by preparative HPLC (column: Phenomenex Gemini 150*25 mm*10 um; mobile phase: [water (0.05% HCl)-ACN]; B %: 33%-63%, 10 min) to give 5-(5-fluoro-3-pyridyl)-7-[2-(1H-indol-3-yl)ethylamino]-N,N-dimethyl-pyrazolo[1,5-a]pyrimidine-3-carboxamide (16.67 mg, 29.67

μmol, 30.9% yield, 98.4% purity, 3HCl) as a yellow solid. $^1H$ NMR (400 MHz, DMSO-$d_6$) δ ppm 10.82 (br s, 1H), 9.12 (s, 1H), 8.69 (d, J=3.2 Hz, 1H), 8.43 (t, J=6.0 Hz, 1H), 8.31 (s, 1H), 8.21 (d, J=10.0 Hz, 1H), 7.63 (d, J=7.6 Hz, 1H), 7.29 (d, J=8.0 Hz, 1H), 7.23 (d, J=1.6 Hz, 1H), 7.07-7.02 (m, 1H), 7.00-6.97 (m, 1H), 6.78 (s, 1H), 3.87 (q, J=6.8 Hz, 2H), 3.16-3.03 (m, 8H); ES-LCMS m/z 444.2 $[M+H]^+$.

Example 56

Synthesis of I-57

I-57

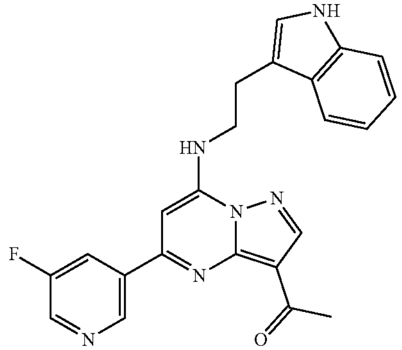 [SMILES: CC(=O)c1cnn2c(NCCc3c[nH]c4ccccc34)cc(-c3cncc(F)c3)nc12]

Synthetic Scheme:

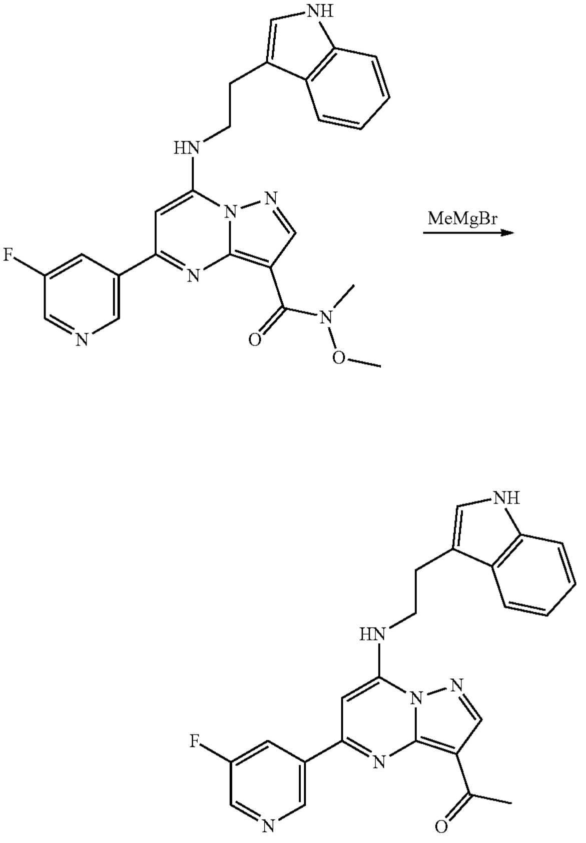

I-57

Step 1: 1-[5-(5-Fluoro-3-pyridyl)-7-[2-(1H-indol-3-yl)ethylamino]pyrazolo[1,5-a]pyrimidin-3-yl]ethanone (I-57)

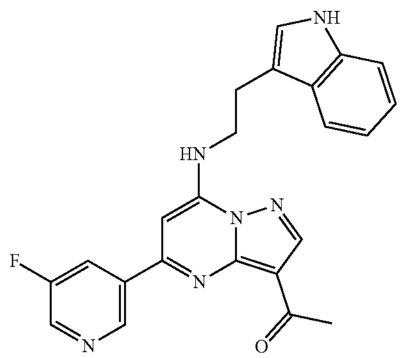

To a solution of 5-(5-fluoro-3-pyridyl)-7-[2-(1H-indol-3-yl)ethylamino]-N-methoxy-N-methyl-pyrazolo[1,5-a]pyrimidine-3-carboxamide (50 mg, 96.85 μmol, 1 eq) in THF (10 mL) was added MeMgBr (3 M in $Et_2O$, 4.68 mL, 145.10 eq) dropwise at 25° C. Then the mixture was stirred at 25° C. for 0.5 h. The mixture was quenched with sat.$NH_4Cl$ (20 mL), extracted with EtOAc (20 mL×3), dried over $Na_2SO_4$, filtered and concentrated under reduced pressure to give a residue which was purified by preparative TLC ($SiO_2$, PE/EA=1/1, $R_f$=0.56), then purified by preparative HPLC (column: Phenomenex Gemini 150*25 mm*10 um; mobile phase: [water(0.05% HCl)-ACN]; B %: 40%-70%, 10 min) to give 1-[5-(5-fluoro-3-pyridyl)-7-[2-(1H-indol-3-yl)ethylamino]pyrazolo[1,5-a]pyrimidin-3-yl]ethanone (17.52 mg, 32.98 μmol, 34.1% yield, 98.6% purity, 3HCl) as a yellow solid. $^1H$ NMR (400 MHz, DMSO-$d_6$) δ ppm 10.81 (br s, 1H), 9.16 (s, 1H), 8.72 (d, J=2.8 Hz, 1H), 8.62 (t, J=6.4 Hz, 1H), 8.53 (s, 1H), 8.23 (d, J=10.0 Hz, 1H), 7.65 (d, J=8.0 Hz, 1H), 7.28 (d, J=8.0 Hz, 1H), 7.20 (d, J=2.0 Hz, 1H), 7.06-7.03 (m, 1H), 7.02-6.99 (m, 1H), 6.87 (s, 1H), 3.89 (q, J=6.8 Hz, 2H), 3.14 (t, J=7.2 Hz, 2H), 2.72 (s, 3H); ES-LCMS m/z 415.2 $[M+H]^+$.

Example 57

Synthesis of I-58

I-58

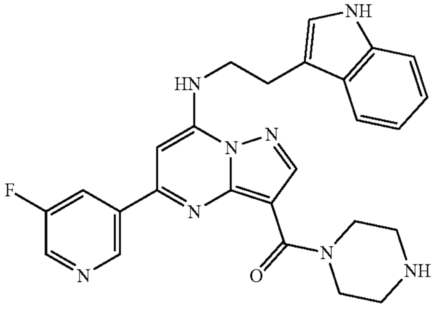

Synthetic Scheme:

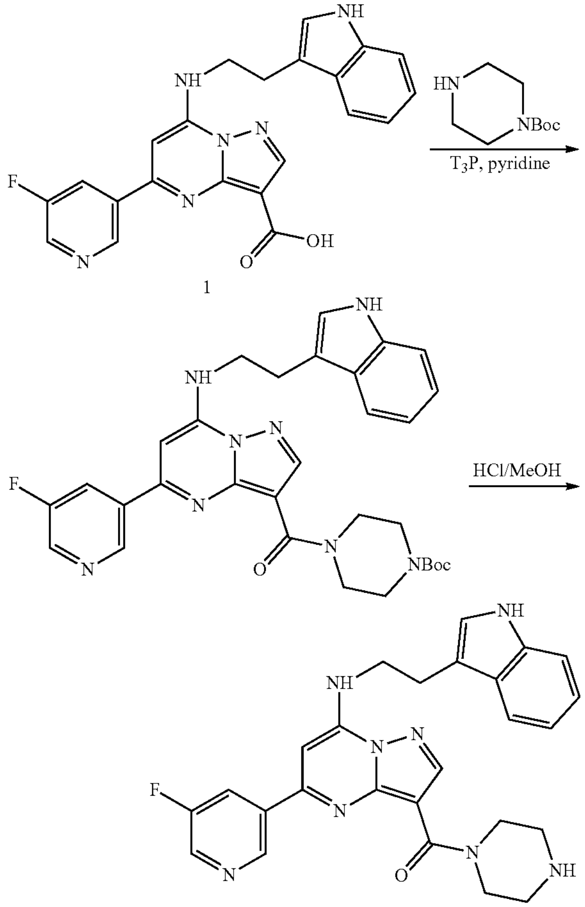

1

I-58

Step 1: tert-Butyl 4-[5-(5-fluoro-3-pyridyl)-7-[2-(1H-indol-3-yl)ethylamino]pyrazolo[1,5-a]pyrimidine-3-carbonyl]piperazine-1-carboxylate

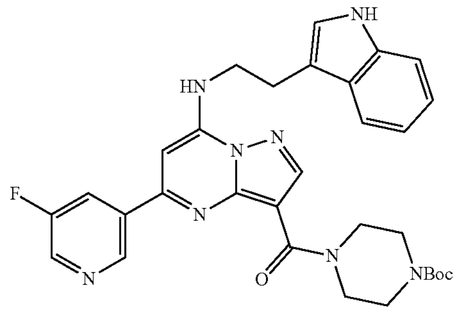 [SMILES: CC(C)(C)OC(=O)N1CCN(C(=O)c2cnn3c(NCCc4c[nH]c5ccccc45)cc(-c4cncc(F)c4)nc23)CC1]

A mixture of 5-(5-fluoro-3-pyridyl)-7-[2-(1H-indol-3-yl)ethyl amino]pyrazolo[1,5-a]pyrimidine-3-carboxylic acid (50 mg, 120.07 μmol, 1 eq), tert-butyl piperazine-1-carboxylate (26.84 mg, 144.09 μmol, 1.2 eq) and $T_3P$ (382.06 mg, 600.37 μmol, 357.06 uL, 50%, 5 eq) in pyridine (1 mL) was stirred at 25° C. for 16 h. The reaction mixture was quenched with water (5 mL) and extracted with EtOAc (10 mL×3). The organic layer was dried over $Na_2SO_4$, filtered and concentrated under reduced pressure to dryness to give tert-butyl 4-[5-(5-fluoro-3-pyridyl)-7-[2-(1H-indol-3-yl) ethylamino]pyrazolo[1,5-a]pyrimidine-3-carbonyl]piperazine-1-carboxylate (100 mg, crude) as a brown solid which was used in the next step directly without further purification.

Step 2: [5-(5-Fluoro-3-pyridyl)-7-[2-(1H-indol-3-y) ethylamino]pyrazolo[1,5-a]pyrimidin-3-yl]-piperazin-1-yl-methanone (I-58)

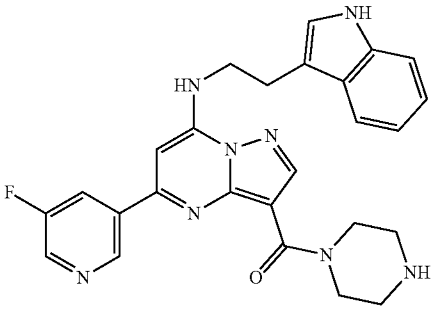 [SMILES: O=C(c1cnn2c(NCCc3c[nH]c4ccccc34)cc(-c3cncc(F)c3)nc12)N1CCNCC1]

To solution of tert-butyl 4-[5-(5-fluoro-3-pyridyl)-7-[2-(1H-indol-3-yl)ethylamino]pyrazolo[1,5-a]pyrimidine-3-carbonyl]piperazine-1-carboxylate (100 mg, 171.04 μmol, 1 eq) in MeOH (3 mL) was added HCl/MeOH (4 M, 3 mL) and then the mixture was stirred at 25° C. for 2 h. The reaction mixture was concentrated under reduced pressure to give a residue which was purified by preparative HPLC (column: Phenomenex Gemini 150*25 mm*10 um; mobile phase: [water (0.05% ammonia hydroxide v/v)-ACN]; B %: 20%-50%, 10 min). The desired fraction was lyophilized to give [5-(5-fluoro-3-pyridyl)-7-[2-(1H-indol-3-yl)ethylamino]pyrazolo[1,5-a]pyrimidin-3-yl]-piperazin-1-yl-methanone (19.42 mg, 39.99 μmol, 23.4% yield, 99.8% purity) as an off-white solid. $^1$H NMR (400 MHz, DMSO-$d_6$) δ ppm 10.80 (s, 1H), 9.12 (s, 1H), 8.69 (d, J=2.8 Hz, 1H), 8.41 (t, J=6.0 Hz, 1H), 8.32 (s, 1H), 8.23-8.16 (m, 1H), 7.63 (d, J=8.4 Hz, 1H), 7.29 (d, J=8.0 Hz, 1H), 7.22 (d, J=2.4 Hz, 1H), 7.05 (t, J=7.2 Hz, 1H), 7.00-6.95 (m, 1H), 6.77 (s, 1H), 3.87 (q, J=6.8 Hz, 2H), 3.54 (m, 4H), 3.13 (t, J=7.2 Hz, 2H), 2.77-2.73 (m, 4H); ES-LCMS m/z 485.2 $[M+H]^+$.

Example 58

Synthesis of I-59

I-59

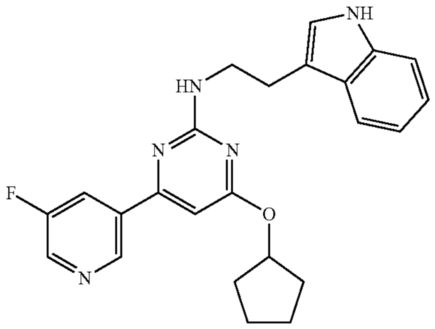

Synthetic Scheme:

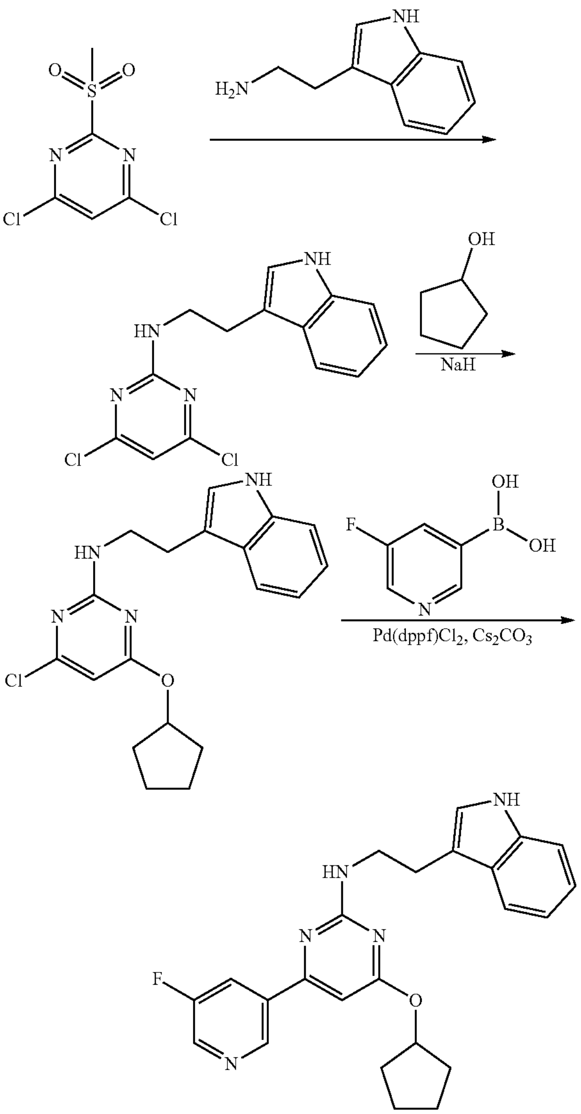

I-59

Step 1: 4,6-Dichloro-N-[2-(1H-indol-3-yl)ethyl] pyrimidin-2-amine

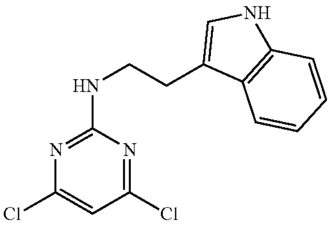 [SMILES: Clc1cc(Cl)nc(NCCc2c[nH]c3ccccc23)n1]

To a suspension of 2-(1H-indol-3-yl)ethanamine (666.18 mg, 4.16 mmol, 1.05 eq) in dry THF (10 mL) was added NaH (223.55 mg, 5.59 mmol, 60% in mineral oil, 1.41 eq) under ice bath and $N_2$ atmosphere. After being stirred for 30 min, the suspension was cooled to −60° C. and a solution of 4,6-dichloro-2-methylsulfonyl-pyrimidine (900 mg, 3.96 mmol, 1.0 eq) in dry THF (10 mL) was added dropwise and kept the temperature below −55° C. The resulting mixture was stirred for 1 h at −55° C. The reaction mixture was poured into water (100 mL) slowly and extracted with EtOAc (50 mL×3). The combined organic layers were washed with brine, dried over $Na_2SO_4$ and concentrated to give the residue which was purified by flash silica gel chromatography (from PE/EtOAc=100/1 to 2/1, TLC: PE/EtOAc=3/1, $R_f$=0.45) to yield 4,6-dichloro-N-[2-(1H-indol-3-yl)ethyl]pyrimidin-2-amine (840 mg, 2.68 mmol, 67.6% yield, 98.0% purity) as a white solid. $^1H$ NMR (400 MHz, $CDCl_3$) δ ppm 8.04 (s, 1H), 7.68 (d, J=7.9 Hz, 1H), 7.36 (d, J=7.9 Hz, 1H), 7.23 (dt, J=1.1, 7.6 Hz, 1H), 7.19-7.14 (m, 1H), 6.98 (d, J=2.2 Hz, 1H), 6.59 (s, 1H), 5.74 (s, 1H), 3.83-3.73 (m, 2H), 3.07 (t, J=6.8 Hz, 2H); ES-LCMS m/z 307.0, 309.0 $[M+H]^+$.

Step 2: 4-Chloro-6-(cyclopentoxy)-N-[2-(1H-indol-3-yl)ethyl]pyrimidin-2-amine

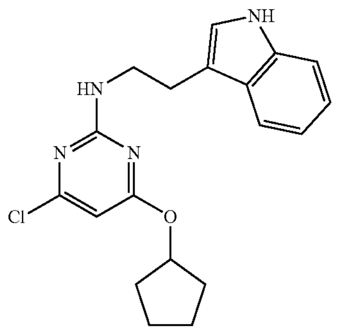 [SMILES: Clc1cc(OC2CCCC2)nc(NCCc2c[nH]c3ccccc23)n1]

To a solution of NaH (30.63 mg, 765.68 μmol, 60% in mineral oil, 1.2 eq) in THF (3 mL) was added cyclopentanol (57.71 mg, 669.97 μmol, 60.81 μL, 1.05 eq). The mixture was stirred at 0° C. for 30 min. 4,6-dichloro-N-[2-(1H-indol-3-yl)ethyl]pyrimidin-2-amine (200 mg, 638.07 μmol, 1 eq) was added into the above solution and the mixture was stirred at 15° C. for 12 h. The reaction mixture was concentrated under reduced pressure to give 4-chloro-6-(cyclopentoxy)-N-[2-(1H-indol-3-yl)ethyl]pyrimidin-2-amine (170 mg, 309.66 μmol, 48.5% yield, 65.0% purity) as a yellow solid which was used in the next step without further purification. $^1H$ NMR (400 MHz, $CDCl_3$) δ ppm 8.03 (s, 1H), 7.66 (t, J=7.5 Hz, 1H), 7.39 (d, J=8.2 Hz, 1H), 7.25-7.19 (m, 1H), 7.18-7.10 (m, 1H), 7.08-7.02 (m, 1H), 6.60 (s, 1H), 5.98 (s, 1H), 5.31 (m, 1H), 3.80-3.72 (m, 2H), 3.11-3.04 (m, 2H), 2.01-1.54 (m, 8H); ES-LCMS m/z 357.1, 358.1 $[M+H]^+$.

Step 3: 4-(Cyclopentoxy)-6-(5-fluoro-3-pyridyl)-N-[2-(1H-indol-3-yl)ethyl]pyrimidin-2-amine (I-59)

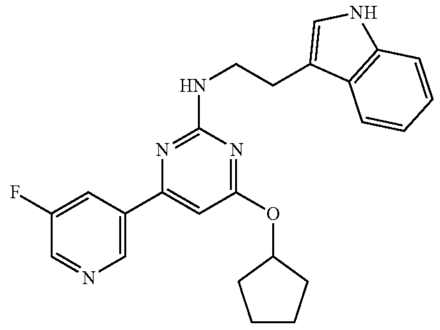 [SMILES: Fc1cncc(-c2cc(OC3CCCC3)nc(NCCc3c[nH]c4ccccc34)n2)c1]

4-Chloro-6-(cyclopentoxy)-N-[2-(1H-indol-3-yl)ethyl]pyrimidin-2-amine (170 mg, 304.89 μmol, 1 eq), (5-fluoro-3-pyridyl)boronic acid (128.88 mg, 914.67 μmol, 3 eq), $Cs_2CO_3$ (298.02 mg, 914.67 μmol, 3.0 eq) and Pd(dppf)$Cl_2$ (22.31 mg, 30.49 μmol, 0.1 eq) were taken up into a microwave tube in 1,4-dioxane (6 mL) and water (1.2 mL). The sealed tube was heated at 80° C. for 30 min under microwave. The reaction mixture was diluted with EtOAc (100 mL) and filtered through a pad of celite. The filtrate was concentrated under reduced pressure to give a residue which was purified by flash silica gel chromatography (from PE/EtOAc=100/1 to 2/1, TLC: PE/EtOAc=3/1, $R_f$=0.40), then re-purified by preparative HPLC (HCl condition, column: Phenomenex Gemini 150×25 mm×10 um; mobile phase: [water(0.05% HCl)-ACN]; B %: 48%-78%, 10 min). The desired fraction was lyophilized to yield 4-(cyclopentoxy)-6-(5-fluoro-3-pyridyl)-N-[2-(1H-indol-3-yl)ethyl]pyrimidin-2-amine (25.91 mg, 48.46 μmol, 15.9% yield, 98.5% purity, 3HCl salt) as a yellow solid. $^1H$ NMR (400 MHz, $CDCl_3$) δ ppm 9.13 (s, 1H), 8.88 (s, 1H), 8.64 (s, 1H), 8.40 (d, J=7.3 Hz, 1H), 8.15 (s, 1H), 7.63 (d, J=7.8 Hz, 1H), 7.38 (d, J=8.0 Hz, 1H), 7.25 (s, 1H), 7.20 (t, J=7.4 Hz, 1H), 7.15-7.09 (m, 1H), 6.32 (s, 1H), 5.27 (s, 1H), 3.85 (q, J=6.5 Hz, 2H), 3.17 (t, J=6.8 Hz, 2H), 1.94 (d, J=5.8 Hz, 2H), 1.84-1.74 (m, 4H), 1.70-1.62 (m, 2H); ES-LCMS m/z 418.2 $[M+H]^+$.

Example 59

Synthesis of I-60

I-60

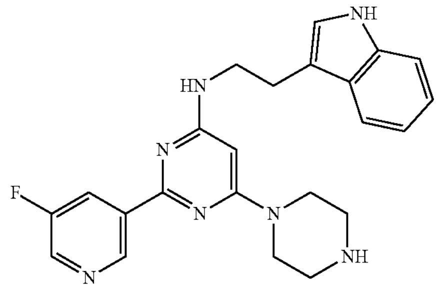 [SMILES: Fc1cncc(-c2nc(NCCc3c[nH]c4ccccc34)cc(N3CCNCC3)n2)c1]

Synthetic Scheme:

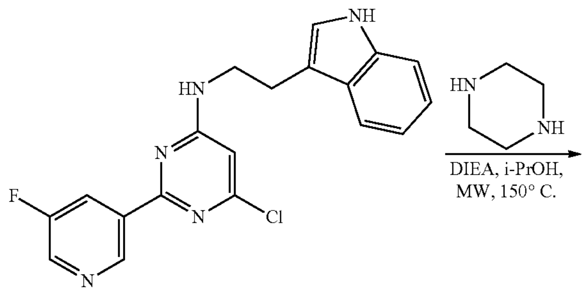

1

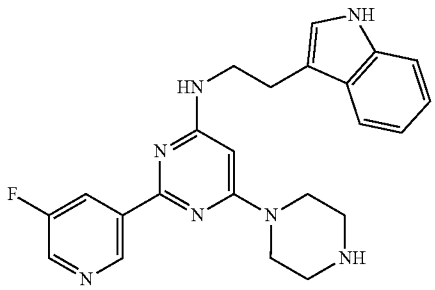

I-60

Step 1: 2-(5-Fluoro-3-pyridyl)-N-[2-(1H-indol-3-yl) ethyl]-6-piperazin-1-yl-pyrimidin-4-amine

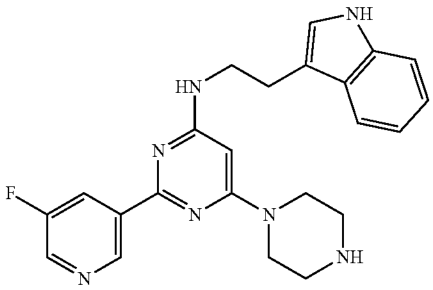

A mixture of 6-chloro-2-(5-fluoro-3-pyridyl)-N-[2-(1H-indol-3-yl)ethyl]pyrimidin-4-amine (60 mg, 161.50 μmol, 1 eq), piperazine (139.11 mg, 1.61 mmol, 10 eq) and DIEA (104.36 mg, 807.49 μmol, 140.65 μL, 5 eq) in i-PrOH (3 mL) was sealed and irradiated under microwave (4 bar) at 150° C. for 2 h. The reaction mixture was concentrated under reduced pressure to dryness to give a residue which was purified by preparative HPLC (column: Phenomenex Gemini C18 250*50 mm*10 um; mobile phase: [water (0.05% HCl)-ACN]; B %: 8%-38%, 10 min). The desired fraction was lyophilized to give 2-(5-fluoro-3-pyridyl)-N-[2-(1H-indol-3-yl)ethyl]-6-piperazin-1-yl-pyrimidin-4-amine (60.34 mg, 106.30 μmol, 65.8% yield, 99.2% purity, 4HCl) as a yellow solid. $^1$H NMR (400 MHz, $CD_3OD$) δ ppm 9.05 (s, 1H), 8.77 (d, J=2.8 Hz, 1H), 8.33 (d, J=9.2 Hz, 1H), 7.64 (d, J=8.0 Hz, 1H), 7.33 (d, J=7.6 Hz, 1H), 7.14 (s, 1H), 7.12-7.07 (m, 1H), 7.06-7.01 (m, 1H), 5.58 (br s, 1H), 3.86-3.72 (m, 6H), 3.27-3.24 (m, 4H), 3.14 (t, J=6.0 Hz, 2H); ES-LCMS m/z 418.1 $[M+H]^+$.

Example 60

Synthesis of I-61

I-61

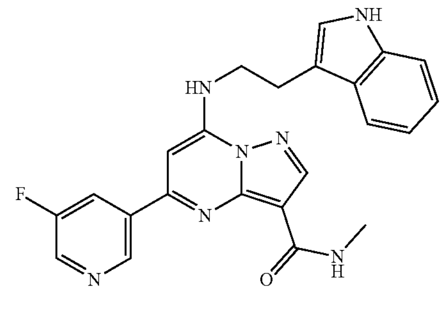

Synthetic Scheme:

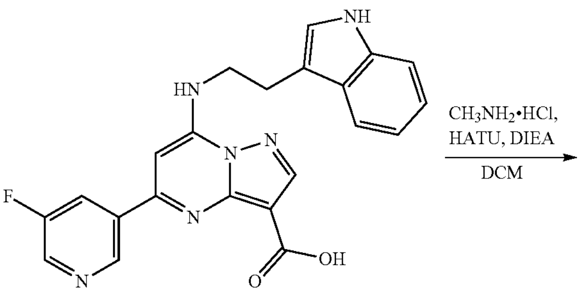

1

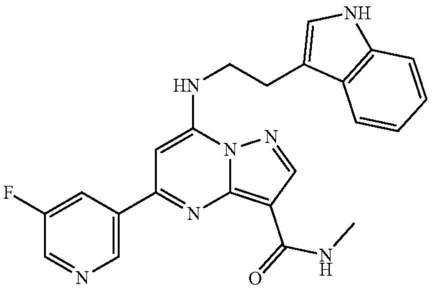 [SMILES: CNC(=O)c1cnn2c(NCCc3c[nH]c4ccccc34)cc(-c3cncc(F)c3)nc12]

I-61

Step 1: 5-(5-Fluoro-3-pyridyl)-7-[2-(1H-indol-3-yl) ethylamino]-N-methyl-pyrazolo[1,5-a]pyrimidine-3-carboxamide (I-61)

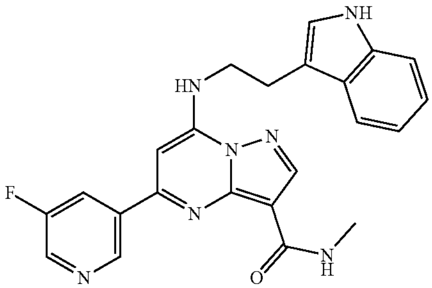

To a solution of 5-(5-fluoro-3-pyridyl)-7-[2-(1H-indol-3-yl)ethylamino]pyrazolo[1,5-a]pyrimidine-3-carboxylic acid (60 mg, 144.09 μmol, 1 eq) in anhydrous DCM (5 mL) was added DIEA (55.87 mg, 432.27 μmol, 75.29 μL, 3 eq), HATU (136.97 mg, 360.22 μmol, 2.5 eq) and methanamine hydrochloride (19.46 mg, 288.18 μmol, 2 eq). The mixture was stirred at 25° C. for 12 h. $H_2O$ (10 mL) was added, the mixture was extracted with DCM (10 mL×3). The combined organic layers were washed with brine (10 mL), dried over anhydrous $Na_2SO_4$, filtered and concentrated to afford the crude product which was purified by preparative HPLC (MeCN/$H_2O$ as eluents, acidic condition, Instrument: Phenomenex Gemini C18 250*50 mm*10 um/Mobile phase: water(0.05% HCl)-ACN/Gradient: B from 35% to 65% in 10 min/Flow rate: 25 mL/min) followed by lyophilization to yield 5-(5-fluoro-3-pyridyl)-7-[2-(1H-indol-3-yl)ethylamino]-N-methyl-pyrazolo[1,5-a]pyrimidine-3-carboxamide (19.25 mg, 35.73 μmol, 24.79% yield, 100% purity, 3HCl) as a yellow solid. $^1H$ NMR (400 MHz, $CD_3OD$) δ ppm 8.73 (d, J=12.5 Hz, 2H), 8.47 (s, 1H), 7.94 (d, J=9.0 Hz, 1H), 7.70 (dd, J=3.0, 6.0 Hz, 1H), 7.15 (dd, J=2.9, 6.1 Hz, 1H), 7.07-7.02 (m, 2H), 6.97 (s, 1H), 6.07 (s, 1H), 3.97 (t, J=6.0 Hz, 2H), 3.23 (t, J=6.1 Hz, 2H), 3.04-2.99 (m, 3H); ES-LCMS m/z 452.1 $[M+Na]^+$.

Example 61

Synthesis of I-62

I-62

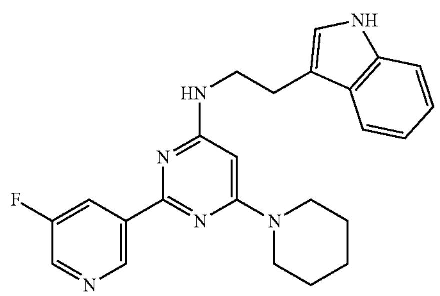

Synthetic Scheme:

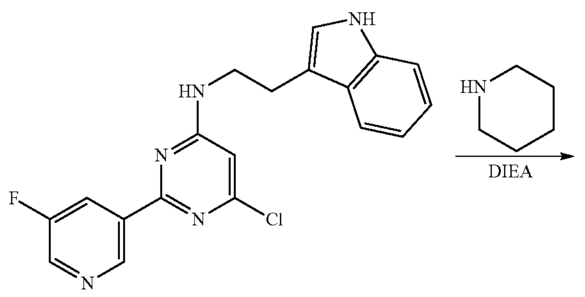

1

-continued

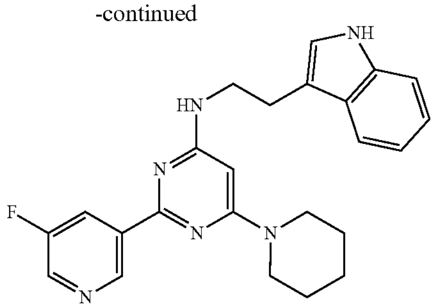

I-62

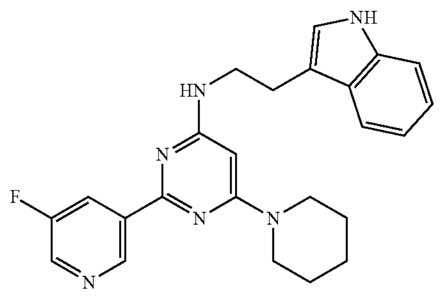 [SMILES: Fc1cncc(-c2nc(NCCc3c[nH]c4ccccc34)cc(N3CCCCC3)n2)c1]

Step 1: 2-(5-Fluoro-3-pyridyl)-N-[2-(1H-indol-3-yl)ethyl]-6-(1-piperidyl)pyrimidin-4-amine (I-62)

6-Chloro-2-(5-fluoro-3-pyridyl)-N-[2-(1H-indol-3-yl)ethyl]pyrimidin-4-amine (60.61 mg, 163.13 μmol, 1.0 eq), piperidine (862.20 mg, 10.13 mmol, 1 mL, 62.07 eq) and DIEA (63.25 mg, 489.39 μmol, 85.24 μL, 3.0 eq) were taken up into a microwave tube in i-PrOH (3 mL). The sealed tube was heated at 150° C. for 3 h under microwave. The reaction mixture was concentrated under reduced pressure to give the residue which was purified by preparative HPLC (HCl condition; column: Phenomenex Gemini C18 250×50 mm×10 um; mobile phase: [water (0.05% HCl)-ACN]; B %: 30%-60%, 10 min) and the desired fraction was lyophilized to yield 2-(5-fluoro-3-pyridyl)-N-[2-(1H-indol-3-yl)ethyl]-6-(1-piperidyl)pyrimidin-4-amine (33.57 mg, 63.84 μmol, 39.1% yield, 100.0% purity, 3HCl salt) as a yellow solid. $^1H$ NMR (400 MHz, $CDCl_3$) δ ppm 10.92 (s, 1H), 9.29 (s, 1H), 8.83 (s, 1H), 8.52 (d, J=6.8 Hz, 1H), 7.98 (s, 1H), 7.59 (d, J=7.7 Hz, 1H), 7.40-7.25 (m, 2H), 7.16-6.91 (m, 2H), 5.77 (s, 1H), 4.17 (s, 4H), 3.63 (d, J=6.6 Hz, 2H), 3.02 (t, J=6.7 Hz, 2H), 1.75-1.47 (m, 6H); ES-LCMS m/z 417.2 $[M+H]^+$.

Example 62

Synthesis of I-63

I-63

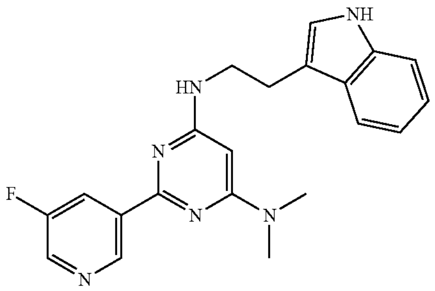

Synthetic Scheme:

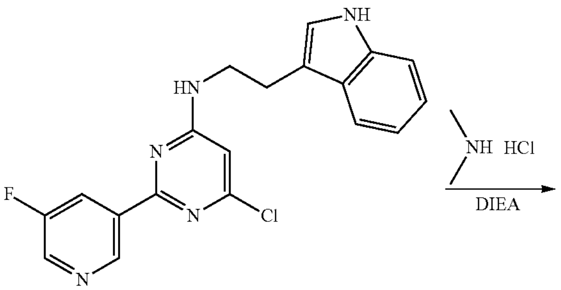

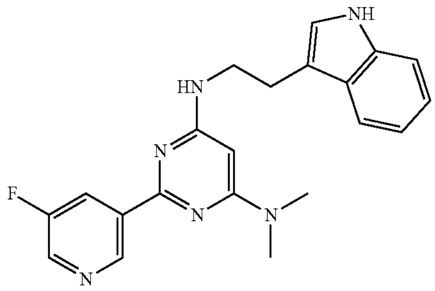

I-63

Step 1: 2-(5-Fluoro-3-pyridyl)-N6-[2-(1H-indol-3-yl)ethyl]-N4,N4-dimethyl-pyrimidine-4,6-diamine (I-63)

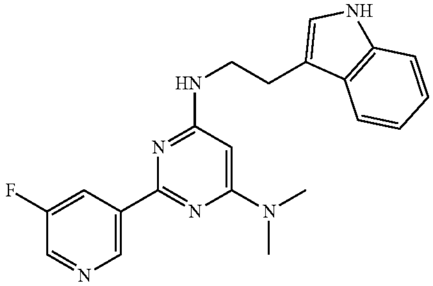 [SMILES: CN(C)c1cc(NCCc2c[nH]c3ccccc23)nc(-c2cncc(F)c2)n1]

6-Chloro-2-(5-fluoro-3-pyridyl)-N-[2-(1H-indol-3-yl)ethyl]pyrimidin-4-amine (80.81 mg, 217.51 umol, 1.0 eq), N-methylmethanamine (177.36 mg, 2.18 mmol, 10 eq, HCl salt) and DIEA (168.66 mg, 1.31 mmol, 227.31 μL, 6.0 eq) in i-PrOH (3 mL) were taken up into a microwave tube. The sealed tube was heated at 150° C. for 3 h under microwave. The reaction mixture was concentrated under reduced pressure to give a residue which was purified by preparative HPLC (HCl condition; column: Phenomenex Gemini 150×25 mm×10 um; mobile phase: [water (0.05% HCl)-ACN]; B %: 20%-50%, 10 min) and the desired fraction was lyophilized to yield 2-(5-fluoro-3-pyridyl)-N6-[2-(1H-indol-3-yl)ethyl]-N4,N4-dimethyl-pyrimidine-4,6-diamine (28.13 mg, 56.54 μmol, 26.0% yield, 97.7% purity, 3HCl salt) as a yellow solid. $^1$H NMR (400 MHz, DMSO-$d_6$) δ ppm 10.93 (s, 1H), 9.31 (s, 1H), 8.85 (d, J=2.0 Hz, 1H), 8.55 (d, J=8.8 Hz, 1H), 8.09 (s, 1H), 7.60 (d, J=7.7 Hz, 1H), 7.42-7.25 (m, 2H), 7.10-7.04 (m, 1H), 7.02-6.96 (m, 1H), 5.59 (s, 1H), 4.04 (s, 6H), 3.62 (t, J=6.7 Hz, 2H), 3.03 (t, J=6.7 Hz, 2H); ES-LCMS m/z 377.2 [M+H]$^+$.

Example 63

Synthesis of I-64

I-64

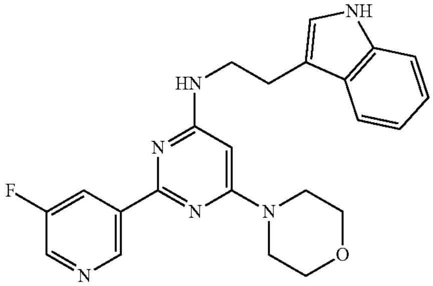 [SMILES: Fc1cncc(-c2nc(NCCc3c[nH]c4ccccc34)cc(N3CCOCC3)n2)c1]

Synthetic Scheme:

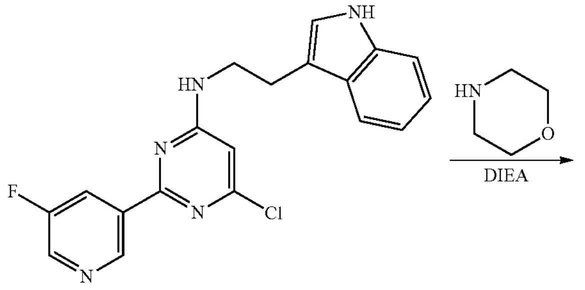

1

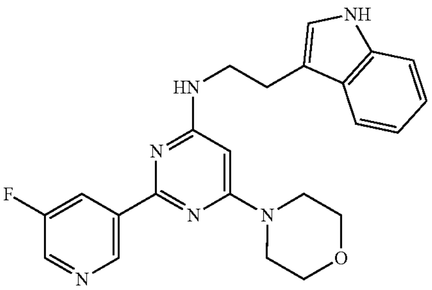

I-64

Step 1: 2-(5-Fluoro-3-pyridyl)-N-[2-(1H-indol-3-yl) ethyl]-6-morpholino-pyrimidin-4-amine (I-64)

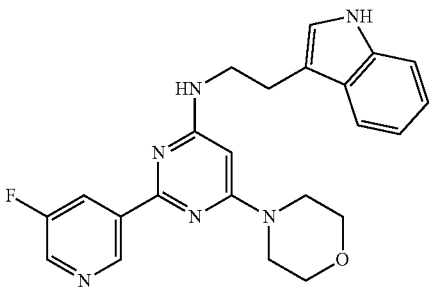

To a solution of 6-chloro-2-(5-fluoro-3-pyridyl)-N-[2-(1H-indol-3-yl)ethyl]pyrimidin-4-amine (60 mg, 161.50 μmol, 1 eq) in i-PrOH (1.5 mL) was added DIEA (208.72 mg, 1.61 mmol, 281.29 μL, 10 eq), morpholine (281.39 mg, 3.23 mmol, 284.24 μL, 20 eq). The mixture was stirred at 150° C. for 1.5 h on microwave. The reaction mixture was concentrated under reduced pressure to give a residue which was purified by preparative HPLC (column: Phenomenex Gemini 150×25 mm×10 μm; mobile phase: [water(0.05% HCl)-ACN]; B %: 25%-55%, 10 min) followed by lyophilization to yield 2-(5-fluoro-3-pyridyl)-N-[2-(1H-indol-3-yl)ethyl]-6-morpholino-pyrimidin-4-amine (53.33 mg, 101.03 μmol, 62.5% yield, 100% purity, 3HCl) as a yellow solid. $^1$H NMR (400 MHz, DMSO-$d_6$) δ ppm 10.87 (s, 1H), 9.30 (s, 1H), 8.86-8.32 (m, 2H), 7.59 (d, J=7.9 Hz, 1H), 7.35 (d, J=7.9 Hz, 1H), 7.25 (s, 1H), 7.11-7.04 (m, 1H), 7.03-6.94 (m, 1H), 5.70 (s, 1H), 3.78-3.60 (m, 11H), 3.01 (t, J=7.1 Hz, 2H); ES-LCMS m/z 419.2 [M+H]$^+$.

Example 64

Synthesis of I-65

I-65

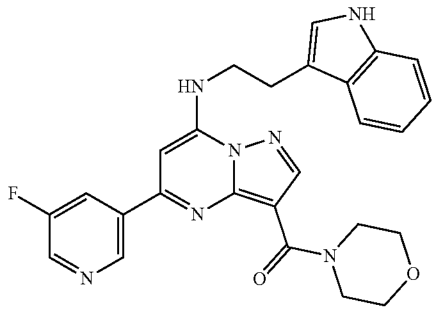

Synthetic Scheme:

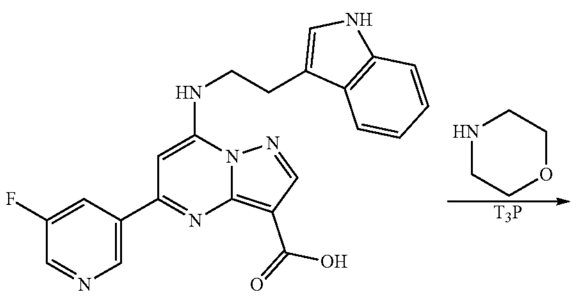

1

-continued

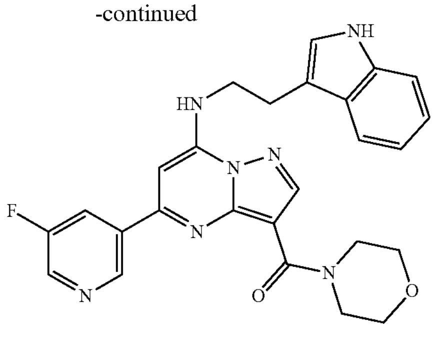

I-65

Step 1: [5-(5-Fluoro-3-pyridyl)-7-[2-(1H-indol-3-yl) ethylamino]pyrazolo[1,5-a]pyrimidin-3-yl]-morpholino-methanone (I-65)

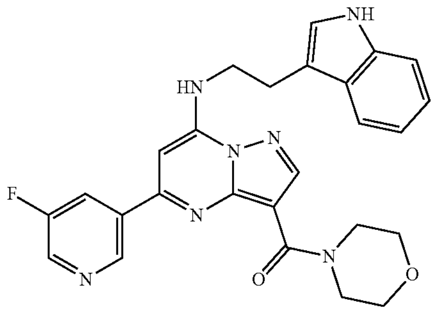 [SMILES: O=C(c1cnn2c(NCCc3c[nH]c4ccccc34)cc(-c3cncc(F)c3)nc12)N1CCOCC1]

To a solution of 5-(5-fluoro-3-pyridyl)-7-[2-(1H-indol-3-yl)ethylamino]pyrazolo[1,5-a]pyrimidine-3-carboxylic acid (40 mg, 96.06 μmol, 1 eq) in pyridine (3 mL) was added $T_3P$ (122.26 mg, 192.12 μmol, 114.26 μL, 50%, 2 eq) and morpholine (16.74 mg, 192.12 μmol, 16.91 μL, 2.0 eq). The mixture was stirred at 25° C. for 12 h. The reaction mixture was quenched by addition of water (50 mL), then extracted with EtOAc (30 mL×3). The combined organic layers were washed with brine (10 mL), dried over $Na_2SO_4$, filtered and concentrated under reduced pressure to give a residue which was purified by preparative HPLC (column: Phenomenex Gemini C18 250×50 mm×10 μm; mobile phase: [water (0.05% HCl)-ACN]; B %: 30%-60%, 10 min) followed by lyophilization to yield [5-(5-fluoro-3-pyridyl)-7-[2-(1H-indol-3-yl)ethylamino]pyrazolo[1,5-a]pyrimidin-3-yl]-morpholino-methanone (19.50 mg, 32.66 μmol, 34.0% yield, 99.6% purity, 3HCl) as a yellow solid. $^1$H NMR (400 MHz, $CD_3OD$) δ ppm 8.71-8.59 (m, 2H), 8.34 (s, 1H), 7.73 (d, J=9.3 Hz, 1H), 7.63 (d, J=7.7 Hz, 1H), 7.14 (d, J=7.7 Hz, 1H), 7.05-6.90 (m, 3H), 6.06 (s, 1H), 3.97 (t, J=6.1 Hz, 2H), 3.75 (s, 8H), 3.22 (t, J=5.8 Hz, 2H); ES-LCMS m/z 486.2 [M+H]$^+$.

Example 65

Synthesis of I-66

I-66

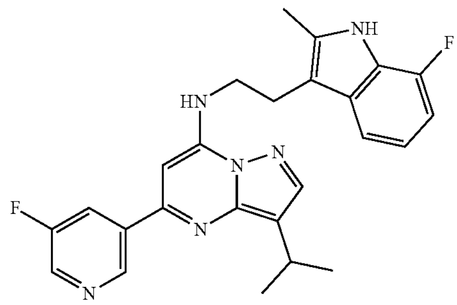

Synthetic Scheme:

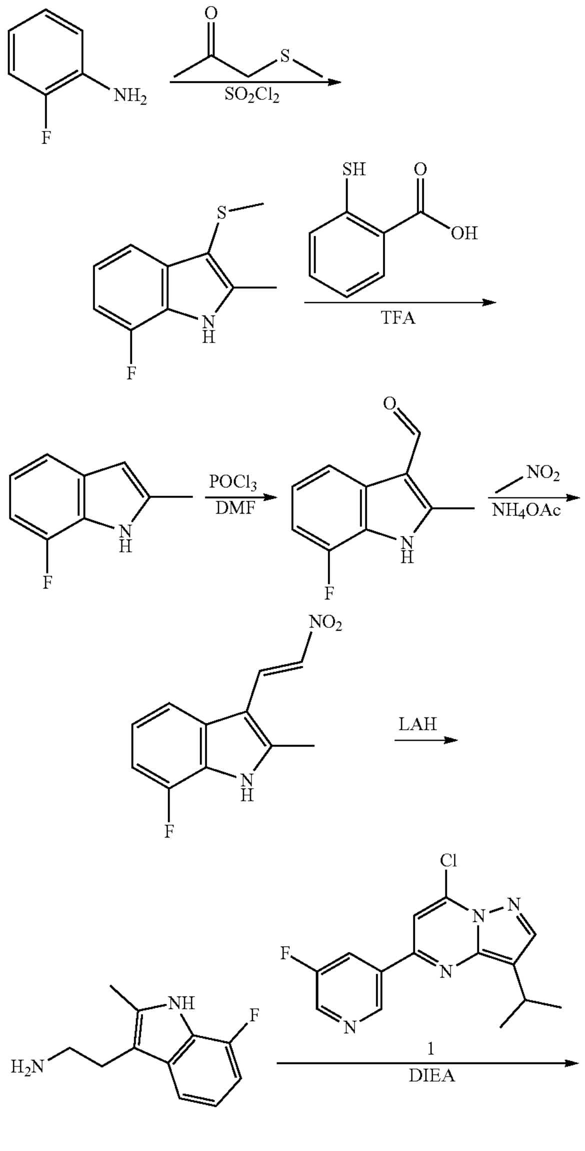

-continued

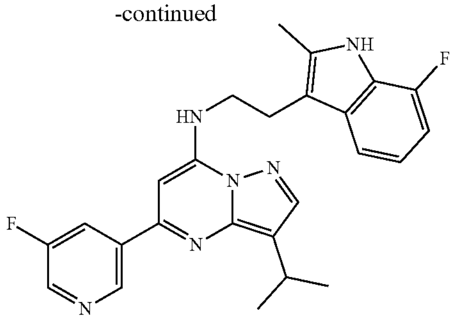

I-66

Step 1: 7-Fluoro-2-methyl-3-methylsulfanyl-1H-indole

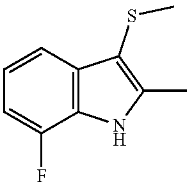

2-Fluoroaniline (0.9 g, 8.10 mmol, 782.61 μL, 1 eq) and 1-methylsulfanylpropan-2-one (371.24 mg, 3.56 mmol, 0.44 eq) were initially introduced into n-butyl acetate (4 ml) and cooled to −30° C. under $N_2$. A solution of sulfuryl chloride (437.28 mg, 3.24 mmol, 323.91 μL, 0.4 eq) in n-butyl acetate (4 ml) was added dropwise. The mixture was stirred for 2 h at −30° C. The reaction mixture was quenched by addition of water (50 mL) at 0° C., then extracted with EtOAc (30 mL×3). The combined organic layers were washed with brine (10 mL), dried over $Na_2SO_4$, filtered and concentrated under reduced pressure to give a residue which was purified by flash silica gel chromatography (from PE/EtOAc=1/0 to 10/1, TLC: PE/EtOAc=20/1, $R_f$=0.34) to yield a product 7-fluoro-2-methyl-3-methylsulfanyl-1H-indole (1 g, 4.56 mmol, 56.3% yield, 89.0% purity) as red-brown oil. $^1$H NMR (400 MHz, $CDCl_3$) δ ppm 8.31 (s, 1H), 7.45 (d, J=7.7 Hz, 1H), 7.07 (dt, J=4.7, 7.9 Hz, 1H), 6.89 (dd, J=7.8, 10.9 Hz, 1H), 2.56 (s, 3H), 2.27 (s, 3H); ES-LCMS m/z 195.9 $[M+H]^+$.

Step 2: 7-Fluoro-2-methyl-1H-indole

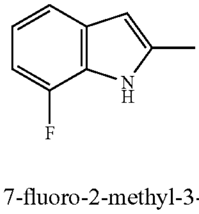

To a solution of 7-fluoro-2-methyl-3-methylsulfanyl-1H-indole (737.08 mg, 3.36 mmol, 1 eq) in TFA(8 mL) was added 2-sulfanylbenzoic acid (1.30 g, 8.40 mmol, 2.5 eq). The mixture was stirred at 25° C. for 2 h. TLC (PE/EtOAc=20/1, $R_f$=0.40) showed the starting material was consumed completely and a new spot formed. The reaction mixture was quenched by addition of water (100 mL), then adjusted to Ph to 10 by 1N aq. NaOH, extracted with EtOAc (50 mL×3). The combined organic layers were washed with brine (30 mL), dried over $Na_2SO_4$, filtered and concentrated under reduced pressure to give a residue which was purified by flash silica gel chromatography (from PE/EtOAc=1/0 to 10/1, TLC: PE/EtOAc=20/1, $R_f$=0.40) to yield 7-fluoro-2-methyl-1H-indole (400 mg, 2.09 mmol, 62.3% yield, 78.0% purity) as yellow oil. $^1$H NMR (400 MHz, DMSO-$d_6$) δ ppm 11.33 (s, 1H), 7.20 (d, J=7.5 Hz, 1H), 6.92-6.74 (m, 2H), 6.19 (s, 1H), 2.38 (s, 3H); ES-LCMS m/z No correct mass was found.

Step 3: 7-Fluoro-2-methyl-1H-indole-3-carbaldehyde

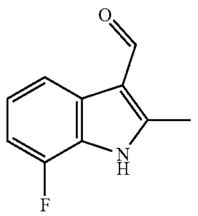

To a solution of DMF (10 mL) was added $POCl_3$ (481.07 mg, 3.14 mmol, 291.56 μL, 2.0 eq) dropwise at −20° C. over a period of 10 min under $N_2$. After 1 h, 7-fluoro-2-methyl-1H-indole (300 mg, 1.57 mmol, 1 eq) in DMF (2 mL) was added to the above solution during which the temperature was maintained below −20° C. The reaction mixture was stirred at 15° C. for 1 h. The reaction mixture was quenched by addition of aq. $NaHCO_3$ (50 mL), then extracted with EtOAc (30 mL×3). The combined organic layers were washed with brine (10 mL), dried over $Na_2SO_4$, filtered and concentrated under reduced pressure to give a residue which was purified by flash silica gel chromatography (from PE/EtOAc=1/0 to 3/1, TLC: PE/EtOAc=3/1, $R_f$=0.40) to yield 7-fluoro-2-methyl-1H-indole-3-carbaldehyde (200 mg, 936.93 μmol, 59.7% yield, 83.0% purity) as a yellow solid. $^1$H NMR (400 MHz, DMSO-$d_6$) δ ppm 12.44 (s, 1H), 10.08 (s, 1H), 7.85 (d, J=7.7 Hz, 1H), 7.13 (dt, J=5.1, 7.8 Hz, 1H), 7.02 (dd, J=7.9, 11.2 Hz, 1H), 2.70 (s, 3H); ES-LCMS m/z 177.9 [M+H]$^+$.

Step 4: 7-Fluoro-2-methyl-3-[(E)-2-nitrovinyl]-1H-indole

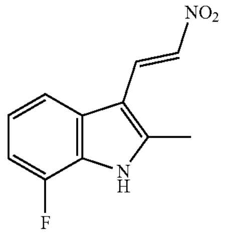 [SMILES: Cc1[nH]c2c(F)cccc2c1/C=C/[N+](=O)[O-]]

To a solution of 7-fluoro-2-methyl-1H-indole-3-carbaldehyde (200 mg, 936.93 μmol, 1 eq) in nitromethane (8 mL) was added $NH_4OAc$ (216.66 mg, 2.81 mmol, 3 eq). The mixture was stirred at 110° C. for 12 h. The reaction mixture was concentrated under reduced pressure to give a residue. The residue was dissolved in EtOAc (50 mL), washed with water (10 mL), brine (10 mL), dried over $Na_2SO_4$, filtered and concentrated under reduced pressure to give a crude which was purified by flash silica gel chromatography (from PE/EtOAc=1/0 to 3/1, TLC: PE/EtOAc=3/1, $R_f$=0.61) to yield 7-fluoro-2-methyl-3-[(E)-2-nitrovinyl]-1H-indole (150 mg, 619.89 μmol, 66.2% yield, 91.0% purity) as a yellow solid. $^1$H NMR (400 MHz, $CDCl_3$) δ ppm 8.82 (br s, 1H), 8.32 (d, J=13.5 Hz, 1H), 7.76 (d, J=13.5 Hz, 1H), 7.46 (d, J=7.9 Hz, 1H), 7.25-7.16 (m, 1H), 7.01 (dd, J=8.2, 10.6 Hz, 1H), 2.67 (s, 3H); ES-LCMS m/z 220.9 [M+H]$^+$.

Step 5: 2-(7-Fluoro-2-methyl-1H-indol-3-yl)ethanamine

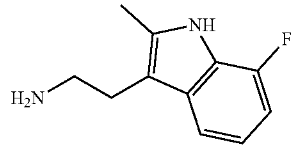

To a solution of 7-fluoro-2-methyl-3-[(E)-2-nitrovinyl]-1H-indole (150 mg, 619.89 μmol, 1 eq) in THF (10 mL) was added dropwise LAH (1 M in THF, 3.10 mL, 5 eq) at 0° C. After addition, the mixture was stirred at 80° C. for 2 h. The reaction mixture was diluted with THF (50 mL), quenched by addition of water (0.05 mL), aq. NaOH (0.05 mL, 10% in water) and water (0.15 mL) in sequence at 0° C. After being stirred for 30 min, the mixture was filtered through celite, the filtrate was concentrated under reduced pressure to give a crude 2-(7-fluoro-2-methyl-1H-indol-3-yl)ethanamine (100 mg, 436.97 μmol, 70.5% yield, 84.0% purity) as yellow oil which was used in the next step directly without further purification. $^1$H NMR (400 MHz, $CD_3OD$) δ ppm 7.23 (d, J=7.8 Hz, 1H), 6.93-6.82 (m, 1H), 6.72 (dd, J=7.9, 11.4 Hz, 1H), 2.90-2.80 (m, 4H), 2.39 (s, 3H); ES-LCMS m/z 193.2 [M+H]$^+$.

Step 6: N-[2-(7-Fluoro-2-methyl-1H-indol-3-yl)ethyl]-5-(5-fluoro-3-pyridyl)-3-isopropyl-pyrazolo (I-66)

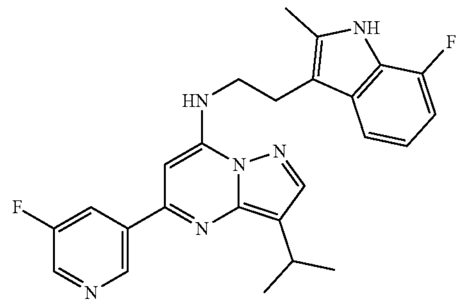 [SMILES: Cc1[nH]c2c(F)cccc2c1CCNc1cc(-c2cncc(F)c2)nc2c(C(C)C)cnn12]

To a solution of 7-chloro-5-(5-fluoro-3-pyridyl)-3-isopropyl-pyrazolo[1,5-a]pyrimidine (40.82 mg, 137.59 μmol, 1 eq) in i-PrOH (3 mL) was added DIEA (53.35 mg, 412.76 μmol, 71.89 μL, 3.0 eq) and 2-(7-fluoro-2-methyl-1H-indol-3-yl)ethanamine (37.78 mg, 165.11 μmol, 1.2 eq). The mixture was stirred at 60° C. for 12 h. The reaction mixture was concentrated under reduced pressure to give a residue which was purified by preparative HPLC (column: Gemini 150×25×5 μm; mobile phase: [water (0.05% ammonia hydroxide v/v)-ACN]; B %: 70%-100%, 10 min) followed by lyophilization to yield N-[2-(7-fluoro-2-methyl-1H-indol-3-yl)ethyl]-5-(5-fluoro-3-pyridyl)-3-isopropyl-pyrazolo[1,5-a]pyrimidin-7-amine (20.36 mg, 45.36 μmol, 33.0% yield, 99.5% purity) as a yellow solid. $^1H$ NMR (400 MHz, $CD_3OD$) δ ppm 8.58 (s, 1H), 8.45 (d, J=2.6 Hz, 1H), 7.89 (s, 1H), 7.64-7.57 (m, 1H), 7.37 (d, J=7.9 Hz, 1H), 6.96 (dt, J=4.6, 7.8 Hz, 1H), 6.69 (dd, J=7.8, 11.6 Hz, 1H), 5.76 (s, 1H), 3.83 (t, J=6.2 Hz, 2H), 3.29-3.22 (m, 1H), 3.13 (t, J=6.1 Hz, 2H), 2.11 (s, 3H), 1.38 (d, J=7.1 Hz, 6H); ES-LCMS m/z 447.2 $[M+H]^+$.

Example 66

Synthesis of I-67

I-67

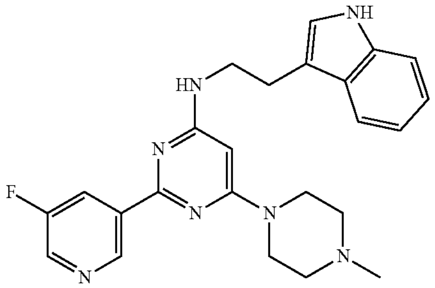

Synthetic Scheme:

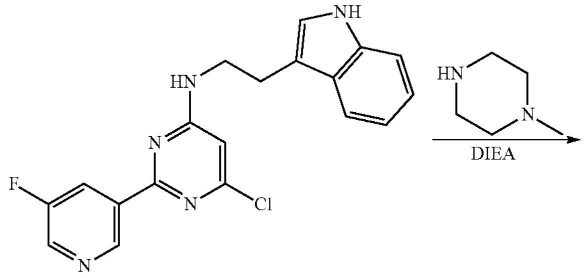

1

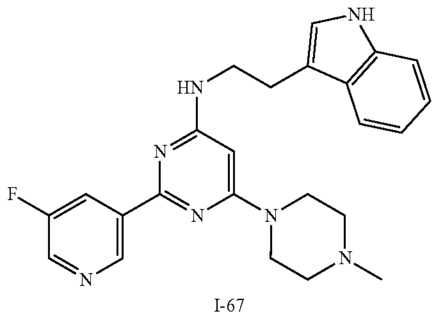

I-67

Step 1: 2-(5-Fluoro-3-pyridyl)-N-[2-(1H-indol-3-yl)ethyl]-6-(4-methylpiperazin-1-yl)pyrimidin-4-amine (I-67)

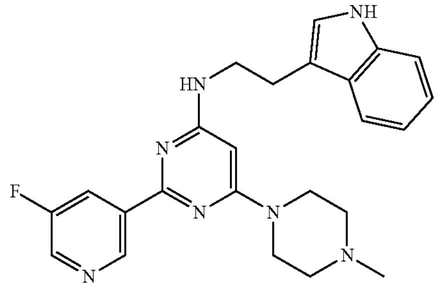 [SMILES: CN1CCN(c2cc(NCCc3c[nH]c4ccccc34)nc(-c3cncc(F)c3)n2)CC1]

To a solution of 6-chloro-2-(5-fluoro-3-pyridyl)-N-[2-(1H-indol-3-yl)ethyl]pyrimidin-4-amine (60 mg, 161.50 μmol, 1 eq) and 1-methylpiperazine (24.26 mg, 242.25 μmol, 26.87 uL, 1.5 eq) in i-PrOH (5 mL) was added DIEA (62.62 mg, 484.49 μmol, 84.39 μL, 3.0 eq). The mixture was stirred at 110° C. for 16 h. LC-MS showed 83% of starting material was remained and 17% of desired compound was detected. The mixture was taken up into a microwave tube. 1-methylpiperazine (500 mg, 5 mmol) was added. The mixture was purged with $N_2$ for 1 min. The sealed tube was heated at 150° C. for 3 h under microwave. The reaction mixture was concentrated under reduced pressure to give a residue which was purified by preparative HPLC (column: Phenomenex Gemini 150*25 mm*10 um; mobile phase: [water (0.05% ammonia hydroxide v/v)-ACN]; B %: 42%-72%, 10 min), followed by lyophilization to yield 2-(5-fluoro-3-pyridyl)-N-[2-(1H-indol-3-yl)ethyl]-6-(4-methylpiperazin-1-yl)pyrimidin-4-amine (49.11 mg, 113.81 μmol, 70.5% yield, 100.0% purity) as a white solid. $^1H$ NMR (400 MHz, DMSO-$d_6$) δ ppm 10.82 (br s, 1H), 9.30 (s, 1H), 8.64 (d, J=2.9 Hz, 1H), 8.32 (d, J=10.1 Hz, 1H), 7.59 (d, J=7.7 Hz, 1H), 7.34 (d, J=7.9 Hz, 1H), 7.20 (d, J=2.0 Hz, 1H), 7.07 (t, J=7.2 Hz, 1H), 6.98 (t, J=7.4 Hz, 2H), 5.59 (br s, 1H), 3.60 (br s, 2H), 3.51 (br s, 4H), 2.97 (t, J=7.3 Hz, 2H), 2.37 (d, J=4.2 Hz, 4H), 2.20 (s, 3H); ES-LCMS m/z 432.2 $[M+H]^+$.

Example 67

Synthesis of I-68

I-68

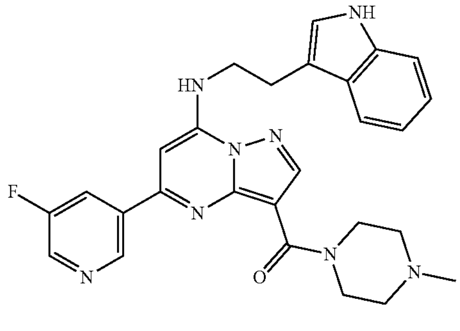 [SMILES: CN1CCN(C(=O)c2cnn3c(NCCc4c[nH]c5ccccc45)cc(-c4cncc(F)c4)nc23)CC1]

Synthetic Scheme:

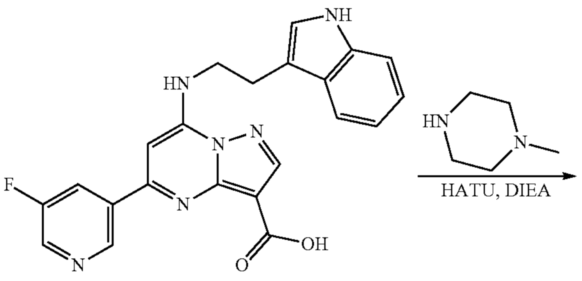

1

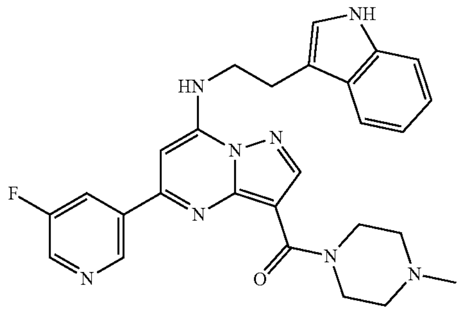

I-68

Step 1: [5-(5-Fluoro-3-pyridyl)-7-[2-(1H-indol-3-yl)ethylamino]pyrazolo[1,5-a]pyrimidin-3-yl]-(4-methylpiperazin-1-yl)methanone (I-68)

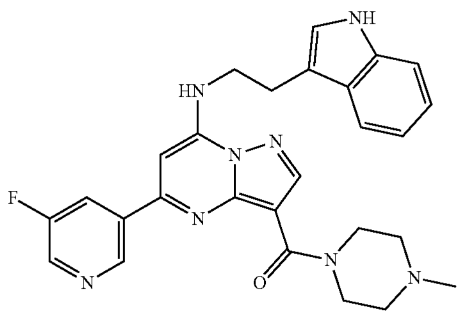

To a solution of 5-(5-fluoro-3-pyridyl)-7-[2-(1H-indol-3-yl)ethylamino]pyrazolo[1,5-a]pyrimidine-3-carboxylic acid (50 mg, 120.07 μmol, 1 eq) and 1-methylpiperazine (18.04 mg, 180.11 μmol, 19.98 μL, 1.5 eq) in DCM (5 mL) was added HATU (54.79 mg, 144.08 μmol, 1.2 eq) and DIEA (46.55 mg, 360.21 μmol, 62.74 μL, 3.0 eq). The mixture was stirred at 25° C. for 16 h. LC-MS showed 42% of starting material was remained and 51% of desired compound was detected. 1-methylpiperazine (18.04 mg, 180.11 μmol, 19.98 μL, 1.5 eq), HATU (54.79 mg, 144.08 μmol, 1.2 eq), DIEA (46.55 mg, 360.21 μmol, 62.74 μL, 3.0 eq) and DMF (2 mL) was added. The mixture was stirred at 25° C. for 5 h. The reaction mixture was diluted with $H_2O$ (20 mL), extracted with DCM (20 mL×3). The combined organic layers were dried over anhydrous $Na_2SO_4$, filtered and concentrated under reduced pressure to give a residue which purified by preparative HPLC (column: Phenomenex Gemini 150*25 mm*10 um; mobile phase: [water (0.05% ammonia hydroxide v/v)-ACN]; B %: 36%-66%, 10 min), followed by lyophilization to yield [5-(5-fluoro-3-pyridyl)-7-[2-(1H-indol-3-yl)ethylamino]pyrazolo[1,5-a]pyrimidin-3-yl]-(4-methylpiperazin-1-yl)methanone (15.94 mg, 31.97 μmol, 26.6% yield, 100.0% purity) as a light yellow solid. $^1H$ NMR (400 MHz, $CD_3OD$) δ ppm 8.63 (s, 1H), 8.48 (d, J=2.9 Hz, 1H), 8.26 (s, 1H), 7.71-7.62 (m, 2H), 7.19-7.13 (m, 1H), 7.07-6.95 (m, 3H), 6.05 (s, 1H), 3.90 (t, J=6.2 Hz, 2H), 3.75 (br s, 4H), 3.19 (t, J=6.1 Hz, 2H), 2.54 (br s, 4H), 2.33 (s, 3H); ES-LCMS m/z 499.2 $[M+H]^+$.

Example 68

Synthesis of I-69

I-69

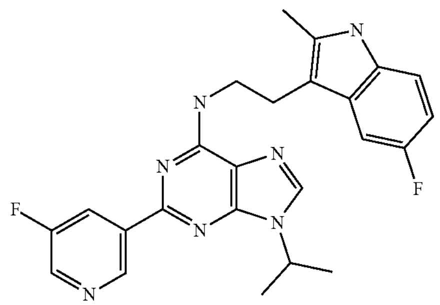

Synthetic Scheme:

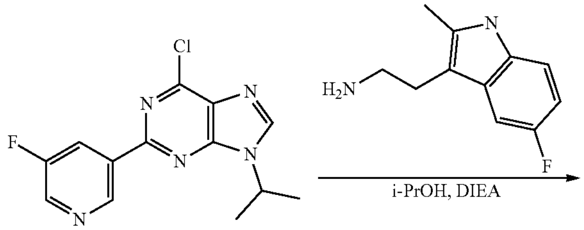

1

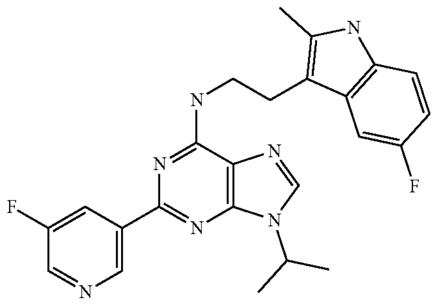 [SMILES: Cc1[nH]c2ccc(F)cc2c1CCNc1nc(-c2cncc(F)c2)nc2c1ncn2C(C)C]

I-69

Step 1: N-[2-(5-Fluoro-2-methyl-1H-indol-3-yl)ethyl]-2-(5-fluoro-3-pyridyl)-9-isopropyl-purin-6-amine (I-69)

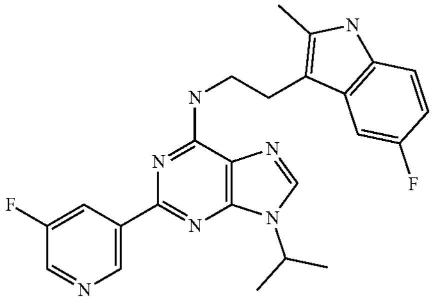

To a solution of 6-chloro-2-(5-fluoro-3-pyridyl)-9-isopropyl-purine (50 mg, 164.55 μmol, eq) in i-PrOH (3 mL) was added DIEA (106.33 mg, 822.73 μmol, 143.31 μL, 5 eq) and 2-(5-fluoro-2-methyl-1H-indol-3-yl)ethanamine (37.96 mg, 197.46 μmol, 1.2 eq). The mixture was stirred at 60° C. for 16 h. The reaction mixture was concentrated under reduced pressure to give a residue which was purified by preparative HPLC (column: Phenomenex Synergi C18 150*25 mm*10 um; mobile phase: [water (0.05% HCl)-ACN]; B %: 45%-75%, 10 min) followed by lyophilization to yield N-[2-(5-fluoro-2-methyl-1H-indol-3-yl)ethyl]-2-(5-fluoro-3-pyridyl)-9-isopropyl-purin-6-amine (32.52 mg, 58.40 μmol, 35.5% yield, 100.0% purity, 3HCl) as a yellow solid. $^1$H NMR (400 MHz, $CD_3OD$) δ ppm 9.35 (s, 1H), 8.93 (s, 1H), 8.77 (s, 1H), 8.62 (d, J=9.3 Hz, 1H), 7.15-6.94 (m, 2H), 6.63 (t, J=8.0 Hz, 1H), 5.10-4.99 (m, 1H), 4.04 (m, 2H), 3.09 (t, J=6.6 Hz, 2H), 2.30 (s, 3H), 1.71 (d, J=6.8 Hz, 6H); ES-LCMS m/z 448.0 $[M+H]^+$.

Example 69

Synthesis of I-70

I-70

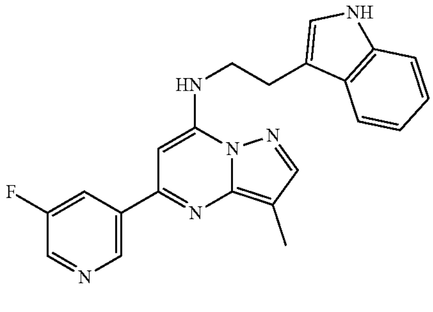

Synthetic Scheme:

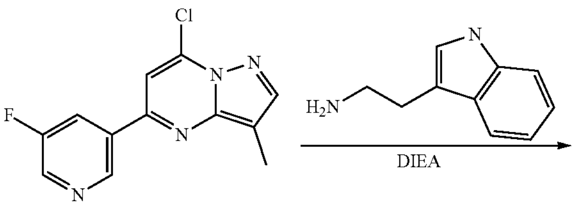

1

-continued

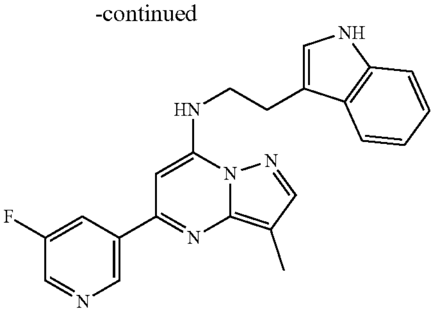

I-70

Step 1: 5-(5-Fluoro-3-pyridyl)-N-[2-(1H-indol-3-yl)ethyl]-3-methyl-pyrazolo[1,5-a]pyrimidin-7-amine (I-70)

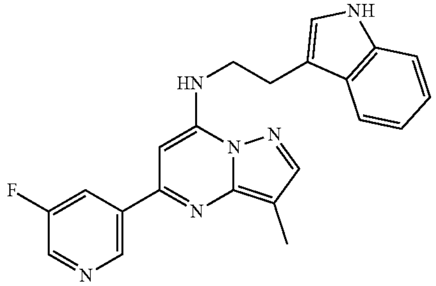 [SMILES: Cc1cnn2c(NCCc3c[nH]c4ccccc34)cc(-c3cncc(F)c3)nc12]

To a solution of 2-(1H-indol-3-yl)ethanamine (29.28 mg, 182.74 μmol, 1.2 eq) in i-PrOH (3 mL) was added DIEA (59.04 mg, 456.85 μmol, 79.57 μL, 3 eq) and 7-chloro-5-(5-fluoro-3-pyridyl)-3-methyl-pyrazolo[1,5-a]pyrimidine (40 mg, 152.28 μmol, 1 eq). The mixture was stirred at 50° C. for 16 h under $N_2$ atmosphere. The reaction mixture was concentrated under reduced pressure to remove i-PrOH to give a residue which was purified by preparative HPLC (column: Phenomenex Synergi C18 150*25 mm*10 um; mobile phase: [water(0.05% HCl)-ACN]; B %: 35%-65%, 10 min) followed by lyophilization to yield 5-(5-fluoro-3-pyridyl)-N-[2-(1H-indol-3-yl)ethyl]-3-methyl-pyrazolo[1,5-a]pyrimidin-7-amine (32.43 mg, 65.15 μmol, 42.8% yield, 99.6% purity, 3HCl) as a yellow solid. $^1$H NMR (400 MHz, $CD_3OD$) δ ppm 8.72 (d, J=2.6 Hz, 1H), 8.35 (s, 1H), 8.10 (s, 1H), 7.56-7.52 (m, 1H), 7.50-7.45 (m, 1H), 7.16-7.10 (m, 1H), 6.98 (s, 1H), 6.97-6.92 (m, 1H), 6.85 (m, 1H), 5.76 (s, 1H), 4.06-3.99 (m, 2H), 3.24-3.19 (m, 2H), 2.30 (s, 3H); ES-LCMS m/z 387.0 $[M+H]^+$.

Example 70

Synthesis of I-71

I-71

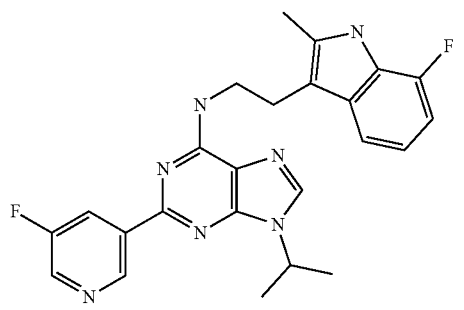

Synthetic Scheme:

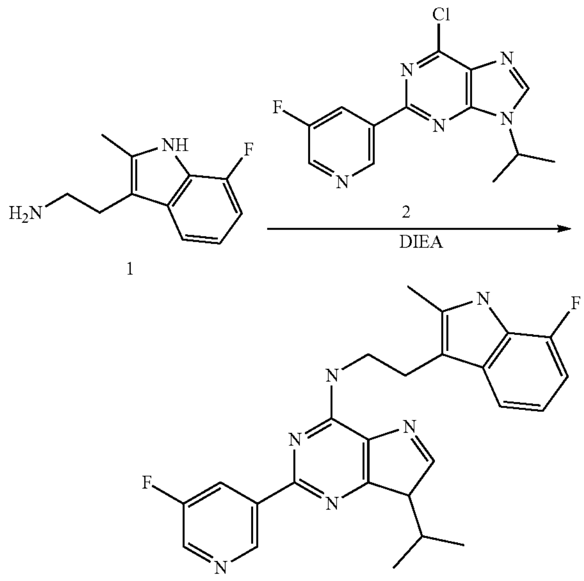

I-71

Step 1: N-[2-(7-Fluoro-2-methyl-H-indol-3-yl) ethyl]-2-(5-fluoro-3-pyridyl)-9-isopropyl-purin-6-amine (I-71)

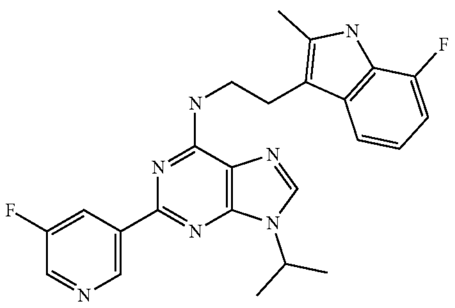 [SMILES: Cc1[nH]c2c(F)cccc2c1CCNc1nc(-c2cncc(F)c2)nc2c1ncn2C(C)C]

To a solution of 6-chloro-2-(5-fluoro-3-pyridyl)-9-isopropyl-purine (41.67 mg, 137.12 μmol, 1 eq) in i-PrOH (3 mL) was added DIEA (53.16 mg, 411.37 μmol, 71.65 μL, 3.0 eq), 2-(7-fluoro-2-methyl-1H-indol-3-yl)ethanamine (37.66 mg, 164.55 μmol, 1.2 eq). The mixture was stirred at 60° C. for 12 h. The reaction mixture was concentrated under reduced pressure to give a residue which was purified by preparative HPLC (column: Phenomenex Gemini 150×25 mm×10 μm; mobile phase: [water(0.05% HCl)-ACN]; B %: 46%-76%, 10 min) followed by lyophilization to yield N-[2-(7-fluoro-2-methyl-1H-indol-3-yl)ethyl]-2-(5-fluoro-3-pyridyl)-9-isopropyl-purin-6-amine (27.83 mg, 49.98 μmol, 36.4% yield, 100.0% purity, 3HCl) as a yellow solid. $^1$H NMR (400 MHz, $CD_3OD$) δ ppm 9.30 (s, 1H), 8.80 (s, 1H), 8.74 (dd, J=1.1, 2.9 Hz, 1H), 8.61-8.56 (m, 1H), 7.28 (d, J=7.9 Hz, 1H), 6.84 (dt, J=4.7, 7.9 Hz, 1H), 6.63 (dd, J=7.9, 11.7 Hz, 1H), 5.03 (td, J=6.9, 13.6 Hz, 1H), 4.04 (m, 2H), 3.12 (t, J=6.6 Hz, 2H), 2.30 (s, 3H), 1.70 (d, J=6.8 Hz, 6H); ES-LCMS m/z 447.9 $[M+H]^+$.

Example 71

Synthesis of I-72

I-72

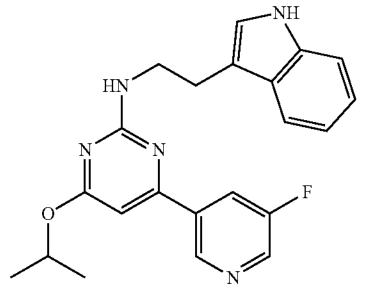

Synthetic Scheme:

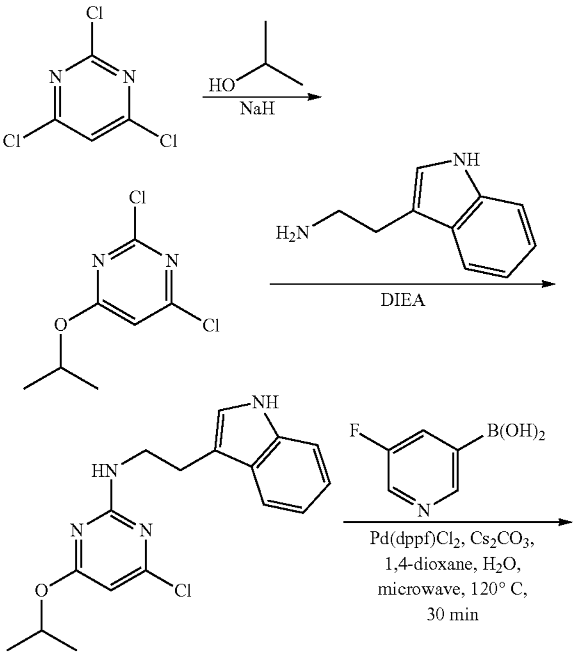

-continued

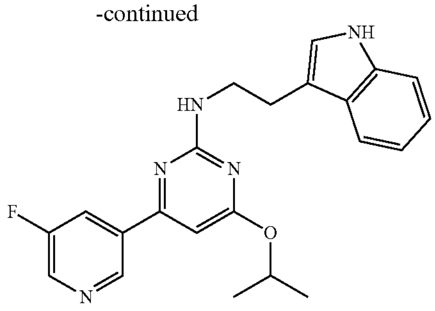

I-72

Step 1: 2,4-Dichloro-6-isopropoxy-pyrimidine

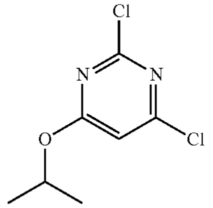

To a solution of i-PrOH (344.04 mg, 5.72 mmol, 438.27 μL, 1.05 eq) in THF (8 mL) was added NaH (261.69 mg, 6.54 mmol, 60% in mineral oil, 1.2 eq). The mixture was stirred at 0° C. for 30 min. 2,4,6-Trichloropyrimidine (1 g, 5.45 mmol, 625.00 μL, 1.0 eq) was added into the above solution and the mixture was stirred at 15° C. for 12 h. The reaction mixture was concentrated under reduced pressure to remove THF. The residue was diluted with water (150 mL), extracted with EtOAc (50 mL×3). The combined organic layers were dried over $Na_2SO_4$, filtered and the filtrate was concentrated under reduced pressure to give a residue which was purified by flash silica gel chromatography (from PE/EtOAc=100/1 to 50/1, TLC: PE/EtOAc=100/1, $R_f$=0.20) to yield mixture 4,6-dichloro-2-isopropoxy-pyrimidine (347 mg, crude) and 2,4-dichloro-6-isopropoxy-pyrimidine (173 mg, crude) as colorless oil. $^1$H NMR (400 MHz, $CDCl_3$) δ ppm 7.00 (s, 1H), 5.35-5.23 (m, 1H), 1.40 (d, J=6.2 Hz, 6H); ES-LCMS m/z 207.1, 209.1 $[M+H]^+$.

Step 2: 4-Chloro-N-[2-(1H-indol-3-yl)ethyl]-6-isopropoxy-pyrimidin-2-amine

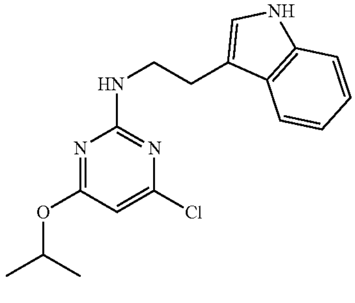 [SMILES: CC(C)Oc1cc(Cl)nc(NCCc2c[nH]c3ccccc23)n1]

To a solution of (2-(1H-indol-3-yl)ethanamine (680.92 mg, 4.25 mmol, 2.2 eq) and 2,4-dichloro-6-isopropoxypyrimidine (100 mg, 482.96 μmol, 0.25 eq) in i-PrOH (5 mL) was added DIEA (749.01 mg, 5.80 mmol, 1.01 mL, 3.0 eq) and 4,6-dichloro-2-isopropoxy-pyrimidine (200 mg, 965.92 μmol, 0.5 eq). The mixture was stirred at 26° C. for 12 h. The reaction mixture was concentrated under reduced pressure to give the residue which was purified by flash silica gel chromatography (from PE/EtOAc=100/1 to 3/1, TLC: PE/EtOAc=3/1, $R_{f1}$=0.55, $R_{f2}$=0.45) to yield 4-chloro-N-[2-(1H-indol-3-yl)ethyl]-6-isopropoxy-pyrimidin-2-amine (90 mg, 220.37 μmol, 11.4% yield, 81.0% purity) as a yellow solid. $^1$H NMR (400 MHz, $CDCl_3$) δ ppm 8.05 (s, 1H), 7.68-7.61 (m, 1H), 7.39 (d, J=8.2 Hz, 1H), 7.25-7.19 (m, 1H), 7.16-7.10 (m, 1H), 7.05 (s, 1H), 5.97 (s, 1H), 3.78-3.69 (m, 2H), 3.10-3.03 (m, 2H), 1.33 (d, J=5.3 Hz, 6H); ES-LCMS m/z 331.1, 332.1 $[M+H]^+$.

Step 3: 4-(5-Fluoro-3-pyridyl)-N-[2-(1H-indol-3-yl)ethyl]-6-isopropoxy-pyrimidin-2-amine (I-72)

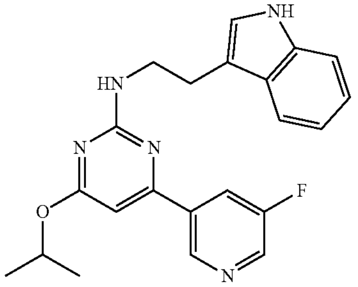 [SMILES: CC(C)Oc1cc(-c2cncc(F)c2)nc(NCCc2c[nH]c3ccccc23)n1]

4-Chloro-N-[2-(1H-indol-3-yl)ethyl]-6-isopropoxy-pyrimidin-2-amine (90.00 mg, 220.37 μmol, 1 eq), (5-fluoro-3-pyridyl)boronic acid (62.10 mg, 440.73 μmol, 2 eq), $Cs_2CO_3$ (215.40 mg, 661.10 μmol, 3.0 eq) and Pd(dppf)$Cl_2$ (16.12 mg, 22.04 μmol, 0.1 eq) were taken up into a microwave tube in 1,4-dioxane (3 mL) and water (0.6 mL). The sealed tube was heated at 120° C. for 30 min under microwave. The reaction mixture was diluted with EtOAc (20 mL) and filtered through a pad of celite. The filtrate was concentrated under reduced pressure to give a residue which was purified by prep-HPLC (HCl condition, column: column: Phenomenex Synergi C18 150×30 mm×4 um; mobile phase: [water (0.05% HCl)-ACN]; B %: 37%-67%, 12 min) and the desired fraction was lyophilized to yield 4-(5-fluoro-3-pyridyl)-N-[2-(1H-indol-3-yl)ethyl]-6-isopropoxy-pyrimidin-2-amine (52.48 mg, 104.79 μmol, 47.5% yield, 100.0% purity, 3HCl salt) as a yellow solid. $^1$H NMR (400 MHz, $CD_3OD$) δ ppm 8.75 (m, 2H), 8.06 (s, 1H), 7.60 (d, J=7.8 Hz, 1H), 7.33 (d, J=8.0 Hz, 1H), 7.14 (s, 1H), 7.12-7.06 (m, 1H), 7.04-6.99 (m, 1H), 6.62 (s, 1H), 5.18 (s, 1H), 3.92 (t, J=6.5 Hz, 2H), 3.15 (t, J=6.5 Hz, 2H), 1.36 (d, J=6.3 Hz, 6H); ES-LCMS m/z 392.2 $[M+H]^+$.

Example 72

Synthesis of I-73

I-73

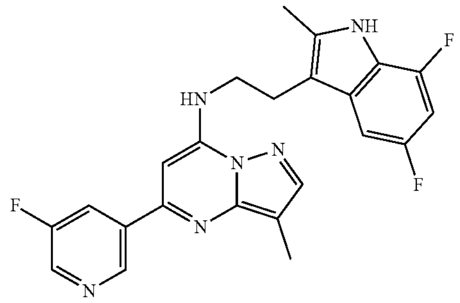 [SMILES: Cc1[nH]c2c(F)cc(F)cc2c1CCNc1cc(-c2cncc(F)c2)nc2c(C)cnn12]

Synthetic Scheme:

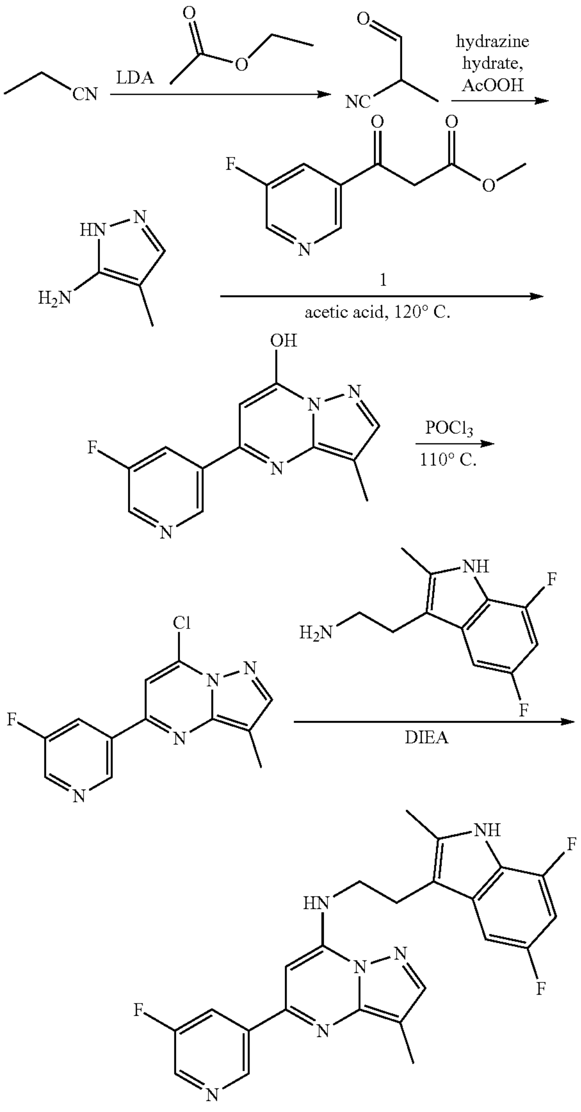

I-73

Step 1: 2-Methyl-3-oxo-propanenitrile

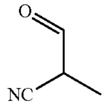

To a solution of DIPA (1.84 g, 18.16 mmol, 2.57 mL, 1 eq) in THF (20 mL) was added n-BuLi (2.5 M in n-hexane, 7.63 mL, 1.05 eq). The mixture was stirred at −65° C. for 30 min. The solution of propanenitrile (1 g, 18.16 mmol, 1.30 mL, 1 eq) in THF (10 mL) was added into the above mixture dropwise. The mixture was stirred at −65° C. for 30 min under $N_2$ atmosphere. A solution of ethyl formate (1.41 g, 19.06 mmol, 1.53 mL, 1.05 eq) in THF (10 mL) was added dropwise and it was stirred at −65° C. for 3 h. TLC (PE/EtOAc=1/1, $R_f$=0.45) showed one major new spot was detected. The reaction mixture was quenched by addition 1 N HCl solution (50 mL) at −65° C., extracted with EtOAc (50 mL×3). The combined organic layers were dried over $Na_2SO_4$, filtered and the filtrate was concentrated under reduced pressure to give 2-methyl-3-oxo-propanenitrile (1.1 g, crude) was obtained as yellow oil which was used in the next step without further purification. $^1H$ NMR (400 MHz, $CDCl_3$) δ ppm 9.60 (s, 1H), 3.54 (d, J=7.5 Hz, 1H), 1.55 (s, 3H).

Step 2: 4-Methyl-1H-pyrazol-5-amine

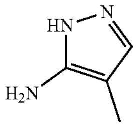

To a solution of 2-methyl-3-oxo-propanenitrile (1.1 g, 13.24 mmol, 1 eq) in EtOH (12 mL) was added AcOH (1.39 g, 23.17 mmol, 1.32 mL, 1.75 eq) and hydrazine (550.00 mg, 17.16 mmol, 620.77 μL, 1.3 eq). The mixture was stirred at 90° C. for 12 h. TLC (PE/EtOAc=1/1, $R_f$=0.10) showed one major new spot was detected. The reaction mixture was concentrated under reduced pressure to give a residue which was diluted with $NaHCO_3$ solution (100 mL), extracted with EtOAc (50 mL×3). The combined organic layers were dried over $Na_2SO_4$, filtered and the filtrate was concentrated under reduced pressure to give a residue which was purified by flash silica gel chromatography (from DCM/MeOH=100/1 to 10/1, TLC: PE/EtOAc=10/1, $R_f$=0.75) to yield compound 4-methyl-1H-pyrazol-5-amine (230 mg, 2.37 mmol, 17.9% yield, crude) as yellow oil. $^1H$ NMR (400 MHz, $CDCl_3$) δ ppm 7.13 (s, 1H), 1.94-1.92 (m, 3H).

Step 3: 5-(5-Fluoro-3-pyridyl)-3-methyl-pyrazolo[1,5-a]pyrimidin-7-ol

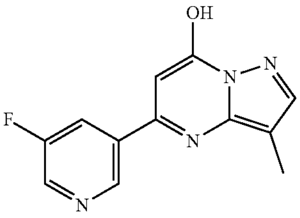

To a solution of methyl 3-(5-fluoro-3-pyridyl)-3-oxo-propanoate (400 mg, 1.99 mmol, 1 eq) in AcOH (6 mL) was added 4-methyl-1H-pyrazol-5-amine (230 mg, 2.37 mmol, 1.19 eq). The mixture was stirred at 120° C. for 2 h. The reaction mixture was concentrated under reduced pressure to give 5-(5-fluoro-3-pyridyl)-3-methyl-pyrazolo[1,5-a]pyrimidin-7-ol (500 mg, crude) was obtained as yellow oil which was used in the next step without further purification. ES-LCMS m/z 245.2 $[M+H]^+$.

Step 4: 7-Chloro-5-(5-fluoro-3-pyridyl)-3-methyl-pyrazolo[1,5-a]pyrimidine

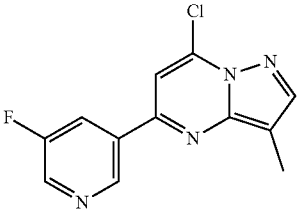

To a solution of 5-(5-fluoro-3-pyridyl)-3-methyl-pyrazolo[1,5-a]pyrimidin-7-ol (500 mg, 655.14 μmol, 1 eq) in $POCl_3$ (5 mL) was stirred at 120° C. for 2 h. The reaction mixture was concentrated under reduced pressure to remove $POCl_3$. The residue was purified by flash silica gel chromatography (from PE/EtOAc=100/1 to 2/1, TLC: PE/EtOAc=3/1, $R_f$=0.40) to yield 7-chloro-5-(5-fluoro-3-pyridyl)-3-methyl-pyrazolo[1,5-a]pyrimidine (145 mg, 552.02 μmol, 84.3% yield, 100.0% purity) as yellow solid $^1$H NMR (400 MHz, $CDCl_3$) δ ppm 9.10 (s, 1H), 8.60 (d, J=2.6 Hz, 1H), 8.24 (dd, J=1.8, 9.3 Hz, 1H), 8.14 (s, 1H), 7.39 (s, 1H), 2.47 (s, 3H); ES-LCMS m/z 262.9, 264.9 $[M+H]^+$.

Step 5: 5-(5-Fluoro-3-pyridyl)-3-methyl-N-[2-(2,5,7-trifluoro-1H-indol-3-yl)ethyl]pyrazolo[1,5-a]pyrimidin-7-amine (I-73)

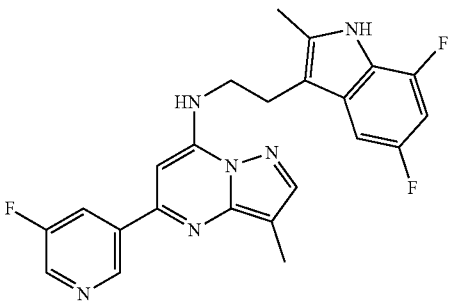

To a solution of 7-chloro-5-(5-fluoro-3-pyridyl)-3-methyl-pyrazolo[1,5-a]pyrimidine (40 mg, 152.28 μmol, 1 eq) in i-PrOH (3 mL) was added DIEA (157.45 mg, 1.22 mmol, 212.19 μL, 8.0 eq) and 2-(5,7-difluoro-2-methyl-1H-indol-3-yl)ethanamine (54.87 mg, 182.74 μmol, 1.2 eq, oxalic acid salt). The mixture was stirred at 50° C. for 12 h. The reaction mixture was concentrated under reduced pressure to give the residue which was purified by preparative HPLC (HCl condition; column: Phenomenex Gemini 150×25 mm×10 um; mobile phase: [water(0.05% HCl)-ACN]; B %: 42%-62%, 10 min) and the desired fraction was lyophilized to yield compound 5-(5-fluoro-3-pyridyl)-3-methyl-N-[2-(2,5,7-trifluoro-1H-indol-3-yl)ethyl]pyrazolo[1,5-a]pyrimidin-7-amine (15.56 mg, 27.91 μmol, 18.3% yield, 98.6% purity, 3HCl salt) as a yellow solid. $^1$H NMR (400 MHz, $CD_3OD$) δ ppm 8.75 (d, J=2.4 Hz, 1H), 8.45 (s, 1H), 8.11 (s, 1H), 7.66-7.61 (m, 1H), 7.00 (dd, J=2.2, 9.3 Hz, 1H), 6.44 (ddd, J=2.2, 9.5, 11.2 Hz, 1H), 5.75 (s, 1H), 4.00 (t, J=5.7 Hz, 2H), 3.16-3.10 (m, 2H), 2.31 (s, 3H), 2.15 (s, 3H); ES-LCMS m/z 437.2 $[M+H]^+$.

Example 73

Synthesis of I-74

I-74

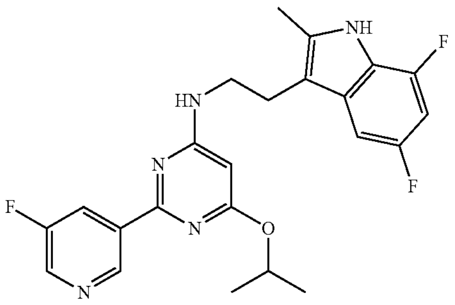

Synthetic Scheme:

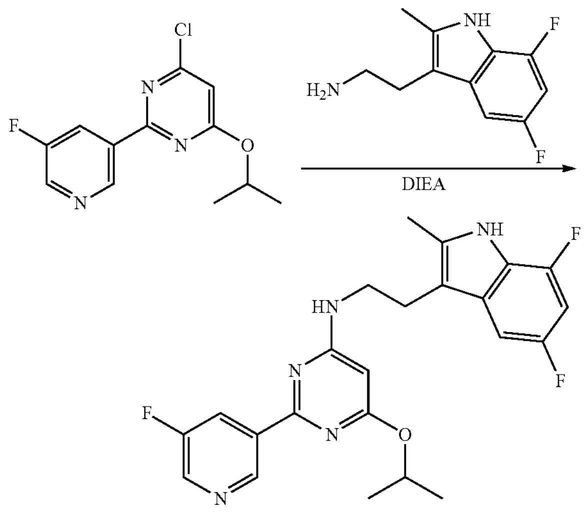

I-74

Step 1: N-[2-(5,7-Difluoro-2-methyl-1H-indol-3-yl)ethyl]-2-(5-fluoro-3-pyridyl)-6-isopropoxy-pyrimidin-4-amine (I-74)

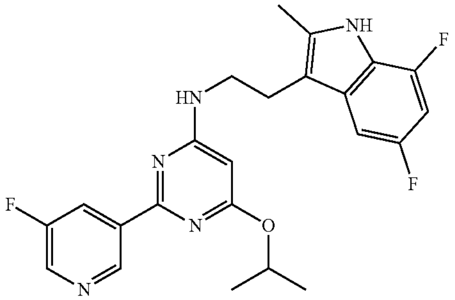 [SMILES: Cc1[nH]c2c(F)cc(F)cc2c1CCNc1cc(OC(C)C)nc(-c2cncc(F)c2)n1]

4-Chloro-2-(5-fluoro-3-pyridyl)-6-isopropoxy-pyrimidine (90 mg, 322.77 μmol, 1.0 eq), 2-(5,7-difluoro-2-methyl-1H-indol-3-yl)ethanamine (145.37 mg, 484.15 μmol, 1.5 eq, oxalic acid salt) and DIEA (333.71 mg, 2.58 mmol, 449.75 uL, 8 eq) in i-PrOH (5 mL) were taken up into a microwave tube. The sealed tube was heated at 150° C. for 6 h under microwave. The reaction mixture was concentrated under reduced pressure to give the residue which was purified by flash silica gel chromatography (from PE/EtOAc=100/1 to 2/1, TLC: PE/EtOAc=3/1, $R_f$=0.50) and then re-purified by preparative HPLC (HCl condition; column: Phenomenex Gemini 150×25 mm×10 um; mobile phase: [water (0.05% HCl)-ACN]; B %: 60%-90%, 10 min) and the desired fraction was lyophilized to yield N-[2-(5,7-difluoro-2-methyl-1H-indol-3-yl)ethyl]-2-(5-fluoro-3-pyridyl)-6-isopropoxy-pyrimidin-4-amine (26.48 mg, 48.07 μmol, 14.9% yield, 100% purity, 3HCl salt) as a yellow solid. $^1H$ NMR (400 MHz, $CD_3OD$) δ ppm 9.10 (s, 1H), 8.71 (d, J=2.6 Hz, 1H), 8.27 (s, 1H), 6.99 (d, J=9.3 Hz, 1H), 6.54 (t, J=9.9 Hz, 1H), 5.69 (s, 1H), 5.05 (s, 1H), 3.74 (m, 2H), 2.97 (t, J=6.6 Hz, 2H), 2.34 (s, 3H), 1.37 (d, J=6.2 Hz, 6H); ES-LCMS m/z 442.2 $[M+H]^+$.

Example 74

Synthesis of I-75a, I-75b and I-75c

I-75a

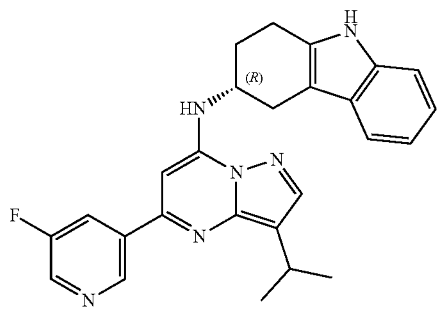

I-75b

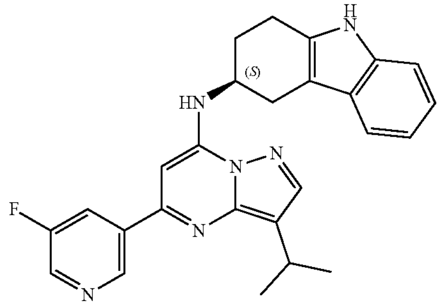

I-75c

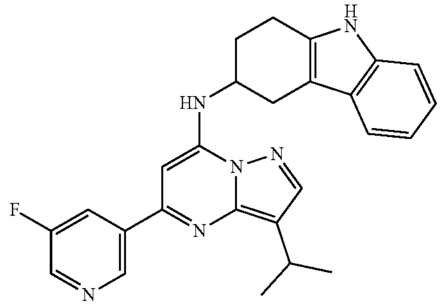

Synthetic Scheme:

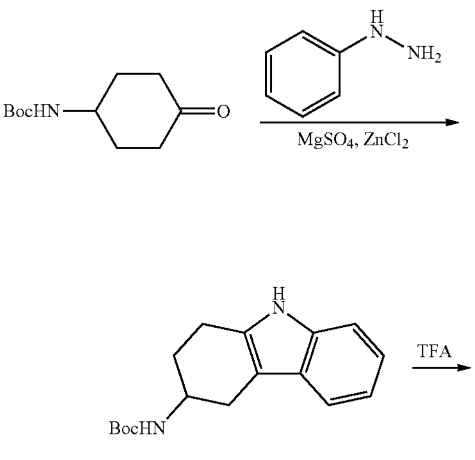

-continued

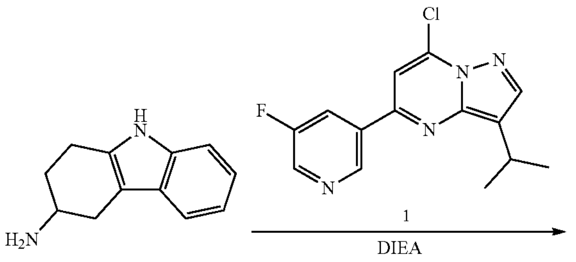

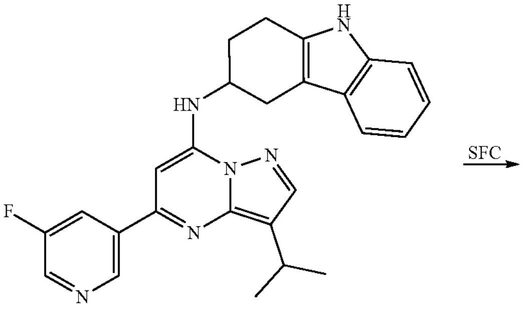

I-75c

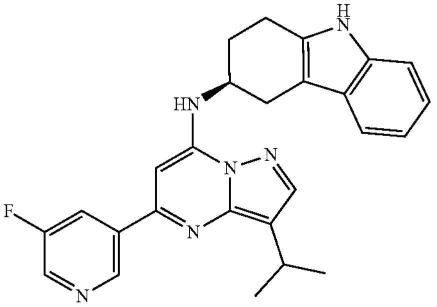

+

I-75b

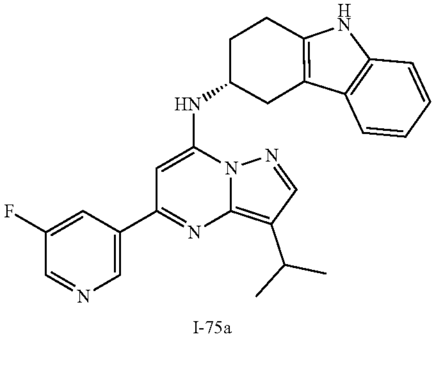

I-75a

Step 1: tert-Butyl N-(2,3,4,9-tetrahydro-1H-carbazol-3-yl)carbamate

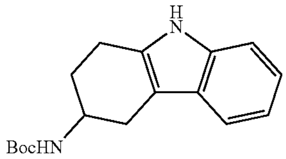 [SMILES: CC(C)(C)OC(=O)NC1CCc2[nH]c3ccccc3c2C1]

To a solution of tert-butyl N-(4-oxocyclohexyl)carbamate (1 g, 4.69 mmol, 1.00 mL, 1 eq) in DCM (30 mL) was added $MgSO_4$ (564.38 mg, 4.69 mmol, 1 eq) and phenylhydrazine (507.05 mg, 4.69 mmol, 460.96 μL, 1 eq). The mixture was stirred at 28° C. for 2 h. Then $MgSO_4$ was filtered off, the filtrate was evaporated under reduced pressure. The resulting brown oil was dissolved in toluene (20 mL), $ZnCl_2$ (3.20 g, 23.44 mmol, 5 eq) was added, the mixture was heated at 110° C. for 4 h. The reaction mixture was concentrated under reduced pressure to give a residue which was purified by flash silica gel chromatography (from PE/EtOAc=100/1 to 3/1, TLC: PE/EtOAc=5/1, $R_f$=0.30) to yield compound tert-butyl N-(2,3,4,9-tetrahydro-1H-carbazol-3-yl)carbamate (700 mg, 1.96 mmol, 41.7% yield, 80.0% purity) as a yellow solid. $^1H$ NMR (400 MHz, $CD_3OD$) δ ppm 7.33 (d, J=7.5 Hz, 1H), 7.23 (td, J=0.9, 7.9 Hz, 1H), 7.04-6.97 (m, 1H), 6.97-6.90 (m, 1H), 3.92-3.79 (m, 1H), 2.92-2.78 (m, 2H), 2.57-2.31 (m, 2H), 1.93-1.68 (m, 2H), 1.47 (s, 9H); ES-LCMS m/z 231.1 $[M-t-Bu+H]^+$.

Step 2: 2,3,4,9-Tetrahydro-1H-carbazol-3-amine

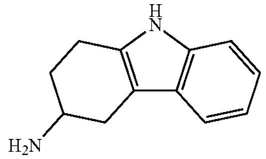 [SMILES: NC1CCc2[nH]c3ccccc3c2C1]

To a solution of tert-butyl N-(2,3,4,9-tetrahydro-1H-carbazol-3-yl)carbamate (700 mg, 1.96 mmol, 1 eq) in DCM (10 mL) was added TFA (3.08 g, 27.01 mmol, 2.0 mL, 13.81 eq). The mixture was stirred at 28° C. for 2 h. TLC (PE/EtOAc=5/1, $R_f$=0) indicated the starting material was consumed completely and one new spot formed. The reaction mixture was concentrated under reduced pressure to give the residue which was diluted with water (30 mL), adjusted pH=10 by 1% NaOH solution. The mixture was extracted with EtOAc (30 mL×3). The combined organic layers were dried over $Na_2SO_4$, filtered and the filtrate was concentrated under reduced pressure to give 2,3,4,9-tetrahydro-1H-carbazol-3-amine (400 mg, 1.80 mmol, 92.3% yield, 84.0% purity) was obtained as a black brown solid which was used in the next step without further purification. $^1H$ NMR (400 MHz, $CDCl_3$) δ ppm 7.80 (s, 1H), 7.44 (d, J=7.7 Hz, 1H), 7.27-7.23 (m, 1H), 7.13-7.04 (m, 2H), 3.34-3.24 (m, 1H), 3.07-2.97 (m, 1H), 2.81 (t, J=6.4 Hz, 2H), 2.50-2.43 (m, 1H), 2.13-2.05 (m, 1H), 1.84-1.76 (m, 1H); ES-LCMS m/z 187.0 $[M+H]^+$.

Step 3: (3S)—N-[5-(5-Fluoro-3-pyridyl)-3-isopropyl-pyrazolo[1,5-a]pyrimidin-7-yl]-2,3,4,9-tetrahydro-1H-carbazol-3-amine (I-75b) & (3R)—N-[5-(5-fluoro-3-pyridyl)-3-isopropyl-pyrazolo[1,5-a]pyrimidin-7-yl]-2,3,4,9-tetrahydro-1H-carbazol-3-amine (I-75a)

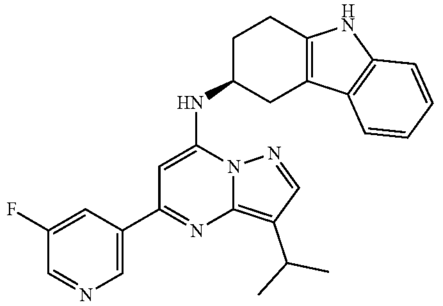

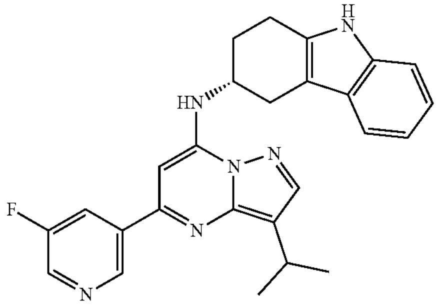

To a solution of 7-chloro-5-(5-fluoro-3-pyridyl)-3-isopropyl-pyrazolo[1,5-a]pyrimidine (153.06 mg, 515.96 μmol, 1.0 eq) in i-PrOH (10 mL) was added DIEA (200.05 mg, 1.55 mmol, 269.60 μL, 3.0 eq) and 2,3,4,9-tetrahydro-1H-carbazol-3-amine (145.09 mg, 654.35 μmol, 1.27 eq). The mixture was stirred at 50° C. for 15 h. The reaction mixture was concentrated under reduced pressure to give a residue which was purified by flash silica gel chromatography (from PE/EtOAc=100/1 to 2/1, TLC: PE/EtOAc=3/1, $R_f$=0.80). The compounds were separated by SFC (condition: column: AD (250 mm×30 mm, 5 um); mobile phase: [0.1% $NH_3H_2O$ EtOH]; B %: 45%-45%, min). The solution after separation were concentrated to afford the crude products which were purified by preparative HPLC (HCl condition; column: Phenomenex Synergi C18 150×30 mm×4 um; mobile phase: [water(0.05% HCl)-ACN]; B %: 60%-90%, 12 min), followed by lyophilization to yield an enantiomer (36.18 mg, 65.79 μmol, 12.8% yield, 100.0% purity, 3HCl salt) (Rt=4.768 min, ee %=100.0 and $[\alpha]^{29}_D$=−3.430 (i-ProH, c=0.107 g/100 mL)) as a yellow solid; $^1$H NMR (400 MHz, $CD_3OD$) δ ppm 9.00 (s, 1H), 8.78 (s, 1H), 8.36-8.29 (m, 1H), 8.24 (d, J=1.3 Hz, 1H), 7.38 (d, J=7.7 Hz, 1H), 7.27 (d, J=7.9 Hz, 1H), 7.08-6.93 (m, 3H), 4.63 (s, 1H), 3.43-3.32 (m, 2H), 3.18-2.93 (m, 3H), 2.43-2.26 (m, 2H), 1.40 (d, J=6.8 Hz, 6H); ES-LCMS m/z 441.2 $[M+H]^+$; and the other enantiomer (36.49 mg, 66.36 μmol, 12.9% yield, 100.0% purity, 3HCl salt) (Rt=5.778 min, ee %=96.4 and $[\alpha]^{29}_D$=+3.121 (i-ProH, c=0.104 g/100 mL)) as a yellow solid. $^1$H NMR (400 MHz, $CD_3OD$) δ ppm 9.03 (s, 1H), 8.73 (d, J=2.6 Hz, 1H), 8.36-8.30 (m, 1H), 8.18 (s, 1H), 7.38 (d, J=7.7 Hz, 1H), 7.29-7.25 (m, 1H), 7.04 (dt, J=1.2, 7.6 Hz, 1H), 7.00-6.93 (m, 2H), 4.60 (s, 1H), 3.40-3.32 (m, 2H), 3.16-2.92 (m, 3H), 2.43-2.24 (m, 2H), 1.40 (d, J=6.8 Hz, 6H); ES-LCMS m/z 441.3 $[M+H]^+$.

Example 75

Synthesis of I-77

I-77

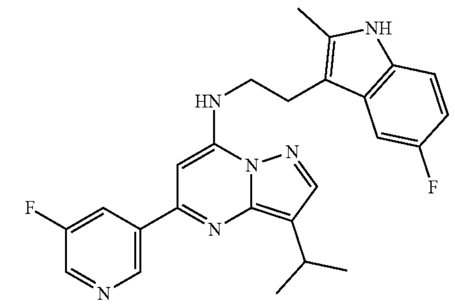

Synthetic Scheme:

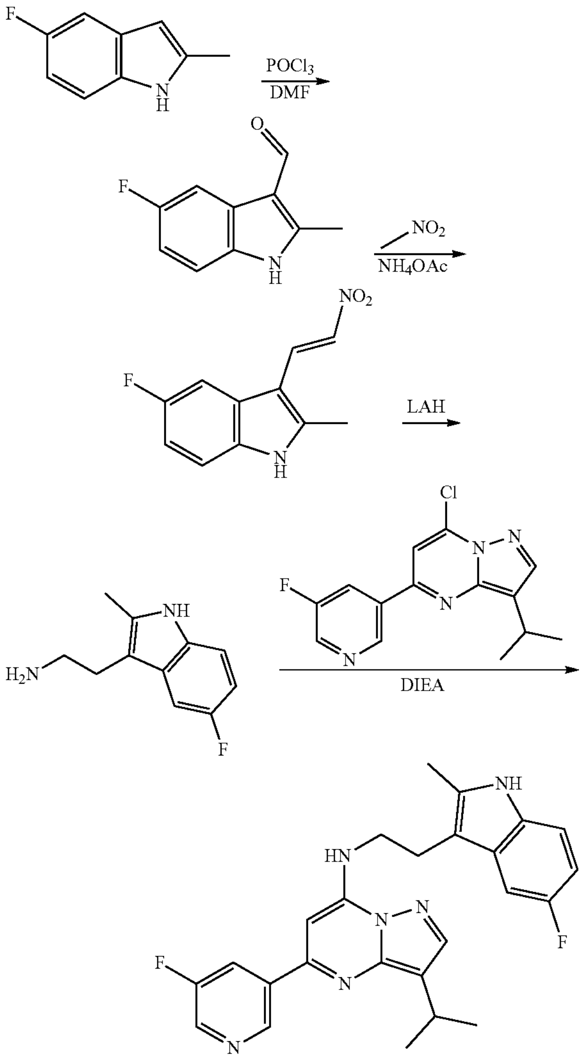

I-77

Step 1: 5-Fluoro-2-methyl-1H-indole-3-carbaldehyde

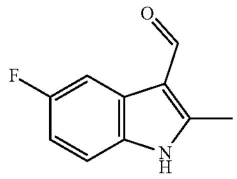

To DMF (40 mH) was added $POCl_3$ (4.11 g, 26.82 mmol, 2.49 mL, 2 eq) dropwise at −20° C. over a period of 10 min under $N_2$ atmosphere. After being stirred for 1 h, 5-fluoro-2-methyl-1H-indole-(2 g, 13.41 mmol, 1 eq) was added to the above solution during which the temperature was maintained below −20° C. The reaction mixture was warmed to 15° C. and stirred for 1 h. The reaction mixture was quenched by saturated aqueous $NaHCO_3$ (100 mL) and extracted with EtOAc (50 mL×3). The combine organic layers were dried over anhydrous $Na_2SO_4$, filtered and concentrated under reduced pressure to give a residue which was purified by flash silica gel chromatography (from PE/EtOAc=1/0 to 1/1, TLC: PE/EtOAc=1/1, $R_f$=0.67) to yield 5-fluoro-2-methyl-1H-indole-3-carbaldehyde (1.3 g, 5.73 mmol, 42.7% yield, 78.1% purity) as a yellow solid. $^1H$ NMR (400 MHz, $CDCl_3$) δ ppm 10.17 (s, 1H), 8.39 (br s, 1H), 7.93 (d, J=9.0 Hz, 1H), 7.08-6.89 (m, 1H), 2.75 (s, 3H); ES-LCMS m/z 178.0 $[M+H]^+$.

Step 2: 5-Fluoro-2-methyl-3-[(E)-2-nitrovinyl]-1H-indole

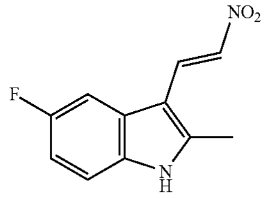 [SMILES: Cc1[nH]c2ccc(F)cc2c1/C=C/[N+](=O)[O-]]

To a solution of 5-fluoro-2-methyl-1H-indole-3-carbaldehyde (1.1 g, 4.85 mmol, 1 eq) in nitronethane (45 mL) was added $NH_4OAc$ (1.12 g, 14.54 mmol, 3 eq). The mixture was stirred at 110° C. for 16 h. The reaction mixture was concentrated under reduced pressure to remove nitronethane. The residue was extracted with EtOAc (50 mL×3). The combine organic layers were dried over $Na_2SO_4$, filtered and concentrated under reduced pressure to give 5-fluoro-2-methyl-3-[(E)-2-nitrovinyl]-1H-indole (0.92 g, crude) as a brown solid which was used in the next step without further purification; ES-LCMS m/z 221.0 $[M+H]^+$.

Step 3: 2-(5-Fluoro-2-methyl-1H-indol-3-yl)ethanamine

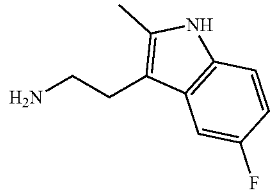

To a solution of 5-fluoro-2-methyl-3-[(E)-2-nitrovinyl]-1H-indole (1.40 g, 6.36 mmol, 1 eq) in THF (30 mL) was added LAH (1 M, 31.79 mL, 5 eq) at 0° C. After addition, the mixture was stirred at 80° C. for 2 h. The reaction mixture was diluted with THF (10 mL) and then was quenched by addition water (1.4 mL), 10% NaOH (1.4 mL) and water (4.2 mL) in sequence at 0° C. After being stirred for 30 min, the mixture was filtered through celite. The filtrate was concentrated under reduced pressure to give 2-(5-fluoro-2-methyl-1H-indol-3-yl)ethanamine (1.0 g, crude) as yellow oil which was used in the next step directly without further purification. $^1H$ NMR (400 MHz, $CD_3OD$) δ ppm 7.14 (dd, J=8.8 Hz, 1H), 7.07 (dd, J=10.0 Hz, 1H), 6.72 (td, J=5.0, 9.1 Hz, 1H), 2.85-2.74 (m, 4H), 2.33 (s, 3H); ES-LCMS m/z 192.1 $[M+H]^+$.

Step 4: N-[2-(5-Fluoro-2-methyl-1H-indol-3-yl) ethyl]-5-(5-fluoro-3-pyridyl)-3-isopropyl-pyrazolo [1,5-a]pyrimidin-7-amine (I-77)

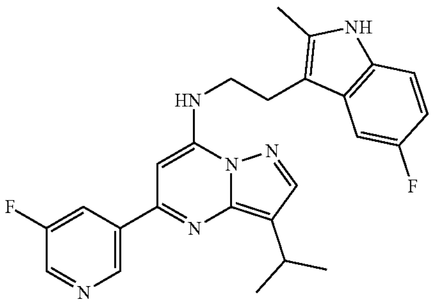 [SMILES: Cc1[nH]c2ccc(F)cc2c1CCNc1cc(-c2cncc(F)c2)nc2c(C(C)C)cnn12]

To a solution of 7-chloro-5-(5-fluoro-3-pyridyl)-3-isopropyl-pyrazolo[1,5-a]pyrimidine (64.30 mg, 216.75 μmol, 1 eq) in i-PrOH (5 mL) was added DIEA (140.07 mg, 1.08 mmol, 188.77 μL, 5 eq) and 2-(5-fluoro-2-methyl-1H-indol-3-yl)ethanamine (50 mg, 260.10 μmol, 1.2 eq) The mixture was stirred at 60° C. for 16 h. The reaction mixture was concentrated under reduced pressure to remove i-PrOH to give a residue which was purified by preparative HPLC (Column: Phenomenex Gemini 150*25 mm*10 um; mobile phase: [water (0.05% HCl)-ACN]; B %: 50%-80%, 7 min). followed by lyophilization to yield N-[2-(5-fluoro-2-methyl-1H-indol-3-yl)ethyl]-5-(5-fluoro-3-pyridyl)-3-isopropyl-pyrazolo[1,5-a]pyrimidin-7-amine (17.49 mg, 31.46 umol, 14.5% yield, 100.0% purity, 3HCl) as a yellow solid. $^1H$ NMR (400 MHz, $CD_3OD$) δ ppm 8.75 (d, J=2.4 Hz, 1H), 8.40 (s, 1H), 8.21 (s, 1H), 7.54 (d, J=8.6 Hz, 1H), 7.07 (dd, J=2.3, 9.8 Hz, 1H), 6.95 (dd, J=4.4, 8.6 Hz, 1H), 6.59 (J=2.4, 9.0 Hz, 1H), 5.71 (s, 1H), 4.03-3.95 (m, 2H), 3.28-3.20 (m, 1H), 3.16-3.09 (m, 2H), 2.16 (s, 3H), 1.34 (d, J=6.8 Hz, 6H); ES-LCMS m/z 447.1 [M+H]$^+$.

Example 76

Synthesis of I-78

I-78

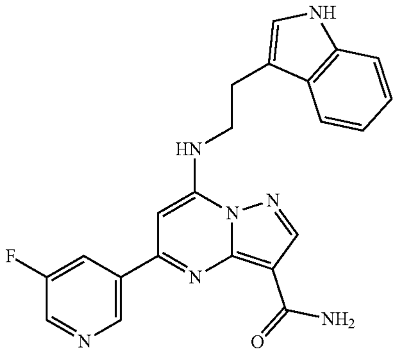 [SMILES: NC(=O)c1cnn2c(NCCc3c[nH]c4ccccc34)cc(-c3cncc(F)c3)nc12]

Synthetic Scheme:

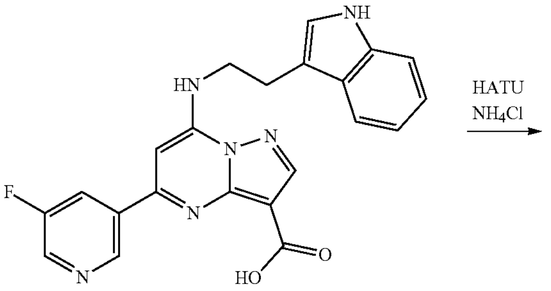

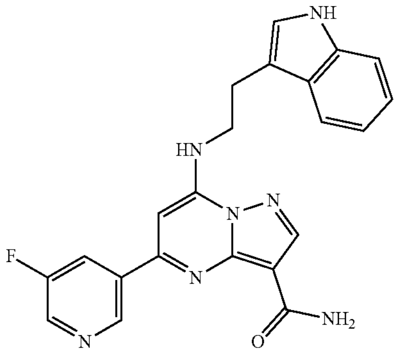

I-78

Step 1: 5-(5-Fluoro-3-pyridyl)-7-[2-(1H-indol-3-yl)ethylamino]pyrazolo[1,5-a]pyrimidine-3-carboxamide (I-78)

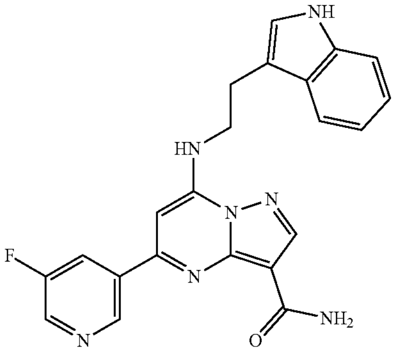

A mixture of 5-(5-fluoro-3-pyridyl)-7-[2-(1H-indol-3-yl)ethyl amino]pyrazolo[1,5-a]pyrimidine-3-carboxylic acid (35 mg, 84.05 μmol, 1 eq), HATU (63.92 mg, 168.10 μmol, 2 eq), DIEA (32.59 mg, 252.16 μmol, 43.92 μL, 3 eq) and $NH_4Cl$ (13.49 mg, 252.16 μmol, 3 eq) in DMF (5 mL) was stirred at 25° C. for 3 h. The mixture was concentrated under reduced pressure to give a residue which was purified by preparative HPLC (column: Phenomenex Gemini 150*25 mm*10 um; mobile phase: [water(0.05% HCl)-ACN]; B %: 36%-56%, 10 min), lyophilized to give 5-(5-fluoro-3-pyridyl)-7-[2-(1H-indol-3-yl)ethylamino]pyrazolo[1,5-a]pyrimidine-3-carboxamide (16.47 mg, 31.08 μmol, 37.0% yield, 99.0% purity, 3HCl) as a yellow solid. $^1H$ NMR (400 MHz, $CD_3OD$) δ ppm 8.85 (s, 1H), 8.73 (s, 1H), 8.51 (s, 1H), 8.03 (d, J=9.2 Hz, 1H), 7.72-7.69 (m, 1H), 7.12 (d, J=8.4 Hz, 1H), 7.04-7.01 (m, 2H), 6.95 (s, 1H), 6.08 (s, 1H), 3.98 (t, J=5.6 Hz, 2H), 3.22 (t, J=5.6 Hz, 2H); ES-LCMS m/z 416.2 [M+H]$^+$.

Example 77

Synthesis of I-79

I-79

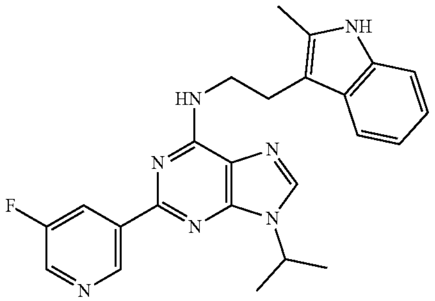 [SMILES: Cc1[nH]c2ccccc2c1CCNc1nc(-c2cncc(F)c2)nc2c1ncn2C(C)C]

Synthetic Scheme:

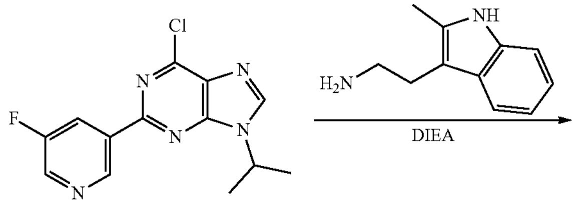

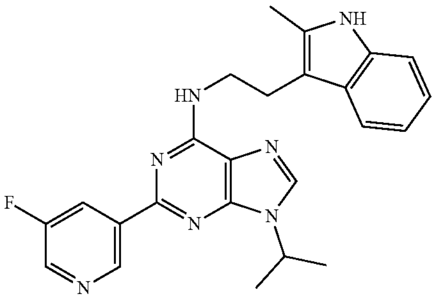

I-79

Step 1: 2-(5-Fluoro-3-pyridyl)-9-isopropyl-N-[2-(2-methyl-1H-indol-3-yl)ethyl]purin-6-amine (I-79)

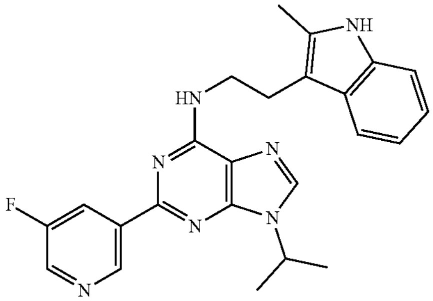

A mixture of 6-chloro-2-(5-fluoro-3-pyridyl)-9-isopropyl-purine (52.08 mg, 171.40 μmol, 1 eq), 2-(2-methyl-1H-indol-3-yl)ethanamine (29.87 mg, 171.40 μmol, 1 eq) and DIEA (66.46 mg, 514.21 μmol, 89.57 μL, 3 eq) in i-PrOH (3 mL) was stirred at 55° C. for 19 h. The reaction mixture was concentrated under reduced pressure to give a residue which was purified by preparative HPLC (column: Phenomenex Synergi C18 150*30 mm*4 um; mobile phase: [water (0.05% HCl)-ACN]; B %: 42%-72%, 12 min) followed by lyophilization to yield 2-(5-fluoro-3-pyridyl)-9-isopropyl-N-[2-(2-methyl-1H-indol-3-yl)ethyl]purin-6-amine (18.99 mg, 34.91 μmol, 20.4% yield, 99.1% purity, 3 HCl salt) as a yellow solid. $^1$H NMR (400 MHz, $CD_3OD$) δ ppm 9.27-9.11 (m, 2H), 8.85 (s, 1H), 8.68 (d, J=8.78 Hz, 1H), 7.51-7.43 (m, 1H), 7.07-7.00 (m, 1H), 6.92-6.83 (m, 2H), 5.13-5.00 (m, 1H), 4.07 (s, 2H), 3.11 (t, J=6.53 Hz, 2H), 2.27 (s, 3H), 1.73 (d, J=6.53 Hz, 6H); ES-LCMS m/z 430.2 $[M+H]^+$.

Example 78

Synthesis of I-80

I-80

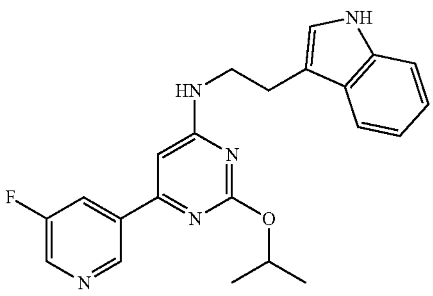

Synthetic Scheme:

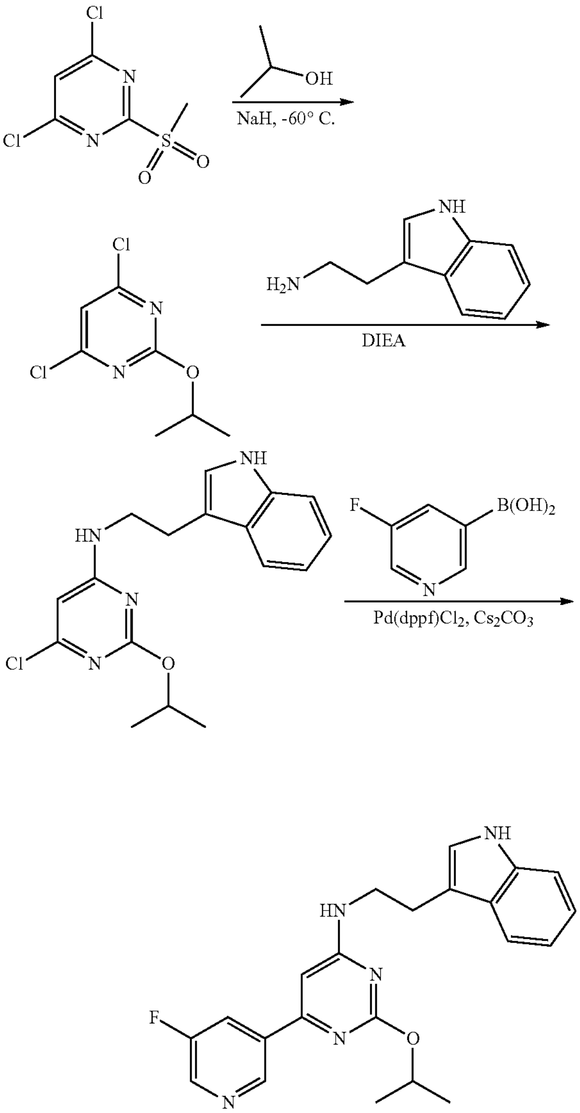

I-80

Step 1: 4,6-Dichloro-2-isopropoxy-pyrimidine

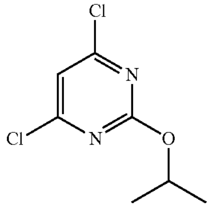

To a suspension of NaH (248.00 mg, 6.20 mmol, 60% in mineral oil, 1.41 eq) in dry THF (10 mL) was added i-PrOH (277.91 mg, 4.62 mmol, 354.03 μL, 1.05 eq) under ice bath and $N_2$ atmosphere. After being stirred for 30 min, the suspension was cooled to −60° C. and 4,6-dichloro-2-methylsulfonyl-pyrimidine (1 g, 4.40 mmol, 625.00 μL, 1.0 eq) in dry THF (10 mL) was added dropwise and kept the temperature below −55° C. The resulting mixture was stirred for 1 h at −55° C. The reaction mixture was poured into water (100 mL) slowly and extracted with EtOAc (30 mL×3). The combined organic layers were washed with brine, dried over $Na_2SO_4$ and concentrated to yield 4,6-dichloro-2-isopropoxy-pyrimidine (565 mg, 2.56 mmol, 58.2% yield, 94% purity) as yellow oil which was used in the next step without further purification. $^1$H NMR (400 MHz, $CDCl_3$) δ ppm 7.02-6.96 (m, 1H), 5.29 (m, 1H), 1.40 (d, J=6.0 Hz, 6H); ES-LCMS m/z 206.9, 208.9 $[M+H]^+$.

Step 2: 6-Chloro-N-[2-(1H-indol-3-yl)ethyl]-2-isopropoxy-pyrimidin-4-amine

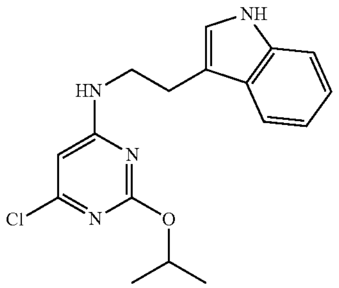 [SMILES: CC(C)Oc1nc(Cl)cc(NCCc2c[nH]c3ccccc23)n1]

To a solution of 4,6-dichloro-2-isopropoxy-pyrimidine (200 mg, 907.96 μmol, 0.5 eq) in i-PrOH (6 mL) was added DIEA (704.07 mg, 5.45 mmol, 948.88 μL, 3.0 eq) and 2-(1H-indol-3-yl)ethanamine (329.00 mg, 2.05 mmol, 1.13 eq). The mixture was stirred at 26° C. for 12 h. The reaction mixture was concentrated under reduced pressure to give the residue which was purified by flash silica gel chromatography (from PE/EtOAc=100/1 to 3/1, TLC: PE/EtOAc=3/1, $R_f$=0.45) to yield 6-chloro-N-[2-(1H-indol-3-yl)ethyl]-2-isopropoxy-pyrimidin-4-amine (290 mg, 841.57 μmol, 46.3% yield, 96% purity) as yellow oil. $^1$H NMR (400 MHz, $CDCl_3$) δ ppm 8.10 (s, 1H), 7.60 (d, J=7.7 Hz, 1H), 7.43-7.37 (m, 1H), 7.24 (dt, J=1.0, 7.6 Hz, 1H), 7.18-7.12 (m, 1H), 7.05 (d, J=2.4 Hz, 1H), 5.95 (s, 1H), 5.26-5.17 (m, 1H), 3.68 (s, 2H), 3.08 (t, J=6.6 Hz, 2H), 1.35 (d, J=6.2 Hz, 6H); ES-LCMS m/z 330.9, 332.0 $[M+H]^+$.

Step 3: 6-(5-Fluoro-3-pyridyl)-N-[2-(1H-indol-3-yl)ethyl]-2-isopropoxy-pyrimidin-4-amine (I-80)

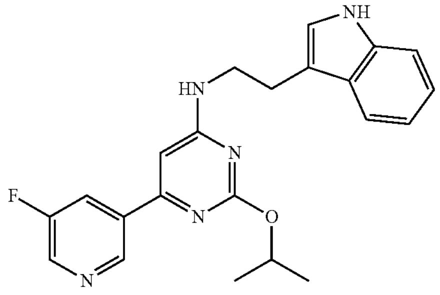 [SMILES: CC(C)Oc1nc(NCCc2c[nH]c3ccccc23)cc(-c2cncc(F)c2)n1]

6-Chloro-N-[2-(1H-indol-3-yl)ethyl]-2-isopropoxy-pyrimidin-4-amine (90 mg, 261.18 μmol, 1 eq), (5-fluoro-3-pyridyl)boronic acid (92.00 mg, 652.94 μmol, 2.5 eq), $Cs_2CO_3$ (255.29 mg, 783.53 μmol, 3.0 eq) and Pd(dppf)$Cl_2$ (19.11 mg, 26.12 μmol, 0.1 eq) were taken up into a microwave tube in water (1.2 mL) and 1,4-dioxane (6 mL). The sealed tube was heated at 120° C. for 30 min under microwave. The reaction mixture was diluted with EtOAc (15 mL) and filtered through a pad of celite. The filtrate was concentrated under reduced pressure to give the residue which was purified by preparative HPLC (HCl condition, column: column: Phenomenex Gemini 150×25 mm×10 um; mobile phase: [water(0.05% HCl)-ACN]; B %: 25%-55%, 10 min) and the desired fraction was lyophilized to yield 6-(5-fluoro-3-pyridyl)-N-[2-(1H-indol-3-yl)ethyl]-2-isopropoxy-pyrimidin-4-amine (43.81 mg, 87.48 μmol, 33.5% yield, 100% purity, 3 HCl salt) as a yellow solid. $^1$H NMR (400 MHz, $CD_3OD$+$Na_2CO_3$) δ ppm 8.92 (s, 1H), 8.53 (m, 1H), 8.12 (m, 1H), 7.61 (m, 1H), 7.33 (m, 1H), 7.09 (d, J=7.0 Hz, 2H), 7.02 (m, 1H), 6.57 (s, 1H), 5.38-5.26 (m, 1H), 3.77 (m, 2H), 3.09 (t, J=7.0 Hz, 2H), 1.40 (d, J=5.8 Hz, 6H); ES-LCMS m/z 392.0 $[M+H]^+$.

Example 79

Synthesis of I-81

I-81

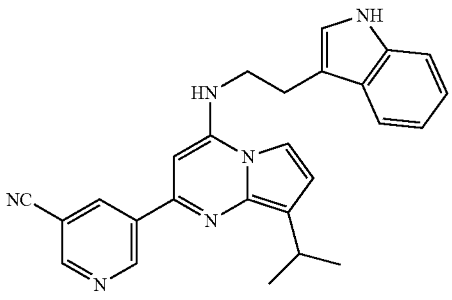

Synthetic Scheme:

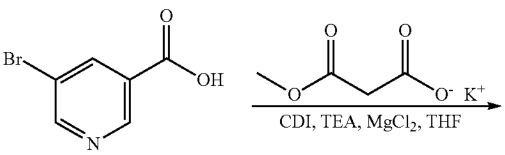

-continued

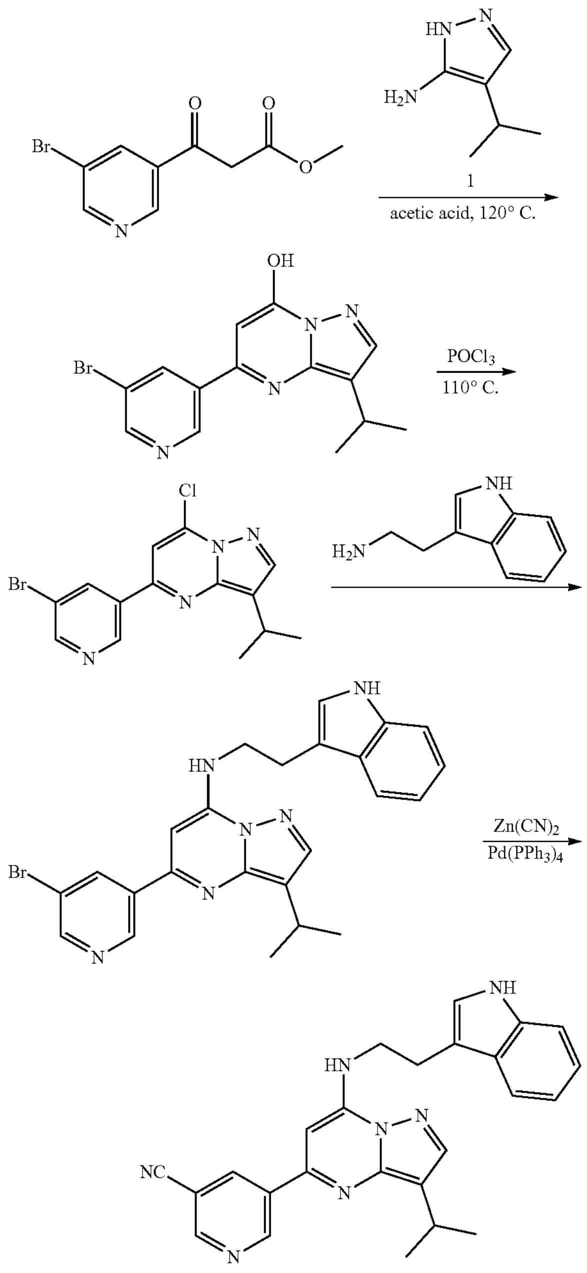

I-81

Step 1: Methyl 3-(5-bromo-3-pyridyl)-3-oxo-propanoate

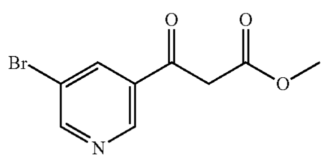

-continued

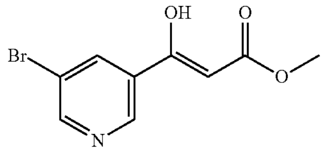

A mixture of 5-bromopyridine-3-carboxylic acid (1 g, 4.95 mmol, 1 eq) and CDI (1.20 g, 7.43 mmol, 1.5 eq) in THF (10 mL) was stirred at 20° C. for 1 h, TEA (500.93 mg, 4.95 mmol, 689.03 μL, 1 eq) was added, the mixture was stirred at 20° C. for 1 h, then (3-methoxy-3-oxo-propanoyl) oxypotassium(1+) (1.55 g, 9.90 mmol, 2 eq) and $MgCl_2$ (942.66 mg, 9.90 mmol, 406.32 μL, 2 eq) were added. The mixture was stirred at 20° C. for 11 h. The reaction mixture was adjust pH to 2 with 2N HCl, extracted with EtOAc (20 mL×3). The combined organic layers were washed with brine (20 mL), dried over $Na_2SO_4$, filtered and concentrated under reduced pressure to give a residue which was purified by flash silica gel chromatography (from PE/EtOAc=10/1 to 5/1, TLC: PE/EtOAc=5/1, $R_f$=0.58) to yield methyl 3-(5-bromo-3-pyridyl)-3-oxo-propanoate (554 mg, 1.50 mmol, 30.4% yield, 70% purity) as a white solid. $^1$H NMR (400 MHz, $CD_3OD$) δ ppm 9.07-9.06 (m, 1H), 8.95 (d, J=1.6 Hz, 1H), 8.89 (d, J=2.0 Hz, 1H), 8.76 (d, J=2.4 Hz, 1H), 8.53-8.52 (m, 1H), 8.42 (t, J=2.0 Hz, 1H), 5.97 (s, 1H), 3.82 (s, 3H), 3.74 (s, 3H); ES-LCMS m/z 259.9, 261.9 $[M+H]^+$.

Step 2: 5-(5-Bromo-3-pyridyl)-3-isopropyl-pyrazolo[1,5-a]pyrimidin-7-ol

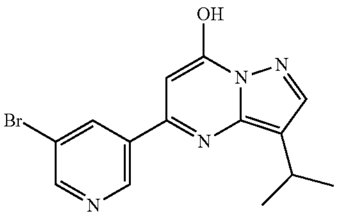 [SMILES: CC(C)c1cnn2c(O)cc(-c3cncc(Br)c3)nc12]

A mixture of methyl 3-(5-bromo-3-pyridyl)-3-oxo-propanoate (300 mg, 813.74 μmol, 1 eq) and 4-isopropyl-1H-pyrazol-5-amine (122.23 mg, 976.49 μmol, 1.2 eq) in AcOH (10 mL) was stirred at 120° C. for 0.5 h. The mixture was concentrated under reduced pressure to give 5-(5-bromo-3-pyridyl)-3-isopropyl-pyrazolo[1,5-a]pyrimidin-7-ol (450 mg, crude) as brown oil which was used in next step without further purification. $^1$H NMR (400 MHz, $CDCl_3$) δ ppm 8.99-8.88 (m, 1H), 8.74-8.73 (m, 1H), 8.39-8.37 (m, 2H), 7.79 (s, 1H), 3.21-3.20 (m, 1H), 1.39-1.33 (m, 6H); ES-LCMS m/z 333.0, 335.0 $[M+H]^+$.

Step 3: 5-(5-Bromo-3-pyridyl)-7-chloro-3-isopropyl-pyrazolo[1,5-a]pyrimidine

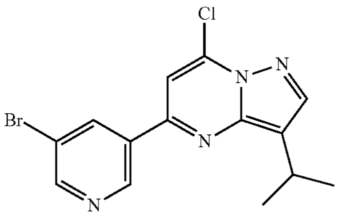 [SMILES: CC(C)c1cnn2c(Cl)cc(-c3cncc(Br)c3)nc12]

A solution of 5-(5-bromo-3-pyridyl)-3-isopropyl-pyrazolo[1,5-a]pyrimidin-7-ol (450 mg, 1.35 mmol, 1 eq) in $POCl_3$ (8.2 g, 53.48 mmol, 4.97 mL, 39.60 eq) was stirred at 110° C. for 1 h. The mixture was concentrated under reduced pressure to give a residue which was purified by flash silica gel chromatography (from PE/EtOAc=10/1 to 5/1, TLC: PE/EtOAc=5/1, $R_f$=0.58) to yield 5-(5-bromo-3-pyridyl)-7-chloro-3-isopropyl-pyrazolo[1,5-a]pyrimidine (331 mg, 847.20 mol, 62.7% yield, 90% purity) as a yellow solid. $^1$H NMR (400 MHz, $CDCl_3$) δ ppm 9.20 (s, 1H), 8.79 (d, J=2.4 Hz, 1H), 8.59 (t, J=2.4 Hz, 1H), 8.14 (s, 1H), 7.37 (s, 1H), 3.42 (s, 1H), 1.45 (d, J=6.8 Hz, 6H); ES-LCMS m/z 350.9, 352.9 $[M+H]^+$.

Step 4: 5-(5-Bromo-3-pyridyl)-N-[2-(1H-indol-3-yl)ethyl]-3-isopropyl-pyrazolo[1,5-a]pyrimidin-7-amine

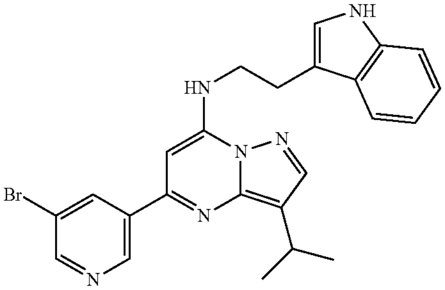 [SMILES: CC(C)c1cnn2c(NCCc3c[nH]c4ccccc34)cc(-c3cncc(Br)c3)nc12]

A mixture of 5-(5-bromo-3-pyridyl)-7-chloro-3-isopropyl-pyrazolo[1,5-a]pyrimidine (60 mg, 153.57 μmol, 1 eq), 2-(1H-indol-3-yl)ethanamine (36.91 mg, 230.36 μmol, 1.5 eq) and DIEA (59.54 mg, 460.71 μmol, 80.25 μL, 3 eq) in i-PrOH (10 mL) was stirred at 80° C. for 2 h. The mixture was concentrated under reduced pressure to give a residue which was purified by preparative TLC ($SiO_2$, PE/EtOAc=1/1, $R_f$=0.28) to yield 5-(5-bromo-3-pyridyl)-N-[2-(1H-indol-3-yl)ethyl]-3-isopropyl-pyrazolo[1,5-a]pyrimidin-7-amine (70 mg, 117.80 μmol, 76.7% yield, 80% purity) as a yellow solid. $^1$H NMR (400 MHz, DMSO-$d_6$) δ ppm 9.21 (d, J=1.6 Hz, 1H), 8.77 (d, J=2.0 Hz, 1H), 8.62 (s, 1H), 7.99-7.95 (m, 2H), 7.64 (d, J=8.0 Hz, 1H), 7.31 (d, J=8.4 Hz, 1H), 7.23 (d, J=2.0 Hz, 1H), 7.09-6.99 (m, 2H), 6.66 (s, 1H), 3.84 (q, J=6.0 Hz, 2H), 3.27-3.22 (m, 1H), 3.13-3.10 (m, 2H), 1.35 (d, J=6.8 Hz, 6H); ES-LCMS m/z 474.9, 476.9 $[M+H]^+$.

Step 5: 5-[7-[2-(1H-Indol-3-yl)ethylamino]-3-isopropyl-pyrazolo[1,5-a]pyrimidin-5-yl]pyridine-3-carbonitrile (I-81)

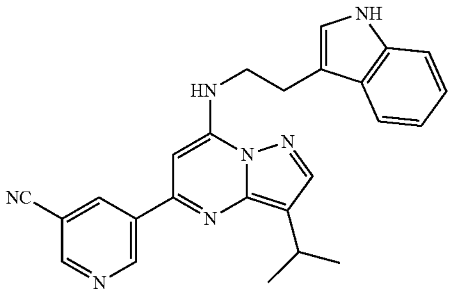 [SMILES: CC(C)c1cnn2c(NCCc3c[nH]c4ccccc34)cc(-c3cncc(C#N)c3)nc12]

A mixture of 5-(5-bromo-3-pyridyl)-N-[2-(1H-indol-3-yl)ethyl]-3-isopropyl-pyrazolo[1,5-a]pyrimidin-7-amine (70 mg, 117.80 μmol, 1 eq), $Pd(PPh_3)_4$ (13.61 mg, 11.78 μmol, 0.1 eq) and $Zn(CN)_2$ (27.67 mg, 235.60 μmol, 2 eq) in DMF (5 mL) was degassed and purged with $N_2$ for 3 times. The mixture was stirred at 85° C. for 12 h under $N_2$ atmosphere. The mixture was concentrated under reduced pressure to give a residue which was purified by preparative HPLC (column: Gemini 150*25 5 u; mobile phase: [water (0.05% ammonia hydroxide v/v)-ACN]; B %: 60%-90%, 10 min) to yield 5-[7-[2-(1H-indol-3-yl)ethylamino]-3-isopropyl-pyrazolo[1,5-a]pyrimidin-5-yl]pyridine-3-carbonitrile (18.46 mg, 43.72 μmol, 37.1% yield, 99.819% purity) as a yellow solid. $^1$H NMR (400 MHz, $CD_3OD$) δ ppm 9.07 (d, J=2.0 Hz, 1H), 8.86 (d, J=1.6 Hz, 1H), 7.97 (t, J=2.0 Hz, 1H), 7.90 (s, 1H), 7.74-7.71 (m, 1H), 7.18-7.17 (m, 1H), 7.13-7.10 (m, 2H), 6.95 (s, 1H), 5.86 (s, 1H), 3.87 (t, J=6.0 Hz, 2H), 3.28-3.19 (m, 1H), 3.18 (t, J=6.0 Hz, 2H), 1.37 (d, J=6.8 Hz, 6H); ES-LCMS m/z 422.0 $[M+H]^+$.

Example 80

Synthesis of I-82a, I-82b and I-82c

I-82a

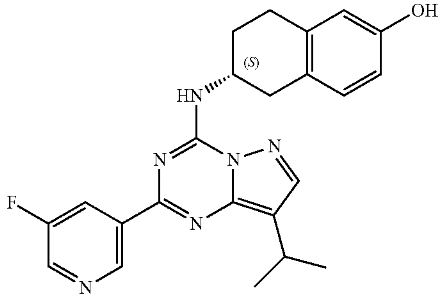

I-82b

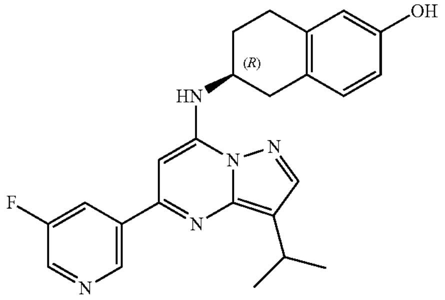

-continued

I-82c

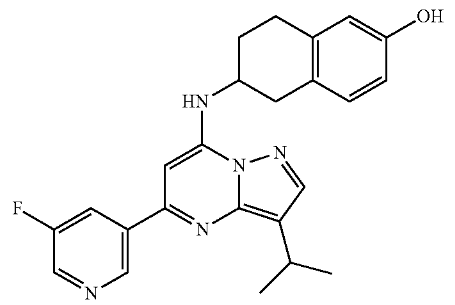

Synthetic Scheme:

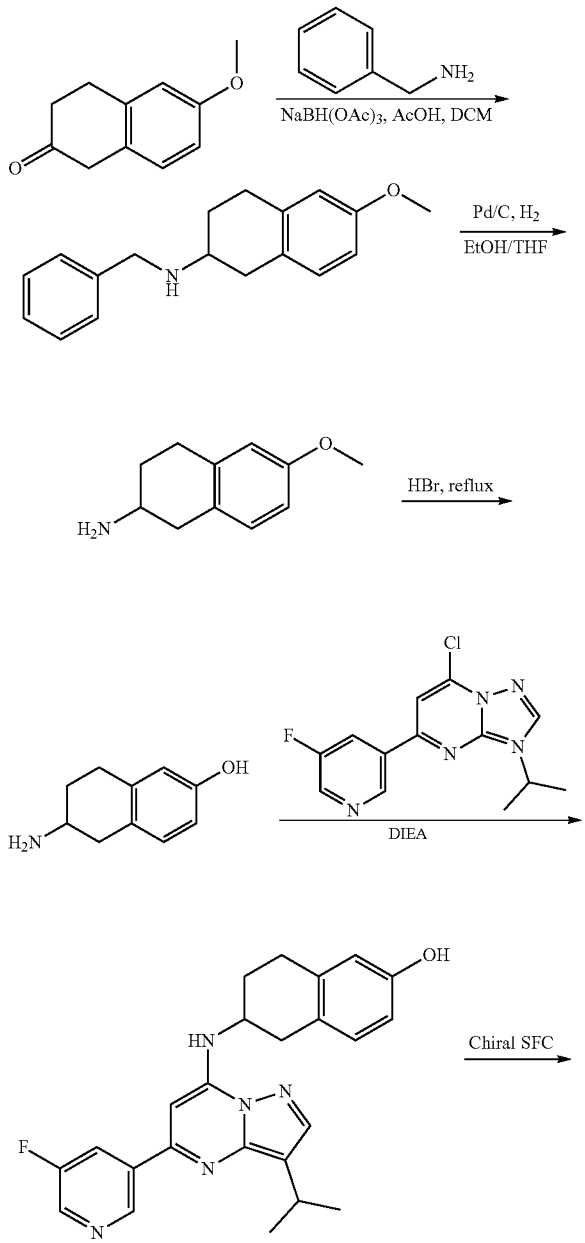

I-82c

-continued

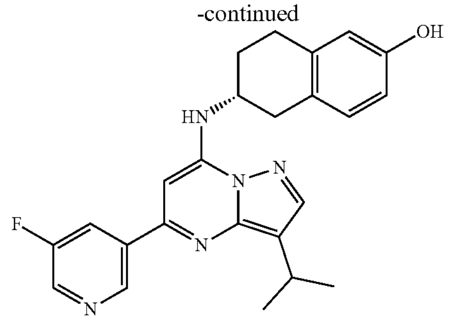

+

I-82a

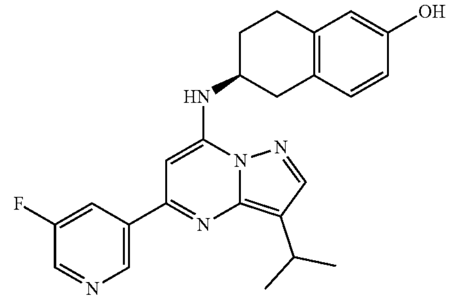

I-82b

Step 1: N-Benzyl-6-methoxy-tetralin-2-amine

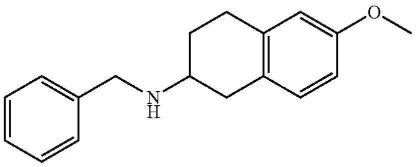 [SMILES: COc1ccc2c(c1)CCC(NCc1ccccc1)C2]

To a solution of 6-methoxytetralin-2-one (300 mg, 1.70 mmol, 1 eq) in anhydrous DCM (5 mL) was added phenylmethanamine (182.43 mg, 1.70 mmol, 185.58 μL, 1 eq), AcOH (102.23 mg, 1.70 mmol, 97.37 μL, 1 eq) and NaBH$(OAc)_3$ (541.24 mg, 2.55 mmol, 1.5 eq). The mixture was stirred at 25° C. for 12 h. Aq. NaOH (1 M, 20 mL) was added and the mixture was extracted with DCM (20 mL×3). The combined organic layers were washed with brine (20 mL), dried over anhydrous $Na_2SO_4$, filtered and concentrated to afford the crude product which was purified on silica gel column chromatography (from PE/EtOAc=1/0 to 10/1, TLC: PE/EtOAc=2/1, $R_f$=0.67) to give N-benzyl-6-methoxy-tetralin-2-amine (255 mg, 883.18 μmol, 51.88% yield, 92.6% purity) as brown oil. $^1$H NMR (400 MHz, $CD_3OD$) δ ppm 7.38-7.28 (m, 4H), 7.26-7.21 (m, 1H), 6.98 (d, J=8.4 Hz, 1H), 6.67 (dd, J=2.5, 8.3 Hz, 1H), 6.61 (d, J=2.4 Hz, 1H), 3.89 (s, 2H), 3.75 (s, 3H), 3.04-2.93 (m, 2H), 2.91-2.72 (m, 2H), 2.64-2.50 (m, 1H), 2.12-1.99 (m, 1H), 1.62-1.56 (m, 2H); ES-LCMS m/z 268.2 [M+H]$^+$.

Step 2: 6-Methoxytetralin-2-amine

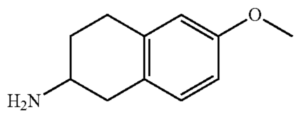

To a solution of N-benzyl-6-methoxy-tetralin-2-amine (255 mg, 883.18 μmol, 1 eq) in anhydrous EtOH (10 mL) and anhydrous THF (10 mL) was added Pd/C (10%, 255 mg) under $N_2$ atmosphere. The suspension was degassed and purged with $H_2$ for 3 times. The mixture was stirred under $H_2$ (50 psi) at 50° C. for 8 h. The mixture was filtered and concentrated to afford the crude product of 6-methoxytetralin-2-amine (210 mg, 874.40 μmol, 99.0% yield, 73.8% purity) as black oil which was used for the next step without further purification. $^1$H NMR (400 MHz, $CD_3OD$) δ ppm 6.94 (d, J=8.4 Hz, 1H), 6.68-6.64 (m, 1H), 6.62 (d, J=2.4 Hz, 1H), 3.74-3.71 (m, 3H), 3.10 (ddt, J=3.3, 5.1, 10.2 Hz, 1H), 2.93 (dd, J=4.1, 15.5 Hz, 1H), 2.88-2.81 (m, 2H), 2.49 (dd, J=9.8, 15.5 Hz, 1H), 2.06-1.97 (m, 1H), 1.64-1.51 (m, 1H); ES-LCMS m/z 178.3 $[M+H]^+$.

Step 3: 2-Aminotetralin-6-ol

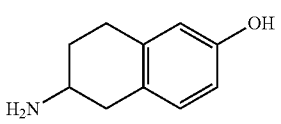 [SMILES: NC1CCc2cc(O)ccc2C1]

A solution of 6-methoxytetralin-2-amine (210 mg, 874.39 μmol, 1 eq) in HBr solution (5 mL) was stirred at 100° C. for 8 h. The mixture was concentrated to give the crude product 2-aminotetralin-6-ol (195 mg, 350.66 μmol, 40.10% yield, 43.9% purity, HBr) as a brown solid which was used for the next step without further purification. $^1$H NMR (400 MHz, $CD_3OD$) δ ppm 6.91 (d, J=8.4 Hz, 1H), 6.58 (dd, J=2.4, 8.4 Hz, 1H), 6.53 (s, 1H), 3.54-3.44 (m, 1H), 3.06 (dd, J=5.1, 15.4 Hz, 1H), 2.86 (dd, J=5.1, 8.2 Hz, 2H), 2.71 (dd, J=10.1, 15.4 Hz, 1H), 2.21-2.12 (m, 1H), 1.85-1.75 (m, 1H); ES-LCMS m/z 164.2 $[M+H]^+$.

Step 4: 2-[[5-(5-Fluoro-3-pyridyl)-3-isopropyl-pyrazolo[1,5-a]pyrimidin-7-yl]amino]tetralin-6-ol

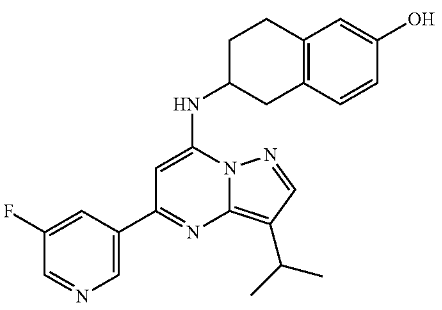 [SMILES: CC(C)c1cnn2c(NC3CCc4cc(O)ccc4C3)cc(-c3cncc(F)c3)nc12]

To a solution of 7-chloro-5-(5-fluoro-3-pyridyl)-3-isopropyl-pyrazolo[1,5-a]pyrimidine (100 mg, 337.09 μmol, 1 eq) in i-prOH (5 mL) was added DIEA (130.70 mg, 1.01 mmol, 176.14 μL, 3 eq) and 2-aminotetralin-6-ol (150.39 mg, 404.51 μmol, 1.2 eq). The mixture was stirred at 120° C. for 3 h under microwave under $N_2$ atmosphere. The mixture was concentrated to remove the solvent. $H_2O$ (10 mL) was added, extracted with EtOAc (10 mL×3). The combined organic layers were washed with brine (10 mL), dried over anhydrous $Na_2SO_4$, filtered and concentrated to afford the crude product which was purified on silica gel column chromatography (from PE/EtOAc=1/0 to 5/1, TLC: PE/EtOAc=1/1, $R_f$=0.60) to give 2-[[5-(5-fluoro-3-pyridyl)-3-isopropyl-pyrazolo[1,5-a]pyrimidin-7-yl]amino]tetralin-6-ol (78 mg, 184.97 μmol, 54.9% yield, 99.0% purity) as a yellow solid. $^1$H NMR (400 MHz, $CD_3OD$) δ ppm 9.15 (s, 1H), 8.51 (d, J=2.6 Hz, 1H), 8.36 (d, J=9.3 Hz, 1H), 7.92 (s, 1H), 6.93 (d, J=7.5 Hz, 1H), 6.74 (s, 1H), 6.61-6.53 (m, 2H), 4.58 (s, 2H), 4.35-4.23 (m, 1H), 2.94-2.81 (m, 2H), 2.35-2.18 (m, 1H), 2.09-1.86 (m, 2H), 1.40 (d, J=7.1 Hz, 6H); ES-LCMS m/z 418.0 $[M+H]^+$.

Step 5: (2R)-2-[[5-(5-fluoro-3-pyridyl)-3-isopropyl-pyrazolo[1,5-a]pyrimidin-7-yl]amino]tetralin-6-ol (I-82b) & (2S)-2-[[5-(5-Fluoro-3-pyridyl)-3-isopropyl-pyrazolo[1,5-a]pyrimidin-7-yl]amino]tetralin-6-ol (I-82a)

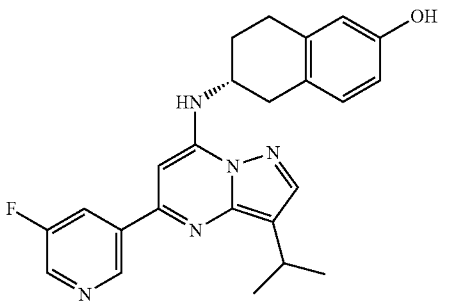

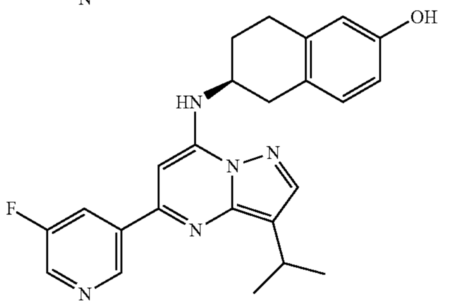

2-[[5-(5-Fluoro-3-pyridyl)-3-isopropyl-pyrazolo[1,5-a]pyrimidin-7-yl]amino]tetralin-6-ol (78 mg, 184.97 μmol, 1 eq) was separated by SFC (column: AD (250 mm*30 mm, 5 μm); mobile phase: [0.1% $NH_3H_2O$ IPA]; B %: 40%-40%, min). The solution after separation were concentrated to afford the crude products which were purified by preparative HPLC (MeCN/$H_2O$ as eluents, acidic condition, Instrument: Phenomenex Synergi C18 150*30 mm*4 um/Mobile phase: water (0.05% HCl)-ACN/Gradient: B from 55% to 85% in 12 min/Flow rate: 25 mL/min), followed by lyophilization to yield an enantiomer (24.75 mg, 50.47 μmol, 27.3% yield, 100% purity, 2HCl, SFC: $T_R$=5.168 min, ee=100%, OR: $[\alpha]^{26.6}{}_D$=167.660) as a yellow solid. $^1$H NMR (400 MHz, $CD_3OD$) δ ppm 8.97 (s, 1H), 8.79 (d, J=2.6 Hz, 1H), 8.34-8.28 (m, 1H), 8.25 (s, 1H), 6.98-6.91 (m, 2H), 6.61-

6.55 (m, 2H), 4.47 (s, 1H), 3.40-3.33 (m, 1H), 3.18 (dd, J=4.6, 15.4 Hz, 1H), 3.09-2.99 (m, 2H), 2.96-2.87 (m, 1H), 2.25 (s, 1H), 2.07 (dq, J=5.5, 11.8 Hz, 1H), 1.38 (d, J=7.1 Hz, 6H); ES-LCMS m/z 418.0 $[M+H]^+$; and the other enantiomer (26.47 mg, 53.98 μmol, 29.2% yield, 100% purity, 2HCl, SFC: $T_R$=5.742 min, ee=100%, OR: $[\alpha]^{26.8}{}_D$=−167.394) as a yellow solid. $^1$H NMR (400 MHz, $CD_3OD$) δ ppm 8.97 (s, 1H), 8.78 (d, J=2.9 Hz, 1H), 8.30 (td, J=2.2, 9.0 Hz, 1H), 8.24 (s, 1H), 6.98-6.91 (m, 2H), 6.62-6.54 (m, 2H), 4.48 (s, 1H), 3.37-3.31 (m, 1H), 3.22-3.13 (m, 1H), 3.09-2.98 (m, 2H), 2.96-2.87 (m, 1H), 2.26 (d, J=10.4 Hz, 1H), 2.07 (tdd, J=5.6, 11.6, 17.7 Hz, 1H), 1.38 (d, J=6.8 Hz, 6H); ES-LCMS m/z 418.0 $[M+H]^+$.

Example 81

Synthesis of I-83

I-83

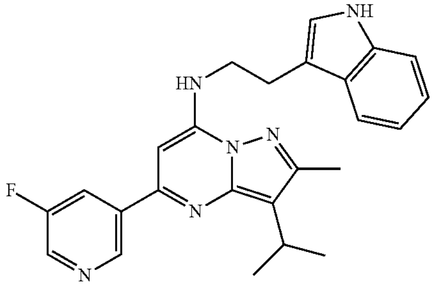

Synthetic Scheme:

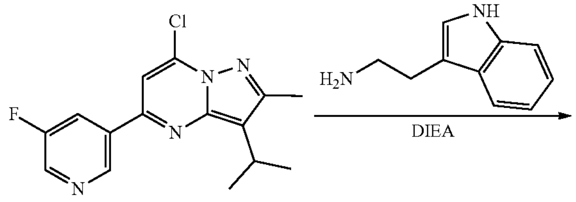

1

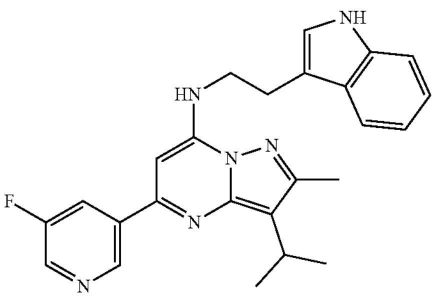

I-83

Step 1: 5-(5-Fluoro-3-pyridyl)-N-[2-(1H-indol-3-yl)ethyl]-3-isopropyl-2-methyl-pyrazolo[1,5-a]pyrimidin-7-amine (I-83)

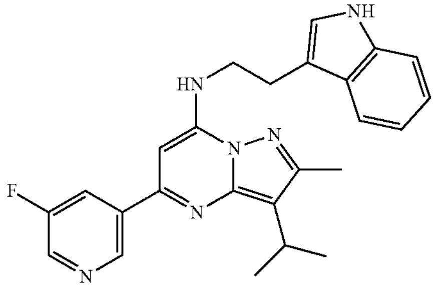 [SMILES: Cc1nn2c(NCCc3c[nH]c4ccccc34)cc(-c3cncc(F)c3)nc2c1C(C)C]

A mixture of 7-chloro-5-(5-fluoro-3-pyridyl)-3-isopropyl-2-methyl-pyrazolo[1,5-a]pyrimidine (50 mg, 160.79 μmol, 1 eq), 2-(1H-indol-3-yl)ethanamine (25.76 mg, 160.79 μmol, 1 eq) and DIEA (62.34 mg, 482.37 μmol, 84.02 μL, 3 eq) in i-PrOH (5 mL) was stirred at 80° C. for 2 h. The mixture was concentrated under reduced pressure to give a residue which was purified by preparative HPLC (column: Phenomenex Synergi C18 150*30 mm*4 um; mobile phase: [water(0.05% HCl)-ACN]; B %: 50%-80%, 12 min) to yield 5-(5-fluoro-3-pyridyl)-N-[2-(1H-indol-3-yl)ethyl]-3-isopropyl-2-methyl-pyrazolo[1,5-a]pyrimidin-7-amine (41.24 mg, 76.67 μmol, 47.7% yield, 100% purity, 3HCl) as a yellow solid. $^1$H NMR (400 MHz, $CD_3OD$) δ ppm 8.68 (d, J=2.8 Hz, 1H), 8.33 (s, 1H), 7.51 (d, J=7.8 Hz, 1H), 7.47-7.45 (m, 1H), 7.15 (d, J=7.6 Hz, 1H), 7.02 (s, 1H), 6.97 (t, J=7.6 Hz, 1H), 6.84-6.82 (m, 1H), 5.71 (s, 1H), 4.01-3.97 (m, 2H), 3.27 (t, J=7.2 Hz, 1H), 3.23-3.19 (m, 2H), 2.57 (s, 3H), 1.36 (d, J=7.2 Hz, 6H); ES-LCMS m/z 429.3 $[M+H]^+$.

Example 82

Synthesis of I-84

I-84

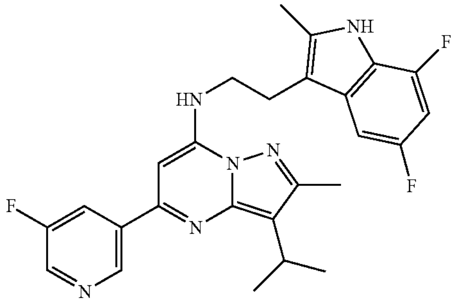

Synthetic Scheme:

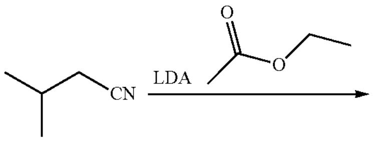

-continued

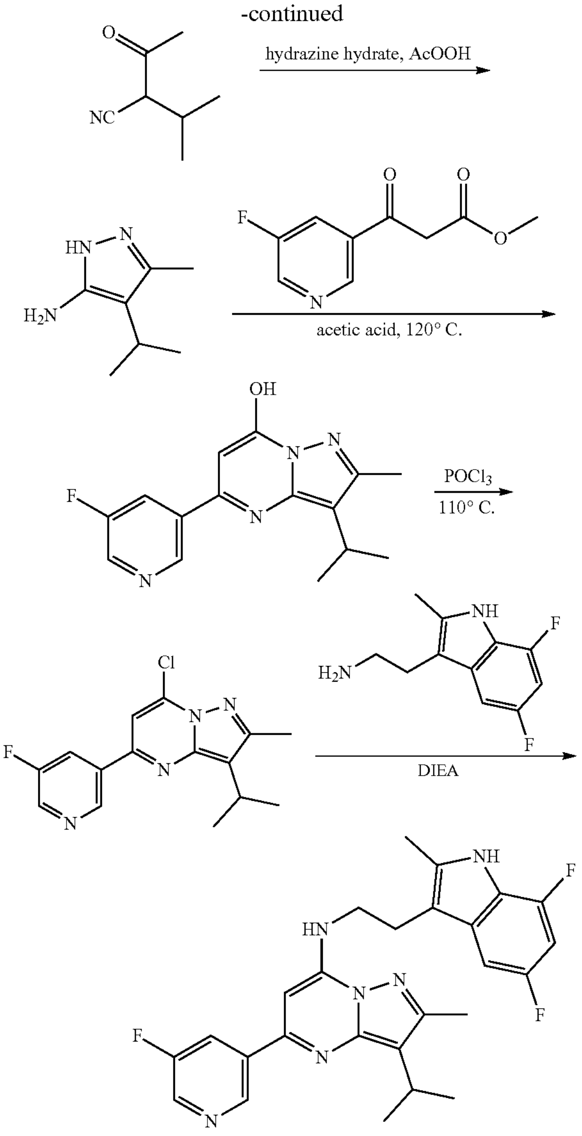

I-84

Step 1: 2-Acetyl-3-methyl-butanenitrile

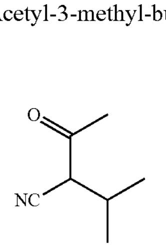

To a mixture of DIPA (1.22 g, 12.03 mmol, 1.70 mL, 1 eq) in THF (10 mL) was added n-BuLi (2.5 M in THF, 5.05 mL, 1.05 eq) dropwise at −78° C. under $N_2$. The mixture was stirred at −78° C. for 15 min, then warmed up to 0° C. and stirred for 1 h. The mixture was cooled to −78° C., 3-methylbutanenitrile (1 g, 12.03 mmol, 1.27 mL, 1 eq) in THF (10 mL) was added dropwise and stirred at −78° C. for 15 min. A solution of ethyl acetate (1.11 g, 12.63 mmol, 1.24 mL, 1.05 eq) in THF (10 mL) was added dropwise. The mixture was stirred at 20° C. for 16 h. TLC (PE/EtOAc=1/1, $R_f$=0.74) indicated one new spot formed. The mixture was quenched with 2N HCl (10 mL), extracted with EtOAc (50 mL×3), washed with brine (20 mL), dried over $Na_2SO_4$, filtered and concentrated under reduced pressure to give a residue which was purified by flash silica gel chromatography (from PE/EtOAc=10/1 to 1/1, TLC: PE/EtOAc=1/1, $R_f$=0.74) to yield 2-acetyl-3-methyl-butanenitrile (661 mg, 4.22 mmol, 35.1% yield, 80.0% purity) as yellow oil. $^1$H NMR (400 MHz, $CDCl_3$) ppm 3.32 (d, J=5.2 Hz, 1H), 2.44-2.38 (m, 1H), 2.37 (s, 3H), 1.11 (d, J=6.8 Hz, 3H), 1.09-1.05 (m, 3H); ES-LCMS: No correct mass was found.

Step 2: 4-Isopropyl-3-methyl-1H-pyrazol-5-amine

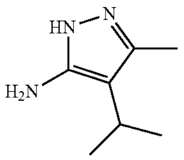

A mixture of 2-acetyl-3-methyl-butanenitrile (750.00 mg, 4.79 mmol, 1 eq), hydrazine hydrate (311.96 mg, 6.23 mmol, 302.87 μL, 1.3 eq) and AcOH (503.76 mg, 8.39 mmol, 479.77 μL, 1.75 eq) in EtOH (20 mL) was stirred at 90° C. for 16 h under $N_2$. The mixture was concentrated under reduced pressure to give a residue which was diluted with sat.$NaHCO_3$ (20 mL) and extracted with DCM (20 mL×3). The combined organic layers were dried over anhydrous $Na_2SO_4$, filtered and concentrated under reduced pressure to give 4-isopropyl-3-methyl-1H-pyrazol-5-amine (560 mg, 3.62 mmol, 75.5% yield, 90.0% purity) as a yellow solid. $^1$H NMR (400 MHz, $CDCl_3$) δ ppm 2.82-2.69 (m, 1H), 2.18 (s, 3H), 1.23 (d, J=6.8 Hz, 6H); ES-LCMS m/z 140.2 $[M+H]^+$.

Step 3: 5-(5-Fluoro-3-pyridyl)-3-isopropyl-2-methyl-pyrazolo[1,5-a]pyrimidin-7-ol

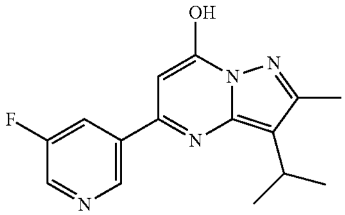 [SMILES: Cc1nn2c(O)cc(-c3cncc(F)c3)nc2c1C(C)C]

A mixture of 4-isopropyl-3-methyl-1H-pyrazol-5-amine (502.05 mg, 3.25 mmol, 0.8 eq) and methyl 3-(5-fluoro-3-pyridyl)-3-oxo-propanoate (816.33 mg, 4.06 mmol, 1 eq) in AcOH (10 mL) was stirred at 120° C. for 3 h. The mixture was concentrated under reduced pressure to give 5-(5-fluoro-3-pyridyl)-3-isopropyl-2-methyl-pyrazolo[1,5-a]pyrimidin-7-ol (1.2 g, crude) as a purple solid which was used in next step without further purification. $^1$H NMR (400 MHz, $CD_3OD$) δ ppm 8.82 (s, 1H), 8.68-8.66 (m, 1H), 8.14-8.08 (m, 2H), 3.30-3.24 (m, 1H), 2.46-2.41 (m, 3H), 1.37 (d, J=7.2 Hz, 6H); ES-LCMS m/z 287.2 $[M+H]^+$.

Step 4: 7-Chloro-5-(5-fluoro-3-pyridyl)-3-isopropyl-2-methyl-pyrazolo[1,5-a]pyrimidine

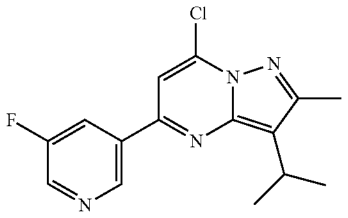

A solution of 5-(5-fluoro-3-pyridyl)-3-isopropyl-2-methyl-pyrazolo[1,5-a]pyrimidin-7-ol (1.2 g, 4.19 mmol, 1 eq) in $POCl_3$ (16.3 g, 106.31 mmol, 9.88 mL, 25.36 eq) was stirred at 110° C. for 2 h. The mixture was concentrated under reduced pressure to give a residue which was purified by flash silica gel chromatography (from PE/EtOAc=10/1 to 1/1, TLC: PE/EtOAc=1/1, $R_f$=0.75) to yield 7-chloro-5-(5-fluoro-3-pyridyl)-3-isopropyl-2-methyl-pyrazolo[1,5-a]pyrimidine (381 mg, 1.23 mmol, 29.2% yield, 98.0% purity) as a yellow solid. $^1H$ NMR (400 MHz, $CD_3OD$) δ ppm 9.08 (s, 1H), 8.57 (d, J=2.4 Hz, 1H), 8.20-8.15 (m, 1H), 7.28 (s, 1H), 3.36-3.24 (m, 1H), 2.57 (s, 3H), 1.48 (d, J=6.8 Hz, 6H); ES-LCMS m/z 305.0 $[M+H]^+$.

Step 5: N-[2-(5,7-Difluoro-2-methyl-1H-indol-3-yl)ethyl]-5-(5-fluoro-3-pyridyl)-3-isopropyl-2-methyl-pyrazolo[1,5-a]pyrimidin-7-amine (I-84)

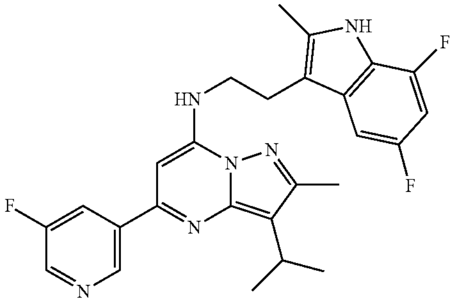 [SMILES: Cc1nn2c(NCCc3c(C)[nH]c4c(F)cc(F)cc34)cc(-c3cncc(F)c3)nc2c1C(C)C]

A mixture of 7-chloro-5-(5-fluoro-3-pyridyl)-3-isopropyl-2-methyl-pyrazolo[1,5-a]pyrimidine (50 mg, 160.79 μmol, 1 eq), 2-(5,7-difluoro-2-methyl-1H-indol-3-yl)ethanamine (33.80 mg, 160.79 μmol, 1 eq) and DIEA (62.34 mg, 482.36 μmol, 84.02 μL, 3 eq) in i-PrOH (10 mL) was stirred at 80° C. for 2 h. The mixture was concentrated under reduced pressure to give a residue which was purified by preparative HPLC (column: Phenomenex Gemini 150*25 mm*10 um; mobile phase: [water(0.05% HCl)-ACN]; B %: 58%-78%, 10 min) to yield N-[2-(5,7-difluoro-2-methyl-1H-indol-3-yl)ethyl]-5-(5-fluoro-3-pyridyl)-3-isopropyl-2-methyl-pyrazolo[1,5-a]pyrimidin-7-amine (32.01 mg, 54.45 μmol, 33.9% yield, 100% purity, 3HCl) as a yellow solid. $^1H$ NMR (400 MHz, $CD_3OD$) δ ppm 8.75 (d, J=2.8 Hz, 1H), 8.43 (s, 1H), 7.66-7.63 (m, 1H), 6.93-6.89 (m, 1H), 6.46-6.39 (m, 1H), 5.73 (s, 1H), 3.97-3.94 (m, 2H), 3.31-3.23 (m, 1H), 3.13-3.09 (m, 2H), 2.57 (s, 3H), 2.23 (s, 3H), 1.36 (d, J=7.2 Hz, 6H); ES-LCMS m/z 479.3 $[M+H]^+$.

Example 83

Synthesis of I-85

I-85

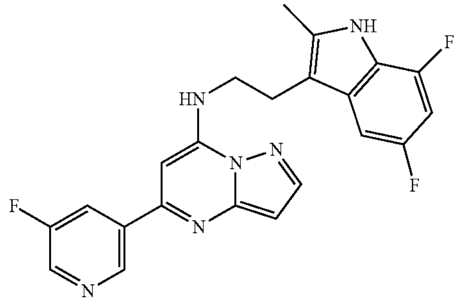 [SMILES: Cc1[nH]c2c(F)cc(F)cc2c1CCNc1cc(-c2cncc(F)c2)nc2ccnn12]

Synthetic Scheme:

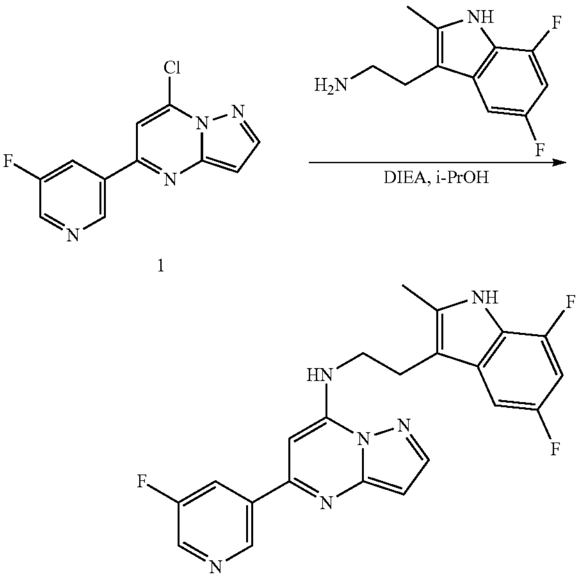

1

I-85

Step 1: N-(2-(5,7-Difluoro-2-methyl-1H-indol-3-yl)ethyl)-5-(5-fluoropyridin-3-yl)pyrazolo[1,5-a]pyrimidin-7-amine (I-85)

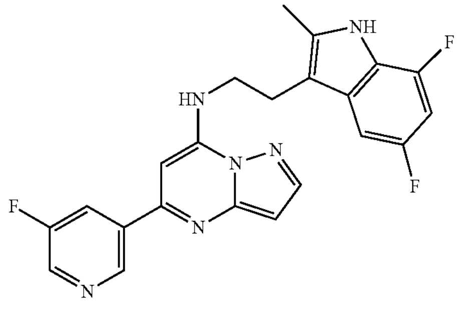

A mixture of 7-chloro-5-(5-fluoro-3-pyridyl)pyrazolo[1,5-a]pyrimidine (40 mg, 147.68 μmol, 1 eq), 2-(5,7-difluoro- 2-methyl-1H-indol-3-yl)ethanamine (60 mg, 153.73 μmol, 1.04 eq, 2 oxalic acid) and DIEA (60.00 mg, 464.24 μmol, 80.86 μL, 3.14 eq) in i-PrOH (3 mL) was stirred at 50° C. for 19 h. The mixture was concentrated under reduced pressure to dryness to give a residue which was purified by preparative HPLC (column: Phenomenex Synergi C18 150×30 mm×4 um; mobile phase: [water(0.05% HCl)-ACN]; B %: 30%-52%, 12 min). The desired fraction was lyophilized to give N-(2-(5,7-difluoro-2-methyl-1H-indol-3-yl)ethyl)-5-(5-fluoropyridin-3-yl)pyrazolo[1,5-a]pyrimidin-7-amine (22.94 mg, 43.14 μmol, 29.2% yield, 100.0% purity, 3HCl) as an off-white solid. $^1$H NMR (400 MHz, $CD_3OD$) δ ppm 8.71 (d, J=2.4 Hz, 1H), 8.47 (s, 1H), 8.22 (d, J=2.4 Hz, 1H), 7.59 (td, J=2.4, 9.2 Hz, 1H), 7.01 (dd, J=2.4, 9.2 Hz, 1H), 6.51 (d, J=2.4 Hz, 1H), 6.44 (ddd, J=2.4, 9.6, 11.2 Hz, 1H), 5.85 (s, 1H), 4.04-3.92 (m, 2H), 3.17-3.08 (m, 2H), 2.13 (s, 3H); ES-LCMS m/z 423.2 $[M+H]^+$.

Example 84

Synthesis of I-86

I-86

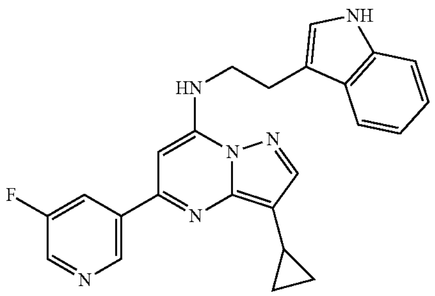

Synthetic Scheme:

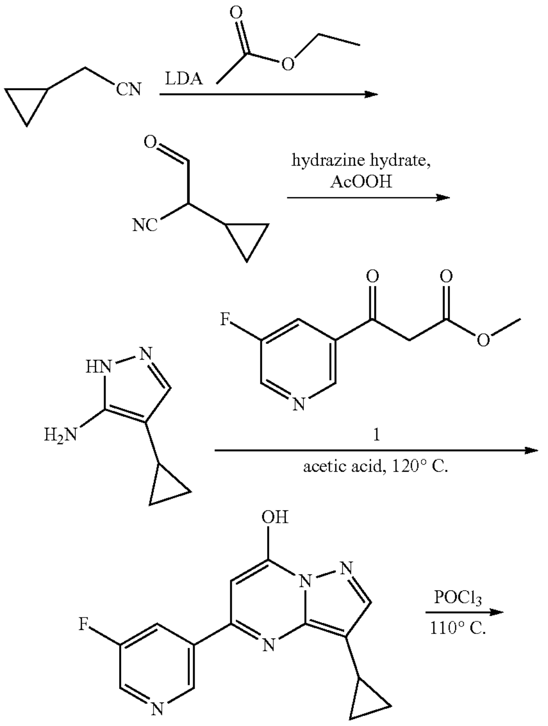

-continued

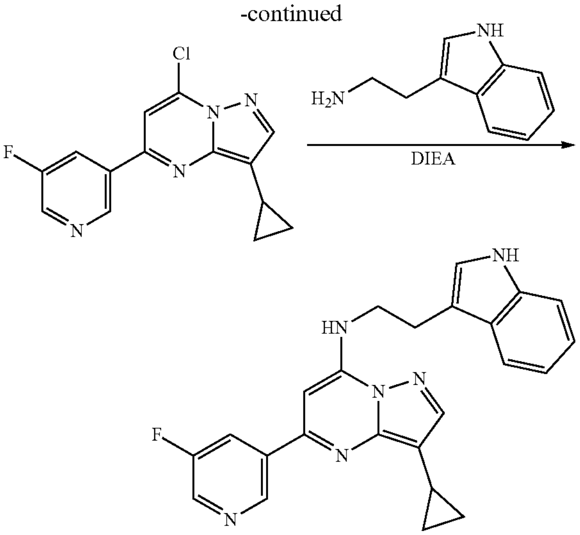

I-86

Step 1: 2-Cyclopropyl-3-oxo-propanenitrile

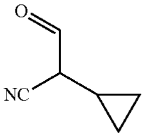

To a solution of DIPA (3.74 g, 36.98 mmol, 5.23 mL, 1 eq) in THF (15 mL) was added n-BuLi (2.5 M in n-hexane, 15.53 mL, 1.05 eq). The mixture was stirred at −78° C. for 10 min. The solution of 2-cyclopropylacetonitrile (3 g, 36.98 mmol, 3.42 mL, 1 eq) in THF (15 mL) was added into the above mixture dropwise. Then the mixture was stirred at −78° C. for 10 min under $N_2$ atmosphere. A solution of ethyl formate (2.88 g, 38.88 mmol, 3.13 mL, 1.05 eq) in THF (15 mL) was added dropwise and stirred at −78° C. for 40 min. Then the reaction mixture was warmed to 25° C. for 12 h. TLC (PE/EtOAc=1/1, $R_f$=0.50) showed one major new spot was detected. The reaction mixture was quenched by addition 1 N HCl solution (50 mL) at 0° C., extracted with EtOAc (50 mL×3). The combined organic layers were dried over $Na_2SO_4$, filtered and concentrated under reduced pressure to give the residue which was purified by flash silica gel chromatography (from PE/EtOAc=100/1 to 1/1, TLC: PE/EtOAc=1/1, $R_f$=0.50) to yield compound 2-cyclopropyl-3-oxo-propanenitrile (3.4 g, crude) as yellow oil. $^1$H NMR (400 MHz, $CDCl_3$) δ ppm 9.61 (d, J=1.1 Hz, 1H), 4.61-4.55 (m, 1H), 4.01-3.84 (m, 1H), 1.92-1.79 (m, 2H), 1.66-1.52 (m, 2H).

Step 2: 4-Cyclopropyl-1H-pyrazol-5-amine $H_2N$

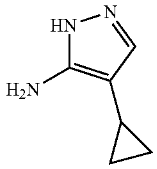

To a solution of 2-cyclopropyl-3-oxo-propanenitrile (3.4 g, 31.16 mmol, 1 eq) in EtOH (30 mL) was added AcOH (3.27 g, 54.52 mmol, 3.12 mL, 1.75 eq) and hydrazine (1.30 g, 40.50 mmol, 1.46 mL, 1.3 eq). The mixture was stirred at 90° C. for 12 h. TLC (PE/EtOAc=1/1, $R_f$=0.10) showed one major new spot was detected. The reaction mixture was concentrated under reduced pressure to give the residue which was diluted with $NaHCO_3$ solution (200 mL) and extracted with EtOAc (100 mL×3). The combined organic layers were dried over $Na_2SO_4$, filtered and concentrated under reduced pressure to give the residue which was purified by flash silica gel chromatography (from DCM/MeOH=100/1 to 10/1, TLC: PE/EtOAc=10/1, $R_f$=0.70) to yield 4-cyclopropyl-1H-pyrazol-5-amine (1.7 g, crude) as a brown solid. $^1$H NMR (400 MHz, $CDCl_3$) δ ppm 7.04 (d, J=0.7 Hz, 1H), 1.49-1.39 (m, 1H), 0.83-0.75 (m, 2H), 0.49-0.41 (m, 2H); ES-LCMS m/z no desired MS was detected.

Step 3: 3-Cyclopropyl-5-(5-fluoro-3-pyridyl)pyrazolo[1,5-a]pyrimidin-7-ol

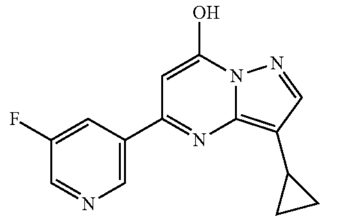 [SMILES: Oc1cc(-c2cncc(F)c2)nc2c(C3CC3)cnn12]

To a solution of methyl 3-(5-fluoro-3-pyridyl)-3-oxo-propanoate (500 mg, 2.49 mmol, 1 eq) in AcOH (6 mL) was added 4-cyclopropyl-1H-pyrazol-5-amine (370.54 mg, 3.01 mmol, 1.21 eq). The mixture was stirred at 120° C. for 2 h. The reaction mixture was concentrated under reduced pressure to yield 3-cyclopropyl-5-(5-fluoro-3-pyridyl)pyrazolo[1,5-a]pyrimidin-7-ol (830 mg, crude) as a yellow solid which was used in the next step without further purification. $^1$H NMR (400 MHz, DMSO-$d_6$) δ ppm 8.90 (s, 1H), 8.80 (d, J=2.6 Hz, 1H), 8.25 (td, J=2.2, 9.7 Hz, 1H), 7.68 (s, 1H), 6.09 (s, 1H), 2.05 (m, 2H), 0.94-0.87 (m, 2H), 0.73-0.64 (m, 2H); ES-LCMS m/z 271.2 [M+H]$^+$.

Step 4: 7-Chloro-3-cyclopropyl-5-(5-fluoro-3-pyridyl)pyrazolo[1,5-a]pyrimidine

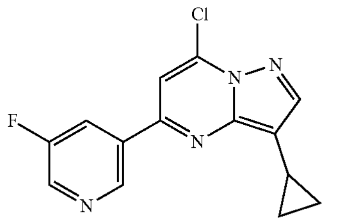 [SMILES: Fc1cncc(-c2cc(Cl)n3ncc(C4CC4)c3n2)c1]

To a solution of 3-cyclopropyl-5-(5-fluoro-3-pyridyl)pyrazolo[1,5-a]pyrimidin-7-ol (830 mg, 3.07 mmol, 1 eq) in $POCl_3$ (5 mL) was stirred at 110° C. for 1 h. The reaction mixture was concentrated under reduced pressure to give the residue which was purified by flash silica gel chromatography (from PE/EtOAc=100/1 to 2/1, TLC: PE/EtOAc=3/1, $R_f$=0.40) to yield compound 7-chloro-3-cyclopropyl-5-(5-fluoro-3-pyridyl)pyrazolo[1,5-a]pyrimidine (290 mg, 924.12 μmol, 30.1% yield, 92.0% purity) as a yellow solid. $^1$H NMR (400 MHz, $CDCl_3$) δ ppm 9.09 (s, 1H), 8.60 (d, J=2.6 Hz, 1H), 8.20 (td, J=2.1, 9.4 Hz, 1H), 8.01 (s, 1H), 7.37 (s, 1H), 2.17 (tt, J=5.2, 8.4 Hz, 1H), 1.11-1.03 (m, 2H), 1.02-0.95 (m, 2H); ES-LCMS m/z 289.0, 291.0 [M+H]$^+$.

Step 5: 3-Cyclopropyl-5-(5-fluoro-3-pyridyl)-N-[2-(1H-indol-3-yl)ethyl]pyrazolo[1,5-a]pyrimidin-7-amine (I-86)

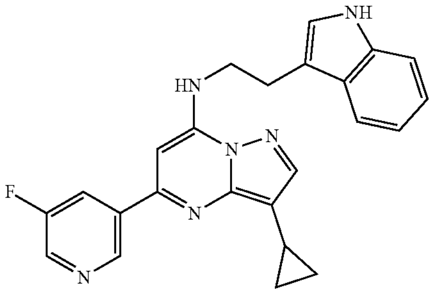 [SMILES: Fc1cncc(-c2cc(NCCc3c[nH]c4ccccc34)n3ncc(C4CC4)c3n2)c1]

To a solution of 7-chloro-3-cyclopropyl-5-(5-fluoro-3-pyridyl)pyrazolo[1,5-a]pyrimidine (45 mg, 143.40 μmol, 1.0 eq) in i-PrOH (3 mL) was added DIEA (55.60 mg, 430.19 μmol, 74.93 μL, 3.0 eq) and 2-(1H-indol-3-yl)ethanamine (29.87 mg, 186.42 μmol, 1.3 eq). The mixture was stirred at 50° C. for 3 h. The reaction mixture was concentrated under reduced pressure to give the residue which was purified by preparative HPLC (HCl condition, column: Phenomenex Gemini 150×25 mm×10 um; mobile phase: [water(0.05% HCl)-ACN]; B %: 43%-73%, 10 min) and the desired fraction was lyophilized to yield 3-cyclopropyl-5-(5-fluoro-3-pyridyl)-N-[2-(1H-indol-3-yl)ethyl]pyrazolo[1,5-a]pyrimidin-7-amine (40.50 mg, 77.61 μmol, 54.1% yield, 100% purity, 3HCl salt) as a yellow solid. $^1$H NMR (400 MHz, $CD_3OD$) δ ppm 8.73 (d, J=2.5 Hz, 1H), 8.36 (s, 1H), 8.00 (s, 1H), 7.54-7.46 (m, 2H), 7.15 (d, J=8.0 Hz, 1H), 7.00 (s, 1H), 6.97 (t, J=7.5 Hz, 1H), 6.85-6.80 (m, 1H), 5.78 (s, 1H), 4.07-3.99 (m, 2H), 3.26-3.19 (m, 2H), 1.96-1.87 (m, 1H), 1.05-0.97 (m, 2H), 0.78-0.70 (m, 2H); ES-LCMS m/z 412.9 [M+H]$^+$.

Example 85

Synthesis of I-87

I-87

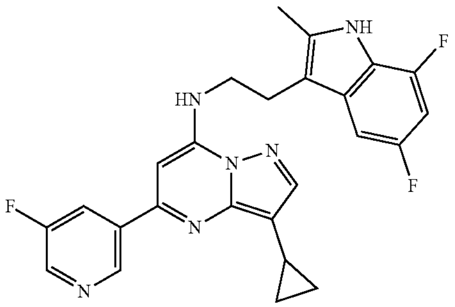

Synthetic Scheme:

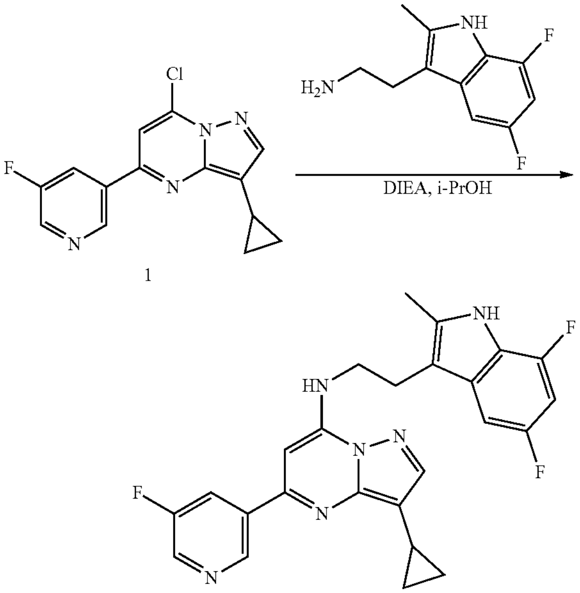

1

I-87

Step 1: 3-Cyclopropyl-N-(2-(5,7-difluoro-2-methyl-1H-indol-3-yl)ethyl)-5-(5-fluoropyridin-3-yl)pyrazolo[1,5-a]pyrimidin-7-amine (I-87)

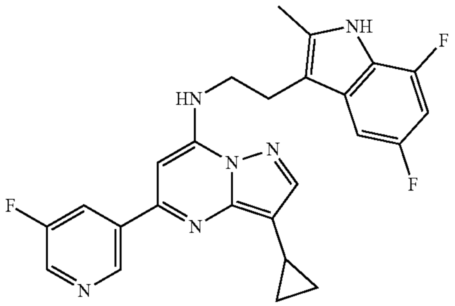 [SMILES: Cc1[nH]c2c(F)cc(F)cc2c1CCNc1cc(-c2cncc(F)c2)nc2c(C3CC3)cnn12]

A mixture of 7-chloro-3-cyclopropyl-5-(5-fluoro-3-pyridyl)pyrazolo[1,5-a]pyrimidine (40 mg, 127.46 μmol, 1 eq), 2-(5,7-difluoro-2-methyl-1H-indol-3-yl)ethanamine (54.72 mg, 140.21 μmol, 1.1 eq, 2 oxalic acid) and DIEA (0.055 g, 425.56 μmol, 74.12 μL, 3.34 eq) in i-PrOH (3 mL) was stirred at 50° C. for 19 h. The mixture was concentrated under reduced pressure to dryness to give a residue which was purified by preparative HPLC (column: Phenomenex Synergi C18 150×30 mm×4 um; mobile phase: [water (0.05% HCl)-ACN]; B %: 45%-75%, 12 min). The desired fraction was lyophilized to give 3-cyclopropyl-N-(2-(5,7-difluoro-2-methyl-1H-indol-3-yl)ethyl)-5-(5-fluoropyridin-3-yl)pyrazolo[1,5-a]pyrimidin-7-amine (22.33 mg, 37.39 μmol, 29.3% yield, 95.7% purity, 3HCl) as an off-white solid. $^1$H NMR (400 MHz, $CD_3OD$) δ ppm 8.73 (d, J=1.6 Hz, 1H), 8.43 (s, 1H), 7.97 (s, 1H), 7.62 (d, J=8.8 Hz, 1H), 6.93 (dd, J=2.0, 9.2 Hz, 1H), 6.49-6.35 (m, 1H), 5.73 (s, 1H), 3.96 (t, J=5.2 Hz, 2H), 3.10 (t, J=5.6 Hz, 2H), 2.14 (s, 3H), 1.98-1.86 (m, 1H), 1.07-0.94 (m, 2H), 0.79-0.67 (m, 2H); ES-LCMS m/z 463.2 $[M+H]^+$.

Example 86

Synthesis of I-88

I-88

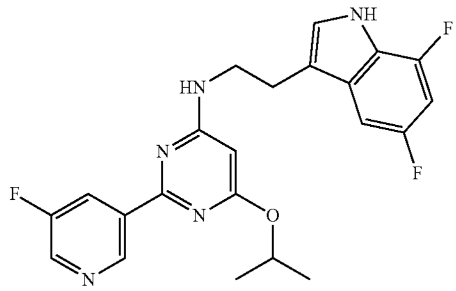

Synthetic Scheme:

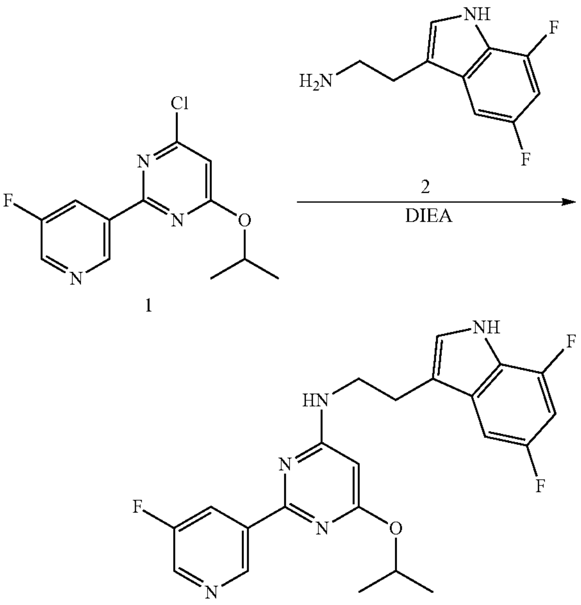

1

I-88

Step 1: N-[2-(5,7-Difluoro-1H-indol-3-yl)ethyl]-2-(5-fluoro-3-pyridyl)-6-isopropoxy-pyrimidin-4-amine (I-88)

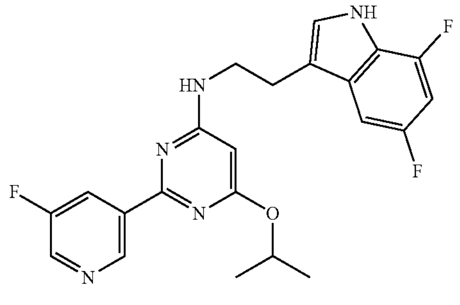 [SMILES: CC(C)Oc1cc(NCCc2c[nH]c3c(F)cc(F)cc23)nc(-c2cncc(F)c2)n1]

4-Chloro-2-(5-fluoro-3-pyridyl)-6-isopropoxy-pyrimidine (55 mg, 172.59 μmol, 1 eq), 2-(5,7-difluoro-1H-indol- 3-yl)ethanamine (50.31 mg, 225.64 μmol, 1.31 eq) and DIEA (66.92 mg, 517.77 μmol, 90.19 μL, 3.0 eq) in i-PrOH (3 mL) were taken up into a microwave tube. The sealed tube was heated at 125° C. for 6 h under microwave. The reaction mixture was concentrated under reduced pressure to give the residue which was purified by preparative HPLC (HCl condition; column: Phenomenex Synergi C18 150×30 mm×4 um; mobile phase: [water (0.05% HCl)-ACN]; B %: 65%-95%, 12 min). The desired fraction was lyophilized to yield N-[2-(5,7-difluoro-1H-indol-3-yl)ethyl]-2-(5-fluoro-3-pyridyl)-6-isopropoxy-pyrimidin-4-amine (15.59 mg, 28.70 mol, 16.6% yield, 98.81% purity, 3HCl salt) as a yellow solid. $^1$H NMR (400 MHz, $CD_3OD$) δ ppm 9.12 (s, 1H), 8.76 (d, J=2.5 Hz, 1H), 8.36 (d, J=8.8 Hz, 1H), 7.21 (s, 1H), 7.11 (dd, J=1.6, 9.2 Hz, 1H), 6.66 (t, J=9.9 Hz, 1H), 5.80 (s, 1H), 5.07 (s, 1H), 3.81 (s, 2H), 3.06 (t, J=6.7 Hz, 2H), 1.39 (d, J=6.0 Hz, 6H); ES-LCMS m/z 428.2 $[M+H]^+$.

Example 87

Synthesis of I-89

I-89

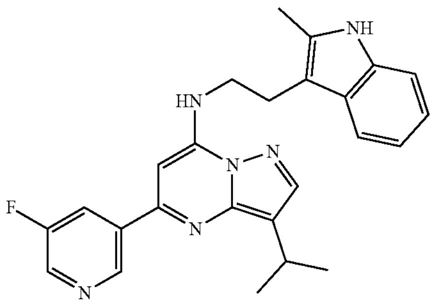 [SMILES: Cc1[nH]c2ccccc2c1CCNc1cc(-c2cncc(F)c2)nc2c(C(C)C)cnn12]

Synthetic Scheme:

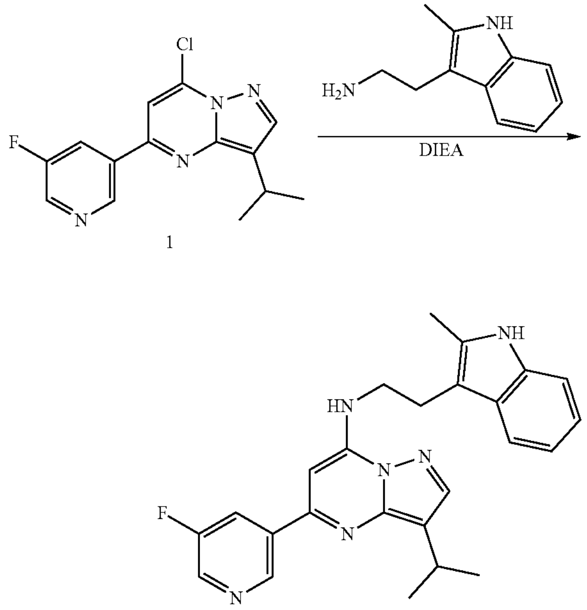

1

I-89

Step 1: 5-(5-Fluoro-3-pyridyl)-3-isopropyl-N-[2-(2-methyl-1H-indol-3-yl)ethyl]pyrazolo[1,5-a]pyrimidin-7-amin (I-89)

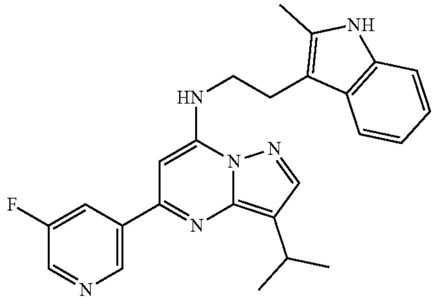

To a solution of 7-chloro-5-(5-fluoro-3-pyridyl)-3-isopropyl-pyrazolo[1,5-a]pyrimidine (40 mg, 132.08 μmol, 1 eq) and 2-(2-methyl-1H-indol-3-yl)ethanamine (34.52 mg, 198.13 μmol, 1.5 eq) in i-PrOH (10 mL) was added DIEA (51.21 mg, 396.25 μmol, 69.02 μL, 3.0 eq). The mixture was stirred at 70° C. for 16 h. The reaction mixture concentrated under reduced pressure to give a residue which was purified by preparative HPLC (column: Phenomenex Synergi C18 150*30 mm*4 um; mobile phase: [water(0.05% HCl)-ACN]; B %: 47%-72%, 12 min) followed by lyophilization to yield 5-(5-fluoro-3-pyridyl)-3-isopropyl-N-[2-(2-methyl-1H-indol-3-yl)ethyl]pyrazolo[1,5-a]pyrimidin-7-amine (47.07 mg, 86.87 μmol, 65.8% yield, 99.3% purity, 3HCl) as a red solid. $^1$H NMR (400 MHz, $CD_3OD$) δ ppm 8.68 (d, J=2.0 Hz, 1H), 8.20 (s, 1H), 8.07 (s, 1H), 7.37 (d, J=8.6 Hz, 1H), 7.32-7.27 (m, 1H), 6.86-6.82 (m, 1H), 6.69 (dquin, J=1.3, 7.0 Hz, 2H), 5.43 (s, 1H), 3.89-3.83 (m, 2H), 3.15-3.07 (m, 1H), 3.03-2.98 (m, 2H), 1.95 (s, 3H), 1.19 (d, J=6.8 Hz, 6H); ES-LCMS m/z 429.3 $[M+H]^+$.

Example 88

Synthesis of I-90

I-90

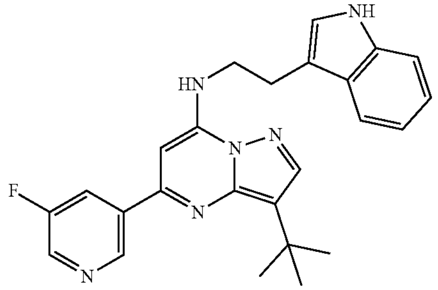

Synthetic Scheme:

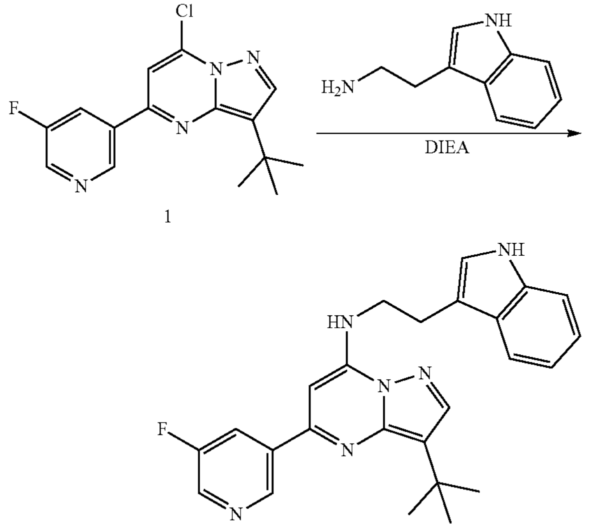

1

I-90

Step 1: 3-tert-Butyl-5-(5-fluoro-3-pyridyl)-N-[2-(1H-indol-3-yl)ethyl]pyrazolo[1,5-a]pyrimidin-7-amine (I-90)

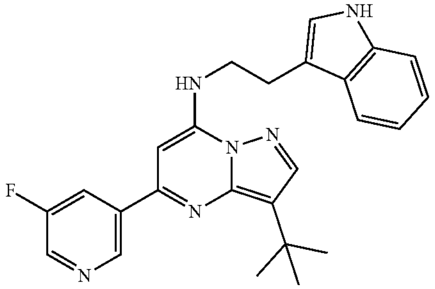 [SMILES: CC(C)(C)c1cnn2c(NCCc3c[nH]c4ccccc34)cc(-c3cncc(F)c3)nc12]

To a solution of 3-tert-butyl-7-chloro-5-(5-fluoro-3-pyridyl)pyrazolo[1,5-a]pyrimidine (40 mg, 128.63 μmol, 1 eq) and 2-(1H-indol-3-yl)ethanamine (30.91 mg, 192.95 μmol, 1.5 eq) in i-PrOH (10 mL) was added DIEA (49.87 mg, 385.89 μmol, 67.21 μL, 3.0 eq). The mixture was stirred at 70° C. for 16 h. The reaction mixture was concentrated under reduced pressure to remove solvent to yield a residue which was purified by preparative HPLC (column: Phenomenex Synergi C18 150*30 mm*4 um; mobile phase: [water (0.05% HCl)-ACN]; B %: 70%-90%, 12 min), followed by lyophilization to yield 3-tert-butyl-5-(5-fluoro-3-pyridyl)-N-[2-(1H-indol-3-yl)ethyl]pyrazolo[1,5-a]pyrimidin-7-amine (42.66 mg, 78.86 μmol, 61.3% yield, 99.4% purity, 3HCl) as a yellow solid. $^1H$ NMR (400 MHz, DMSO-$d_6$) δ ppm 10.82 (br s, 1H), 9.13 (s, 1H), 8.67 (d, J=2.2 Hz, 1H), 8.22 (d, J=8.6 Hz, 1H), 8.04 (br s, 1H), 7.94 (s, 1H), 7.64 (d, J=7.9 Hz, 1H), 7.31 (d, J=7.9 Hz, 1H), 7.23 (d, J=2.0 Hz, 1H), 7.10-6.95 (m, 2H), 6.64 (s, 1H), 3.83 (q, J=6.9 Hz, 2H), 3.11 (t, J=7.1 Hz, 2H), 1.46 (s, 9H); ES-LCMS m/z 429.3 $[M+H]^+$.

Example 89

Synthesis of I-91

I-91

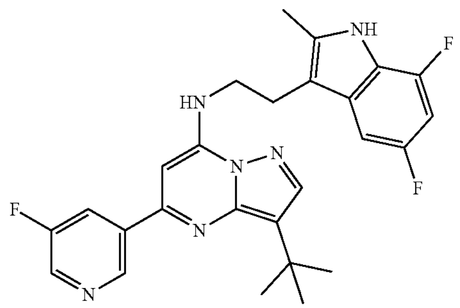

Synthetic Scheme:

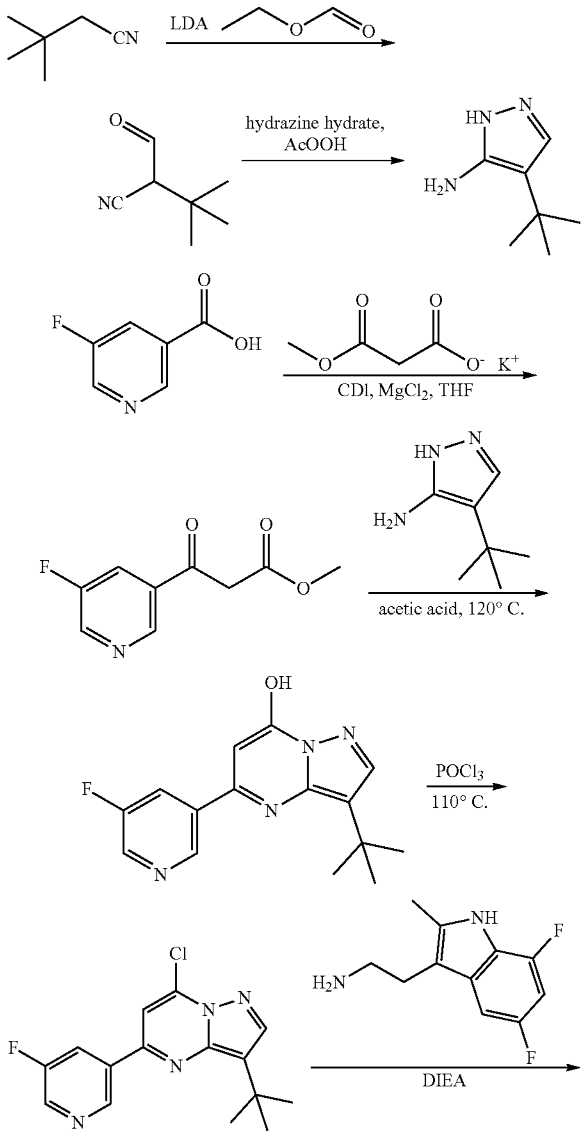

-continued

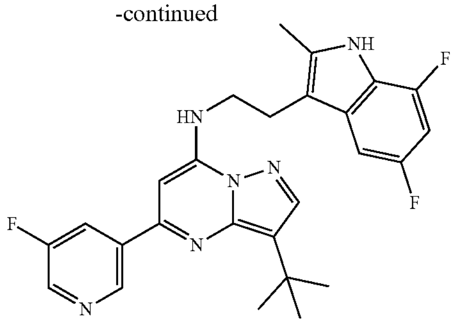

I-91

Step 1: 2-Formyl-3,3-dimethyl-butanenitrile

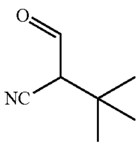

To a mixture of DIPA (833.20 mg, 8.23 mmol, 1.16 mL, 1 eq) in THF (20 mL) was added n-BuLi (2.5 M, 3.46 mL, 1.05 eq) dropwise at −78° C. under $N_2$. The mixture was stirred at −78° C. for 10 min, then heated to 0° C. and stirred for 1 h. The mixture was cooled to −78° C., 3,3-dimethylbutanenitrile (800 mg, 8.23 mmol, 12.66 mL, 1 eq) dissolved in THF (15 mL, anhydrous) was added dropwise and stirred at −78° C. for 10 min. A solution of ethyl formate (640.46 mg, 8.65 mmol, 695.40 μL, 1.05 eq) in THF (15 mL, anhydrous) was added dropwise and stirred at −78° C. for 40 min, then the mixture was warmed to 5-14° C. for 16 h. TLC (PE/EtOAc=3/1, $R_f$=0.34) indicated one major new spot was detected. The reaction mixture was quenched by addition 1N HCl solution (50) mL at −78° C., extracted with DCM (50 mL×3). The combined organic layers were dried over anhydrous $Na_2SO_4$, filtered and concentrated under reduced pressure to give a residue which was purified on silica gel column chromatography (from PE/EtOAc=1/0 to 10/3, TLC: PE/EtOAc=3/1, $R_f$=0.34) to give the product 2-formyl-3,3-dimethyl-butanenitrile (750 mg, 5.39 mmol, 65.5% yield, 90.0% purity) as a yellow oil. $^1$H NMR (400 MHz, $CDCl_3$) δ ppm 9.66 (d, J=2.2 Hz, 1H), 3.27 (d, J=2.4 Hz, 1H), 1.23 (s, 9H).

Step 2: 4-tert-Butyl-1H-pyrazol-5-amine

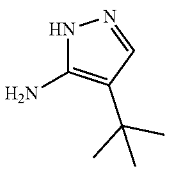

A mixture of 2-formyl-3,3-dimethyl-butanenitrile (750 mg, 5.39 mmol, 1 eq), hydrazine (224.65 mg, 7.01 mmol, 253.56 μL, 1.3 eq) and AcOH (566.71 mg, 9.44 mmol, 539.73 μL, 1.75 eq) in EtOH (20 mL) was degassed and purged with $N_2$ for 3 times. Then the mixture was stirred at 80-90° C. (reflux) for 16 h under $N_2$ atmosphere. TLC (PE/EtOAc=1/1, $R_f$=0.55) indicated most of starting material was consumed and one major new spot with larger polarity was detected. The reaction mixture concentrated under reduced pressure. The residue was diluted with $H_2O$ (20 mL), adjusted to pH to 9-10 with $NaHCO_3$ solid and extracted with DCM (20 mL×3). The combined organic layers were dried over anhydrous $Na_2SO_4$, filtered and concentrated under reduced pressure to give the crude product 4-tert-butyl-1H-pyrazol-5-amine (750 mg, 5.39 mmol, 99.9% yield, crude purity) as a yellow solid which was used in the next step without further purification. $^1$H NMR (400 MHz, $CDCl_3$) δ ppm 7.12 (s, 1H), 1.30 (s, 9H).

Step 3: 5-(5-Fluoro-3-pyridyl)-3-isopropyl-pyrazolo[1,5-a]pyrimidin-7-ol

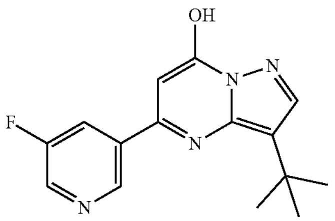 [SMILES: CC(C)(C)c1cnn2c(O)cc(-c3cncc(F)c3)nc12]

To a solution of methyl 3-(5-fluoro-3-pyridyl)-3-oxo-propanoate (1.08 g, 5.37 mmol, 1 eq) in AcOH (20 mL) was added 4-tert-butyl-1H-pyrazol-5-amine (747.23 mg, 5.37 mmol, 1 eq). The mixture was stirred at 120° C. for 0.5 h. The reaction mixture was concentrated under reduced pressure to remove solvent to give crude product 5-(5-fluoro-3-pyridyl)-3-isopropyl-pyrazolo[1,5-a]pyrimidin-7-ol (1.46 g, 5.36 mmol, 100.0% yield, crude) as a yellow oil which was used in the next step without further purification.

Step 4: 3-tert-Butyl-7-chloro-5-(5-fluoro-3-pyridyl)pyrazolo[1,5-a]pyrimidine

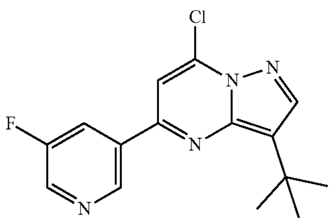 [SMILES: CC(C)(C)c1cnn2c(Cl)cc(-c3cncc(F)c3)nc12]

A mixture of 3-tert-butyl-5-(5-fluoro-3-pyridyl)pyrazolo[1,5-a]pyrimidin-7-ol (1.67 g, 5.83 mmol, 1 eq) in $POCl_3$ (37.81 g, 246.59 mmol, 22.92 mL, 42.28 eq) was degassed and purged with $N_2$ for 3 times. Then the mixture was stirred at 110° C. for 3 h under $N_2$ atmosphere. The reaction mixture was concentrated under reduced pressure to remove solvent. The residue was diluted with DCM (50 mL×2) and concentrated under reduced pressure to give a residue which was purified on silica gel column chromatography (from PE/EtOAc=1/0 to 10/3, TLC: PE/EtOAc=3/1, $R_f$=0.48) to give the product 3-tert-butyl-7-chloro-5-(5-fluoro-3-pyridyl)pyrazolo[1,5-a]pyrimidine (950 mg, 3.05 mmol, 52.4% yield, 98.0% purity) as a yellow solid. $^1$H NMR (400 MHz, $CDCl_3$) δ ppm 9.13 (t, J=1.5 Hz, 1H), 8.61 (d, J=2.8

Hz, 1H), 8.22-8.16 (m, 1H), 8.12 (s, 1H), 7.41 (s, 1H), 1.56 (s, 9H); ES-LCMS m/z 305.1, 307.1 $[M+H]_+$.

Step 5: 3-tert-Butyl-N-[2-(5,7-difluoro-2-methyl-1H-indol-3-yl)ethyl]-5-(5-fluoro-3-pyridyl)pyrazolo[1,5-a]pyrimidin-7-amine (I-91)

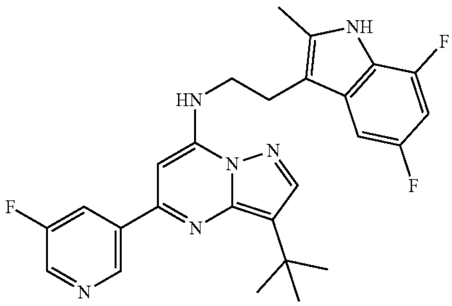 [SMILES: Cc1[nH]c2c(F)cc(F)cc2c1CCNc1cc(-c2cncc(F)c2)nc2c(C(C)(C)C)cnn12]

To a solution of 3-tert-butyl-7-chloro-5-(5-fluoro-3-pyridyl)pyrazolo[1,5-a]pyrimidine (40 mg, 128.63 μmol, 1 eq) and 2-(5,7-difluoro-2-methyl-1H-indol-3-yl)ethanamine (57.93 mg, 192.95 μmol, 1.5 eq, oxalic acid) in i-PrOH (10 mL) was added DIEA (49.87 mg, 385.89 μmol, 67.21 μL, 3.0 eq). The mixture was stirred at 70° C. for 16 h. The reaction mixture concentrated under reduced pressure to give a residue which was purified by preparative HPLC (column: Phenomenex Synergi C18 150*30 mm*4 um; mobile phase: [water(0.05% HCl)-ACN]; B %: 70%-90%, 12 min) 3-tert-butyl-N-[2-(5,7-difluoro-2-methyl-1H-indol-3-yl)ethyl]-5-(5-fluoro-3-pyridyl)pyrazolo[1,5-a]pyrimidin-7-amine (34.14 mg, 57.39 μmol, 44.6% yield, 98.8% purity, 3HCl) as a orange solid. $^1H$ NMR (400 MHz, DMSO-$d_6$) δ ppm 11.21 (s, 1H), 9.06-8.98 (m, 1H), 8.66 (d, J=2.6 Hz, 1H), 8.13-8.01 (m, 2H), 7.95 (s, 1H), 7.22 (dd, J=2.1, 9.6 Hz, 1H), 6.76 (ddd, J=2.2, 9.6, 11.4 Hz, 1H), 6.42 (s, 1H), 3.71 (q, J=6.8 Hz, 2H), 3.01 (t, J=6.6 Hz, 2H), 2.20 (s, 3H), 1.47 (s, 9H); ES-LCMS m/z 479.3 $[M+H]^+$.

Example 90

Synthesis of I-92

I-92

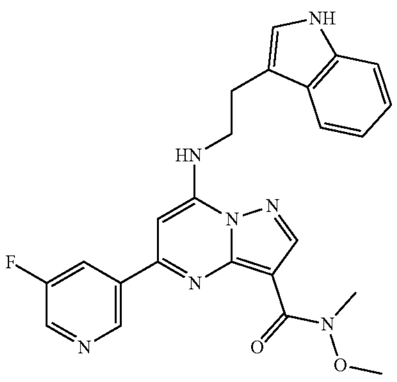

Synthetic Scheme:

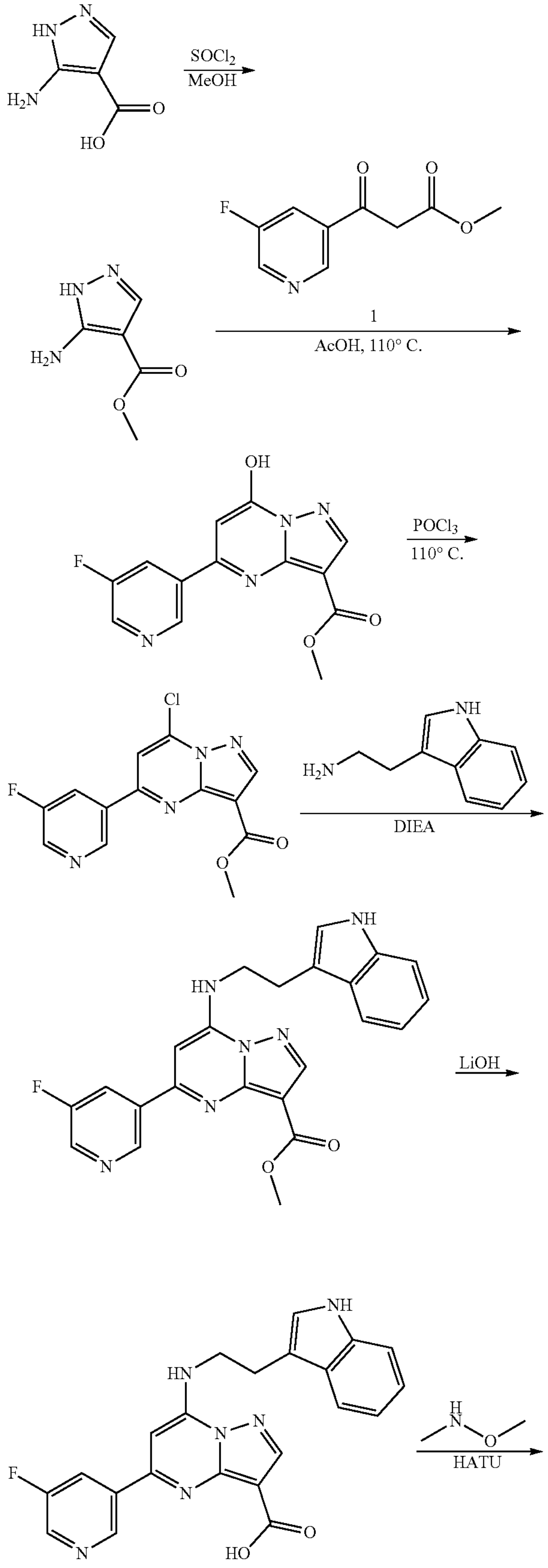

-continued

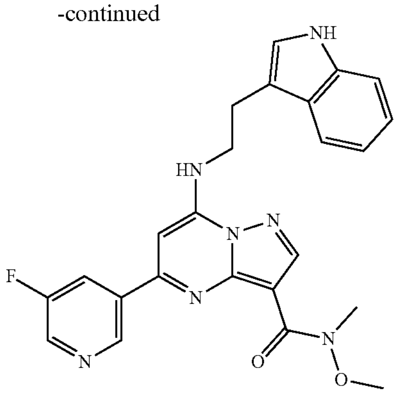

I-92

Step 1: Methyl 5-amino-1H-pyrazole-4-carboxylate

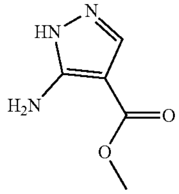

A solution of 5-amino-1H-pyrazole-4-carboxylic acid (1 g, 7.87 mmol, 1 eq) in HCl/MeOH (4 M, 40 mL, 20.34 eq) was stirred at 60° C. for 12 hr. The reaction mixture was concentrated under reduced pressure to give methyl 5-amino-1H-pyrazole-4-carboxylate (1.4 g, 7.49 mmol, 95.2% yield, 95.0% purity, HCl) as a white solid which was used in the next step without further purification. $^1$H NMR (400 MHz, $CD_3OD$) δ ppm 8.31 (s, 1H), 3.84 (s, 3H); ES-LCMS m/z 142.2 $[M+H]^+$.

Step 2: Methyl 5-(5-fluoro-3-pyridyl)-7-hydroxy-pyrazolo[1,5-a]pyrimidine-3-carboxylate

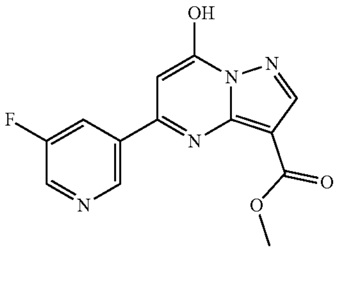 [SMILES: COC(=O)c1cnn2c(O)cc(-c3cncc(F)c3)nc12]

To a solution of methyl 3-(5-fluoro-3-pyridyl)-3-oxo-propanoate (160 mg, 795.28 μmol, 1 eq) in AcOH (5 mL) was added methyl 5-amino-1H-pyrazole-4-carboxylate (148.67 mg, 795.28 μmol, 1 eq, HCl). The mixture was stirred at 120° C. for 4 h. The reaction mixture was concentrated to yield methyl 5-(5-fluoro-3-pyridyl)-7-hydroxy-pyrazolo[1,5-a]pyrimidine-3-carboxylate (230 mg, crude) as a yellow solid which was used in the next step without further purification. $^1$H NMR (400 MHz, $CD_3OD$) δ ppm 8.83 (s, 1H), 8.72 (d, J=2.6 Hz, 1H), 8.29 (s, 1H), 8.22 (s, 1H), 6.34 (s, 1H), 3.92 (s, 3H); ES-LCMS m/z 289.2 $[M+H]^+$.

Step 3: Methyl 7-chloro-5-(5-fluoro-3-pyridyl)pyrazolo[1,5-a]pyrimidine-3-carboxylate

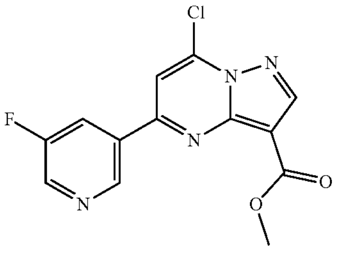 [SMILES: COC(=O)c1cnn2c(Cl)cc(-c3cncc(F)c3)nc12]

A solution of methyl 5-(5-fluoro-3-pyridyl)-7-hydroxy-pyrazolo[1,5-a]pyrimidine-3-carboxylate (230 mg, 797.96 μmol, 1 eq) in $POCl_3$ (5 mL) was stirred at 110° C. for 1 h. The reaction mixture was concentrated under reduced pressure to give the residue which was purified by flash silica gel chromatography (ISCO®; 12 g SepaFlash® Silica Flash Column, Eluent of 0-50% Ethyl acetate/Petroleum ethergradient @ 30 mL/min) to yield methyl 7-chloro-5-(5-fluoro-3-pyridyl)pyrazolo[1,5-a]pyrimidine-3-carboxylate (180 mg, 516.50 μmol, 64.7% yield, 88.0% purity) as a white solid. $^1$H NMR (400 MHz, $CDCl_3$) δ ppm 9.08 (s, 1H), 8.65 (s, 1H), 8.59 (d, J=2.6 Hz, 1H), 7.69 (s, 1H), 7.56 (s, 1H), 3.93 (s, 3H); ES-LCMS m/z 307.1, 309.1 $[M+H]^+$.

Step 4: Methyl 5-(5-fluoro-3-pyridyl)-7-[2-(1H-indol-3-yl)ethylamino]pyrazolo[1,5-a]pyrimidine-3-carboxylate

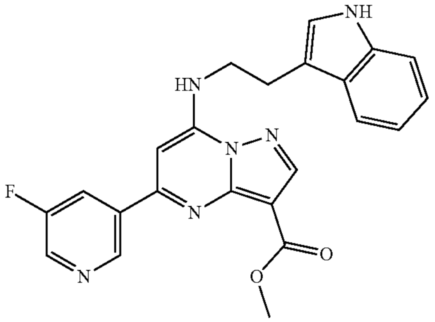 [SMILES: COC(=O)c1cnn2c(NCCc3c[nH]c4ccccc34)cc(-c3cncc(F)c3)nc12]

To a solution of methyl 7-chloro-5-(5-fluoro-3-pyridyl) pyrazolo[1,5-a]pyrimidine-3-carboxylate (180 mg, 516.50 μmol, 1 eq), 2-(1H-indol-3-yl)ethanamine (82.75 mg, 516.50 μmol, 1 eq) in i-PrOH (10 mL) was added DIEA (200.26 mg, 1.55 mmol, 269.90 μL, 3 eq). Then the mixture was stirred at 60° C. for 3 h. The reaction mixture was concentrated under reduced pressure to give methyl 5-(5-fluoro-3-pyridyl)-7-[2-(1H-indol-3-yl)ethyl amino]pyrazolo[1,5-a]pyrimidine-3-carboxylate (120 mg, 242.55 μmol, 47.0% yield, 87.0% purity) as an off white solid which was used in the next step without further purification. $^1$H NMR (400 MHz, $CD_3OD$) δ ppm 8.59 (s, 1H), 8.46 (d, J=2.9 Hz, 1H), 8.41 (s, 1H), 7.84 (br s, 1H), 7.15-7.15 (m, 1H), 7.13-7.08 (m, 3H), 6.94 (s, 1H), 6.07 (s, 1H), 3.86 (s, 3H), 3.11-3.05 (m, 4H); ES-LCMS m/z 431.1 $[M+H]^+$.

Step 5: 5-(5-Fluoro-3-pyridyl)-7-[2-(1H-indol-3-yl)ethylamino]pyrazolo[1,5-a]pyrimidine-3-carboxylic Acid

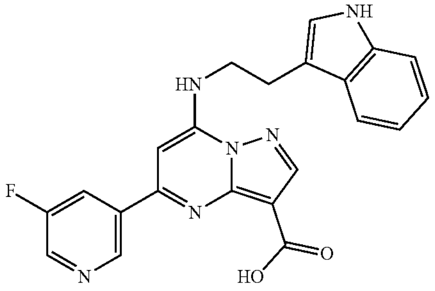 [SMILES: O=C(O)c1cnn2c(NCCc3c[nH]c4ccccc34)cc(-c3cncc(F)c3)nc12]

To a solution of methyl 5-(5-fluoro-3-pyridyl)-7-[2-(1H-indol-3-yl)ethylamino]pyrazolo[1,5-a]pyrimidine-3-carboxylate (60 mg, 121.27 μmol, 1 eq) in MeOH (2 mL) THF (2 mL) and Water (4 mL) was added LiOH—$H_2O$ (72.00 mg, 1.72 mmol, 14.15 eq) and the mixture was stirred at 50° C. for 1 h. The reaction mixture was concentrated under reduced pressure to give a residue which diluted with EtOAc (20 mL) and extracted with EtOAc (20 mL×2). The combined organic layers were washed with brine (20 mL), dried over $Na_2SO_4$, filtered and concentrated under reduced pressure to give 5-(5-fluoro-3-pyridyl)-7-[2-(1H-indol-3-yl)ethylamino]pyrazolo[1,5-a]pyrimidine-3-carboxylic acid (50 mg, 84.05 μmol, 69.3% yield, 70.0% purity) as a brown solid which was used in the next step without further purification. $^1$H NMR (400 MHz, $CD_3OD$) δ ppm 8.58 (s, 1H), 8.46 (d, J=2.4 Hz, 1H), 8.40 (s, 1H), 7.62 (s, 1H), 7.54 (d, J=7.7 Hz, 1H), 7.35 (d, J=8.2 Hz, 1H), 7.10 (d, J=7.9 Hz, 1H), 6.95 (m, 2H), 6.07 (s, 1H), 3.90 (t, J=6.2 Hz, 2H), 3.13-3.08 (m, 2H); ES-LCMS m/z 417.2 $[M+H]^+$.

Step 6: 5-(5-Fluoro-3-pyridyl)-7-[2-(1H-indol-3-yl)ethylamino]-N-methoxy-N-methyl-pyrazolo[1,5-a]pyrimidine-3-carboxamide (I-92)

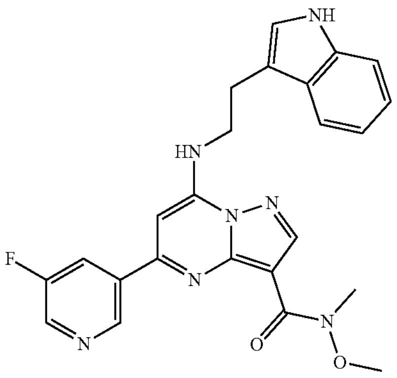 [SMILES: CON(C)C(=O)c1cnn2c(NCCc3c[nH]c4ccccc34)cc(-c3cncc(F)c3)nc12]

To a solution of 5-(5-fluoro-3-pyridyl)-7-[2-(1H-indol-3-yl)ethylamino]pyrazolo[1,5-a]pyrimidine-3-carboxylic acid (50 mg, 84.05 μmol, 1 eq) and N-methoxymethanamine (12.30 mg, 126.08 μmol, 1.5 eq, HCl) in DCM (5 mL) was added HATU (47.94 mg, 126.08 μmol, 1.5 eq) and TEA (17.01 mg, 168.10 μmol, 23.40 μL, 2 eq). Then the mixture was stirred at 20° C. for 1 h. The reaction mixture was concentrated under reduced pressure to give the residue which was diluted with EtOAc (20 mL) and extracted with EtOAc(20 mL×2). The combined organic layers were washed with brine (20 mL), dried over $Na_2SO_4$, filtered and concentrated under reduced pressure to yield a residue which was purified by preparative HPLC (column: Phenomenex Gemini 150*25 mm*10 um; mobile phase: [water (0.05% HCl)-ACN]; B %: 30%-60%, 10 min). The desired fraction was evaporated to afford 5-(5-fluoro-3-pyridyl)-7-[2-(1H-indol-3-yl)ethylamino]-N-methoxy-N-methyl-pyrazolo[1,5-a]pyrimidine-3-carboxamide (20.19 mg, 35.14 μmol, 41.8% yield, 99.0% purity, 3HCl) as a light yellow solid. $^1$H NMR (400 MHz, $CD_3OD$) δ ppm 8.74 (d, J=2.6 Hz, 1H), 8.61 (s, 1H), 8.40 (s, 1H), 7.57-7.51 (m, 2H), 7.10 (d, J=8.4 Hz, 1H), 7.01 (s, 1H), 6.94 (t, J=7.3 Hz, 1H), 6.87-6.81 (m, 1H), 6.04 (s, 1H), 4.07 (t, J=5.8 Hz, 2H), 3.85 (s, 3H), 3.37 (s, 3H), 3.24 (t, J=5.7 Hz, 2H); ES-LCMS m/z 460.4 $[M+H]^+$.

Example 91

Synthesis of I-93

I-93

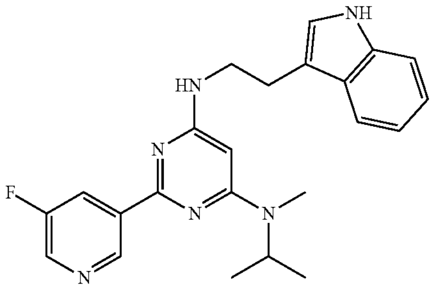 [SMILES: CC(C)N(C)c1cc(NCCc2c[nH]c3ccccc23)nc(-c2cncc(F)c2)n1]

Synthetic Scheme:

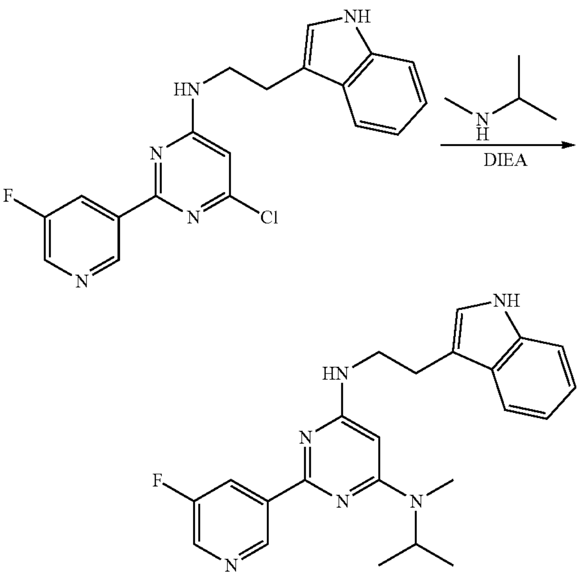

I-93

Step 1: 2-(5-Fluoro-3-pyridyl)-N6-[2-(1H-indol-3-yl)ethyl]-N4-isopropyl-N4-methyl-pyrimidine-4,6-diamine (I-93)

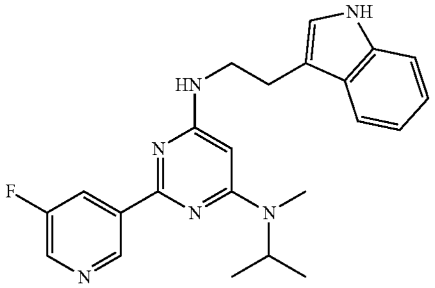

6-Chloro-2-(5-fluoro-3-pyridyl)-N-[2-(1H-indol-3-yl)ethyl]pyrimidin-4-amine (60 mg, 163.13 mol, 1.0 eq), N-methylpropan-2-amine (702.00 mg, 9.60 mmol, 1 mL, 58.84 eq) and DIEA (63.25 mg, 489.39 μmol, 85.24 μL, 3.0 eq) in i-PrOH (2 mL) were taken up into a microwave tube. The sealed tube was heated at 125° C. for 10 h under microwave. The reaction mixture was concentrated under reduced pressure to give the residue which was purified by preparative HPLC (HCl condition; column: column: Phenomenex Synergi C18 150×30 mm×4 um; mobile phase: [water(0.05% HCl)-ACN]; B %: 22%-52%, 12 min) and the desired fraction was lyophilized to yield 2-(5-fluoro-3-pyridyl)-N6-[2-(1H-indol-3-yl)ethyl]-N4-isopropyl-N4-methyl-pyrimidine-4,6-diamine (19.96 mg, 49.25 μmol, 30.2% yield, 99.80% purity, 3 HCl salt) as a yellow solid. $^1$H NMR (400 MHz, $CD_3OD+Na_2CO_3$) δ ppm 9.26 (s, 1H), 8.47 (d, J=2.6 Hz, 1H), 8.39-8.33 (m, 1H), 7.65-7.59 (m, 1H), 7.35-7.31 (m, 1H), 7.12-7.06 (m, 2H), 7.04-6.98 (m, 1H), 5.34 (s, 1H), 4.95 (s, 1H), 3.66 (t, J=6.9 Hz, 2H), 3.07 (t, J=6.9 Hz, 2H), 2.79 (s, 3H), 1.18 (d, J=6.8 Hz, 6H); ES-LCMS m/z 405.3 $[M+H]^+$.

Example 92

Synthesis of I-94a

I-94a

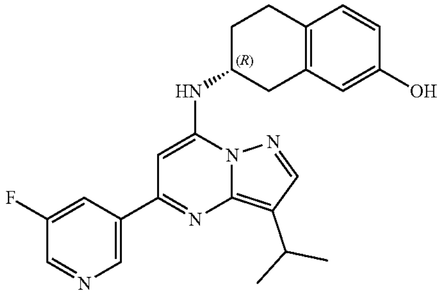

Synthetic Scheme:

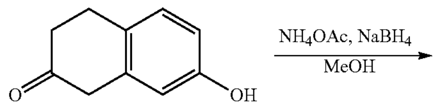

-continued

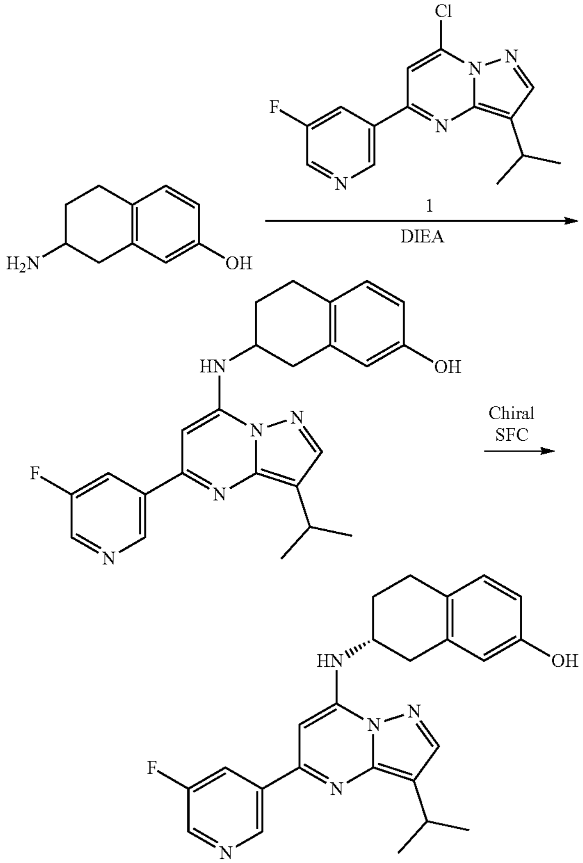

I-94

Step 1: 3-Aminotetralin-6-ol

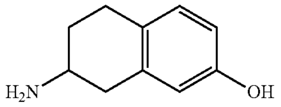

To a solution of 7-hydroxytetralin-2-one (500 mg, 3.08 mmol, 1 eq) in anhydrous MeOH (5 mL) was added $NH_4OAc$ (7.13 g, 92.49 mmol, 30 eq). After stirring for 5 h, $NaBH_4$ (349.88 mg, 9.25 mmol, 3 eq) was added. The mixture was stirred at 25° C. for 3 h. The mixture was concentrated to remove the solvent. $H_2O$ (10 mL) was added, the mixture was extracted with EtOAc (20 mL×2). The aqueous was adjusted by 3 N HCl to pH=6-7, extracted with EtOAc (10 mL×2). The aqueous was adjusted by 1 N NaOH to pH=6-7. Then the mixture was lyophilized to give the solid. The solid was dissolved in i-PrOH (10 mL). The resulting mixture was filtered and concentrated to give 3-aminotetralin-6-ol (550 mg, 2.66 mmol, 86.4% yield, 79.0% purity) as a yellow oil which was used in the next step without further purification. $^1$H NMR (400 MHz, $CD_3OD$) δ ppm 6.91 (d, J=8.2 Hz, 1H), 6.58 (dd, J=2.4, 8.4 Hz, 1H), 6.51 (s, 1H), 3.53-3.42 (m, 1H), 3.06 (dd, J=5.4, 15.5 Hz, 1H), 2.89-2.73 (m, 3H), 2.17 (d, J=10.1 Hz, 1H), 1.84-1.74 (m, 1H); ES-LCMS m/z 164.3 $[M+H]^+$.

Step 2: 3-[[5-(5-Fluoro-3-pyridyl)-3-isopropyl-pyrazolo[1,5-a]pyrimidin-7-yl]amino]tetralin-6-ol

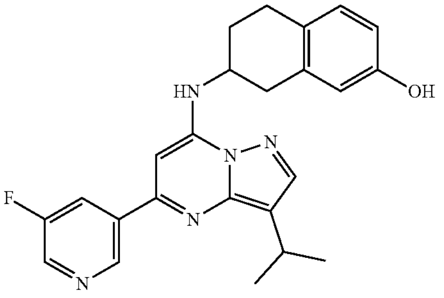 [SMILES: CC(C)c1cnn2c(NC3CCc4ccc(O)cc4C3)cc(-c3cncc(F)c3)nc12]

To a solution of 7-chloro-5-(5-fluoro-3-pyridyl)-3-isopropyl-pyrazolo[1,5-a]pyrimidine (100 mg, 330.21 μmol, 1 eq) in i-PrOH (10 mL) was added DIEA (128.03 mg, 990.63 μmol, 172.55 μL, 3 eq) and 3-aminotetralin-6-ol (204.67 mg, 990.63 μmol, 3 eq). The mixture was stirred at 120° C. for 3 h under microwave under $N_2$ atmosphere. The mixture was concentrated to remove the solvent. $H_2O$ (10 mL) was added, the mixture was extracted with EtOAc (10 mL×3). The combined organic layers were washed with brine (10 mL), dried over anhydrous $Na_2SO_4$, filtered and concentrated to afford the crude product which was purified on silica gel column chromatography (from PE/EtOAc=1/0 to 3/1, TLC: PE/EtOAc=2/1, $R_f$=0.50) to give 3-[[5-(5-fluoro-3-pyridyl)-3-isopropyl-pyrazolo[1,5-a]pyrimidin-7-yl]amino]tetralin-6-ol (63 mg, 138.83 mol, 42.0% yield, 92.0% purity) as a yellow solid. $^1H$ NMR (400 MHz, $CD_3OD$) δ ppm 9.19 (s, 1H), 8.56 (d, J=2.5 Hz, 1H), 8.45-8.37 (m, 1H), 7.96 (s, 1H), 6.98 (d, J=8.3 Hz, 1H), 6.78 (s, 1H), 6.66-6.56 (m, 2H), 4.62 (s, 2H), 4.32 (s, 1H), 3.01-2.89 (m, 3H), 2.28 (s, 1H), 2.03 (d, J=5.5 Hz, 1H), 1.44 (d, J=7.0 Hz, 6H); ES-LCMS m/z 418.2 $[M+H]^+$.

Step 3: (3R)-3-[[5-(5-fluoro-3-pyridyl)-3-isopropyl-pyrazolo[1,5-a]pyrimidin-7-yl]amino]tetralin-6-ol (I-94)

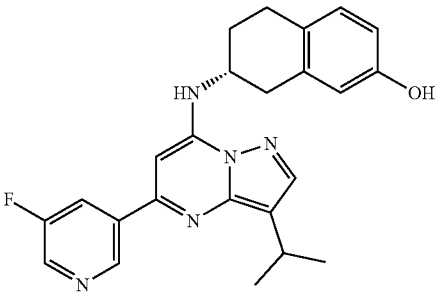 [SMILES: CC(C)c1cnn2c(N[C@@H]3CCc4ccc(O)cc4C3)cc(-c3cncc(F)c3)nc12]

3-[[5-(5-fluoro-3-pyridyl)-3-isopropyl-pyrazolo[1,5-a]pyrimidin-7-yl]amino]tetralin-6-ol (100 mg, 220.37 μmol, 1 eq) was separation by SFC (column: Chiralcel OD 250*30 5 u; mobile phase: [0.1% $NH_3.H_2O$ EtOH]; B %: 45%-45%, min) to yield the product (Rt=3.922 min) which was purified by preparative HPLC (MeCN/$H_2O$ as eluents, acidic condition, Instrument: Phenomenex Gemini 150*25 mm*10 um/Mobile phase: water (0.05% HCl)-ACN/Gradient: B from 50% to 80% in 10 min/Flow rate: 25 mL/min) followed by lyophilization to yield (3R)-3-[[5-(5-fluoro-3-pyridyl)-3-isopropyl-pyrazolo[1,5-a]pyrimidin-7-yl]amino]tetralin-6-ol (19.02 mg, 45.10 μmol, 20.47% yield, 99.0% purity) ($[\alpha]^{25}_D$=−23.996) as a yellow solid. $^1H$ NMR (400 MHz, $CD_3OD$) δ ppm 8.99 (s, 1H), 8.81 (d, J=2.4 Hz, 1H), 8.38-8.31 (m, 1H), 8.25 (s, 1H), 7.00-6.91 (m, 2H), 6.60 (dd, J=2.5, 8.3 Hz, 1H), 6.55 (d, J=2.4 Hz, 1H), 4.50 (s, 1H), 3.41-3.32 (m, 1H), 3.23-3.15 (m, 1H), 3.11-3.02 (m, 1H), 3.01-2.94 (m, 1H), 2.94-2.86 (m, 1H), 2.32-2.21 (m, 1H), 2.14-2.02 (m, 1H), 1.38 (d, J=6.8 Hz, 6H); ES-LCMS m/z 418.2 $[M+H]^+$.

Example 93

Synthesis of I-95

I-95

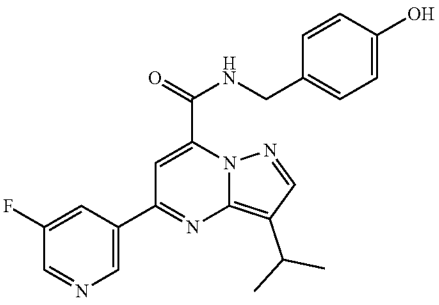

Synthetic Scheme:

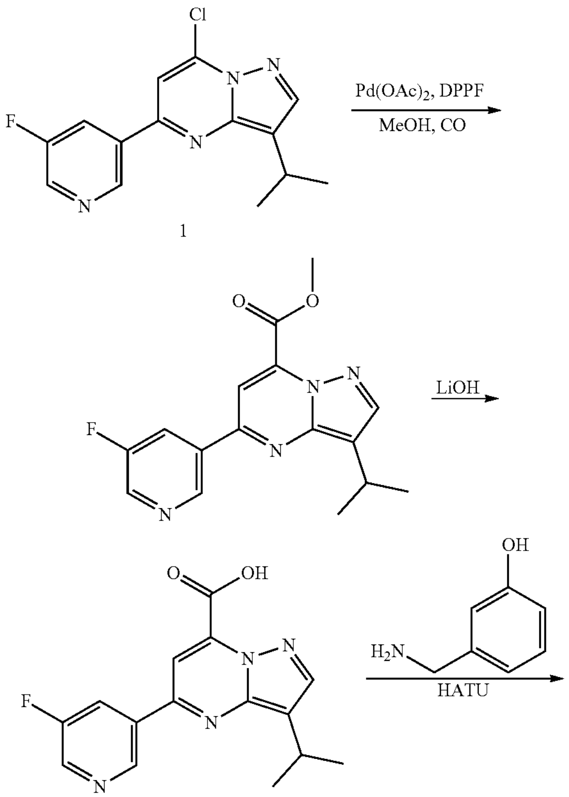

-continued

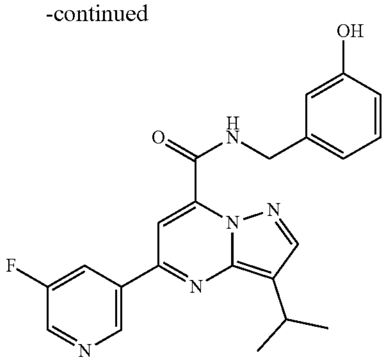

I-95

Step 1: Methyl 5-(5-fluoro-3-pyridyl)-3-isopropyl-pyrazolo[1,5-a]pyrimidine-7-carboxylate

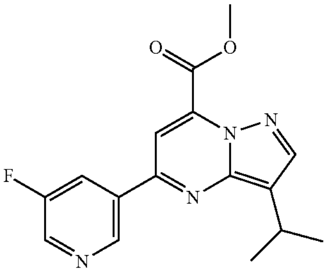 [SMILES: COC(=O)c1cc(-c2cncc(F)c2)nc2c(C(C)C)cnn12]

To a solution of 7-chloro-5-(5-fluoro-3-pyridyl)-3-isopropyl-pyrazolo[1,5-a]pyrimidine (270 mg, 659.39 μmol, 1 eq, 71.0%) in DMF (10 mL) and MeOH (8 mL) was added $Et_3N$ (333.62 mg, 3.30 mmol, 458.90 μL, 5.0 eq), $Pd(OAc)_2$ (22.21 mg, 98.91 μmol, 0.15 eq) and DPPF (54.83 mg, 98.91 μmol, 0.15 eq). The mixture was purged with CO (50 psi) three times and stirred at 70° C. for 24 hr under CO (50 psi). The reaction mixture concentrated under high vacuum to give a residue which was purified on silica gel column chromatography (from PE/EtOAc=1/0 to 10/3, TLC: PE/EtOAc=3/1, $R_f$=0.47) to give the product methyl 5-(5-fluoro-3-pyridyl)-3-isopropyl-pyrazolo[1,5-a]pyrimidine-7-carboxylate (180 mg, 538.32 μmol, 81.6% yield, 94.0% purity) as a yellow solid. $^1$H NMR (400 MHz, $CDCl_3$) δ ppm 9.17 (d, J=6.8 Hz, 1H), 8.62 (d, J=5.3 Hz, 1H), 8.22 (dd, J=7.9, 17.9 Hz, 2H), 7.81 (d, J=8.2 Hz, 1H), 4.22-4.00 (m, 3H), 3.47-3.45 (m, 1H), 1.47 (t, J=7.4 Hz, 6H); ES-LCMS m/z 315.3 $[M+H]^+$.

Step 2: 5-(5-Fluoro-3-pyridyl)-3-isopropyl-pyrazolo[1,5-a]pyrimidine-7-carboxylic Acid

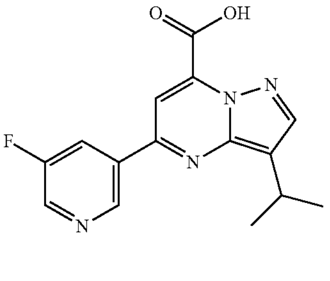 [SMILES: CC(C)c1cnn2c(C(=O)O)cc(-c3cncc(F)c3)nc12]

To a solution of methyl 5-(5-fluoro-3-pyridyl)-3-isopropyl-pyrazolo[1,5-a]pyrimidine-7-carboxylate (180 mg, 538.32 μmol, 1 eq) in MeOH (10 mL) and THF (10 mL), $H_2O$ (5 mL) was added LiOH (128.92 mg, 5.38 mmol, 10 eq). The mixture was stirred at 50° C. for 2 h. The reaction mixture was concentrated under reduced pressure. The residue was diluted with $H_2O$ (20 mL), adjusted to pH=3-4 with 1N HCl solution, extracted with DCM (20 mL×3). The combined organic layers were dried over anhydrous $Na_2SO_4$, filtered and concentrated under reduced pressure to give the crude product 5-(5-fluoro-3-pyridyl)-3-isopropyl-pyrazolo[1,5-a]pyrimidine-7-carboxylic acid (100 mg, 293.05 μmol, 54.4% yield, 88.0% purity) as a yellow solid which was used in the next step without further purification. $^1$H NMR (400 MHz, $CDCl_3$) δ ppm 9.23 (s, 1H), 8.65 (d, J=2.6 Hz, 1H), 8.26 (td, J=2.3, 9.3 Hz, 1H), 8.22 (s, 1H), 8.14 (s, 1H), 3.59-3.35 (m, 1H), 1.49 (d, J=6.8 Hz, 6H); ES-LCMS m/z 301.1 $[M+H]^+$.

Step 3: 5-(5-Fluoro-3-pyridyl)-N-[(3-hydroxyphenyl)methyl]-3-isopropyl-pyrazolo[1,5-a]pyrimidine-7-carboxamide (I-95)

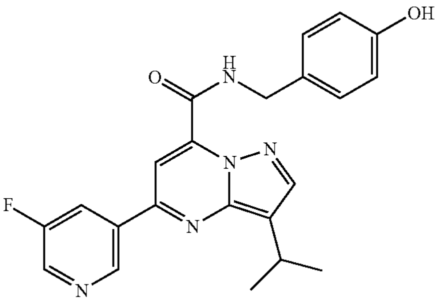 [SMILES: CC(C)c1cnn2c(C(=O)NCc3ccc(O)cc3)cc(-c3cncc(F)c3)nc12]

To a solution of 5-(5-fluoro-3-pyridyl)-3-isopropyl-pyrazolo[1,5-a]pyrimidine-7-carboxylic acid (70 mg, 205.14 μmol, 1 eq) and 3-(aminomethyl)phenol (50.53 mg, 410.27 μmol, 2.0 eq) in DCM (20 mL) was added HATU (117.00 mg, 307.71 μmol, 1.5 eq) and DIEA (79.54 mg, 615.41 μmol, 107.19 μL, 3.0 eq). The mixture was stirred at 25° C. for 16 h. The combined reaction mixture was diluted with $H_2O$ (20 mL), extracted with EtOAc (20 mL×3). The combined organic layers were dried over anhydrous $Na_2SO_4$, filtered and concentrated under reduced pressure to give a residue which was purified by preparative HPLC (column: Phenomenex Synergi C18 150*30 mm*4 um; mobile phase: [water(0.05% HCl)-ACN]; B %: 47%-77%, 12 min), followed by lyophilization to yield 5-(5-fluoro-3-pyridyl)-N-[(3-hydroxyphenyl)methyl]-3-isopropyl-pyrazolo[1,5-a]pyrimidine-7-carboxamide (16.16 mg, 33.78 μmol, 16.5% yield, 100.0% purity, 2HCl) as a yellow solid. $^1$H NMR (400 MHz, DMSO-$d_6$) δ ppm 10.41 (t, J=5.8 Hz, 1H), 9.34-9.27 (m, 1H), 8.76 (d, J=2.9 Hz, 1H), 8.62-8.49 (m, 1H), 8.35 (s, 1H), 8.20 (s, 1H), 7.15 (t, J=7.7 Hz, 1H), 6.88-6.80 (m, 2H), 6.72-6.61 (m, 1H), 4.62 (d, J=6.0 Hz, 2H), 3.42-3.35 (m, 1H), 1.41 (d, J=7.1 Hz, 6H); ES-LCMS m/z 406.2 $[M+H]^+$.

Example 94

Synthesis of I-96

I-96

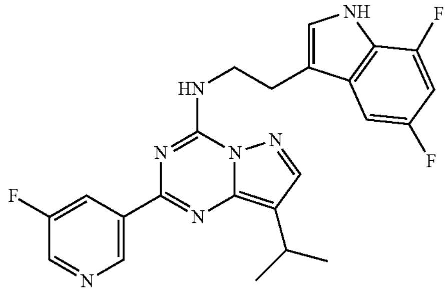 [SMILES: CC(C)c1cnn2c(NCCc3c[nH]c4c(F)cc(F)cc34)nc(-c3cncc(F)c3)nc12]

Synthetic Scheme:

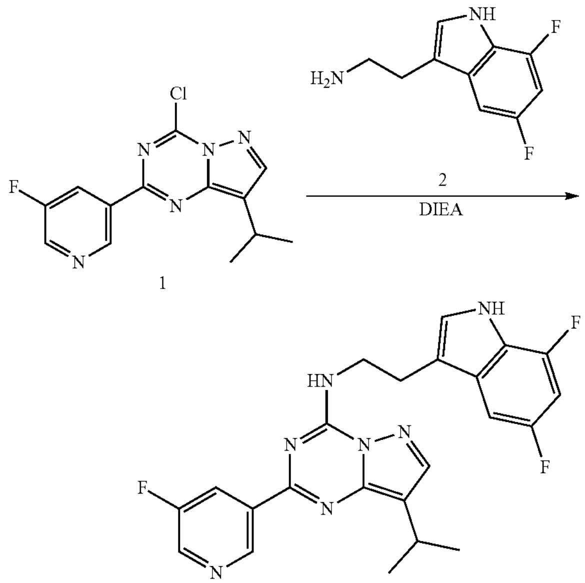

1

I-96

Step 1: N-[2-(5,7-Difluoro-1H-indol-3-yl)ethyl]-2-(5-fluoro-3-pyridyl)-8-isopropyl-pyrazolo[1,5-a][1,3,5]triazin-4-amine (I-96)

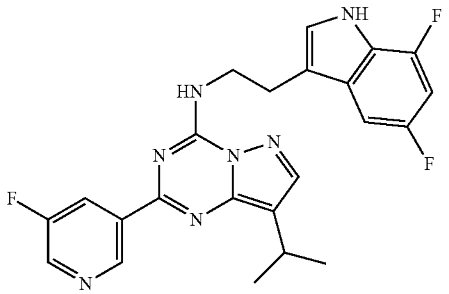

A mixture of 4-chloro-2-(5-fluoro-3-pyridyl)-8-isopropyl-pyrazolo[1,5-a][1,3,5]triazine (40 mg, 137.12 μmol, 1 eq), 2-(5,7-difluoro-1H-indol-3-yl)ethanamine (45.86 mg, 205.68 μmol, 1.5 eq) and DIEA (17.72 mg, 137.12 μmol, 23.88 μL, 1 eq) in i-PrOH (10 mL) was stirred at 80° C. for 2 h. The mixture was concentrated under reduced pressure to give a residue which was washed with MeOH (10 mL), filtered and dried under reduced pressure to yield N-[2-(5,7-difluoro-1H-indol-3-yl)ethyl]-2-(5-fluoro-3-pyridyl)-8-isopropyl-pyrazolo[1,5-a][1,3,5]triazin-4-amine (18.95 μmg, 41.98 μmol, 30.6% yield, 100% purity) as a white solid. $^1$H NMR (400 MHz, DMSO-$d_6$) δ ppm 11.37 (s, 1H), 9.29 (t, J=1.6 Hz, 1H), 9.03-9.01 (m, 1H), 8.70 (d, J=2.8 Hz, 1H), 8.26-8.22 (m, 1H), 8.10 (s, 1H), 7.34 (d, J=2.0 Hz, 1H), 7.27 (dd, J=2.0, 7.2 Hz, 1H), 6.91-6.87 (m, 1H), 3.92 (q, J=6.8 Hz, 2H), 3.22-3.15 (m, 1H), 3.09 (t, J=7.2 Hz, 2H), 1.35 (d, J=6.8 Hz, 6H); ES-LCMS m/z 452.2 [M+H]$^+$.

Example 95

Synthesis of I-97a

I-97a

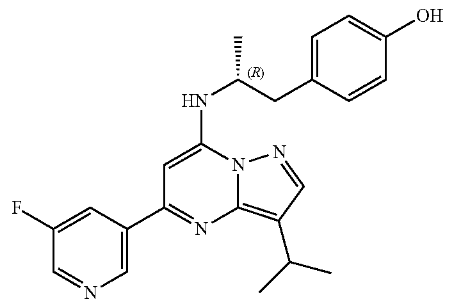

Synthetic Scheme:

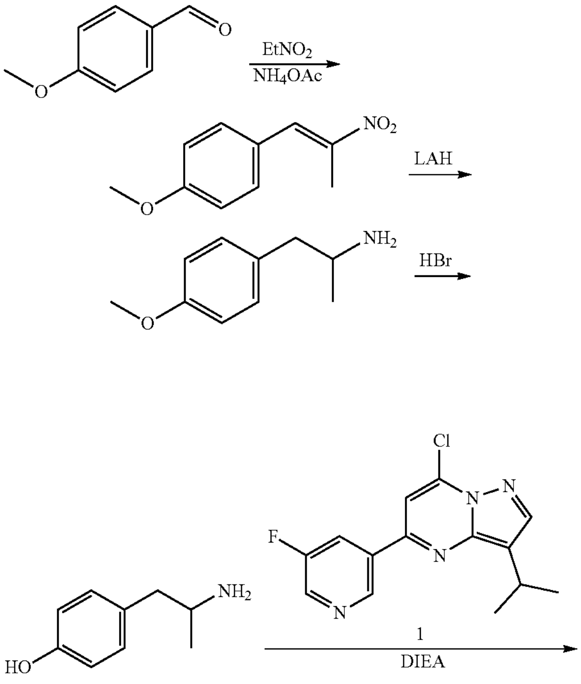

-continued

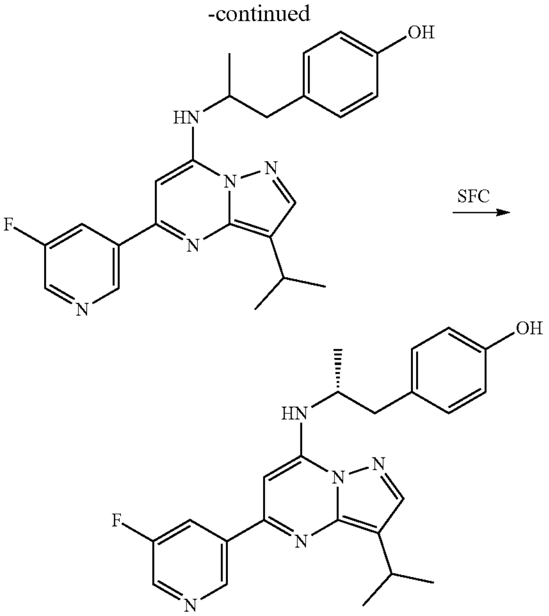

I-97

Step 1: 1-Methoxy-4-[(E)-2-nitroprop-1-enyl]benzene $NO_2$

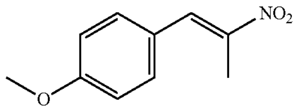

A mixture of 4-methoxybenzaldehyde (5 g, 36.72 mmol, 4.46 mL, 1 eq), $NH_4OAc$ (566.17 mg, 7.34 mmol, 0.2 eq) in $EtNO_2$ (50 mL) was stirred at 110° C. for 5 h under $N_2$ atmosphere. Then the mixture was stirred at 110° C. for another 40 h. TLC (PE/EtOAc=5/1, $R_f$=0.73) indicated starting material was consumed completely and one new spot formed. The mixture was concentrated under reduced pressure to give a residue which was purified by flash silica gel chromatography (from PE/EtOAc=10/1 to 5/1, TLC: PE/EtOAc=5/1, $R_f$=0.73) to yield 1-methoxy-4-[(E)-2-nitroprop-1-enyl]benzene (3.7 g, 18.19 mmol, 49.5% yield, 95% purity) as a yellow solid. $^1H$ NMR (400 MHz, $CD_3OD$) δ ppm 8.06 (s, 1H), 7.52-7.49 (m, 2H), 7.05-7.02 (m, 2H), 3.85 (s, 3H), 2.45 (s, 3H); ES-LCMS m/z 194.0 $[M+H]^+$.

Step 2: 1-(4-Methoxyphenyl)propan-2-amine $NH_2$

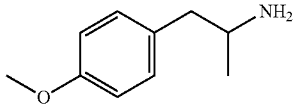

A mixture of 1-methoxy-4-[(E)-2-nitroprop-1-enyl]benzene (1 g, 4.92 mmol, 1 eq) and LAH (1 M in THF, 14.75 mL, 3 eq) in THF (10 mL) was stirred at 60° C. for 14 h. The mixture was quenched with water (0.5 mL), 15% NaOH (0.5 mL) and water (1.5 mL), the mixture was stirred for 3 h at 20° C. The mixture was filtered and concentrated under reduced pressure to yield 1-(4-methoxyphenyl)propan-2-amine (800 mg, crude) as yellow oil. $^1H$ NMR (400 MHz, $CD_3OD$) δ ppm 7.08 (d, J=8.4 Hz, 2H), 6.86-6.81 (m, 2H), 3.72 (s, 3H), 2.96-2.91 (m, 1H), 2.51-2.42 (m, 2H), 0.92 (d, J=6.4 Hz, 3H); ES-LCMS m/z 166.2 $[M+H]^+$.

Step 3: 4-(2-Aminopropyl)phenol

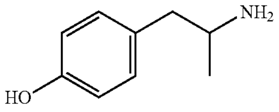

A mixture of 1-(4-methoxyphenyl) propan-2-amine (1.2 g, 7.26 mmol, 1 eq) in a solution of HBr (8 mL) solution in $H_2O$ (3 mL) was stirred at 100° C. for 3 h. The mixture was extracted with EtOAc (20 mL), pH was adjusted to 9 with 15% NaOH, the aqueous solution was extracted with EtOAc (20 mL×3), dried over $Na_2SO_4$, filtered and concentrated under reduced pressure to give 4-(2-aminopropyl) phenol (445 mg, crude) as a brown solid which was used in the next step without further purification. $^1H$ NMR (400 MHz, $CD_3OD$) δ ppm 7.00 (d, J=8.4 Hz, 2H), 6.73-6.70 (m, 2H), 3.07-3.01 (m, 1H), 2.56-2.51 (m, 2H), 1.07 (d, J=6.4 Hz, 3H); ES-LCMS m/z 152.2 $[M+H]^+$.

Step 4: 4-[(2R)-2-[[5-(5-Fluoro-3-pyridyl)-3-isopropyl-pyrazolo[1,5-a]pyrimidin-7-yl]amino]propyl]phenol (I-97)

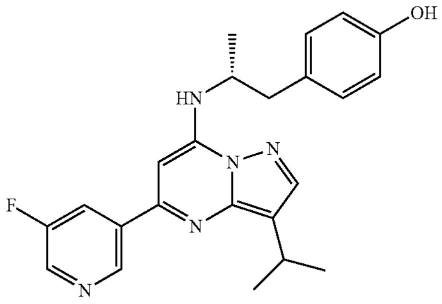 [SMILES: CC(C)c1cnn2c(N[C@H](C)Cc3ccc(O)cc3)cc(-c3cncc(F)c3)nc12]

A mixture of 7-chloro-5-(5-fluoro-3-pyridyl)-3-isopropyl-pyrazolo[1,5-a]pyrimidine (100 mg, 330.21 μmol, 1 eq), 4-(2-aminopropyl)phenol (99.86 mg, 660.42 μmol, 2 eq) and DIEA (128.03 mg, 990.63 μmol, 172.55 μL, 3 eq) in i-PrOH (10 mL) was degassed and purged with $N_2$ for 3 times, the mixture was stirred at 80° C. for 12 h under $N_2$ atmosphere. The mixture was concentrated under reduced pressure to give a residue which was purified by SFC (column: Chiralpak AS-H 250*30 5 u; mobile phase: [0.1% $NH_3H_2O$ EtOH]; B %: 20%-20%, min) to give 4-[(2R)-2-[[5-(5-fluoro-3-pyridyl)-3-isopropyl-pyrazolo[1,5-a]pyrimidin-7-yl]amino]propyl]phenol (Rt=4.781 min, 50 mg) and preparative HPLC (column: Phenomenex Synergi C18 150*30 mm*4 m; mobile phase: [water (0.05% HCl)-ACN]; B %: 52%-62%, 12 min) to yield 4-[(2R)-2-[[5-(5-fluoro-3-pyridyl)-3-isopropyl-pyrazolo[1,5-a]pyrimidin-7-yl]amino]propyl]phenol (27.45 mg, 57.15 umol, 17.3% yield, 99.6% purity, 2HCl) ($[\alpha]^{25}_D$=−90.432) as a yellow solid. $^1H$ NMR (400 MHz, $CD_3OD$) δ ppm 8.81-8.76 (m, 2H), 8.25 (s, 1H), 8.12-8.07 (m, 1H), 7.04 (d, J=8.4 Hz, 2H), 6.54 (d, J=8.4 Hz, 2H), 6.34 (s, 1H), 4.42 (br s, 1H), 3.31-3.29 (m, 1H), 3.04 (dd, J=4.4, 13.6 Hz, 1H), 2.87-2.83 (m, 1H), 1.54 (d, J=6.4 Hz, 3H), 1.36 (t, J=6.8 Hz, 6H); ES-LCMS m/z 406.2 $[M+H]^+$.

Example 96

Synthesis of I-98a

I-98a

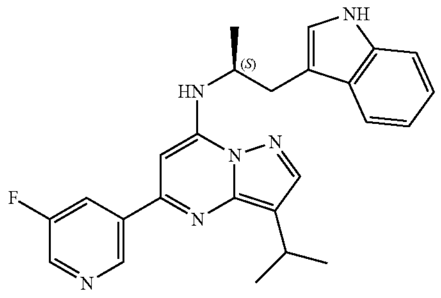

Synthetic Scheme:

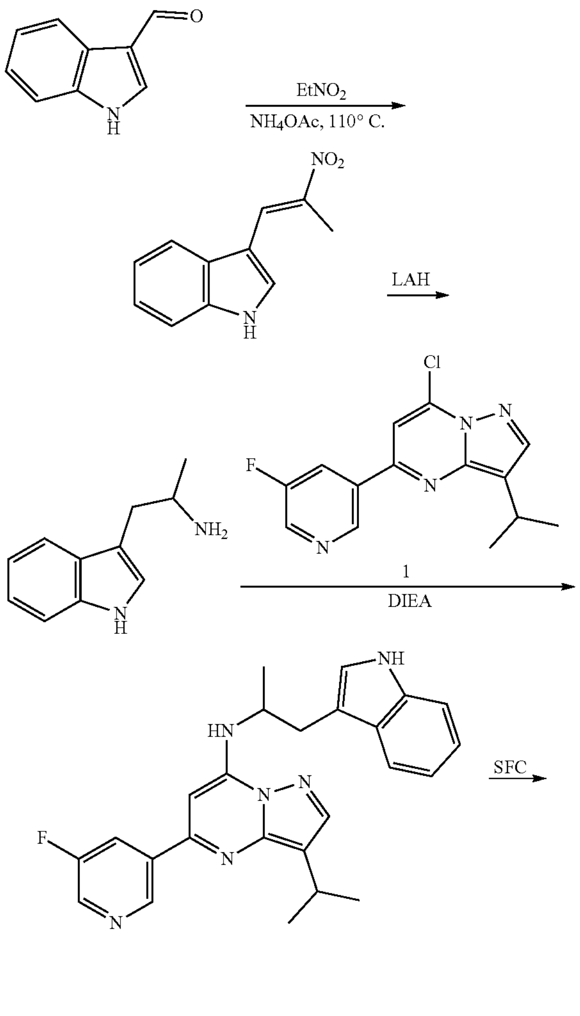

-continued

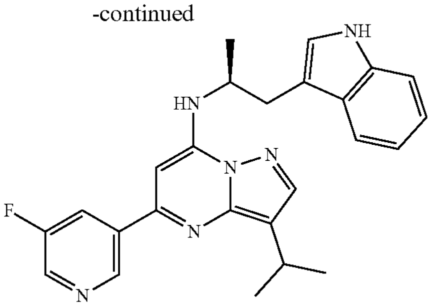

I-98

Step 1: 3-[(E)-2-Nitroprop-1-enyl]-1H-indole

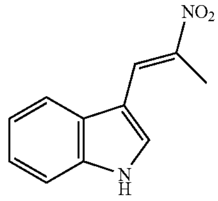

A mixture of 1H-indole-3-carbaldehyde (5 g, 34.45 mmol, 1 eq), $NH_4OAc$ (531.02 mg, 6.89 mmol, 0.2 eq) in nitroethane (50 mL) was stirred at 110° C. for 24 h. TLC (DCM/MeOH=10/1, $R_f$=0.8) indicated starting material was consumed completely and one new spot formed. The mixture was cooled to 0° C. The mixture was filtered and the filtered cake was dried under reduced pressure to give 3-[(E)-2-nitroprop-1-enyl]-1H-indole (5.1 g, 25.22 mmol, 73.2% yield, 100% purity) as a brown solid. $^1H$ NMR (400 MHz, $CD_3OD$) δ ppm 8.53 (s, 1H), 7.79-7.75 (m, 2H), 7.46 (d, J=8.0 Hz, 1H), 7.26-7.20 (m, 2H), 2.52 (s, 3H); ES-LCMS m/z 203.0 $[M+H]^+$.

Step 2: 1-(1H-Indol-3-yl)propan-2-amine

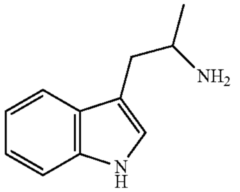

To a solution of 3-[(E)-2-nitroprop-1-enyl]-1H-indole (1 g, 4.95 mmol, 1 eq) in THF (10 mL) was added LAH (1 M in THF, 14.84 mL, 3 eq) at 0° C. Then the mixture was stirred at 60° C. for 2 h. The mixture was diluted with EtOAc (200 mL), quenched with water (0.5 mL), 15% NaOH (0.5 mL), water (1.5 mL), stirred for 3 h, filtered and concentrated under reduced pressure to give 1-(1H-indol-3-yl)propan-2-amine (1.3 g, 3.73 mmol, 75.4% yield, 50% purity) as yellow oil which was used in the next step without further purification. $^1H$ NMR (400 MHz, $CD_3OD$) δ ppm 7.56-7.53 (m, 1H), 7.35-7.30 (m, 1H), 7.10-7.06 (m, 2H), 7.01-6.97 (m, 1H), 3.21-3.17 (m, 1H), 2.85-2.79 (m, 1H), 2.73-2.69 (m, 1H), 1.15-1.10 (m, 3H); ES-LCMS m/z 175.2 $[M+H]^+$.

Step 3: 5-(5-Fluoro-3-pyridyl)-N-[(1S)-2-(1H-indol-3-yl)-1-methyl-ethyl]-3-isopropyl-pyrazolo[1,5-a]pyrimidin-7-amine (I-98)

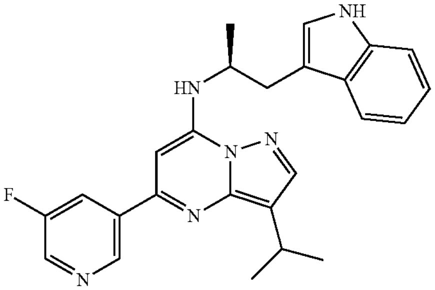 [SMILES: CC(C)c1cnn2c(N[C@@H](C)Cc3c[nH]c4ccccc34)cc(-c3cncc(F)c3)nc12]

A mixture of 1-(1H-indol-3-yl)propan-2-amine (172.61 mg, 495.32 μmol, 1.5 eq), 7-chloro-5-(5-fluoro-3-pyridyl)-3-isopropyl-pyrazolo[1,5-a]pyrimidine (100 mg, 330.21 μmol, 1 eq) and DIEA (42.68 mg, 330.21 μmol, 57.52 μL, 1 eq) in i-PrOH (10 mL) was degassed and purged with $N_2$ for 3 times, the mixture was stirred at 50° C. for 3 h under $N_2$ atmosphere. The mixture was concentrated under reduced pressure to give a residue which was purified by flash silica gel chromatography ($SiO_2$, PE/EtOAc=10/1 to 1/1, TLC: PE/EtOAc=1/1, $R_f$=0.55) and further separated by SFC (column: OD(250 mm*30 mm, 5 μm); mobile phase: [0.1% $NH_3/H_2O$ EtOH]; B %: 30%-30%, min) to give 5-(5-fluoro-3-pyridyl)-N-[(1S)-2-(1H-indol-3-yl)-1-methyl-ethyl]-3-isopropyl-pyrazolo[1,5-a]pyrimidin-7-amine (Rt=3.870 min, 30 mg) which was purified by preparative HPLC (column: Phenomenex Synergi C18 150*30 mm*4 m; mobile phase: [water (0.05% HCl)-ACN]; B %: 50%-80%, 12 min) to yield 5-(5-fluoro-3-pyridyl)-N-[(1S)-2-(1H-indol-3-yl)-1-methyl-ethyl]-3-isopropyl-pyrazolo[1,5-a]pyrimidin-7-amine (16.33 mg, 29.93 mol, 9.1% yield, 98.6% purity, 3HCl) ($[\alpha]^{25}_{D}$=−261.788) as a yellow solid. $^1$H NMR (400 MHz, $CD_3OD$) δ ppm 8.67 (d, J=2.4 Hz, 1H), 8.34 (s, 1H), 8.18 (s, 1H), 7.54 (d, J=7.6 Hz, 1H), 7.45 (d, J=2.0, 8.8 Hz, 1H), 7.14 (d, J=8.4 Hz, 1H), 6.99 (s, 1H), 6.95 (t, J=7.5 Hz, 1H), 6.83-6.81 (m, 1H), 5.80 (s, 1H), 4.48-4.43 (m, 1H), 3.28 (d, J=2.8 Hz, 1H), 3.23-3.17 (m, 1H), 3.05-3.01 (m, 1H), 1.64 (d, J=6.4 Hz, 3H), 1.34 (t, J=7.2 Hz, 6H); ES-LCMS m/z 429.3 $[M+H]^+$.

Example 97

Synthesis of I-99

I-99

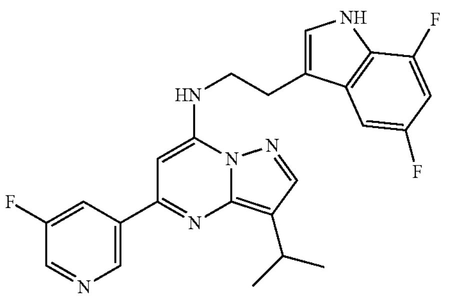

Synthetic Scheme:

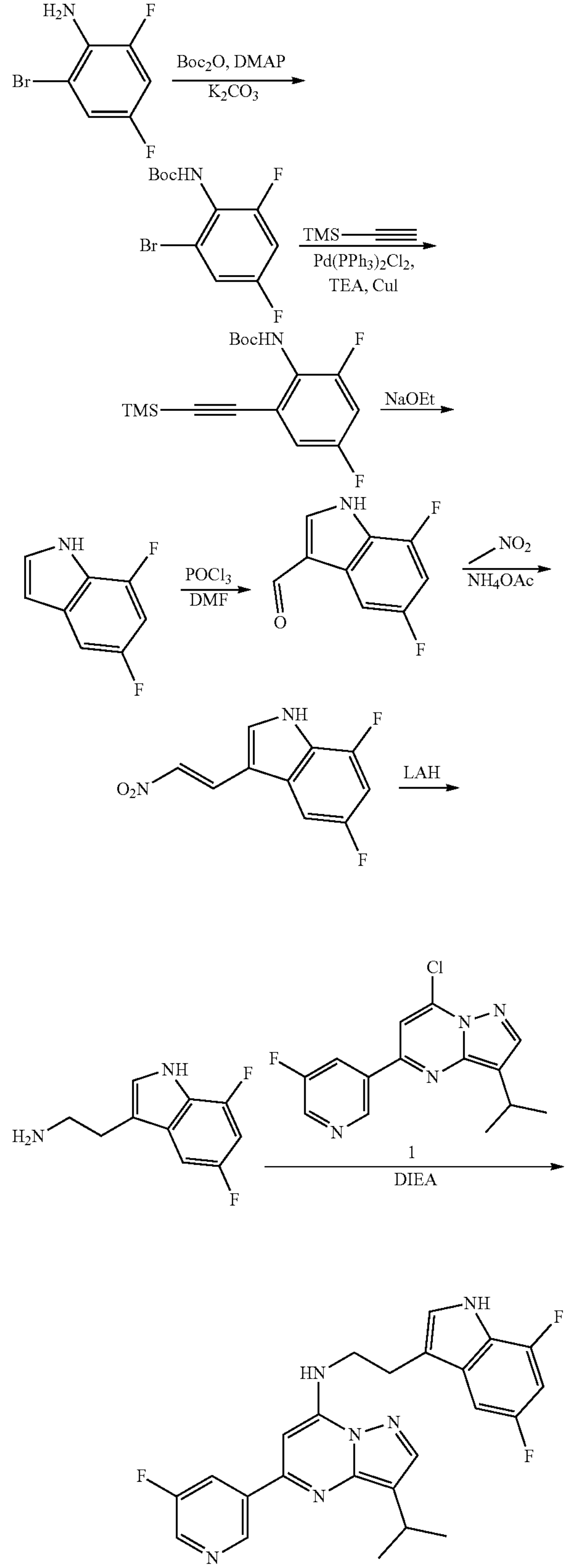

I-99

Step 1: tert-Butyl N-(2-bromo-4,6-difluoro-phenyl)carbamate

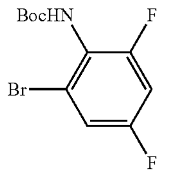

A mixture of 2-bromo-4,6-difluoro-aniline (10 g, 48.08 mmol, 1 eq), $Boc_2O$ (31.48 g, 144.23 mmol, 33.13 mL, 3 eq), DMAP (587.34 mg, 4.81 mmol, 0.1 eq) in THF (100 mL) was degassed and purged with $N_2$ for 3 times. The mixture was stirred at 70° C. for 16 h under $N_2$. The reaction mixture was concentrated under reduced pressure to give a residue which was dissolved in MeOH (100 mL), added $K_2CO_3$ (19.93 g, 144.23 mmol, 3 eq) and stirred at 70° C. for 4 h. The reaction mixture was filtered and the filtrate was concentrated under reduced pressure. To the crude mixture was added water (100 mL), extracted with EtOAc (100 mL×3). The combined organic layers were washed with brine (30 mL), dried over $Na_2SO_4$, filtered, concentrated under reduced pressure to give a residue which was purified by flash silica gel chromatography (from PE/EtOAc=1/0 to 10/1, TLC: PE/EtOAc=10/1, $R_f$=0.36) to yield tert-butyl N-(2-bromo-4,6-difluoro-phenyl)carbamate (12.5 g, 40.57 mmol, 84.3% yield, 100% purity) as a white solid. $^1H$ NMR (400 MHz, $CDCl_3$) δ ppm 7.10 (td, J=2.3, 7.7 Hz, 1H), 6.86-6.77 (m, 1H), 5.84 (s, 1H), 1.43 (s, 9H); ES-LCMS m/z 251.9, 253.9 $[M-t-Bu+H]^+$.

Step 2: tert-Butyl N-[2,4-difluoro-6-(2-trimethylsilylethynyl)phenyl]carbamate

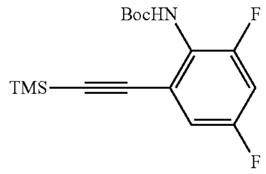 [SMILES: CC(C)(C)OC(=O)Nc1c(F)cc(F)cc1C#C[Si](C)(C)C]

A mixture of tert-butyl N-(2-bromo-4,6-difluoro-phenyl)carbamate (4 g, 12.98 mmol, 1 eq), ethynyl(trimethyl)silane (1.91 g, 19.47 mmol, 2.70 mL, 1.5 eq), TEA (3.94 g, 38.95 mmol, 5.42 mL, 3.0 eq), CuI (247.24 mg, 1.30 mmol, 0.1 eq) and $Pd(PPh_3)_2Cl_2$ (455.60 mg, 649.10 μmol, 0.05 eq) in DMF (80 mL) was degassed and purged with $N_2$ for 3 times, then stirred at 100° C. for 16 h under $N_2$. The reaction mixture was quenched by addition of water (300 mL), then extracted with EtOAc (200 mL×3). The combined organic layers were washed with brine (50 mL), dried over anhydrous $Na_2SO_4$, filtered and concentrated under reduced pressure to give a residue which was purified by flash silica gel chromatography (from PE/EtOAc=1/0 to 10/1, TLC: PE/EtOAc=20/1, $R_f$=0.31) to yield tert-butyl N-[2,4-difluoro-6-(2-trimethylsilylethynyl)phenyl]carbamate (3.0 g, 8.20 mmol, 63.2% yield, 89.0% purity) as a black brown solid. $^1H$ NMR (400 MHz, $CDCl_3$) δ ppm 7.00-6.93 (m, 1H), 6.90-6.81 (m, 1H), 6.09 (s, 1H), 1.49 (s, 9H), 0.26 (s, 9H); ES-LCMS m/z 270.1 $[M-t-Bu+H]^+$.

Step 3: 5,7-Difluoro-1H-indole

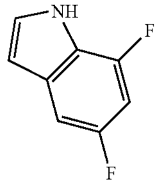 [SMILES: Fc1cc(F)c2[nH]ccc2c1]

To a solution of EtOH (150 mL) was added Na (1.51 g, 65.64 mmol, 8 eq) slowly. After being stirred for 1 h at 15° C. while Na was dissolved completely, to the mixture was added tert-butyl N-[2,4-difluoro-6-(2-trimethylsilylethynyl)phenyl]carbamate (3.0 g, 8.20 mmol, 1 eq) and the mixture was stirred at 85° C. for 16 h. The reaction mixture was concentrated under reduced pressure to remove EtOH. To the residue was added water (100 mL), extracted with EtOAc (60 mL×3). The combined organic layers were washed with brine (30 mL), dried over $Na_2SO_4$, filtered and concentrated under reduced pressure to give a residue which was purified by flash silica gel chromatography (from PE/EtOAc=1/0 to 10/1, TLC: PE/EtOAc=10/1, $R_f$=0.17) to yield 5,7-difluoro-1H-indole (600 mg, 3.68 mmol, 44.8% yield, 94.0% purity) as yellow oil. $^1H$ NMR (400 MHz, $CDCl_3$) δ ppm 8.36 (s, 1H), 7.27-7.25 (m, 1H), 7.09 (dd, J=2.0, 9.0 Hz, 1H), 6.74 (dt, J=2.1, 10.2 Hz, 1H), 6.60-6.47 (m, 1H); ES-LCMS m/z No mass was found.

Step 4: 5,7-Difluoro-1H-indole-3-carbaldehyde

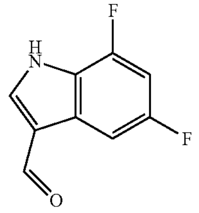 [SMILES: O=Cc1c[nH]c2c(F)cc(F)cc12]

To a solution of DMF (18 mL) was added $POCl_3$ (1.13 g, 7.37 mmol, 684.54 μL, 2.0 eq) dropwise at −20° C. over a period of 10 min under $N_2$. After 1 h, 5,7-difluoro-1H-indole (600 mg, 3.68 mmol, 1 eq) in DMF (2 mL) was added to the above solution during which the temperature was maintained below −20° C. The reaction mixture was warmed to 15° C. and stirred at 15° C. for 1 h. TLC (PE/EtOAc=1/1, $R_f$=0.40) showed the starting material was consumed completely and one new spot formed. The reaction mixture was quenched by addition of $NaHCO_3$ (100 mL) at 0° C., extracted with EtOAc (100 mL×3). The combined organic layers were washed with brine (30 mL), dried over $Na_2SO_4$, filtered and concentrated under reduced pressure to give a residue which was purified by flash silica gel chromatography (from PE/EtOAc=1/0 to 1/2, TLC: PE/EtOAc=1/1, $R_f$=0.40) to yield 5,7-difluoro-1H-indole-3-carbaldehyde (500 mg, 2.35 mmol, 63.7% yield, 85.0% purity) as a yellow solid. $^1H$ NMR (400 MHz, Acetone) δ ppm 11.72 (s, 1H), 10.05 (s, 1H), 8.36 (s, 1H), 7.73 (dd, J=2.4, 9.0 Hz, 1H), 7.02 (ddd, J=2.2, 9.4, 11.3 Hz, 1H); ES-LCMS m/z 182.1 $[M+H]^+$.

Step 5: 5,7-Difluoro-3-[(E)-2-nitrovinyl]-1H-indole

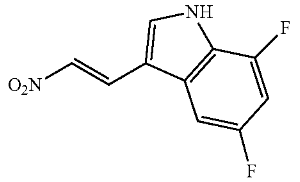 [SMILES: O=[N+]([O-])/C=C/c1c[nH]c2c(F)cc(F)cc12]

To a solution of 5,7-difluoro-1H-indole-3-carbaldehyde (500 mg, 2.35 mmol, 1 eq) in nitromethane (15 mL) was added $NH_4OAc$ (542.57 mg, 7.04 mmol, 3.0 eq). The mixture was stirred at 110° C. for 16 h. The reaction mixture was concentrated under reduced pressure to remove nitromethane. The residue was diluted in EtOAc (50 mL), washed with water (10 mL), brine (10 mL), dried over $Na_2SO_4$, filtered and concentrated under reduced pressure to give a residue which was purified by flash silica gel chromatography (from PE/EtOAc=1/0 to 3/1, TLC: PE/EtOAc=1/1, $R_f$=0.70) to yield 5,7-difluoro-3-[(E)-2-nitrovinyl]-1H-indole (420 mg, 1.82 mmol, 77.4% yield, 97.0% purity) as a yellow solid. $^1H$ NMR (400 MHz, $CDCl_3$) δ ppm 8.23 (d, J=13.5 Hz, 1H), 7.76-7.57 (m, 2H), 7.25-7.16 (m, 1H), 6.91-6.78 (m, 1H); ES-LCMS m/z 225.1 $[M+H]^+$.

Step 6: 2-(5,7-Difluoro-1H-indol-3-yl)ethanamine

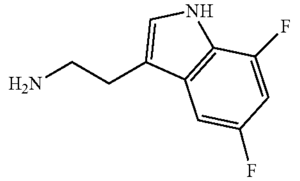 [SMILES: NCCc1c[nH]c2c(F)cc(F)cc12]

To a solution of 5,7-difluoro-3-[(E)-2-nitrovinyl]-1H-indole (420 mg, 1.82 mmol, 1 eq) in THF (15 mL) was added dropwise LAH (1 M in THF, 6.36 mL, 3.5 eq) at 0° C. After addition, the mixture was stirred at 80° C. for 2 h. TLC (PE/EtOAc=3/1, $R_f$=0.04) showed the starting material was consumed completely and a new spot formed. The reaction mixture was diluted with THF (75 mL), quenched by addition of water (0.25 mL), aq. NaOH (0.25 mL, 10% in water), water (0.75 mL) at 0° C. in sequence. After being stirred for 20 min, the mixture was filtered through celite. The filtrate was concentrated under reduced pressure to yield a crude 2-(5,7-difluoro-1H-indol-3-yl)ethanamine (320 mg, 1.44 mmol, 78.9% yield, 88.0% purity) as a brown solid which was used in the next step directly without further purification. $^1H$ NMR (400 MHz, $CD_3OD$) δ ppm 7.18 (s, 1H), 7.08 (dd, J=2.1, 9.4 Hz, 1H), 6.70 (ddd, J=2.3, 9.5, 11.3 Hz, 1H), 2.94-2.82 (m, 4H); ES-LCMS m/z 197.1 $[M+H]^+$.

Step 7: N-[2-(5,7-Difluoro-1H-indol-3-yl)ethyl]-5-(5-fluoro-3-pyridyl)-3-isopropyl-pyrazolo[1,5-a]pyrimidin-7-amine (I-99)

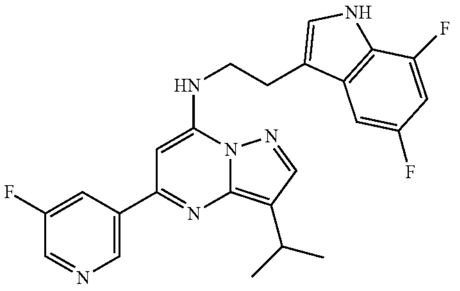 [SMILES: CC(C)c1cnn2c(NCCc3c[nH]c4c(F)cc(F)cc34)cc(-c3cncc(F)c3)nc12]

To a solution of 7-chloro-5-(5-fluoro-3-pyridyl)-3-isopropyl-pyrazolo[1,5-a]pyrimidine (40 mg, 132.08 μmol, 1 eq), 2-(5,7-difluoro-1H-indol-3-yl)ethanamine (44.17 mg, 198.13 μmol, 1.5 eq) in i-PrOH (3 mL) was added DIEA (85.35 mg, 660.42 μmol, 115.03 μL, 5 eq). The mixture was stirred at 60° C. for 16 h. The reaction mixture was concentrated under reduced pressure to yield a residue which was purified by preparative TLC (DCM/MeOH=20/1, TLC: DCM/MeOH=20/1, $R_f$=0.48) to yield N-[2-(5,7-difluoro-1H-indol-3-yl)ethyl]-5-(5-fluoro-3-pyridyl)-3-isopropyl-pyrazolo[1,5-a]pyrimidin-7-amine (30.31 mg, 66.35 μmol, 50.2% yield, 98.6% purity) as a yellow solid. $^1H$ NMR (400 MHz, $CD_3OD$) δ ppm 8.82 (t, J=1.4 Hz, 1H), 8.49 (d, J=2.6 Hz, 1H), 7.97-7.85 (m, 2H), 7.21-7.11 (m, 2H), 6.72-6.58 (m, 1H), 6.11 (s, 1H), 3.85 (t, J=6.5 Hz, 2H), 3.30-3.24 (m, 1H), 3.15 (t, J=6.3 Hz, 2H), 1.38 (d, J=7.1 Hz, 6H); ES-LCMS m/z 451.3 $[M+H]^+$.

Example 98

Synthesis of I-100

I-100

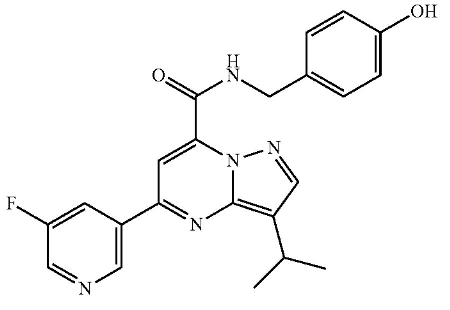 [SMILES: CC(C)c1cnn2c(C(=O)NCc3ccc(O)cc3)cc(-c3cncc(F)c3)nc12]

Synthetic Scheme:

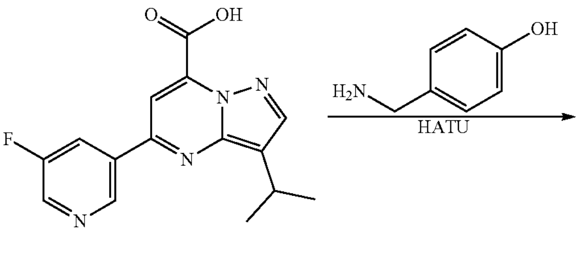

-continued

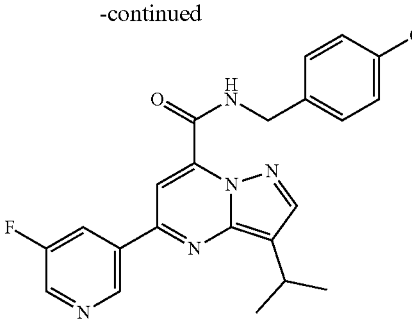

I-100

Step 1: 5-(5-Fluoro-3-pyridyl)-N-[(4-hydroxyphenyl)methyl]-3-isopropyl-pyrazolo[1,5-a]pyrimidine-7-carboxamide (I-100)

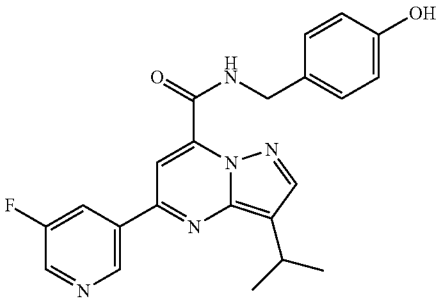

To a solution of 5-(5-fluoro-3-pyridyl)-3-isopropyl-pyrazolo[1,5-a]pyrimidine-7-carboxylic acid (40 mg, 130.54 μmol, 1 eq) and 4-(aminomethyl)phenol (19.29 mg, 156.65 μmol, 1.2 eq) in DCM (20 mL) was added HATU (74.45 mg, 195.81 μmol, 1.5 eq) and DIEA (50.61 mg, 391.63 μmol, 68.21 μL, 3.0 eq). The mixture was stirred at 25° C. for 16 h. The combined reaction mixture was diluted with $H_2O$ (20 mL), extracted with EtOAc (20 mL×3). The combined organic layers were dried over anhydrous $Na_2SO_4$, filtered and concentrated under reduced pressure to give a residue which was purified by preparative HPLC (column: Phenomenex Synergi C18 150*30 mm*4 um; mobile phase: [water (0.05% HCl)-ACN]; B %: 47%-77%, 12 min), followed by lyophilization to yield 5-(5-fluoro-3-pyridyl)-N-[(4-hydroxyphenyl)methyl]-3-isopropyl-pyrazolo[1,5-a]pyrimidine-7-carboxamide (14.42 mg, 29.79 μmol, 22.8% yield, 98.8% purity, 2HCl) as a yellow solid. $^1H$ NMR (400 MHz, DMSO-$d_6$) δ ppm 9.35 (s, 1H), 8.77 (d, J=2.9 Hz, 1H), 8.69 (d, J=9.3 Hz, 1H), 8.31 (s, 1H), 8.22 (s, 1H), 7.26 (d, J=8.6 Hz, 2H), 6.82-6.72 (m, 2H), 4.66 (s, 2H), 3.48-3.42 (m, 1H), 1.46 (d, J=6.8 Hz, 6H); ES-LCMS m/z 406.1 $[M+H]^+$.

Example 99

Synthesis of I-101

I-101

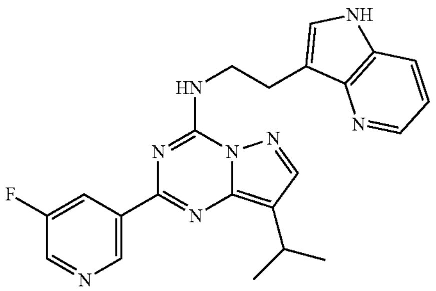 [SMILES: CC(C)c1cnn2c(NCCc3c[nH]c4cccnc34)nc(-c3cncc(F)c3)nc12]

Synthetic Scheme:

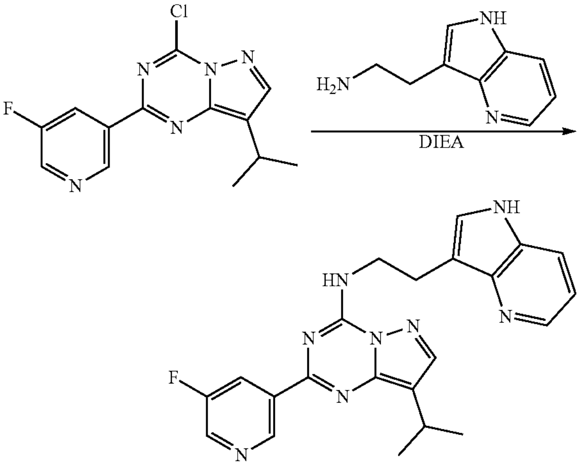

I-101

Step 1: 2-(5-Fluoro-3-pyridyl)-8-isopropyl-N-[2-(1H-pyrrolo[3,2-b]pyridin-3-yl)ethyl]pyrazolo[1,5-a][1,3,5]triazin-4-amine (I-101)

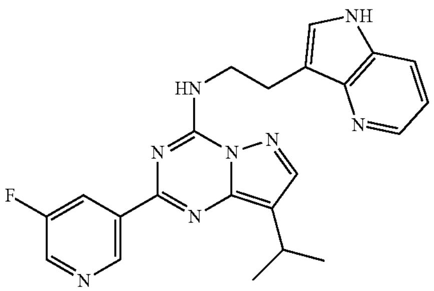

To a solution of 4-chloro-2-(5-fluoro-3-pyridyl)-8-isopropyl-pyrazolo[1,5-a][1,3,5]triazine (40 mg, 137.12 umol, 1 eq) and 2-(1H-pyrrolo[3,2-b]pyridin-3-yl)ethanamine (33.58 mg, 164.55 mol, 1.2 eq) in i-PrOH (10 mL) was added DIEA (53.17 mg, 411.37 μmol, 71.65 μL, 3 eq). The mixture was stirred at 90° C. for 3 h. The mixture was concentrated under reduced pressure to give a residue which was purified by prep-HPLC (column: Phenomenex Synergi C18 150*30 mm*4 um; mobile phase: [water (0.05% HCl)-ACN]; B %: 20%-50%, 12 min) to yield 2-(5-fluoro-3-pyridyl)-8-isopropyl-N-[2-(1H-pyrrolo[3,2-b]pyridin-3-yl) ethyl]pyrazolo[1,5-a][1,3,5]triazin-4-amine (26.15 mg, 49.73 μmol, 36.27% yield, 100% purity, 3HCl) as a yellow solid. $^1$H NMR (400 MHz, $CD_3OD$) δ ppm 9.43-9.38 (m, 1H), 9.00-8.93 (m, 2H), 8.49 (d, J=5.6 Hz, 1H), 8.41 (d, J=8.2 Hz, 1H), 8.01 (s, 2H), 7.59-7.54 (m, 1H), 4.19 (t, J=6.4 Hz, 2H), 3.41-3.37 (m, 2H), 3.29-3.22 (m, 1H), 1.39 (d, J=6.8 Hz, 6H); ES-LCMS m/z 417.3 $[M+H]^+$.

Example 100

Synthesis of I-102

I-102

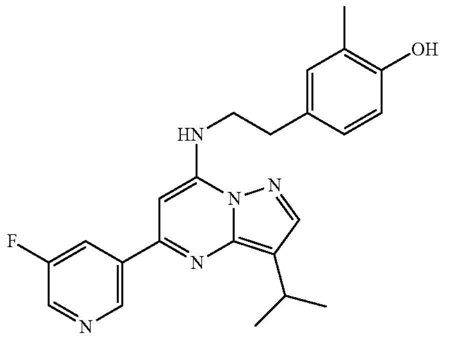

Synthetic Scheme:

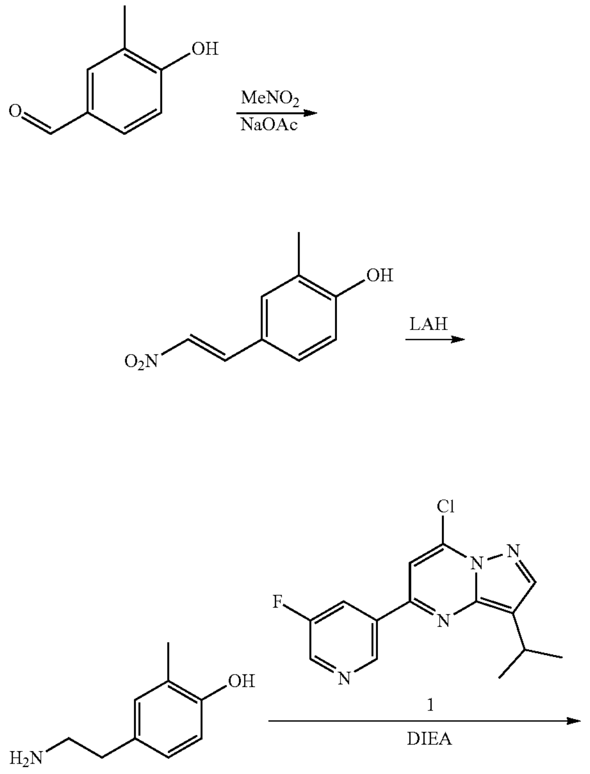

-continued

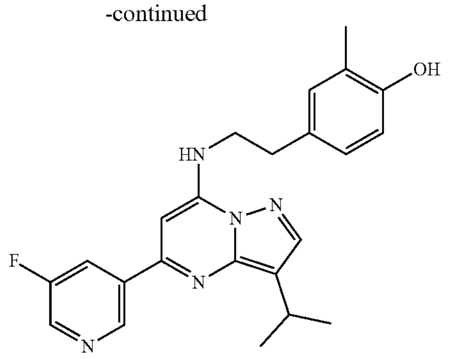

I-102

Step 1: 2-Methyl-4-[(E)-2-nitrovinyl]phenol

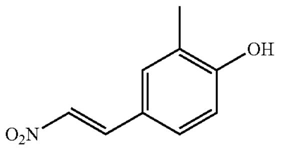

A mixture of 4-hydroxy-3-methyl-benzaldehyde (1 g, 7.34 mmol, 1 eq) and NaOAc (602.53 mg, 7.34 mmol, 1 eq) in $CH_3NO_2$ (10 mL) was stirred at 110° C. for 48 h. TLC (PE/EtOAc=5/1, $R_f$=0.23) indicated starting material was consumed completely and one new spot formed. The mixture was concentrated under reduced pressure to give a residue which was purified by flash silica gel chromatography (from PE/EtOAc=1/0 to 5/1, TLC: PE/EtOAc=5/1, $R_f$=0.23) to yield 2-methyl-4-[(E)-2-nitrovinyl]phenol (400 mg, 1.12 mmol, 15.2% yield, 50% purity) as a yellow solid. $^1$H NMR (400 MHz, $CD_3OD$) δ ppm 7.98 (d, J=13.6 Hz, 1H), 7.75 (d, J=13.6 Hz, 1H), 7.65-7.59 (m, 1H), 7.46-7.37 (m, 1H), 6.88 (d, J=8.4 Hz, 1H), 2.24 (s, 3H); ES-LCMS m/z 180.1 $[M+H]^+$ Step 2: 4-(2-Aminoethyl)-2-methyl-phenol

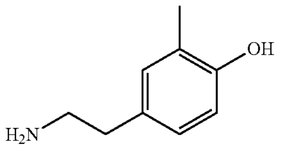

To a solution of 2-methyl-4-[(E)-2-nitrovinyl]phenol (400 mg, 1.12 mmol, 1 eq) in THF (10 mL) was added LAH (1 M, 3.35 mL, 3 eq) at 0° C. Then the mixture was stirred at 70° C. for 2 h. The mixture was quenched with water (0.25 mL), 15% NaOH (0.25 mL) and water (0.75 mL). Then the mixture was stirred at 20° C. for 3 h. The mixture was filtered and concentrated under reduced pressure to yield 4-(2-aminoethyl)-2-methyl-phenol (350 mg, crude) as a brown oil which was used in next step without further purification. $^1$H NMR (400 MHz, $CD_3OD$) δ ppm 7.05 (s, 1H), 6.92 (s, 1H), 6.85-6.84 (m, 1H), 3.58-3.55 (m, 2H), 2.17 (s, 3H), 1.60-1.57 (m, 2H); ES-LCMS m/z 152.1 $[M+H]^+$.

Step 3: 4-[2-[[5-(5-Fluoro-3-pyridyl)-3-isopropyl-pyrazolo[1,5-a]pyrimidin-7-yl]amino]ethyl]-2-methyl-phenol (I-102)

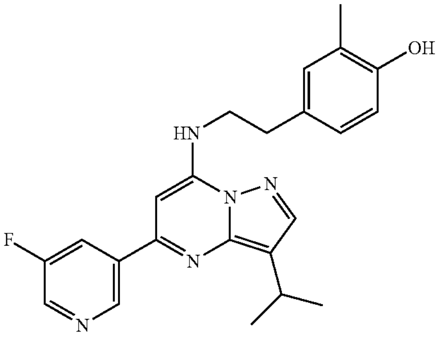 [SMILES: Cc1cc(CCNc2cc(-c3cncc(F)c3)nc3c(C(C)C)cnn23)ccc1O]

To a solution of 7-chloro-5-(5-fluoro-3-pyridyl)-3-isopropyl-pyrazolo[1,5-a]pyrimidine (50 mg, 165.11 μmol, 1.0 eq) and 4-(2-aminoethyl)-2-methyl-phenol (29.96 mg, 198.13 μmol, 1.2 eq) in i-PrOH (10 mL) was added DIEA(64.02 mg, 495.33 μmol, 86.28 μL, 3 eq). The mixture was stirred at 80° C. for 12 h. The mixture was concentrated under reduced pressure to give a residue which was washed with MeOH (20 mL), filtered. The filtered cake was lyophilized to yield 4-[2-[[5-(5-fluoro-3-pyridyl)-3-isopropyl-pyrazolo[1,5-a]pyrimidin-7-yl]amino]ethyl]-2-methyl-phenol (26.08 mg, 63.29 μmol, 38.3% yield, 98.4% purity) as a white solid. $^1$H NMR (400 MHz, DMSO-$d_6$) δ ppm 9.24 (s, 1H), 9.03 (s, 1H), 8.67 (s, 1H), 8.40-8.36 (m, 1H), 7.99 (s, 1H), 7.92 (t, J=6.0 Hz, 1H), 7.02 (s, 1H), 6.90 (dd, J=2.0, 8.2 Hz, 1H), 6.73 (s, 1H), 6.64 (d, J=8.2 Hz, 1H), 3.74-3.67 (m, 2H), 3.27-3.19 (m, 1H), 2.85 (t, J=7.6 Hz, 2H), 2.07 (s, 3H), 1.36 (d, J=6.8 Hz, 6H); ES-LCMS m/z 406.2 $[M+H]_+$.

Example 101

Synthesis of I-103

I-103

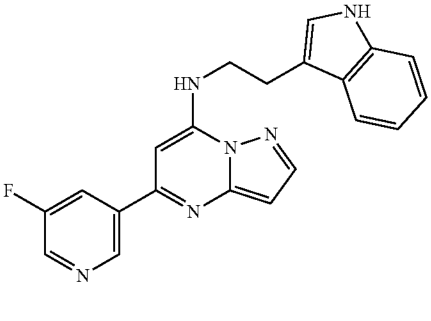 [SMILES: Fc1cncc(-c2cc(NCCc3c[nH]c4ccccc34)n3nccc3n2)c1]

Synthetic Scheme:

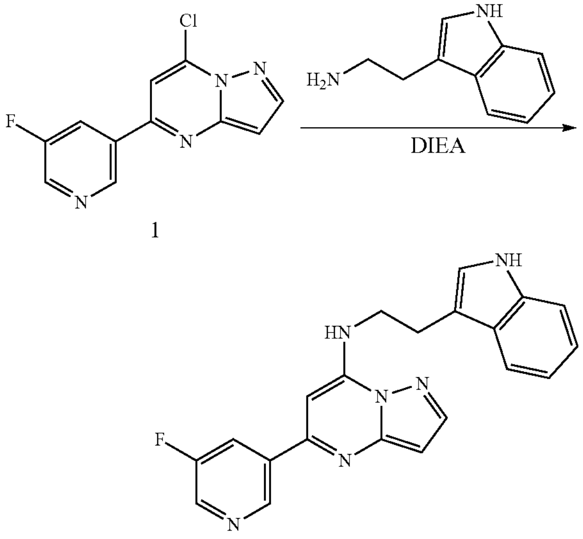

1

I-103

Step 1: 5-(5-Fluoro-3-pyridyl)-N-[2-(1H-indol-3-yl)ethyl]pyrazolo[1,5-a]pyrimidin-7-amine (I-103)

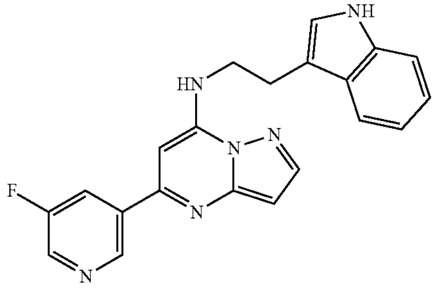

To a solution of 7-chloro-5-(5-fluoro-3-pyridyl)pyrazolo[1,5-a]pyrimidine (30 mg, 110.76 μmol, 1.0 eq) in i-PrOH (3 mL) was added DIEA (42.94 mg, 332.28 μmol, 57.88 μL, 3.0 eq) and 2-(1H-indol-3-yl)ethanamine (24.00 mg, 149.80 μmol, 1.35 eq). The mixture was stirred at 50° C. for 3 h. The reaction mixture was concentrated under reduced pressure to give the residue which was purified by preparative HPLC (HCl condition; column: Phenomenex Gemini 150×25 mm×10 um; mobile phase: [water (0.05% HCl)-ACN]; B %: 29%-49%, 10 min). The desired fraction was lyophilized to yield 5-(5-fluoro-3-pyridyl)-N-[2-(1H-indol-3-yl)ethyl]pyrazolo[1,5-a]pyrimidin-7-amine (25.41 mg, 52.74 μmol, 47.62% yield, 100% purity, 3HCl salt) as a yellow solid. $^1$H NMR (400 MHz, $CD_3OD$) δ ppm 8.73 (d, J=2.5 Hz, 1H), 8.38 (s, 1H), 8.26 (d, J=2.3 Hz, 1H), 7.56 (d, J=7.8 Hz, 1H), 7.46 (td, J=2.3, 9.0 Hz, 1H), 7.12 (d, J=8.0 Hz, 1H), 7.00 (s, 1H), 6.96 (t, J=7.2 Hz, 1H), 6.89-6.84 (m, 1H), 6.52 (d, J=2.3 Hz, 1H), 5.88 (s, 1H), 4.07 (t, J=5.9 Hz, 2H), 3.27-3.23 (m, 2H); ES-LCMS m/z 373.3 $[M+H]^+$.

Example 102

Synthesis of I-104

I-104

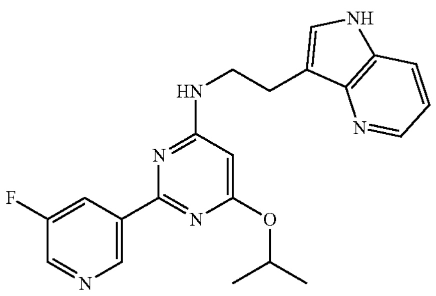

Synthetic Scheme:

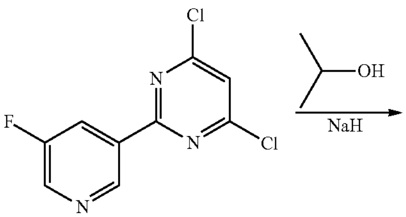

1

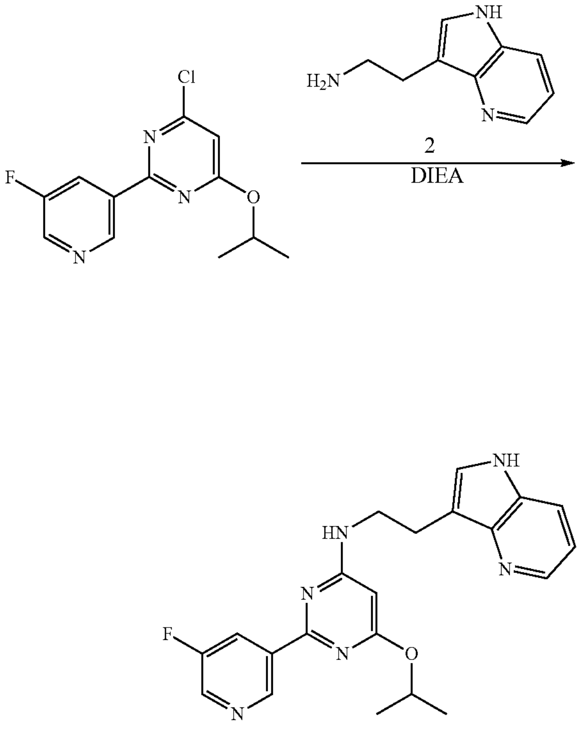

I-104

Step 1: 4-Chloro-2-(5-fluoro-3-pyridyl)-6-isopropoxy-pyrimidine

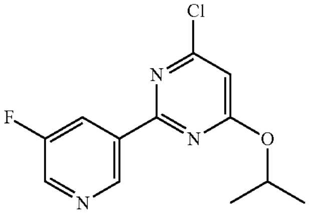 [SMILES: CC(C)Oc1cc(Cl)nc(-c2cncc(F)c2)n1]

To a solution of i-PrOH (43.10 mg, 717.06 μmol, 54.90 μL, 1 eq) in THE (8 mL) was added NaH (34.42 mg, 860.47 μmol, 60% purity, 1.2 eq). The mixture was stirred at 0° C. for 30 min. 4,6-dichloro-2-(5-fluoro-3-pyridyl)pyrimidine (175 mg, 717.06 μmol, 1.0 eq) was added into the above solution and the mixture was stirred at 15° C. for 12 h. The reaction mixture was concentrated under reduced pressure to remove THF. The residue was diluted with water (50 mL) and extracted with EtOAc (30 mL×3). The combined organic layers were dried over $Na_2SO_4$, filtered and concentrated under reduced pressure to give 4-chloro-2-(5-fluoro-3-pyridyl)-6-isopropoxy-pyrimidine (220 mg, 690.36 μmol, 96.2% yield, 84.0% purity) as a yellow solid which was used in the next step without further purification. $^1H$ NMR (400 MHz, $CDCl_3$) δ ppm 9.41 (s, 1H), 8.58 (d, J=2.8 Hz, 1H), 8.40-8.31 (m, 1H), 6.67 (s, 1H), 5.53 (m, 1H), 1.43 (d, J=6.3 Hz, 6H); ES-LCMS m/z 268.1, 270.1 $[M+H]^+$.

Step 2: 2-(5-Fluoro-3-pyridyl)-6-isopropoxy-N-[2-(1H-pyrrolo[3,2-b]pyridin-3-yl)ethyl]pyrimidin-4-amine (I-104)

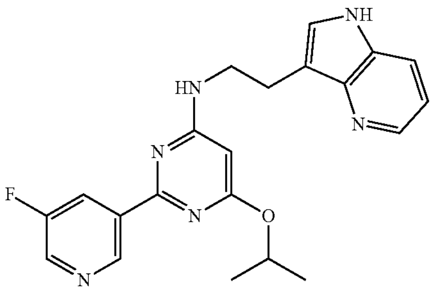 [SMILES: CC(C)Oc1cc(NCCc2c[nH]c3cccnc23)nc(-c2cncc(F)c2)n1]

4-Chloro-2-(5-fluoro-3-pyridyl)-6-isopropoxy-pyrimidine (60 mg, 188.28 μmol, 1.0 eq), 2-(1H-pyrrolo[3,2-b]pyridin-3-yl)ethanamine (45 mg, 220.53 μmol, 1.17 eq) and DIEA (73.00 mg, 564.84 μmol, 98.38 μL, 3.0 eq) in i-PrOH (3 mL) were taken up into a microwave tube. The sealed tube was heated at 125° C. for 6 h under microwave. The reaction mixture was concentrated under reduced pressure to remove solvent. The residue was purified by preparative HPLC (HCl condition; column: Phenomenex Gemini 150×25 mm×10 um; mobile phase: [water (0.05% HCl)-ACN]; B %: 25%-55%, 10 min). The desired fraction was lyophilized to yield 2-(5-fluoro-3-pyridyl)-6-isopropoxy-N-[2-(1H-pyrrolo[3,2-b]pyridin-3-yl)ethyl]pyrimidin-4-amine (20.08 mg, 38.97 μmol, 20.7% yield, 97.4% purity, 3HCl salt) as a yellow solid. $^1H$ NMR (400 MHz, $CD_3OD$) δ ppm 9.20 (s, 1H), 8.93 (dd, J=1.0, 2.5 Hz, 1H), 8.62 (s, 1H), 8.53-8.46 (m, 2H), 8.06 (s, 1H), 7.65-7.58 (m, 1H), 6.03 (s, 1H), 5.22 (s, 1H), 5.29-5.16 (m, 1H), 3.96 (m, 2H), 3.30-3.27 (m, 2H), 1.42 (d, J=6.0 Hz, 6H); ES-LCMS m/z 393.2 $[M+H]^+$.

Example 103

Synthesis of I-105

I-105

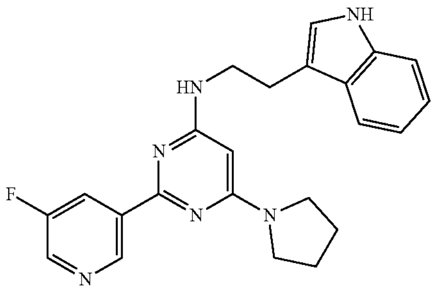 [SMILES: Fc1cncc(-c2nc(NCCc3c[nH]c4ccccc34)cc(N3CCCC3)n2)c1]

Synthetic Scheme:

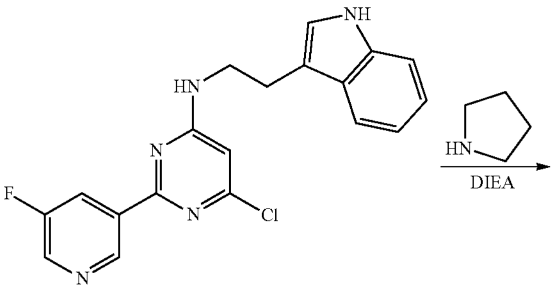

1

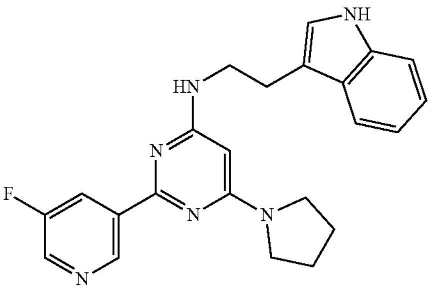

I-105

Step 1: 2-(5-Fluoro-3-pyridyl)-N-[2-(1H-indol-3-yl)ethyl]-6-pyrrolidin-1-yl-pyrimidin-4-amine (I-105)

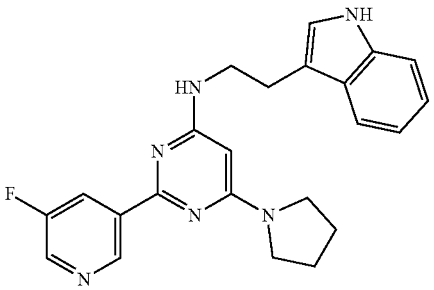

6-Chloro-2-(5-fluoro-3-pyridyl)-N-[2-(1H-indol-3-yl)ethyl]pyrimidin-4-amine (80 mg, 215.33 mol, 1.0 eq), pyrrolidine (1.28 g, 17.97 mmol, 1.5 mL, 83.45 eq) and DIEA (139.15 mg, 1.08 mmol, 187.53 μL, 5.0 eq) were taken up into a microwave tube in i-PrOH (1.5 mL). The sealed tube was heated at 130° C. for 3 h under microwave. The reaction mixture was concentrated under reduced pressure to remove solvent. The residue was purified by preparative HPLC (HCl condition; column: Phenomenex Gemini 150×25 mm×10 um; mobile phase: [water (0.05% HCl)-ACN]; B %: 25%-55%, 10 min). The desired fraction was lyophilized to yield 2-(5-fluoro-3-pyridyl)-N-[2-(1H-indol-3-yl)ethyl]-6-pyrrolidin-1-yl-pyrimidin-4-amine (47.28 mg, 91.26 μmol, 42.3% yield, 98.8% purity, 3HCl salt) as a yellow solid. $^1H$ NMR (400 MHz, $CD_3OD$) δ ppm 9.00 (s, 1H), 8.77 (s, 1H), 8.22 (s, 1H), 7.64 (d, J=7.3 Hz, 1H), 7.33 (d, J=7.9 Hz, 1H), 7.16-6.98 (m, 4H), 3.72 (d, J=6.0 Hz, 4H), 3.15 (t, J=5.8 Hz, 4H), 2.00 (s, 4H); ES-LCMS m/z 403.3 $[M+H]^+$.

Example 104

Synthesis of I-106

I-106

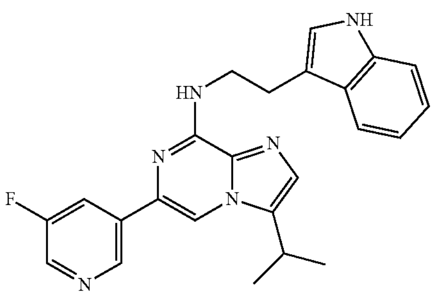

Synthetic Scheme:

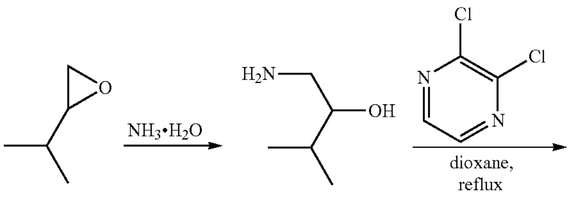

-continued

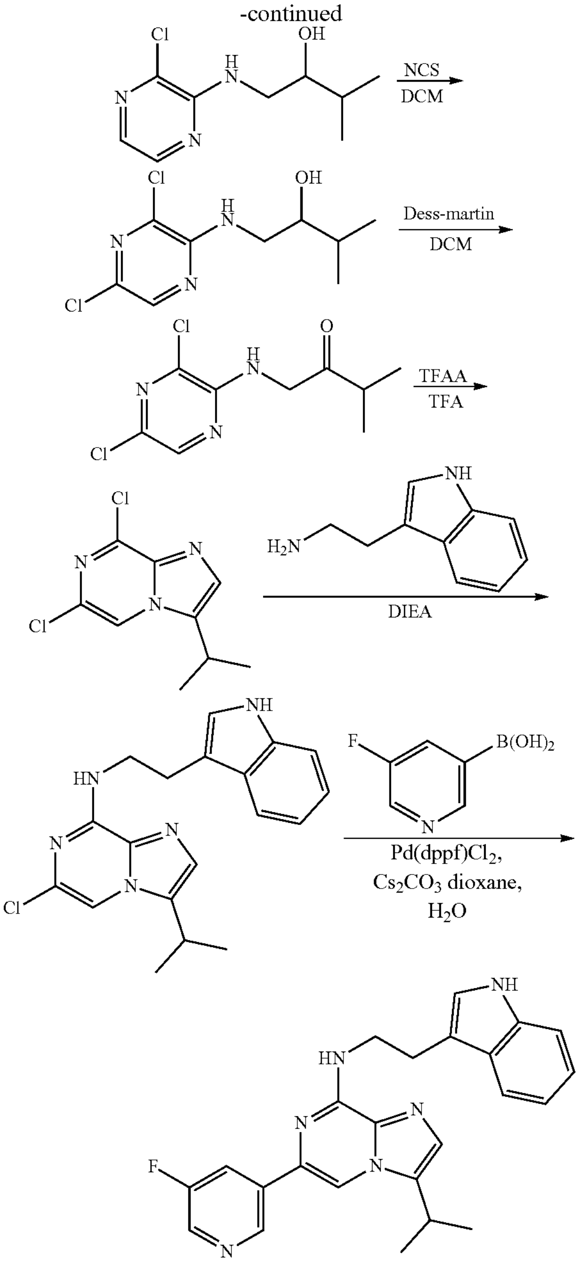

I-106

Step: 1-Amino-3-methyl-butan-2-ol

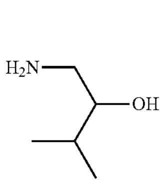

A mixture of 2-isopropyloxirane (600 mg, 6.97 mmol, 1 eq) in $NH_3.H_2O$ (5 mL) was degassed and purged with $N_2$ for 3 times. Then the mixture was stirred at 10-15° C. for 16 h under $N_2$ atmosphere. The reaction mixture was concentrated under reduced pressure to give the crude product 1-amino-3-methyl-butan-2-ol (700 mg, 6.79 mmol, 97.4% yield, crude) as colorless oil which was used in the next step without further purification. $^1$H NMR (400 MHz, $CDCl_3$) δ ppm 3.39-3.22 (m, 1H), 2.91-2.72 (m, 1H), 2.60-2.49 (m, 1H), 1.71-1.62 (m, 1H), 0.98-0.91 (m, 6H); ES-LCMS m/z No correct mass was found.

Step 2: 1-[(3-Chloropyrazin-2-yl)amino]-3-methyl-butan-2-ol

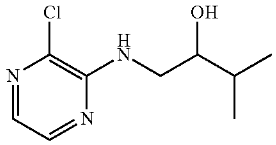

A mixture of 2,3-dichloropyrazine (670 mg, 4.50 mmol, 1 eq) and 1-amino-3-methyl-butan-2-ol (695.93 mg, 6.75 mmol, 1.5 eq) in 1,4-dioxane (3 mL) was degassed and purged with $N_2$ for 3 times. The mixture was stirred at 110° C. for 16 h under $N_2$ atmosphere. TLC (PE/EtOAc=5/1, $R_f$=0.54) showed the starting material was not consumed completely and a new spots was found. The reaction mixture was concentrated under reduced pressure to give a residue which was purified on silica gel column chromatography (from PE/EtOAc=1/0 to 5/1, TLC: PE/EtOAc=5/1, $R_f$=0.54) to give the product 1-[(3-chloropyrazin-2-yl)amino]-3-methyl-butan-2-ol (500 mg, 2.27 mmol, 50.5% yield, 98.0% purity) as colorless oil. $^1$H NMR (400 MHz, $CDCl_3$) δ ppm 7.92 (d, J=2.9 Hz, 1H), 7.60 (d, J=2.6 Hz, 1H), 5.61 (br s, 1H), 3.74 (ddd, J=2.4, 6.5, 13.8 Hz, 1H), 3.59-3.58 (m, 1H), 3.44-3.37 (m, 1H), 2.83 (d, J=4.4 Hz, 1H), 1.89-1.72 (m, 1H), 1.03 (dd, J=6.8, 10.6 Hz, 6H); ES-LCMS m/z 216.0, 218.1 $[M+H]^+$.

Step 3: 1-[(3,5-Dichloropyrazin-2-yl)amino]-3-methyl-butan-2-ol

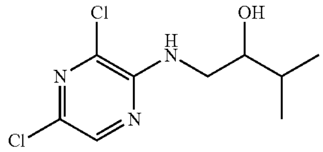

A mixture of 1-[(3-chloropyrazin-2-yl)amino]-3-methyl-butan-2-ol (380 mg, 1.73 mmol, 1 eq) and NCS (276.68 mg, 2.07 mmol, 1.2 eq) in $CHCl_3$ (10 mL) was degassed and purged with $N_2$ for 3 times and stirred at 70° C. for 2 h under $N_2$ atmosphere. The reaction mixture was concentrated under reduced pressure to give a residue which was purified on silica gel column chromatography (from PE/EtOAc=1/0 to 10/3, TLC: PE/EtOAc=3/1, $R_f$=0.46) to give the product of 1-[(3,5-dichloropyrazin-2-yl)amino]-3-methyl-butan-2-ol (345 mg, 1.23 mmol, 71.1% yield, 89.0% purity) as yellow oil. $^1$H NMR (400 MHz, $CDCl_3$) δ ppm 7.95 (s, 1H), 5.59 (br s, 1H), 3.74 (ddd, J=2.8, 6.7, 13.7 Hz, 1H), 3.58-3.56 (m, 1H), 3.38-3.33 (m, 1H), 1.83-1.73 (m, 1H), 1.03 (dd, J=6.8, 10.1 Hz, 6H); ES-LCMS m/z 250.0, 252.0 $[M+H]^+$.

Step 4: 1-[(3,5-Dichloropyrazin-2-yl)amino]-3-methyl-butan-2-one

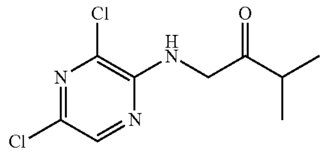

To a solution of 1-[(3,5-dichloropyrazin-2-yl)amino]-3-methyl-butan-2-ol (405 mg, 1.44 mmol, 1 eq) in DCM (30 mL) was added Dess-Martin (733.47 mg, 1.73 mmol, 1.2 eq). The mixture was stirred at 20° C. for 2 h. TLC (PE/EtOAc=3/1, $R_f$=0.51) showed about 50% of starting material was remained. Dess-Martin (300 mg, 0.71 mmol) was added and the reaction was stirred at 20° C. for 16 h. TLC (PE/EtOAc=3/1, $R_f$=0.51) showed about 20% of starting material was remained. The reaction mixture was quenched by addition sat $Na_2S_2O_3$ solution (50 mL), extracted with EtOAc (50 mL×3). The combined organic layers were dried over anhydrous $Na_2SO_4$, filtered and concentrated under reduced pressure to give a residue which was purified on silica gel column chromatography (from PE/EtOAc=1/0 to 3/1, TLC: PE/EtOAc=3/1, $R_f$=0.51) to give the product of 1-[(3,5-dichloropyrazin-2-yl)amino]-3-methyl-butan-2-one (200 mg, 669.06 μmol, 46.4% yield, 83.0% purity) as a yellow oil. $^1H$ NMR (400 MHz, $CDCl_3$) δ ppm 7.96 (s, 1H), 6.03 (br s, 1H), 4.35 (d, J=4.4 Hz, 2H), 2.76 (m, 1H), 1.22 (d, J=6.8 Hz, 6H); ES-LCMS m/z 247.9, 249.9 $[M+H]^+$.

Step 5: 6,8-Dichloro-3-isopropyl-imidazo[1,2-a]pyrazine

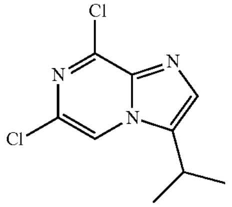

To a solution of 1-[(3,5-dichloropyrazin-2-yl)amino]-3-methyl-butan-2-one (180 mg, 602.16 μmol, 1 eq) in TFA (2 mL) was added TFAA (379.41 mg, 1.81 mmol, 251.27 μL, 3 eq). The mixture was stirred at 20° C. for 5 h. The reaction mixture was concentrated under reduced pressure to give a residue which was purified on silica gel column chromatography (from PE/EtOAc=1/0 to 10/3, TLC: PE/EtOAc=3/1, $R_f$=0.48) to give the product 6,8-dichloro-3-isopropyl-imidazo[1,2-a]pyrazine (120 mg, 521.53 μmol, 86.6% yield, 100.0% purity) as a light yellow solid. $^1H$ NMR (400 MHz, $CDCl_3$) δ ppm 7.94 (s, 1H), 7.69 (s, 1H), 3.22-3.16 (m, 1H), 1.44 (d, J=6.8 Hz, 6H); ES-LCMS m/z 230.0, 232.0 $[M+H]^+$.

Step 6: 6-Chloro-N-[2-(1H-indol-3-yl)ethyl]-3-isopropyl-imidazo[1,2-a]pyrazin-8-amine

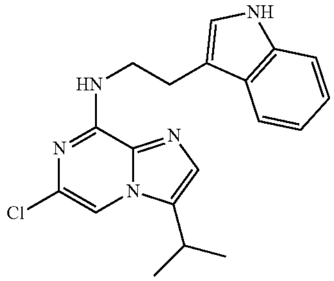 [SMILES: CC(C)c1cnc2c(NCCc3c[nH]c4ccccc34)nc(Cl)cn12]

To a solution of 6,8-dichloro-3-isopropyl-imidazo[1,2-a]pyrazine (50 mg, 217.30 μmol, 1 eq) and 2-(1H-indol-3-yl)ethanamine (41.78 mg, 260.76 μmol, 1.2 eq) in i-PrOH (3 mL) was added DIEA (84.25 mg, 651.91 μmol, 113.55 μL, 3.0 eq). The mixture was stirred at 45° C. for 3 h. The reaction mixture was concentrated under reduced pressure to give a residue which was purified on silica gel column chromatography (from PE/EtOAc=1/0 to 10/3, TLC: PE/EtOAc=1/1, $R_f$=0.44) to give the product 6-chloro-N-[2-(1H-indol-3-yl)ethyl]-3-isopropyl-imidazo[1,2-a]pyrazin-8-amine (60 mg, 162.78 μmol, 74.9% yield, 96.0% purity) as brown oil. $^1H$ NMR (400 MHz, $CDCl_3$) (ppm 8.07 (br s, 1H), 7.71 (d, J=7.9 Hz, 1H), 7.38 (d, J=7.9 Hz, 1H), 7.30 (s, 1H), 7.24-7.19 (m, 2H), 7.17-7.12 (m, 1H), 7.11 (d, J=2.2 Hz, 1H), 6.21 (br s, 1H), 4.02-3.89 (m, 2H), 3.17 (t, J=6.8 Hz, 2H), 3.12-3.02 (m, 1H), 1.37 (d, J=7.1 Hz, 6H); ES-LCMS m/z 354.0, 356.1 $[M+H]^+$.

Step 7: 6-(5-Fluoro-3-pyridyl)-N-[2-(1H-indol-3-yl)ethyl]-3-isopropyl-imidazo[1,2-a]pyrazin-8-amine (I-106)

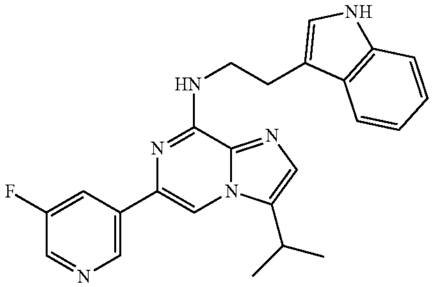 [SMILES: CC(C)c1cnc2c(NCCc3c[nH]c4ccccc34)nc(-c3cncc(F)c3)cn12]

6-Chloro-N-[2-(1H-indol-3-yl)ethyl]-3-isopropyl-imidazo[1,2-a]pyrazin-8-amine (60 mg, 162.78 μmol, 1 eq), (5-fluoro-3-pyridyl)boronic acid (45.87 mg, 325.56 μmol, 2.0 eq), $Pd(dppf)Cl_2$ (11.91 mg, 16.28 μmol, 0.1 eq) and $Cs_2CO_3$ (159.11 mg, 488.35 μmol, 3.0 eq) were taken up into a microwave tube in 1,4-dioxane (2 mL) and $H_2O$ (0.5 mL). The mixture was purged with $N_2$ for 3 min. The sealed tube was heated at 110° C. for 30 min under microwave. The reaction mixture was diluted with (20 mL) and extracted with ethyl acetate (20 mL×3). The combined organic layers were dried over anhydrous $Na_2SO_4$, filtered and concentrated under reduced pressure to give a residue which was purified by preparative HPLC (column: Phenomenex Synergi C18 150*30 mm*4 um; mobile phase: [water(0.05%

HCl)-ACN]; B %: 30%-60%, 12 min), followed by lyophilization to yield 6-(5-fluoro-3-pyridyl)-N-[2-(1H-indol-3-yl)ethyl]-3-isopropyl-imidazo[1,2-a]pyrazin-8-amine (50.13 mg, 94.00 μmol, 57.8% yield, 98.2% purity, 3HCl) as a yellow solid. $^1$H NMR (400 MHz, $CD_3OD$) δ ppm 9.21 (br s, 1H), 8.86 (br s, 1H), 8.74 (d, J=9.0 Hz, 1H), 8.57 (s, 1H), 7.89 (s, 1H), 7.51 (d, J=7.8 Hz, 1H), 7.18 (d, J=8.3 Hz, 1H), 7.09 (s, 1H), 6.94 (t, J=7.5 Hz, 1H), 6.89-6.81 (m, 1H), 4.06 (t, J=6.1 Hz, 2H), 3.46 (d, J=6.0 Hz, 1H), 3.18 (t, J=6.3 Hz, 2H), 1.42 (d, J=6.3 Hz, 6H); ES-LCMS m/z 415.3 [M+H]$^+$.

Example 105

Synthesis of I-107

I-107

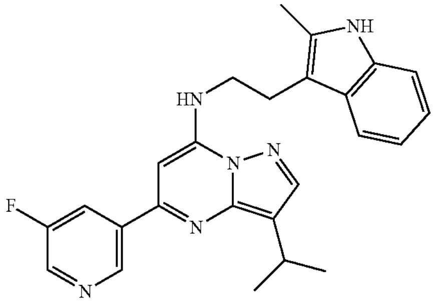 [SMILES: Cc1[nH]c2ccccc2c1CCNc1cc(-c2cncc(F)c2)nc2c(C(C)C)cnn12]

Synthetic Scheme:

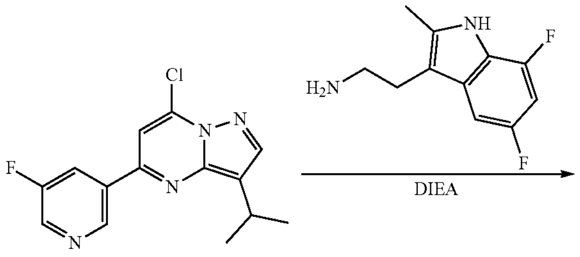

1

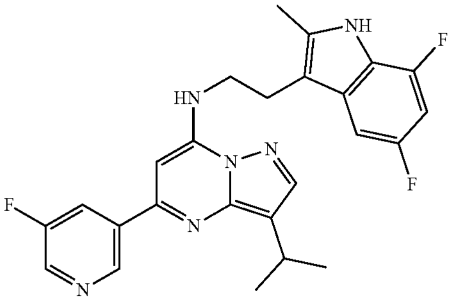

I-107

Step 1: N-[2-(5,7-Difluoro-2-methyl-1H-indol-3-yl)ethyl]-5-(5-fluoro-3-pyridyl)-3-isopropyl-pyrazolo[1,5-a]pyrimidin-7-amine (I-107)

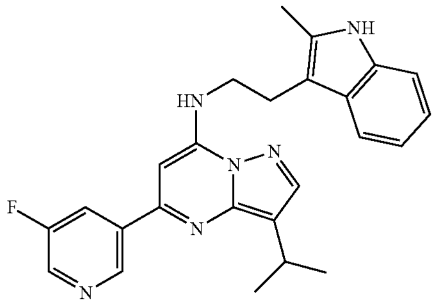

To a solution of 7-chloro-5-(5-fluoro-3-pyridyl)-3-isopropyl-pyrazolo[1,5-a]pyrimidine (120 mg, 404.51 μmol, 1 eq) and 2-(5,7-difluoro-2-methyl-1H-indol-3-yl)ethanamine (182.19 mg, 606.76 μmol, 1.5 eq, oxalic acid) in i-PrOH (20 mL) was added DIEA (261.40 mg, 2.02 mmol, 352.29 μL, 5.0 eq). The mixture was stirred at 70° C. for 18 h. The reaction mixture concentrated under reduced pressure to give a residue which was purified by preparative HPLC (column: Phenomenex Gemini 150*25 mm*10 um; mobile phase: [water (0.05% ammonia hydroxide v/v)-ACN]; B %: 63%-93%, 10 min), followed by lyophilization to yield N-[2-(5,7-difluoro-2-methyl-1H-indol-3-yl)ethyl]-5-(5-fluoro-3-pyridyl)-3-isopropyl-pyrazolo[1,5-a]pyrimidin-7-amine (94.41 mg, 196.14 μmol, 48.5% yield, 96.5% purity, 92.85 mg was for delivery) as a light yellow solid. $^1$H NMR (400 MHz, DMSO-$d_6$) δ ppm 11.16 (s, 1H), 8.96 (s, 1H), 8.61 (d, J=2.8 Hz, 1H), 8.06-7.95 (m, 3H), 7.20 (dd, J=2.0, 9.5 Hz, 1H), 6.80-6.68 (m, 1H), 6.34 (s, 1H), 3.69 (q, J=6.5 Hz, 2H), 3.19 (spt, J=6.8 Hz, 1H), 2.99 (t, J=6.7 Hz, 2H), 2.16 (s, 3H), 1.33 (d, J=7.0 Hz, 6H); ES-LCMS m/z 465.3 [M+H]$^+$.

Example 106

Synthesis of I-108

I-108

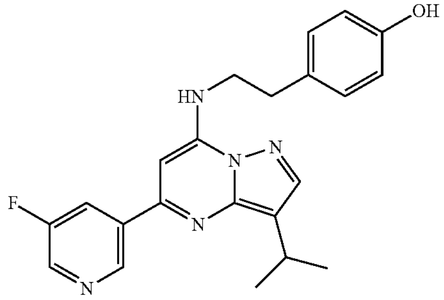 [SMILES: CC(C)c1cnn2c(NCCc3ccc(O)cc3)cc(-c3cncc(F)c3)nc12]

Synthetic Scheme:

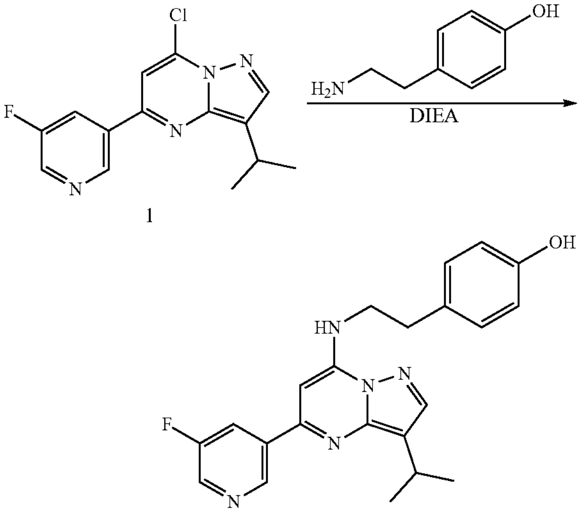

1

I-108

Step 1: 4-[2-[[5-(5-Fluoro-3-pyridyl)-3-isopropyl-pyrazolo[1,5-a]pyrimidin-7-yl]amino]ethyl]phenol (I-108)

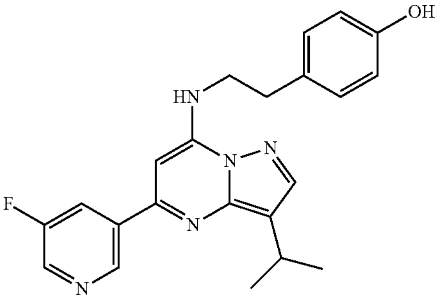

To a solution of 7-chloro-5-(5-fluoro-3-pyridyl)-3-isopropyl-pyrazolo[1,5-a]pyrimidine (52.08 mg, 171.99 umol, 1 eq) in i-PrOH (3 mL) was added 4-(2-aminoethyl)phenol (28.31 mg, 206.38 μmol, 1.2 eq) and DIEA (66.68 mg, 515.96 μmol, 89.87 μL, 3 eq). The mixture was stirred at 60° C. for 16 h. The mixture was concentrated to afford the crude product which was purified by preparative HPLC (MeCN/$H_2O$ as eluents, acidic condition, Instrument: Phenomenex Gemini 150*25 mm*10 μm/Mobile phase: water(0.05% HCl)-CAN/Gradient: B from 42% to 72% in 10 min/Flow rate: 25 mL/min), followed by lyophilization to yield 4-[2-[[5-(5-fluoro-3-pyridyl)-3-isopropyl-pyrazolo[1,5-a]pyrimidin-7-yl]amino]ethyl]phenol (49.37 mg, 105.68 μmol, 61.5% yield, 99.4% purity, 2HCl) as a yellow solid. $^1H$ NMR (400 MHz, $CD_3OD$) δ ppm 8.83 (d, J=2.5 Hz, 2H), 8.27 (s, 1H), 8.16 (dd, J=1.8, 8.8 Hz, 1H), 7.08 (d, J=8.3 Hz, 2H), 6.63 (d, J=8.3 Hz, 2H), 6.38 (s, 1H), 3.97 (t, J=6.5 Hz, 2H), 3.38-3.34 (m, 1H), 3.01 (t, J=6.5 Hz, 2H), 1.39 (d, J=7.0 Hz, 6H); ES-LCMS m/z 392.1 $[M+H]^+$.

Example 107

Synthesis of I-109

I-109

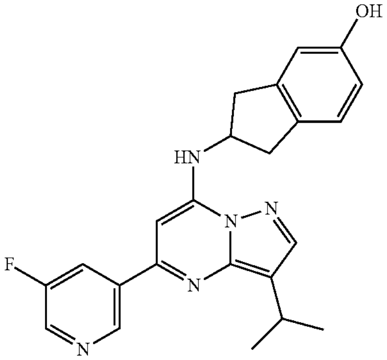

Synthetic Scheme:

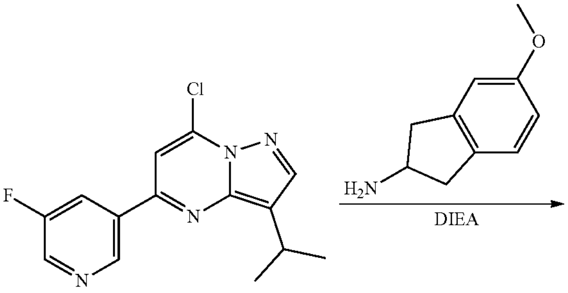

1

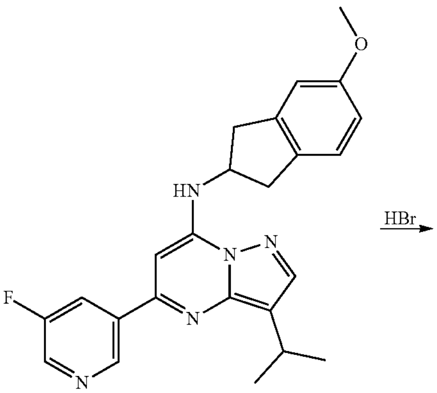

-continued

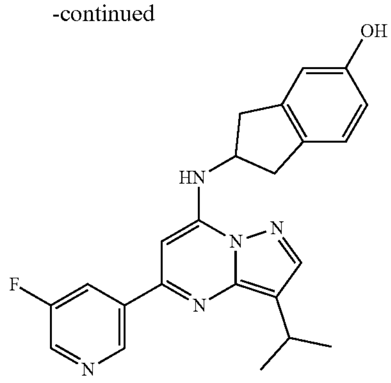

I-109

Step 1: 5-(5-Fluoro-3-pyridyl)-3-isopropyl-N-(5-methoxyindan-2-yl)pyrazolo[1,5-a]pyrimidin-7-amine

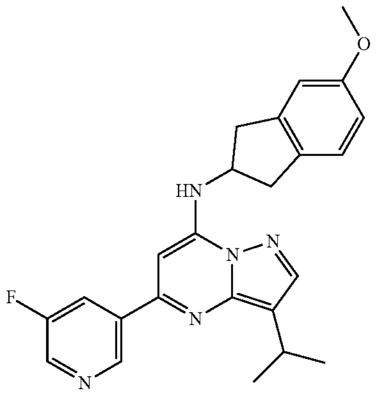 [SMILES: COc1ccc2c(c1)CC(Nc1cc(-c3cncc(F)c3)nc3c(C(C)C)cnn13)C2]

To a solution of 7-chloro-5-(5-fluoro-3-pyridyl)-3-isopropyl-pyrazolo[1,5-a]pyrimidine (80 mg, 264.17 μmol, 1.0 eq) in i-PrOH (3 mL) was added DIEA (102.42 mg, 792.51 μmol, 138.04 μL, 3.0 eq) and 5-methoxyindan-2-amine (60 mg, 367.61 μmol, 1.39 eq). The mixture was stirred at 50° C. for 15 h. The reaction mixture was concentrated under reduced pressure to give a residue which was purified by flash silica gel chromatography (from PE/EtOAc=100/1 to 2/1, TLC: PE/EtOAc=3/1, $R_f$=0.70) to yield 5-(5-fluoro-3-pyridyl)-3-isopropyl-N-(5-methoxyindan-2-yl)pyrazolo[1,5-a]pyrimidin-7-amine (120 mg, 155.51 μmol, 58.9% yield, 54.1% purity) as a yellow oil. $^1$H NMR (400 MHz, $CDCl_3$) δ ppm 9.08 (s, 1H), 8.55 (d, J=2.8 Hz, 1H), 8.21 (td, J=2.3, 9.5 Hz, 1H), 7.87 (s, 1H), 7.18 (d, J=8.3 Hz, 1H), 6.83 (s, 1H), 6.57 (d, J=7.5 Hz, 1H), 6.41 (s, 1H), 4.70-4.60 (m, 1H), 3.81 (s, 3H), 3.50 (ddd, J=6.8, 12.6, 15.7 Hz, 2H), 3.42-3.30 (m, 1H), 3.08 (dt, J=4.5, 16.1 Hz, 2H), 1.42 (d, J=6.8 Hz, 6H); ES-LCMS m/z 418.1 $[M+H]^+$.

Step 2: 2-[[5-(5-Fluoro-3-pyridyl)-3-isopropyl-pyrazolo[1,5-a]pyrimidin-7-yl]amino]indan-5-ol (I-109)

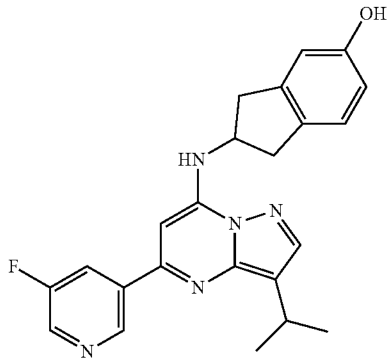 [SMILES: CC(C)c1cnn2c(NC3Cc4ccc(O)cc4C3)cc(-c3cncc(F)c3)nc12]

To a solution of 5-(5-fluoro-3-pyridyl)-3-isopropyl-N-(5-methoxyindan-2-yl)pyrazolo[1,5-a]pyrimidin-7-amine (95 mg, 123.11 μmol, 1 eq) in HBr (9 mL) was stirred at 120° C. for 2 h. The reaction mixture was concentrated under reduced pressure to give a residue which was purified by preparative HPLC (HCl condition; column: Phenomenex Gemini 150×25 mm×10 um; mobile phase: [water (0.05% HCl)-ACN]; B %: 49%-79%, 10 min). The desired fraction was lyophilized to yield 2-[[5-(5-fluoro-3-pyridyl)-3-isopropyl-pyrazolo[1,5-a]pyrimidin-7-yl]amino]indan-5-ol (30.69 mg, 61.40 μmol, 49.8% yield, 95.3% purity, 2HCl salt) as a yellow solid. $^1$H NMR (400 MHz, $CD_3OD$) δ ppm 9.00 (s, 1H), 8.83 (d, J=2.5 Hz, 1H), 8.35 (td, J=2.3, 9.0 Hz, 1H), 8.24 (s, 1H), 7.08 (d, J=8.3 Hz, 1H), 6.96 (s, 1H), 6.71 (s, 1H), 6.65 (dd, J=2.3, 8.0 Hz, 1H), 5.02 (t, J=6.9 Hz, 1H), 3.51-3.40 (m, 2H), 3.40-3.32 (m, 1H), 3.25-3.12 (m, 2H), 1.39 (d, J=7.0 Hz, 6H); ES-LCMS m/z 404.2 $[M+H]^+$.

Example 108

Synthesis of I-110

I-110

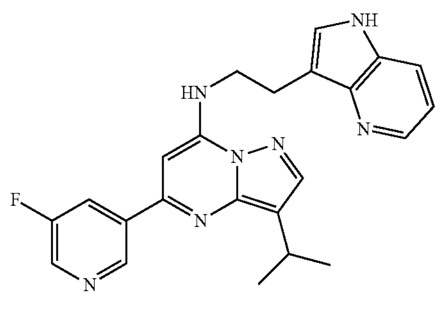 [SMILES: CC(C)c1cnn2c(NCCc3c[nH]c4cccnc34)cc(-c3cncc(F)c3)nc12]

Synthetic Scheme:

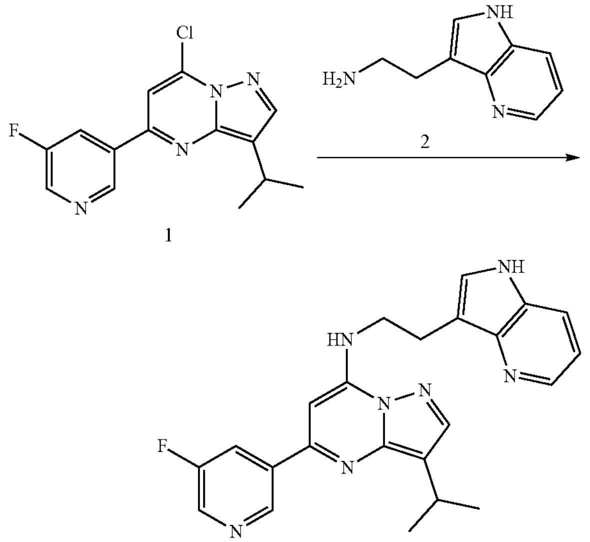

1

I-110

Step 1: 5-(5-Fluoro-3-pyridyl)-3-isopropyl-N-[2-(1H-pyrrolo[3,2-b]pyridin-3-yl)ethyl]pyrazolo[1,5-a]pyrimidin-7-amine (I-110)

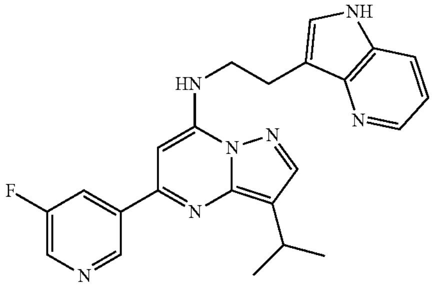

To a solution of 7-chloro-5-(5-fluoro-3-pyridyl)-3-isopropyl-pyrazolo[1,5-a]pyrimidine (45 mg, 123.83 umol, 1.0 eq) in i-PrOH (2 mL) was added DIEA (48.01 mg, 371.49 μmol, 64.70 μL, 3.0 eq) and 2-(1H-pyrrolo[3,2-b]pyridin-3-yl)ethanamine (25 mg, 155.08 μmol, 1.25 eq). The mixture was stirred at 50° C. for 15 h. The reaction mixture was concentrated under reduced pressure to give the residue which was purified by preparative HPLC (HCl condition; column: Phenomenex Gemini 150×25 mm×10 um; mobile phase: [water(0.05% HCl)-ACN]; B %: 20%-50%, 10 min). The desired fraction was lyophilized to yield 5-(5-fluoro-3-pyridyl)-3-isopropyl-N-[2-(1H-pyrrolo[3,2-b]pyridin-3-yl)ethyl]pyrazolo[1,5-a]pyrimidin-7-amine (16.32 mg, 30.38 μmol, 24.5% yield, 97.7% purity, 3HCl salt) as a yellow solid. $^1$H NMR (400 MHz, $CD_3OD$) δ ppm 8.97 (s, 1H), 8.84 (d, J=2.4 Hz, 1H), 8.57-8.52 (m, 2H), 8.35 (td, J=2.1, 9.0 Hz, 1H), 8.23 (s, 1H), 8.10 (s, 1H), 7.70-7.65 (m, 1H), 6.90 (s, 1H), 4.15 (t, J=6.9 Hz, 2H), 3.45 (t, J=6.9 Hz, 2H), 3.38-3.33 (m, 1H), 1.38 (d, J=6.8 Hz, 6H); ES-LCMS m/z 416.2 $[M+H]^+$.

Example 109

Synthesis of I-120

I-120

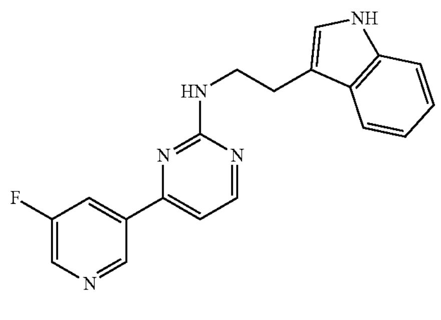

Synthetic Scheme:

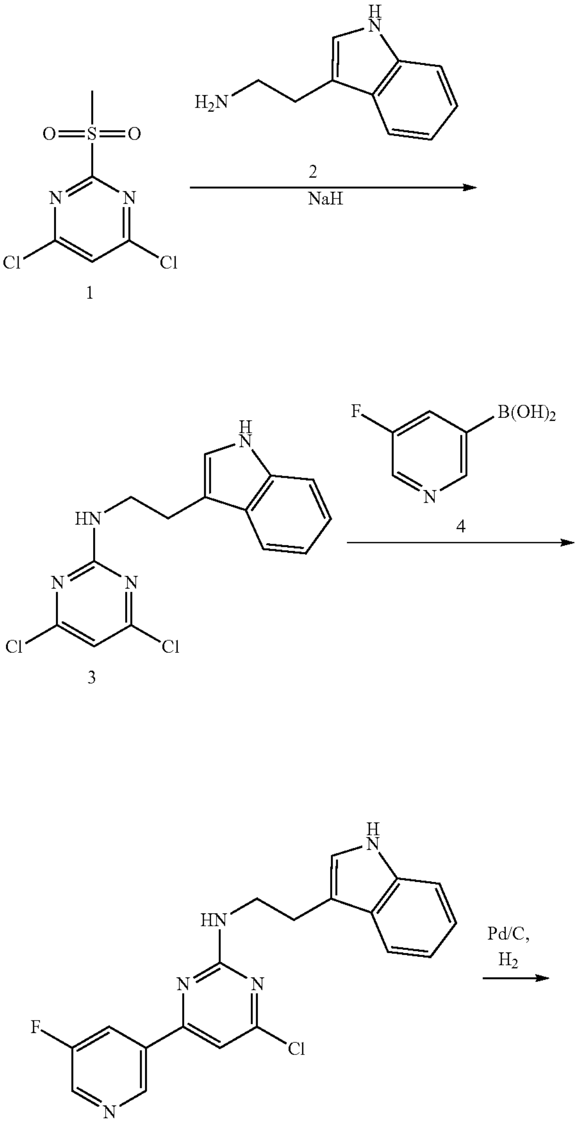

1

3

5

-continued

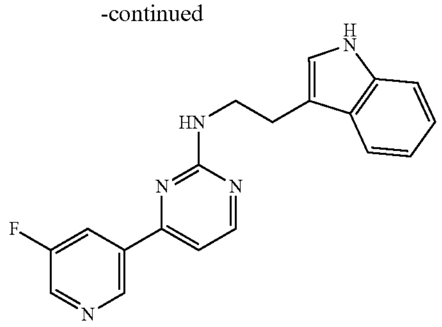

I-120

Step 1: 4,6-Dichloro-N-[2-(1H-indol-3-yl)ethyl]pyrimidin-2-amine

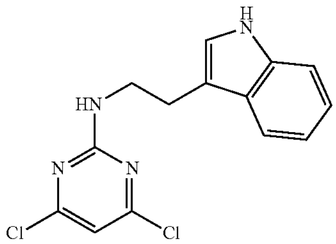 [SMILES: Clc1cc(Cl)nc(NCCc2c[nH]c3ccccc23)n1]

To a mixture of 2-(1H-indol-3-yl)ethanamine (2.96 g, 18.50 mmol, 1.05 eq) in THF (50 mL) was added NaH (1.06 g, 26.42 mmol, 1.5 eq). The mixture was stirred for 30 min at 0° C. under $N_2$ atmosphere. A solution of 4,6-dichloro-2-methylsulfonyl-pyrimidine (4 g, 17.62 mmol, 1 eq) in THF (50 mL) was added to the mixture dropwise. The mixture was stirred at −55° C. for 12 h. To the reaction mixture was added 1N $NH_4Cl$ solution (5 mL) and concentrated. The residue was purified by flash silica gel chromatography (PE/EtOAc=3/1, $R_f$=0.5) to yield 4,6-dichloro-N-[2-(1H-indol-3-yl)ethyl]pyrimidin-2-amine (2.1 g, 5.81 mmol, 33.0% yield, 85% purity) as a yellow solid. $^1H$ NMR (400 MHz, $CDCl_3$) δ ppm 8.68 (s, 1H), 8.00 (d, J=10.8 Hz, 1H), 7.64 (t, J=6.1 Hz, 1H), 7.39-7.33 (m, 1H), 7.26-7.20 (m, 1H), 7.16-7.09 (m, 1H), 7.08-6.99 (m, 1H), 6.61-6.53 (m, 1H), 3.84-3.70 (m, 2H), 3.05 (d, J=6.1 Hz, 2H); ES-LCMS m/z 307.0, 309.1 $[M+H]^+$.

Step 2: 4-Chloro-6-(5-fluoro-3-pyridyl)-N-[2-(1H-indol-3-yl)ethyl]pyrimidin-2-amine

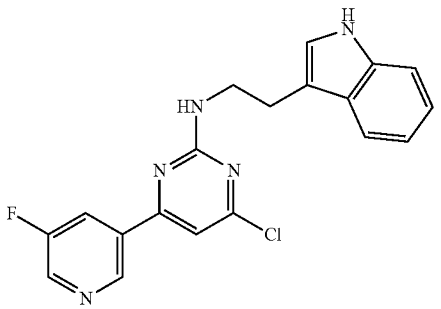 [SMILES: Fc1cncc(-c2cc(Cl)nc(NCCc3c[nH]c4ccccc34)n2)c1]

To a mixture of 4,6-dichloro-N-[2-(1H-indol-3-yl)ethyl]pyrimidin-2-amine (300 mg, 830.14 mol, 1 eq) and (5-fluoro-3-pyridyl)boronic acid (93.58 mg, 664.11 mol, 0.8 eq) in 1,4-dioxane (3 mL) and $H_2O$ (2 mL) was added $Cs_2CO_3$ (540.95 mg, 1.66 mmol, 2 eq) and $Pd(dppf)Cl_2$ (60.74 mg, 83.01 mol, 0.1 eq) under $N_2$ atmosphere. The mixture was stirred at 110° C. for 20 min under microwave. The reaction mixture was concentrated. The residue was purified on silica gel column chromatography (from pure PE to PE/EtOAc=3/1, TLC: PE/EtOAc=3/1, $R_f$=0.33) to yield 4-chloro-6-(5-fluoro-3-pyridyl)-N-[2-(1H-indol-3-yl)ethyl]pyrimidin-2-amine (70 mg, 171.29 mol, 20.6% yield, 90% purity) as a light yellow solid. $^1H$ NMR (400 MHz, $CDCl_3$) δ ppm 8.91 (br s, 1H), 8.50 (br s, 1H), 7.97 (br s, 2H), 7.60 (d, J=7.1 Hz, 1H), 7.32 (d, J=8.1 Hz, 1H), 7.15 (t, J=7.6 Hz, 1H), 7.10-7.04 (m, 1H), 7.02 (br s, 1H), 6.92 (s, 1H), 5.39 (br s, 1H), 3.79 (br s, 2H), 3.05 (t, J=6.7 Hz, 2H); ES-LCMS m/z 368.1, 370.1 $[M+H]^+$.

Step 3: 4-(5-Fluoro-3-pyridyl)-N-[2-(1H-indol-3-yl)ethyl]pyrimidin-2-amine (I-120)

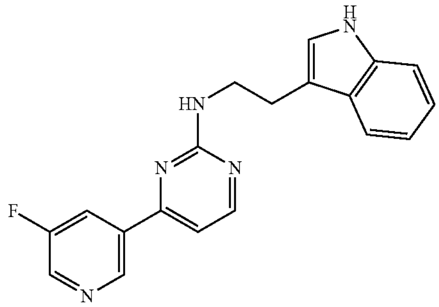 [SMILES: Fc1cncc(-c2ccnc(NCCc3c[nH]c4ccccc34)n2)c1]

To a solution of 4-chloro-6-(5-fluoro-3-pyridyl)-N-[2-(1H-indol-3-yl)ethyl]pyrimidin-2-amine (70 mg, 171.29 mol, 1 eq) in MeOH (5 mL) and $NH_3$—$H_2O$ (0.2 mL) was added Pd/C (30 mg, 10% purity). The suspension was degassed under vacuum and purged with $H_2$ several times. The mixture was stirred under $H_2$ (15 psi) atmosphere at 10° C. for 0.5 h. The reaction mixture was filtered and concentrated. The residue was purified by preparative HPLC (column: Agela ASB 150*25 mm*5 um; mobile phase: [water (0.05% HCl)-ACN]; B %: 33%-63%, 8 min), followed by lyophilization to yield 4-(5-fluoro-3-pyridyl)-N-[2-(1H-indol-3-yl)ethyl]pyrimidin-2-amine (20.8 mg, 50.20 □mol, 29.3% yield, 98.1% purity, 2 HCl) as a yellow solid. $^1H$ NMR (400 MHz, $CD_3OD$) δ ppm 9.06 (br s, 1H), 8.74 (br s, 1H), 8.32-8.06 (m, 2H), 7.59-7.55 (m, 1H), 7.43 (d, J=6.6 Hz, 1H), 7.24-7.04 (m, 2H), 7.01-6.93 (m, 2H), 4.05-3.96 (m, 2H), 3.15 (t, J=6.4 Hz, 2H); ES-LCMS m/z 334.1 $[M+H]^+$.

Example 110

Synthesis of I-121

I-121

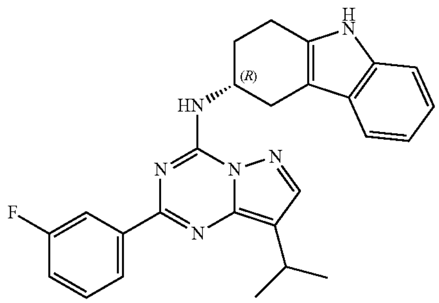

Synthetic Scheme:

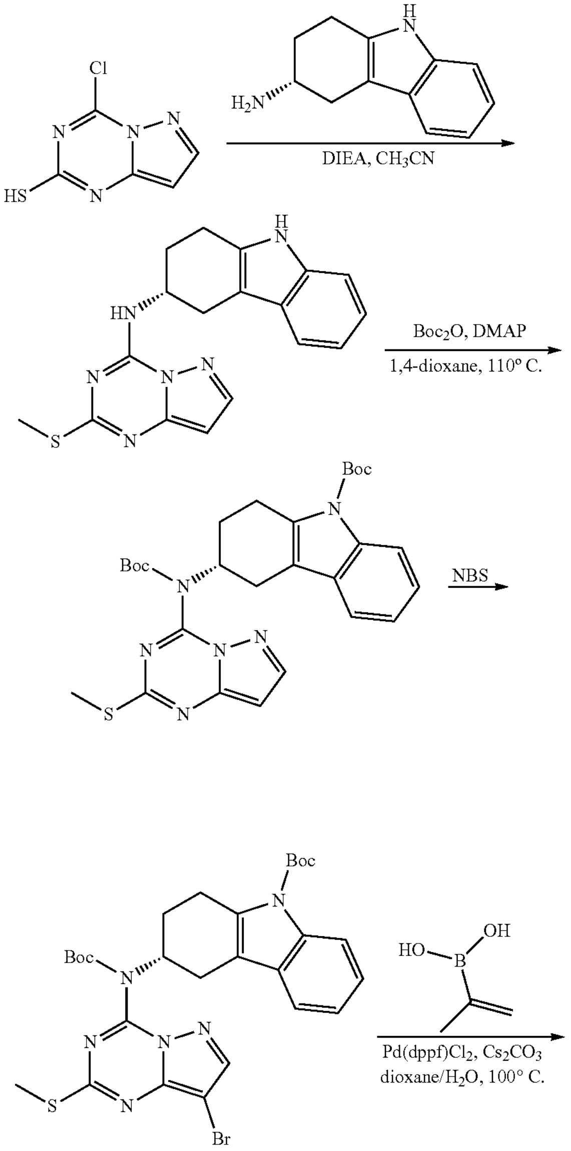

-continued

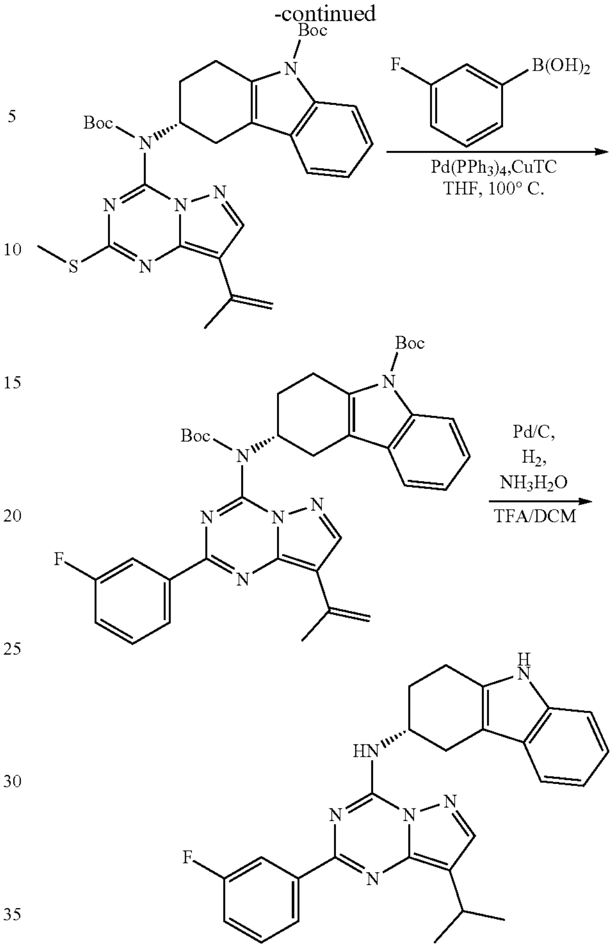

I-121

Step 1: (3R)—N-(2-Methylsulfanylpyrazolo[1,5-a][1,3,5]triazin-4-yl)-2,3,4,9-tetrahydro-1H-carbazol-3-amine

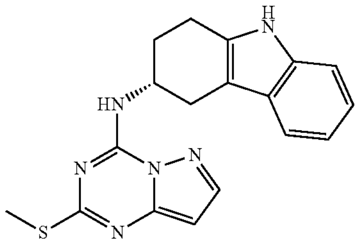 [SMILES: CSc1nc(N[C@@H]2CCc3[nH]c4ccccc4c3C2)n2nccc2n1]

To a solution of 4-chloro-2-methylsulfanyl-pyrazolo[1,5-a][1,3,5]triazine (500 mg, 1.69 mmol, 1 eq, HCl) in MeCN (30 mL) was added DIEA (1.31 g, 10.12 mmol, 1.76 mL, 6 eq) and (3R)-2,3,4,9-tetrahydro-1H-carbazol-3-amine (314.20 mg, 1.69 mmol, 1 eq). The mixture was stirred at 50° C. for 2 h. The mixture was concentrated. The crude material was purified on silica gel column chromatography (from pure PE to PE/EtOAc=2/1, TLC: PE/EtOAc=3/1, $R_f$=0.4) to yield (3R)—N-(2-methylsulfanylpyrazolo[1,5-a][1,3,5]triazin-4-yl)-2,3,4,9-tetrahydro-1H-carbazol-3-amine (300 mg, 770.46 μmol, 45.7% yield, 90% purity) as a yellow solid. $^1$H NMR (400 MHz, $CDCl_3$) δ ppm 7.90-7.77 (m, 2H), 7.44 (d, J=7.8 Hz, 1H), 7.30 (d, J=8.1 Hz, 1H), 7.18-7.12 (m, 1H), 7.11-7.06 (m, 1H), 6.61 (d, J=8.3 Hz, 1H), 6.21 (s, 1H), 3.28 (dd, J=5.0, 15.5 Hz, 1H), 3.00-2.78 (m, 4H), 2.55 (s, 3H), 2.31-2.15 (m, 2H); ES-LCMS m/z 351.2 $[M+H]^+$.

Step 2: tert-Butyl (3R)-3-[tert-butoxycarbonyl-(2-methylsulfanylpyrazolo[1,5-a][1,3,5]triazin-4-yl)amino]-1,2,3,4-tetrahydrocarbazole-9-carboxylate

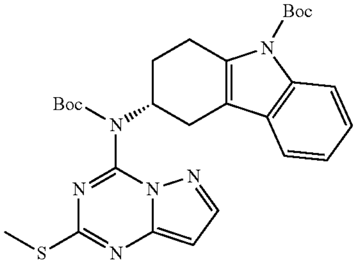 [SMILES: CSc1nc(N(C(=O)OC(C)(C)C)[C@@H]2CCc3c(c4ccccc4n3C(=O)OC(C)(C)C)C2)n2nccc2n1]

To a solution of (3R)—N-(2-methylsulfanylpyrazolo[1,5-a][1,3,5]triazin-4-yl)-2,3,4,9-tetrahydro-1H-carbazol-3-amine (200 mg, 513.64 μmol, 1 eq) in 1,4-dioxane (30 mL) was added DMAP (188.25 mg, 1.54 mmol, 3 eq) and $Boc_2O$ (672.60 mg, 3.08 mmol, 708.00 μL, 6 eq). The mixture was stirred at 110° C. for 24 h. The mixture was concentrated. The crude material was purified on silica gel column chromatography (from pure PE to PE/EtOAc=3/1, TLC: PE/EtOAc=5/1, $R_f$=0.5) to yield tert-butyl (3R)-3-[tert-butoxycarbonyl-(2-methylsulfanylpyrazolo[1,5-a][1,3,5]triazin-4-yl)amino]-1,2,3,4-tetrahydrocarbazole-9-carboxylate (300 mg, 492.49 μmol, 95.9% yield, 90.4% purity) as an off white solid. $^1$H NMR (400 MHz, $CDCl_3$) δ ppm 8.11-8.02 (m, 2H), 7.33 (d, J=7.6 Hz, 1H), 7.23-7.14 (m, 2H), 6.41 (s, 1H), 4.79-4.72 (m, 1H), 3.31-3.01 (m, 4H), 2.56 (s, 3H), 2.41-2.17 (m, 2H), 1.64 (s, 9H), 1.32 (s, 9H); ES-LCMS m/z 551.3 $[M+H]^+$.

Step 3: tert-Butyl (3R)-3-[(8-bromo-2-methylsulfanyl-pyrazolo[1,5-a][1,3,5]triazin-4-yl)-tert-butoxycarbonyl-amino]-1,2,3,4-tetrahydrocarbazole-9-carboxylate

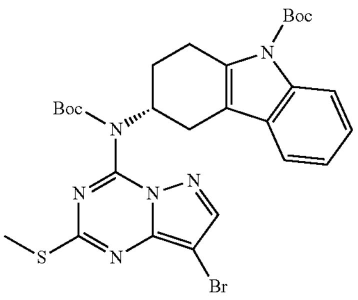 [SMILES: CSc1nc(N(C(=O)OC(C)(C)C)[C@@H]2CCc3c(c4ccccc4n3C(=O)OC(C)(C)C)C2)n2ncc(Br)c2n1]

To a solution of tert-butyl (3R)-3-[tert-butoxycarbonyl-(2-methylsulfanylpyrazolo[1,5-a][1,3,5]triazin-4-yl)amino]-1,2,3,4-tetrahydrocarbazole-9-carboxylate (260 mg, 426.82 μmol, 1 eq) in MeCN (20 mL) and DCM (20 mL) was added NBS (79.76 mg, 448.17 μmol, 1.05 eq). The mixture was stirred at 10° C. for 30 min. The mixture was concentrated. The residue was purified on silica gel column chromatography (from PE/EtOAc=5/1 to 2/1, TLC: PE/EtOAc=5/1, $R_f$=0.58) to yield tert-butyl (3R)-3-[(8-bromo-2-methyl sulfanyl-pyrazolo[1,5-a][1,3,5]triazin-4-yl)-tert-butoxycarbonyl-amino]-1,2,3,4-tetrahydrocarbazole-9-carboxylate (200 mg, 299.89 μmol, 70.3% yield, 94.4% purity) as a yellow solid. $^1$H NMR (400 MHz, $CDCl_3$) δ ppm 8.09 (d, J=7.8 Hz, 1H), 8.05 (s, 1H), 7.34 (d, J=8.0 Hz, 1H), 7.25-7.17 (m, 2H), 4.83-4.73 (m, 1H), 3.34-3.25 (m, 1H), 3.23-3.02 (m, 3H), 2.62 (s, 3H), 2.36 (td, J=6.2, 12.0 Hz, 1H), 2.23-2.21 (m, 1H), 1.66 (s, 9H), 1.36 (s, 9H); ES-LCMS m/z 629.2, 631.2 $[M+H]^+$.

Step 4: tert-Butyl (3R)-3-[tert-butoxycarbonyl-(8-isopropenyl-2-methylsulfanyl-pyrazolo[1,5-a][1,3,5]triazin-4-yl)amino]-1,2,3,4-tetrahydrocarbazole-9-carboxylate

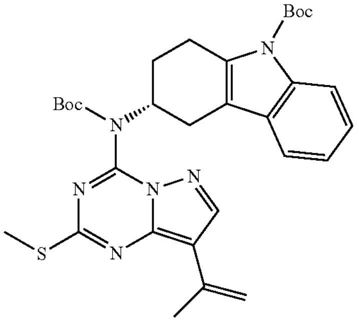 [SMILES: C=C(C)c1cnn2c(N(C(=O)OC(C)(C)C)[C@@H]3CCc4c(c5ccccc5n4C(=O)OC(C)(C)C)C3)nc(SC)nc12]

To a solution of tert-butyl (3R)-3-[(8-bromo-2-methylsulfanyl-pyrazolo[1,5-a][1,3,5]triazin-4-yl)-tert-butoxycarbonyl-amino]-1,2,3,4-tetrahydrocarbazole-9-carboxylate (200 mg, 299.89 μmol, 1 eq), 2-isopropenyl-4,4,5,5-tetramethyl-1,3,2-dioxaborolane (75.59 mg, 449.83 μmol, 1.5 eq) in 1,4-dioxane (4 mL) and $H_2O$ (2 mL) was added $Cs_2CO_3$ (293.13 mg, 899.67 μmol, 3 eq) and Pd(dppf)$Cl_2$ (21.94 mg, 29.99 μmol, 0.1 eq) under $N_2$ atmosphere. The mixture was stirred at 110° C. for 1 h under microwave. After filtration, the filtrate was concentrated. The crude material was purified on silica gel column chromatography (from pure PE to PE/EtOAc=5/1, TLC: PE/EtOAc=5/1, $R_f$=0.65) to yield tert-butyl (3R)-3-[tert-butoxycarbonyl-(8-isopropenyl-2-methyl sulfanyl-pyrazolo[1,5-a][1,3,5]triazin-4-yl)amino]-1,2,3,4-tetrahydrocarbazole-9-carboxylate (180 mg, 274.23 μmol, 91.5% yield, 90% purity) as a yellow solid. $^1$H NMR (400 MHz, $CDCl_3$) δ ppm 8.13-8.05 (m, 2H), 7.32 (d, J=7.6 Hz, 1H), 7.23-7.15 (m, 2H), 5.86 (s, 1H), 5.12 (s, 1H), 4.79-4.74 (m, 1H), 3.29-3.01 (m, 4H), 2.57 (s, 3H), 2.33-2.18 (m, 5H), 1.34 (s, 9H), 1.26 (s, 9H); ES-LCMS m/z 591.3 $[M+H]^+$.

Step 5: tert-Butyl (3R)-3-[tert-butoxycarbonyl-[2-(3-fluorophenyl)-8-isopropenyl-pyrazolo[1,5-a][1,3,5]triazin-4-yl]amino]-1,2,3,4-tetrahydrocarbazole-9-carboxylate

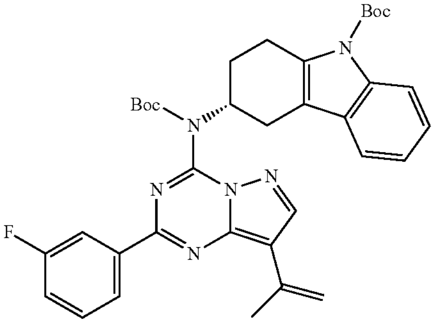 [SMILES: C=C(C)c1cnn2c(N(C(=O)OC(C)(C)C)[C@@H]3CCc4c(c5ccccc5n4C(=O)OC(C)(C)C)C3)nc(-c3cccc(F)c3)nc12]

A mixture of tert-butyl (3R)-3-[tert-butoxycarbonyl-(8-isopropenyl-2-methylsulfanyl-pyrazolo[1,5-a][1,3,5]triazin-4-yl)amino]-1,2,3,4-tetrahydrocarbazole-9-carboxylate (140 mg, 213.29 μmol, 1 eq), (3-fluorophenyl)boronic acid (89.53 mg, 639.88 μmol, 3 eq), $Pd(PPh_3)_4$ (24.65 mg, 21.33 umol, 0.1 eq) and CuTC (122.02 mg, 639.88 μmol, 3 eq) in THF (2 mL) was taken up into a microwave tube under $N_2$ atmosphere. The mixture was stirred at 100° C. for 3 h under microwave. After filtration, the filtrate was concentrated. The residue was purified with preparative TLC (PE/EtOAc=5/1, $R_f$=0.68) to afford tert-butyl (3R)-3-[tert-butoxycarbonyl-[2-(3-fluorophenyl)-8-isopropenyl-pyrazolo [1,5-a][1,3,5]triazin-4-yl]amino]-1,2,3,4-tetrahydrocarbazole-9-carboxylate (70 mg, 64.11 μmol, 30.1% yield, 58.5% purity) as a yellow solid. $^1$H NMR (400 MHz, $CDCl_3$) δ ppm 8.21-8.13 (m, 2H), 8.02 (d, J=8.1 Hz, 2H), 7.31-7.23 (m, 2H), 7.13-7.06 (m, 3H), 5.97 (s, 1H), 5.17 (s, 1H), 4.85-4.83 (m, 1H), 3.10-2.97 (m, 4H), 2.22-2.14 (m, 5H), 1.29 (d, J=4.4 Hz, 18H); ES-LCMS m/z 639.4 $[M+H]^+$.

Step 6: (3R)—N-[2-(3-Fluorophenyl)-8-isopropyl-pyrazolo[1,5-a][1,3,5]triazin-4-yl]-2,3,4,9-tetrahydro-1H-carbazol-3-amine (I-121)

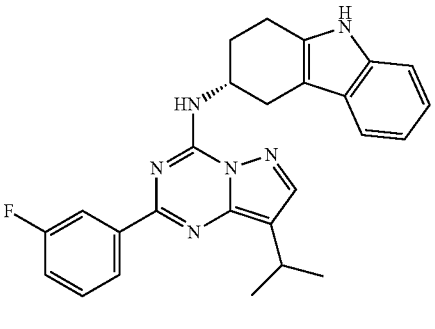 [SMILES: CC(C)c1cnn2c(N[C@@H]3CCc4[nH]c5ccccc5c4C3)nc(-c3cccc(F)c3)nc12]

To a solution of tert-butyl (3R)-3-[tert-butoxycarbonyl-[2-(3-fluorophenyl)-8-isopropenyl-pyrazolo[, 5-a][1,3,5]triazin-4-yl]amino]-1,2,3,4-tetrahydrocarbazole-9-carboxylate (60 mg, 54.95 μmol, 1 eq) and $NH_3H_2O$ (546.00 mg, 4.36 mmol, 600.00 μL, 28% purity, 79.38 eq) in MeOH (15 mL) was added Pd/C (30 mg, 9.16 umol, 10% purity). The mixture was stirred under $H_2$ atmosphere (15 psi) at 25° C. for 6 h. After filtration, the filtrate was concentrated. To the residue was added DCM (3 mL) and TFA (1.54 g, 13.51 mmol, 1 mL, 245.78 eq). The mixture was stirred at 15° C. for 1 h. The mixture was concentrated to yield a residue which was purified by preparative HPLC (column: Agela ASB 150*25 mm*5 um; mobile phase: [water (0.05% HCl)-ACN]; B %: 80%-100%, 8 min), followed by lyophilization to yield (3R)—N-[2-(3-fluorophenyl)-8-isopropyl-pyrazolo[1,5-a][1,3,5]triazin-4-yl]-2,3,4,9-tetrahydro-1H-carbazol-3-amine (12.51 mg, 26.23 mol, 9.8% yield, 100% purity, HCl, OR: $[\alpha]^{22.4}_D$=+9.972, (MeOH, c=0.071 g/100 mL)) as a yellow solid. $^1$H NMR (400 MHz, $CD_3OD$) δ ppm 8.24 (d, J=8.1 Hz, 1H), 8.09 (d, J=10.3 Hz, 1H), 7.95 (s, 1H), 7.45 (dt, J=5.9, 7.9 Hz, 1H), 7.37 (d, J=7.8 Hz, 1H), 7.26 (d, J=7.8 Hz, 1H), 7.20 (dt, J=2.1, 8.3 Hz, 1H), 7.02 (t, J=7.2 Hz, 1H), 6.97-6.91 (m, 1H), 4.89-4.85 (m, 1H), 3.28-3.23 (m, 1H), 3.08-2.87 (m, 3H), 2.43-2.33 (m, 1H), 2.30-2.19 (m, 1H), 1.39 (d, J=6.8 Hz, 6H); ES-LCMS m/z 441.3 $[M+H]^+$.

Example 111

Synthesis of I-122

I-122

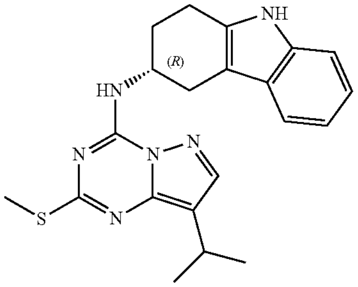

Synthetic Scheme:

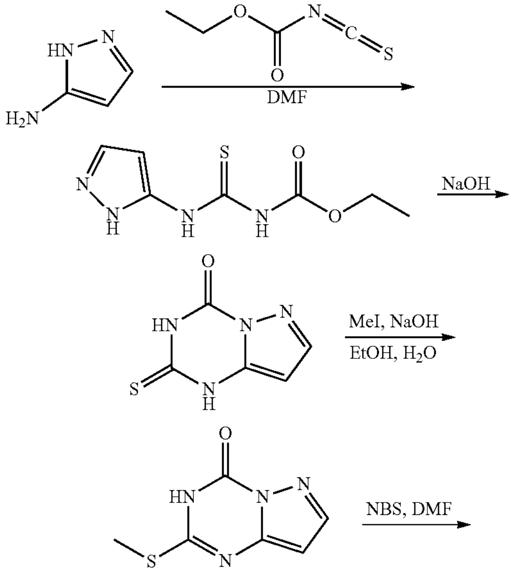

-continued

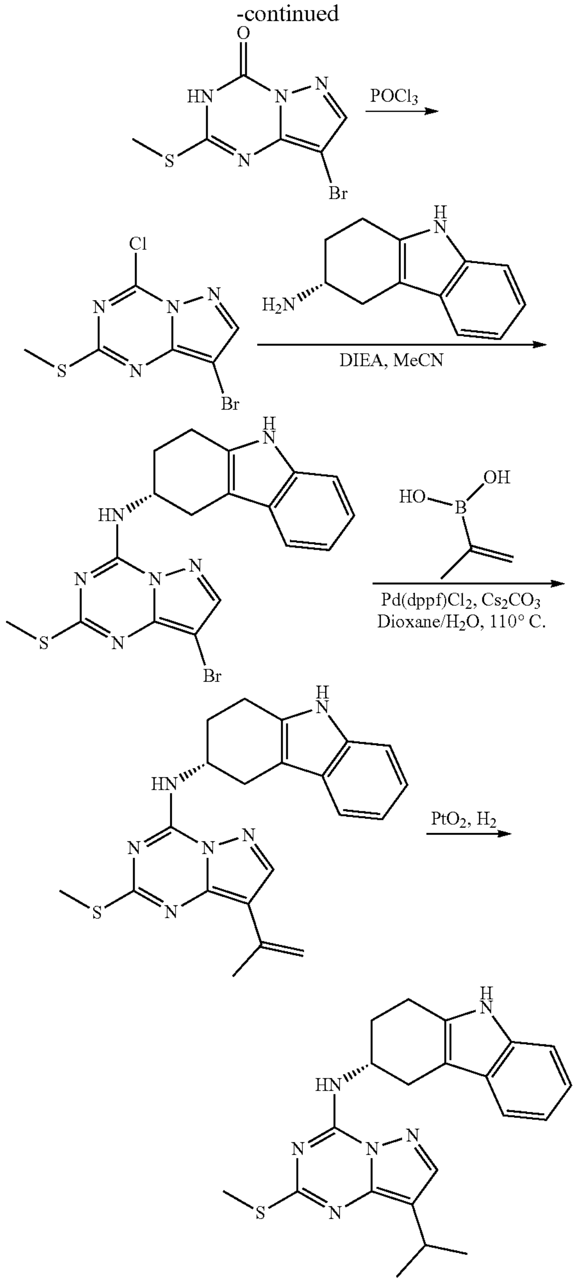

I-122

Step 1: Ethyl N-(1H-pyrazol-5-ylcarbamothioyl)carbamate

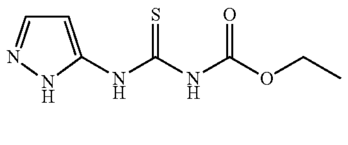

To a suspension of 3H-pyrazol-3-amine (15.84 g, 190.62 mmol, 1 eq) in DCM (160 mL) was added ethoxycarbonyl isothiocyanate (25 g, 190.62 mmol, 22.52 mL, 1 eq) at 0° C. The mixture was stirred at 25° C. for 12 h under $N_2$ atmosphere. The mixture was filtered. The filter cake was washed with DCM (20 mL×2), dried to yield ethyl N-(1H-pyrazol-5-ylcarbamothioyl)carbamate (26 g, 109.22 mmol, 57.3% yield, 90% purity) as a white solid. $^1H$ NMR (400 MHz, $CD_3OD$) δ ppm 7.59 (d, J=2.2 Hz, 1H), 7.12 (s, 1H), 4.27 (q, J=7.2 Hz, 2H), 1.34 (t, J=7.1 Hz, 3H); ES-LCMS m/z 215.1 $[M+H]^+$.

Step 2: 2-Thioxo-1H-pyrazolo[1,5-a][1,3,5]triazin-4-one

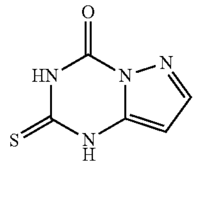 [SMILES: O=c1[nH]c(=S)[nH]c2ccnn12]

To a mixture of ethyl N-(1H-pyrazol-5-ylcarbamothioyl) carbamate (25.5 g, 107.12 mmol, 1 eq) in MeCN (300 mL) was added $K_2CO_3$ (44.42 g, 321.36 mmol, 3 eq). The mixture was stirred at 85° C. for 4 h. The mixture diluted with water (100 mL) and adjusted pH to 5-6 with 2 N HCl. The solvents were evaporated and the residue was suspended in water (600 mL). The solid was filtered off, washed with water (60 mL×2), dried to yield 2-thioxo-1H-pyrazolo[1,5-a][1,3,5]triazin-4-one (16 g, 90.38 mmol, 84.4% yield, 95% purity) as a white solid. $^1H$ NMR (400 MHz, $CD_3OD$) & ppm 7.83 (s, 1H), 5.93 (d, J=1.7 Hz, 1H); ES-LCMS m/z 169.1 $[M+H]^+$.

Step 3: 2-Methylsulfanyl-3H-pyrazolo[1,5-a][1,3,5]triazin-4-one

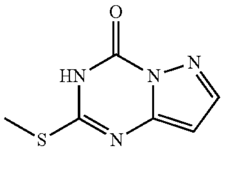

To a suspension of 2-thioxo-1H-pyrazolo[1,5-a][1,3,5]triazin-4-one (16 g, 90.38 mmol, 1 eq) in EtOH (120 mL) was added NaOH (7.23 g, 180.76 mmol, 2 eq) in $H_2O$ (9.6 mL), MeI (15.96 g, 112.44 mmol, 7.0 mL, 1.24 eq) was added dropwise. The mixture was stirred at 15° C. for 1 h. The mixture was acidified with 1N aq. HCl (80 mL) and EtOH was evaporated. The mixture was filtered, washed with $H_2O$ (50 mL×2). The filter cake was dried to yield 2-methylsulfanyl-3H-pyrazolo[1,5-a][1,3,5]triazin-4-one (16 g, 83.42 mmol, 92.3% yield, 95% purity) as a white solid. $^1H$ NMR (400 MHz, $CD_3OD$) δ ppm 7.74 (d, J=2.0 Hz, 1H), 5.99 (d, J=2.2 Hz, 1H), 2.48 (s, 3H); ES-LCMS m/z 183.2 $[M+H]^+$.

Step 4: 8-Bromo-2-methylsulfanyl-3H-pyrazolo[1,5-a][1,3,5]triazin-4-on

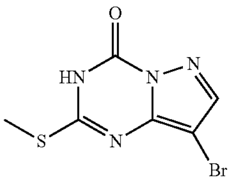

To a solution of 2-methylsulfanyl-3H-pyrazolo[1,5-a][1,3,5]triazin-4-one (3.0 g, 15.64 mmol, 1 eq) in DMF (30 mL) was added NBS (2.51 g, 14.08 mmol, 0.9 eq). The mixture was stirred at 15° C. for 0.5 h. The mixture was concentrated to yield 8-bromo-2-methylsulfanyl-3H-pyrazolo[1,5-a][1,3,5]triazin-4-one (4 g, 12.26 mmol, 78.4% yield, 80% purity) as green oil. $^1$H NMR (400 MHz, $CD_3OD$) δ ppm 7.72 (s, 1H), 2.49 (s, 3H); ES-LCMS m/z 261.0, 263.0 $[M+H]^+$.

Step 5: 8-Bromo-4-chloro-2-methylsulfanyl-pyrazolo[1,5-a][1,3,5]triazine

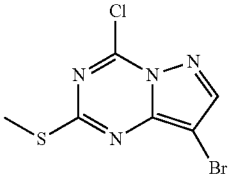

A suspension of 8-bromo-2-methylsulfanyl-3H-pyrazolo[1,5-a][1,3,5]triazin-4-one (2.0 g, 6.13 mmol, 1 eq) and N,N-dimethylaniline (742.58 mg, 6.13 mmol, 776.76 μL, 1 eq) in $POCl_3$ (16.50 g, 107.61 mmol, 10 mL, 17.56 eq) was stirred at 130° C. for 4 h. The mixture was added into water (100 mL) at 0° C., extracted with EtOAc (200 mL×3). The combined organic layers were washed with brine (50 mL), dried over $Na_2SO_4$, filtered and concentrated. The crude material was purified on silica gel column chromatography (from pure PE to PE/EtOAc=3/1, TLC: PE/EtOAc=3/1, $R_f$=0.8) to yield 8-bromo-4-chloro-2-methylsulfanyl-pyrazolo[1,5-a][1,3,5]triazine (600 mg, 2.08 mmol, 33.9% yield, 97% purity) as a white solid. $^1$H NMR (400 MHz, $CDCl_3$) δ ppm 8.12 (s, 1H), 2.66 (s, 3H); ES-LCMS m/z 278.9, 280.9 $[M+H]^+$.

Step 6: (3R)—N-(8-Bromo-2-methylsulfanyl-pyrazolo[1,5-a][1,3,5]triazin-4-yl)-2,3,4,9-tetrahydro-1H-carbazol-3-amine

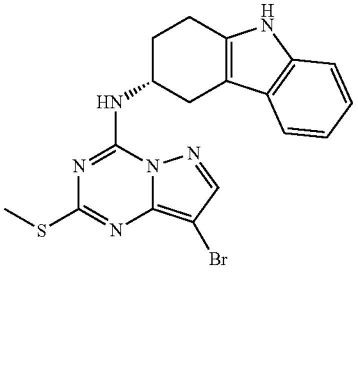 [SMILES: CSc1nc(N[C@@H]2CCc3[nH]c4ccccc4c3C2)n2ncc(Br)c2n1]

To a solution of 8-bromo-4-chloro-2-methylsulfanyl-pyrazolo[1,5-a][1,3,5]triazine (600 mg, 2.08 mmol, 1 eq) in i-PrOH (12 mL) was added DIEA (807.22 mg, 6.25 mmol, 1.09 mL, 3 eq) and (3R)-2,3,4,9-tetrahydro-1H-carbazol-3-amine (426.55 mg, 2.29 mmol, 1.10 eq). The mixture was stirred at 50° C. for 2 h. The mixture was concentrated, extracted with EtOAc (60 mL×3). The combined organic layers were washed with brine (50 mL), dried over $Na_2SO_4$, filtered and concentrated to yield (3R)—N-(8-bromo-2-methylsulfanyl-pyrazolo[1,5-a][1,3,5]triazin-4-yl)-2,3,4,9-tetrahydro-1H-carbazol-3-amine (800 mg, 1.68 mmol, 80.6% yield, 90% purity) as a yellow solid. $^1$H NMR (400 MHz, $CDCl_3$) δ ppm 7.86-7.80 (m, 2H), 7.45 (d, J=7.6 Hz, 1H), 7.32 (d, J=8.1 Hz, 1H), 7.17 (t, J=6.8 Hz, 1H), 7.13-7.07 (m, 1H), 6.59 (d, J=8.3 Hz, 1H), 4.82-4.78 (m, 1H), 3.31-3.26 (m, 1H), 2.99-2.84 (m, 3H), 2.61 (s, 3H), 2.30-2.20 (m, 2H); ES-LCMS m/z 429.1, 431.1 $[M+H]^+$.

Step 7: (3R)—N-(8-Isopropenyl-2-methylsulfanyl-pyrazolo[1,5-a][1,3,5]triazin-4-yl)-2,3,4,9-tetrahydro-1H-carbazol-3-amine

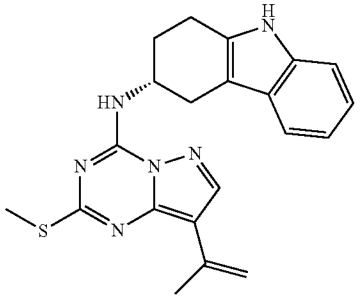 [SMILES: C=C(C)c1cnn2c(N[C@@H]3CCc4[nH]c5ccccc5c4C3)nc(SC)nc12]

To a mixture of (3R)—N-(8-bromo-2-methylsulfanyl-pyrazolo[1,5-a][1,3,5]triazin-4-yl)-2,3,4,9-tetrahydro-1H-carbazol-3-amine (400 mg, 838.50 μmol, 1 eq), $Pd(dppf)Cl_2$ (61.35 mg, 83.85 μmol, 0.1 eq), $Cs_2CO_3$ (683.00 mg, 2.10 mmol, 2.5 eq) in 1,4-dioxane (10 mL) and $H_2O$ (2.5 mL) was added 2-isopropenyl-4,4,5,5-tetramethyl-1,3,2-dioxaborolane (704.51 mg, 4.19 mmol, 5 eq) under $N_2$ atmosphere. The mixture was stirred at 110° C. for 1.5 h under $N_2$ atmosphere under microwave. The combined reaction mixture was concentrated, extracted with EtOAc (50 mL×3). The combined organic layers were washed with brine (50 mL), dried over $Na_2SO_4$, filtered and concentrated. The crude material was purified on silica gel column chromatography (from pure PE to PE/EtOAc=3/1, TLC: PE/EtOAc=3/1, $R_f$=0.46) to yield (3R)—N-(8-isopropenyl-2-methylsulfanyl-pyrazolo[1,5-a][1,3,5]triazin-4-yl)-2,3,4,9-tetrahydro-1H-carbazol-3-amine (250 mg, 550.57 μmol, 65.6% yield, 86% purity) as a yellow solid. $^1$H NMR (400 MHz, $CDCl_3$) δ ppm 7.87 (s, 1H), 7.81 (s, 1H), 7.45 (d, J=7.8 Hz, 1H), 7.32 (d, J=7.8 Hz, 1H), 7.17 (t, J=7.5 Hz, 1H), 7.13-7.08 (m, 1H), 6.57 (d, J=8.6 Hz, 1H), 5.86 (s, 1H), 5.06 (s, 1H), 4.82-4.77 (m, 1H), 3.29 (dd, J=4.8, 15.5 Hz, 1H), 2.99-2.82 (m, 3H), 2.58 (s, 3H), 2.32-2.23 (m, 2H), 2.21 (s, 3H); ES-LCMS m/z 391.2 $[M+H]^+$.

Step 8: (3R)—N-(8-Isopropyl-2-methylsulfanyl-pyrazolo[1,5-a][1,3,5]triazin-4-yl)-2,3,4,9-tetra-hydro-1H-carbazol-3-amine (I-122)

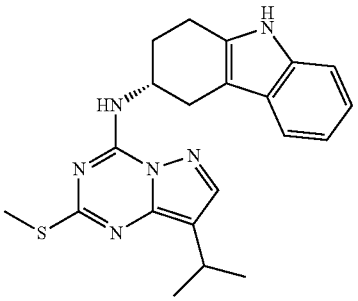 [SMILES: CSc1nc(N[C@@H]2CCc3[nH]c4ccccc4c3C2)n2ncc(C(C)C)c2n1]

To a mixture of (3R)—N-(8-isopropenyl-2-methyl sulfanyl-pyrazolo[1,5-a][1,3,5]triazin-4-yl)-2,3,4,9-tetrahydro-1H-carbazol-3-amine (100 mg, 220.23 μmol, 1 eq) in EtOAc (12 mL) was added $PtO_2$ (250 mg, 1.10 mmol, 5.00 eq) under $N_2$ atmosphere. The mixture was stirred at 15° C. for 20 min under $H_2$ (15 psi) atmosphere. The mixture was filtered. The filtrate was concentrated. The residue was purified by preparative HPLC (column: Agela ASB 150*25 mm*5 μm; mobile phase: [water (0.05% HCl)-ACN]; B %: 70%-100%, 8 min), followed by lyophilization to yield (3R)—N-(8-isopropyl-2-methylsulfanyl-pyrazolo[1,5-a][1,3,5]triazin-4-yl)-2,3,4,9-tetrahydro-1H-carbazol-3-amine (50 mg, 116.56 μmol, 52.9% yield, 100% purity, HCl) as a white solid. $^1H$ NMR (400 MHz, $CD_3OD$) δ ppm 7.90 (s, 1H), 7.37 (d, J=7.6 Hz, 1H), 7.26 (d, J=7.6 Hz, 1H), 7.08-7.00 (m, 1H), 6.96 (t, J=7.3 Hz, 1H), 4.73-4.68 (m, 1H), 3.23 (dd, J=4.9, 14.7 Hz, 1H), 3.14-3.11 (m, 1H), 2.95 (s, 2H), 2.91-2.82 (m, 1H), 2.58 (s, 3H), 2.30 (s, 1H), 2.21 (d, J=6.4 Hz, 1H), 1.33 (d, J=6.8 Hz, 6H); ES-LCMS m/z 393.2 $[M+H]^+$.

Example 112

Synthesis of I-123

I-123

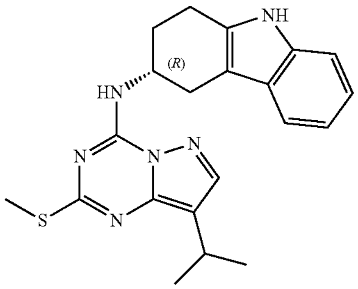

Synthetic Scheme:

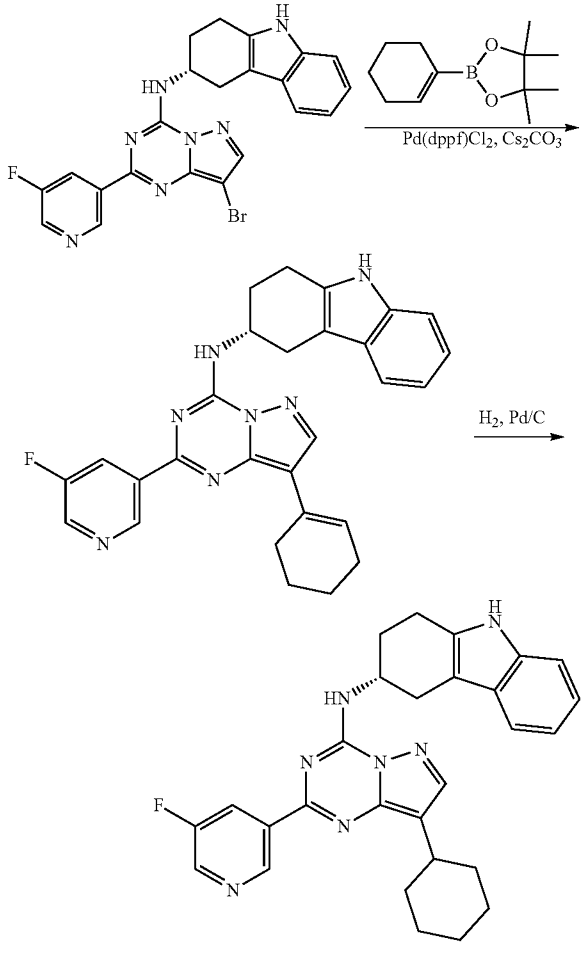

I-123

Step 1: (3R)—N-[8-(Cyclohexen-1-yl)-2-(5-fluoro-3-pyridyl)pyrazolo[1,5-a][1,3,5]triazin-4-yl]-2,3,4,9-tetrahydro-1H-carbazol-3-amine

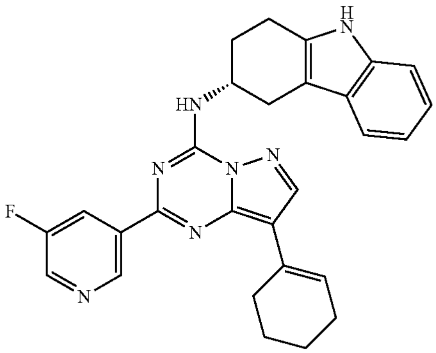 [SMILES: Fc1cncc(-c2nc(N[C@@H]3CCc4[nH]c5ccccc5c4C3)n3ncc(C4=CCCCC4)c3n2)c1]

A mixture of (3R)—N-[8-bromo-2-(5-fluoro-3-pyridyl)pyrazolo[1,5-a][1,3,5]triazin-4-yl]-2,3,4,9-tetrahydro-1H-carbazol-3-amine (200 mg, 408.10 μmol, 1 eq), 2-(cyclohexen-1-yl)-4,4,5,5-tetramethyl-1,3,2-dioxaborolane (84.94 mg, 408.10 μmol, 87.75 μL, 1 eq), Pd(dppf)$Cl_2$ (29.87 mg, 40.81 μmol, 0.1 eq), $Cs_2CO_3$ (332.47 mg, 1.02 mmol, 2.5 eq) in $H_2O$ (2 mL) and 1,4-dioxane (6 mL) was degassed and purged with $N_2$ for 3 times, the mixture was stirred at 90° C. for 2 h under $N_2$ atmosphere. The reaction mixture was filtered and concentrated under reduced pressure to yield a residue which was purified by flash silica gel chromatography (from PE/EA=1/0 to 1/1, TLC: PE/EtOAc=1/1, $R_f$=0.7) to yield (3R)—N-[8-(cyclohexen-1-yl)-2-(5-fluoro-3-pyridyl)pyrazolo[1,5-a][1,3,5]triazin-4-yl]-2,3,4,9-tetrahydro-1H-carbabazol-3-amine (110 mg, 193.83 μmol, 47.5% yield, 84.5% purity) as a yellow solid. $^1$H NMR (400 MHz, DMSO-$d_6$) δ ppm 10.79 (s, 1H), 9.38 (s, 1H), 9.08 (d, J=8.6 Hz, 1H), 8.79-8.66 (m, 1H), 8.48-8.37 (m, 1H), 8.28 (s, 1H), 7.35 (d, J=7.8 Hz, 1H), 7.27 (d, J=8.1 Hz, 1H), 7.05-6.97 (m, 1H), 6.96-6.88 (m, 1H), 6.73 (br s, 1H), 4.84-4.82 (m, 1H), 3.64 (s, 2H), 3.12 (dd, J=5.1, 14.9 Hz, 1H), 3.07-2.83 (m, 3H), 2.24-2.15 (m, 4H), 1.77-1.75 (m, 2H), 1.67-1.65 (m, 2H); ES-LCMS m/z 480.3 $[M+H]^+$.

Step 2: (3R)—N-[8-Cyclohexyl-2-(5-fluoro-3-pyridyl)pyrazolo[1,5-a][1,3,5]triazin-4-yl]-2,3,4,9-tetrahydro-1H-carbazol-3-amine (I-123)

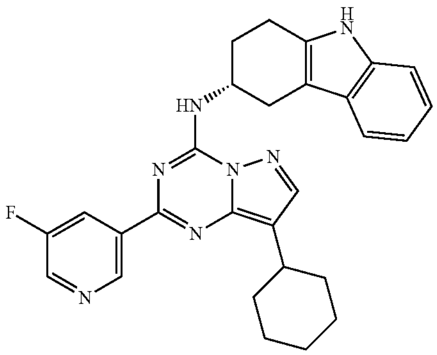 [SMILES: Fc1cncc(-c2nc(N[C@@H]3CCc4[nH]c5ccccc5c4C3)n3ncc(C4CCCCC4)c3n2)c1]

To a solution of (3R)—N-[8-(cyclohexen-1-yl)-2-(5-fluoro-3-pyridyl)pyrazolo[1,5-a][1,3,5]triazin-4-yl]-2,3,4,9-tetrahydro-1H-carbazol-3-amine (90 mg, 158.59 μmol, 1 eq) in EtOAc (5 mL) was added Pd/C (50 mg, 10% purity) under $N_2$. The suspension was degassed and purged with $H_2$ several times. The mixture was stirred under $H_2$ (15 psi) at 10° C. for 12 h. The reaction mixture was filtered and the filtrate was concentrated to yield a residue which was purified by preparative HPLC (HCl condition; column: Agela ASB 150*25 mm*5 um; mobile phase: [water (0.05% HCl)-ACN]; B %: 85%-100%, 8 min), followed by lyophilization to yield (3R)—N-[8-cyclohexyl-2-(5-fluoro-3-pyridyl)pyrazolo[1,5-a][1,3,5]triazin-4-yl]-2,3,4,9-tetrahydro-1H-carbazol-3-amine (16.46 mg, 28.78 μmol, 18.2% yield, 96.9% purity, 2HCl, OR: $[\alpha]^{24.6}_D$=9.235 (7.5 mg/10 mL in MeOH)) as a yellow solid (Optical Rotation: $[\alpha]^{25}_D$=9.235 (7.5 mg/10 mL in MeOH)). $^1$H NMR (400 MHz, DMSO-$d_6$) δ ppm 10.79 (s, 1H), 9.37 (s, 1H), 9.02 (d, J=8.6 Hz, 1H), 8.70 (d, J=2.7 Hz, 1H), 8.44 (dd, J=1.6, 9.9 Hz, 1H), 8.13 (s, 1H), 7.34 (d, J=7.6 Hz, 1H), 7.27 (d, J=7.8 Hz, 1H), 7.07-6.97 (m, 1H), 6.96-6.88 (m, 1H), 4.90-4.75 (m, 1H), 3.15-3.07 (m, 1H), 3.05-2.80 (m, 4H), 2.20-2.19 (m, 2H), 1.82-1.79 (m, 2H), 1.87-1.69 (m, 3H), 1.62-1.59 (m, 2H), 1.44-1.41 (m, 2H), 1.31-1.22 (m, 1H); ES-LCMS m/z 482.3 $[M+H]^+$.

Example 113

Synthesis of I-124

I-124

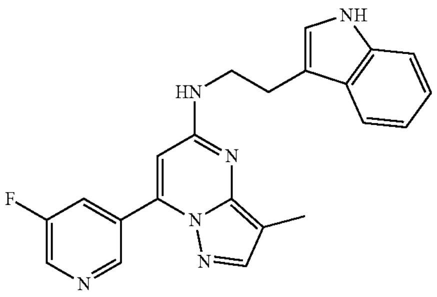

Synthetic Scheme:

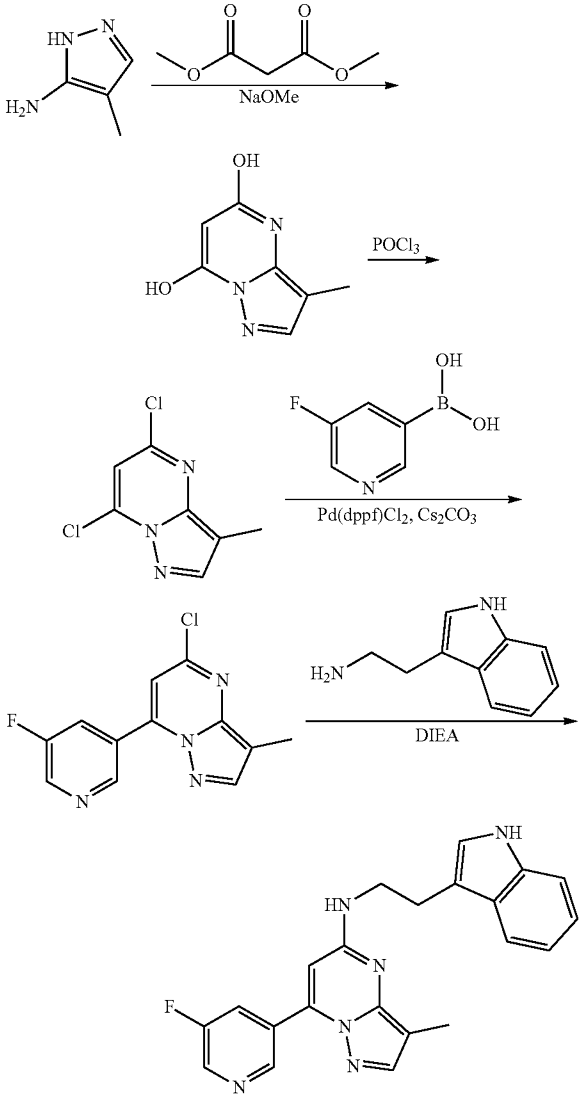

I-123

Step 1: 3-Methylpyrazolo[1,5-a]pyrimidine-5,7-diol

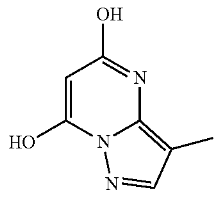

To a solution of 4-methyl-1H-pyrazol-5-amine (2 g, 20.59 mmol, 1 eq) and dimethyl propanedioate (2.86 g, 21.62 mmol, 2.48 mL, 1.05 eq) in MeOH (20 mL) was added a solution of Na (946.88 mg, 41.19 mmol, 976.16 μL, 2.0 eq) in MeOH (20 mL) under $N_2$ at 20° C. The mixture was stirred at 80° C. for 12 h. The reaction mixture was cooled to 20° C., filtered and collected the white solid. The solid was diluted with 1NHCl (20 mL) and stirred for 10 min, filtered and the solid was dried under reduced pressure to yield product of 3-methylpyrazolo[1,5-a]pyrimidine-5,7-diol (2 g, 12.11 mmol, 58.8% yield, crude purity) as a white solid which was used in the next step without further purification. $^1$H NMR (400 MHz, DMSO-$d_6$) δ ppm 10.54 (br s, 1H), 7.31 (s, 1H), 4.21 (br s, 1H), 1.96 (s, 3H).

Step 2: 5,7-Dichloro-3-methyl-pyrazolo[1,5-a]pyrimidine

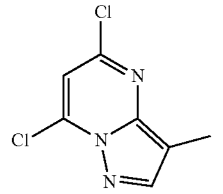

A solution of 3-methylpyrazolo[1,5-a]pyrimidine-5,7-diol (500 mg, 3.03 mmol, 1 eq) in $POCl_3$ (5 mL) was stirred at 110° C. for 3 h. The reaction mixture was concentrated under reduced pressure. The residue was diluted DCM (20 mL×2) and concentrated under reduced pressure. The residue was diluted DCM (20 mL), adjusted to pH to 9-10 with DIEA and concentrated under reduced pressure to yield a residue which was purified on silica gel column chromatography (from PE/EtOAc=1/0 to 5/1, TLC: PE/EtOAc=10/1, $R_f$=0.68) to yield product of 5,7-dichloro-3-methyl-pyrazolo[1,5-a]pyrimidine (400 mg, 1.98 mmol, 65.3% yield, 99.8% purity) as a white solid. $^1$H NMR (400 MHz, $CDCl_3$) δ ppm 8.09 (s, 1H), 6.93 (s, 1H), 2.37 (s, 3H); ES-LCMS m/z 202.0, 204.0 [M+H]$^+$.

Step 3: 5-Chloro-7-(5-fluoro-3-pyridyl)-3-methyl-pyrazolo[1,5-a]pyrimidine

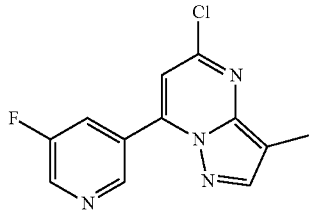 [SMILES: Cc1cnn2c(-c3cncc(F)c3)cc(Cl)nc12]

5,7-Dichloro-3-methyl-pyrazolo[1,5-a]pyrimidine (190 mg, 938.52 μmol, 1 eq), (5-fluoro-3-pyridyl)boronic acid (138.86 mg, 985.45 μmol, 1.05 eq), Pd(dppf)$Cl_2$ (68.67 mg, 93.85 μmol, 0.1 eq) and $Cs_2CO_3$ (611.58 mg, 1.88 mmol, 2 eq) were taken up into a microwave tube in 1,4-dioxane (3 mL) and $H_2O$ (1 mL). The sealed tube was heated at 110° C. for 1 h under microwave. The mixture was concentrated and water (10 mL) was added. The mixture was extracted with EtOAc (20 mL×3). The combined organic layers were dried over $Na_2SO_4$, filtered and concentrated to yield a residue which was purified on silica gel column chromatography (from PE/EtOAc=1/0 to 10/3, TLC: PE/EtOAc=3/1, $R_f$=0.50) to yield 5-chloro-7-(5-fluoro-3-pyridyl)-3-methyl-pyrazolo[1,5-a]pyrimidine (130 mg, 494.92 μmol, 52.7% yield, 100.0% purity) as a yellow solid. $^1$H NMR (400 MHz, $CDCl_3$) δ ppm 8.97 (s, 1H), 8.69 (d, J=2.7 Hz, 1H), 8.38-8.31 (m, 1H), 8.04 (s, 1H), 6.92 (s, 1H), 2.40 (s, 3H); ES-LCMS m/z 263.0, 265.0 [M+H]$^+$.

Step 4: 7-(5-Fluoro-3-pyridyl)-N-[2-(1H-indol-3-yl)ethyl]-3-methyl-pyrazolo[1,5-a]pyrimidin-5-amine (I-124)

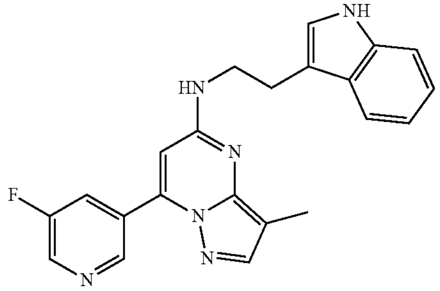 [SMILES: Cc1cnn2c(-c3cncc(F)c3)cc(NCCc3c[nH]c4ccccc34)nc12]

5-Chloro-7-(5-fluoro-3-pyridyl)-3-methyl-pyrazolo[1,5-a]pyrimidine (70 mg, 266.49 μmol, 1 eq), 2-(1H-indol-3-yl)ethanamine (64.04 mg, 399.74 μmol, 1.5 eq) and DIEA (103.33 mg, 799.48 μmol, 139.26 μL, 3 eq) were taken up into a microwave tube in i-PrOH (2 mL). The sealed tube was heated at 150° C. for 3 h under microwave. The reaction mixture was concentrated under reduced pressure to yield a residue which was purified by preparative HPLC (column: Agela Durashell C18 150*25 5 u; mobile phase: [water (0.05% HCl)-ACN]; B %: 32%-55%, 9 min), followed by lyophilization to yield 7-(5-fluoro-3-pyridyl)-N-[2-(1H-indol-3-yl)ethyl]-3-methyl-pyrazolo[1,5-a]pyrimidin-5-amine (28.21 mg, 59.77 μmol, 22.4% yield, 97.3% purity, 2HCl) as a yellow solid. $^1$H NMR (400 MHz, $CD_3OD$+$Na_2CO_3$) δ ppm 8.80 (br s, 1H), 8.62 (d, J=2.7 Hz, 1H), 8.18 (br s, 1H), 7.74-7.65 (m, 2H), 7.31 (d, J=8.1 Hz, 1H), 7.12-7.04 (m, 2H), 7.03-6.97 (m, 1H), 6.27 (br s, 1H), 3.78 (t, J=7.2 Hz, 2H), 3.11 (t, J=7.3 Hz, 2H), 2.24 (s, 3H); ES-LCMS m/z 387.1 $[M+H]^+$.

Example 114

Synthesis of I-125

I-125

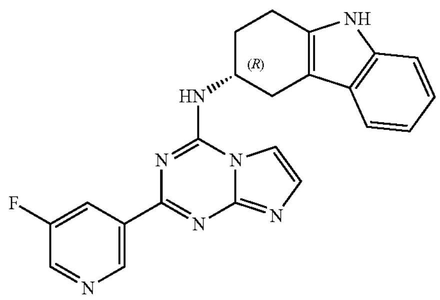

Synthetic Scheme:

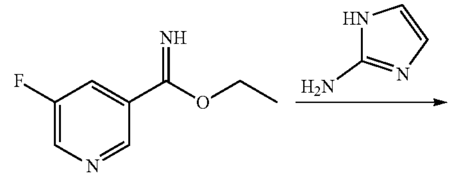

1

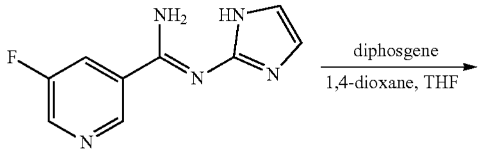

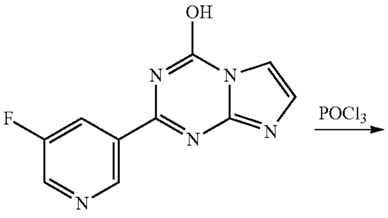

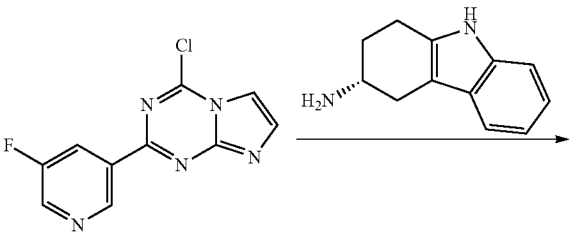

-continued

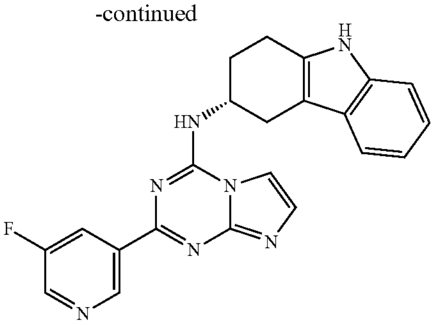

I-125

Step 1: 5-Fluoro-N'-(1H-imidazol-2-yl)pyridine-3-carboxamidine

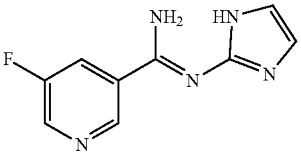 [SMILES: N/C(=N\c1ncc[nH]1)c1cncc(F)c1]

To a mixture of ethyl 5-fluoropyridine-3-carboximidate (1 g, 5.65 mmol, 1 eq) and 1H-imidazol-2-amine (563.27 mg, 6.78 mmol, 1.2 eq) in ACN (15 mL) was added AcONa (926.84 mg, 11.30 mmol, 2 eq). The mixture was stirred at 80° C. for 25 h under $N_2$ atmosphere. The reaction mixture was concentrated under reduced pressure to yield a residue which was purified on silica gel column chromatography (from PE/EtOAc=1/0 to 2/1, TLC: PE/EtOAc=2/1, $R_f$=0.35) to yield 5-fluoro-N'-(1H-imidazol-2-yl)pyridine-3-carboxamidine (400 mg, 1.75 mmol, 31.1% yield, 90.0% purity) as a yellow solid. $^1H$ NMR (400 MHz, DMSO-$d_6$) δ ppm 11.67 (br s, 1H), 9.97 (br s, 1H), 9.05 (s, 1H), 8.70 (d, J=2.4 Hz, 1H), 8.29-8.12 (m, 2H), 6.92 (s, 1H), 6.85 (s, 1H); ES-LCMS m/z 206.1 $[M+H]^+$.

Step 2: 2-(5-Fluoro-3-pyridyl)imidazo[1,2-a][1,3,5]triazin-4-ol

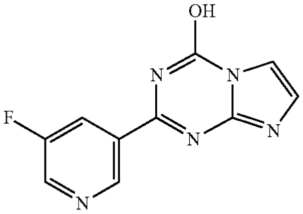 [SMILES: Oc1nc(-c2cncc(F)c2)nc2nccn12]

To a solution of 5-fluoro-N'-(1H-imidazol-2-yl)pyridine-3-carboxamidine (400 mg, 1.75 mmol, 1 eq) in THF (5 mL) and 1,4-dioxane (5 mL) was added diphosgene (694.18 mg, 3.51 mmol, 423.28 μL, 2 eq). The mixture was stirred at 80° C. for 2 h under $N_2$ atmosphere. The reaction mixture was concentrated under reduced pressure to yield a residue which was washed with DMF (5 mL), filtered and concentrated to yield 2-(5-fluoro-3-pyridyl)imidazo[1,2-a][1,3,5]triazin-4-ol (250 mg, 973.24 μmol, 55.5% yield, 90.0% purity) as a white solid which was used in the next step without further purification. $^1H$ NMR (400 MHz, DMSO-$d_6$) δ ppm 13.64 (br s, 1H), 9.29 (s, 1H), 8.78 (d, J=2.7 Hz, 1H), 8.35 (J=10.0 Hz, 1H), 7.73-7.65 (m, 2H); ES-LCMS m/z 232.0 $[M+H]^+$.

Step 3: 4-Chloro-2-(5-fluoro-3-pyridyl)imidazo[1,2-a][1,3,5]triazine

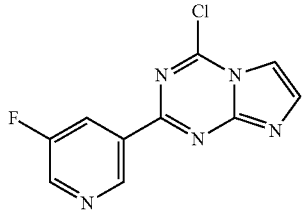

To a solution of 2-(5-fluoro-3-pyridyl)imidazo[1,2-a][1,3,5]triazin-4-ol (100 mg, 389.30 μmol, 1 eq) in $POCl_3$ (12 mL) was added DIEA (1.48 g, 11.48 mmol, 2 mL, 29.49 eq). The mixture was stirred at 120° C. for 3 h under $N_2$ atmosphere. The reaction mixture was concentrated under reduced pressure to yield 4-chloro-2-(5-fluoro-3-pyridyl)imidazo[1,2-a][1,3,5]triazine (90 mg, 360.53 μmol, 92.6% yield, crude) as a black solid which was used in the next step without further purification. ES-LCMS m/z 350.1 $[M+H]^+$.

Step 4: (3R)—N-[2-(5-Fluoro-3-pyridyl)imidazo[1,2-a][1,3,5]triazin-4-yl]-2,3,4,9-tetrahydro-1H-carbazol-3-amine (I-125)

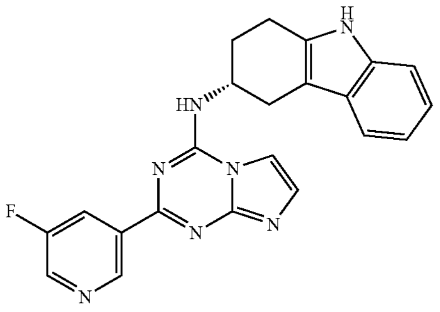 [SMILES: Fc1cncc(-c2nc(N[C@@H]3CCc4[nH]c5ccccc5c4C3)n3ccnc3n2)c1]

To a mixture of 4-chloro-2-(5-fluoro-3-pyridyl)imidazo[1,2-a][1,3,5]triazine (90 mg, 360.53 μmol, 1 eq) and (3R)-2,3,4,9-tetrahydro-1H-carbazol-3-amine (80.58 mg, 432.64 μmol, 1.2 eq) in ACN (10 mL) was added DIEA (5.34 g, 41.34 mmol, 7.20 mL, 114.65 eq). The mixture was stirred at 80° C. for 2 h under $N_2$ atmosphere. The reaction mixture was concentrated to yield a residue which was purified by preparative HPLC (column: Agela DuraShell 150 mm_25 mm_5 μm; mobile phase: [water (0.05% HCl)-ACN]; B %: 23%-53%, 8.5 min), followed by lyophilization to yield a product which was purified by preparative HPLC (column: Phenomenex Gemini 150*25 mm*10 μm; mobile phase: [water (0.05% ammonia hydroxide v/v)-ACN]; B %: 40%-70%, 8 min), followed by lyophilization to yield (3R)—N-[2-(5-fluoro-3-pyridyl)imidazo[1,2-a][1,3,5]triazin-4-yl]-2,3,4,9-tetrahydro-1H-carbazol-3-amine (15.11 mg, 37.83 μmol, 10.5% yield, 100.0% purity, $[\alpha]^{24}_D$=98.97 (MeOH, c=0.050 g/100 mL)) as a yellow solid. $^1H$ NMR (400 MHz, $CD_3OD$) δ ppm 9.39 (s, 1H), 8.55-8.47 (m, 2H), 7.93 (d, J=1.7 Hz, 1H), 7.56 (s, 1H), 7.36 (d, J=7.6 Hz, 1H), 7.25 (d, J=8.1 Hz, 1H), 7.05-6.98 (m, 1H), 6.97-6.90 (m, 1H), 4.85-4.79 (m, 1H), 3.36 (J=5.1 Hz, 1H), 3.08-2.83 (m, 3H), 2.44 (J=9.8 Hz, 1H), 2.26-2.14 (m, 1H); ES-LCMS m/z 400.2 $[M+H]^+$.

Example 115

Synthesis of I-126

I-126

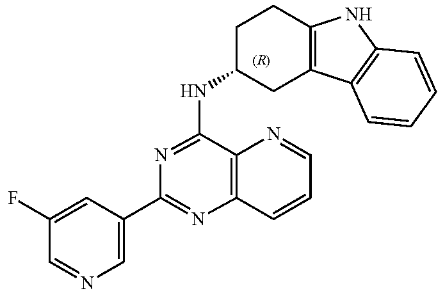

Synthetic Scheme:

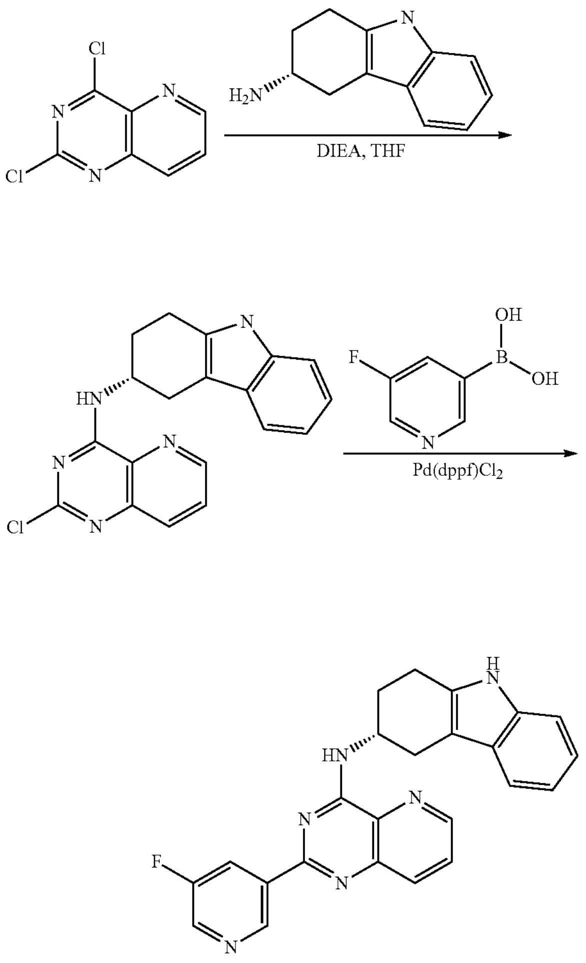

I-126

Step 1: (3R)—N-(2-Chloropyrido[3,2-d]pyrimidin-4-yl)-2,3,4,9-tetrahydro-1H-carbazol-3-amine

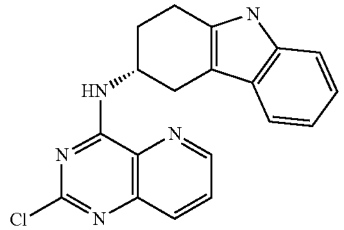 [SMILES: Clc1nc(N[C@@H]2CCc3[nH]c4ccccc4c3C2)c2ncccc2n1]

To a solution of 2,4-dichloropyrido[3,2-d]pyrimidine (100 mg, 499.94 μmol, 1 eq) in THF (3 mL) was added DIEA (193.84 mg, 1.50 mmol, 261.24 μL, 3 eq) and (3R)-2,3,4,9-tetrahydro-1H-carbazol-3-amine (93.11 mg, 499.94 μmol, 1 eq). The mixture was stirred at 60° C. for 3 h. The reaction mixture was concentrated under reduced pressure to yield a residue which was purified by flash silica gel chromatography (from PE/EtOAC=100/1 to 1/1, TLC: PE/EtOAc=1/1, $R_f$=0.5) to yield (3R)—N-(2-chloropyrido[3,2-d]pyrimidin-4-yl)-2,3,4,9-tetrahydro-1H-carbazol-3-amine (150 mg, 428.80 μmol, 85.8% yield, 100.0% purity) as a yellow solid. $^1$H NMR (400 MHz, $CD_3OD$) δ ppm 8.72 (dd, J=1.5, 4.4 Hz, 1H), 7.95 (dd, J=1.5, 8.3 Hz, 1H), 7.75 (dd, J=4.2, 8.6 Hz, 1H), 7.37 (d, J=7.6 Hz, 1H), 7.26 (d, J=8.1 Hz, 1H), 7.07-7.00 (m, 1H), 6.98-6.92 (m, 1H), 4.80-4.68 (m, 1H), 3.21 (dd, J=5.1, 15.2 Hz, 1H), 3.06-2.80 (m, 3H), 2.37-2.12 (m, 2H); ES-LCMS m/z 350.1 $[M+H]^+$.

Step 2. (3R)—N-[2-(5-Fluoro-3-pyridyl)pyrido[3,2-d]pyrimidin-4-yl]-2,3,4,9-tetrahydro-1H-carbazol-3-amine (I-126)

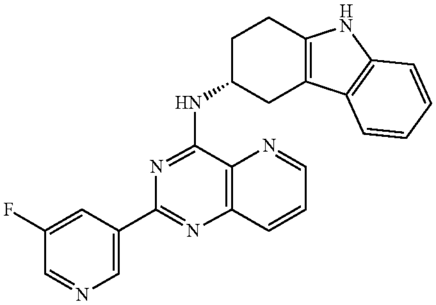 [SMILES: Fc1cncc(-c2nc(N[C@@H]3CCc4[nH]c5ccccc5c4C3)c3ncccc3n2)c1]

(3R)—N-(2-chloropyrido[3,2-d]pyrimidin-4-yl)-2,3,4,9-tetrahydro-1H-carbazol-3-amine (60 mg, 171.52 μmol, 1 eq), (5-fluoro-3-pyridyl)boronic acid (29.00 mg, 205.82 μmol, 1.2 eq), $Pd(dppf)Cl_2$ (12.55 mg, 17.15 μmol, 0.1 eq) and $Cs_2CO_3$ (167.65 mg, 514.56 μmol, 3 eq) were taken up into a microwave tube in 1,4-dioxane (2 mL) and $H_2O$ (0.5 mL). The sealed tube was heated at 110° C. for 0.5 h under microwave. The reaction mixture was diluted with water (5 mL) and extracted with EtOAc (10 mL×3). The combined organic layers were dried over $Na_2SO_4$, filtered and concentrated under reduced pressure to give a residue which was purified by preparative HPLC (column: Agela ASB 150*25 mm*5 um; mobile phase: [water(0.05% HCl)-ACN]; B %: 55%-85%, 8 min), followed by lyophilization to yield (3R)—N-[2-(5-fluoro-3-pyridyl)pyrido[3,2-d]pyrimidin-4-yl]-2,3,4,9-tetrahydro-1H-carbazol-3-amine (39.09 mg, 95.24 μmol, 55.5% yield, 100.0% purity, OR: $[\alpha]^{23.6}_D$=0.471 (MeOH, c=0.110 g/100 mL).) as a yellow solid. $^1$H NMR (400 MHz, $CD_3OD$) δ ppm 9.32 (s, 1H), 9.01 (dd, J=1.2, 4.4 Hz, 1H), 8.83 (d, J=2.4 Hz, 1H), 8.61-8.49 (m, 1H), 8.32 (dd, J=1.2, 8.6 Hz, 1H), 8.04 (dd, J=4.4, 8.6 Hz, 1H), 7.33 (d, J=7.6 Hz, 1H), 7.25 (d, J=8.1 Hz, 1H), 6.98 (t, J=7.5 Hz, 1H), 6.91-6.81 (m, 1H), 5.22-5.04 (m, 1H), 3.28 (s, 1H), 3.12-2.86 (m, 3H), 2.43-2.27 (m, 2H); ES-LCMS m/z 411.2 $[M+H]^+$.

Example 116

Synthesis of I-128a

I-128a

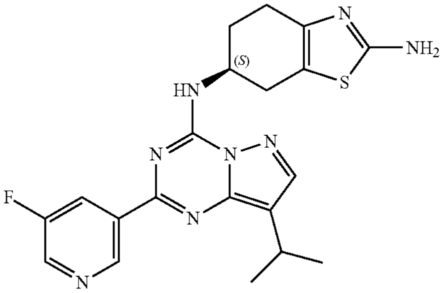

Synthetic Scheme:

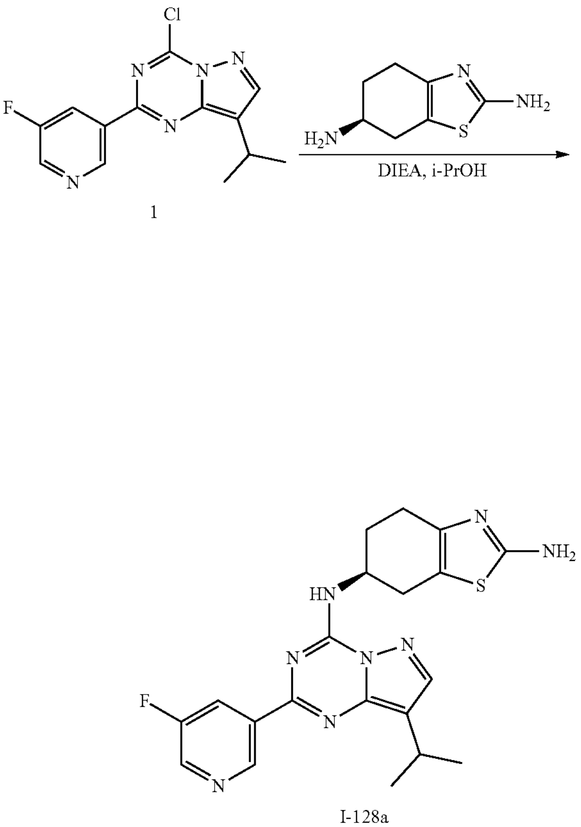

1

I-128a

Step 1: (6S)-N6-[2-(5-Fluoro-3-pyridyl)-8-isopropyl-pyrazolo[1,5-a][1,3,5]triazin-4-yl]-4,5,6,7-tetrahydro-1,3-benzothiazole-2,6-diamine (I-128a)

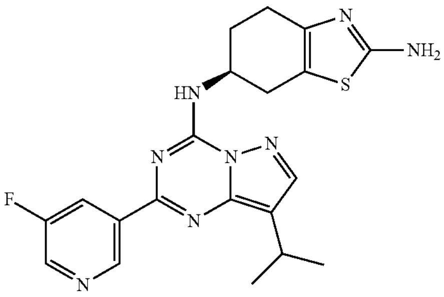 [SMILES: CC(C)c1cnn2c(N[C@H]3CCc4nc(N)sc4C3)nc(-c3cncc(F)c3)nc12]

A mixture of 4-chloro-2-(5-fluoro-3-pyridyl)-8-isopropyl-pyrazolo[1,5-a][1,3,5]triazine (70 mg, 236.12 μmol, 1 eq), (6S)-4,5,6,7-tetrahydro-1,3-benzothiazole-2,6-diamine (43.96 mg, 259.74 mol, 1.1 eq) and DIEA (91.55 mg, 708.37 μmol, 123.39 μL, 3 eq) in i-PrOH (10 mL) was stirred at 80° C. for 2 h. The mixture was concentrated under reduced pressure to give a residue which was washed with MeOH (20 mL×2) to yield (6S)-N6-[2-(5-fluoro-3-pyridyl)-8-isopropyl-pyrazolo[1,5-a][1,3,5]triazin-4-yl]-4,5,6,7-tetrahydro-1,3-benzothiazole-2,6-diamine (22.62 mg, 53.29 μmol, 22.6% yield, 100.0% purity, SFC: Rt=5.691 min, ee=99.8%, OR: $[\alpha]^{21.9}{}_D$=−34.176 ($CHCl_3$, c=0.104 g/100 mL)) as a white solid. $^1$H NMR (400 MHz, DMSO-$d_6$) δ ppm 9.37 (s, 1H), 8.97 (br s, 1H), 8.71 (d, J=2.8 Hz, 1H), 8.44 (d, J=10.0 Hz, 1H), 8.13 (s, 1H), 6.72 (s, 2H), 4.75-4.72 (m, 1H), 3.49-3.19 (m, 1H), 2.90-2.83 (m, 2H), 2.65-2.58 (m, 1H), 2.54-2.50 (m, 1H), 2.09-2.05 (m, 2H), 1.36 (d, J=6.8 Hz, 6H); ES-LCMS m/z 425.2 $[M+H]^+$ Example 117

Synthesis of I-128b

I-128b

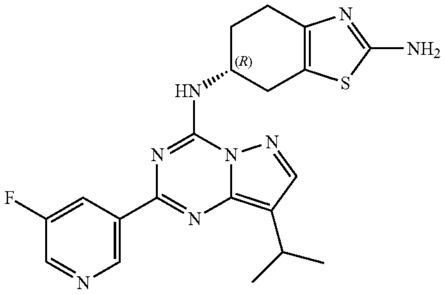

Synthetic Scheme:

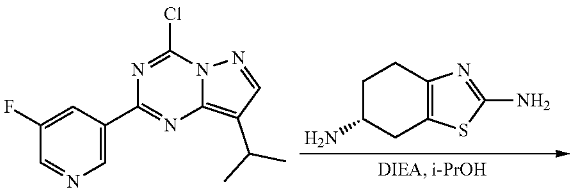

1

-continued

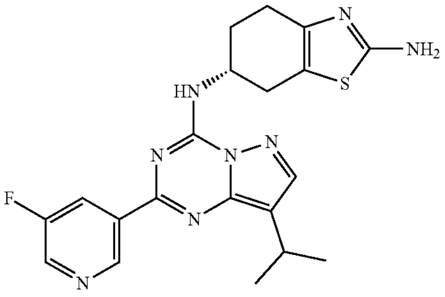

I-128b

Step 1: (6R)-N6-[2-(5-Fluoro-3-pyridyl)-8-isopropyl-pyrazolo[1,5-a][1,3,5]triazin-4-yl]-4,5,6,7-tetrahydro-1,3-benzothiazole-2,6-diamine(I-128b)

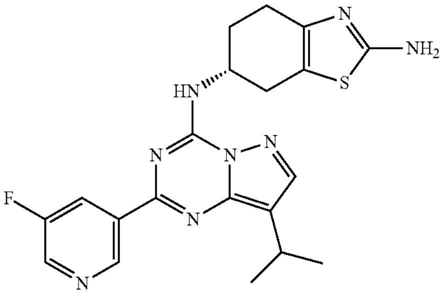 [SMILES: CC(C)c1cnn2c(N[C@@H]3CCc4nc(N)sc4C3)nc(-c3cncc(F)c3)nc12]

A mixture of 4-chloro-2-(5-fluoro-3-pyridyl)-8-isopropyl-pyrazolo[1,5-a][1,3,5]triazine (70 mg, 236.12 μmol, 1 eq), (6R)-4,5,6,7-tetrahydro-1,3-benzothiazole-2,6-diamine (43.96 mg, 259.74 mol, 1.1 eq) and DIEA (91.55 mg, 708.37 μmol, 123.38 μL, 3 eq) in i-PrOH (10 mL) was stirred at 80° C. for 2 h. The mixture was concentrated under reduced pressure to yield a residue which was washed with MeOH (20 mL×2) to yield (6R)-N6-[2-(5-fluoro-3-pyridyl)-8-isopropyl-pyrazolo[1,5-a][1,3,5]triazin-4-yl]-4,5,6,7-tetrahydro-1,3-benzothiazole-2,6-diamine (20.56 mg, 48.43 μmol, 20.5% yield, 100.0% purity, SFC: Rt=7.228 min, ee=98.44%, OR: $[\alpha]^{22.1}{}_D$=29.753 ($CHCl_3$, c=0.100 g/100 mL)) as a white solid. $^1$H NMR (400 MHz, DMSO-$d_6$) δ ppm 9.37 (s, 1H), 8.97 (d, J=8.4 Hz, 1H), 8.71 (d, J=2.8 Hz, 1H), 8.46-8.42 (m, 1H), 8.13 (s, 1H), 6.72 (s, 2H), 4.77-4.72 (m, 1H), 3.23-3.17 (m, 1H), 2.90-2.83 (m, 2H), 2.67-2.64 (m, 1H), 2.58-2.53 (m, 1H), 2.07-2.05 (m, 2H), 1.36 (d, J=6.8 Hz, 6H); ES-LCMS m/z 425.2 $[M+H]^+$.

Example 118

Synthesis of I-129

I-129

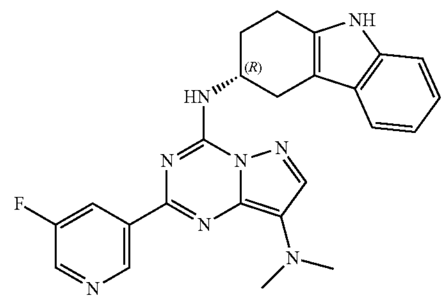

Synthetic Scheme:

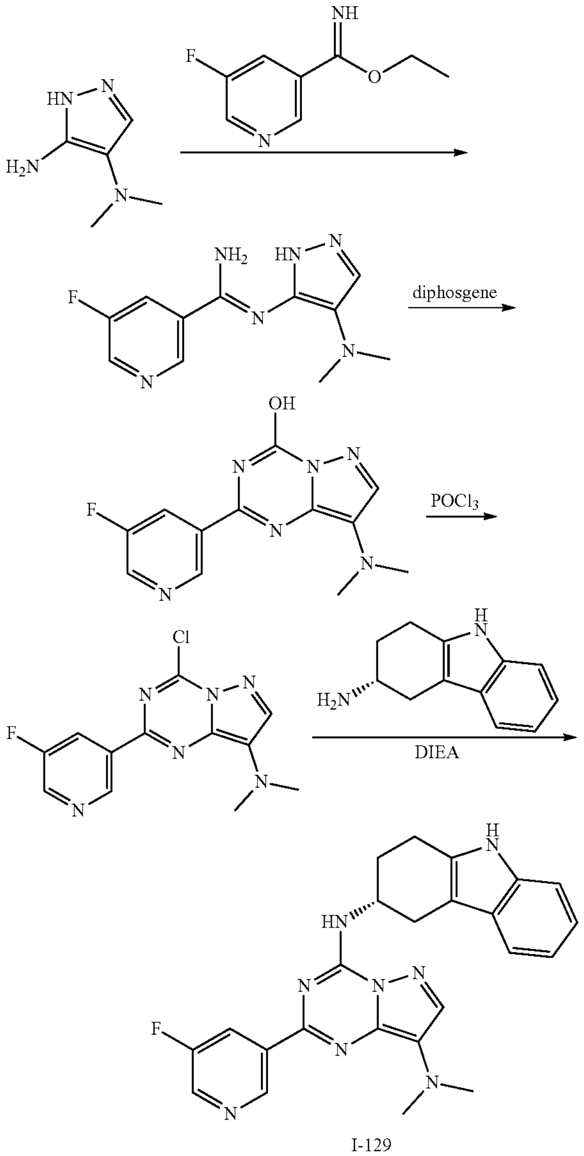

I-129

Step 1: N'-[4-(Dimethylamino)-1H-pyrazol-5-yl]-5-fluoro-pyridine-3-carboxamidine

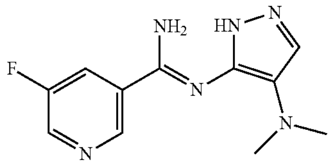 [SMILES: CN(C)c1cn[nH]c1/N=C(\N)c1cncc(F)c1]

To a solution of N4,N4-dimethyl-1H-pyrazole-4,5-diamine (1.2 g, 6.27 mmol, 1 eq, HCl) in ACN (20 mL) was added ethyl 5-fluoropyridine-3-carboximidate (1.11 g, 6.27 mmol, 1 eq). The mixture was stirred at 60° C. for 12 h under N2 atmosphere. The reaction mixture was concentrated under reduced pressure to yield a residue which was purified on silica gel column chromatography (from DCM/MeOH=1/0 to 5/1, TLC: DCM/MeOH=10/1, $R_f$=0.3) to yield N'-[4-(dimethylamino)-1H-pyrazol-5-yl]-5-fluoro-pyridine-3-carboxamidine (700 mg, 2.52 mmol, 40.2% yield, 89.5% purity) as a yellow solid. $^1$H NMR (400 MHz, DMSO-$d_6$) δ ppm 11.96 (br s, 1H), 9.07 (s, 1H), 8.66 (d, J=2.0 Hz, 1H), 8.17 (d, J=10.0 Hz, 1H), 7.18 (s, 1H), 2.72 (br s, 6H); ES-LCMS m/z 248.9 $[M+H]^+$.

Step 2: 2-8-(Dimethylamino)-2-(5-Fluoro-3-pyridyl)pyrazolo[1,5-a][1,3,5]triazin-4-ol

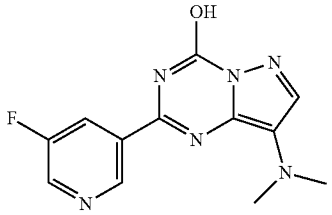 [SMILES: CN(C)c1cnn2c(O)nc(-c3cncc(F)c3)nc12]

To a solution of N'-[4-(dimethylamino)-1H-pyrazol-5-yl]-5-fluoro-pyridine-3-carboxamidine (160 mg, 576.82 μmol, 1 eq) in THF (1 mL) and toluene (8 mL) was added diphosgene (342.34 mg, 1.73 mmol, 208.74 μL, 3 eq) under $N_2$ at 15° C., the mixture was stirred at 15° C. for 0.5 h. Then the mixture was stirred at 130° C. for 2 h under $N_2$ atmosphere. The reaction mixture was concentrated under reduced pressure to yield 8-(dimethylamino)-2-(5-fluoro-3-pyridyl)pyrazolo[1,5-a][1,3,5]triazin-4-ol (150 mg, crude) as a yellow solid which was used in the next step without further purification. $^1$H NMR (400 MHz, DMSO-$d_6$) δ ppm 9.15 (s, 1H), 9.07 (s, 1H), 8.92 (d, J=2.3 Hz, 1H), 8.79 (d, J=2.8 Hz, 1H), 8.03 (s, 1H), 3.03 (s, 6H); ES-LCMS m/z 275.1 $[M+H]^+$.

Step 3 4-Chloro-2-(5-fluoro-3-pyridyl)-N,N-dimethyl-pyrazolo[1,5-a][1,3,5]triazin-8-amine

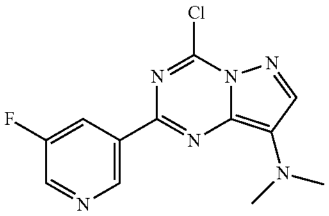

A mixture of 8-(dimethylamino)-2-(5-fluoro-3-pyridyl) pyrazolo[1,5-a][1,3,5]triazin-4-ol (150 mg, 546.94 μmol, 1 eq) in $POCl_3$ (9 g, 58.70 mmol, 5.45 mL, 107.32 eq) was degassed and purged with $N_2$ for 3 times, stirred at 120° C. for 1 h under $N_2$ atmosphere. The reaction mixture was concentrated under reduced pressure to yield a residue which was quenched by addition of water (50 mL), adjusted pH to 8 by aq. $NaHCO_3$, extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 3/1, TLC: PE/EtOAc=3/1, $R_f$=0.31) to yield 4-chloro-2-(5-fluoro-3-pyridyl)-N,N-dimethyl-pyrazzolo[1,5-a][1,3,5]triazin-8-amine (25 mg, 76.87 mol, 14.0% yield, 90% purity) as a yellow solid. $^1$H NMR (400 MHz, $CDCl_3$) δ ppm 9.35 (s, 1H), 8.51 (br s, 1H), 8.27 (d, J=8.8 Hz, 1H), 7.85 (s, 1H), 3.05 (s, 6H); ES-LCMS m/z 293.1, 295.0 $[M+H]^+$.

Step 4: 2-(5-Fluoro-3-pyridyl)-N8,N8-dimethyl-N4-[(3R)-2,3,4,9-tetrahydro-1H-carbazol-3-yl]pyrazolo[1,5-a][1,3,5]triazine-4,8-diamine (I-129)

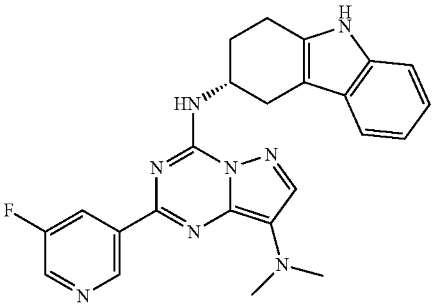 [SMILES: CN(C)c1cnn2c(N[C@@H]3CCc4[nH]c5ccccc5c4C3)nc(-c3cncc(F)c3)nc12]

To a solution of 4-chloro-2-(5-fluoro-3-pyridyl)-N,N-dimethyl-pyrazolo[1,5-a][1,3,5]triazin-8-amine (25 mg, 76.87 μmol, 1 eq) in i-PrOH (3 mL) was added (3R)-2,3,4,9-tetrahydro-1H-carbazol-3-amine (17.18 mg, 92.24 μmol, 1.2 eq). The mixture was stirred at 40° C. for 2 h. The reaction mixture was concentrated to yield a residue which was purified by preparative HPLC (column: Agela ASB 150*25 mm*5 m; mobile phase: [water (0.05% HCl)-ACN]; B %: 38%-68%, 8 min) twice, followed by lyophilization to yield 2-(5-fluoro-3-pyridyl)-N8,N8-dimethyl-N4-[(3R)-2,3,4,9-tetrahydro-1H-carbazol-3-yl]pyrazolo[1,5-a][1,3,5]triazine-4,8-diamine (34.45 mg, 62.30 μmol, 81.0% yield, 99.8% purity, 3HCl, $[\alpha]^{20.6}_D$=+36.080 (MeOH, c=0.1 g/100 mL)) as a yellow solid. $^1$H NMR (400 MHz, $CD_3OD$) δ ppm 9.51 (br s, 1H), 8.74 (m, 2H), 8.42 (br s, 1H), 7.37 (d, J=7.8 Hz, 1H), 7.28 (d, J=8.3 Hz, 1H), 7.04 (t, J=7.5 Hz, 1H), 6.99-6.92 (m, 1H), 5.00-4.92 (m, 1H), 3.53 (br s, 6H), 3.28-2.89 (m, 4H), 2.44-2.23 (m, 2H); ES-LCMS m/z 443.2 $[M+H]^+$.

Example 119

Synthesis of I-130

I-130

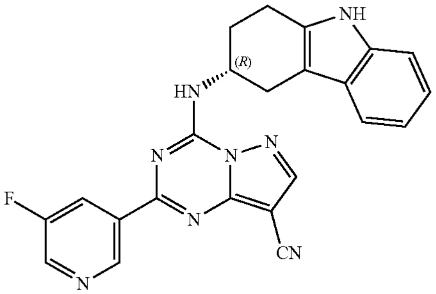

Synthetic Scheme:

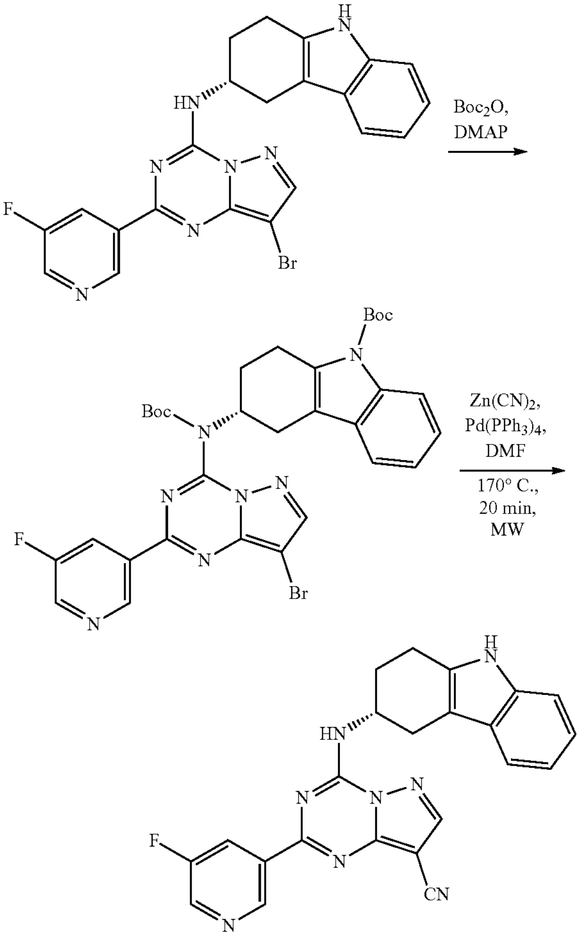

I-130

Step 1: tert-Butyl (3R)-3-[[8-bromo-2-(5-fluoro-3-pyridyl)pyrazolo[1,5-a][1,3,5]triazin-4-yl]-tert-butoxycarbonyl-aminol]1,2,3,4-tetrahydrocarbazole-9-carboxylate

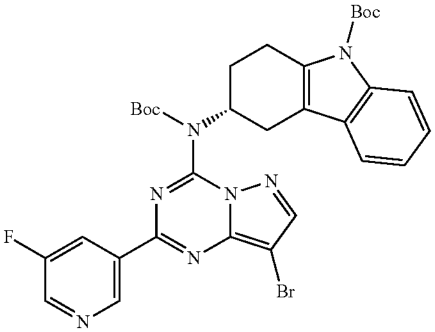

A mixture of (3R)—N-[8-bromo-2-(5-fluoro-3-pyridyl)pyrazolo[1,5-a][1,3,5]triazin-4-yl]-2,3,4,9-tetrahydro-1H-carbazol-3-amine (560 mg, 1.09 mmol, 1 eq), $Boc_2O$ (1.43 g, 6.57 mmol, 1.51 mL, 6 eq) and DMAP (534.93 mg, 4.38 mmol, 4 eq) in 1,4-dioxane (50 mL) was stirred at 110° C. for 12 h. TLC (PE/EtOAc=5/1, $R_f$=0.65) showed the starting material was consumed completely. The reaction mixture was concentrated under reduced pressure to yield a residue which was purified by flash silica gel chromatography (from PE/EtOAc=1/0 to 10/1, TLC: PE/EtOAc=5/1, $R_f$=0.65) to yield tert-butyl (3R)-3-[[8-bromo-2-(5-fluoro-3-pyridyl)pyrazolo[1,5-a][1,3,5]triazin-4-yl]-tert-butoxycarbonyl-amino]-1,2,3,4-tetrahydrocarbazole-9-carboxylate (660 mg, 972.66 μmol, 88.9% yield, 100.0% purity) as a white solid. $^1$H NMR (400 MHz, $CDCl_3$) δ ppm 9.49 (s, 1H), 8.60 (d, J=2.8 Hz, 1H), 8.44 (d, J=8.4 Hz, 1H), 8.23 (s, 1H), 8.10 (d, J=8.4 Hz, 1H), 7.33 (d, J=7.8 Hz, 1H), 7.22-7.16 (m, 2H), 4.92 (br s, 1H), 3.34 (d, J=16.8 Hz, 1H), 3.25-3.11 (m, 3H), 2.50 (m, 1H), 2.33 (m, 1H), 1.67 (s, 9H), 1.39 (s, 9H); ES-LCMS m/z 678.2, 680.2 $[M+H]^+$.

Step 2: 2-(5-Fluoro-3-pyridyl)-4-[[(3R)-2,3,4,9-tetrahydro-1H-carbazol-3-yl]amino]pyrazolo[1,5-a][1,3,5]triazine-8-carbonitrile (I-130)

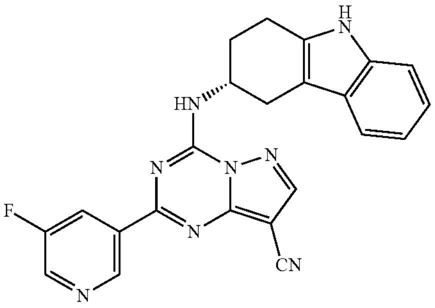

A mixture of tert-butyl (3R)-3-[[8-bromo-2-(5-fluoro-3-pyridyl)pyrazolo[1,5-a][1,3,5]triazin-4-yl]-tert-butoxycarbonyl-amino]-1,2,3,4-tetrahydrocarbazole-9-carboxylate (50 mg, 72.36 μmol, 1 eq), $Zn(CN)_2$ (33.99 mg, 289.44 μmol, 18.37 μL, 4 eq) and $Pd(PPh_3)_4$ (16.72 mg, 14.47 μmol, 0.2 eq) in DMF (3 mL) were taken up into a microwave tube and then purged with $N_2$ for 1 min. The sealed tube was stirred at 170° C. for 20 min under microwave (1 bar). The reaction mixture was extracted with EtOAc (20 mL×3). The combined organic layers were dried over $Na_2SO_4$, filtered and concentrated to yield a residue which was purified by preparative HPLC (column: Agela ASB 150*25 mm*5 um; mobile phase: [water (0.05% HCl)-ACN]; B %: 55%-85%, 8 min), followed by lyophilization to yield 2-(5-fluoro-3-pyridyl)-4-[[(3R)-2,3,4,9-tetrahydro-1H-carbazol-3-yl]amino]pyrazolo[1,5-a][1,3,5]triazine-8-carbonitrile (15.36 mg, 29.98 umol, 41.4% yield, 97.1% purity, 2HCl, $[\alpha]^{18.1}_D$=45.287, (MeOH, c=0.078 g/100 mL)) as a yellow solid. $^1$H NMR (400 MHz, $CD_3OD$) δ ppm 9.48 (s, 1H), 8.80-8.71 (m, 2H), 8.43 (s, 1H), 7.32 (d, J=7.6 Hz, 1H), 7.24 (d, J=8.1 Hz, 1H), 7.00 (t, J=7.5 Hz, 1H), 6.94-6.88 (m, 1H), 4.83 (m, 1H), 3.26 (m, 1H), 3.08-2.88 (m, 3H), 2.37-2.35 (m, 1H), 2.31-2.18 (m, 1H); ES-LCMS m/z 425.2 $[M+H]^+$.

Example 120

Synthesis of I-131

I-131

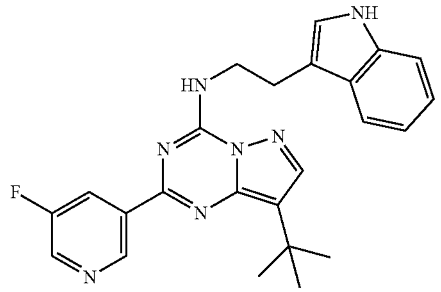 [SMILES: CC(C)(C)c1cnn2c(NCCc3c[nH]c4ccccc34)nc(-c3cncc(F)c3)nc12]

Synthetic Scheme:

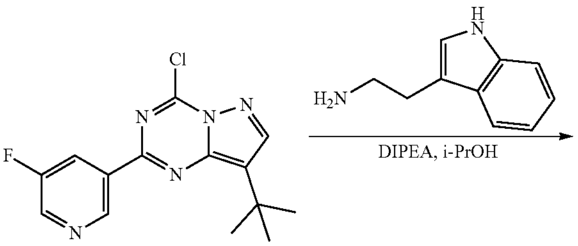

1

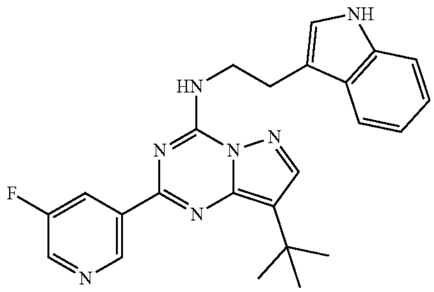

I-131

Step 1: N-(2-(1H-Indol-3-yl)ethyl)-8-(tert-butyl)-2-(5-fluoropyridin-3-yl)pyrazolo[1,5-a][1,3,5]triazin-4-amine (I-131)

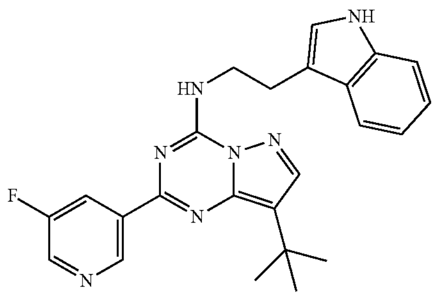

To a solution of 8-tert-butyl-4-chloro-2-(5-fluoro-3-pyridyl)pyrazolo[1,5-a][1,3,5]triazine (60 mg, 176.62 μmol, 1 eq) in i-PrOH (3 mL) was added 2-(1H-indol-3-yl)ethanamine (29.43 mg, 183.68 μmol, 1.04 eq) and DIPEA (114.13 mg, 883.10 μmol, 153.82 □μL, 5 eq). The reaction mixture was stirred at 50° C. for 3 h. The reaction mixture was concentrated under reduced pressure to give a residue which was purified by preparative HPLC (column: Agela Durashell C18 150*25 5 u; mobile phase: [water (0.05% HCl)-ACN]; B %: 75%-95%, 8 min), followed by lyophilization to yield 8-tert-butyl-2-(5-fluoro-3-pyridyl)-N-[2-(1H-indol-3-yl)ethyl]pyrazolo[1,5-a][1,3,5]triazin-4-amine (27.49 mg, 54.18 μmol, 30.7% yield, 99.0% purity, 2HCl) as a yellow solid. $^1$H NMR (400 MHz, $CD_3OD$) δ ppm 9.13 (s, 1H), 8.80 (s, 1H), 8.55 (d, J=8.6 Hz, 1H), 7.95 (s, 1H), 7.69-7.62 (m, 1H), 7.19-7.12 (m, 1H), 7.01-6.93 (m, 3H), 4.02 (J=6.7 Hz, 2H), 3.16 (t, J=6.7 Hz, 2H), 1.48 (s, 9H); ES-LCMS m/z 430.3 $[M+H]^+$.

Example 121

Synthesis of I-132

I-132

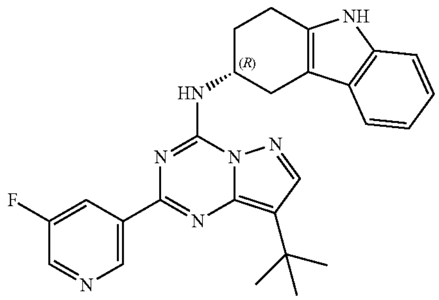

Synthetic Scheme:

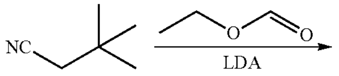

-continued

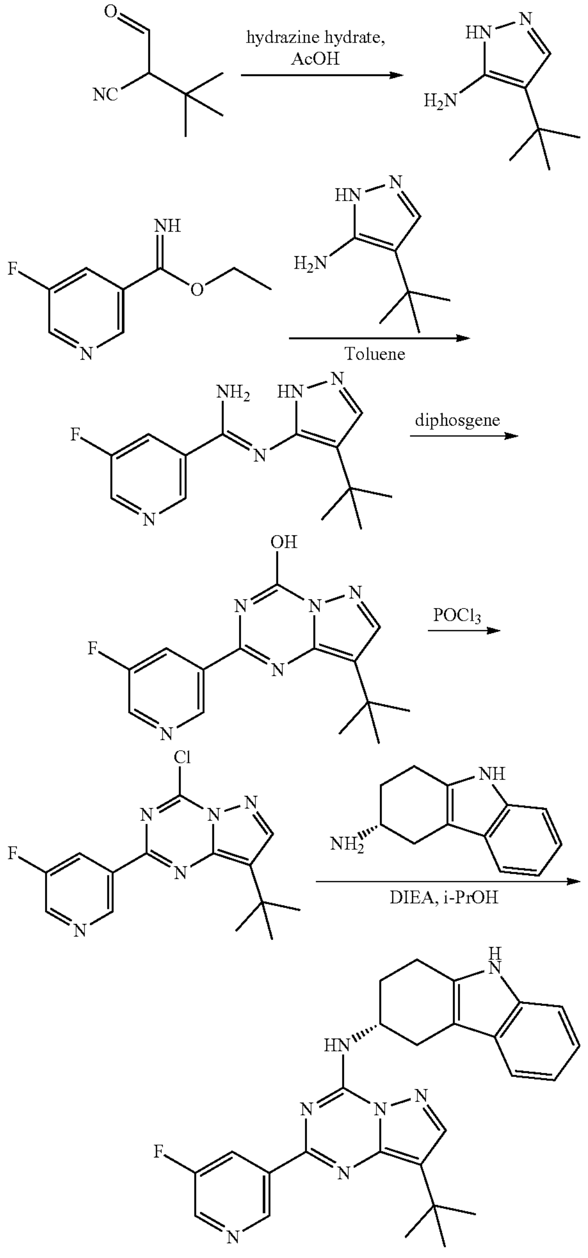

I-131

Step 1: (Z)—N'-(4-(tert-Butyl)-1H-pyrazol-5-yl)-5-fluoronicotinimidamide

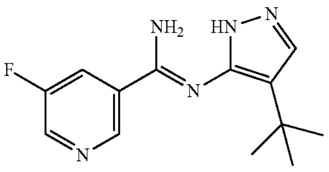 [SMILES: CC(C)(C)c1cn[nH]c1/N=C(\N)c1cncc(F)c1]

To a solution of ethyl 5-fluoropyridine-3-carboximidate (400 mg, 2.26 mmol, 1 eq) in toluene (15 mL) was added 4-tert-butyl-1H-pyrazol-5-amine (314.54 mg, 2.26 mmol, 1 eq). The mixture was stirred at 130° C. for 24 h under $N_2$. The reaction mixture was concentrated under reduced pressure to yield a residue which was purified on silica gel column chromatography (from PE/EtOAc=1/0 to 5/1, TLC: PE/EtOAc=1/1, $R_f$=0.23) to yield N-(4-tert-butyl-1H-pyrazol-5-yl)-5-fluoro-pyridine-3-carboxamidine (400 mg, 1.45 mmol, 64.4% yield, 95.0% purity) as a white solid. $^1H$ NMR (400 MHz, $CDCl_3$) δ ppm 9.59 (s, 1H), 8.94 (s, 1H), 8.57-8.48 (m, 1H), 8.02 (d, J=9.5 Hz, 1H), 7.23 (s, 1H), 1.41 (s, 9H); ES-LCMS m/z 262.1 $[M+H]^+$.

Step 2: 8-(tert-Butyl)-2-(5-fluoropyridin-3-yl)pyrazolo[1,5-a][1,3,5]triazin-4-ol

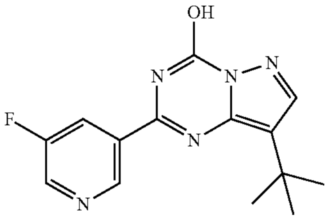 [SMILES: CC(C)(C)c1cnn2c(O)nc(-c3cncc(F)c3)nc12]

To a solution of N'-(4-tert-butyl-1H-pyrazol-5-yl)-5-fluoro-pyridine-3-carboxamidine (400 mg, 1.45 mmol, 1 eq) in 1,4-dioxane (5 mL) and THF (5 mL) was added diphosgene (575.40 mg, 2.91 mmol, 350.85 μL, 2 eq). The mixture was stirred at 80° C. for 7 h under $N_2$. The reaction mixture was concentrated under reduced pressure to yield 8-tert-butyl-2-(5-fluoro-3-pyridyl)pyrazolo[1,5-a][1,3,5]triazin-4-ol (400 mg, 1.32 mmol, 91.0% yield, 95.0% purity) as a yellow solid which was used in next step without further purification. $^1H$ NMR (400 MHz, $CD_3OD$) δ ppm 9.22 (s, 1H), 8.89 (s, 1H), 8.55 (d, J=9.0 Hz, 1H), 8.03 (s, 1H), 1.49 (s, 9H); ES-LCMS m/z 287.8 $[M+H]^+$.

Step 3: 8-(tert-Butyl)-4-chloro-2-(5-fluoropyridin-3-yl)pyrazolo[1,5-a][1,3,5]triazine

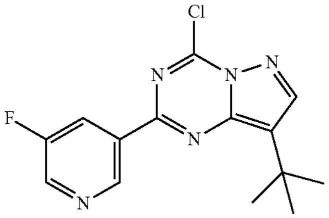 [SMILES: CC(C)(C)c1cnn2c(Cl)nc(-c3cncc(F)c3)nc12]

A solution of 8-tert-butyl-2-(5-fluoro-3-pyridyl)pyrazolo[1,5-a][1,3,5]triazin-4-ol (400 mg, 1.32 mmol, 1 eq) in $POCl_3$ (2 g, 13.04 mmol, 1.21 mL, 9.86 eq) was stirred at 110° C. for 2 h under $N_2$ atmosphere. The reaction mixture was concentrated under reduced pressure. The residue was dissolved in ice-water (10 mL) and extracted with DCM (10 mL×3). The organic layer was dried over $Na_2SO_4$, filtered and concentrated to yield a residue which was purified on silica gel column chromatography (from PE/EtOAc=1/0 to 5/1, TLC: PE/EtOAc=3/1, $R_f$=0.7) to yield 8-tert-butyl-4-chloro-2-(5-fluoro-3-pyridyl)pyrazolo[1,5-a][1,3,5]triazine (130 mg, 382.68 μmol, 28.9% yield, 90.0% purity) as a yellow solid. $^1H$ NMR (400 MHz, $CDCl_3$) δ ppm 9.44 (s, 1H), 8.56 (s, 1H), 8.35 (d, J=9.0 Hz, 1H), 8.11 (s, 1H), 1.47 (s, 9H); ES-LCMS m/z 305.7 $[M+H]^+$.

Step 4: (R)—N-(8-(tert-Butyl)-2-(5-fluoropyridin-3-yl)pyrazolo[1,5-a][1,3,5]triazin-4-yl)-2,3,4,9-tetrahydro-1H-carbazol-3-amine (I-132)

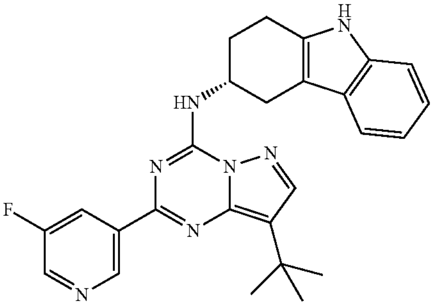 [SMILES: CC(C)(C)c1cnn2c(N[C@@H]3CCc4[nH]c5ccccc5c4C3)nc(-c3cncc(F)c3)nc12]

To a solution of 8-tert-butyl-4-chloro-2-(5-fluoro-3-pyridyl)pyrazolo[1,5-a][1,3,5]triazine (60 mg, 176.62 μmol, 1 eq) in i-PrOH (3 mL) was added (3R)-2,3,4,9-tetrahydro-1H-carbazol-3-amine (34.21 mg, 183.69 μmol, 1.04 eq) and DIPEA (114.14 mg, 883.11 μmol, 153.82 μL, 5 eq). The reaction mixture was stirred at 50° C. for 3 h. The reaction mixture was concentrated under reduced pressure to yield a residue which was purified by preparative HPLC (column: Agela Durashell C18 150*25 5 u; mobile phase: [water (0.05% HCl)-ACN]; B %: 75%-95%, 8 min), followed by lyophilization to yield (3R)—N-[8-tert-butyl-2-(5-fluoro-3-pyridyl)pyrazolo[1,5-a][1,3,5]triazin-4-yl]-2,3,4,9-tetrahydro-1H-carbazol-3-amine (28.87 mg, 53.29 μmol, 30.2% yield, 97.6% purity, 2HCl, $[\alpha]^{21}_D$=18.883 (MeOH, c=0.100 g/100 mL)) as a yellow solid. $^1H$ NMR (400 MHz, $CD_3OD$) δ ppm 9.41 (s, 1H), 8.69-8.61 (m, 2H), 7.94 (s, 1H), 7.35 (d, J=7.8 Hz, 1H), 7.25 (d, J=8.1 Hz, 1H), 7.01 (t, J=7.5 Hz, 1H), 6.97-6.87 (m, 1H), 4.81 (m, 1H), 3.25 (d, J=4.9 Hz, 1H), 3.10-2.84 (m, 3H), 2.35 (m, 1H), 2.29-2.18 (m, 1H), 1.50 (s, 9H); ES-LCMS m/z 456.3 $[M+H]^+$.

Example 122

Synthesis of I-133

I-133

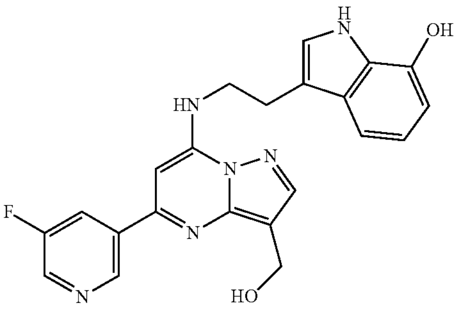

Synthetic Scheme:

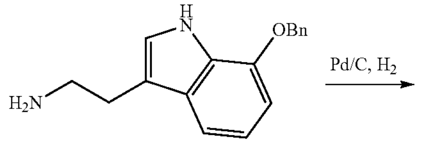

1

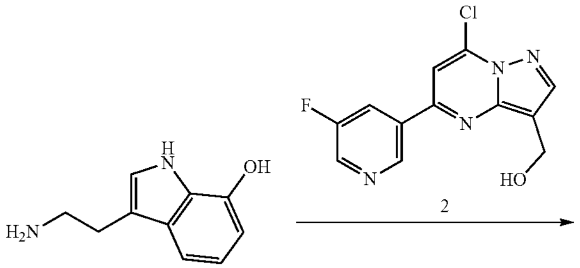

2

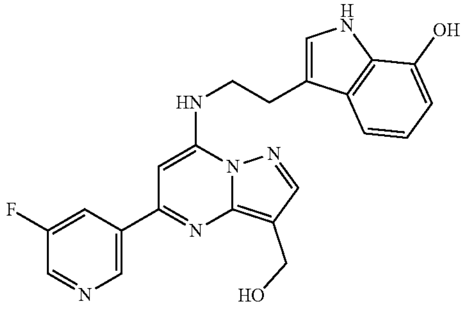

I-133

Step 1: 3-(2-Aminoethyl)-1H-indol-7-ol

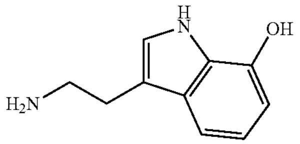 [SMILES: NCCc1c[nH]c2c(O)cccc12]

To a solution of 2-(7-benzyloxy-1H-indol-3-yl)ethanamine (150 mg, 563.19 μmol, 1 eq) in MeOH (10 mL) was added Pd/C (50 mg, 10%). The mixture was degassed and purged with $H_2$ for 3 times and stirred at 50° C. for 1 h. The mixture was filtered and concentrated to yield 3-(2-aminoethyl)-1H-indol-7-ol (90 mg, 510.74 μmol, 90.7% yield) as yellow solid which was used in the next step without further purification. $^1$H NMR (400 MHz, $CD_3OD$) δ ppm 7.06-7.00 (m, 2H), 6.85-6.77 (m, 1H), 6.50 (d, J=7.6 Hz, 1H), 2.96-2.83 (m, 4H).

Step 2: 3-[2-[[5-(5-Fluoro-3-pyridyl)-3-(hydroxymethyl)pyrazolo[1,5-a]pyrimidin-7-yl]amino]ethyl]-1H-indol-7-ol (I-133)

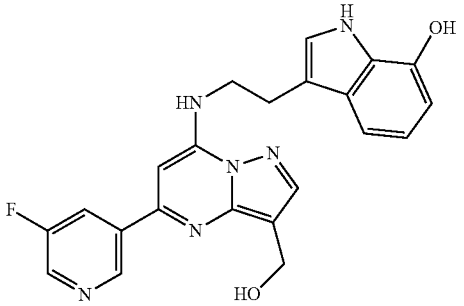 [SMILES: OCc1cnn2c(NCCc3c[nH]c4c(O)cccc34)cc(-c3cncc(F)c3)nc12]

A mixture of [7-chloro-5-(5-fluoro-3-pyridyl)pyrazolo[1,5-a]pyrimidin-3-yl]methanol (55 mg, 171.12 μmol, 1 eq), 3-(2-aminoethyl)-1H-indol-7-ol (39.20 mg, 222.45 μmol, 1.3 eq) and DIEA (66.35 mg, 513.35 μmol, 89.42 μL, 3 eq) in i-PrOH (10 mL) was degassed and purged with $N_2$ for 3 times. The mixture was stirred at 80° C. for 5 h under $N_2$ atmosphere. The reaction mixture was concentrated under reduced pressure to yield a residue which was purified by preparative HPLC (column: Xtimate C18 150*25 mm*5 μm; mobile phase: [Water-ACN]; B %: 17%-47%, 8.5 min), followed by lyophilization to yield 3-[2-[[5-(5-fluoro-3-pyridyl)-3-(hydroxymethyl)pyrazolo[1,5-a]pyrimidin-7-yl]amino]ethyl]-1H-indol-7-ol (16.9 mg, 38.27 μmol, 22.4% yield, 94.8% purity) as a gray solid. $^1$H NMR (400 MHz, $CD_3OD$) δ ppm 8.67 (s, 1H), 8.47 (d, J=2.4 Hz, 1H), 8.06 (s, 1H), 7.73-7.67 (m, 1H), 7.21 (d, J=8.1 Hz, 1H), 6.94-6.87 (m, 2H), 6.51 (d, J=7.3 Hz, 1H), 5.96 (s, 1H), 4.80 (s, 2H), 3.88 (t, J=6.1 Hz, 2H), 3.21-3.11 (m, 2H); ES-LCMS m/z 419.1 $[M+H]^+$.

Example 123

Synthesis of I-135

I-135

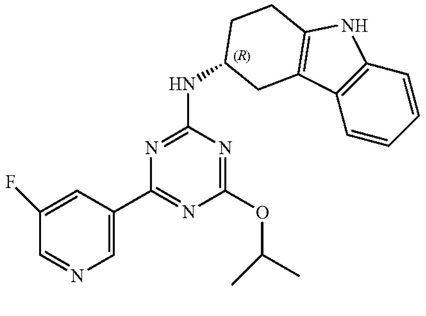

Synthetic Scheme:

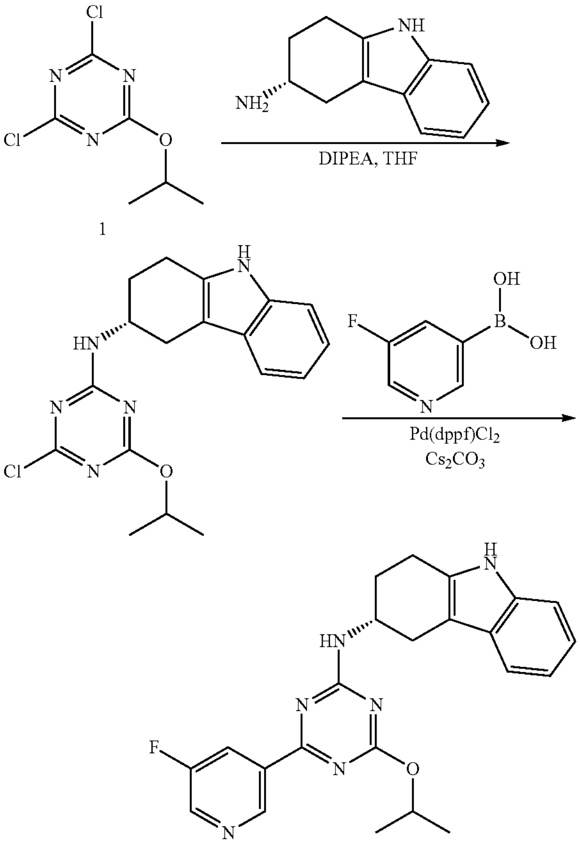

1

I-135

Step 1: (3R)—N-(4-Chloro-6-isoprpoxy-1,3,5-triazine-2-yl)-2,3,4,9-tetrahydro-1H-carbazol-3-amine

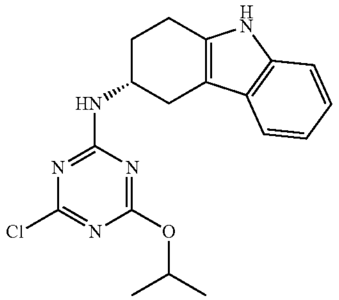 [SMILES: CC(C)Oc1nc(Cl)nc(N[C@@H]2CCc3[nH]c4ccccc4c3C2)n1]

To a solution of 2,4-dichloro-6-isopropoxy-1,3,5-triazine (150 mg, 648.90 μmol, 1 eq) in THE (5 mL) was added DIPEA (119.93 mg, 927.92 μmol, 161.63 □μL, 1.43 eq) and (3R)-2,3,4,9-tetrahydro-1H-carbazol-3-amine (125.69 mg, 674.85 μmol, 1.04 eq) in THF (5 mL) dropwise at 0° C. The mixture was stirred at 0° C. for 1 h and concentrated under reduced pressure to yield a residue which was purified on silica gel column chromatography (from PE/EtOAc=1/0 to 3/1, TLC: PE/EtOAc=1/1, $R_f$=0.47) to yield (3R)—N-(4-chloro-6-isopropoxy-1,3,5-triazin-2-yl)-2,3,4,9-tetrahydro-1H-carbazol-3-amine (220 mg, 553.33 μmol, 85.3% yield, 90.0% purity) as a yellow solid. $^1$H NMR (400 MHz, $CDCl_3$) δ ppm 7.80 (d, J=6.4 Hz, 1H), 7.45-7.38 (m, 1H), 7.29 (dd, J=3.1, 7.7 Hz, 1H), 7.18-7.05 (m, 2H), 6.06-5.59 (m, 1H), 5.41-4.98 (m, 1H), 4.65-4.51 (m, 1H), 3.16 (d, J=15.4 Hz, 1H), 2.96-2.66 (m, 3H), 2.18-2.06 (m, 2H), 1.31 (d, J=5.1 Hz, 6H); ES-LCMS m/z 358.1 $[M+H]^+$.

Step 2: (3R)—N-[4-(5-Fluoro-3-pyridyl)-6-isopropoxy-1,3,5-triazin-2-yl]-2,3,4,9-tetrahydro-1H-carbazol-3-amine (I-135)

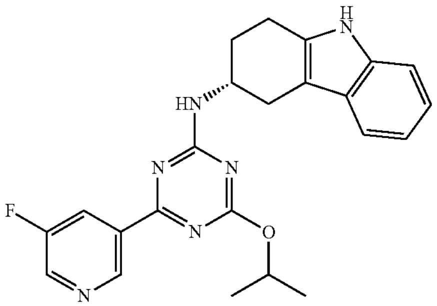 [SMILES: CC(C)Oc1nc(N[C@@H]2CCc3[nH]c4ccccc4c3C2)nc(-c2cncc(F)c2)n1]

To a solution of (3R)—N-(4-chloro-6-isopropoxy-1,3,5-triazin-2-yl)-2,3,4,9-tetrahydro-1H-carbazol-3-amine (200 mg, 503.02 μmol, 1 eq) in 1,4-dioxane (3 mL) and $H_2O$ (1 mL) was added (5-fluoro-3-pyridyl)boronic acid (70.88 mg, 503.02 μmol, 1 eq), Pd(dppf)$Cl_2$ (36.81 mg, 50.30 μmol, 0.1 eq) and $Cs_2CO_3$ (491.68 mg, 1.51 mmol, 3 eq) under $N_2$. The mixture was stirred at 100° C. for 3 h under $N_2$. The reaction mixture was concentrated to yield a residue which was purified by preparative HPLC (HCl condition; column: Agela ASB 150*25 mm*5 um; mobile phase: [water (0.05% HCl)-ACN]; B %: 60%-90%, 8 min) to yield (3R)—N-[4-(5-fluoro-3-pyridyl)-6-isopropoxy-1,3,5-triazin-2-yl]-2,3,4,9-tetrahydro-1H-carbazol-3-amine (55.56 mg, 113.07 μmol, 22.5% yield, 100.0% purity, 2HCl, $[\alpha]^{21.2}_D$=56.652 (MeOH, c=0.100 g/100 mL)) as a yellow solid. $^1$H NMR (400 MHz, $CD_3OD$) δ ppm 9.26 (s, 1H), 8.75 (s, 1H), 8.50 (d, J=7.6 Hz, 1H), 7.30 (d, J=7.6 Hz, 1H), 7.20 (d, J=7.8 Hz, 1H), 7.03-6.86 (m, 2H), 5.44 (s, 1H), 4.65-4.37 (m, 1H), 3.16 (d, J=14.7 Hz, 1H), 2.89 (s, 2H), 2.70 (dd, J=8.8, 14.2 Hz, 1H), 2.24 (s, 1H), 2.03 (s, 1H), 1.41 (d, J=5.1 Hz, 6H); ES-LCMS m/z 419.0 $[M+H]^+$.

Example 124

Synthesis of I-136

I-136

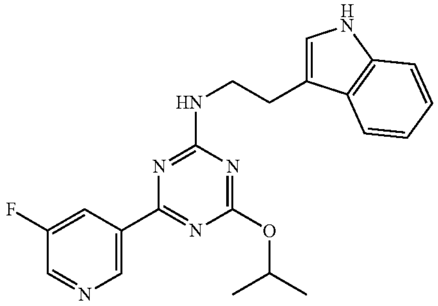

Synthetic Scheme:

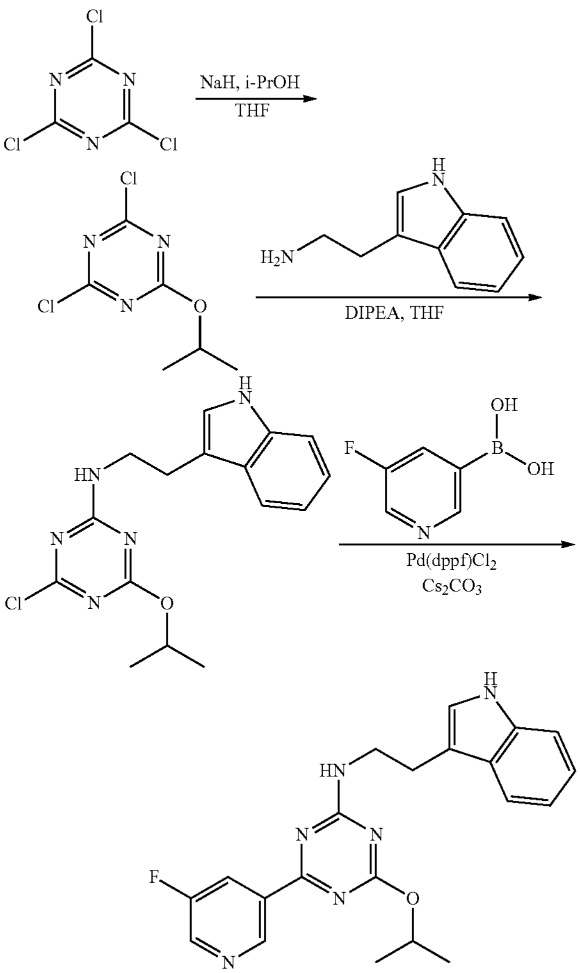

I-136

Step 1: 2,4-Dichloro-6-isopropoxy-1,3,5-triazine

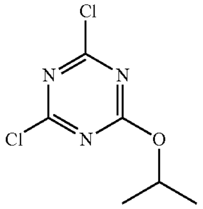

To a solution of i-PrOH (322.62 mg, 5.37 mmol, 410.98 μL, 1.1 eq) in THF (12 mL) was added NaH (253.76 mg, 6.34 mmol, 60% purity, 1.3 eq) at 0° C. under $N_2$. The mixture was stirred at 0° C. for 0.5 h. Then 2,4,6-trichloro-1,3,5-triazine (1 g, 4.88 mmol, 1 eq) in THF (8 mL) was added to the mixture dropwise at 0° C. The mixture was stirred at 10° C. for 11.5 h under $N_2$. TLC (PE/EtOAc=6:1, $R_f$=0.6) showed the reaction was completed. The reaction mixture was dissolved in water (50 mL) at 0° C. slowly. The mixture was extracted with EtOAc (50 mL×3). The combined organic layers were washed with brine (50 mL), dried over $Na_2SO_4$, filtered and concentrated to yield a residue which was purified on silica gel column chromatography (from PE/EtOAc=1/0 to 20/1, TLC: PE/EtOAc=6/1, $R_f$=0.6) to yield 2,4-dichloro-6-isopropoxy-1,3,5-triazine (430 mg, 1.86 mmol, 38.1% yield, 90.0% purity) as a white solid. $^1$H NMR (400 MHz, $CDCl_3$) δ ppm 5.40-5.25 (m, 1H), 1.37 (d, J=6.1 Hz, 6H).

Step 2: 4-Chloro-N-[2-(1H-indol-3-yl)ethyl]-6-isopropoxy-1,3,5-triazin-2-amine

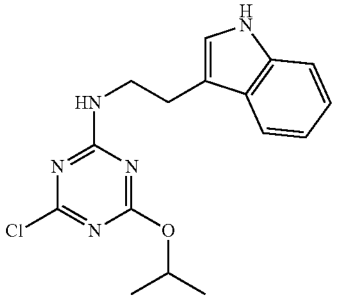 [SMILES: CC(C)Oc1nc(Cl)nc(NCCc2c[nH]c3ccccc23)n1]

To a solution of 2,4-dichloro-6-isopropoxy-1,3,5-triazine (100 mg, 432.60 μmol, 1 eq) in THF (10 mL) was added DIPEA (79.95 mg, 618.62 μmol, 107.75 μL, 1.43 eq) and 2-(1H-indol-3-yl)ethanamine (72.08 mg, 449.90 umol, 1.04 eq) in THF (5 mL) dropwise at 0° C. The mixture was stirred at 0° C. for 1 h and concentrated under reduced pressure to yield a residue which was purified on silica gel column chromatography (from PE/EtOAc=1/0 to 3/1, TLC: PE/EtOAc=1/1, $R_f$=0.47) to yield 4-chloro-N-[2-(1H-indol-3-yl)ethyl]-6-isopropoxy-1,3,5-triazin-2-amine (90 mg, 244.12 μmol, 56.4% yield, 90.0% purity) as a yellow solid. $^1$H NMR (400 MHz, $CDCl_3$) δ ppm 8.13-7.96 (m, 1H), 7.59-7.47 (m, 1H), 7.33-7.24 (m, 1H), 7.16-7.10 (m, 1H), 7.09-7.04 (m, 1H), 6.96 (t, J=10.9 Hz, 1H), 5.39-4.97 (m, 1H), 3.84-3.59 (m, 2H), 3.48 (d, J=4.9 Hz, 1H), 3.09-2.86 (m, 2H), 1.25-1.19 (m, 6H); ES-LCMS m/z 332.1, 334.1 $[M+H]^+$.

Step 3: 4-(5-Fluoro-3-pyridyl)-N-[2-(1H-indol-3-yl)ethyl]-6-isopropoxy-1,3,5-triazin-2-amine (I-136)

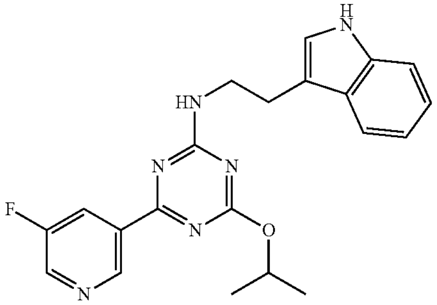 [SMILES: CC(C)Oc1nc(NCCc2c[nH]c3ccccc23)nc(-c2cncc(F)c2)n1]

To a solution of 4-chloro-N-[2-(1H-indol-3-yl)ethyl]-6-isopropoxy-1,3,5-triazin-2-amine (90 mg, 244.12 μmol, 1 eq) in 1,4-dioxane (3 mL) and $H_2O$ (1 mL) was added (5-fluoro-3-pyridyl)boronic acid (34.40 mg, 244.12 μmol, 1 eq), $Cs_2CO_3$ (238.62 mg, 732.37 μmol, 3 eq) and Pd(dppf)

$Cl_2$ (17.86 mg, 24.41 μmol, 0.1 eq) under $N_2$. The mixture was stirred at 100° C. for 3 h under $N_2$. The reaction mixture was filtered and concentrated to yield a residue which was purified by preparative HPLC (HCl condition; column: Agela ASB 150*25 mm*5 μm; mobile phase: [water (0.05% HCl)-ACN]; B %: 55%-85%, 8 min) to yield 4-(5-fluoro-3-pyridyl)-N-[2-(1H-indol-3-yl)ethyl]-6-isopropoxy-1,3,5-triazin-2-amine (25.60 mg, 55.01 μmol, 22.5% yield, 100.0% purity, 2HCl) as a yellow solid. $^1H$ NMR (400 MHz, DMSO-$d_6$) δ ppm 10.80 (s, 1H), 9.24 (d, J=16.1 Hz, 1H), 8.75 (s, 1H), 8.38-8.18 (m, 2H), 7.56 (dd, J=8.2, 13.8 Hz, 1H), 7.29 (t, J=8.4 Hz, 1H), 7.16 (s, 1H), 7.06-6.99 (m, 1H), 6.98-6.90 (m, 1H), 5.36-5.16 (m, 1H), 3.75-3.51 (m, 2H), 2.95 (s, 2H), 1.34-1.26 (m, 6H); ES-LCMS m/z 393.1 $[M+H]^+$.

Example 125

Synthesis of I-137a, I-137b and I-137c

I-137a

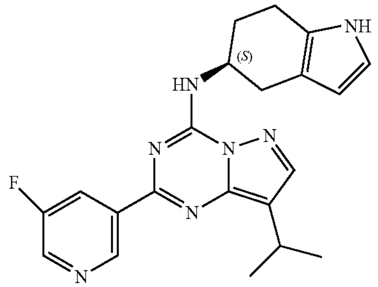

I-137b

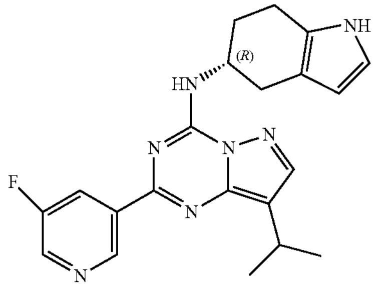

I-137c

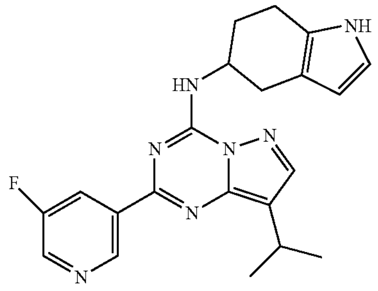

Synthetic Scheme:

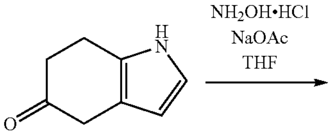

-continued

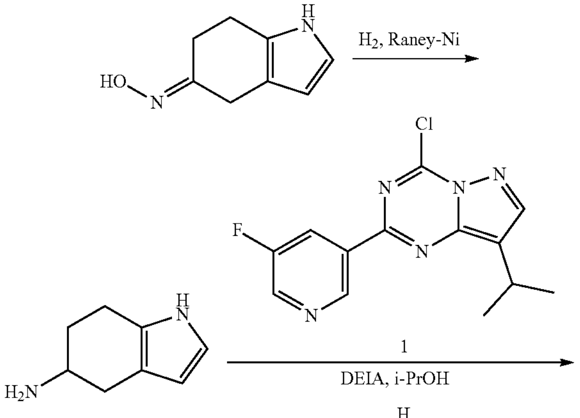

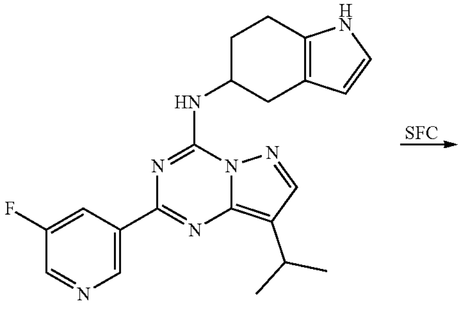

I-137c

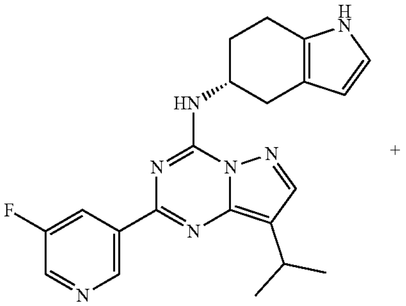

I-137b

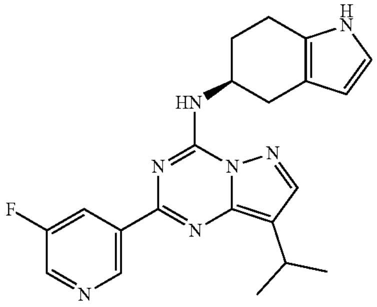

I-137a

Step 1: 1,4,6,7-Tetrahydroindol-5-one oxime

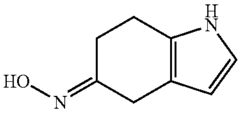 [SMILES: O/N=C1\CCc2[nH]ccc2C1]

A mixture of 1,4,6,7-tetrahydroindol-5-one (150 mg, 1.11 mmol, 1 eq), $NH_2OH$.HCl (92.54 mg, 1.33 mmol, 1.2 eq) and NaOAc (136.56 mg, 1.66 mmol, 1.5 eq) in THF (10 mL) was stirred at 60° C. for 3 h. TLC (PE/EtOAc=1/1, $R_f$=0.20) showed the starting material was consumed completely. The reaction mixture was diluted with $H_2O$ (20 mL) and extracted with EtOAc (20 mL×3). The organic layer was dried over $Na_2SO_4$, filtered and concentrated under reduced pressure to yield 1,4,6,7-tetrahydroindol-5-one oxime (160 mg, crude) as a brown gum which was used in the next step without further purification. $^1$H NMR (400 MHz, $CDCl_3$) δ 7.81 (br s, 1H), 6.69-6.64 (m, 1H), 6.06-5.98 (m, 1H), 3.63-3.35 (m, 2H), 2.81-2.74 (m, 2H), 2.68-2.53 (m, 2H); ES-LCMS m/z 151.1 $[M+H]^+$.

Step 2: 4,5,6,7-Tetrahydro-1H-indol-5-amine

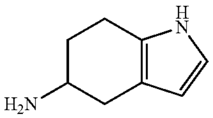

A mixture of 1,4,6,7-tetrahydroindol-5-one oxime (160 mg, 1.07 mmol, 1 eq) and Raney-Ni (200 mg) in MeOH (10 mL) was stirred under $H_2$ (15 Psi) at 10° C. for 12 h. The reaction mixture was filtered. The filtrate was concentrated under reduced pressure to yield 4,5,6,7-tetrahydro-1H-indol-5-amine (140 mg, crude) as a brown solid which was used in the next step without further purification. $^1$H NMR (400 MHz, $CD_3OD$) δ ppm 6.55 (d, J=2.4 Hz, 1H), 5.80 (d, J=2.4 Hz, 1H), 3.17-3.05 (m, 1H), 2.79 (dd, J=4.8, 14.8 Hz, 1H), 2.71-2.63 (m, 2H), 2.33 (dd, J=8.8, 14.8 Hz, 1H), 2.06-1.96 (m, 1H), 1.77-1.64 (m, 1H); ES-LCMS m/z 137.2 $[M+H]^+$.

Step 3: 2-(5-fluoro-3-pyridyl)-8-isopropyl-N-[(5S)-4,5,6,7-tetrahydro-1H-indol-5-yl]pyrazolo[1,5-a][1,3,5]triazin-4-amine (I-137a) and 2-(5-fluoro-3-pyridyl)-8-isopropyl-N-[(5R)-4,5,6,7-tetrahydro-1H-indol-5-yl]pyrazolo[1,5-a][1,3,5]triazin-4-amine (I-137b)

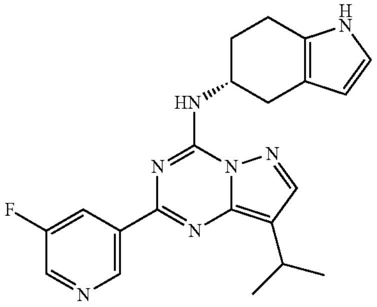

-continued

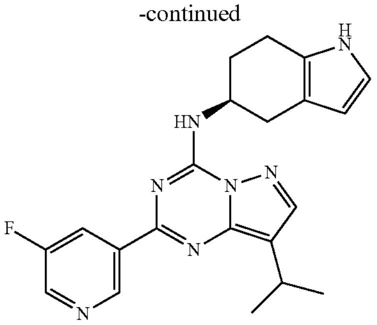

To a solution of 4-chloro-2-(5-fluoro-3-pyridyl)-8-isopropyl-pyrazolo[1,5-a][1,3,5]triazine (120.48 mg, 330.41 μmol, 1 eq) and 4,5,6,7-tetrahydro-1H-indol-5-amine (45 mg, 330.41 μmol, 1 eq) in i-PrOH (10 mL) was added DIEA (341.63 mg, 2.64 mmol, 460.41 μL, 8 eq). The mixture was stirred at 50° C. for 2 h. TLC (PE/EtOAc=3/1, $R_f$=0.5) indicated the starting material was consumed completely. The reaction mixture was concentrated under reduced pressure to yield a residue which was purified by flash silica gel chromatography (from PE/EtOAc=1/0 to 3/1, TLC: PE/EtOAc=3/1, $R_f$=0.50) to yield product which was separated by chiral SFC (column: DAICEL CHIRALCEL OJ-H (250 mm*30 mm, 5 um); mobile phase: [0.10% $NH_3H_2O$ MeOH]; B %: 35%-35%) to yield peak 1 (SFC: Rt=3.442) and peak 2 (SFC: Rt=3.780). Peak 1 was concentrated to yield a residue which was purified by preparative HPLC (column: Xtimate C18 150*25 mm*5 um; mobile phase: [water(0.05% HCl)-ACN]; B %: 75%-100%, 8 min), followed by lyophilization to yield an enantiomer (17.61 mg, 35.16 μmol, 10.6% yield, 100.0% purity, 3HCl, SFC: Rt=3.442, ee=100%, OR: $[\alpha]^{20.2}_D$=−0.069 (MeOH c=0.086 g/100 mL)) as a gray solid. $^1$H NMR (400 MHz, DMSO-$d_6$) δ ppm 10.37 (br s, 1H), 9.36 (s, 1H), 8.87 (d, J=8.8 Hz, 1H), 8.71 (d, J=2.7 Hz, 1H), 8.46-8.39 (m, 1H), 8.13 (s, 1H), 6.56 (t, J=2.4 Hz, 1H), 5.77 (t, J=2.4 Hz, 1H), 4.66 (br s, 1H), 3.27-3.17 (m, 1H), 2.86-2.74 (m, 3H), 2.68 (d, J=7.8 Hz, 1H), 2.12-1.97 (m, 2H), 1.36 (d, J=6.8 Hz, 6H); ES-LCMS m/z 392.2 $[M+H]^+$. Peak 2 (SFC: Rt=3.780) was concentrated to yield a residue which was purified by preparative HPLC (column: Xtimate C18 150*25 mm*5 um; mobile phase: [water(0.05% HCl)-ACN]; B %: 75%-100%, 8 min), followed by lyophilization to yield the other enantiomer (16.18 mg, 32.31 μmol, 9.8% yield, 100.0% purity, 3HCl, SFC: Rt=3.780, ee=99.12%, OR: $[\alpha]^{20.3}_D$=0.066 (MeOH c=0.084 g/100 mL)) as a gray solid. $^1$H NMR (400 MHz, DMSO-$d_6$) δ ppm 10.38 (br s, 1H), 9.36 (s, 1H), 8.88 (d, J=8.6 Hz, 1H), 8.71 (d, J=2.4 Hz, 1H), 8.46-8.38 (m, 1H), 8.13 (s, 1H), 6.56 (br s, 1H), 5.77 (br s, 1H), 4.66 (br s, 1H), 3.21 (td, J=6.8, 13.7 Hz, 1H), 2.84-2.72 (m, 3H), 2.71-2.66 (m, 1H), 2.12-1.99 (m, 2H), 1.36 (d, J=6.8 Hz, 6H); ES-LCMS m/z 392.2 $[M+H]^+$.

Example 126
Synthesis of I-139a, I-139b and I-139c
I-139a
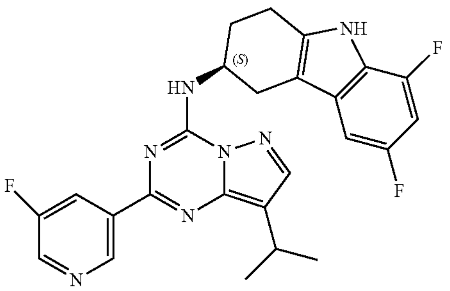
I-139b
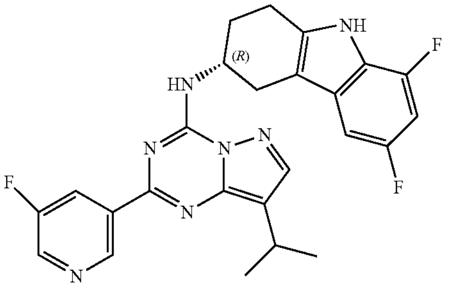
I-139c
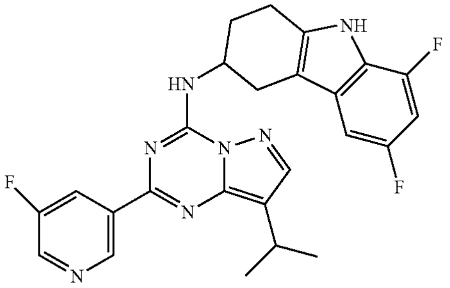
Synthetic Scheme:
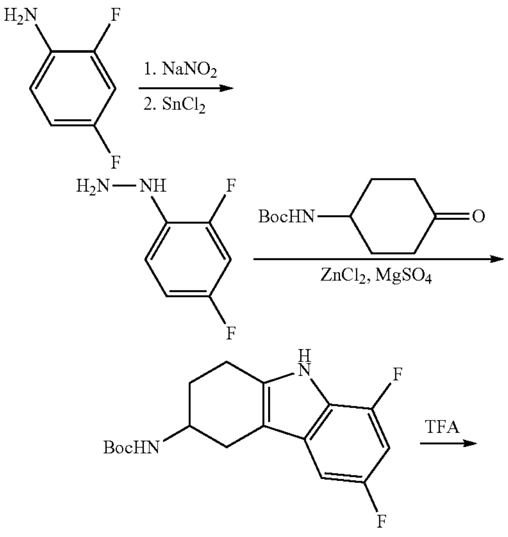
-continued
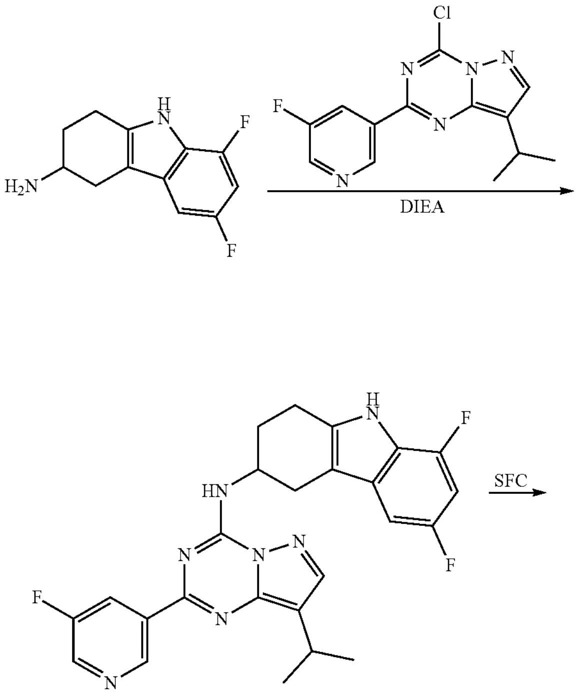
I-139c
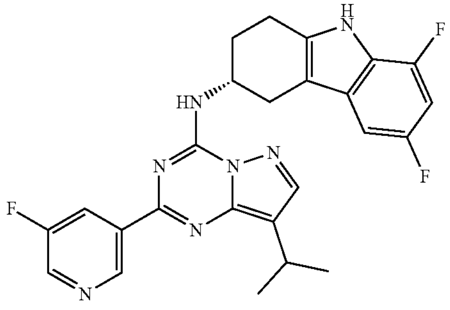
+
I-139b
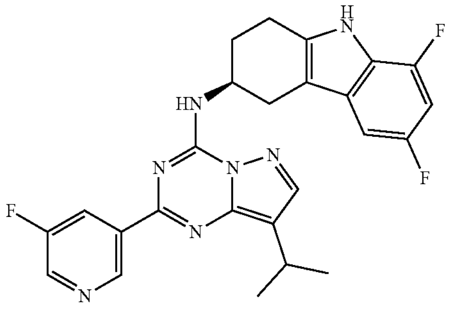
I-139a Step 1: (3S)-6,8-difluoro-N-[2-(5-fluoro-3-pyridyl)-8-isopropyl-pyrazolo[1,5-a][1,3,5]triazin-4-yl]-2,3,4,9-tetrahydro-1H-carbazol-3-amine (I-139a) and (3R)-6,8-difluoro-N-[2-(5-fluoro-3-pyridyl)-8-isopropyl-pyrazolo[1,5-a][1,3,5]triazin-4-yl]-2,3,4,9-tetrahydro-1H-carbazol-3-amine (I-139b)

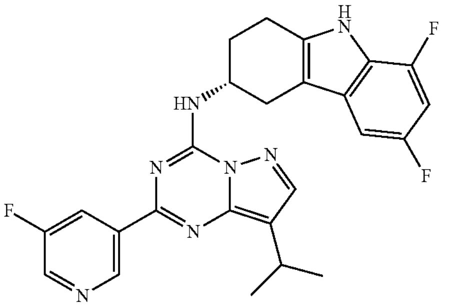

+

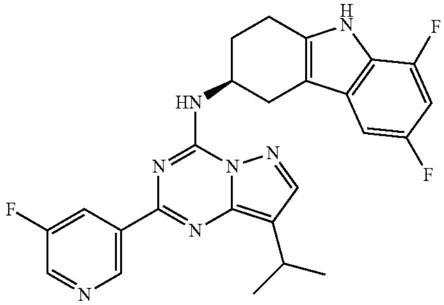

To a solution of 6,8-difluoro-2,3,4,9-tetrahydro-1H-carbazol-3-amine (180 mg, 509.83 μmol, 1 eq, TFA) and 4-chloro-2-(5-fluoro-3-pyridyl)-8-isopropyl-pyrazolo[1,5-a][1,3,5]triazine (221.40 mg, 607.18 μmol, 1.19 eq) in i-PrOH (10 mL) was added DIEA (527.13 mg, 4.08 mmol, 710.42 μL, 8 eq). The mixture was stirred at 50° C. for 2 h. TLC (PE/EtOAc=3/1, $R_f$=0.5) indicated the starting material was consumed completely. The reaction mixture was concentrated under reduced pressure to dryness to yield a residue which was purified by flash silica gel chromatography (from PE/EtOAc=1/0 to 3/1, TLC: PE/EtOAc=3/1, $R_f$=0.50). The desired fraction was concentrated under reduced pressure to yield a product which was separated by chiral SFC (column: DAICEL CHIRALPAK AD(250 mm*30 mm, 10 um); mobile phase: [0.10% $NH_3H_2O$ IPA]; B %: 45%-45%, min) to yield peak 1 (SFC: Rt=1.851) and peak 2 (SFC: Rt=2.254). Peak 1 was concentrated to yield a residue which was purified by preparative HPLC (column: Agela ASB 150*25 mm*5 um; mobile phase: [water (0.05% HCl)-ACN]; B %: 75%-100%, 8 min). The desired fraction was lyophilized to yield an enantiomer (64.24 mg, 114.88 μmol, 22.5% yield, 98.4% purity, 2HCl, SFC: Rt=1.851, ee=100%, OR: $[\alpha]^{20.2}_{D}$=0.206 (MeOH c=0.110 g/100 mL)) as a yellow solid. $^1$H NMR (400 MHz, DMSO-$d_6$) δ ppm 11.38 (s, 1H), 9.38 (s, 1H), 9.06 (d, J=8.6 Hz, 1H), 8.69 (d, J=2.2 Hz, 1H), 8.44 (d, J=10.0 Hz, 1H), 8.15 (s, 1H), 7.02 (d, J=9.0 Hz, 1H), 6.86 (m, J=10.6 Hz, 1H), 4.84 (br s, 1H), 3.22 (d, J=7.1, 14.0 Hz, 1H), 3.12-2.98 (m, 2H), 2.88 (d, J=15.4 Hz, 2H), 2.20 (br s, 2H), 1.37 (d, J=6.8 Hz, 6H); ES-LCMS m/z 478.3 $[M+H]^+$. Peak 2 was concentrated to yield a residue which was purified by preparative HPLC (column: Agela ASB 150*25 mm*5 um; mobile phase: [water(0.05% HCl)-ACN]; B %: 75%-100%, 8 min). The desired fraction was lyophilized to yield the other enantiomer (70.3 mg, 125.02 μmol, 24.5% yield, 97.9% purity, 2HCl, SFC: Rt=2.254, ee=99.79%, OR: $[\alpha]^{20.2}_{D}$=−0.239 (MeOH c=0.117 g/100 mL)) as a yellow solid. $^1$H NMR (400 MHz, DMSO-$d_6$) δ ppm 11.38 (s, 1H), 9.38 (s, 1H), 9.05 (d, J=8.6 Hz, 1H), 8.69 (d, J=2.9 Hz, 1H), 8.49-8.38 (m, 1H), 8.15 (s, 1H), 7.02 (dd, J=1.8, 9.4 Hz, 1H), 6.91-6.80 (m, 1H), 4.94-4.75 (m, 1H), 3.22 (d, J=6.9, 13.8 Hz, 1H), 3.13-2.98 (m, 2H), 2.96-2.83 (m, 2H), 2.28-2.13 (m, 2H), 1.37 (d, J=6.8 Hz, 6H); ES-LCMS m/z 478.2 $[M+H]^+$.

Example 127

Synthesis of I-141

I-141

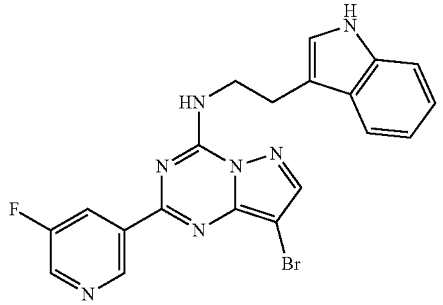 [SMILES: Fc1cncc(-c2nc(NCCc3c[nH]c4ccccc34)n3ncc(Br)c3n2)c1]

Synthetic Scheme:

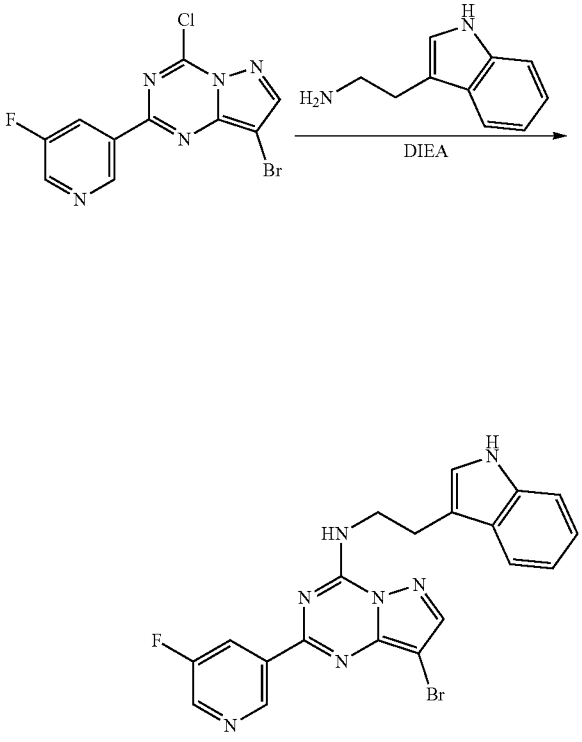

I-141

Step 1: 8-Bromo-2-(5-fluoro-3-pyridyl)-N-[2-(1H-indol-3-yl)ethyl]pyrazolo[1,5-a][1,3,5]triazin-4-amine (I-141)

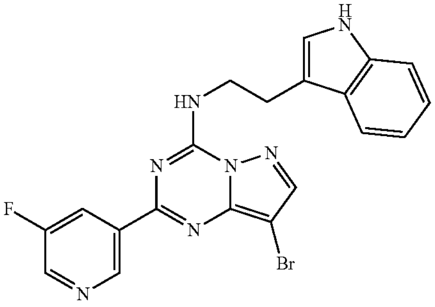

To a solution of 8-bromo-4-chloro-2-(5-fluoro-3-pyridyl) pyrazolo[1,5-a][1,3,5]triazine (50 mg, 152.19 μmol, 1 eq) in i-PrOH (3 mL) was added DIEA (59.01 mg, 456.58 μmol, 79.53 μL, 3 eq) and 2-(1H-indol-3-yl)ethanamine (29.26 mg, 182.63 μmol, 1.2 eq). The mixture was stirred at 60° C. for 2 h. The reaction mixture was concentrated under reduced pressure to yield a residue which was purified by preparative HPLC (column: Xtimate C18 150*25 mm*5 um; mobile phase: [water (0.05% HCl)-ACN]; B %: 55%-85%, 8 min), followed by lyophilization to yield 8-bromo-2-(5-fluoro-3-pyridyl)-N-[2-(1H-indol-3-yl)ethyl]pyrazolo[1,5-a][1,3,5] triazin-4-amine (19.80 mg, 37.70 μmol, 24.8% yield, 100.0% purity, 2HCl) as a yellow solid. $^1$H NMR (400 MHz, DMSO-$d_6$) δ ppm 10.81 (s, 1H), 9.34 (s, 2H), 8.76 (s, 1H), 8.38 (s, 1H), 8.29 (d, J=9.8 Hz, 1H), 7.66 (d, J=7.6 Hz, 1H), 7.29 (d, J=8.1 Hz, 1H), 7.20 (s, 1H), 7.04 (t, J=7.6 Hz, 1H), 7.00-6.91 (m, 1H), 3.95 (t, J=7.2 Hz, 2H), 3.13 (t, J=7.2 Hz, 2H); ES-LCMS m/z 452.1, 454.1 $[M+H]^+$.

Example 128

Synthesis of I-143

I-143

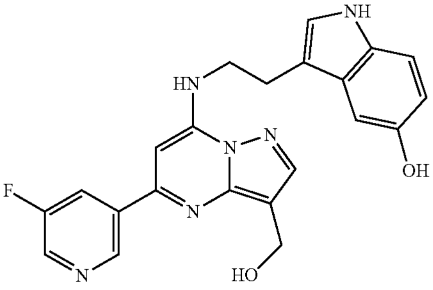

Synthetic Scheme:

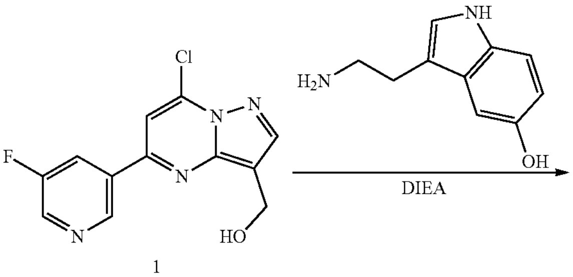

1

I-143

Step 1: 3-[2-[[5-(5-Fluoro-3-pyridyl)-3-(hydroxymethyl)pyrazolo[1,5-a]pyrimidin-7-yl]amino]ethyl]-1H-indol-5-ol (I-143)

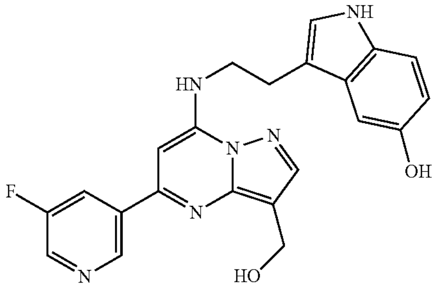 [SMILES: OCc1cnn2c(NCCc3c[nH]c4ccc(O)cc34)cc(-c3cncc(F)c3)nc12]

To a solution of [7-chloro-5-(5-fluoro-3-pyridyl)pyrazolo [1,5-a]pyrimidin-3-yl]methanol (80 mg, 287.08 μmol, 1 eq) in i-PrOH (4 mL) was added 3-(2-aminoethyl)-1H-indol-5-ol (50.59 mg, 287.08 μmol, 1 eq) and DIEA (111.31 mg, 861.24 μmol, 150.01 μL, 3 eq). The mixture was stirred at 90° C. for 3 h under $N_2$ atmosphere. The reaction mixture was concentrated under reduced pressure to yield a residue which was purified by preparative HPLC (column: Phenomenex Gemini 150*25 mm*10 μm; mobile phase: [water (0.05% ammonia hydroxide v/v)-ACN]; B %: 20%-50%, 8 min), followed by lyophilization to yield 3-[2-[[5-(5-fluoro-3-pyridyl)-3-(hydroxymethyl)pyrazolo[1,5-a]pyrimidin-7-yl]amino]ethyl]-1H-indol-5-ol (3.76 mg, 8.99 μmol, 3.1% yield, 100% purity) as a white solid. $^1$H NMR (400 MHz, $CD_3OD$) δ ppm 8.73 (s, 1H), 8.48 (s, 1H), 8.06 (s, 1H), 7.78 (d, J=9.5 Hz, 1H), 7.09-7.02 (m, 2H), 6.93 (s, 1H), 6.67 (d, J=8.8 Hz, 1H), 6.05 (s, 1H), 4.80 (s, 2H), 3.86 (t, J=6.1 Hz, 2H), 3.13 (t, J=5.9 Hz, 2H); ES-LCMS m/z 440.8 $[M+Na]^+$.

Example 129

Synthesis of I-144a

I-144a

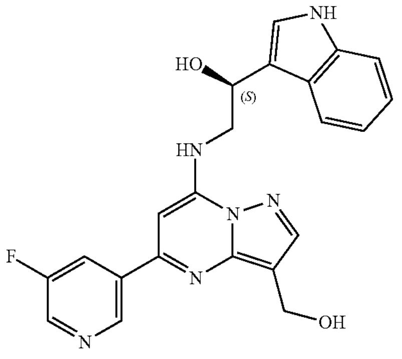

Synthetic Scheme:

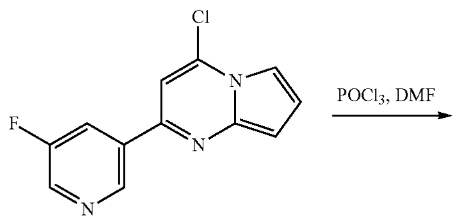

1

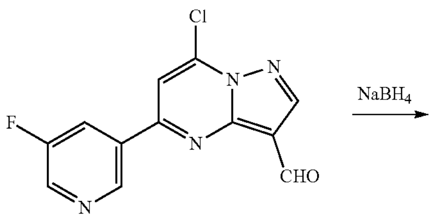

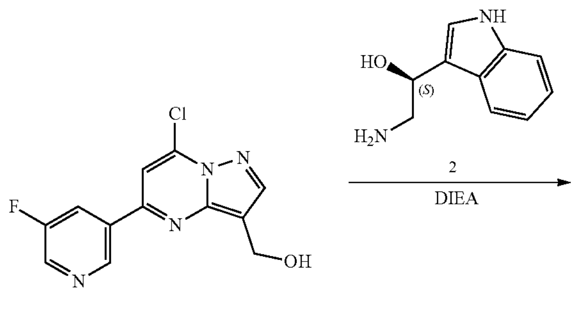

-continued

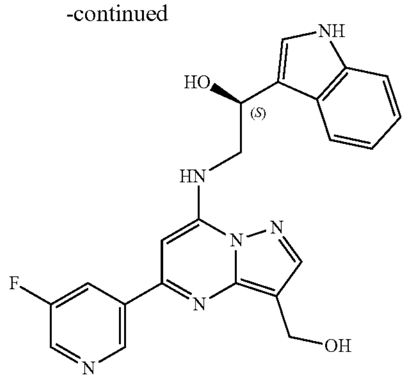

I-144a

Step 1: 7-Chloro-5-(5-fluoro-3-pyridyl)pyrazolo[1,5-a]pyrimidine-3-carbaldehyde

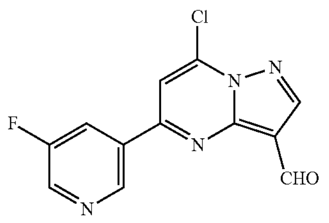 [SMILES: O=Cc1cnn2c(Cl)cc(-c3cncc(F)c3)nc12]

To a solution of DMF(10 mL) was added $POCl_3$ (5 g) dropwise at −20° C. over a period of 12 mins under $N_2$ atmosphere. After 1 h, 7-chloro-5-(5-fluoro-3-pyridyl)pyrazolo[1,5-a]pyrimidine (1 g, 3.76 mmol, 1 eq) in DMF (5 mL) was added to the above solution during which the temperature was maintained below −20° C. The mixture was warmed to 20° C. and stirred for 12 h under $N_2$ atmosphere. $POCl_3$ (12.85 g) in DMF (10 mL) was added to the above solution. The mixture was stirred at 20° C. for 12 h under $N_2$ atmosphere. The mixture was concentrated and water (200 mL) was added. The mixture was extracted with DCM (50 mL×3). The combined organic layers were washed with 5% LiCl (50 mL), dried over $Na_2SO_4$, filtered and concentrated to yield 7-chloro-5-(5-fluoro-3-pyridyl)pyrazolo[1,5-a]pyrimidine-3-carbaldehyde (800 mg, 2.77 mmol, 73.5% yield, 95.7% purity) as a yellow solid which was used in the next step without further purification. $^1H$ NMR (400 MHz, $CD_3OD$) δ ppm 10.29 (s, 1H), 9.42 (s, 1H), 8.9-8.79 (m, 2H), 8.63 (d, J=10.0 Hz, 1H), 8.52 (s, 1H); ES-LCMS m/z 277.0 $[M+H]^+$.

Step 2: [7-Chloro-5-(5-fluoro-3-pyridyl)pyrazolo[1,5-a]pyrimidin-3-yl]methanol

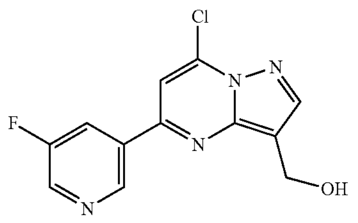 [SMILES: OCc1cnn2c(Cl)cc(-c3cncc(F)c3)nc12]

A mixture of 7-chloro-5-(5-fluoro-3-pyridyl)pyrazolo[1,5-a]pyrimidine-3-carbaldehyde (400 mg, 1.38 mmol, 1 eq) in THF (10 mL) was added $NaBH_4$ (78.52 mg, 2.08 mmol, 1.5 eq) at 0° C., the mixture was stirred at 20° C. for 12 h under $N_2$ atmosphere. To the reaction mixture was added 0.5 N aq.HCl (0.05 mL). The mixture was concentrated under reduced pressure to yield a residue which was purified on silica gel column chromatography (from PE/EtOAc=1/0 to 1/1, TLC: PE/EtOAc=1/1, $R_f$=0.27) to yield [7-chloro-5-(5-fluoro-3-pyridyl)pyrazolo[1,5-a]pyrimidin-3-yl]methanol (130 mg, 421.25 μmol, 30.4% yield, 90.3% purity) as a yellow solid. $^1$H NMR (400 MHz, DMSO-$d_6$) δ ppm 10.28 (s, 1H), 9.70 (d, J=2.2 Hz, 1H), 9.48 (d, J=10.3 Hz, 1H), 9.33 (s, 1H), 9.15 (s, 1H), 6.10 (br s, 1H), 5.71 (br s, 2H); ES-LCMS m/z 279.0 [M+H]$^+$.

Step 3: (1S)-2-[[5-(5-Fluoro-3-pyridyl)-3-(hydroxymethyl)pyrazolo[1,5-a]pyrimidin-7-yl]amino]-1-(1H-indol-3-yl)ethanol (I-144a)

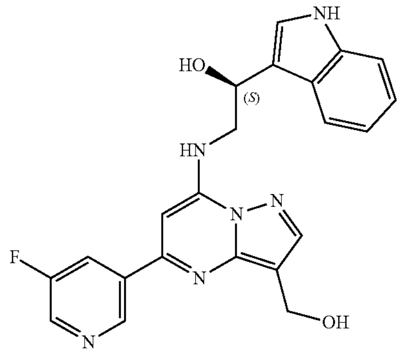

To a solution of [7-chloro-5-(5-fluoro-3-pyridyl)pyrazolo[1,5-a]pyrimidin-3-yl]methanol (55 mg, 178.22 μmol, 1 eq) in i-PrOH (3 mL) was added (1S)-2-amino-1-(1H-indol-3-yl)ethanol (36.95 mg, 178.22 μmol, 1 eq) and DIEA (69.10 mg, 534.66 μmol, 93.13 μL, 3 eq). The mixture was stirred at 90° C. for 3 h under $N_2$ atmosphere. The reaction mixture was concentrated under reduced pressure to yield a residue which was purified by preparative HPLC (column: Phenomenex Gemini 150*25 mm*10 μm; mobile phase: [water (0.05% ammonia hydroxide v/v)-ACN]; B %: 25%-55%, 8 min), followed by lyophilization to yield (1S)-2-[[5-(5-fluoro-3-pyridyl)-3-(hydroxymethyl)pyrazolo[1,5-a]pyrimidin-7-yl]amino]-1-(1H-indol-3-yl)ethanol (40 mg, 94.55 μmol, 53.0% yield, 98.9% purity, SFC: Rt=4.476, ee=99.1%, $[\alpha]^{19.6}_D$=−11.254 (MeOH, c=0.106 g/100 mL)) as a white solid. $^1$H NMR (400 MHz, $CD_3OD$) δ ppm 8.73 (s, 1H), 8.48 (d, J=2.2 Hz, 1H), 8.07 (s, 1H), 7.88-7.81 (m, 2H), 7.29-7.21 (m, 1H), 7.18 (s, 1H), 7.13-7.05 (m, 2H), 6.16 (s, 1H), 5.30 (t, J=5.6 Hz, 1H), 4.81 (s, 2H), 4.07-3.95 (m, 2H); ES-LCMS m/z 419.1 [M+H]$^+$.

Example 130

Synthesis of I-144b

I-144b

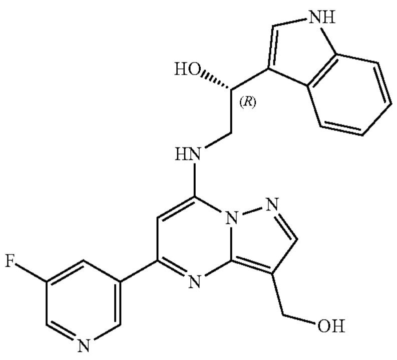

Synthetic Scheme:

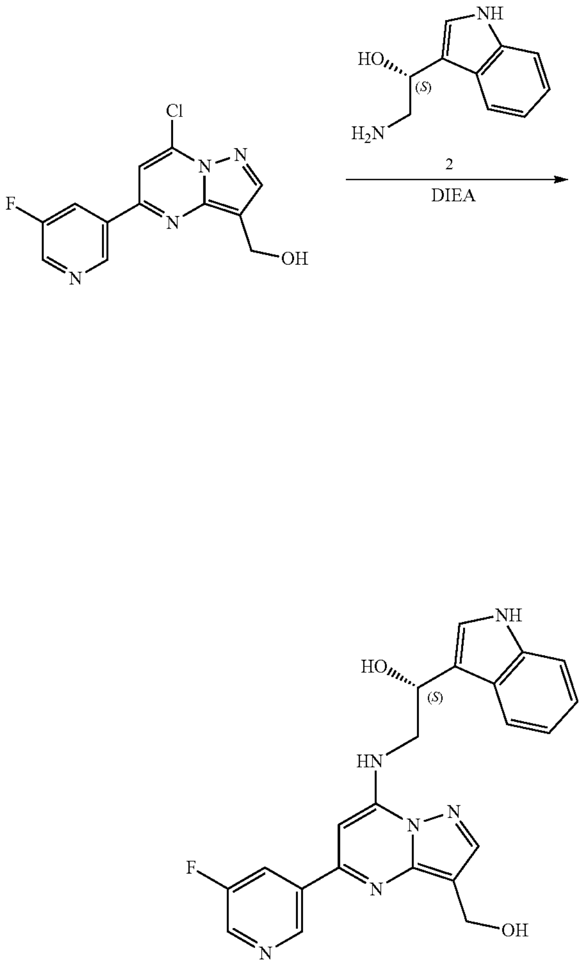

I-144b

Step 1: (1R)-2-[[5-(5-Fluoro-3-pyridyl)-3-(hydroxymethyl)pyrazolo[1,5-a]pyrimidin-7-yl]amino]-1-(1H-indol-3-yl)ethanol (I-144b)

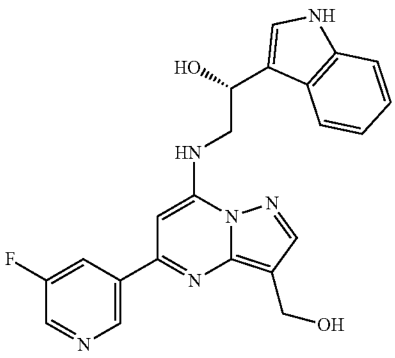 [SMILES: OCc1cnn2c(NC[C@H](O)c3c[nH]c4ccccc34)cc(-c3cncc(F)c3)nc12]

To a solution of [7-chloro-5-(5-fluoro-3-pyridyl)pyrazolo[1,5-a]pyrimidin-3-yl]methanol (66.45 mg, 215.31 μmol, 1 eq) in i-PrOH (3 mL) was added DIEA (83.48 mg, 645.93 μmol, 112.51 μL, 3 eq) and (1R)-2-amino-1-(1H-indol-3-yl) ethanol (53.32 mg, 279.90 μmol, 1.3 eq). The reaction mixture was stirred at 80° C. for 12 h. The reaction mixture was concentrated under reduced pressure to yield a residue which was purified by preparative HPLC twice (basic condition; column: Phenomenex Gemini 150*25 mm*10 μm; mobile phase: [water (0.05% ammonia hydroxide v/v)-ACN]; B %: 25%-55%, 8 min). The desired fraction was lyophilized to yield (1R)-2-[[5-(5-fluoro-3-pyridyl)-3-(hydroxymethyl)pyrazolo[1,5-a]pyrimidin-7-yl]amino]-1-(1H-indol-3-yl)ethanol (18.50 mg, 44.21 μmol, 20.5% yield, 100.0% purity, SFC: Rt=3.628 min, ee=99.4%, $[\alpha]^{19.5}{}_D$=+12.650 (MeOH, c=0.106 g/100 mL)) as a yellow solid. $^1$H NMR (400 MHz, $CD_3OD$) δ ppm 8.74 (s, 1H), 8.48 (d, J=2.4 Hz, 1H), 8.08 (s, 1H), 7.90-7.80 (m, 2H), 7.25 (d, J=8.3 Hz, 1H), 7.18 (s, 1H), 7.13-7.05 (m, 2H), 6.17 (s, 1H), 5.31 (t, J=5.7 Hz, 1H), 4.81 (s, 2H), 4.09-3.95 (m, 2H); ES-LCMS m/z 419.1 $[M+H]^+$.

Example 131

Synthesis of I-150a

I-150a

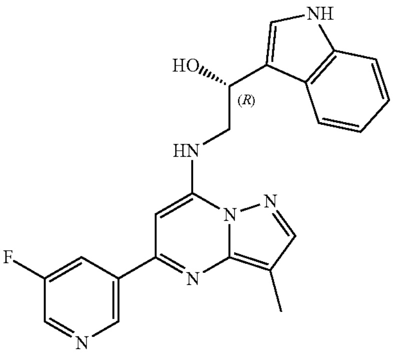

Synthetic Scheme:

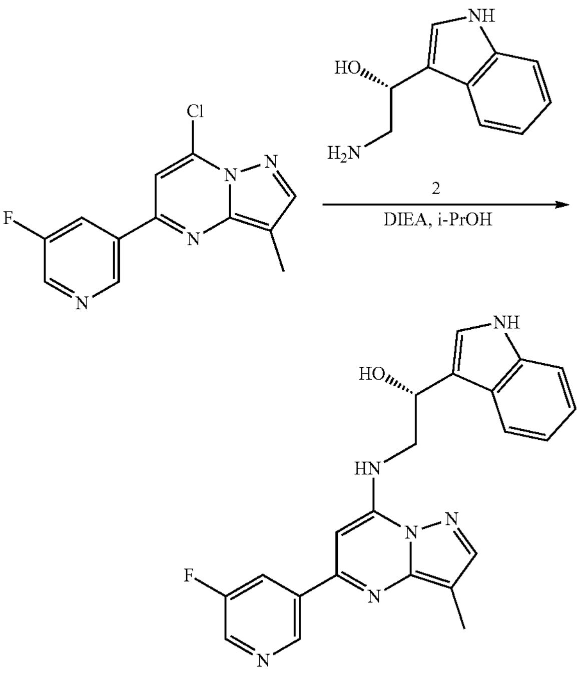

I-150a

Step 1: (1R)-2-[[5-(5-Fluoro-3-pyridyl)-3-methyl-pyrazolo[1,5-a]pyrimidin-7-yl]amino]-1-(1H-indol-3-yl)ethanol (I-150a)

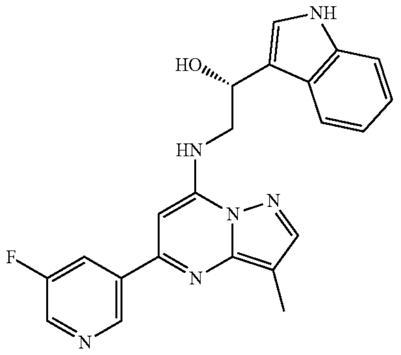 [SMILES: Cc1cnn2c(NC[C@H](O)c3c[nH]c4ccccc34)cc(-c3cncc(F)c3)nc12]

To a solution of 7-chloro-5-(5-fluoro-3-pyridyl)-3-methyl-pyrazolo[1,5-a]pyrimidine (50 mg, 185.97 μmol, 1 eq) in i-PrOH (3 mL) was added DIEA (120.18 mg, 929.87 mol, 161.96 μL, 5 eq) and (1R)-2-amino-1-(1H-indol-3-yl) ethanol (46.06 mg, 241.77 μmol, 1.3 eq). The mixture was stirred at 90° C. for 12 h. The reaction mixture was concentrated under reduced pressure to yield a residue which was purified by flash silica gel chromatography (from PE/EtOAc=1/0 to 1/2, TLC: PE/EtOAc=1/1, $R_f$=0.12) to yield (1R)-2-[[5-(5-fluoro-3-pyridyl)-3-methyl-pyrazolo[1,5-a]pyrimidin-7-yl]amino]-1-(1H-indol-3-yl)ethanol (15.35 mg, 38.14 mol, 20.5% yield, 100% purity, SFC: Rt=1.560, ee=99.008%, $[\alpha]^{22.1}{}_D$=+6.048 (MeOH, c=0.133 g/100 mL)) as a yellow solid. $^1$H NMR (400 MHz, $CD_3OD$) δ ppm 8.73

(s, 1H), 8.48 (d, J=2.8 Hz, 1H), 7.89 (s, 1H), 7.85-7.79 (m, 2H), 7.25 (d, J=7.0 Hz, 1H), 7.19 (s, 1H), 7.12-7.05 (m, 2H), 6.11 (s, 1H), 5.30 (t, J=5.6 Hz, 1H), 4.06-3.96 (m, 2H), 2.31 (s, 3H); ES-LCMS m/z 403.1 [M+H]$^+$.

Example 132

Synthesis of I-150b

I-150b

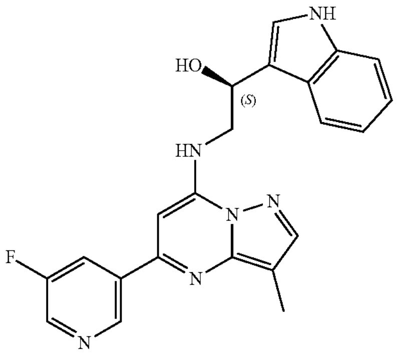

Synthetic Scheme:

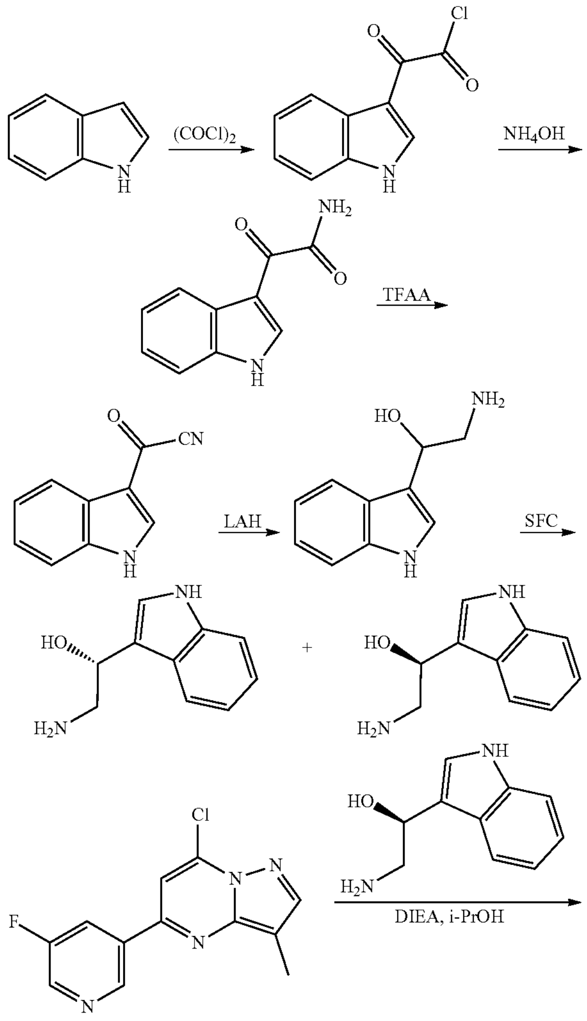

-continued

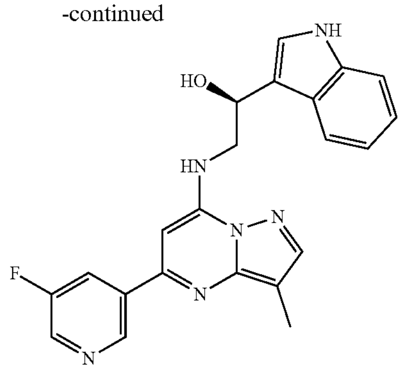

I-150b

Step 1: 2-(1H-Indol-3-yl)-2-oxo-acetyl chloride

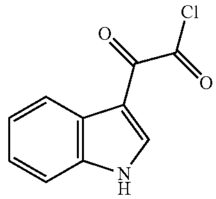 [SMILES: O=C(Cl)C(=O)c1c[nH]c2ccccc12]

To a solution of indole (10 g, 85.36 mmol, 1 eq) in THF (100 mL) was added drop-wise $(COCl)_2$ (11.05 g, 87.07 mmol, 7.62 mL, 1.02 eq) at 0-5° C. under $N_2$. The mixture was stirred at 0-5° C. for 3 h. The yellow slurry was filtered, the cake was washed with PE (10 mL×2), dried under reduced pressure to yield crude 2-(1H-indol-3-yl)-2-oxo-acetyl chloride (15 g, 72.25 mmol, 84.6% yield, 100% purity) as a yellow solid which was used in the next step without further purification. $^1$H NMR (400 MHz, $CDCl_3$) δ ppm 13.31 (br s, 1H), 8.64-8.57 (m, 1H), 8.34-8.25 (m, 1H), 7.45-7.38 (m, 1H), 7.26-7.15 (m, 2H).

Step 2: 2-(1H-Indol-3-yl)-2-oxo-acetamide

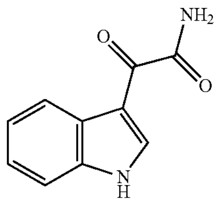 [SMILES: NC(=O)C(=O)c1c[nH]c2ccccc12]

To a solution of $NH_3.H_2O$ (42.20 g, 337.17 mmol, 46.37 mL, 28%, 10 eq) in EtOH (100 mL) was added 2-(1H-indol-3-yl)-2-oxo-acetyl chloride (7 g, 33.72 mmol, 1 eq). The mixture was stirred at 0° C. for 1.5 h. The slurry was filtered, the filter cake was washed with water (20 mL×2), dried under reduced pressure to yield 2-(1H-indol-3-yl)-2-oxo-acetamide (5.5 g, 28.00 mmol, 83.0% yield, 95.8% purity) as a white solid which was used in the next step without further purification. $^1$H NMR (400 MHz, DMSO-$d_6$) δ ppm 12.18 (br s, 1H), 8.69 (s, 1H), 8.27-8.17 (m, 1H), 8.08 (br s, 1H), 7.71 (br s, 1H), 7.58-7.48 (m, 1H), 7.30-7.19 (m, 2H); ES-LCMS m/z 189.1 $[M+H]^+$.

Step 3: 1H-Indole-3-carbonyl cyanide

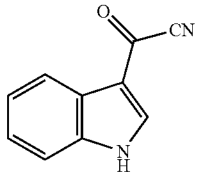 [SMILES: N#CC(=O)c1c[nH]c2ccccc12]

To a solution of 2-(1H-indol-3-yl)-2-oxo-acetamide (5.5 g, 28.00 mmol, 1 eq) and pyridine (6.64 g, 84.00 mmol, 6.78 mL, 3 eq) in EtOAc (100 mL) was added TFAA (8.82 g, 42.00 mmol, 5.84 mL, 1.5 eq) at 10° C. under $N_2$. The mixture was stirred at 10° C. for 4 h. The reaction mixture was quenched by addition of $NaHCO_3$ (100 mL), extracted with EtOAc (80 mL×3). The combined organic layers were washed with 0.5N aq. HCl (20 mL), brine (20 mL), dried over $Na_2SO_4$, filtered and concentrated under reduced pressure to yield crude 1H-indole-3-carbonyl cyanide (3.2 g, 12.73 mmol, 45.5% yield, 67.7% purity) as a white solid which was used in the next step without further purification. $^1H$ NMR (400 MHz, DMSO-$d_6$) δ ppm 12.88 (br s, 1H), 8.63 (s, 1H), 8.07-8.01 (m, 1H), 7.58 (dd, J=1.3, 7.0 Hz, 1H), 7.34 (dq, J=1.3, 7.2 Hz, 2H); ES-LCMS m/z 171.1 $[M+H]^+$.

Step 4: (1S)-2-Amino-1-(1H-indol-3-yl)ethanol

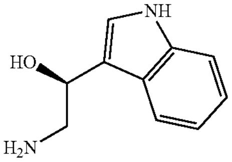 [SMILES: NC[C@@H](O)c1c[nH]c2ccccc12]

To a solution of 1H-indole-3-carbonyl cyanide (1 g, 3.98 mmol, 1 eq) in THF (40 mL) was added LAH (302.00 mg, 7.96 mmol, 2 eq) at 0° C. under $N_2$. The mixture was stirred at 15° C. for 2 h. TLC (PE/EtOAc=3/1, $R_f$=0.18) showed the starting material was consumed completely. The mixture was diluted with THF (50 mL), cooled to 0° C., quenched by water (0.3 mL), 10% aq. NaOH (0.3 mL), water (0.9 mL) in sequence. After being stirred for 30 min, the mixture was filtered through a celite. The filtrate was concentrated under reduced pressure to yield a residue which was purified by flash silica gel chromatography (from EtOAc/MeOH=1/0 to 1/1, TLC: EtOAc/MeOH=10/1, $R_f$=0.18) to yield product which was purified by SFC separation twice (first: DAICEL CHIRALPAK IC (250 mm*30 mm, 10 μm); mobile phase: [0.1% $NH_3H_2O$ IPA]; B %: 35%-35%. second: column: DAICEL CHIRALPAK IC (250 mm*30 mm, 5 m); mobile phase: [0.1% $NH_3H_2O$ IPA]; B %: 45%-45%) to yield (1R)-2-amino-1-(1H-indol-3-yl)ethanol (120 mg, 629.91 mol, 15.8% yield, 92.5% purity, ee=92.5%) as yellow oil. $^1H$ NMR (400 MHz, $CD_3OD$) δ ppm 7.66 (d, J=7.8 Hz, 1H), 7.35 (d, J=8.3 Hz, 1H), 7.22 (s, 1H), 7.10 (t, J=7.2 Hz, 1H), 7.05-6.95 (m, 1H), 4.96 (t, J=6.3 Hz, 1H), 3.02 (d, J=6.3 Hz, 2H); ES-LCMS m/z 159.2 $[M-H_2O+H]^+$. And (1S)-2-amino-1-(1H-indol-3-yl)ethanol (125 mg, 602.96 mol, 15.2% yield, 85.0% purity, ee=98.698%) as yellow oil. $^1H$ NMR (400 MHz, $CD_3OD$) δ ppm 7.67 (d, J=8.0 Hz, 1H), 7.35 (d, J=8.0 Hz, 1H), 7.23 (s, 1H), 7.11 (t, J=7.2 Hz, 1H), 7.05-6.99 (m, 1H), 4.99 (t, J=6.3 Hz, 1H), 3.08-3.02 (m, 2H); ES-LCMS m/z 159.2 $[M-H_2O+H]^+$.

Step 5 (1S)-2-[[5-(5-Fluoro-3-pyridyl)-3-methyl-pyrazolo[1,5-a]pyrimidin-7-yl]amino]-1-(1H-indol-3-yl)ethanol (I-150b)

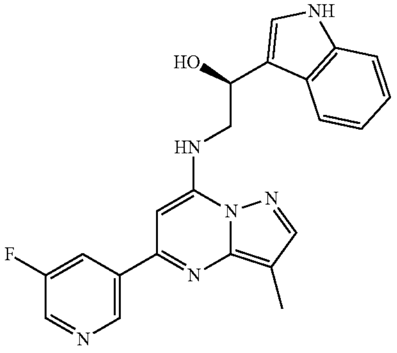 [SMILES: Cc1cnn2c(NC[C@@H](O)c3c[nH]c4ccccc34)cc(-c3cncc(F)c3)nc12]

To a solution of 7-chloro-5-(5-fluoro-3-pyridyl)-3-methyl-pyrazolo[1,5-a]pyrimidine (50 mg, 185.97 mol, 1 eq) in i-PrOH (3 mL) was added DIEA (72.11 mg, 557.92 mol, 97.18 μL, 3 eq) and (1S)-2-amino-1-(1H-indol-3-yl) ethanol (57.47 mg, 277.22 μmol, 1.49 eq). The mixture was stirred at 90° C. for 12 h. The reaction mixture was concentrated under reduced pressure to yield a residue which was purified by flash silica gel chromatography (from PE/EtOAc=1/0 to 1/2, TLC: PE/EtOAc=1/1, $R_f$=0.18) to yield (1S)-2-[[5-(5-fluoro-3-pyridyl)-3-methyl-pyrazolo[1,5-a]pyrimidin-7-yl]amino]-1-(1H-indol-3-yl)ethanol (29.26 mg, 71.26 mol, 38.3% yield, 98.0% purity, SFC: Rt=2.204, ee=98.378, $[\alpha]^{21.4}_D$=−8.227 (MeOH, c=0.10 g/100 mL)) as a yellow solid. $^1H$ NMR (400 MHz, $CD_3OD$) δ ppm 8.72 (s, 1H), 8.48 (d, J=2.2 Hz, 1H), 7.89 (s, 1H), 7.82 (d, J=5.9 Hz, 2H), 7.25 (d, J=8.3 Hz, 1H), 7.19 (s, 1H), 7.14-7.02 (m, 2H), 6.10 (s, 1H), 5.30 (t, J=5.7 Hz, 1H), 4.08-3.95 (m, 2H), 2.31 (s, 3H); ES-LCMS m/z 403.2 $[M+H]^+$.

Example 133

Synthesis of I-152a, I-152b, I-152c

I-152a

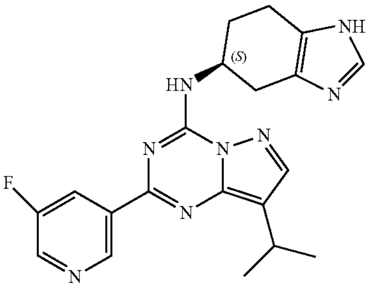

-continued
I-152b
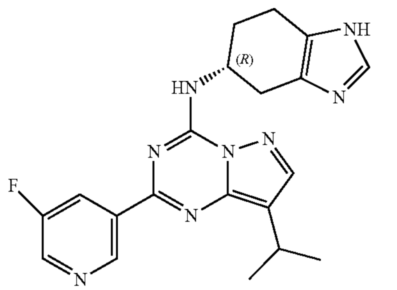
I-152c
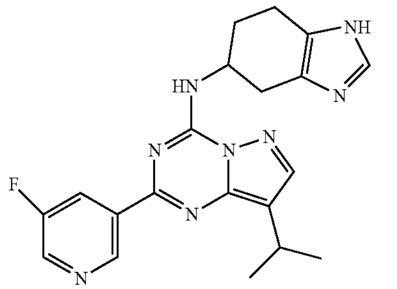
Synthetic Scheme:
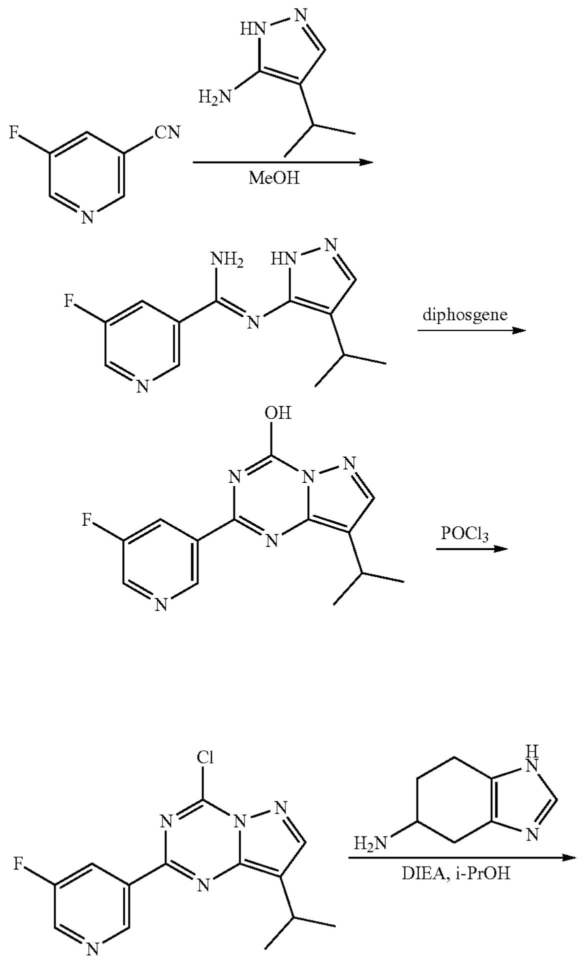
-continued
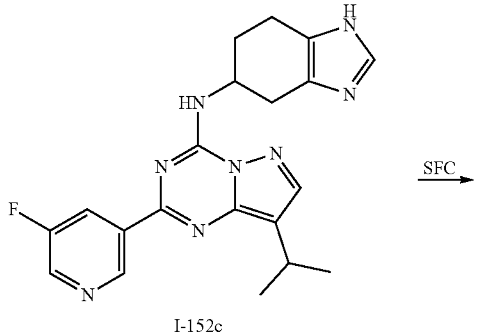
I-152c
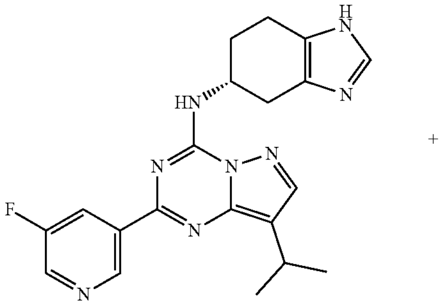
I-152b
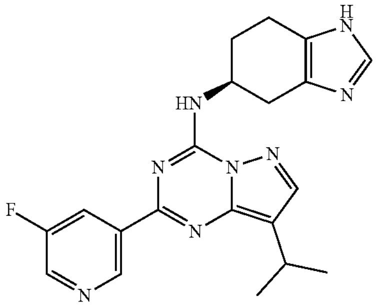
I-152a
Step 1: (3R)-6,8-difluoro-N-[2-(5-fluoro-3-pyridyl)-8-isopropyl-pyrazolo[1,5-a][1,3,5]triazin-4-yl]-2,3,4,9-tetrahydro-1H-carbazol-3-amine (I-152b) and (3S)-6,8-difluoro-N-[2-(5-fluoro-3-pyridyl)-8-isopropyl-pyrazolo[1,5-a][1,3,5]triazin-4-yl]-2,3,4,9-tetrahydro-1H-carbazol-3-amine (I-152a)
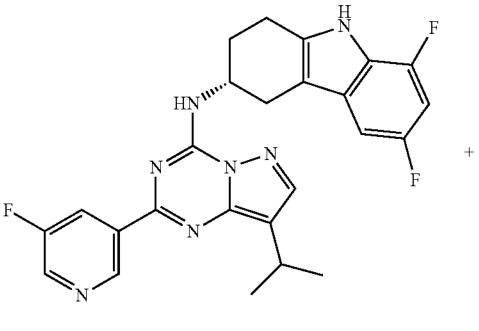

-continued

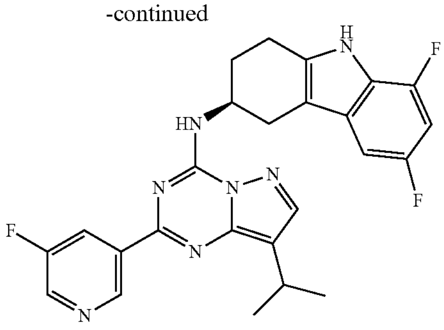

To a solution of 6,8-difluoro-2,3,4,9-tetrahydro-1H-carbazol-3-amine (180 mg, 509.83 μmol, 1 eq, TFA) and 4-chloro-2-(5-fluoro-3-pyridyl)-8-isopropyl-pyrazolo[1,5-a][1,3,5]triazine (221.40 mg, 607.18 μmol, 1.19 eq) in i-PrOH (10 mL) was added DIEA (527.13 mg, 4.08 mmol, 710.42 μL, 8 eq). The mixture was stirred at 50° C. for 2 h. TLC (PE/EtOAc=3/1, $R_f$=0.5) indicated the starting material was consumed completely. The reaction mixture was concentrated under reduced pressure to dryness to yield a residue which was purified by flash silica gel chromatography (from PE/EtOAc=1/0 to 3/1, TLC: PE/EtOAc=3/1, $R_f$=0.50). The desired fraction was concentrated under reduced pressure to yield a product which was separated by chiral SFC (column: DAICEL CHIRALPAK AD(250 mm*30 mm, 10 um); mobile phase: [0.1% $NH_3H_2O$ IPA]; B %: 45%-45%, min) to yield peak 1 (SFC: Rt=1.851) and peak 2 (SFC: Rt=2.254). Peak 1 was concentrated to yield a residue which was purified by preparative HPLC (column: Agela ASB 150*25 mm*5 um; mobile phase: [water (0.05% HCl)-ACN]; B %: 75%-100%, 8 min). The desired fraction was lyophilized to yield an enantiomer (64.24 mg, 114.88 μmol, 22.5% yield, 98.4% purity, 2HCl, SFC: Rt=1.851, ee=100%, OR: $[\alpha]^{20.2}_D$=0.206 (MeOH c=0.110 g/100 mL)) as a yellow solid. $^1$H NMR (400 MHz, DMSO-$d_6$) δ ppm 11.38 (s, 1H), 9.38 (s, 1H), 9.06 (d, J=8.6 Hz, 1H), 8.69 (d, J=2.2 Hz, 1H), 8.44 (d, J=10.0 Hz, 1H), 8.15 (s, 1H), 7.02 (d, J=9.0 Hz, 1H), 6.86 (m, J=10.6 Hz, 1H), 4.84 (br s, 1H), 3.22 (d, J=7.1, 14.0 Hz, 1H), 3.12-2.98 (m, 2H), 2.88 (d, J=15.4 Hz, 2H), 2.20 (br s, 2H), 1.37 (d, J=6.8 Hz, 6H); ES-LCMS m/z 478.3 $[M+H]^+$. Peak 2 was concentrated to yield a residue which was purified by preparative HPLC (column: Agela ASB 150*25 mm*5 um; mobile phase: [water(0.05% HCl)-ACN]; B %: 75%-100%, 8 min). The desired fraction was lyophilized to yield the other enantiomer (70.3 mg, 125.02 μmol, 24.5% yield, 97.9% purity, 2HCl, SFC: Rt=2.254, ee=99.79%, OR: $[\alpha]^{20.2}_D$=−0.239 (MeOH c=0.117 g/100 mL)) as a yellow solid. $^1$H NMR (400 MHz, DMSO-$d_6$) δ ppm 11.38 (s, 1H), 9.38 (s, 1H), 9.05 (d, J=8.6 Hz, 1H), 8.69 (d, J=2.9 Hz, 1H), 8.49-8.38 (m, 1H), 8.15 (s, 1H), 7.02 (dd, J=1.8, 9.4 Hz, 1H), 6.91-6.80 (m, 1H), 4.94-4.75 (m, 1H), 3.22 (d, J=6.9, 13.8 Hz, 1H), 3.13-2.98 (m, 2H), 2.96-2.83 (m, 2H), 2.28-2.13 (m, 2H), 1.37 (d, J=6.8 Hz, 6H); ES-LCMS m/z 478.2 $[M+H]^+$.

Example 134

Synthesis of I-154

I-154

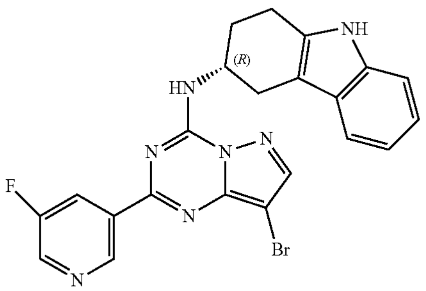

Synthetic Scheme:

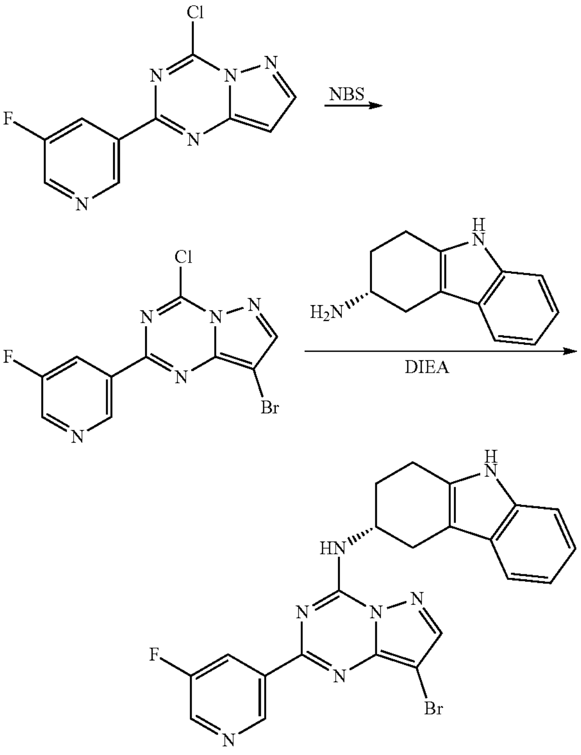

I-154

Step 1: 8-Bromo-4-chloro-2-(5-fluoro-3-pyridyl)pyrazolo[1,5-a][1,3,5]triazine

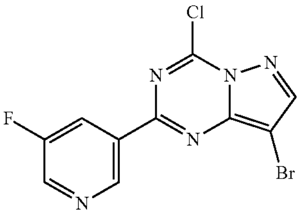 [SMILES: Fc1cncc(-c2nc(Cl)n3ncc(Br)c3n2)c1]

To a solution of 4-chloro-2-(5-fluoro-3-pyridyl)pyrazolo[1,5-a][1,3,5]triazine (110 mg, 423.02 μmol, 1 eq) in MeCN (2 mL) and DCM (1 mL) was added NBS (82.82 mg, 465.33 μmol, 1.1 eq). The mixture was stirred at 30° C. for 2 h. The reaction mixture was concentrated under reduced pressure to yield 8-bromo-4-chloro-2-(5-fluoro-3-pyridyl)pyrazolo[1,5-a][1,3,5]triazine (120 mg, 365.27 μmol, 86.4% yield) as a yellow solid which was used in the next step without further purification. $^1$H NMR (400 MHz, $CDCl_3$) δ ppm 9.56 (s, 1H), 8.68 (d, J=2.4 Hz, 1H), 8.51 (d, J=9.3 Hz, 1H), 8.32 (s, 1H); ES-LCMS m/z 327.9, 329.9 $[M+H]^+$.

Step 2: (3R)—N-[8-Bromo-2-(5-fluoro-3-pyridyl)pyrazolo[1,5-a][1,3,5]triazin-4-yl]-2,3,4,9-tetrahydro-1H-carbazol-3-amine (I-154)

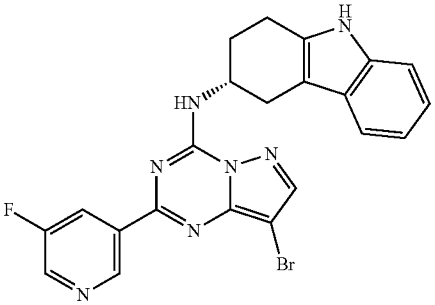 [SMILES: Fc1cncc(-c2nc(N[C@@H]3CCc4[nH]c5ccccc5c4C3)n3ncc(Br)c3n2)c1]

A mixture of 8-bromo-4-chloro-2-(5-fluoro-3-pyridyl)pyrazolo[1,5-a][1,3,5]triazine (70 mg, 204.55 μmol, 1 eq), (3R)-2,3,4,9-tetrahydro-1H-carbazol-3-amine (41.91 mg, 225.00 μmol, 1.1 eq) and DIEA (79.31 mg, 613.65 μmol, 106.89 μL, 3 eq) in i-PrOH (3 mL) was degassed and purged with $N_2$ for 3 times The mixture was stirred at 60° C. for 3 h under $N_2$ atmosphere. The reaction mixture was concentrated under reduced pressure to yield a residue which was purified by preparative HPLC (column: Agela ASB 150*25 mm*5 um; mobile phase: [water(0.05% HCl)-ACN]; B %: 63%-93%, 8 min), followed by lyophilization to yield (3R)—N-[8-bromo-2-(5-fluoro-3-pyridyl)pyrazolo[1,5-a][1,3,5]triazin-4-yl]-2,3,4,9-tetrahydro-1H-carbazol-3-amine (32.48 mg, 58.92 μmol, 28.8% yield, 100.0% purity, 2HCl, OR: $[\alpha]^{22.1}_D$=0.234 (MeOH, c=0.105 g/100 mL) as a yellow solid. $^1$H NMR (400 MHz, $CD_3OD$) δ ppm 9.45 (s, 1H), 8.85-8.72 (m, 2H), 8.12 (s, 1H), 7.34 (d, J=7.8 Hz, 1H), 7.25 (d, J=8.1 Hz, 1H), 7.02 (t, J=7.6 Hz, 1H), 6.97-6.89 (m, 1H), 4.89-4.83 (m, 1H), 3.27 (m, 1H), 3.08-2.86 (m, 3H), 2.43-2.17 (m, 2H); ES-LCMS m/z 480.1, 482.1 $[M+H]^+$.

Example 135

Synthesis of I-155

I-155

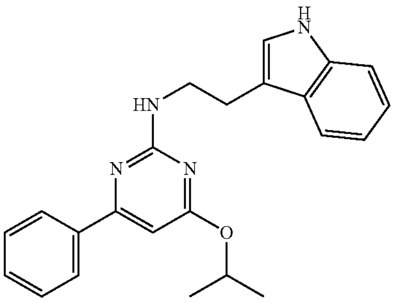

Synthetic Scheme:

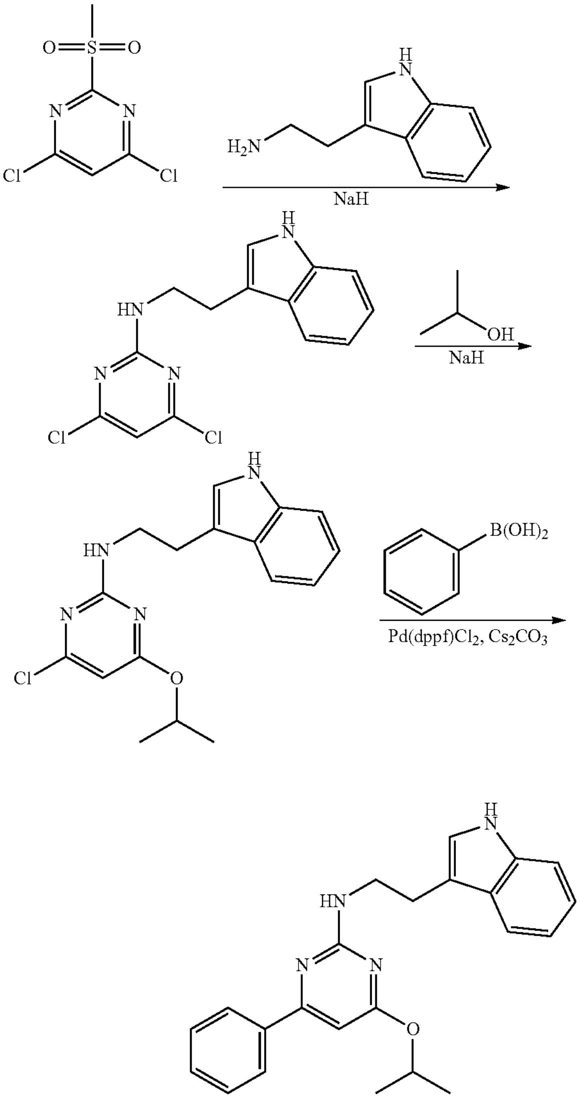

I-155

Step 1: 4,6-Dichloro-N-[2-(1H-indol-3-yl)ethyl]pyrimidin-2-amine

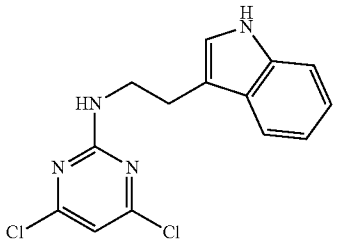 [SMILES: Clc1cc(Cl)nc(NCCc2c[nH]c3ccccc23)n1]

To a mixture of 2-(1H-indol-3-yl)ethanamine (666.77 mg, 4.16 mmol, 1.05 eq) in dry THF (10 mL) was added NaH (237.58 mg, 5.94 mmol, 1.5 eq) under ice bath at $N_2$ atmosphere. After being stirred for 30 min, the mixture was cooled to −60° C. and 4,6-dichloro-2-methylsulfonyl-pyrimidine (900 mg, 3.96 mmol, 1 eq) in dry THF (10 mL) was added dropwise and kept the temperature below −55° C. The resulting mixture was stirred for 1 h at −55° C. The reaction mixture was quenched by addition of $H_2O$ (15 mL), diluted with $H_2O$ (15 mL) and extracted with EtOAc (20 mL×3). The combined organic layers were washed with $H_2O$ (15 mL×2), dried over $Na_2SO_4$, filtered and concentrated. The residue was purified by flash silica gel chromatography (from PE/EtOAc=1/0 to 3/1, TLC: PE/EtOAc=1/3, $R_f$=0.43) to yield 4,6-dichloro-N-[2-(1H-indol-3-yl)ethyl]pyrimidin-2-amine (570 mg, 1.48 mmol, 37.5% yield, 80% purity) as a yellow solid. $^1H$ NMR (400 MHz, $CDCl_3$) δ ppm 7.96 (br s, 1H), 7.59 (d, J=7.8 Hz, 1H), 7.31 (d, J=8.1 Hz, 1H), 7.15 (t, J=7.6 Hz, 1H), 7.11-7.05 (m, 1H), 6.99 (d, J=2.0 Hz, 1H), 6.52 (s, 1H), 5.37 (br s, 1H), 3.73-3.68 (m, 2H), 3.00 (t, J=6.7 Hz, 2H); ES-LCMS m/z 307.0, 309.0 $[M+H]^+$.

Step 2: 4-Chloro-N-[2-(1H-indol-3-yl)ethyl]-6-isopropoxy-pyrimidin-2-amine

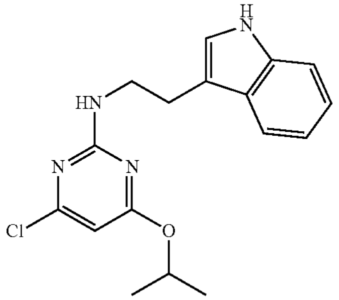 [SMILES: CC(C)Oc1cc(Cl)nc(NCCc2c[nH]c3ccccc23)n1]

To a solution of i-PrOH (75.12 mg, 1.25 mmol, 95.70 μL, 1.2 eq) in THF (3 mL) was added NaH (62.50 mg, 1.56 mmol, 1.5 eq), the mixture was stirred at 0° C. for 30 min. To the mixture was added a solution of 4,6-dichloro-N-[2-(1H-indol-3-yl)ethyl]pyrimidin-2-amine (400 mg, 1.04 mmol, 1 eq) in THF (3 mL), the mixture was stirred at 60° C. for 12 h. To the mixture was added $H_2O$ (3 mL) and concentrated to yield a residue which was purified with preparative TLC (PE/EtOAc=3/1, $R_f$=0.5) to yield 4-chloro-N-[2-(1H-indol-3-yl)ethyl]-6-isopropoxy-pyrimidin-2-amine (470 mg, 710.37 μmol, 68.2% yield, 50% purity) as yellow oil. $^1H$ NMR (400 MHz, $CDCl_3$) δ ppm 8.03 (br s, 1H), 7.66-7.60 (m, 1H), 7.36 (d, J=8.1 Hz, 1H), 7.20 (t, J=7.6 Hz, 1H), 7.15-7.09 (m, 1H), 7.03 (s, 1H), 6.57 (s, 1H), 5.26 (d, J=19.3 Hz, 1H), 3.78-3.69 (m, 2H), 3.05 (t, J=6.4 Hz, 2H), 1.62-1.18 (m, 6H); ES-LCMS m/z 331.1 $[M+H]^+$.

Step 3: N-(2-(1H-Indol-3-yl)ethyl)-4-isopropoxy-6-phenylpyrimidin-2-amine (I-155)

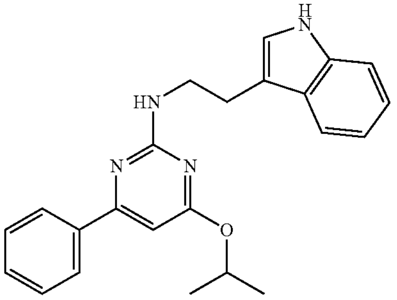 [SMILES: CC(C)Oc1cc(-c2ccccc2)nc(NCCc2c[nH]c3ccccc23)n1]

To a mixture of 4-chloro-N-[2-(1H-indol-3-yl)ethyl]-6-isopropoxy-pyrimidin-2-amine (450 mg, 680.15 μmol, 1 eq) and phenylboronic acid (124.39 mg, 1.02 mmol, 1.5 eq) in 1,4-dioxane (10 mL) and $H_2O$ (2 mL) was added Pd(dppf)$Cl_2$ (49.77 mg, 68.01 μmol, 0.1 eq) and $Cs_2CO_3$ (664.81 mg, 2.04 mmol, 3 eq) under $N_2$ atmosphere. The mixture was taken up into a microwave tube and heated at 110° C. for 30 min. The mixture was concentrated to yield a residue which was purified by preparative HPLC (column: Agela ASB 150*25 mm*5 μm; mobile phase: [water (0.05% HCl)-ACN]; B %: 40%-70%, 8 min), followed by lyophilization to yield N-[2-(1H-indol-3-yl)ethyl]-4-isopropoxy-6-phenyl-pyrimidin-2-amine (19.18 mg, 44.68 μmol, 6.6% yield, 95.3% purity, HCl) as a yellow solid. $^1H$ NMR (400 MHz, $CD_3OD$) δ ppm 7.76 (d, J=7.3 Hz, 2H), 7.69-7.62 (m, 1H), 7.58 (t, J=6.6 Hz, 3H), 7.31 (d, J=8.1 Hz, 1H), 7.12 (s, 1H), 7.07 (t, J=7.3 Hz, 1H), 7.01-6.96 (m, 1H), 6.50 (s, 1H), 5.13 (td, J=6.1, 12.2 Hz, 1H), 3.89 (t, J=6.6 Hz, 2H), 3.13 (t, J=6.6 Hz, 2H), 1.32 (d, J=6.1 Hz, 6H); ES-LCMS m/z 373.3 $[M+H]^+$.

Example 136

Synthesis of I-160a, I-160b and I-160c)

I-160a

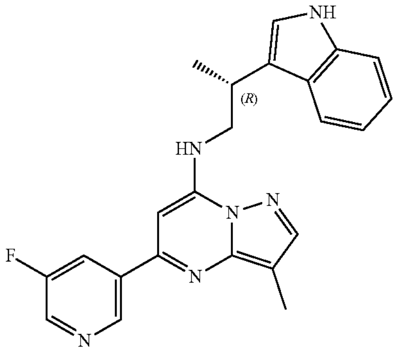

-continued
I-160b
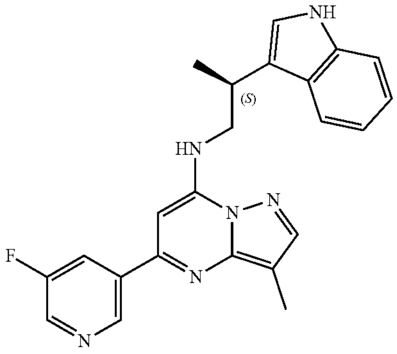
I-160c
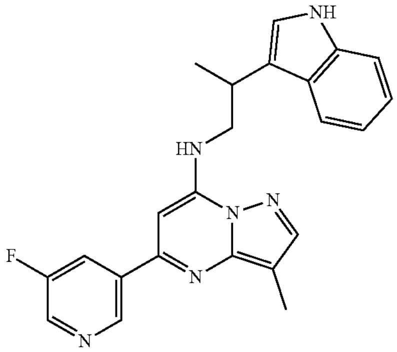
Synthetic Scheme:
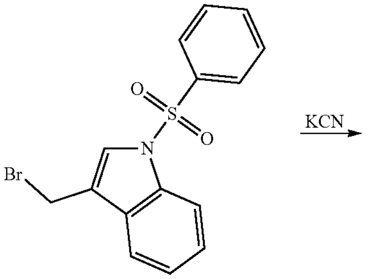
1
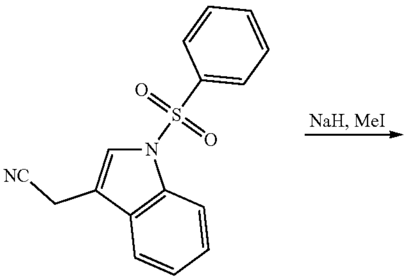
-continued
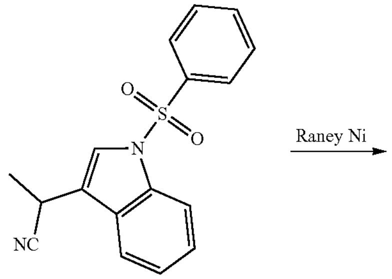
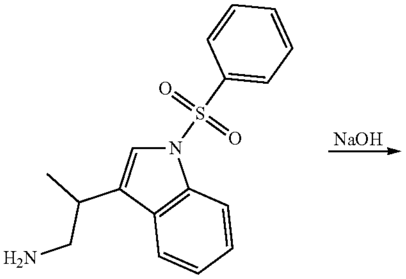
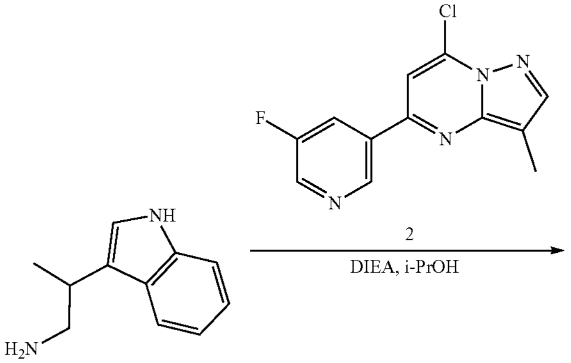
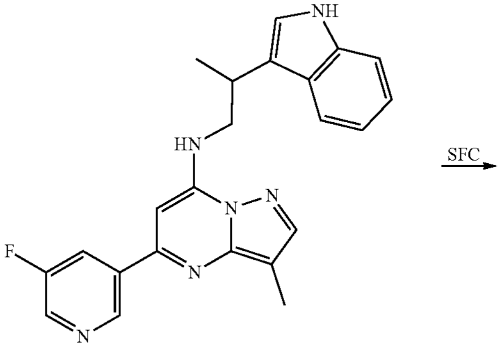
I-160c
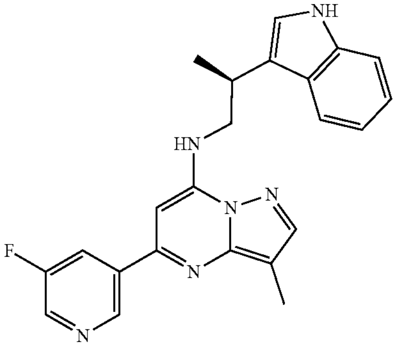
+
I-160c -continued

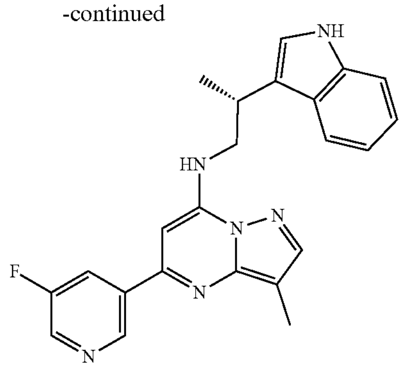

I-160c

Step 1: 2-[1-(Benzenesulfonyl)indol-3-yl]acetonitrile

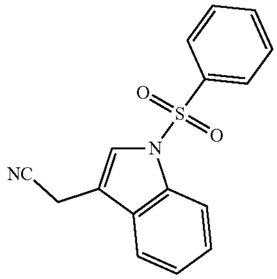 [SMILES: N#CCc1cn(S(=O)(=O)c2ccccc2)c2ccccc12]

A solution of 1-(benzenesulfonyl)-3-(bromomethyl)indole (7 g, 19.99 mmol, 1 eq) in THF (50 mL) was added to a well-stirred suspension KCN (2.07 g, 31.79 mmol, 1.59 eq) in DMSO (50 mL) and THF (20 mL) dropwise at 0° C. under N2 atmosphere. The mixture was warmed to 25° C. and stirred for 15.5 h under N2 atmosphere. TLC (PE/EtOAc=3/1, $R_f$=0.30) indicated one major new spot was detected and starting material was remained. KCN (1.76 g, 27.03 mmol, 1.35 eq) was added to the mixture. The mixture was stirred for 16 h under $N_2$ atmosphere. Ice water (200 mL) was added to the mixture. The mixture was extracted with EtOAc (200 mL×3). The combined organic layers were washed with brine (150 mL), dried over $Na_2SO_4$, filtered and concentrated to yield a residue which was purified on silica gel column chromatography (from PE/EtOAc=1/0 to 10/3, TLC: PE/EtOAc=3/1, $R_f$=0.30) to yield 2-[1-(benzenesulfonyl)indol-3-yl]acetonitrile (2.0 g, 5.47 mmol, 27.6% yield, 81.0% purity) as a yellow solid. $^1$H NMR (400 MHz, $CD_3OD$) δ ppm 8.02 (d, J=8.3 Hz, 1H), 7.97-7.93 (m, 2H), 7.71 (s, 1H), 7.64-7.59 (m, 2H), 7.55-7.49 (m, 2H), 7.42-7.37 (m, 1H), 7.33-7.28 (m, 1H), 3.97 (d, J=1.0 Hz, 2H); ES-LCMS m/z 297.1 $[M+H]^+$.

Step 2: 2-[1-(Benzenesulfonyl)indol-3-yl]propanenitrile

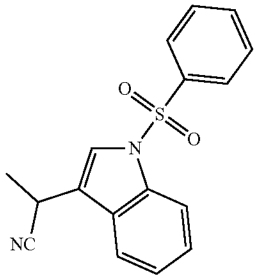 [SMILES: CC(C#N)c1cn(S(=O)(=O)c2ccccc2)c2ccccc12]

To a solution of 2-[1-(benzenesulfonyl)indol-3-yl]acetonitrile (1 g, 2.73 mmol, 1 eq) in THF (50 mL) was added n-BuLi (2.5 M, 1.09 mL, 1 eq) dropwise at −78° C. under $N_2$ atmosphere. The mixture was stirred at −78° C. under $N_2$ atmosphere for 1 h. A solution of MeI (387.96 mg, 2.73 mmol, 170.16 μL, 1 eq) in THF (5 mL) was added dropwise to the mixture. The mixture was stirred at 20° C. under $N_2$ atmosphere for 3 h. TLC (PE/EtOAc=3/1, $R_f$=0.38) indicated one major new spot was detected. Ice water (30 mL) was added to the mixture, the mixture was extracted with EtOAc (50 mL×3). The combined organic layers were washed with brine (50 mL), dried over $Na_2SO_4$, filtered and concentrated to yield a residue which was purified on silica gel column chromatography (from PE/EtOAc=1/0 to 5/1, TLC: PE/EtOAc=3/1, $R_f$=0.38) to yield 2-[1-(benzenesulfonyl)indol-3-yl]propanenitrile (420 mg, 1.14 mmol, 41.6% yield, 84.0% purity) as a yellow solid. $^1$H NMR (400 MHz, $CDCl_3$) δ ppm 8.03 (d, J=8.3 Hz, 1H), 7.94-7.89 (m, 2H), 7.62-7.55 (m, 3H), 7.52-7.46 (m, 2H), 7.42-7.37 (m, 1H), 7.34-7.29 (m, 1H), 4.13 (q, J=7.1 Hz, 1H), 1.75 (d, J=7.1 Hz, 3H); ES-LCMS m/z 311.1 $[M+H]^+$.

Step 3: 2-[1-(Benzenesulfonyl)indol-3-yl]propan-1-amine

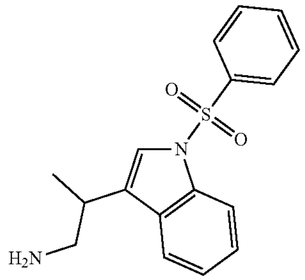 [SMILES: CC(CN)c1cn(S(=O)(=O)c2ccccc2)c2ccccc12]

To a solution of 2-[1-(benzenesulfonyl)indol-3-yl]propanenitrile (420 mg, 1.14 mmol, 1 eq) in MeOH (10 mL) was added Raney-Ni (453.70 mg, 5.30 mmol, 4.66 eq) and $NH_3.H_2O$ (910.00 mg, 6.49 mmol, 1 mL, 5.71 eq). The mixture was degassed and purged with $H_2$ for 3 times, stirred at 25° C. for 16 h. TLC (PE/EtOAc=3/1, $R_f$=0.16) indicated one major new spot was detected. The reaction mixture was filtered and concentrated to yield 2-[1-(benzenesulfonyl) indol-3-yl]propan-1-amine (330 mg, 818.70 μmol, 72.0% yield, 78.0% purity) as white solid which was used in the next step without further purification. $^1$H NMR (400 MHz, $CDCl_3$) δ ppm 8.01 (d, J=8.3 Hz, 1H), 7.87 (d, J=7.5 Hz, 2H), 7.58-7.51 (m, 2H), 7.48-7.40 (m, 2H), 7.38-7.30 (m, 2H), 7.26-7.21 (m, 1H), 4.93 (br s, 2H), 3.08-2.93 (m, 2H), 2.92-2.86 (m, 1H), 1.34 (d, J=6.8 Hz, 3H); ES-LCMS m/z 315.1 $[M+H]^+$.

Step 4: 2-(1H-Indol-3-yl)propan-1-amine

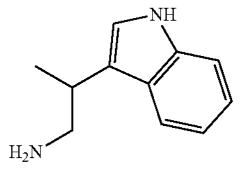

To a solution of 2-[1-(benzenesulfonyl)indol-3-yl]propan-1-amine (330 mg, 818.70 μmol, 1 eq) in MeOH (10 mL) was added NaOH (327.46 mg, 8.19 mmol, 10 eq). The mixture was stirred at 50° C. for 4 h under $N_2$ atmosphere. TLC (DCM/MeOH=10/1, $R_f$=0.20) indicated one major new spot was detected. The mixture was concentrated and water (10 mL) was added. The mixture was extracted with EtOAc (10 mL×3). The combined organic layers were dried over $Na_2SO_4$, filtered and concentrated to yield 2-(1H-indol-3-yl)propan-1-amine (130 mg, 746.09 μmol, 91.1% yield, crude) as white solid which was used in the next step without further purification. $^1$H NMR (400 MHz, $CDCl_3$) δ ppm 8.05 (br s, 1H), 7.67 (d, J=8.1 Hz, 1H), 7.42-7.36 (m, 1H), 7.21 (t, J=7.5 Hz, 1H), 7.12 (t, J=7.6 Hz, 1H), 7.03 (d, J=2.0 Hz, 1H), 3.18-3.10 (m, 1H), 3.05-2.92 (m, 2H), 1.40-1.36 (m, 3H).

Step 5: 5-(5-Fluoro-3-pyridyl)-N-[(2S)-2-(1H-indol-3-yl)propyl]-3-methyl-pyrazolo[1,5-a]pyrimidin-7-amine & 5-(5-Fluoro-3-pyridyl)-N-[(2R)-2-(1H-indol-3-yl)propyl]-3-methyl-pyrazolo[1,5-a]pyrimidin-7-amine (I-160a, I-160b)

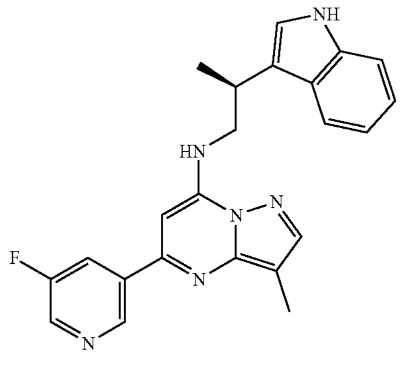

-continued

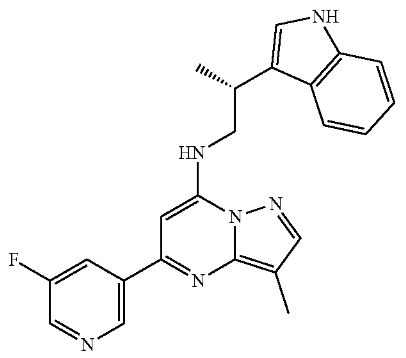

To a mixture of 2-(1H-indol-3-yl)propan-1-amine (130 mg, 746.09 μmol, 1 eq) and 7-chloro-5-(5-fluoro-3-pyridyl)-3-methyl-pyrazolo[1,5-a]pyrimidine (200.59 mg, 746.09 μmol, 1 eq) in i-PrOH (10 mL) was added DIEA (289.28 mg, 2.24 mmol, 389.87 μL, 3 eq). The mixture was stirred at 80° C. for 15 h under $N_2$ atmosphere and concentrated under reduced pressure to yield a residue which was purified on silica gel column chromatography (from PE/EtOAc=1/0 to 10/3, TLC: PE/EtOAc=3/1, $R_f$=0.34) to yield 5-(5-fluoro-3-pyridyl)-N-[2-(1H-indol-3-yl)propyl]-3-methyl-pyrazolo[1,5-a]pyrimidin-7-amine (300 mg, 689.22 μmol, 92.4% yield, 92.0% purity) as a yellow solid which were separated by SFC (column: DAICEL CHIRALCEL OJ (250 mm*30 mm, 10 μm); mobile phase: [0.1% $NH_3.H_2O$ EtOH]; B %: 40%-40%, min). The solution were concentrated to yield a crude products which were purified by preparative HPLC (column: Agela ASB 150*25 mm*5 μm; mobile phase: [water (0.05% HCl)-ACN]; B %: 48%-68%, 8 min), followed by lyophilization to yield an enantiomer (27.27 mg, 57.61 μmol, 8.4% yield, 100.0% purity, 2HCl, SFC: Rt=3.079 min, ee=98.49%, OR: $[\alpha]^{23.9}_D$=+48.385 (MeOH, c=0.110 g/100 mL)) as a yellow solid. $^1$H NMR (400 MHz, $CD_3OD$) δ ppm 8.73 (d, J=2.7 Hz, 1H), 8.39 (s, 1H), 8.09 (s, 1H), 7.54 (d, J=8.1 Hz, 2H), 7.11 (d, J=8.1 Hz, 1H), 7.05 (s, 1H), 6.91 (t, J=7.6 Hz, 1H), 6.76 (t, J=7.1 Hz, 1H), 5.74 (s, 1H), 4.00-3.94 (m, 2H), 3.58-3.51 (m, 1H), 2.27 (s, 3H), 1.59 (d, J=7.1 Hz, 3H); ES-LCMS m/z 401.1 $[M+H]^+$; and the other enantiomer (64.75 mg, 136.78 μmol, 19.85% yield, 100% purity, 2HCl, SFC: Rt=3.374 min, ee=98.93%, OR: $[\alpha]^{23.8}_D$=−32.08 (MeOH, c=0.120 g/100 mL)) as a yellow solid. $^1$H NMR (400 MHz, $CD_3OD$) δ ppm 8.73 (d, J=2.7 Hz, 1H), 8.39 (s, 1H), 8.09 (s, 1H), 7.57-7.51 (m, 2H), 7.12 (d, J=8.3 Hz, 1H), 7.06 (s, 1H), 6.92 (t, J=7.6 Hz, 1H), 6.76 (t, J=7.5 Hz, 1H), 5.75 (s, 1H), 4.02-3.92 (m, 2H), 3.59-3.51 (m, 1H), 2.28 (s, 3H), 1.60 (d, J=7.1 Hz, 3H); ES-LCMS m/z 401.1 $[M+H]^+$.

Example 137

Synthesis of I-162

I-162

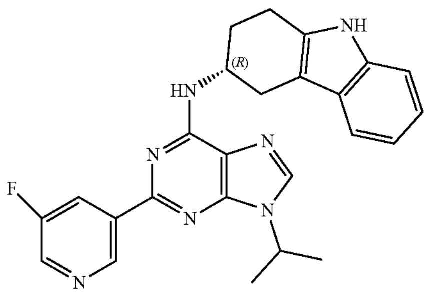

Synthetic Scheme:

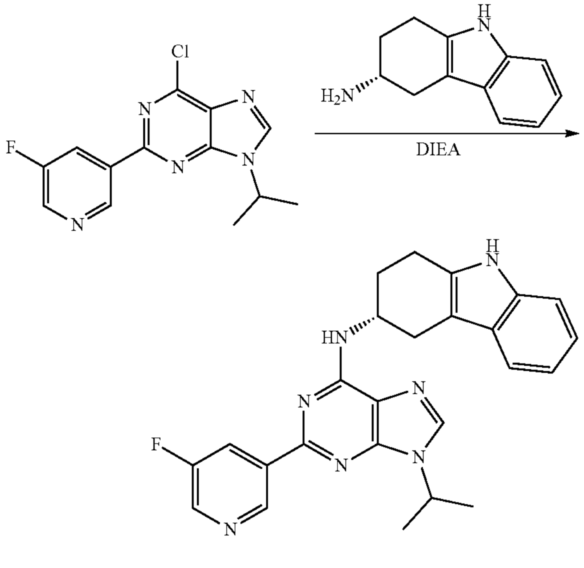

I-162

Step 1: (3R)—N-[2-(5-Fluoro-3-pyridyl)-9-isopropyl-purin-6-yl]-2,3,4,9-tetrahydro-1H-carbazol-3-amine (I-162)

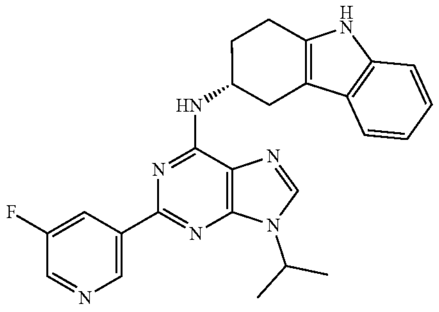 [SMILES: CC(C)n1cnc2c(N[C@@H]3CCc4[nH]c5ccccc5c4C3)nc(-c3cncc(F)c3)nc21]

A mixture of 6-chloro-2-(5-fluoro-3-pyridyl)-9-isopropyl-purine (60 mg, 187.17 μmol, 1 eq), (3R)-2,3,4,9-tetrahydro-1H-carbazol-3-amine (38.35 mg, 205.89 μmol, 1.1 eq) and DIEA (72.57 mg, 561.51 μmol, 97.81 μL, 3 eq) in i-PrOH (6 mL) was degassed and purged with $N_2$ for 3 times. The mixture was stirred at 80° C. for 15 h under $N_2$ atmosphere. The reaction mixture was concentrated under reduced pressure to yield a residue which was purified by preparative HPLC (column: Agela ASB 150*25 mm*5 μm; mobile phase: [water (0.05% HCl)-ACN]; B %: 60%-90%, 8 min), followed by lyophilization to yield (3R)—N-[2-(5-fluoro-3-pyridyl)-9-isopropyl-purin-6-yl]-2,3,4,9-tetrahydro-1H-carbazol-3-amine (30.19 mg, 58.51 μmol, 31.3% yield, 99.7% purity, 2HCl, $[\alpha]^{22.3}_{D}$=−22.78 (MeOH, c=0.149 g/100 mL) as a yellow solid. $^1$H NMR (400 MHz, $CD_3OD$) δ ppm 9.57 (br s, 1H), 9.40 (s, 1H), 9.14 (J=8.0 Hz, 1H), 8.99 (br s, 1H), 7.31 (J=7.5 Hz, 1H), 7.23 (d, J=8.0 Hz, 1H), 7.00 (t, J=7.5 Hz, 1H), 6.94-6.87 (m, 1H), 5.23-5.12 (m, 1H), 5.01 (m, 1H), 3.28 (J=5.0 Hz, 1H), 3.01-2.94 (m, 2H), 2.90 (J=6.8, 15.3 Hz, 1H), 2.42-2.32 (m, 1H), 2.27 (td, J=7.0, 13.7 Hz, 1H), 1.78-1.74 (m, 6H); ES-LCMS m/z 442.1 $[M+H]^+$.

Example 138

Synthesis of I-163

I-163

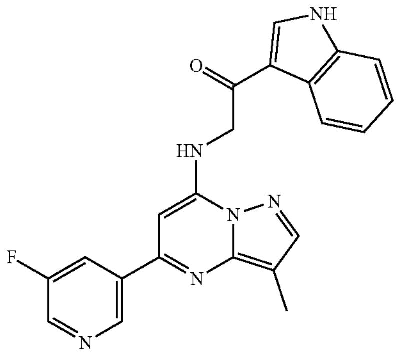 [SMILES: Cc1cnn2c(NCC(=O)c3c[nH]c4ccccc34)cc(-c3cncc(F)c3)nc12]

Synthetic Scheme:

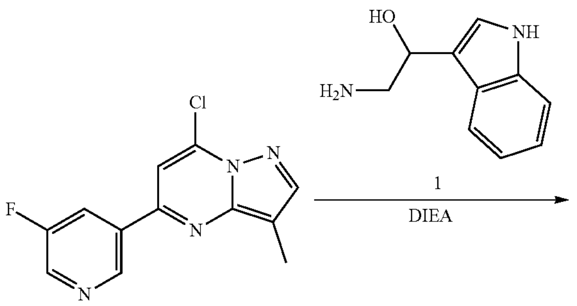

-continued

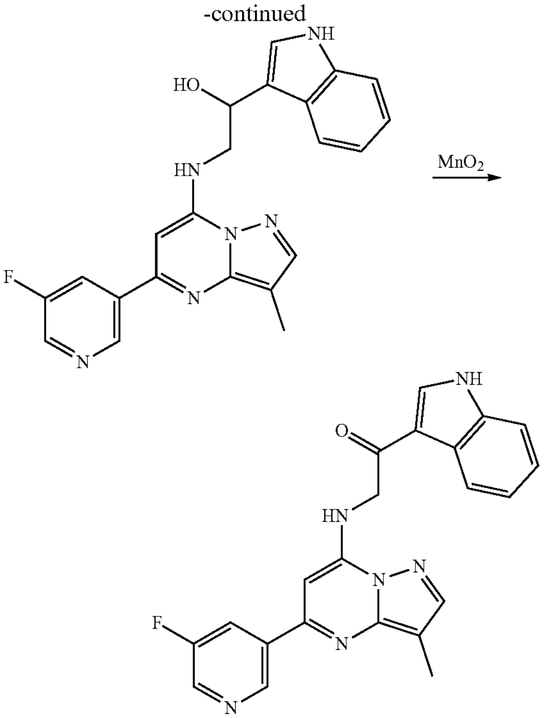

I-163

Step 1: 2-[[5-(5-Fluoro-3-pyridyl)-3-methyl-pyrazolo[1,5-a]pyrimidin-7-yl]aminol-1-(1H-indol-3-yl) ethanol

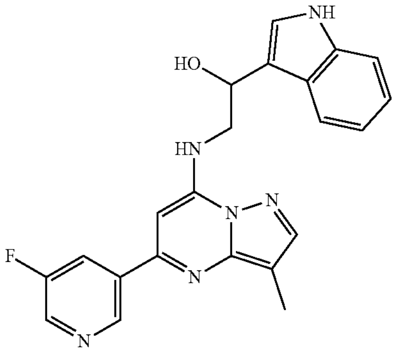

A mixture of 7-chloro-5-(5-fluoro-3-pyridyl)-3-methyl-pyrazolo[1,5-a]pyrimidine (70 mg, 260.36 μmol, 1 eq), 2-amino-1-(1H-indol-3-yl)ethanol (53.72 mg, 260.36 μmol, 1 eq), DIEA (100.95 mg, 781.09 μmol, 136.05 μL, 3 eq) in i-PrOH (15 mL) was stirred at 80° C. for 12 h. The reaction mixture was concentrated to yield a residue which was purified on silica gel column chromatography (from pure DCM to DCM/MeOH=10/1, TLC: DCM/MeOH=10/1, $R_f$=0.60) to yield 2-[[5-(5-fluoro-3-pyridyl)-3-methyl-pyrazolo[1,5-a]pyrimidin-7-yl]amino]-1-(1H-indol-3-yl)ethanol (80 mg, 152.08 μmol, 58.4% yield, 76.5% purity) as a brown solid. $^1$H NMR (400 MHz, $CDCl_3$) δ ppm 8.77 (s, 1H), 8.46 (s, 1H), 8.24 (s, 1H), 7.91 (d, J=8.3 Hz, 1H), 7.82 (s, 1H), 7.78 (d, J=7.6 Hz, 1H), 7.35 (d, J=8.1 Hz, 1H), 7.20 (d, J=2.2 Hz, 1H), 6.83-6.76 (m, 1H), 6.07 (s, 1H), 5.38 (t, J=5.4 Hz, 1H), 3.92 (t, J=5.9 Hz, 2H), 2.35 (s, 3H); ES-LCMS m/z 403.2 $[M+H]^+$.

Step 2: 2-[[5-(5-Fluoro-3-pyridyl)-3-methyl-pyrazolo[1,5-a]pyrimidin-7-yl]amino]-1-(1H-indol-3-yl) ethanone (I-163)

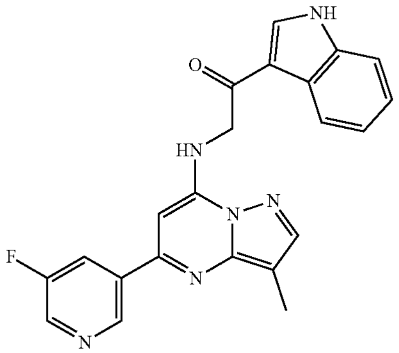

To a solution of 2-[[5-(5-fluoro-3-pyridyl)-3-methyl-pyrazolo[1,5-a]pyrimidin-7-yl]amino]-1-(1H-indol-3-yl) ethanol (80 mg, 152.08 μmol, 1 eq) in DCM (10 mL) was added $MnO_2$ (396.64 mg, 4.56 mmol, 30 eq). The reaction mixture was stirred at 20° C. for 12 h. The reaction mixture was concentrated to yield a residue which was purified by preparative HPLC (column: Agela DuraShell 150 mm_25 mm_5 m; mobile phase: water (0.05% HCl)-ACN; B %: 40%-70%, 8 min) twice, followed by lyophilization to yield 2-[[5-(5-fluoro-3-pyridyl)-3-methyl-pyrazolo[1,5-a]pyrimidin-7-yl]amino]-1-(1H-indol-3-yl)ethanone (13.82 mg, 27.88 μmol, 18.3% yield, 95.5% purity, 2HCl) as a yellow solid. $^1$H NMR (400 MHz, $CD_3OD$) δ ppm 8.95 (s, 1H), 8.76 (d, J=2.7 Hz, 1H), 8.38 (d, J=3.2 Hz, 1H), 8.28-8.24 (m, 1H), 8.23-8.18 (m, 2H), 7.48 (d, J=7.1 Hz, 1H), 7.29-7.20 (m, 2H), 6.87 (s, 1H), 5.24 (s, 2H), 2.40 (s, 3H); ES-LCMS m/z 401.2 $[M+H]^+$.

Example 139

Synthesis of I-164

I-164

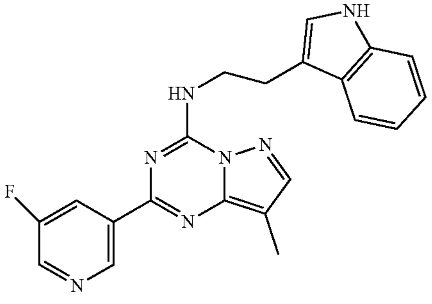

Synthetic Scheme:

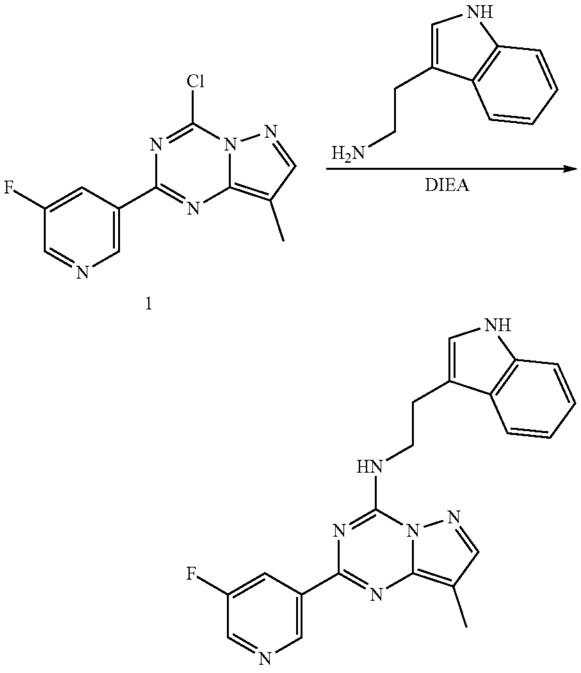

1

I-164

Step 1: 2-(5-Fluoro-3-pyridyl)-N-[2-(1H-indol-3-yl)ethyl]-8-methyl-pyrazolo[1,5-a][1,3,5]triazin-4-amine (I-164)

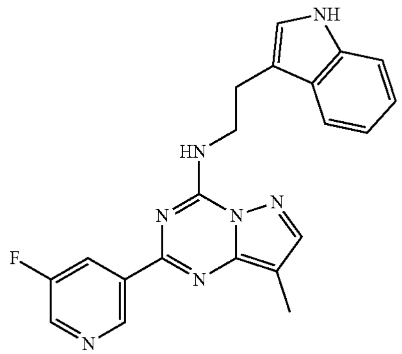 [SMILES: Cc1cnn2c(NCCc3c[nH]c4ccccc34)nc(-c3cncc(F)c3)nc12]

To a solution of 4-chloro-2-(5-fluoro-3-pyridyl)-8-methyl-pyrazolo[1,5-a][1,3,5]triazine (50 mg, 182.24 μmol, 1 eq) and 2-(1H-indol-3-yl)ethanamine (32.12 mg, 200.47 μmol, 1.1 eq) in i-PrOH (10 mL) was added DIEA (188.43 mg, 1.46 mmol, 253.95 μL, 8 eq). The mixture was stirred at 50° C. for 3 h. TLC (PE/EtOAc=3/1, $R_f$=0.2) indicated the starting material was consumed completely. The reaction mixture was concentrated under reduced pressure to yield a residue which was purified by preparative HPLC (HCl condition; column: Agela DuraShell 150 mm_25 mm_5 um; mobile phase: [water (0.05% HCl)-ACN]; B %: 45%-75%, 9 min). The desired fraction was lyophilized to yield 2-(5-fluoro-3-pyridyl)-N-[2-(1H-indol-3-yl)ethyl]-8-methyl-pyrazolo[1,5-a][1,3,5]triazin-4-amine (22.72 mg, 48.65 μmol, 26.7% yield, 98.6% purity, 2HCl) as a yellow solid. $^1$H NMR (400 MHz, $CD_3OD$) δ ppm 9.15 (s, 1H), 8.83 (br s, 1H), 8.59 (d, J=9.0 Hz, 1H), 7.95 (s, 1H), 7.68 (dd, J=2.4, 6.1 Hz, 1H), 7.20-7.12 (m, 1H), 7.05-6.91 (m, 3H), 4.05 (t, J=6.7 Hz, 2H), 3.19 (t, J=6.7 Hz, 2H), 2.29 (s, 3H); ES-LCMS m/z 388.2 $[M+H]^+$.

Example 140

Synthesis of I-165

I-165

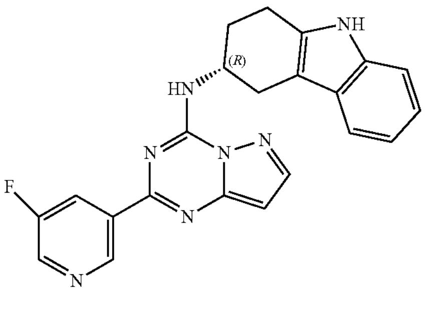

Synthetic Scheme:

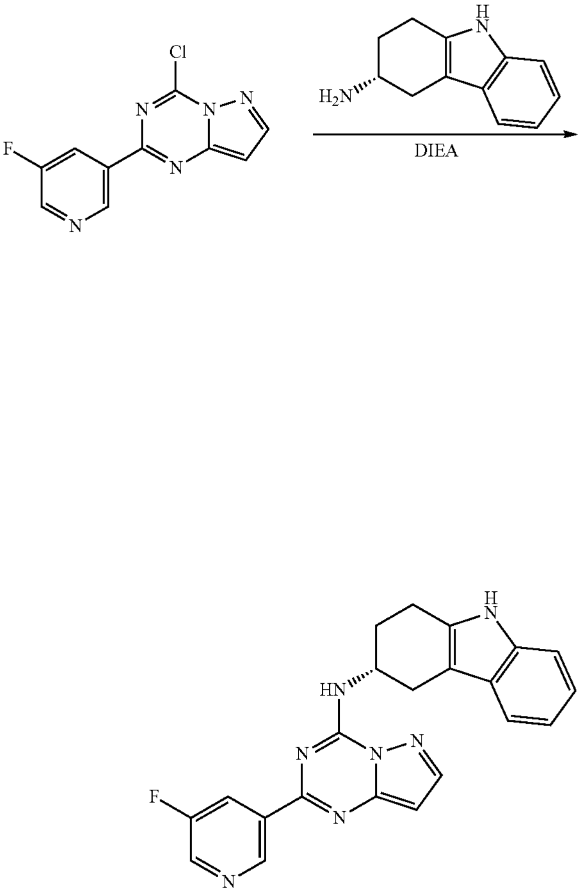

I-165

Step 1: (3R)—N-[2-(5-Fluoro-3-pyridyl)pyrazolo[1,5-a][1,3,5]triazin-4-yl]-2,3,4,9-tetrahydro-1H-carbazol-3-amine (I-165)

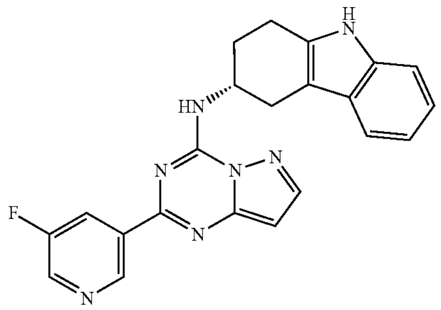 [SMILES: Fc1cncc(-c2nc(N[C@@H]3CCc4[nH]c5ccccc5c4C3)n3nccc3n2)c1]

A mixture of 4-chloro-2-(5-fluoro-3-pyridyl)pyrazolo[1,5-a][1,3,5]triazine (44.89 mg, 172.65 μmol, 1 eq), (3R)-2,3,4,9-tetrahydro-1H-carbazol-3-amine (39.30 mg, 189.92 μmol, 1.1 eq) and DIEA (66.94 mg, 517.95 μmol, 90.22 μL, 3 eq) in i-PrOH (3 mL) was degassed and purged with $N_2$ for 3 times. The mixture was stirred at 80° C. for 12 h under $N_2$ atmosphere. The reaction mixture was concentrated under reduced pressure to yield a residue which was purified by preparative HPLC (column: Agela ASB 150*25 mm*5 μm; mobile phase: [water (0.05% HCl)-ACN]; B %: 55%-85%, 8 min), followed by lyophilization to yield (3R)—N-[2-(5-fluoro-3-pyridyl)pyrazolo[1,5-a][1,3,5]triazin-4-yl]-2,3,4,9-tetrahydro-1H-carbazol-3-amine (20.39 mg, 42.52 μmol, 24.6% yield, 98.5% purity, 2HCl) as a yellow solid. $^1H$ NMR (400 MHz, $CD_3OD$) δ ppm 9.46 (s, 1H), 8.90 (d, J=9.0 Hz, 1H), 8.82 (s, 1H), 8.13 (d, J=2.2 Hz, 1H), 7.35 (d, J=7.8 Hz, 1H), 7.25 (d, J=8.1 Hz, 1H), 7.06-6.98 (m, 1H), 6.97-6.91 (m, 1H), 6.57 (d, J=2.0 Hz, 1H), 4.89 (m, 1H), 3.31-3.26 (m, 1H), 3.11-2.88 (m, 3H), 2.42-2.34 (m, 1H), 2.33-2.21 (m, 1H); ES-LCMS m/z 400.2 $[M+H]^+$; Optical rotation ($[\alpha]^{21.4}_D$=0.396 (MeOH, c=0.102 g/100 mL).

Example 141

Synthesis of I-166

I-166

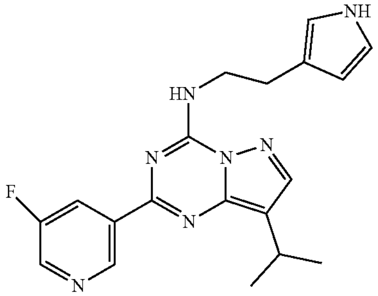

Synthetic Scheme:

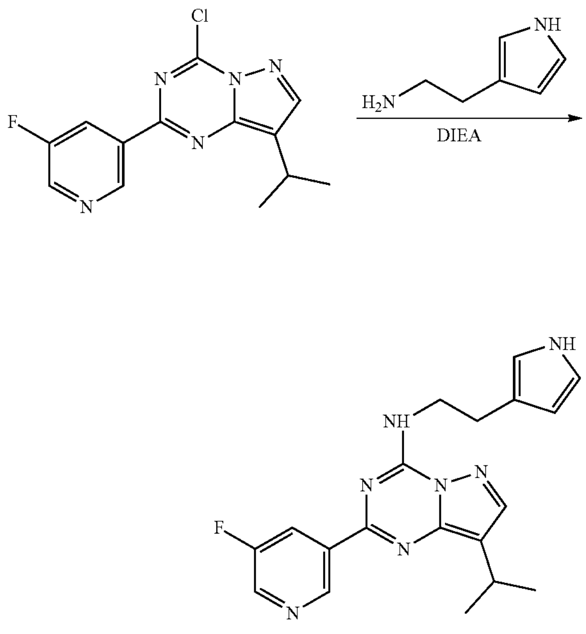

I-166

Step 1: 2-(5-Fluoro-3-pyridyl)-8-isopropyl-N-[2-(1H-pyrrol-3-yl)ethyl]pyrazolo[1,5-a][1,3,5]triazin-4-amine (i-166)

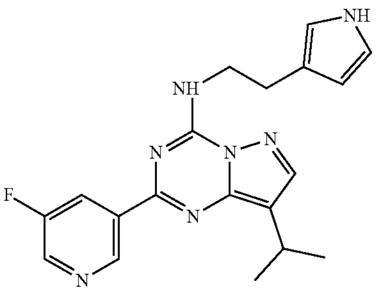 [SMILES: CC(C)c1cnn2c(NCCc3cc[nH]c3)nc(-c3cncc(F)c3)nc12]

To a solution of 4-chloro-2-(5-fluoro-3-pyridyl)-8-isopropyl-pyrazolo[1,5-a][1,3,5]triazine (50 mg, 168.66 μmol, 1 eq) in i-PrOH (3 mL) was added DIEA (21.80 mg, 168.66 μmol, 29.38 μL, 1 eq) and 2-(1H-pyrrol-3-yl)ethanamine (27.87 mg, 252.99 μmol, 1.5 eq). The mixture was stirred at 60° C. for 3 h. The reaction mixture was concentrated under reduced pressure to yield a residue which was purified by preparative HPLC (column: Agela ASB 150*25 mm*5 um; mobile phase: [water (0.05% HCl)-ACN]; B %: 60%-90%, 8 min), followed by lyophilization to yield 2-(5-fluoro-3-pyridyl)-8-isopropyl-N-[2-(1H-pyrrol-3-yl)ethyl]pyrazolo[1,5-a][1,3,5]triazin-4-amine (15.28 mg, 32.18 μmol, 19.1% yield, 100.0% purity, 3HCl) as a yellow solid. $^1H$ NMR (400 MHz, DMSO-$d_6$) δ ppm 10.52 (s, 1H), 9.39 (s, 1H), 8.93 (t, J=5.6 Hz, 1H), 8.73 (d, J=2.9 Hz, 1H), 8.41 (d, J=8.8 Hz, 1H), 8.11 (s, 1H), 6.65 (d, J=2.4 Hz, 2H), 5.98 (s, 1H), 3.84-3.75 (m, 2H), 3.23-3.16 (m, 1H), 2.84 (t, J=7.3 Hz, 2H), 1.35 (d, J=6.8 Hz, 6H); ES-LCMS m/z 366.2 $[M+H]^+$.

Example 142

Synthesis of I-169

Synthetic Scheme:

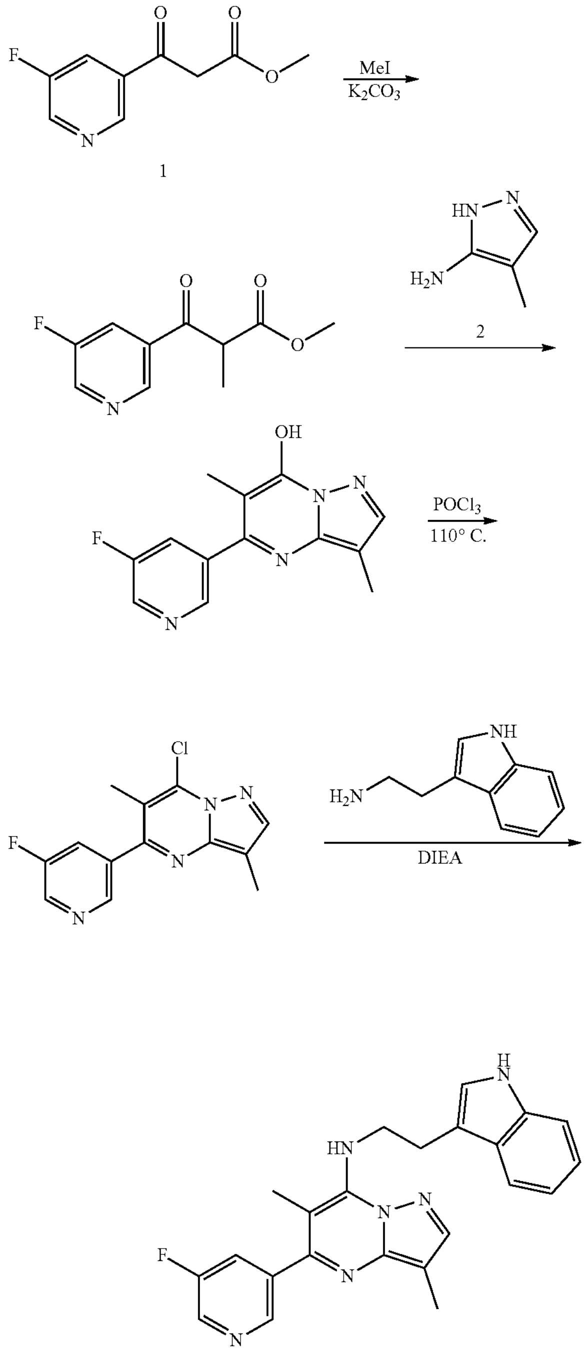

I-169

Step 1: Methyl 3-(5-fluoro-3-pyridyl)-2-methyl-3-oxo-propanoate

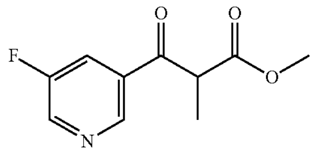

To a solution of methyl (Z)-3-(5-fluoro-3-pyridyl)-3-hydroxy-prop-2-enoate (600.00 mg, 2.83 μmol, 1 eq) and MeI (401.71 mg, 2.83 μmol, 176.19 μL, 1 eq) in DMF (20 mL) was added $K_2CO_3$ (391.14 mg, 2.83 μmol, 1 eq). The mixture was stirred at 20° C. for 3 h. The reaction mixture was quenched by addition $H_2O$ (50 mL), extracted with EtOAc (50 mL×3). The combined organic layers were dried over anhydrous $Na_2SO_4$, filtered and concentrated under reduced pressure to yield a residue which was purified on silica gel column chromatography (from PE/EtOAc=1/0 to 10/1, TLC: PE/EtOAc=10/1, $R_f$=0.37) to yield the product of methyl 3-(5-fluoro-3-pyridyl)-2-methyl-3-oxo-propanoate (605 mg, 2.69 μmol, 95.0% yield, 93.9% purity) as a yellow oil. $^1$H NMR (400 MHz $CDCl_3$) δ ppm 9.00 (d, J=1.5 Hz, 1H), 8.78-8.61 (m, 1H), 8.03-7.90 (m, 1H), 4.36 (q, J=7.1 Hz, 1H), 3.71 (s, 3H), 1.57-1.52 (m, 3H); ES-LCMS m/z 212.1 $[M+H]^+$.

Step 2: 5-(5-Fluoro-3-pyridyl)-3,6-dimethyl-pyrazolo[1,5-a]pyrimidin-7-ol

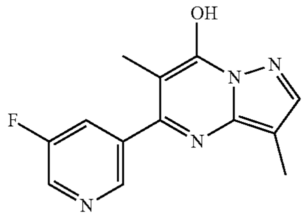 [SMILES: Cc1c(-c2cncc(F)c2)nc2c(C)cnn2c1O]

Methyl 3-(5-fluoro-3-pyridyl)-2-methyl-3-oxo-propanoate (300 mg, 1.33 μmol, 1 eq), 4-methyl-1H-pyrazol-5-amine (647.37 mg, 6.67 μmol, 5 eq) were taken up into a microwave tube in AcOH (5 mL). The sealed tube was heated at 150° C. for 1 h under microwave. The mixture was concentrated under reduced pressure to yield 5-(5-fluoro-3-pyridyl)-3,6-dimethyl-pyrazolo[1,5-a]pyrimidin-7-ol (300 mg, 1.16 μmol, 87.14% yield) as a white solid which was used in the next step without further purification.

Step 3: 7-Chloro-5-(5-fluoro-3-pyridyl)-3,6-dimethyl-pyrazolo[1,5-a]pyrimidine

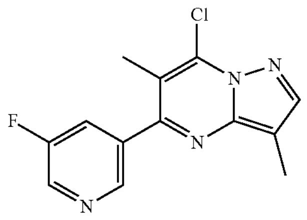 [SMILES: Cc1c(-c2cncc(F)c2)nc2c(C)cnn2c1Cl]

A solution of 5-(5-fluoro-3-pyridyl)-3,6-dimethyl-pyrazolo[1,5-a]pyrimidin-7-ol (270 mg, 1.05 μmol, 1 eq) in $POCl_3$ (8.25 g, 53.80 μmol, 5.00 mL, 51.46 eq) was stirred at 110° C. for 3 h. The reaction mixture was pour into ice water (50 g), extracted with DCM (50 mL×3). The combined organic layers were dried over anhydrous $Na_2SO_4$, filtered and concentrated under reduced pressure to yield a residue which was purified on silica gel column chromatography (from PE/EtOAc=1/0 to 3/1, TLC: PE/EtOAc=3/1, $R_f$=0.51) to yield 7-chloro-5-(5-fluoro-3-pyridyl)-3,6-dimethyl-pyrazolo[1,5-a]pyrimidine (200 mg, 337.55 μmol, 32.3% yield, 46.7% purity) as a yellow solid. $^1$H NMR (400 MHz, $CDCl_3$) δ ppm 9.01 (d, J=1.2 Hz, 1H), 8.68 (s, 1H), 8.61 (s, 1H), 8.08 (s, 1H), 2.65 (s, 3H), 2.63 (s, 3H); ES-LCMS m/z 277.1 $[M+H]^+$.

Step 4: 5-(5-Fluoro-3-pyridyl)-N-[2-(1H-indol-3-yl)ethyl]-3,6-dimethyl-pyrazolo[1,5-a]pyrimidin-7-amine (I-169)

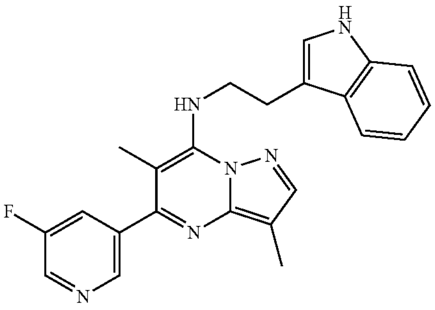 [SMILES: Cc1c(-c2cncc(F)c2)nc2c(C)cnn2c1NCCc1c[nH]c2ccccc12]

To a solution of 7-chloro-5-(5-fluoro-3-pyridyl)-3,6-dimethyl-pyrazolo[1,5-a]pyrimidine (100 mg, 168.78 μmol, 1 eq) and 2-(1H-indol-3-yl)ethanamine (40.56 mg, 253.17 μmol, 1.5 eq) in i-PrOH (4 mL) was added DIEA (87.25 mg, 675.11 μmol, 117.59 μL, 4 eq). The mixture was stirred at 70° C. for 3 h and concentrated to yield a residue which was purified by preparative HPLC (Phenomenex Gemini 150*25 mm*10 um; mobile phase: [water (0.05% ammonia hydroxide v/v)-ACN]; B %: 50%-80%, 8 min), followed by lyophilization to yield 5-(5-fluoro-3-pyridyl)-N-[2-(1H-indol-3-yl)ethyl]-3,6-dimethyl-pyrazolo[1,5-a]pyrimidin-7-amine (33.61 mg, 83.93 μmol, 49.7% yield, 100.0% purity) as a yellow solid. $^1$H NMR (400 MHz, $CD_3OD$) δ ppm 8.49 (d, J=2.7 Hz, 1H), 8.13 (s, 1H), 7.89 (s, 1H), 7.52 (d, J=7.8 Hz, 1H), 7.30-7.26 (m, 1H), 7.20 (d, J=8.1 Hz, 1H), 7.07 (t, J=7.5 Hz, 1H), 6.98 (d, J=7.8 Hz, 1H), 6.71 (s, 1H), 4.16-4.12 (m, 2H), 3.12-3.09 (m, 2H), 2.26 (s, 3H), 1.88 (s, 3H); ES-LCMS m/z 401.2 $[M+H]^+$.

Example 143

Synthesis of I-171

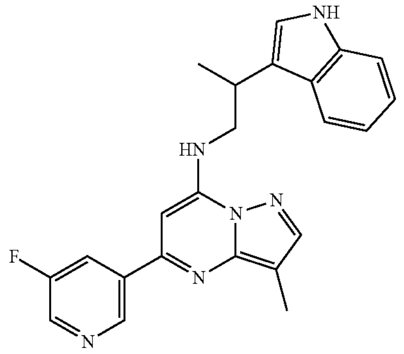 [SMILES: Cc1cnn2c(NCC(C)c3c[nH]c4ccccc34)cc(-c3cncc(F)c3)nc12]

Synthetic Scheme:

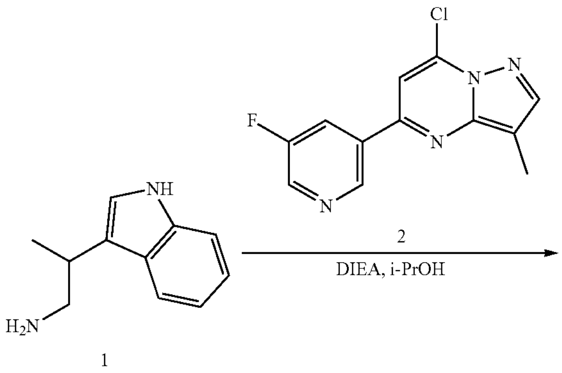

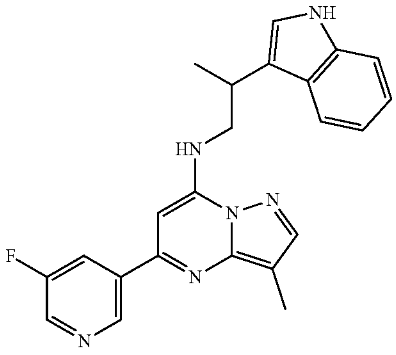

I-171

Step 1: 5-(5-Fluoro-3-pyridyl)-N-[2-(1H-indol-3-yl)propyl]-3-methyl-pyrazolo[1,5-a]pyrimidin-7-amine (I-171)

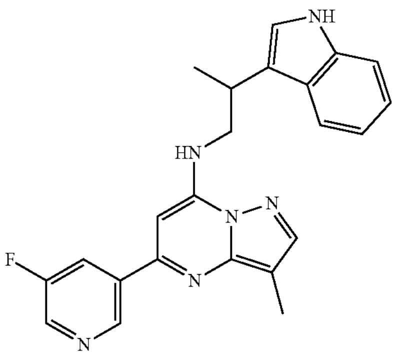 [SMILES: Cc1cnn2c(NCC(C)c3c[nH]c4ccccc34)cc(-c3cncc(F)c3)nc12]

A mixture of 2-(1H-indol-3-yl)propan-1-amine (30 mg, 172.17 μmol, 1 eq) and 7-chloro-5-(5-fluoro-3-pyridyl)-3-methyl-pyrazolo[1,5-a]pyrimidine (46.29 mg, 172.17 μmol, 1 eq) in i-PrOH (6 mL) was added DIEA (66.76 mg, 516.52 μmol, 89.97 μL, 3 eq). The mixture was stirred at 80° C. for 15 h under $N_2$ atmosphere. The reaction mixture was concentrated under reduced pressure to yield a residue which was purified by preparative HPLC (column: Agela ASB 150*25 mm*5 μm; mobile phase: [water (0.05% HCl)-ACN]; B %: 48%-68%, 8 min), followed by lyophilization to yield 5-(5-fluoro-3-pyridyl)-N-[2-(1H-indol-3-yl)propyl]-3-methyl-pyrazolo[1,5-a]pyrimidin-7-amine (18.71 mg, 39.52 μmol, 23.0% yield, 100.0% purity, 2HCl) as an orange solid. $^1H$ NMR (400 MHz, $CD_3OD$) δ ppm 8.80 (br s, 1H), 8.44 (br s, 1H), 8.09 (s, 1H), 7.64 (br s, 1H), 7.56 (d, J=8.1 Hz, 1H), 7.12 (d, J=8.1 Hz, 1H), 7.05 (s, 1H), 6.92 (t, J=7.3 Hz, 1H), 6.80-6.74 (m, 1H), 5.75 (s, 1H), 4.04-3.92 (m, 2H), 3.59-3.50 (m, 1H), 2.28 (s, 3H), 1.59 (d, J=7.3 Hz, 3H); ES-LCMS m/z 401.1 $[M+H]^+$.

Example 144

Synthesis of I-172

I-172

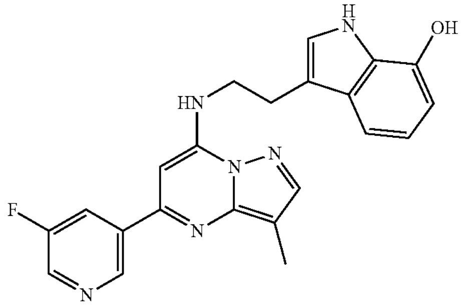

Synthetic Scheme:

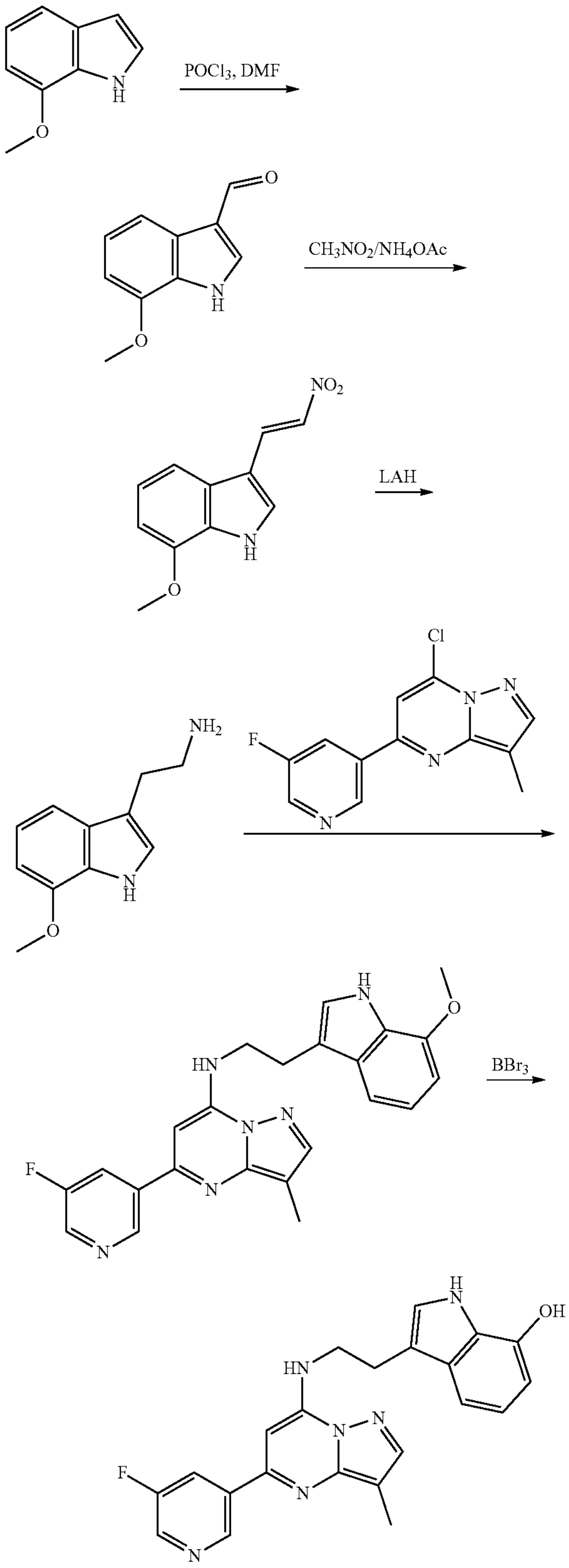

I-172

Step 1: 7-Methoxy-1H-indole-3-carbaldehyde

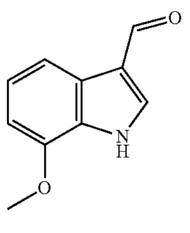

To a solution of $POCl_3$ (1.13 g, 7.37 mmol, 684.85 μL, 1.08 eq) in DMF (12 mL) was added 7-methoxy-1H-indole (1 g, 6.79 mmol, 884.96 μL, 1 eq) at 0° C. The mixture was stirred at 0~20° C. for 3 h under $N_2$ atmosphere. TLC (PE/EtOAc=3/1, $R_f$=0.25) indicated one major new spot was detected. The mixture was adjusted pH to 10~12 with 2 N NaOH. The mixture was extracted with DCM (30 mL×3). The combined organic layers were dried over $Na_2SO_4$, filtered and concentrated to yield a residue which was purified on silica gel column chromatography (from PE/EtOAc=1/0 to 5/2, TLC: PE/EtOAc=3/1, $R_f$=0.25) to yield 7-methoxy-1H-indole-3-carbaldehyde (900 mg, 5.03 mmol, 74.1% yield, 98.0% purity) as a pink solid. $^1H$ NMR (400 MHz, $CDCl_3$) δ ppm 10.07 (s, 1H), 9.18 (br s, 1H), 7.89 (d, J=7.9 Hz, 1H), 7.81 (d, J=3.1 Hz, 1H), 7.24 (t, J=7.9 Hz, 1H), 6.78 (d, J=7.7 Hz, 1H), 3.98 (s, 3H); ES-LCMS m/z 176.1 $[M+H]^+$.

Step 2: 7-Methoxy-3-[(E)-2-nitrovinyl]-1H-indole

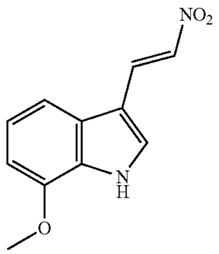 [SMILES: COc1cccc2c(/C=C/[N+](=O)[O-])c[nH]c12]

A mixture of 7-methoxy-1H-indole-3-carbaldehyde (900 mg, 5.03 mmol, 1 eq) and $NH_4OAc$ (504.52 mg, 6.55 mmol, 1.3 eq) in THF (10 mL) was added $CH_3NO_2$ (11.30 g, 185.12 mmol, 10 mL, 36.77 eq). The mixture was degassed and purged with $N_2$ for 3 times and stirred at 80° C. for 19 h under $N_2$ atmosphere. TLC (PE/EtOAc=1/1, $R_f$=0.60) indicated one major new spot was detected. The reaction mixture was concentrated under reduced pressure to yield a residue which was purified on silica gel column chromatography (from PE/EtOAc=1/0 to 5/2, TLC: PE/EtOAc=1/1, $R_f$=0.60) to yield 7-methoxy-3-[(E)-2-nitrovinyl]-1H-indole (660 mg, 2.87 mmol, 57.1% yield, 95.0% purity) as a orange solid. $^1H$ NMR (400 MHz, $CDCl_3$) δ ppm 8.92 (br s, 1H), 8.29 (d, J=13.5 Hz, 1H), 7.79 (d, J=13.5 Hz, 1H), 7.63 (d, J=3.1 Hz, 1H), 7.38 (d, J=8.2 Hz, 1H), 7.26-7.24 (m, 1H), 6.80 (d, J=7.7 Hz, 1H), 4.00 (s, 3H).

Step 3: 2-(7-Methoxy-1H-indol-3-yl)ethanamine $NH_2$

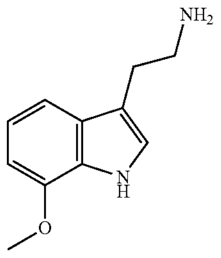

To a solution of 7-methoxy-3-[(E)-2-nitrovinyl]-1H-indole (300 mg, 1.31 mmol, 1 eq) in THF (10 mL) was added $LiAlH_4$ (247.86 mg, 6.53 mmol, 5 eq). The mixture was stirred at 80° C. for 2 h under $N_2$ atmosphere. TLC (PE/EtOAc=3/1, $R_f$=0.10) indicated one major new spot was detected. 2 mL $H_2O$ and 1 mL 2N NaOH was added to the mixture. The mixture was filtered and concentrated to yield 2-(7-methoxy-1H-indol-3-yl)ethanamine (240 mg, 1.20 mmol, 91.8% yield, 95.0% purity) as yellow solid which was used in the next step without further purification. $^1H$ NMR (400 MHz, $CDCl_3$) δ ppm 8.22 (br s, 1H), 7.23 (d, J=7.8 Hz, 1H), 7.07-7.01 (m, 2H), 6.66 (d, J=7.6 Hz, 1H), 3.97 (s, 3H), 3.06-3.01 (m, 2H), 2.93-2.87 (m, 2H).

Step 4: 5-(5-Fluoro-3-pyridyl)-N-[2-(7-methoxy-1H-indol-3-yl)ethyl]-3-methyl-pyrazolo[1,5-a]pyrimidin-7-amine

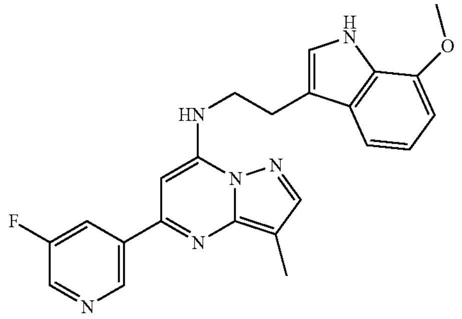 [SMILES: COc1cccc2c(CCNc3cc(-c4cncc(F)c4)nc4c(C)cnn34)c[nH]c12]

A mixture of 7-chloro-5-(5-fluoro-3-pyridyl)-3-methyl-pyrazolo[1,5-a]pyrimidine (230 mg, 855.48 μmol, 1 eq), 2-(7-methoxy-1H-indol-3-yl)ethanamine (217.00 mg, 1.03 mmol, 1.2 eq) and DIEA (331.70 mg, 2.57 mmol, 447.03 μL, 3 eq) in i-PrOH (10 mL) was degassed and purged with $N_2$ for 3 times. The mixture was stirred at 80° C. for 16 h under $N_2$ atmosphere. The reaction mixture was concentrated under reduced pressure to yield a residue which was purified by preparative HPLC (column: Agela DuraShell 150 mm_25 mm_5 um; mobile phase: [water (0.05% HCl)-ACN]; B %: 35%-65%, 9 min), followed by lyophilization to yield 5-(5-fluoro-3-pyridyl)-N-[2-(7-methoxy-1H-indol-3-yl)ethyl]-3-methyl-pyrazolo[1,5-a]pyrimidin-7-amine (240 mg, 490.42 μmol, 57.3% yield, 100.0% purity, 2HCl) as a yellow solid. $^1H$ NMR (400 MHz, $CD_3OD$) δ ppm 8.72 (d, J=2.7 Hz, 1H), 8.30 (s, 1H), 8.10 (s, 1H), 7.43 (td, J=2.3, 9.0 Hz, 1H), 7.15 (d, J=7.8 Hz, 1H), 6.87 (s, 1H), 6.80 (t, J=7.8 Hz, 1H), 6.48

(d, J=7.6 Hz, 1H), 5.62 (s, 1H), 4.04-3.98 (m, 2H), 3.81 (s, 3H), 3.21-3.16 (m, 2H), 2.29 (s, 3H); ES-LCMS m/z 417.1 $[M+H]^+$.

Step 5: 3-[2-[[5-(5-Fluoro-3-pyridyl)-3-methyl-pyrazolo[1,5-a]pyrimidin-7-yl]amino]ethyl]-1H-indol-7-ol (I-172)

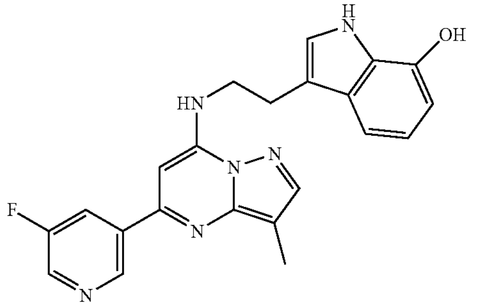 [SMILES: Cc1cnn2c(NCCc3c[nH]c4c(O)cccc34)cc(-c3cncc(F)c3)nc12]

To a solution of 5-(5-fluoro-3-pyridyl)-N-[2-(7-methoxy-1H-indol-3-yl)ethyl]-3-methyl-pyrazolo[1,5-a]pyrimidin-7-amine (200 mg, 480.25 μmol, 1 eq) in DCM (10 mL) was added $BBr_3$ (240.63 mg, 960.50 μmol, 92.55 μL, 2 eq) at 0° C. The mixture was stirred at 0-20° C. for 0.5 h under $N_2$ atmosphere. 1 mL MeOH was added to the mixture. The mixture was concentrated under reduced pressure to yield a residue which was purified by preparative HPLC (column: Agela ASB 150*25 mm*5 μm; mobile phase: [water (0.05% HCl)-ACN]; B %: 35%-65%, 8 min) followed by lyophilization to yield 3-[2-[[5-(5-fluoro-3-pyridyl)-3-methyl-pyrazolo[1,5-a]pyrimidin-7-yl]amino]ethyl]-1H-indol-7-ol (22.74 mg, 45.54 μmol, 9.5% yield, 95.2% purity, 2HCl) as a orange solid. $^1H$ NMR (400 MHz, $CD_3OD$) δ ppm 8.71 (d, J=2.7 Hz, 1H), 8.35 (s, 1H), 8.10 (s, 1H), 7.43 (J=9.0 Hz, 1H), 7.04 (d, J=7.8 Hz, 1H), 6.87 (s, 1H), 6.69 (td, J=3.8, 7.9 Hz, 1H), 6.36 (d, J=7.6 Hz, 1H), 5.65 (s, 1H), 4.04-3.98 (m, 2H), 3.21-3.15 (m, 2H), 2.29 (s, 3H); ES-LCMS m/z 403.1 $[M+H]^+$.

Example 145

Synthesis of I-175

I-175

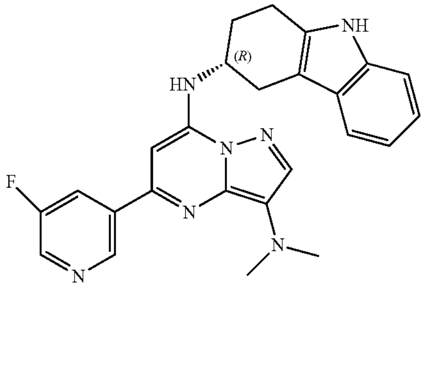

Synthetic Scheme:

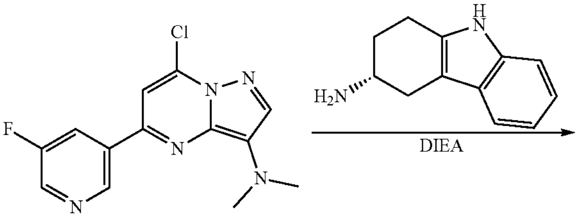

1

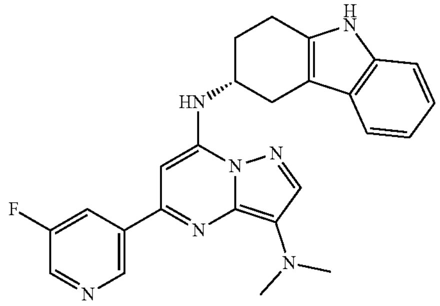

I-175

Step 1: 5-(5-Fluoro-3-pyridyl)-N3,N3-dimethyl-N7-[(3R)-2,3,4,9-tetrahydro-1H-carbazol-3-yl]pyrazolo[1,5-a]pyrimidine-3,7-diamine (I-175)

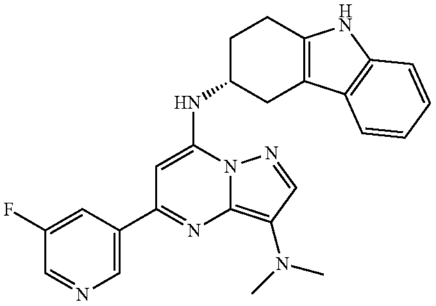 [SMILES: CN(C)c1cnn2c(N[C@@H]3CCc4[nH]c5ccccc5c4C3)cc(-c3cncc(F)c3)nc12]

To a solution of 7-chloro-5-(5-fluoro-3-pyridyl)-N,N-dimethyl-pyrazolo[1,5-a]pyrimidin-3-amine (50 mg, 171.40 μmol, 1 eq) in i-PrOH (5 mL) was added DIEA (66.46 mg, 514.21 μmol, 89.56 μL, 3 eq) and (3R)-2,3,4,9-tetrahydro-1H-carbazol-3-amine (35.12 mg, 188.54 μmol, 1.1 eq). The mixture was stirred at 90° C. for 12 h under N2 atmosphere. The reaction mixture was concentrated under reduced pressure to yield a residue which was purified by preparative HPLC (column: Agela DuraShell 150 mm 25 mm 5 μm; mobile phase: [water (0.05% HCl)-ACN]; B %: 30%-60%, 8 min), followed by lyophilization to yield 5-(5-fluoro-3-pyridyl)-N3,N3-dimethyl-N7-[(3R)-2,3,4,9-tetrahydro-1H-carbazol-3-yl]pyrazolo[1,5-a]pyrimidine-3,7-diamine (22.71 mg, 43.35 μmol, 25.3% yield, 98.2% purity, 2HCl) as a yellow solid. $^1H$ NMR (400 MHz, DMSO-$d_6$) δ ppm 10.82 (s, 1H), 9.41 (s, 1H), 8.72 (s, 1H), 8.66-8.55 (m, 2H), 8.49 (br s, 1H), 7.36 (d, J=7.6 Hz, 1H), 7.31-7.25 (m, 2H), 7.04-6.98 (m, 1H), 6.96-6.91 (m, 1H), 4.56 (br s, 1H), 3.37 (s, 6H), 3.18-3.01 (m, 2H), 2.99-2.82 (m, 2H), 2.28-2.09 (m, 2H); ES-LCMS m/z 442.3 $[M+H]^+$.

Example 146

Synthesis of I-177

I-177

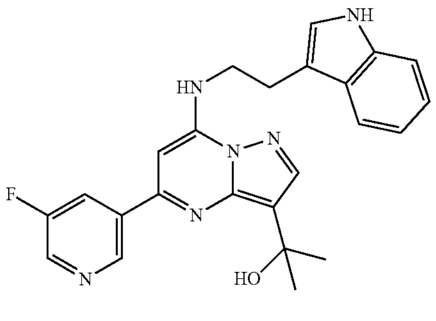 [SMILES: CC(C)(O)c1cnn2c(NCCc3c[nH]c4ccccc34)cc(-c3cncc(F)c3)nc12]

Synthetic Scheme:

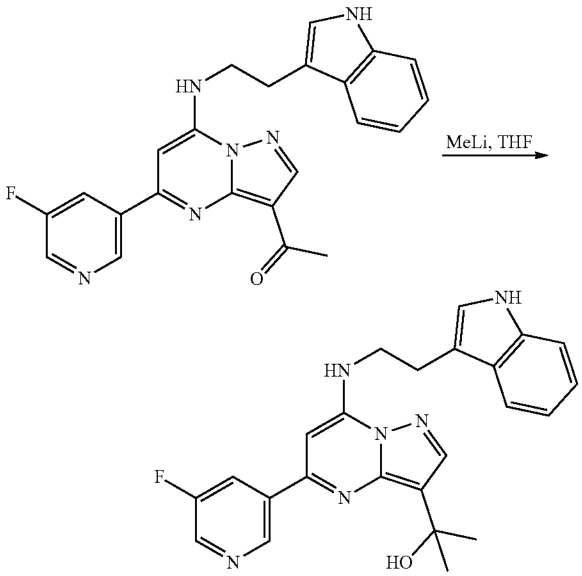

I-177

Step 1: 2-[5-(5-Fluoro-3-pyridyl)-7-[2-(1H-indol-3-yl)ethylamino]pyrazolo[1,5-a]pyrimidin-3-yl]propan-2-ol (I-177)

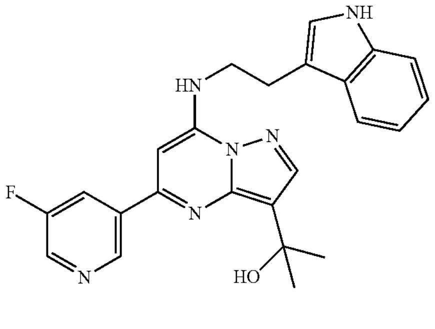

To MeLi (1.3 M, 5 mL, 57.13 eq) was added a solution of 1-[5-(5-fluoro-3-pyridyl)-7-[2-(1H-indol-3-yl)ethylamino]pyrazolo[1,5-a]pyrimidin-3-yl]ethanone (50 mg, 113.77 μmol, 1 eq) in THF (2 mL) dropwise under $N_2$ atmosphere at −20° C. The mixture was stirred under $N_2$ atmosphere at −20° C. for 0.5 h. The reaction was quenched with water (10 mL) and extracted with EtOAc (50 mL×3). The organic layer was dried over $Na_2SO_4$, filtered and concentrated under reduced pressure to yield a residue which was purified by preparative HPLC (column: Agela Durashell C18 150*30 5 u; mobile phase: [water (10 mM $NH_4HCO_3$)-ACN]; B %: 40%-60%, 9 min). The desired fraction was lyophilized to yield 2-[5-(5-fluoro-3-pyridyl)-7-[2-(1H-indol-3-yl)ethylamino]pyrazolo[1,5-a]pyrimidin-3-yl]propan-2-ol (13.48 mg, 31.31 μmol, 27.5% yield, 100.0% purity) as a yellow solid. $^1$H NMR (400 MHz, $CD_3OD$) δ ppm 8.69 (s, 1H), 8.43 (d, J=2.8 Hz, 1H), 7.98 (s, 1H), 7.74 (td, J=2.0, 9.6 Hz, 1H), 7.68 (dd, J=2.8, 6.0 Hz, 1H), 7.24-7.16 (m, 1H), 7.09-7.02 (m, 2H), 6.98 (s, 1H), 6.00 (s, 1H), 3.86 (t, J=6.0 Hz, 2H), 3.18 (t, J=6.0 Hz, 2H), 1.72 (s, 6H); ES-LCMS m/z 431.1 $[M+H]^+$.

Example 147

Synthesis of I-179

I-179

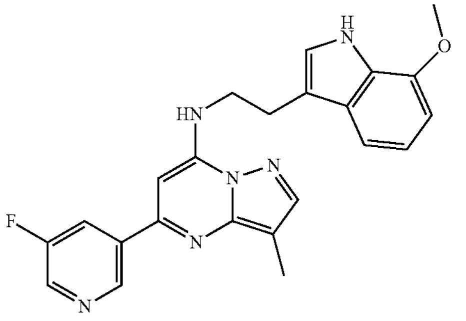

Synthetic Scheme:

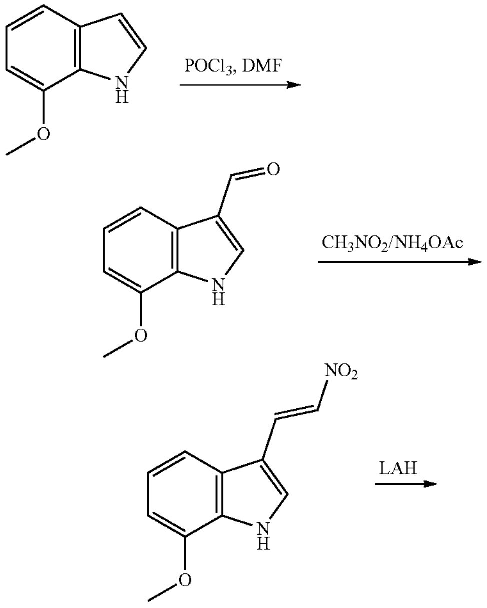

-continued

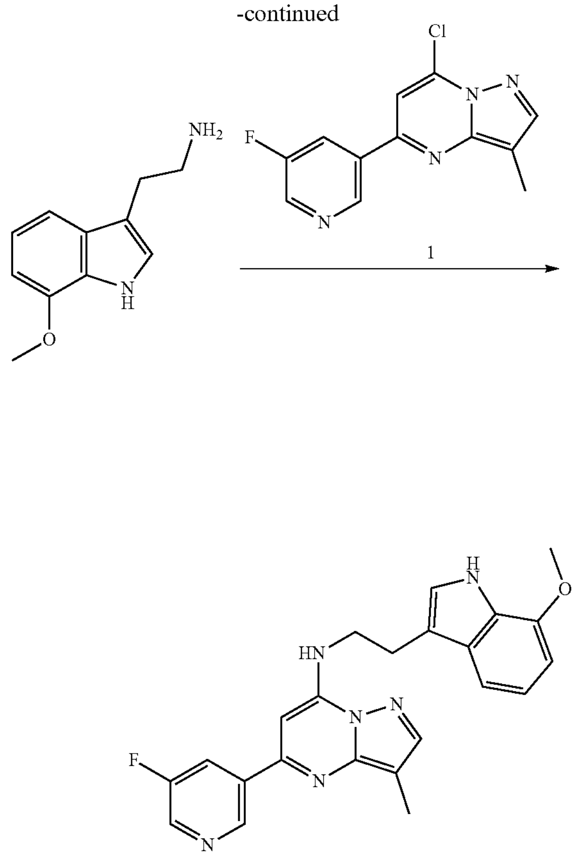

I-179

Step 1: 7-Methoxy-1H-indole-3-carbaldehyde

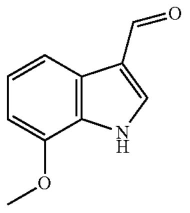

To a solution of $POCl_3$ (1.13 g, 7.37 mmol, 684.85 μL, 1.08 eq) in DMF (12 mL) was added 7-methoxy-1H-indole (1 g, 6.79 mmol, 884.96 μL, 1 eq) at 0° C. The mixture was stirred at 0-20° C. for 3 h under $N_2$ atmosphere. TLC (PE/EtOAc=3/1, $R_f$=0.25) indicated one major new spot was detected. The mixture was adjusted pH to 10-12 with 2 N NaOH. The mixture was extracted with DCM (30 mL×3). The combined organic layers were dried over $Na_2SO_4$, filtered and concentrated to yield the residue which was purified on silica gel column chromatography (from PE/EtOAc=1/0 to 5/2, TLC: PE/EtOAc=3/1, $R_f$=0.25) to yield 7-methoxy-1H-indole-3-carbaldehyde (900 mg, 5.03 mmol, 74.1% yield, 98.0% purity) as a pink solid. $^1H$ NMR (400 MHz, $CDCl_3$) δ ppm 10.07 (s, 1H), 9.18 (br s, 1H), 7.89 (d, J=7.9 Hz, 1H), 7.81 (d, J=3.1 Hz, 1H), 7.24 (t, J=7.9 Hz, 1H), 6.78 (d, J=7.7 Hz, 1H), 3.98 (s, 3H); ES-LCMS m/z 176.1 $[M+H]^+$.

Step 2: 7-Methoxy-3-[(E)-2-nitrovinyl]-1H-indole

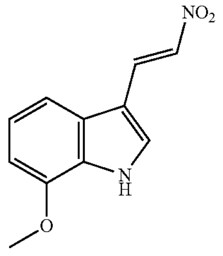 [SMILES: COc1cccc2c(/C=C/[N+](=O)[O-])c[nH]c12]

A mixture of 7-methoxy-1H-indole-3-carbaldehyde (900 mg, 5.03 mmol, 1 eq) and $NH_4OAc$ (504.52 mg, 6.55 mmol, 1.3 eq) in THF (10 mL) was added $CH_3NO_2$ (11.30 g, 185.12 mmol, 10 mL, 36.77 eq). The mixture was degassed and purged with $N_2$ for 3 times and stirred at 80° C. for 19 h under $N_2$ atmosphere. TLC (PE/EtOAc=1/1, $R_f$=0.60) indicated one major new spot was detected. The reaction mixture was concentrated under reduced pressure to yield a residue which was purified on silica gel column chromatography (from PE/EtOAc=1/0 to 5/2, TLC: PE/EtOAc=1/1, $R_f$=0.60) to yield 7-methoxy-3-[(E)-2-nitrovinyl]-1H-indole (660 mg, 2.87 mmol, 57.1% yield, 95.0% purity) as a orange solid. $^1H$ NMR (400 MHz, $CDCl_3$) δ ppm 8.92 (br s, 1H), 8.29 (d, J=13.5 Hz, 1H), 7.79 (d, J=13.5 Hz, 1H), 7.63 (d, J=3.1 Hz, 1H), 7.38 (d, J=8.2 Hz, 1H), 7.26-7.24 (m, 1H), 6.80 (d, J=7.7 Hz, 1H), 4.00 (s, 3H).

Step 3: 2-(7-Methoxy-1H-indol-3-yl)ethanamine

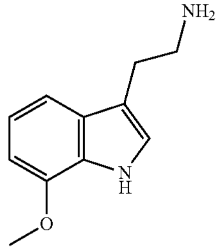

To a solution of 7-methoxy-3-[(E)-2-nitrovinyl]-1H-indole (300 mg, 1.31 mmol, 1 eq) in THF (10 mL) was added $LiAlH_4$ (247.86 mg, 6.53 mmol, 5 eq). The mixture was stirred at 80° C. for 2 h under $N_2$ atmosphere. TLC (PE/EtOAc=3/1, $R_f$=0.10) indicated one major new spot was detected. $H_2O$ (2 mL) was added, followed by 2N NaOH (1 mL) to the mixture. The mixture was filtered and concentrated to yield 2-(7-methoxy-1H-indol-3-yl)ethanamine (240 mg, 1.20 mmol, 91.8% yield, 95.0% purity) as yellow solid which was used in the next step without further purification. $^1H$ NMR (400 MHz, $CDCl_3$) δ ppm 8.22 (br s, 1H), 7.23 (d, J=7.8 Hz, 1H), 7.07-7.01 (m, 2H), 6.66 (d, J=7.6 Hz, 1H), 3.97 (s, 3H), 3.06-3.01 (m, 2H), 2.93-2.87 (m, 2H).

Step 4: 5-(5-Fluoro-3-pyridyl)-N-[2-(7-methoxy-1H-indol-3-yl)ethyl]-3-methyl-pyrazolo[1,5-a]pyrimidin-7-amine (I-179)

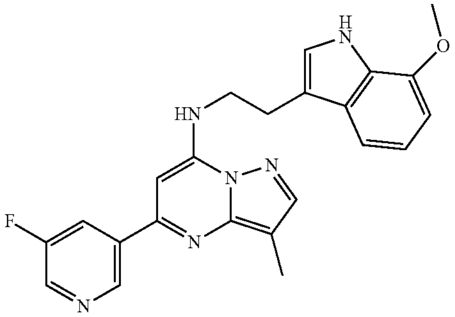 [SMILES: COc1cccc2c(CCNc3cc(-c4cncc(F)c4)nc4c(C)cnn34)c[nH]c12]

A mixture of 7-chloro-5-(5-fluoro-3-pyridyl)-3-methyl-pyrazolo[1,5-a]pyrimidine (230 mg, 855.48 μmol, 1 eq), 2-(7-methoxy-1H-indol-3-yl)ethanamine (217.00 mg, 1.03 mmol, 1.2 eq) and DIEA (331.70 mg, 2.57 mmol, 447.03 μL, 3 eq) in i-PrOH (10 mL) was degassed and purged with $N_2$ for 3 times. The mixture was stirred at 80° C. for 16 h under $N_2$ atmosphere. The reaction mixture was concentrated under reduced pressure to yield a residue which was purified by preparative HPLC (column: Agela DuraShell 150 mm_25 mm_5 μm; mobile phase: [water (0.05% HCl)-ACN]; B %: 35%-65%, 9 min), followed by lyophilization to yield 5-(5-fluoro-3-pyridyl)-N-[2-(7-methoxy-1H-indol-3-yl)ethyl]-3-methyl-pyrazolo[1,5-a]pyrimidin-7-amine (240 mg, 490.42 μmol, 57.3% yield, 100.0% purity, 2HCl) as a yellow solid. $^1H$ NMR (400 MHz, $CD_3OD$) δ ppm 8.72 (d, J=2.7 Hz, 1H), 8.30 (s, 1H), 8.10 (s, 1H), 7.43 (td, J=2.3, 9.0 Hz, 1H), 7.15 (d, J=7.8 Hz, 1H), 6.87 (s, 1H), 6.80 (t, J=7.8 Hz, 1H), 6.48 (d, J=7.6 Hz, 1H), 5.62 (s, 1H), 4.04-3.98 (m, 2H), 3.81 (s, 3H), 3.21-3.16 (m, 2H), 2.29 (s, 3H); ES-LCMS m/z 417.1 $[M+H]^+$.

Example 148

Synthesis of I-180

I-180

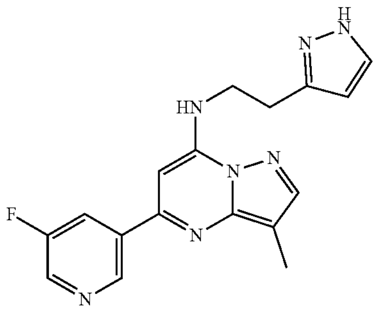

Synthetic Scheme:

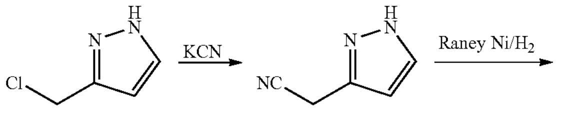

-continued

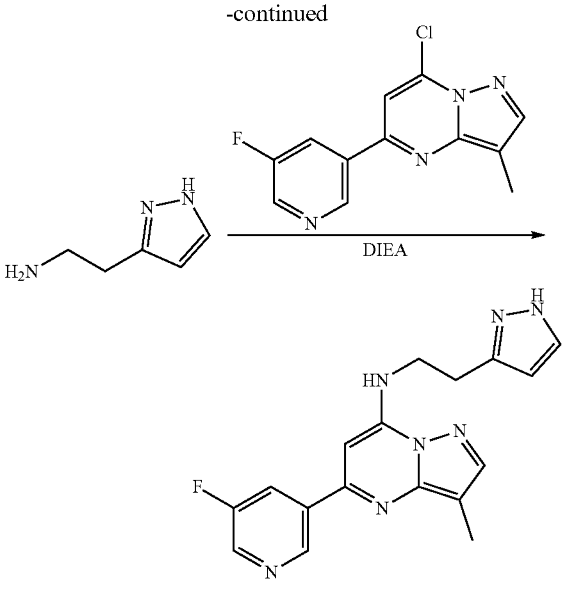

I-180

Step 1: 2-(1H-Pyrazol-3-yl)acetonitrile

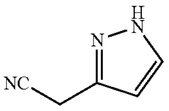

To a solution of 3-(chloromethyl)-1H-pyrazole (350 mg, 2.29 mmol, 1 eq, HCl) in $CH_3CN$ (5 mL) was added KCN (300 mg, 4.61 mmol, 197.37 μL, 2.01 eq) and $H_2O$ (1 mL). The mixture was stirred at 50° C. for 12 h. TLC (DCM/MeOH=10/1, $R_f$=0.4) indicated starting material was consumed completely and one new spot formed. The reaction mixture was diluted with $H_2O$ (10 mL) and extracted with EtOAc (20 mL×3). The combined organic layers were dried over $Na_2SO_4$, filtered and concentrated under reduced pressure to yield 2-(1H-pyrazol-3-yl)acetonitrile (150 mg, 1.33 mmol, 58.2% yield, 95.0% purity) as a yellow oil which was used in the next step without further purification. $^1H$ NMR (400 MHz, DMSO-$d_6$) δ ppm 12.84 (s, 1H), 7.73 (s, 1H), 6.23 (s, 1H), 3.95 (s, 2H); ES-LCMS: No correct mass was found.

Step 2. 2-(1H-Pyrazol-3-yl)ethanamine

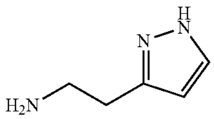

To a solution of 2-(1H-pyrazol-3-yl)acetonitrile (150 mg, 1.33 mmol, 1 eq) in MeOH (10 mL) was added Raney-Ni (600 mg, 7.00 mmol, 5.26 eq) under Ar atmosphere. The suspension was degassed and purged with $H_2$ for 3 times. The mixture was stirred under $H_2$ (15 psi) at 20° C. for 12 h. TLC (DCM/MeOH=10/1, $R_f$=0.4) indicated starting material was consumed completely. The reaction mixture was filtered and concentrated under reduced pressure to yield 2-(1H-pyrazol-3-yl)ethanamine (100 mg, 899.73 μmol, 67.6% yield, crude) as a brown solid which was used in the next step without further purification. $^1$H NMR (400 MHz, DMSO-$d_6$) δ ppm 12.64 (s, 1H), 7.42-7.35 (m, 1H), 5.98 (s, 1H), 3.10-2.94 (m, 2H), 2.82 (d, J=17.6 Hz, 2H); ES-LCMS: No correct mass was found.

Step 3: 5-(5-Fluoro-3-pyridyl)-3-methyl-N-[2-(1H-pyrazol-3-yl)ethyl]pyrazolo[1,5-a]pyrimidin-7-amine (I-180)

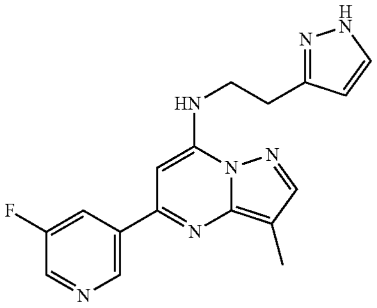 [SMILES: Cc1cnn2c(NCCc3cc[nH]n3)cc(-c3cncc(F)c3)nc12]

To a solution of 7-chloro-5-(5-fluoro-3-pyridyl)-3-methyl-pyrazolo[1,5-a]pyrimidine (75 mg, 279.53 μmol, 1 eq) in i-PrOH (3 mL) was added DIEA (180.64 mg, 1.40 mmol, 243.45 μL, 5 eq) and 2-(1H-pyrazol-3-yl)ethanamine (62.14 mg, 559.07 μmol, 2 eq). The mixture was stirred at 80° C. for 12 h. The reaction mixture was concentrated under reduced pressure to yield a residue which was purified by preparative HPLC (column: Phenomenex Gemini 150*25 mm*10 um; mobile phase: [water (0.05% HCl)-ACN]; B %: 15%-45%, 9 min), followed by lyophilization to yield 5-(5-fluoro-3-pyridyl)-3-methyl-N-[2-(1H-pyrazol-3-yl)ethyl]pyrazolo[1,5-a]pyrimidin-7-amine (21.84 mg, 48.89 μmol, 17.5% yield, 100.0% purity, 3HCl) as a yellow solid. $^1$H NMR (400 MHz, $CD_3OD$) δ ppm 9.07 (s, 1H), 8.88 (d, J=2.4 Hz, 1H), 8.45 (td, J=2.3, 8.9 Hz, 1H), 8.21 (d, J=2.7 Hz, 1H), 8.16 (s, 1H), 7.01 (s, 1H), 6.80 (d, J=2.7 Hz, 1H), 4.16 (t, J=7.0 Hz, 2H), 3.37 (t, J=7.0 Hz, 2H), 2.40 (s, 3H); ES-LCMS m/z 338.1 $[M+H]^+$.

Example 149

Synthesis of I-186

I-186

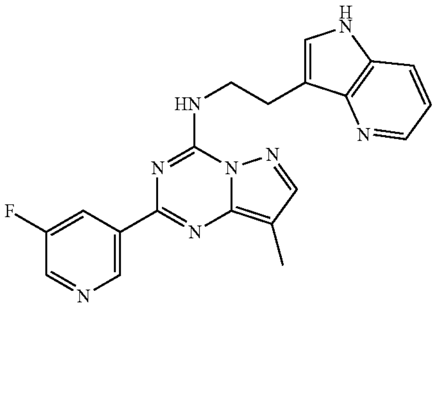 [SMILES: Cc1cnn2c(NCCc3c[nH]c4cccnc34)nc(-c3cncc(F)c3)nc12]

Synthetic Scheme:

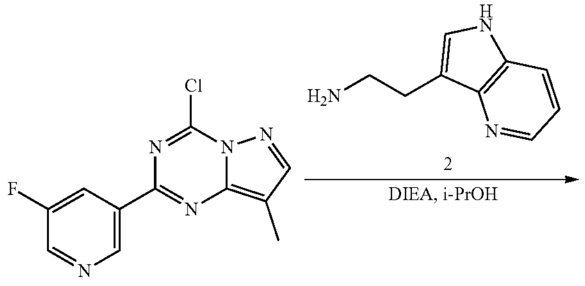

1

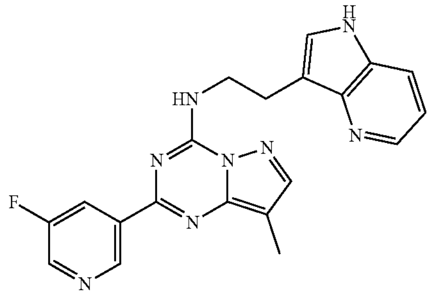

I-186

Step 1: 2-(5-Fluoro-3-pyridyl)-8-methyl-N-[2-(1H-pyrrolo[3,2-b]pyridin-3-yl)ethyl]pyrazolo[1,5-a][1,3,5]triazin-4-amine (I-186)

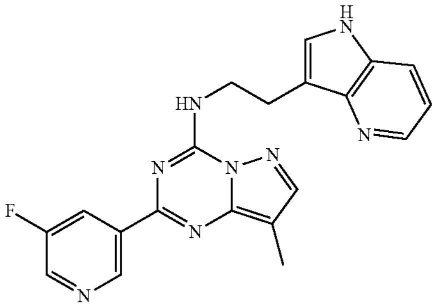

To a solution of 4-chloro-2-(5-fluoro-3-pyridyl)-8-methyl-pyrazolo[1,5-a][1,3,5]triazine (50 mg, 189.64 μmol, 1 eq) in i-PrOH (5 mL) was added DIEA (73.53 mg, 568.92 μmol, 99.09 μL, 3 eq) and 2-(1H-pyrrolo[3,2-b]pyridin-3-yl)ethanamine (40 mg, 248.13 μmol, 1.31 eq). The mixture was stirred at 80° C. for 12 h. The reaction mixture was concentrated under reduced pressure to give the residue which was purified by preparative HPLC (HCl condition; column: Phenomenex Gemini 150*25 mm*10 um; mobile phase: [water(0.05% HCl)-ACN]; B %: 10%-40%, 9 min). The desired fraction was lyophilized to yield 2-(5-fluoro-3-pyridyl)-8-methyl-N-[2-(1H-pyrrolo[3,2-b]pyridin-3-yl)ethyl]pyrazolo[1,5-a][1,3,5]triazin-4-amine (30.06 mg, 60.39 μmol, 31.8% yield, 100.0% purity, 3HCl) as a yellow solid. $^1$H NMR (400 MHz, $CD_3OD$) δ ppm 9.37 (d, J=1.3 Hz, 1H), 8.92 (d, J=2.3 Hz, 1H), 8.82 (d, J=8.8 Hz, 1H), 8.48 (d, J=5.8 Hz, 1H), 8.40 (d, J=8.3 Hz, 1H), 7.98 (d, J=10.5 Hz, 2H), 7.55 (dd, J=5.9, 8.2 Hz, 1H), 4.19 (t, J=6.3 Hz, 2H), 3.38 (t, J=6.4 Hz, 2H), 2.29 (s, 3H); ES-LCMS m/z 389.1 $[M+H]^+$.

Example 150

Synthesis of I-187b

I-187b

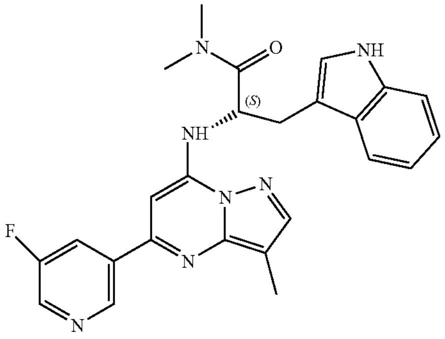

Synthetic Scheme:

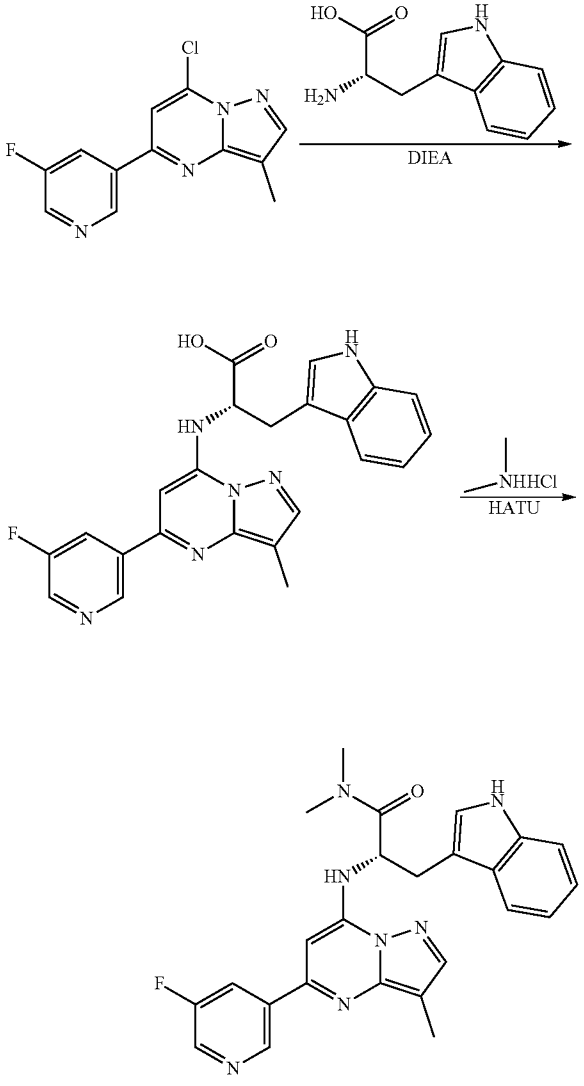

I-187b

Step 1: (2S)-2-[[5-(5-Fluoro-3-pyridyl)-3-methyl-pyrazolo[1,5-a]pyrimidin-7-yl]amino]-3-(1H-indol-3-yl)propanoic Acid

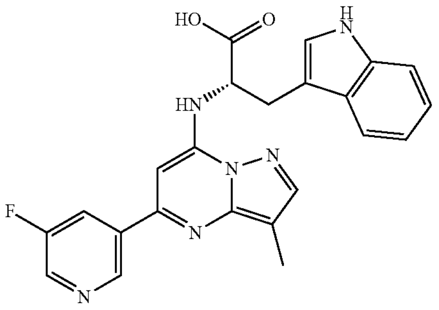 [SMILES: Cc1cnn2c(N[C@@H](Cc3c[nH]c4ccccc34)C(=O)O)cc(-c3cncc(F)c3)nc12]

A mixture of 7-chloro-5-(5-fluoro-3-pyridyl)-3-methyl-pyrazolo[1,5-a]pyrimidine (100 mg, 380.71 μmol, 1 eq), (2S)-2-amino-3-(1H-indol-3-yl)propanoic acid (77.75 mg, 380.71 μmol, 1 eq), DIEA (147.61 mg, 1.14 mmol, 198.93 μL, 3 eq) in i-PrOH (10 mL) was stirred at 80° C. for 12 h. The reaction mixture was concentrated to yield (2S)-2-[[5-(5-fluoro-3-pyridyl)-3-methyl-pyrazolo[1,5-a]pyrimidin-7-yl]amino]-3-(1H-indol-3-yl)propanoic acid (160 mg, 371.72 μmol, 97.6% yield, 100.0% purity) as brown oil which was used in the next step without further purification. $^1$H NMR (400 MHz, DMSO-$d_6$) δ ppm 10.69 (s, 1H), 8.91 (s, 1H), 8.57 (d, J=2.7 Hz, 1H), 7.96 (d, J=10.0 Hz, 1H), 7.88 (s, 1H), 7.59-7.50 (m, 2H), 7.19 (d, J=8.1 Hz, 1H), 7.02-6.94 (m, 2H), 6.91-6.85 (m, 1H), 6.29 (s, 1H), 4.62 (s, 1H), 3.58-3.54 (m, 1H), 2.94 (s, 2H), 2.21 (s, 3H); ES-LCMS m/z 431.2 $[M+H]^+$.

Step 2: (2S)-2-[[5-(5-Fluoro-3-pyridyl)-3-methyl-pyrazolo[1,5-a]pyrimidin-7-yl]amino]-3-(1H-indol-3-yl)-N,N-dimethyl-propanamide (I-187b)

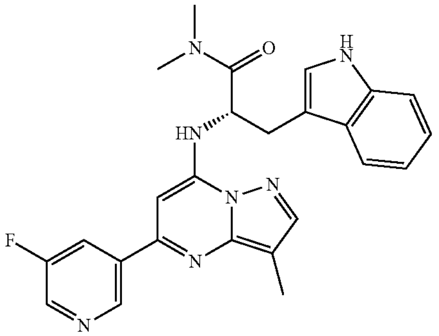 [SMILES: Cc1cnn2c(N[C@@H](Cc3c[nH]c4ccccc34)C(=O)N(C)C)cc(-c3cncc(F)c3)nc12]

To a solution of (2S)-2-[[5-(5-fluoro-3-pyridyl)-3-methyl-pyrazolo[1,5-a]pyrimidin-7-yl]amino]-3-(1H-indol-3-yl) propanoic acid (80 mg, 183.26 μmol, 1 eq) and N-methyl-methanamine; hydrochloride (29.89 mg, 366.52 μmol, 2.0 eq) in DMF (20 mL) was added HATU (139.36 mg, 366.52 μmol, 2.0 eq) and $Et_3N$ (92.72 mg, 916.30 μmol, 127.54 μL, 5.0 eq). The mixture was stirred at 25° C. for 12 h. The reaction mixture was concentrated under reduced pressure to yield a residue which was purified by preparative HPLC (column: Phenomenex Gemini 150*25 mm*10 μm; mobile phase: [water(0.05% HCl)-ACN]; B %: 30%-60%, 9 min), followed by lyophilization to yield (2S)-2-[[5-(5-fluoro-3-pyridyl)-3-methyl-pyrazolo[1,5-a]pyrimidin-7-yl]amino]-3-(1H-indol-3-yl)-N,N-dimethyl-propanamide (17.77 mg, 32.74 μmol, 17.9% yield, 97.7% purity, 2HCl) as a yellow solid. $^1$H NMR (400 MHz, $CD_3OD$) δ ppm 8.73 (d, J=2.3 Hz, 1H), 8.39 (s, 1H), 8.11 (s, 1H), 7.57 (d, J=8.3 Hz, 1H), 7.45 (d, J=8.0 Hz, 1H), 7.07 (d, J=8.0 Hz, 1H), 7.01 (s, 1H), 6.91 (t, J=7.4 Hz, 1H), 6.84-6.77 (m, 1H), 5.83 (s, 1H), 5.40 (d, J=8.5 Hz, 1H), 3.52 (dd, J=3.0, 14.6 Hz, 1H), 3.31 (s, 3H), 3.13-3.07 (m, 1H), 3.04 (s, 3H), 2.27 (s, 3H); ES-LCMS m/z 458.3 $[M+H]^+$.

Example 151

Synthesis of I-192

I-192

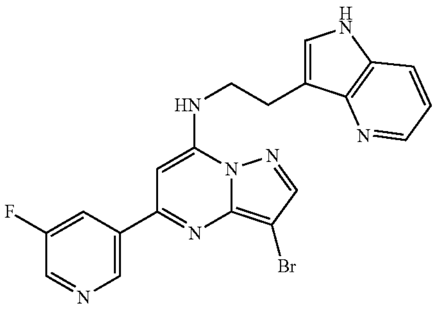 [SMILES: Fc1cncc(-c2cc(NCCc3c[nH]c4cccnc34)n3ncc(Br)c3n2)c1]

Synthetic Scheme:

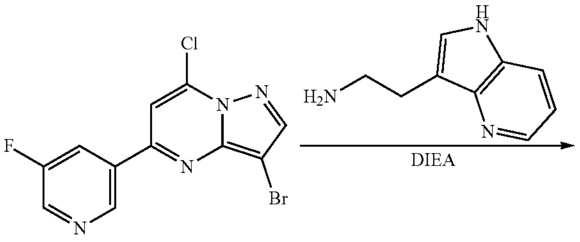

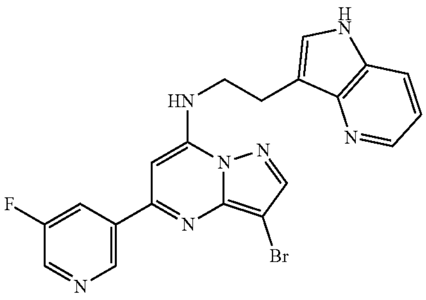

I-192

Step 1: 3-Bromo-5-(5-fluoro-3-pyridyl)-N-[2-(1H-pyrrolo[3,2-b]pyridin-3-yl)ethyl]pyrazolo[1,5-a]pyrimidin-7-amine (I-192)

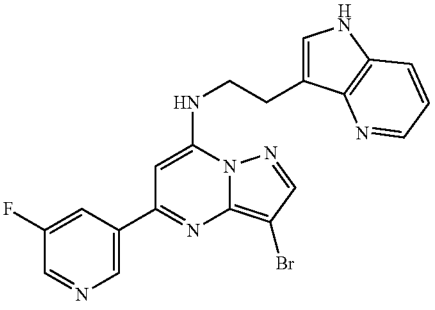

To a solution of 3-bromo-7-chloro-5-(5-fluoro-3-pyridyl)pyrazolo[1,5-a]pyrimidine (100 mg, 305.31 μmol, 1 eq) in i-PrOH (5 mL) was added 2-(1H-pyrrolo[3,2-b]pyridin-3-yl)ethanamine (50 mg, 310.17 μmol, 1.02 eq) and DIEA (118.38 mg, 915.92 μmol, 159.54 μL, 3 eq). The mixture was stirred at 60° C. for 12 h under $N_2$ atmosphere. The reaction mixture was concentrated under reduced pressure to yield a residue which was purified by preparative HPLC (column: Phenomenex Gemini 150*25 mm*10 μm; mobile phase: [water(0.05% HCl)-ACN]; B %: 25%-55%, 9 min), followed by lyophilization to yield 3-bromo-5-(5-fluoro-3-pyridyl)-N-[2-(1H-pyrrolo[3,2-b]pyridin-3-yl)ethyl]pyrazolo[1,5-a]pyrimidin-7-amine (37.41 mg, 65.74 μmol, 21.5% yield, 98.7% purity, 3HCl) as a yellow solid. $^1$H NMR (400 MHz, $CD_3OD$) δ ppm 9.11 (s, 1H), 8.72 (d, J=2.5 Hz, 1H), 8.50-8.47 (m, 2H), 8.46 (s, 1H), 8.12 (s, 1H), 8.05 (s, 1H), 7.62 (dd, J=5.9, 8.2 Hz, 1H), 6.69 (s, 1H), 4.03 (t, J=6.7 Hz, 2H), 3.39 (t, J=6.8 Hz, 2H); ES-LCMS m/z 452.0, 454.0 $[M+H]^+$.

Example 152

Synthesis of I-195

I-195

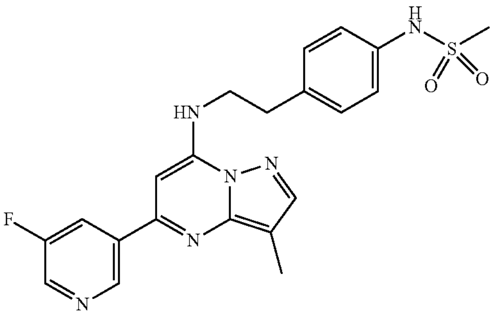

Synthetic Scheme:

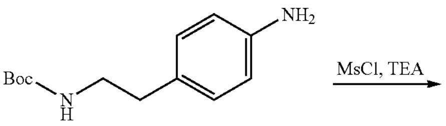

1

-continued

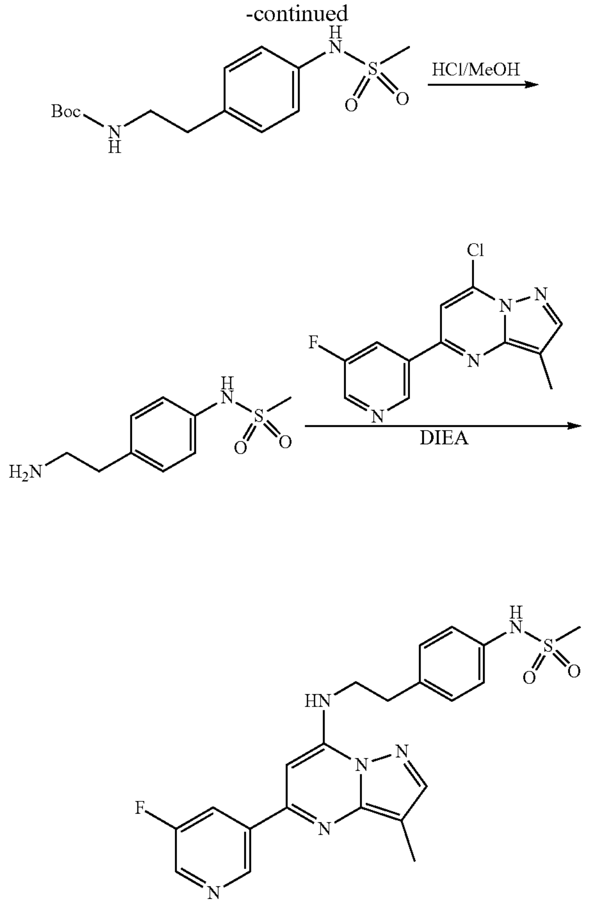

I-195

Step 1: tert-Butyl N-[2-[4-(methanesulfonamido)phenyl]ethyl]carbamate

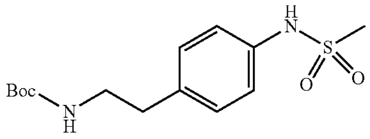 [SMILES: CC(C)(C)OC(=O)NCCc1ccc(NS(C)(=O)=O)cc1]

To a solution of tert-butyl N-[2-(4-aminophenyl)ethyl]carbamate (150 mg, 634.76 μmol, 1 eq) in DCM (10 mL) was added MsCl (327.20 mg, 2.86 mmol, 221.08 μL, 4.5 eq) and TEA (321.16 mg, 3.17 mmol, 441.76 μL, 5 eq). The mixture was stirred at 20° C. for 20 h. The reaction mixture was quenched by addition of saturated $NaHCO_3$ (50 mL), extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 1/1, TLC: PE/EtOAc=1/1, $R_f$=0.37) to yield tert-butyl N-[2-[4-(methanesulfonamido)phenyl]ethyl]carbamate (190 mg, 186.13 μmol, 29.3% yield, 30.8% purity) as colorless oil. $^1$H NMR (400 MHz, $CDCl_3$) δ ppm 7.25-7.11 (m, 4H), 6.45 (br s, 1H), 4.58-4.49 (m, 1H), 3.37 (d, J=6.8 Hz, 2H), 3.01 (s, 3H), 2.79 (t, J=7.0 Hz, 2H), 1.44 (s, 9H); ES-LCMS m/z 337.1 $[M+Na]^+$.

Step 2: N-[4-(2-Aminoethyl)phenyl]methanesulfonamide

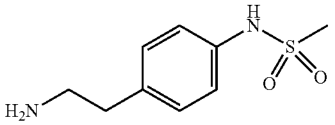

To a solution of tert-butyl N-[2-[4-(methanesulfonamido)phenyl]ethyl]carbamate (190 mg, 186.13 mol, 1 eq) in DCM (3 mL) was added TFA (212.23 mg, 1.86 mmol, 137.81 μL, 10 eq). The mixture was stirred at 20° C. for 20 min. TLC (PE/EtOAc=1/1, $R_f$=0.06) showed that the starting material was consumed. The reaction mixture was concentrated under reduced pressure to yield a crude N-[4-(2-aminoethyl)phenyl]methanesulfonamide (61 mg, crude, TFA) as yellow oil which was used in the next step without further purification.

Step 3: N-[4-[2-[[5-(5-Fluoro-3-pyridyl)-3-methyl-pyrazolo[1,5-a]pyrimidin-7-yl]amino]ethyl]phenyl]methanesulfonamide (I-195)

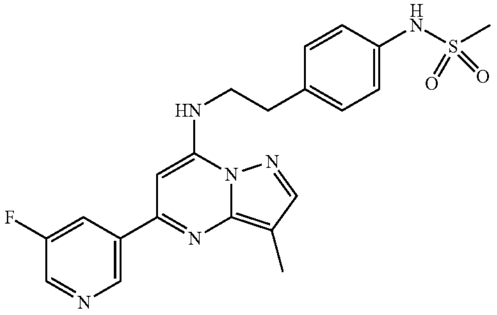 [SMILES: Cc1cnn2c(NCCc3ccc(NS(C)(=O)=O)cc3)cc(-c3cncc(F)c3)nc12]

To a solution of 7-chloro-5-(5-fluoro-3-pyridyl)-3-methyl-pyrazolo[1,5-a]pyrimidine (48.80 mg, 185.80 μmol, 1 eq) in i-PrOH (10 mL) was added DIEA (120.07 mg, 929.01 μmol, 161.81 μL, 5 eq) and N-[4-(2-aminoethyl)phenyl]methanesulfonamide (61 mg, 185.80 μmol, 1 eq, TFA). The mixture was stirred at 60° C. for 12 h. The reaction mixture was concentrated under reduced pressure to yield a residue which was purified by preparative HPLC (column: Phenomenex Gemini C18 250*50 mm*10 m; mobile phase: [water (0.05% HCl)-ACN]; B %: 25%-55%, 9 min), followed by lyophilization to yield N-[4-[2-[[5-(5-fluoro-3-pyridyl)-3-methyl-pyrazolo[1,5-a]pyrimidin-7-yl]amino]ethyl]phenyl]methanesulfonamide (50.35 mg, 95.81 μmol, 51.5% yield, 97.7% purity, 2HCl) as a yellow solid. $^1$H NMR (400 MHz, $CD_3OD$) δ ppm 8.89 (s, 1H), 8.85 (d, J=2.3 Hz, 1H), 8.27-8.22 (m, 1H), 8.14 (s, 1H), 7.26 (d, J=8.3 Hz, 2H), 7.08 (d, J=8.5 Hz, 2H), 6.53 (s, 1H), 4.01 (t, J=6.7 Hz, 2H), 3.08 (t, J=6.7 Hz, 2H), 2.87 (s, 3H), 2.36 (s, 3H); ES-LCMS m/z 441.0 $[M+H]^+$.

Example 153

Synthesis of I-196

I-196

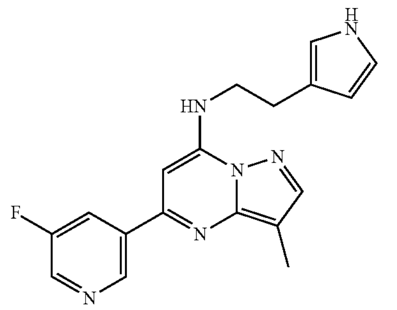

Synthetic Scheme:

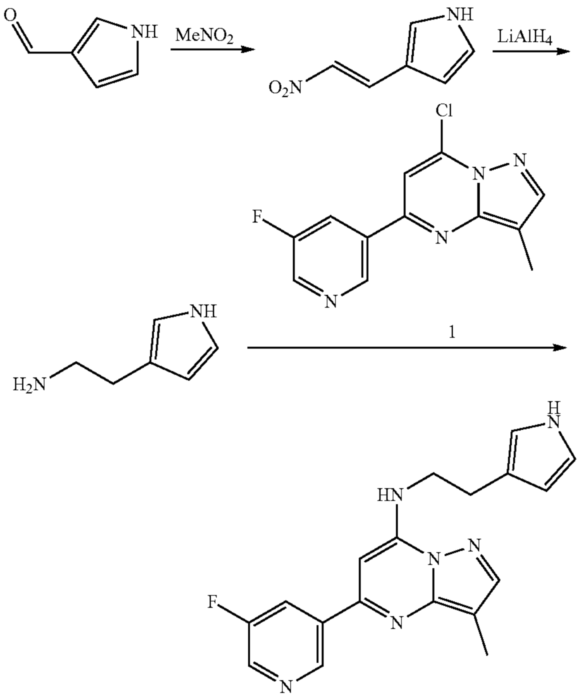

I-196

Step 1: 3-[(E)-2-Nitrovinyl]-1H-pyrrole

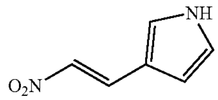

To a solution of 1H-pyrrole-3-carbaldehyde (1 g, 10.52 mmol, 1 eq) in $CH_3NO_2$ (10 mL) and THF (10 mL) was added $NH_4OAc$ (891.60 mg, 11.57 mmol, 1.1 eq). The mixture was stirred at 80° C. for 12 h. TLC (TLC: PE/EtOAc=3/1, $R_f$=0.45) indicated no starting material was remained and one major new spot with lower polarity was detected. The reaction mixture was concentrated under reduced pressure to yield a residue which was purified on silica gel column chromatography (from PE/EtOAc=1/0 to 10/3, TLC: PE/EtOAc=3/1, $R_f$=0.45) to yield the product 3-[(E)-2-nitrovinyl]-1H-pyrrole (1.2 g, 7.82 mmol, 74.4% yield, 90.0% purity) as a yellow solid. $^1$H NMR (400 MHz, $CDCl_3$) δ ppm 8.64 (br s, 1H), 8.03 (d, J=13.4 Hz, 1H), 7.44 (d, J=13.3 Hz, 1H), 7.22 (td, J=1.6, 2.8 Hz, 1H), 6.88 (q, J=2.4 Hz, 1H), 6.49-6.43 (m, 1H).

Step 2: 2-(1H-Pyrrol-3-yl)ethanamine

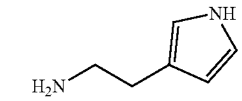

To a solution of 3-[(E)-2-nitrovinyl]-1H-pyrrole (300 mg, 1.95 mmol, 1 eq) in THF (20 mL) was added $LiAlH_4$ (370.96 mg, 9.77 mmol, 5.0 eq) under ice-baths. The mixture was stirred at 80° C. for 2 h. TLC (TLC: PE/EtOAc=3/1, $R_f$=0.56) indicated no starting material was remained and one major new spot with larger polarity was detected. The reaction mixture was quenched by addition $H_2O$ (1.5 mL), 1N NaOH (1.5 mL) and $H_2O$ (1.5 mL) under ice-baths, filtered and concentrated under reduced pressure to yield the crude product 2-(1H-pyrrol-3-yl)ethanamine (180 mg, 1.63 mmol, 83.6% yield, crude purity) as brown oil which was used in the next step without further purification. $^1$H NMR (400 MHz, $CDCl_3$) δ ppm 8.12 (br s, 1H), 6.80-6.72 (m, 1H), 6.63 (d, J=1.3 Hz, 1H), 6.14-6.08 (m, 1H), 2.93-2.85 (m, 2H), 2.63 (t, J=6.7 Hz, 2H).

Step 3: 5-(5-Fluoro-3-pyridyl)-3-methyl-N-[2-(1H-pyrrol-3-yl)ethyl]pyrazolo[1,5-a]pyrimidin-7-amine (I-196)

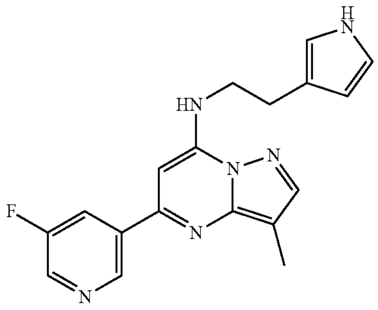 [SMILES: Cc1cnn2c(NCCc3cc[nH]c3)cc(-c3cncc(F)c3)nc12]

To a solution of 7-chloro-5-(5-fluoro-3-pyridyl)-3-methyl-pyrazolo[1,5-a]pyrimidine (50 mg, 190.35 μmol, 1 eq) and 2-(1H-pyrrol-3-yl)ethanamine (41.94 mg, 380.71 μmol, 2.0 eq) in i-PrOH (10 mL) was added DIEA (73.81 mg, 571.06 μmol, 99.47 μL, 3.0 eq). The mixture was stirred at 70° C. for 3 h. The reaction mixture was concentrated under reduced pressure to yield a residue which was purified by preparative HPLC (column: Agela ASB 150*25 mm*5 um; mobile phase: [water (0.05% HCl)-ACN]; B %: 30%-60%, 9 min) to yield the residue which was purified by preparative HPLC (column: Phenomenex Gemini 150*25 mm*10 um; mobile phase: [water (0.05% ammonia hydroxide v/v)-ACN]; B %: 35%-65%, 10 min), followed by lyophilization to yield 5-(5-fluoro-3-pyridyl)-3-methyl-N-

[2-(1H-pyrrol-3-yl)ethyl]pyrazolo[1,5-a]pyrimidin-7-amine (15.72 mg, 46.73 μmol, 24.6% yield, 100.0% purity) as a yellow solid. $^1$H NMR (400 MHz, $CD_3OD$) δ ppm 9.03 (s, 1H), 8.53 (d, J=2.7 Hz, 1H), 8.19 (d, J=9.5 Hz, 2H), 7.87 (s, 1H), 6.80 (d, J=2.4 Hz, 1H), 6.72 (s, 1H), 6.48 (br s, 1H), 6.27 (s, 1H), 6.19 (br s, 1H), 3.69 (q, J=6.4 Hz, 2H), 2.99 (t, J=6.8 Hz, 2H), 2.39 (s, 3H); ES-LCMS m/z 337.2 $[M+H]^+$.

Example 154

Synthesis of I-197

I-197

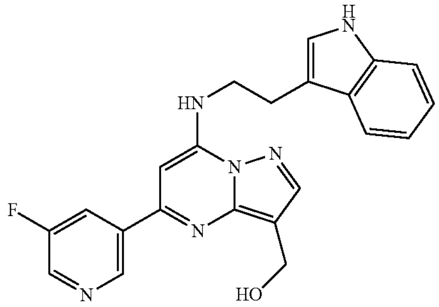 [SMILES: OCc1cnn2c(NCCc3c[nH]c4ccccc34)cc(-c3cncc(F)c3)nc12]

Synthetic Scheme:

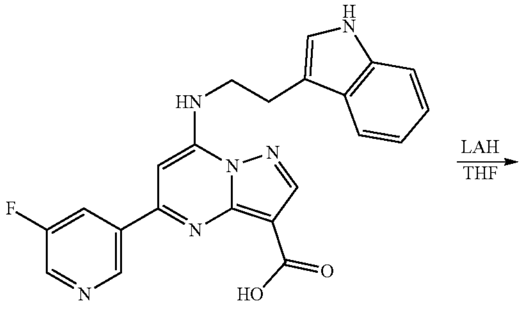

1

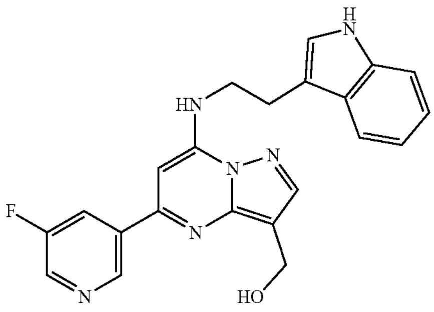

I-197

Step 1: [5-(5-Fluoro-3-pyridyl)-7-[2-(1H-indol-3-yl)ethylamino]pyrazolo[1,5-a]pyrimidin-3-yl]methanol (I-197)

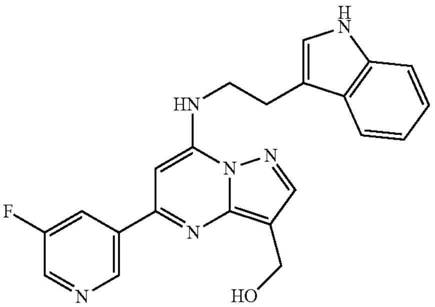

To a solution of 5-(5-fluoro-3-pyridyl)-7-[2-(1H-indol-3-yl)ethylamino]pyrazolo[1,5-a]pyrimidine-3-carboxylic acid (50 mg, 110.71 μmol, 1 eq) in THF (8 mL) was added LAH (50 mg, 1.32 mmol, 11.90 eq) at 0° C. The mixture was stirred at 80° C. for 12 h under $N_2$ atmosphere. The reaction mixture was diluted with THF (40 mL), quenched by addition of water (0.5 mL), 10% NaOH (0.5 mL) and water (1.5 mL) in sequence at 0° C. After being stirred for 30 min, the mixture was filtered through celite. The filtrate was concentrated under reduced pressure to yield a residue which was purified by preparative HPLC (column: Xbridge 150*30 mm*10 μm; mobile phase: [water (0.05% ammonia hydroxide v/v)-ACN]; B %: 25%-55%, 8 min), followed by lyophilization to yield [5-(5-fluoro-3-pyridyl)-7-[2-(1H-indol-3-yl)ethylamino]pyrazolo[1,5-a]pyrimidin-3-yl]methanol (6 mg, 14.91 μmol, 13.5% yield, 100% purity) as a yellow solid. $^1$H NMR (400 MHz, $CD_3OD$) δ ppm 8.65 (s, 1H), 8.47 (d, J=2.7 Hz, 1H), 8.06 (s, 1H), 7.74 (d, J=9.8 Hz, 1H), 7.71-7.66 (m, 1H), 7.24-7.18 (m, 1H), 7.12-7.02 (m, 2H), 6.98 (s, 1H), 6.00 (s, 1H), 4.80 (s, 2H), 3.88 (t, J=6.2 Hz, 2H), 3.20 (t, J=6.1 Hz, 2H); ES-LCMS m/z 403.2 $[M+H]^+$.

Example 155

Synthesis of I-198a, I-198b and I-198c

I-198a

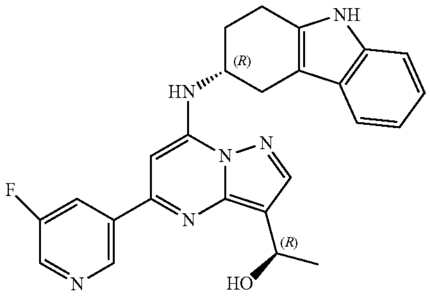

-continued
I-198b
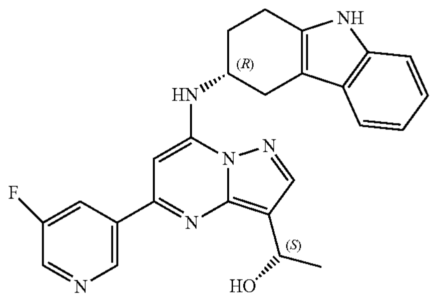
I-198c
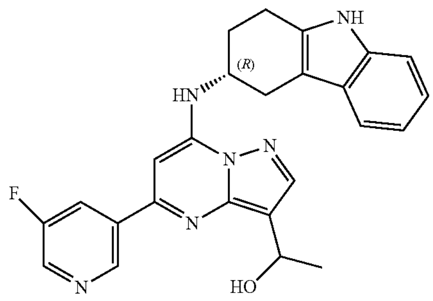
Synthetic Scheme:
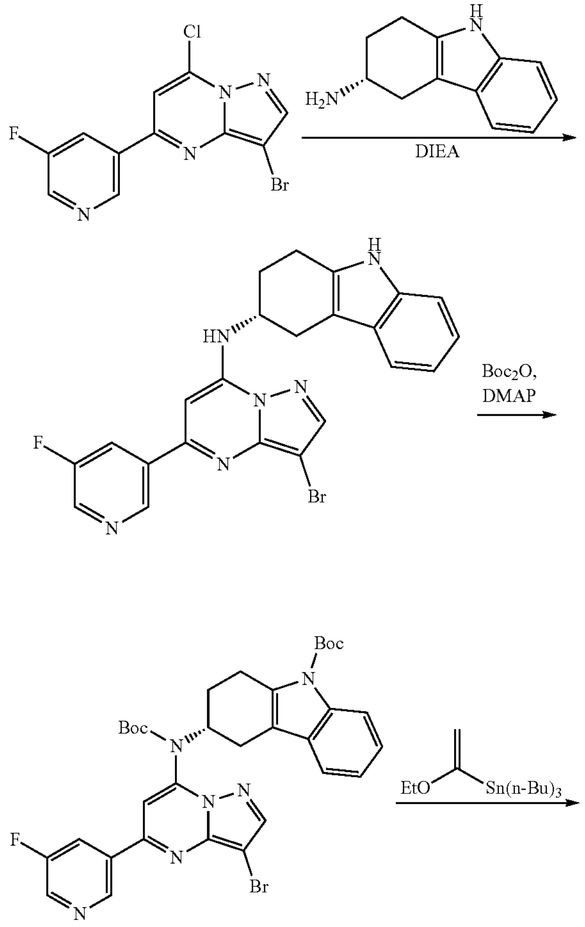
-continued
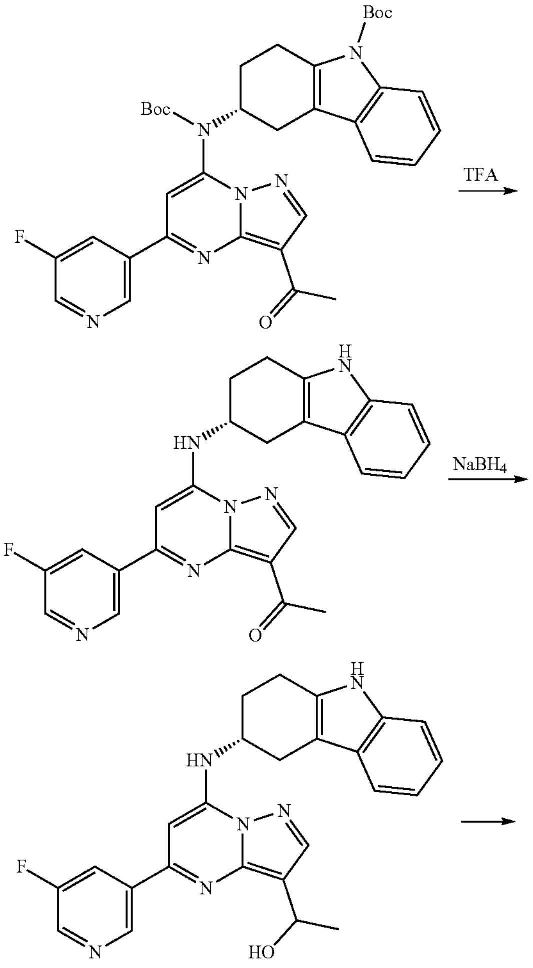
I-198c
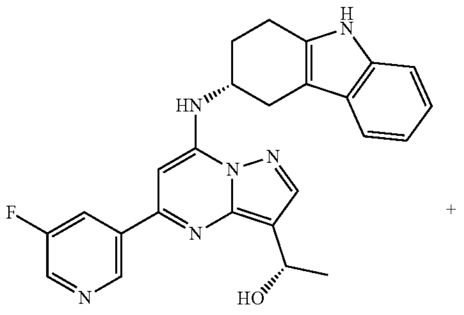
+
I-198b
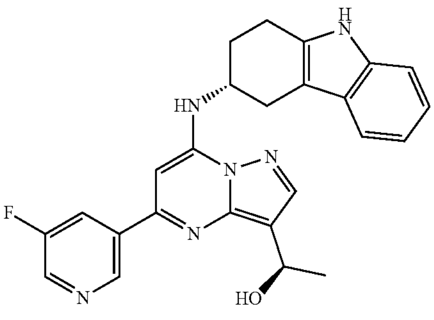
I-198a Step 1: (3R)—N-[3-bromo-5-(5-fluoro-3-pyridyl)pyrazolo[1,5-a]pyrimidin-7-yl]-2,3,4,9-tetrahydro-1H-carbazol-3-amine

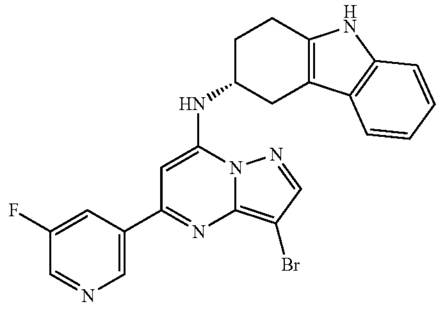 [SMILES: Fc1cncc(-c2cc(N[C@@H]3CCc4[nH]c5ccccc5c4C3)n3ncc(Br)c3n2)c1]

A mixture of 3-bromo-7-chloro-5-(5-fluoro-3-pyridyl)pyrazolo[1,5-a]pyrimidine (440 mg, 1.34 mmol, 1 eq), (3R)-2,3,4,9-tetrahydro-1H-carbazol-3-amine (274.54 mg, 1.47 mmol, 1.1 eq) and DIEA (519.56 mg, 4.02 mmol, 700.21 μL, 3 eq) in i-PrOH (10 mL) was stirred at 80° C. for 12 h. The reaction mixture was concentrated to yield the residue which was purified on silica gel column chromatography (from PE/EtOAc=1/0 to 2/1, TLC: PE/EtOAc=2/1, $R_f$=0.25) to yield (3R)—N-[3-bromo-5-(5-fluoro-3-pyridyl)pyrazolo[1,5-a]pyrimidin-7-yl]-2,3,4,9-tetrahydro-1H-carbazol-3-amine (520 mg, 1.06 mmol, 79.2% yield, 97.4% purity) as a yellow solid. $^1$H NMR (400 MHz, DMSO-$d_6$) δ ppm 10.76 (s, 1H), 9.30 (s, 1H), 8.65 (d, J=2.9 Hz, 1H), 8.46 (td, J=2.2, 10.4 Hz, 1H), 8.32-8.24 (m, 2H), 7.33 (d, J=7.5 Hz, 1H), 7.24 (d, J=7.9 Hz, 1H), 7.15 (s, 1H), 7.02-6.86 (m, 2H), 4.49 (td, J=4.8, 9.4 Hz, 1H), 3.14-2.98 (m, 2H), 2.94-2.79 (m, 2H), 2.23-2.10 (m, 2H); ES-LCMS m/z 477.1, 479.1 $[M+H]^+$.

Step 2: tert-Butyl (3R)-3-[[3-bromo-5-(5-fluoro-3-pyridyl)pyrazolo[1,5-a]pyrimidin-7-yl]-tert-butoxy-carbonyl-amino]-1,2,3,4-tetrahydrocarbazole-9-carboxylate

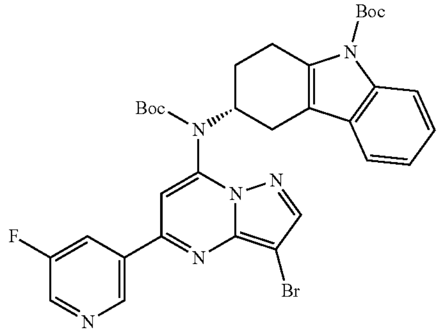 [SMILES: CC(C)(C)OC(=O)N(c1cc(-c2cncc(F)c2)nc2c(Br)cnn12)[C@@H]1CCc2c(c3ccccc3n2C(=O)OC(C)(C)C)C1]

A mixture of (3R)—N-[3-bromo-5-(5-fluoro-3-pyridyl)pyrazolo[1,5-a]pyrimidin-7-yl]-2,3,4,9-tetrahydro-1H-carbazol-3-amine (500 mg, 1.02 mmol, 1 eq), $Boc_2O$ (556.67 mg, 2.55 mmol, 585.97 μL, 2.5 eq) and DMAP (373.93 mg, 3.06 mmol, 3 eq) in 1,4-dioxane (10 mL) was stirred at 110° C. for 5 h. The reaction mixture was concentrated to yield a residue which was purified by flash silica gel chromatography (from pure PE to PE/EtOAc=3/1, TLC: PE/EtOAc=3/1, $R_f$=0.7) to yield tert-butyl (3R)-3-[[3-bromo-5-(5-fluoro-3-pyridyl)pyrazolo[1,5-a]pyrimidin-7-yl]-tert-butoxycarbonyl-amino]-1,2,3,4-tetrahydrocarbazole-9-carboxylate (600 mg, 664.15 umol, 65.1% yield, 75.0% purity) as a yellow solid. $^1$H NMR (400 MHz, $CDCl_3$) δ ppm 9.06 (s, 1H), 8.60 (d, J=3.0 Hz, 1H), 8.26-8.18 (m, 2H), 8.06 (d, J=8.0 Hz, 1H), 7.29 (s, 1H), 7.25-7.13 (m, 3H), 4.86-4.76 (m, 1H), 3.26-3.16 (m, 2H), 2.66 (d, J=10.5 Hz, 1H), 2.36 (m, 1H), 2.10-1.92 (m, 2H), 1.64 (s, 9H), 1.34 (s, 9H); ES-LCMS m/z 677.2, 679.2 $[M+H]^+$.

Step 3: tert-Butyl (3R)-3-[[3-acetyl-5-(5-fluoro-3-pyridyl)pyrazolo[1,5-a]pyrimidin-7-yl]-tert-butoxy-carbonyl-amino]-1,2,3,4-tetrahydrocarbazole-9-carboxylate

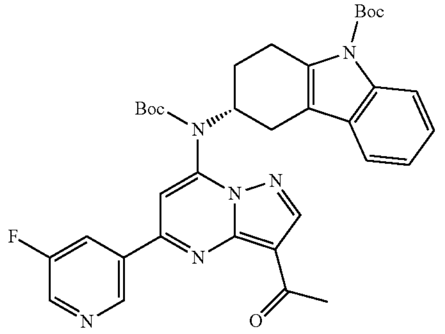 [SMILES: CC(=O)c1cnn2c(N(C(=O)OC(C)(C)C)[C@@H]3CCc4c(c5ccccc5n4C(=O)OC(C)(C)C)C3)cc(-c3cncc(F)c3)nc12]

tert-Butyl (3R)-3-[[3-bromo-5-(5-fluoro-3-pyridyl)pyrazolo[1,5-a]pyrimidin-7-yl]-tert butoxycarbonyl-amino]-1,2,3,4-tetrahydrocarbazole-9-carboxylate (550 mg, 608.80 μmol, 1 eq), tributyl(1-ethoxyvinyl)stannane (1.02 g, 2.82 mmol, 953.27 μL, 4.64 eq) and Pd(dppf)$Cl_2$ (89.09 mg, 121.76 μmol, 0.2 eq) in toluene (8 mL) were taken up into a microwave tube and then purged with $N_2$ for 1 min. The sealed tube was heated at 120° C. for 5 h under microwave (1 bar). To the mixture was added aqueous KF (10 mL, 1 g/10 mL). The mixture was stirred at 25° C. for 30 minutes and extracted with EtOAc (30 mL×3). The organic layer was dried over $Na_2SO_4$, filtered and concentrated to yield a residue which was purified by flash silica gel chromatography (from pure PE to PE/EtOAc=3/1, TLC: PE/EtOAc=3/1, $R_f$=0.45) to yield tert-butyl (3R)-3-[[3-acetyl-5-(5-fluoro-3-pyridyl)pyrazolo[1,5-a]pyrimidin-7-yl]-tert-butoxycarbonyl-amino]-1,2,3,4-tetrahydrocarbazole-9-carboxylate (340 mg, 524.83 μmol, 91.0% yield, 98.9% purity) as a yellow solid. $^1$H NMR (400 MHz, $CDCl_3$) δ ppm 9.12 (s, 1H), 8.73 (s, 1H), 8.64 (d, J=2.5 Hz, 1H), 8.15 (d, J=9.5 Hz, 1H), 8.05 (d, J=8.0 Hz, 1H), 7.28 (s, 1H), 7.25-7.19 (m, 1H), 7.18-7.13 (m, 1H), 4.83 (s, 1H), 3.27-3.11 (m, 3H), 2.90 (s, 3H), 2.72-2.62 (m, 1H), 2.37 (s, 1H), 2.13-2.06 (m, 1H), 2.05 (s, 1H), 1.64 (s, 9H), 1.34 (s, 9H); ES-LCMS m/z 641.4 $[M+H]^+$.

Step 4: 1-[5-(5-Fluoro-3-pyridyl)-7-[[(3R)-2,3,4,9-tetrahydro-1H-carbazol-3-yl]amino]pyrazolo[1,5-a]pyrimidin-3-yl]ethanone

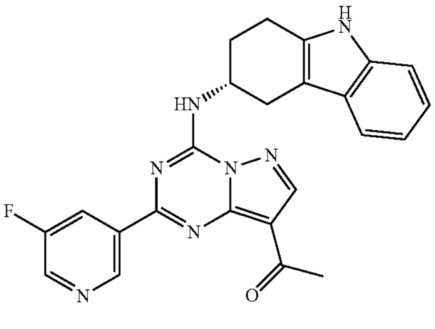 [SMILES: CC(=O)c1cnn2c(N[C@@H]3CCc4[nH]c5ccccc5c4C3)nc(-c3cncc(F)c3)nc12]

To a solution of tert-butyl (3R)-3-[[3-acetyl-5-(5-fluoro-3-pyridyl)pyrazolo[1,5-a]pyrimidin-7-yl]-tert-butoxycarbonyl-amino]-1,2,3,4-tetrahydrocarbazole-9-carboxylate (340 mg, 524.83 mol, 1 eq) in DCM (8 mL) was added TFA (3.08 g, 27.01 mmol, 2 mL, 51.47 eq). The reaction mixture was stirred at 20° C. for 30 min. The reaction mixture was concentrated. The residue was dissolved in water (10 mL), basified with saturated aqueous $NaHCO_3$ until pH=8 and extracted with DCM (30 mL×3). The organic layer was dried over $Na_2SO_4$, filtered and concentrated to yield 1-[5-(5-fluoro-3-pyridyl)-7-[[(3R)-2,3,4,9-tetrahydro-1H-carbazol-3-yl]amino]pyrazolo[1,5-a]pyrimidin-3-yl]ethanone (250 mg, 515.36 μmol, 98.2% yield, 90.8% purity) as a yellow solid which was used in the next step without further purification. $^1H$ NMR (400 MHz, $CDCl_3$) δ ppm 9.11 (s, 1H), 8.58 (d, J=2.9 Hz, 1H), 8.49 (s, 1H), 8.20 (td, J=2.4, 9.4 Hz, 1H), 7.90 (s, 1H), 7.44 (d, J=7.9 Hz, 1H), 7.33 (d, J=8.2 Hz, 1H), 7.17 (t, J=7.6 Hz, 1H), 7.13-7.07 (m, 1H), 6.76 (d, J=8.4 Hz, 1H), 6.63 (s, 1H), 4.34 (s, 1H), 3.38 (dd, J=4.9, 15.0 Hz, 1H), 3.02-2.91 (m, 3H), 2.84 (s, 3H), 2.35 (m, 1H), 2.31-2.23 (m, 1H); ES-LCMS m/z 441.3 $[M+H]^+$.

Step 5: (1R)-1-[5-(5-Fluoro-3-pyridyl)-7-[[(3R)-2,3,4,9-tetrahydro-1H-carbazol-3-yl]amino]pyrazolo[1,5-a]pyrimidin-3-yl]ethanol (I-198a) & (1S)-1-[5-(5-fluoro-3-pyridyl)-7-[[(3R)-2,3,4,9-tetrahydro-1H-carbazol-3-yl]amino]pyrazolo[1,5-a]pyrimidin-3-yl]ethanol (I-198b)

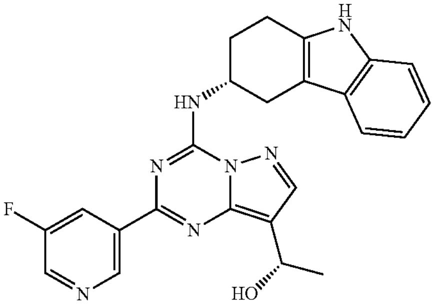

-continued

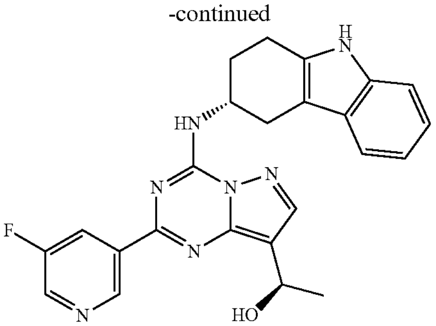

To a solution of 1-[5-(5-fluoro-3-pyridyl)-7-[[(3R)-2,3,4,9-tetrahydro-1H-carbazol-3-yl]amino]pyrazolo[1,5-a]pyrimidin-3-yl]ethanone (100 mg, 206.14 μmol, 1 eq) in MeOH (2.5 mL) and EtOH (2.5 mL) was added $NaBH_4$ (31.19 mg, 824.57 μmol, 4 eq) in portions at 20° C. The reaction mixture was stirred at 20° C. for 0.5 h. $H_2O$ (10 mL) was added to quench the reaction and extracted with DCM (30 mL×3). The combined organic layers were dried over $Na_2SO_4$, filtered and concentrated to yield a residue which was purified by preparative HPLC (column: Gemini 150*25 5 u; mobile phase: [water (0.05% ammonia hydroxide v/v)-ACN]; B %: 55%-70%, 8 min), followed by lyophilization to yield an enantiomer (12.50 mg, 28.25 μmol, 13.7% yield, 100.0% purity) (SFC: Rt=6.742, ee=100%) as a yellow solid. $^1H$ NMR (400 MHz, DMSO-$d_6$) δ ppm 10.79 (s, 1H), 9.34 (s, 1H), 8.66 (d, J=2.8 Hz, 1H), 8.50 (td, J=2.2, 10.4 Hz, 1H), 8.12 (s, 1H), 7.99 (d, J=9.3 Hz, 1H), 7.37 (d, J=7.8 Hz, 1H), 7.28 (d, J=8.0 Hz, 1H), 7.07 (s, 1H), 7.04-6.98 (m, 1H), 6.97-6.91 (m, 1H), 5.20-5.12 (m, 1H), 5.05 (d, J=4.5 Hz, 1H), 4.50 (d, J=8.8 Hz, 1H), 3.18-3.00 (m, 2H), 2.98-2.82 (m, 2H), 2.24-2.13 (m, 2H), 1.57 (d, J=6.3 Hz, 3H); ES-LCMS m/z 443.2 $[M+H]^+$; and the other enantiomer (18.17 mg, 40.22 umol, 19.5% yield, 97.9% purity) (SFC: Rt=5.398, ee=82.9%) as a yellow solid. $^1H$ NMR (400 MHz, DMSO-$d_6$) δ ppm 10.75 (s, 1H), 9.30 (s, 1H), 8.62 (d, J=2.7 Hz, 1H), 8.50-8.43 (m, 1H), 8.08 (s, 1H), 7.95 (d, J=9.3 Hz, 1H), 7.32 (d, J=7.8 Hz, 1H), 7.24 (d, J=7.8 Hz, 1H), 7.03 (s, 1H), 7.00-6.94 (m, 1H), 6.93-6.87 (m, 1H), 5.16-5.08 (m, 1H), 4.99 (d, J=4.4 Hz, 1H), 4.46 (d, J=8.8 Hz, 1H), 3.13-2.98 (m, 2H), 2.92-2.79 (m, 2H), 2.14 (m, 2H), 1.53 (d, J=6.4 Hz, 3H); ES-LCMS m/z 443.2 $[M+H]^+$.

Example 156

Synthesis of I-200

I-200

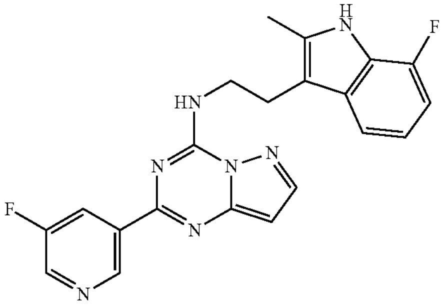

Synthetic Scheme:

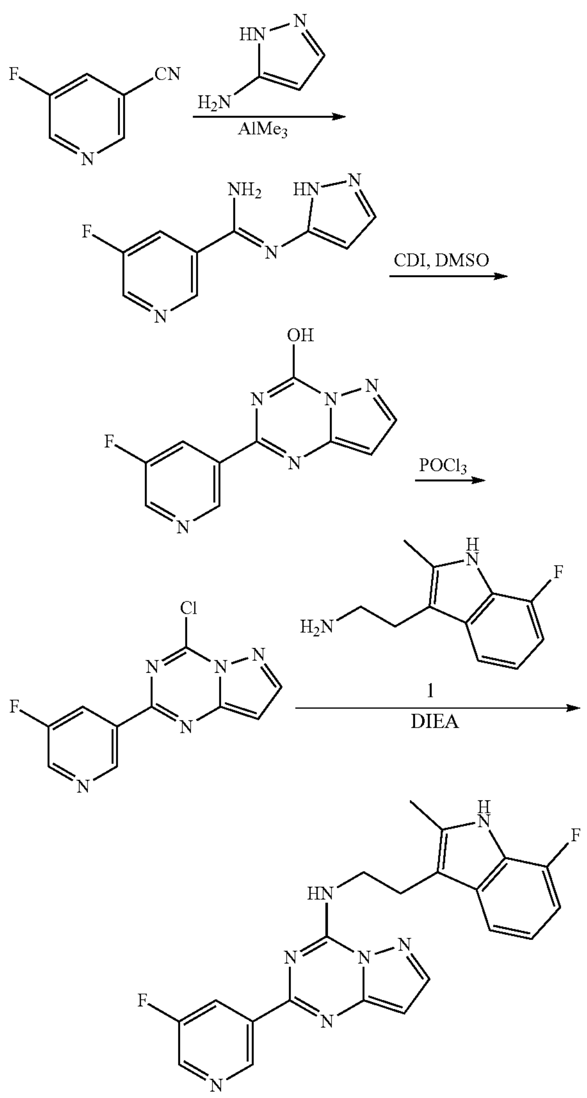

I-200

Step 1: 5-Fluoro-21-(1H-pyrazol-5-yl)pyridine-3-carboxamidine

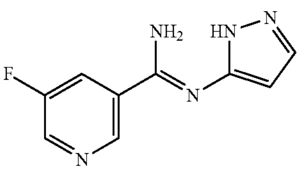 [SMILES: N/C(=N\c1ccn[nH]1)c1cncc(F)c1]

A mixture of 5-fluoropyridine-3-carbonitrile (1 g, 7.78 mmol, 1 eq) and 1H-pyrazol-5-amine (775.80 mg, 9.34 mmol, 1.2 eq) in xylene (15 mL) was stirred at 70° C. for 30 min, then $AlMe_3$ (2 M, 7.78 mL, 2 eq) (2 M in toluene, 19.45 mL, 1 eq) was added in one portion at 70° C. The mixture was stirred at 100° C. for 12 h. The reaction mixture was concentrated under reduced pressure to yield a residue which was purified by flash silica gel chromatography (from DCM/MeOH=100/1 to 10/1, TLC: DCM/MeOH=10/1, $R_f$=0.3) to yield 5-fluoro-N'-(1H-pyrazol-5-yl)pyridine-3-carboxamidine (700 mg, 2.73 mmol, 35.1% yield, 80.0% purity) as a yellow solid. $^1$H NMR (400 MHz, $CD_3OD$) δ ppm 8.89 (s, 1H), 8.59 (d, J=2.7 Hz, 1H), 8.06 (d, J=9.3 Hz, 1H), 7.56 (d, J=2.2 Hz, 1H), 6.16 (d, J=2.2 Hz, 1H); ES-LCMS m/z 206.3 $[M+H]^+$.

Step 2: 2-(5-Fluoro-3-pyridyl)pyrazolo[1,5-a][1,3,5]triazin-4-ol

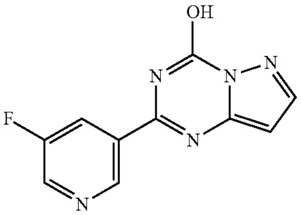 [SMILES: Oc1nc(-c2cncc(F)c2)nc2ccnn12]

A mixture of 5-fluoro-N-(1H-pyrazol-5-yl)pyridine-3-carboxamidine (600 mg, 2.34 mmol, 1 eq), CDI (758.62 mg, 4.68 mmol, 2 eq) and DMAP (142.89 mg, 1.17 mmol, 0.5 eq) in DMSO (10 mL) was stirred at 130° C. for 12 h. The mixture was purified by preparative HPLC (column: Agela ASB 150*25 mm*5 um; mobile phase: [water (0.05% HCl)-ACN]; B %: 15%-43%, 9 min), followed by lyophilization to yield 2-(5-fluoro-3-pyridyl)pyrazolo[1,5-a][1,3,5]triazin-4-ol (150 mg, 627.42 μmol, 26.8% yield, 96.7% purity) as a yellow solid. $^1$H NMR (400 MHz, $CD_3OD$) δ ppm 9.17 (s, 1H), 8.82 (d, J=2.4 Hz, 1H), 8.55-8.36 (m, 1H), 8.10 (d, J=2.0 Hz, 1H), 6.65 (d, J=2.0 Hz, 1H); ES-LCMS m/z 232.1 $[M+H]^+$.

Step 3: 4-Chloro-2-(5-fluoro-3-pyridyl)pyrazolo[1,5-a][1,3,5]triazine

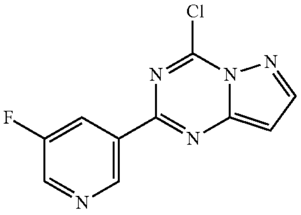 [SMILES: Fc1cncc(-c2nc(Cl)n3nccc3n2)c1]

A mixture of 2-(5-fluoro-3-pyridyl)pyrazolo[1,5-a][1,3,5]triazin-4-ol (150 mg, 627.42 μmol, 1 eq) and N,N-dimethylaniline (304.12 mg, 2.51 mmol, 318.12 μL, 4 eq) in $POCl_3$ (59.33 g, 386.94 mmol, 35.96 mL, 616.72 eq) was degassed and purged with $N_2$ for 3 times. The mixture was stirred at 110° C. for 3 h under $N_2$ atmosphere. The reaction mixture was concentrated under reduced pressure to yield a residue which was diluted with ice-water, then saturated $NaHCO_3$ was added to above solution until pH=8, extracted with EtOAc (30 mL×3). The combined organic layers were dried over $Na_2SO_4$, filtered and concentrated under reduced pressure to yield a residue which was purified by flash silica gel chromatography (from PE/EtOAC=100/1 to 3/1, TLC: PE/EtOAc=3/1, $R_f$=0.5) to yield 4-chloro-2-(5-fluoro-3-pyridyl)pyrazolo[1,5-a][1,3,5]triazine (50 mg, 172.65 μmol, 27.5% yield, 86.2% purity) as a yellow solid. $^1$H NMR (400 MHz, $CDCl_3$) δ ppm 9.51 (s, 1H), 8.65 (d, J=2.7 Hz, 1H), 8.50-8.42 (m, 1H), 8.34 (d, J=2.2 Hz, 1H), 6.86 (d, J=2.2 Hz, 1H); ES-LCMS m/z 250.0, 252.1 $[M+H]^+$.

Step 4: N-[2-(7-Fluoro-2-methyl-1H-indol-3-yl) ethyl]-2-(5-fluoro-3-pyridyl)pyrazolo[1,5-a][1,3,5] triazin-4-amine (I-200)

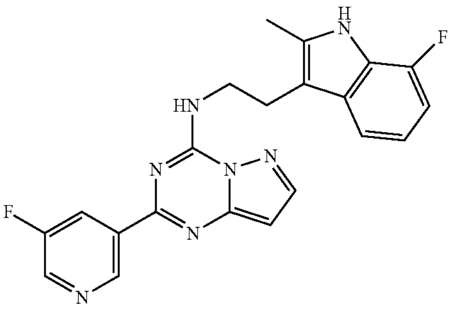 [SMILES: Cc1[nH]c2c(F)cccc2c1CCNc1nc(-c2cncc(F)c2)nc2ccnn12]

A mixture of 4-chloro-2-(5-fluoro-3-pyridyl)pyrazolo[1,5-a][1,3,5]triazine (50 mg, 172.65 μmol, 1 eq), 2-(7-fluoro-2-methyl-1H-indol-3-yl)ethanamine (57.03 mg, 224.45 umol, 1.3 eq, HCl) and DIEA (111.57 mg, 863.27 μmol, 150.37 μL, 5 eq) in i-PrOH (2 mL) was degassed and purged with $N_2$ for 3 times. The mixture was stirred at 80° C. for 12 h. The reaction mixture was concentrated under reduced pressure to yield a residue which was purified by preparative HPLC (column: Phenomenex Gemini 150*25 mm*10 um; mobile phase: [water (0.05% HCl)-ACN]; B %: 55%-85%, 9 min), followed by lyophilization to yield N-[2-(7-fluoro-2-methyl-1H-indol-3-yl)ethyl]-2-(5-fluoro-3-pyridyl)pyrazolo[1,5-a][1,3,5]triazin-4-amine (19.54 mg, 40.85 μmol, 23.7% yield, 100.0% purity, 2HCl) as a white solid. $^1$H NMR (400 MHz, $CD_3OD$) δ ppm 9.15 (s, 1H), 8.53 (d, J=2.9 Hz, 1H), 8.12 (d, J=9.5 Hz, 1H), 8.05 (d, J=2.0 Hz, 1H), 7.33 (d, J=7.8 Hz, 1H), 6.86 (dt, J=4.6, 7.8 Hz, 1H), 6.61 (dd, J=7.8, 11.2 Hz, 1H), 6.43 (d, J=2.0 Hz, 1H), 3.98 (t, J=6.8 Hz, 2H), 3.13 (t, J=6.8 Hz, 2H), 2.26 (s, 3H); ES-LCMS m/z 406.1 $[M+H]^+$.

Example 157

Synthesis of I-201

I-201

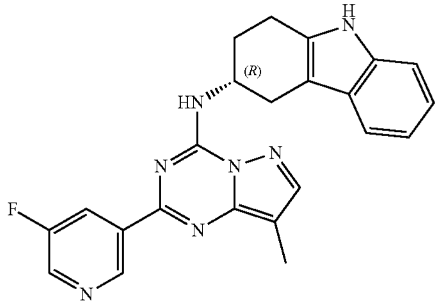

Synthetic Scheme:

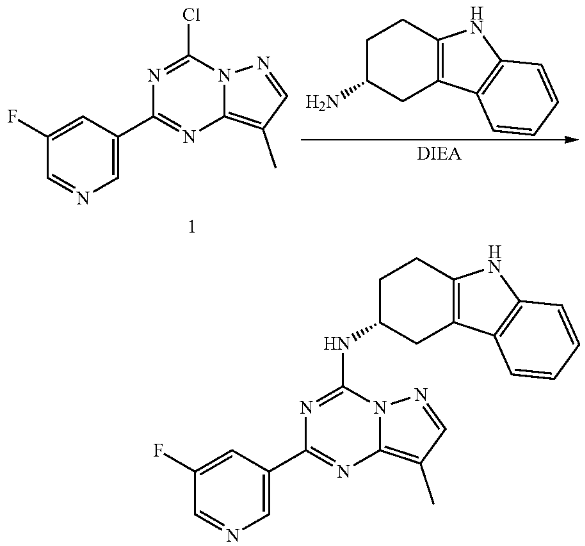

1

I-201

Step 1: (3R)—N-[2-(5-Fluoro-3-pyridyl)-8-methyl-pyrazolo[1,5-a][1,3,5]triazin-4-yl]-2,3,4,9-tetrahydro-1H-carbazol-3-amine (I-201)

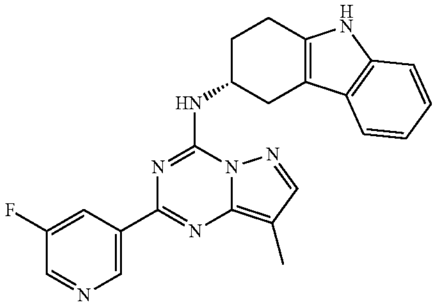 [SMILES: Cc1cnn2c(N[C@@H]3CCc4[nH]c5ccccc5c4C3)nc(-c3cncc(F)c3)nc12]

A mixture of 4-chloro-2-(5-fluoro-3-pyridyl)-8-methyl-pyrazolo[1,5-a][1,3,5]triazine (11 mg, 24.27 μmol, 1 eq), (3R)-2,3,4,9-tetrahydro-1H-carbazol-3-amine (5.43 mg, 29.13 μmol, 1.2 eq) and DIEA (15.69 mg, 121.37 μmol, 21.14 μL, 5 eq) in i-PrOH (2 mL) was stirred at 80° C. for 12 h. The reaction mixture was concentrated under reduced pressure to yield a residue which was purified by preparative HPLC (column: Agela ASB 150*25 mm*5 um; mobile phase: [water (0.05% HCl)-ACN]; B %: 60%-90%, 9 min), followed by lyophilization to yield (3R)—N-[2-(5-fluoro-3-pyridyl)-8-methyl-pyrazolo[1,5-a][1,3,5]triazin-4-yl]-2,3,4,9-tetrahydro-1H-carbazol-3-amine (4.32 mg, 8.72 μmol, 35.9% yield, 98.2% purity, 2HCl) as a yellow solid. $^1$H NMR (400 MHz, $CD_3OD$) δ ppm 9.48 (s, 1H), 8.94 (d, J=9.2 Hz, 1H), 8.82 (br s, 1H), 7.96 (s, 1H), 7.34 (d, J=7.6 Hz, 1H), 7.25 (d, J=8.0 Hz, 1H), 7.04-6.98 (m, 1H), 6.96-6.90 (m, 1H), 4.86 (m, 1H), 3.25 (d, J=5.6 Hz, 1H), 3.12-2.84 (m, 3H), 2.40-2.33 (m, 1H), 2.32 (s, 3H), 2.29-2.17 (m, 1H); ES-LCMS m/z 414.2 $[M+H]^+$.

Example 158

Synthesis of I-202

I-202

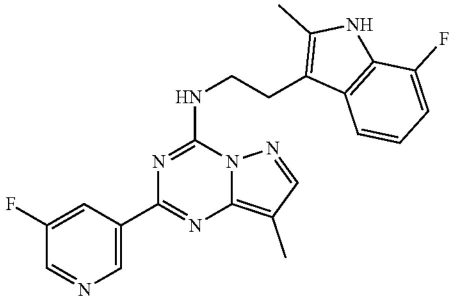

Synthetic Scheme:

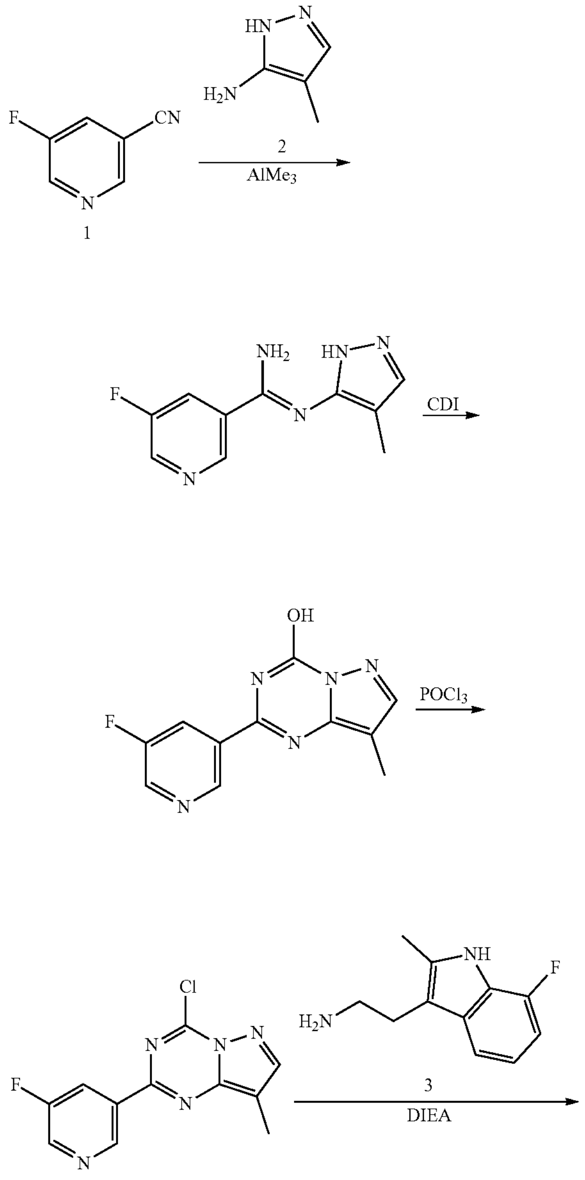

-continued

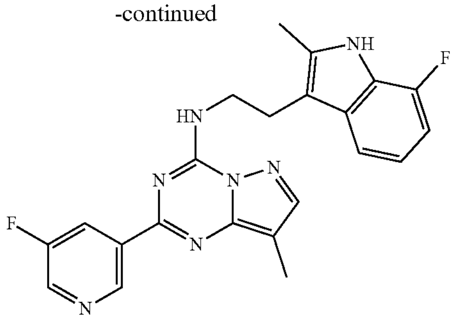

I-202

Step 1: 5-Fluoro-1V'-(4-methyl-1H-pyrazol-5-yl) pyridine-3-carboxamidine

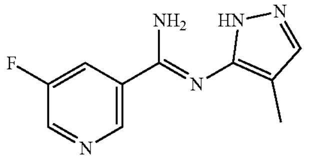 [SMILES: Cc1cn[nH]c1/N=C(\N)c1cncc(F)c1]

A mixture of 5-fluoropyridine-3-carbonitrile (1 g, 6.55 mmol, 1 eq) and 4-methyl-1H-pyrazol-5-amine (707.02 mg, 6.55 mmol, 1 eq) in xylene (10 mL) was stirred at 70° C. for 0.5 h. Then $AlMe_3$ (2 M, 3.93 mL, 1.2 eq) was added to the mixture in one portion at 100° C. The mixture was stirred at 100° C. for 16 h. The mixture was quenched with MeOH (30 mL) and concentrated under reduced pressure. The residue was purified by flash silica gel chromatography (from DCM/MeOH=1/0 to 5/1, TLC: DCM/MeOH=5/1, $R_f$=0.40) to yield product of 5-fluoro-N-(4-methyl-1H-pyrazol-5-yl)pyridine-3-carboxamidine (1.09 g, 3.86 mmol, 58.9% yield, 77.7% purity) as yellow oil. $^1$H NMR (400 MHz, $CD_3OD$) δ ppm 8.98 (s, 1H), 8.60 (d, J=2.4 Hz, 1H), 7.38 (s, 1H), 7.17 (s, 1H), 2.14 (s, 3H); ES-LCMS m/z 220.2 $[M+H]^+$.

Step 2: 2-(5-Fluoro-3-pyridyl)-8-methyl-pyrazolo[1,5-a][1,3,5]triazin-4-ol

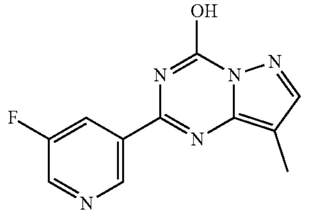 [SMILES: Cc1cnn2c(O)nc(-c3cncc(F)c3)nc12]

A mixture of 5-fluoro-N-(4-methyl-1H-pyrazol-5-yl)pyridine-3-carboxamidine (600 mg, 2.46 mmol, 1 eq), CDI (799.20 mg, 4.93 mmol, 2 eq) and DMAP (301.07 mg, 2.46 mmol, 1 eq) in DMSO (15 mL) was stirred under $N_2$ atmosphere at 130° C. for 12 h. The reaction mixture was concentrated under reduced pressure. The residue was purified by preparative HPLC (column: Phenomenex Gemini 150*25 mm*10 um; mobile phase: [water(0.05% HCl)-ACN]; B %: 14%-44%, 9 min), followed by lyophilization to yield 2-(5-fluoro-3-pyridyl)-8-methyl-pyrazolo[1,5-a][1,3,5]triazin-4-ol (120 mg, 412.82 μmol, 16.8% yield, 96.9% purity, HCl) as a yellow solid. $^1$H NMR (400 MHz, $CD_3OD$) δ ppm 9.12 (s, 1H), 8.72 (s, 1H), 8.34 (s, 1H), 7.95 (s, 1H), 2.28 (s, 3H); ES-LCMS m/z 246.1 $[M+H]^+$.

Step 3: 4-Chloro-2-(5-fluoro-3-pyridyl)-8-methyl-pyrazolo[1,5-a][1,3,5]triazine

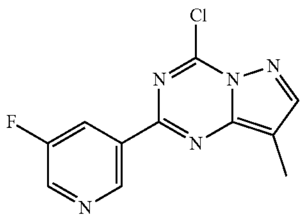 [SMILES: Cc1cnn2c(Cl)nc(-c3cncc(F)c3)nc12]

A mixture of 2-(5-fluoro-3-pyridyl)-8-methyl-pyrazolo[1,5-a][1,3,5]triazin-4-ol (150 mg, 422.79 μmol, 1 eq, 2HCl), N,N-dimethylaniline (69.12 mg, 570.36 μmol, 72.30 μL, 1.35 eq) and $POCl_3$ (11.40 g, 74.38 mmol, 6.91 mL, 175.91 eq) was stirred at 110° C. for 3 h. The reaction mixture was concentrated under reduced pressure. To the residue was added ice-water (50 mL). The mixture was basified with $NaHCO_3$ until pH=8 and extracted with EtOAc (50 mL×3). The organic layer was dried over $Na_2SO_4$, filtered and concentrated under reduced pressure to yield a residue which was purified by flash silica gel chromatography (from PE/EtOAc=1/0 to 2/1, TLC: PE/EtOAc=2/1, $R_f$=0.40) to yield 4-chloro-2-(5-fluoro-3-pyridyl)-8-methyl-pyrazolo[1,5-a][1,3,5]triazine (100 mg, 379.28 μmol, 89.7% yield, 100.0% purity) as a white solid. $^1$H NMR (400 MHz, $CDCl_3$) δ ppm 9.52 (s, 1H), 8.63 (d, J=2.8 Hz, 1H), 8.46 (d, J=9.2 Hz, 1H), 8.19 (s, 1H), 2.44 (s, 3H); ES-LCMS m/z 264.0, 266.0 $[M+H]^+$.

Step 4: N-[2-(7-Fluoro-2-methyl-1H-indol-3-yl)ethyl]-2-(5-fluoro-3-pyridyl)-8-methyl-pyrazolo[1,5-a][1,3,5]triazin-4-amine (I-202)

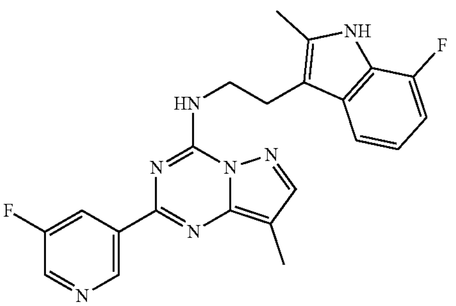 [SMILES: Cc1[nH]c2c(F)cccc2c1CCNc1nc(-c2cncc(F)c2)nc2c(C)cnn12]

A mixture of 4-chloro-2-(5-fluoro-3-pyridyl)-8-methyl-pyrazolo[1,5-a][1,3,5]triazine (20 mg, 75.86 μmol, 1 eq), 2-(7-fluoro-2-methyl-1H-indol-3-yl)ethanamine (21.20 mg, 83.44 μmol, 1.1 eq, HCl) and DIEA (49.02 mg, 379.28 μmol, 66.06 μL, 5 eq) in i-PrOH (2 mL) was stirred at 90° C. for 10 h. The mixture was concentrated under reduced pressure to yield a residue which was purified by preparative HPLC (column: Phenomenex Gemini 150*25 mm*10 um; mobile phase: [water (0.05% HCl)-ACN]; B %: 55%-85%, 9 min) to yield N-[2-(7-fluoro-2-methyl-1H-indol-3-yl)ethyl]-2-(5-fluoro-3-pyridyl)-8-methyl-pyrazolo[1,5-a][1,3,5]triazin-4-amine (4.66 mg, 9.21 μmol, 12.1% yield, 97.3% purity, 2HCl) as a yellow solid. $^1$H NMR (400 MHz, $CD_3OD$) δ ppm 9.17 (s, 1H), 8.53 (d, J=2.0 Hz, 1H), 8.18 (d, J=8.8 Hz, 1H), 7.88 (s, 1H), 7.33 (d, J=7.6 Hz, 1H), 6.92-6.76 (m, 1H), 6.60 (dd, J=7.6, 11.2 Hz, 1H), 3.95 (t, J=6.8 Hz, 2H), 3.10 (t, J=6.8 Hz, 2H), 2.27 (s, 3H), 2.23 (s, 3H); ES-LCMS m/z 420.2 $[M+H]^+$.

Example 159

Synthesis of I-203

I-203

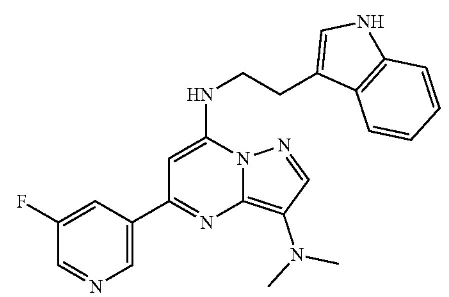

Synthetic Scheme:

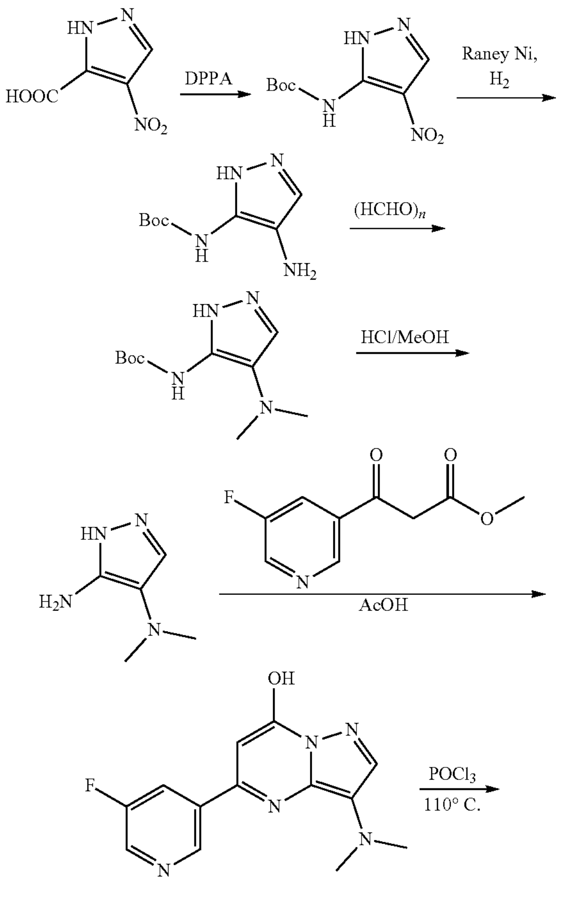

-continued

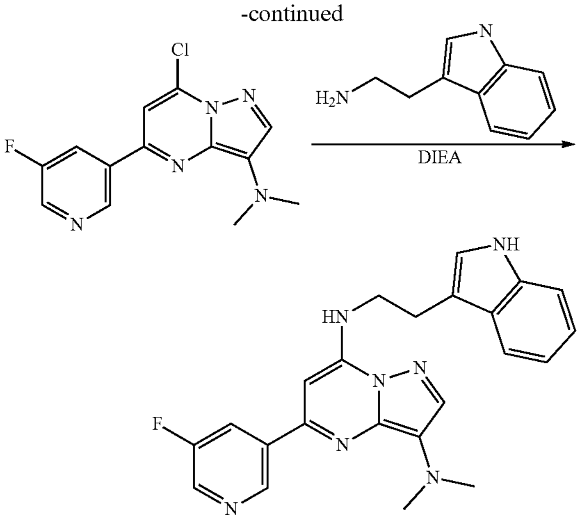

I-203

Step 1: tert-Butyl N-(4-nitro-1H-pyrazol-5-yl)carbamate

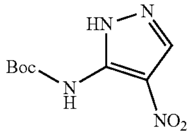 [SMILES: CC(C)(C)OC(=O)Nc1[nH]ncc1[N+](=O)[O-]]

To a solution of 4-nitro-1H-pyrazole-5-carboxylic acid (14 g, 89.12 mmol, 1 eq) in toluene (280 mL) was added TEA (22.55 g, 222.81 mmol, 31.01 mL, 2.5 eq) and DPPA (26.98 g, 98.04 mmol, 21.24 mL, 1.1 eq) at 25° C. The mixture was stirred at 25° C. for 1.5 h. t-BuOH (66.06 g, 891.24 mmol, 85.24 mL, 10 eq) was added to the above solution, the mixture was stirred at 130° C. for 12 h under $N_2$. TLC (PE/EtOAc=1/1, $R_f$=0.49) showed the starting material was consumed completely and a major spot formed. The reaction mixture was quenched by addition of saturated $NaHCO_3$ (100 mL), extracted with EtOAc (80 mL×3). The combined organic layers were washed with brine (20 mL), dried over $Na_2SO_4$, filtered and concentrated under reduced pressure to yield a residue which was purified by flash silica gel chromatography (from PE/EtOAc=1/0 to 1/1, TLC: PE/EtOAc=1/1, $R_f$=0.49) to yield tert-butyl N-(4-nitro-1H-pyrazol-5-yl)carbamate (6.0 g, 21.03 mmol, 23.6% yield, 80% purity) as a white solid. $^1$H NMR (400 MHz, DMSO-$d_6$) δ ppm 13.80-13.47 (m, 1H), 9.35 (br s, 1H), 8.58-7.94 (m, 1H), 1.44 (br s, 9H).

Step 2: tert-Butyl N-(4-amino-1H-pyrazol-5-yl)carbamate

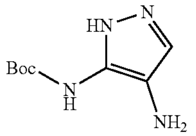 [SMILES: CC(C)(C)OC(=O)Nc1[nH]ncc1N]

A mixture of tert-butyl N-(4-nitro-1H-pyrazol-5-yl)carbamate (5 g, 17.53 mmol, 1 eq), Raney-Ni (5 g, in water) and $NH_3H_2O$ (2.19 g, 17.53 mmol, 2.41 mL, 28%, 1 eq) in MeOH (100 mL) was degassed and purged with $H_2$ for 3 times, the mixture was stirred at 20° C. for 2 h under $H_2$ (15 psi). The reaction mixture was filtered and the filtrate was concentrated under reduced pressure to yield a crude product of tert-butyl N-(4-amino-1H-pyrazol-5-yl)carbamate (3.47 g, 16.44 mmol, 93.7% yield, 93.9% purity) as a purple solid which was used in the next step without further purification. $^1$H NMR (400 MHz, DMSO-$d_6$) δ ppm 11.65 (br s, 1H), 8.76 (br s, 1H), 7.00 (s, 1H), 3.50 (br s, 2H), 1.50-1.36 (m, 9H); ES-LCMS m/z 143.1 $[M-t-Bu+H]^+$.

Step 3: tert-Butyl N-[4-(dimethylamino)-1H-pyrazol-5-yl]carbamate

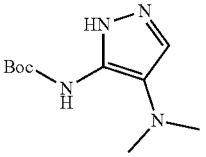 [SMILES: CN(C)c1cn[nH]c1NC(=O)OC(C)(C)C]

To a solution of tert-butyl N-(4-amino-1H-pyrazol-5-yl) carbamate (1.5 g, 7.11 mmol, 1 eq) in MeOH (30 mL) was added HCHO (938.76 mg, 31.26 mmol, 4.4 eq) and $NaBH_3CN$ (4.47 g, 71.06 mmol, 10 eq). The mixture was stirred at 50° C. for 12 h. The reaction mixture was concentrated under reduced pressure to yield a residue which was quenched by addition of water (100 mL), extracted with EtOAc (80 mL×3). The combined organic layers were washed with brine (30 mL), dried over $Na_2SO_4$, filtered and concentrated under reduced pressure to yield a residue which was purified by flash silica gel chromatography (from PE/EtOAc=1/0 to 0/1, TLC: PE/EtOAc=1/1, $R_f$=0.20) to yield tert-butyl N-[4-(dimethylamino)-1H-pyrazol-5-yl]carbamate (1.2 g, 3.87 mmol, 54.4% yield, 73.0% purity) as red brown oil. $^1$H NMR (400 MHz, $CD_3OD$) δ ppm 7.29 (s, 1H), 2.64 (s, 6H), 1.49 (s, 9H).

Step 4: N4,N4-Dimethyl-1H-pyrazole-4,5-diamine

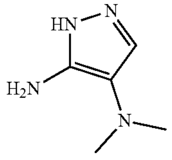

A mixture of tert-butyl N-[4-(dimethylamino)-1H-pyrazol-5-yl]carbamate (1.2 g, 3.87 mmol, 1 eq) in HCl/MeOH (4 M, 15 mL) was degassed and purged with $N_2$ for 3 times, the mixture was stirred at 15° C. for 12 h under $N_2$ atmosphere. The reaction mixture was concentrated under reduced pressure to yield a crude product of N4,N4-dimethyl-1H-pyrazole-4,5-diamine (629 mg, crude, HCl) as a white solid which was used in the next step without further purification. $^1$H NMR (400 MHz, $CD_3OD$) δ ppm 8.47 (s, 1H), 3.32 (s, 6H).

Step 5: 3-(Dimethylamino)-5-(5-fluoro-3-pyridyl)pyrazolo[1,5-a]pyrimidin-7-ol

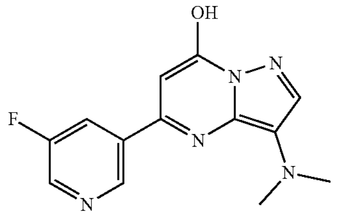 [SMILES: CN(C)c1cnn2c(O)cc(-c3cncc(F)c3)nc12]

N4,N4-Dimethyl-1H-pyrazole-4,5-diamine (300 mg, 1.57 mmol, 1 eq, HCl) was dissolved in MeOH (10 mL), then adjusted pH to 9-10 by 2N aq. NaOH. The mixture was concentrated under reduced pressure to yield a residue. The residue and methyl (Z)-3-(5-fluoro-3-pyridyl)-3-hydroxy-prop-2-enoate (332.44 mg, 1.57 mmol, 1 eq) in AcOH (15 mL) was stirred at 120° C. for 2 h. The reaction mixture was concentrated under reduced pressure to yield a crude product of 3-(dimethylamino)-5-(5-fluoro-3-pyridyl)pyrazolo[1,5-a]pyrimidin-7-ol (616 mg, crude, 2HOAC) as a yellow solid which was used in the next step without further purification. $^1$H NMR (400 MHz, DMSO-$d_6$) δ ppm 10.71 (s, 1H), 9.05 (s, 1H), 8.89 (d, J=1.5 Hz, 1H), 8.30 (s, 1H), 7.97 (s, 1H), 6.37 (s, 1H), 2.72-2.52 (m, 6H); ES-LCMS m/z 274.2 $[M+H]^+$.

Step 6: 7-Chloro-5-(5-fluoro-3-pyridyl)-N,N-dimethyl-pyrazolo[1,5-a]pyrimidin-3-amine

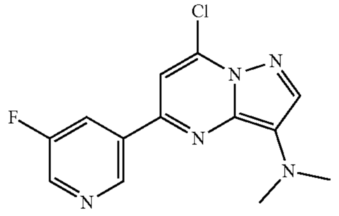

A solution of 3-(dimethylamino)-5-(5-fluoro-3-pyridyl)pyrazolo[1,5-a]pyrimidin-7-ol (616 mg, 1.57 mmol, 1 eq, 2HOAC) in $POCl_3$ (16.50 g, 10 mL) was degassed and purged with $N_2$ for 3 times, the mixture was stirred at 110° C. for 4 h under $N_2$ atmosphere. The reaction mixture was concentrated under reduced pressure to yield a residue which was quenched by addition of ice-water (100 mL) at 0° C., adjusted pH to 9-10 by saturated $NaHCO_3$, extracted with EtOAc (80 mL×3). The combined organic layers were washed with brine (20 mL), dried over $Na_2SO_4$, filtered and concentrated under reduced pressure to yield a residue which was purified by flash silica gel chromatography (from PE/EtOAc=1/0 to 1/1, TLC: PE/EtOAc=3/1, $R_f$=0.21) to yield 7-chloro-5-(5-fluoro-3-pyridyl)-N,N-dimethyl-pyrazolo[1,5-a]pyrimidin-3-amine (190 mg, 651.33 μmol, 41.5% yield, 100% purity) as a red solid. $^1$H NMR (400 MHz, $CDCl_3$) δ ppm 9.08 (s, 1H), 8.57 (d, J=2.8 Hz, 1H), 8.18-8.10 (m, 1H), 7.87 (s, 1H), 7.30 (s, 1H), 3.10 (s, 6H); ES-LCMS m/z 292.2, 294.2 $[M+H]^+$.

Step 7: 5-(5-Fluoro-3-pyridyl)-N7-[2-(1H-indol-3-yl)ethyl]-N3,N3-dimethyl-pyrazolo[1,5-a]pyrimidine-3,7-diamine (I-203)

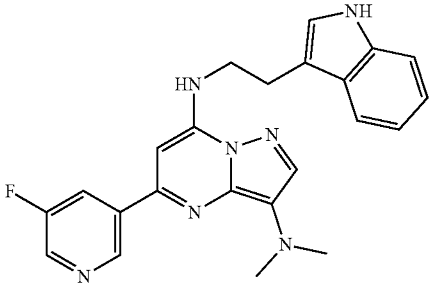

To a solution of 7-chloro-5-(5-fluoro-3-pyridyl)-N,N-dimethyl-pyrazolo[1,5-a]pyrimidin-3-amine (40 mg, 137.12 μmol, 1 eq) in i-PrOH (5 mL) was added DIEA (53.17 mg, 411.37 μmol, 71.65 μL, 3 eq) and 2-(1H-indol-3-yl)ethanamine (28.56 mg, 178.26 μmol, 1.3 eq). The mixture was stirred at 90° C. for 12 h. The reaction mixture was concentrated under reduced pressure to yield a residue which was purified by preparative HPLC (column: Phenomenex Gemini C18 250*50 mm*10 m; mobile phase: [water (0.05% HCl)-ACN]; B %: 25%-55%, 9 min), followed by lyophilization to yield 5-(5-fluoro-3-pyridyl)-N7-[2-(1H-indol-3-yl)ethyl]-N3,N3-dimethyl-pyrazolo[1,5-a]pyrimidine-3,7-diamine (27.03 mg, 55.35 μmol, 40.3% yield, 100% purity, 2HCl) as a yellow solid. $^1$H NMR (400 MHz, $CD_3OD$) δ ppm 8.87 (d, J=1.0 Hz, 1H), 8.82 (d, J=1.2 Hz, 1H), 8.36 (s, 1H), 8.17-8.12 (m, 1H), 7.71-7.67 (m, 1H), 7.17-7.11 (m, 1H), 7.07-7.00 (m, 2H), 6.98 (s, 1H), 6.18 (s, 1H), 3.96 (t, J=6.1 Hz, 2H), 3.48 (s, 6H), 3.21 (t, J=6.0 Hz, 2H); ES-LCMS m/z 416.1 $[M+H]^+$.

Example 160

Synthesis of I-204a

I-204a

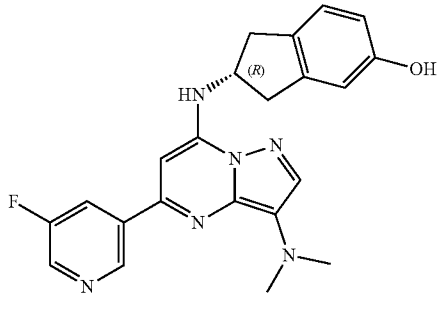

Synthetic Scheme:

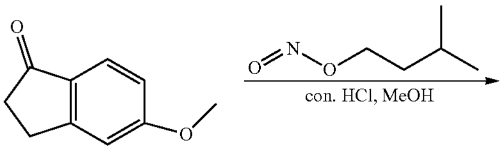

-continued

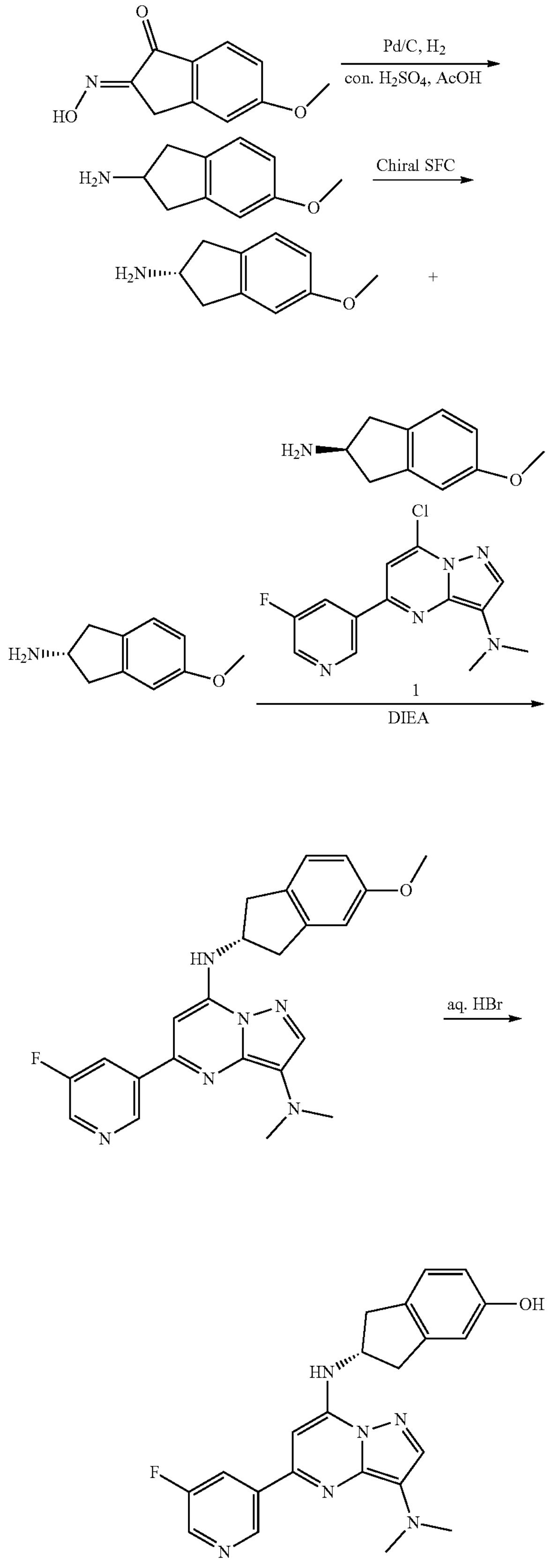

I-204a

Step 1: (2E)-2-Hydroxyimino-5-methoxy-indan-1-one

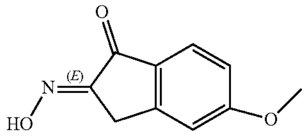

A solution of 5-methoxyindan-1-one (5 g, 30.83 mmol, 1 eq) in MeOH (500 mL) was heated to 45° C., isopentyl nitrite (5.42 g, 46.24 mmol, 6.23 mL, 1.5 eq) and con. HCl (12 M, 5.14 mL, 2 eq) was added. The mixture was stirred at 45° C. for 2 h. The mixture was concentrate under reduced pressure to yield a residue and MeOH (30 mL) was added. The slurry was filtered, dried in vacuo to yield (2E)-2-hydroxyimino-5-methoxy-indan-1-one (5.0 g, 22.75 mmol, 73.8% yield, 87.0% purity) as a brown solid which was used in the next step without further purification. $^1$H NMR (400 MHz, DMSO-$d_6$) δ ppm 12.47 (s, 1H), 7.68 (d, J=8.5 Hz, 1H), 7.14 (d, J=2.0 Hz, 1H), 7.01 (dd, J=2.3, 8.5 Hz, 1H), 3.92-3.84 (m, 3H), 3.71 (s, 2H); ES-LCMS m/z 192.1 $[M+H]^+$.

Step 2: (2R)-5-Methoxyindan-2-amine

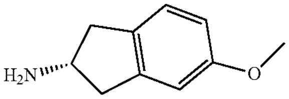

To a solution of (2E)-2-hydroxyimino-5-methoxy-indan-1-one (5 g, 22.75 mmol, 1 eq) in AcOH (250 mL) and con. $H_2SO_4$ (3.5 mL) was added Pd/C (1 g, 10%). The mixture was stirred at 25° C. for 12 h under $H_2$ (15 psi). The mixture was filtered, the filtrate was concentrated under reduced pressure to yield a residue which was poured into ice-water (200 mL), adjusted pH to 10-11 with 2 N NaOH, extracted with EtOAc (150 mL×3). The combined organic layers were washed with brine (50 mL), dried over $Na_2SO_4$, filtered and concentrated under reduced pressure to yield a crude product of 5-methoxyindan-2-amine (2.0 g, 11.48 mmol, 50.4% yield, 93.7% purity) as a brown solid. 5-methoxyindan-2-amine (1 g, 5.74 mmol) was separated by chiral SFC (column: AD-3_EtOH (DEA), AD (250 mm×30 mm, 10 μm); mobile phase: [0.1% $NH_3H_2O$ IPA]; B %: 55%-55%, min) for three times to yield (2R)-5-methoxyindan-2-amine (220 mg, 1.35 mmol, 23.4% yield, 100% purity) (Rt=3.581 min, ee=100%, $[\alpha]^{22}_D$=24.733 (13.5 mg/10 mL, $CHCl_3$)) as brown oil. $^1$H NMR (400 MHz, $CDCl_3$) δ ppm 7.11 (d, J=8.2 Hz, 1H), 6.78 (s, 1H), 6.72 (dd, J=2.5, 8.3 Hz, 1H), 3.88-3.81 (m, 1H), 3.79 (s, 3H), 3.15 (dt, J=6.7, 14.6 Hz, 2H), 2.71-2.59 (m, 2H); ES-LCMS m/z 164.2 $[M+H]^+$. And (2S)-5-methoxyindan-2-amine (350 mg, 2.14 mmol, 37.3% yield, 100% purity) (Rt=3.762 min, ee=100%, $[\alpha]^{22}_D$=−16.666 (10.3 mg/10 mL, $CHCl_3$)) as brown oil. $^1$H NMR (400 MHz, $CDCl_3$) δ ppm 7.11 (d, J=7.9 Hz, 1H), 6.78 (s, 1H), 6.72 (dd, J=2.5, 8.3 Hz, 1H), 3.87-3.81 (m, 1H), 3.79 (s, 3H), 3.15 (dt, J=6.8, 14.7 Hz, 2H), 2.71-2.57 (m, 2H); ES-LCMS m/z 164.2 $[M+H]^+$.

Step 3: 5-(5-Fluoro-3-pyridyl)-N7-[(2R)-5-methoxyindan-2-yl]-N3,N3-dimethyl-pyrazolo[1,5-a]pyrimidine-3,7-diamine

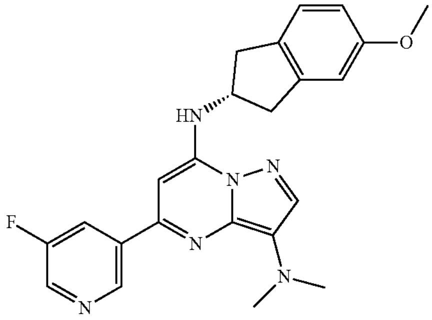 [SMILES: COc1ccc2c(c1)C[C@H](Nc1cc(-c3cncc(F)c3)nc3c(N(C)C)cnn13)C2]

To a solution of 7-chloro-5-(5-fluoro-3-pyridyl)-N,N-dimethyl-pyrazolo[1,5-a]pyrimidin-3-amine (50 mg, 171.40 μmol, 1 eq) in i-PrOH (5 mL) was added DIEA (66.46 mg, 514.21 μmol, 89.56 μL, 3 eq) and (2R)-5-methoxyindan-2-amine (36.37 mg, 222.82 μmol, 1.3 eq). The mixture was stirred at 70° C. for 12 h. The reaction mixture was concentrated under reduced pressure to yield a crude 5-(5-fluoro-3-pyridyl)-N7-[(2R)-5-methoxyindan-2-yl]-N3,N3-dimethyl-pyrazolo[1,5-a]pyrimidine-3,7-diamine (71 mg, 123.18 μmol, 71.9% yield, 72.6% purity) as red brown oil which was used in the next step without further purification. $^1$H NMR (400 MHz, $CDCl_3$) δ ppm 9.01 (s, 1H), 8.44 (d, J=2.7 Hz, 1H), 8.17-8.10 (m, 1H), 7.58 (s, 1H), 7.10 (d, J=8.3 Hz, 1H), 6.75 (s, 1H), 6.71 (dd, J=2.3, 8.2 Hz, 1H), 6.43 (d, J=7.6 Hz, 1H), 6.29 (s, 1H), 4.63-4.55 (m, 1H), 3.73 (s, 3H), 3.58-3.54 (m, 2H), 3.46-3.37 (m, 2H), 2.93 (s, 6H); ES-LCMS m/z 419.2 $[M+H]^+$.

Step 4: (2R)-2-[[3-(Dimethylamino)-5-(5-fluoro-3-pyridyl)pyrazolo[1,5-a]pyrimidin-7-yl]amino]indan-5-ol (I-204a)

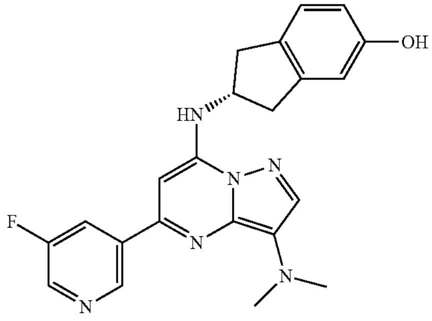 [SMILES: CN(C)c1cnn2c(N[C@@H]3Cc4ccc(O)cc4C3)cc(-c3cncc(F)c3)nc12]

A solution of 5-(5-fluoro-3-pyridyl)-N7-[(2R)-5-methoxyindan-2-yl]-N3,N3-dimethyl-pyrazolo[1,5-a]pyrimidine-3,7-diamine (71 mg, 123.18 μmol, 1 eq) in aq. HBr (5 mL, 60%) was stirred at 120° C. for 2 h under $N_2$ atmosphere. The reaction mixture was concentrated under reduced pressure to yield a residue which was purified by preparative HPLC (column: Agela ASB 150*25 mm*5 m; mobile phase: [water (0.05% HCl)-ACN]; B %: 23%-53%, 8 min) followed by lyophilization to yield (2R)-2-[[3-(dimethylamino)-5-(5-fluoro-3-pyridyl)pyrazolo[1,5-a]pyrimidin-7-yl]amino]indan-5-ol (33.84 mg, 67.84 μmol, 55.1% yield, 95.7% purity, 2HCl) as a yellow solid. $^1$H NMR (400 MHz, $CD_3OD$) δ ppm 9.68 (s, 1H), 9.31 (d, J=9.0 Hz, 1H), 9.12 (s, 1H), 8.43 (s, 1H), 7.24 (s, 1H), 7.07 (d, J=8.1 Hz, 1H), 6.72 (s, 1H), 6.65 (d, J=8.1 Hz, 1H), 4.97-4.94 (m, 1H), 3.54 (s, 6H), 3.52-3.43 (m, 2H), 3.19-3.02 (m, 2H); ES-LCMS m/z 405.2 $[M+H]^+$.

Example 161

Synthesis of I-204b

I-204b

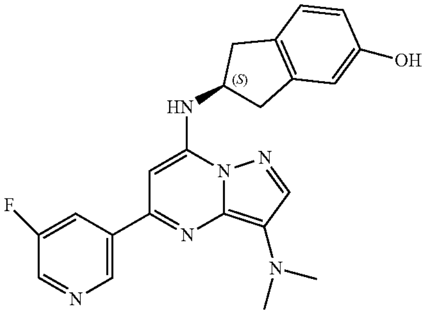

Synthetic Scheme:

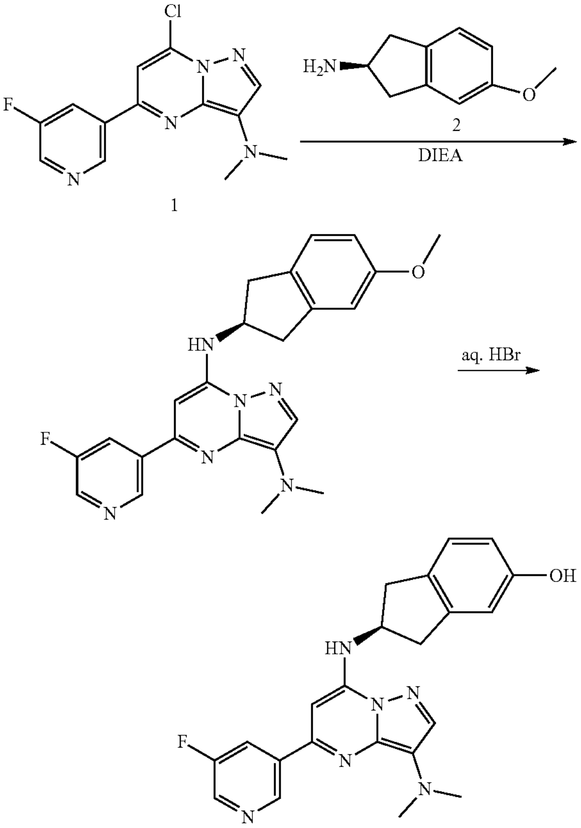

I-204b

Step 1: 5-(5-Fluoro-3-pyridyl)-N7-[(2S)-5-methoxy-indan-2-yl]-N3,N3-dimethyl-pyrazolo[1,5-a]pyrimidine-3,7-diamine

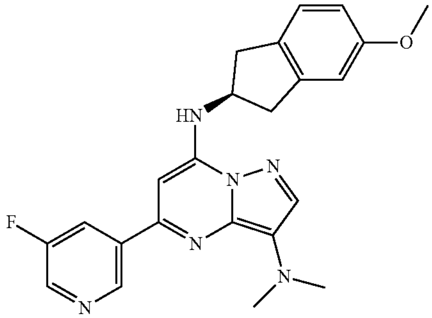 [SMILES: COc1ccc2c(c1)C[C@@H](Nc1cc(-c3cncc(F)c3)nc3c(N(C)C)cnn13)C2]

To a solution of 7-chloro-5-(5-fluoro-3-pyridyl)-N,N-dimethyl-pyrazolo[1,5-a]pyrimidin-3-amine (50 mg, 171.40 μmol, 1 eq) in i-PrOH (5 mL) was added DIEA (66.46 mg, 514.20 μmol, 89.56 μL, 3 eq) and (2S)-5-methoxyindan-2-amine (27.98 mg, 171.40 μmol, 1 eq). The mixture was stirred at 70° C. for 12 h. The reaction mixture was concentrated under reduced pressure to yield a crude 5-(5-fluoro-3-pyridyl)-N7-[(2S)-5-methoxyindan-2-yl]-N3,N3-dimethyl-pyrazolo[1,5-a]pyrimidine-3,7-diamine (71 mg, 128.27 μmol, 74.8% yield, 75.6% purity) as red brown oil which was used in the next step without further purification. $^1$H NMR (400 MHz, $CDCl_3$) δ ppm 9.12-9.05 (m, 1H), 8.52 (d, J=2.7 Hz, 1H), 8.21 (td, J=2.2, 9.8 Hz, 1H), 7.66 (s, 1H), 7.18 (d, J=8.3 Hz, 1H), 6.86-6.76 (m, 2H), 6.51 (d, J=7.6 Hz, 1H), 6.37 (s, 1H), 4.72-4.57 (m, 1H), 3.81 (s, 3H), 3.66 (d, J=4.9 Hz, 2H), 3.50 (ddd, J=7.0, 12.6, 15.9 Hz, 2H), 3.01 (s, 6H); ES-LCMS m/z 419.2 $[M+H]^+$.

Step 2: (2S)-2-[[3-(Dimethylamino)-5-(5-fluoro-3-pyridyl)pyrazolo[1,5-a]pyrimidin-7-yl]amino]indan-5-ol (I-204b)

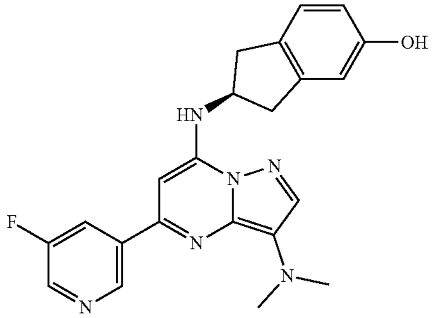

A solution of 5-(5-fluoro-3-pyridyl)-N7-[(2S)-5-methoxyindan-2-yl]-N3,N3-dimethyl-pyrazolo[1,5-a]pyrimidine-3,7-diamine (71 mg, 128.27 μmol, 1 eq) in aq. HBr (5 mL, 60%) was stirred at 120° C. for 2 h. The reaction mixture was concentrated under reduced pressure to yield a residue which was purified by preparative HPLC (column: Agela ASB 150*25 mm*5 m; mobile phase: [water (0.05% HCl)-ACN]; B %: 20%-50%, 8 min), followed by lyophilization to yield (2S)-2-[[3-(dimethylamino)-5-(5-fluoro-3-pyridyl)pyrazolo[1,5-a]pyrimidin-7-yl]amino]indan-5-ol (32.5 mg, 77.95 μmol, 60.7% yield, 97.0% purity) as a yellow solid. $^1$H NMR (400 MHz, $CD_3OD$) δ ppm 9.64 (s, 1H), 9.25 (d, J=9.3 Hz, 1H), 9.08 (s, 1H), 8.43 (s, 1H), 7.22 (s, 1H), 7.08 (d, J=8.1 Hz, 1H), 6.72 (s, 1H), 6.65 (d, J=8.1 Hz, 1H), 4.97-4.92 (m, 1H), 3.54 (s, 6H), 3.44-3.41 (m, 2H), 3.18-3.03 (m, 2H); ES-LCMS m/z 405.2 $[M+H]^+$.

Example 162

Synthesis of I-208

I-208

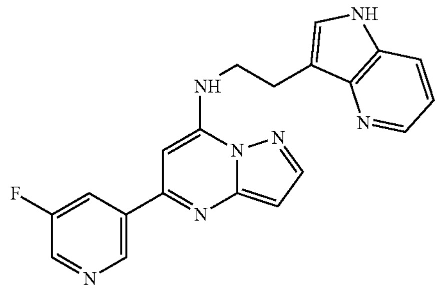 [SMILES: Fc1cncc(-c2cc(NCCc3c[nH]c4cccnc34)n3nccc3n2)c1]

Synthetic Scheme:

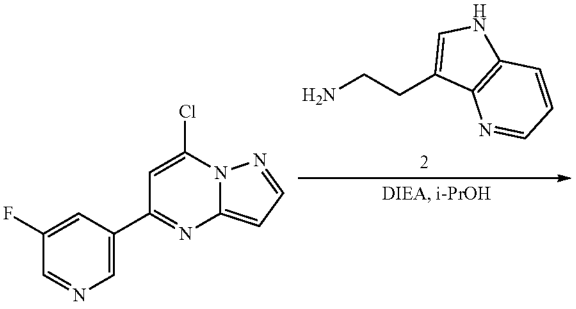

1

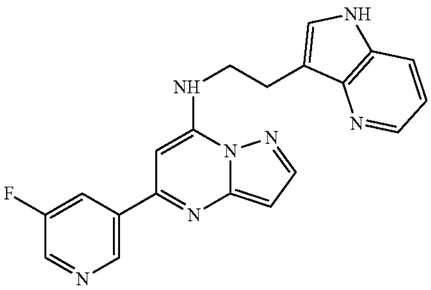

I-208

Step 1: 5-(5-Fluoro-3-pyridyl)-N-[2-(1H-pyrrolo[3,2-b]pyridin-3-yl)ethyl]pyrazolo[1,5-a]pyrimidin-7-amine (I-208)

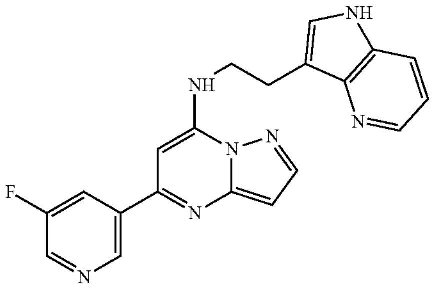

A mixture of 7-chloro-5-(5-fluoro-3-pyridyl)pyrazolo[1,5-a]pyrimidine (60 mg, 225.62 μmol, 1 eq), 2-(1H-pyrrolo[3,2-b]pyridin-3-yl)ethanamine (43.65 mg, 270.75 μmol, 1.2 eq), DIEA (87.48 mg, 676.87 μmol, 117.90 μL, 3 eq) in i-PrOH (10 mL) was stirred at 80° C. for 12 h. The reaction mixture was concentrated to give the residue which was purified by preparative HPLC (column: Agela ASB 150*25 mm*5 m; mobile phase: [water (0.05% HCl)-ACN]; B %: 5%-35%, 9 min), followed by lyophilization to yield 5-(5-fluoro-3-pyridyl)-N-[2-(1H-pyrrolo[3,2-b]pyridin-3-yl)ethyl]pyrazolo[1,5-a]pyrimidin-7-amine (37.11 mg, 75.38 μmol, 33.4% yield, 98.7% purity, 3 HCl) as a yellow solid. $^1$H NMR (400 MHz, $CD_3OD$) δ ppm 8.99 (s, 1H), 8.82 (s, 1H), 8.56-8.50 (m, 2H), 8.35 (d, J=8.8 Hz, 1H), 8.26 (s, 1H), 8.10 (s, 1H), 7.69-7.63 (m, 1H), 7.04 (s, 1H), 6.65 (d, J=2.0 Hz, 1H), 4.22-4.13 (m, 2H), 3.46 (t, J=6.6 Hz, 2H); ES-LCMS m/z 374.2 $[M+H]^+$.

Example 163

Synthesis of I-209

I-209

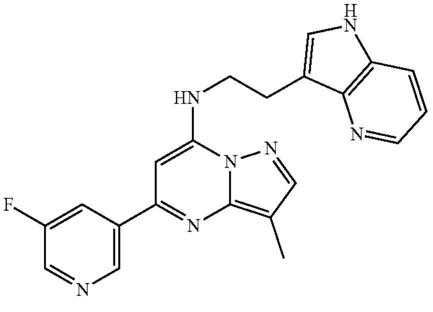 [SMILES: Cc1cnn2c(NCCc3c[nH]c4cccnc34)cc(-c3cncc(F)c3)nc12]

Synthetic Scheme:

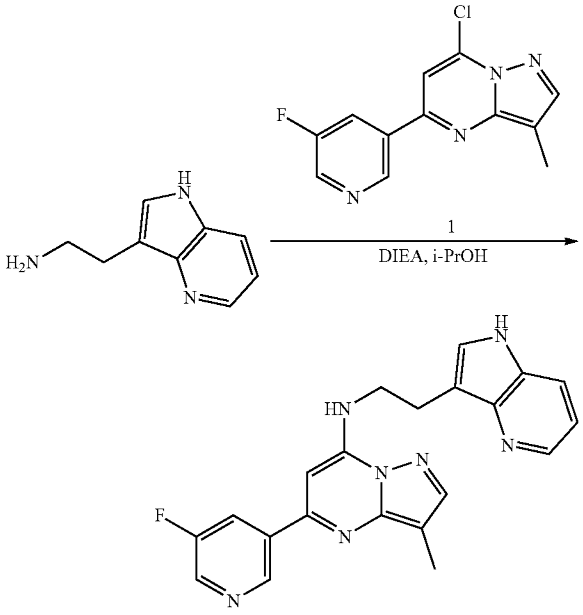

I-209

Step 1: 5-(5-Fluoro-3-pyridyl)-3-methyl-N-[2-(1H-pyrrolo[3,2-b]pyridin-3-yl)ethyl]pyrazolo[1,5-a]pyrimidin-7-amine (1-209)

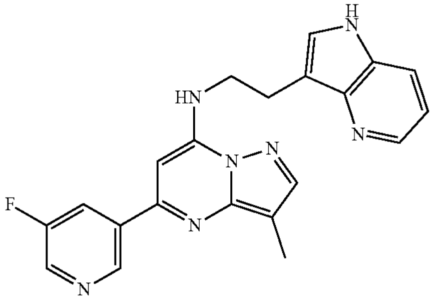

To a solution of 7-chloro-5-(5-fluoro-3-pyridyl)-3-methyl-pyrazolo[1,5-a]pyrimidine (60 mg, 228.42 mol, 1 eq) in —PrOH (5 mL) was added DIA (88.56 mg, 685.27 μmol, 119.36 μL, 3 eq) and 2-(1H-pyrrolo[3,2-b]pyridin-3-yl)ethanamine (45 mg, 279.15 μmol, 1.22 eq). The mixture was stirred at 80° C. for 12 h. The reaction mixture was concentrated under reduced pressure to yield a residue which was purified by preparative HPLC (HCl condition; column: Agela ASB 150*25 mm*5 um; mobile phase: [water (0.05% HCl)-ACN]; B %: 15%-45%, 9 min). The desired fraction was lyophilized to yield 5-(5-fluoro-3-pyridyl)-3-methyl-N-[2-(1H-pyrrolo[3,2-b]pyridin-3-yl)ethyl]pyrazolo[1,5-a]pyrimidin-7-amine (28.89 mg, 56.64 μmol, 24.8% yield, 97.4% purity, 3HCl) as a yellow solid. $^1$H NMR (400 MHz, $CD_3OD$) δ ppm 8.94 (s, 1H), 8.79 (d, J=2.7 Hz, 1H), 8.57-8.50 (m, 2H), 8.31-8.24 (m, 1H), 8.09 (d, J=7.6 Hz, 2H), 7.71-7.63 (m, 1H), 6.80 (s, 1H), 4.12 (t, J=7.0 Hz, 2H), 3.43 (t, J=6.8 Hz, 2H), 2.37 (s, 3H); ES-LCMS m z 388.2 $[M+H]^+$.

Example 164

Synthesis of I-210

I-210

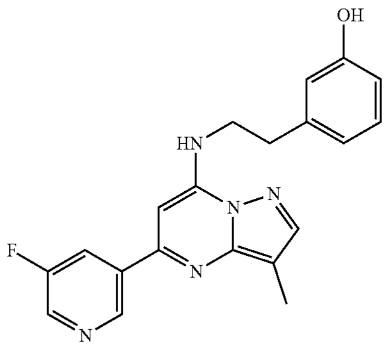

Synthetic Scheme:

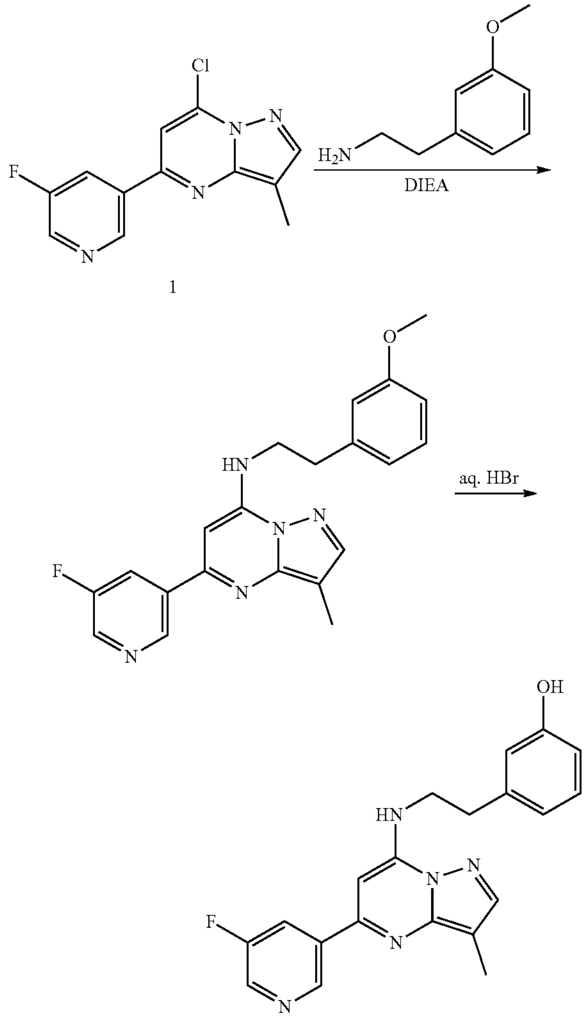

1

I-210

Step 1: 5-(5-Fluoro-3-pyridyl)-N-[2-(3-methoxyphenyl)ethyl]-3-methyl-pyrazolo[1,5-a]pyrimidin-7-amine

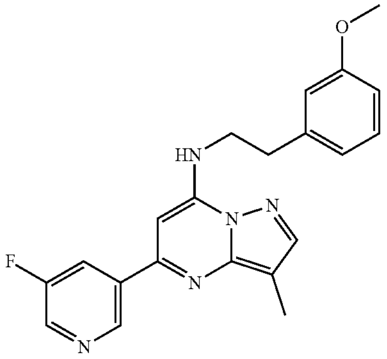 [SMILES: COc1cccc(CCNc2cc(-c3cncc(F)c3)nc3c(C)cnn23)c1]

To a solution of 7-chloro-5-(5-fluoro-3-pyridyl)-3-methyl-pyrazolo[1,5-a]pyrimidine (50 mg, 190.35 μmol, 1 eq) in i-PrOH (3 mL) was added 2-(3-methoxyphenyl) ethanamine (43.17 mg, 285.53 μmol, 41.92 μL, 1.5 eq) and DIEA (73.81 mg, 571.06 μmol, 99.47 μL, 3 eq). The mixture was stirred at 60° C. for 3 h under $N_2$ atmosphere. The reaction mixture was concentrated under reduced pressure to yield 5-(5-fluoro-3-pyridyl)-N-[2-(3-methoxyphenyl)ethyl]-3-methyl-pyrazolo[1,5-a]pyrimidin-7-amine (70 mg, 185.47 μmol, 97.4% yield) as a yellow solid which was used in the next step without further purification. $^1H$ NMR (400 MHz, $CD_3OD$) δ ppm 9.01 (s, 1H), 8.54 (d, J=2.5 Hz, 1H), 8.25-8.18 (m, 1H), 7.89 (s, 1H), 7.18-7.10 (m, 1H), 6.89-6.83 (m, 2H), 6.73-6.65 (m, 1H), 6.36 (s, 1H), 3.83 (t, J=6.8 Hz, 2H), 3.67 (s, 3H), 3.03 (t, J=6.8 Hz, 2H), 2.33 (s, 3H); ES-LCMS m/z 378.2 $[M+H]^+$.

Step 2: 3-[2-[[5-(5-Fluoro-3-pyridyl)-3-methyl-pyrazolo[1,5-a]pyrimidin-7-yl]amino]ethyl]phenol (I-210)

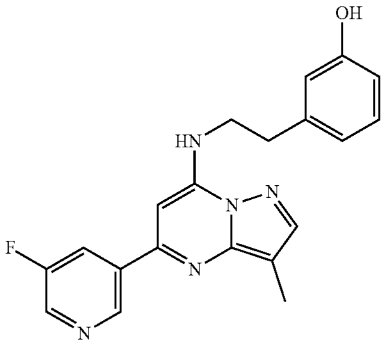 [SMILES: Cc1cnn2c(NCCc3cccc(O)c3)cc(-c3cncc(F)c3)nc12]

A mixture of 5-(5-fluoro-3-pyridyl)-N-[2-(3-methoxyphenyl)ethyl]-3-methyl-pyrazolo[1,5-a]pyrimidin-7-amine (70 mg, 185.47 μmol, 1 eq) and aq. HBr (4.47 g, 33.15 mmol, 3 mL, 60% purity, 178.72 eq) was degassed and purged with $N_2$ for 3 times. The mixture was stirred at 120° C. for 1 h under $N_2$ atmosphere. The reaction mixture was concentrated under reduced pressure to yield a residue which was purified by preparative HPLC (column: Phenomenex Gemini C18 250*50 mm*10 μm; mobile phase: [water (0.05% HCl)-ACN]; B %: 35%-65%, 10 min), followed by lyophilization to yield 3-[2-[[5-(5-fluoro-3-pyridyl)-3-methyl-pyrazolo[1,5-a]pyrimidin-7-yl]amino]ethyl]phenol (40.74 mg, 93.37 μmol, 50.3% yield, 100% purity, 2HCl) as a yellow solid. $^1$H NMR (400 MHz, $CO_3OD$) δ ppm 8.87-8.85 (m, 2H), 8.22 (d, J=8.8 Hz, 1H), 8.14 (s, 1H), 7.06-6.95 (m, 1H), 6.77-6.68 (m, 2H), 6.60-6.51 (m, 1H), 6.44 (s, 1H), 4.01 (t, J=6.5 Hz, 2H), 3.02 (t, J=6.4 Hz, 2H), 2.36 (s, 3H); ES-LCMS m/z 364.1 $[M+H]^+$.

Example 165

Synthesis of I-211

I-211

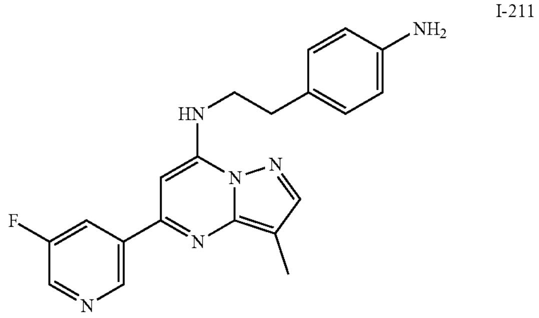 [SMILES: Cc1cnn2c(NCCc3ccc(N)cc3)cc(-c3cncc(F)c3)nc12]

Synthetic Scheme:

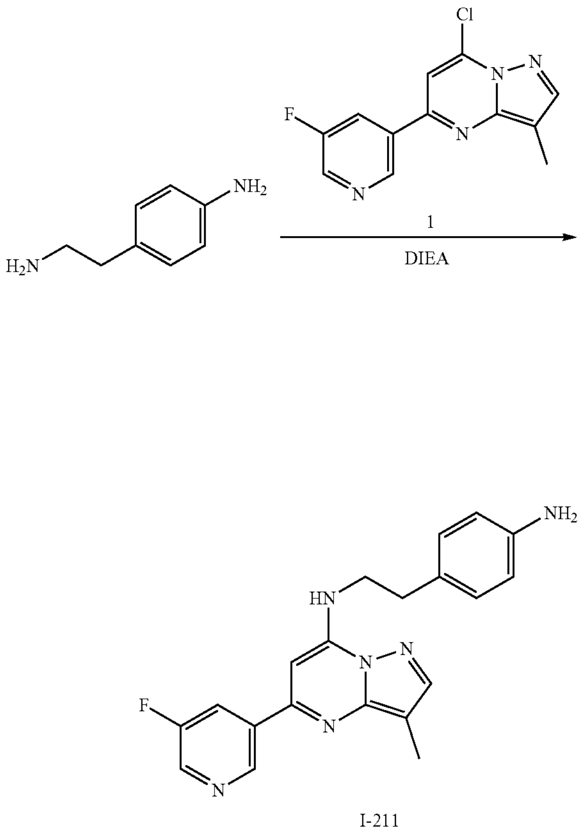

I-211

Step 1: N-[2-(4-Aminophenyl)ethyl]-5-(5-fluoro-3-pyridyl)-3-methyl-pyrazolo[1,5-a]pyrimidin-7-amine (I-211)

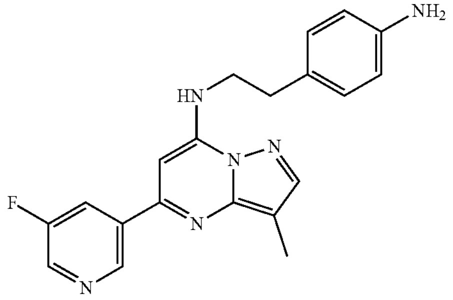 [SMILES: Cc1cnn2c(NCCc3ccc(N)cc3)cc(-c3cncc(F)c3)nc12]

To a solution of 4-(2-aminoethyl)aniline (25.92 mg, 190.35 μmol, 1 eq) in i-PrOH (3 mL) was added 7-chloro-5-(5-fluoro-3-pyridyl)-3-methyl-pyrazolo[1,5-a]pyrimidine (50 mg, 190.35 μmol, 1 eq) and DIEA (73.81 mg, 571.06 μmol, 99.47 μL, 3 eq). The mixture was stirred at 50° C. for 12 h. The reaction mixture was concentrated under reduced pressure to yield a residue which was purified by preparative HPLC (column: Agela ASB 150*25 mm*5 μm; mobile phase: [water (0.05% HCl)-ACN]; B %: 20%-50%, 8 min) followed by lyophilization to yield N-[2-(4-aminophenyl)ethyl]-5-(5-fluoro-3-pyridyl)-3-methyl-pyrazolo[1,5-a]pyrimidin-7-amine (73.99 mg, 155.10 μmol, 81.5% yield, 98.9% purity, 3HCl) as a yellow solid. $^1$H NMR (400 MHz, $CD_3OD$) δ ppm 8.94 (s, 1H), 8.80 (d, J=2.7 Hz, 1H), 8.28 (td, J=2.4, 8.9 Hz, 1H), 8.11 (s, 1H), 7.54 (d, J=8.6 Hz, 2H), 7.35 (d, J=8.3 Hz, 2H), 6.80 (s, 1H), 4.02 (t, J=7.2 Hz, 2H), 3.19 (t, J=7.2 Hz, 2H), 2.37 (s, 3H); ES-LCMS m/z 363.3 $[M+H]^+$.

Example 166

Synthesis of I-213

I-213

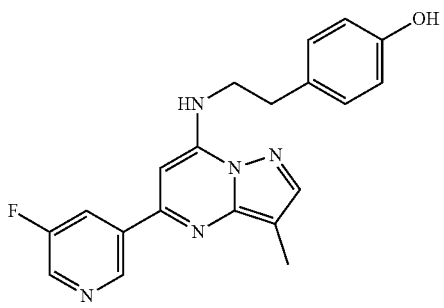 [SMILES: Cc1cnn2c(NCCc3ccc(O)cc3)cc(-c3cncc(F)c3)nc12]

Synthetic Scheme:

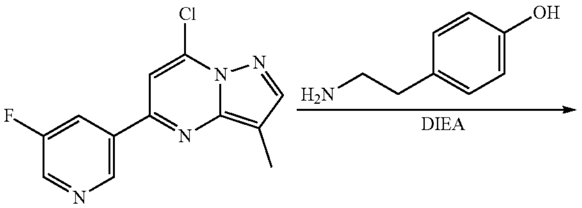

1

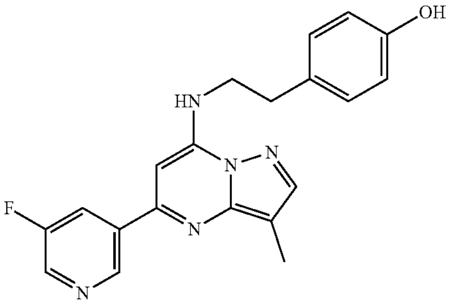

I-213

Step 1: 4-[2-[[5-(5-Fluoro-3-pyridyl)-3-methyl-pyrazolo[1,5-a]pyrimidin-7-yl]amino]ethyl]phenol (I-213)

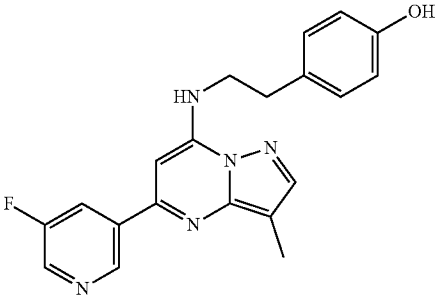

To a mixture of 7-chloro-5-(5-fluoro-3-pyridyl)-3-methyl-pyrazolo[1,5-a]pyrimidine (60 mg, 228.42 mol, 1 eq) and 4-(2-aminoethyl)phenol (37.60 mg, 274.11 μmol, 1.2 eq) in i-PrOH (12 mL) was added DIEA (88.57 mg, 685.27 μmol, 119.36 μL, 3 eq). The mixture was stirred at 75° C. for 19 h under $N_2$ atmosphere. The reaction mixture was concentrated under reduced pressure to yield a residue which was purified by preparative HPLC (column: Agela ASB 150*25 mm*5 μm; mobile phase: [water (0.05% HCl)-ACN]; B %: 30%-60%, 9 min), followed by lyophilization to yield 4-[2-[[5-(5-fluoro-3-pyridyl)-3-methyl-pyrazolo[1,5-a]pyrimidin-7-yl]amino]ethyl]phenol (55.37 mg, 126.91 μmol, 55.6% yield, 100.0% purity, 2HCl) as a yellow solid. $^1$H NMR (400 MHz, $CD_3OD$) δ ppm 8.84 (br s, 2H), 8.23-8.12 (m, 2H), 7.06 (d, J=8.6 Hz, 2H), 6.63-6.57 (m, 2H), 6.36 (s, 1H), 3.96 (t, J=6.5 Hz, 2H), 2.99 (t, J=6.5 Hz, 2H), 2.36 (s, 3H); ES-LCMS m/z 364.0 $[M+H]^+$.

Example 167

Synthesis of I-214

I-214

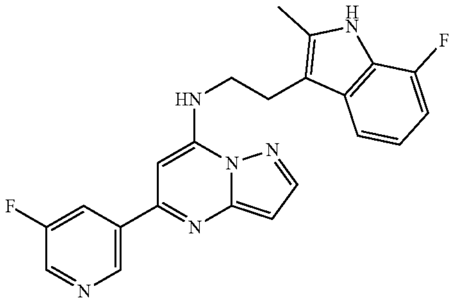

Synthetic Scheme:

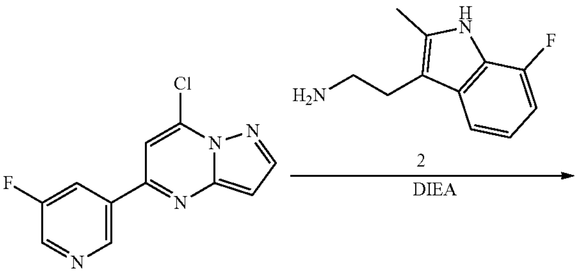

1

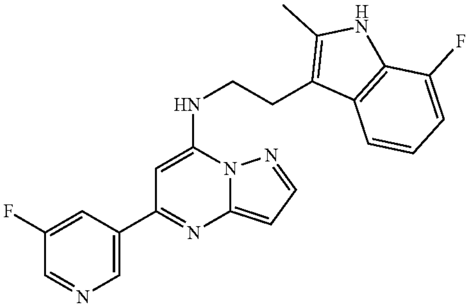

I-214

Step 1: N-[2-(7-Fluoro-2-methyl-1H-indol-3-yl)ethyl]-5-(5-fluoro-3-pyridyl)pyrazolo[1,5-a]pyrimidin-7-amine (I-214)

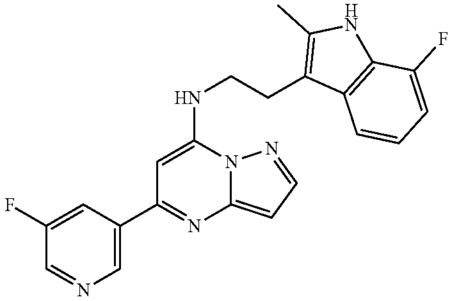 [SMILES: Cc1[nH]c2c(F)cccc2c1CCNc1cc(-c2cncc(F)c2)nc2ccnn12]

To a mixture of 7-chloro-5-(5n-fluoro-3-pyridyl)pyrazolo[1,5-a]pyrimidine (100 mg, 376.04 mol, 1 eq) in DIEA (5 mL) and i-PrOH (3 mL) was added 2-(7-fluoro-2-methyl-1H-indol-3-yl)ethanamine (95.55 mg, 376.04 μmol, 1 eq, HCl). The mixture was stirred at 80° C. for 12 h. The reaction mixture was concentrated under reduced pressure to yield a residue which was purified by preparative HPLC (column: Gemini 150*25 5 u; mobile phase: [water (0.05% ammonia hydroxide v/v)-ACN]; B %: 45%-75%, 8 min), followed by lyophilization to yield N-[2-(7-fluoro-2-methyl-1H-indol-3-yl)ethyl]-5-(5-fluoro-3-pyridyl)pyrazolo[1,5-a]pyrimidin-7-amine (58.73 mg, 141.11 μmol, 37.5% yield, 97.2% purity) as a yellow solid. $^1$H NMR (400 MHz, $CDCl_3$) δ ppm 8.70 (s, 1H), 8.44 (d, J=2.8 Hz, 1H), 7.93 (d, J=2.4 Hz, 1H), 7.81-7.76 (m, 1H), 7.25 (d, J=7.6 Hz, 1H), 6.99 (dt, J=4.8, 8.0 Hz, 1H), 6.83-6.79 (m, 1H), 6.47 (d, J=2.4 Hz, 1H), 5.99 (s, 1H), 3.72 (q, J=6.4 Hz, 2H), 3.11 (t, J=6.4 Hz, 2H), 2.24 (s, 3H); ES-LCMS m/z 405.2 $[M+H]^+$.

Example 168

Synthesis of I-215

I-215

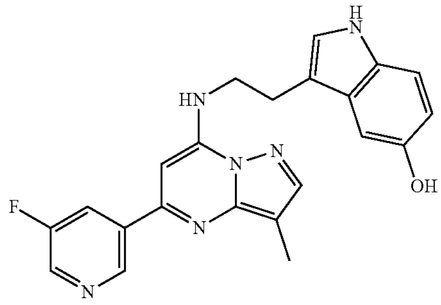

Synthetic Scheme:

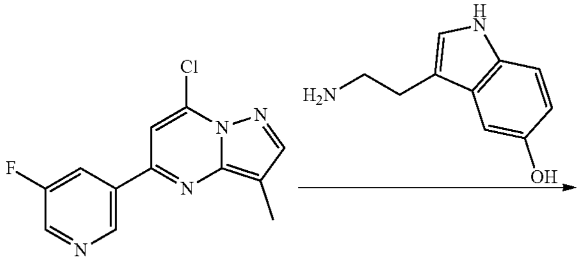

1

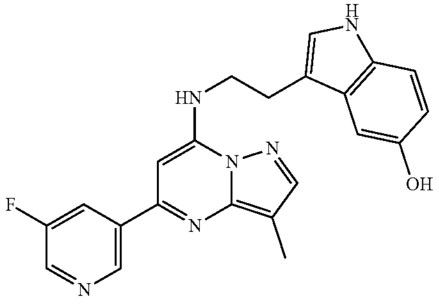

I-215

Step 1: 3-[2-[[5-(5-Fluoro-3-pyridyl)-3-methyl-pyrazolo[1,5-a]pyrimidin-7-yl]amino]ethyl]-1H-indol-5-ol (I-215)

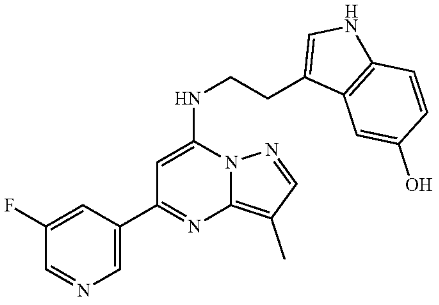 [SMILES: Cc1cnn2c(NCCc3c[nH]c4ccc(O)cc34)cc(-c3cncc(F)c3)nc12]

To a solution of 7-chloro-5-(5-fluoro-3-pyridyl)-3-methyl-pyrazolo[1,5-a]pyrimidine (60 mg, 228.42 μmol, 1 eq), 3-(2-aminoethyl)-1H-indol-5-ol (60.37 mg, 283.87 μmol, 1.24 eq, HCl) in i-PrOH (5 mL) was added DIEA (147.61 mg, 1.14 μmol, 198.94 μL, 5 eq). The mixture was stirred at 60° C. for 4 h. The reaction mixture was concentrated to yield a residue which was purified on silica gel column chromatography (from PE/EtOAc=1/0 to 1/1, TLC: PE/EtOAc=1/1, $R_f$=0.25) to yield the product 3-[2-[[5-(5-fluoro-3-pyridyl)-3-methyl-pyrazolo[1,5-a]pyrimidin-7-yl]amino]ethyl]-1H-indol-5-ol (73.19 mg, 179.69 μmol, 78.7% yield, 98.8% purity) as a yellow solid. $^1$H NMR (400 MHz, DMSO-$d_6$) δ ppm 10.52 (br s, 1H), 9.16 (s, 1H), 8.77-8.55 (m, 2H), 8.27 (d, J=9.7 Hz, 1H), 8.07-7.93 (m, 2H), 7.20-7.02 (m, 2H), 6.91 (d, J=1.8 Hz, 1H), 6.65 (s, 1H), 6.62-6.58 (m, 1H), 3.91-3.74 (m, 2H), 3.03 (t, J=7.1 Hz, 2H), 2.28 (s, 3H); ES-LCMS m/z 403.2 $[M+H]^+$.

Example 169

Synthesis of I-216a

I-216a

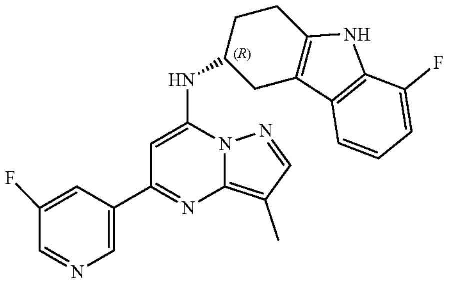

Synthetic Scheme:

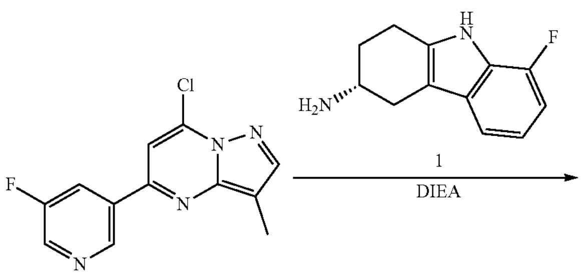

-continued

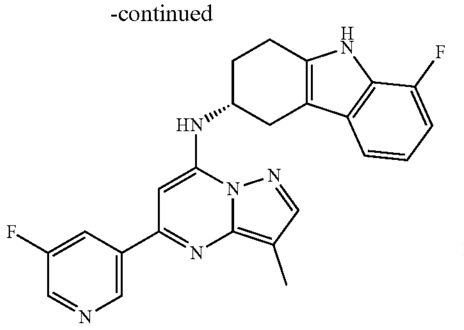

I-216a

Step 1: (3R)-8-Fluoro-N-[5-(5-fluoro-3-pyridyl)-3-methyl-pyrazolo[1,5-a]pyrimidin-7-yl]-2,3,4,9-tetrahydro-1H-carbazol-3-amine (I-216a)

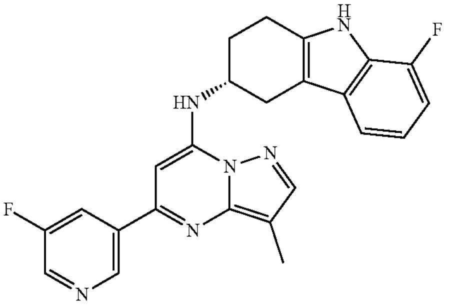 [SMILES: Cc1cnn2c(N[C@@H]3CCc4[nH]c5c(F)cccc5c4C3)cc(-c3cncc(F)c3)nc12]

A mixture of 7-chloro-5-(5-fluoro-3-pyridyl)-3-methyl-pyrazolo[1,5-a]pyrimidine (50 mg, 190.35 μmol, 1 eq), (3R)-8-fluoro-2,3,4,9-tetrahydro-1H-carbazol-3-amine (47.36 mg, 209.39 μmol, 1.1 eq) and DIEA (123.01 mg, 951.76 μmol, 165.78 μL, 5 eq) in i-PrOH (2 mL) was stirred at 90° C. for 12 h. The reaction mixture was concentrated under reduced pressure to yield a residue which was purified by preparative HPLC (column: Phenomenex Gemini C18 250*50 mm*10 um; mobile phase: [water (0.05% HCl)-ACN]; B %: 50%-80%, 10 min). The desired fraction was lyophilized to yield (3R)-8-fluoro-N-[5-(5-fluoro-3-pyridyl)-3-methyl-pyrazolo[1,5-a]pyrimidin-7-yl]-2,3,4,9-tetrahydro-1H-carbazol-3-amine (21.98 mg, 51.06 μmol, 26.8% yield, 100.0% purity) as a yellow solid (SFC: Rt=2.106, ee %=97.3%). $^1H$ NMR (400 MHz, $CD_3OD$) δ ppm 8.97 (s, 1H), 8.75 (d, J=2.4 Hz, 1H), 8.29 (td, J=2.0, 9.2 Hz, 1H), 8.13 (s, 1H), 7.16 (d, J=8.0 Hz, 1H), 7.00 (s, 1H), 6.89 (dt, J=4.8, 8.0 Hz, 1H), 6.76 (dd, J=8.0, 11.6 Hz, 1H), 4.62 (m, 1H), 3.32 (s, 1H), 3.16-3.06 (m, 1H), 3.03-2.95 (m, 2H), 2.37 (s, 3H), 2.36-2.23 (m, 2H); ES-LCMS m/z 431.2 $[M+H]^+$.

Example 170

Synthesis of I-218

I-218

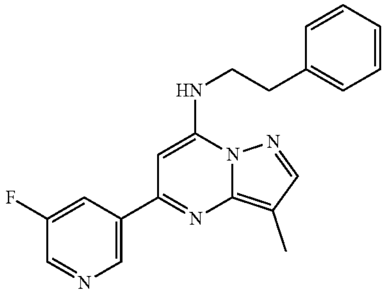 [SMILES: Cc1cnn2c(NCCc3ccccc3)cc(-c3cncc(F)c3)nc12]

Synthetic Scheme:

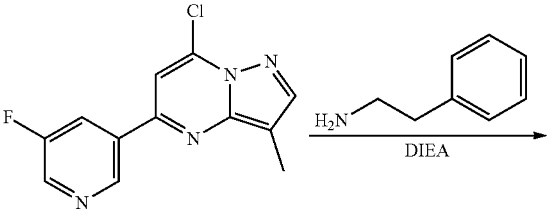

1

I-218

Step 1: 5-(5-Fluoro-3-pyridyl)-3-methyl-N-(2-phenylethyl)pyrazolo[1,5-a]pyrimidin-7-amine (I-218)

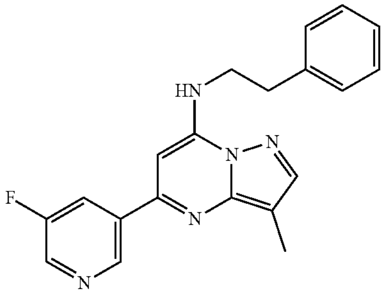

To a solution of 7-chloro-5-(5-fluoro-3-pyridyl)-3-methyl-pyrazolo[1,5-a]pyrimidine (50 mg, 190.35 μmol, 1 eq) in i-PrOH (3 mL) was added DIEA (73.80 mg, 571.06 μmol, 99.47 μL, 3 eq) and 2-phenylethanamine (34.60 mg, 285.53 μmol, 35.86 μL, 1.5 eq). The mixture was stirred at 60° C. for 12 h. The reaction mixture was concentrated under reduced pressure to yield a residue which was purified by preparative HPLC (column: Agela ASB 150*25 mm*5 m; mobile phase: [water (0.05% HCl)-ACN]; B %: 45%-75%, 9 min), followed by lyophilization to yield 5-(5-fluoro-3-pyridyl)-3-methyl-N-(2-phenylethyl)pyrazolo[1,5-a]pyrimidin-7-amine (37.43 mg, 89.05 μmol, 46.78% yield, 100% purity, 2HCl) as a yellow solid. $^1$H NMR (400 MHz, $CD_3OD$) δ ppm 8.83-8.78 (m, 2H), 8.17-8.13 (m, 2H), 7.32-7.27 (m, 2H), 7.23 (t, J=7.3 Hz, 2H), 7.18-7.13 (m, 1H), 6.51 (s, 1H), 4.01 (t, J=6.7 Hz, 2H), 3.09 (t, J=6.7 Hz, 2H), 2.34 (s, 3H); ES-LCMS m/z 348.2 $[M+H]^+$.

Example 171

Synthesis of I-219

I-219

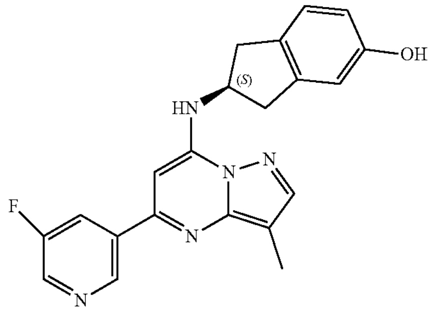

Synthetic Scheme:

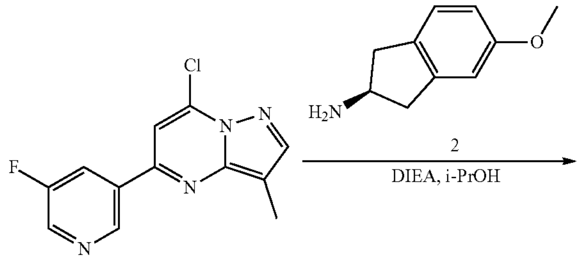

1

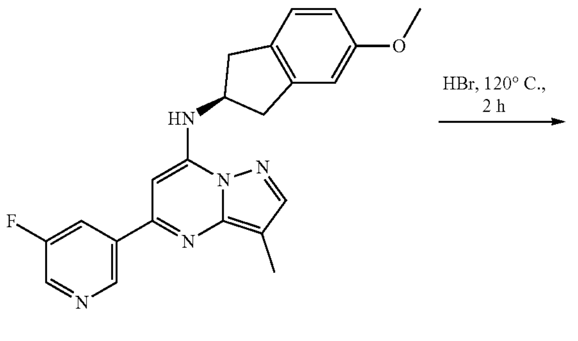

-continued

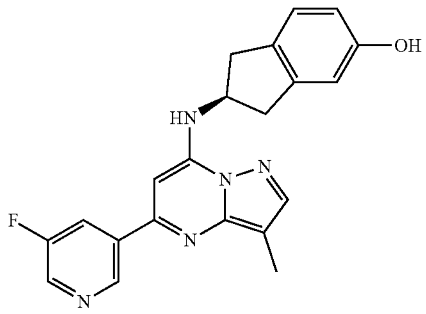

I-219

Step 1: 5-(5-Fluoro-3-pyridyl)-N-[(2S)-5-methoxy-indan-2-yl]-3-methyl-pyrazolo[1,5-a]pyrimidin-7-amine

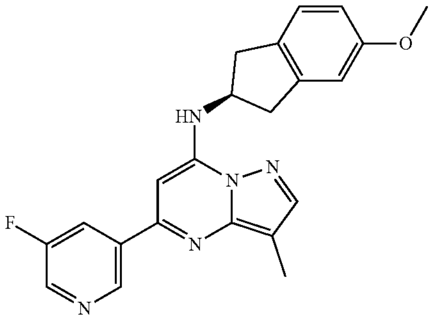 [SMILES: COc1ccc2c(c1)C[C@@H](Nc1cc(-c3cncc(F)c3)nc3c(C)cnn13)C2]

A mixture of 7-chloro-5-(5-fluoro-3-pyridyl)-3-methyl-pyrazolo[1,5-a]pyrimidine (50 mg, 190.35 mol, 1 eq), (2S)-5-methoxyindan-2-amine (33.05 mg, 190.35 μmol, 1 eq), DIEA (73.80 mg, 571.06 μmol, 99.47 μL, 3 eq) in i-PrOH (10 mL) was stirred at 80° C. for 12 h. The reaction mixture was concentrated to yield 5-(5-fluoro-3-pyridyl)-N-[(2S)-5-methoxyindan-2-yl]-3-methyl-pyrazolo[1,5-a]pyrimidin-7-amine (60 mg, 122.03 μmol, 64.1% yield, 79.2% purity) as brown oil which was used in the next step without further purification. $^1$H NMR (400 MHz, $CDCl_3$) δ ppm 9.06-8.95 (m, 1H), 8.58-8.43 (m, 1H), 8.22-8.09 (m, 1H), 7.79 (s, 1H), 7.15-7.00 (m, 1H), 6.80-6.61 (m, 2H), 6.53 (d, J=7.1 Hz, 1H), 6.32 (s, 1H), 4.59 (s, 1H), 3.74 (s, 3H), 3.60 (d, J=6.4 Hz, 2H), 3.06-3.02 (m, 2H), 2.31 (s, 3H); ES-LCMS m/z 390.2 $[M+H]^+$.

Step 2: (2S)-2-[[5-(5-Fluoro-3-pyridyl)-3-methyl-pyrazolo[1,5-a]pyrimidin-7-yl]amino]indan-5-ol (I-219)

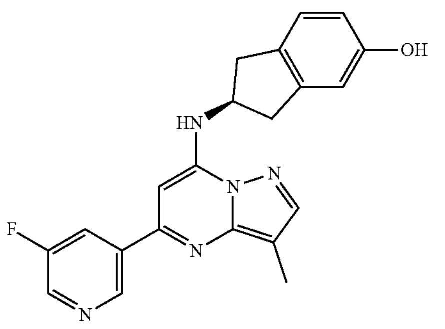

5-(5-Fluoro-3-pyridyl)-N-[(2S)-5-methoxyindan-2-yl]-3-methyl-pyrazolo[1,5-a]pyrimidin-7-amine (60 mg, 122.03 μmol, 1 eq) in HBr (5 mL, 60% in water) was stirred at 120° C. for 2 h. The reaction mixture was concentrated to yield a residue which was purified by preparative HPLC (column: Phenomenex Gemini C18 250*50 mm*10 m; mobile phase: [water (0.05% HCl)-ACN]; B %: 30%-60%, 10 min), followed by lyophilization to yield (2S)-2-[[5-(5-fluoro-3-pyridyl)-3-methyl-pyrazolo[1,5-a]pyrimidin-7-yl]amino]indan-5-ol (23.51 mg, 52.44 μmol, 43.0% yield, 100.0% purity, 2 HCl) ((SFC: Rt=2.090, ee=100%) as a yellow solid. $^1$H NMR (400 MHz, $CD_3OD$) δ ppm 9.08 (s, 1H), 8.90 (s, 1H), 8.45 (d, J=9.0 Hz, 1H), 8.16 (s, 1H), 7.09 (d, J=8.0 Hz, 1H), 7.01 (s, 1H), 6.73 (s, 1H), 6.66 (dd, J=2.0, 8.0 Hz, 1H), 5.11-5.02 (m, 1H), 3.54-3.42 (m, 2H), 3.28-3.14 (m, 2H), 2.41 (s, 3H); ES-LCMS m/z 376.2 $[M+H]^+$.

Example 172

Synthesis of I-220

I-220

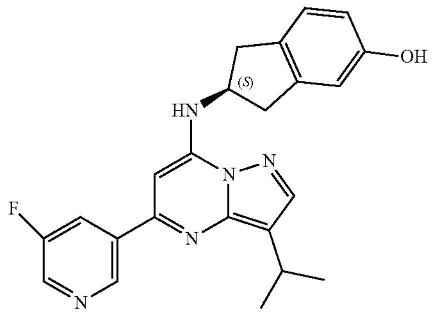

Synthetic Scheme:

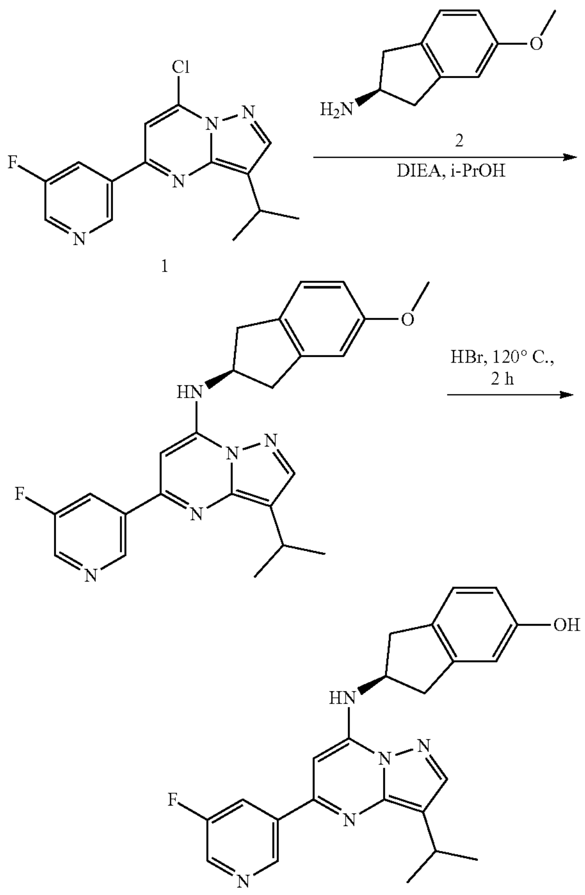

I-220

Step 1: 5-(5-Fluoro-3-pyridyl)-3-isopropyl-N-[(2S)-5-methoxyindan-2-yl]pyrazolo[1,5-a]pyrimidin-7-amine

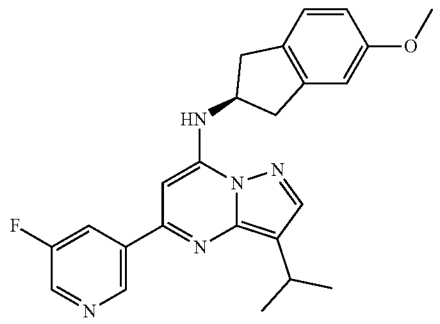 [SMILES: COc1ccc2c(c1)C[C@@H](Nc1cc(-c3cncc(F)c3)nc3c(C(C)C)cnn13)C2]

A mixture of 7-chloro-5-(5-fluoro-3-pyridyl)-3-isopropyl-pyrazolo[1,5-a]pyrimidine (50 mg, 154.79 μmol, 1 eq), (2S)-5-methoxyindan-2-amine (26.88 mg, 154.79 μmol, 1 eq) and DIEA (60.02 mg, 464.36 μmol, 80.88 μL, 3 eq) in i-PrOH (10 mL) was stirred at 80° C. for 12 h. The reaction mixture was concentrated to yield 5-(5-fluoro-3-pyridyl)-3-isopropyl-N-[(2S)-5-methoxyindan-2-yl]pyrazolo[1,5-a]pyrimidin-7-amine (60 mg, 115.69 μmol, 74.7% yield, 80.5% purity) as brown oil which was used in the next step without further purification. $^1$H NMR (400 MHz, $CDCl_3$) δ ppm 9.06-8.93 (m, 1H), 8.54-8.42 (m, 1H), 8.13 (d, J=7.3 Hz, 1H), 7.79 (s, 1H), 7.10 (d, J=7.9 Hz, 1H), 6.79-6.58 (m, 2H), 6.51 (d, J=7.3 Hz, 1H), 6.33 (s, 1H), 4.57 (s, 1H), 3.75-3.62 (m, 3H), 3.59 (d, J=6.8 Hz, 2H), 3.02 (d, J=8.6 Hz, 3H), 1.15 (d, J=2.2 Hz, 6H); ES-LCMS m/z 418.2[M+H]$^+$.

Step 2: (2S)-2-[[5-(5-Fluoro-3-pyridyl)-3-isopropyl-pyrazolo[1,5-a]pyrimidin-7-yl]amino]indan-5-ol (I-220)

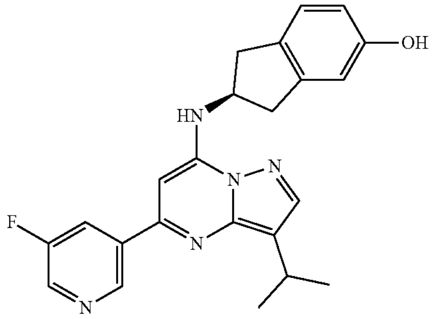

5-(5-Fluoro-3-pyridyl)-3-isopropyl-N-[(2S)-5-methoxy-indan-2-yl]pyrazolo[1,5-a]pyrimidin-7-amine (60 mg, 115.69 μmol, 1 eq) in HBr (5 mL, 60% in water) was stirred at 120° C. for 2 h. The reaction mixture was concentrated to yield the residue which was purified by preparative HPLC (column: Phenomenex Gemini C18 250*50 mm*10 um; mobile phase: [water (0.05% HCl)-ACN]; B %: 40%-70%, 10 min) followed by lyophilization to yield (2S)-2-[[5-(5-fluoro-3-pyridyl)-3-isopropyl-pyrazolo[1,5-a]pyrimidin-7-yl]amino]indan-5-ol (17.20 mg, 36.11 μmol, 31.2% yield, 100.0% purity, 2 HCl) (SFC: Rt=2.050, ee=99.374%) as a yellow solid. $^1$H NMR (400 MHz, $CD_3OD$) δ ppm 9.04 (s, 1H), 8.86 (d, J=2.0 Hz, 1H), 8.40 (d, J=9.0 Hz, 1H), 8.26 (s, 1H), 7.09 (d, J=8.0 Hz, 1H), 6.99 (s, 1H), 6.73 (s, 1H), 6.66 (dd, J=2.5, 8.0 Hz, 1H), 5.09-5.01 (m, 1H), 3.54-3.43 (m, 2H), 3.39 (td, J=6.8, 13.9 Hz, 1H), 3.26-3.15 (m, 2H), 1.41 (d, J=7.0 Hz, 6H); ES-LCMS m/z 404.2 [M+H]$^+$.

Example 173

Synthesis of I-222a, I-222b and I-222c

I-222a

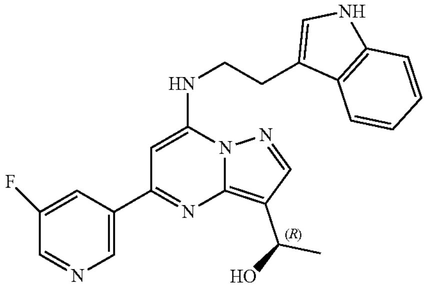

-continued

I-222b

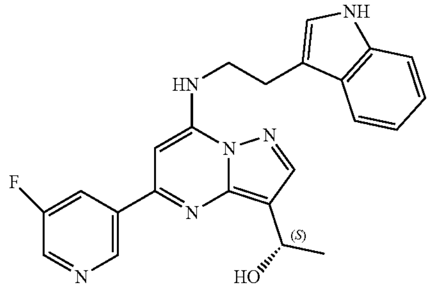

I-222c

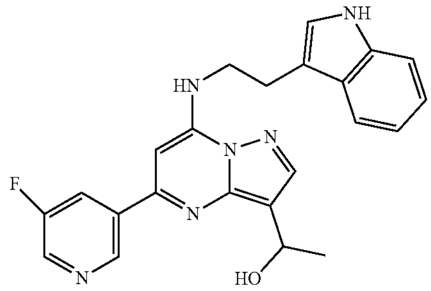

Synthetic Scheme:

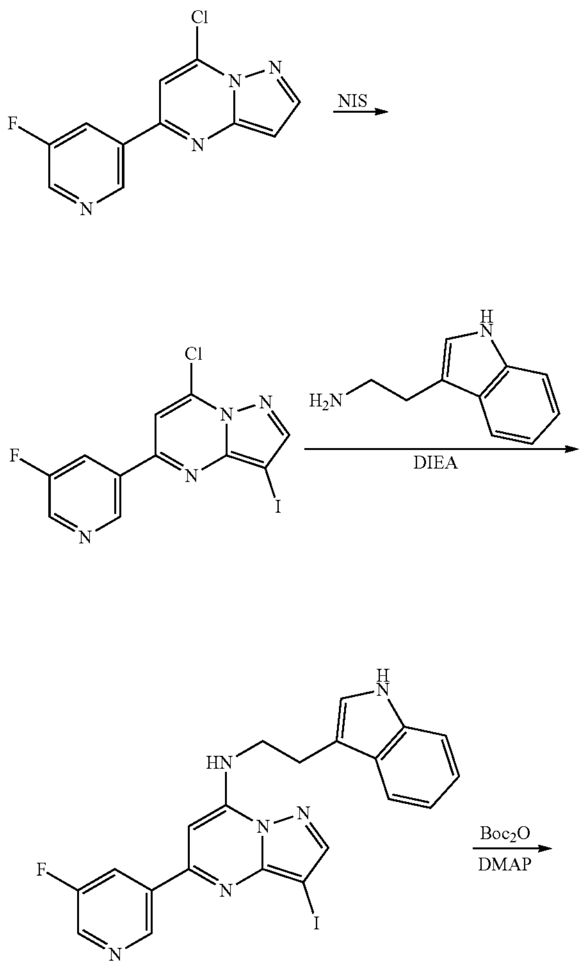

-continued

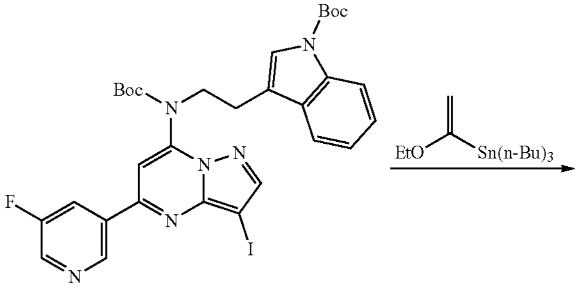

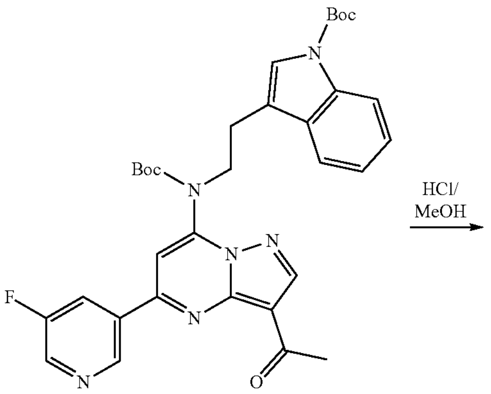

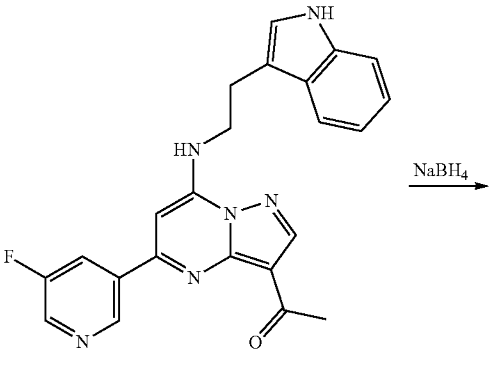

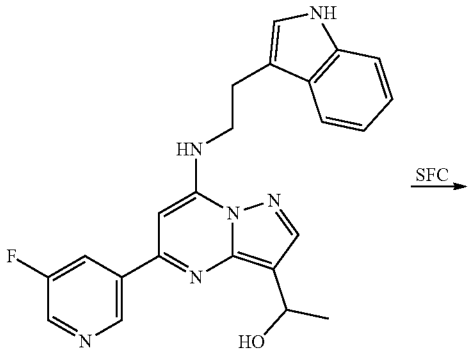

I-222c

-continued

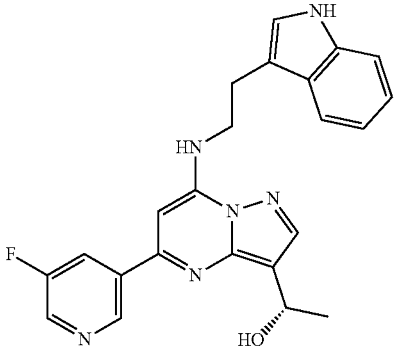

I-222b

+

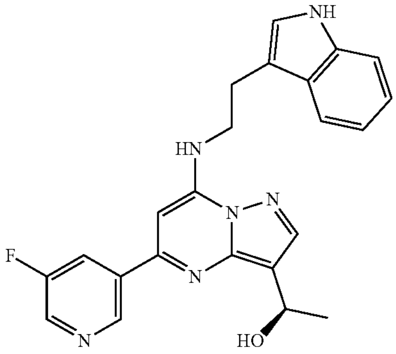

I-222a

Step 1: 7-Chloro-5-(5-fluoro-3-pyridyl)-3-iodo-pyrazolo[1,5-a]pyrimidine

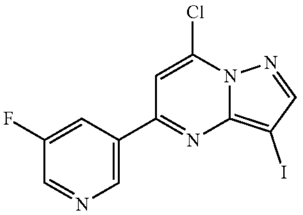

To a solution of 7-chloro-5-(5-fluoro-3-pyridyl)pyrazolo [1,5-a]pyrimidine (600 mg, 2.24 mmol, 1 eq) in DCM (25 mL) and MeCN (25 mL) was added NIS (1.01 g, 4.48 mmol, 2 eq) partwise and the mixture was stirred at 20° C. for 24 h. TLC (PE/EtOAc=3/1, $R_f$=0.41) showed the starting material was consumed completely. The reaction mixture was quenched with saturated $Na_2S_2O_3$ (100 mL) and concentrated under reduced pressure to remove DCM and MeCN. The residue was extracted with EtOAc (100 mL×3). The organic layer was dried over $Na_2SO_4$, filtered and concentrated under reduced pressure to yield a residue which was purified by flash silica gel chromatography (from PE/EtOAc=1/0 to 4/1, TLC: PE/EtOAc=3/1, $R_f$=0.41) to yield 7-chloro-5-(5-fluoro-3-pyridyl)-3-iodo-pyrazolo[1,5-a]pyrimidine (1.03 g, 2.75 mmol, 61.4% yield, 100.0% purity) as a yellow solid. $^1H$ NMR (400 MHz, $CDCl_3$) δ ppm 9.12 (s, 1H), 8.64 (d, J=2.8 Hz, 1H), 8.34-8.26 (m, 2H), 7.53-7.45 (m, 1H); ES-LCMS m/z 374.9 $[M+H]^+$.

Step 2: 5-(5-Fluoro-3-pyridyl)-N-[2-(1H-indol-3-yl)ethyl]-3-iodo-pyrazolo[1,5-a]pyrimidin-7-amine

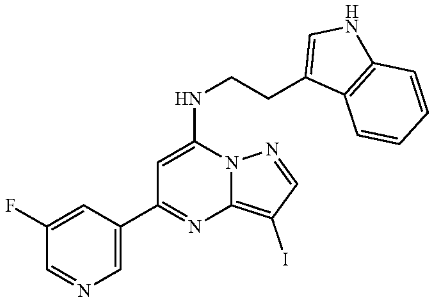 [SMILES: Fc1cncc(-c2cc(NCCc3c[nH]c4ccccc34)n3ncc(I)c3n2)c1]

A mixture of 7-chloro-5-(5-fluoro-3-pyridyl)-3-iodo-pyrazolo[1,5-a]pyrimidine (650 mg, 1.74 mmol, 1 eq), 2-(1H-indol-3-yl)ethanamine (333.66 mg, 2.08 mmol, 1.2 eq) and DIEA (672.89 mg, 5.21 mmol, 906.86 μL, 3 eq) in i-PrOH (50 mL) was stirred at 60° C. for 12 h. TLC (PE/EtOAc=2/1, $R_f$=0.30) showed the starting material was consumed completely. The reaction mixture was cooled to 20° C. and filtered. The solid was washed with i-PrOH (5 mL), dried under reduced pressure to yield 5-(5-fluoro-3-pyridyl)-N-[2-(1H-indol-3-yl)ethyl]-3-iodo-pyrazolo[1,5-a]pyrimidin-7-amine (620 mg, 1.24 mmol, 71.3% yield, 99.3% purity) as a yellow solid. $^1$H NMR (400 MHz, $CDCl_3$) δ ppm 8.78 (s, 1H), 8.52 (d, J=2.4 Hz, 1H), 8.10-7.90 (m, 3H), 7.68 (d, J=7.6 Hz, 1H), 7.39-7.32 (m, 1H), 7.24-7.18 (m, 2H), 7.06 (s, 1H), 6.57 (br s, 1H), 6.12 (s, 1H), 3.86 (q, J=6.4 Hz, 2H), 3.27 (t, J=6.4 Hz, 2H); ES-LCMS m/z 499.1 $[M+H]^+$.

Step 3: tert-Butyl 3-[2-[tert-butoxycarbonyl-[5-(5-fluoro-3-pyridyl)-3-iodo-pyrazolo[1,5-a]pyrimidin-7-yl]amino]ethyl]indole-1-carboxylate

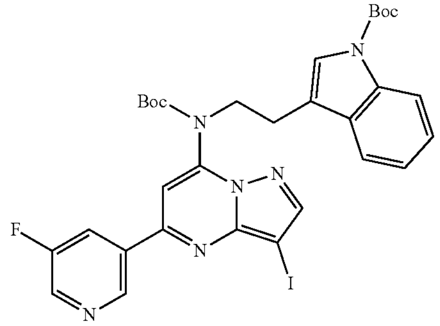 [SMILES: CC(C)(C)OC(=O)N(CCc1cn(C(=O)OC(C)(C)C)c2ccccc12)c1cc(-c2cncc(F)c2)nc2c(I)cnn12]

A mixture of 5-(5-fluoro-3-pyridyl)-N-[2-(1H-indol-3-yl)ethyl]-3-iodo-pyrazolo[1,5-a]pyrimidin-7-amine (900 mg, 1.81 mmol, 1 eq), $Boc_2O$ (1.58 g, 7.22 mmol, 1.66 mL, 4 eq) and DMAP (1.10 g, 9.03 mmol, 5 eq) in 1,4-dioxane (60 mL) was stirred at 120° C. for 12 h. TLC (PE/EtOAc=3/1, $R_f$=0.60) showed the starting material was consumed completely. The reaction mixture was concentrated under reduced pressure to yield a residue which was purified by flash silica gel chromatography (from PE/EtOAc=1/0 to 5/1, TLC: PE/EtOAc=3/1, $R_f$=0.60) to yield tert-butyl 3-[2-[tert-butoxycarbonyl-[5-(5-fluoro-3-pyridyl)-3-iodo-pyrazolo[1,5-a]pyrimidin-7-yl]amino]ethyl]indole-1-carboxylate (1 g, 1.41 mmol, 78.2% yield, 98.7% purity) as a yellow solid. $^1$H NMR (400 MHz, $CDCl_3$) δ ppm 8.73 (s, 1H), 8.55 (d, J=2.4 Hz, 1H), 8.15 (s, 1H), 7.98 (br s, 1H), 7.90 (d, J=7.6 Hz, 1H), 7.42 (d, J=7.6 Hz, 1H), 7.25-7.23 (m, 2H), 7.19-7.12 (m, 1H), 6.55 (s, 1H), 4.24-4.18 (m, 2H), 3.15-3.06 (m, 2H), 1.59 (s, 9H), 1.39 (s, 9H); ES-LCMS m/z 699.2 $[M+H]^+$.

Step 4: tert-Butyl 3-[2-[[3-acetyl-5-(5-fluoro-3-pyridyl)pyrazolo[1,5-a]pyrimidin-7-yl]-tert-butoxy-carbonyl-amino]ethyl]indole-1-carboxylate

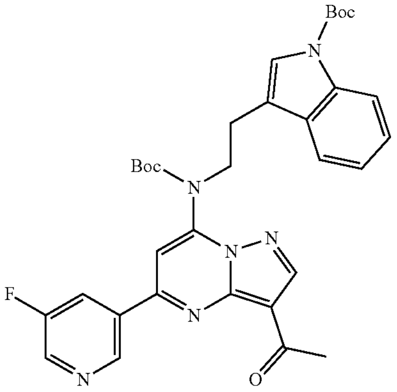 [SMILES: CC(=O)c1cnn2c(N(CCc3cn(C(=O)OC(C)(C)C)c4ccccc34)C(=O)OC(C)(C)C)cc(-c3cncc(F)c3)nc12]

A mixture of tert-butyl 3-[2-[tert-butoxycarbonyl-[5-(5-fluoro-3-pyridyl)-3-iodo-pyrazolo[1,5-a]pyrimidin-7-yl]amino]ethyl]indole-1-carboxylate (200 mg, 282.60 μmol, 1 eq), tributyl(1-ethoxyvinyl)stannane (880 mg, 2.44 mmol, 822.43 μL, 8.62 eq) and Pd(dppf)$Cl_2$ (206.78 mg, 282.60 μmol, 1 eq) in toluene (6 mL) was bubbled with $N_2$ for 2 minutes and sealed. The reaction mixture was irradiated under microwave (1 bar) at 100° C. for 2 h. The reactions were carried out in parallel 5 times. KF(100 mL, 2M) was added to the combined mixture. The mixture was stirred at 25° C. for 1 h and extracted with EtOAc (100 mL×3). The organic layer was dried over $Na_2SO_4$, filtered and concentrated under reduced pressure to yield a residue which was purified by flash silica gel chromatography (from PE/EtOAc=1/0 to 4/1, TLC: PE/EtOAc=3/1, $R_f$=0.40) to yield tert-butyl 3-[2-[[3-acetyl-5-(5-fluoro-3-pyridyl)pyrazolo[1,5-a]pyrimidin-7-yl]-tert-butoxycarbonyl-amino]ethyl]indole-1-carboxylate (450 mg, 732.11 μmol, 51.8% yield, 100.0% purity) as a yellow solid. $^1$H NMR (400 MHz, $CDCl_3$) δ ppm 8.79 (s, 1H), 8.66 (s, 1H), 8.61 (d, J=2.4 Hz, 1H), 7.97 (d, J=6.4 Hz, 1H), 7.80 (td, J=2.4, 9.2 Hz, 1H), 7.42 (d, J=7.6 Hz, 1H), 7.26-7.20 (m, 2H), 7.17-7.11 (m, 1H), 6.65 (s, 1H), 4.30 (t, J=6.4 Hz, 2H), 3.18-3.12 (m, 2H), 2.84 (s, 3H), 1.59 (s, 9H), 1.43 (s, 9H); ES-LCMS m/z 615.3 $[M+H]^+$.

Step 5: 1-[5-(5-Fluoro-3-pyridyl)-7-[2-(1H-indol-3-yl)ethylamino]pyrazolo[1,5-a]pyrimidin-3-yl]ethanone

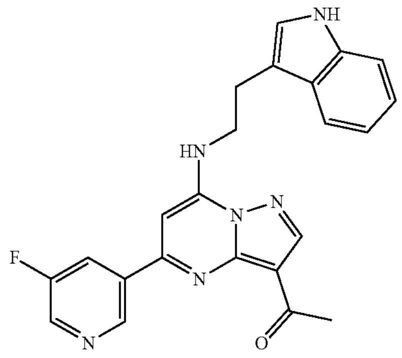 [SMILES: CC(=O)c1cnn2c(NCCc3c[nH]c4ccccc34)cc(-c3cncc(F)c3)nc12]

To a mixture of tert-butyl 3-[2-[[3-acetyl-5-(5-fluoro-3-pyridyl)pyrazolo[1,5-a]pyrimidin-7-yl]-tert-butoxycarbonyl-amino]ethyl]indole-1-carboxylate (450 mg, 732.11 μmol, 1 eq) in MeOH (50 mL) was added $HCl/H_2O$ (6 M, 150 mL, 1229.33 eq) at 20° C. The mixture was stirred at 35° C. for 3 h. The mixture was basified with aqueous NaOH (15%) until pH=8 and concentrated under reduced pressure to remove MeOH. The residue was extracted with EtOAc (50 mL×3). The organic layer was dried over $Na_2SO_4$, filtered and concentrated under reduced pressure to yield 1-[5-(5-fluoro-3-pyridyl)-7-[2-(1H-indol-3-yl)ethylamino]pyrazolo[1,5-a]pyrimidin-3-yl]ethanone (300 mg, 723.88 μmol, 98.9% yield, 100.0% purity) as a yellow solid which was used in the next step without further purification. $^1H$ NMR (400 MHz, DMSO-$d_6$) δ ppm 10.77 (br s, 1H), 9.11 (s, 1H), 8.67 (d, J=2.4 Hz, 1H), 8.60 (t, J=6.0 Hz, 1H), 8.49 (s, 1H), 8.18 (d, J=10.4 Hz, 1H), 7.61 (d, J=7.6 Hz, 1H), 7.24 (d, J=7.6 Hz, 1H), 7.16 (d, J=1.6 Hz, 1H), 7.05-6.99 (m, 1H), 6.98-6.93 (m, 1H), 6.82 (s, 1H), 3.84 (q, J=6.4 Hz, 2H), 3.09 (t, J=6.8 Hz, 2H), 2.67 (s, 3H); ES-LCMS m/z 415.1 $[M+H]^+$.

Step 6: (1S)-1-[5-(5-Fluoro-3-pyridyl)-7-[2-(1H-indol-3-yl)ethylamino]pyrazolo[1,5-a]pyrimidin-3-yl]ethanol (I-222b) & (1R)-1-[5-(5-Fluoro-3-pyridyl)-7-[2-(1H-indol-3-yl)ethylamino]pyrazolo[1,5-a]pyrimidin-3-yl]ethanol (I-222a)

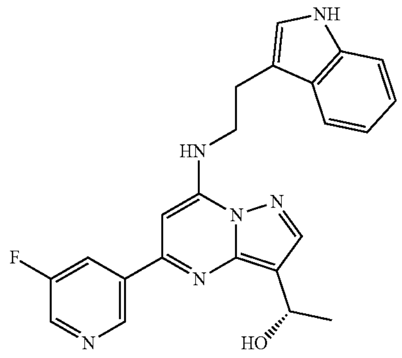 [SMILES: C[C@H](O)c1cnn2c(NCCc3c[nH]c4ccccc34)cc(-c3cncc(F)c3)nc12]

+

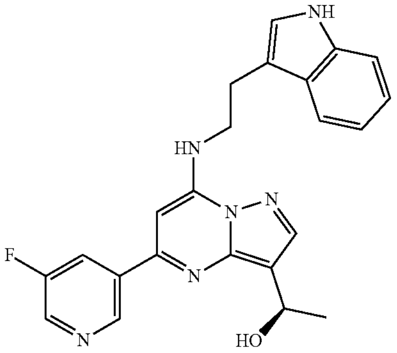 [SMILES: C[C@@H](O)c1cnn2c(NCCc3c[nH]c4ccccc34)cc(-c3cncc(F)c3)nc12]

To a solution of 1-[5-(5-fluoro-3-pyridyl)-7-[2-(1H-indol-3-yl)ethylamino]pyrazolo[1,5-a]pyrimidin-3-yl]ethanone (250 mg, 603.23 μmol, 1 eq) in THF (50 mL) and EtOH (20 mL) was added $NaBH_4$ (114.11 mg, 3.02 mmol, 5 eq) partwise at 20° C. The mixture was stirred at 20° C. for 3 h. The reaction mixture was quenched with water (50 mL) and concentrated under reduced pressure at 30° C. to remove EtOH and THF. The residue was extracted with EtOAc (80 mL×3), dried over $Na_2SO_4$, filtered and concentrated under reduced pressure to yield a residue which was separated by chiral SFC (column: DAICEL CHIRALPAK AD-H (250 mm*30 mm, 5 um); mobile phase: [0.1% $NH_3.H_2O$/EtOH]; B %: 40%-40%). Peak 1 was concentrated under reduced pressure to yield a residue which was purified by preparative HPLC (column: Phenomenex Gemini 150*25 mm*10 um; mobile phase: [water (0.05% ammonia hydroxide v/v)-ACN]; B %: 40%-70%, 10 min). The desired fraction was lyophilized to yield an enantiomer (32.78 mg, 76.81 μmol, 12.7% yield, 97.6% purity) as a white solid (SFC: Rt=6.825, ee=98.8%; Optical Rotation: $[\alpha]^{22.3}_D$=−9.540 (10.04 mg/10 mL in MeOH)). $^1H$ NMR (400 MHz, $CDCl_3$) δ ppm 8.78 (s, 1H), 8.51 (d, J=2.4 Hz, 1H), 8.07 (br s, 1H), 7.95 (s, 1H), 7.87-7.80 (m, 1H), 7.68 (d, J=7.6 Hz, 1H), 7.40-7.32 (m, 1H), 7.26-7.18 (m, 2H), 7.06 (s, 1H), 6.56 (br s, 1H), 6.08 (s, 1H), 5.34 (d, J=6.0 Hz, 1H), 3.89-3.83 (m, 2H), 3.29-3.24 (m, 3H), 1.70 (d, J=6.4 Hz, 3H); ES-LCMS m/z 417.2 $[M+H]^+$. Peak 2 was concentrated under reduced pressure to yield a residue which was purified by preparative HPLC (column: Phenomenex Gemini 150*25 mm*10 um; mobile phase: [water (0.05% ammonia hydroxide v/v)-ACN]; B %: 40%-70%, 10 min). The desired fraction was lyophilized to yield the residue which was separated by chiral SFC (column: DAICEL CHIRALPAK AD-H (250 mm*30 mm, 5 um); mobile phase: [0.1% $NH_3$—$H_2O$/EtOH]; B %: 40%-40%) again. The desired fraction was concentrated under reduced pressure to yield a residue which was purified by preparative HPLC (column: Phenomenex Gemini 150*25 mm*10 um; mobile phase: [water (0.05% ammonia hydroxide v/v)-ACN]; B %: 42%-72%, 10 min). The desired fraction was lyophilized to yield the other enantiomer (30.13 mg, 72.35 μmol, 12.0% yield, 100.0% purity) as a white solid (SFC: Rt=7.042, ee=99.0%; Optical Rotation: $[\alpha]^{22.2}_D$=1.916 (6.44 mg/10 mL in MeOH)). $^1H$ NMR (400 MHz, $CDCl_3$) δ ppm 8.77 (s, 1H), 8.51 (d, J=2.4 Hz, 1H), 8.11 (br s, 1H), 7.95 (s, 1H), 7.83 (td, J=2.0, 9.6 Hz, 1H), 7.68 (d, J=7.6 Hz, 1H), 7.36 (d, J=8.0 Hz, 1H), 7.27-7.18 (m, 2H), 7.06 (d, J=2.0 Hz, 1H), 6.58 (t, J=5.6 Hz, 1H), 6.07 (s, 1H), 5.42-5.26 (m, 1H), 3.85 (q, J=6.4 Hz, 2H), 3.34-3.22 (m, 3H), 1.70 (d, J=6.4 Hz, 3H); ES-LCMS m/z 417.2 $[M+H]^+$.

Example 174

Synthesis of I-224

I-224

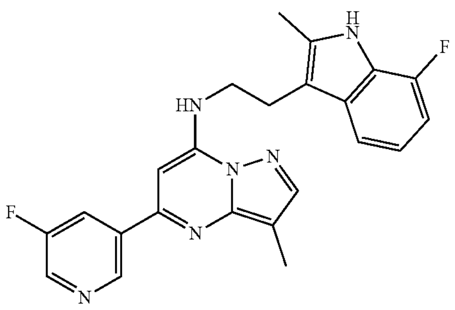 [SMILES: Cc1[nH]c2c(F)cccc2c1CCNc1cc(-c2cncc(F)c2)nc2c(C)cnn12]

Synthetic Scheme:

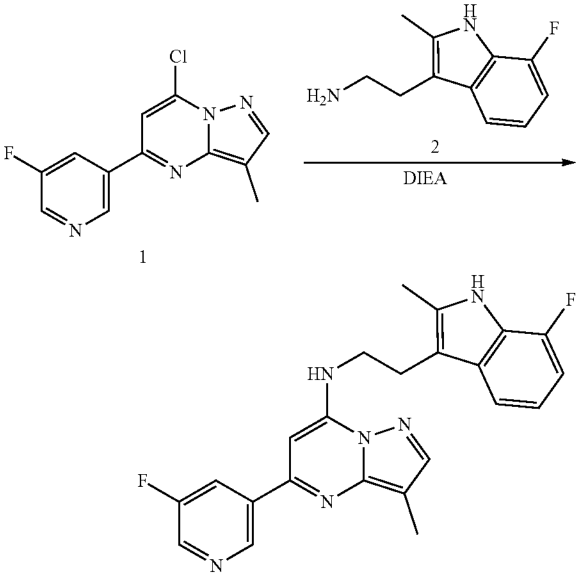

1

I-224

Step 1: N-[2-(7-Fluoro-2-methyl-1H-indol-3-yl) ethyl]-5-(5-fluoro-3-pyridyl)-3-methyl-pyrazolo (I-224)

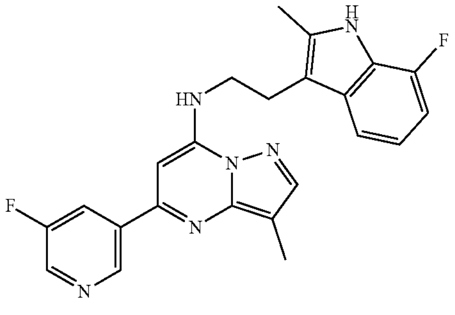

A mixture of 7-chloro-5-(5-fluoro-3-pyridyl)-3-methyl-pyrazolo[1,5-a]pyrimidine (60 mg, 228.42 μmol, 1 eq) and 2-(7-fluoro-2-methyl-1H-indol-3-yl)ethanamine (79.89 mg, 296.95 μmol, 1.3 eq, HCl) in i-PrOH (10 mL) was added DIEA (88.57 mg, 685.27 μmol, 119.36 μL, 3 eq) and purged with $N_2$ for 3 times. The mixture was stirred at 80° C. for 16 h under $N_2$ atmosphere. The reaction mixture was concentrated under reduced pressure to give a residue which was purified by preparative HPLC (column: Agela Durashell C18 150*25 5 u; mobile phase: [water (0.05% HCl)-ACN]; B %: 30%-60%, 12 min) to yield a product which was purified by preparative HPLC (column: Gemini 150*25 5 u; mobile phase: [water (0.05% ammonia hydroxide v/v)-ACN]; B %: 55%-85%, 8 min), followed by lyophilization to yield N-[2-(7-fluoro-2-methyl-1H-indol-3-yl)ethyl]-5-(5-fluoro-3-pyridyl)-3-methyl-pyrazolo[1,5-a]pyrimidin-7-amine (16.79 mg, 40.13 μmol, 17.6% yield, 100.0% purity) as a yellow solid. $^1$H NMR (400 MHz, $CDCl_3$) δ ppm 8.80 (s, 1H), 8.50 (d, J=2.6 Hz, 1H), 8.00 (br s, 1H), 7.95-7.82 (m, 2H), 7.32 (d, J=7.9 Hz, 1H), 7.10-7.03 (m, 1H), 6.89 (dd, J=8.2, 11.0 Hz, 1H), 6.49 (br s, 1H), 6.01 (s, 1H), 3.78 (q, J=6.5 Hz, 2H), 3.21-3.13 (m, 2H), 2.38 (s, 3H), 2.29 (s, 3H); ES-LCMS m/z 419.2 $[M+H]^+$.

Example 175

Synthesis of I-225

I-225

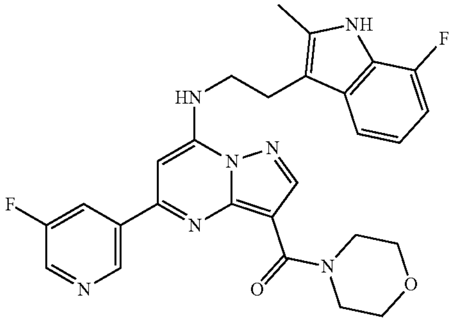

Synthetic Scheme:

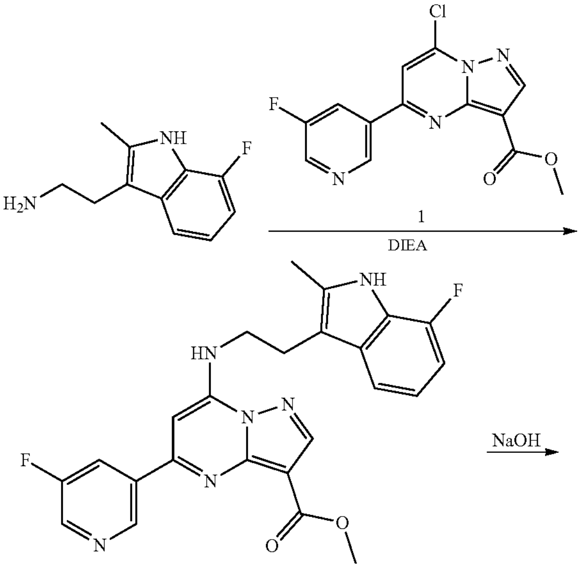

-continued

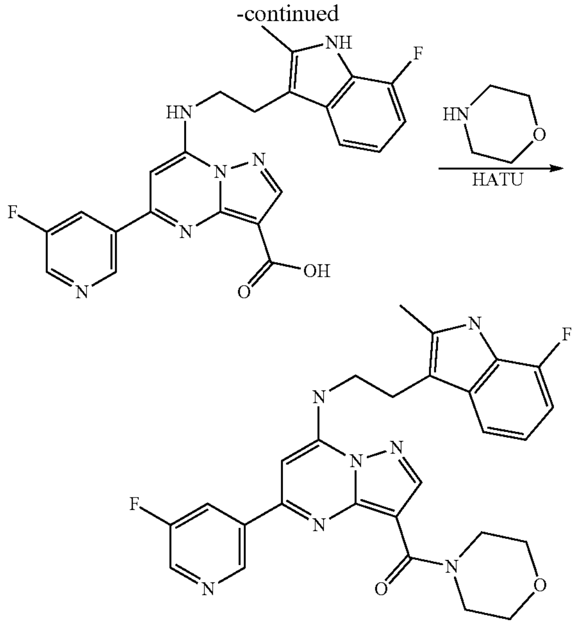

I-225

Step 1: Methyl 7-[2-(7-fluoro-2-methyl-1H-indol-3-yl)ethylamino]-5-(5-fluoro-3-pyridyl)pyrazolo[1,5-a]pyrimidine-3-carboxylate

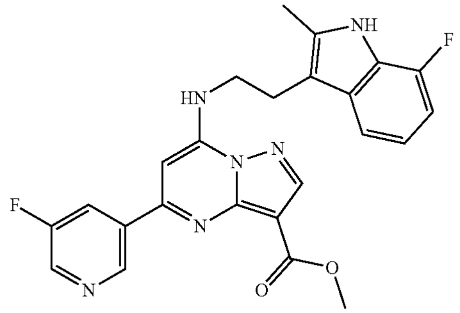 [SMILES: COC(=O)c1cnn2c(NCCc3c(C)[nH]c4c(F)cccc34)cc(-c3cncc(F)c3)nc12]

To a solution of 2-(7-fluoro-2-methyl-1H-indol-3-yl)ethanamine (50 mg, 196.77 μmol, 1 eq, HCl) in i-PrOH (5 mL) was added methyl 7-chloro-5-(5-fluoro-3-pyridyl)pyrazolo[1,5-a]pyrimidine-3-carboxylate (63.52 mg, 196.77 μmol, 1 eq) and DIEA (76.29 mg, 590.31 μmol, 102.82 μL, 3 eq). The mixture was stirred at 60° C. for 3 h under $N_2$ atmosphere. The mixture was concentrated under reduced pressure and water (50 mL) was added. The mixture was extracted with EtOAc (30 mL×3). The combined organic layers were washed with brine (20 mL), dried over $Na_2SO_4$, filtered and concentrated to yield methyl 7-[2-(7-fluoro-2-methyl-1H-indol-3-yl)ethylamino]-5-(5-fluoro-3-pyridyl)pyrazolo[1,5-a]pyrimidine-3-carboxylate (90 mg, 173.79 μmol, 88.3% yield, 89.3% purity) as a yellow solid which was used in the next step without further purification. $^1H$ NMR (400 MHz, $CD_3OD$) δ ppm 8.51-8.46 (m, 2H), 8.41 (s, 1H), 7.72-7.65 (m, 1H), 7.38 (d, J=8.0 Hz, 1H), 6.98-6.92 (m, 1H), 6.69-6.60 (m, 1H), 5.85 (s, 1H), 3.88 (s, 3H), 3.83 (br s, 2H), 3.16-3.07 (m, 2H), 2.08 (s, 3H); ES-LCMS m/z 463.2 $[M+H]^+$.

Step 2: 7-[2-(7-Fluoro-2-methyl-1H-indol-3-yl)ethylamino]-5-(5-fluoro-3-pyridyl)pyrazolo[1,5-a]pyrimidine-3-carboxylic Acid

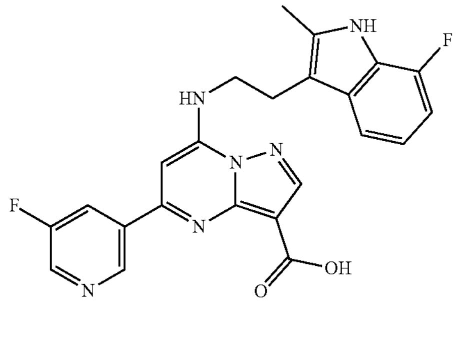 [SMILES: Cc1[nH]c2c(F)cccc2c1CCNc1cc(-c2cncc(F)c2)nc2c(C(=O)O)cnn12]

To a solution of methyl 7-[2-(7-fluoro-2-methyl-1H-indol-3-yl)ethylamino]-5-(5-fluoro-3-pyridyl)pyrazolo[1,5-a]pyrimidine-3-carboxylate (90 mg, 173.79 μmol, 1 eq) in MeOH (5 mL) was added NaOH (2 M, 4.96 mL, 57.09 eq). The mixture was stirred at 50° C. for 4 h under $N_2$ atmosphere. The mixture was concentrated under reduced pressure. The residue was dissolved in water (50 mL), adjusted to pH to 3 by 1N HCl solution, extracted with EtOAc (20 mL×3). The combined organic layers were washed with brine (20 mL), dried over $Na_2SO_4$, filtered and concentrated to yield 7-[2-(7-fluoro-2-methyl-1H-indol-3-yl)ethylamino]-5-(5-fluoro-3-pyridyl)pyrazolo[1,5-a]pyrimidine-3-carboxylic acid (80 mg, 160.56 μmol, 92.4% yield, 90.0% purity) as a yellow solid which was used in the next step without further purification. $^1H$ NMR (400 MHz, $CD_3OD$) δ ppm 8.48 (s, 2H), 8.41 (s, 1H), 7.68 (d, J=9.8 Hz, 1H), 7.38 (d, J=7.8 Hz, 1H), 6.95 (dt, J=4.5, 7.9 Hz, 1H), 6.68-6.60 (m, 1H), 5.85 (s, 1H), 3.89-3.83 (m, 2H), 3.15-3.08 (m, 2H), 2.08 (s, 3H); ES-LCMS m/z 449.2 $[M+H]^+$.

Step 3: [7-[2-(7-Fluoro-2-methyl-1H-indol-3-yl)ethylamino]-5-(5-fluoro-3-pyridyl)pyrazolo[1,5-a]pyrimidin-3-yl]-morpholino-methanone (I-225)

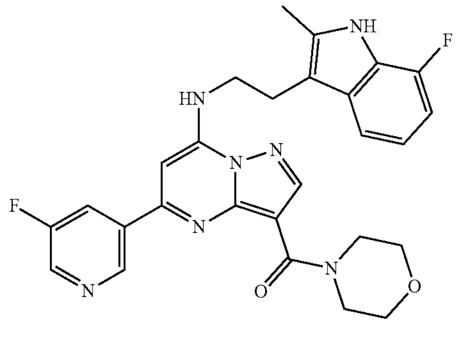 [SMILES: Cc1[nH]c2c(F)cccc2c1CCNc1cc(-c2cncc(F)c2)nc2c(C(=O)N3CCOCC3)cnn12]

To a solution of 7-[2-(7-fluoro-2-methyl-1H-indol-3-yl)ethylamino]-5-(5-fluoro-3-pyridyl)pyrazolo[1,5-a]pyrimidine-3-carboxylic acid (80 mg, 160.56 μmol, 1 eq) in DCM (10 mL) was added morpholine (20.98 mg, 240.84 μmol, 21.19 μL, 1.5 eq), HATU (91.58 mg, 240.84 μmol, 1.5 eq) and TEA (32.49 mg, 321.12 μmol, 44.70 μL, 2 eq). The mixture was stirred at 20° C. for 1 h under $N_2$ atmosphere. The mixture was concentrated under reduced pressure, water (30 mL) was added. The mixture was extracted with EtOAc (20 mL×3). The combined organic layers were washed with brine (30 mL), dried over $Na_2SO_4$, filtered and concentrated to yield a residue which was purified by preparative HPLC (column: Phenomenex Gemini C18 250*50 mm*10 μm; mobile phase: [water (0.05% HCl)-ACN]; B %: 33%-63%, 10 min), followed by lyophilization to yield [7-[2-(7-fluoro-2-methyl-1H-indol-3-yl)ethylamino]-5-(5-fluoro-3-pyridyl) pyrazolo[1,5-a]pyrimidin-3-yl]-morpholino-methanone (29.09 mg, 56.21 μmol, 35.0% yield, 100% purity) as a yellow solid. $^1$H NMR (400 MHz, $CD_3OD$) δ ppm 8.78 (d, J=2.5 Hz, 1H), 8.60 (s, 1H), 8.38 (s, 1H), 7.79-7.70 (m, 1H), 7.34 (d, J=8.0 Hz, 1H), 6.87 (dt, J=4.7, 7.8 Hz, 1H), 6.60 (dd, J=7.7, 11.4 Hz, 1H), 5.88 (s, 1H), 4.01-3.93 (m, 2H), 3.76 (s, 8H), 3.20-3.14 (m, 2H), 2.12 (s, 3H); ES-LCMS m/z 518.3 $[M+H]^+$.

Example 176

Synthesis of I-226

I-226

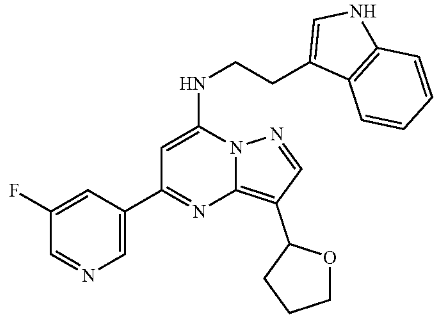

Synthetic Scheme:

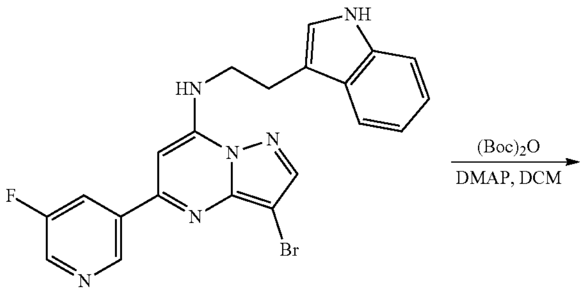

1

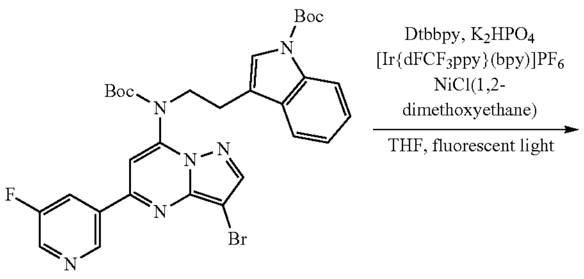

-continued

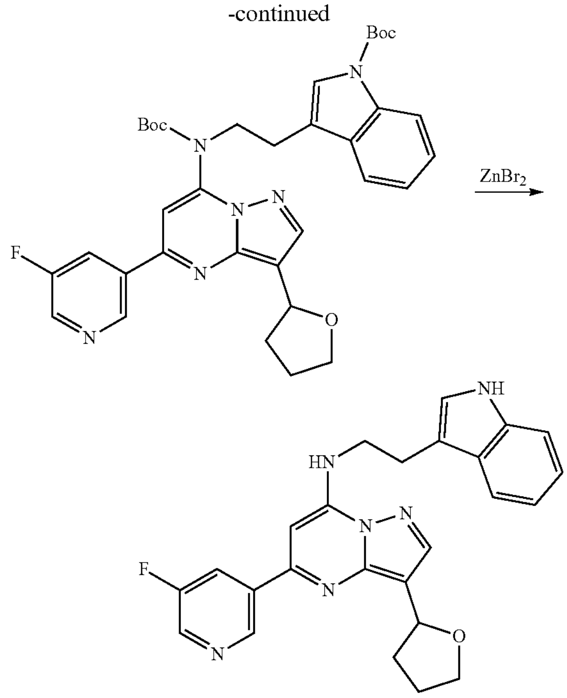

I-226

Step 1: tert-Butyl 3-[2-[[3-bromo-5-(5-fluoro-3-pyridyl)pyrazolo[1,5-a]pyrimidin-7-yl]-tert-butoxy-carbonyl-amino]ethyl]indole-1-carboxylate

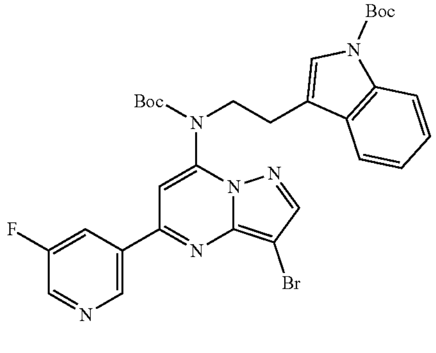 [SMILES: CC(C)(C)OC(=O)N(CCc1cn(C(=O)OC(C)(C)C)c2ccccc12)c1cc(-c2cncc(F)c2)nc2c(Br)cnn12]

To a solution of 3-bromo-5-(5-fluoro-3-pyridyl)-N-[2-(1H-indol-3-yl)ethyl]pyrazolo[1,5-a]pyrimidin-7-amine (750 mg, 1.63 mmol, 1 eq) in 1,4-dioxane (30 mL) was added DMAP (596.31 mg, 4.88 mmol, 3 eq) and $(Boc)_2O$ (887.73 mg, 4.07 mmol, 934.45 μL, 2.5 eq). The mixture was stirred at 110° C. for 5 h. The reaction mixture was concentrated under reduced pressure to yield a residue which was purified by flash silica gel chromatography (from PE/EtOAc=100/1 to 3/1, TLC: PE/EtOAc=3/1, $R_f$=0.75) to yield tert-butyl 3-[2-[[3-bromo-5-(5-fluoro-3-pyridyl)pyrazolo[1,5-a]pyrimidin-7-yl]-tert-butoxycarbonyl-amino] ethyl]indole-1-carboxylate (950 mg, 1.46 mmol, 89.6% yield, 100.0% purity) as a yellow solid. $^1$H NMR (400 MHz, $CDCl_3$) δ ppm 8.73 (s, 1H), 8.57 (d, J=2.8 Hz, 1H), 8.16 (s, 1H), 8.00 (d, J=7.0 Hz, 1H), 7.91 (td, J=2.1, 9.3 Hz, 1H), 7.45 (d, J=7.8 Hz, 1H), 7.27-7.21 (m, 2H), 7.21-7.14 (m, 1H), 6.57 (s, 1H), 4.24 (t, J=6.8 Hz, 2H), 3.12 (t, J=6.7 Hz, 2H), 1.62 (s, 9H), 1.42 (s, 9H); ES-LCMS m/z 651.2, 652.2 $[M+H]^+$.

Step 2: tert-Butyl 3-[2-[tert-butoxycarbonyl-[5-(5-fluoro-3-pyridyl)-3-tetrahydrofuran-2-yl-pyrazolo[1,5-a]pyrimidin-7-yl]amino]ethyl]indole-1-carboxylate

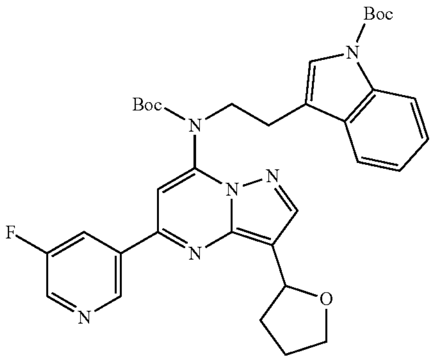 [SMILES: CC(C)(C)OC(=O)N(CCc1cn(C(=O)OC(C)(C)C)c2ccccc12)c1cc(-c2cncc(F)c2)nc2c(C3CCCO3)cnn12]

4-tert-Butyl-2-(4-tert-butyl-2-pyridyl)pyridine (24.72 mg, 92.09 μmol, 0.1 eq) and dichloronickel; 1,2-dimethoxyethane (20.23 mg, 92.09 μmol, 0.1 eq) were added into THF (4 mL). The mixture was stirred at 50° C. under $N_2$ atmosphere until a green solution was obtained. $[Ir\{dFCF_3ppy\}_2(bpy)]PF_6$ (51.66 mg, 46.05 μmol, 0.05 eq), $K_2HPO_4$ (320.81 mg, 1.84 mmol, 2 eq) and a solution of tert-butyl 3-[2-[[3-bromo-5-(5-fluoro-3-pyridyl)pyrazolo[1,5-a]pyrimidin-7-yl]-tert-butoxycarbonyl-amino]ethyl]indole-1-carboxylate (600 mg, 920.92 μmol, 1 eq) in THF (20 mL) were added into the above mixture under $N_2$ atmosphere. The resulting mixture was stirred and irradiated with a standard 72 W LED strip light bulb at 25° C. for 12 h. The reaction mixture was concentrated to yield a residue which was purified by flash silica gel chromatography (from PE/EtOAc=100/1 to 3/1, TLC: PE/EtOAc=3/1, $R_f$=0.45) to yield tert-butyl 3-[2-[tert-butoxycarbonyl-[5-(5-fluoro-3-pyridyl)-3-tetrahydrofuran-2-yl-pyrazolo[1,5-a]pyrimidin-7-yl]amino]ethyl]indole-1-carboxylate (190 mg, 274.04 μmol, 29.8% yield, 92.7% purity) as yellow oil. $^1H$ NMR (400 MHz, $CDCl_3$) δ ppm 8.83-8.76 (m, 1H), 8.55 (s, 1H), 8.18 (s, 1H), 8.05 (s, 1H), 7.90-7.79 (m, 1H), 7.47 (t, J=6.9 Hz, 1H), 7.31 (d, J=8.8 Hz, 1H), 7.19 (t, J=7.6 Hz, 2H), 6.59 (s, 1H), 5.38-5.29 (m, 1H), 4.21-4.15 (m, 2H), 4.10 (m, 1H), 4.01-3.92 (m, 1H), 3.11 (t, J=6.9 Hz, 2H), 2.45-2.35 (m, 1H), 2.33-2.24 (m, 1H), 2.23-2.16 (m, 1H), 2.15-2.07 (m, 1H), 1.60 (s, 9H), 1.46-1.39 (m, 9H); ES-LCMS m/z 643.3 $[M+H]^+$.

Step 3: 5-(5-Fluoro-3-pyridyl)-N-[2-(1H-indol-3-yl)ethyl]-3-tetrahydrofuran-2-yl-pyrazolo[1,5-a]pyrimidin-7-amine (I-226)

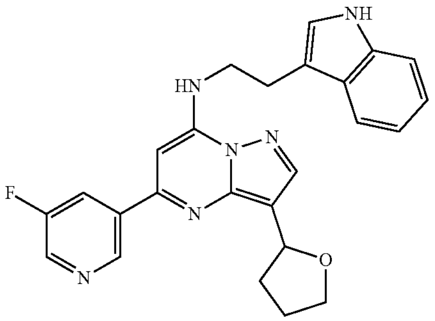 [SMILES: Fc1cncc(-c2cc(NCCc3c[nH]c4ccccc34)n3ncc(C4CCCO4)c3n2)c1]

To a stirred solution of tert-butyl 3-[2-[tert-butoxycarbonyl-[5-(5-fluoro-3-pyridyl)-3-tetrahydrofuran-2-yl-pyrazolo[1,5-a]pyrimidin-7-yl]amino]ethyl]indole-1-carboxylate (70 mg, 100.96 μmol, 1 eq) in DCM (8 mL) was added $ZnBr_2$ (2.27 g, 10.10 mmol, 100 eq). The reaction mixture was stirred at 25° C. for 15 h. TLC (PE/EtOAc=1/1, $R_f$=0.35) indicated one major new spot was detected. MeOH (30 mL) was added into the reaction mixture and diluted with water (50 mL), adjusted pH to 8-9 with saturated $NaHCO_3$ solution, extracted with EtOAc (30 mL×3). The combined organic layers were dried over $Na_2SO_4$, filtered and concentrated under reduced pressure to yield a residue which was purified by flash silica gel chromatography (from PE/EtOAc=100/1 to 2/1, TLC: PE/EtOAc=1/1, $R_f$=0.35) to yield a residue which was re-purified by preparative HPLC (basic condition; column: Gemini 150*25 5 u; mobile phase: [water (0.05% ammonia hydroxide v/v)-ACN]; B %: 55%-75%, 8 min). The desired fraction was lyophilized to yield 5-(5-fluoro-3-pyridyl)-N-[2-(1H-indol-3-yl)ethyl]-3-tetrahydrofuran-2-yl-pyrazolo[1,5-a]pyrimidin-7-amine (5.91 mg, 12.85 μmol, 12.7% yield, 96.2% purity) as a white solid. $^1H$ NMR (400 MHz, $CDCl_3$) δ ppm 8.80 (s, 1H), 8.50 (s, 1H), 8.03 (s, 2H), 7.85 (d, J=9.5 Hz, 1H), 7.69 (d, J=7.5 Hz, 1H), 7.36 (d, J=7.7 Hz, 1H), 7.26-7.18 (m, 2H), 7.05 (d, J=2.0 Hz, 1H), 6.54 (s, 1H), 6.07 (s, 1H), 5.29 (t, J=7.3 Hz, 1H), 4.12 (q, J=7.3 Hz, 1H), 3.99-3.90 (m, 1H), 3.85 (q, J=6.3 Hz, 2H), 3.25 (t, J=6.5 Hz, 2H), 2.39-2.28 (m, 2H), 2.24-2.15 (m, 1H), 2.14-2.04 (m, 1H); ES-LCMS m/z 443.2 $[M+H]^+$.

Example 177

Synthesis of I-227

I-227

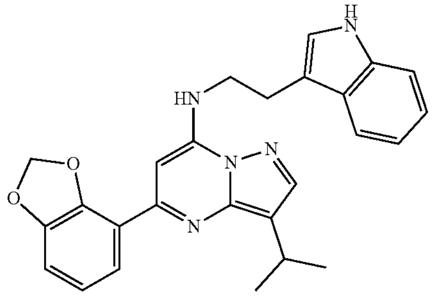

Synthetic Scheme:

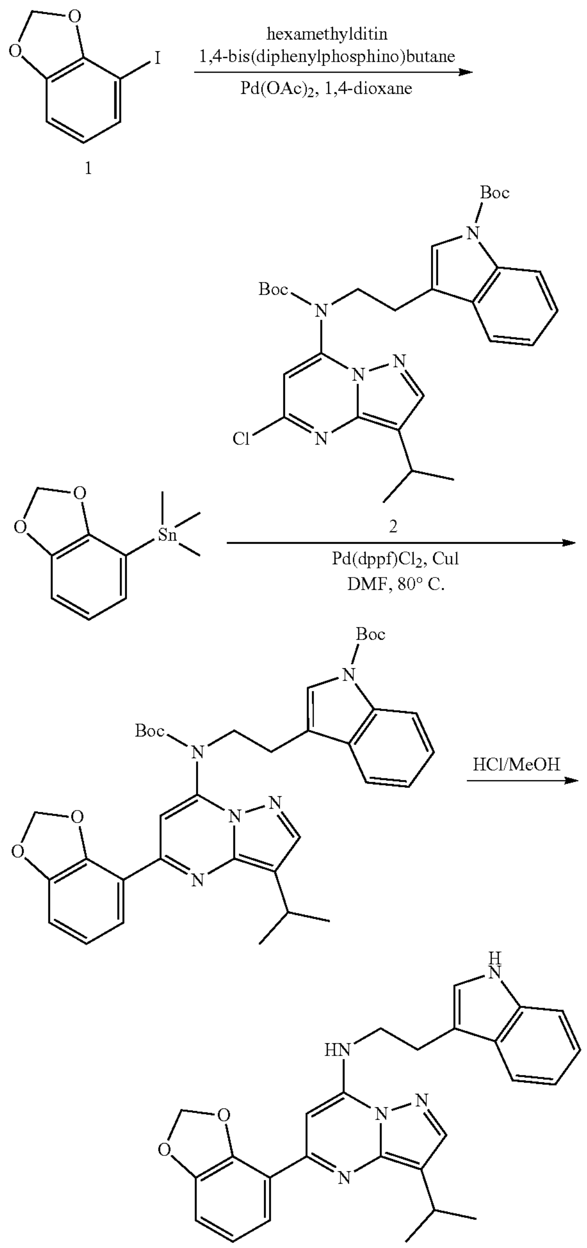

I-227

Step 1: 1,3-Benzodioxol-4-yl(trimethyl)stannane

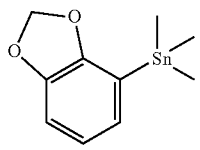

To a solution of 4-iodo-1,3-benzodioxole (100 mg, 403.20 μmol, 1 eq) in 1,4-dioxane (5 mL) was added trimethyl (trimethylstannyl)stannane (132.10 mg, 403.20 μmol, 83.61 μL, 1 eq) and 4-diphenylphosphanylbutyl(diphenyl)phosphane (17.20 mg, 40.32 μmol, 0.1 eq) was purged with $N_2$ for 15 min. $Pd(OAc)_2$ (9.05 mg, 40.32 μmol, 0.1 eq) was added and the mixture was stirred at 110° C. for 3 h. TLC (PE/EtOAc=10/1, $R_f$=0.44) indicated one major new spot with lower polarity was detected. The reaction mixture was concentrated under reduced pressure to yield a residue which was purified on silica gel column chromatography (from PE/EtOAc=1/0 to 10/3, TLC: PE/EtOAc=3/1, $R_f$=0.44) to yield the product 1,3-benzodioxol-4-yl(trimethyl)stannane (80 mg, 252.70 μmol, 62.7% yield, 90.0% purity) as colorless oil. $^1$H NMR (400 MHz, $CDCl_3$) δ ppm 6.88-6.76 (m, 3H), 5.91 (s, 2H), 0.42-0.26 (s, 9H).

Step 2: tert-Butyl 3-[2-[[5-(1,3-benzodioxol-4-yl)-3-isopropyl-pyrazolo[1,5-a]pyrimidin-7-yl]-tert-butoxycarbonyl-amino]ethyl]indole-1-carboxylate

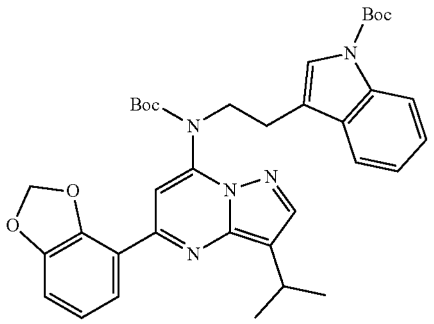 [SMILES: CC(C)c1cnn2c(N(CCc3cn(C(=O)OC(C)(C)C)c4ccccc34)C(=O)OC(C)(C)C)cc(-c3cccc4c3OCO4)nc12]

To a solution of 1,3-benzodioxol-4-yl(trimethyl)stannane (50 mg, 157.94 μmol, 1 eq) and tert-butyl 3-[2-[tert-butoxycarbonyl-(5-chloro-3-isopropyl-pyrazolo[1,5-a]pyrimidin-7-yl) amino]ethyl]indole-1-carboxylate (75.06 mg, 134.25 μmol, 0.85 eq) in DMF (5 mL) was purged with $N_2$ for 25 min. $Pd(dppf)Cl_2$ (10.98 mg, 15.00 μmol, 0.095 eq) and CuI (2.86 mg, 15.00 μmol, 0.095 eq) was added and the mixture was stirred at 110° C. for 2 h under microwave. The reaction mixture was filtered and concentrated under reduced pressure to yield a residue which was purified by preparative TLC (TLC: PE/EtOAc=10/1, $R_f$=0.46) to yield the product tert-butyl 3-[2-[[5-(1,3-benzodioxol-4-yl)-3-isopropyl-pyrazolo[1,5-a]pyrimidin-7-yl]-tert-butoxycarbonyl-amino] ethyl]indole-1-carboxylate (80 mg, 106.42 μmol, 67.4% yield, 85.1% purity) as yellow oil. $^1$H NMR (400 MHz, $CDCl_3$) δ ppm 8.03 (s, 2H), 7.99 (s, 1H), 7.87 (d, J=7.7 Hz, 1H), 7.50 (d, J=7.1 Hz, 1H), 7.39 (br s, 2H), 7.23-7.14 (m, 1H), 7.03-6.96 (m, 1H), 6.95-6.90 (m, 1H), 6.09-6.04 (m, 2H), 4.19 (t, J=7.5 Hz, 2H), 3.46-3.37 (m, 1H), 3.06 (t, J=6.9 Hz, 2H), 1.63 (s, 9H), 1.45 (d, J=6.4 Hz, 6H), 1.36 (s, 9H); ES-LCMS m/z 640.4 $[M+H]^+$.

Step 3: 5-(1,3-Benzodioxol-4-yl)-N-[2-(1H-indol-3-yl)ethyl]-3-isopropyl-pyrazolo[1,5-a]pyrimidin-7-amine (I-227)

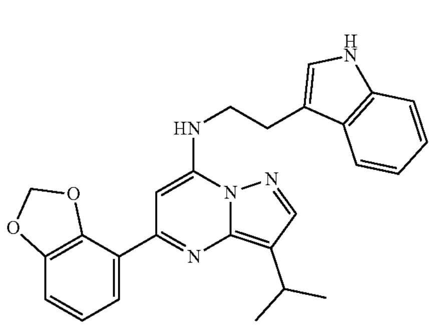 [SMILES: CC(C)c1cnn2c(NCCc3c[nH]c4ccccc34)cc(-c3cccc4c3OCO4)nc12]

A solution of tert-butyl 3-[2-[[5-(1,3-benzodioxol-4-yl)-3-isopropyl-pyrazolo[1,5-a]pyrimidin-7-yl]-tert-butoxycarbonyl-amino]ethyl]indole-1-carboxylate (80 mg, 106.42 μmol, 1 eq) in HCl/MeOH (4 M, 5 mL, 187.94 eq) was was stirred at 25° C. for 12 h. LC-MS showed the starting material was not consumed completely. The mixture was stirred at 25° C. for another 12 h. The reaction mixture was concentrated under reduced pressure to yield a residue which was purified by preparative HPLC (column: Phenomenex Gemini 150*25 mm*10 um; mobile phase: [water (0.05% HCl)-ACN]; B %: 35%-65%, 9 min) followed by lyophilization to yield 5-(1,3-benzodioxol-4-yl)-N-[2-(1H-indol-3-yl)ethyl]-3-isopropyl-pyrazolo[1,5-a]pyrimidin-7-amine (47.73 mg, 100.08 μmol, 94.0% yield, 99.8% purity, HCl) as a yellow solid. $^1H$ NMR (400 MHz, $CD_3OD$) δ ppm 8.16 (s, 1H), 7.51 (d, J=7.8 Hz, 1H), 7.14 (d, J=8.0 Hz, 1H), 7.05-7.00 (m, 2H), 6.97-6.92 (m, 2H), 6.86-6.80 (m, 1H), 6.53 (d, J=8.0 Hz, 1H), 6.07 (s, 2H), 5.76 (s, 1H), 3.96 (t, J=5.8 Hz, 2H), 3.23-3.18 (m, 3H), 1.33 (d, J=6.8 Hz, 6H); ES-LCMS m/z 440.3 $[M+H]^+$.

Example 178

Synthesis of I-229

I-229

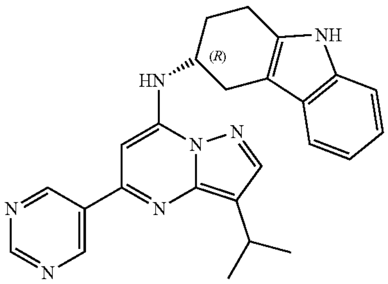

Synthetic Scheme:

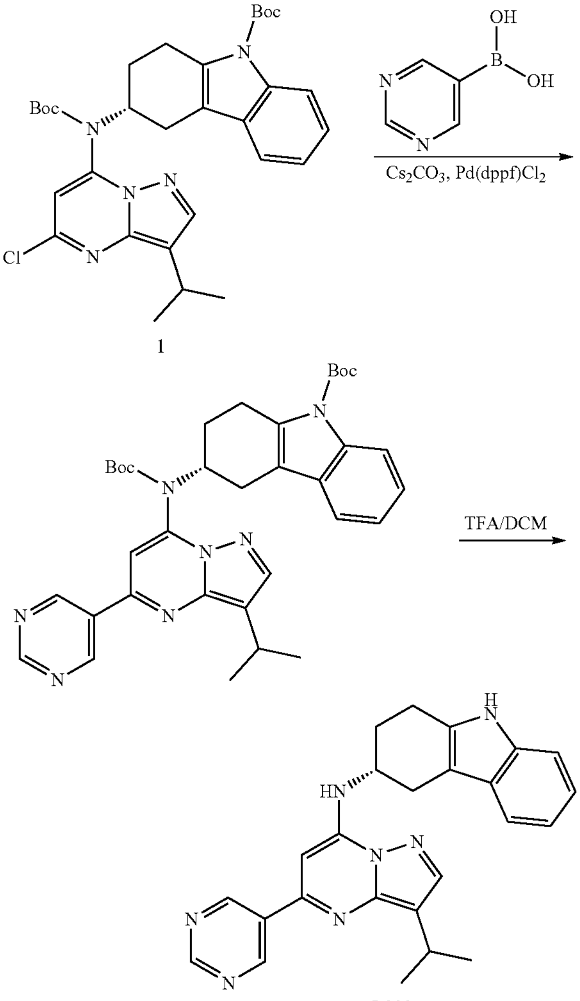

Step 1: tert-Butyl (3R)-3-[tert-butoxycarbonyl-(3-isopropyl-5-pyrimidin-5-yl-pyrazolo[1,5-a]pyrimidin-7-yl)amino]-1,2,3,4-tetrahydrocarbazole-9-carboxylate

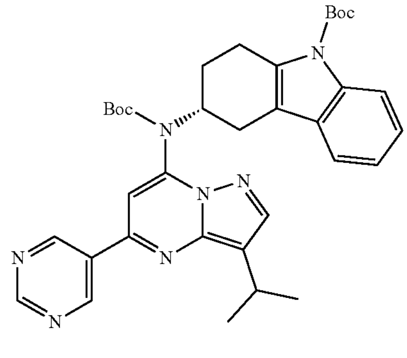 [SMILES: CC(C)c1cnn2c(N(C(=O)OC(C)(C)C)[C@@H]3CCc4c(c5ccccc5n4C(=O)OC(C)(C)C)C3)cc(-c3cncnc3)nc12]

tert-Butyl (3R)-3-[tert-butoxycarbonyl-(5-chloro-3-isopropyl-pyrazol[1,5-a]pyrimidin-7-yl) amino]-1,2,3,4-tetrahydrocarbazole-9-carboxylate (200 mg, 316.66 μmol, 1 eq), pyrimidin-5-ylboronic acid (47.08 mg, 379.99 μmol, 1.2 eq), $Cs_2CO_3$ (309.52 mg, 949.98 μmol, 3 eq) and $Pd(dppf)Cl_2$ (23.17 mg, 31.67 μmol, 0.1 eq) were taken up into a microwave tube in 1,4-dioxane (6 mL) and $H_2O$ (2 mL). The sealed tube was heated at 110° C. for 1 h under microwave(2 bar). The mixture was concentrated and then saturated $NaHCO_3$ (10 mL) was added, extracted with EtOAc (10 mL×3). The combined organic layers were dried over $Na_2SO_4$, filtered and concentrated to yield a residue which was purified on silica gel column chromatography (from PE/EtOAc=1/0 to 10/3, TLC: PE/EtOAc=3/1, $R_f$=0.30) to yield tert-butyl (3R)-3-[tert-butoxycarbonyl-(3-isopropyl-5-pyrimidin-5-yl-pyrazolo[1,5-a]pyrimidin-7-yl)amino]-1,2,3,4-tetrahydrocarbazole-9-carboxylate (180 mg, 288.58 μmol, 91.1% yield, 100.0% purity) as a yellow gum. $^1H$ NMR (400 MHz, $CD_3OD$) δ ppm 9.39 (s, 2H), 9.22 (s, 1H), 8.14 (s, 1H), 7.94 (d, J=7.9 Hz, 1H), 7.46 (s, 1H), 7.19 (br s, 1H), 7.14-7.02 (m, 2H), 4.79 (m, 1H), 3.48 (m, 1H), 3.43-3.36 (m, 2H), 3.18-3.08 (m, 2H), 2.36-2.28 (m, 2H), 1.63 (s, 9H), 1.45 (d, J=7.1 Hz, 6H), 1.30 (s, 9H); ES-LCMS m/z 624.4 $[M+H]^+$.

Step 2: (3R)—N-(3-Isopropyl-5-pyrimidin-5-yl-pyrazolo[1,5-a]pyrimidin-7-yl)-2,3,4,9-tetrahydro-1H-carbazol-3-amine (I-229)

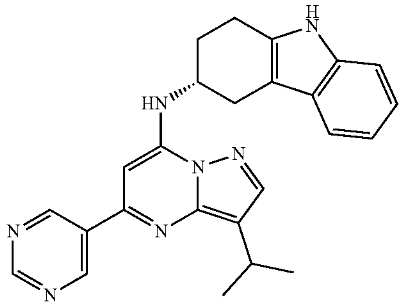 [SMILES: CC(C)c1cnn2c(N[C@@H]3CCc4[nH]c5ccccc5c4C3)cc(-c3cncnc3)nc12]

To a solution of tert-butyl (3R)-3-[tert-butoxycarbonyl-(3-isopropyl-5-pyrimidin-5-yl-pyrazolo[1,5-a]pyrimidin-7-yl)amino]-1,2,3,4-tetrahydrocarbazole-9-carboxylate (180 mg, 288.58 μmol, 1 eq) in DCM (5 mL) was added TFA (1 mL). The mixture was degassed and purged with $N_2$ for 3 times, the mixture was stirred under $N_2$ atmosphere at 20° C. for 3 h. The reaction mixture was concentrated under reduced pressure to yield a residue which was purified by preparative HPLC (column: Phenomenex Gemini 150*25 mm*10 μm; mobile phase: [water (0.05% HCl)-ACN]; B %: 50%-80%, 9 min) to yield the residue which was purified by preparative HPLC (column: Phenomenex Gemini 150*25 mm*10 μm; mobile phase: [water (0.05% ammonia hydroxide v/v)-ACN]; B %: 56%-86%, 10 min) followed by lyophilization to yield (3R)—N-(3-isopropyl-5-pyrimidin-5-yl-pyrazolo[1,5-a]pyrimidin-7-yl)-2,3,4,9-tetrahydro-1H-carbazol-3-amine (12 mg, 28.33 μmol, 9.8% yield, 100.0% purity) as a yellow solid. $^1H$ NMR (400 MHz, $CD_3OD$) δ ppm 9.51 (s, 2H), 9.21 (s, 1H), 7.95 (s, 1H), 7.39 (d, J=7.7 Hz, 1H), 7.27 (d, J=8.2 Hz, 1H), 7.07-7.01 (m, 1H), 6.99-6.93 (m, 1H), 6.84 (s, 1H), 4.47 (m, J=8.6 Hz, 1H), 3.37-3.34 (m, 2H), 3.14-3.03 (m, 1H), 3.00-2.88 (m, 2H), 2.41-2.33 (m, 1H), 2.28-2.19 (m, 1H), 1.42 (d, J=6.8 Hz, 6H); ES-LCMS m/z 424.2 $[M+H]^+$.

Example 179

Synthesis of I-230

I-230

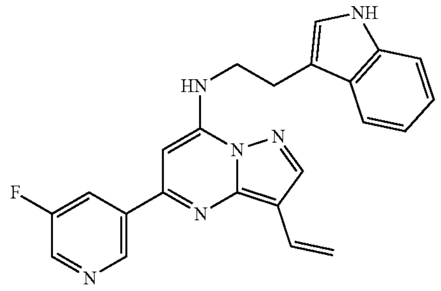 [SMILES: C=Cc1cnn2c(NCCc3c[nH]c4ccccc34)cc(-c3cncc(F)c3)nc12]

Synthetic Scheme:

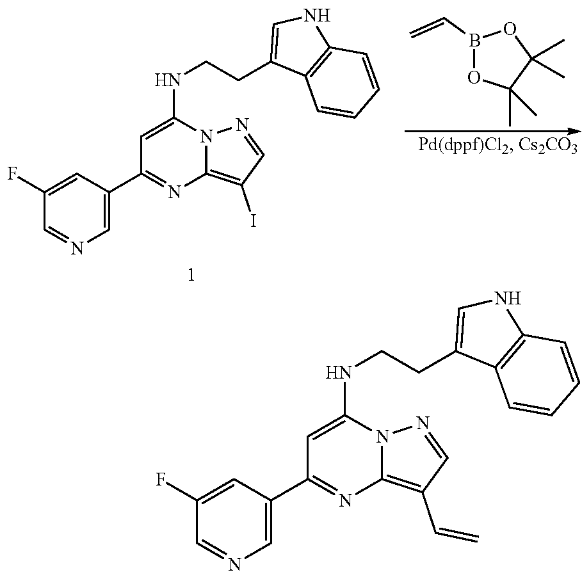

1

I-230

Step 1: 5-(5-Fluoro-3-pyridyl)-N-[2-(1H-indol-3-yl)ethyl]-3-vinyl-pyrazolo[1,5-a]pyrimidin-7-amine (I-230)

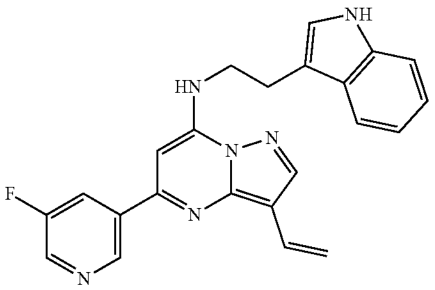

A mixture of 5-(5-fluoro-3-pyridyl)-N-[2-(1H-indol-3-yl)ethyl]-3-iodo-pyrazolo[1,5-a]pyrimidin-7-amine (55 mg, 109.71 μmol, 1 eq), 4,4,5,5-tetramethyl-2-vinyl-1,3,2-dioxaborolane (50.69 mg, 329.14 μmol, 55.83 μL, 3 eq), $Cs_2CO_3$ (178.74 mg, 548.57 μmol, 5 eq) and $Pd(dppf)Cl_2$ (40.14 mg, 54.86 μmol, 0.5 eq) in 1,4-dioxane (3 mL) and $H_2O$ (1.5 mL) was bubbled with $N_2$ for 2 minutes and sealed. The reaction mixture was irradiated under microwave (2 bar) at 120° C. for 2 h. The reaction mixture was diluted with $H_2O$ (10 mL) and extracted with EtOAc (10 mL×3). The organic layer was dried over $Na_2SO_4$, filtered and concentrated under reduced pressure to yield a residue which was purified by preparative TLC (PE/EtOAc=2/1, $R_f$=0.23) and then by preparative HPLC (column: Gemini 150*25 5 u; mobile phase: [water (0.05% ammonia hydroxide v/v)-ACN]; B %: 60%-90%, 8 min). The desired fraction was lyophilized to yield 5-(5-fluoro-3-pyridyl)-N-[2-(1H-indol-3-yl)ethyl]-3-vinyl-pyrazolo[1,5-a]pyrimidin-7-amine (15.4 mg, 38.65 μmol, 35.2% yield, 100.0% purity) as a yellow solid. $^1H$ NMR (400 MHz, $CDCl_3$) δ ppm 8.82 (s, 1H), 8.51 (d, J=2.4 Hz, 1H), 8.06 (s, 2H), 7.95-7.88 (m, 1H), 7.69 (d, J=7.6 Hz, 1H), 7.39-7.33 (m, 1H), 7.27-7.18 (m, 2H), 7.06 (d, J=2.0 Hz, 1H), 6.90 (dd, J=11.2, 17.6 Hz, 1H), 6.55 (t, J=6.4 Hz, 1H), 6.11 (s, 1H), 6.07 (dd, J=1.6, 17.6 Hz, 1H), 5.27 (dd, J=2.0, 11.2 Hz, 1H), 3.85 (q, J=6.4 Hz, 2H), 3.27 (t, J=6.4 Hz, 2H); ES-LCMS m/z 399.2 $[M+H]^+$.

Example 180

Synthesis of I-232

I-232

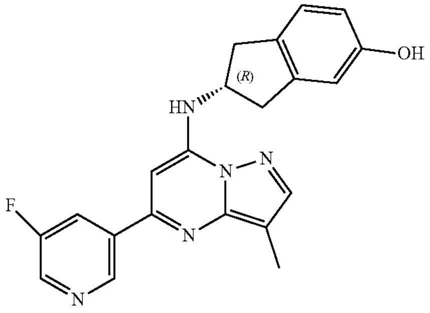

Synthetic Scheme:

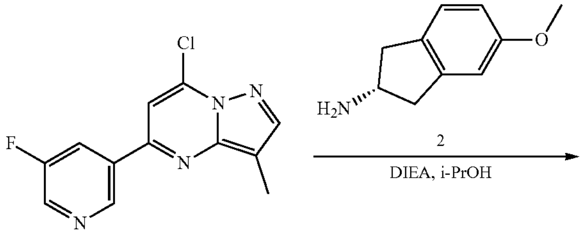

1

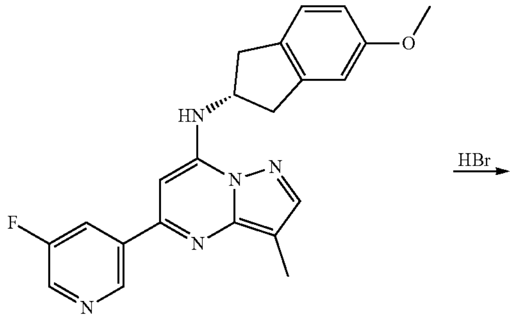

-continued

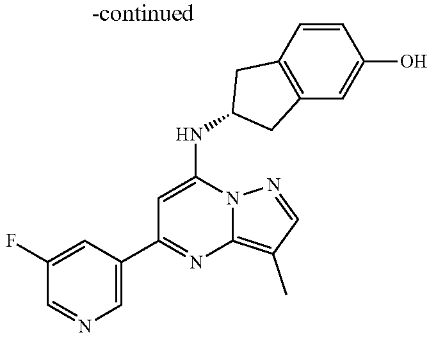

I-232

Step 1: 5-(5-Fluoro-3-pyridyl)-N-[(2R)-5-methoxy-indan-2-yl]-3-methyl-pyrazolo[1,5-a]pyrimidin-7-amine

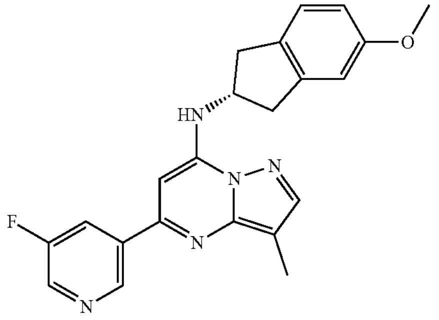 [SMILES: COc1ccc2c(c1)C[C@H](Nc1cc(-c3cncc(F)c3)nc3c(C)cnn13)C2]

To a mixture of 7-chloro-5-(5-fluoro-3-pyridyl)-3-methyl-pyrazolo[1,5-a]pyrimidine (50 mg, 190.35 μmol, 1 eq), (2R)-5-methoxyindan-2-amine (38.01 mg, 190.35 μmol, 1 eq, HCl) in i-PrOH (5 mL) was added DIEA (73.80 mg, 571.06 μmol, 99.47 uL, 3 eq). The mixture was stirred at 80° C. for 12 h. The mixture was concentrated to yield a crude compound 5-(5-fluoro-3-pyridyl)-N-[(2R)-5-methoxyindan-2-yl]-3-methyl-pyrazolo[1,5-a]pyrimidin-7-amine (70 mg, 130.90 μmol, 68.8% yield, 72.8% purity) as yellow oil which was used in the next step without further purification; ES-LCMS m/z 390.2$[M+H]^+$.

Step 2: (2R)-2-[[5-(5-Fluoro-3-pyridyl)-3-methyl-pyrazolo[1,5-a]pyrimidin-7-yl]amino]indan-5-ol (I-232)

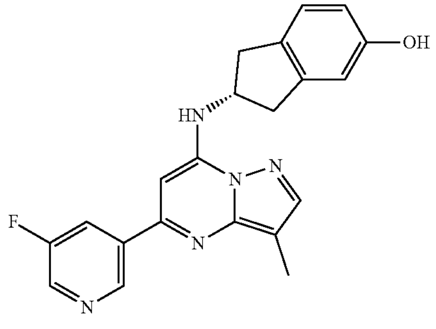

A mixture of 5-(5-fluoro-3-pyridyl)-N-[(2R)-5-methoxyindan-2-yl]-3-methyl-pyrazolo[1,5-a]pyrimidin-7-amine (70 mg, 130.90 μmol, 1 eq) in HBr solution (7.45 g, 55.25 mmol, 5 mL, 60%, 422.06 eq) was stirred at 80° C. for 1 h. The mixture was concentrated to yield a residue was purified by preparative HPLC (column: Phenomenex Gemini 150*25 mm*10 um; mobile phase: [water (0.05% HCl)-ACN]; B %: 30%-60%, 6 min). The desired fraction was lyophilized to yield (2R)-2-[[5-(5-fluoro-3-pyridyl)-3-methyl-pyrazolo[1,5-a]pyrimidin-7-yl]amino]indan-5-ol (17.22 mg, 38.27 μmol, 29.2% yield, 99.6% purity, 2HCl, ee=98.2%) as a yellow solid. $^1$H NMR (400 MHz, $CD_3OD$) δ ppm 8.98 (s, 1H), 8.80 (d, J=2.4 Hz, 1H), 8.29 (td, J=2.4, 9.2 Hz, 1H), 8.11 (s, 1H), 7.06 (d, J=8.0 Hz, 1H), 6.94 (s, 1H), 6.69 (s, 1H), 6.63 (dd, J=2.4, 8.0 Hz, 1H), 5.07-4.96 (m, 1H), 3.47-3.39 (m, 2H), 3.23-3.15 (m, 2H), 2.36 (s, 3H); ES-LCMS m/z 376.1 $[M+H]^+$.

Example 181

Synthesis of I-234

I-234

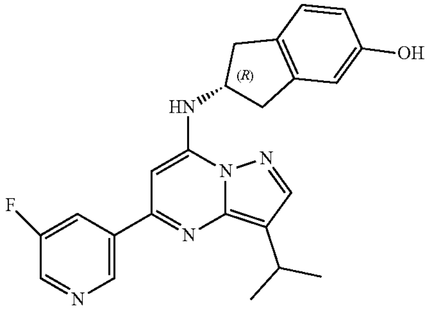

Synthetic Scheme:

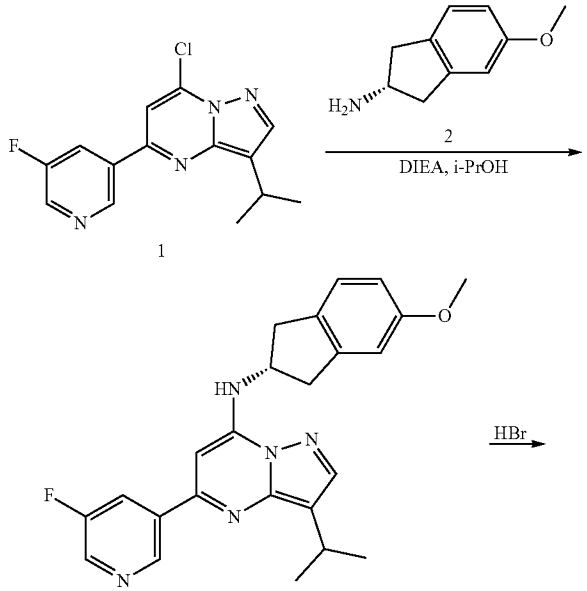

-continued

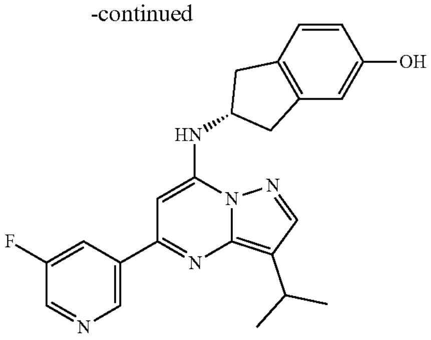

I-234

Step 1: 5-(5-Fluoro-3-pyridyl)-3-isopropyl-N-[(2R)-5-methoxyindan-2-yl]pyrazolo[1,5-a]pyrimidin-7-amine

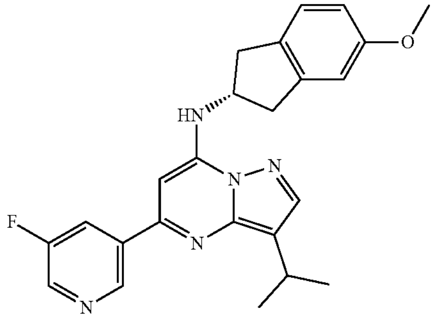 [SMILES: COc1ccc2c(c1)C[C@H](Nc1cc(-c3cncc(F)c3)nc3c(C(C)C)cnn13)C2]

To a mixture of 7-chloro-5-(5-fluoro-3-pyridyl)-3-isopropyl-pyrazolo[1,5-a]pyrimidine (50 mg, 154.79 μmol, 1 eq), (2R)-5-methoxyindan-2-amine (27.79 mg, 170.27 μmol, 1.1 eq) in i-PrOH (5 mL) was added DIEA (60.01 mg, 464.36 μmol, 80.88 μL, 3 eq). The mixture was stirred at 80° C. for 12 h. The mixture was concentrated to yield the product of 5-(5-fluoro-3-pyridyl)-3-isopropyl-N-[(2R)-5-methoxyindan-2-yl]pyrazolo[1,5-a]pyrimidin-7-amine (60 mg, 102.65 μmol, 66.3% yield, 71.4% purity) as yellow oil which was used in the next step without further purification. ES-LCMS m/z 418.2$[M+H]^+$.

Step 2: (2R)-2-[[5-(5-Fluoro-3-pyridyl)-3-isopropyl-pyrazolo[1,5-a]pyrimidin-7-yl]amino]indan-5-ol (I-234)

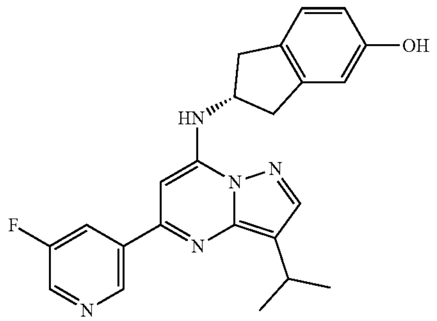

A mixture of 5-(5-fluoro-3-pyridyl)-3-isopropyl-N-[(2R)-5-methoxyindan-2-yl]pyrazolo[1,5-a]pyrimidin-7-amine(60 mg, 102.04 μmol, 1 eq) in HBr solution (5.29 g, 39.22 mmol, 3.55 mL, 60%, 384.39 eq) was stirred at 120° C. for 2 h. The mixture was concentrated to yield a residue which was purified by preparative HPLC (column: Phenomenex Gemini 150*25 mm*10 um; mobile phase: [water (0.05% HCl)-ACN]; B %: 45%-75%, 9 min). The desired fraction was lyophilized to yield (2R)-2-[[5-(5-fluoro-3-pyridyl)-3-isopropyl-pyrazolo[1,5-a]pyrimidin-7-yl]amino]indan-5-ol (13.92 mg, 31.34 μmol, 30.7% yield, 99.0% purity, HCl) (97.1% ee) as a yellow solid. $^1$H NMR (400 MHz, $CD_3OD$) δ ppm 8.98 (s, 1H), 8.80 (d, J=2.0 Hz, 1H), 8.32-8.29 (m, 1H), 8.21 (s, 1H), 7.05 (d, J=8.0 Hz, 1H), 6.92 (s, 1H), 6.62 (dd, J=2.4, 8.4 Hz, 1H), 6.61 (m, 1H), 5.02-4.93 (m, 1H), 3.49-3.40 (m, 2H), 3.37-3.31 (m, 1H), 3.21-3.09 (m, 2H), 1.36 (d, J=6.8 Hz, 6H); ES-LCMS m/z 404.3 $[M+H]^+$.

Example 182

Synthesis of I-235

I-235

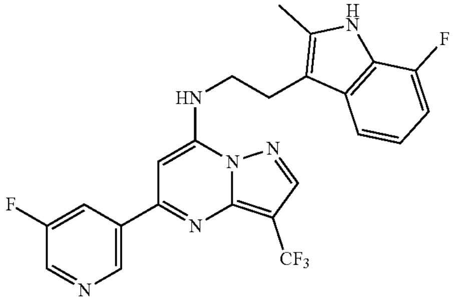

Synthetic Scheme:

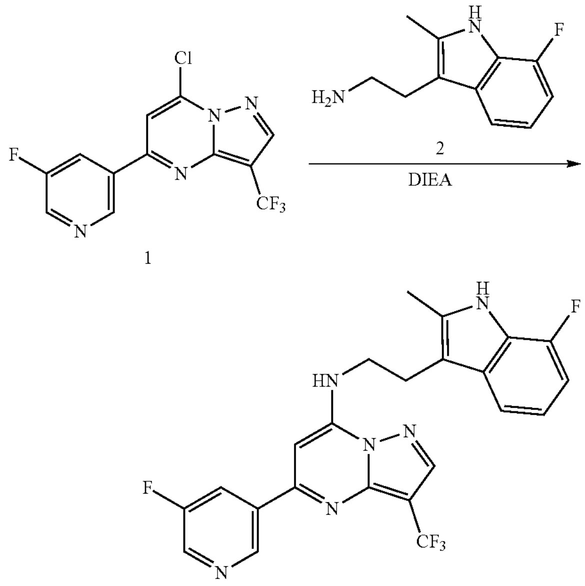

1

I-235

Step 1: N-[2-(7-Fluoro-2-methyl-1H-indol-3-yl)ethyl]-5-(5-fluoro-3-pyridyl)-3-(trifluoromethyl)pyrazolo[1,5-a]pyrimidin-7-amine (I-235)

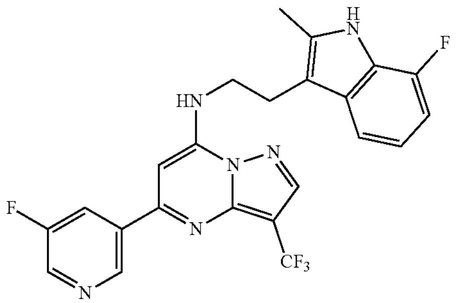 [SMILES: Cc1[nH]c2c(F)cccc2c1CCNc1cc(-c2cncc(F)c2)nc2c(C(F)(F)F)cnn12]

To a solution of 7-chloro-5-(5-fluoro-3-pyridyl)-3-(trifluoromethyl)pyrazolo[1,5-a]pyrimidine (30 mg, 87.92 μmol, 1 eq) and 2-(7-fluoro-2-methyl-1H-indol-3-yl)ethanamine (24.15 mg, 105.51 μmol, 1.2 eq) in i-PrOH (5 mL) was added DIEA (34.09 mg, 263.77 μmol, 45.94 μL, 3.0 eq). The mixture was stirred at 80° C. for 9 h. The reaction mixture was concentrated under reduced pressure to yield a residue which was purified by preparative HPLC (column: Phenomenex Gemini 150*25 mm*10 um; mobile phase: [water (0.05% HCl)-ACN]; B %: 50%-80%, 10 min) followed by lyophilization to yield N-[2-(7-fluoro-2-methyl-1H-indol-3-yl)ethyl]-5-(5-fluoro-3-pyridyl)-3-(trifluoromethyl)pyrazolo[1,5-a]pyrimidin-7-amine (10.90 mg, 19.97 μmol, 22.7% yield, 99.9% purity, 2HCl) as a yellow solid. $^1$H NMR (400 MHz, $CD_3OD$) δ ppm 8.86 (dd, J=1.3, 2.5 Hz, 1H), 8.74 (d, J=1.5 Hz, 1H), 8.34 (s, 1H), 7.94 (td, J=2.3, 8.7 Hz, 1H), 7.42 (d, J=8.0 Hz, 1H), 6.98 (dt, J=4.8, 7.9 Hz, 1H), 6.67 (dd, J=7.9, 11.4 Hz, 1H), 5.92 (s, 1H), 3.98-3.91 (m, 2H), 3.21-3.14 (m, 2H), 2.13-2.05 (m, 3H); ES-LCMS m/z 473.2 $[M+H]^+$.

Example 183

Synthesis of I-237

I-237

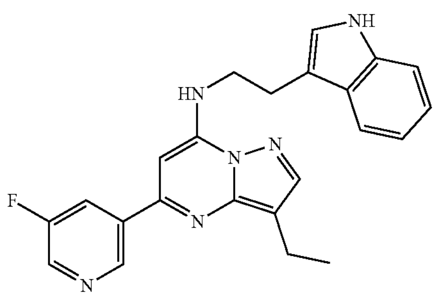 [SMILES: CCc1cnn2c(NCCc3c[nH]c4ccccc34)cc(-c3cncc(F)c3)nc12]

Synthetic Scheme:

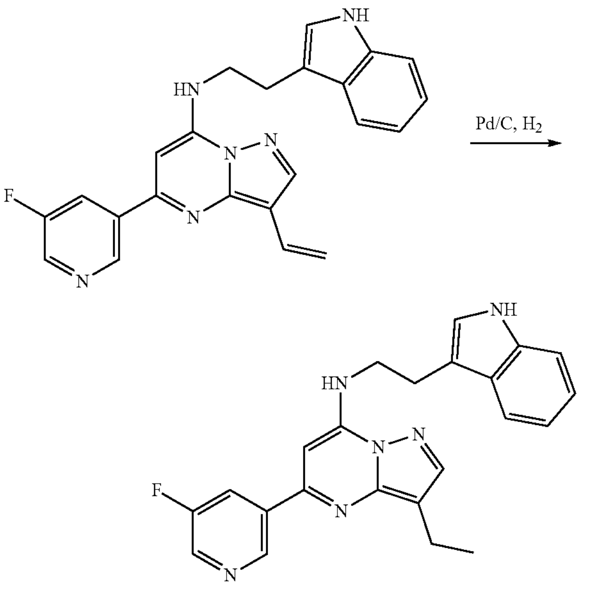

I-237

Step 1: 3-Ethyl-5-(5-fluoro-3-pyridyl)-N-[2-(1H-indol-3-yl)ethyl]pyrazolo[1,5-a]pyrimidin-7-amine (I-237)

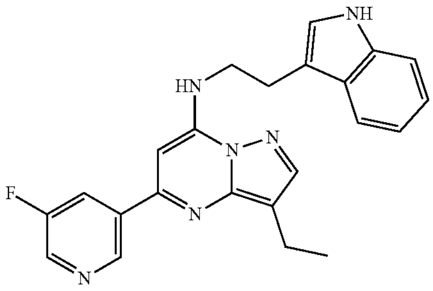

A mixture of 5-(5-fluoro-3-pyridyl)-N-[2-(1H-indol-3-yl)ethyl]-3-vinyl-pyrazolo[1,5-a]pyrimidin-7-amine (140 mg, 196.77 μmol, 1 eq) and Pd/C (50 mg, 10% purity) in EtOAc (20 mL) was stirred under $H_2$ (15 Psi) at 25° C. for 12 h. The reaction mixture was filtered. The filtrate was concentrated under reduced pressure to yield a residue which was purified by preparative HPLC (column: Phenomenex Gemini C18 250*50 mm*10 μm; mobile phase: [water (0.05% HCl)-ACN]; B %: 35%-65%, 10 min). The desired fraction was lyophilized to yield 3-ethyl-5-(5-fluoro-3-pyridyl)-N-[2-(1H-indol-3-yl)ethyl]pyrazolo[1,5-a]pyrimidin-7-amine (7.13 mg, 15.06 μmol, 7.7% yield, 100.0% purity, 2HCl) as a yellow solid. $^1$H NMR (400 MHz, $CD_3OD$) δ ppm 8.65 (d, J=2.4 Hz, 1H), 8.37 (s, 1H), 8.11 (s, 1H), 7.53 (d, J=8.0 Hz, 1H), 7.50-7.46 (m, 1H), 7.14 (d, J=8.0 Hz, 1H), 6.99 (s, 1H), 6.96 (t, J=7.6 Hz, 1H), 6.87-6.82 (m, 1H), 5.78 (s, 1H), 3.98 (t, J=5.6 Hz, 2H), 3.20 (t, J=5.6 Hz, 2H), 2.72 (q, J=7.6 Hz, 2H), 1.28 (t, J=7.6 Hz, 3H); ES-LCMS m/z 401.2 $[M+H]^+$.

Example 184

Synthesis of I-240

I-240

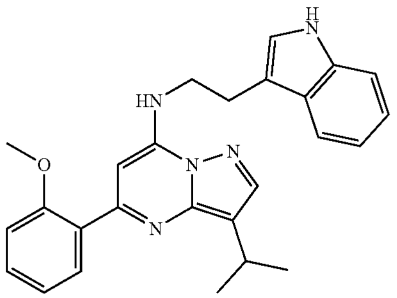

Synthetic Scheme:

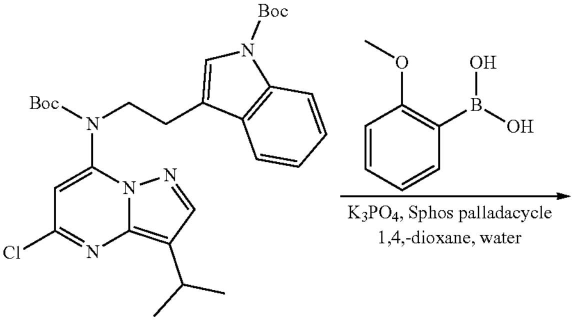

1

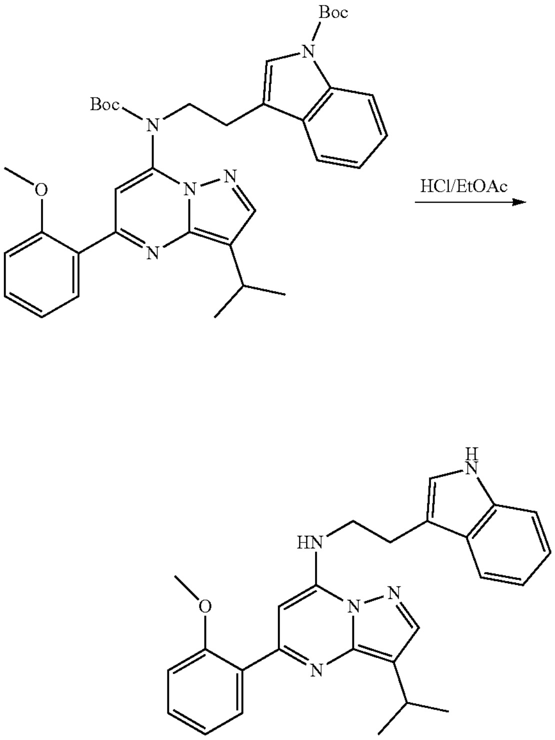

I-240

Step 1: tert-Butyl 3-[2-[tert-butoxycarbonyl-[3-isopropyl-5-(2-methoxyphenyl)pyrazolo[1,5-a]pyrimidin-7-yl]amino]ethyl]indole-1-carboxylate

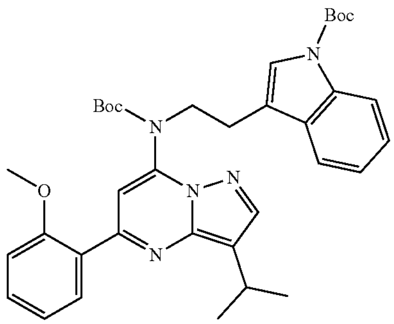 [SMILES: COc1ccccc1-c1cc(N(CCc2cn(C(=O)OC(C)(C)C)c3ccccc23)C(=O)OC(C)(C)C)n2ncc(C(C)C)c2n1]

To a solution of tert-butyl 3-[2-[tert-butoxycarbonyl-(5-chloro-3-isopropyl-pyrazolo[1,5-a]pyrimidin-7-yl)amino]ethyl]indole-1-carboxylate (100 mg, 178.86 μmol, 1 eq) in 1,4-dioxane (6 mL) and water (2 mL) was added (2-methoxyphenyl)boronic acid (81.53 mg, 536.57 μmol, 3 eq), $K_3PO_4$ (113.89 mg, 536.57 μmol, 3 eq) and sphos palladacycle (13.61 mg, 17.89 μmol, 0.1 eq). The mixture was stirred at 110° C. for 1 h under $N_2$ atmosphere. The mixture was concentrated under reduced pressure, then water (30 mL) was added. The mixture was extracted with EtOAc (50 mL×3). The combined organic layers were washed with brine (50 mL), dried over $Na_2SO_4$, filtered and concentrated to yield tert-butyl 3-[2-[tert-butoxycarbonyl-[3-isopropyl-5-(2-methoxyphenyl)pyrazolo[1,5-a]pyrimidin-7-yl]amino]ethyl]indole-1-carboxylate (200 μmg, 164.28 μmol, 91.8% yield, 51.4% purity) as yellow oil which was used in the next step without further purification. $^1$H NMR (400 MHz, $CD_3OD$) δ ppm 7.96 (s, 1H), 7.92-7.87 (m, 1H), 7.73 (dd, J=1.7, 7.6 Hz, 1H), 7.65-7.60 (m, 1H), 7.47 (dd, J=1.4, 8.7 Hz, 1H), 7.19-7.13 (m, 2H), 7.07 (s, 1H), 6.97-6.94 (m, 1H), 6.94-6.91 (m, 2H), 4.1 (m, 2H), 3.81 (s, 3H), 3.36 (s, 1H), 3.06 (t, J=6.4 Hz, 2H), 1.61-1.55 (m, 9H), 1.48-1.45 (m, 6H), 1.37-1.35 (m, 9H); ES-LCMS m/z 626.4 $[M+H]^+$.

Step 2: N-[2-(1H-Indol-3-yl)ethyl]-3-isopropyl-5-(2-methoxyphenyl)pyrazolo[1,5-a]pyrimidin-7-amine (I-240_

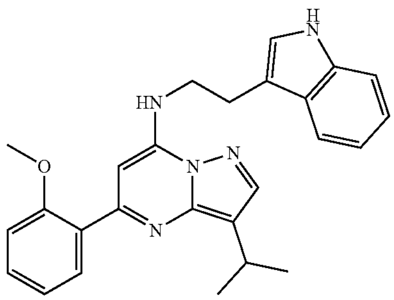 [SMILES: COc1ccccc1-c1cc(NCCc2c[nH]c3ccccc23)n2ncc(C(C)C)c2n1]

To a solution of tert-butyl 3-[2-[tert-butoxycarbonyl-[3-isopropyl-5-(2-methoxyphenyl) pyrazolo[1,5-a]pyrimidin-7-yl]amino]ethyl]indole-1-carboxylate (185 mg, 151.96 μmol, 1 eq) in DCM (10 mL) was added TFA (3.08 g, 27.01 mmol, 2 mL, 177.76 eq). The mixture was stirred at 25° C. for 2 h under $N_2$ atmosphere. The reaction mixture was concentrated under reduced pressure to yield a residue which was purified by preparative HPLC (column: Phenomenex Gemini 150*25 mm*10 μm; mobile phase: [water (0.05% HCl)-ACN]; B %: 23%-53%, 10 min) followed by lyophilization to yield N-[2-(1H-indol-3-yl)ethyl]-3-isopropyl-5-(2-methoxyphenyl)pyrazolo[1,5-a]pyrimidin-7-amine (27.57 mg, 63.69 μmol, 41.9% yield, 98.3% purity) as a yellow solid. $^1$H NMR (400 MHz, $CD_3OD$) δ ppm 8.11 (s, 1H), 7.57-7.47 (m, 2H), 7.25 (d, J=8.0 Hz, 1H), 7.13 (d, J=8.3 Hz, 1H), 7.06-6.95 (m, 3H), 6.84 (t, J=7.5 Hz, 2H), 5.79 (s, 1H), 3.93 (t, J=6.1 Hz, 2H), 3.83 (s, 3H), 3.21 (t, J=6.1 Hz, 2H), 3.19-3.12 (m, 1H), 1.33 (d, J=6.8 Hz, 6H); ES-LCMS m/z 426.2 $[M+H]^+$.

Example 185

Synthesis of I-241

I-241

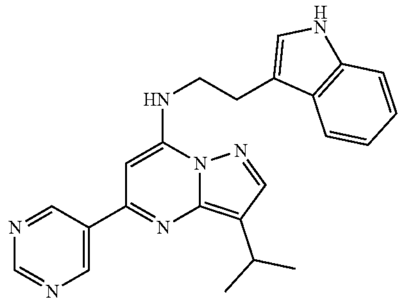

Synthetic Scheme:

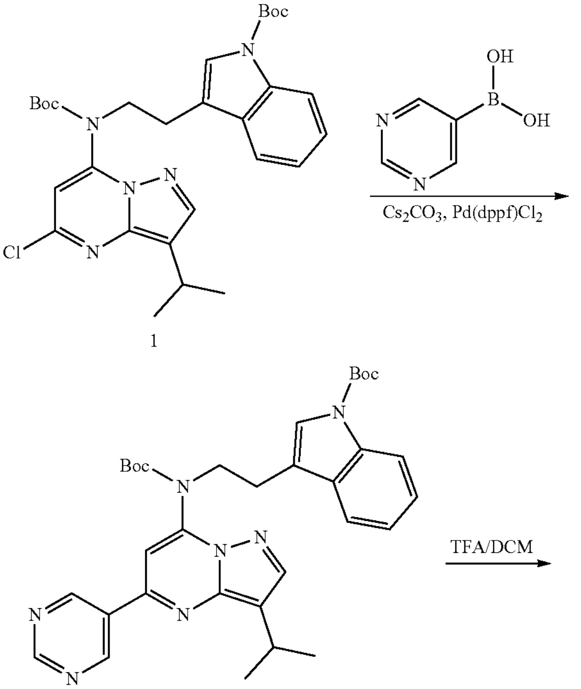

-continued

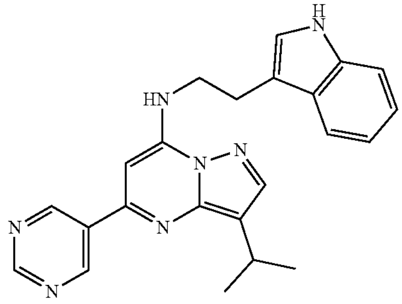

I-241

Step 1: tert-Butyl 3-[2-[tert-butoxycarbonyl-(3-isopropyl-5-pyrimidin-5-yl-pyrazolo[1,5-a]pyrimidin-7-yl)amino]ethyl]indole-1-carboxylate

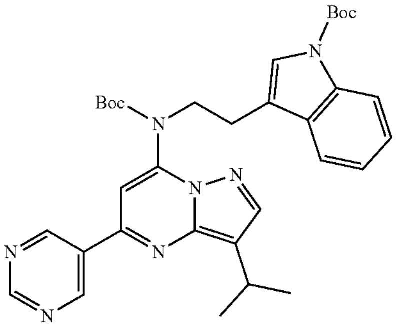 [SMILES: CC(C)c1cnn2c(N(CCc3cn(C(=O)OC(C)(C)C)c4ccccc34)C(=O)OC(C)(C)C)cc(-c3cncnc3)nc12]

Tert-butyl 3-[2-[tert-butoxycarbonyl-(5-chloro-3-isopropyl-pyrazolo[1,5-a]pyrimidin-7-yl) amino]ethyl]indole-1-carboxylate (100 mg, 178.86 μmol, 1 eq), pyrimidin-5-ylboronic acid (22.16 mg, 178.86 μmol, 1 eq), $Pd(dppf)Cl_2$ (13.09 mg, 17.89 μmol, 0.1 eq) and $Cs_2CO_3$ (174.82 mg, 536.57 μmol, 3 eq) were taken up into a microwave tube in $H_2O$ (2 mL) and 1,4-dioxane (6 mL). The sealed tube was heated at 110° C. for 1 h under microwave. The mixture was concentrated and saturated $NaHCO_3$ (10 mL) was added, extracted with EtOAc (10 mL×3). The combined organic layers were dried over $Na_2SO_4$, filtered and concentrated to yield tert-butyl 3-[2-[tert-butoxycarbonyl-(3-isopropyl-5-pyrimidin-5-yl-pyrazolo[1,5-a]pyrimidin-7-yl)amino]ethyl] indole-1-carboxylate (100 mg, 167.31 μmol, 93.5% yield, crude) as brown solid which was used in the next step without further purification. $^1H$ NMR (400 MHz, $CD_3OD$) δ ppm 9.23-9.22 (m, 1H), 9.21-9.20 (m, 1H), 8.97 (s, 1H), 7.81 (d, J=7.6 Hz, 1H), 7.45 (d, J=7.6 Hz, 2H), 7.41 (d, J=8.4 Hz, 1H), 7.09-7.02 (m, 2H), 6.93 (t, J=8.0 Hz, 1H), 4.33 (d, J=6.4 Hz, 2H), 4.30 (s, 1H), 3.11 (t, J=6.4 Hz, 2H), 1.59 (s, 9H), 1.39 (s, 6H), 1.37 (s, 9H); ES-LCMS m z 598.4 $[M+H]^+$.

Step 2: N-[2-(1H-Indol-3-yl)ethyl]-3-isopropyl-5-pyrimidin-5-yl-pyrazolo[1,5-a]pyrimidin-7-amine (I-241)

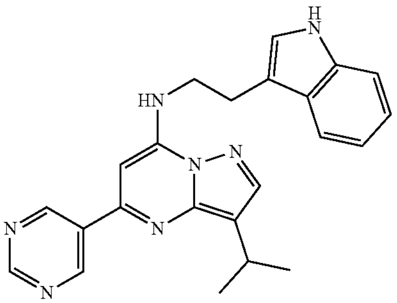 [SMILES: CC(C)c1cnn2c(NCCc3c[nH]c4ccccc34)cc(-c3cncnc3)nc12]

To a solution of tert-butyl 3-[2-[tert-butoxycarbonyl-(3-isopropyl-5-pyrimidin-5-yl-pyrazolo[1,5-a]pyrimidin-7-yl) amino]ethyl]indole-1-carboxylate (100 mg, 167.31 μmol, 1 eq) in DCM (7.5 mL) was added TFA (1.5 mL). The mixture was degassed and purged with $N_2$ for 3 times and stirred under $N_2$ atmosphere at 20° C. for 3 h. The reaction mixture was concentrated under reduced pressure to give a residue which was purified by preparative HPLC (column: Phenomenex Gemini C18 250*50 mm*10 Gm; mobile phase: [water (0.05% HCl)-ACN]; B %: 35%-65%, 10 min). The desired fraction was lyophilized to yield N-[2-(1H-indol-3-yl) ethyl]-3-isopropyl-5-pyrimidin-5-yl-pyrazolo[1,5-a]pyrimidin-7-amine (17.94 mg, 34.12 μmol, 20.4% yield, 96.4% purity, 3HCl) as a yellow solid. $^1H$ NMR (400 MHz, $CD_3OD$) δ ppm 9.31 (s, 1H), 8.68 (s, 2H), 8.18 (s, 1H), 7.50 (d, J=7.9 Hz, 1H), 7.16 (d, J=8.0 Hz, 1H), 7.03 (s, 1H), 6.99-6.92 (m, 1H), 6.83-6.77 (m, 1H), 5.83 (s, 1H), 4.04-3.97 (m, 2H), 3.25-3.16 (m, 3H), 1.35 (d, J=6.8 Hz, 6H); ES-LCMS m/z 398.1 $[M+H]^+$.

Example 186

Synthesis of I-242

I-242

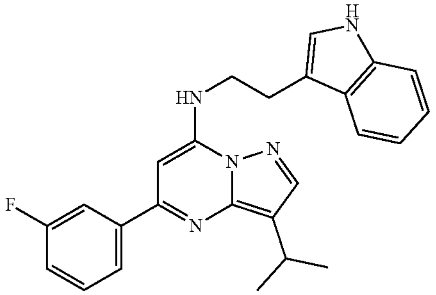

Synthetic Scheme:

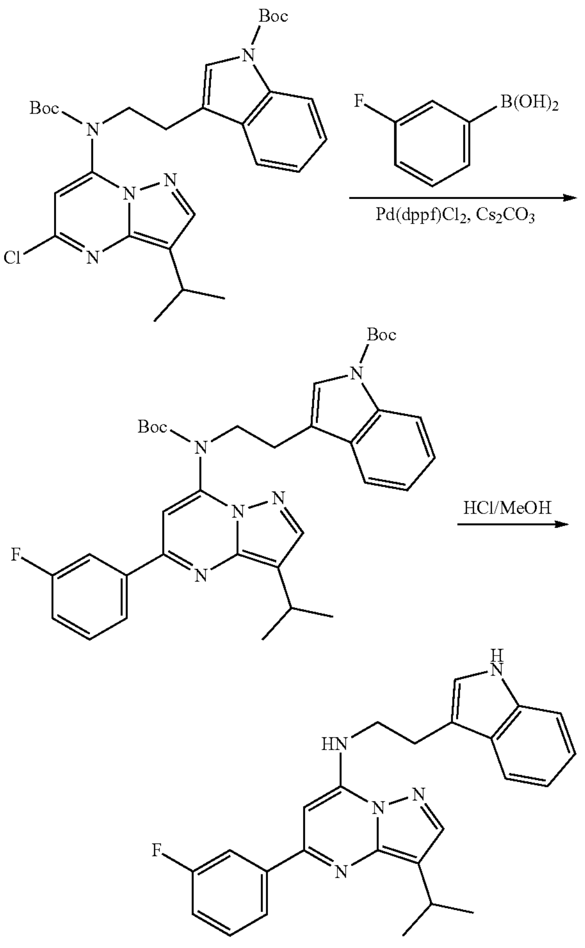

I-242

Step 1: tert-Butyl N-(2-bromo-4,6-difluoro-phenyl)carbamate

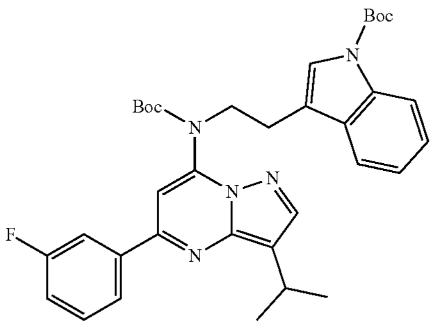 [SMILES: CC(C)c1cnn2c(N(CCc3cn(C(=O)OC(C)(C)C)c4ccccc34)C(=O)OC(C)(C)C)cc(-c3cccc(F)c3)nc12]

tert-Butyl 3-[2-[tert-butoxycarbonyl-(5-chloro-3-isopropyl-pyrazolo[1,5-a]pyrimidin-7-yl) amino]ethyl]indole-1-carboxylate (100 mg, 178.86 μmol, 1 eq), (3-fluorophenyl) boronic acid (75.08 mg, 536.57 μmol, 3 eq), Pd(dppf)$Cl_2$ (13.09 mg, 17.89 μmol, 0.1 eq), $Cs_2CO_3$ (174.82 mg, 536.57 μmol, 3 eq) and $H_2O$ (2 mL) were taken up into a microwave tube in 1,4-dioxane (6 mL). The sealed tube was heated at 110° C. for 1 h under microwave. The reaction mixture was concentrated under reduced pressure to give a residue which was diluted with aq. $NaHCO_3$ (20 mL) and extracted with EtOAc (50 mL×3). The combined organic layers were dried over $Na_2SO_4$, filtered and concentrated under reduced pressure to yield tert-butyl3-[2-[tert-butoxycarbonyl-[5-(3-fluorophenyl)-3-isopropyl-pyrazolo[1,5-a]pyrimidin-7-yl] amino]ethyl]indole-1-carboxylate (100 mg, 97.77 μmol, 54.7% yield, 60.0% purity) as a brown solid which was used in the next step without further purification. $^1$H NMR (400 MHz, $CD_3OD$) δ ppm 7.98 (s, 1H), 7.94 (d, J=7.6 Hz, 1H), 7.59 (d, J=1.2 Hz, 1H), 7.56 (d, J=2.4 Hz, 1H), 7.53 (s, 1H), 7.51 (s, 1H), 7.48 (d, J=3.6 Hz, 1H), 7.46 (d, J=2.0 Hz, 1H), 7.26 (s, 1H), 7.19-7.15 (m, 1H), 6.65-6.57 (m, 1H), 4.24-4.21 (m, 2H), 3.58-3.44 (m, 1H), 3.11 (t, J=6.4 Hz, 2H), 1.56 (s, 9H), 1.50-1.45 (m, 6H), 1.37 (s, 9H); ES-LCMS m/z 614.3 $[M+H]^+$.

Step 2: 5-(3-Fluorophenyl)-N-[2-(1H-indol-3-yl) ethyl]-3-isopropyl-pyrazolo[1,5-a]pyrimidin-7-amine (I-242)

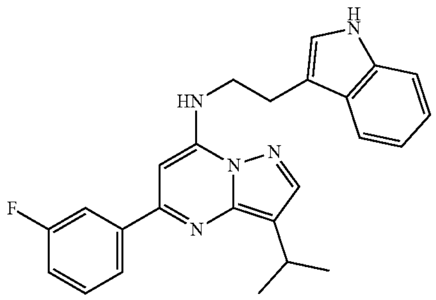 [SMILES: CC(C)c1cnn2c(NCCc3c[nH]c4ccccc34)cc(-c3cccc(F)c3)nc12]

A solution of tert-butyl 3-[2-[tert-butoxycarbonyl-[5-(3-fluorophenyl)-3-isopropyl-pyrazolo[1,5-a]pyrimidin-7-yl] amino]ethyl]indole-1-carboxylate (80 mg, 78.21 μmol, 1 eq) in HCl/MeOH (4 M, 3 mL, 153.43 eq) was stirred at 25° C. for 2 h under $N_2$ atmosphere. The reaction mixture was concentrated under reduced pressure to give a residue which was purified by preparative HPLC (column: Phenomenex Gemini C18 250*50 mm*10 um; mobile phase: [water (0.05% HCl)-ACN]; B %: 35%-65%, 10 min) followed by lyophilization to yield 5-(3-fluorophenyl)-N-[2-(1H-indol-3-yl)ethyl]-3-isopropyl-pyrazolo[1,5-a]pyrimidin-7-amine (38.32 mg, 76.97 μmol, 98.4% yield, 97.7% purity, 2HCl) as a yellow solid. $^1$H NMR (400 MHz, $CD_3OD$) δ ppm 8.16 (s, 1H), 7.55-7.46 (m, 2H), 7.31-7.36 (m, 1H), 7.20 (d, J=8.0 Hz, 1H), 7.10 (d, J=8.8 Hz, 1H), 7.06-6.92 (m, 3H), 6.85 (t, J=7.6 Hz, 1H), 5.74 (s, 1H), 4.08-3.92 (m, 2H), 3.29-3.24 (m, 1H), 3.24-3.19 (m, 2H), 1.34 (d, J=6.8 Hz, 6H); ES-LCMS m/z 414.2 $[M+H]^+$.

Example 187

Synthesis of I-245

I-245

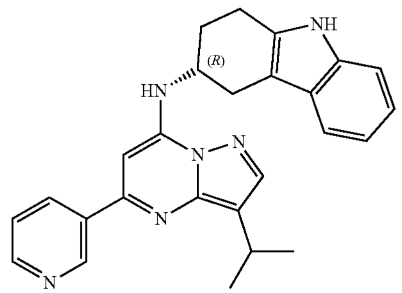

Synthetic Scheme:

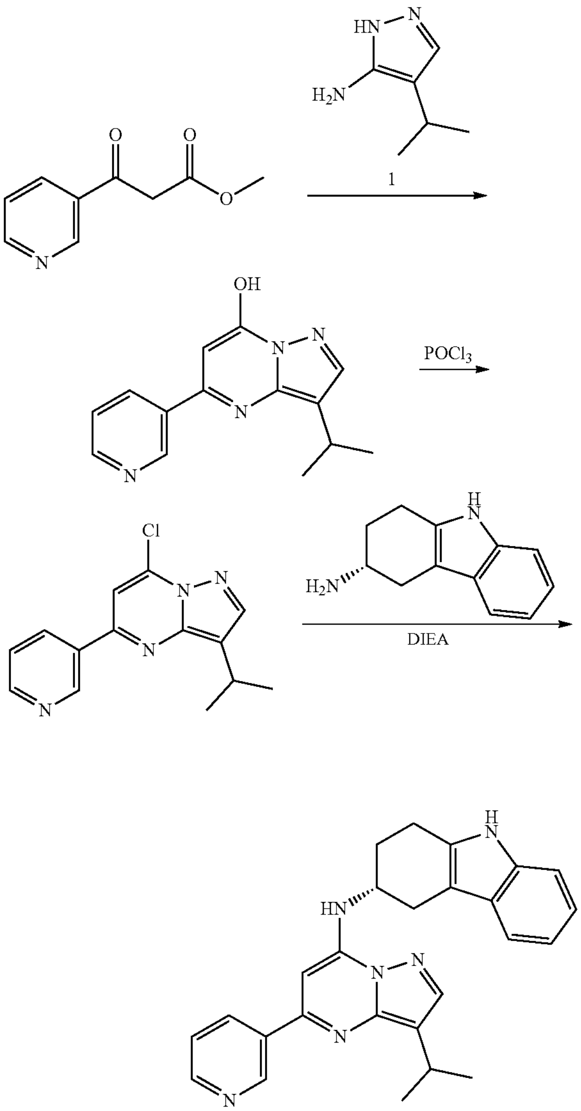

I-245

Step 1: 3-Isopropyl-5-(3-pyridyl)pyrazolo[1,5-a]pyrimidin-7-ol

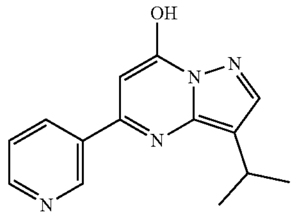

A mixture of methyl 3-oxo-3-(3-pyridyl)propanoate (440 mg, 2.46 mmol, 1 eq) and 4-isopropyl-1H-pyrazol-5-amine (307.39 mg, 2.46 mmol, 1 eq) in AcOH (20 mL) was stirred at 120° C. for 0.5 h. The reaction mixture was concentrated under reduced pressure to yield 3-isopropyl-5-(3-pyridyl)pyrazolo[1,5-a]pyrimidin-7-ol (600 mg, 1.60 mmol, 65.3% yield, crude, 2HOAC) as brown oil which was used in the next step without further purification. $^1$H NMR (400 MHz, $CDCl_3$) δ ppm 9.19-9.17 (m, 1H), 8.83-8.78 (m, 1H), 8.27 (td, J=1.9, 8.0 Hz, 1H), 7.50-7.42 (m, 2H), 7.14 (s, 1H), 2.84-2.75 (m, 1H), 1.22 (d, J=2.0 Hz, 6H); ES-LCMS m/z 255.1 $[M+H]^+$.

Step 2: 7-Chloro-3-isopropyl-5-(3-pyridyl)pyrazolo[1,5-a]pyrimidine

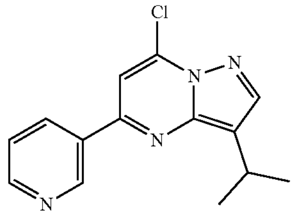 [SMILES: CC(C)c1cnn2c(Cl)cc(-c3cccnc3)nc12]

A solution of 3-isopropyl-5-(3-pyridyl)pyrazolo[1,5-a]pyrimidin-7-ol (600 mg, 1.60 mmol, 1 eq, 2HOAC) in $POCl_3$ (15 mL) was degassed and purged with $N_2$ for 3 times. The mixture was stirred at 110° C. for 3 h. The reaction mixture was concentrated under reduced pressure to yield a residue which adjusted to pH to 7-8 with TEA. The residue was purified on silica gel column chromatography (from PE/EtOAc=1/0 to 10/3, TLC: PE/EtOAc=3/1, $R_f$=0.35) to yield 7-chloro-3-isopropyl-5-(3-pyridyl)pyrazolo[1,5-a]pyrimidine (100 mg, 322.66 μmol, 20.1% yield, 88.0% purity) as a green solid. $^1$H NMR (400 MHz, $CDCl_3$) δ ppm 9.33 (d, J=1.8 Hz, 1H), 8.74 (dd, J=1.5, 4.9 Hz, 1H), 8.46 (td, J=2.0, 7.9 Hz, 1H), 8.13 (s, 1H), 7.50 (dd, J=4.7, 8.0 Hz, 1H), 7.40 (s, 1H), 3.42 (td, J=6.9, 13.8 Hz, 1H), 1.46 (d, J=7.1 Hz, 6H); ES-LCMS m/z 273.0 $[M+H]^+$.

Step 3: (3R)—N-[3-Isopropyl-5-(3-pyridyl)pyrazolo[1,5-a]pyrimidin-7-yl]-2,3,4,9-tetrahydro-1H-carbazol-3-amine (I-245)

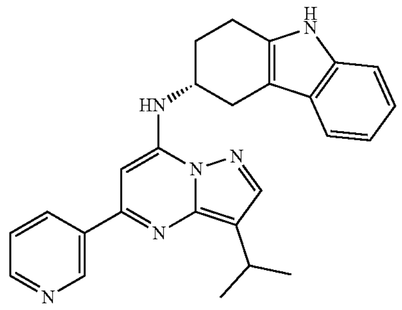 [SMILES: CC(C)c1cnn2c(N[C@@H]3CCc4[nH]c5ccccc5c4C3)cc(-c3cccnc3)nc12]

A mixture of 7-chloro-3-isopropyl-5-(3-pyridyl)pyrazolo[1,5-a]pyrimidine (60 mg, 193.60 μmol, 1 eq), (3R)-2,3,4,9-tetrahydro-1H-carbazol-3-amine (36.06 mg, 193.60 μmol, 1 eq) and DIEA (75.06 mg, 580.79 μmol, 101.16 μL, 3 eq) in i-PrOH (10 mL) was degassed and purged with $N_2$ for 3 times. The mixture was stirred at 80° C. for 3 h under $N_2$ atmosphere. The reaction mixture was concentrated under reduced pressure to yield a residue which was purified by preparative HPLC (column: Phenomenex Gemini 150*25 mm*10 μm; mobile phase: [water (0.05% HCl)-ACN]; B %: 42%-70%, 7 min) followed by lyophilization to yield (3R)—N-[3-isopropyl-5-(3-pyridyl)pyrazolo[1,5-a]pyrimidin-7-yl]-2,3,4,9-tetrahydro-1H-carbazol-3-amine (40.65 mg, 76.42 μmol, 39.5% yield, 100.0% purity, 3HCl) as a red solid. $^1H$ NMR (400 MHz, $CD_3OD$) δ ppm 9.52 (s, 1H), 9.17 (J=8.2 Hz, 1H), 8.97 (J=5.3 Hz, 1H), 8.21-8.15 (m, 2H), 7.34 (d, J=7.7 Hz, 1H), 7.23 (d, J=7.9 Hz, 1H), 7.10 (s, 1H), 7.00 (t, J=7.2 Hz, 1H), 6.95-6.88 (m, 1H), 4.62 (br s, 1H), 3.41 (td, J=7.0, 13.8 Hz, 1H), 3.27 (J=4.9 Hz, 1H), 3.13 (J=9.7 Hz, 1H), 3.01-2.91 (m, 2H), 2.42-2.22 (m, 2H), 1.42 (dd, J=3.1, 6.8 Hz, 6H); ES-LCMS m/z 423.2 $[M+H]^+$.

Example 188

Synthesis of I-246

I-246

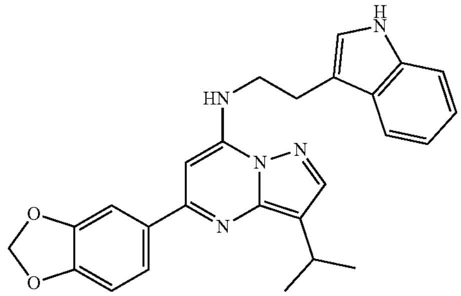

Synthetic Scheme:

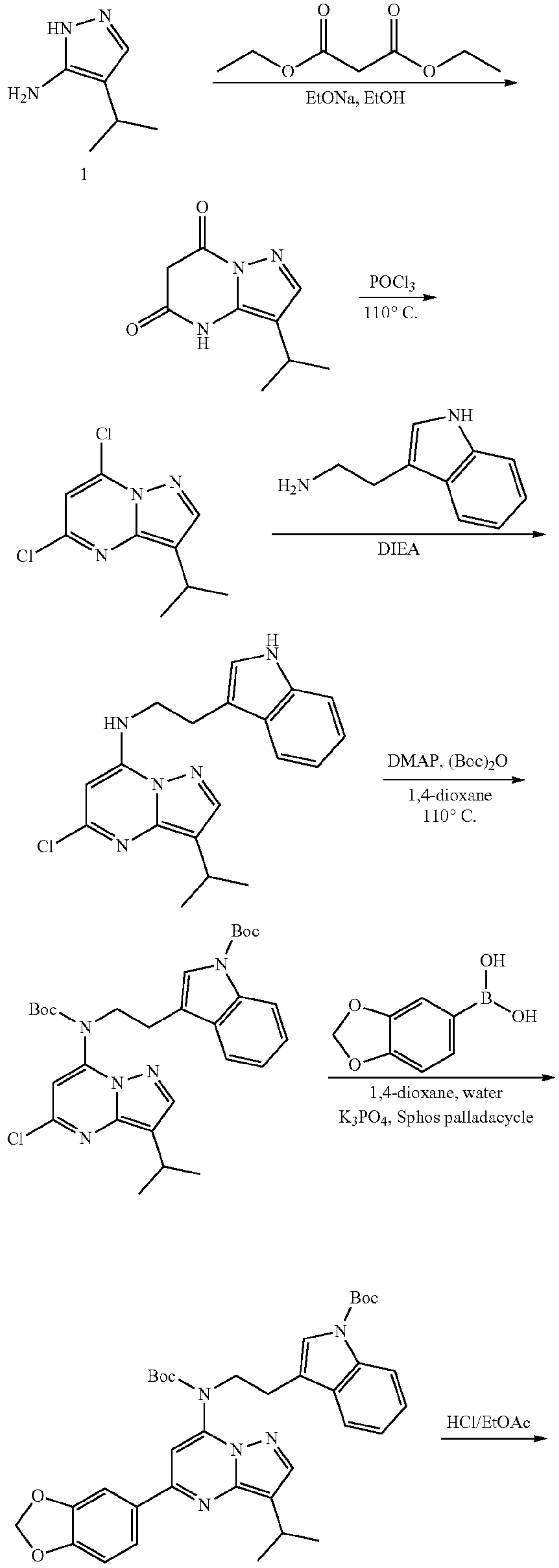

-continued

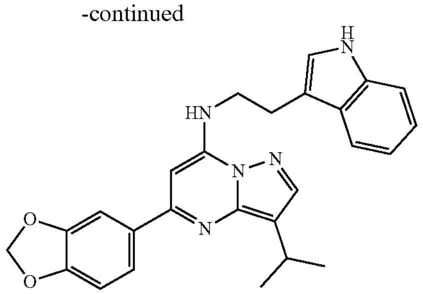

I-246

Step 1: 3-Isopropyl-4H-pyrazolo[1,5-a]pyrimidine-5,7-dione

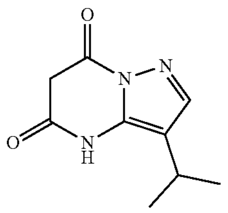

Na (367.33 mg, 15.98 mmol, 2 eq) was added into EtOH (25 mL) and the mixture was stirred at 24° C. for 2 h. 4-Isopropyl-1H-pyrazol-5-amine (1 g, 7.99 mmol, 1 eq) and diethyl propanedioate (1.41 g, 8.79 mmol, 1.33 mL, 1.1 eq) were added into the above reaction mixture and stirred at 80° C. for 5 h. The solution was cooled to room temperature and filtered. The obtained solid was washed with EtOH and dissolved in water (20 mL). Then the solution was acidified to pH=1-2 with concentrated hydrochloric acid in an ice-bath. The precipitate was filtered, washed with water and dried under reduced pressure to yield 3-isopropyl-4H-pyrazolo[1,5-a]pyrimidine-5,7-dione (300 mg, 1.55 mmol, 19.4% yield, 100.0% purity) as a yellow solid which was used in the next step without further purification. $^1$H NMR (400 MHz, $CD_3OD$) δ ppm 7.80-7.73 (m, 2H), 3.02 (td, J=6.7, 13.7 Hz, 1H), 1.28 (d, J=7.1 Hz, 6H); ES-LCMS m/z 194.2 $[M+H]^+$.

Step 2: 5,7-Dichloro-3-isopropyl-pyrazolo[1,5-a]pyrimidine

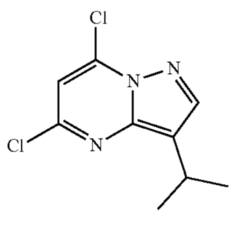

3-Isopropyl-4H-pyrazolo[1,5-a]pyrimidine-5,7-dione (285 mg, 1.48 mmol, 1 eq) was added into $POCl_3$ (20 mL). The reaction mixture was stirred at 110° C. for 12 h. The reaction mixture was concentrated under reduced pressure to give a residue which was purified by flash silica gel chromatography (from PE/EtOAc=100/1 to 5/1, TLC: PE/EtOAc=10/1, $R_f$=0.30) to yield 5,7-dichloro-3-isopropyl-pyrazolo[1,5-a]pyrimidine (300 mg, 1.30 mmol, 88.4% yield, 100.0% purity) as a yellow solid. $^1$H NMR (400 MHz, $CDCl_3$) δ ppm 8.10 (s, 1H), 6.94-6.90 (m, 1H), 3.37-3.26 (m, 1H), 1.37 (d, J=6.8 Hz, 6H); ES-LCMS m/z 230.1, 232.1 $[M+H]^+$.

Step 3: 5-Chloro-N-[2-(1H-indol-3-yl)ethyl]-3-isopropyl-pyrazolo[1,5-a]pyrimidin-7-amine

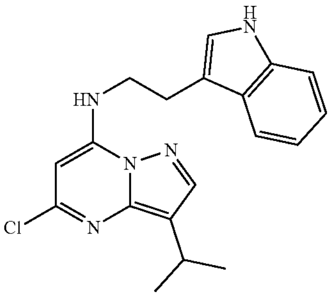 [SMILES: CC(C)c1cnn2c(NCCc3c[nH]c4ccccc34)cc(Cl)nc12]

To a solution of 5,7-dichloro-3-isopropyl-pyrazolo[1,5-a]pyrimidine (200 mg, 869.21 μmol, 1 eq) in i-PrOH (6 mL) was added DIEA (337.02 mg, 2.61 mmol, 454.20 μL, 3 eq) and 2-(1H-indol-3-yl)ethanamine (167.11 mg, 1.04 mmol, 1.2 eq). The mixture was stirred at 90° C. for 12 h. The reaction mixture was concentrated under reduced pressure to give a residue which was purified by flash silica gel chromatography (from PE/EtOAc=100/1 to 3/1, TLC: PE/EtOAc=3/1, $R_f$=0.60) to yield 5-chloro-N-[2-(1H-indol-3-yl)ethyl]-3-isopropyl-pyrazolo[1,5-a]pyrimidin-7-amine (240 mg, 672.83 μmol, 77.4% yield, 99.2% purity) as yellow solid. $^1$H NMR (400 MHz, $CDCl_3$) δ ppm 8.11 (s, 1H), 7.81 (s, 1H), 7.62 (d, J=7.8 Hz, 1H), 7.41 (d, J=8.3 Hz, 1H), 7.27-7.22 (m, 1H), 7.20-7.13 (m, 1H), 7.11 (d, J=2.3 Hz, 1H), 6.45 (s, 1H), 5.88 (s, 1H), 3.71 (q, J=6.6 Hz, 2H), 3.33-3.18 (m, 3H), 1.33 (d, J=7.0 Hz, 6H); ES-LCMS m/z 354.1, 355.1 $[M+H]^+$.

Step 4: tert-Butyl 3-[2-[tert-butoxycarbonyl-(5-chloro-3-isopropyl-pyrazolo[1,5-a]pyrimidin-7-yl)amino]ethyl]indole-1-carboxylate

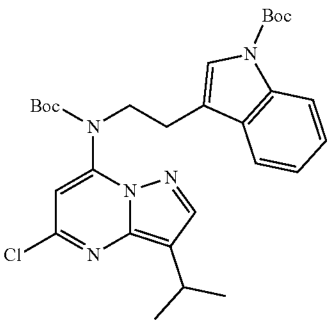 [SMILES: CC(C)c1cnn2c(N(CCc3cn(C(=O)OC(C)(C)C)c4ccccc34)C(=O)OC(C)(C)C)cc(Cl)nc12]

To a solution of 5-chloro-N-[2-(1H-indol-3-yl)ethyl]-3-isopropyl-pyrazolo[1,5-a]pyrimidin-7-amine (120 mg, 336.42 μmol, 1 eq) in 1,4-dioxane (6 mL) was added DMAP (123.30 mg, 1.01 mmol, 3 eq) and $(Boc)_2O$ (183.56 mg, 841.04 μmol, 193.22 μL, 2.5 eq). The mixture was stirred at 110° C. for 5 h. The reaction mixture was concentrated under reduced pressure to give a residue which was purified by flash silica gel chromatography (from PE/EtOAc=100/1 to 3/1, TLC: PE/EtOAc=3/1, $R_f$=0.75) to yield tert-butyl 3-[2-[tert-butoxycarbonyl-(5-chloro-3-isopropyl-pyrazolo[1,5-a]pyrimidin-7-yl)amino]ethyl]indole-1-carboxylate (150 mg, 262.33 μmol, 77.9% yield, 96.9% purity) as a yellow solid. $^1$H NMR (400 MHz, $CDCl_3$) δ ppm 8.09 (d, J=6.4 Hz, 1H), 7.97 (s, 1H), 7.43 (d, J=7.9 Hz, 1H), 7.35 (s, 1H), 7.32-7.27 (m, 1H), 7.20-7.13 (m, 1H), 6.39 (s, 1H), 4.21-4.15 (m, 2H), 3.28 (td, J=7.0, 13.9 Hz, 1H), 3.06 (t, J=7.4 Hz, 2H), 1.67 (s, 9H), 1.41 (s, 9H), 1.36 (d, J=7.1 Hz, 6H); ES-LCMS m/z 554.3, 556.3 $[M+H]^+$.

Step 5: 5-(1,3-Benzodioxol-5-yl)-N-[2-(1H-indol-3-yl)ethyl]-3-isopropyl-pyrazolo[1,5-a]pyrimidin-7-amine (I-246)

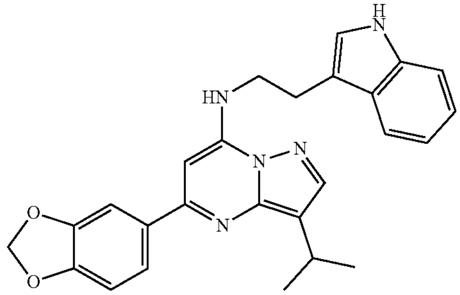 [SMILES: CC(C)c1cnn2c(NCCc3c[nH]c4ccccc34)cc(-c3ccc4c(c3)OCO4)nc12]

To a solution of tert-butyl 3-[2-[tert-butoxycarbonyl-(5-chloro-3-isopropyl-pyrazolo[1,5-a]pyrimidin-7-yl)amino]ethyl]indole-1-carboxylate (100 mg, 174.88 μmol, 1 eq) in 1,4-dioxane (6 mL) and water (2 mL) was added $K_3PO_4$ (111.37 mg, 524.65 μmol, 3 eq), sphos palladacycle (13.30 mg, 17.49 μmol, 0.1 eq) and 1,3-benzodioxol-5-ylboronic acid (87.06 mg, 524.65 μmol, 3 eq). The mixture was degassed and purged with $N_2$ three times and stirred at 110° C. for 1 h under microwave. The reaction mixture was diluted with EtOAc (50 mL) and filtered through a pad of celite. The filtrate was concentrated under reduced pressure to give a residue which was dissolved in DCM (1 mL) and HCl/EtOAc (1 mL, 4M) was added. The reaction mixture was stirred at 25° C. for 14 h. The reaction mixture was diluted with water (50 mL) and adjusted to pH=2 by 10% aq. NaOH solution. The mixture was extracted with EtOAc (50 mL×3), dried over anhydrous $Na_2SO_4$, filtered and the filtrate was concentrated to give the residue which was purified by preparative HPLC (HCl condition; column: Phenomenex Gemini 150*25 mm*10 m; mobile phase: [water (0.05% HCl)-ACN]; B %: 30%-60%, 10 min). The desired fraction was lyophilized to yield 5-(1,3-benzodioxol-5-yl)-N-[2-(1H-indol-3-yl)ethyl]-3-isopropyl-pyrarazolo[1,5-a]pyrimidin-7-amine (22.10 mg, 43.13 μmol, 25.1% yield, 100.0% purity, 2 HCl) as a yellow solid. $^1$H NMR (400 MHz, $CD_3OD$) δ ppm 8.09 (s, 1H), 7.56 (d, J=7.9 Hz, 1H), 7.22 (d, J=8.2 Hz, 1H), 7.08-7.02 (m, 2H), 6.92-6.86 (m, 2H), 6.80 (d, J=1.8 Hz, 1H), 6.73 (dd, J=1.9, 8.3 Hz, 1H), 6.08 (s, 2H), 5.70 (s, 1H), 3.99-3.93 (m, 2H), 3.28-3.18 (m, 3H), 1.33 (d, J=6.8 Hz, 6H); ES-LCMS m/z 440.2 $[M+H]^+$.

Example 189

Synthesis of I-249a, I-249b and I-249c

I-249a

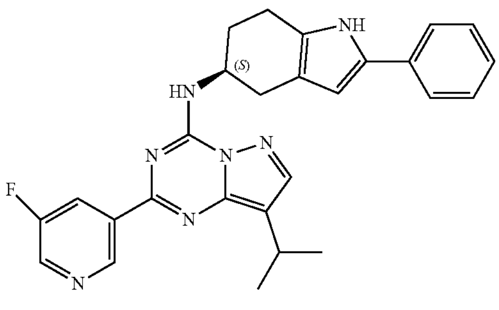

I-249b

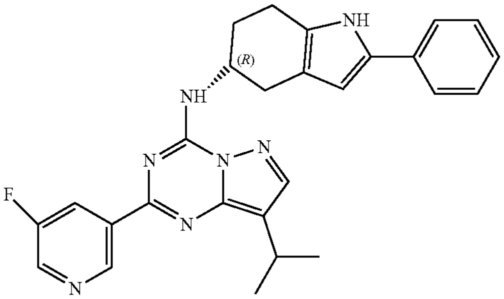

I-249c

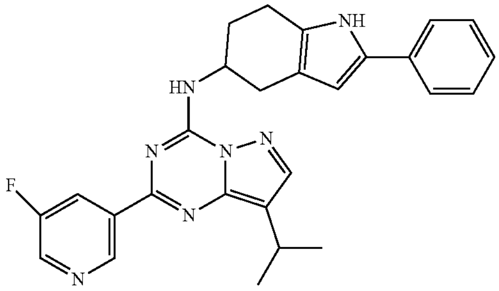

Synthetic Scheme:

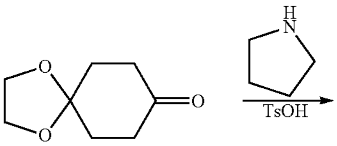

1

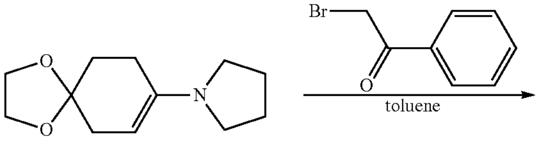

2

-continued

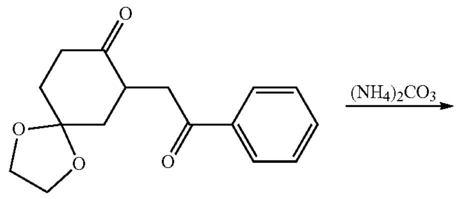

3

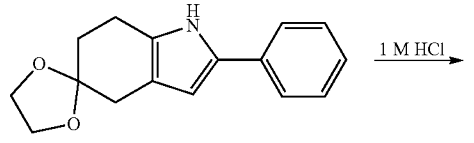

4

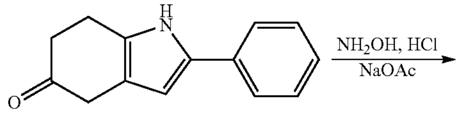

5

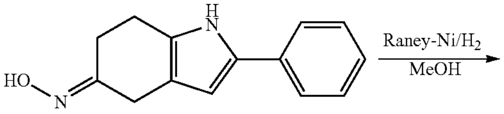

6

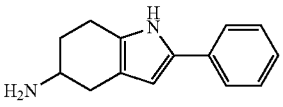

7

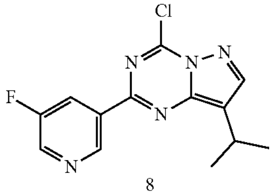

8

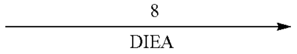

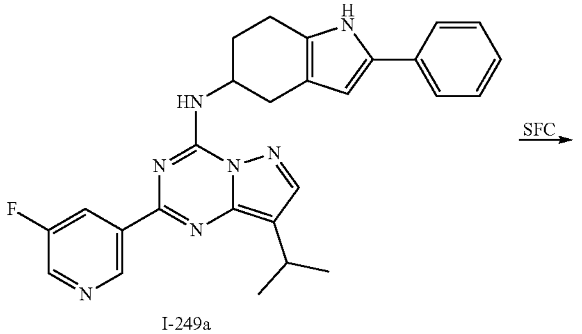

I-249a

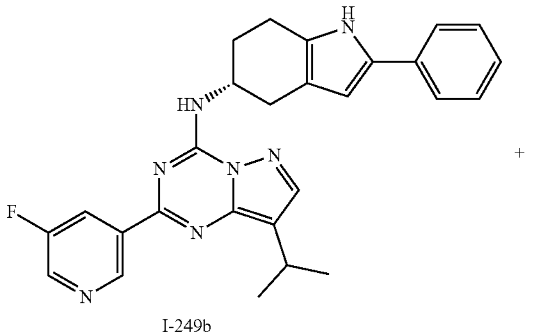

I-249b

-continued

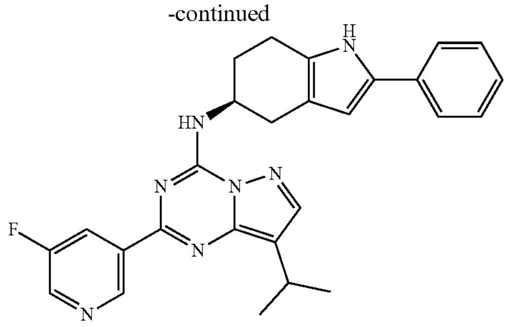

I-249a

Step 1: 1-(1,4-Dioxaspiro[4.5]dec-7-en-8-yl)pyrrolidine

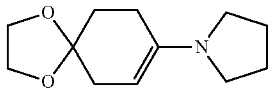 [SMILES: C1=C(N2CCCC2)CCC2(C1)OCCO2]

To a mixture of 1,4-dioxaspiro[4.5]decan-8-one (18 g, 115.25 mmol, 1 eq), TsOH (198.47 mg, 1.15 mmol, 0.01 eq) in toluene (200 mL) was added pyrrolidine (12.30 g, 172.88 mmol, 14.43 mL, 1.5 eq) under $N_2$ atmosphere. The mixture was stirred at 110° C. for 12 h under $N_2$ atmosphere. The reaction mixture was concentrated to yield 1-(1,4-dioxaspiro[4.5]dec-7-en-8-yl)pyrrolidine (24 g, 103.21 mmol, 89.6% yield, 90% purity) as brown oil. $^1H$ NMR (400 MHz, $CDCl_3$) δ ppm 4.17 (t, J=3.7 Hz, 1H), 4.11 (s, 2H), 4.07-4.05 (m, 2H), 3.12 (t, J=6.5 Hz, 2H), 2.97 (t, J=6.2 Hz, 2H), 2.59 (t, J=7.1 Hz, 2H), 2.54-2.49 (m, 1H), 2.45-2.43 (m, 1H), 2.09 (t, J=7.1 Hz, 2H), 1.94-1.90 (m, 2H), 1.87-1.73 (m, 2H).

Step 2: 7-Phenacyl-1,4-dioxaspiro[4.5]decan-8-one

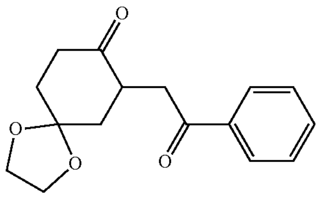 [SMILES: O=C(CC1CC2(CCC1=O)OCCO2)c1ccccc1]

A solution of 1-(1,4-dioxaspiro[4.5]dec-7-en-8-yl)pyrrolidine (24 g, 103.21 mmol, 1 eq) in toluene (200 mL) was heated to reflux under $N_2$ atmosphere and 2-bromo-1-phenyl-ethanone (20.54 g, 103.21 mmol, 1 eq) in toluene (60 mL) was added slowly. The mixture was stirred at 110° C. for 2 h under $N_2$ atmosphere. Then $H_2O$ (60 mL) was added and the mixture was stirred at 110° C. for further 2 h under $N_2$ atmosphere. The mixture was concentrated and water (50 mL) was added, extracted with EtOAc (100 mL×3). The combined organic layers were washed with brine (50 mL), dried over $Na_2SO_4$, filtered and concentrated. The crude material was purified on silica gel column chromatography (from pure PE to PE/EtOAc=2/1, TLC: PE/EtOAc=3/1, $R_f$=0.4) to yield 7-phenacyl-1,4-dioxaspiro[4.5]decan-8-one (13 g, 42.65 mmol, 41.3% yield, 90% purity) as a yellow solid. $^1$H NMR (400 MHz, $CDCl_3$) δ ppm 8.01-7.93 (m, 2H), 7.59-7.53 (m, 1H), 7.49-7.43 (m, 2H), 4.17-4.06 (m, 2H), 4.05-3.96 (m, 2H), 3.64-3.45 (m, 2H), 2.85-2.68 (m, 2H), 2.48-2.39 (m, 1H), 2.25-2.14 (m, 1H), 2.13-2.02 (m, 2H), 1.89-1.77 (m, 1H); ES-LCMS m/z 275.1 $[M+H]^+$.

Step 3: 2'-Phenylspiro[1,3-dioxolane-2,5'-1,4,6,7-tetrahydroindole]

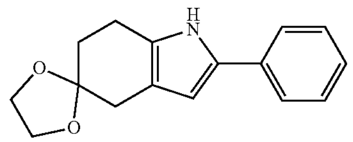 [SMILES: c1ccc(-c2cc3c([nH]2)CCC2(C3)OCCO2)cc1]

A mixture of 7-phenacyl-1,4-dioxaspiro[4.5]decan-8-one (5 g, 16.40 mmol, 1 eq) and $(NH_4)_2CO_3$ (5.00 g, 52.04 mmol, 5.56 mL, 3.17 eq) in sealed tube was stirred at 110° C. for 2 h under $N_2$ atmosphere. To the mixture was added water (50 mL), extracted with EtOAc (100 mL×2). The combined organic layers were washed with brine (40 mL), dried over $Na_2SO_4$, filtered and concentrated to yield 2'-phenylspiro[1,3-dioxolane-2,5'-1,4,6,7-tetrahydroindole](4 g, 14.10 mmol, 86.0% yield, 90% purity) as a brown solid. $^1$H NMR (400 MHz, $CDCl_3$) δ ppm 8.07-7.86 (m, 1H), 7.40 (d, J=7.8 Hz, 2H), 7.36-7.29 (m, 2H), 7.20-7.10 (m, 1H), 6.25 (d, J=2.4 Hz, 1H), 4.08-3.99 (m, 4H), 2.84 (t, J=6.6 Hz, 2H), 2.80 (s, 2H), 2.02 (t, J=6.5 Hz, 2H); ES-LCMS m/z 256.1 $[M+H]^+$.

Step 4: 2-Phenyl-1,4,6,7-tetrahydroindol-5-one

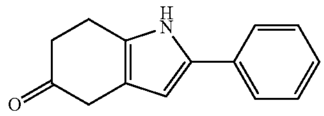 [SMILES: O=C1CCc2[nH]c(-c3ccccc3)cc2C1]

To a solution of 2'-phenylspiro[1,3-dioxolane-2,5'-1,4,6,7-tetrahydroindole](3.9 g, 13.75 mmol, 1 eq) in acetone (30 mL) was added HCl (1 M, 13.75 mL, 1 eq), the mixture was stirred at 50° C. for 3 h. The mixture was concentrated and adjusted pH to 7 with saturated $NaHCO_3$ solution, extracted with EtOAc (80 mL×2). The combined organic layers were washed with brine (50 mL), dried over $Na_2SO_4$, filtered and concentrated. The crude material was purified on silica gel column chromatography (from pure PE to PE/EtOAc=2/1, TLC: PE/EtOAc=3/1, $R_f$=0.3) to yield 2-phenyl-1,4,6,7-tetrahydroindol-5-one (0.7 g, 2.32 mmol, 16.9% yield, 70.0% purity) as a yellow solid. $^1$H NMR (400 MHz, $CDCl_3$) δ ppm 8.15 (s, 1H), 7.44 (d, J=7.6 Hz, 2H), 7.36 (t, J=7.7 Hz, 2H), 7.23-7.17 (m, 1H), 6.29 (d, J=2.4 Hz, 1H), 3.45 (s, 2H), 3.09-3.03 (m, 2H), 2.74 (t, J=6.8 Hz, 2H); ES-LCMS m/z 212.1 $[M+H]^+$.

Step 5: 2-Phenyl-1,4,6,7-tetrahydroindol-5-one oxime

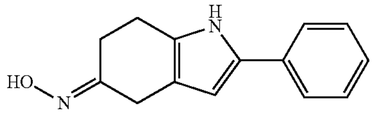 [SMILES: O/N=C1\CCc2[nH]c(-c3ccccc3)cc2C1]

To a solution of 2-phenyl-1,4,6,7-tetrahydroindol-5-one (600 mg, 1.99 mmol, 1 eq) in THF (15 mL) was added NaOAc (244.64 mg, 2.98 mmol, 1.5 eq) and $NH_2OH.HCl$ (165.78 mg, 2.39 mmol, 1.2 eq). The mixture was stirred at 60° C. for 3 h. The mixture was filtered. The filtrate was concentrated to yield a residue which was purified on silica gel column chromatography (from pure PE to PE/EtOAc=1/1, TLC: PE/EtOAc=1/1, $R_f$=0.4) to yield 2-phenyl-1,4,6,7-tetrahydroindol-5-one oxime (350 mg, 1.24 mmol, 62.2% yield, 80% purity) as a red solid. $^1$H NMR (400 MHz, $CDCl_3$) δ ppm 8.02 (s, 1H), 7.47-7.41 (m, 2H), 7.38-7.33 (m, 2H), 7.21-7.16 (m, 1H), 6.32 (d, J=2.4 Hz, 1H), 3.66 (s, 2H), 2.89-2.81 (m, 2H), 2.71-2.63 (m, 1H); ES-LCMS m/z 227.1 $[M+H]^+$.

Step 6: 2-Phenyl-4,5,6,7-tetrahydro-1H-indol-5-amine

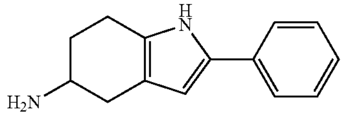

To a solution of 2-phenyl-1,4,6,7-tetrahydroindol-5-one oxime (350 mg, 1.24 mmol, 1 eq) in MeOH (6 mL) was added Raney-Ni (200 mg, 2.33 mmol, 1.89 eq) under $N_2$ atmosphere. The mixture was stirred at 20° C. for 1 h under $H_2$ (15 psi) atmosphere. The mixture was filtered. The filtrate was concentrated to yield 2-phenyl-4,5,6,7-tetrahydro-1H-indol-5-amine (250 mg, 942.11 mol, 76.1% yield, 80% purity) was obtained as a black brown solid. $^1$H NMR (500 MHz, $CD_3OD$) δ ppm 7.50-7.46 (m, 2H), 7.26 (t, J=7.9 Hz, 2H), 7.09-7.03 (m, 1H), 6.18 (s, 1H), 3.12-3.04 (m, 1H), 2.86-2.63 (m, 3H), 2.30 (dd, J=8.9, 14.8 Hz, 1H), 2.05-1.97 (m, 1H), 1.73-1.64 (m, 1H); ES-LCMS m/z 213.2 $[M+H]^+$.

Step 7: 2-(5-Fluoro-3-pyridyl)-8-isopropyl-N-[(5R)-2-phenyl-4,5,6,7-tetrahydro-1H-indol-5-yl]pyrazolo[1,5-a][1,3,5]triazin-4-amine (I-249b) and 2-(5-Fluoro-3-pyridyl)-8-isopropyl-N-[(5S)-2-phenyl-4,5,6,7-tetrahydro-1H-indol-5-yl]pyrazolo[1,5-a][1,3,5]triazin-4-amine (I-249a)

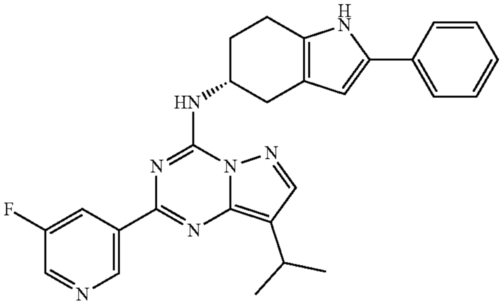

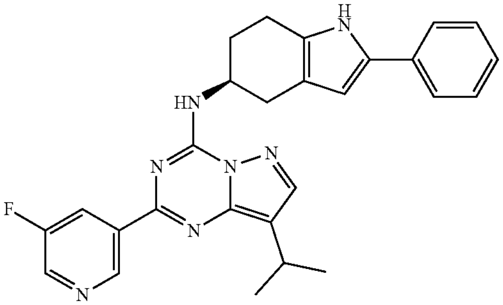

To a solution of 2-phenyl-4,5,6,7-tetrahydro-1H-indol-5-amine (207.84 mg, 783.24 umol, 1.2 eq) and DIEA (253.07 mg, 1.96 mmol, 341.07 μL, 3 eq) in i-PrOH (15 mL) was added 4-chloro-2-(5-fluoro-3-pyridyl)-8-isopropyl-pyrazolo[1,5-a][1,3,5]triazine (200 mg, 652.70 μmol, 1 eq). The mixture was stirred at 50° C. for 2 h. The mixture was concentrated. The crude material was purified on silica gel column chromatography (from pure PE to PE/EtOAc=2/1, TLC: PE/EtOAc=2/1, $R_f$=0.5) to yield the residue which was separated by SFC (column: DAICEL CHIRALCEL OJ-H (250 mm*30 mm, 5 m); mobile phase: [0.1% $NH_3H_2O$ EtOH]; B %: 40%-40%, min) to yield Peak 1 and Peak 2. Peak 1 was concentrated and purified by preparative HPLC (column: Agela ASB 150*25 mm*5 m; mobile phase: [water (0.05% HCl)-ACN]; B %: 75%-100%, 8 min), followed by lyophilization to yield an enantiomer (18.68 mg, 31.16 μmol, 4.8% yield, 96.249% purity, 3 HCl. SFC: Rt=5.229 min, ee=95.522%, $[\alpha]^{26.5}_D$=+24.339, ($CHCl_3$, c=0.1015 g/100 mL)) as a yellow solid. $^1H$ NMR (400 MHz, DMSO-$d_6$) δ ppm 10.89 (s, 1H), 9.38 (s, 1H), 8.89 (d, J=8.6 Hz, 1H), 8.70 (d, J=2.9 Hz, 1H), 8.43 (td, J=2.2, 9.8 Hz, 1H), 8.18-8.07 (m, 1H), 7.55 (d, J=7.6 Hz, 2H), 7.30 (t, J=7.7 Hz, 2H), 7.14-7.03 (m, 1H), 6.27 (d, J=2.2 Hz, 1H), 4.77-4.60 (m, 1H), 3.26-3.15 (m, 1H), 2.93-2.71 (m, 4H), 2.17-2.00 (m, 2H), 1.36 (d, J=7.1 Hz, 6H); ES-LCMS m/z 468.3 $[M+H]^+$. Peak 2 was concentrated to yield a residue which was dissolved in MeCN (20 mL), 1 M HCl solution (1.2 mL) and $H_2O$ (40 mL), followed by lyophilization to yield the other enantiomer (23.41 mg, 40.58 μmol, 6.2% yield, 100% purity, 3 HCl. SFC: Rt=6.074 min, ee=100%, $[\alpha]^{26.5}_D$=−26.002, ($CHCl_3$, c=0.1002 g/100 mL)) as a yellow solid. $^1H$ NMR (400 MHz, DMSO-$d_6$) δ ppm 10.90 (br s, 1H), 9.38 (s, 1H), 8.89 (d, J=8.6 Hz, 1H), 8.70 (d, J=2.7 Hz, 1H), 8.43 (d, J=9.8 Hz, 1H), 8.23-8.04 (m, 1H), 7.55 (d, J=7.6 Hz, 2H), 7.30 (t, J=7.8 Hz, 2H), 7.17-7.03 (m, 1H), 6.27 (d, J=2.2 Hz, 1H), 4.68 (d, J=5.1 Hz, 1H), 3.27-3.13 (m, 1H), 2.92-2.66 (m, 4H), 2.19-2.00 (m, 2H), 1.36 (d, J=6.8 Hz, 6H); ES-LCMS m/z 468.3 $[M+H]^+$.

Example 190

Synthesis of I-252a, I-252b and I-252c

I-252a

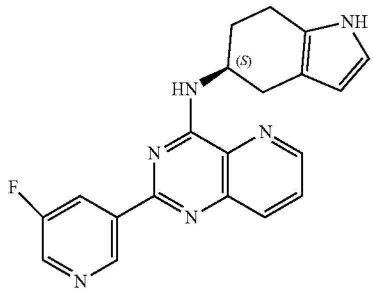

I-252b

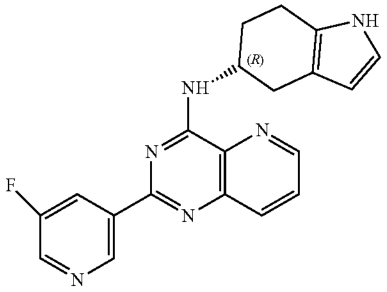

I-252c

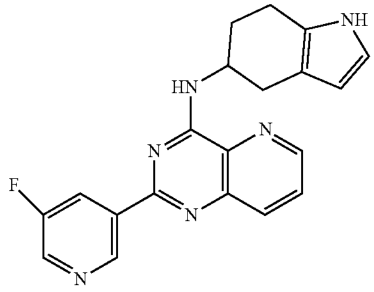

Synthetic Scheme:

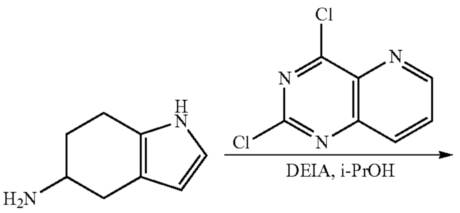

-continued

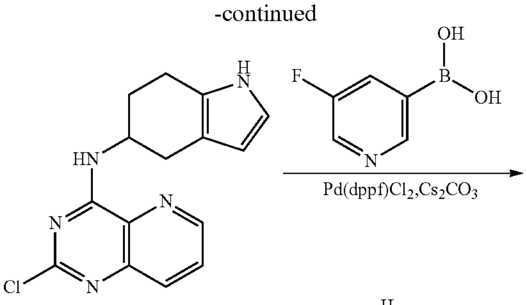

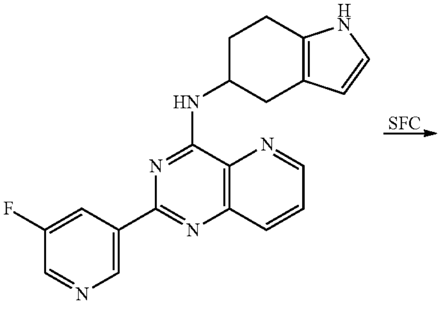

I-252c

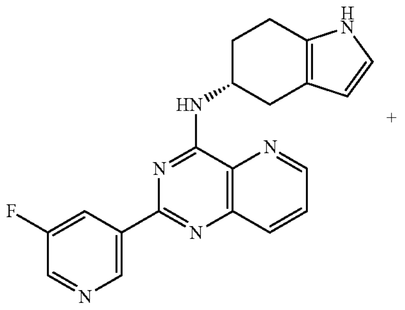

I-252b

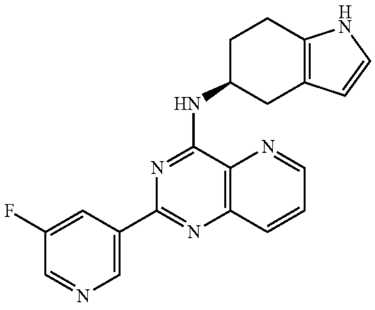

I-252a

Step 1: 2-Chloro-N-(4,5,6,7-tetrahydro-1H-indol-5-yl)pyrido[3,2-d]pyrimidin-4-amine

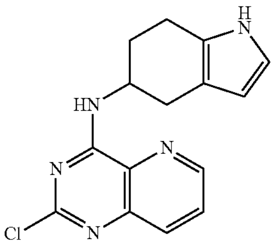 [SMILES: Clc1nc(NC2CCc3[nH]ccc3C2)c2ncccc2n1]

A mixture of 2,4-dichloropyrido[3,2-d]pyrimidine (150 mg, 749.91 μmol, 1 eq), 4,5,6,7-tetrahydro-1H-indol-5-amine (113.48 mg, 749.91 μmol, 1 eq) and DIEA (387.68 mg, 3.00 mmol, 522.48 μL, 4 eq) in i-PrOH (10 mL) was stirred at 55° C. for 2 h. The reaction mixture was concentrated to yield the residue which was purified on silica gel column chromatography (from PE/EtOAc=3/1 to 1/1, TLC: PE/EtOAc=1/1, $R_f$=0.50) to yield 2-chloro-N-(4,5,6,7-tetrahydro-1H-indol-5-yl)pyrido[3,2-d]pyrimidin-4-amine (120 mg, 397.52 μmol, 53.0% yield, 99.3% purity) as a yellow solid. $^1$H NMR (400 MHz, $CDCl_3$) δ ppm 8.64 (dd, J=1.5, 4.3 Hz, 1H), 8.01 (dd, J=1.5, 8.5 Hz, 1H), 7.85 (s, 1H), 7.64 (dd, J=4.3, 8.3 Hz, 1H), 7.44 (d, J=8.5 Hz, 1H), 6.70 (t, J=2.6 Hz, 1H), 6.04 (t, J=2.6 Hz, 1H), 4.80-4.70 (m, 1H), 3.10 (dd, J=5.3, 15.3 Hz, 1H), 2.99-2.45 (m, 3H), 2.24-2.08 (m, 2H); ES-LCMS m/z 300.1 $[M+H]^+$.

Step 2: 2-(5-Fluoro-3-pyridyl)-N-[(5R)-4,5,6,7-tetrahydro-1H-indol-5-yl]pyrido[3,2-d]pyrimidin-4-amine (I-252b) and 2-(5-Fluoro-3-pyridyl)-N-[(5S)-4,5,6,7-tetrahydro-1H-indol-5-yl]pyrido[3,2-d]pyrimidin-4-amine (I-252a)

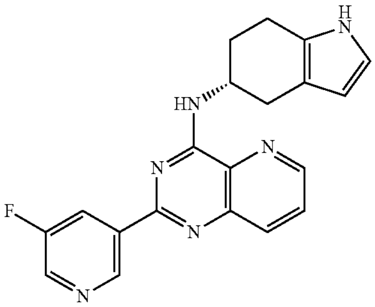

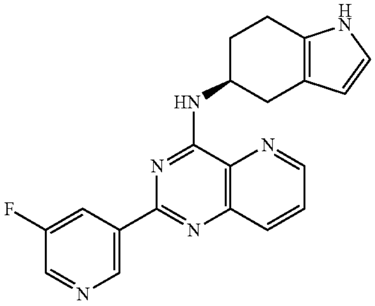

2-Chloro-N-(4,5,6,7-tetrahydro-1H-indol-5-yl)pyrido[3,2-d]pyrimidin-4-amine (120 mg, 397.52 mol, 1 eq), (5-fluoro-3-pyridyl)boronic acid (168.04 mg, 1.19 mmol, 3 eq), Pd(dppf)$Cl_2$ (29.09 mg, 39.75 μmol, 0.1 eq) and $Cs_2CO_3$ (518.08 mg, 1.59 mmol, 4 eq) in 1,4-dioxane (3 mL) and $H_2O$ (1 mL) were taken up into a microwave tube and purged with $N_2$ atmosphere for 1 min. The sealed tube was heated at 110° C. for 1 h under microwave. The reaction mixture was concentrated. The residue was purified by flash silica gel chromatography (from pure PE to PE/EtOAc=1/1, TLC: PE/EtOAc=2/1, $R_f$=0.40) to yield a residue which was separated by chiral SFC (column: DAICEL CHIRALCEL OJ-H (250 mm*30 mm, 5 μm); mobile phase: [0.1% $NH_3H_2O$ EtOH]; B %: 40%-40%) to yield an enantiomer (19.36 mg, 52.04 μmol, 13.1% yield, 96.9% purity, SFC: Rt=4.040, ee=100%, Optical rotation: $[\alpha]^{23.9}_D$=−8.542 ($CHCl_3$, c=0.075 g/100 mL)) as a red solid. $^1$H NMR (400

MHz, $CD_3OD$) δ ppm 9.43 (s, 1H), 8.71 (dd, J=1.5, 4.2 Hz, 1H), 8.56-8.48 (m, 2H), 8.15 (dd, J=1.5, 8.6 Hz, 1H), 7.76-7.73 (m, 1H), 6.62 (d, J=2.4 Hz, 1H), 5.90 (d, J=2.4 Hz, 1H), 4.84-4.78 (m, 1H), 3.09 (dd, J=4.9, 15.2 Hz, 1H), 2.85-2.69 (m, 3H), 2.27 (d, J=12.5 Hz, 1H), 2.14 (d, J=6.6 Hz, 1H); ES-LCMS m/z 361.2 $[M+H]^+$ and the other enantiomer (17.54 mg, 47.86 μmol, 12.0% yield, 98.3% purity) as a red solid (SFC: Rt=4.941, ee=100%, Optical rotation: $[t]^{25}_D$=+10.973 ($CHCl_3$, c=0.054 g/100 mL)). $^1H$ NMR (400 MHz, $CD_3OD$) δ ppm 9.44 (s, 1H), 8.71 (dd, J=1.2, 4.2 Hz, 1H), 8.57-8.49 (m, 2H), 8.16 (dd, J=1.2, 8.6 Hz, 1H), 7.75 (dd, J=4.2, 8.6 Hz, 1H), 6.64 (s, 1H), 5.92 (d, J=2.4 Hz, 1H), 4.86-4.81 (m, 1H), 3.11 (dd, J=5.0, 15.0 Hz, 1H), 2.88-2.70 (m, 3H), 2.28 (d, J=9.8 Hz, 1H), 2.19-2.11 (m, 1H); ES-LCMS m/z 361.2 $[M+H]^+$.

Example 191

Synthesis of I-253

I-253

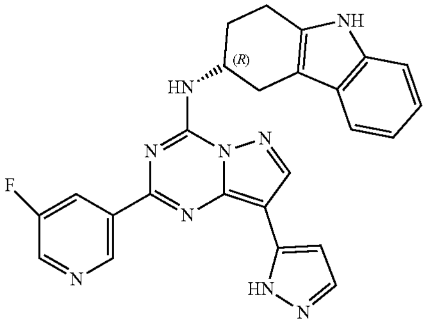

Synthetic Scheme:

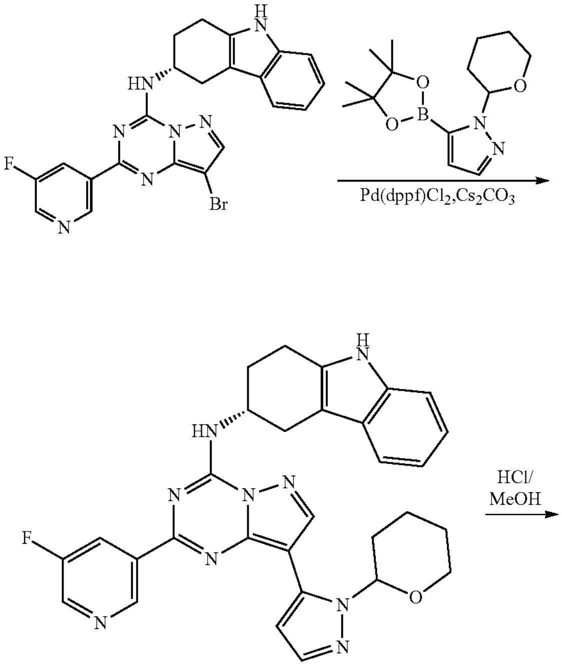

-continued

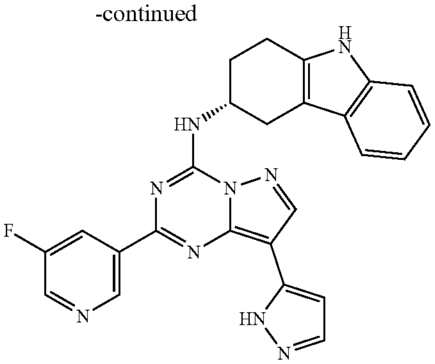

I-253

Step 1: (3R)—N-[2-(5-Fluoro-3-pyridyl)-8-(2-tetrahydropyran-2-ylpyrazol-3-yl)pyrazolo[1,5-a][1,3,5]triazin-4-yl]-2,3,4,9-tetrahydro-1H-carbazol-3-amine

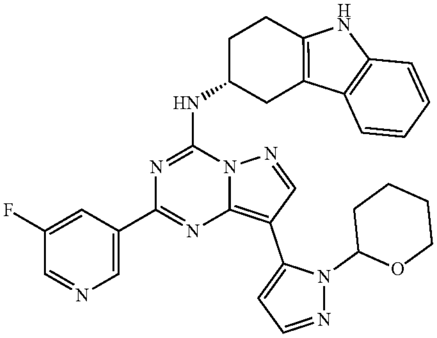 [SMILES: Fc1cncc(-c2nc(N[C@@H]3CCc4[nH]c5ccccc5c4C3)n3ncc(-c4ccnn4C4CCCCO4)c3n2)c1]

(3R)—N-[8-bromo-2-(5-fluoro-3-pyridyl)pyrazolo[1,5-a][1,3,5]triazin-4-yl]-2,3,4,9-tetrahydro-1H-carbazol-3-amine (100 mg, 202.79 μmol, 1 eq), $Cs_2CO_3$ (66.07 mg, 202.79 μmol, 1 eq), Pd(dppf)$Cl_2$ (148.39 mg, 202.79 μmol, 1 eq) and 1-tetrahydropyran-2-yl-5-(4,4,5,5-tetramethyl-1,3,2-dioxaborolan-2-yl)pyrazole (56.41 mg, 202.79 μmol, 1 eq) were taken up into a microwave tube in 1,4-dioxane (6 mL) and $H_2O$ (2 mL). The sealed tube was heated at 110° C. for 30 min under microwave. TLC (PE/EtOAc=1/1, $R_f$=0.4) indicated the starting material was consumed completely. The reaction mixture was concentrated under reduced pressure to yield a residue which was purified by flash silica gel chromatography (from PE/EA=1/0 to 1/1, TLC: PE/EtOAc=1/1, $R_f$=0.4) to yield (3R)—N-[2-(5-fluoro-3-pyridyl)-8-(2-tetrahydropyran-2-ylpyrazol-3-yl)pyrazolo[1,5-a][1,3,5]triazin-4-yl]-2,3,4,9-tetrahydro-1H-carbazol-3-amine (70 mg, 122.27 μmol, 60.3% yield, 96.0% purity) as a yellow solid. $^1H$ NMR (400 MHz, DMSO-$d_6$) δ ppm 10.82 (s, 1H), 9.41-9.38 (m, 2H), 8.73 (d, J=2.7 Hz, 1H), 8.49-8.47 (d, J=9.0 Hz, 1H), 8.38 (s, 1H), 7.64 (s, 1H), 7.37-7.35 (d, J=7.8 Hz, 1H), 7.29-7.27 (d, J=7.8 Hz, 1H), 7.02-6.99 (m, 1H), 6.95-6.92 (m, 1H), 6.74 (s, 1H), 5.66-5.64 (d, J=9.0 Hz, 1H), 4.89 (d, 1H), 3.95-3.91 (m, 2H), 3.59-3.57 (m, 1H), 3.15-2.88 (m, 4H), 2.23 (br s, 2H), 1.64-1.52 (m, 3H), 1.23 (m, 1H), 0.85-0.83 (d, J=7.8 Hz, 1H); ES-LCMS m/z 550.3 $[M+H]^+$.

Step 2: (3R)—N-[2-(5-Fluoro-3-pyridyl)-8-(1H-pyrazol-5-yl)pyrazolo[1,5-a][1,3,5]triazin-4-yl]-2,3,4,9-tetrahydro-1H-carbazol-3-amine (I-253)

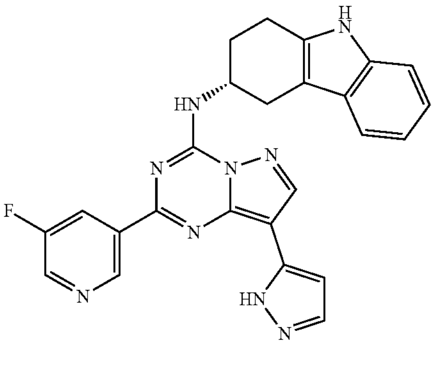 [SMILES: Fc1cncc(-c2nc(N[C@@H]3CCc4[nH]c5ccccc5c4C3)n3ncc(-c4ccn[nH]4)c3n2)c1]

A solution of (3R)—N-[2-(5-fluoro-3-pyridyl)-8-(2-tetrahydropyran-2-ylpyrazol-3-yl)pyrazolo[1,5-a][1,3,5]triazin-4-yl]-2,3,4,9-tetrahydro-1H-carbazol-3-amine (70 mg, 122.27 μmol, 1 eq) in HCl/MeOH (10 mL) was stirred at 15° C. for 20 min. The reaction mixture was basified with aqueous $NaHCO_3$ solution until pH to 7-8, extracted with EtOAc (50 mL×3), dried over $Na_2SO_4$, filtered and concentrated under reduced pressure to yield a residue which was purified by preparative HPLC (HCl condition; column: Agela ASB 150*25 mm*5 μm; mobile phase: [water (0.05% HCl)-ACN]; B %: 53%-83%, 8 min) to yield (3R)—N-[2-(5-fluoro-3-pyridyl)-8-(1H-pyrazol-5-yl)pyrazolo[1,5-a][1,3,5]triazin-4-yl]-2,3,4,9-tetrahydro-1H-carbazol-3-amine (19.45 mg, 33.83 μmol, 27.7% yield, 100.0% purity, 3HCl, $[\alpha]^{26.4}_{D}$=+13.329 (MeOH, c=0.098 g/100 mL)) as a yellow solid. $^1H$ NMR (400 MHz, DMSO-$d_6$) δ ppm 10.82 (s, 1H), 9.51 (s, 1H), 9.29-9.27 (d, J=8.6 Hz, 1H), 8.75 (d, J=2.7 Hz, 1H), 8.68 (d, J=10.0 Hz, 1H), 8.64 (s, 1H), 7.84-7.83 (d, J=2.0 Hz, 1H), 7.37-7.35 (d, J=7.6 Hz, 1H), 7.29-7.27 (d, J=8.1 Hz, 1H), 7.04-7.00 (m, 2H), 6.95-6.93 (m, 1H), 4.89-4.87 (d, J=7.6 Hz, 1H), 3.17-3.12 (m, J=5.5, 14.8 Hz, 1H), 3.04-2.88 (m, 3H), 2.24-2.23 (d, J=3.7 Hz, 2H); ES-LCMS m/z 466.2 $[M+H]^+$.

Example 192

Synthesis of I-254

I-254

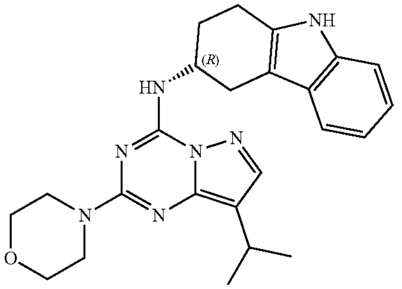

Synthetic Scheme:

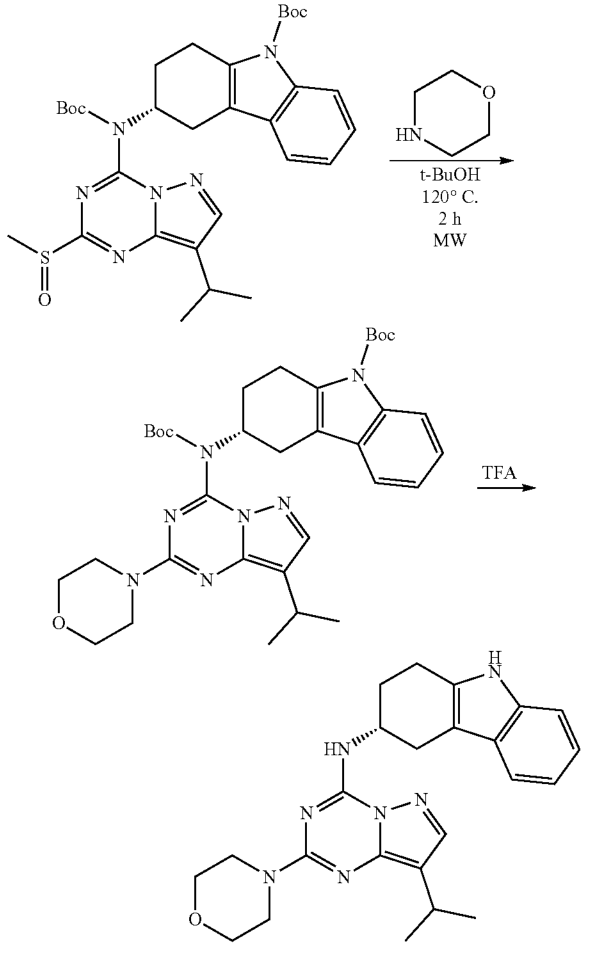

I-253

Step 1: tert-Butyl (3R)-3-[tert-butoxycarbonyl-(8-isopropyl-2-morpholino-pyrazolo[1,5-a][1,3,5]triazin-4-yl)amino]-1,2,3,4-tetrahydrocarbazole-9-carboxylate

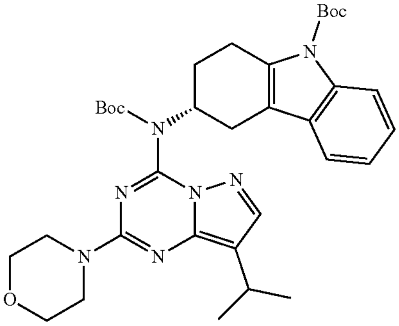 [SMILES: CC(C)c1cnn2c(N(C(=O)OC(C)(C)C)[C@@H]3CCc4c(c5ccccc5n4C(=O)OC(C)(C)C)C3)nc(N3CCOCC3)nc12]

tert-Butyl-(3R)-3-[tert-butoxycarbonyl-(8-isopropyl-2-methyl sulfinyl-pyrazolo[1,5-a][1,3,5]triazin-4-yl)amino]-1,2,3,4-tetrahydrocarbazole-9-carboxylate (100 mg, 156.06 μmol, 1 eq) and morpholine (40.79 mg, 468.17 μmol, 41.20

μL, 3 eq) in t-BuOH (4 mL) were taken up into a microwave tube and purged with $N_2$ for 1 min. The sealed tube was heated at 120° C. for 2 h under microwave. The reaction mixture was concentrated to yield tert-butyl (3R)-3-[tert-butoxycarbonyl-(8-isopropyl-2-morpholino-pyrazolo[1,5-a][1,3,5]triazin-4-yl)amino]-1,2,3,4-tetrahydrocarbazole-9-carboxylate (100 mg, 142.46 μmol, 91.3% yield, 90% purity) as yellow oil which was used in the next step without purification. $^1$H NMR (400 MHz, $CDCl_3$) δ ppm 8.10 (d, J=8.0 Hz, 1H), 7.82 (s, 1H), 7.35 (d, J=7.5 Hz, 1H), 7.22 (dd, J=6.7, 13.9 Hz, 2H), 4.74 (s, 1H), 3.79-3.74 (m, 8H), 3.23 (d, J=10.8 Hz, 2H), 3.15-3.07 (m, 3H), 2.26 (d, J=4.3 Hz, 2H), 1.65 (s, 9H), 1.36 (s, 9H), 1.33 (d, J=7.0 Hz, 6H); ES-LCMS m/z 632.3 $[M+H]^+$.

Step 2: (3R)—N-(8-Isopropyl-2-morpholino-pyrazolo[1,5-a][1,3,5]triazin-4-yl)-2,3,4,9-tetrahydro-1H-carbazol-3-amine (I-254)

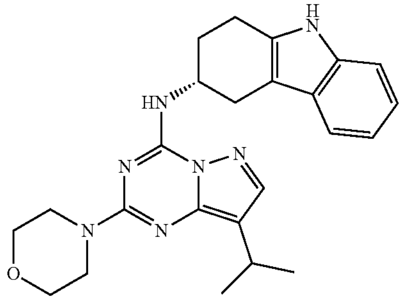 [SMILES: CC(C)c1cnn2c(N[C@@H]3CCc4[nH]c5ccccc5c4C3)nc(N3CCOCC3)nc12]

To a solution of tert-butyl (3R)-3-[tert-butoxycarbonyl-(8-isopropyl-2-morpholino-pyrazolo[1,5-a][1,3,5]triazin-4-yl)amino]-1,2,3,4-tetrahydrocarbazole-9-carboxylate (100 mg, 142.46 μmol, 1 eq) in DCM (4 mL) was added TFA (1.54 g, 13.51 mmol, 1 mL, 94.81 eq). The reaction mixture was stirred at 20° C. for 0.5 h. The reaction mixture was concentrated. The residue was purified by preparative HPLC (column: Agela ASB 150*25 mm*5 m; mobile phase: [water (0.05% HCl)-ACN]; B %: 50%-80%, 8 min), followed by lyophilization to yield (3R)—N-(8-isopropyl-2-morpholino-pyrazolo[1,5-a][1,3,5]triazin-4-yl)-2,3,4,9-tetrahydro-1H-carbazol-3-amine (28.19 mg, 59.32 μmol, 41.6% yield, 98.5% purity, HCl, $[\alpha]^{24.7}_D$=+84.327, MeOH, c=0.074 g/100 mL) as a white solid. $^1$H NMR (400 MHz, $CD_3OD$) δ ppm 7.95 (s, 1H), 7.37 (d, J=7.8 Hz, 1H), 7.28 (d, J=8.0 Hz, 1H), 7.08-7.02 (m, 1H), 7.00-6.94 (m, 1H), 4.72-4.63 (m, 1H), 3.93-3.87 (m, 4H), 3.83-3.78 (m, 4H), 3.27-3.19 (m, 2H), 3.03-2.86 (m, 3H), 2.35-2.18 (m, 2H), 1.32 (d, J=6.8 Hz, 6H); ES-LCMS m/z 432.3 $[M+H]^+$.

Example 193

Synthesis of I-255

I-255

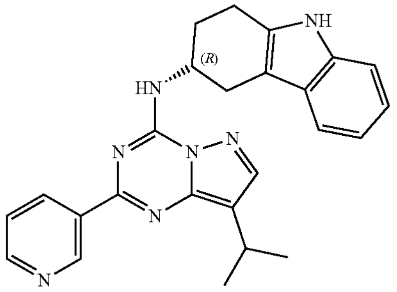

Synthetic Scheme:

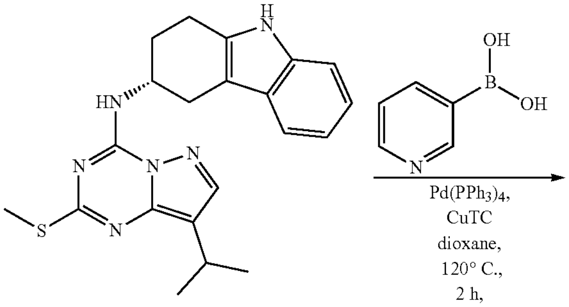

1

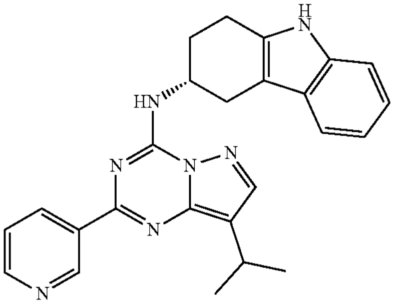 [SMILES: CC(C)c1cnn2c(N[C@@H]3CCc4[nH]c5ccccc5c4C3)nc(-c3cccnc3)nc12]

I-255

Step 1: (3R)—N-[8-Isopropyl-2-(3-pyridyl)pyrazolo[1,5-a][1,3,5]triazin-4-yl]-2,3,4,9-tetrahydro-1H-carbazol-3-amine (I-255)

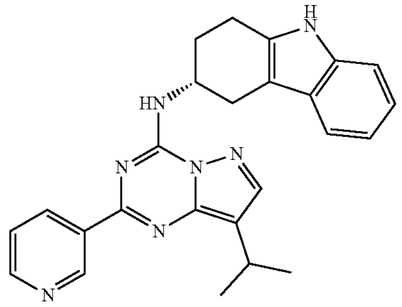

(3R)—N-(8-isopropyl-2-methylsulfanyl-pyrazolo[1,5-a][1,3,5]triazin-4-yl)-2,3,4,9-tetrahydro-1H-carbazol-3-amine (100 mg, 242.03 μmol, 1 eq), 3-pyridylboronic acid (89.25 mg, 726.08 μmol, 3 eq), $Pd(PPh_3)_4$ (27.97 mg, 24.20 μmol, 0.1 eq) and thiophene-2-carbonyloxycopper (138.46 mg, 726.08 μmol, 3 eq) in 1,4-dioxane (3 mL) were taken up into a microwave tube and purged with $N_2$ for 1 min. The sealed tube was heated at 120° C. for 2 h under microwave. The reaction mixture was filtered and concentrated to give the residue which was purified by preparative HPLC (column: Xtimate C18 150*25 mm*5 m; mobile phase: [water (0.05% HCl)-ACN]; B %: 35%-65%, 8 min) twice, followed by lyophilization to yield (3R)—N-[8-isopropyl-2-(3-pyridyl)pyrazolo[1,5-a][1,3,5]triazin-4-yl]-2,3,4,9-tetrahydro-1H-carbazol-3-amine (28.39 mg, 56.08 μmol, 23.2% yield, 98.1% purity, 2 HCl, $[\alpha]^{25.1}_D$=+34.261 (MeOH, c=0.071 g/100 mL)) as a yellow solid. $^1$H NMR (400 MHz, $CD_3OD$) δ ppm 9.69 (s, 1H), 9.49 (d, J=8.3 Hz, 1H), 8.89 (d, J=4.5 Hz, 1H), 8.16-8.10 (m, 1H), 8.06 (s, 1H), 7.38 (d, J=7.8 Hz, 1H), 7.29 (d, J=8.0 Hz, 1H), 7.08-7.03 (m, 1H), 7.00-6.94 (m, 1H), 4.90-4.88 (m, 1H), 3.37-3.34 (m, 1H), 3.30 (d, J=7.0 Hz, 1H), 3.13-2.90 (m, 3H), 2.44-2.24 (m, 2H), 1.45 (d, J=7.0 Hz, 6H); ES-LCMS m/z 424.3 $[M+H]^+$.

Example 194

Synthesis of I-256

I-256

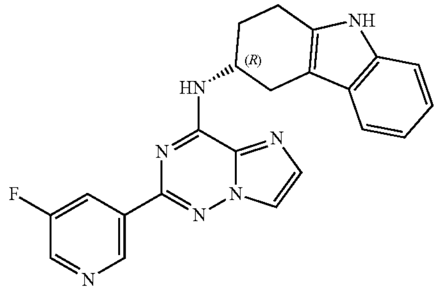

Synthetic Scheme:

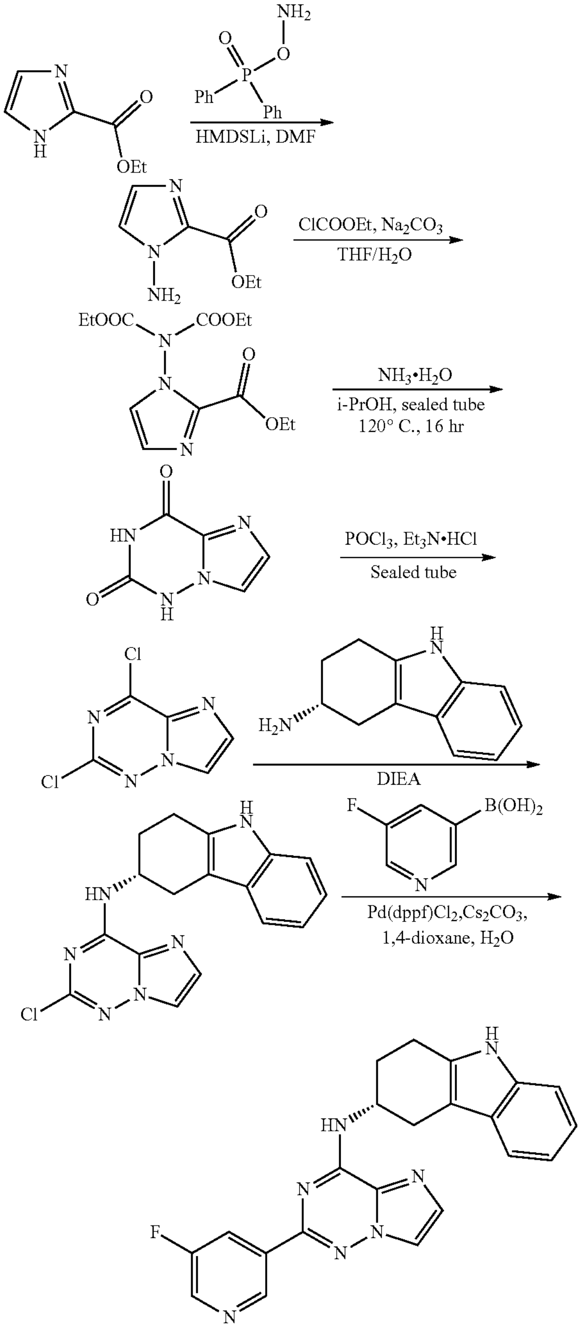

I-256

Step 1: Ethyl 1-aminoimidazole-2-carboxylate

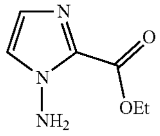

To a solution of ethyl 1H-imidazole-2-carboxylate (1 g, 7.14 mmol, 1 eq) in DMF (80 mL) cooled to −10° C. was added LiHMDS (1 M, 7.85 mL, 1.1 eq). The mixture was stirred at −10° C. for 0.5 h. To the mixture was added N-diphenylphosphorylhydroxylamine (1.83 g, 7.85 mmol, 1.1 eq). The mixture was stirred at 15° C. for 11.5 h. The mixture was quenched with saturated aqueous $NH_4Cl$ solution (50 mL) at −10° C. The mixture was concentrated and to the residue was added EtOAc (100 mL). After filtration, washed with EtOAc (50 mL×3), the filtrate was concentrated to yield ethyl 1-aminoimidazole-2-carboxylate (3 g, crude) as a yellow solid which was used in the next step without further purification. $^1H$ NMR (400 MHz, $CDCl_3$) δ ppm 7.10 (s, 1H), 6.98 (s, 1H), 5.74 (s, 2H), 4.33 (q, J=7.2 Hz, 2H), 1.36-1.33 (m, 3H); ES-LCMS m/z 156.0 $[M+H]^+$.

Step 2: Ethyl 1-[bis(ethoxycarbonyl)amino]imidazole-2-carboxylate

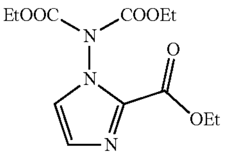 [SMILES: CCOC(=O)c1nccn1N(C(=O)OCC)C(=O)OCC]

To a solution of ethyl 1-aminoimidazole-2-carboxylate (5.3 g, 17.08 mmol, 1 eq) in THF (80 mL) and $H_2O$ (80 mL) was added $Na_2CO_3$ (12.67 g, 119.56 mmol, 7 eq) and ethyl carbonochloridate (8.47 g, 78.05 mmol, 7.43 mL, 4.57 eq). The mixture was stirred at 15° C. for 2 h. To the mixture was added $H_2O$ (100 mL), extracted with EtOAc (100 mL×2). The combined organic layers were dried over $Na_2SO_4$, filtered and concentrated. The residue was purified on silica gel column chromatography (from pure PE to PE/EtOAc=3/1, TLC: PE/EtOAc=3/1, $R_f$=0.6) to yield ethyl 1-[bis(ethoxycarbonyl)amino]imidazole-2-carboxylate (2.69 g, 6.29 mmol, 36.8% yield, 70% purity) as a yellow solid. $^1H$ NMR (400 MHz, $CDCl_3$) δ ppm 7.30 (d, J=1.0 Hz, 1H), 7.10 (s, 1H), 4.44-4.33 (m, 4H), 4.19-4.08 (m, 2H), 1.39 (td, J=7.3, 16.3 Hz, 6H), 1.08 (t, J=7.2 Hz, 3H); ES-LCMS m/z 300.1 $[M+H]^+$.

Step 3: 1H-Imidazo[2,1-f][1,2,4]triazine-2,4-dione

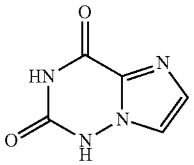 [SMILES: O=c1[nH]c(=O)c2nccn2[nH]1]

A solution of ethyl 1-[bis(ethoxycarbonyl)amino]imidazole-2-carboxylate (2.1 g, 4.91 mmol, 1 eq) and $NH_3H_2O$ (97.50 g, 778.99 mmol, 107.14 mL, 158.59 eq) in i-PrOH (20 mL) was stirred in a sealed tube at 120° C. for 16 h. The mixture was concentrated. To the residue was added PE/MeOH (10/1, 50 mL) and stirred at room temperature for 10 min. After filtration, washed with PE/MeOH (10/1, 15 mL), the filter cake was dried in vacuo. The crude product (1 g) was purified on silica gel column chromatography (from DCM/MeOH=10/1 to 1/2, TLC: DCM/MeOH=10/1, $R_f$=0.3) to yield 1H-imidazo[2,1-f][1,2,4]triazine-2,4-dione (0.9 g, 96.4% yield, 80.0% purity). $^1H$ NMR (400 MHz, DMSO-$d_6$) δ ppm 10.02 (br s, 1H), 7.24 (s, 1H), 7.13 (br s, 1H), 7.07 (s, 1H).

Step 4: 2,4-Dichloroimidazo[2,1-f][1,2,4]triazine

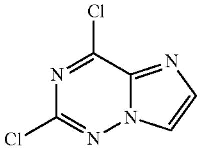 [SMILES: Clc1nc(Cl)c2nccn2n1]

A mixture of 1H-imidazo[2,1-f][1,2,4]triazine-2,4-dione (500 mg, 2.63 mmol, 1 eq), N,N-diethylethanamine, hydrochloride (723.95 mg, 5.26 mmol, 2 eq) and $POCl_3$ (87.18 g, 568.57 mmol, 52.84 mL, 216.21 eq) was stirred in a sealed tube at 120° C. for 24 h. The mixture was concentrated and to the residue was added DCM (30 mL). The mixture was poured into ice cold water (50 mL), extracted with DCM (30 mL×2). The combined organic layers were washed with brine (50 mL), dried over $Na_2SO_4$, filtered and concentrated to yield 2,4-dichloroimidazo[2,1-f][1,2,4]triazine (400 mg, 1.27 mmol, 48.3% yield, 60% purity) as a yellow solid. $^1H$ NMR (400 MHz, $CDCl_3$) δ ppm 8.09 (s, 1H), 8.02 (s, 1H); ES-LCMS m/z 189.2, 191.1 $[M+H]^+$.

Step 5: (3R)—N-(2-chloroimidazo[2,1-f][1,2,4]triazin-4-yl)-2,3,4,9-tetrahydro-1H-carbazol-3-amine

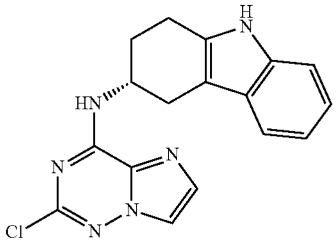 [SMILES: Clc1nc(N[C@@H]2CCc3[nH]c4ccccc4c3C2)c2nccn2n1]

A mixture of 2,4-dichloroimidazo[2,1-f][1,2,4]triazine (400 mg, 1.27 mmol, 1 eq), DIEA (492.34 mg, 3.81 mmol, 663.53 μL, 3 eq) and (3R)-2,3,4,9-tetrahydro-1H-carbazol-3-amine (236.51 mg, 1.27 mmol, 1 eq) in $CH_3CN$ (15 mL) was stirred at 70° C. for 6 h. The mixture was concentrated. The residue was purified on silica gel column chromatography (from PE/EtOAc=5/1 to 1/2, TLC: PE/EtOAc=1/1, $R_f$=0.4) to yield (3R)—N-(2-chloroimidazo[2,1-f][1,2,4]triazin-4-yl)-2,3,4,9-tetrahydro-1H-carbazol-3-amine (220 mg, 636.38 μmol, 50.1% yield, 98.0% purity) as a yellow solid. $^1H$ NMR (400 MHz, $CDCl_3$) δ ppm 7.83 (br s, 1H), 7.67 (s, 1H), 7.48-7.36 (m, 2H), 7.30 (d, J=7.8 Hz, 1H), 7.18-7.12 (m, 1H), 7.11-7.04 (m, 1H), 6.84 (d, J=7.3 Hz, 1H), 4.86-4.84 (m, 1H), 3.27 (dd, J=4.9, 15.7 Hz, 1H), 2.98-2.80 (m, 3H), 2.29-2.17 (m, 2H); ES-LCMS m/z 339.1 $[M+H]^+$.

Step 6: (3R)—N-[2-(5-fluoro-3-pyridyl)imidazo[2,1-f][1,2,4]triazin-4-yl]-2,3,4,9-tetrahydro-1H-carbazol-3-amine (I-256)

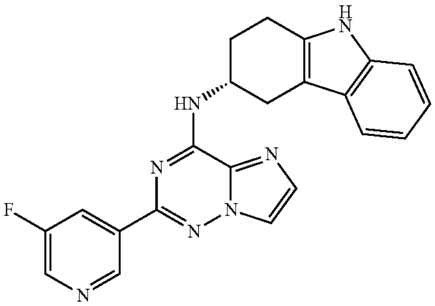 [SMILES: Fc1cncc(-c2nc(N[C@@H]3CCc4[nH]c5ccccc5c4C3)c3nccn3n2)c1]

A mixture of (3R)—N-(2-chloroimidazo[2,1-f][1,2,4]triazin-4-yl)-2,3,4,9-tetrahydro-1H-carbazol-3-amine (100 mg, 289.26 μmol, 1 eq), (5-fluoro-3-pyridyl)boronic acid (81.52 mg, 578.52 μmol, 2 eq), $Cs_2CO_3$ (282.74 mg, 867.78 μmol, 3 eq) and $Pd(dppf)Cl_2$ (21.17 mg, 28.93 μmol, 0.1 eq) in 1,4-dioxane (2 mL) and $H_2O$ (0.5 mL) was stirred at 110° C. for 2 h under $N_2$ atmosphere. After filtration, the filtrate was concentrated. The residue was purified by preparative TLC (PE/EtOAc=1/1, $R_f$=0.3) to yield (3R)—N-[2-(5-fluoro-3-pyridyl)imidazo[2,1-f][1,2,4]triazin-4-yl]-2,3,4,9-tetrahydro-1H-carbazol-3-amine (60.97 mg, 152.65 μmol, 52.8% yield, 100% purity, $[\alpha]^{26.9}_{D}$=+9.272 (MeOH, c=0.101 g/100 mL)) as a yellow solid. $^1H$ NMR (400 MHz, $CD_3OD$) δ ppm 9.30 (s, 1H), 8.54 (d, J=2.7 Hz, 1H), 8.42 (td, J=2.1, 9.8 Hz, 1H), 7.96 (d, J=1.0 Hz, 1H), 7.55 (s, 1H), 7.36 (d, J=7.6 Hz, 1H), 7.25 (d, J=8.1 Hz, 1H), 7.05-6.97 (m, 1H), 6.96-6.89 (m, 1H), 4.98-4.90 (m, 1H), 3.26 (br s, 1H), 2.97 (t, J=5.7 Hz, 2H), 2.90 (dd, J=7.2, 15.3 Hz, 1H), 2.40-2.32 (m, 1H), 2.31-2.21 (m, 1H); ES-LCMS m/z 399.9 $[M+H]^+$.

Example 195

Synthesis of I-257

I-257

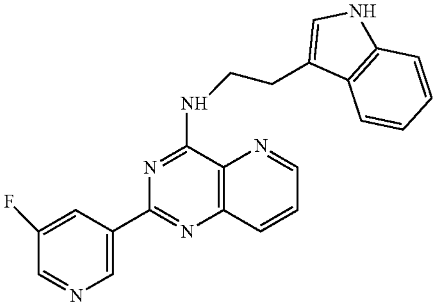

Synthetic Scheme:

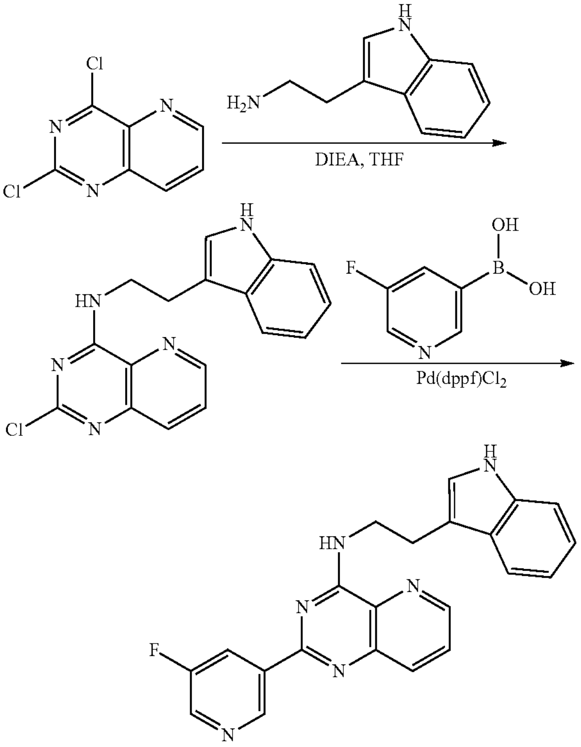

I-257

Step 1: 2-Chloro-N-[2-(1H-indol-3-yl)ethyl]pyrido[3,2-d]pyrimidin-4-amine

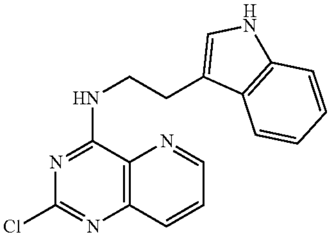 [SMILES: Clc1nc(NCCc2c[nH]c3ccccc23)c2ncccc2n1]

To a solution of 2,4-dichloropyrido[3,2-d]pyrimidine (100 mg, 499.94 μmol, 1 eq) in THF (3 mL) was added DIEA (193.84 mg, 1.50 mmol, 261.24 μL, 3 eq) and 2-(1H-indol-3-yl)ethanamine (88.11 mg, 549.93 μmol, 1.1 eq). The mixture was stirred at 60° C. for 2 h. The reaction mixture was concentrated under reduced pressure to yield a residue which was purified by flash silica gel chromatography (from PE/EtOAc=100/1 to 3/1, TLC: PE/EtOAc=3/1, $R_f$=0.2) to yield 2-chloro-N-[2-(1H-indo-3-yl)ethyl]pyrido[3,2-d]pyrimidin-4-amine (90 mg, 271.57 μmol, 54.3% yield, 97.7% purity) as a yellow solid. $^1H$ NMR (400 MHz, $CDCl_3$) δ ppm 8.61 (dd, J=1.3, 4.3 Hz, 1H), 8.07 (s, 1H), 8.01 (dd, J=1.3, 8.4 Hz, 1H), 7.71 (d, J=7.8 Hz, 1H), 7.63 (dd, J=4.3, 8.4 Hz, 1H), 7.47 (s, 1H), 7.41 (d, J=8.1 Hz, 1H), 7.24 (t, J=7.5 Hz, 1H), 7.18-7.12 (m, 2H), 4.03 (q, J=6.7 Hz, 2H), 3.22 (t, J=6.8 Hz, 2H); ES-LCMS m/z 324.1 $[M+H]^+$.

Step 2: 2-(5-Fluoro-3-pyridyl)-N-[2-(1H-indol-3-yl)ethyl]pyrido[3,2-d]pyrimidin-4-amine (I-257)

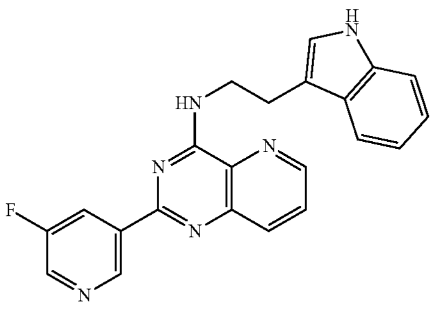 [SMILES: Fc1cncc(-c2nc(NCCc3c[nH]c4ccccc34)c3ncccc3n2)c1]

2-Chloro-N-[2-(1H-indol-3-yl)ethyl]pyrido[3,2-d]pyrimidin-4-amine (50 mg, 150.87 μmol, 1 eq), (5-fluoro-3-pyridyl)boronic acid (25.51 mg, 181.05 μmol, 1.2 eq), $Pd(dppf)Cl_2$ (11.04 mg, 15.09 μmol, 0.1 eq) and $Cs_2CO_3$ (147.47 mg, 452.62 μmol, 3 eq) were taken up into a microwave tube in 1,4-dioxane (2 mL) and $H_2O$ (1 mL). The sealed tube was heated at 110° C. for 0.5 h under microwave. The reaction mixture was diluted with water (5 mL) and extracted with EtOAc (10 mL×3). The combined organic layers were dried over $Na_2SO_4$, filtered and concentrated under reduced pressure to yield a residue which was purified by preparative HPLC (column: Xtimate C18 150*25 mm*5 m; mobile phase: [water (0.05% HCl)-ACN]; B %: 45%-75%, 8 min), followed by lyophilization to yield 2-(5-fluoro-3-pyridyl)-N-[2-(1H-indol-3-yl)ethyl]pyrido[3,2-d]pyrimidin-4-amine (24.02 mg, 51.42 μmol, 34.1% yield, 97.9% purity, 2HCl) as a yellow solid. $^1H$ NMR (400 MHz, $CD_3OD$) δ ppm 9.03 (s, 1H), 9.01 (dd, J=1.3, 4.3 Hz, 1H), 8.82 (d, J=2.7 Hz, 1H), 8.20 (dd, J=1.5, 8.6 Hz, 1H), 8.10-8.05 (m, 1H), 8.01 (dd, J=4.3, 8.7 Hz, 1H), 7.56 (d, J=7.8 Hz, 1H), 7.14 (d, J=8.1 Hz, 1H), 7.05 (s, 1H), 6.92 (t, J=7.2 Hz, 1H), 6.85-6.71 (m, 1H), 4.26 (t, J=6.6 Hz, 2H), 3.26 (t, J=6.6 Hz, 2H); ES-LCMS m/z 385.2 $[M+H]^+$.

Example 196

Synthesis of I-258

I-258

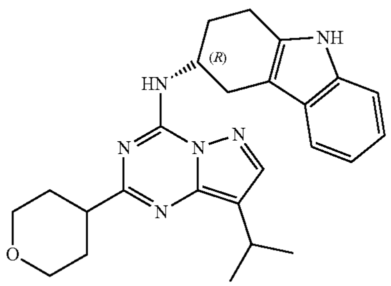

Synthetic Scheme:

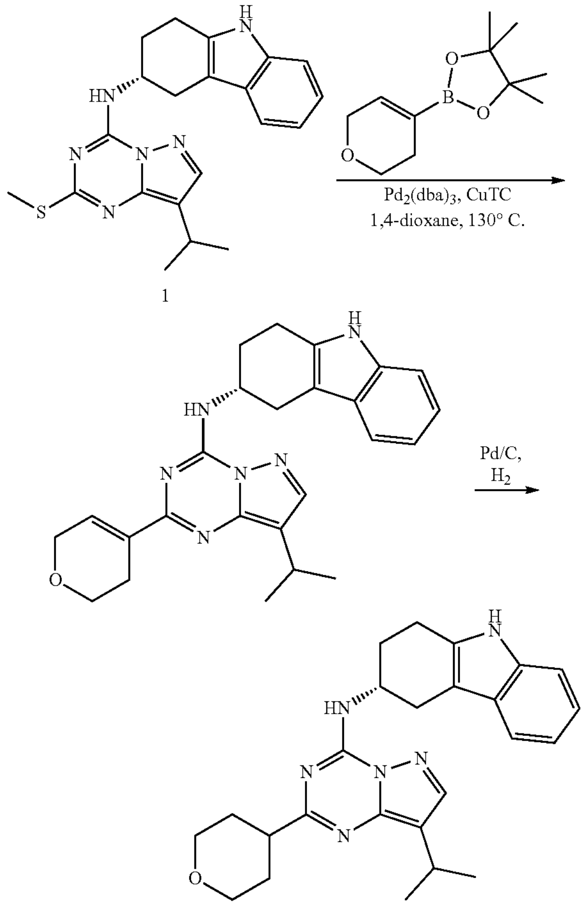

I-258

Step 1: (3R)—N-[2-(3,6-Dihydro-2H-pyran-4-yl)-8-isopropyl-pyrazolo[1,5-a][1,3,5]triazin-4-yl]-2,3,4,9-tetrahydro-1H-carbazol-3-amine

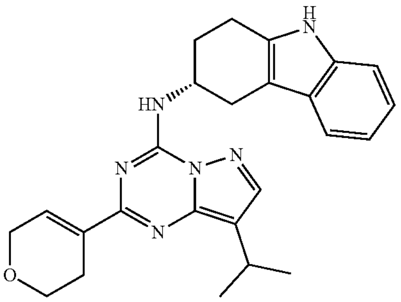 [SMILES: CC(C)c1cnn2c(N[C@@H]3CCc4[nH]c5ccccc5c4C3)nc(C3=CCOCC3)nc12]

To a stirred solution of (3R)—N-(8-isopropyl-2-methylsulfanyl-pyrazolo[1,5-a][1,3,5]triazin-4-yl)-2,3,4,9-tetrahydro-1H-carbazol-3-amine (300 mg, 703.15 μmol, 1 eq) and 2-(3,6-dihydro-2H-pyran-4-yl)-4,4,5,5-tetramethyl-1,3,2-dioxaborolane (443.15 mg, 2.11 mmol, 3 eq) in 1,4-dioxane (15 mL) was degassed and purged with $N_2$ then added thiophene-2-carbonyloxycopper (268.17 mg, 1.41 mmol, 2 eq) and $Pd_2(dba)_3$ (64.39 mg, 70.31 μmol, 0.1 eq).

The reaction mixture was stirred at 130° C. for 12 h under $N_2$ atmosphere. The reaction mixture was filtered through a pad of celite. The filtrate was concentrated to yield a residue which was purified by flash silica gel chromatography (from PE/EtOAc=100/1 to 3/1, TLC: PE/EtOAc=3/1, $R_f$=0.55) to yield (3R)—N-[2-(3,6-dihydro-2H-pyran-4-yl)-8-isopropyl-pyrazolo[1,5-a][1,3,5]triazin-4-yl]-2,3,4,9-tetrahydro-1H-carbazol-3-amine (60 mg, 127.97 μmol, 18.2% yield, 91.4% purity) as a white solid. $^1$H NMR (400 MHz, $CD_3OD$) δ ppm 7.87 (s, 1H), 7.37 (d, J=7.6 Hz, 1H), 7.29-7.20 (m, 2H), 7.03 (t, J=7.1 Hz, 1H), 6.98-6.92 (m, 1H), 4.73 (s, 1H), 4.34 (d, J=2.7 Hz, 2H), 3.89 (t, J=5.5 Hz, 2H), 3.29-3.15 (m, 2H), 3.00-2.91 (m, 2H), 2.86 (dd, J=8.9, 15.0 Hz, 1H), 2.69 (d, J=1.7 Hz, 2H), 2.32 (s, 1H), 2.26-2.17 (m, 1H), 1.35 (d, J=7.1 Hz, 6H); ES-LCMS m/z 429.3 $[M+H]^+$.

Step 2: (3R)—N-(8-Isopropyl-2-tetrahydropyran-4-yl-pyrazolo[1,5-a][1,3,5]triazin-4-yl)-2,3,4,9-tetrahydro-1H-carbazol-3-amine (I-258)

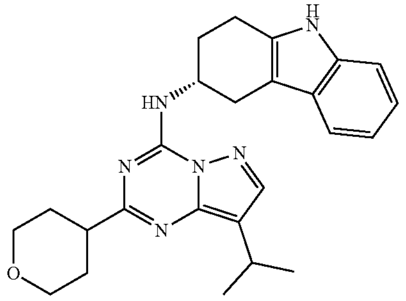 [SMILES: CC(C)c1cnn2c(N[C@@H]3CCc4[nH]c5ccccc5c4C3)nc(C3CCOCC3)nc12]

To a stirred solution of (3R)—N-[2-(3,6-dihydro-2H-pyran-4-yl)-8-isopropyl-pyrazolo[1,5-a][1,3,5]triazin-4-yl]-2,3,4,9-tetrahydro-1H-carbazol-3-amine (55 mg, 117.31 μmol, 1 eq) in MeOH (20 mL) was added Pd/C (0.1 g, 10% wt). The reaction mixture was stirred at 20° C. for 5 h under $H_2$ atmosphere (15 psi). The reaction mixture was filtered through a pad of celite. The filtrate was concentrated to yield a residue which was purified by preparative HPLC (HCl condition; column: Agela ASB 150*25 mm*5 m; mobile phase: [water (0.05% HCl)-ACN]; B %: 55%-85%, 8 min). The desired fraction was lyophilized to yield (3R)—N-(8-isopropyl-2-tetrahydropyran-4-yl-pyrazolo[1,5-a][1,3,5]triazin-4-yl)-2,3,4,9-tetrahydro-1H-carbazol-3-amine (16.60 mg, 36.74 μmol, 31.3% yield, 95.3% purity, $[\alpha]^{25.0}_D$=+9.739 (MeOH, c=0.098 g/100 mL)) as a white solid. $^1$H NMR (400 MHz, $CD_3OD$) δ ppm 8.08 (s, 1H), 7.37 (d, J=7.8 Hz, 1H), 7.27 (d, J=8.0 Hz, 1H), 7.07-7.01 (m, 1H), 6.99-6.93 (m, 1H), 4.86-4.77 (m, 1H), 4.05 (dd, J=2.0, 11.5 Hz, 2H), 3.61-3.50 (m, 2H), 3.28-3.17 (m, 2H), 3.10-2.88 (m, 4H), 2.39-2.20 (m, 2H), 2.11-1.98 (m, 2H), 1.96-1.87 (m, 2H), 1.35 (d, J=6.8 Hz, 6H); ES-LCMS m/z 431.3 $[M+H]^+$.

Example 197

Synthesis of I-259a, I-259b and I-259c

I-259a

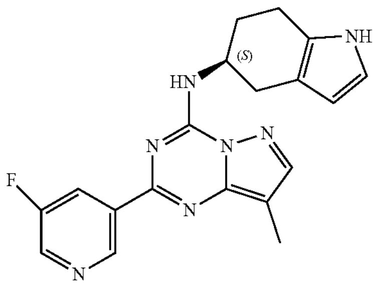

I-259b

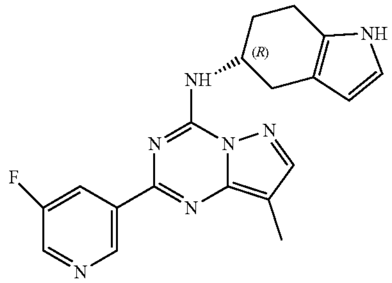

I-259c

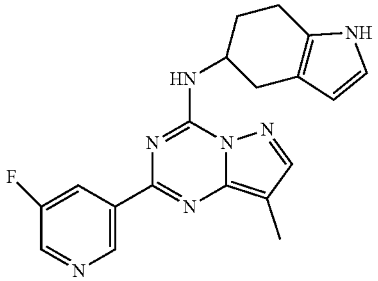

Synthetic Scheme:

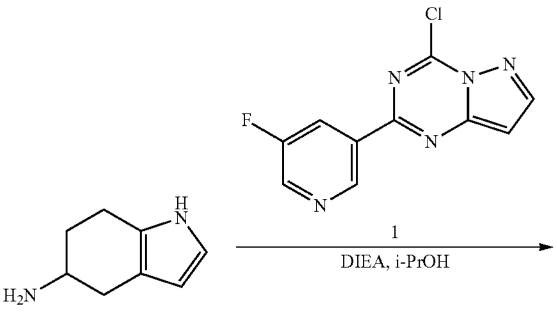

-continued

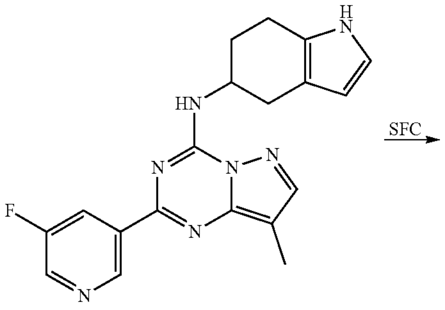

I-259c

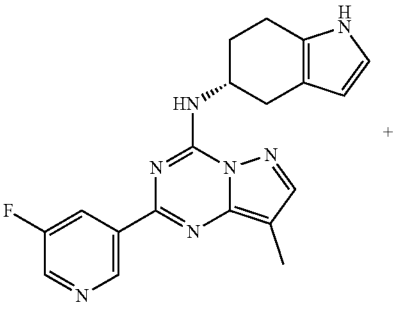

+

I-259b

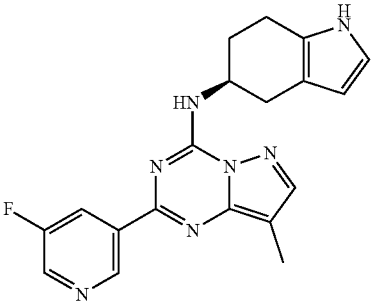

I-259a

Step 1: 2-(5-Fluoro-3-pyridyl)-8-methyl-N-[(5R)-4,5,6,7-tetrahydro-1H-indol-5-yl]pyrazolo[1,5-a][1,3,5]triazin-4-amine (I-259b) and 2-(5-fluoro-3-pyridyl)-8-methyl-N-[(5S)-4,5,6,7-tetrahydro-1H-indol-5-yl]pyrazolo[1,5-a][1,3,5]triazin-4-amine (I-259a)

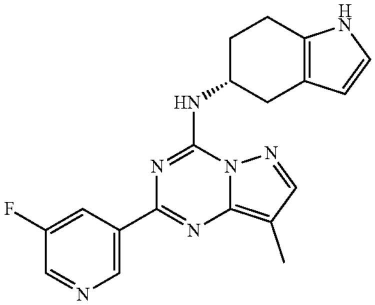

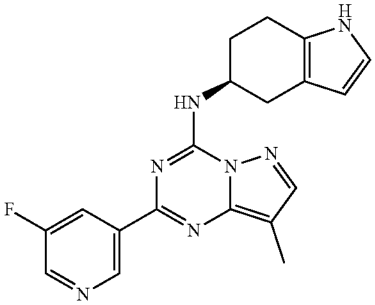

A mixture of 4-chloro-2-(5-fluoro-3-pyridyl)-8-methyl-pyrazolo[1,5-a][1,3,5]triazine (100 mg, 379.28 μmol, 1 eq), 4,5,6,7-tetrahydro-1H-indol-5-amine (56.82 mg, 417.21 μmol, 1.1 eq) and DIEA (147.06 mg, 1.14 mmol, 198.19 μL, 3 eq) in i-PrOH (3 mL) was stirred at 60° C. for 2 h. The reaction mixture was concentrated under reduced pressure to yield a residue which was purified by flash silica gel chromatography (from PE/EtOAc=1/0 to 2/1, TLC: PE/EtOAc=1/1, $R_f$=0.60) to yield crude product which was separated by chiral SFC (column: DAICEL CHIRALPAK AD (250 mm*50 mm, 10 um); mobile phase: [0.1% $NH_3H_2O$/IPA]; B %: 40%-40%) to yield Peak 1 and Peak 2. Peak 1 was concentrated under reduced pressure to yield a residue which was dissolved in MeCN (20 mL) and $H_2O$ (40 mL) and lyophilized to yield an enantiomer (20.50 mg, 56.41 μmol, 14.9% yield, 100.0% purity, SFC: Rt=1.488, ee=100%, $[\alpha]^{26.1}_D$=−32.731 ($CHCl_3$, c=0.108 g/100 mL)) as an off-white solid. $^1$H NMR (400 MHz, $CDCl_3$) δ ppm 9.51 (s, 1H), 8.56 (d, J=2.8 Hz, 1H), 8.50-8.41 (m, 1H), 7.94-7.87 (m, 1H), 7.85 (s, 1H), 6.72 (t, J=2.4 Hz, 1H), 6.66 (d, J=8.0 Hz, 1H), 6.05 (t, J=2.4 Hz, 1H), 4.88-4.77 (m, 1H), 3.17 (dd, J=4.8, 15.2 Hz, 1H), 2.88-2.71 (m, 3H), 2.35 (s, 3H), 2.28 (dq, J=2.4, 6.0 Hz, 1H), 2.23-2.12 (m, 1H); ES-LCMS m/z 364.2 $[M+H]^+$. Peak 2 was concentrated under reduced pressure to yield a residue which was dissolved in MeCN (20 mL) and $H_2O$ (40 mL) and lyophilized to yield the other enantiomer (19.32 mg, 53.17 μmol, 14.0% yield, 100.0% purity, SFC: Rt=1.691, ee=100%, $[\alpha]^{26.0}_D$=+10.595 ($CHCl_3$, c=0.102 g/100 mL)) as an off-white solid. $^1$H NMR (400 MHz, $CDCl_3$) δ ppm 9.51 (br s, 1H), 8.56 (br s, 1H), 8.46 (d, J=9.2 Hz, 1H), 7.90 (s, 1H), 7.85 (s, 1H), 6.72 (s, 1H), 6.66 (d, J=8.4 Hz, 1H), 6.05 (s, 1H), 4.90-4.80 (m, 1H), 3.16 (d, J=10.8 Hz, 1H), 2.87-2.73 (m, 3H), 2.35 (s, 3H), 2.30-2.22 (m, 1H), 2.20-2.10 (m, 1H); ES-LCMS m/z 364.2 $[M+H]^+$.

Example 198

Synthesis of I-262

I-262

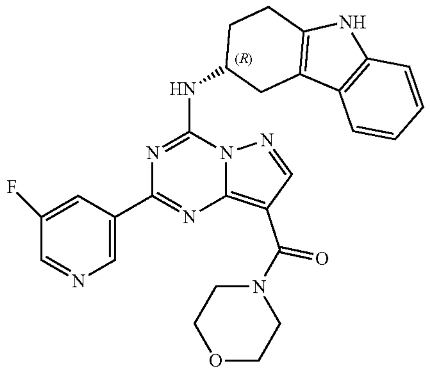

Synthetic Scheme:

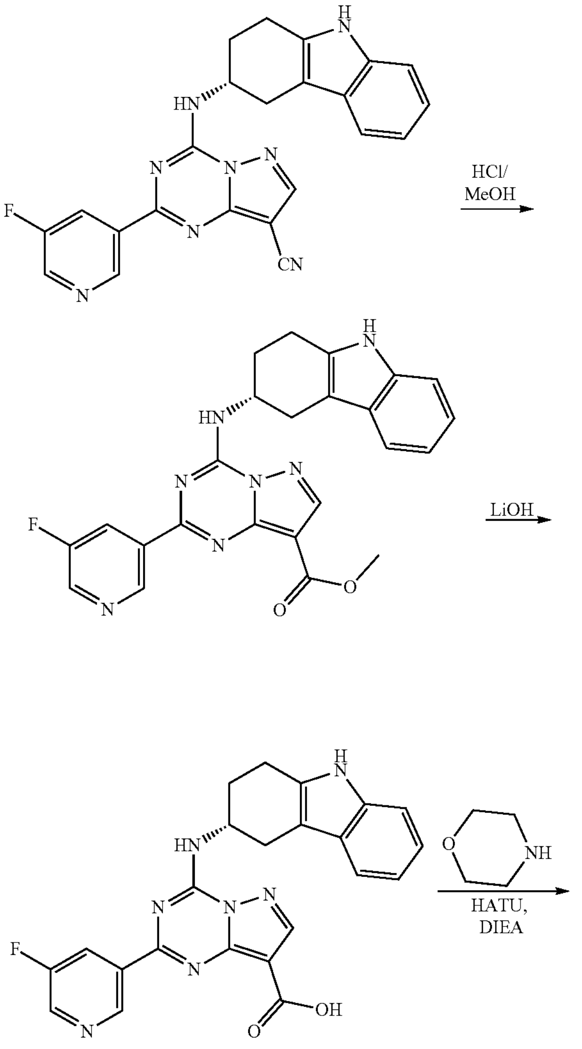

-continued

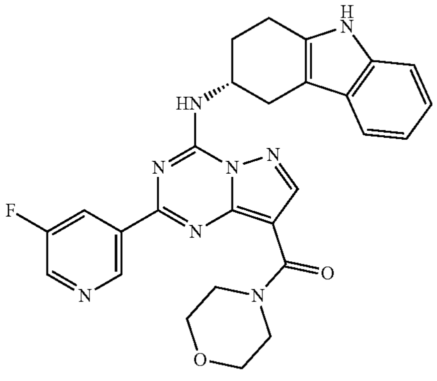

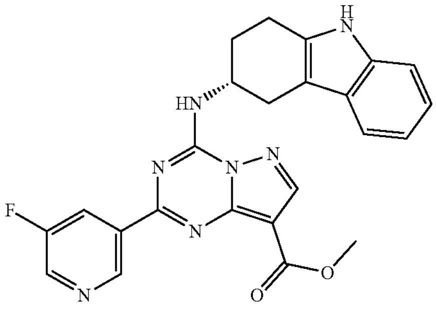 [SMILES: COC(=O)c1cnn2c(N[C@@H]3CCc4[nH]c5ccccc5c4C3)nc(-c3cncc(F)c3)nc12]

I-262

Step 1: 2-(5-fluoro-3-pyridyl)-4-[[(3R)-2,3,4,9-tetrahydro-1H-carbazol-3-yl]amino]pyrazolo[1,5-a][1,3,5]triazine-8-carboxylate A solution of 2-(5-fluoro-3-pyridyl)-4-[[(3R)-2,3,4,9-tetrahydro-1H-carbazol-3-yl]amino]pyrazolo[1,5-a][1,3,5]triazine-8-carbonitrile (200 mg, 335.51 μmol, 1 eq) in HCl/MeOH (4 M, 10 mL) was stirred at 70° C. for 12 h in sealed tube. The reaction mixture was concentrated under reduced pressure to give a residue which was quenched by addition of water (50 mL), adjusted pH to 9 by aqueous $NaHCO_3$, extracted with EtOAc (50 mL×3). The combined organic layers were washed with brine (20 mL), dried over $Na_2SO_4$, filtered and concentrated under reduced pressure to yield a residue which was purified by preparative TLC (PE/EtOAc=1/2, TLC: PE/EtOAc=1/2, $R_f$=0.53) to yield methyl 2-(5-fluoro-3-pyridyl)-4-[[(3R)-2,3,4,9-tetrahydro-1H-carbazol-3-yl]amino]pyrazolo[1,5-a][1,3,5]triazine-8-carboxylate (50 mg, 96.84 μmol, 28.80 yield, 88.6% purity) as a yellow solid. $^1H$ NMR (400 MHz, $CDCl_3$) δ ppm 9.57 (br s, 1H), 8.67-8.48 (m, 2H), 8.41 (s, 1H), 7.98 (s, 1H), 7.55-7.42 (m, 1H), 7.36 (d, J=8.1 Hz, 1H), 7.19 (t, J=7.7 Hz, 1H), 7.15-7.10 (m, 1H), 6.96 (d, J=8.1 Hz, 1H), 4.99 (s, 1H), 3.98 (s, 3H), 3.39 (dd, J=4.8, 15.3 Hz, 1H), 3.09-2.97 (m, 3H), 2.43-2.32 (m, 2H); ES-LCMS m/z 458.2 $[M+H]^+$.

Step 2: 2-(5-Fluoro-3-pyridyl)-4-[[(3R)-2,3,4,9-tetrahydro-1H-carbazol-3-yl]amino]pyrazolo[1,5-a][1,3,5]triazine-8-carboxylic Acid

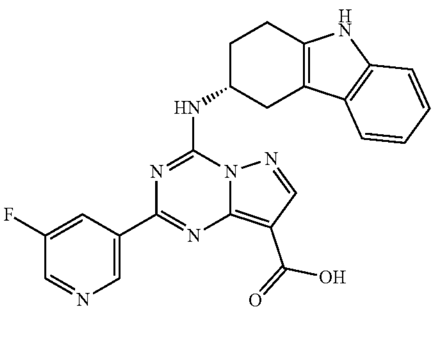 [SMILES: O=C(O)c1cnn2c(N[C@@H]3CCc4[nH]c5ccccc5c4C3)nc(-c3cncc(F)c3)nc12]

To a solution of methyl 2-(5-fluoro-3-pyridyl)-4-[[(3R)-2,3,4,9-tetrahydro-1H-carbazol-3-yl]amino]pyrazolo[1,5-a][1,3,5]triazine-8-carboxylate (140 mg, 306.04 μmol, 1 eq) in THF (2 mL), MeOH (2 mL) and $H_2O$ (1 mL) was added LiOH (73.29 mg, 3.06 mmol, 10 eq) was stirred at 50° C. for 12 h. The solution was adjusted pH to 6 by 2N aqueous HCl solution, concentrated to yield 2-(5-fluoro-3-pyridyl)-4-[[(3R)-2,3,4,9-tetrahydro-1H-carbazol-3-yl]amino]pyrazolo[1,5-a][1,3,5]triazine-8-carboxylic acid (120 mg, 187.00 μmol, 61.1% yield, 69.1% purity) as a yellow solid which was used in the next step without further purification. $^1$H NMR (400 MHz, $CD_3OD$) δ ppm 9.69 (s, 1H), 9.21 (d, J=6.6 Hz, 1H), 8.93 (s, 1H), 8.49 (s, 1H), 7.36 (d, J=7.8 Hz, 1H), 7.29-7.17 (m, 1H), 7.08-6.89 (m, 2H), 4.93 (d, J=4.2 Hz, 1H), 3.30-3.20 (m, 1H), 3.19-2.88 (m, 3H), 2.53-2.08 (m, 2H); ES-LCMS m/z 444.1 $[M+H]^+$.

Step 3: [2-(5-Fluoro-3-pyridyl)-4-[[(3R)-2,3,4,9-tetrahydro-1H-carbazol-3-yl]amino]pyrazolo[1,5-a][1,3,5]triazin-8-yl]-morpholino-methanone (I-262)

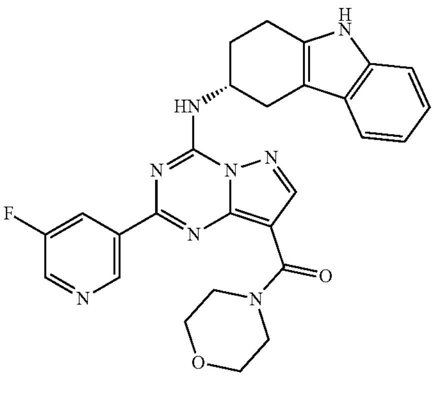 [SMILES: O=C(c1cnn2c(N[C@@H]3CCc4[nH]c5ccccc5c4C3)nc(-c3cncc(F)c3)nc12)N1CCOCC1]

To a solution of 2-(5-fluoro-3-pyridyl)-4-[[(3R)-2,3,4,9-tetrahydro-1H-carbazol-3-yl]amino]pyrazolo[1,5-a][1,3,5]triazine-8-carboxylic acid (50 mg, 77.91 μmol, 1 eq), morpholine (20.36 mg, 233.74 μmol, 20.57 μL, 3 eq) in DMF (2 mL) was added HATU (35.55 mg, 93.50 mol, 1.2 eq) and TEA (23.65 mg, 233.74 μmol, 32.53 μL, 3 eq). The mixture was stirred at 15° C. for 12 h. The reaction mixture was quenched by addition of water (50 mL), extracted with EtOAc (30 mL×3). The combined organic layers were washed with brine (10 mL), dried over $Na_2SO_4$, filtered and concentrated under reduced pressure to yield a residue which was purified by preparative HPLC (column: DuraShell 150*25 mm*5 m; mobile phase: [water (0.05% HCl)-ACN]; B %: 32%-62%, 7 min), followed by lyophilization to yield [2-(5-fluoro-3-pyridyl)-4-[[(3R)-2,3,4,9-tetrahydro-1H-carbazol-3-yl]amino]pyrazolo[1,5-a][1,3,5]triazin-8-yl]-morpholino-methanone (15.18 mg, 25.93 μmol, 33.2% yield, 100% purity, 2HCl, $[\alpha]^{24.3}_{D}$=+20.863 (MeOH, c=0.059 g/100 mL)) as a yellow solid. $^1$H NMR (400 MHz, $CD_3OD$) δ ppm 9.52 (s, 1H), 8.90 (dd, J=1.5, 9.0 Hz, 1H), 8.85 (s, 1H), 8.35 (s, 1H), 7.37 (d, J=7.6 Hz, 1H), 7.28 (d, J=8.1 Hz, 1H), 7.04 (t, J=7.0 Hz, 1H), 6.99-6.93 (m, 1H), 4.99-4.92 (m, 1H), 3.81 (s, 8H), 3.29 (d, J=5.6 Hz, 1H), 3.17-2.91 (m, 3H), 2.46-2.23 (m, 2H); ES-LCMS m/z 513.3 $[M+H]^+$.

Example 199

Synthesis of I-263a, I-263b and I-263c

I-263a

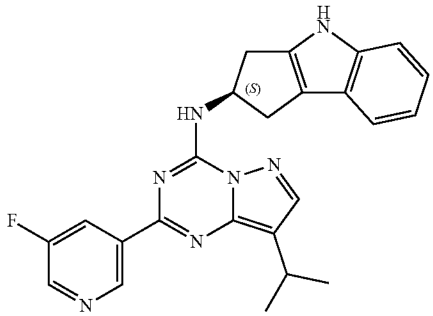

I-263b

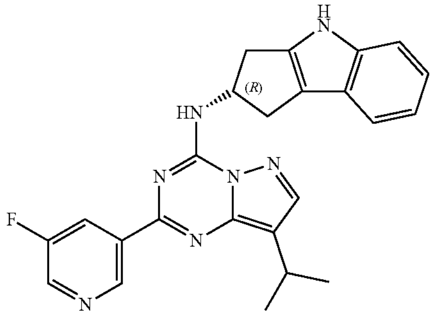

I-263c

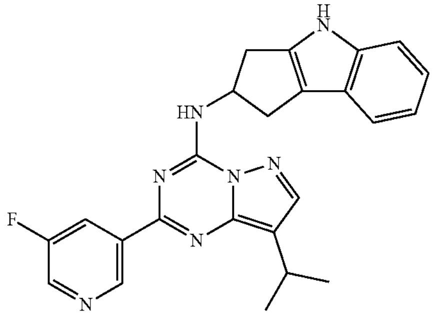

Synthetic Scheme:

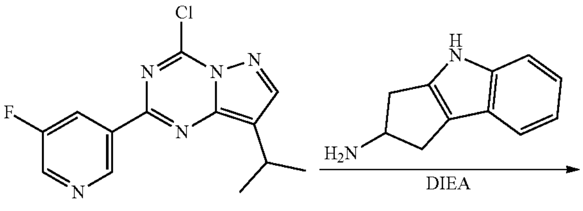

1

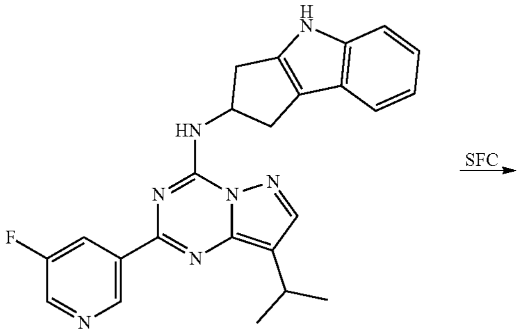

I-263c

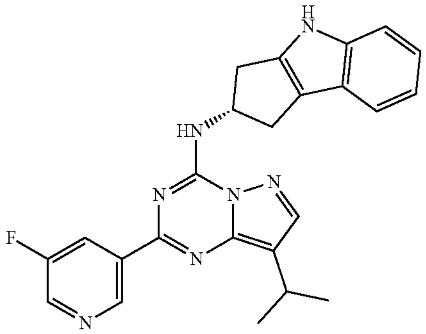

+

I-263b

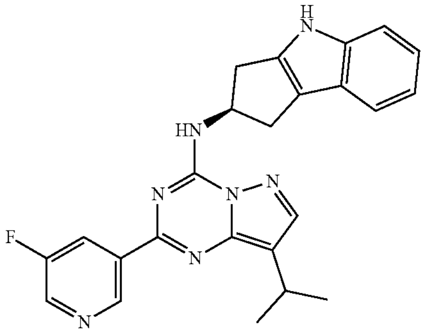

I-263a

Step 1: (2S)—N-[2-(5-Fluoro-3-pyridyl)-8-isopropyl-pyrazolo[1,5-a][1,3,5]triazin-4-yl]-1,2,3,4-tetrahydrocyclopenta[b]indol-2-amine (I-263a) and (2R)—N-[2-(5-fluoro-3-pyridyl)-8-isopropyl-pyrazolo[1,5-a][1,3,5]triazin-4-yl]-1,2,3,4-tetrahydrocyclopenta[b]indol-2-amine (I-263b)

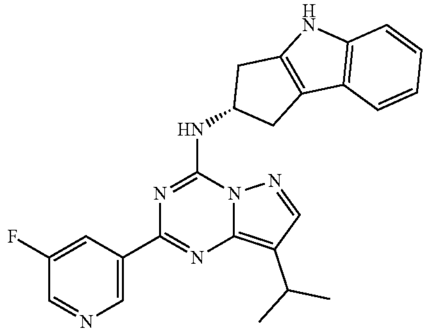

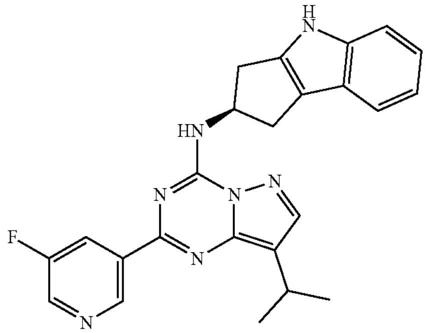

To a solution of 4-chloro-2-(5-fluoro-3-pyridyl)-8-isopropyl-pyrazolo[1,5-a][1,3,5]triazine (120 mg, 391.62 μmol, 1 eq) and 1,2,3,4-tetrahydrocyclopenta[b]indol-2-amine (67.45 mg, 391.62 μmol, 1 eq) in i-PrOH (10 mL) was added DIEA (404.91 mg, 3.13 mmol, 545.71 μL, 8 eq). The mixture was stirred at 50° C. for 2 h and concentrated to yield N-[2-(5-fluoro-3-pyridyl)-8-isopropyl-pyrazolo[1,5-a][1,3,5]triazin-4-yl]-1,2,3,4-tetrahydrocyclopenta[b]indol-2-amine (120 mg, 274.65 μmol, 70.1% yield, 97.8% purity) which was separated by chiral SFC (column: DAICEL CHIRALCEL OJ-H (250 mm*30 mm, 5 μm); mobile phase: [0.1% $NH_3H_2O$ EtOH]; B %: 40%-40%) to yield peak 1 and peak 2. Peak 1 was concentrated under reduced pressure to yield a residue which was purified by preparative HPLC (column: Agela ASB 150*25 mm*5 um; mobile phase: [water (0.05% HCl)-ACN]; B %: 68%-98%, 8 min). The desired fraction was lyophilized to yield an enantiomer (31.51 mg, 62.97 μmol, 16.1% yield, 100.0% purity, 2HCl, SFC: Rt=5.092, ee=99.41%, $[\alpha]^{24.5}_{D}$=+37.706 (MeOH, c=0.093 g/100 mL)) as a yellow solid. $^1$H NMR (400 MHz, DMSO-$d_6$) δ ppm 10.94 (s, 1H), 9.43-9.40 (m, 2H), 8.71 (d, J=2.9 Hz, 1H), 8.45-8.41 (m, 1H), 8.15 (s, 1H), 7.35-7.31 (m, 2H), 7.00-6.95 (m, 2H), 5.65-5.60 (m, 1H), 3.43-3.34 (m, 2H), 3.24-3.19 (m, 2H), 3.03 (dd, J=6.6, 13.9 Hz, 1H), 1.37 (d, J=6.8 Hz, 6H); ES-LCMS m/z 428.2 $[M+H]^+$. Peak 2 was concentrated under reduced pressure to yield a residue which was purified by preparative HPLC (column: Agela ASB 150*25 mm*5 um; mobile phase: [water (0.05% HCl)-ACN]; B %: 68%-98%, 8 min). The desired fraction was lyophilized to yield the other enantiomer (24.54 mg, 49.04 μmol, 12.5% yield, 100.0% purity, 2HCl, SFC:

Rt=6.749, ee=99.76%, $[\alpha]^{24.6}_{D}$=−41.018 (MeOH, c=0.087 g/100 mL)) as a yellow solid. $^{1}$H NMR (400 MHz, DMSO-$d_6$) δ ppm 10.93 (s, 1H), 9.43-9.40 (m, 2H), 8.71 (d, J=2.7 Hz, 1H), 8.45-8.41 (m, 1H), 8.15 (s, 1H), 7.35-7.31 (m, 2H), 7.02-6.95 (m, J=7.0, 15.1 Hz, 2H), 5.67-5.60 (m, 1H), 3.41-3.34 (m, 2H), 3.24-3.21 (m, J=7.2, 14.1 Hz, 2H), 3.04-2.99 (dd, J=6.4, 13.9 Hz, 1H), 1.37 (d, J=6.8 Hz, 6H); ES-LCMS m/z 428.2 $[M+H]^{+}$.

Example 200

Synthesis of I-264

I-264

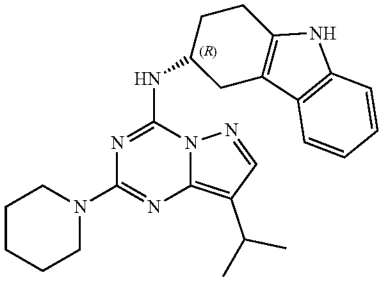

Synthetic Scheme:

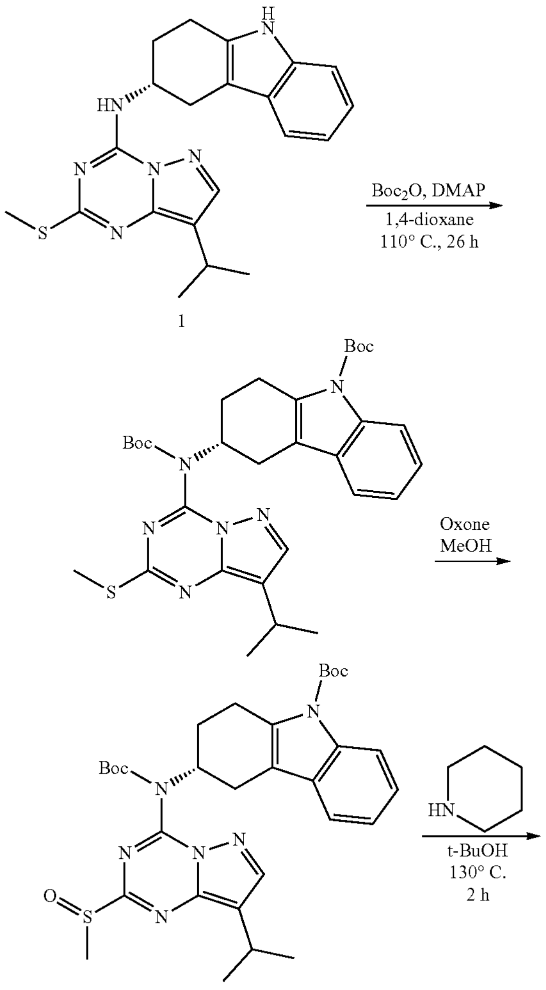

-continued

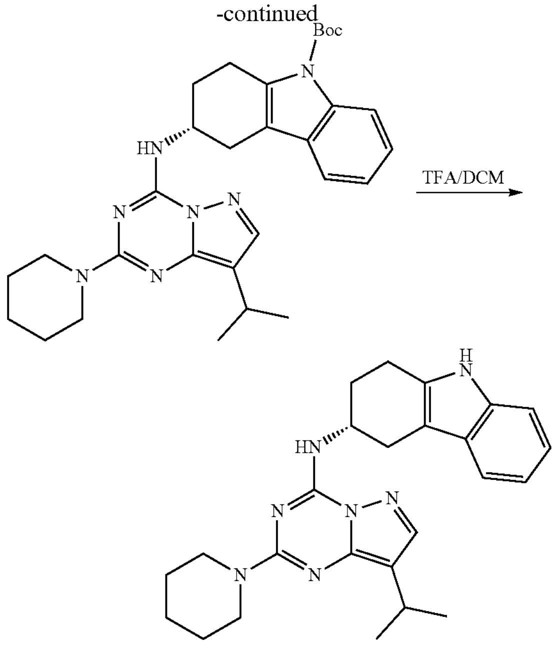

I-264

Step 1: tert-Butyl (3R)-3-[tert-butoxycarbonyl-(8-isopropyl-2-methylsulfanyl-pyrazolo[1,5-a][1,3,5]triazin-4-yl)amino]-1,2,3,4-tetrahydrocarbazole-9-carboxylate

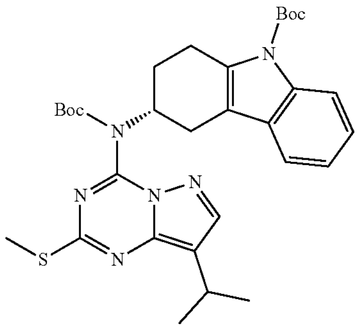 [SMILES: CSc1nc(N(C(=O)OC(C)(C)C)[C@@H]2CCc3c(c4ccccc4n3C(=O)OC(C)(C)C)C2)n2ncc(C(C)C)c2n1]

To a solution of (3R)—N-(8-isopropyl-2-methylsulfanyl-pyrazolo[1,5-a][1,3,5]triazin-4-yl)-2,3,4,9-tetrahydro-1H-carbazol-3-amine (300 mg, 726.08 μmol, 1 eq) in 1,4-dioxane (30 mL) was added DMAP (266.12 mg, 2.18 mmol, 3 eq) and Boc$_2$O (950.78 mg, 4.36 mmol, 1.00 mL, 6 eq). The mixture was stirred at 110° C. for 10 h. To the mixture was added Boc$_2$O (950.78 mg, 4.36 mmol, 1.00 mL, 6 eq). The mixture was stirred at 110° C. for another 16 h. The mixture was concentrated. The crude material was purified on silica gel column chromatography (from pure PE to PE/EtOAc=3/1, TLC: PE/EtOAc=5/1, $R_f$=0.7) to yield tert-butyl (3R)-3-[tert-butoxycarbonyl-(8-isopropyl-2-methyl-sulfanyl-pyrazolo[1,5-a][1,3,5]triazin-4-yl)amino]-1,2,3,4-tetrahydrocarbazole-9-carboxylate (420 mg, 637.71 μmol, 87.8% yield, 90.0% purity) as a yellow solid. $^{1}$H NMR (400 MHz, $CDCl_3$) δ ppm 8.10-8.04 (m, 1H), 7.93 (s, 1H), 7.33 (d, J=7.3 Hz, 1H), 7.23-7.13 (m, 2H), 4.76-4.74 (m, 1H), 3.33-2.97 (m, 5H), 2.59-2.51 (m, 3H), 2.37-2.27 (m, 1H), 2.24-2.26 (m, 1H), 1.63 (s, 9H), 1.54 (s, 9H), 1.36 (d, J=6.8 Hz, 6H); ES-LCMS m/z 593.3 $[M+H]^+$.

Step 2: tert-Butyl (3R)-3-[tert-butoxycarbonyl-(8-isopropyl-2-methylsulfinyl-pyrazolo[1,5-a][1,3,5]triazin-4-yl)amino]-1,2,3,4-tetrahydrocarbazole-9-carboxylate

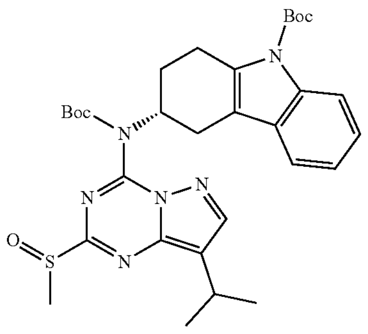 [SMILES: CC(C)c1cnn2c(N(C(=O)OC(C)(C)C)[C@@H]3CCc4c(c5ccccc5n4C(=O)OC(C)(C)C)C3)nc(S(C)=O)nc12]

To a solution of tert-butyl (3R)-3-[tert-butoxycarbonyl-(8-isopropyl-2-methylsulfanyl-pyrazolo[1,5-a][1,3,5]triazin-4-yl)amino]-1,2,3,4-tetrahydrocarbazole-9-carboxylate (400 μmg, 607.34 μmol, 1 eq) in MeOH (20 mL) was added oxone (373.37 mg, 607.34 μmol, 1 eq). The mixture was stirred at 15° C. for 3 h. After being filtered, to the filtration was added EtOAc (80 mL) and quenched by addition with saturated $Na_2SO_3$ solution (50 mL). The aqueous layer was extracted with EtOAc (30 mL×3) and the combined organic layers were washed with brine (50 mL), dried over $Na_2SO_4$, filtered and concentrated. The crude material was purified on silica gel column chromatography (from PE/EtOAc=10/1 to 2/1, TLC: PE/EtOAc=5/1, $R_f$=0.2) to yield tert-butyl (3R)-3-[tert-butoxycarbonyl-(8-isopropyl-2-methylsulfinyl-pyrazolo[1,5-a][1,3,5]triazin-4-yl)amino]-1,2,3,4-tetrahydrocarbazole-9-carboxylate (250 mg, 403.70 μmol, 66.5% yield, 98.3% purity) as a yellow solid. $^1H$ NMR (400 MHz, $CDCl_3$) δ ppm 8.16 (s, 1H), 8.07 (d, J=8.1 Hz, 1H), 7.32 (d, J=7.6 Hz, 1H), 7.24-7.14 (m, 2H), 4.85-4.83 (m, 1H), 3.40 (td, J=6.8, 13.8 Hz, 1H), 3.34-3.01 (m, 4H), 2.94 (d, J=2.7 Hz, 3H), 2.43 (d, J=12.0 Hz, 1H), 2.27 (d, J=8.1 Hz, 1H), 1.64 (s, 9H), 1.45-1.29 (m, 15H); ES-LCMS m/z 631.3 $[M+Na]^+$.

Step 3: tert-Butyl (3R)-3-[[8-isopropyl-2-(1-piperidyl)pyrazolo[1,5-a][1,3,5]triazin-4-yl]amino]-1,2,3,4-tetrahydrocarbazole-9-carboxylate

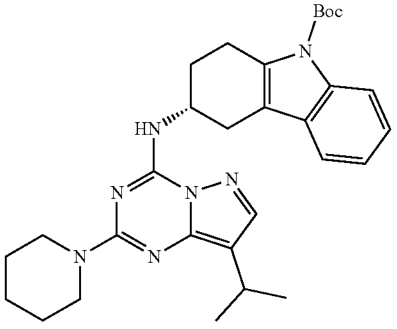 [SMILES: CC(C)c1cnn2c(N[C@@H]3CCc4c(c5ccccc5n4C(=O)OC(C)(C)C)C3)nc(N3CCCCC3)nc12]

A solution of tert-butyl (3R)-3-[tert-butoxycarbonyl-(8-isopropyl-2-methylsulfinyl-pyrazolo[1,5-a][1,3,5]triazin-4-yl)amino]-1,2,3,4-tetrahydrocarbazole-9-carboxylate (100 mg, 161.48 μmol, 1 eq) and piperidine (172.44 mg, 2.03 mmol, 0.2 mL, 12.54 eq) in t-BuOH (1 mL) was irradiated and stirred at 120° C. for 2 h under microwave. The mixture was concentrated to yield tert-butyl (3R)-3-[[8-isopropyl-2-(1-piperidyl)pyrazolo[1,5-a][1,3,5]triazin-4-yl]amino]-1,2,3,4-tetrahydrocarbazole-9-carboxylate (80 mg, 137.44 μmol, 85.1% yield, 91.0% purity) as a yellow solid. $^1H$ NMR (400 MHz, $CDCl_3$) δ ppm 8.11 (d, J=8.3 Hz, 1H), 7.57 (s, 1H), 7.35 (d, J=7.1 Hz, 1H), 7.27 (br s, 1H), 7.23-7.17 (m, 1H), 6.26 (d, J=7.8 Hz, 1H), 4.60-4.59 (m, 1H), 3.79 (d, J=4.6 Hz, 4H), 3.35 (d, J=5.1 Hz, 3H), 3.27-3.14 (m, 3H), 3.02 (td, J=6.8, 13.8 Hz, 1H), 2.72 (dd, J=7.7, 14.6 Hz, 1H), 2.25 (br s, 1H), 2.12 (d, J=8.3 Hz, 1H), 1.54-1.39 (m, 12H), 1.28 (d, J=6.8 Hz, 6H); ES-LCMS m/z 530.4 $[M+H]^+$.

Step 4: (3R)—N-[8-Isopropyl-2-(1-piperidyl)pyrazolo[1,5-a][1,3,5]triazin-4-yl]-2,3,4,9-tetrahydro-1H-carbazol-3-amine (I-264)

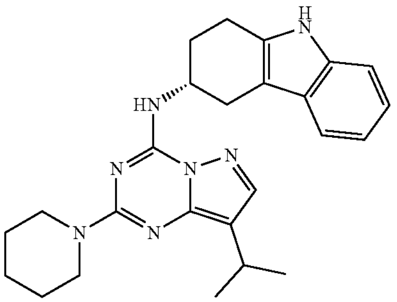

A solution of tert-butyl (3R)-3-[[8-isopropyl-2-(1-piperidyl)pyrazolo[1,5-a][1,3,5]triazin-4-yl]amino]-1,2,3,4-tetrahydrocarbazole-9-carboxylate (80 mg, 137.44 μmol, 1 eq) and TFA (1.12 g, 9.83 mmol, 728.00 μL, 71.54 eq) in DCM (5 mL) was stirred at 20° C. for 2 h. The mixture was concentrated. The residue was purified by preparative HPLC (column: Agela ASB 150*25 mm*5 m; mobile phase: [water (0.05% HCl)-ACN]; B %: 50%-80%, 8 min), followed by lyophilization to yield (3R)—N-[8-isopropyl-2-(1-piperidyl)pyrazolo[1,5-a][1,3,5]triazin-4-yl]-2,3,4,9-tetrahydro-1H-carbazol-3-amine (34.59 mg, 71.55 μmol, 52.1% yield, 96.4% purity, HCl; Optical rotation: $[\alpha]^{22.2}_D$=+82.409, (MeOH, c=0.096 g/100 mL)) as a yellow solid. $^1H$ NMR (400 MHz, $CD_3OD$) δ ppm 7.89 (s, 1H), 7.37 (d, J=7.8 Hz, 1H), 7.28 (d, J=8.0 Hz, 1H), 7.04 (t, J=7.5 Hz, 1H), 7.00-6.93 (m, 1H), 4.69-4.57 (m, 1H), 3.87 (br s, 4H), 3.28-3.16 (m, 2H), 2.97 (br s, 2H), 2.93-2.82 (m, 1H), 2.37-2.15 (m, 2H), 1.74 (br s, 6H), 1.31 (d, J=6.8 Hz, 6H); ES-LCMS m/z 430.3 $[M+H]^+$.

Example 201

Synthesis of I-265

I-265

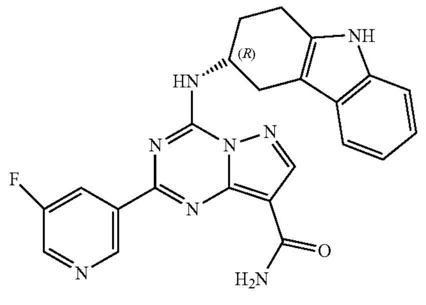

Synthetic Scheme:

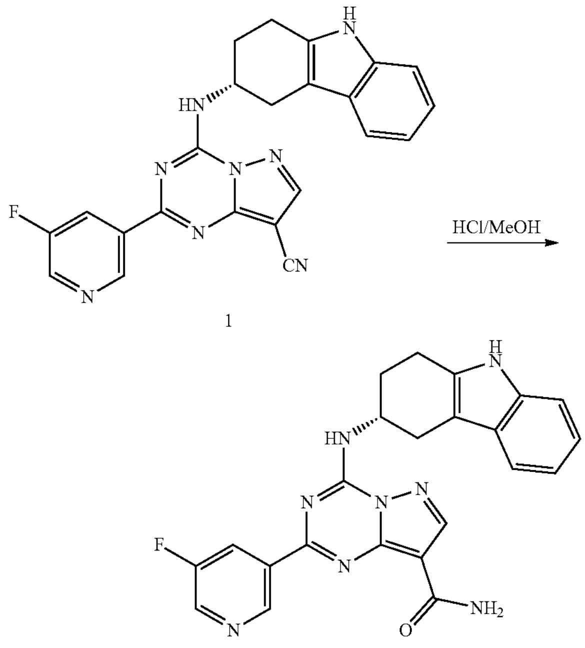

Step 1: 2-(5-Fluoro-3-pyridyl)-4-[[(3R)-2,3,4,9-tetrahydro-1H-carbazol-3-yl]amino]pyrazolo[1,5-a][1,3,5]triazine-8-carboxamide (I-265)

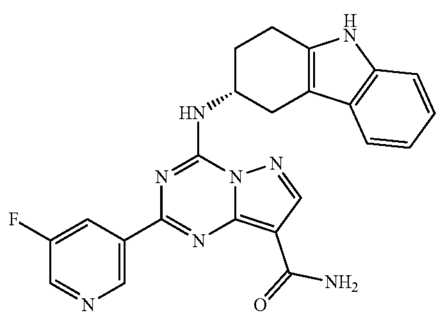 [SMILES: NC(=O)c1cnn2c(N[C@@H]3CCc4[nH]c5ccccc5c4C3)nc(-c3cncc(F)c3)nc12]

A solution of 2-(5-fluoro-3-pyridyl)-4-[[(3R)-2,3,4,9-tetrahydro-1H-carbazol-3-yl]amino]pyrazolo[1,5-a][1,3,5]triazine-8-carbonitrile (170 mg, 396.53 μmol, 1 eq) in HCl/MeOH (4 M in MeOH, 30 mL) was stirred at 80° C. for 12 h. The reaction mixture was concentrated under reduced pressure to yield a residue which was quenched by addition of saturated aqueous $NaHCO_3$ (50 mL), extracted with EtOAc (30 mL×3). The combined organic layers were washed with brine (10 mL), dried over $Na_2SO_4$, filtered and concentrated under reduced pressure to yield a residue. The residue was purified by flash silica gel chromatography (from PE/EtOAc=1/0 to 0/1, TLC: PE/EtOAc=1/1, $R_f$=0.11) to yield 2-(5-fluoro-3-pyridyl)-4-[[(3R)-2,3,4,9-tetrahydro-1H-carbazol-3-yl]amino]pyrazolo[1,5-a][1,3,5]triazine-8-carboxamide (60 mg, 135.61 μmol, 34.2% yield, 100% purity, $[\alpha]^{23.7}{}_D$=+21.368 (MeOH, c=0.088 g/100 mL)) as a yellow solid. $^1$H NMR (400 MHz, DMSO-$d_6$) δ ppm 10.79 (s, 1H), 9.56-9.41 (m, 2H), 8.78-8.67 (m, 2H), 8.50 (s, 1H), 7.52 (s, 1H), 7.45 (s, 1H), 7.34 (d, J=7.8 Hz, 1H), 7.28 (d, J=7.8 Hz, 1H), 7.05-6.98 (m, 1H), 6.97-6.89 (m, 1H), 4.86 (s, 1H), 3.23-2.77 (m, 4H), 2.22 (s, 2H); ES-LCMS m/z 443.1 $[M+H]^+$.

Example 202

Synthesis of I-267

I-267

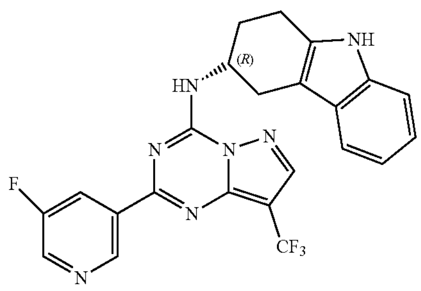

Synthetic Scheme:

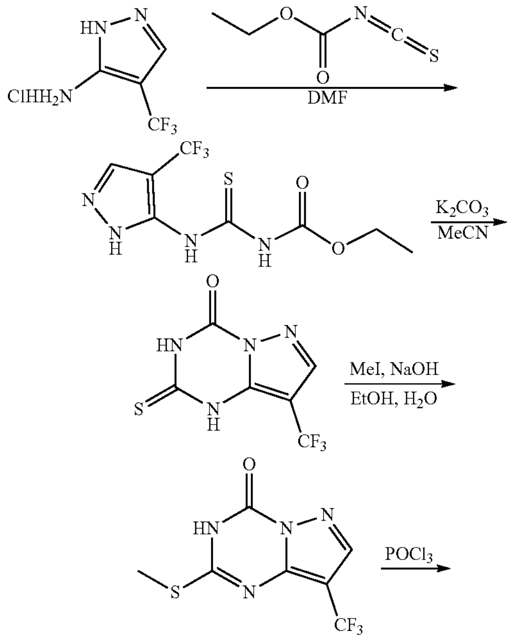

-continued

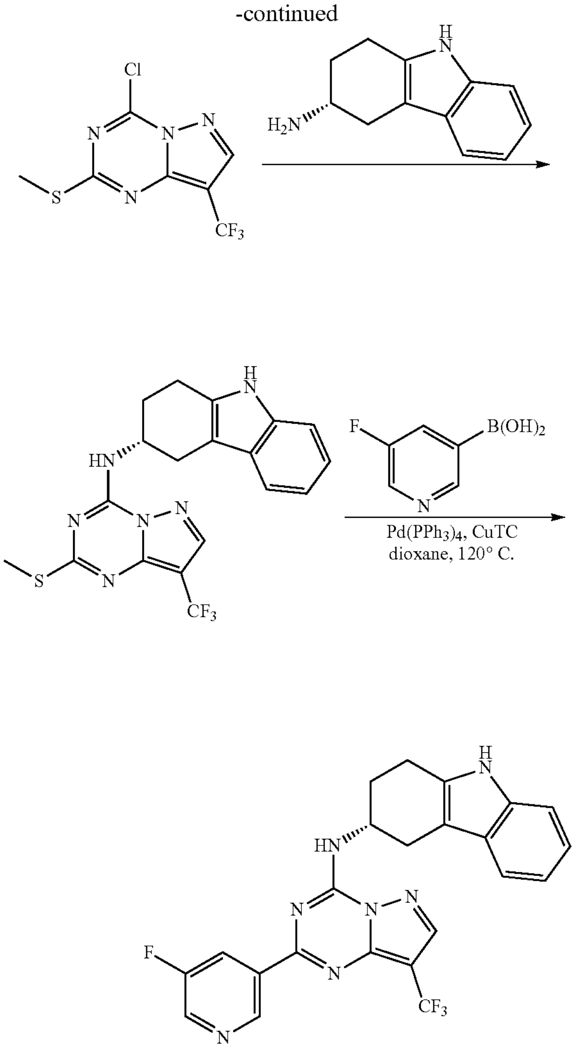

I-267

Step 1: Ethyl N-[[4-(trifluoromethyl)-1H-pyrazol-5-yl]carbamothioyl]carbamate

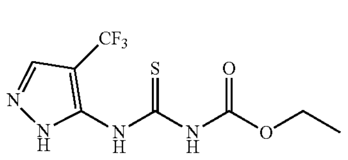 [SMILES: CCOC(=O)NC(=S)Nc1[nH]ncc1C(F)(F)F]

A solution of 4-(trifluoromethyl)-1H-pyrazol-5-amine; hydrochloride (1 g, 4.46 mmol, 1 eq, HCl) and ethyl N-(thioxomethylene)carbamate (585.47 mg, 4.46 mmol, 1 eq) in DCM (10 mL) and DMF (10 mL) was stirred at 20° C. for 2.5 h. The reaction mixture was concentrated under reduced pressure to yield a residue of ethyl N-[[4-(trifluoromethyl)-1H-pyrazol-5-yl]carbamothioyl]carbamate (1.1 g, 3.90 mmol, 87.3% yield, crude purity) as a yellow solid which was used in the next step without further purification. $^1H$ NMR (400 MHz, DMSO-$d_6$) δ ppm 11.52 (s, 1H), 11.06 (s, 1H), 8.34 (s, 1H), 4.21 (q, J=7.0 Hz, 2H), 1.25 (t, J=7.0 Hz, 3H); ES-LCMS m/z 283.0 $[M+H]^+$.

Step 2: 2-Thioxo-8-(trifluoromethyl)-1H-pyrazolo[1,5-a][1,3,5]triazin-4-one

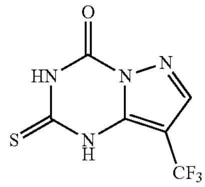 [SMILES: O=c1[nH]c(=S)[nH]c2c(C(F)(F)F)cnn12]

To a solution of ethyl N-[[4-(trifluoromethyl)-1H-pyrazol-5-yl]carbamothioyl]carbamate (1.1 g, 3.90 mmol, 1 eq) in $CH_3CN$ (5 mL) was added $K_2CO_3$ (1.62 g, 11.69 mmol, 3.0 eq). The mixture was stirred at 60° C. for 3 h. The reaction mixture was quenched by AcOH solution (6 mL), diluted with $H_2O$ (50 mL) and extracted with EtOAc (50 mL×3). The combined organic layers were dried over anhydrous $Na_2SO_4$, filtered and concentrated under reduced pressure to yield a residue. The residue was diluted with EtOAc/PE (2 mL/10 mL), filtered and collected the solid to yield 2-thioxo-8-(trifluoromethyl)-1H-pyrazolo[1,5-a][1,3,5]triazin-4-one (900 mg, 3.33 mmol, 85.4% yield, 87.3% purity) as a yellow solid which was used in the next step without further purification. $^1H$ NMR (400 MHz, DMSO-$d_6$) δ ppm 12.65 (br s, 1H), 8.16 (s, 1H); ES-LCMS m/z 237.0 $[M+H]^+$.

Step 3: 2-Methylsulfanyl-8-(trifluoromethyl)-3H-pyrazolo[1,5-a][1,3,5]triazin-4-one

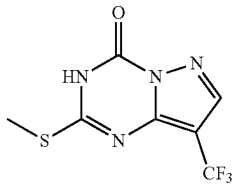 [SMILES: CSc1nc2c(C(F)(F)F)cnn2c(=O)[nH]1]

To a solution of 2-thioxo-8-(trifluoromethyl)-1H-pyrazolo[1,5-a][1,3,5]triazin-4-one (900 mg, 3.33 mmol, 1 eq) in EtOH (15 mL) was added a solution of NaOH (266.12 mg, 6.65 mmol, 2 eq) in $H_2O$ (6 mL) and then MeI (472.20 mg, 3.33 mmol, 207.11 μL, 1 eq) was added dropwise. The mixture was stirred at 20° C. for 1 h. The reaction mixture was acidified with 1NHCl solution (10 mL) and concentrated under reduced pressure to remove EtOH, solid was formed, filtered and collected the solid to yield 2-methylsulfanyl-8-(trifluoromethyl)-3H-pyrazolo[1,5-a][1,3,5]triazin-4-one (800 mg, 3.00 mmol, 90.2% yield, 93.8% purity) as a yellow solid which was used in the next step without further purification. $^1H$ NMR (400 MHz, $CD_3OD$) δ ppm 8.16 (s, 1H), 2.64 (s, 3H); ES-LCMS m/z 251.1 $[M+H]^+$.

Step 4: 4-Chloro-2-methylsulfanyl-8-(trifluoromethyl)pyrazolo[1,5-a][1,3,5]triazine

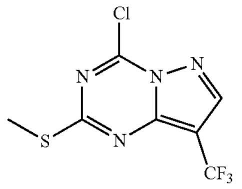 [SMILES: CSc1nc(Cl)n2ncc(C(F)(F)F)c2n1]

A solution of 2-methylsulfanyl-8-(trifluoromethyl)-3H-pyrazolo[1,5-a][1,3,5]triazin-4-one (200 mg, 749.80 μmol, 1 eq) and DIEA (290.72 mg, 2.25 mmol, 391.80 μL, 3.0 eq) in $POCl_3$ (34.43 g, 224.55 mmol, 20.87 mL, 299.47 eq) was stirred at 130° C. for 12 h under $N_2$ atmosphere. The reaction mixture was concentrated under reduced pressure to yield 4-chloro-2-methylsulfanyl-8-(trifluoromethyl)pyrazolo[1,5-a][1,3,5]triazine (200 mg, 744.47 μmol, 99.3% yield, crude purity) as a black brown oil which was used in the next step without further purification. $^1$H NMR (400 MHz, $CDCl_3$) δ ppm 8.29 (s, 1H), 2.66-2.64 (m, 3H).

Step 5: (3R)—N-[2-Methylsulfanyl-8-(trifluoromethyl)pyrazolo[1,5-a][1,3,5]triazin-4-yl]-2,3,4,9-tetrahydro-1H-carbazol-3-amine

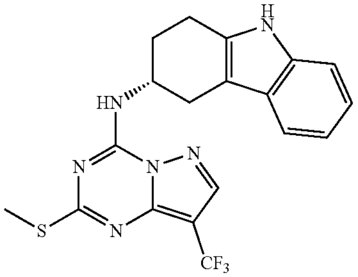 [SMILES: CSc1nc(N[C@@H]2CCc3[nH]c4ccccc4c3C2)n2ncc(C(F)(F)F)c2n1]

To a solution of 4-chloro-2-methylsulfanyl-8-(trifluoromethyl)pyrazolo[1,5-a][1,3,5]triazine (200 mg, 744.47 μmol, 1 eq) and (3R)-2,3,4,9-tetrahydro-1H-carbazol-3-amine (166.39 mg, 893.37 μmol, 1.2 eq) in ACN (10 mL) was added DIEA (962.18 mg, 7.44 mmol, 1.30 mL, 10 eq). The mixture was stirred at 60° C. for 3 h. The reaction mixture was concentrated under reduced pressure to yield a residue which was purified on silica gel column chromatography (from PE/EtOAc=1/0 to 10/3, TLC: PE/EtOAc=3/1, $R_f$=0.32) to yield the product of (3R)—N-[2-methylsulfanyl-8-(trifluoromethyl)pyrazolo[1,5-a][1,3,5]triazin-4-yl]-2,3,4,9-tetrahydro-1H-carbazol-3-amine (150 mg, 353.10 μmol, 47.4% yield, 98.5% purity) as a brown oil. $^1$H NMR (400 MHz, $CDCl_3$) δ ppm 7.99 (s, 1H), 7.84 (br s, 1H), 7.47 (d, J=7.5 Hz, 1H), 7.34 (d, J=7.8 Hz, 1H), 7.24-7.08 (m, 2H), 6.65 (d, J=9.3 Hz, 1H), 4.82 (m, 1H), 3.31 (dd, J=5.4, 15.4 Hz, 1H), 3.03-2.84 (m, 3H), 2.60 (s, 3H), 2.31-2.21 (m, 2H); ES-LCMS m/z 419.1 [M+H]$^+$.

Step 6: (3R)—N-[2-(5-Fluoro-3-pyridyl)-8-(trifluoromethyl)pyrazolo[1,5-a][1,3,5]triazin-4-yl]-2,3,4,9-tetrahydro-1H-carbazol-3-amine (I-267)

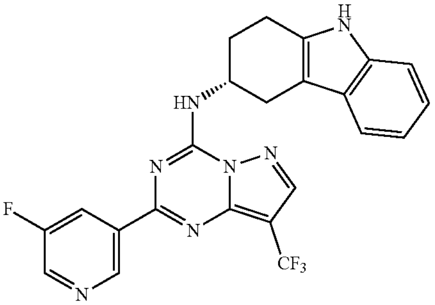 [SMILES: Fc1cncc(-c2nc(N[C@@H]3CCc4[nH]c5ccccc5c4C3)n3ncc(C(F)(F)F)c3n2)c1]

To a solution of (3R)—N-[2-methylsulfanyl-8-(trifluoromethyl)pyrazzolo[1,5-a][1,3,5]triazin-4-yl]-2,3,4,9-tetrahydro-1H-carbazol-3-amine (100 mg, 235.40 μmol, 1 eq) and (5-fluoro-3-pyridyl)boronic acid (99.51 mg, 706.20 μmol, 3.0 eq) in 1,4-dioxane (6 mL) was added $Pd(PPh_3)_4$ (27.20 mg, 23.54 μmol, 0.1 eq) and thiophene-2-carbonyloxycopper (89.78 mg, 470.80 μmol, 2.0 eq). The mixture was purged with $N_2$ for 1 min and stirred at 120° C. for 5 h under microwave. The reaction mixture was filtered and concentrated under reduced pressure to yield a residue which was purified on silica gel column chromatography (from PE/EtOAc=1/0 to 10/3, TLC: PE/EtOAc=3/1, $R_f$=0.38) and preparative HPLC (column: DuraShell 150*25 mm*5 um; mobile phase: [water (0.05% HCl)-ACN]; B %: 45%-75%, 8 min), followed by lyophilization to yield the product of (3R)—N-[2-(5-fluoro-3-pyridyl)-8-(trifluoromethyl)pyrazolo[1,5-a][1,3,5]triazin-4-yl]-2,3,4,9-tetrahydro-1H-carbazol-3-amine (36.04 mg, 66.30 μmol, 28.2% yield, 99.4% purity, 2HCl, Optical rotation: ($[\alpha]^{24.3}_D$=+51.474, (MeOH, c=0.048 g/100 mL)) as a yellow solid. $^1$H NMR (400 MHz, $CD_3OD$) δ ppm 9.48 (br s, 1H), 8.71 (d, J=8.8 Hz, 2H), 8.35 (s, 1H), 7.36 (d, J=7.8 Hz, 1H), 7.26 (d, J=8.3 Hz, 1H), 7.06-6.99 (m, 1H), 6.97-6.88 (m, 1H), 4.91 (d, J=3.8 Hz, 1H), 3.29 (d, J=5.5 Hz, 1H), 3.10-2.90 (m, 3H), 2.45-2.35 (m, 1H), 2.33-2.21 (m, 1H); ES-LCMS m/z 468.2 [M+H]$^+$.

Example 203

Synthesis of I-270

I-270

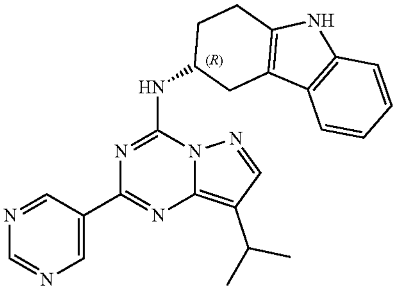

Synthetic Scheme:

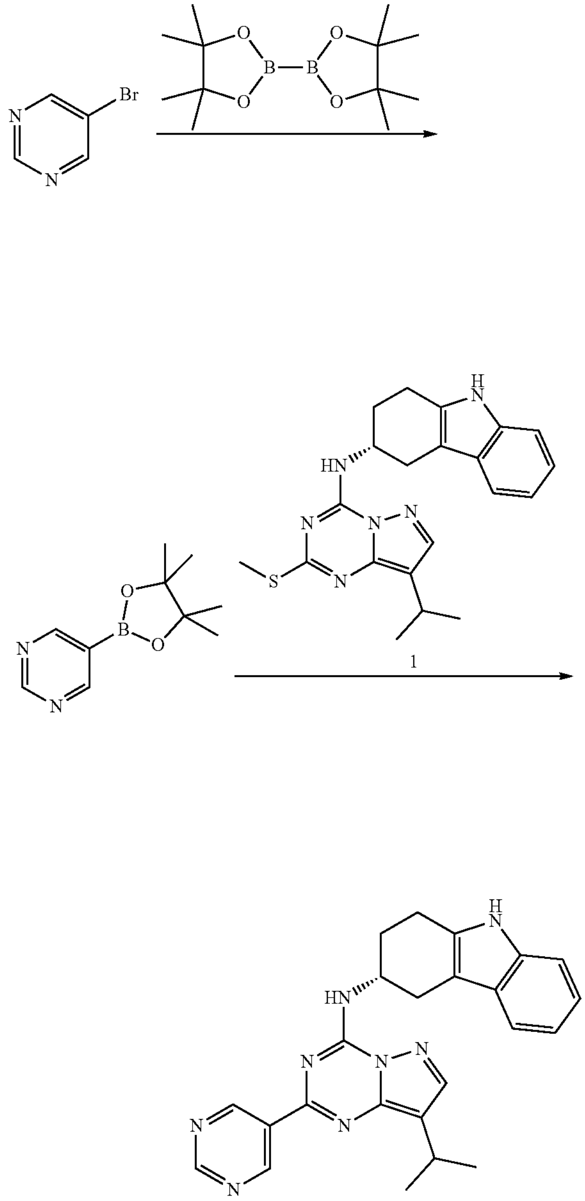

I-270

Step 1: 5-(4,4,5,5-Tetramethyl-1,3,2-dioxaborolan-2-yl)pyrimidine

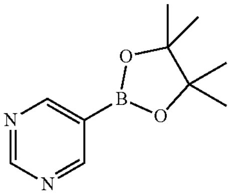

A mixture of 5-bromopyrimidine (1 g, 6.29 mmol, 1 eq), 4,4,5,5-tetramethyl-2-(4,4,5,5-tetramethyl-1,3,2-dioxaborolan-2-yl)-1,3,2-dioxaborolane (1.76 g, 6.93 mmol, 1.10 eq), $Pd(dppf)Cl_2.CH_2Cl_2$ (513.66 mg, 628.99 μmol, 0.1 eq), KOAc (1.85 g, 18.87 mmol, 3 eq) in 1,4-dioxane (40 mL) and DMF (10 mL) was stirred at 100° C. for 2 h under N2 atmosphere. The mixture was concentrated. The residue was purified on silica gel column chromatography (from PE/EtOAc=1/0 to 3/1, TLC: PE/EtOAc=3/1, $R_f$=0.23) to yield 5-(4,4,5,5-tetramethyl-1,3,2-dioxaborolan-2-yl)pyrimidine (1.5 g, 5.82 mmol, 92.6% yield, 80% purity) as red oil. $^1$H NMR (400 MHz, $CDCl_3$) δ ppm 9.25 (s, 1H), 9.00 (br s, 2H), 1.33 (s, 12H).

Step 2: (3R)—N-(8-Isopropyl-2-pyrimidin-5-yl-pyrazolo[1,5-a][1,3,5]triazin-4-yl)-2,3,4,9-tetrahydro-1H-carbazol-3-amine (I-270)

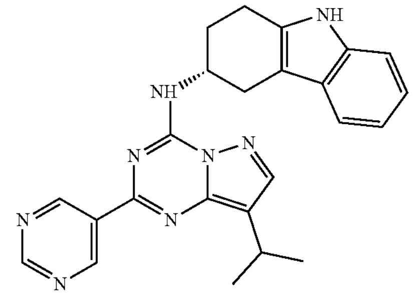 [SMILES: CC(C)c1cnn2c(N[C@@H]3CCc4[nH]c5ccccc5c4C3)nc(-c3cncnc3)nc12]

A mixture of (3R)—N-(8-isopropyl-2-methylsulfanyl-pyrazolo[1,5-a][1,3,5]triazin-4-yl)-2,3,4,9-tetrahydro-1H-carbazol-3-amine (150 mg, 351.57 μmol, 1 eq), 5-(4,4,5,5-tetramethyl-1,3,2-dioxaborolan-2-yl)pyrimidine (271.66 mg, 1.05 mmol, 3 eq), $Pd_2(dba)_3$ (32.19 mg, 35.16 μmol, 0.1 eq) and copper (I) thiophene-2-carbonyloxy (134.08 mg, 703.15 μmol, 2 eq) in 1,4-dioxane (4 mL) was stirred at 110° C. for 12 h under $N_2$ atmosphere. The mixture was concentrated to yield crude material which was purified on silica gel column chromatography (from PE/EtOAc=1/0 to 2/1, TLC: PE/EtOAc=3/1, $R_f$=0.25) to yield a gray solid which was slurry with $MeCN/H_2O/DMF$ (3/1/0.5, 10 mL). After filtration, the filter cake was washed with MeCN (10 mL×3) and dried under vacuum to yield (3R)—N-(8-isopropyl-2-pyrimidin-5-yl-pyrazolo[1,5-a][1,3,5]triazin-4-yl)-2,3,4,9-tetrahydro-1H-carbazol-3-amine (42.34 mg, 99.74 μmol, 28.4% yield, 100% purity, $[\alpha]^{24.5}_D$=+83.175 (DMSO, c=0.102 g/100 mL)) as a gray solid. $^1$H NMR (400 MHz, DMSO) δ ppm 10.75 (s, 1H), 9.57 (s, 2H), 9.26 (s, 1H), 9.01 (br s, 1H), 8.12 (s, 1H), 7.31 (d, J=7.6 Hz, 1H), 7.24 (d, J=8.1 Hz, 1H), 7.01-6.94 (m, 1H), 6.93-6.86 (m, 1H), 4.80-4.77 (m, 1H), 3.11-3.00 (m, 2H), 2.99-2.81 (m, 3H), 2.18 (m, 2H), 1.34 (d, J=6.8 Hz, 6H); ES-LCMS m/z 425.2 $[M+H]^+$.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method for treating an AHR-mediated disorder in a patient in need thereof, comprising administering to said patient a compound selected from any one of formulae IX-a, IX-b and IX-c:

IX-a

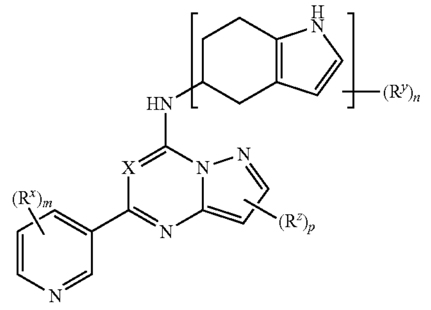

IX-b

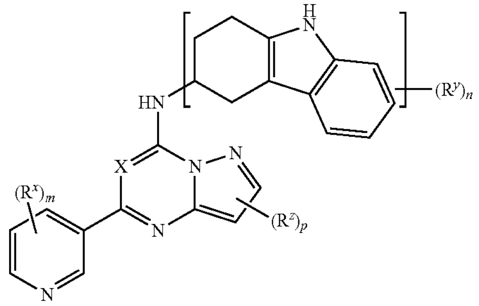

and

IX-c

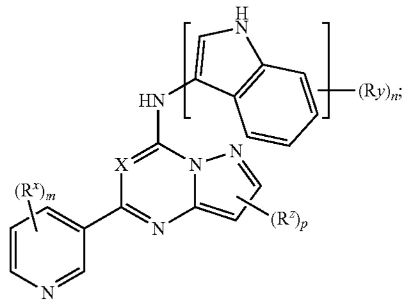

or a pharmaceutically acceptable salt thereof, wherein X is N or CH;

each or $R^x$, $R^y$, and $R^z$ is independently selected from R, halogen, cyano, nitro, —OR, —SR, —$N(R)_2$, —N(R)C(O)R, —$C(O)N(R)_2$, —C(O)N(R)OR, —N(R)C(O)N$(R)_2$, —N(R)C(O)OR, —$OC(O)N(R)_2$, —$N(R)SO_2R$, —$SO_2RN(R)_2$, —C(O)R, —C(O)OR, —OC(O)R, —C(O)OR, —S(O)R, or —$SO_2R$, or:

two $R^x$ on the same carbon are taken together to form ═O or ═S; or:

two $R^y$ on the same carbon are taken together to form ═O or ═S;

each R is independently hydrogen, deuterium, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or two R on the same nitrogen are taken together with their intervening atoms to form a 4-7 membered saturated, partially unsaturated, or aromatic ring having 1-2 heteroatoms in addition to the nitrogen independently selected from oxygen, nitrogen, or sulfur;

each p is independently 0, 1, or 2, as valency will allow; and each of m and n is independently 1, 2, 3, 4, or 5.

2. The method according to claim 1, wherein the AHR-mediated disorder is a cancer.

3. The method according to claim 1, wherein the AHR-mediated disorder is an inflammatory disorder.

4. A method for treating an AHR-mediated disorder in a patient in need thereof, comprising administering to said patient a compound selected from any one of formulae X-a, X-b, X-c, X-d, X-e, X-f, X-g, X-h and X-i:

X-a

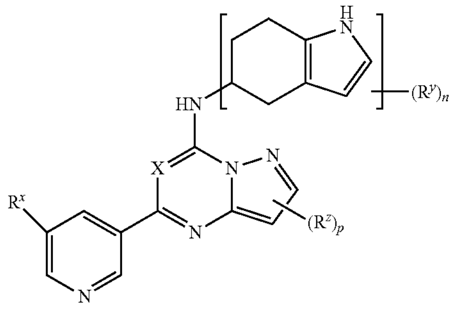

X-b

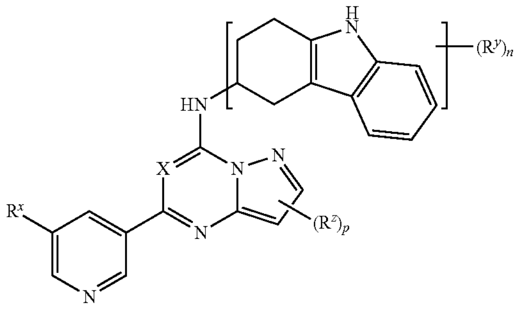

X-c

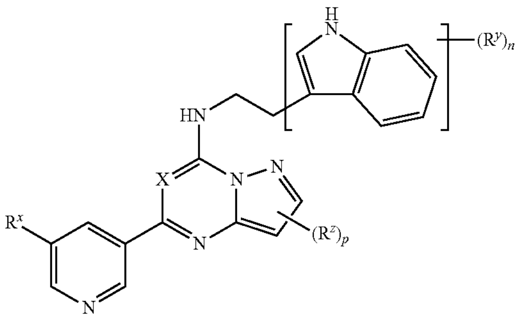

-continued

X-d

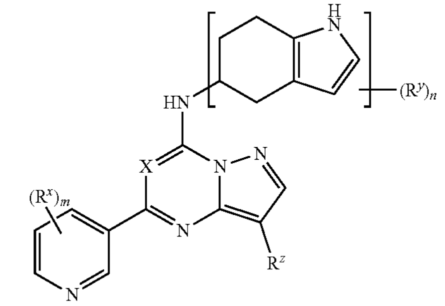

X-e

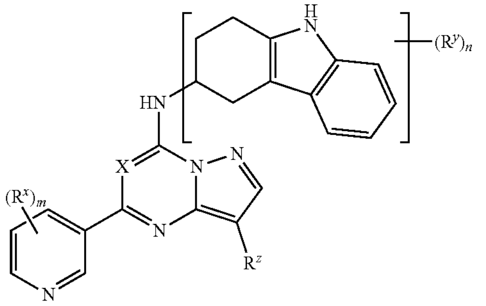

X-f

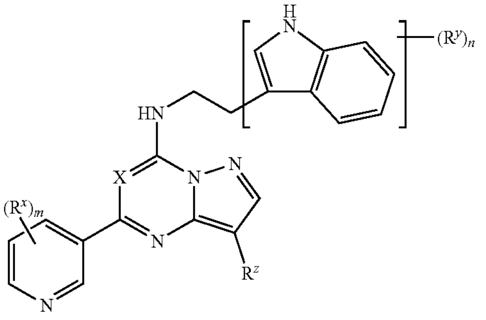

X-g

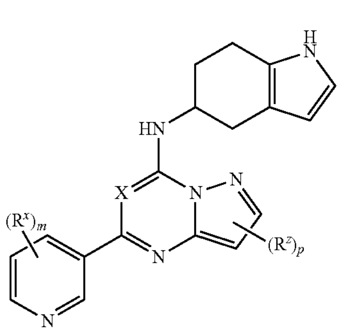

-continued

X-h

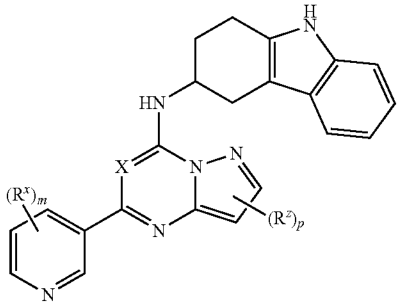

and

X-i

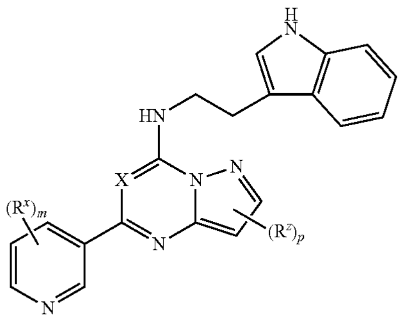

;

or a pharmaceutically acceptable salt thereof, wherein X is N or CH;

each or $R^x$, $R^y$, and $R^z$ is independently selected from R, halogen, cyano, nitro, —OR, —SR, —N(R)$_2$, —N(R)C(O)R, —C(O)N(R)$_2$, —C(O)N(R)OR, —N(R)C(O)N(R)$_2$, N(R)C(O)OR, —OC(O)N(R)$_2$, —N(R)SO$_2$R, —SO$_2$RN(R)$_2$, —C(O)R, —C(O)OR, —OC(O)R, —C(O)OR, —S(O)R, or —SO$_2$R, or:

two $R^x$ on the same carbon are taken together to form =O or =S; or:

two $R^y$ on the same carbon are taken together to form =O or =S;

each R is independently hydrogen, deuterium, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or two R on the same nitrogen are taken together with their intervening atoms to form a 4-7 membered saturated, partially unsaturated, or aromatic ring having 1-2 heteroatoms in addition to the nitrogen independently selected from oxygen, nitrogen, or sulfur;

each p is independently 0, 1, or 2, as valency will allow; and each of m and n is independently 1, 2, 3, 4, or 5.

5. The method according to claim 4, wherein the compound is selected from any one of formulae XI-a, XI-b, XI-c, XI-d, XI-e, XI-f, XI-g, XI-h and XI-i:

XI-a
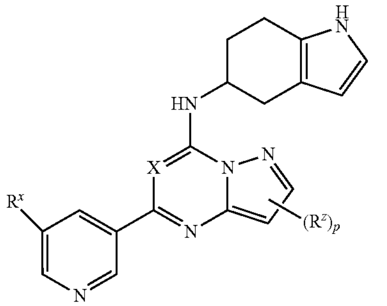
XI-b
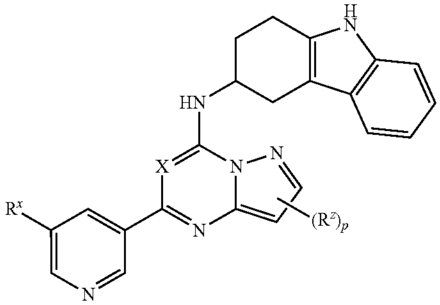
XI-c
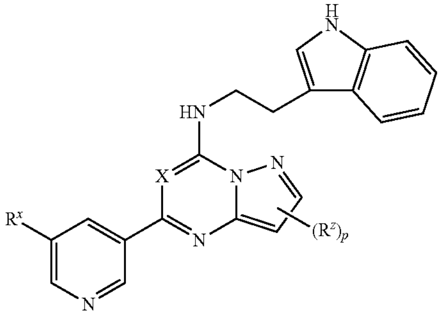
XI-d
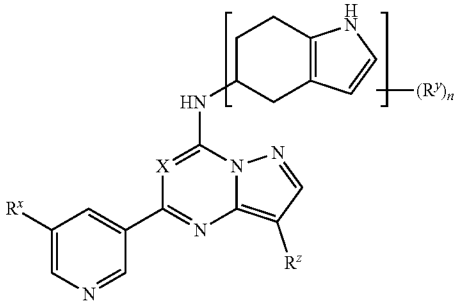
XI-e
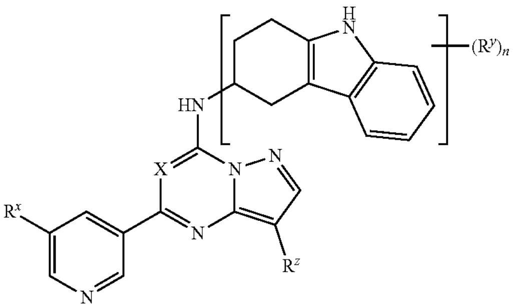
-continued
XI-f
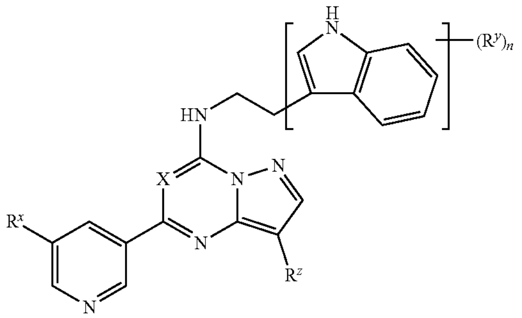
XI-g
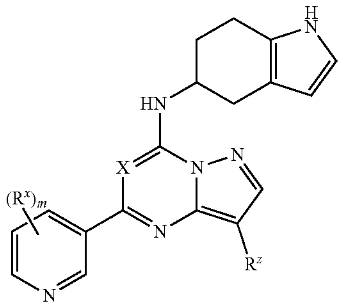
XI-h
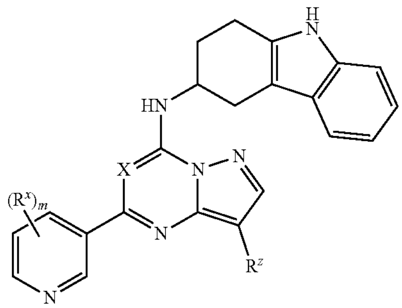
and
XI-i
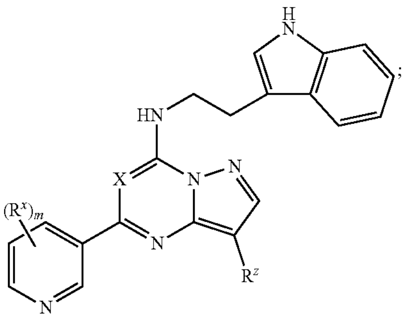
or a pharmaceutically acceptable salt thereof.
6. The method according to claim 4, wherein the compound is selected from any one of formulae XII-a, XII-b and XI-c:

XII-a
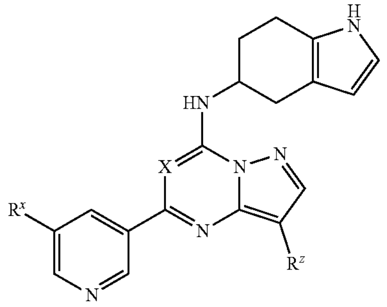
XII-b
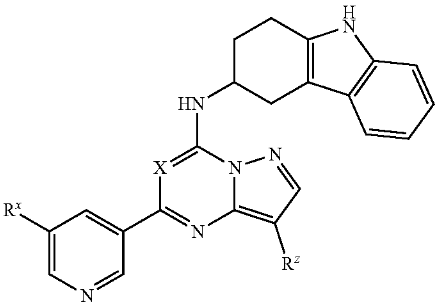
and
XII-c
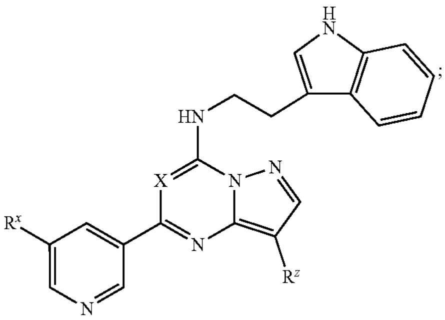
or a pharmaceutically acceptable salt thereof.
7. The method according to claim 4, wherein the compound is selected from:
I-2
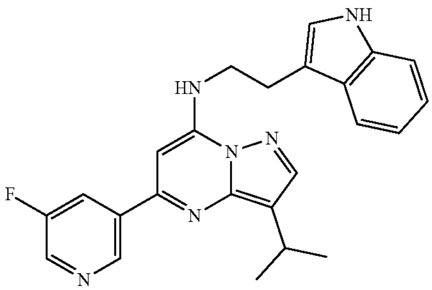 [SMILES: CC(C)c1cnn2c(NCCc3c[nH]c4ccccc34)cc(-c3cncc(F)c3)nc12]
-continued
I-16
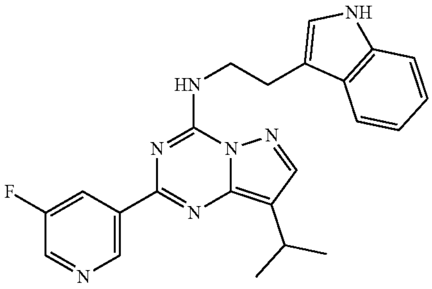 [SMILES: CC(C)c1cnn2c(NCCc3c[nH]c4ccccc34)nc(-c3cncc(F)c3)nc12]
I-24
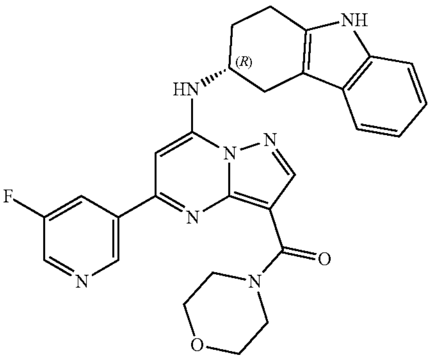
I-25
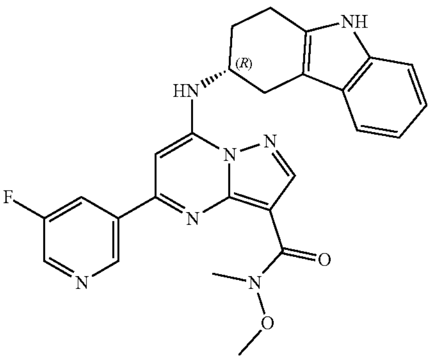
I-29
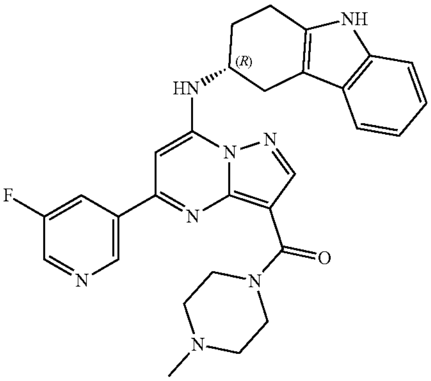

-continued
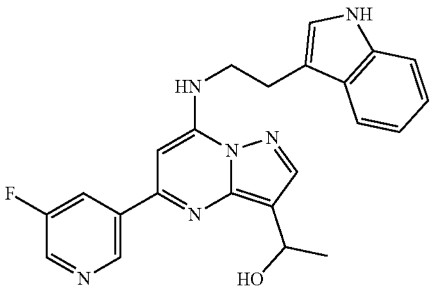 [SMILES: CC(O)c1cnn2c(NCCc3c[nH]c4ccccc34)cc(-c3cncc(F)c3)nc12]
I-33
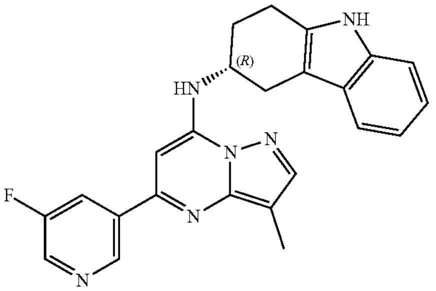
I-34
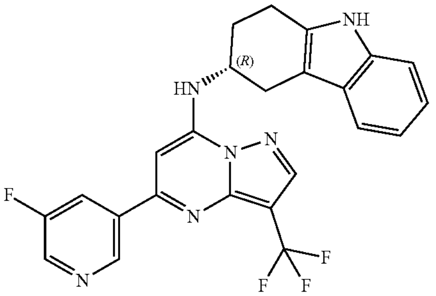
I-35
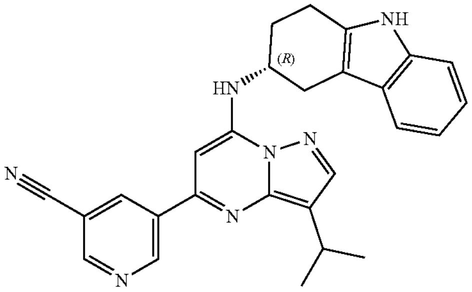
I-38
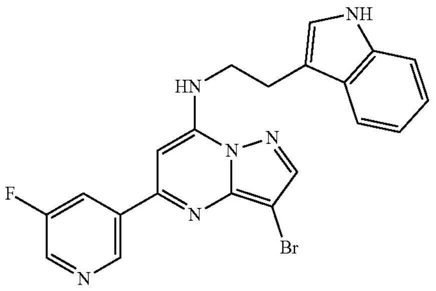 [SMILES: Fc1cncc(-c2cc(NCCc3c[nH]c4ccccc34)n3ncc(Br)c3n2)c1]
I-39
-continued
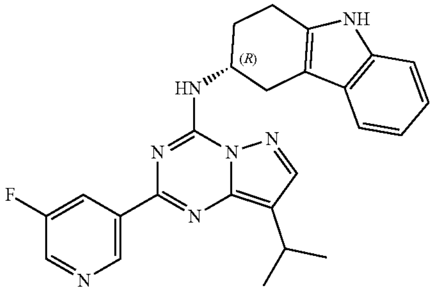
I-40
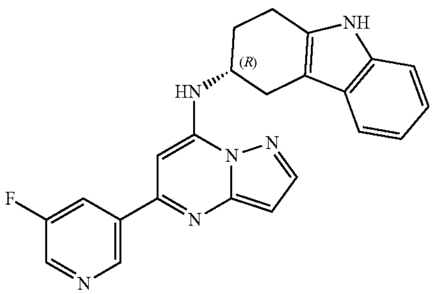
I-41
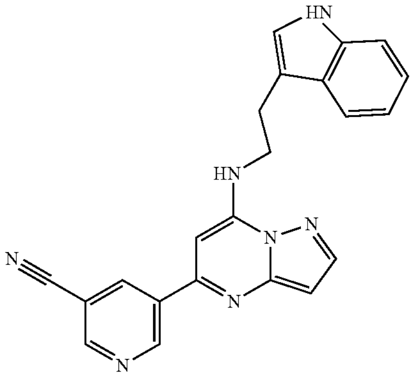 [SMILES: N#Cc1cncc(-c2cc(NCCc3c[nH]c4ccccc34)n3nccc3n2)c1]
I-43
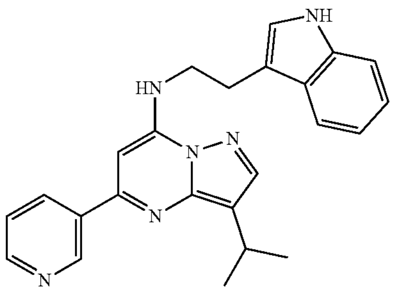 [SMILES: CC(C)c1cnn2c(NCCc3c[nH]c4ccccc34)cc(-c3cccnc3)nc12]
I-46
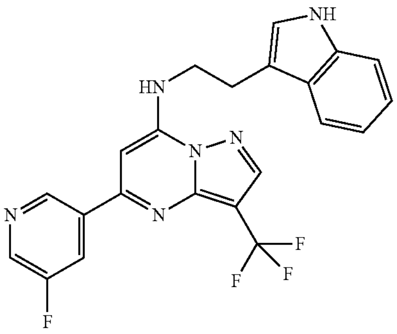 [SMILES: Fc1cncc(-c2cc(NCCc3c[nH]c4ccccc34)n3ncc(C(F)(F)F)c3n2)c1]
I-47

-continued
I-55
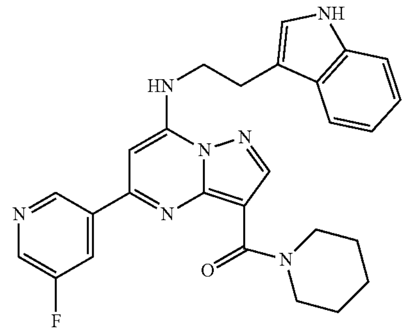 [SMILES: O=C(c1cnn2c(NCCc3c[nH]c4ccccc34)cc(-c3cncc(F)c3)nc12)N1CCCCC1]
I-56
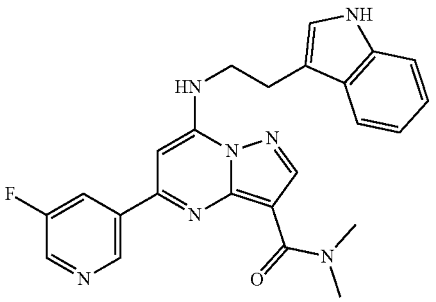 [SMILES: CN(C)C(=O)c1cnn2c(NCCc3c[nH]c4ccccc34)cc(-c3cncc(F)c3)nc12]
I-57
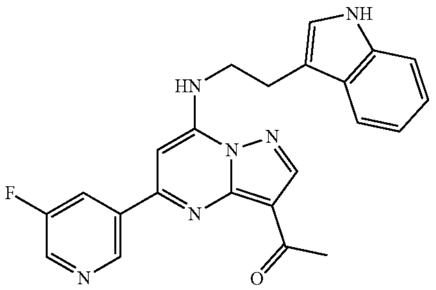 [SMILES: CC(=O)c1cnn2c(NCCc3c[nH]c4ccccc34)cc(-c3cncc(F)c3)nc12]
I-58
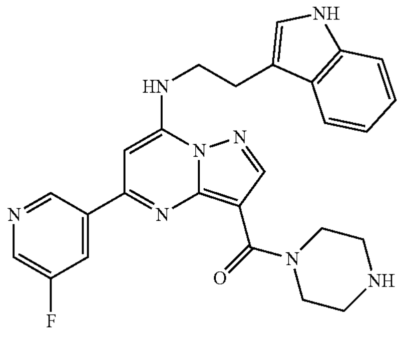 [SMILES: O=C(c1cnn2c(NCCc3c[nH]c4ccccc34)cc(-c3cncc(F)c3)nc12)N1CCNCC1]
I-61
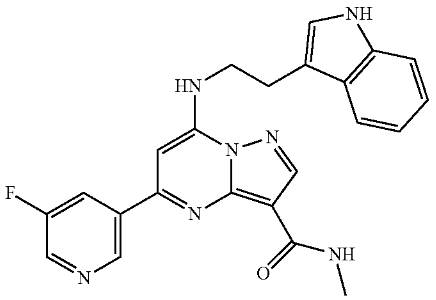 [SMILES: CNC(=O)c1cnn2c(NCCc3c[nH]c4ccccc34)cc(-c3cncc(F)c3)nc12]
-continued
I-65
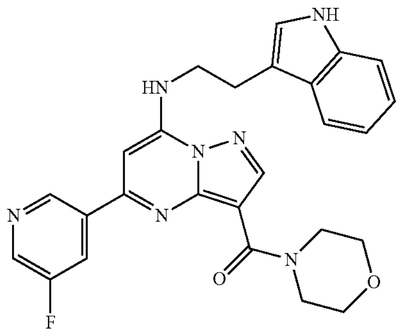 [SMILES: O=C(c1cnn2c(NCCc3c[nH]c4ccccc34)cc(-c3cncc(F)c3)nc12)N1CCOCC1]
I-66
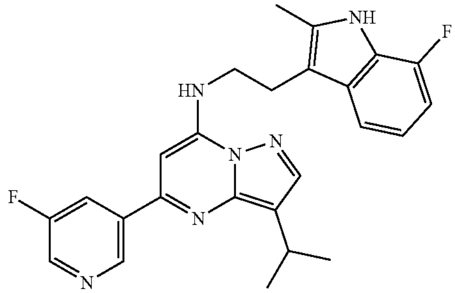 [SMILES: Cc1[nH]c2c(F)cccc2c1CCNc1cc(-c2cncc(F)c2)nc2c(C(C)C)cnn12]
I-68
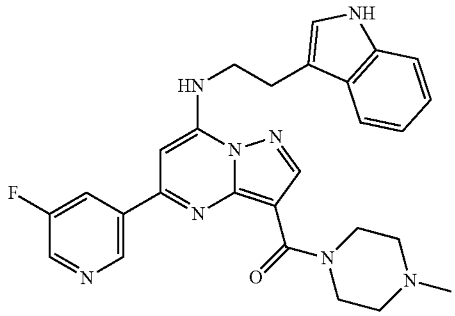 [SMILES: CN1CCN(C(=O)c2cnn3c(NCCc4c[nH]c5ccccc45)cc(-c4cncc(F)c4)nc23)CC1]
I-70
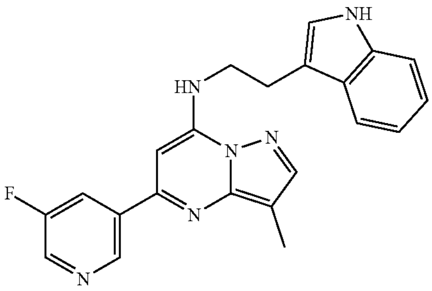 [SMILES: Cc1cnn2c(NCCc3c[nH]c4ccccc34)cc(-c3cncc(F)c3)nc12]
I-73
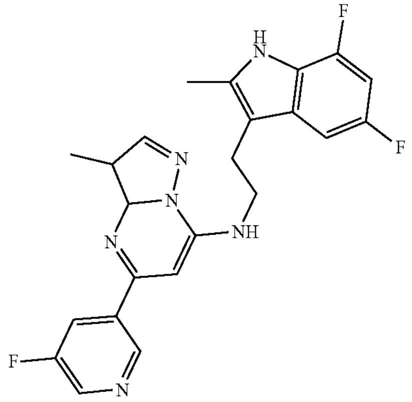 [SMILES: Cc1[nH]c2c(F)cc(F)cc2c1CCNC1=CC(c2cncc(F)c2)=NC2C(C)C=NN12]

-continued
I-75a
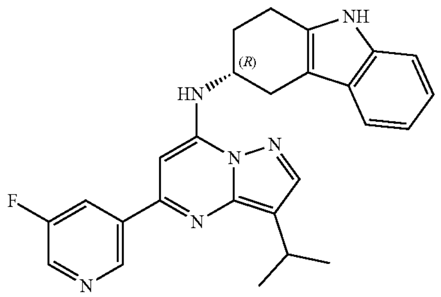
I-75b
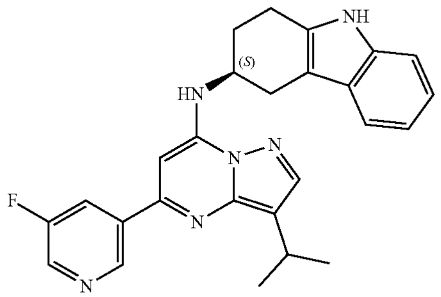
I-75c
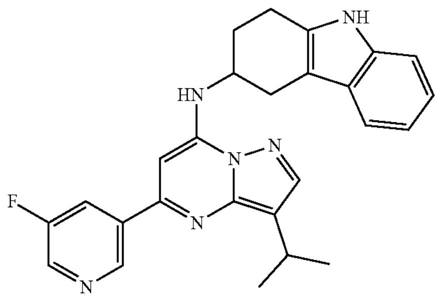 [SMILES: CC(C)c1cnn2c(NC3CCc4[nH]c5ccccc5c4C3)cc(-c3cncc(F)c3)nc12]
I-78
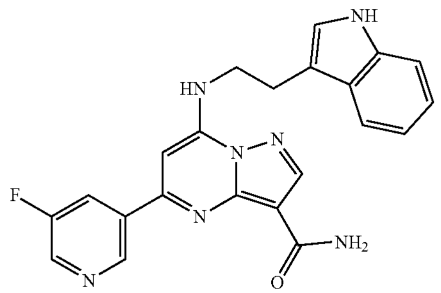 [SMILES: NC(=O)c1cnn2c(NCCc3c[nH]c4ccccc34)cc(-c3cncc(F)c3)nc12]
I-81
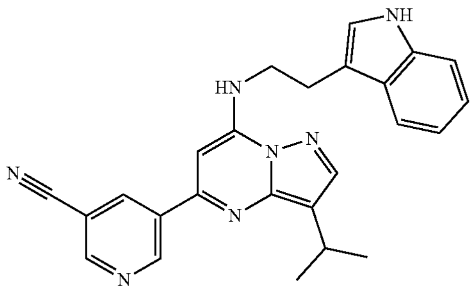 [SMILES: CC(C)c1cnn2c(NCCc3c[nH]c4ccccc34)cc(-c3cncc(C#N)c3)nc12]
-continued
I-83
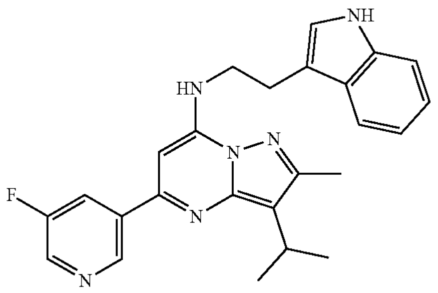 [SMILES: Cc1nn2c(NCCc3c[nH]c4ccccc34)cc(-c3cncc(F)c3)nc2c1C(C)C]
I-84
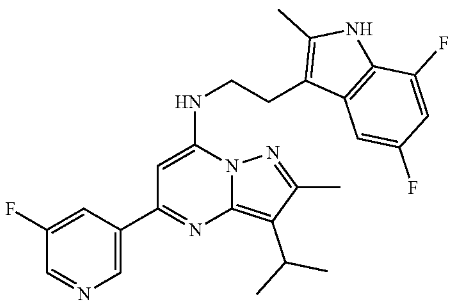 [SMILES: Cc1nn2c(NCCc3c(C)[nH]c4c(F)cc(F)cc34)cc(-c3cncc(F)c3)nc2c1C(C)C]
I-85
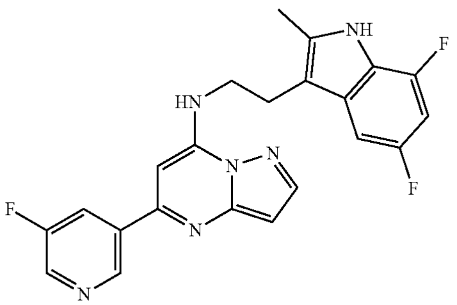
I-86
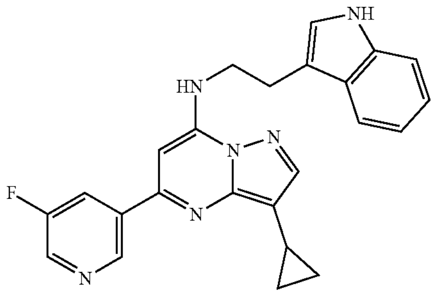 [SMILES: Fc1cncc(-c2cc(NCCc3c[nH]c4ccccc34)n3ncc(C4CC4)c3n2)c1]
I-87
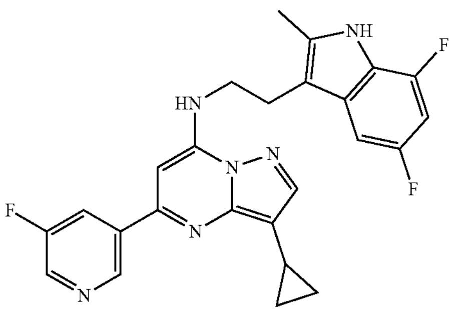 [SMILES: Cc1[nH]c2c(F)cc(F)cc2c1CCNc1cc(-c2cncc(F)c2)nc2c(C3CC3)cnn12]

-continued
I-89
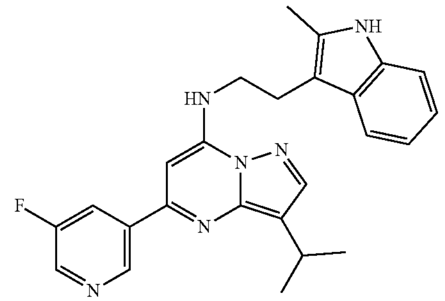 [SMILES: Cc1[nH]c2ccccc2c1CCNc1cc(-c2cncc(F)c2)nc2c(C(C)C)cnn12]
I-90
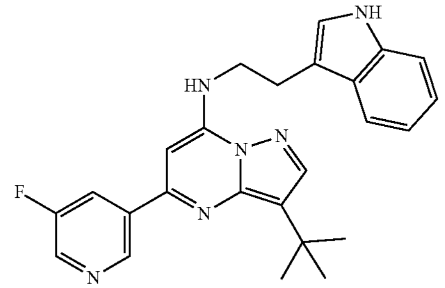 [SMILES: CC(C)(C)c1cnn2c(NCCc3c[nH]c4ccccc34)cc(-c3cncc(F)c3)nc12]
I-91
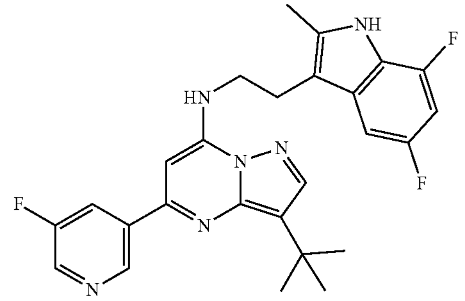 [SMILES: Cc1[nH]c2c(F)cc(F)cc2c1CCNc1cc(-c2cncc(F)c2)nc2c(C(C)(C)C)cnn12]
I-92
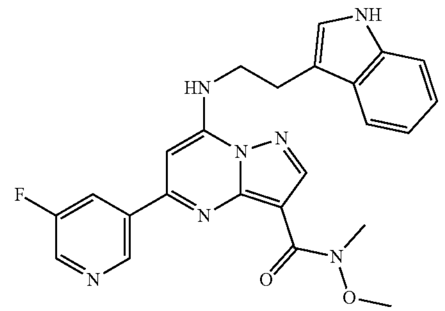 [SMILES: CON(C)C(=O)c1cnn2c(NCCc3c[nH]c4ccccc34)cc(-c3cncc(F)c3)nc12]
I-96
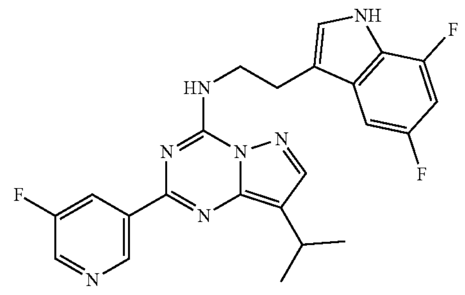 [SMILES: CC(C)c1cnn2c(NCCc3c[nH]c4c(F)cc(F)cc34)nc(-c3cncc(F)c3)nc12]
-continued
I-99
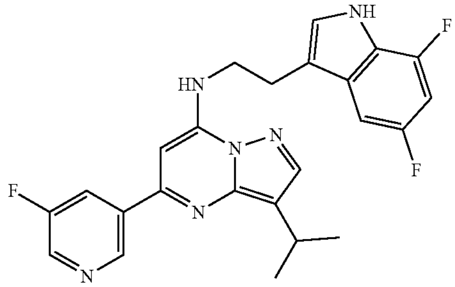 [SMILES: CC(C)c1cnn2c(NCCc3c[nH]c4c(F)cc(F)cc34)cc(-c3cncc(F)c3)nc12]
I-103
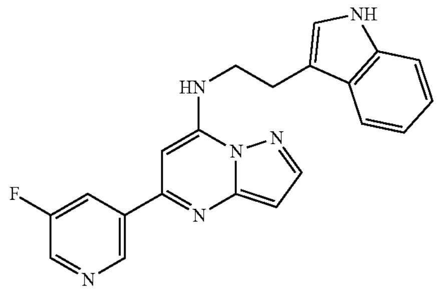 [SMILES: Fc1cncc(-c2cc(NCCc3c[nH]c4ccccc34)n3nccc3n2)c1]
I-107
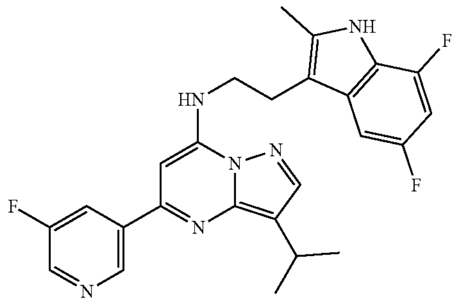 [SMILES: Cc1[nH]c2c(F)cc(F)cc2c1CCNc1cc(-c2cncc(F)c2)nc2c(C(C)C)cnn12]
I-112
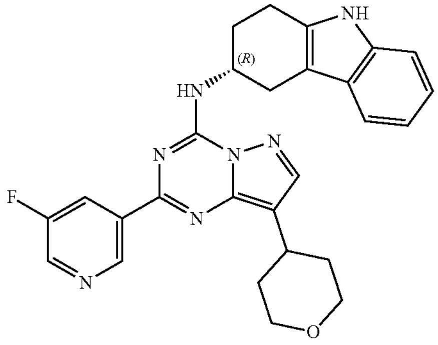
I-115
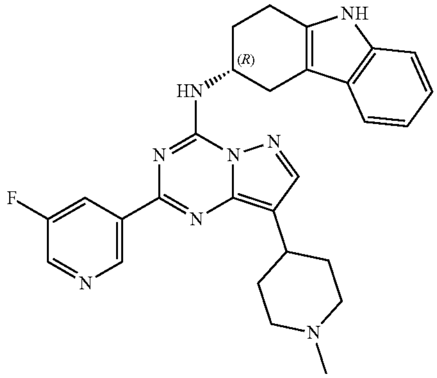

-continued
I-117
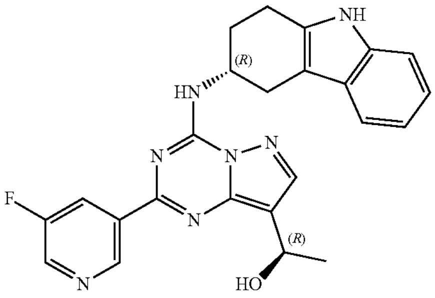
I-118
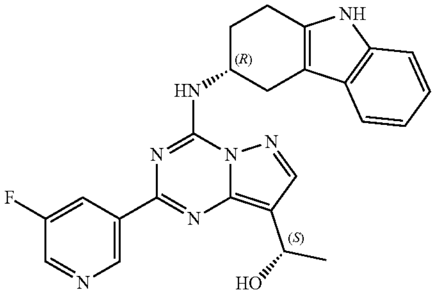
I-123
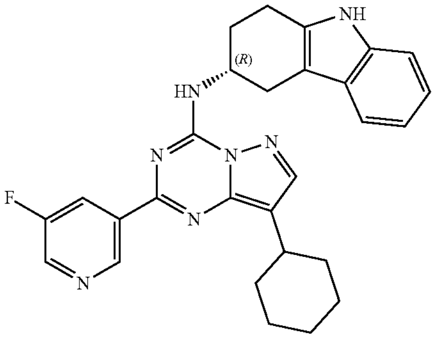
I-129
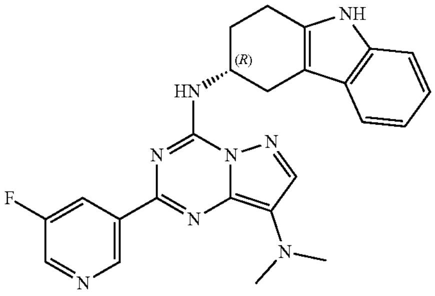
I-130
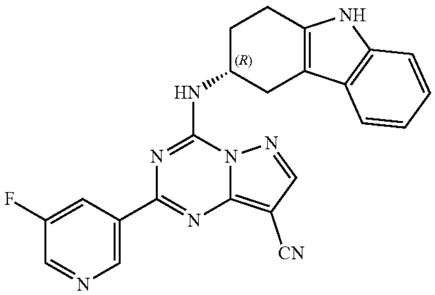
-continued
I-131
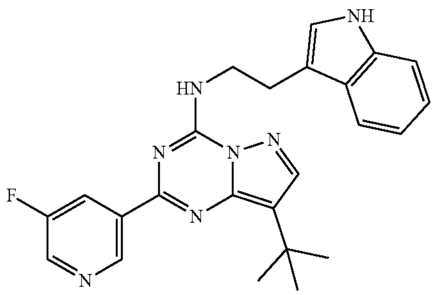 [SMILES: CC(C)(C)c1cnn2c(NCCc3c[nH]c4ccccc34)nc(-c3cncc(F)c3)nc12]
I-132
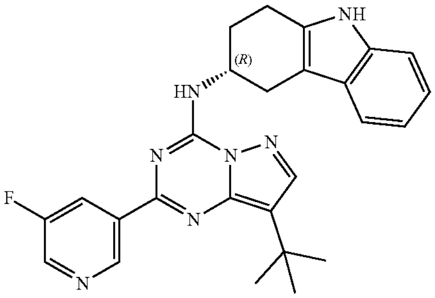
I-133
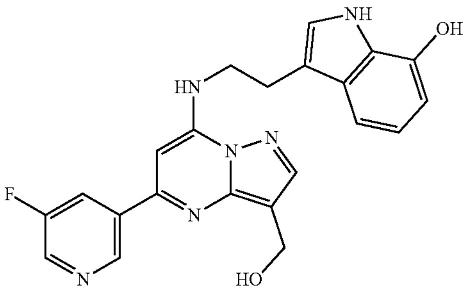 [SMILES: OCc1cnn2c(NCCc3c[nH]c4c(O)cccc34)cc(-c3cncc(F)c3)nc12]
I-137a
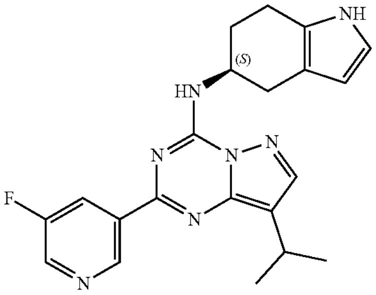
I-137b
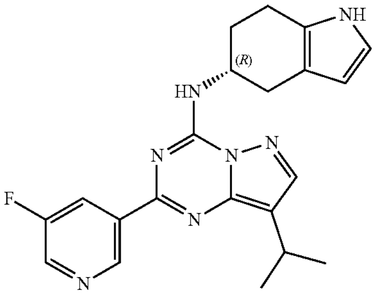

-continued
I-137c
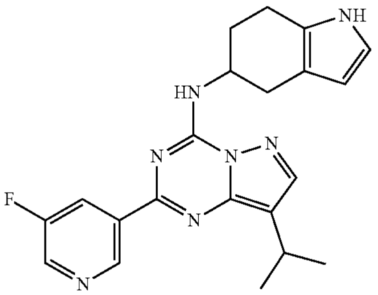 [SMILES: CC(C)c1cnn2c(NC3CCc4[nH]ccc4C3)nc(-c3cncc(F)c3)nc12]
I-139a
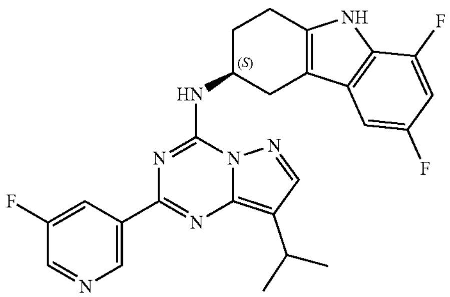
I-139b
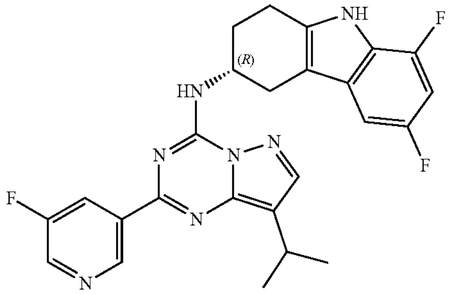
I-139c
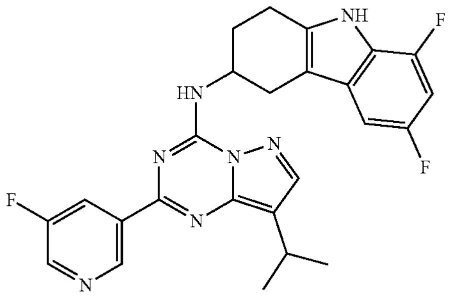 [SMILES: CC(C)c1cnn2c(NC3CCc4[nH]c5c(F)cc(F)cc5c4C3)nc(-c3cncc(F)c3)nc12]
I-141
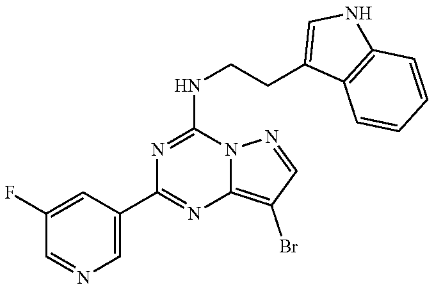 [SMILES: Fc1cncc(-c2nc(NCCc3c[nH]c4ccccc34)n3ncc(Br)c3n2)c1]
-continued
I-142
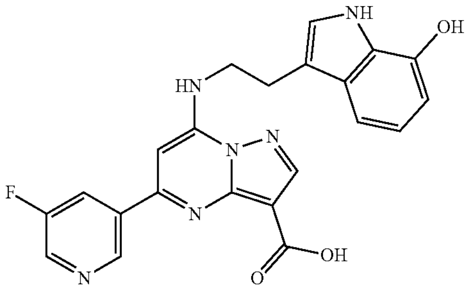 [SMILES: O=C(O)c1cnn2c(NCCc3c[nH]c4c(O)cccc34)cc(-c3cncc(F)c3)nc12]
I-143
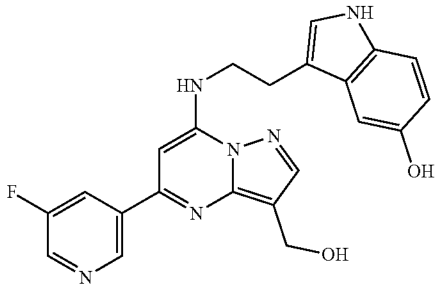 [SMILES: OCc1cnn2c(NCCc3c[nH]c4ccc(O)cc34)cc(-c3cncc(F)c3)nc12]
I-149
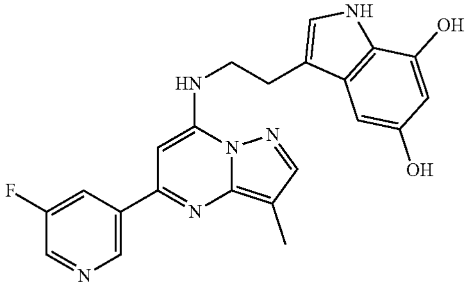 [SMILES: Cc1cnn2c(NCCc3c[nH]c4c(O)cc(O)cc34)cc(-c3cncc(F)c3)nc12]
I-154
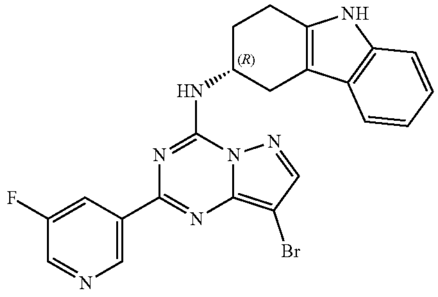
I-157
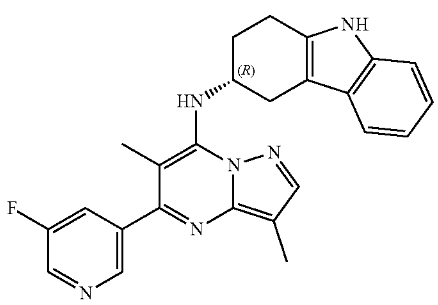

-continued
I-164
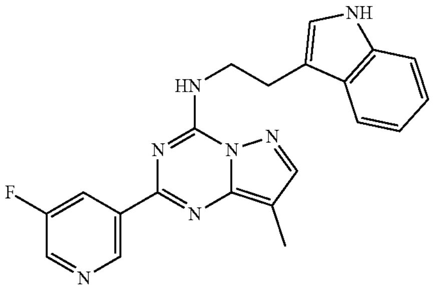 [SMILES: Cc1cnn2c(NCCc3c[nH]c4ccccc34)nc(-c3cncc(F)c3)nc12]
I-165
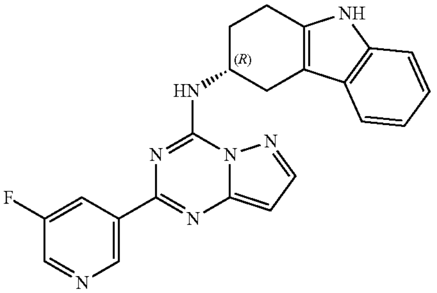
I-168
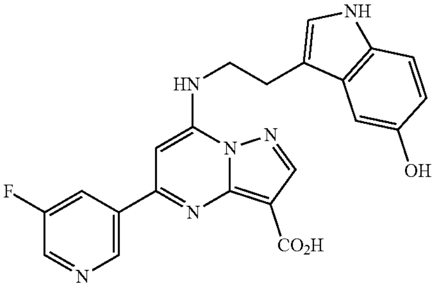 [SMILES: O=C(O)c1cnn2c(NCCc3c[nH]c4ccc(O)cc34)cc(-c3cncc(F)c3)nc12]
I-169
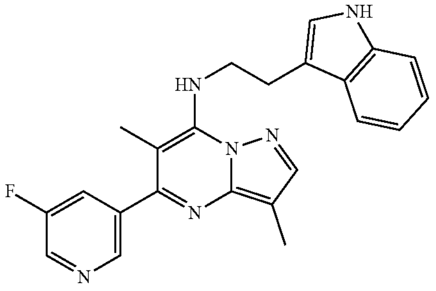 [SMILES: Cc1c(-c2cncc(F)c2)nc2c(C)cnn2c1NCCc1c[nH]c2ccccc12]
I-172
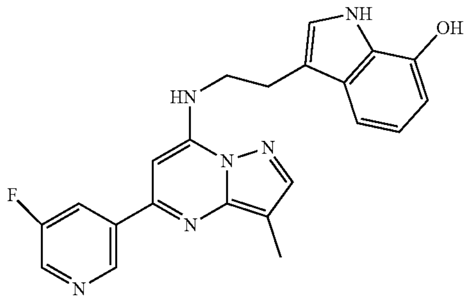 [SMILES: Cc1cnn2c(NCCc3c[nH]c4c(O)cccc34)cc(-c3cncc(F)c3)nc12]
-continued
I-177
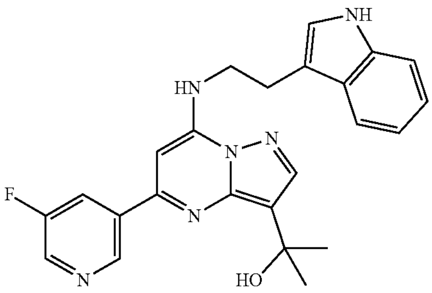 [SMILES: CC(C)(O)c1cnn2c(NCCc3c[nH]c4ccccc34)cc(-c3cncc(F)c3)nc12]
I-179
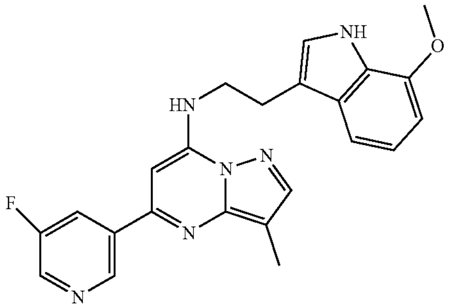 [SMILES: COc1cccc2c(CCNc3cc(-c4cncc(F)c4)nc4c(C)cnn34)c[nH]c12]
I-183
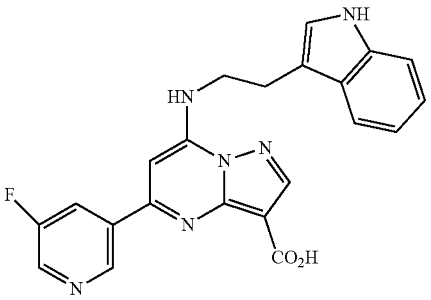 [SMILES: O=C(O)c1cnn2c(NCCc3c[nH]c4ccccc34)cc(-c3cncc(F)c3)nc12]
I-197
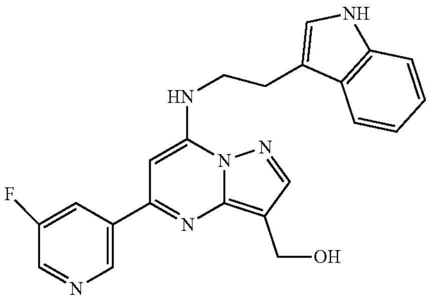 [SMILES: OCc1cnn2c(NCCc3c[nH]c4ccccc34)cc(-c3cncc(F)c3)nc12]
I-198a
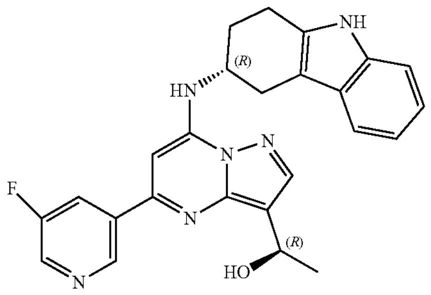

-continued
I-198b
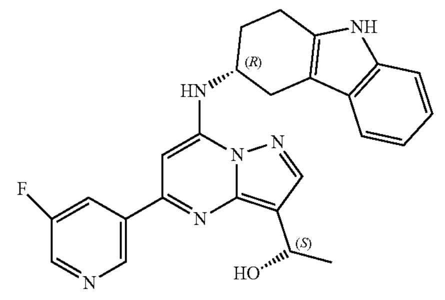
I-198c
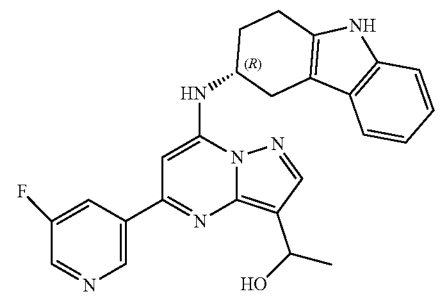
I-200
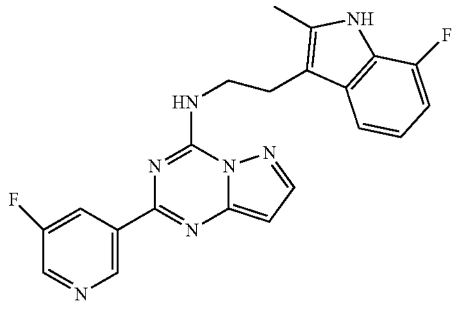 [SMILES: Cc1[nH]c2c(F)cccc2c1CCNc1nc(-c2cncc(F)c2)nc2ccnn12]
I-202
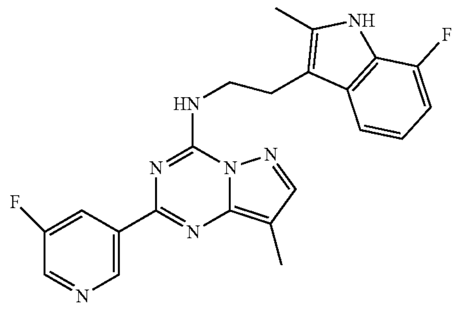 [SMILES: Cc1[nH]c2c(F)cccc2c1CCNc1nc(-c2cncc(F)c2)nc2c(C)cnn12]
I-203
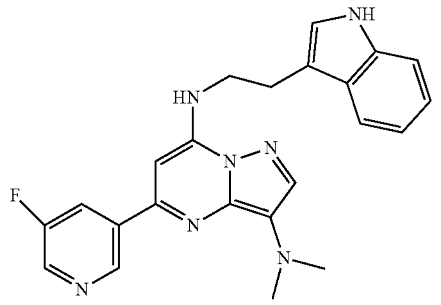 [SMILES: CN(C)c1cnn2c(NCCc3c[nH]c4ccccc34)cc(-c3cncc(F)c3)nc12]
-continued
I-212
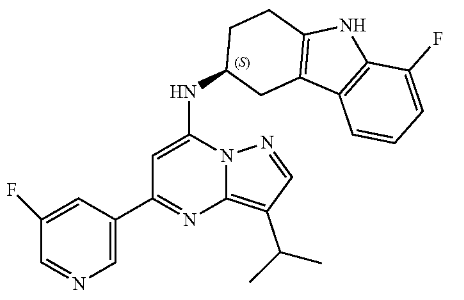
I-214
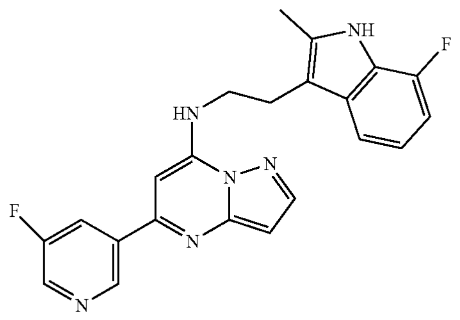 [SMILES: Cc1[nH]c2c(F)cccc2c1CCNc1cc(-c2cncc(F)c2)nc2ccnn12]
I-215
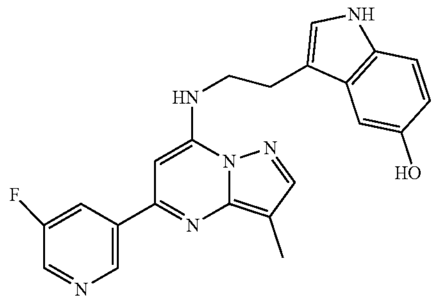 [SMILES: Cc1cnn2c(NCCc3c[nH]c4ccc(O)cc34)cc(-c3cncc(F)c3)nc12]
I-216a
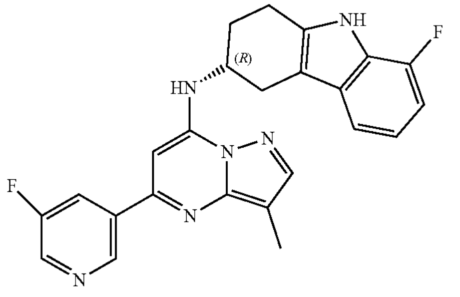
I-216b
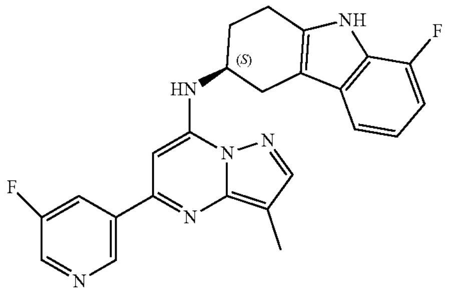

-continued
I-221
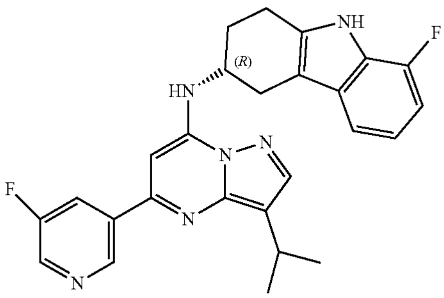
I-222a
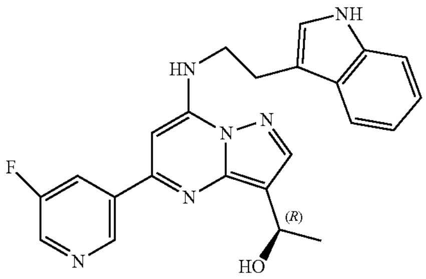
I-222b
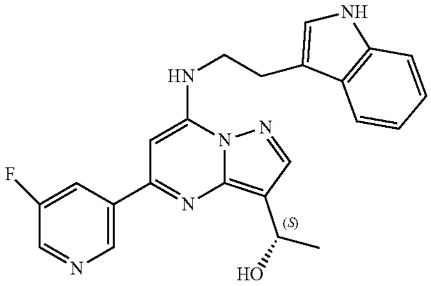
I-222c
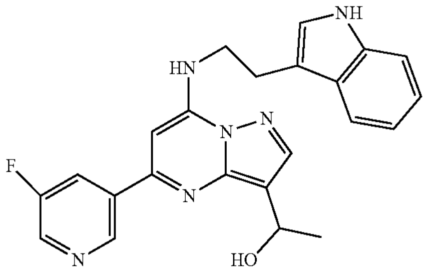 [SMILES: CC(O)c1cnn2c(NCCc3c[nH]c4ccccc34)cc(-c3cncc(F)c3)nc12]
I-224
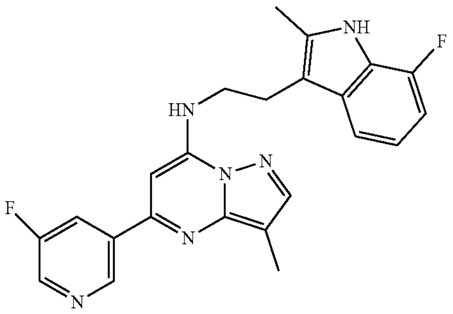 [SMILES: Cc1[nH]c2c(F)cccc2c1CCNc1cc(-c2cncc(F)c2)nc2c(C)cnn12]
-continued
I-225
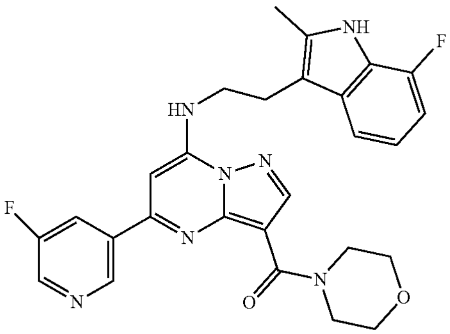 [SMILES: Cc1[nH]c2c(F)cccc2c1CCNc1cc(-c2cncc(F)c2)nc2c(C(=O)N3CCOCC3)cnn12]
I-226
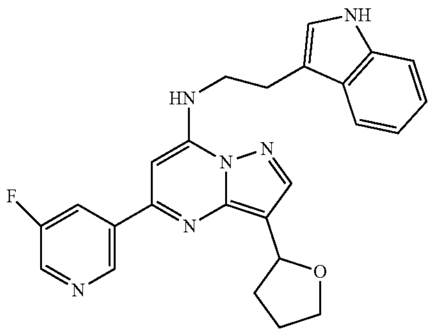 [SMILES: Fc1cncc(-c2cc(NCCc3c[nH]c4ccccc34)n3ncc(C4CCCO4)c3n2)c1]
I-230
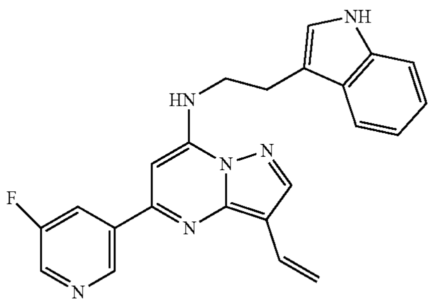 [SMILES: C=Cc1cnn2c(NCCc3c[nH]c4ccccc34)cc(-c3cncc(F)c3)nc12]
I-231
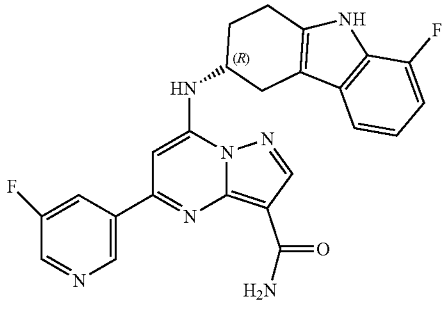
I-235
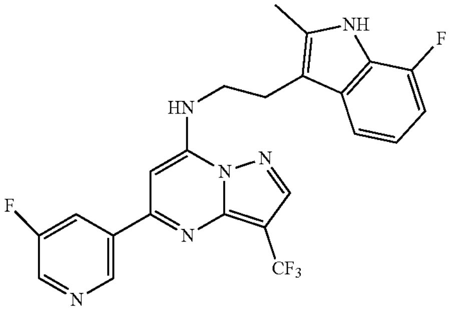 [SMILES: Cc1[nH]c2c(F)cccc2c1CCNc1cc(-c2cncc(F)c2)nc2c(C(F)(F)F)cnn12]

-continued
I-236
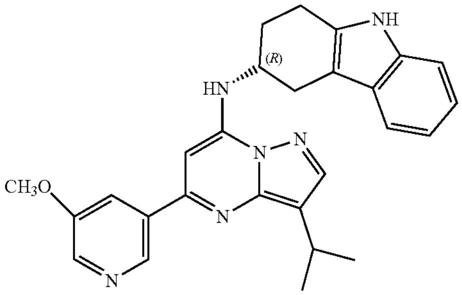
I-237
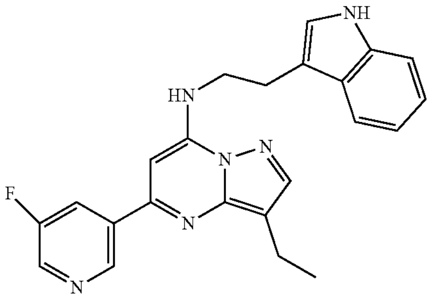 [SMILES: CCc1cnn2c(NCCc3c[nH]c4ccccc34)cc(-c3cncc(F)c3)nc12]
I-243a
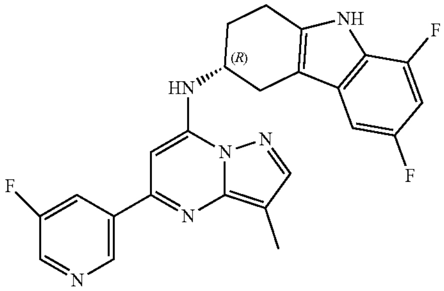
I-243b
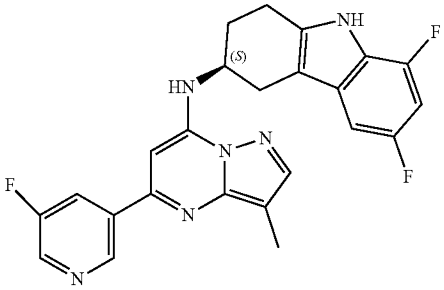
I-245
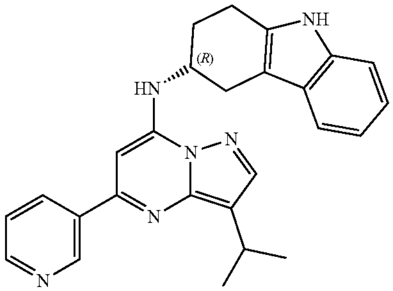
-continued
I-247a
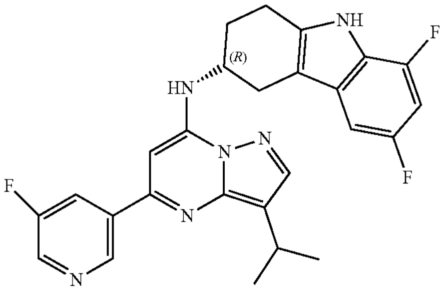
I-247b
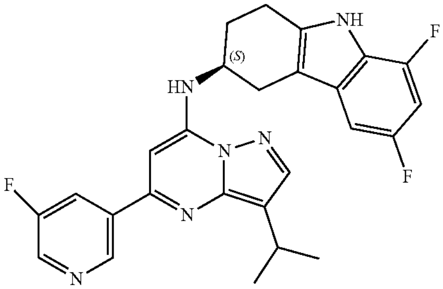
I-249a
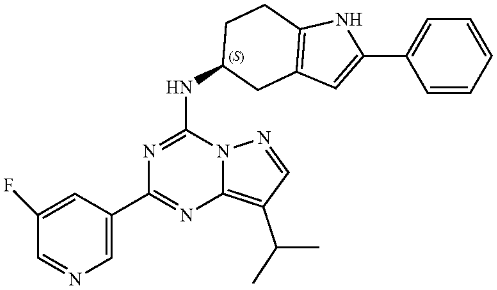
I-249b
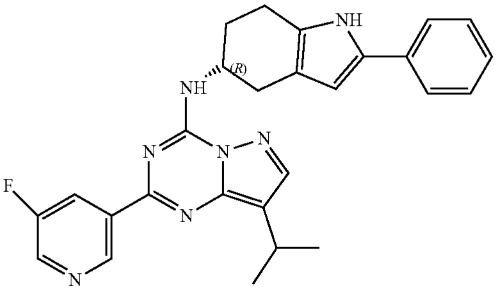
I-249c
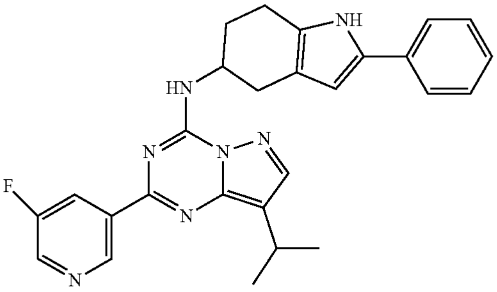 [SMILES: CC(C)c1cnn2c(NC3CCc4[nH]c(-c5ccccc5)cc4C3)nc(-c3cncc(F)c3)nc12]

-continued
I-251
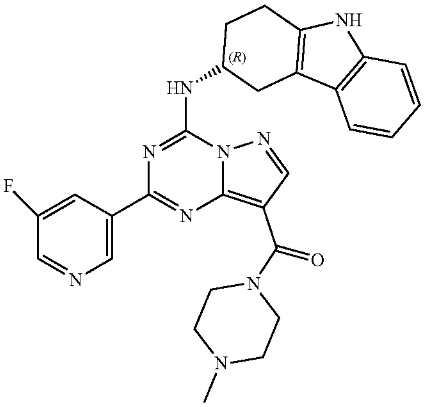
I-253
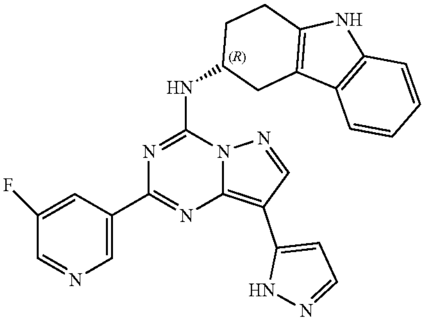
I-255
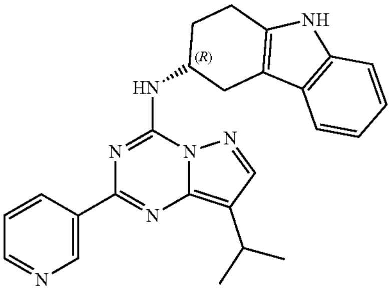
I-259a
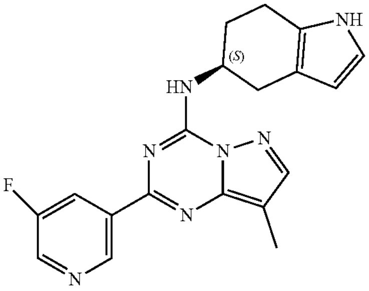
I-259b
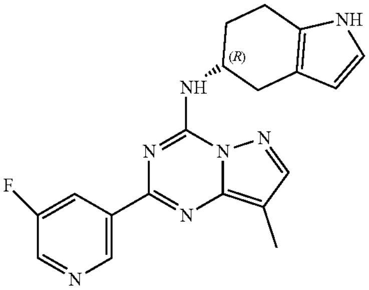
-continued
I-259c
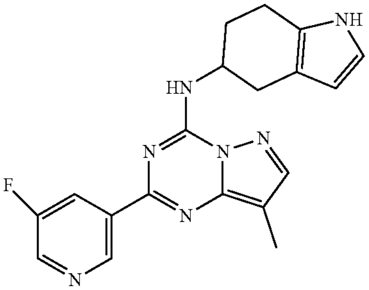 [SMILES: Cc1cnn2c(NC3CCc4[nH]ccc4C3)nc(-c3cncc(F)c3)nc12]
I-262
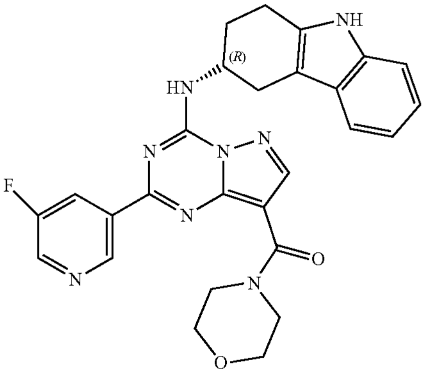
I-265
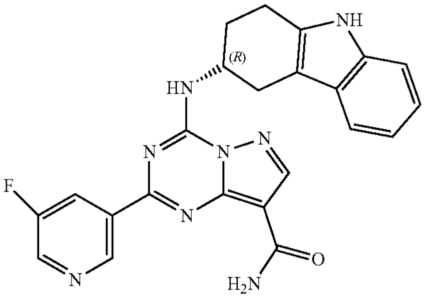
I-267
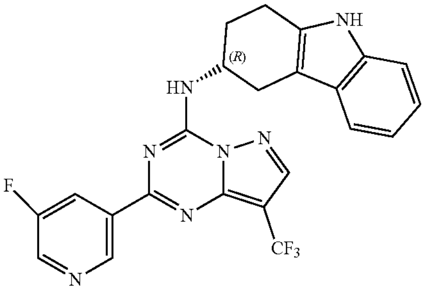
I-273
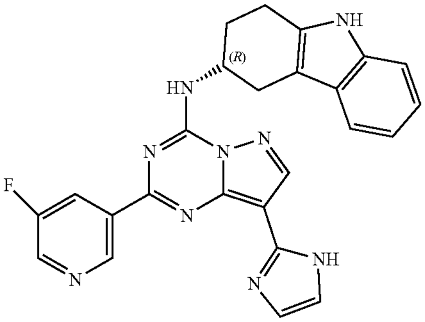

I-274
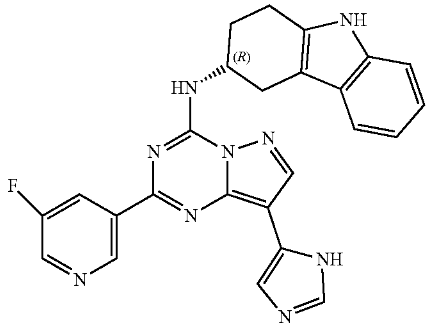
I-275
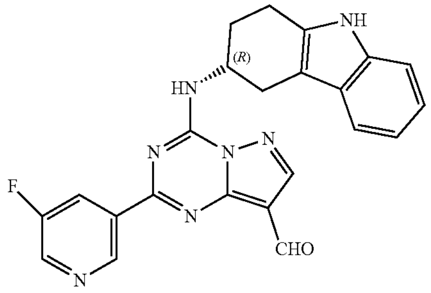
I-276
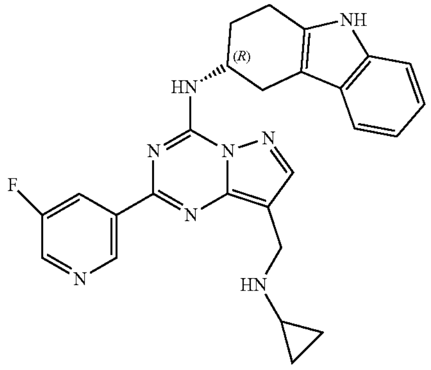
I-277
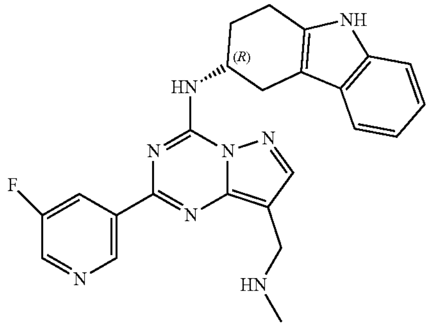
I-278
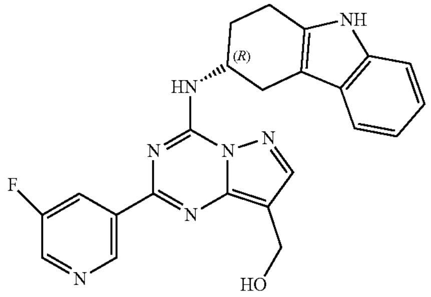
I-279
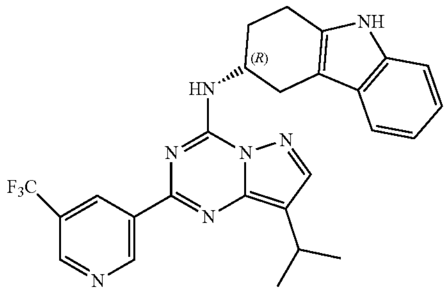
I-280
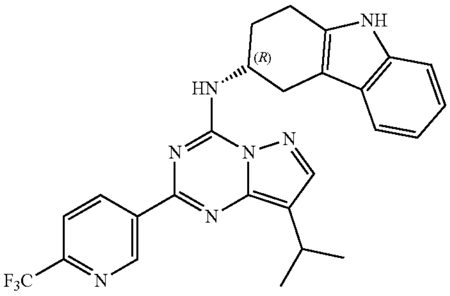
I-281
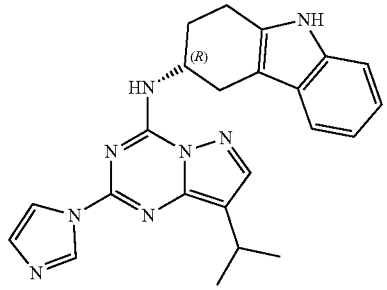
I-282
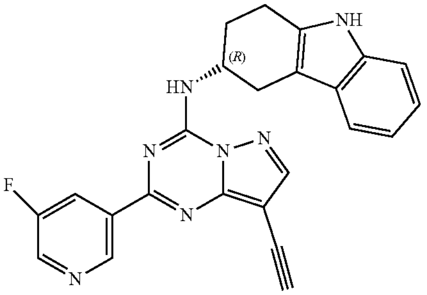
I-283
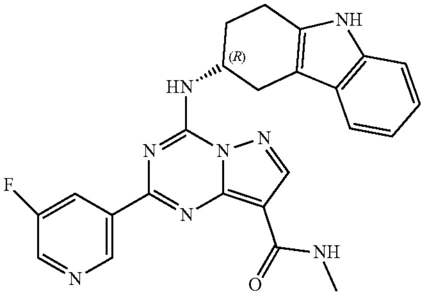

-continued
I-285
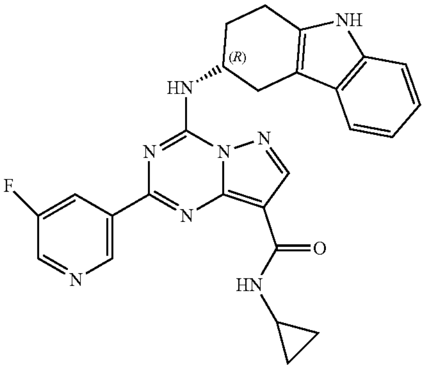
I-286
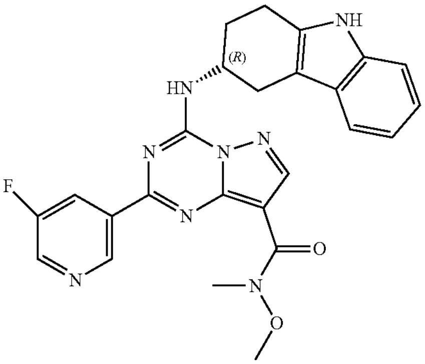
I-287
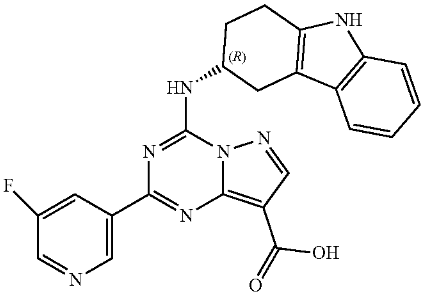
I-288
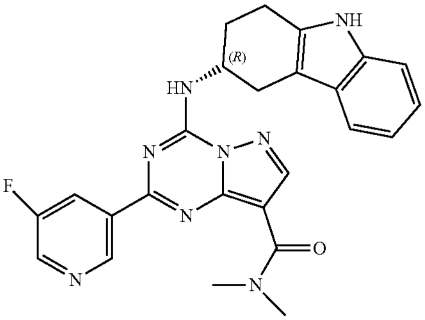
or a pharmaceutically acceptable salt thereof.
8. The method according to claim 4, wherein the compound is selected from
I-129
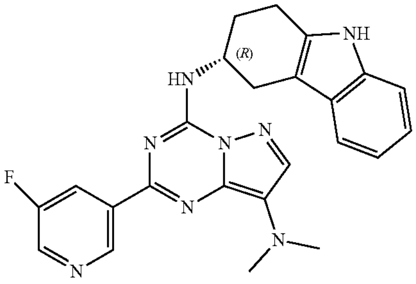
I-255
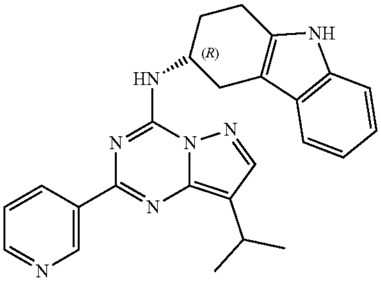
I-118
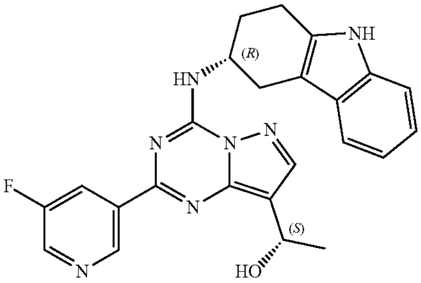
I-112
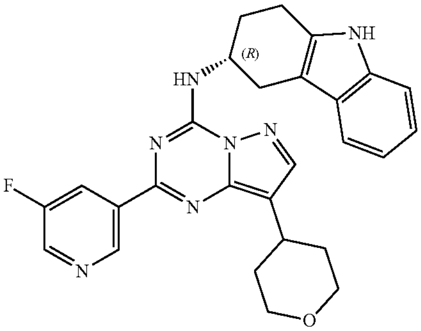
I-40
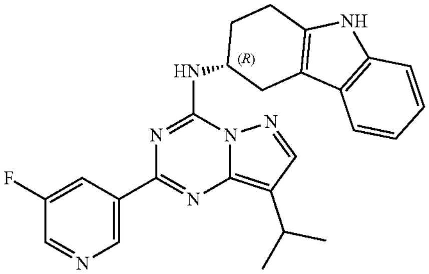

-continued

I-130

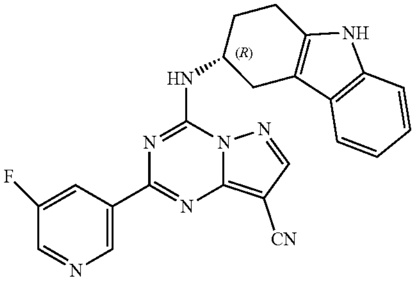

I-276

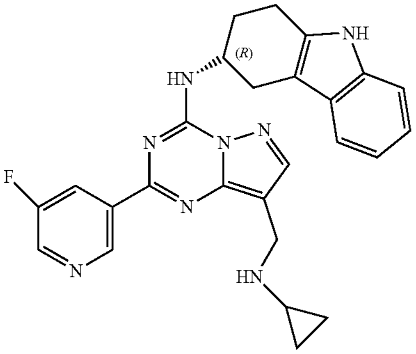

I-137b

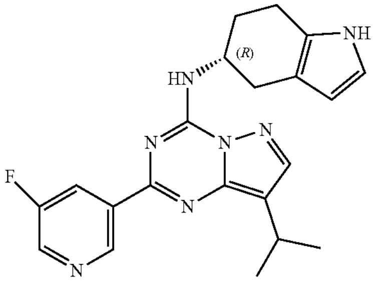

I-259b

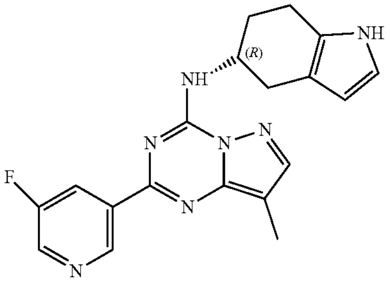

I-165

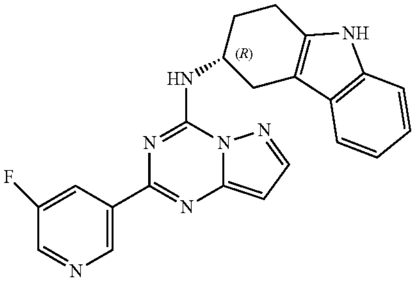

or a pharmaceutically acceptable salt thereof.

9. The method according to claim 4, wherein the compound is

I-129

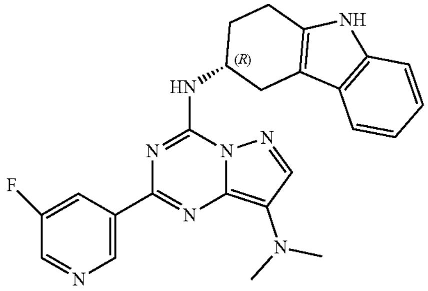

or a pharmaceutically acceptable salt thereof.

10. The method according to claim 4, wherein the compound is

I-137b

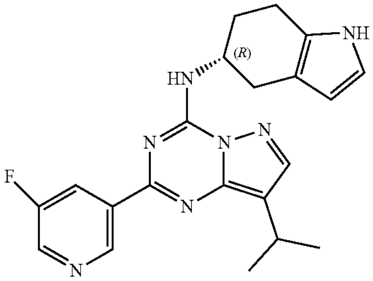

or a pharmaceutically acceptable salt thereof.

11. The method according to claim 4, wherein the compound is

I-40

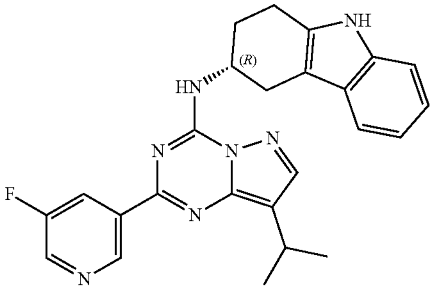

or a pharmaceutically acceptable salt thereof.

12. The method according to claim 4, wherein the compound is

I-259b

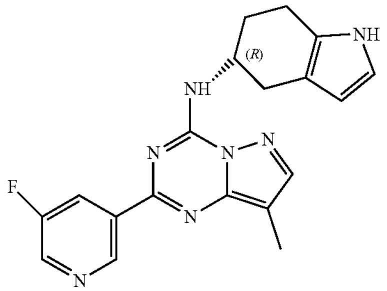

or a pharmaceutically acceptable salt thereof.

13. The method according to claim 4, wherein the AHR-mediated disorder is a cancer.

14. The method according to claim 4, wherein the AHR-mediated disorder is an inflammatory disorder.

15. The method according to claim 13, wherein the cancer is selected from bladder cancer, melanoma, ovarian cancer, head and neck squamous cell carcinoma (HNSCC), lung cancer, kidney cancer, stomach cancer, esophageal cancer, and acute myeloid leukemia (AML).

16. A method for treating a cancer in a patient in need thereof, comprising administering to said patient a compound selected from:

I-2

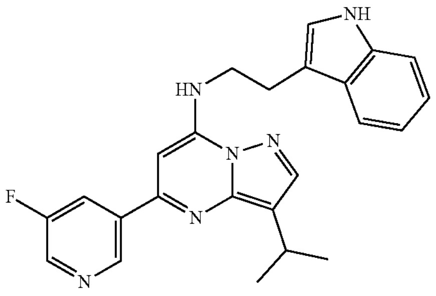

I-16

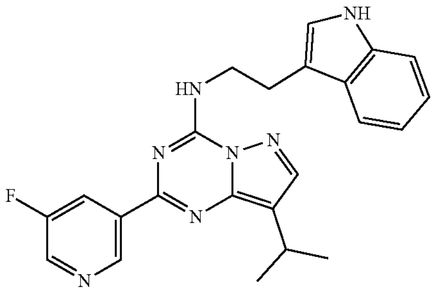 [SMILES: CC(C)c1cnn2c(NCCc3c[nH]c4ccccc34)nc(-c3cncc(F)c3)nc12]

-continued

I-24

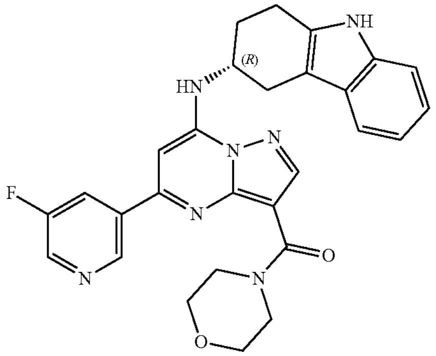

I-25

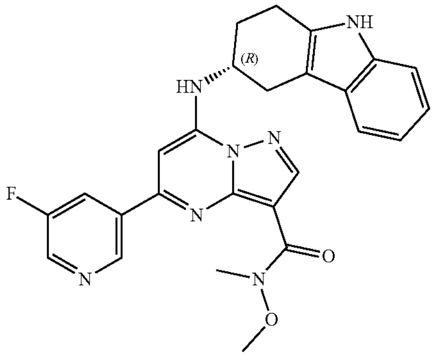

I-29

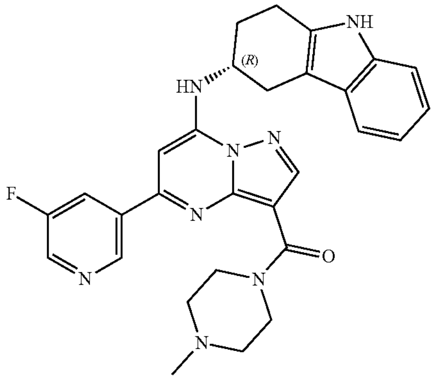

I-33

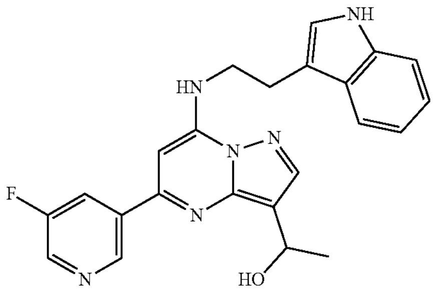 [SMILES: CC(O)c1cnn2c(NCCc3c[nH]c4ccccc34)cc(-c3cncc(F)c3)nc12]

-continued
I-34
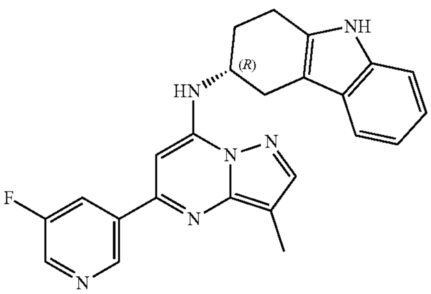
I-35
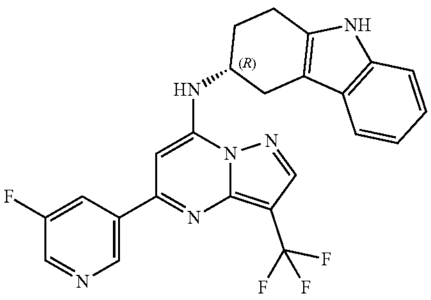
I-38
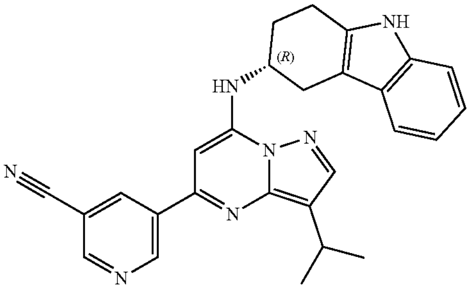
I-39
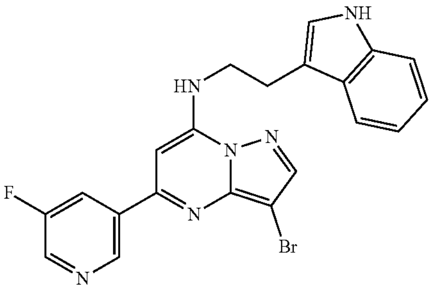 [SMILES: Fc1cncc(-c2cc(NCCc3c[nH]c4ccccc34)n3ncc(Br)c3n2)c1]
I-40
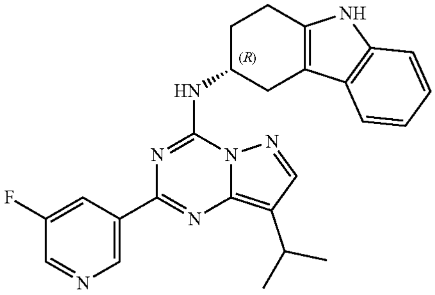
-continued
I-41
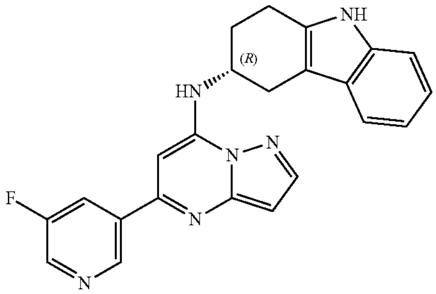
I-43
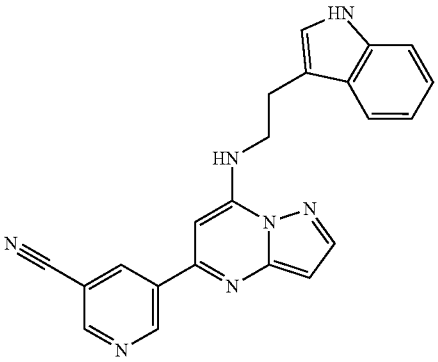 [SMILES: N#Cc1cncc(-c2cc(NCCc3c[nH]c4ccccc34)n3nccc3n2)c1]
I-46
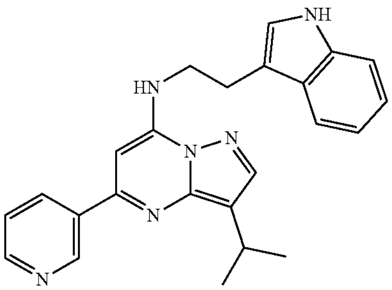 [SMILES: CC(C)c1cnn2c(NCCc3c[nH]c4ccccc34)cc(-c3cccnc3)nc12]
I-47
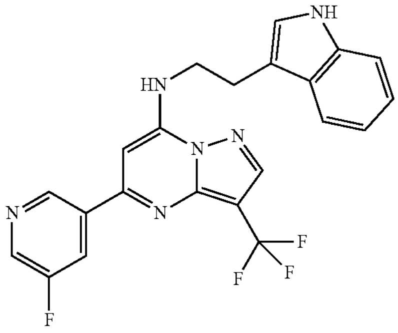 [SMILES: Fc1cncc(-c2cc(NCCc3c[nH]c4ccccc34)n3ncc(C(F)(F)F)c3n2)c1]
I-55
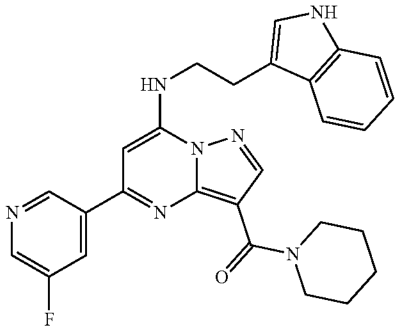 [SMILES: O=C(c1cnn2c(NCCc3c[nH]c4ccccc34)cc(-c3cncc(F)c3)nc12)N1CCCCC1]

-continued
I-56
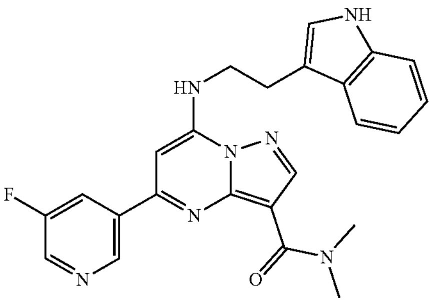 [SMILES: CN(C)C(=O)c1cnn2c(NCCc3c[nH]c4ccccc34)cc(-c3cncc(F)c3)nc12]
I-57
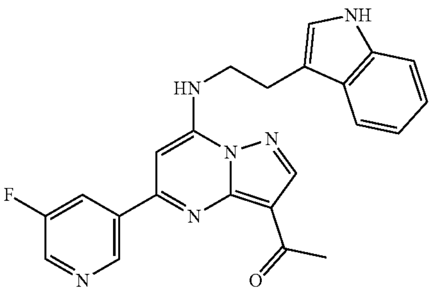 [SMILES: CC(=O)c1cnn2c(NCCc3c[nH]c4ccccc34)cc(-c3cncc(F)c3)nc12]
I-58
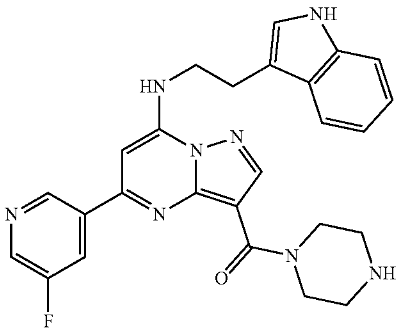 [SMILES: O=C(c1cnn2c(NCCc3c[nH]c4ccccc34)cc(-c3cncc(F)c3)nc12)N1CCNCC1]
I-61
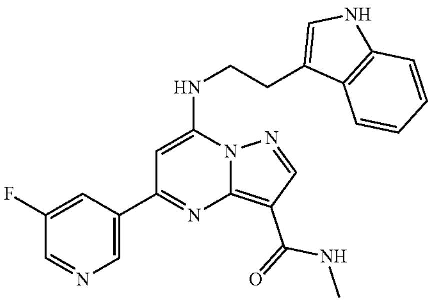 [SMILES: CNC(=O)c1cnn2c(NCCc3c[nH]c4ccccc34)cc(-c3cncc(F)c3)nc12]
I-65
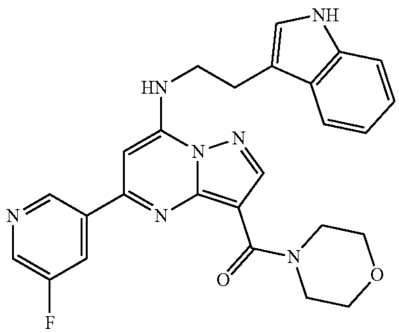 [SMILES: O=C(c1cnn2c(NCCc3c[nH]c4ccccc34)cc(-c3cncc(F)c3)nc12)N1CCOCC1]
-continued
I-66
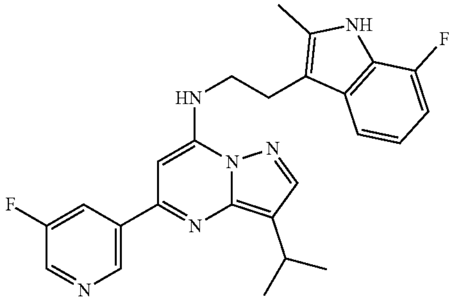
I-68
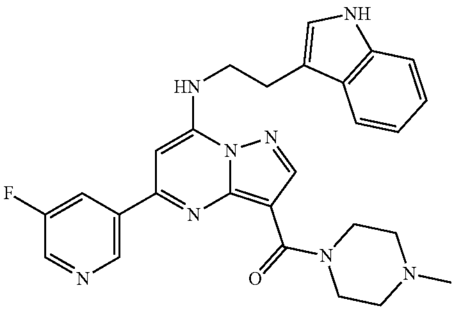 [SMILES: CN1CCN(C(=O)c2cnn3c(NCCc4c[nH]c5ccccc45)cc(-c4cncc(F)c4)nc23)CC1]
I-70
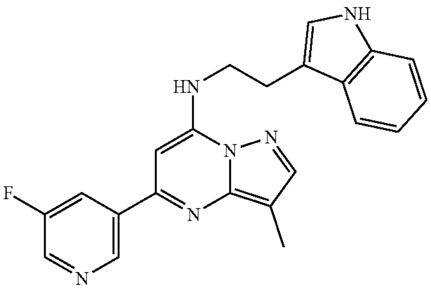 [SMILES: Cc1cnn2c(NCCc3c[nH]c4ccccc34)cc(-c3cncc(F)c3)nc12]
I-73
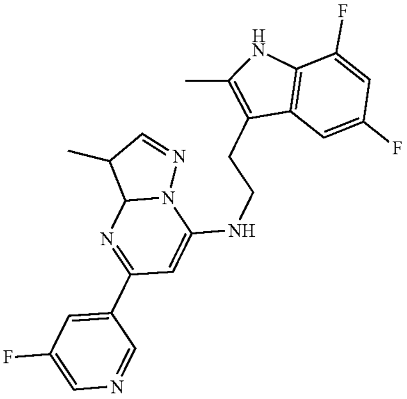 [SMILES: Cc1[nH]c2c(F)cc(F)cc2c1CCNC1=CC(c2cncc(F)c2)=NC2C(C)C=NN12]
I-75a
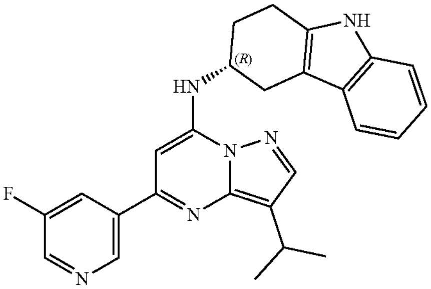

-continued
I-75b
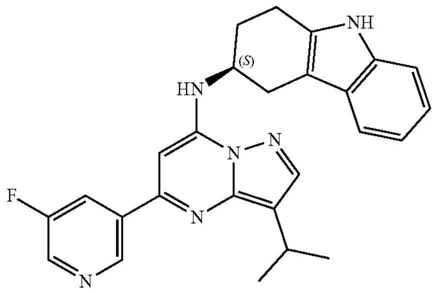
I-75c
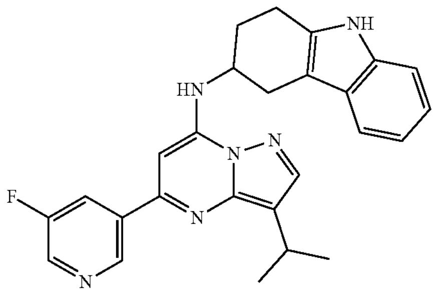 [SMILES: CC(C)c1cnn2c(NC3CCc4[nH]c5ccccc5c4C3)cc(-c3cncc(F)c3)nc12]
I-78
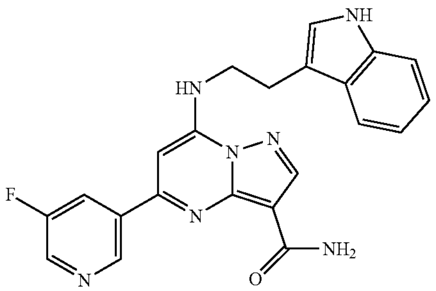 [SMILES: NC(=O)c1cnn2c(NCCc3c[nH]c4ccccc34)cc(-c3cncc(F)c3)nc12]
I-81
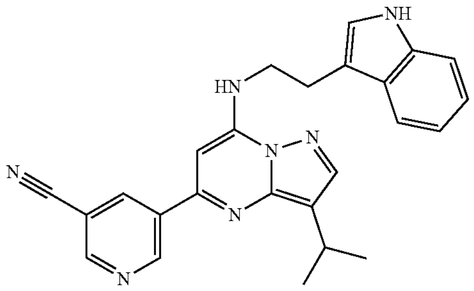 [SMILES: CC(C)c1cnn2c(NCCc3c[nH]c4ccccc34)cc(-c3cncc(C#N)c3)nc12]
I-83
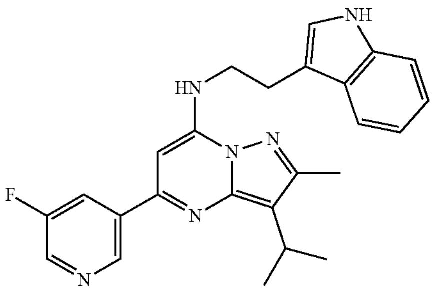 [SMILES: Cc1nn2c(NCCc3c[nH]c4ccccc34)cc(-c3cncc(F)c3)nc2c1C(C)C]
-continued
I-84
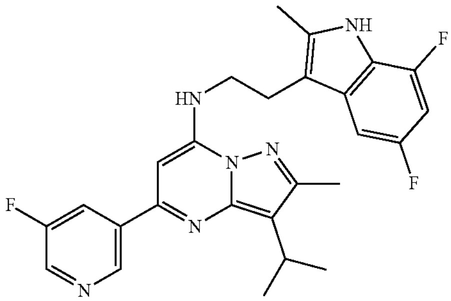 [SMILES: Cc1nn2c(NCCc3c(C)[nH]c4c(F)cc(F)cc34)cc(-c3cncc(F)c3)nc2c1C(C)C]
I-85
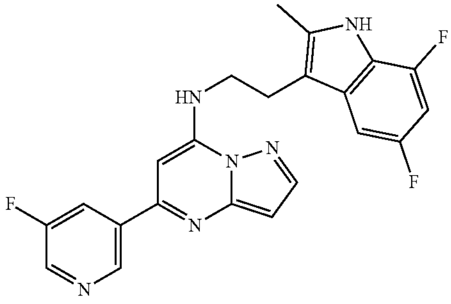 [SMILES: Cc1[nH]c2c(F)cc(F)cc2c1CCNc1cc(-c2cncc(F)c2)nc2ccnn12]
I-86
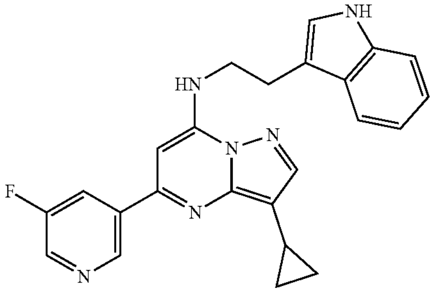 [SMILES: Fc1cncc(-c2cc(NCCc3c[nH]c4ccccc34)n3ncc(C4CC4)c3n2)c1]
I-87
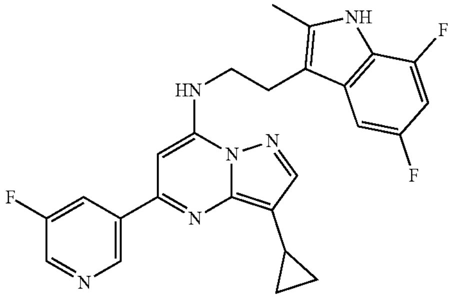 [SMILES: Cc1[nH]c2c(F)cc(F)cc2c1CCNc1cc(-c2cncc(F)c2)nc2c(C3CC3)cnn12]
I-89
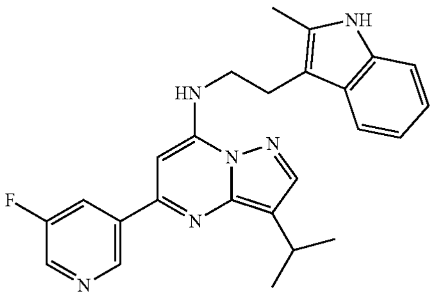 [SMILES: Cc1[nH]c2ccccc2c1CCNc1cc(-c2cncc(F)c2)nc2c(C(C)C)cnn12]

-continued
I-90
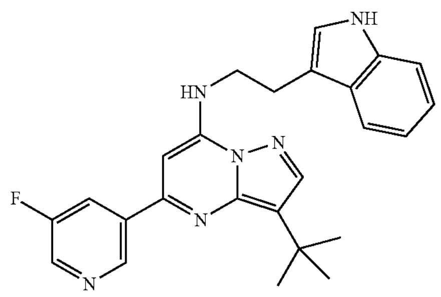 [SMILES: CC(C)(C)c1cnn2c(NCCc3c[nH]c4ccccc34)cc(-c3cncc(F)c3)nc12]
I-91
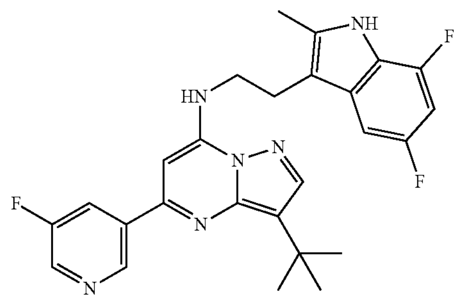 [SMILES: Cc1[nH]c2c(F)cc(F)cc2c1CCNc1cc(-c2cncc(F)c2)nc2c(C(C)(C)C)cnn12]
I-92
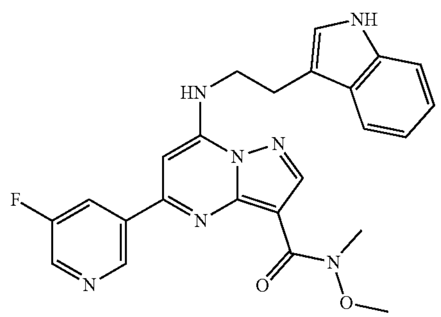 [SMILES: CON(C)C(=O)c1cnn2c(NCCc3c[nH]c4ccccc34)cc(-c3cncc(F)c3)nc12]
I-96
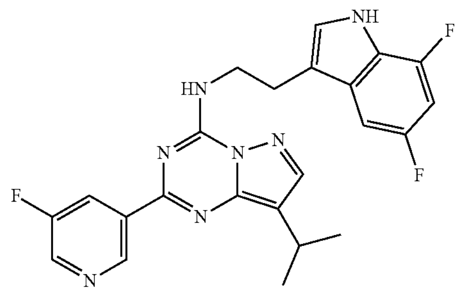 [SMILES: CC(C)c1cnn2c(NCCc3c[nH]c4c(F)cc(F)cc34)nc(-c3cncc(F)c3)nc12]
I-99
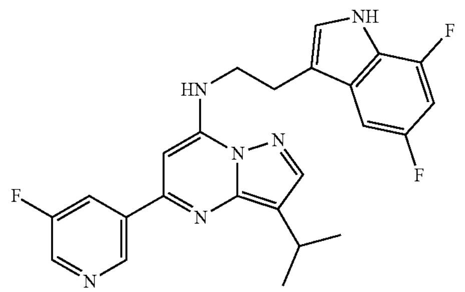 [SMILES: CC(C)c1cnn2c(NCCc3c[nH]c4c(F)cc(F)cc34)cc(-c3cncc(F)c3)nc12]
-continued
I-103
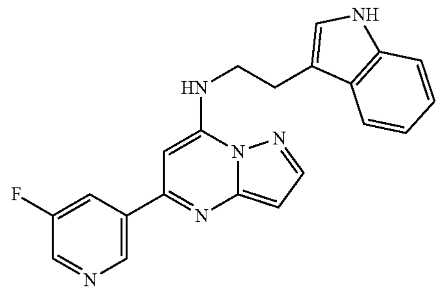 [SMILES: Fc1cncc(-c2cc(NCCc3c[nH]c4ccccc34)n3nccc3n2)c1]
I-107
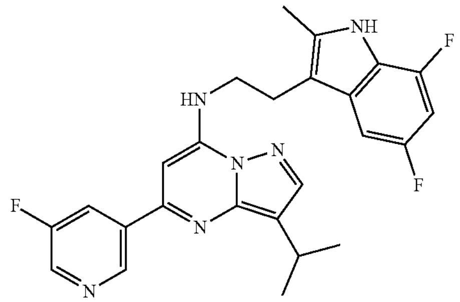 [SMILES: Cc1[nH]c2c(F)cc(F)cc2c1CCNc1cc(-c2cncc(F)c2)nc2c(C(C)C)cnn12]
I-112
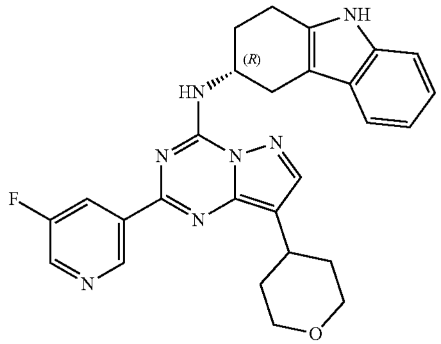
I-115
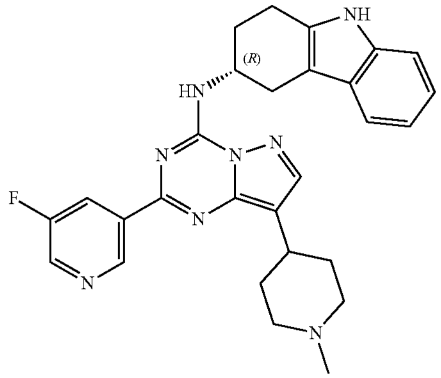
I-117
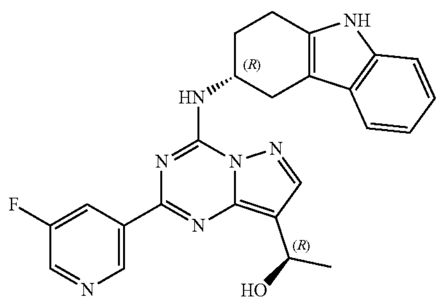

I-118
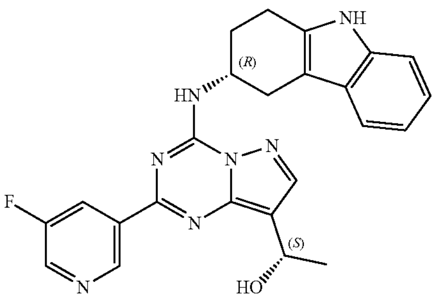
I-123
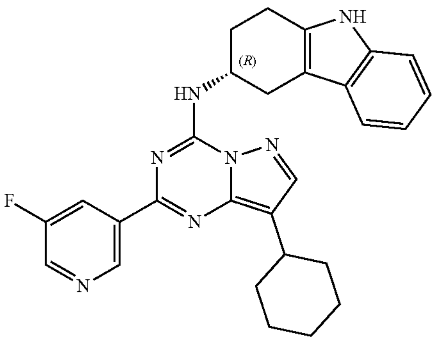
I-129
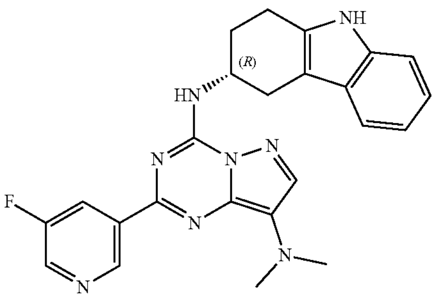
I-130
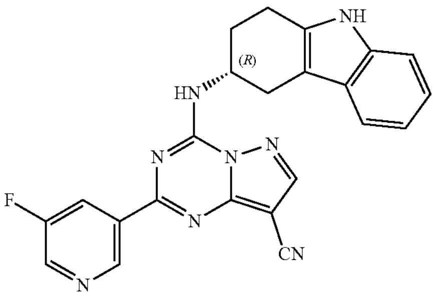
I-131
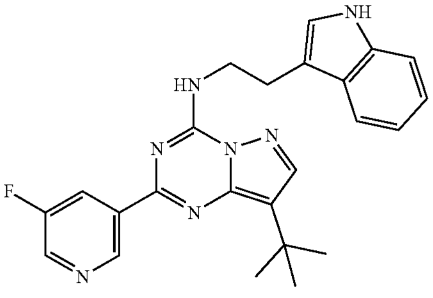 [SMILES: CC(C)(C)c1cnn2c(NCCc3c[nH]c4ccccc34)nc(-c3cncc(F)c3)nc12]
I-132
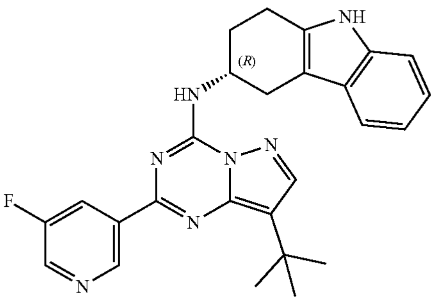
I-133
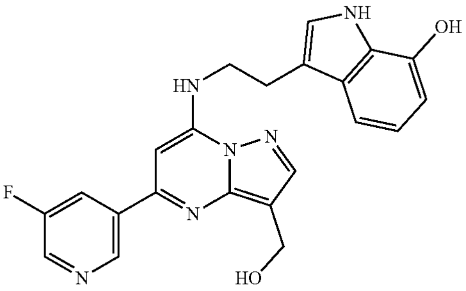 [SMILES: OCc1cnn2c(NCCc3c[nH]c4c(O)cccc34)cc(-c3cncc(F)c3)nc12]
I-137a
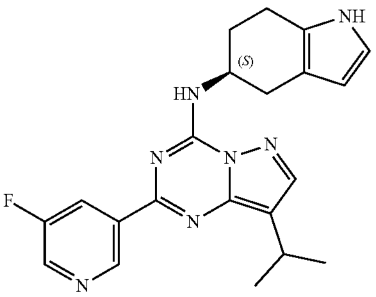
I-137b
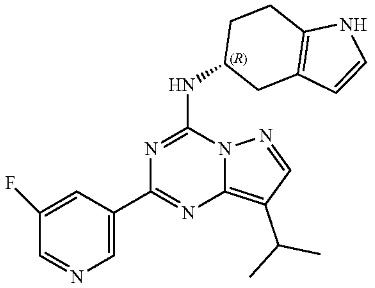
I-137c
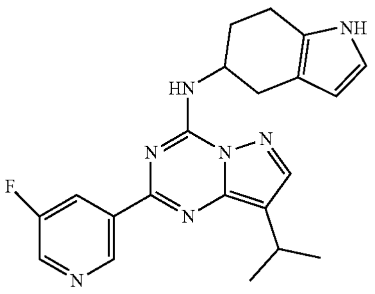 [SMILES: CC(C)c1cnn2c(NC3CCc4[nH]ccc4C3)nc(-c3cncc(F)c3)nc12]

-continued
I-139a
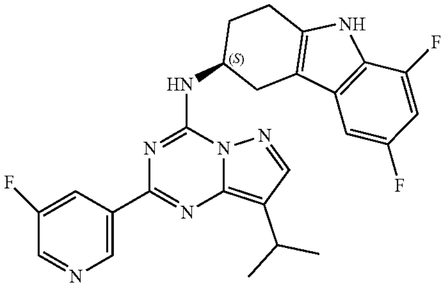
I-139b
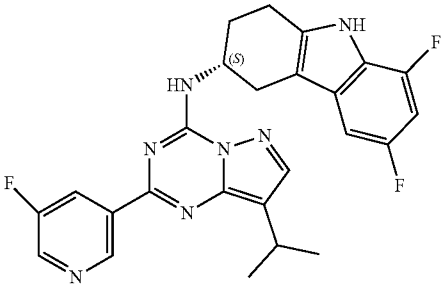
I-139c
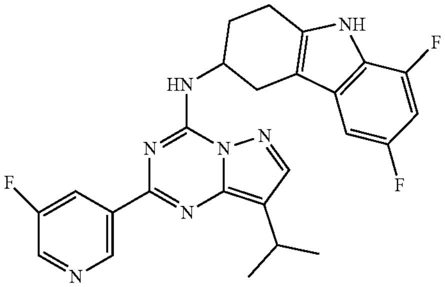 [SMILES: CC(C)c1cnn2c(NC3CCc4[nH]c5c(F)cc(F)cc5c4C3)nc(-c3cncc(F)c3)nc12]
I-141
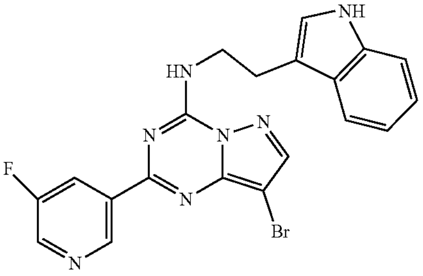 [SMILES: Fc1cncc(-c2nc(NCCc3c[nH]c4ccccc34)n3ncc(Br)c3n2)c1]
I-142
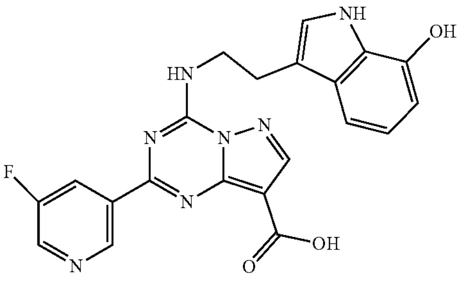 [SMILES: O=C(O)c1cnn2c(NCCc3c[nH]c4c(O)cccc34)nc(-c3cncc(F)c3)nc12]
-continued
I-143
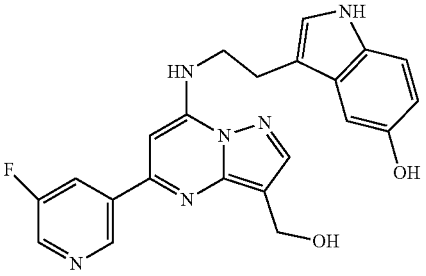 [SMILES: OCc1cnn2c(NCCc3c[nH]c4ccc(O)cc34)cc(-c3cncc(F)c3)nc12]
I-149
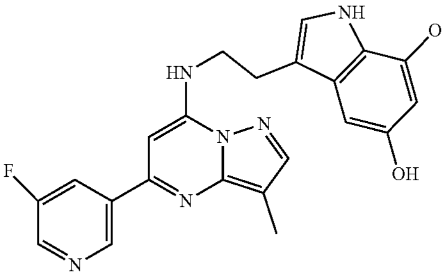 [SMILES: Cc1cnn2c(NCCc3c[nH]c4c(O)cc(O)cc34)cc(-c3cncc(F)c3)nc12]
I-154
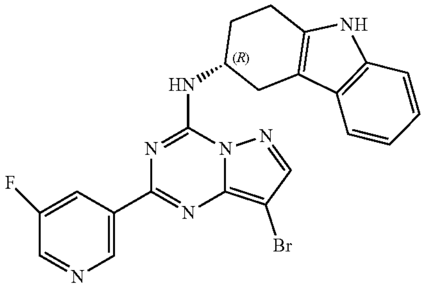
I-157
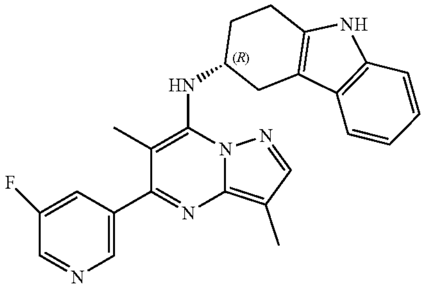
I-164
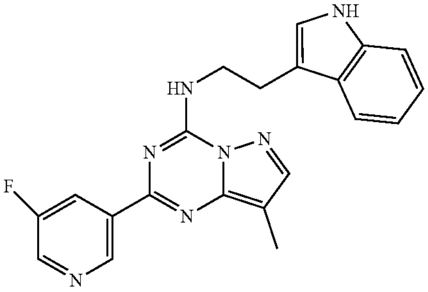 [SMILES: Cc1cnn2c(NCCc3c[nH]c4ccccc34)nc(-c3cncc(F)c3)nc12]

I-165
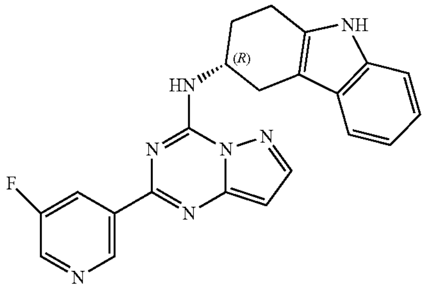
I-168
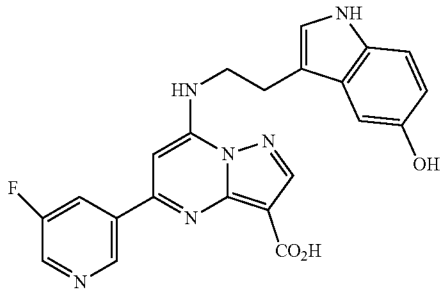 [SMILES: O=C(O)c1cnn2c(NCCc3c[nH]c4ccc(O)cc34)cc(-c3cncc(F)c3)nc12]
I-169
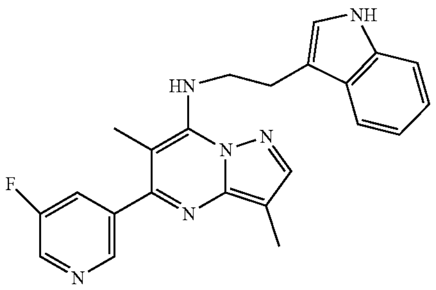 [SMILES: Cc1c(-c2cncc(F)c2)nc2c(C)cnn2c1NCCc1c[nH]c2ccccc12]
I-172
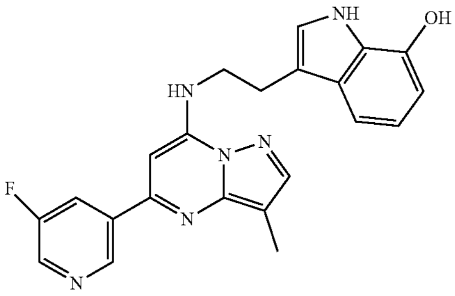 [SMILES: Cc1cnn2c(NCCc3c[nH]c4c(O)cccc34)cc(-c3cncc(F)c3)nc12]
I-177
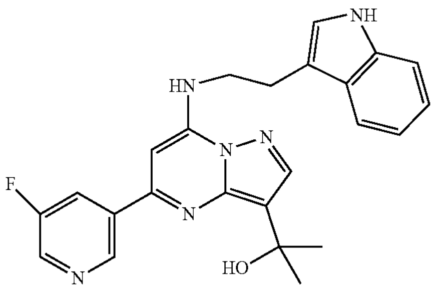 [SMILES: CC(C)(O)c1cnn2c(NCCc3c[nH]c4ccccc34)cc(-c3cncc(F)c3)nc12]
I-179
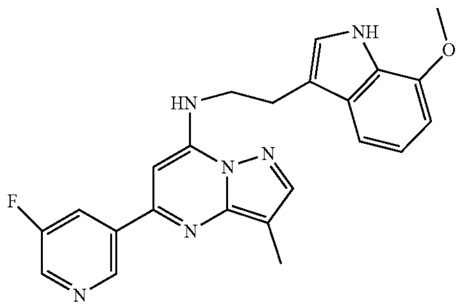 [SMILES: COc1cccc2c(CCNc3cc(-c4cncc(F)c4)nc4c(C)cnn34)c[nH]c12]
I-183
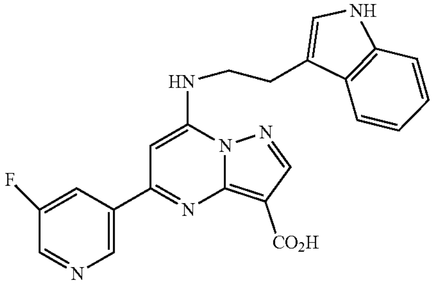 [SMILES: O=C(O)c1cnn2c(NCCc3c[nH]c4ccccc34)cc(-c3cncc(F)c3)nc12]
I-197
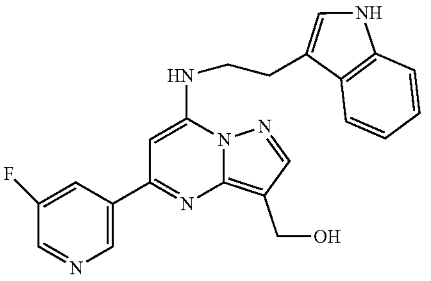 [SMILES: OCc1cnn2c(NCCc3c[nH]c4ccccc34)cc(-c3cncc(F)c3)nc12]
I-198a
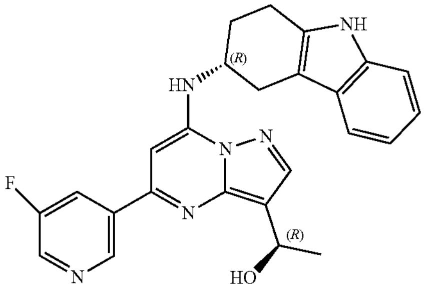
I-198b
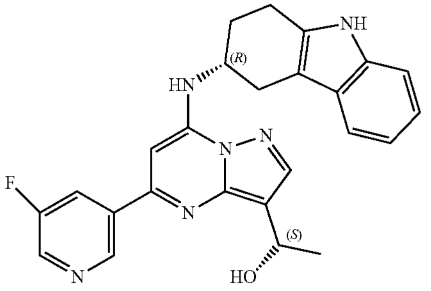

-continued
I-198c
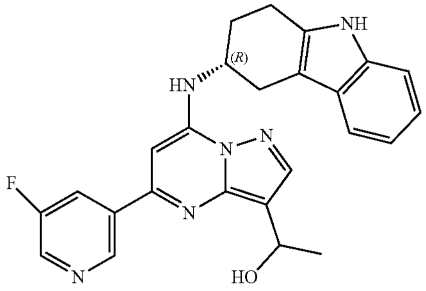
I-200
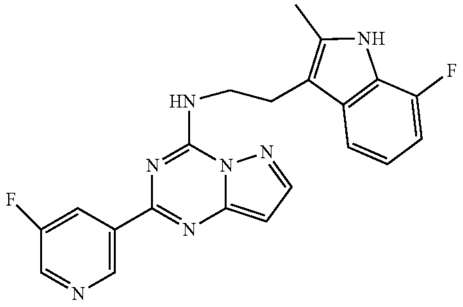 [SMILES: Cc1[nH]c2c(F)cccc2c1CCNc1nc(-c2cncc(F)c2)nc2ccnn12]
I-202
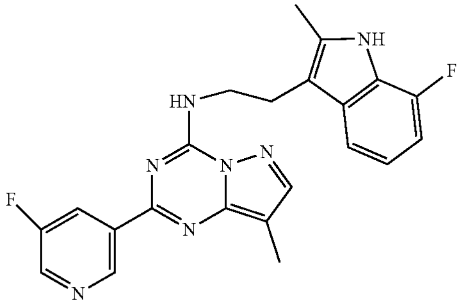 [SMILES: Cc1[nH]c2c(F)cccc2c1CCNc1nc(-c2cncc(F)c2)nc2c(C)cnn12]
I-203
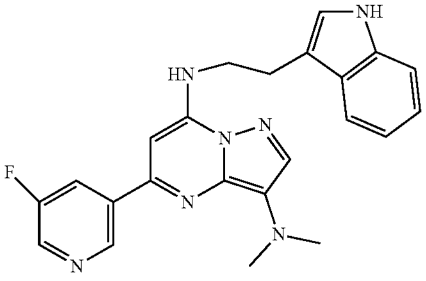 [SMILES: CN(C)c1cnn2c(NCCc3c[nH]c4ccccc34)cc(-c3cncc(F)c3)nc12]
I-212
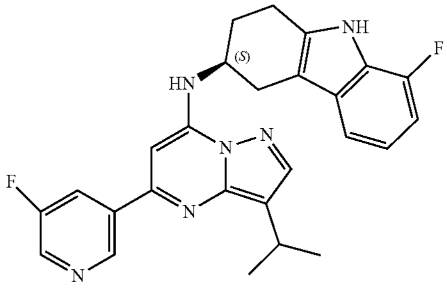
-continued
I-214
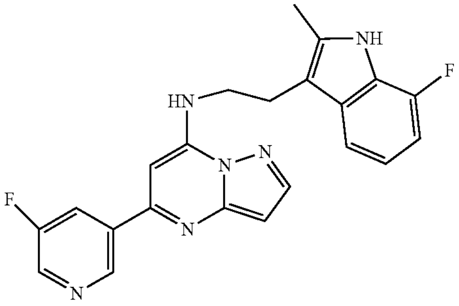 [SMILES: Cc1[nH]c2c(F)cccc2c1CCNc1cc(-c2cncc(F)c2)nc2ccnn12]
I-215
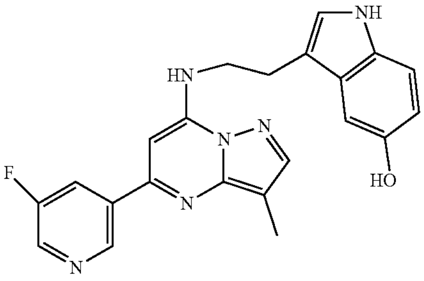 [SMILES: Cc1cnn2c(NCCc3c[nH]c4ccc(O)cc34)cc(-c3cncc(F)c3)nc12]
I-216a
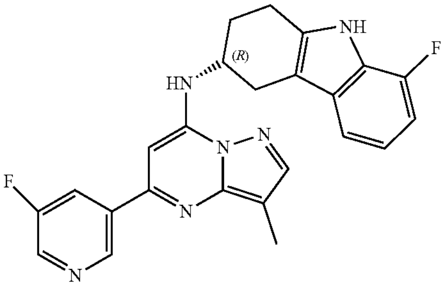
I-216b
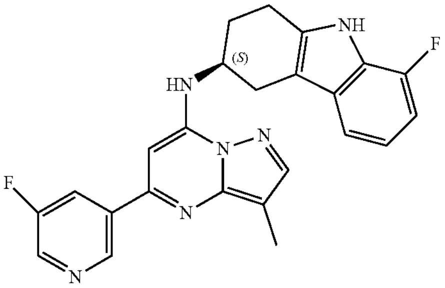
I-221
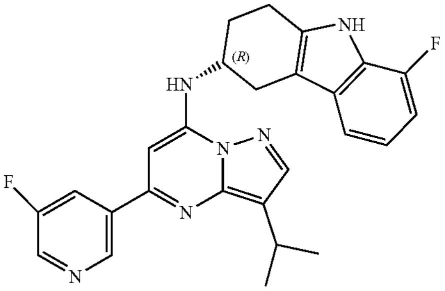

-continued
I-222a
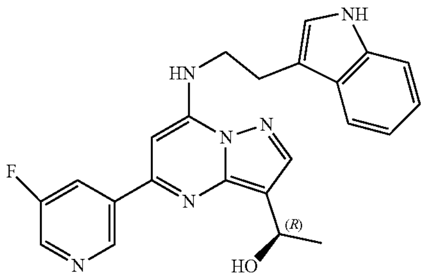
I-222b
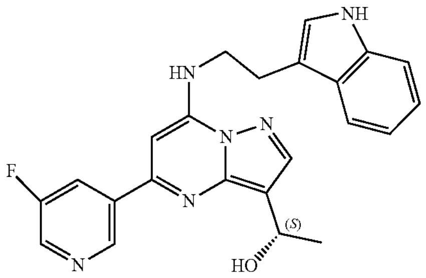
I-222c
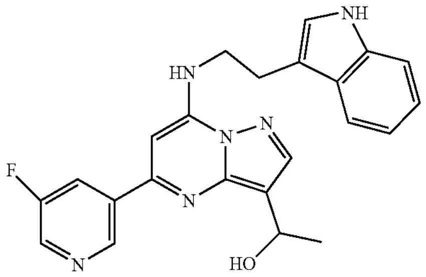 [SMILES: CC(O)c1cnn2c(NCCc3c[nH]c4ccccc34)cc(-c3cncc(F)c3)nc12]
I-224
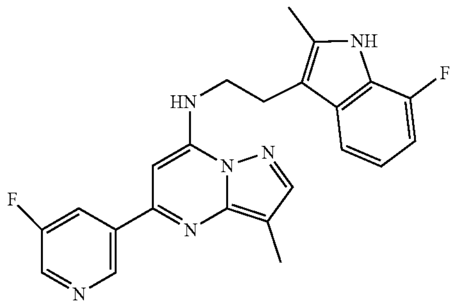 [SMILES: Cc1[nH]c2c(F)cccc2c1CCNc1cc(-c2cncc(F)c2)nc2c(C)cnn12]
I-225
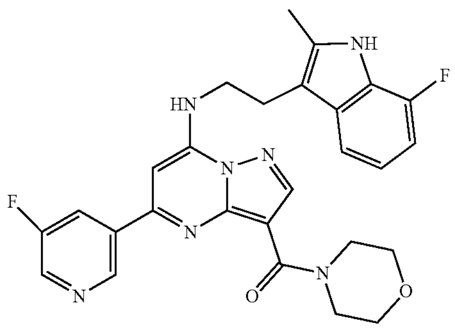 [SMILES: Cc1[nH]c2c(F)cccc2c1CCNc1cc(-c2cncc(F)c2)nc2c(C(=O)N3CCOCC3)cnn12]
-continued
I-226
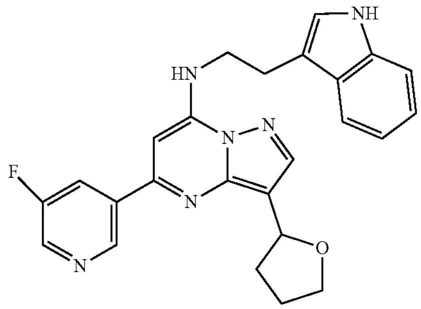 [SMILES: Fc1cncc(-c2cc(NCCc3c[nH]c4ccccc34)n3ncc(C4CCCO4)c3n2)c1]
I-230
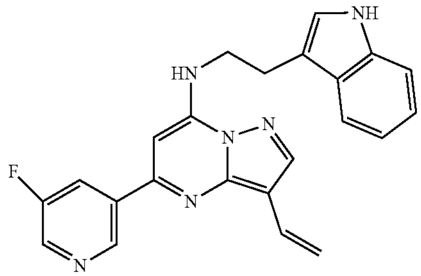 [SMILES: C=Cc1cnn2c(NCCc3c[nH]c4ccccc34)cc(-c3cncc(F)c3)nc12]
I-231
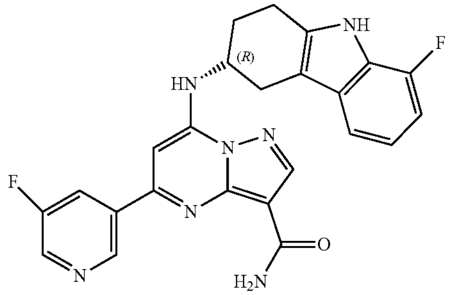
I-235
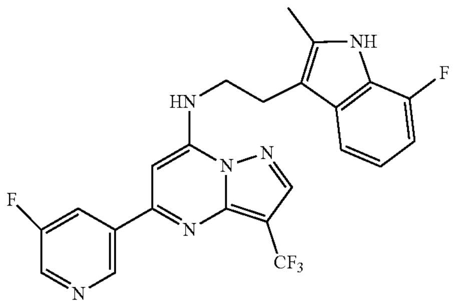 [SMILES: Cc1[nH]c2c(F)cccc2c1CCNc1cc(-c2cncc(F)c2)nc2c(C(F)(F)F)cnn12]
I-236
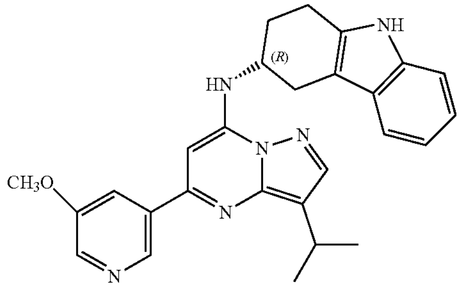

-continued
I-237
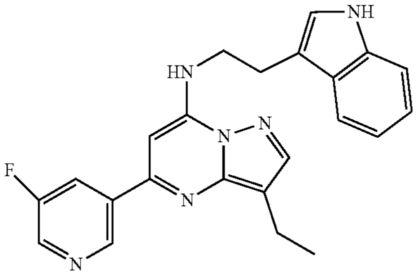 [SMILES: CCc1cnn2c(NCCc3c[nH]c4ccccc34)cc(-c3cncc(F)c3)nc12]
I-243a
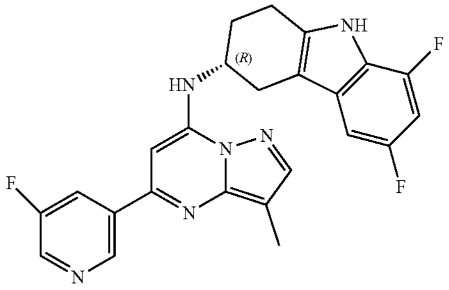
I-243b
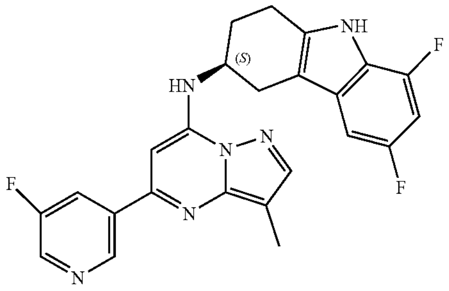
I-245
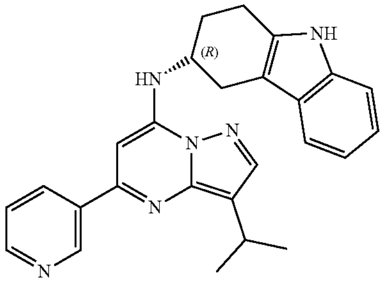
I-247a
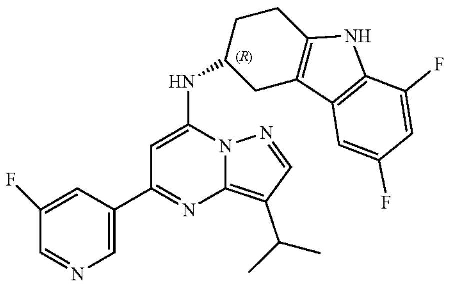
-continued
I-247b
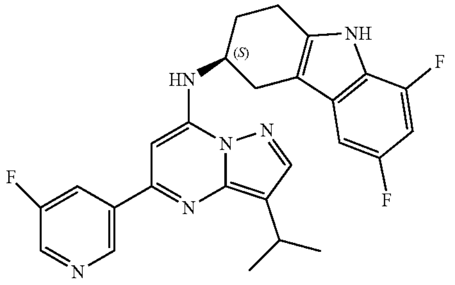
I-249a
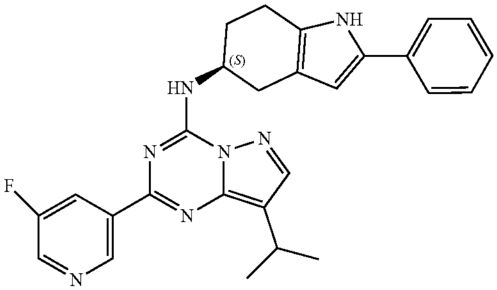
I-249b
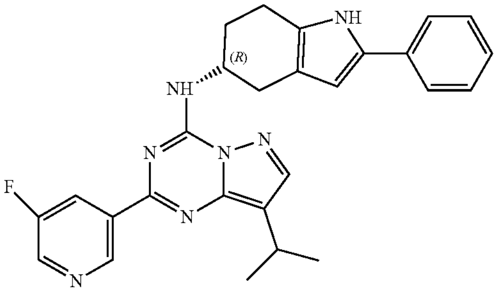
I-249c
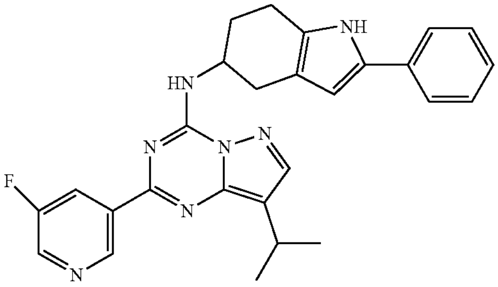 [SMILES: CC(C)c1cnn2c(NC3CCc4[nH]c(-c5ccccc5)cc4C3)nc(-c3cncc(F)c3)nc12]
I-251
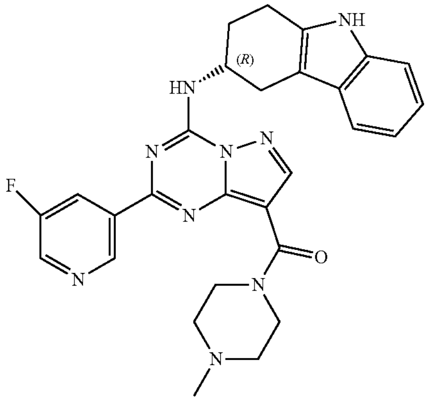

-continued
I-253
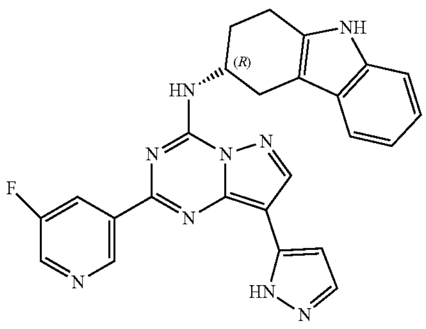
I-255
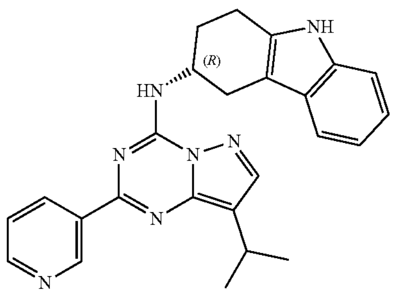
I-259a
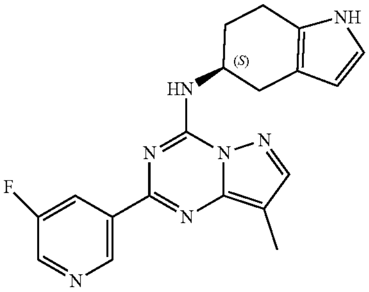
I-259b
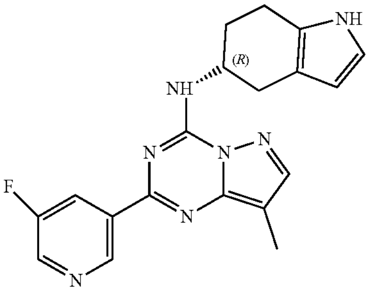
I-259c
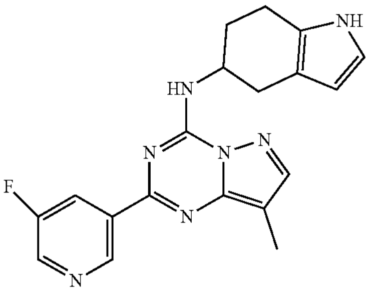 [SMILES: Cc1cnn2c(NC3CCc4[nH]ccc4C3)nc(-c3cncc(F)c3)nc12]
-continued
I-262
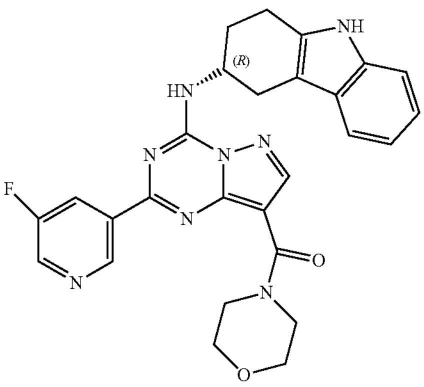
I-265
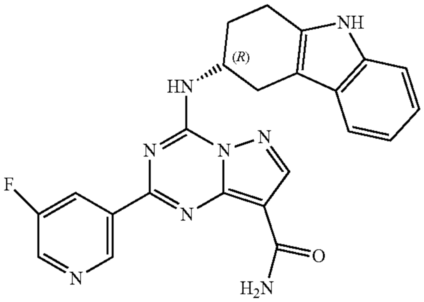
I-267
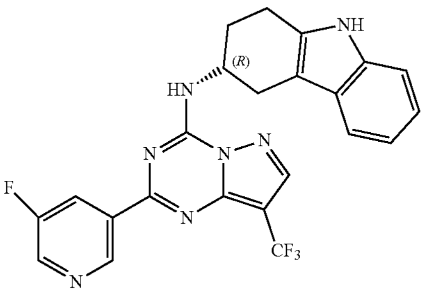
I-273
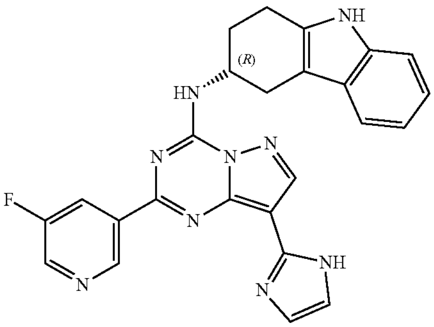

-continued
I-274
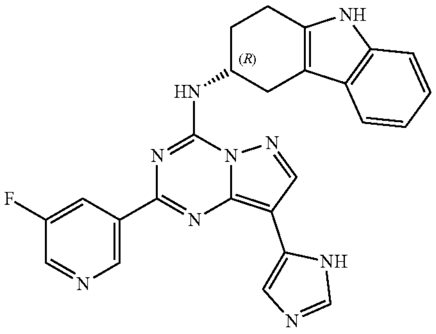
I-275
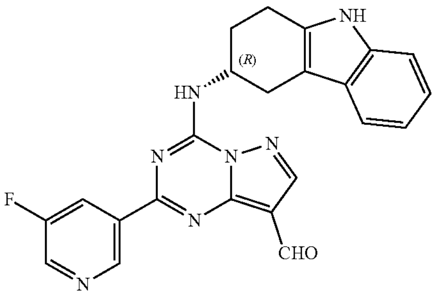
I-276
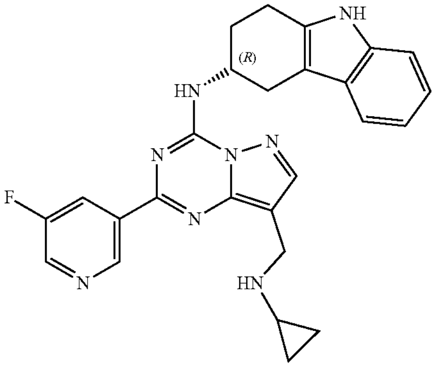
I-277
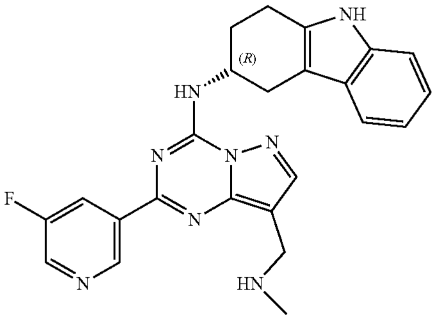
I-278
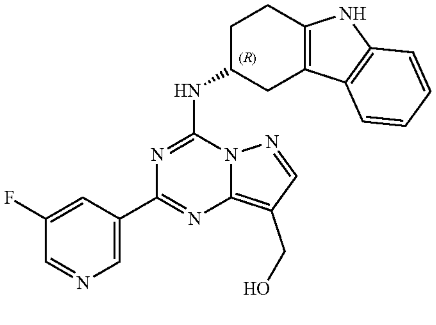
-continued
I-279
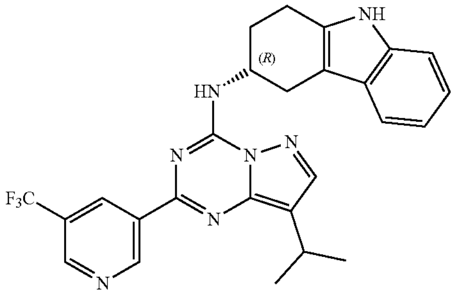
I-280
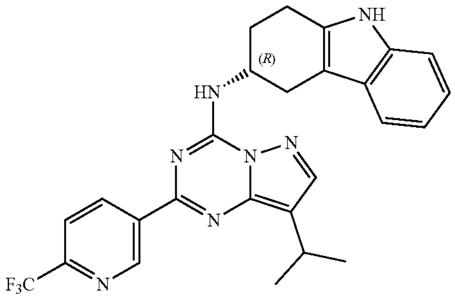
I-281
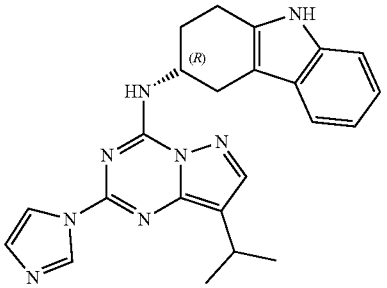
I-282
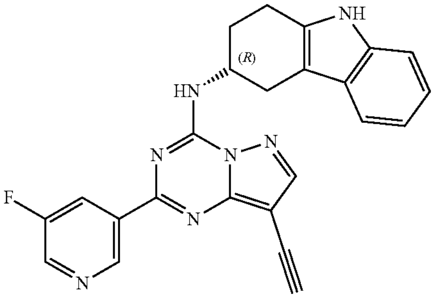
I-283
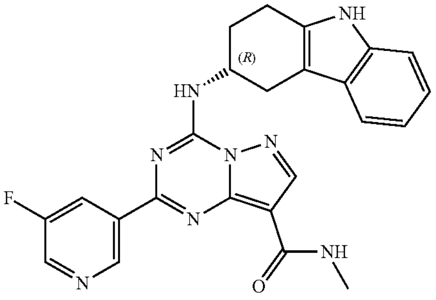

-continued

I-285

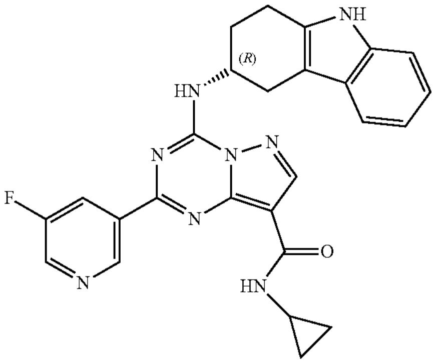

I-286

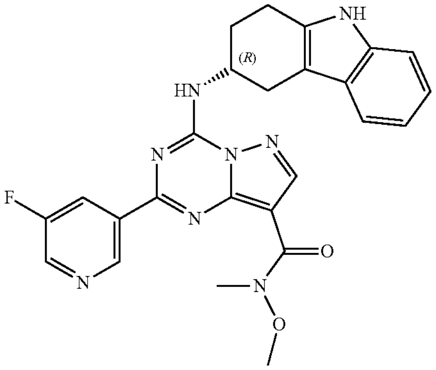

I-287

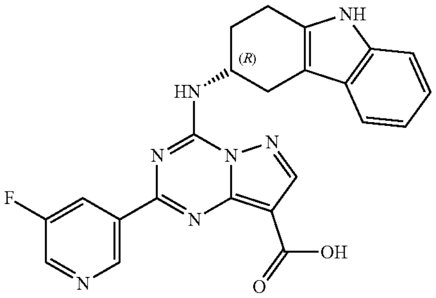

I-288

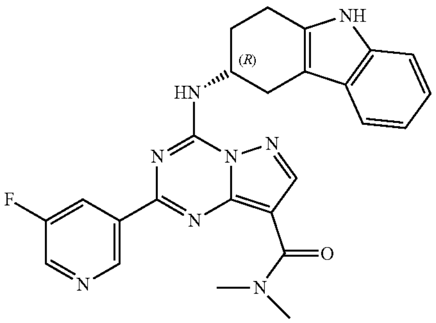

or a pharmaceutically acceptable salt thereof.

17. The method according to claim 16, wherein the compound is

I-129

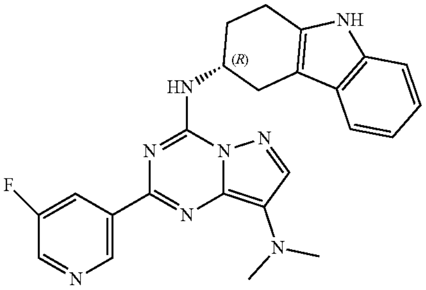

or a pharmaceutically acceptable salt thereof.

18. The method according to claim 16, wherein the compound is

I-137b

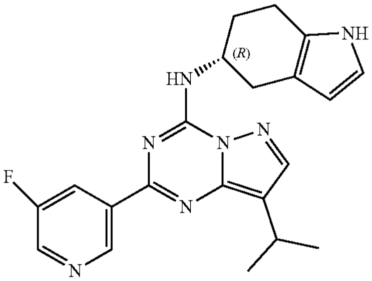

or a pharmaceutically acceptable salt thereof.

19. The method according to claim 16, wherein the compound is

I-40

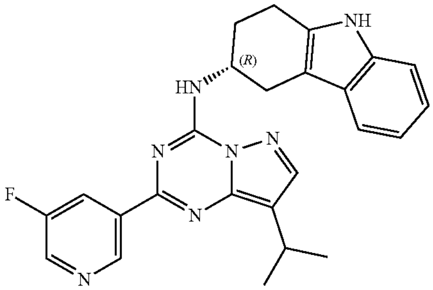

or a pharmaceutically acceptable salt thereof.

20. The method according to claim 16, wherein the compound is
I-259b
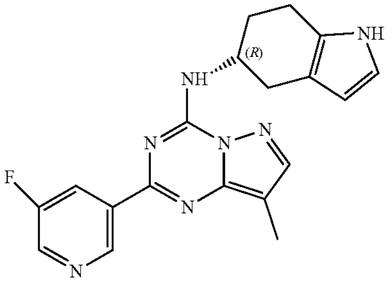
or a pharmaceutically acceptable salt thereof.
* * * * *